United States Patent [19]
Chien

[11] Patent Number: 6,150,087
[45] Date of Patent: Nov. 21, 2000

[54] NANBV DIAGNOSTICS AND VACCINES

[75] Inventor: David Y. Chien, Alamo, Calif.

[73] Assignee: Chiron Corporation, Emeryville, Calif.

[21] Appl. No.: 08/444,818

[22] Filed: May 18, 1995

Related U.S. Application Data

[62] Division of application No. 08/403,590, Mar. 14, 1995, which is a continuation of application No. 07/722,489, Jun. 24, 1991.

[51] Int. Cl.[7] .............................. C12Q 1/70; C07K 14/18
[52] U.S. Cl. .................. 435/5; 424/189.1; 424/228.1; 530/324; 530/325; 530/326; 530/327; 530/328; 530/329; 530/350
[58] Field of Search ................................. 530/324–329, 530/350; 435/5; 424/189.1, 228.1

[56] References Cited

U.S. PATENT DOCUMENTS

| | | | |
|---|---|---|---|
| 5,106,726 | 4/1992 | Wang | 435/5 |
| 5,312,737 | 5/1994 | Bolling et al. | 435/69.1 |
| 5,350,671 | 9/1994 | Houghton et al. | 435/5 |
| 5,371,017 | 12/1994 | Houghton et al. | 435/320.1 |
| 5,372,928 | 12/1994 | Miyamura et al. | 435/5 |
| 5,443,965 | 8/1995 | Reyes et al. | 435/69.3 |

FOREIGN PATENT DOCUMENTS

| | | | |
|---|---|---|---|
| 0 318 216 | 5/1989 | European Pat. Off. | C12N 15/00 |
| 0 388 232 A1 | 3/1990 | European Pat. Off. | C12N 15/51 |
| 0 419 182 A1 | 3/1991 | European Pat. Off. | C12N 15/51 |
| 0 435 229 A1 | 7/1991 | European Pat. Off. | C07K 15/00 |
| 0 463 848 A2 | 1/1992 | European Pat. Off. | C12N 15/40 |
| 0 464 287 | 1/1992 | European Pat. Off. | C12N 15/40 |
| 0 468 527 A2 | 1/1992 | European Pat. Off. | C07K 7/10 |
| 0 468 657 A2 | 1/1992 | European Pat. Off. | C12N 15/40 |
| 0 472 207 A2 | 2/1992 | European Pat. Off. | C12N 15/62 |
| 0 475 182 A2 | 3/1992 | European Pat. Off. | C12N 15/51 |
| 0 484 787 A2 | 5/1992 | European Pat. Off. | C07K 7/08 |
| 0 485 209 A1 | 5/1992 | European Pat. Off. | C12N 15/40 |
| 0 489 968 A1 | 6/1992 | European Pat. Off. | C07K 7/10 |
| 0 507 615 A1 | 10/1992 | European Pat. Off. | C07K 15/00 |
| 0 518 313 A2 | 12/1992 | European Pat. Off. | C12N 15/51 |
| 0 521 318 | 1/1993 | European Pat. Off. | C12N 15/51 |
| 0 442 394 A2 | 8/1994 | European Pat. Off. | C07K 7/08 |
| 0 644 202 A1 | 3/1995 | European Pat. Off. | C07K 14/18 |
| 0 445 423 B1 | 9/1995 | European Pat. Off. | G01N 33/576 |
| 5 068 562 | of 0000 | Japan . | |
| 3-103180 | 4/1991 | Japan | C12N 15/51 |
| 3-190898 | 8/1991 | Japan | C07K 7/10 |
| 4-004880 | 1/1992 | Japan | C12N 15/51 |
| 4-046196 | 2/1992 | Japan | C07K 13/00 |
| 4-121193 | 4/1992 | Japan | C12N 15/62 |
| 4-126086 | 4/1992 | Japan | C12N 15/51 |
| 4-144686 | 5/1992 | Japan | C12N 15/51 |
| 4-159298 | 6/1992 | Japan | C07K 7/08 |
| 4-179482 | 6/1992 | Japan | C12N 15/51 |
| 4-187090 | 7/1992 | Japan | C12N 15/51 |
| 4-305156 | 10/1992 | Japan | G01N 33/576 |
| 4-356500 | 12/1992 | Japan | C07K 13/00 |
| 5-91884 | 4/1993 | Japan | C12N 15/51 |
| 2 239 245 | 6/1991 | United Kingdom | C12N 15/51 |
| 2212511 | 1/1992 | United Kingdom | C12N 7/00 |
| 91/01376 | 2/1991 | WIPO . | |
| 91/15516 | 10/1991 | WIPO | C07K 15/00 |
| 92/02642 | 2/1992 | WIPO | C12Q 1/70 |
| 92/03458 | 3/1992 | WIPO | C07H 15/12 |
| 92/09634 | 6/1992 | WIPO | C07K 15/04 |
| 92/13892 | 8/1992 | WIPO | C07K 15/28 |
| 92/21759 | 12/1992 | WIPO | C12N 15/51 |
| 92/22571 | 12/1992 | WIPO | C07K 7/00 |

*Primary Examiner*—Michael P. Woodward
*Attorney, Agent, or Firm*—Robins & Associates; Alisa A. Harbin; Robert P. Blackburn

[57] ABSTRACT

We have discovered epitopes of the HCV viral proteins which are immunoreactive with immune serum. The epitopes are useful in immunodiagnostic assays and as immunogens.

10 Claims, 168 Drawing Sheets

FIG. 1

```
    AlaSerCysLeuAsnCysSerAlaSerIleIleProAspArgGluValLeuTyrArgGlu
  1 GGCCTCCTGCTTGAACTGCTCGGCGAGCATCATACCTGACAGGGAAGTCCTCTACCGAGA
    CCGGAGGACGAACTTGACGAGCCGCTCGTAGTATGGACTGTCCCTTCAGGAGATGGCTCT

PheAspGluMetGluGluCysSerGlnHisLeuProTyrIleGluGlnGlyMetMetLeu
 61 GTTCGATGAGATGGAAGAGTGCTCTCAGCACTTACCGTACATCGAGCAAGGGATGATGCT
    CAAGCTACTCTACCTTCTCACGAGAGTCGTGAATGGCATGTAGCTCGTTCCCTACTACGA

AlaGluGlnPheLysGlnLysAlaLeuGlyLeu
121 CGCCGAGCAGTTCAAGCAGAAGGCCCTCGGCCTCC
    GCGGCTCGTCAAGTTCGTCTTCCGGGAGCCGGAGG
```

FIG. 3

```
    GlyCysValValIleValGlyArgValValLeuSerGlyLysProAlaIleIleProAsp
  1 CTGGCTGCGTGGTCATAGTGGGCAGGGTCGTCTTGTCCGGGAAGCCGGCAATCATACCTG
    GACCGACGCACCAGTATCACCCGTCCCAGCAGAACAGGCCCTTCGGCCGTTAGTATGGAC

T
    ArgGluValLeuTyrArgGluPheAspGluMetGluGluCysSerGlnHisLeuProTyr
 61 ACAGGGAAGTCCTCTACCGAGAGTTCGATGAGATGGAAGAGTGCTCTCAGCACTTACCGT
    TGTCCCTTCAGGAGATGGCTCTCAAGCTACTCTACCTTCTCACGAGAGTCGTGAATGGCA
                       A

IleGluGlnGlyMetMetLeuAlaGluGlnPheLysGlnLysAlaLeuGlyLeuLeuGln
121 ACATCGAGCAAGGGATGATGCTCGCCGAGCAGTTCAAGCAGAAGGCCCTCGGCCTCCTGC
    TGTAGCTCGTTCCCTACTACGAGCGGCTCGTCAAGTTCGTCTTCCGGGAGCCGGAGGACG

ThrAlaSerArgGlnAlaGluValIleAlaProAlaValGlnThrAsnTrpGlnLysLeu
181 AGACCGCGTCCCGTCAGGCAGAGGTTATCGCCCCTGCTGTCCAGACCAACTGGCAAAAAC
    TCTGGCGCAGGGCAGTCCGTCTCCAATAGCGGGGACGACAGGTCTGGTTGACCGTTTTTG

GluThrPheTrpAlaLysHisMetTrpAsnPheIleSerGlyIleGlnTyrLeuAlaGly
241 TCGAGACCTTCTGGGCGAAGCATATGTGGAACTTCATCAGTGGGATACAATACTTGGCGG
    AGCTCTGGAAGACCCGCTTCGTATACACCTTGAAGTAGTCACCCTATGTTATGAACCGCC

LeuSerThrLeuProGlyAsnProAlaIleAlaSerLeuMetAlaPheThrAlaAlaVal
301 GCTTGTCAACGCTGCCTGGTAACCCCGCCATTGCTTCATTGATGGCTTTTACAGCTGCTG
    CGAACAGTTGCGACGGACCATTGGGGCGGTAACGAAGTAACTACCGAAAATGTCGACGAC

ThrSerProLeuThrThrSerGln
361 TCACCAGCCCACTAACCACTAGCCAAA
    AGTGGTCGGGTGATTGGTGATCGGTTT
```

FIG. 2

```
5-1-1   1                                         [ggcctcctgcttgaactgctcggcgagc]ATCATACCTGACAGGGAAG
                                                                              ||||||||||||||||||
  81    1                                         GTCCGGGAAGCCGGCAATCATACCTGACAGGGAAG
                                                  ||||||||||||||||||||||||||||||||||
  91    1    ctggctgcgtGGTCATAGTGGGCAGGGTCGTCTTGTCCGGGAAGCCGGCAATCATACCTGACAGGGAAG
                       ||||||||||||||||||||||||||||||||||||||||||||||||||||||||||
  1-2   1                 GGTCATAGTGGGCAGGGTCGTCTTGTCCGGGAAGCCGGCAATCATACCTGACAGGGAAG 5-1-1  48   TCCTCTACCGAGAGTTCGATGAGATGGAAGAGTGCTCTCAGCACTTACCGTACATCGAGCAAGGGATGATGC
            ||||||||||||||||||||||||||||||||||||||||||||||||||||||||||||||||||||||
  81   36   TCCTCTACCGAGAGTTCGATGAGATGGAAGAGTGCTCTCAGCACTTACCGTACATCGAGCAAGGGATGATGC
            ||||||||||||||||||||||||||||||||||||||||||||||||||||||||||||||||||||||
  91   70   TCCTCTACCGAGAGTTCGATGAGATGGAAGAGTGCTCTCAGCACTTACCGTACATCGAGCAAGGGATGATGC
            ||||| |||| |||||||||||||||||||||||||||||||||||||||||||||||||||||||||||
  1-2  60   TCCTCTAtCGAGAGTTCGATGAGATGGAAGAGTGCTCTCAGCACTTACCGTACATCGAGCAAGGGATGATGC 5-1-1 120   TCGCCGAGCAGTTCAAGCAGAAGGCCCTCGGCCTCC
            ||||||||||||||||||||||||||||||||||||
  81  108   TCGCCGAGCAGTTCAAGCAGAAGGCCCTCGGCCCTCCTGCAGAACCGCGTCCCGTCAGGCAGAGGTTATCGCCC
            ||||||||||||||||||||||||||||||||||||||||||||||||||||||||||||||||||||||||
  91  142   TCGCCGAGCAGTTCAAGCAGAAGGCCCTCGGCCCTCCTGCAGAACCGCGTCCCGTCAGGCAGAGGTTATCGCCC
            ||||||||||||||||||||||||||||||||
  1-2 132   TCGCCGAGCAGTTCAAGCAGAAGGCCCTCGGCC 81  180   CTGCTGTCCAGACCAACTGGCAAAAACTCGAGACCTTTCTGGGCGAAGCATATGTGGAACTTCATCAGTGGGA
            ||||||||||||||||||||||||||||||||||||||||||||||||||||||||||||||||||||||||
  91  214   CTGCTGTCCAGACCAACTGGCAAAAACTCGAGACCTTTCTGGGCGAAGCATATGTGGAACTTCATCAGTGGGA 81  252   TACAATACTTGGCGGGCTTGTCAACGCTGCCTGGtaaccccgccattgcttcattgatggctttacagctg
            ||||||||||||||||||||||||||||||||||
  91  286   TACAATACTTGGCGGGCTTGTCAACGCTGCCTGG 81  324   ctgtcaccagcccactaaccactagccaaa
```

FIG. 4

```
    SerGlyLysProAlaIleIleProAspArgGluValLeuTyrArgGluPheAspGluMet
  1 GTCCGGGAAGCCGGCAATCATACCTGACAGGAAGTCCTCTACCGAGAGTTCGATGAGAT
    CAGGCCCTTCGGCCGTTAGTATATGGACTGTCCTTCAGGAGATGGCTCTCAAGCTACTCTA

GluGluCysSerGlnHisLeuProTyrIleGluGlnPheMetMetLeuAlaGluGlnPhe
 61 GGAAGAGTGCTCTCAGCACTTACCGTACATCGAGCAAGGATGATGCTCGCCGAGCAGTT
    CCTTCTCACGAGAGTCGTGAATGGCATGTAGCTCGTTCCTACTACGAGCGGCTCGTCAA

LysGlnLysAlaLeuLeuGlyLeuLeuGlnThrAlaSerArgGlnAlaGluValIleAlaPro
121 CAAGCAGAAGGCCCTCCTCGGCCTCCTGCAGACCGCGTCCCGTCAGGCAGAGGTTATCGCCCC
    GTTCGTCTTCCGGGAGCCGGACGTCTGGCGCAGGGCAGTCCGTCTCCAATAGCGGGG

AlaValGlnThrAsnTrpGlnLysLeuLeuGluThrPheTrpAlaLysHisMetTrpAsnPhe
181 TGCTGTCCAGACCAACTGGCAAAAACTCGAGACCTTCTGGGCAAAGCATATGTGGAACTT
    ACGACAGGTCTGGTTGACCGTTTTTGAGCTCTGGAAGACCCGTTTCGTATACACCTTGAA

IleSerGlyIleGlnTyrLeuAlaGlyLeuSerThrLeuProGlyAsnProAlaIleAla
241 CATCAGTGGGATACAATACTTGGCGGGCTTGTCAACGCTGGTAACCCCGCCATTGC
    GTAGTCACCCTATGTTATGAACCGCCCGAACAGTTGCGACCATTGGGGCGGTAACG

SerLeuMetAlaPheThrAlaAlaValThrSerProLeuThrThrSerGln
301 TTCATTGATGGCTTTACAGCTGCTGTCACCAGCCCACTAACCACTAGCCAAA
    AAGTAACTACCGAAAATGTCGACGACAGTGGTCGGGTGATTGGTGATCGGTTT
```

FIG. 5

```
    AspAlaHisPheLeuSerGlnThrLysGlnSerGlyGluAsnLeuProTyrLeuValAla
  1 GATGCCCACTTTCTATCCCAGACAACAAAGCAGAGTGGGGAGAACCTTCCTTACCTGGTAGCG
    CTACGGGTGAAAGATAGGGTCTGTTTCGTCTCACCCCTCTTGGAAGGAATGGACCATCGC

TyrGlnAlaThrValCysAlaArgAlaGlnAlaProProSerTrpAspGlnMetTrp
 61 TACCAAGCCACCGTGTGCGCTAGGGCTCAAGCCCCTCCCCCATGTGGGACCAGATGTGG
    ATGGTTCGGTGGCACACGCGATCCCGAGTTCGGGAGGGGTAGCACCCTGGTCTACACC

LysCysLeuIleArgLeuLysProThrLeuHisGlyProThrProLeuTyrArgLeu
121 AAGTGTTTGATTCGCCTCAAGCCCACCCTCCATGGCCCAACACCCTCTATACAGACTG
    TTCACAAACTAAGCGGAGTTCGGGTGGGAGGTACCCGGTTGTGGGACGATATGTCTGAC

GlyAlaValGlnAsnGluIleThrLeuHisProValThrLysTyrIleMetThrCys
181 GGGGCTGTTCAGAATGAAATCACCCTGCACCCCAGTCACCAAATCATGACATG
    CCGCGACAAGTCTTACTTTAGTGGGACTGTCAGTGGTCAGTGGTTTAGTAGTACTGTACG

MetSerAlaAspLeuGluValValThrSerThrTrpValLeuValGlyGlyValLeuAla
241 ATGTCGGCCGACCTGGAGGTCGTCACGAGCACCTGGGTGCTCGTTGGCGGTCCTGGCT
    TACAGCCGGCTGGACCTCCAGCAGTGCTCGTGGACCCACGAGCAACCGCCAGGACCGA

AlaLeuAlaAlaTyrCysLeuSerThrGlyCysValValIleValGlyArgValLeu
301 GCTTTGGCCGCGTATTGCCTGTCAACAGGCTGCGTGGTGATAGTGGGCAGGGTCGTCTTG
    CGAAACCGGCGCATAACGGACAGTTGTCCGACGCACCAGTATCACCCGTCCCAGCAGAAC

---------Overlap with 81---------
    SerGlyLysProAlaIleIleProAspArgGluValLeuTyrArg
361 TCCGGAAGCCGGCAATCATACCTGACAGGAAGTCCTCTACCGAG
    AGGCCCTTCGGCCGTTAGTATGGACTGTCCCTTCAGGAGATGGCTC
```

FIG. 6

```
       AspAlaHisPheLeuSerGlnThrLysGlnSerGlyGluAsnLeuProTyrLeuValAla
  1    GATGCCCACTTTCTATCCCAGACAAAGCAGAGTGGGGAGAACCTTCCTTACCTGGTAGCG
       CTACGGGTGAAAGATAGGGTCTGTTTCGTCTCACCCCTCTTGGAAGGAATGGACCATCGC

TyrGlnAlaThrValCysAlaArgAlaGlnAlaProProProSerTrpAspGlnMetTrp
  61   TACCAAGCCACCGTGTGCGCTAGGGCTCAAGCCCCTCCCCCATCGTGGGACCAGATGTGG
       ATGGTTCGGTGGCACACGCGATCCCGAGTTCGGGGAGGGGGTAGCACCCTGGTCTACACC

LysCysLeuIleArgLeuLysProThrLeuHisGlyProThrProLeuLeuTyrArgLeu
 121   AAGTGTTTGATTCGCCTCAAGCCCACCCTCCATGGGCCAACACCCCTGCTATACAGACTG
       TTCACAAACTAAGCGGAGTTCGGGTGGGAGGTACCCGGTTGTGGGGACGATATGTCTGAC

GlyAlaValGlnAsnGluIleThrLeuThrHisProValThrLysTyrIleMetThrCys
 181   GGCGCTGTTCAGAATGAAATCACCCTGACGCACCCAGTCACCAAATACATCATGACATGC
       CCGCGACAAGTCTTACTTTAGTGGGACTGCGTGGGTCAGTGGTTTATGTAGTACTGTACG

MetSerAlaAspLeuGluValValThrSerThrTrpValLeuValGlyGlyValLeuAla
 241   ATGTCGGCCGACCTGGAGGTCGTCACGAGCACCTGGGTGCTCGTTGGCGGCGTCCTGGCT
       TACAGCCGGCTGGACCTCCAGCAGTGCTCGTGGACCCACGAGCAACCGCCGCAGGACCGA

AlaLeuAlaAlaTyrCysLeuSerThrGlyCysValValIleValGlyArgValValLeu
 301   GCTTTGGCCGCGTATTGCCTGTCAACAGGCTGCGTGGTCATAGTGGGCAGGGTCGTCTTG
       CGAAACCGGCGCATAACGGACAGTTGTCCGACGCACCAGTATCACCCGTCCCAGCAGAAC

SerGlyLysProAlaIleIleProAspArgGluValLeuTyrArgGluPheAspGluMet
 361   TCCCGGAAGCCGGCAATCATACCTGACAGGGAAGTCCTCTACCGAGAGTTCGATGAGATG
       AGGGCCTTCGGCCGTTAGTATGGACTGTCCCTTCAGGAGATGGCTCTCAAGCTACTCTAC

GluGluCysSerGlnHisLeuProTyrIleGluGlnGlyMetMetLeuAlaGluGlnPhe
 421   GAAGAGTGCTCTCAGCACTTACCGTACATCGAGCAAGGGATGATGCTCGCCGAGCAGTTC
       CTTCTCACGAGAGTCGTGAATGGCATGTAGCTCGTTCCCTACTACGAGCGGCTCGTCAAG

LysGlnLysAlaLeuGlyLeuLeuGlnThrAlaSerArgGlnAlaGluValIleAlaPro
 481   AAGCAGAAGGCCCTCGGCCTCCTGCAGACCGCGTCCCGTCAGGCAGAGGTTATCGCCCCT
       TTCGTCTTCCGGGAGCCGGAGGACGTCTGGCGCAGGGCAGTCCGTCTCCAATAGCGGGGA

AlaValGlnThrAsnTrpGlnLysLeuGluThrPheTrpAlaLysHisMetTrpAsnPhe
 541   GCTGTCCAGACCAACTGGCAAAAACTCGAGACCTTCTGGGCGAAGCATATGTGGAACTTC
       CGACAGGTCTGGTTGACCGTTTTTGAGCTCTGGAAGACCCGCTTCGTATACACCTTGAAG

IleSerGlyIleGlnTyrLeuAlaGlyLeuSerThrLeuProGlyAsnProAlaIleAla
 601   ATCAGTGGGATACAATACTTGGCGGGCTTGTCAACGCTGCCTGGTAACCCCGCCATTGCT
       TAGTCACCCTATGTTATGAACCGCCCGAACAGTTGCGACGGACCATTGGGGCGGTAACGA

SerLeuMetAlaPheThrAlaAlaValThrSerProLeuThrThrSerGln
 661   TCATTGATGGCTTTTACAGCTGCTGTCACCAGCCCACTAACCACTAGCCAAA
       AGTAACTACCGAAAATGTCGACGACAGTGGTCGGGTGATTGGTGATCGGTTT
```

FIG. 7

```
        ------Overlap with 81--------------------
        PheThrAlaAlaValThrSerProLeuThrThrSerGlnThrLeuLeuPheAsnIleLeu
  1     CTTTTACAGCTGCTGTCACCAGCCCACTAACCACTAGCCAAACCCTCCTCTTCAACATAT .
        GAAAATGTCGACGACAGTGGTCGGGTGATTGGTGATCGGTTTGGGAGGAGAAGTTGTATA GlyGlyTrpValAlaAlaGlnLeuAlaAlaProGlyAlaAlaThrAlaPheValGlyAla
  61    TGGGGGGGTGGGTGGCTGCCCAGCTCGCCGCCCCGGTGCCGCTACTGCCTTTGTGGGCG
        ACCCCCCCACCCACCGACGGGTCGAGCGGCGGGGGCCACGGCGATGACGGAAACACCCGC GlyLeuAlaGlyAlaAlaIleGlySerValGlyLeuGlyLysValLeuIleAspIleLeu
  121   CTGGCTTAGCTGGCGCCGCCATCGGCAGTGTTGGACTGGGGAAGGTCCTCATAGACATCC
        GACCGAATCGACCGCGGCGGTAGCCGTCACAACCTGACCCCTTCCAGGAGTATCTGTAGG AlaGlyTyrGlyAlaGlyValAlaGlyAlaLeuValAlaPheLysIleMetSerGlyGlu
  181   TTGCAGGGTATGGCGCGGGCGTGGCGGGAGCTCTTGTGGCATTCAAGATCATGAGCGGTG
        AACGTCCCATACCGCGCCCGCACCGCCCTCGAGAACACCGTAAGTTCTAGTACTCGCCAC ValProSerThrGluAspLeuValAsnLeuLeuProAlaIleLeuSerProGlyAlaLeu
  241   AGGTCCCCTCCACGGAGGACCTGGTCAATCTACTGCCCGCCATCCTCTCGCCCGGAGCCC
        TCCAGGGGAGGTGCCTCCTGGACCAGTTAGATGACGGGCGGTAGGAGAGCGGGCCTCGGG ValValGlyValValCysAlaAlaIleLeuArgArgHisValGlyProGlyGluGlyAla
  301   TCGTAGTCGGCGTGGTCTGTGCAGCAATACTGCGCCGGCACGTTGGCCCGGGCGAGGGGG
        AGCATCAGCCGCACCAGACACGTCGTTATGACGCGGCCGTGCAACCGGGCCCGCTCCCCC ValGlnTrpMetAsnArgLeuIleAlaPheAlaSerArgGlyAsnHisValSer
  361   CAGTGCAGTGGATGAACCGGCTGATAGCCTTCGCCTCCCGGGGGAACCATGTTTCCCC
        GTCACGTCACCTACTTGGCCGACTATCGGAAGCGGAGGGCCCCCTTGGTACAAAGGGG
```

FIG. 8A

```
    SerIleGluThrIleThrLeuProGlnAspAlaValSerArgArgThrGlnArgArgGlyArg
  1 TCCATTGAGACAATCACGCTCCCCAGGATGCTGTCTCCCGCACTCAACGTCGGGGCAGG
    AGGTAACTCTGTTAGTGCGAGGGGTCCTACGACAGAGGGCGTGAGTTGCAGCCCCGTCC

ThrGlyArgGlyLysProGlyIleTyrArgPheValAlaProGlyGluArgProSerGly
 61 ACTGGCAGGGGGAAGCCAGGCCATCTACAGATTTGTGGCACCGGGGGAGCGCCCTCCGGC
    TGACCGTCCCCCTTCGGTCCGGTAGATGTCTAAACACCGTGGCCCCCTCGCGGGAGGCCG

MetPheAspSerSerValLeuCysGluCysTyrAspAlaGlyCysAlaTrpTyrGluLeu
121 ATGTTCGACTCGAGTGTCCTCTGTGAGTGCTATGACGCAGGCTGTGCTTGGTATGAGCTC
    TACAAGCTGAGCTCACAGGAGGACACTCACGATACTGCGTCCGACACGAACCATACTCGAG

ThrProAlaGluThrThrValArgLeuArgAlaTyrMetAsnThrProGlyLeuProVal
181 ACGCCCGCGGAGACTACAGTTAGGCTACGAGCGTACATGAACACCCCGGGCTTCCCGTG
    TGCGGGCGCCTCTGATGTCAATCCGATGCTCGCATGTACTTGTGGGCCCCGAAGGGCAC
```

FIG. 8B

```
     CysGlnAspHisLeuGluPheTrpGluGlyValPheThrGlyLeuThrHisIleAspAla
241  TGCCAGGACCATCTTGAACTTTGGGAGGCGTCTTTACAGGCCTCACTCATATAGATGCC
     ACGGTCCTGGTAGAACTTGAAACCCTCCGCAGAAATGTCCGGAGTGAGTATATCTACGG

HisPheLeuSerGlnThrLysGlnSerGlyGluAsnLeuProTyrLeuValAlaTyrGln
301  CACTTTCTATCCCAGACAAAGCAGAGTGGGGAGAACCTTCCTTACCTGGTAGCGTACCAA
     GTGAAAGATAGGGTCTGTTTCGTCTCACCCCCTCTTGGAAGGAATGGACCATCGCATGGTT

---------Overlap with 36---------
     AlaThrValCysAlaArgAlaAlaGlnAlaProProSerTrpAspGlnMetTrpLysCys
361  GCCACCGTGTGCGCTAGGGCTGCTCAAGCCTCCCCCATCGTGGGACCAGATGTGGAAGTGT
     CGGTGGCACACGCGATCCCGAGTTCGGAGGGGTAGCACCCTGGTCTACACCTTCACA LeuIleArgLeuLysProThrLeuHisGlyProThrProLeuLeuTyrArgLeuGlyAla
421  TTGATTCGCCTCAAGCCCACCCTCCATGGCCCAACACCCCTGCTATACAGACTGGGCGCT
     AACTAAGCGGAGTTCGGGTGGGAGGTACCGGGTTGTGGGGACGATATGTCTGACCCGCGA
```

FIG. 9A

```
    SerIleGluThrIleThrLeuProGlnAspAlaValSerArgThrGlnArgArgGlyArg
  1 TCCATTGAGACAATCACGCTCCCCCAGGATGCTGTCTCCCGCACTCAACGTCGGGGCAGG
    AGGTAACTCTGTTAGTGCGAGGGGGTCCTACGACAGAGGGCGTGAGTTGCAGCCCCGTCC

ThrGlyArgGlyLysProGlyIleTyrArgPheValAlaProGlyGluArgProSerGly
 61 ACTGGCAGGGGGAAGCCAGGCATCTACAGATTTGTGGCACCGGGGGAGCGCCCCTCCGGC
    TGACCGTCCCCCTTCGGTCCGTAGATGTCTAAACACCGTGGCCCCCTCGCGGGGAGGCCG

MetPheAspSerSerValLeuCysGluCysTyrAspAlaGlyCysAlaTrpTyrGluLeu
121 ATGTTCGACTCGTCCGTCCTCTGTGAGTGCTATGACGCAGGCTGTGCTTGGTATGAGCTC
    TACAAGCTGAGCAGGCAGGAGACACTCACGATACTGCGTCCGACACGAACCATACTCGAG

ThrProAlaGluThrThrValArgLeuArgAlaTyrMetAsnThrProGlyLeuProVal
181 ACGCCCGCCGAGACTACAGTTAGGCTACGAGCGTACATGAACACCCCGGGGCTTCCCGTG
    TGCGGGCGGCTCTGATGTCAATCCGATGCTCGCATGTACTTGTGGGGCCCCGAAGGGCAC

CysGlnAspHisLeuGluPheTrpGluGlyValPheThrGlyLeuThrHisIleAspAla
241 TGCCAGGACCATCTTGAATTTTGGGAGGGCGTCTTTACAGGCCTCACTCATATAGATGCC
    ACGGTCCTGGTAGAACTTAAAACCCTCCCGCAGAAATGTCCGGAGTGAGTATATCTACGG

HisPheLeuSerGlnThrLysGlnSerGlyGluAsnLeuProTyrLeuValAlaTyrGln
301 CACTTTCTATCCCAGACAAAGCAGAGTGGGGAGAACCTTCCTTACCTGGTAGCGTACCAA
    GTGAAAGATAGGGTCTGTTTCGTCTCACCCCTCTTGGAAGGAATGGACCATCGCATGGTT

AlaThrValCysAlaArgAlaGlnAlaProProProSerTrpAspGlnMetTrpLysCys
361 GCCACCGTGTGCGCTAGGGCTCAAGCCCCTCCCCCATCGTGGGACCAGATGTGGAAGTGT
    CGGTGGCACACGCGATCCCGAGTTCGGGGAGGGGGTAGCACCCTGGTCTACACCTTCACA

LeuIleArgLeuLysProThrLeuHisGlyProThrProLeuLeuTryArgLeuGlyAla
421 TTGATTCGCCTCAAGCCCACCCTCCATGGGCCAACACCCCTGCTATACAGACTGGGCGCT
    AACTAAGCGGAGTTCGGGTGGGAGGTACCCGGTTGTGGGGACGATATGTCTGACCCGCGA

ValGlnAsnGluIleThrLeuThrHisProValThrLysTyrIleMetThrCysMetSer
481 GTTCAGAATGAAATCACCCTGACGCACCCAGTCACCAAATACATCATGACATGCATGTCG
    CAAGTCTTACTTTAGTGGGACTGCGTGGGTCAGTGGTTTATGTAGTACTGTACGTACAGC

AlaAspLeuGluValValThrSerThrTrpValLeuValGlyGlyValLeuAlaAlaLeu
541 GCCGACCTGGAGGTCGTCACGAGCACCTGGGTGCTCGTTGGCGGCGTCCTGGCTGCTTTG
    CGGCTGGACCTCCAGCAGTGCTCGTGGACCCACGAGCAACCGCCGCAGGACCGACGAAAC

AlaAlaTyrCysLeuSerThrGlyCysValValIleValGlyArgValValLeuSerGly
601 GCCGCGTATTGCCTGTCAACAGGCTGCGTGGTCATAGTGGGCAGGGTCGTCTTGTCCGGG
    CGGCGCATAACGGACAGTTGTCCGACGCACCAGTATCACCCGTCCCAGCAGAACAGGCCC

LysProAlaIleIleProAspArgGluValLeuTyrArgGluPheAspGluMetGluGlu
661 AAGCCGGCAATCATACCTGACAGGGAAGTCCTCTACCGAGAGTTCGATGAGATGGAAGAG
    TTCGGCCGTTAGTATGGACTGTCCCTTCAGGAGATGGCTCTCAAGCTACTCTACCTTCTC

CysSerGlnHisLeuProTyrIleGluGlnGlyMetMetLeuAlaGluGlnPheLysGln
721 TGCTCTCAGCACTTACCGTACATCGAGCAAGGGATGATGCTCGCCGAGCAGTTCAAGCAG
    ACGAGAGTCGTGAATGGCATGTAGCTCGTTCCCTACTACGAGCGGCTCGTCAAGTTCGTC

LysAlaLeuGlyLeuLeuGlnThrAlaSerArgGlnAlaGluValIleAlaProAlaVal
781 AAGGCCCTCGGCCTCCTGCAGACCGCGTCCCGTCAGGCAGAGGTTATCGCCCCTGCTGTC
    TTCCGGGAGCCGGAGGACGTCTGGCGCAGGGCAGTCCGTCTCCAATAGCGGGGACGACAG
```

FIG. 9B

```
        GlnThrAsnTrpGlnLysLeuGluThrPheTrpAlaLysHisMetTrpAsnPheIleSer
  841   CAGACCAACTGGCAAAAACTCGAGACCTTCTGGGCGAAGCATATGTGGAACTTCATCAGT
        GTCTGGTTGACCGTTTTTGAGCTCTGGAAGACCCGCTTCGTATACACCTTGAAGTAGTCA

GlyIleGlnTyrLeuAlaGlyLeuSerThrLeuProGlyAsnProAlaIleAlaSerLeu
  901   GGGATACAATACTTGGCGGGCTTGTCAACGCTGCCTGGTAACCCCGCCATTGCTTCATTG
        CCCTATGTTATGAACCGCCCGAACAGTTGCGACGGACCATTGGGGCGGTAACGAAGTAAC

MetAlaPheThrAlaAlaValThrSerProLeuThrThrSerGlnThrLeuLeuPheAsn
  961   ATGGCTTTTACAGCTGCTGTCACCAGCCCACTAACCACTAGCCAAACCCTCCTCTTCAAC
        TACCGAAAATGTCGACGACAGTGGTCGGGTGATTGGTGATCGGTTTGGGAGGACAAGTTG

IleLeuGlyGlyTrpValAlaAlaGlnLeuAlaAlaProGlyAlaAlaThrAlaPheVal
 1021   ATATTGGGGGGTGGGTGGCTGCCCAGCTCGCCGCCCCGGTGCCGCTACTGCCTTTGTG
        TATAACCCCCCCACCCACCGACGGGTCGAGCGGCGGGGGCCACGGCGATGACGGAAACAC

GlyAlaGlyLeuAlaGlyAlaAlaIleGlySerValGlyLeuGlyLysValLeuIleAsp
 1081   GGCGCTGGCTTAGCTGGCGCCGCCATCGGCAGTGTTGGACTGGGGAAGGTCCTCATAGAC
        CCGCGACCGAATCGACCGCGGCGGTAGCCGTCACAACCTGACCCCTTCCAGGAGTATCTG

IleLeuAlaGlyTyrGlyAlaGlyValAlaGlyAlaLeuValAlaPheLysIleMetSer
 1141   ATCCTTGCAGGGTATGGCGCGGGCGTGGCGGGAGCTCTTGTGGCATTCAAGATCATGAGC
        TAGGAACGTCCCATACCGCGCCCGCACCGCCCTCGAGAACACCGTAAGTTCTAGTACTCG

GlyGluValProSerThrGluAspLeuValAsnLeuLeuProAlaIleLeuSerProGly
 1201   GGTGAGGTCCCCTCCACGGAGGACCTGGTCAATCTACTGCCCGCCATCCTCTCGCCCGGA
        CCACTCCAGGGGAGGTGCCTCCTGGACCAGTTAGATGACGGGCGGTAGGAGAGCGGGCCT

AlaLeuValValGlyValValCysAlaAlaIleLeuArgArgHisValGlyProGlyGlu
 1261   GCCCTCGTAGTCGGCGTGGTCTGTGCAGCAATACTGCGCCGGCACGTTGGCCCGGGCGAG
        CGGGAGCATCAGCCGCACCAGACACGTCGTTATGACGCGGCCGTGCAACCGGGCCCGCTC

GlyAlaValGlnTrpMetAsnArgLeuIleAlaPheAlaSerArgGlyAsnHisValSer
 1321   GGGGCAGTGCAGTGGATGAACCGGCTGATAGCCTTCGCCTCCCGGGGGAACCATGTTTCCCC
        CCCCGTCACGTCACCTACTTGGCCGACTATCGGAAGCGGAGGGCCCCCTTGGTACAAAGGGG
```

FIG. 10

```
    LeuAlaAlaLysLeuValAlaAlaLeuGlyIleAsnAlaValAlaAlaTyrTyrArgGlyLeuAsp
  1 CTCGCCCGCAAAGCTGGTCGCCGCATTGGGCATCAATGCCGTGGCCGCCTACTACCGCGGTCTTGAC
    GAGCGGGCGTTTCGACCAGCTACCCGTAGTTACGGCACCGGATGATGGCGCCAGAACTG

ValSerValIleProThrSerGlyAspValValValValAlaThrAspAlaLeuMetThr
 61 GTGTCCGTCATCCCGACCAGCGGCGATGTTGTCGTGGCAACCGATGCCCTCATGACC
    CACAGGCAGTAGGGCTGGTCGCCGCTACAACAGCAGCACCGTTGGCTACGGAGTACTGG

GlyTyrThrGlyAspPheAspSerValIleAspTyrAsnThrCysValThrGlnThrVal
121 GGCTATACCGGCGACTTCGACTCGGTGATAGACTACAATACGTGTGTCACCCAGACAGTC
    CCGATATGGCCGCTGAAGCTGAGCCACTATCTGATGTTATGCACACAGTGGGTCTGTCAG

---------Overlap with
    AspPheSerLeuAspProThrPheThrIleGluThrIleThrLeuProGlnAspAlaVal
181 GATTTCAGCCTTGACCCTACCTTCACCATTGAGACAATCACGCTCCCCCAGGATGCTGTC
    CTAAAGTCGGAACTGGGATGGAAGTGGTAACTCTGTTAGTGCGAGGGGTCCTACGACAG clone 35---------
    SerArgThrGlnArgArgGlyArgThr
241 TCCCGCACTCAACGTCGGGGGCAGGACTG
    AGGGCGTGAGTTGCAGCCCCGTCCTGAC
```

FIG. 11

```
        -------Overlap with 32---------------------
         MetAsnArgLeuIleAlaPheAlaSerArgGlyAsnHisValSerProThrHisTyrVal
  1   GATGAACCGGCTGATAGCCTTCGCCTCCCGGGGGAACCATGTTTCCCCCACGCACTACGT
      CTACTTGGCCGACTATCGGAAGCGGAGGGCCCCCTTGGTACAAAGGGGGTGCGTGATGCA ProGluSerAspAlaAlaAlaArgValThrAlaIleLeuSerSerLeuThrValThrGln
 61   GCCGGAGAGCGATGCAGCTGCCCGCGTCACTGCCATACTCAGCAGCCTCACTGTAACCCA
      CGGCCTCTCGCTACGTCGACGGGCGCAGTGACGGTATGAGTCGTCGGAGTGACATTGGGT LeuLeuArgArgLeuHisGlnTrpIleSerSerGluCysThrThrProCysSerGlySer
121   GCTCCTGAGGCGACTGCACCAGTGGATAAGCTCGGAGTGTACCACTCCATGCTCCGGTTC
      CGAGGACTCCGCTGACGTGGTCACCTATTCGAGCCTCACATGGTGAGGTACGAGGCCAAG TrpLeuArgAspIleTrpAspTrpIleCysGluValLeuSerAspPheLysThrTrpLeu
181   CTGGCTAAGGGACATCTGGGACTGGATATGCGAGGTGTTGAGCGACTTTAAGACCTGGCT
      GACCGATTCCCTGTAGACCCTGACCTATACGCTCCACAACTCGCTGAAATTCTGGACCGA LysAlaLysLeuMetProGlnLeuProGlyIleProPheValSerCysGlnArgGlyTyr
241   AAAAGCTAAGCTCATGCCACAGCTGCCTGGGATCCCCTTTGTGTCCTGCCAGCGCGGGTA
      TTTTCGATTCGAGTACGGTGTCGACGGACCCTAGGGGAAACACAGGACGGTCGCGCCCAT LysGlyValTrpArgVal
301   TAAGGGGGTCTGGCGAGTG
      ATTCCCCCAGACCGCTCAC
```

```
     AlaTyrMetSerLysAlaHisGlyIleAspProAsnIleArgThrGlyValArgThrIle
  1  GGCTTACATGTCCAAGGCTCATGGGATCGATCCTAACATCAGGACCGGGTGAGAACAAT
     CCGAATGTACAGGTTCCGAGTACCCTAGCTAGGATTGTAGTCCTGGCCCACTCTTGTTA

ThrThrGlySerProIleThrTyrSerThrTyrGlyLysPheLeuAlaAspGlyGlyCys
 61  TACCACTGGCAGCCCATCACGTACTCCACCTACGGCAAGTTCCTTGCCGACGGCGGGTG
     ATGGTGACCGTCGGGTAGTGCATGAGGTGGATGCCGTTCAAGGAACGGCTGCCGCCCAC

SerGlyGlyAlaTyrAspIleIleIleCysAspGluCysHisSerThrAspAlaThrSer
121  CTCGGGGGCGCTTATGACATAATAATTTGTGACGAGTGCCACTCCACGGATGCCACATC
     GAGCCCCCCGAATACTGTATTATTAAACACTGCTCACGGTGAGGTGCCTACGGTGTAG

IleLeuGlyIleGlyThrValLeuAspGlnAlaGluThrAlaGluGlyAlaArgLeuValVal
181  CATCTTGGGCATCGGCACTGTCCTTGACCAAGCAGAGACTGCGGGGGCGAGACTGGTTGT
     GTAGAACCCGTAGCCGTGACAGGAACTGGTTCGTCTGTCTGACGCCCCGCTCTGACCAACA

LeuAlaThrProProGlySerValThrValProHisProAsnIleProHisGluValVal
241  GCTCGCCACGCCACCCGGCTCCGGGCTCCGTACTGTCCCCATCCAACATCGAGAGGT
     CGAGCGGTGGCGGTGGGCCGAGGCAGTGACACGGTAGGTTGTAGCTCTCCA

AlaLeuSerThrThrGlyIleGluIleProPheTyrGlyLysAlaIleProLeuValIle
301  TGCTCTGTCCACCACGGTGGCCTCTCTAGGCAAGGCTATCCCCCTGAAGTAAT
     ACGAGACAGGTGGTGGCCACCGGAGAGATCCGTTCCGATAGGGGAGCTTCATTA

LysGlyArgHisSerLeuIlePheCysHisSerLysLysLysAspGluAlaAla
361  CAAGGGGGGAGACATCTCATCTTCTGTCATTCAAAGAAGAAGTGCGACGAACTGCCGC
     GTTCCCCCCCTCTGTAGAGTAGAAGACAGTAAGTTTCTTCTTCACGCTGCTTGAGCGCG

LysLeuValAlaLeuGlyIleAsnAlaValAlaTyrTyrArgGlyLeuAspValSerVal
421  AAAGCTGGTCGCATTGGGCATCAATGCCGTGGCCTACTACCGGGTCTTGACGTGTCCGT
     TTTCGACCAGCGTAACCCGTAGTTACGGCACCGGATGATGGCCCAGAACTGCACAGGCA

IleProThr
481  CATCCCGACCAG
     GTAGGGCTGGTC
```

```
                CysSerLeuThrValThrGlnLeuLeuArgArgLeuHisGlnTrpIleSerSerGluCys
  1     ACTGCAGCCTCACTGTAACCCAGCTCCTGAGGCGACTGCACCAGTGGATAAGCTCGGAGT
        TGACGTCGGAGTGACATTGGGTCGAGGACTCCGCTGACGTGGTCACCTATTCGAGCCTCA

ThrThrProCysSerGlySerTrpLeuArgAspIleTrpAspTrpIleCysGluValLeu
 61     GTACCACTCCATGCTCCGGTTCCTGGCTAAGGGACATCTGGGACTGGATATGCGAGGTGT
        CATGGTGAGGTACGAGGCCAAGGACCGATTCCCTGTAGACCCTGACCTATACGCTCCACA.

---------------Overlap with 33b-------------------------------
                SerAspPheLysThrTrpLeuLysAlaLysLeuMetProGlnLeuProGlyIleProPhe
121     TGAGCGACTTTAAGACCTGGCTAAAAGCTAAGCTCATGCCACAGCTGCCTGGGATCCCCT
        ACTCGCTGAAATTCTGGACCGATTTTCGATTCGAGTACGGTGTCGACGGACCCTAGGGGA ValSerCysGlnArgGlyTyrLysGlyValTrpArgGlyAspGlyIleMetHisThrArg
181     TTGTGTCCTGCCAGCGCGGGTATAAGGGGGTCTGGCGAGGGGACGGCATCATGCACACTC
        AACACAGGACGGTCGCGCCCATATTCCCCCAGACCGCTCCCCTGCCGTAGTACGTGTGAG CysHisCysGlyAlaGluIleThrGlyHisValLysAsnGlyThrMetArgIleValGly
241     GCTGCCACTGTGGAGCTGAGATCACTGGACATGTCAAAAACGGGACGATGAGGATCGTCG
        CGACGGTGACACCTCGACTCTAGTGACCTGTACAGTTTTTGCCCTGCTACTCCTAGCAGC ProArgThrCysArgAsnMetTrpSerGlyThrPheProIleAsnAlaTyrThrThrGly
301     GTCCTAGGACCTGCAGGAACATGTGGAGTGGGACCTTCCCCATTAATGCCTACACCACGG
        CAGGATCCTGGACGTCCTTGTACACCTCACCCTGGAAGGGGTAATTACGGATGTGGTGCC ProCysThrProLeuProAlaProAsnTyrThrPheAlaLeuTrpArgValSerAlaGlu
361     GCCCCTGTACCCCCCTTCCTGCGCCGAACTACACGTTCGCGCTATGGAGGGTGTCTGCAG
        CGGGGACATGGGGGGAAGGACGCGGCTTGATGTGCAAGCGCGATACCTCCCACAGACGTC GluTyrValGluIleArgGlnValGlyAspPheHisTyrValThrGlyMetThrThrAsp
421     AGGAATATGTGGAGATAAGGCAGGTGGGGGACTTCCACTACGTGACGGGTATGACTACTG
        TCCTTATACACCTCTATTCCGTCCACCCCCTGAAGGTGATGCACTGCCCATACTGATGAC AsnLeuLysCysProCysGlnValProSerProGluPhePheThrGlu
481     ACAATCTCAAATGCCCGTGCCAGGTCCCATCGCCCGAATTTTTCACAGAAT
        TGTTAGAGTTTACGGGCACGGTCCAGGGTAGCGGGCTTAAAAAGTGTCTTA
```

FIG. 14A

```
    AlaTyrMetSerLysAlaHisGlyIleAspProAsnIleArgThrGlyValArgThrIle
  1 TGCTTACATGTCCAAGGCTCATGGGATCGATCCTAACATCAGGACCGGGGTGAGAACAAT
    ACGAATGTACAGGTTCCGAGTACCCTAGCTAGGATTGTAGTCCTGGCCCCACTCTTGTTA

ThrThrGlySerProIleThrTyrSerThrTyrGlyLysPheLeuAlaAspGlyGlyCys
 61 TACCACTGGCAGCCCCATCACGTACTCCACCTACGGCAAGTTCCTTGCCGACGGCGGGTG
    ATGGTGACCGTCGGGGTAGTGCATGAGGTGGATGCCGTTCAAGGAACGGCTGCCGCCCAC

SerGlyGlyAlaTyrAspIleIleIleCysAspGluCysHisSerThrAspAlaThrSer
121 CTCGGGGGGCGCTTATGACATAATAATTTGTGACGAGTGCCACTCCACGGATGCCACATC
    GAGCCCCCCGCGAATACTGTATTATTAAACACTGCTCACGGTGAGGTGCCTACGGTGTAG

IleLeuGlyIleGlyThrValLeuAspGlnAlaGluThrAlaGlyAlaArgLeuValVal
181 CATCTTGGGCATCGGCACTGTCCTTGACCAAGCAGAGACTGCGGGGGCGAGACTGGTTGT
    GTAGAACCCGTAGCCGTGACAGGAACTGGTTCGTCTCTGACGCCCCGCTCTGACCAACA

LeuAlaThrAlaThrProProGlySerValThrValProHisProAsnIleGluGluVal
241 GCTCGCCACCGCCACCCCTCCGGGCTCCGTCACTGTGCCCCATCCCAACATCGAGGAGGT
    CGAGCGGTGGCGGTGGGGAGGCCCGAGGCAGTGACACGGGGTAGGGTTGTAGCTCCTCCA

AlaLeuSerThrThrGlyGluIleProPheTyrGlyLysAlaIleProLeuGluValIle
301 TGCTCTGTCCACCACCGGAGAGATCCCTTTTTACGGCAAGGCTATCCCCCTCGAAGTAAT
    ACGAGACAGGTGGTGGCCTCTCTAGGGAAAAATGCCGTTCCGATAGGGGGAGCTTCATTA

LysGlyGlyArgHisLeuIlePheCysHisSerLysLysLysCysAspGluLeuAlaAla
361 CAAGGGGGGGAGACATCTCATCTTCTGTCATTCAAAGAAGAAGTGCGACGAACTCGCCGC
    GTTCCCCCCCTCTGTAGAGTAGAAGACAGTAAGTTTCTTCTTCACGCTGCTTGAGCGGCG

LysLeuValAlaLeuGlyIleAsnAlaValAlaTyrTyrArgGlyLeuAspValSerVal
421 AAAGCTGGTCGCATTGGGCATCAATGCCGTGGCCTACTACCGCGGTCTTGACGTGTCCGT
    TTTCGACCAGCGTAACCCGTAGTTACGGCACCGGATGATGGCGCCAGAACTGCACAGGCA

IleProThrSerGlyAspValValValValAlaThrAspAlaLeuMetThrGlyTyrThr
481 CATCCCGACCAGCGGCGATGTTGTCGTCGTGGCAACCGATGCCCTCATGACCGGCTATAC
    GTAGGGCTGGTCGCCGCTACAACAGCAGCACCGTTGGCTACGGGAGTACTGGCCGATATG

GlyAspPheAspSerValIleAspTyrAsnThrCysValThrGlnThrValAspPheSer
541 CGGCGACTTCGACTCGGTGATAGACTACAATACGTGTGTCACCCAGACAGTCGATTTCAG
    GCCGCTGAAGCTGAGCCACTATCTGATGTTATGCACACAGTGGGTCTGTCAGCTAAAGTC

LeuAspProThrPheThrIleGluThrIleThrLeuProGlnAspAlaValSerArgThr
601 CCTTGACCCTACCTTCACCATTGAGACAATCACGCTCCCCCAGGATGCTGTCTCCCGCAC
    GGAACTGGGATGGAAGTGGTAACTCTGTTAGTGCGAGGGGGTCCTACGACAGAGGGCGTG

GlnArgArgGlyArgThrGlyArgGlyLysProGlyIleTyrArgPheValAlaProGly
661 TCAACGTCGGGGCAGGACTGGCAGGGGGAAGCCAGGCATCTACAGATTTGTGGCACCGGG
    AGTTGCAGCCCCCTCCTGACCGTCCCCCTTCGGTCCGTAGATGTCTAAACACCGTGGCCC

GluArgProSerGlyMetPheAspSerSerValLeuCysGluCysTyrAspAlaGlyCys
721 GGAGCGCCCCTCCGGCATGTTCGACTCGTCCGTCCTCTGTGAGTGCTATGACGCAGGCTG
    CCTCGCGGGGAGGCCGTACAAGCTGAGCAGGCAGGAGACACTCACGATACTGCGTCCGAC

AlaTrpTyrGluLeuThrProAlaGluThrThrValArgLeuArgAlaTyrMetAsnThr
781 TGCTTGGTATGAGCTCACGCCCGCCGAGACTACAGTTAGGCTACGAGCGTACATGAACAC
    ACGAACCATACTCGAGTGCGGGCGGCTCTGATGTCAATCCGATGCTCGCATGTACTTGTG

ProGlyLeuProValCysGlnAspHisLeuGluPheTrpGluGlyValPheThrGlyLeu
841 CCCGGGGCTTCCCGTGTGCCAGGACCATCTTGAATTTTGGGAGGGCGTCTTTACAGGCCT
    GGGCCCCGAAGGGCACACGGTCCTGGTAGAACTTAAAACCCTCCCGCAGAAATGTCCGGA
```

FIG. 14B

```
         ThrHisIleAspAlaHisPheLeuSerGlnThrLysGlnSerGlyGluAspLeuProTyr
   901   CACTCATATAGATGCCCACTTTCTATCCAGACAAAGCAGAGTGGGGAGAACCTTCCTTA
         GTGAGTATATCTACGGGTGAAAGATAGGGTCTGTTTCGTCTCACCCCTCTTGGAAGGAAT

LeuValAlaTyrGlnAlaThrValCysAlaArgAlaGlnAlaProProProSerTrpAsp
   961   CCTGGTAGCGTACCAAGCCACCGTGTGCGCTAGGGCTCAAGCCCCTCCCCCATCGTGGGA
         GGACCATCGCATGGTTCGGTGGCACACGCGATCCCGAGTTCGGGGAGGGGGTAGCACCCT

GlnMetTrpLysCysLeuIleArgLeuLysProThrLeuHisGlyProThrProLeuLeu
  1021   CCAGATGTGGAAGTGTTTGATTCGCCTCAAGCCCACCCTCCATGGGCCAACACCCCTGCT
         GGTCTACACCTTCACAAACTAAGCGGAGTTCGGGTGGGAGGTACCCGGTTGTGGGGACGA

TyrArgLeuGlyAlaValGlnAsnGluIleThrLeuThrHisProValThrLysTyrIle
  1081   ATACAGACTGGGCGCTGTTCAGAATGAAATCACCCTGACGCACCCAGTCACCAAATACAT
         TATGTCTGACCCGCGACAAGTCTTACTTTAGTGGGACTGCGTGGGTCAGTGGTTTATGTA

MetThrCysMetSerAlaAspLeuGluValValThrSerThrTrpValLeuValGlyGly
  1141   CATGACATGCATGTCGGCCGACCTGGAGGTCGTCACGAGCACCTGGGTGCTCGTTGGCGG
         GTACTGTACGTACAGCCGGCTGGACCTCCAGCAGTGCTCGTGGACCCACGAGCAACCGCC

ValLeuAlaAlaLeuAlaAlaTyrCysLeuSerThrGlyCysValValIleValGlyArg
  1201   CGTCCTGGCTGCTTTGGCCGCGTATTGCCTGTCAACAGGCTGCGTGGTCATAGTGGGCAG
         GCAGGACCGACGAAACCGGCGCATAACGGACAGTTGTCCGACGCACCAGTATCACCCGTC

ValValLeuSerGlyLysProAlaIleIleProAspArgGluValLeuTyrArgGluPhe
  1261   GGTCGTCTTGTCCGGGAAGCCGGCAATCATACCTGACAGGGAAGTCCTCTACCGAGAGTT
         CCAGCAGAACAGGCCCTTCGGCCGTTAGTATGGACTGTCCCTTCAGGAGATGGCTCTCAA

AspGluMetGluGluCysSerGlnHisLeuProTyrIleGluGlnGlyMetMetLeuAla
  1321   CGATGAGATGGAAGAGTGCTCTCAGCACTTACCGTACATCGAGCAAGGGATGATGCTCGC
         GCTACTCTACCTTCTCACGAGAGTCGTGAATGGCATGTAGCTCGTTCCCTACTACGAGCG

GluGlnPheLysGlnLysAlaLeuGlyLeuLeuGlnThrAlaSerArgGlnAlaGluVal
  1381   CGAGCAGTTCAAGCAGAAGGCCCTCGGCCTCCTGCAGACCGCGTCCCGTCAGGCAGAGGT
         GCTCGTCAAGTTCGTCTTCCGGGAGCCGGAGGACGTCTGGCGCAGGGCAGTCCGTCTCCA

IleAlaProAlaValGlnThrAsnTrpGlnLysLeuGluThrPheTrpAlaLysHisMet
  1441   TATCGCCCCTGCTGTCCAGACCAACTGGCAAAAACTCGAGACCTTCTGGGCGAAGCATAT
         ATAGCGGGGACGACAGGTCTGGTTGACCGTTTTTGAGCTCTGGAAGACCCGCTTCGTATA

TrpAsnPheIleSerGlyIleGlnTyrLeuAlaGlyLeuSerThrLeuProGlyAsnPro
  1501   GTGGAACTTCATCAGTGGGATACAATACTTGGCGGGCTTGTCAACGCTGCCTGGTAACCC
         CACCTTGAAGTAGTCACCCTATGTTATGAACCGCCCGAACAGTTGCGACGGACCATTGGG

AlaIleAlaSerLeuMetAlaPheThrAlaAlaValThrSerProLeuThrThrSerGln
  1561   CGCCATTGCTTCATTGATGGCTTTTACAGCTGCTGTCACCAGCCCACTAACCACTAGCCA
         GCGGTAACGAAGTAACTACCGAAAATGTCGACGACAGTGGTCGGGTGATTGGTGATCGGT

ThrLeuLeuPheAsnIleLeuGlyGlyTrpValAlaAlaGlnLeuAlaAlaProGlyAla
  1621   AACCCTCCTCTTCAACATATTGGGGGGTGGGTGGCTGCCCAGCTCGCCGCCCCGGTGC
         TTGGGAGGAGAAGTTGTATAACCCCCCACCCACCGACGGGTCGAGCGGCGGGGCCACG

AlaThrAlaPheValGlyAlaGlyLeuAlaGlyAlaAlaIleGlySerValGlyLeuGly
  1681   CGCTACTGCCTTTGTGGGCGCTGGCTTAGCTGGCGCCGCCATCGGCAGTGTTGGACTGGG
         GCGATGACGGAAACACCCGCGACCGAATCGACCGCGGCGGTAGCCGTCACAACCTGACCC
```

FIG. 14C

```
         LysValLeuIleAspIleLeuAlaGlyTyrGlyAlaGlyValAlaGlyAlaLeuValAla
1741 GAAGGTCCTCATAGACATCCTTGCAGGGTATGGCGCGGGCGTGGCGGGAGCTCTTGTGGC
     CTTCCAGGAGTATCTGTAGGAACGTCCCATACCGCGCCCGCACCGCCCTCGAGAACACCG

PheLysIleMetSerGlyGluValProSerThrGluAspLeuValAsnLeuLeuProAla
1801 ATTCAAGATCATGAGCGGTGAGGTCCCCTCCACGGAGGACCTGGTCAATCTACTGCCCGC
     TAAGTTCTAGTACTCGCCACTCCAGGGGAGGTGCCTCCTGGACCAGTTAGATGACGGGCG

IleLeuSerProGlyAlaLeuValValGlyValValCysAlaAlaIleLeuArgArgHis
1861 CATCCTCTCGCCCGGAGCCCTCGTAGTCGGCGTGGTCTGTGCAGCAATACTGCGCCGGCA
     GTAGGAGAGCGGGCCTCGGGAGCATCAGCCGCACCAGACACGTCGTTATGACGCGGCCGT

ValGlyProGlyGluGlyAlaValGlnTrpMetAsnArgLeuIleAlaPheAlaSerArg
1921 CGTTGGCCCGGGCGAGGGGGCAGTGCAGTGGATGAACCGGCTGATAGCCTTCGCCTCCCG
     GCAACCGGGCCCGCTCCCCCGTCACGTCACCTACTTGGCCGACTATCGGAAGCGGAGGGC

GlyAsnHisValSerProThrHisTyrValProGluSerAspAlaAlaAlaArgValThr
1981 GGGGAACCATGTTTCCCCCACGCACTACGTGCCGGAGAGCGATGCAGCTGCCCGCGTCAC
     CCCCTTGGTACAAAGGGGGTGCGTGATGCACGGCCTCTCGCTACGTCGACGGGCGCAGTG

AlaIleLeuSerSerLeuThrValThrGlnLeuLeuArgArgLeuHisGlnTrpIleSer
2041 TGCCATACTCAGCAGCCTCACTGTAACCCAGCTCCTGAGGCGACTGCACCAGTGGATAAG
     ACGGTATGAGTCGTCGGAGTGACATTGGGTCGAGGACTCCGCTGACGTGGTCACCTATTC

SerGluCysThrThrProCysSerGlySerTrpLeuArgAspIleTrpAspTrpIleCys *
2101 CTCGGAGTGTACCACTCCATGCTCCGGTTCCTGGCTAAGGGACATCTGGGACTGGATATG
     GAGCCTCACATGGTGAGGTACGAGGCCAAGGACCGATTCCCTGTAGACCCTGACCTATAC

GluValLeuSerAspPheLysThrTrpLeuLysAlaLysLeuMetProGlnLeuProGly
2161 CGAGGTGTTGAGCGACTTTAAGACCTGGCTAAAAGCTAAGCTCATGCCACAGCTGCCTGG
     GCTCCACAACTCGCTGAAATTCTGGACCGATTTTCGATTCGAGTACGGTGTCGACGGACC

IleProPheValSerCysGlnArgGlyTyrLysGlyValTrpArgValAspGlyIleMet
2221 GATCCCCTTTGTGTCCTGCCAGCGCGGGTATAAGGGGGTCTGGCGAGTGGACGGCATCAT
     CTAGGGGAAACACAGGACGGTCGCGCCCATATTCCCCCAGACCGCTCACCTGCCGTAGTA

HisThrArgCysHisCysGlyAlaGluIleThrGlyHisValLysAsnGlyThrMetArg
2281 GCACACTCGCTGCCACTGTGGAGCTGAGATCACTGGACATGTCAAAAACGGGACGATGAG
     CGTGTGAGCGACGGTGACACCTCGACTCTAGTGACCTGTACAGTTTTTGCCCTGCTACTC

IleValGlyProArgThrCysArgAsnMetTrpSerGlyThrPheProIleAsnAlaTyr
2341 GATCGTCGGTCCTAGGACCTGCAGGAACATGTGGAGTGGGACCTTCCCCATTAATGCCTA
     CTAGCAGCCAGGATCCTGGACGTCCTTGTACACCTCACCCTGGAAGGGGTAATTACGGAT

ThrThrGlyProCysThrProLeuProAlaProAsnTyrThrPheAlaLeuTrpArgVal
2401 CACCACGGGCCCCTGTACCCCCCTTCCTGCGCCGAACTACACGTTCGCGCTATGGAGGGT
     GTGGTGCCCGGGGACATGGGGGGAAGGACGCGGCTTGATGTGCAAGCGCGATACCTCCCA

SerAlaGluGluTyrValGluIleArgGlnValGlyAspPheHisTyrValThrGlyMet
2461 GTCTGCAGAGGAATATGTGGAGATAAGGCAGGTGGGGGACTTCCACTACGTGACGGGTAT
     CAGACGTCTCCTTATACACCTCTATTCCGTCCACCCCCTGAAGGTGATGCACTGCCCATA

ThrThrAspAsnLeuLysCysProCysGlnValProSerProGluPhePheThrGlu
2521 GACTACTGACAATCTCAAATGCCCGTGCCAGGTCCCATCGCCCGAATTTTTCACAGAAT
     CTGATGACTGTTAGAGTTTACGGGCACGGTCCAGGGTAGCGGGCTTAAAAAGTGTCTTA
```

FIG. 15

```
      AlaValAspPheIleProValGluAsnLeuGluThrThrMetArgSerProValPheThr
  1   GGCGGTGGACTTTATCCCTGTGGAGAACCTAGAGACAACCATGAGGTCCCCGGTGTTCAC
      CCGCCACCTGAAATAGGGACACCTCTTGGATCTCTGTTGGTACTCCAGGGGCCACAAGTG

AspAsnSerSerProProValValProGlnSerPheGlnValAlaHisLeuHisAlaPro
 61   GGATAACTCCTCTCCACCAGTAGTGCCCCAGAGCTTCCAGGTGGCTCACCTCCATGCTCC
      CCTATTGAGGAGAGGTGGTCATCACGGGGTCTCGAAGGTCCACCGAGTGGAGGTACGAGG

ThrGlySerGlyLysSerThrLysValProAlaAlaTyrAlaAlaGlnGlyTyrLysVal
121   CACAGGCAGCGGCAAAAGCACCAAGGTCCCGGCTGCATATGCAGCTCAGGGCTATAAGGT
      GTGTCCGTCGCCGTTTTCGTGGTTCCAGGGCCGACGTATACGTCGAGTCCCGATATTCCA
                                                        ------------------
      LeuValLeuAsnProSerValAlaAlaThrLeuGlyPheGlyAlaTyrMetSerLysAla
181   GCTAGTACTCAACCCCTCTGTTGCTGCAACACTGGGCTTTGGTGCTTACATGTCCAAGGC
      CGATCATGAGTTGGGGAGACAACGACGTTGTGACCCGAAACCACGAATGTACAGGTTCCG
      ----------Overlap with 40b----------------------------------
      HisGlyIleAspProAsnIleArgThrGlyValArgThrIleThrThrGlySerProIle
241   TCATGGGATCGATCCTAACATCAGGACCGGGGTGAGAACAATTACCACTGGCAGCCCCAT
      AGTACCCTAGCTAGGATTGTAGTCCTGGCCCCACTCTTGTTAATGGTGACCGTCGGGGTA ThrTyrSerThrTyrGlyLysPheLeuAlaAspGlyGlyCysSerGlyGlyAlaTyrAsp
301   CACGTACTCCACCTACGGCAAGTTCCTTGCCGACGGCGGGTGCTCGGGGGGCGCTTATGA
      GTGCATGAGGTGGATGCCGTTCAAGGAACGGCTGCCGCCCACGAGCCCCCCGCGAATACT IleIleIleCysAspGluCysHisSerThrAspAlaThrSerIleLeuGlyIleGlyThr
361   CATAATAATTTGTGACGAGTGCCACTCCACGGATGCCACATCCATCTTGGGCATTGGCAC
      GTATTATTAAACACTGCTCACGGTGAGGTGCCTACGGTGTAGGTAGAACCCGTAACCGTG ValLeuAspGlnAlaGluThrAlaGlyAlaArgLeuValValLeuAlaThrAlaThrPro
421   TGTCCTTGACCAAGCAGAGACTGCGGGGGCGAGACTGGTTGTGCTCGCCACCGCCACCCC
      ACAGGAACTGGTTCGTCTCTGACGCCCCCGCTCTGACCAACACGAGCGGTGGCGGTGGGG ProGlySerValThrValProHisProAsnIleGluGluValAlaLeuSerThrThrGly
481   TCCGGGCTCCGTCACTGTGCCCCATCCCAACATCGAGGAGGTTGCTCTGTCCACCACCGG
      AGGCCCGAGGCAGTGACACGGGGTAGGGTTGTAGCTCCTCCAACGAGACAGGTGGTGGCC GluIleProPheTyrGlyLysAlaIleProLeuGluValIleLysGlyGlyArgHisLeu
541   AGAGATCCCTTTTTACGGCAAGGCTATCCCCCTCGAAGTAATCAAGGGGGGGAGACATCT
      TCTCTAGGGAAAAATGCCGTTCCGATAGGGGGAGCTTCATTAGTTCCCCCCCTCTGTAGA IlePheCysHisSerLysLysLysCysAspGluLeuAlaAlaLysLeuValAlaLeuGly
601   CATCTTCTGTCATTCAAAGAAGAAGTGCGACGAACTCGCCGCAAAGCTGGTCGCATTGGG
      GTAGAAGACAGTAAGTTTCTTCTTCACGCTGCTTGAGCGGCGTTTCGACCAGCGTAACCC
      ------------------------------------------------------------
      IleAsnAlaValAlaTyrTyrArgGlyLeuAspValSerValIleProThrSerGlyAsp
661   CATCAATGCCGTGGCCTACTACCGCGGTCTTGACGTGTCCGTCATCCCGACCAGCGGCGA
      GTAGTTACGGCACCGGATGATGGCGCCAGAACTGCACAGGCAGTAGGGCTGGTCGCCGCT ValValValValAlaThrAspAlaLeuMetThrGlyTyrThrGlyAspPheAspSerVal
721   TGTTGTCGTCGTGGCAACCGATGCCCTCATGACCGGCTATACCGGCGACTTCGACTCGGT
      ACAACAGCAGCACCGTTGGCTACGGGAGTACTGGCCGATATGGCCGCTGAAGCTGAGCCA IleAspCysAsnThrCys
781   GATAGACTGCAATACGTGTG
      CTATCTGACGTTATGCACAC
```

FIG. 16

```
       ProCysThrCysGlySerSerAspLeuTyrLeuValThrArgHisAlaAspValIlePro
  1 CTCCCTGCACTTGCGGCTCCTCGGACCTTTACCTGGTCACGAGGCACGCCGATGTCATTC
    GAGGGACGTGAACGCCGAGGAGCCTGGAAATGGACCAGTGCTCCGTGCGGCTACAGTAAG

ValArgArgArgGlyAspSerArgGlySerLeuLeuSerProArgProIleSerTyrLeu
 61 CCGTGCGCCGGCGGGGTGATAGCAGGGGCAGCCTGCTGTCGCCCCGGCCCATTTCCTACT
    GGCACGCGGCCGCCCCACTATCGTCCCCGTCGGACGACAGCGGGGCCGGGTAAAGGATGA

LysGlySerSerGlyGlyProLeuLeuCysProAlaGlyHisAlaValGlyIlePheArg
121 TGAAAGGCTCCTCGGGGGGTCCGCTGTTGTGCCCCGCGGGGCACGCCGTGGGCATATTTA
    ACTTTCCGAGGAGCCCCCCAGGCGACAACACGGGGCGCCCCGTGCGGCACCCGTATAAAT

-----------------Overlap with
       AlaAlaValCysThrArgGlyValAlaLysAlaValAspPheIleProValGluAsnLeu
181 GGGCCGCGGTGTGCACCCGTGGAGTGGCTAAGGCGGTGGACTTTATCCCTGTGGAGAACC
    CCCGGCGCCACACGTGGGCACCTCACCGATTCCGCCACCTGAAATAGGGACACCTCTTGG 33c-------------------------------------
       GluThrThrMetArgSerProValPheThrAspAsnSer
241 TAGAGACAACCATGAGGTCCCCGGTGTTCACGGATAACTCCTC
    ATCTCTGTTGGTACTCCAGGGGCCACAAGTGCCTATTGAGGAG
```

FIG. 17

```
       GlyTrpArgLeuLeuAlaProIleThrAlaTyrAlaGlnGlnThrArgGlyLeuLeuGly
  1 GGGGTGGAGGTTGCTGGCGCCCATCACGGCGTACGCCCAGCAGACAAGGGGCCTCCTAGG
    CCCCACCTCCAACGACCGCGGGTAGTGCCGCATGCGGGTCGTCTGTTCCCCGGAGGATCC

CysIleIleThrSerLeuThrGlyArgAspLysAsnGlnValGluGlyGluValGlnIle
 61 GTGCATAATCACCAGCCTAACTGGCCGGGACAAAAACCAAGTGGAGGGTGAGGTCCAGAT
    CACGTATTAGTGGTCGGATTGACCGGCCCTGTTTTTGGTTCACCTCCCACTCCAGGTCTA

ValSerThrAlaAlaGlnThrPheLeuAlaThrCysIleAsnGlyValCysTrpThrVal
121 TGTGTCAACTGCTGCCCAAACCTTCCTGGCAACGTGCATCAATGGGGTGTGCTGGACTGT
    ACACAGTTGACGACGGGTTTGGAAGGACCGTTGCACGTAGTTACCCCACACGACCTGACA

TyrHisGlyAlaGlyThrArgThrIleAlaSerProLysGlyProValIleGlnMetTyr
181 CTACCACGGGGCCGGAACGAGGACCATCGCGTCACCCAAGGGTCCTGTCATCCAGATGTA
    GATGGTGCCCCGGCCTTGCTCCTGGTAGCGCAGTGGGTTCCCAGGACAGTAGGTCTACAT

ThrAsnValAspGlnAspLeuValGlyTrpProAlaProGlnGlySerArgSerLeuThr
241 TACCAATGTAGACCAAGACCTTGTGGGCTGGCCCGCTCCGCAAGGTAGCCGCTCATTGAC
    ATGGTTACATCTGGTTCTGGAACACCCGACCGGGCGAGGCGTTCCATCGGCGAGTAACTG

----------Overlap with 8h---------------------
       ProCysThrCysGlySerSerAspLeuTyrLeuValThrArgHis
301 ACCCTGCACTTGCGGCTCCTCGGACCTTTACCTGGTCACGAGGCACG
    TGGGACGTGAACGCCGAGGAGCCTGGAAATGGACCAGTGCTCCGTGC
```

FIG. 18

```
         AsnMetTrpSerGlyThrPheProIleAsnAlaTyrThrThrGlyProCysThrProLeu
  1 GAACATGTGGAGTGGGACCTTCCCCATTAATGCCTACACCACGGGCCCCTGTACCCCCCT
    CTTGTACACCTCACCCTGGAAGGGGTAATTACGGATGTGGTGCCCGGGGACATGGGGGGA

----------Overlap with 25c----------
         ProAlaProAsnTyrThrPheAlaLeuTrpArgValSerAlaGluGluTyrValGluIle
 61 TCCTGCGCCGAACTACACGTTCGCGCTATGGAGGGTGTCTGCAGAGGAATACGTGGAGAT
    AGGACGCGGCTTGATGTGCAAGCGCGATACCTCCCACAGACGTCTCCTTATGCACCTCTA ArgGlnValGlyAspPheHisTyrValThrGlyMetThrThrAspAsnLeuLysCysPro
121 AAGGCAGGTGGGGGACTTCCACTACGTGACGGGTATGACTACTGACAATCTTAAATGCCC
    TTCCGTCCACCCCCTGAAGGTGATGCACTGCCCATACTGATGACTGTTAGAATTTACGGG CysGlnValProSerProGluPhePheThrGluLeuAspGlyValArgLeuHisArgPhe
181 GTGCCAGGTCCCATCGCCCGAATTTTTCACAGAATTGGACGGGGTGCGCCTACATAGGTT
    CACGGTCCAGGGTAGCGGGCTTAAAAAGTGTCTTAACCTGCCCCACGCGGATGTATCCAA AlaProProCysLysProLeuLeuArgGluGluValSerPheArgValGlyLeuHisGlu
241 TGCGCCCCCCTGCAAGCCCTTGCTGCGGGAGGAGGTATCATTCAGAGTAGGACTCCACGA
    ACGCGGGGGGACGTTCGGGAACGACGCCCTCCTCCATAGTAAGTCTCATCCTGAGGTGCT TyrProValGlySerGlnLeuProCysGluProGluProAspValAlaValLeuThrSer
301 ATACCCGGTAGGGTCGCAATTACCTTGCGAGCCCGAACCGGACGTGGCCGTGTTGACGTC
    TATGGGCCATCCCAGCGTTAATGGAACGCTCGGGCTTGGCCTGCACCGGCACAACTGCAG MetLeuThrAspProSerHisIleThrAlaGluAlaAlaGlyArgArgLeuAlaArgGly
361 CATGCTCACTGATCCCTCCCATATAACAGCAGAGGCGGCCGGGCGAAGGTTGGCGAGGGG
    GTACGAGTGACTAGGGAGGGTATATTGTCGTCTCCGCCGGCCCGCTTCCAACCGCTCCCC SerProProSerValAlaSerSerSerAlaSerGlnLeuSerAlaProSerLeuLysAla
421 ATCACCCCCCTCTGTGGCCAGCTCCTCGGCTAGCCAGCTATCCGCTCCATCTCTCAAGGC
    TAGTGGGGGGAGACACCGGTCGAGGAGCCGATCGGTCGATAGGCGAGGTAGAGAGTTCCG ThrCysThrAlaAsnHisAspSerProAsp
481 AACTTGCACCGCTAACCATGACTCCCCTGAT
    TTGAACGTGGCGATTGGTACTGAGGGGACTA
```

FIG. 19

```
                    ---------------------------------Overlap with 14c-------------
       SerSerSerAlaSerGlnLeuSerAlaProSerLeuLysAlaThrCysThrAlaAspHis
   1   AGCTCCTCGGCTAGCCAGCTATCCGCTCCATCTCTCAAGGCAACTTGCACCGCTAACCAT
       TCGAGGAGCCGATCGGTCGATAGGCGAGGTAGAGAGTTCCGTTGAACGTGGCGATTGGTA
       -------------
       AspSerProAspAlaGluLeuIleGluAlaAsnLeuLeuTrpArgGlnGluMetGlyGlu
  61   GACTCCCCTGATGCTGAGCTCATAGAGGCCAACCTCCTATGGAGGCAGGAGATGGGCGGC
       CTGAGGGGACTACGACTCGAGTATCTCCGGTTGGAGGATACCTCCGTCCTCTACCCGCCG AsnIleThrArgValGluSerGluAsnLysValValIleLeuAspSerPheAspProLeu
 121   AACATCACCAGGGTTGAGTCAGAAAACAAAGTGGTGATTCTGGACTCCTTCGATCCGCTT
       TTGTAGTGGTCCCAACTCAGTCTTTTGTTTCACCACTAAGACCTGAGGAAGCTAGGCGAA ValAlaGluGluAspGluArgGluIleSerValProAlaGluIleLeuArgLysSerArg
 181   GTGGCGGAGGAGGACGAGCGGGAGATCTCCGTACCCGCAGAAATCCTGCGGAAGTCTCGG
       CACCGCCTCCTCCTGCTCGCCCTCTAGAGGCATGGGCGTCTTTAGGACGCCTTCAGAGCC ArgPheAlaGlnAlaLeuProValTrpAlaArgProAspTyrAsnProProLeuValGlu
 241   AGATTCGCCCAGGCCCTGCCCGTTTGGGCGCGGCCGGACTATAACCCCCCGCTAGTGGAG
       TCTAAGCGGGTCCGGGACGGGCAAACCCGCGCCGGCCTGATATTGGGGGGCGATCACCTC ThrTrpLysLysProAspTyrGluProProValValHisGlyCysProLeuProProPro
 301   ACGTGGAAAAAGCCCGACTACGAACCACCTGTGGTCCATGGCTGTCCGCTTCCACCTCCA
       TGCACCTTTTTCGGGCTGATGCTTGGTGGACACCAGGTACCGACAGGCGAAGGTGGAGGT LysSerProProValPro
 361   AAGTCCCCTCCTGTGCCG
       TTCAGGGGAGGACACGGC
```

FIG. 20

```
       ------------------------------------------------------------
       ValTrpAlaArgProAspTyrAsnProProLeuValGluThrTrpLysLysProAspTyr
   1   CGTTTGGGCGCGGCCGGACTATAACCCCCCGCTAGTGGAGACGTGGAAAAAGCCCGACTA
       GCAAACCCGCGCCGGCCTGATATTGGGGGGCGATCACCTCTGCACCTTTTTCGGGCTGAT

------------------Overlap with 8f-------------------------
       GluProProValValHisGlyCysProLeuProProProLysSerProProValProPro
  61   CGAACCACCTGTGGTCCATGGCTGCCCGCTTCCACCTCCAAAGTCCCCTCCTGTGCCTCC
       GCTTGGTGGACACCAGGTACCGACGGGCGAAGGTGGAGGTTTCAGGGGAGGACACGGAGG ProArgLysLysArgThrValValLeuThrGluSerThrLeuSerThrAlaLeuAlaGlu
 121   GCCTCGGAAGAAGCGGACGGTGGTCCTCACTGAATCAACCCTATCTACTGCCTTGGCCGA
       CGGAGCCTTCTTCGCCTGCCACCAGGAGTGACTTAGTTGGGATAGATGACGGAACCGGCT LeuAlaThrArgSerPheGlySerSerSerThrSerGlyIleThrGlyAspAsnThrThr
 181   GCTCGCCACCAGAAGCTTTGGCAGCTCCTCAACTTCCGGCATTACGGGCGACAATACGAC
       CGAGCGGTGGTCTTCGAAACCGTCGAGGAGTTGAAGGCCGTAATGCCCGCTGTTATGCTG ThrSerSerGluProAlaProSerGlyCysProProAspSerAspAlaGluSerPhe
 241   AACATCCTCTGAGCCCGCCCCTTCTGGCTGCCCCCCCGACTCCGACGCTGAGTCCTTTGC
       TTGTAGGAGACTCGGGCGGGGAAGACCGACGGGGGGGCTGAGGCTGCGACTCAGGAAACG
```

FIG. 21

```
         AlaSerArgSerPheGlySerSerSerThrSerGlyIleThrGlyAspAsnThrThrThr
   1 GCCTCCAGAAGCTTTGGCAGCTCCTCAACTTCCGGCATTACGGGCGACAATACGACAACA
     CGGAGGTCTTCGAAACCGTCGAGGAGTTGAAGGCCGTAATGCCCGCTGTTATGCTGTTGT

---------------Overlap with 33f-----------------------
         SerSerGluProAlaProSerGlyCysProProAspSerAspAlaGluSerTyrSerSer
  61 TCCTCTGAGCCCGCCCCTTCTGGCTGCCCCCCCGACTCCGACGCTGAGTCCTATTCCTCC
     AGGAGACTCGGGCGGGGAAGACCGACGGGGGGGCTGAGGCTGCGACTCAGGATAAGGAGG MetProProLeuGluGlyGluProGlyAspProAspLeuSerAspGlySerTrpSerThr
 121 ATGCCCCCCCTGGAGGGGGAGCCTGGGGATCCGGATCTTAGCGACGGGTCATGGTCAACG
     TACGGGGGGGACCTCCCCCTCGGACCCCTAGGCCTAGAATCGCTGCCCAGTACCAGTTGC ValSerSerGluAlaAsnAlaGluAspValValCysCysSerMetSerTyrSerTrpThr
 181 GTCAGTAGTGAGGCCAACGCGGAGGATGTCGTGTGCTGCTCAATGTCTTACTCTTGGACA
     CAGTCATCACTCCGGTTGCGCCTCCTACAGCACACGACGAGTTACAGAATGAGAACCTGT GlyAlaLeuValThrProCysAlaAlaGluGluGlnLysLeuProIleAsnAlaLeuSer
 241 GGCGCACTCGTCACCCCGTGCGCCGCGGAAGAACAGAAACTGCCCATCAATGCACTAAGC
     CCGCGTGAGCAGTGGGGCACGCGGCGCCTTCTTGTCTTTGACGGGTAGTTACGTGATTCG AsnSerLeuLeuArgHisHisAsnLeuValTyrSerThrThrSerArgSer
 301 AACTCGTTGCTACGTCACCACAATTTGGTGTATTCCACCACCTCACGCAGTG
     TTGAGCAACGATGCAGTGGTGTTAAACCACATAAGGTGGTGGAGTGCGTCAC
```

FIG. 22

```
         GlyThrTyrValTyrAsnHisLeuThrProLeuArgAspTrpAlaHisAsnGlyLeuArg
   1 GGCACCTATGTTTATAACCATCTGACTCCTCTTCGGGACTGGGCGCACAACGGCTTGCGA
     CCGTGGATACAAATATTGGTAGAGTGAGGAGAAGCCCTGACCCGCGTGTTGCCGAACGCT

AspLeuAlaValAlaValGluProValValPheSerGlnMetGluThrLysLeuIleThr
  61 GATCTGGCCGTGGCTGTAGAGCCAGTCGTCTTCTCCCAAATGGAGACCAAGCTCATCACG
     CTAGACCGGCACCGACATCTCGGTCAGCAGAAGAGGGTTTACCTCTGGTTCGAGTAGTGC

TrpGlyAlaAspThrAlaAlaCysGlyAspIleIleAsnGlyLeuProValSerAlaArg
 121 TGGGGGGCAGATACCGCCGCGTGCGGTGACATCATCAACGGCTTGCCTGTTTCCGCCCGC
     ACCCCCCGTCTATGGCGGCGCACGCCACTGTAGTAGTTGCCGAACGGACAAAGGCGGGCG

ArgGlyArgGluIleLeuLeuGlyProAlaAspGlyMetValSerLysGlyTrpArgLeu
 181 AGGGGCCGGGAGATACTGCTCGGGCCAGCCGATGGAATGGTCTCCAAGGGTTGGAGGTTG
     TCCCCGGCCCTCTATGACGAGCCCGGTCGGCTACCTTACCAGAGGTTCCCAACCTCCAAC

LeuAlaProIleThrAlaTyrAlaGlnGlnThrArgGlyLeuLeuGlyCysIleIleThr
 241 CTGGCGCCCATCACGGCGTACGCCCAGCAGACAAGGGGCCTCCTAGGGTGCATAATCACC
     GACCGCGGGTAGTGCCGCATGCGGGTCGTCTGTTCCCCGGAGGATCCCACGTATTAGTGG

---------------Overlap with 7e-----------------------
         SerLeuThrGlyArgAspLysAsnGlnValGluGlyGluValGlnIleValSerThrAla
 301 AGCCTAACTGGCCGGGACAAAAACCAAGTGGAGGGTGAGGTCCAGATTGTGTCAACTGCT
     TCGGATTGACCGGCCCTGTTTTTGGTTCACCTCCCACTCCAGGTCTAACACAGTTGACGA AlaGlnThrPheLeuAlaThrCysIleAsnGlyValCysTrp
 361 GCCCAAACCTTCCTGGCAACGTGCATCAATGGGGTGTGCTGG
     CGGGTTTGGAAGGACCGTTGCACGTAGTTACCCCACACGACC
```

FIG. 23

```
        GlyGlyValValLeuValGlyLeuMetAlaLeuThrLeuSerProTyrTyrLysArgTyr
  1     GGCGGTGTTGTTCTCGTCGGGTTGATGGCGCTGACTCTGTCACCATATTACAAGCGCTAT
        CCGCCACAACAAGAGCAGCCCAACTACCGCGACTGAGACAGTGGTATAATGTTCGCGATA

IleSerTrpCysLeuTrpTrpLeuGlnTyrPheLeuThrArgValGluAlaGlnLeuHis
 61     ATCAGCTGGTGCTTGTGGTGGCTTCAGTATTTTCTGACCAGAGTGGAAGCGCAACTGCAC
        TAGTCGACCACGAACACCACCGAAGTCATAAAAGACTGGTCTCACCTTCGCGTTGACGTG

ValTrpIleProProLeuAsnValArgGlyGlyArgAspAlaValIleLeuLeuMetCys
121     GTGTGGATTCCCCCCCTCAACGTCCGAGGGGGGCGCGACGCCGTCATCTTACTCATGTGT
        CACACCTAAGGGGGGGAGTTGCAGGCTCCCCCCGCGCTGCGGCAGTAGAATGAGTACACA

AlaValHisProThrLeuValPheAspIleThrLysLeuLeuLeuAlaValPheGlyPro
181     GCTGTACACCCGACTCTGGTATTTGACATCACCAAATTGCTGCTGGCCGTCTTCGGACCC
        CGACATGTGGGCTGAGACCATAAACTGTAGTGGTTTAACGACGACCGGCAGAAGCCTGGG

LeuTrpIleLeuGlnAlaSerLeuLeuLysValProTyrPheValArgValGlnGlyLeu
241     CTTTGGATTCTTCAAGCCAGTTTGCTTAAAGTACCCTACTTTGTGCGCGTCCAAGGCCTT
        GAAACCTAAGAAGTTCGGTCAAACGAATTTCATGGGATGAAACACGCGCAGGTTCCGGAA

.euArgPheCysAlaLeuAlaArgLysMetIleGlyGlyHisTyrValGlnMetValIle
301     CTCCGGTTCTGCGCGTTAGCGCGGAAGATGATCGGAGGCCATTACGTGCAAATGGTCATC
        GAGGCCAAGACGCGCAATCGCGCCTTCTACTAGCCTCCGGTAATGCACGTTTACCAGTAG
        ------------------------------------------------
        IleLysLeuGlyAlaLeuThrGlyThrTyrValTyrAsnHisLeuThrProLeuArgAsp
361     ATTAAGTTAGGGGCGCTTACTGGCACCTATGTTTATAACCATCTCACTCCTCTTCGGGAC
        TAATTCAATCCCCGCGAATGACCGTGGATACAAATATTGGTAGAGTGAGGAGAAGCCCTG

------------------Overlap with 7f ------------------
        TrpAlaHisAsnGlyLeuArgAspLeuAlaValAlaValGluProValValPheSerGln
421     TGGGCGCACAACGGCTTGCGAGATCTGGCCGTGGCTGTAGAGCCAGTCGTCTTCTCCCAA
        ACCCGCGTGTTGCCGAACGCTCTAGACCGGCACCGACATCTCGGTCAGCAGAAGAGGGTT ------------------------------
        MetGluThrLysLeuIleThrTrpGly
481     ATGGAGACCAAGCTCATCACGTGGGGGGC
        TACCTCTGGTTCGAGTAGTGCACCCCCCG
```

FIG. 24

```
         GluTyrValValLeuLeuPheLeuLeuLeuAlaAspAlaArgValCysSerCysLeuTrp
  1   GGGAGTACGTCGTTCTCCTGTTCCTTCTGCTTGCAGACGCGCGCGTCTGCTCCTGCTTGT
      CCCTCATGCAGCAAGAGGACAAGGAAGACGAACGTCTGCGCGCGCAGACGAGGACGAACA

MetMetLeuLeuIleSerGlnAlaGluAlaAlaLeuGluAsnLeuValIleLeuAsnAla
 61   GGATGATGCTACTCATATCCCAAGCGGAGGCGGCTTTGGAGAACCTCGTAATACTTAATG
      CCTACTACGATGAGTATAGGGTTCGCCTCCGCCGAAACCTCTTGGAGCATTATGAATTAC

AlaSerLeuAlaGlyThrHisGlyLeuValSerPheLeuValPhePheCysPheAlaTrp
121   CAGCATCCCTGGCCGGGACGCACGGTCTTGTATCCTTCCTCGTGTTCTTCTGCTTTGCAT
      GTCGTAGGGACCGGCCCTGCGTGCCAGAACATAGGAAGGAGCACAAGAAGACGAAACGTA

TyrLeuLysGlyLysTrpValProGlyAlaValTyrThrPheTyrGlyMetTrpProLeu
181   GGTATTTGAAGGGTAAGTGGGTGCCCGGAGCGGTCTACACCTTCTACGGGATGTGGCCTC
      CCATAAACTTCCCATTCACCCACGGGCCTCGCCAGATGTGGAAGATGCCCTACACCGGAG

LeuLeuLeuLeuLeuAlaLeuProGlnArgAlaTyrAlaLeuAspThrGluValAlaAla
241   TCCTCCTGCTCCTGTTGGCGTTGCCCCAGCGGGCGTACGCGCTGGACACGGAGGTGGCCG
      AGGAGGACGAGGACAACCGCAACGGGGTCGCCCGCATGCGCGACCTGTGCCTCCACCGGC

---------------Overlap with 11b----------------
         SerCysGlyGlyValValLeuValGlyLeuMetAlaLeuThrLeuSerProTyrTyrLys
301   CGTCGTGTGGCGGTGTTGTTCTCGTCGGGTTGATGGCGCTGACTCTGTCACCATATTACA
      GCAGCACACCGCCACAACAAGAGCAGCCCAACTACCGCGACTGAGACAGTGGTATAATGT
      ----------------------------------------
         ArgTyrIleSerTrpCysLeuTrpTrpLeuGln
361   AGCGCTATATCAGCTGGTGCTTGTGGTGGCTTCAGAA
      TCGCGATATAGTCGACCACGAACACCACCGAAGTCTT
```

FIG. 25

```
      ------------------------------------------------------------
         ProAlaProSerGlyCysProProAspSerAspAlaGluSerTyrSerSerMetProPro
  1   CCAGCCCCTTCTGGCTGCCCCCCCGACTCCGACGCTGAGTCCTATTCCTCCATGCCCCCC
      GGTCGGGGAAGACCGACGGGGGGGCTGAGGCTGCGACTCAGGATAAGGAGGTACGGGGGG
      ------------------------------------------------------------
         LeuGluGlyGluProGlyAspProAspLeuSerAspGlySerTrpSerThrValSerSer
 61   CTGGAGGGGGAGCCTGGGGATCCGGATCTTAGCGACGGGTCATGGTCAACAGTCAGTAGT
      GACCTCCCCCTCGGACCCCTAGGCCTAGAATCGCTGCCCAGTACCAGTTGTCAGTCATCA

---------------Overlap with 33g---------------
         GluAlaAsnAlaGluAspValValCysCysSerMetSerTyrSerTrpThrGlyAlaLeu
121   GAGGCCAACGCGGAGGATGTCGTGTGCTGCTCAATGTCCTACTCTTGGACAGGCGCACTC
      CTCCGGTTGCGCCTCCTACAGCACACGACGAGTTACAGGATGAGAACCTGTCCGCGTGAG
      ------------------------------------------------------------
         ValThrProCysAlaAlaGluGluGlnLysLeuProIleAsnAlaLeuSerAsnSerLeu
181   GTCACCCCGTGCGCCGCGGAAGAACAGAAACTGCCCATCAATGCACTGAGCAACTCGTTG
      CAGTGGGGCACGCGGCGCCTTCTTGTCTTTGACGGGTAGTTACGTGACTCGTTGAGCAAC LeuArgHisHisAsnLeuValTyrSerThrThrSerArgSerAlaCysGlnArgGlnLys
241   CTACGTCACCACAATTTGGTGTATTCCACCACCTCACGCAGTGCTTGCCAAAGGCAGAAG
      GATGCAGTGGTGTTAAACCACATAAGGTGGTGGAGTGCGTCACGAACGGTTTCCGTCTTC LysValThrPheAspArgLeuGlnValLeuAspSerHisTyrGlnAspValLeuLysGly
301   AAAGTCACATTTGACAGACTGCAAGTTCTGGACAGCCATTACCAGGACGTACTCAAGGAG
      TTTCAGTGTAAACTGTCTGACGTTCAAGACCTGTCGGTAATGGTCCTGCATGAGTTCCTC ValLysAlaAlaAlaSerLysValLysAlaAsnPhe
361   GTTAAAGCAGCGGCGTCAAAAGTGAAGGCTAACTTC
      CAATTTCGTCGCCGCAGTTTTCACTTCCGATTGAAG
```

FIG. 26A

```
          GluTyrValValLeuLeuPheLeuLeuLeuAlaAspAlaArgValCysSerCysLeuTrp
  1 GGGAGTACGTCGTTCTCCTGTTCCTTCTGCTTGCAGACGCGCGCGTCTGCTCCTGCTTGT
    CCCTCATGCAGCAAGAGGACAAGGAAGACGAACGTCTGCGCGCGCAGACGAGGACGAACA

MetMetLeuLeuIleSerGlnAlaGluAlaAlaLeuGluAsnLeuValIleLeuAsnAla
 61 GGATGATGCTACTCATATCCCAAGCGGAGGCGGCTTTGGAGAACCTCGTAATACTTAATG
    CCTACTACGATGAGTATAGGGTTCGCCTCCGCCGAAACCTCTTGGAGCATTATGAATTAC

AlaSerLeuAlaGlyThrHisGlyLeuValSerPheLeuValPhePheCysPheAlaTrp
121 CAGCATCCCTGGCCGGGACGCACGGTCTTGTATCCTTCCTCGTGTTCTTCTGCTTTGCAT
    GTCGTAGGGACCGGCCCTGCGTGCCAGAACATAGGAAGGAGCACAAGAAGACGAAACGTA

TyrLeuLysGlyLysTrpValProGlyAlaValTyrThrPheTyrGlyMetTrpProLeu
181 GGTATTTGAAGGGTAAGTGGGTGCCCGGAGCGGTCTACACCTTCTACGGGATGTGGCCTC
    CCATAAACTTCCCATTCACCCACGGGCCTCGCCAGATGTGGAAGATGCCCTACACCGGAG

LeuLeuLeuLeuLeuAlaLeuProGlnArgAlaTyrAlaLeuAspThrGluValAlaAla
241 TCCTCCTGCTCCTGTTGGCGTTGCCCCAGCGGGCGTACGCGCTGGACACGGAGGTGGCCG
    AGGAGGACGAGGACAACCGCAACGGGGTCGCCCGCATGCGCGACCTGTGCCTCCACCGGC

SerCysGlyGlyValValLeuValGlyLeuMetAlaLeuThrLeuSerProTyrTyrLys
301 CGTCGTGTGGCGGTGTTGTTCTCGTCGGGTTGATGGCGCTGACTCTGTCACCATATTACA
    GCAGCACACCGCCACAACAAGAGCAGCCCAACTACCGCGACTGAGACAGTGGTATAATGT

ArgTyrIleSerTrpCysLeuTrpTrpLeuGlnTyrPheLeuThrArgValGluAlaGln
361 AGCGCTATATCAGCTGGTGCTTGTGGTGGCTTCAGTATTTTCTGACCAGAGTGGAAGCGC
    TCGCGATATAGTCGACCACGAACACCACCGAAGTCATAAAAGACTGGTCTCACCTTCGCG

LeuHisValTrpIleProProLeuAsnValArgGlyGlyArgAspAlaValIleLeuLeu
421 AACTGCACGTGTGGATTCCCCCCCTCAACGTCCGAGGGGGGCGCGACGCCGTCATCTTAC
    TTGACGTGCACACCTAAGGGGGGGAGTTGCAGGCTCCCCCCGCGCTGCGGCAGTAGAATG

MetCysAlaValHisProThrLeuValPheAspIleThrLysLeuLeuLeuAlaValPhe
481 TCATGTGTGCTGTACACCCGACTCTGGTATTTGACATCACCAAATTGCTGCTGGCCGTCT
    AGTACACACGACATGTGGGCTGAGACCATAAACTGTAGTGGTTTAACGACGACCGGCAGA

GlyProLeuTrpIleLeuGlnAlaSerLeuLeuLysValProTyrPheValArgValGln
541 TCGGACCCCTTTGGATTCTTCAAGCCAGTTTGCTTAAAGTACCCTACTTTGTGCGCGTCC
    AGCCTGGGGAAACCTAAGAAGTTCGGTCAAACGAATTTCATGGGATGAAACACGCGCAGG

GlyLeuLeuArgPheCysAlaLeuAlaArgLysMetIleGlyGlyHisTyrValGlnMet
601 AAGGCCTTCTCCGGTTCTGCGCGTTAGCGCGGAAGATGATCGGAGGCCATTACGTGCAAA
    TTCCGGAAGAGGCCAAGACGCGCAATCGCGCCTTCTACTAGCCTCCGGTAATGCACGTTT

ValIleIleLysLeuGlyAlaLeuThrGlyThrTyrValTyrAsnHisLeuThrProLeu
661 TGGTCATCATTAAGTTAGGGGCGCTTACTGGCACCTATGTTTATAACCATCTCACTCCTC
    ACCAGTAGTAATTCAATCCCCGCGAATGACCGTGGATACAAATATTGGTAGAGTGAGGAG

ArgAspTrpAlaHisAsnGlyLeuArgAspLeuAlaValAlaValGluProValValPhe
721 TTCGGGACTGGGCGCACAACGGCTTGCGAGATCTGGCCGTGGCTGTAGAGCCAGTCGTCT
    AAGCCCTGACCCGCGTGTTGCCGAACGCTCTAGACCGGCACCGACATCTCGGTCAGCAGA

SerGlnMetGluThrLysLeuIleThrTrpGlyAlaAspThrAlaAlaCysGlyAspIle
781 TCTCCCAAATGGAGACCAAGCTCATCACGTGGGGGGCAGATACCGCCGCGTGCGGTGACA
    AGAGGGTTTACCTCTGGTTCGAGTAGTGCACCCCCGTCTATGGCGGCGCACGCCACTGT

IleAsnGlyLeuProValSerAlaArgArgGlyArgGluIleLeuLeuGlyProAlaAsp
841 TCATCAACGGCTTGCCTGTTTCCGCCCGCAGGGGCCGGGAGATACTGCTCGGGCCAGCCG
    AGTAGTTGCCGAACGGACAAAGGCGGGCGTCCCCGGCCCTCTATGACGAGCCCGGTCGGC

GlyMetValSerLysGlyTrpArgLeuLeuAlaProIleThrAlaTyrAlaGlnGlnThr
901 ATGGAATGGTCTCCAAGGGGTGGAGGTTGCTGGCGCCCATCACGGCGTACGCCCAGCAGA
    TACCTTACCAGAGGTTCCCCACCTCCAACGACCGCGGGTAGTGCCGCATGCGGGTCGTCT
```

FIG. 26B

```
         ArgGlyLeuLeuGlyCysIleIleThrSerLeuThrGlyArgAspLysAsnGlnValGlu
 961 CAAGGGGCCTCCTAGGGTGCATAATCACCAGCCTAACTGGCCGGGACAAAAACCAAGTGG
     GTTCCCCGGAGGATCCCACGTATTAGTGGTCGGATTGACCGGCCCTGTTTTTGGTTCACC

GlyGluValGlnIleValSerThrAlaAlaGlnThrPheLeuAlaThrCysIleAsnGly
1021 AGGGTGAGGTCCAGATTGTGTCAACTGCTGCCCAAACCTTCCTGGCAACGTGCATCAATG
     TCCCACTCCAGGTCTAACACAGTTGACGACGGGTTTGGAAGGACCGTTGCACGTAGTTAC

ValCysTrpThrValTyrHisGlyAlaGlyThrArgThrIleAlaSerProLysGlyPro
1081 GGGTGTGCTGGACTGTCTACCACGGGGCCGGAACGAGGACCATCGCGTCACCCAAGGGTC
     CCCACACGACCTGACAGATGGTGCCCCGGCCTTGCTCCTGGTAGCGCAGTGGGTTCCCAG

ValIleGlnMetTyrThrAsnValAspGlnAspLeuValGlyTrpProAlaProGlnGly
1141 CTGTCATCCAGATGTATACCAATGTAGACCAAGACCTTGTGGGCTGGCCCGCTCCGCAAG
     GACAGTAGGTCTACATATGGTTACATCTGGTTCTGGAACACCCGACCGGGCGAGGCGTTC

SerArgSerLeuThrProCysThrCysGlySerSerAspLeuTyrLeuValThrArgHis
1201 GTAGCCGCTCATTGACACCCTGCACTTGCGGCTCCTCGGACCTTTACCTGGTCACGAGGC
     CATCGGCGAGTAACTGTGGGACGTGAACGCCGAGGAGCCTGGAAATGGACCAGTGCTCCG

AlaAspValIleProValArgArgArgGlyAspSerArgGlySerLeuLeuSerProArg
1261 ACGCCGATGTCATTCCCGTGCGCCGGCGGGGTGATAGCAGGGGCAGCCTGCTGTCGCCCC
     TGCGGCTACAGTAAGGGCACGCGGCCGCCCCACTATCGTCCCCGTCGGACGACAGCGGGG

ProIleSerTyrLeuLysGlySerSerGlyGlyProLeuLeuCysProAlaGlyHisAla
1321 GGCCCATTTCCTACTTGAAAGGCTCCTCGGGGGGTCCGCTGTTGTGCCCCGCGGGGCACG
     CCGGGTAAAGGATGAACTTTCCGAGGAGCCCCCCAGGCGACAACACGGGGCGCCCCGTGC

ValGlyIlePheArgAlaAlaValCysThrArgGlyValAlaLysAlaValAspPheIle
1381 CCGTGGGCATATTTAGGGCCGCGGTGTGCACCCGTGGAGTGGCTAAGGCGGTGGACTTTA
     GGCACCCGTATAAATCCCGGCGCCACACGTGGGCACCTCACCGATTCCGCCACCTGAAAT

ProValGluAsnLeuGluThrThrMetArgSerProValPheThrAspAsnSerSerPro
1441 TCCCTGTGGAGAACCTAGAGACAACCATGAGGTCCCCGGTGTTCACGGATAACTCCTCTC
     AGGGACACCTCTTGGATCTCTGTTGGTACTCCAGGGGCCACAAGTGCCTATTGAGGAGAG

ProValValProGlnSerPheGlnValAlaHisLeuHisAlaProThrGlySerGlyLys
1501 CACCAGTAGTGCCCCAGAGCTTCCAGGTGGCTCACCTCCATGCTCCCACAGGCAGCGGCA
     GTGGTCATCACGGGGTCTCGAAGGTCCACCGAGTGGAGGTACGAGGGTGTCCGTCGCCGT

SerThrLysValProAlaAlaTyrAlaAlaGlnGlyTyrLysValLeuValLeuAsnPro
1561 AAAGCACCAAGGTCCCCGGCTGCATATGCAGCTCAGGGCTATAAGGTGCTAGTACTCAACC
     TTTCGTGGTTCCAGGGCCGACGTATACGTCGAGTCCCGATATTCCACGATCATGAGTTGG

SerValAlaAlaThrLeuGlyPheGlyAlaTyrMetSerLysAlaHisGlyIleAspPro
1621 CCTCTGTTGCTGCAACACTGGGCTTTGGTGCTTACATGTCCAAGGCTCATGGGATCGATC
     GGAGACAACGACGTTGTGACCCGAAACCACGAATGTACAGGTTCCGAGTACCCTAGCTAG

AsnIleArgThrGlyValArgThrIleThrThrGlySerProIleThrTyrSerThrTyr
1681 CTAACATCAGGACCGGGGTGAGAACAATTACCACTGGCAGCCCCATCACGTACTCCACCT
     GATTGTAGTCCTGGCCCCACTCTTGTTAATGGTGACCGTCGGGGTAGTGCATGAGGTGGA

GlyLysPheLeuAlaAspGlyGlyCysSerGlyGlyAlaTyrAspIleIleIleCysAsp
1741 ACGGCAAGTTCCTTGCCGACGGCGGGTGCTCGGGGGGCGCTTATGACATAATAATTTGTG
     TGCCGTTCAAGGAACGGCTGCCGCCCACGAGCCCCCCGCGAATACTGTATTATTAAACAC

GluCysHisSerThrAspAlaThrSerIleLeuGlyIleGlyThrValLeuAspGlnAla
1801 ACGAGTGCCACTCCACGGATGCCACATCCATCTTGGGCATCGGCACTGTCCTTGACCAAG
     TGCTCACGGTGAGGTGCCTACGGTGTAGGTAGAACCCGTAGCCGTGACAGGAACTGGTTC

GluThrAlaGlyAlaArgLeuValValLeuAlaThrAlaThrProProGlySerValThr
1861 CAGAGACTGCGGGGGCGAGACTGGTTGTGCTCGCCACCGCCACCCCTCCGGGCTCCGTCA
     GTCTCTGACGCCCCGCTCTGACCAACACGAGCGGTGGCGGTGGGGAGGCCCGAGGCAGT

ValProHisProAsnIleGluGluValAlaLeuSerThrThrGlyGluIleProPheTyr
1921 CTGTGCCCCATCCCAACATCGAGGAGGTTGCTCTGTCCACCACCGGAGAGATCCCTTTTT
     GACACGGGGTAGGGTTGTAGCTCCTCCAACGAGACAGGTGGTGGCCTCTCTAGGGAAAAA
```

FIG. 26C

```
         GlyLysAlaIleProLeuGluValIleLysGlyGlyArgHisLeuIlePheCysHisSer
1981 ACGGCAAGGCTATCCCCCTCGAAGTAATCAAGGGGGGGAGACATCTCATCTTCTGTCATT
     TGCCGTTCCGATAGGGGGAGCTTCATTAGTTCCCCCCCTCTGTAGAGTAGAAGACAGTAA

LysLysLysCysAspGluLeuAlaAlaLysLeuValAlaLeuGlyIleAsnAlaValAla
2041 CAAAGAAGAAGTGCGACGAACTCGCCGCAAAGCTGGTCGCATTGGGCATCAATGCCGTGG
     GTTTCTTCTTCACGCTGCTTGAGCGGCGTTTCGACCAGCGTAACCCGTAGTTACGGCACC

TyrTyrArgGlyLeuAspValSerValIleProThrSerGlyAspValValValValAla
2101 CCTACTACCGCGGTCTTGACGTGTCCGTCATCCCGACCAGCGGCGATGTTGTCGTCGTGG
     GGATGATGGCGCCAGAACTGCACAGGCAGTAGGGCTGGTCGCCGCTACAACAGCAGCACC

ThrAspAlaLeuMetThrGlyTyrThrGlyAspPheAspSerValIleAspCysAsnThr
2161 CAACCGATGCCCTCATGACCGGCTATACCGGCGACTTCGACTCGGTGATAGACTGCAATA
     GTTGGCTACGGGAGTACTGGCCGATATGGCCGCTGAAGCTGAGCCACTATCTGACGTTAT

CysValThrGlnThrValAspPheSerLeuAspProThrPheThrIleGluThrIleThr
2221 CGTGTGTCACCCAGACAGTCGATTTCAGCCTTGACCCTACCTTCACCATTGAGACAATCA
     GCACACAGTGGGTCTGTCAGCTAAAGTCGGAACTGGGATGGAAGTGGTAACTCTGTTAGT

LeuProGlnAspAlaValSerArgThrGlnArgArgGlyArgThrGlyArgGlyLysPro
2281 CGCTCCCCCAGGATGCTGTCTCCCGCACTCAACGTCGGGGCAGGACTGGCAGGGGGAAGC
     GCGAGGGGGTCCTACGACAGAGGGCGTGAGTTGCAGCCCCGTCCTGACCGTCCCCCTTCG

GlyIleTyrArgPheValAlaProGlyGluArgProSerGlyMetPheAspSerSerVal
2341 CAGGCATCTACAGATTTGTGGCACCGGGGGAGCGCCCCTCCGGCATGTTCGACTCGTCCG
     GTCCGTAGATGTCTAAACACCGTGGCCCCCTCGCGGGGAGGCCGTACAAGCTGAGCAGGC

LeuCysGluCysTyrAspAlaGlyCysAlaTrpTyrGluLeuThrProAlaGluThrThr
2401 TCCTCTGTGAGTGCTATGACGCAGGCTGTGCTTGGTATGAGCTCACGCCCGCCGAGACTA
     AGGAGACACTCACGATACTGCGTCCGACACGAACCATACTCGAGTGCGGGCGGCTCTGAT

ValArgLeuArgAlaTyrMetAsnThrProGlyLeuProValCysGlnAspHisLeuGlu
2461 CAGTTAGGCTACGAGCGTACATGAACACCCCGGGGCTTCCCGTGTGCCAGGACCATCTTG
     GTCAATCCGATGCTCGCATGTACTTGTGGGGCCCCGAAGGGCACACGGTCCTGGTAGAAC

PheTrpGluGlyValPheThrGlyLeuThrHisIleAspAlaHisPheLeuSerGlnThr
2521 AATTTTTGGGAGGGCGTCTTTACAGGCCTCACTCATATAGATGCCCACTTTCTATCCCAGA
     TTAAAACCCTCCCGCAGAAATGTCCGGAGTGAGTATATCTACGGGTGAAAGATAGGGTCT

LysGlnSerGlyGluAsnLeuProTyrLeuValAlaTyrGlnAlaThrValCysAlaArg
2581 CAAAGCAGAGTGGGGAGAACCTTCCTTACCTGGTAGCGTACCAAGCCACCGTGTGCGCTA
     GTTTCGTCTCACCCCTCTTGGAAGGAATGGACCATCGCATGGTTCGGTGGCACACGCGAT

AlaGlnAlaProProProSerTrpAspGlnMetTrpLysCysLeuIleArgLeuLysPro
2641 GGGCTCAAGCCCCTCCCCCATCGTGGGACCAGATGTGGAAGTGTTTGATTCGCCTCAAGC
     CCCGAGTTCGGGGAGGGGGTAGCACCCTGGTCTACACCTTCACAAACTAAGCGGAGTTCG

ThrLeuHisGlyProThrProLeuLeuTyrArgLeuGlyAlaValGlnAsnGluIleThr
2701 CCACCCTCCATGGGCCAACACCCCTGCTATACAGACTGGGCGCTGTTCAGAATGAAATCA
     GGTGGGAGGTACCCGGTTGTGGGGACGATATGTCTGACCCGCGACAAGTCTTACTTTAGT

LeuThrHisProValThrLysTyrIleMetThrCysMetSerAlaAspLeuGluValVal
2761 CCCTGACGCACCCAGTCACCAAATACATCATGACATGCATGTCGGCCGACCTGGAGGTCG
     GGGACTGCGTGGGTCAGTGGTTTATGTAGTACTGTACGTACAGCCGGCTGGACCTCCAGC

ThrSerThrTrpValLeuValGlyGlyValLeuAlaAlaLeuAlaAlaTyrCysLeuSer
2821 TCACGAGCACCTGGGTGCTCGTTGGCGGCGTCCTGGCTGCTTTGGCCGCGTATTGCCTGT
     AGTGCTCGTGGACCCACGAGCAACCGCCGCAGGACCGACGAAACCGGCGCATAACGGACA

ThrGlyCysValValIleValGlyArgValValLeuSerGlyLysProAlaIleIlePro
2881 CAACAGGCTGCGTGGTCATAGTGGGCAGGGTCGTCTTGTCCGGGAAGCCGGCAATCATAC
     GTTGTCCGACGCACCAGTATCACCCGTCCCAGCAGAACAGGCCCTTCGGCCGTTAGTATG

AspArgGluValLeuTyrArgGluPheAspGluMetGluGluCysSerGlnHisLeuPro
2941 CTGACAGGGAAGTCCTCTACCGAGAGTTCGATGAGATGGAAGAGTGCTCTCAGCACTTAC
     GACTGTCCCTTCAGGAGATGGCTCTCAAGCTACTCTACCTTCTCACGAGAGTCGTGAATG
```

FIG. 26D

```
         TyrIleGluGlnGlyMetMetLeuAlaGluGlnPheLysGlnLysAlaLeuGlyLeuLeu
3001 CGTACATCGAGCAAGGGATGATGCTCGCCGAGCAGTTCAAGCAGAAGGCCCTCGGCCTCC
     GCATGTAGCTCGTTCCCTACTACGAGCGGCTCGTCAAGTTCGTCTTCCGGGAGCCGGAGG

GlnThrAlaSerArgGlnAlaGluValIleAlaProAlaValGlnThrAsnTrpGlnLys
3061 TGCAGACCGCGTCCCGTCAGGCAGAGGTTATCGCCCCTGCTGTCCAGACCAACTGGCAAA
     ACGTCTGGCGCAGGGCAGTCCGTCTCCAATAGCGGGGACGACAGGTCTGGTTGACCGTTT

LeuGluThrPheTrpAlaLysHisMetTrpAsnPheIleSerGlyIleGlnTyrLeuAla
3121 AACTCGAGACCTTCTGGGCGAAGCATATGTGGAACTTCATCAGTGGGATACAATACTTGG
     TTGAGCTCTGGAAGACCCGCTTCGTATACACCTTGAAGTAGTCACCCTATGTTATGAACC

GlyLeuSerThrLeuProGlyAsnProAlaIleAlaSerLeuMetAlaPheThrAlaAla
3181 CGGGCTTGTCAACGCTGCCTGGTAACCCCGCCATTGCTTCATTGATGGCTTTTACAGCTG
     GCCCGAACAGTTGCGACGGACCATTGGGGCGGTAACGAAGTAACTACCGAAAATGTCGAC

ValThrSerProLeuThrThrSerGlnThrLeuLeuPheAsnIleLeuGlyGlyTrpVal
3241 CTGTCACCAGCCCACTAACCACTAGCCAAACCCTCCTCTTCAACATATTGGGGGGGTGGG
     GACAGTGGTCGGGTGATTGGTGATCGGTTTGGGAGGAGAAGTTGTATAACCCCCCCACCC

AlaAlaGlnLeuAlaAlaProGlyAlaAlaThrAlaPheValGlyAlaGlyLeuAlaGly
3301 TGGCTGCCCAGCTCGCCGCCCCGGTGCCGCTACTGCCTTTGTGGGCGCTGGCTTAGCTG
     ACCGACGGGTCGAGCGGCGGGGGCCACGGCGATGACGGAAACACCCGCGACCGAATCGAC

AlaAlaIleGlySerValGlyLeuGlyLysValLeuIleAspIleLeuAlaGlyTyrGly
3361 GCGCCGCCATCGGCAGTGTTGGACTGGGGAAGGTCCTCATAGACATCCTTGCAGGGTATG
     CGCGGCGGTAGCCGTCACAACCTGACCCCTTCCAGGAGTATCTGTAGGAACGTCCCATAC

AlaGlyValAlaGlyAlaLeuValAlaPheLysIleMetSerGlyGluValProSerThr
3421 GCGCGGGCGTGGCGGGAGCTCTTGTGGCATTCAAGATCATGAGCGGTGAGGTCCCCTCCA
     CGCGCCCGCACCGCCCTCGAGAACACCGTAAGTTCTAGTACTCGCCACTCCAGGGGAGGT

GluAspLeuValAsnLeuLeuProAlaIleLeuSerProGlyAlaLeuValValGlyVal
3481 CGGAGGACCTGGTCAATCTACTGCCCGCCATCCTCTCGCCCGGAGCCCTCGTAGTCGGCG
     GCCTCCTGGACCAGTTAGATGACGGGCGGTAGGAGAGCGGGCCTCGGGAGCATCAGCCGC

ValCysAlaAlaIleLeuArgArgHisValGlyProGlyGluGlyAlaValGlnTrpMet
3541 TGGTCTGTGCAGCAATACTGCGCCGGCACGTTGGCCCGGGCGAGGGGCAGTGCAGTGGA
     ACCAGACACGTCGTTATGACGCGGCCGTGCAACCGGGCCCGCTCCCCCGTCACGTCACCT

AsnArgLeuIleAlaPheAlaSerArgGlyAsnHisValSerProThrHisTyrValPro
3601 TGAACCGGCTGATAGCCTTCGCCTCCCGGGGGAACCATGTTTCCCCCACGCACTACGTGC
     ACTTGGCCGACTATCGGAAGCGGAGGGCCCCCTTGGTACAAAGGGGGTGCGTGATGCACG

GluSerAspAlaAlaAlaArgValThrAlaIleLeuSerSerLeuThrValThrGlnLeu
3661 CGGAGAGCGATGCAGCTGCCCGCGTCACTGCCATACTCAGCAGCCTCACTGTAACCCAGC
     GCCTCTCGCTACGTCGACGGGCGCAGTGACGGTATGAGTCGTCGGAGTGACATTGGGTCG

LeuArgArgLeuHisGlnTrpIleSerSerGluCysThrThrProCysSerGlySerTrp
3721 TCCTGAGGCGACTGCACCAGTGGATAAGCTCGGAGTGTACCACTCCATGCTCCGGTTCCT
     AGGACTCCGCTGACGTGGTCACCTATTCGAGCCTCACATGGTGAGGTACGAGGCCAAGGA

LeuArgAspIleTrpAspTrpIleCysGluValLeuSerAspPheLysThrTrpLeuLys
3781 GGCTAAGGGACATCTGGGACTGGATATGCGAGGTGTTGAGCGACTTTAAGACCTGGCTAA
     CCGATTCCCTGTAGACCCTGACCTATACGCTCCACAACTCGCTGAAATTCTGGACCGATT

AlaLysLeuMetProGlnLeuProGlyIleProPheValSerCysGlnArgGlyTyrLys
3841 AAGCTAAGCTCATGCCACAGCTGCCTGGGATCCCCTTTGTGTCCTGCCAGCGCGGGTATA
     TTCGATTCGAGTACGGTGTCGACGGACCCTAGGGGAAACACAGGACGGTCGCGCCCATAT

GlyValTrpArgValAspGlyIleMetHisThrArgCysHisCysGlyAlaGluIleThr
3901 AGGGGGTCTGGCGAGTGGACGGCATCATGCACACTCGCTGCCACTGTGGAGCTGAGATCA
     TCCCCCAGACCGCTCACCTGCCGTAGTACGTGTGAGCGACGGTGACACCTCGACTCTAGT

GlyHisValLysAsnGlyThrMetArgIleValGlyProArgThrCysArgAsnMetTrp
3961 CTGGACATGTCAAAAACGGGACGATGAGGATCGTCGGTCCTAGGACCTGCAGGAACATGT
     GACCTGTACAGTTTTTGCCCTGCTACTCCTAGCAGCCAGGATCCTGGACGTCCTTGTACA
```

FIG. 26E

```
      SerGlyThrPheProIleAsnAlaTyrThrThrGlyProCysThrProLeuProAlaPro
4021 GGAGTGGGACCTTCCCCATTAATGCCTACACCACGGGCCCCTGTACCCCCCTTCCTGCGC
     CCTCACCCTGGAAGGGGTAATTACGGATGTGGTGCCCGGGGACATGGGGGGAAGGACGCG

AsnTyrThrPheAlaLeuTrpArgValSerAlaGluGluTyrValGluIleArgGlnVal
4081 CGAACTACACGTTCGCGCTATGGAGGGTGTCTGCAGAGGAATATGTGGAGATAAGGCAGG
     GCTTGATGTGCAAGCGCGATACCTCCCACAGACGTCTCCTTATACACCTCTATTCCGTCC

GlyAspPheHisTyrValThrGlyMetThrThrAspAsnLeuLysCysProCysGlnVal
4141 TGGGGGACTTCCACTACGTGACGGGTATGACTACTGACAATCTCAAATGCCCGTGCCAGG
     ACCCCCTGAAGGTGATGCACTGCCCATACTGATGACTGTTAGAGTTTACGGGCACGGTCC

ProSerProGluPhePheThrGluLeuAspGlyValArgLeuHisArgPheAlaProPro
4201 TCCCATCGCCCGAATTTTTCACAGAATTGGACGGGGTGCGCCTACATAGGTTTGCGCCCC
     AGGGTAGCGGGCTTAAAAAGTGTCTTAACCTGCCCCACGCGGATGTATCCAAACGCGGGG

CysLysProLeuLeuArgGluGluValSerPheArgValGlyLeuHisGluTyrProVal
4261 CCTGCAAGCCCTTGCTGCGGGAGGAGGTATCATTCAGAGTAGGACTCCACGAATACCCGG
     GGACGTTCGGGAACGACGCCCTCCTCCATAGTAAGTCTCATCCTGAGGTGCTTATGGGCC

GlySerGlnLeuProCysGluProGluProAspValAlaValLeuThrSerMetLeuThr
4321 TAGGGTCGCAATTACCTTGCGAGCCCGAACCGGACGTGGCCGTGTTGACGTCCATGCTCA
     ATCCCAGCGTTAATGGAACGCTCGGGCTTGGCCTGCACCGGCACAACTGCAGGTACGAGT

AspProSerHisIleThrAlaGluAlaAlaGlyArgArgLeuAlaArgGlySerProPro
4381 CTGATCCCTCCCATATAACAGCAGAGGCGGCCGGGCGAAGGTTGGCGAGGGGATCACCCC
     GACTAGGGAGGGTATATTGTCGTCTCCGCCGGCCCGCTTCCAACCGCTCCCCTAGTGGGG

SerValAlaSerSerSerAlaSerGlnLeuSerAlaProSerLeuLysAlaThrCysThr
4441 CCTCTGTGGCCAGCTCCTCGGCTAGCCAGCTATCCGCTCCATCTCTCAAGGCAACTTGCA
     GGAGACACCGGTCGAGGAGCCGATCGGTCGATAGGCGAGGTAGAGAGTTCCGTTGAACGT

AlaAsnHisAspSerProAspAlaGluLeuIleGluAlaAsnLeuLeuTrpArgGlnGlu
4501 CCGCTAACCATGACTCCCCTGATGCTGAGCTCATAGAGGCCAACCTCCTATGGAGGCAGG
     GGCGATTGGTACTGAGGGGACTACGACTCGAGTATCTCCGGTTGGAGGATACCTCCGTCC

MetGlyGlyAsnIleThrArgValGluSerGluAsnLysValValIleLeuAspSerPhe
4561 AGATGGGCGGCAACATCACCAGGGTTGAGTCAGAAAACAAAGTGGTGATTCTGGACTCCT
     TCTACCCGCCGTTGTAGTGGTCCCAACTCAGTCTTTTGTTTCACCACTAAGACCTGAGGA

AspProLeuValAlaGluGluAspGluArgGluIleSerValProAlaGluIleLeuArg
4621 TCGATCCGCTTGTGGCGGAGGAGGACGAGCGGGAGATCTCCGTACCCGCAGAAATCCTGC
     AGCTAGGCGAACACCGCCTCCTCCTGCTCGCCCTCTAGAGGCATGGGCGTCTTTAGGACG

LysSerArgArgPheAlaGlnAlaLeuProValTrpAlaArgProAspTyrAsnProPro
4681 GGAAGTCTCGGAGATTCGCCCAGGCCCTGCCCGTTTGGGCGCGGCCGGACTATAACCCCC
     CCTTCAGAGCCTCTAAGCGGGTCCGGGACGGGCAAACCCGCGCCGGCCTGATATTGGGGG

LeuValGluThrTrpLysLysProAspTyrGluProProValValHisGlyCysProLeu
4741 CGCTAGTGGAGACGTGGAAAAAGCCCGACTACGAACCACCTGTGGTCCATGGCTGTCCGC
     GCGATCACCTCTGCACCTTTTTCGGGCTGATGCTTGGTGGACACCAGGTACCGACAGGCG

ProProProLysSerProProValProProProArgLysLysArgThrValValLeuThr
4801 TTCCACCTCCAAAGTCCCCTCCTGTGCCTCCGCCTCGGAAGAAGCGGACGGTGGTCCTCA
     AAGGTGGAGGTTTCAGGGGAGGACACGGAGGCGGAGCCTTCTTCGCCTGCCACCAGGAGT

GluSerThrLeuSerThrAlaLeuAlaGluLeuAlaThrArgSerPheGlySerSerSer
4861 CTGAATCAACCCTATCTACTGCCTTGGCCGAGCTCGCCACCAGAAGCTTTGGCAGCTCCT
     GACTTAGTTGGGATAGATGACGGAACCGGCTCGAGCGGTGGTCTTCGAAACCGTCGAGGA

ThrSerGlyIleThrGlyAspAsnThrThrThrSerSerGluProAlaProSerGlyCys
4921 CAACTTCCGGCATTACGGGCGACAATACGACAACATCCTCTGAGCCCGCCCCTTCTGGCT
     GTTGAAGGCCGTAATGCCCGCTGTTATGCTGTTGTAGGAGACTCGGGCGGGGAAGACCGA

ProProAspSerAspAlaGluSerTyrSerSerMetProProLeuGluGlyGluProGly
4981 GCCCCCCCGACTCCGACGCTGAGTCCTATTCCTCCATGCCCCCCCTGGAGGGGGAGCCTG
     CGGGGGGGCTGAGGCTGCGACTCAGGATAAGGAGGTACGGGGGGGACCTCCCCCTCGGAC
```

FIG. 26F

```
       AspProAspLeuSerAspGlySerTrpSerThrValSerSerGluAlaAsnAlaGluAsp
5041 GGGATCCGGATCTTAGCGACGGGTCATGGTCAACGGTCAGTAGTGAGGCCAACGCGGAGG
     CCCTAGGCCTAGAATCGCTGCCCAGTACCAGTTGCCAGTCATCACTCCGGTTGCGCCTCC

ValValCysCysSerMetSerTyrSerTrpThrGlyAlaLeuValThrProCysAlaAla
5101 ATGTCGTGTGCTGCTCAATGTCTTACTCTTGGACAGGCGCACTCGTCACCCCGTGCGCCG
     TACAGCACACGACGAGTTACAGAATGAGAACCTGTCCGCGTGAGCAGTGGGGCACGCGGC

GluGluGlnLysLeuProIleAsnAlaLeuSerAsnSerLeuLeuArgHisHisAsnLeu
5161 CGGAAGAACAGAAACTGCCCATCAATGCACTAAGCAACTCGTTGCTACGTCACCACAATT
     GCCTTCTTGTCTTTGACGGGTAGTTACGTGATTCGTTGAGCAACGATGCAGTGGTGTTAA

ValTyrSerThrThrSerArgSerAlaCysGlnArgGlnLysLysValThrPheAspArg
5221 TGGTGTATTCCACCACCTCACGCAGTGCTTGCCAAAGGCAGAAGAAAGTCACATTTGACA
     ACCACATAAGGTGGTGGAGTGCGTCACGAACGGTTTCCGTCTTCTTTCAGTGTAAACTGT

LeuGlnValLeuAspSerHisTyrGlnAspValLeuLysGluValLysAlaAlaAlaSer
5281 GACTGCAAGTTCTGGACAGCCATTACCAGGACGTACTCAAGGAGGTTAAAGCAGCGGCGT
     CTGACGTTCAAGACCTGTCGGTAATGGTCCTGCATGAGTTCCTCCAATTTCGTCGCCGCA

LysValLysAlaAsnLeu
5341 CAAAAGTGAAGGCTAACTTG
     GTTTTCACTTCCGATTGAAC
```

FIG. 30

```
      ---------------------------------------------------------------
        GlyGlyGluAsnCysGlyTyrArgArgCysArgAlaSerGlyValLeuThrThrSerCys
   1  GGGGGGGAGAACTGCGGCTATCGCAGGTGCCGCGCAAGCGGCGTACTGACAACTAGCTGT
      CCCCCCCTCTTGACGCCGATAGCGTCCACGGCGCGTTCGCCGCATGACTGTTGATCGACA

GlyAsnThrLeuThrCysTyrIleLysAlaArgAlaAlaCysArgAlaAlaGlyLeuGln
  61  GGTAACACCCTCACTTGTTACATCAAGGCCCGAGCAGCCTGTCGAGCCGCAGGGCTCCAG
      CCATTGTGGGAGTGAACAATGTAGTTCCGGGCTCGTCGGACAGCTCGGCGTCCCGAGGTC

-------------Overlap with 19g----------------------------------
        AspCysThrMetLeuValCysGlyAspAspLeuValValIleCysGluSerAlaGlyVal
 121  GACTGCACCATGCTCGTGTGTGGCGACGACTTAGTCGTTATCTGTGAAAGCGCGGGGGTC
      CTGACGTGGTACGAGCACACACCGCTGCTGAATCAGCAATAGACACTTTCGCGCCCCCAG
      ----------------

GlnGluAspAlaAlaSerLeuArgAlaPheThrGluAlaMetThrArgTyrSerAlaPro
 181  CAGGAGGACGCGGCGAGCCTGAGAGCCTTCACGGAGGCTATGACCAGGTACTCCGCCCCC
      GTCCTCCTGCGCCGCTCGGACTCTCGGAAGTGCCTCCGATACTGGTCCATGAGGCGGGGG

ProGlyAspProProGlnProGluTyrAspLeuGluLeuIleThrSerCysSerSerAsn
 241  CCTGGGGACCCCCCACAACCAGAATACGACTTGGAGCTCATAACATCATGCTCCTCCAAC
      GGACCCCTGGGGGGTGTTGGTCTTATGCTGAACCTCGAGTATTGTAGTACGAGGAGGTTG

ValSerValAlaHisAspGlyAlaGlyLysArgValTyrTyrLeuThrArgAspProThr
 301  GTGTCAGTCGCCCACGACGGCGCTGGAAAGAGGGTCTACTACCTCACCCGTGACCCTACA
      CACAGTCAGCGGGTGCTGCCGCGACCTTTCTCCCAGATGATGGAGTGGGCACTGGGATGT

ThrProLeuAlaArgAlaAlaTrpGluThrAlaArgHisThrProValAsnSerTrpLeu
 361  ACCCCCCTCGCGAGAGCTGCGTGGGAGACAGCAAGACACACTCCAGTCAATTCCTGGCTA
      TGGGGGGAGCGCTCTCGACGCACCCTCTGTCGTTCTGTGTGAGGTCAGTTAAGGACCGAT

GlyAsnIleIleMetPheAlaProThrLeuTrpAla
 421  GGCAACATAATCATGTTTGCCCCCACACTGTGGGCG
      CCGTTGTATTAGTACAAACGGGGGTGTGACACCCGC
```

FIG. 27

```
    IlePheLysIleArgMetTyrValGlyLysValGluHisArgLeuGluAlaAlaCysAsn
  1 CCATATTAAAATCAGGATGTACGTGGGAGGGTCGAACACAGGCTGGAAGCTGCCTGCA
    GGTATAATTTTAGTCCTACATGCACCCTCCCAGCTTGTGTCCGACCTTCGACGACGT
    TrpThrArgGlyGlyGluArgCysAspLeuGluAspArgArgSerGluLeuSerProLeu
 61 ACTGGACGCGGGGGAACGTTGCGATCTGGAAGACAGGAGGTCCGAGCTCAGCCCGT
    TGACCTGCGCCCCGCTTGCAACGCTAGACCTTCTGTCCCGTCCAGGCTCGAGTCGGGCA
    LeuLeuThrThrThrGlnTrpGlnValLeuProCysSerPheThrThrLeuProAlaLeu
121 TACTGCTGACCACTACACAGTGGCAGGTCCTCCCGTGTTCCTTCACAACCCTACCAGCCT
    ATGACGACTGGTGATGTGTCACCGTCCAGGAGGGCACACAAGGAAGTGTTGGGATGGTCGGA
    SerThrGlyLeuIleHisLeuHisGlnAsnIleValAspValGlnTyrLeuTyrGlyVal
181 TGTCCACCGGCCTCATCCACTCCACCAGAACATTGGACGTGCAGTACTGTACGGGG
    ACAGGTGGCCGGAGTAGGTGGAGGTGGTCTTGTAACACCTGCACGTCATGAACATGCCCC
    GlySerSerIleAlaSerTrpAlaIleLysTrpGluTyrValValLeuLeuPheLeuLeu
241 TGGGGTCAAGCATCGCGTCCTGGGCCATTAAGTGGGAGTACGTTCGTTCTCCTGTTCCTTC
    ACCCCAGTTCGTAGCGCAGGACCCGGTAATTCACCTCATGCAAGCAAGAGACAAGGAAG
    LeuAlaAspAlaArgValCysSerCysLeuTrpMetMetLeuLeuIleSerGlnAlaGlu
301 TGCTTGCAGACGCGCGCGTCTGCTCCTGTGGATGATGCTACTCATATCCCAAGCGG
    ACGAACGTCTGCGCGCGCAGACGAGGACGAGGACACCTACTACGATGAGTATAGGGTTCGCC
    ------ Overlap with 14i ------
    AlaAlaLeuGluAsnLeuValIleLeuAsnAlaAlaSerLeuAlaGlyThrHisGlyLeu
361 AGGCGGCTTTGGAGAACCTCGTAATACTTAATGCAGCATCCCTGGCCGGGACGCACGGTC
    TCCGCCGAAACCTCTTGGAGCATTATGAATTACGTCGTAGGGACCGGCCCTGCGTGCCAG
    Val
421 TTGTATC
    AACATAG
```

FIG. 28

```
         ----------Overlap with 39c--------------------
         LeuLysGluValLysAlaAlaAlaSerLysValLysAlaAsnLeuLeuSerValGluGlu
   1     TGCTCAAGGAGGTTAAAGCAGCGGCGTCAAAAGTGAAGGCTAACTTGCTATCCGTAGAGG
         ACGAGTTCCTCCAATTTCGTCGCCGCAGTTTTCACTTCCGATTGAACGATAGGCATCTCC AlaCysSerLeuThrProProHisSerAlaLysSerLysPheGlyTyrGlyAlaLysAsp
  61     AAGCTTGCAGCCTGACGCCCCCACACTCAGCCAAATCCAAGTTTGGTTATGGGGCAAAAG
         TTCGAACGTCGGACTGCGGGGGTGTGAGTCGGTTTAGGTTCAAACCAATACCCCGTTTTC ValArgCysHisAlaArgLysAlaValThrHisIleAsnSerValTrpLysAspLeuLeu
 121     ACGTCCGTTGCCATGCCAGAAAGGCCGTAACCCACATCAACTCCGTGTGGAAAGACCTTC
         TGCAGGCAACGGTACGGTCTTTCCGGCATTGGGTGTAGTTGAGGCACACCTTTCTGGAAG GluAspAsnValThrProIleAspThrThrIleMetAlaLysAsnGluValPheCysVal
 181     TGGAAGACAATGTAACACCAATAGACACTACCATCATGGCTAAGAACGAGGTTTTCTGCG
         ACCTTCTGTTACATTGTGGTTATCTGTGATGGTAGTACCGATTCTTGCTCCAAAAGACGC GlnProGluLysGlyGlyArgLysProAlaArgLeuIleValPheProAspLeuGlyVal
 241     TTCAGCCTGAGAAGGGGGGTCGTAAGCCAGCTCGTCTCATCGTGTTCCCCGATCTGGGCG
         AAGTCGGACTCTTCCCCCCAGCATTCGGTCGAGCAGAGTAGCACAAGGGGCTAGACCCGC ArgValCysGluLysMetAlaLeuTyrAspValValThrLysLeuProLeuAlaValMet
 301     TGCGCGTGTGCGAAAGATGGCTTTGTACGACGTGGTTACAAAGCTCCCCTTGGCCGTGA
         ACGCGCACACGCTTTTCTACCGAAACATGCTGCACCAATGTTTCGAGGGGAACCGGCACT GlySerSerTyrGlyPheGlnTyrSerProGlyGlnArgValGluPheLeuValGlnAla
 361     TGGGAAGCTCCTACGGATTCCAATACTCACCAGGACAGCGGGTTGAATTCCTCGTGCAAG
         ACCCTTCGAGGATGCCTAAGGTTATGAGTGGTCCTGTCGCCCAACTTAAGGAGCACGTTC TrpLysSerLysLysThrProMetGlyPheSerTyrAspThrArgCysPheAspSerThr
 421     CGTGGAAGTCCAAGAAAACCCCAATGGGGTTCTCGTATGATACCCGCTGCTTTGACTCCA
         GCACCTTCAGGTTCTTTTGGGGTTACCCCAAGAGCATACTATGGGCGACGAAACTGAGGT ValThrGluSerAspIleArgThrGluGluAla
 481     CAGTCACTGAGAGCGACATCCGTACGGAGGAGGCA
         GTCAGTGACTCTCGCTGTAGGCATGCCTCCTCCGT
```

FIG. 29

```
           GluPheLeuValGlnAlaTrpLysSerLysLysThrProMetGlyPheSerTyrAspThr
  1        GAATTCCTCGTGCAAGCGTGGAAGTCCAAGAAAACCCCAATGGGGTTCTCGTATGATACC
           CTTAAGGAGCACGTTCGCACCTTCAGGTTCTTTTGGGGTTACCCCAAGAGCATACTATGC

--------------Overlap with 35f--------------------------
           ArgCysPheAspSerThrValThrGluSerAspIleArgThrGluGluAlaIleTyrGln
  61       CGCTGCTTTGACTCCACAGTCACTGAGAGCGACATCCGTACGGAGGAGGCAATCTACCAA
           GCGACGAAACTGAGGTGTCAGTGACTCTCGCTGTAGGCATGCCTCCTCCGTTAGATGGTT CysCysAspLeuAspProGlnAlaArgValAlaIleLysSerLeuThrGluArgLeuTyr
  121      TGTTGTGACCTCGACCCCCAAGCCCGCGTGGCCATCAAGTCCCTCACCGAGAGGCTTTAT
           ACAACACTGGAGCTGGGGGTTCGGGCGCACCGGTAGTTCAGGGAGTGGCTCTCCGAAATA ValGlyGlyProLeuThrAsnSerArgGlyGluAsnCysGlyTyrArgArgCysArgAla
  181      GTTGGGGGCCCTCTTACCAATTCAAGGGGGGAGAACTGCGGCTATCGCAGGTGCCGCGCG
           CAACCCCCGGGAGAATGGTTAAGTTCCCCCCTCTTGACGCCGATAGCGTCCACGGCGCGC SerGlyValLeuThrThrSerCysGlyAsnThrLeuThrCysTyrIleLysAlaArgAla
  241      AGCGGCGTACTGACAACTAGCTGTGGTAACACCCTCACTTGCTACATCAAGGCCCGGGCA
           TCGCCGCATGACTGTTGATCGACACCATTGTGGGAGTGAACGATGTAGTTCCGGGCCCGT AlaCysArgAlaAlaGlyLeuGlnAspCysThrMetLeuValCysGlyAspAspLeuVal
  301      GCCTGTCGAGCCGCAGGGCTCCAGGACTGCACCATGCTCGTGTGTGGCGACGACTTAGTC
           CGGACAGCTCGGCGTCCCGAGGTCCTGACGTGGTACGAGCACACACCGCTGCTGAATCAG ValIleCysGluSerAlaGlyValGlnGluAspAlaAla
  361      GTTATCTGTGAAAGCGCGGGGGTCCAGGAGGACGCGGCGAG
           CAATAGACACTTTCGCGCCCCCAGGTCCTCCTGCGCCGCTC
```

FIG. 31

```
     GlyAlaGlyLysArgValTyrTyrLeuThrArgAspProThrProLeuAlaArgAla
  1  CGGGCTGGAAAGAGGGTCTACTACCTCACCCGTGACCCTACAACCCCTCGGAGAGC
     GCCGGCGACCTTTCTCCAGATGATGAGTGGGCACTGGGATGTTGGGGGAGCGCTCTCG

----------Overlap with 26g----------
     AlaTrpGluThrAlaArgHisThrProValAsnSerTrpLeuGlyAsnIleIleMetPhe
 61  TGCGTGGGAGACAAGCAAGACACACTCCAGTGACACTCCTGGCTAGCAACATAATCATGTT
     ACGCACCCTCTGTCGTTCTGTGTGAGGTCAGTGTCAGTTAAGGACCGATCCGTTGTATTAGTACAA AlaProThrLeuTrpAlaArgMetIleLeuMetThrHisPhePheSerValLeuIleAla
121  TGCCCCCACACTGTGGGCGGAGGATGATACTGATGACCCATTTCTTTAGCGTCCTTATAGC
     ACGGGGGTGTGACACCCGCTCCTACTATGACTACTGGGTAAAGAAATCGCAGGAATATCG ArgAspGlnLeuGluGlnAlaLeuAspCysGluIleTyrGlyAlaCysTyrSerIleGlu
181  CAGGGACCAGCTTGAACAGGCCCTCGATTGCGAGATCTACGGGGCCTGCTACTCCATAGA
     GTCCCTGGTCGAACTTGTCCGGGAGCTAACGCTCTAGATGCCCCGGACGATGAGGTATCT ProLeuAspLeuProProIleIleGlnArgLeu
241  ACCACTTGATCTACCTCCAATCATTCAAAGACTC
     TGGTGAACTAGATGGAGGTTAGTAAGTTTCTGAG
```

FIG. 32A

```
      IlePheLysIleArgMetTyrValGlyGlyValGluHisArgLeuGluAlaAlaCysAsn
  1 CCATATTTAAAAATCAGGATGTACGTGGGAGGGGTCGAACACAGGCTGGAAGCTGCCTGCA
    GGTATAAATTTTAGTCCTACATGCACCCTCCCCAGCTTGTGTCCGACCTTCGACGGACGT

TrpThrArgGlyGluArgCysAspLeuGluAspArgAspArgSerGluLeuSerProLeu
 61 ACTGGACGCGGGGCGAACGTTGCGATCTGGAAGACAGGGACAGGTCCGAGCTCAGCCCGT
    TGACCTGCGCCCCGCTTGCAACGCTAGACCTTCTGTCCCTGTCCAGGCTCGAGTCGGGCA

LeuLeuThrThrThrGlnTrpGlnValLeuProCysSerPheThrThrLeuProAlaLeu
121 TACTGCTGACCACTACACAGTGGCAGGTCCTCCCGTGTTCCTTCACAACCCTACCAGCCT
    ATGACGACTGGTGATGTGTCACCGTCCAGGAGGGCACAAGGAAGTGTTGGGATGGTCGGA

SerThrGlyLeuIleHisLeuHisGlnAsnIleValAspValGlnTyrLeuTyrGlyVal
181 TGTCCACCGGCCTCATCCACCTCCACCAGAACATTGTGGACGTGCAGTACTTGTACGGGG
    ACAGGTGGCCGGAGTAGGTGGAGGTGGTCTTGTAACACCTGCACGTCATGAACATGCCCC

GlySerSerIleAlaSerTrpAlaIleLysTrpGluTyrValValLeuLeuPheLeuLeu
241 TGGGGTCAAGCATCGCGTCCTGGGCCATTAAGTGGGAGTACGTCGTTCTCCTGTTCCTTC
    ACCCCAGTTCGTAGCGCAGGACCCGGTAATTCACCCTCATGCAGCAAGAGGACAAGGAAG

LeuAlaAspAlaArgValCysSerCysLeuTrpMetMetLeuLeuIleSerGlnAlaGlu
301 TGCTTGCAGACGCGCGCGTCTGCTCCTGCTTGTGGATGATGCTACTCATATCCCAAGCGG
    ACGAACGTCTGCGCGCGCAGACGAGGACGAACACCTACTACGATGAGTATAGGGTTCGCC

AlaAlaLeuGluAsnLeuValIleLeuAsnAlaAlaSerLeuAlaGlyThrHisGlyLeu
361 AGGCGGCTTTGGAGAACCTCGTAATACTTAATGCAGCATCCCTGGCCGGGACGCACGGTC
    TCCGCCGAAACCTCTTGGAGCATTATGAATTACGTCGTAGGGACCGGCCCTGCGTGCCAG

ValSerPheLeuValPhePheCysPheAlaTrpTyrLeuLysGlyLysTrpValProGly
421 TTGTATCCTTCCTCGTGTTCTTCTGCTTTGCATGGTATTTGAAGGGTAAGTGGGTGCCCG
    AACATAGGAAGGAGCACAAGAAGACGAAACGTACCATAAACTTCCCATTCACCCACGGGC

AlaValTyrThrPheTyrGlyMetTrpProLeuLeuLeuLeuLeuLeuAlaLeuProGln
481 GAGCGGTCTACACCTTCTACGGGATGTGGCCTCTCCTCCTGCTCCTGTTGGCGTTGCCCC
    CTCGCCAGATGTGGAAGATGCCCTACACCGGAGAGGAGGACGAGGACAACCGCAACGGGG

ArgAlaTyrAlaLeuAspThrGluValAlaAlaSerCysGlyGlyValValLeuValGly
541 AGCGGGCGTACGCGCTGGACACGGAGGTGGCCGCGTCGTGTGGCGGTGTTGTTCTCGTCG
    TCGCCCGCATGCGCGACCTGTGCCTCCACCGGCGCAGCACACCGCCACAACAAGAGCAGC

LeuMetAlaLeuThrLeuSerProTyrTyrLysArgTyrIleSerTrpCysLeuTrpTrp
601 GGTTGATGGCGCTGACTCTGTCACCATATTACAAGCGCTATATCAGCTGGTGCTTGTGGT
    CCAACTACCGCGACTGAGACAGTGGTATAATGTTCGCGATATAGTCGACCACGAACACCA

LeuGlnTyrPheLeuThrArgValGluAlaGlnLeuHisValTrpIleProProLeuAsn
661 GGCTTCAGTATTTTCTGACCAGAGTGGAAGCGCAACTGCACGTGTGGATTCCCCCCCTCA
    CCGAAGTCATAAAAGACTGGTCTCACCTTCGCGTTGACGTGCACACCTAAGGGGGGAGT

ValArgGlyGlyArgAspAlaValIleLeuLeuMetCysAlaValHisProThrLeuVal
721 ACGTCCGAGGGGGGCGCGACGCCGTCATCTTACTCATGTGTGCTGTACACCCGACTCTGG
    TGCAGGCTCCCCCCGCGCTGCGGCAGTAGAATGAGTACACACGACATGTGGGCTGAGACC

PheAspIleThrLysLeuLeuLeuAlaValPheGlyProLeuTrpIleLeuGlnAlaSer
781 TATTTGACATCACCAAATTGCTGCTGGCCGTCTTCGGACCCCTTTGGATTCTTCAAGCCA
    ATAAACTGTAGTGGTTTAACGACGACCGGCAGAAGCCTGGGGAAACCTAAGAAGTTCGGT

LeuLeuLysValProTyrPheValArgValGlnGlyLeuLeuArgPheCysAlaLeuAla
841 GTTTGCTTAAAGTACCCTACTTTGTGCGCGTCCAAGGCCTTCTCCGGTTCTGCGCGTTAG
    CAAACGAATTTCATGGGATGAAACACGCGCAGGTTCCGGAAGAGGCCAAGACGCGCAATC
```

FIG. 32B

```
         ArgLysMetIleGlyGlyHisTyrValGlnMetValIleIleLysLeuGlyAlaLeuThr
 901 CGCGGAAGATGATCGGAGGCCATTACGTGCAAATGGTCATCATTAAGTTAGGGGCGCTTA
     GCGCCTTCTACTAGCCTCCGGTAATGCACGTTTACCAGTAGTAATTCAATCCCCGCGAAT

GlyThrTyrValTyrAsnHisLeuThrProLeuArgAspTrpAlaHisAsnGlyLeuArg
 961 CTGGCACCTATGTTTATAACCATCTCACTCCTCTTCGGGACTGGGCGCACAACGGCTTGC
     GACCGTGGATACAAATATTGGTAGAGTGAGGAGAAGCCCTGACCCGCGTGTTGCCGAACG

AspLeuAlaValAlaValGluProValValPheSerGlnMetGluThrLysLeuIleThr
1021 GAGATCTGGCCGTGGCTGTAGAGCCAGTCGTCTTCTCCCAAATGGAGACCAAGCTCATCA
     CTCTAGACCGGCACCGACATCTCGGTCAGCAGAAGAGGGTTTACCTCTGGTTCGAGTAGT

TrpGlyAlaAspThrAlaAlaCysGlyAspIleIleAsnGlyLeuProValSerAlaArg
1081 CGTGGGGGGCAGATACCGCCGCGTGCGGTGACATCATCAACGGCTTGCCTGTTTCCGCCC
     GCACCCCCCGTCTATGGCGGCGCACGCCACTGTAGTAGTTGCCGAACGGACAAAGGCGGG

ArgGlyArgGluIleLeuLeuGlyProAlaAspGlyMetValSerLysGlyTrpArgLeu
1141 GCAGGGGCCGGGAGATACTGCTCGGGCCAGCCGATGGAATGGTCTCCAAGGGGTGGAGGT
     CGTCCCCGGCCCTCTATGACGAGCCCGGTCGGCTACCTTACCAGAGGTTCCCCACCTCCA

LeuAlaProIleThrAlaTyrAlaGlnGlnThrArgGlyLeuLeuGlyCysIleIleThr
1201 TGCTGGCGCCCATCACGGCGTACGCCCAGCAGACAAGGGGCCTCCTAGGGTGCATAATCA
     ACGACCGCGGGTAGTGCCGCATGCGGGTCGTCTGTTCCCCGGAGGATCCCACGTATTAGT

SerLeuThrGlyArgAspLysAsnGlnValGluGlyGluValGlnIleValSerThrAla
1261 CCAGCCTAACTGGCCGGGACAAAAACCAAGTGGAGGGTGAGGTCCAGATTGTGTCAACTG
     GGTCGGATTGACCGGCCCTGTTTTTGGTTCACCTCCCACTCCAGGTCTAACACAGTTGAC

AlaGlnThrPheLeuAlaThrCysIleAsnGlyValCysTrpThrValTyrHisGlyAla
1321 CTGCCCAAACCTTCCTGGCAACGTGCATCAATGGGGTGTGCTGGACTGTCTACCACGGGG
     GACGGGTTTGGAAGGACCGTTGCACGTAGTTACCCCACACGACCTGACAGATGGTGCCCC

GlyThrArgThrIleAlaSerProLysGlyProValIleGlnMetTyrThrAsnValAsp
1381 CCGGAACGAGGACCATCGCGTCACCCAAGGGTCCTGTCATCCAGATGTATACCAATGTAG
     GGCCTTGCTCCTGGTAGCGCAGTGGGTTCCCAGGACAGTAGGTCTACATATGGTTACATC

GlnAspLeuValGlyTrpProAlaProGlnGlySerArgSerLeuThrProCyrThrCys
1441 ACCAAGACCTTGTGGGCTGGCCCGCTCCGCAAGGTAGCCGCTCATTGACACCCTGCACTT
     TGGTTCTGGAACACCCGACCGGGCGAGGCGTTCCATCGGCGAGTAACTGTGGGACGTGAA

GlySerSerAspLeuTyrLeuValThrArgHisAlaAspValIleProValArgArgArg
1501 GCGGCTCCTCGGACCTTTACCTGGTCACGAGGCACGCCGATGTCATTCCCGTGCGCCGGC
     CGCCGAGGAGCCTGGAAATGGACCAGTGCTCCGTGCGGCTACAGTAAGGGCACGCGGCCG

GlyAspSerArgGlySerLeuLeuSerProArgProIleSerTyrLeuLysGlySerSer
1561 GGGGTGATAGCAGGGGCAGCCTGCTGTCGCCCCGGCCCATTTCCTACTTGAAAGGCTCCT
     CCCCACTATCGTCCCCGTCGGACGACAGCTGGGCCGGGTAAAGGATGAACTTTCCGAGGA

GlyGlyProLeuLeuCysProAlaGlyHisAlaValGlyIlePheArgAlaAlaValCys
1621 CGGGGGGTCCGCTGTTGTGCCCCGCGGGGCACGCCGTGGGCATATTTAGGGCCGCGGTGT
     GCCCCCCAGGCGACAACACGGGGCGCCCCGTGCGGCACCCGTATAAATCCCGGCGCCACA

ThrArgGlyValAlaLysAlaValAspPheIleProValGluAsnLeuGluThrThrMet
1681 GCACCCGTGGAGTGGCTAAGGCGGTGGACTTTATCCCTGTGGAGAACCTAGAGACAACCA
     CGTGGGCACCTCACCGATTCCGCCACCTGAAATAGGGACACCTCTTGGATCTCTGTTGGT
```

FIG. 32C

```
          ArgSerProValPheThrAspAsnSerSerProProValValProGlnSerPheGlnVal
1741 TGAGGTCCCCGGTGTTCACGGATAACTCCTCTCCACCAGTAGTGCCCCAGAGCTTCCAGG
     ACTCCAGGGGCCACAAGTGCCTATTGAGGAGAGGTGGTCATCACGGGGTCTCGAAGGTCC

AlaHisLeuHisAlaProThrGlySerGlyLysSerThrLysValProAlaAlaTyrAla
1801 TGGCTCACCTCCATGCTCCCACAGGCAGCGGCAAAAGCACCAAGGTCCCGGCTGCATATG
     ACCGAGTGGAGGTACGAGGGTGTCCGTCGCCGTTTTCGTGGTTCCAGGGCCGACGTATAC

AlaGlnGlyTyrLysValLeuValLeuAsnProSerValAlaAlaThrLeuGlyPheGly
1861 CAGCTCAGGGCTATAAGGTGCTAGTACTCAACCCCTCTGTTGCTGCAACACTGGGCTTTG
     GTCGAGTCCCGATATTCCACGATCATGAGTTGGGGAGACAACGACGTTGTGACCCGAAAC

AlaTyrMetSerLysAlaHisGlyIleAspProAsnIleArgThrGlyValArgThrIle
1921 GTGCTTACATGTCCAAGGCTCATGGGATCGATCCTAACATCAGGACCGGGGTGAGAACAA
     CACGAATGTACAGGTTCCGAGTACCCTAGCTAGGATTGTAGTCCTGGCCCCACTCTTGTT

ThrThrGlySerProIleThrTyrSerThrTyrGlyLysPheLeuAlaAspGlyGlyCys
1981 TTACCACTGGCAGCCCCATCACGTACTCCACCTACGGCAAGTTCCTTGCCGACGGCGGGT
     AATGGTGACCGTCGGGGTAGTGCATGAGGTGGATGCCGTTCAAGGAACGGCTGCCGCCCA

SerGlyGlyAlaTyrAspIleIleIleCysAspGluCysHisSerThrAspAlaThrSer
2041 GCTCGGGGGGCGCTTATGACATAATAATTTGTGACGAGTGCCACTCCACGGATGCCACAT
     CGAGCCCCCCGCGAATACTGTATTATTAAACACTGCTCACGGTGAGGTGCCTACGGTGTA

IleLeuGlyIleGlyThrValLeuAspGlnAlaGluThrAlaGlyAlaArgLeuValVal
2101 CCATCTTGGGCATCGGCACTGTCCTTGACCAAGCAGAGACTGCGGGGGCGAGACTGGTTG
     GGTAGAACCCGTAGCCGTGACAGGAACTGGTTCGTCTCTGACGCCCCCGCTCTGACCAAC

LeuAlaThrAlaThrProProGlySerValThrValProHisProAsnIleGluGluVal
2161 TGCTCGCCACCGCCACCCCTCCGGGCTCCGTCACTGTGCCCCATCCCAACATCGAGGAGG
     ACGAGCGGTGGCGGTGGGGAGGCCCGAGGCAGTGACACGGGGTAGGGTTGTAGCTCCTCC

AlaLeuSerThrThrGlyGluIleProPheTyrGlyLysAlaIleProLeuGluValIle
2221 TTGCTCTGTCCACCACCGGAGAGATCCCTTTTTACGGCAAGGCTATCCCCCTCGAAGTAA
     AACGAGACAGGTGGTGGCCTCTCTAGGGAAAAATGCCGTTCCGATAGGGGGAGCTTCATT

LysGlyGlyArgHisLeuIlePheCysHisSerLysLysLysCysAspGluLeuAlaAla
2281 TCAAGGGGGGGAGACATCTCATCTTCTGTCATTCAAAGAAGAAGTGCGACGAACTCGCCG
     AGTTCCCCCCCTCTGTAGAGTAGAAGACAGTAAGTTTCTTCTTCACGCTGCTTGAGCGGC

LysLeuValAlaLeuGlyIleAsnAlaValAlaTyrTyrArgGlyLeuAspValSerVal
2341 CAAAGCTGGTCGCATTGGGCATCAATGCCGTGGCCTACTACCGCGGTCTTGACGTGTCCG
     GTTTCGACCAGCGTAACCCGTAGTTACGGCACCGGATGATGGCGCCAGAACTGCACAGGC

IleProThrSerGlyAspValValValValAlaThrAspAlaLeuMetThrGlyTyrThr
2401 TCATCCCGACCAGCGGCGATGTTGTCGTCGTGGCAACCGATGCCCTCATGACCGGCTATA
     AGTAGGGCTGGTCGCCGCTACAACAGCAGCACCGTTGGCTACGGGAGTACTGGCCGATAT

GlyAspPheAspSerValIleAspCysAsnThrCysValThrGlnThrValAspPheSer
2461 CCGGCGACTTCGACTCGGTGATAGACTGCAATACGTGTGTCACCCAGACAGTCGATTTCA
     GGCCGCTGAAGCTGAGCCACTATCTGACGTTATGCACACAGTGGGTCTGTCAGCTAAAGT

LeuAspProThrPheThrIleGluThrIleThrLeuProGlnAspAlaValSerArgThr
2521 GCCTTGACCCTACCTTCACCATTGAGACAATCACGCTCCCCCAGGATGCTGTCTCCCGCA
     CGGAACTGGGATGGAAGTGGTAACTCTGTTAGTGCGAGGGGGTCCTACGACAGAGGGCGT

GlnArgArgGlyArgThrGlyArgGlyLysProGlyIleTyrArgPheValAlaProGly
2581 CTCAACGTCGGGGCAGGACTGGCAGGGGAAGCCAGGCATCTACAGATTTGTGGCACCGG
     GAGTTGCAGCCCCGTCCTGACCGTCCCCCTTCGGTCCGTAGATGTCTAAACACCGTGGCC

GluArgProSerGlyMetPheAspSerSerValLeuCysGluCysTyrAspAlaGlyCys
2641 GGGAGCGCCCCTCCGGCATGTTCGACTCGTCCGTCCTCTGTGAGTGCTATGACGCAGGCT
     CCCTCGCGGGGAGGCCGTACAAGCTGAGCAGGCAGGAGACACTCACGATACTGCGTCCGA

AlaTrpTyrGluLeuThrProAlaGluThrThrValArgLeuArgAlaTyrMetAsnThr
2701 GTGCTTGGTATGAGCTCACGCCCGCCGAGACTACAGTTAGGCTACGAGCGTACATGAACA
     CACGAACCATACTCGAGTGCGGGCGGCTCTGATGTCAATCCGATGCTCGCATGTACTTGT
```

FIG. 32D

```
          ProGlyLeuProValCysGlnAspHisLeuGluPheTrpGluGlyValPheThrGlyLeu
2761 CCCCGGGGCTTCCCGTGTGCCAGGACCATCTTGAATTTTGGGAGGGCGTCTTTACAGGCC
     GGGGCCCCGAAGGGCACACGGTCCTGGTAGAACTTAAAACCCTCCCGCAGAAATGTCCGG

ThrHisIleAspAlaHisPheLeuSerGlnThrLysGlnSerGlyGluAsnLeuProTyr
2821 TCACTCATATAGATGCCCACTTTCTATCCCAGACAAAGCAGAGTGGGGAGAACCTTCCTT
     AGTGAGTATATCTACGGGTGAAAGATAGGGTCTGTTTCGTCTCACCCCTCTTGGAAGGAA

LeuValAlaTyrGlnAlaThrValCysAlaArgAlaGlnAlaProProProSerTrpAsp
2881 ACCTGGTAGCGTACCAAGCCACCGTGTGCGCTAGGGCTCAAGCCCCTCCCCCATCGTGGG
     TGGACCATCGCATGGTTCGGTGGCACACGCGATCCCGAGTTCGGGGAGGGGGTAGCACCC

GlnMetTrpLysCysLeuIleArgLeuLysProThrLeuHisGlyProThrProLeuLeu
2941 ACCAGATGTGGAAGTGTTTGATTCGCCTCAAGCCCACCCTCCATGGGCCAACACCCCTGC
     TGGTCTACACCTTCACAAACTAAGCGGAGTTCGGGTGGGAGGTACCCGGTTGTGGGGACG

TyrArgLeuGlyAlaValGlnAsnGluIleThrLeuThrHisProValThrLysTyrIle
3001 TATACAGACTGGGCGCTGTTCAGAATGAAATCACCCTGACGCACCCAGTCACCAAATACA
     ATATGTCTGACCCGCGACAAGTCTTACTTTAGTGGGACTGCGTGGGTCAGTGGTTTATGT

MetThrCysMetSerAlaAspLeuGluValValThrSerThrTrpValLeuValGlyGly
3061 TCATGACATGCATGTCGGCCGACCTGGAGGTCGTCACGAGCACCTGGGTGCTCGTTGGCG
     AGTACTGTACGTACAGCCGGCTGGACCTCCAGCAGTGCTCGTGGACCCACGAGCAACCGC

ValLeuAlaAlaLeuAlaAlaTyrCysLeuSerThrGlyCysValValIleValGlyArg
3121 GCGTCCTGGCTGCTTTGGCCGCGTATTGCCTGTCAACAGGCTGCGTGGTCATAGTGGGCA
     CGCAGGACCGACGAAACCGGCGCATAACGGACAGTTGTCCGACGCACCAGTATCACCCGT

ValValLeuSerGlyLysProAlaIleIleProAspArgGluValLeuTyrArgGluPhe
3181 GGGTCGTCTTGTCCGGGAAGCCGGCAATCATACCTGACAGGGAAGTCCTCTACCGAGAGT
     CCCAGCAGAACAGGCCCTTCGGCCGTTAGTATGGACTGTCCCTTCAGGAGATGGCTCTCA

AspGluMetGluGluCysSerGlnHisLeuProTyrIleGluGlnGlyMetMetLeuAla
3241 TCGATGAGATGGAAGAGTGCTCTCAGCACTTACCGTACATCGAGCAAGGGATGATGCTCG
     AGCTACTCTACCTTCTCACGAGAGTCGTGAATGGCATGTAGCTCGTTCCCTACTACGAGC

GluGlnPheLysGlnLysAlaLeuGlyLeuLeuGlnThrAlaSerArgGlnAlaGluVal
3301 CCGAGCAGTTCAAGCAGAAGGCCCTCGGCCTCCTGCAGACCGCGTCCCGTCAGGCAGAGG
     GGCTCGTCAAGTTCGTCTTCCGGGAGCCGGAGGACGTCTGGCGCAGGGCAGTCCGTCTCC

IleAlaProAlaValGlnThrAsnTrpGlnLysLeuGluThrPheTrpAlaLysHisMet
3361 TTATCGCCCCTGCTGTCCAGACCAACTGGCAAAAACTCGAGACCTTCTGGGCGAAGCATA
     AATAGCGGGGACGACAGGTCTGGTTGACCGTTTTTGAGCTCTGGAAGACCCGCTTCGTAT

TrpAsnPheIleSerGlyIleGlnTyrLeuAlaGlyLeuSerThrLeuProGlyAsnPro
3421 TGTGGAACTTCATCAGTGGGATACAATACTTGGCGGGCTTGTCAACGCTGCCTGGTAACC
     ACACCTTGAAGTAGTCACCCTATGTTATGAACCGCCCGAACAGTTGCGACGGACCATTGG

AlaIleAlaSerLeuMetAlaPheThrAlaAlaValThrSerProLeuThrThrSerGln
3481 CCGCCATTGCTTCATTGATGGCTTTTACAGCTGCTGTCACCAGCCCACTAACCACTAGCC
     GGCGGTAACGAAGTAACTACCGAAAATGTCGACGACAGTGGTCGGGTGATTGGTGATCGG

ThrLeuLeuPheAsnIleLeuGlyGlyTrpValAlaAlaGlnLeuAlaAlaProGlyAla
3541 AAACCCTCCTCTTCAACATATTGGGGGGTGGGTGGCTGCCCAGCTCGCCGCCCCCGGTG
     TTTGGGAGGAGAAGTTGTATAACCCCCCACCCACCGACGGGTCGAGCGGCGGGGGCCAC

AlaThrAlaPheValGlyAlaGlyLeuAlaGlyAlaAlaIleGlySerValGlyLeuGly
3601 CCGCTACTGCCTTTGTGGGCGCTGGCTTAGCTGGCGCCGCCATCGGCAGTGTTGGACTGG
     GGCGATGACGGAAACACCCGCGACCGAATCGACCGCGGCGGTAGCCGTCACAACCTGACC

LysValLeuIleAspIleLeuAlaGlyTyrGlyAlaGlyValAlaGlyAlaLeuValAla
3661 GGAAGGTCCTCATAGACATCCTTGCAGGGTATGGCGCGGGCGTGGCGGGAGCTCTTGTGG
     CCTTCCAGGAGTATCTGTAGGAACGTCCCATACCGCGCCCGCACCGCCCTCGAGAACACC

PheLysIleMetSerGlyGluValProSerThrGluAspLeuValAsnLeuLeuProAla
3721 CATTCAAGATCATGAGCGGTGAGGTCCCCTCCACGGAGGACCTGGTCAATCTACTGCCCG
     GTAAGTTCTAGTACTCGCCACTCCAGGGGAGGTGCCTCCTGGACCAGTTAGATGACGGGC
```

FIG. 32E

```
         IleLeuSerProGlyAlaLeuValValGlyValValCysAlaAlaIleLeuArgArgHis
3781 CCATCCTCTCGCCCGGAGCCCTCGTAGTCGGCGTGGTCTGTGCAGCAATACTGCGCCGGC
     GGTAGGAGAGCGGGCCTCGGGAGCATCAGCCGCACCAGACACGTCGTTATGACGCGGCCG

ValGlyProGlyGluGlyAlaValGlnTrpMetAsnArgLeuIleAlaPheAlaSerArg
3841 ACGTTGGCCCGGGCGAGGGGGCAGTGCAGTGGATGAACCGGCTGATAGCCTTCGCCTCCC
     TGCAACCGGGCCCGCTCCCCCGTCACGTCACCTACTTGGCCGACTATCGGAAGCGGAGGG

GlyAsnHisValSerProThrHisTyrValProGluSerAspAlaAlaAlaArgValThr
3901 GGGGGAACCATGTTTCCCCCACGCACTACGTGCCGGAGAGCGATGCAGCTGCCCGCGTCA
     CCCCCTTGGTACAAAGGGGGTGCGTGATGCACGGCCTCTCGCTACGTCGACGGGCGCAGT

AlaIleLeuSerSerLeuThrValThrGlnLeuLeuArgArgLeuHisGlnTrpIleSer
3961 CTGCCATACTCAGCAGCCTCACTGTAACCCAGCTCCTGAGGCGACTGCACCAGTGGATAA
     GACGGTATGAGTCGTCGGAGTGACATTGGGTCGAGGACTCCGCTGACGTGGTCACCTATT

SerGluCysThrThrProCysSerGlySerTrpLeuArgAspIleTrpAspTrpIleCys
4021 GCTCGGAGTGTACCACTCCATGCTCCGGTTCCTGGCTAAGGGACATCTGGGACTGGATAT
     CGAGCCTCACATGGTGAGGTACGAGGCCAAGGACCGATTCCCTGTAGACCCTGACCTATA

GluValLeuSerAspPheLysThrTrpLeuLysAlaLysLeuMetProGlnLeuProGly
4081 GCGAGGTGTTGAGCGACTTTAAGACCTGGCTAAAAGCTAAGCTCATGCCACAGCTGCCTG
     CGCTCCACAACTCGCTGAAATTCTGGACCGATTTTCGATTCGAGTACGGTGTCGACGGAC

IleProPheValSerCysGlnArgGlyTyrLysGlyValTrpArgValAspGlyIleMet
4141 GGATCCCCTTTGTGTCCTGCCAGCGCGGGTATAAGGGGGTCTGGCGAGTGGACGGCATCA
     CCTAGGGGAAACACAGGACGGTCGCGCCCATATTCCCCAGACCGCTCACCTGCCGTAGT

HisThrArgCysHisCysGlyAlaGluIleThrGlyHisValLysAsnGlyThrMetArg
4201 TGCACACTCGCTGCCACTGTGGAGCTGAGATCACTGGACATGTCAAAAACGGGACGATGA
     ACGTGTGAGCGACGGTGACACCTCGACTCTAGTGACCTGTACAGTTTTTGCCCTGCTACT

IleValGlyProArgThrCysArgAsnMetTrpSerGlyThrPheProIleAsnAlaTyr
4261 GGATCGTCGGTCCTAGGACCTGCAGGAACATGTGGAGTGGGACCTTCCCCATTAATGCCT
     CCTAGCAGCCAGGATCCTGGACGTCCTTGTACACCTCACCCTGGAAGGGGTAATTACGGA

ThrThrGlyProCysThrProLeuProAlaProAsnTyrThrPheAlaLeuTrpArgVal
4321 ACACCACGGGCCCCTGTACCCCCCTTCCTGCGCCGAACTACACGTTCGCGCTATGGAGGG
     TGTGGTGCCCGGGGACATGGGGGGAAGGACGCGGCTTGATGTGCAAGCGCGATACCTCCC

SerAlaGluGluTyrValGluIleArgGlnValGlyAspPheHisTyrValThrGlyMet
4381 TGTCTGCAGAGGAATATGTGGAGATAAGGCAGGTGGGGGACTTCCACTACGTGACGGGTA
     ACAGACGTCTCCTTATACACCTCTATTCCGTCCACCCCCTGAAGGTGATGCACTGCCCAT

ThrThrAspAsnLeuLysCysProCysGlnValProSerProGluPhePheThrGluLeu
4441 TGACTACTGACAATCTCAAATGCCCGTGCCAGGTCCCATCGCCCGAATTTTTCACAGAAT
     ACTGATGACTGTTAGAGTTTACGGGCACGGTCCAGGGTAGCGGGCTTAAAAAGTGTCTTA

AspGlyValArgLeuHisArgPheAlaProProCysLysProLeuLeuArgGluGluVal
4501 TGGACGGGGTGCGCCTACATAGGTTTGCGCCCCCTGCAAGCCCTTGCTGCGGGAGGAGG
     ACCTGCCCCACGCGGATGTATCCAAACGCGGGGGGACGTTCGGGAACGACGCCCTCCTCC

SerPheArgValGlyLeuHisGluTyrProValGlySerGlnLeuProCysGluProGlu
4561 TATCATTCAGAGTAGGACTCCACGAATACCCGGTAGGGTCGCAATTACCTTGCGAGCCCG
     ATAGTAAGTCTCATCCTGAGGTGCTTATGGGCCATCCCAGCGTTAATGGAACGCTCGGGC

ProAspValAlaValLeuThrSerMetLeuThrAspProSerHisIleThrAlaGluAla
4621 AACCGGACGTGGCCGTGTTGACGTCCATGCTCACTGATCCCTCCCATATAACAGCAGAGG
     TTGGCCTGCACCGGCACAACTGCAGGTACGAGTGACTAGGGAGGGTATATTGTCGTCTCC

AlaGlyArgArgLeuAlaArgGlySerProProSerValAlaSerSerSerAlaSerGln
4681 CGGCCGGGCGAAGGTTGGCGAGGGGATCACCCCCCTCTGTGGCCAGCTCCTCGGCTAGCC
     GCCGGCCCGCTTCCAACCGCTCCCCTAGTGGGGGGAGACACCGGTCGAGGAGCCGATCGG

LeuSerAlaProSerLeuLysAlaThrCysThrAlaAsnHisAspSerProAspAlaGlu
4741 AGCTATCCGCTCCATCTCTCAAGGCAACTTGCACCGCTAACCATGACTCCCCTGATGCTG
     TCGATAGGCGAGGTAGAGAGTTCCGTTGAACGTGGCGATTGGTACTGAGGGGACTACGAC
```

FIG. 32F

```
           LeuIleGluAlaAsnLeuLeuTrpArgGlnGluMetGlyGlyAsnIleThrArgValGlu
4801 AGCTCATAGAGGCCAACCTCCTATGGAGGCAGGAGATGGGCGGCAACATCACCAGGGTTG
     TCGAGTATCTCCGGTTGGAGGATACCTCCGTCCTCTACCCGCCGTTGTAGTGGTCCCAAC

SerGluAsnLysValValIleLeuAspSerPheAspProLeuValAlaGluGluAspGlu
4861 AGTCAGAAAACAAAGTGGTGATTCTGGACTCCTTCGATCCGCTTGTGGCGGAGGAGGACG
     TCAGTCTTTTGTTTCACCACTAAGACCTGAGGAAGCTAGGCGAACACCGCCTCCTCCTGC

ArgGluIleSerValProAlaGluIleLeuArgLysSerArgArgPheAlaGlnAlaLeu
4921 AGCGGGAGATCTCCGTACCCGCAGAAATCCTGCGGAAGTCTCGGAGATTCGCCCAGGCCC
     TCGCCCTCTAGAGGCATGGGCGTCTTTAGGACGCCTTCAGAGCCTCTAAGCGGGTCCGGG

ProValTrpAlaArgProAspTyrAsnProProLeuValGluThrTrpLysLysProAsp
4981 TGCCCGTTTGGGCGCGGCCGGACTATAACCCCCCGCTAGTGGAGACGTGGAAAAAGCCCG
     ACGGGCAAACCCGCGCCGGCCTGATATTGGGGGGCGATCACCTCTGCACCTTTTTCGGGC

TyrGluProProValValHisGlyCysProLeuProProProLysSerProProValPro
5041 ACTACGAACCACCTGTGGTCCATGGCTGTCCGCTTCCACCTCCAAAGTCCCCTCCTGTGC
     TGATGCTTGGTGGACACCAGGTACCGACAGGCGAAGGTGGAGGTTTCAGGGGAGGACACG

ProProArgLysLysArgThrValValLeuThrGluSerThrLeuSerThrAlaLeuAla
5101 CTCCGCCTCGGAAGAAGCGGACGGTGGTCCTCACTGAATCAACCCTATCTACTGCCTTGG
     GAGGCGGAGCCTTCTTCGCCTGCCACCAGGAGTGACTTAGTTGGGATAGATGACGGAACC

GluLeuAlaThrArgSerPheGlySerSerSerThrSerGlyIleThrGlyAspAsnThr
5161 CCGAGCTCGCCACCAGAAGCTTTGGCAGCTCCTCAACTTCCGGCATTACGGGCGACAATA
     GGCTCGAGCGGTGGTCTTCGAAACCGTCGAGGAGTTGAAGGCCGTAATGCCCGCTGTTAT

ThrThrSerSerGluProAlaProSerGlyCysProProAspSerAspAlaGluSerTyr
5221 CGACAACATCCTCTGAGCCCGCCCCTTCTGGCTGCCCCCCGACTCCGACGCTGAGTCCT
     GCTGTTGTAGGAGACTCGGGCGGGGAAGACCGACGGGGGGCTGAGGCTGCGACTCAGGA

SerSerMetProProLeuGluGlyGluProGlyAspProAspLeuSerAspGlySerTrp
5281 ATTCCTCCATGCCCCCCCTGGAGGGGGAGCCTGGGGATCCGGATCTTAGCGACGGGTCAT
     TAAGGAGGTACGGGGGGGACCTCCCCCTCGGACCCCTAGGCCTAGAATCGCTGCCCAGTA

SerThrValSerSerGluAlaAsnAlaGluAspValValCysCysSerMetSerTyrSer
5341 GGTCAACGGTCAGTAGTGAGGCCAACGCGGAGGATGTCGTGTGCTGCTCAATGTCTTACT
     CCAGTTGCCAGTCATCACTCCGGTTGCGCCTCCTACAGCACACGACGAGTTACAGAATGA

TrpThrGlyAlaLeuValThrProCysAlaAlaGluGluGlnLysLeuProIleAsnAla
5401 CTTGGACAGGCGCACTCGTCACCCCGTGCGCCGCGGAAGAACAGAAACTGCCCATCAATG
     GAACCTGTCCGCGTGAGCAGTGGGGCACGCGGCGCCTTCTTGTCTTTGACGGGTAGTTAC

LeuSerAsnSerLeuLeuArgHisHisAsnLeuValTyrSerThrThrSerArgSerAla
5461 CACTAAGCAACTCGTTGCTACGTCACCACAATTTGGTGTATTCCACCACCTCACGCAGTG
     GTGATTCGTTGAGCAACGATGCAGTGGTGTTAAACCACATAAGGTGGTGGAGTGCGTCAC

CysGlnArgGlnLysLysValThrPheAspArgLeuGlnValLeuAspSerHisTyrGln
5521 CTTGCCAAAGGCAGAAGAAAGTCACATTTGACAGACTGCAAGTTCTGGACAGCCATTACC
     GAACGGTTTCCGTCTTCTTTCAGTGTAAACTGTCTGACGTTCAAGACCTGTCGGTAATGG

AspValLeuLysGluValLysAlaAlaAlaSerLysValLysAlaAsnLeuLeuSerVal
5581 AGGACGTACTCAAGGAGGTTAAAGCAGCGGCGTCAAAAGTGAAGGCTAACTTGCTATCCG
     TCCTGCATGAGTTCCTCCAATTTCGTCGCCGCAGTTTTCACTTCCGATTGAACGATAGGC

GluGluAlaCysSerLeuThrProProHisSerAlaLysSerLysPheGlyTyrGlyAla
5641 TAGAGGAAGCTTGCAGCCTGACGCCCCCACACTCAGCCAAATCCAAGTTTGGTTATGGGG
     ATCTCCTTCGAACGTCGGACTGCGGGGGTGTGAGTCGGTTTAGGTTCAAACCAATACCCC

LysAspValArgCysHisAlaArgLysAlaValThrHisIleAsnSerValTrpLysAsp
5701 CAAAAGACGTCCGTTGCCATGCCAGAAAGGCCGTAACCCACATCAACTCCGTGTGGAAAG
     GTTTTCTGCAGGCAACGGTACGGTCTTTCCGGCATTGGGTGTAGTTGAGGCACACCTTTC

LeuLeuGluAspAsnValThrProIleAspThrThrIleMetAlaLysAsnGluValPhe
5761 ACCTTCTGGAAGACAATGTAACACCAATAGACACTACCATCATGGCTAAGAACGAGGTTT
     TGGAAGACCTTCTGTTACATTGTGGTTATCTGTGATGGTAGTACCGATTCTTGCTCCAAA
```

FIG. 32G

```
            CysValGlnProGluLysGlyGlyArgLysProAlaArgLeuIleValPheProAspLeu
5821 TCTGCGTTCAGCCTGAGAAGGGGGGTCGTAAGCCAGCTCGTCTCATCGTGTTCCCCGATC
     AGACGCAAGTCGGACTCTTCCCCCCAGCATTCGGTCGAGCAGAGTAGCACAAGGGGCTAG

GlyValArgValCysGluLysMetAlaLeuTyrAspValValThrLysLeuProLeuAla
5881 TGGGCGTGCGCGTGTGCGAAAAGATGGCTTTGTACGACGTGGTTACAAAGCTCCCCTTGG
     ACCCGCACGCGCACACGCTTTTCTACCGAAACATGCTGCACCAATGTTTCGAGGGGAACC

ValMetGlySerSerTyrGlyPheGlnTyrSerProGlyGlnArgValGluPheLeuVal
5941 CCGTGATGGGAAGCTCCTACGGATTCCAATACTCACCAGGACAGCGGGTTGAATTCCTCG
     GGCACTACCCTTCGAGGATGCCTAAGGTTATGAGTGGTCCTGTCGCCCAACTTAAGGAGC

GlnAlaTrpLysSerLysLysThrProMetGlyPheSerTyrAspThrArgCysPheAsp
6001 TGCAAGCGTGGAAGTCCAAGAAAACCCCAATGGGGTTCTCGTATGATACCCGCTGCTTTG
     ACGTTCGCACCTTCAGGTTCTTTTGGGGTTACCCCAAGAGCATACTATGGGCGACGAAAC

SerThrValThrGluSerAspIleArgThrGluGluAlaIleTyrGlnCysCysAspLeu
6061 ACTCCACAGTCACTGAGAGCGACATCCGTACGGAGGAGGCAATCTACCAATGTTGTGACC
     TGAGGTGTCAGTGACTCTCGCTGTAGGCATGCCTCCTCCGTTAGATGGTTACAACACTGG

AspProGlnAlaArgValAlaIleLysSerLueThrGluArgLeuTyrValGlyGlyPro
6121 TCGACCCCCAAGCCCGCGTGGCCATCAAGTCCCTCACCGAGAGGCTTTATGTTGGGGGCC
     AGCTGGGGGTTCGGGCGCACCGGTAGTTCAGGGAGTGGCTCTCCGAAATACAACCCCCGG

LeuThrAsnSerArgGlyGluAsnCysGlyTyrArgArgCysArgAlaSerGlyValLeu
6181 CTCTTACCAATTCAAGGGGGGAGAACTGCGGCTATCGCAGGTGCCGCGCGAGCGGCGTAC
     GAGAATGGTTAAGTTCCCCCCTCTTGACGCCGATAGCGTCCACGGCGCGCTCGCCGCATG

ThrThrSerCysGlyAsnThrLeuThrCysTyrIleLysAlaArgAlaAlaCysArgAla
6241 TGACAACTAGCTGTGGTAACACCCTCACTTGCTACATCAAGGCCCGGGCAGCCTGTCGAG
     ACTGTTGATCGACACCATTGTGGGAGTGAACGATGTAGTTCCGGGCCCGTCGGACAGCTC

AlaGlyLeuGlnAspCysThrMetLeuValCysGlyAspAspLeuValValIleCysGlu
6301 CCGCAGGGCTCCAGGACTGCACCATGCTCGTGTGTGGCGACGACTTAGTCGTTATCTGTG
     GGCGTCCCGAGGTCCTGACGTGGTACGAGCACACACCGCTGCTGAATCAGCAATAGACAC

SerAlaGlyValGlnGluAspAlaAlaSerLeuArgAlaPheThrGluAlaMetThrArg
6361 AAAGCGCGGGGGTCCAGGAGGACGCGGCGAGCCTGAGAGCCTTCACGGAGGCTATGACCA
     TTTCGCGCCCCCAGGTCCTCCTGCGCCGCTCGGACTCTCGGAAGTGCCTCCGATACTGGT

TyrSerAlaProProGlyAspProProGlnProGluTyrAspLeuGluLeuIleThrSer
6421 GGTACTCCGCCCCCCCTGGGGACCCCCCACAACCAGAATACGACTTGGAGCTCATAACAT
     CCATGAGGCGGGGGGGACCCCTGGGGGGTGTTGGTCTTATGCTGAACCTCGAGTATTGTA

CysSerSerAsnValSerValAlaHisAspGlyAlaGlyLysArgValTyrTyrLeuThr
6481 CATGCTCCTCCAACGTGTCAGTCGCCCACGACGGCGCTGGAAAGAGGGTCTACTACCTCA
     GTACGAGGAGGTTGCACAGTCAGCGGGTGCTGCCGCGACCTTTCTCCCAGATGATGGAGT

ArgAspProThrThrProLeuAlaArgAlaAlaTrpGluThrAlaArgHisThrProVal
6541 CCCGTGACCCTACAACCCCCCTCGCGAGAGCTGCGTGGGAGACAGCAAGACACACTCCAG
     GGGCACTGGGATGTTGGGGGGAGCGCTCTCGACGCACCCTCTGTCGTTCTGTGTGAGGTC

AsnSerTrpLeuGlyAsnIleIleMetPheAlaProThrLeuTrpAlaArgMetIleLeu
6601 TCAATTCCTGGCTAGGCAACATAATCATGTTTGCCCCCACACTGTGGGCGAGGATGATAC
     AGTTAAGGACCGATCCGTTGTATTAGTACAAACGGGGGTGTGACACCCGCTCCTACTATG

MetThrHisPhePheSerValLeuIleAlaArgAspGlnLeuGluGlnAlaLeuAspCys
6661 TGATGACCCATTTCTTTAGCGTCCTTATAGCCAGGGACCAGCTTGAACAGGCCCTCGATT
     ACTACTGGGTAAAGAAATCGCAGGAATATCGGTCCCTGGTCGAACTTGTCCGGGAGCTAA

GluIleTyrGlyAlaCysTyrSerIleGluProLeuAspLeuProProIleIleGlnArg
6721 GCGAGATCTACGGGGCCTGCTACTCCATAGAACCACTTGATCTACCTCCAATCATTCAAA
     CGCTCTAGATGCCCCGGACGATGAGGTATCTTGGTGAACTAGATGGAGGTTAGTAAGTTT

Leu
6781 GACTC
     CTGAG
```

FIG. 33

| Lane Number | Chimp Reference Number | Infection Type | Sample date (days) (0=inoculation day) | ALT (alanine) aminotransferase level in sera)mµ/ml) |
|---|---|---|---|---|
| 1 | 1 | NANB | 0 | 0 |
| 2 | 1 | NANB | 76 | 71 |
| 3 | 1 | NANB | 118 | 19 |
| 4 | 1 | NANB | 154 | N/A |
| 5 | 2 | NANB | 0 | 0 |
| 6 | 2 | NANB | 21 | 52 |
| 7 | 2 | NANB | 73 | 13 |
| 8 | 2 | NANB | 138 | N/A |
| 9 | 3 | NANB | 0 | 8 |
| 10 | 3 | NANB | 43 | 205 |
| 11 | 3 | NANB | 53 | 14 |
| 12 | 3 | NANB | 159 | 6 |
| 13 | 4 | NANB | -3 | 11 |
| 14 | 4 | NANB | 55 | 132 |
| 15 | 4 | NANB | 83 | N/A |
| 16 | 4 | NANB | 140 | N/A |
| 17 | 5 | HAV | 0 | 4 |
| 18 | 5 | HAV | 25 | 147 |
| 19 | 5 | HAV | 40 | 18 |
| 20 | 5 | HAV | 268 | 5 |
| 21 | 6 | HAV | -8 | N/A |
| 22 | 6 | HAV | 15 | 100 |
| 23 | 6 | HAV | 41 | 10 |
| 24 | 6 | HAV | 129 | N/A |
| 26 | 7 | HAV | 0 | 7 |
| 27 | 7 | HAV | 22 | 83 |
| 28 | 7 | HAV | 115 | 5 |
| 29 | 7 | HAV | 139 | N/A |
| 30 | 8 | HAV | 0 | 15 |
| 31 | 8 | HAV | 26 | 130 |
| 32 | 8 | HAV | 74 | 8 |
| 33 | 8 | HAV | 205 | 5 |
| 34 | 9 | HBV | -290 | N/A |
| 35 | 9 | HBV | 379 | 9 |
| 36 | 9 | HBV | 435 | 6 |
| 37 | 10 | HBV | 0 | 8 |
| 38 | 10 | HBV | 111-118 (pool) | 96-156 (pool) |
| 39 | 10 | HBV | 205 | 9 |
| 40 | 10 | HBV | 240 | 13 |
| 41 | 11 | HBV | 0 | 11 |
| 42 | 11 | HBV | 28-56 (pool) | 8-100 (pool) |
| 43 | 11 | HBV | 169 | 9 |
| 44 | 11 | HBV | 223 | 10 |

FIG. 34

| Lane Number | Patient Reference Number | Diagnosis | ALT Level (mμ/ml) |
|---|---|---|---|
| 1 | 1[1] | NANB | 1354 |
| 2 | 1[1] | NANB | 31 |
| 3 | 2[1] | NANB | 14 |
| 4 | 2[1] | NANB | 79 |
| 5 | 2[1] | NANB | 26 |
| 6 | 3[1] | NANB | 78 |
| 7 | 3[1] | NANB | 87 |
| 8 | 3[1] | NANB | 25 |
| 9 | 4[1] | NANB | 60 |
| 10 | 4[1] | NANB | 13 |
| 11 | 5[1] | NANB | 298 |
| 12 | 5[1] | NANB | 101 |
| 13 | 6[1] | NANB | 474 |
| 14 | 6[1] | NANB | 318 |
| 15 | 7[1] | NANB | 20 |
| 16 | 7[1] | NANB | 163 |
| 17 | 8[1] | NANB | 44 |
| 18 | 8[1] | NANB | 50 |
| 19 | 9 | NANB | N/A |
| 20 | 10 | NANB | N/A |
| 21 | 11 | NANB | N/A |
| 22 | 12 | Normal | N/A |
| 23 | 13 | Normal | N/A |
| 24 | 14 | Normal | N/A |
| 26 | 30174 | Normal | N/A |
| 27 | 30105 | Normal | N/A |
| 28 | 30072 | Normal | N/A |
| 29 | 30026 | Normal | N/A |
| 30 | 30146 | Normal | N/A |
| 31 | 30250 | Normal | N/A |
| 32 | 30071 | Normal | N/A |
| 33 | 15 | AcuteHAV | N/A |
| 34 | 16 | AcuteHAV | N/A |
| 35 | 17 | AcuteHAV | N/A |
| 36 | 18 | AcuteHAV | N/A |
| 37 | 48088 | AcuteHAV | N/A |
| 38 | 47288 | AcuteHAV | N/A |
| 39 | 47050 | AcuteHAV | N/A |
| 40 | 46997 | AcuteHAV | N/A |
| 41 | 19 | Convalescent HBV | N/A |
| 42 | 20 | (anti-HBSag+ve; | N/A |
| 43 | 21 | anti-HBCag+ve) | N/A |
| 44 | 22 | (anti-HBSag+ve; | N/A |
| 45 | 23 | anti-HBCag+ve) | N/A |
| 46 | 24 | (anti-HBSag+ve; | N/A |
| 47 | 25 | anti-HBCag+ve) | N/A |
| 48 | 26 | (anti-HBSag+ve; | N/A |
| 49 | 27 | anti-HBSag+ve) | N/A |

[1] Sequential serum samples were assayed from these patients

FIG. 36A

```
          --------SOD-----------COOH][--adaptor----][NANBHpolypeptide>
          AlaCysGlyValIleGlyIleAlaGlnAsnLeuGlyIleArgAspAlaHisPheLeuSer
      1   GCTTGTGGTGTAATTGGGATCGCCCAGAATTTGGGAATTCGGGATGCCCACTTTCTATCC
          CGAACACCACATTAACCCTAGCGGGTCTTAAACCCTTAAGCCCTACGGGTGAAAGATAGG >>>>>>>>>>>>>>>>>>>>>
          GlnThrLysGlnSerGlyGluAsnLeuProTyrLeuValAlaTyrGlnAlaThrValCys
     61   CAGACAAAGCAGAGTGGGGAGAACCTTCCTTACCTGGTAGCGTACCAAGCCACCGTGTGC
          GTCTGTTTCGTCTCACCCCTCTTGGAAGGAATGGACCATCGCATGGTTCGGTGGCACACG AlaArgAlaGlnAlaProProProSerTrpAspGlnMetTrpLysCysLeuIleArgLeu
    121   GCTAGGGCTCAAGCCCCTCCCCCATCGTGGGACCAGATGTGGAAGTGTTTGATTCGCCTC
          CGATCCCGAGTTCGGGGAGGGGGTAGCACCCTGGTCTACACCTTCACAAACTAAGCGGAG LysProThrLeuHisGlyProThrProLeuLeuTyrArgLeuGlyAlaValGlnAsnGlu
    181   AAGCCCACCCTCCATGGGCCAACACCCCTGCTATACAGACTGGGCGCTGTTCAGAATGAA
          TTCGGGTGGGAGGTACCCGGTTGTGGGGACGATATGTCTGACCCGCGACAAGTCTTACTT IleThrLeuThrHisProValThrLysTyrIleMetThrCysMetSerAlaAspLeuGlu
    241   ATCACCCTGACGCACCCAGTCACCAAATACATCATGACATGCATGTCGGCCGACCTGGAG
          TAGTGGGACTGCGTGGGTCAGTGGTTTATGTAGTACTGTACGTACAGCCGGCTGGACCTC ValValThrSerThrTrpValLeuValGlyGlyValLeuAlaAlaLeuAlaAlaTyrCys
    301   GTCGTCACGAGCACCTGGGTGCTCGTTGGCGGCGTCCTGGCTGCTTTGGCCGCGTATTGC
          CAGCAGTGCTCGTGGACCCACGAGCAACCGCCGCAGGACCGACGAAACCGGCGCATAACG LeuSerThrGlyCysValValIleValGlyArgValValLeuSerGlyLysProAlaIle
    361   CTGTCAACAGGCTGCGTGGTCATAGTGGGCAGGGTCGTCTTGTCCGGGAAGCCGGCAATC
          GACAGTTGTCCGACGCACCAGTATCACCCGTCCCAGCAGAACAGGCCCTTCGGCCGTTAG IleProAspArgGluValLeuTyrArgGluPheAspGluMetGluGluCysSerGlnHis
    421   ATACCTGACAGGGAAGTCCTCTACCGAGAGTTCGATGAGATGGAAGAGTGCTCTCAGCAC
          TATGGACTGTCCCTTCAGGAGATGGCTCTCAAGCTACTCTACCTTCTCACGAGAGTCGTG LeuProTyrIleGluGlnGlyMetMetLeuAlaGluGlnPheLysGlnLysAlaLeuGly
    481   TTACCGTACATCGAGCAAGGGATGATGCTCGCCGAGCAGTTCAAGCAGAAGGCCCTCGGC
          AATGGCATGTAGCTCGTTCCCTACTACGAGCGGCTCGTCAAGTTCGTCTTCCGGGAGCCG LeuLeuGlnThrAlaSerArgGlnAlaGluValIleAlaProAlaValGlnThrAsnTrp
    541   CTCCTGCAGACCGCGTCCCGTCAGGCAGAGGTTATCGCCCCTGCTGTCCAGACCAACTGG
          GAGGACGTCTGGCGCAGGGCAGTCCGTCTCCAATAGCGGGGACGACAGGTCTGGTTGACC GlnLysLeuGluThrPheTrpAlaLysHisMetTrpAsnPheIleSerGlyIleGlnTyr
    601   CAAAAACTCGAGACCTTCTGGGCGAAGCATATGTGGAACTTCATCAGTGGGATACAATAC
          GTTTTTGAGCTCTGGAAGACCCGCTTCGTATACACCTTGAAGTAGTCACCCTATGTTATG LeuAlaGlyLeuSerThrLeuProGlyAsnProAlaIleAlaSerLeuMetAlaPheThr
    661   TTGGCGGGCTTGTCAACGCTGCCTGGTAACCCCGCCATTGCTTCATTGATGGCTTTTACA
          AACCGCCCGAACAGTTGCGACGGACCATTGGGGCGGTAACGAAGTAACTACCGAAAATGT AlaAlaValThrSerProLeuThrThrSerGlnThrLeuLeuPheAsnIleLeuGlyGly
    721   GCTGCTGTCACCAGCCCACTAACCACTAGCCAAACCCTCCTCTTCAACATATTGGGGGGG
          CGACGACAGTGGTCGGGTGATTGGTGATCGGTTTGGGAGGAGAAGTTGTATAACCCCCCC TrpValAlaAlaGlnLeuAlaAlaProGlyAlaAlaThrAlaPheValGlyAlaGlyLeu
    781   TGGGTGGCTGCCCAGCTCGCCGCCCCGGTGCCGCTACTGCCTTTGTGGGCGCTGGCTTA
          ACCCACCGACGGGTCGAGCGGCGGGGGCCACGGCGATGACGGAAACACCCGCGACCGAAT
```

FIG. 36B

```
         AlaGlyAlaAlaIleGlySerValGlyLeuGlyLysValLeuIleAspIleLeuAlaGly
 841 GCTGGCGCCGCCATCGGCAGTGTTGGACTGGGGAAGGTCCTCATAGACATCCTTGCAGGG
     CGACCGCGGCGGTAGCCGTCACAACCTGACCCCTTCCAGGAGTATCTGTAGGAACGTCCC

TyrGlyAlaGlyValAlaGlyAlaLeuValAlaPheLysIleMetSerGlyGluValPro
 901 TATGGCGCGGGCGTGGCGGGAGCTCTTGTGGCATTCAAGATCATGAGCGGTGAGGTCCCC
     ATACCGCGCCCGCACCGCCCTCGAGAACACCGTAAGTTCTAGTACTCGCCACTCCAGGGG

SerThrGluAspLeuValAsnLeuLeuProAlaIleLeuSerProGlyAlaLeuValVal
 961 TCCACGGAGGACCTGGTCAATCTACTGCCCGCCATCCTCTCGCCCGGAGCCCTCGTAGTC
     AGGTGCCTCCTGGACCAGTTAGATGACGGGCGGTAGGAGAGCGGGCCTCGGGAGCATCAG

GlyValValCysAlaAlaIleLeuArgArgHisValGlyProGlyGluGlyAlaValGln
1021 GGCGTGGTCTGTGCAGCAATACTGCGCCGGCACGTTGGCCCGGGCGAGGGGCAGTGCAG
     CCGCACCAGACACGTCGTTATGACGCGGCCGTGCAACCGGGCCCGCTCCCCCGTCACGTC

<<<<<<<<<<<<<<<<<<<NANBH][---extra
         TrpMetAsnArgLeuIleAlaPheAlaSerArgGlyAsnHisValSerProValHisHis
1081 TGGATGAACCGGCTGATAGCCTTCGCCTCCCGGGGGAACCATGTTTCCCCAGTCCATCAT
     ACCTACTTGGCCGACTATCGGAAGCGGAGGGCCCCCTTGGTACAAAGGGGTCAGGTAGTA -----]
     LysArgOP
1141 AAGCGTTGACGCTCCCTACGGGTGGACTGTGGAGAGACAGGGCACTGCTAAGGCCCAAAT
     TTCGCAACTGCGAGGGATGCCCACCTGACACCTCTCTGTCCCGTGACGATTCCGGGTTTA 1201 CTCAGCCATGCATCGAGGGGTACAATCCGTATGGCCAACAACTAGCGCGTACGTAAAGTC
     GAGTCGGTACGTAGCTCCCCATGTTAGGCATACCGGTTGTTGATCGCGCATGCATTTCAG 1261 TCCTTTCTCGATGGTCCATACCTTAGATGCGTTAGCATTAATCCGAATTC
     AGGAAAGAGCTACCAGGTATGGAATCTACGCAATCGTAATTAGGCTTAAG
```

FIG. 42A

```
              10        20        30        40        50
HCV       EYVVLLFLLLADARVCSCLWMMLLISQAEAALENLVILNAASLAGTHGLVSFLVFFCFA
MNWVD1    AVSFVTLITGNMSFRDLGRVMVMVGATMTDDIGMGVTYLALLAAFKVRPTFAAGLLLRKL
              130       140       150       160       170       180

60        70        80        90        100       110
HCV       WYLKGKWVPGAVYTFYGMWPLLLLLLLALPQRAYALDTEVAASCGGVVLVGLMALTLSPYY
MNWVD1    TSKELMMTTIGIVLLSQSTIPETILELTDALALGMMVLKMVRKMEKYQLAVTIMAILCVP
              190       200       210       220       230       240

120       130       140       150       160       170
HCV       KRYISWCLWWLQYFLTRVEAQLHVWIPPLNVRGGRDAVILLMCAVHPTLVFDITKLLLAV
MNWVD1    NAVILQNAWKVSCTILAVVSVSPLFLTSSQQKADWIPLALTIKGLNPTAIF-LTTLSRTN
              250       260       270       280       290

180       190       200       210       220       230
HCV       FGPLWILQASLLKVPYF-VRVQGLLRF-CALARKMIGGHYVQMVIIKLGALTGTYVYNHL
MNWVD1    KKRSWPLNEAIMAVGMVSILASSLLKNDIPMTGPLVAGGLLTVCYV-LTGRSADLELERA
              300       310       320       330       340       350

240       250       260       270       280       290
HCV       TPLRDWAHNGLRDLAVAVEPVVFSQMETKLITWGADTAACGDIINGLPVSARRGREILLG
MNWVD1    ADVK-WEDQAEISGSSPILSITISE-DGSMSIKNEEEEQTLTILIRTGLLVISG---LFP
              360       370       380       390       400       410

300       310       320       330       340       350
HCV       PADGMVSKGWRLLAPITAYAQQTRGLLGCIITSLTGRDKNQVEGEVQIVSTAAQTFLATC
MNWVD1    VSIPITAAAWYLWEVKKQRAGVLWDVPSPPPVGKAELEDGAYRIKQKGILGYSQIGAGVY
              420       430       440       450       460       470

360       370       380       390       400       410
HCV       INGVCWTVYHGAGTRTIASPKGPVIQMYTNVDQDLV----GWPAPQGSRSLTPCTGSSD
MNWVD1    KEGTFHTMWHVTRGAVLMHKGKRIEPSWADVKKDLVSCGGGWKLEGEWKEGEEVQVLALE
              480       490       500       510       520       530

420       430       440       450       460       470
HCV       LYLVTRHADVIPVRRRGDSRGSLLSPRPISYLKGSSGGPLLCPAGHAVGIFRAAVCTRGV
MNWVD1    PGKNPRAVQTKPGLFKTN--AGTIGAVSLDFSPGTSGSPIIDKKGKVVGLYGNGVVTRSG
              540       550       560       570       580       590
```

FIG. 42B

```
              480       490       500       510       520       530
HCV      AKAVDFIPVENLETTMRSPVFTDNSSPPVVPQSFQVAHLHAPTGSGKS--TKVPAAYAAQ
          : :: :  : :    : :: : : :: :     : :: :  ::    :  ::
MNWVD1   AYVSAIAQTEK--SIEDNPEIEDDIFRK---RKLTIMDLHPGAGKTKRYLPAIVRGAIKR
              600       610       620       630       640

540       550       560       570       580
HCV      GYKVLVLNPS--VAATLGFGAYMSKAHGIDPNIRTGVRTITTGSPITYSTYGKFLADGGC
          : :: :  :   :::  :  :   : ::  ::  :  ::: ::::   ::    :
MNWVD1   GLRTLILAPTRVVAAEMEEALRGLPIRYQTPAIRAEHTGREIVDLMCHATFTMRLL-SPV
              650       660       670       680       690       700

590       600       610       620       630       640
HCV      SGGAYDIIICDECHSTDATSILGIGTVLDQAETAGARLVVLATATPPGSVTVPHPNIEEV
                 X                                              _ v.
          : :  : :: :: : : ::  :  :: : :  :  :  ::: ::::: ::  :::
MNWVD1   RVPNYNLIIMDEAHFTDPASIAARGYISTRVE-MGEAAGIFMTATPPGSRD-PFPQSNAP
              710       720       730       740       750       760

650       660       670       680       690       700
HCV      ALSTTGEIPFYGKAIPLEVIKGGRHLIFCHSKKKCDELAAKLVALGINAVAYYRGLDVSV
          : :  : :
MNWVD1   IMDEEREIPERSWSSGHEWVTDFKGKTVWFVPSIKAGNDTAACLRKNGKKVTQLSRKTFD
              770       780       790       800       810       820

710       720       730       740       750       760
HCV      IPTSGDVVVVATDALMTGYTGDFDSVIDCNTCVTQTVDFSLDPTFTIETITLPQDAVSRT

MNWVD1   SEYVKTRTNDWNFVVTTDISEMGANFKAERVIDPRRCMKPVILTDGEERVILAGPMPVTH
              830       840       850       860       870       880

770       780       790       800       810       820
HCV      QRRGRTGRGKPGIYRFVAPGERPSGMFDSSVLCECYDAGCAWYELTPAETTVRLRAYMNT

MNWVD1   SS
```

FIG. 45

| Name | Common Sequence | Variable Sequence |
|---|---|---|
| 5'-3-1 | AAGCTTGATCGAATTC | CGATCTTGC |
| -2 | | CGATCCTGC |
| -3 | | CGATCATGC |
| -4 | | CGATCGTGC |
| -5 | | CGAAGTTGC |
| -6 | | CGAAGCTGC |
| -7 | | AGATCTTGC |
| -8 | | AGATCCTGC |
| -9 | | AGATCATGC |
| -10 | | AGATCGTGC |
| -11 | | AGAAGTTGC |
| -12 | | AGAAGCTGC |
| -13 | | CGATCTTGT |
| -14 | | CGATCCTGT |
| -15 | | CGATCATGT |
| -16 | | CGATCGTGT |
| -17 | | CGAAGTTGT |
| -18 | | CGAAGCTGT |
| -19 | | AGATCTTGT |
| -20 | | AGATCCTGT |
| -21 | | AGATCATGT |
| -22 | | AGATCGTGT |
| -23 | | AGAAGTTGT |
| -24 | | AGAAGCTGT |
| -25 | | CGCTCTTGC |
| -26 | | CGCTCCTGC |
| -27 | | CGCTCATGC |
| -28 | | CGCTCGTGC |
| -29 | | CGCAGTTGC |
| -30 | | CGCAGCTGC |
| -31 | | CGCTCTTGT |
| -32 | | CGCTCCTGT |
| -33 | | CGCTCATGT |
| -34 | | CGCTCGTGT |
| -35 | | CGCAGTTGT |
| -36 | | CGCAGCTGT |

FIG. 46A

```
      GlyCysProGluArgLeuAlaSerCysArgProLeuThrAspPheAspGlnGlyTrpGly
  1   CAGGCTGTCCTGAGAGGCTAGCCAGCTGCCGGACCCCTTACCGATTTGACCAGGGCTGGG
      GTCCGACAGGACTCTCCGATCGGTCGACGGCTGGGGAATGGCTAAAACTGGTCCCGACCC

ProIleSerTyrAlaAsnGlySerGlyProAspGlnArgProTyrCysTrpHisTyrPro
 61   GCCCTATATCAGTTATGCCAACGGAAGCGGCCCCAGCGCCCCTACTGCTGGCACTACC
      CGGGATAGTCAATACGGTTGCCTTCGCCGGGGTCGCGGGGATGACGACCGTGATGG

ProLysProCysGlyIleValProAlaLysSerValCysGlyProValTyrCysPheThr
121   CCCAAAACCTTGCGGTATTGTGCCCGCGAAGAGTGTGTGTCCGGTATATTGCTTCA
      GGGGTTTTGAACGCCATAACACGGGCGCTTCTCACACAACAGGCCATATAACGAAGT

ProSerProValValGlyThrThrAspArgSerGlyAlaProThrTyrSerTrpGly
181   CTCCCAGCCCGTGGTGGGAACCGACAGGTCGGGGCGCCCACCTACAGCTGGG
      GAGGGTCGGGGCACCACCCTTGCTGTCCAGCCCGCGGGTGACGATGTCGACCC

GluAsnAspThrAspValPheValLeuAsnAsnThrArgProProLeuGlyAsnTrpPhe
241   GTGAAAATGATACGGACGTCTTCGTCCTTAACAATACCAGGCCACCGCTGGGCAATTGGT
      CACTTTTACTATGCCTGCAGAAGCAGGAATTGTTATGGTCCGGTGGCGACCCGTTAACCA

GlyCysThrTrpMetAsnSerThrGlyPheThrLysValCysGlyAlaProProCysVal
301   TCGGTTGTACCTGGATGAACTCAACTGATTCACCAAAGTGCGAGCCTCCTTGTG
      AGCCAACATGGACCTACTTGAGTTGACCTAAGTGGTTTCACACGCCTCGCGGAGGAACAC
```

FIG. 46B

```
    IleGlyGlyAlaGlyAsnThrLeuHisCysProThrAspCysPheArgLysHisPro
361 TCATCGGAGGGGCAACAACACCCTGCACTGCCCCACTGATTGCTTCCGCAAGCATC
    AGTAGCCTCCCCGCCGTTGTTGTGGGACGTGACGGGGACTAACGAAGGCGTTCGTAG

AspAlaThrTyrSerArgCysGlySerGlyProTrpIleThrProArgCysLeuValAsp
421 CGGAGCGCCACATACTCTCGGTGCGGCTCCGGTCCCTGGATCACACCCAGGTGCCTGGTCG
    GCCTCGCGGTGTATGAGAGCCACGCCGAGGGCCAGGACCTAGTGTGGGTCCACGGACCAGC

TyrProTyrArgLeuTrpHisTyrProCysThrIleAsnTyrThrIlePheLysIleArg
481 ACTACCCGTATAGGCTTTGGCATTATCCTTGTACCATCAACTACACTATATTTAAAATCA
    TGATGGGCATATCCGAAACCGTAATAGGAACATGGTAGTTGATGTGATATAAATTTTAGT

MetTyrValGlyGlyValGluHisArgLeuGluAlaAlaCysAsnTrpThrArgGlyGlu
541 GGATGTACGTGGGAGGGGTCGAGCAGGCTGGAAGCCTGCAACTGGACGCGGGGGCG
    CCTACACATGCACCCTCCCCAGCTCGTCCGACCTTCGACGTTGACCTGCGCCCCGC

ArgCysAspLeuGluAspArgArgSerGluLeuSerProLeuLeuThrThrThr
601 AACGTTGCGATCTGGAAGATAGGGACAGGTCCGAGCTCAGCCCGTTACTGCTGACCACTA
    TTGCAACGCTAGACCTTCTATCCCTGTCCAGGCTCGAGTCGGGCAATGACGACTGGTGAT

GlnTrpGlnValLeuProCysSerPheThrThrLeuProAlaLeuSerThrGlyLeuIle
661 CACAGTGGCAGGTCCTCCCGTGTCCTTCACAACCTGCCAGCCTTGTCCACCGGCCTCA
    GTGTCACCGTCCAGGAGGGCACAAGGAAGTGTTGGACGTCGGAACAGGTGCCGGAGT
```

FIG. 46C

```
-----Overlap with Combined ORF of DNAs 12f through 15e-----
       HisLeuHisGlnAsnIleValAspValGlnTyrLeuTyrGlyValGlySerIleAla
721 TCCACCTCCACCAGAACATTGTGGACGTGCAGTACTTGTACGGGGTGGGGTCAAGCATCG
      AGGTGGAGGTGGTCTTGTAACACCTGCACGTCATGAACATGCCCCACCCCAGTTCGTAGC SerTrpAlaIleLysTrpGluTyrValValLeuPheLeuLeuLeuAlaAspAlaArg
781 CGTCCTGGGCCATTAAGTGGGAGTACGTCGTCCTCTTCCTTCTGCTTGCAGACGCGC
      GCAGGACCCGGTAATTCACCCTCATGCAGCAGGAGGACGAAGGAAGACGAACGTCTGCGCG ValCysSerCysLeuTrpMetMetLeuLeuIleSerGlnAlaGluAlaAlaLeuGluAsn
841 GCGTCTGCTCCTGCTGTGTGGATGATGCTACTCATATCCCAAGCGGAAGCGGCTTTGAGA
      CGCAGACGAGGACGAACACCTACTACGATGAGTATAGGGTTCGCCTTCGCGAAACCTCT LeuValIleLeuAsnAlaAlaSerLeuLeuAlaGlyThrHisGlyLeuValSerPheLeuVal
901 ACCTCGTAATACTTAATGCAGCATCCCTGGCGGACCGCACGGTCTTGTATCCTTCCTCG
      TGGAGCATTATGAATTACGTCGTAGGGACCGCCTGGCGTGCCAGAACATAGGAAGGAGC PhePheCysPheAlaTrpTyrLeuLysGlyLysTrpValProGlyAlaValTyrThrPhe
961 TGTTCTTCTGCTTTGCATGGTATCTGAAGGGTAAGTGGGTGCCCGGAGCGGTCTACACCT
      ACAAGAAGACGAAACGTACCATAGACTTCCCATTCACCCACGGGCCTCGCCAGATGTGGA
```

FIG. 46D

```
     TyrGlyMetTrpProLeuLeuLeuLeuAlaLeuLeuProGlnArgAlaTyrAlaLeu
1021 TCTACGGGATGTGGCCCTTCCTCCTCCTGTGCCGTTGGCTGCCCCAGCGGGCGTACGCGC
     AGATGCCCTACACCGGAGAGGAGGACACGGCAACCGACAACCGGGGTCGCCCGCATGCGCG

AspThrGluValAlaAlaSerCysGlyGlyValValLeuValValGlyLeuMetAlaLeuThr
1081 TGGACACGGAGGTGGCCGCGTCGTGTGGCGGTGTTGTTCTCGTCGGGTTGATGGCGCTAA
     ACCTGTGCCTCCACCGGCGCAGCGCAGCACACCGCCACAACAAGAGCAGCCCAACTACCGATT

LeuSerProTyrTyrTyrLysArgTyrIleSerTrpCysLeuTrpTrpLeuGlnTyrPheLeu
1141 CTCTGTCCACCATATTACAAGCGCTATATCAGCTGGTGCTTGTGGCTTCAGTATTTC
     GAGACAGGTGGTATAATGTTCGCGATATAGTCGACCACGAACACCACCGAAGTCATAAAAG

ThrArgValGluAlaGlnLeuHisValTrpIleProProLeuAsnValArgGlyGlyArg
1201 TGACCAGAGTGGAAGCGCAACTGCACGTGTGGATTCCCCCTCAACGTCCGAGGGGGGC
     ACTGGTCTCACCTTCGCGTTGACGTGCACACCTAAGGGGGAGTTGCAGGCTCCCCCG

AspAlaValIleLeuLeuMetCysAlaValHisProThrLeuValPheAspIleThrLys
1261 GCGAGCGTCATCTTACTATGTGCTGTGTACACCCGACTCTGGTATTGACATCACCA
     CGCTCGCAGTAGAATGAGTACACACGACACATGGGCTGAGACCATAAACTGTAGTGGT

LeuLeuLeuAlaValPheGlyProLeuTrpIleLeuGlnAla
1321 AATTGCTGCTGGCCGTCTTCGGACCCCTTTGGATTCTTCAAGCCAG
     TTAACGACGACCGGCAGAAGCCTGGGAAACCTAAGAAGTTCGGTC
```

FIG. 47A

```
           GlyCysProGluArgLeuAlaSerCysArgProLeuThrAspPheAspGlnGlyTrpGly
  1  CAGGCTGTCCTGAGAGGCTAGCCAGCTGCCGACCCCTTACCGATTTTGACCAGGGCTGGG
       GTCCGACAGGACTCTCCGATCGGTCGACGGCTGGGGAATGGCTAAAACTGGTCCCGACCC

ProIleSerTyrAlaAsnGlySerGlyProAspGlnArgProTyrCysTrpHisTyrPro
 61  GCCCTATCAGTTATGCCAACGGAAGCGGCCCCGACCAGCGCCCCTACTGCTGGCACTACC
       CGGGATAGTCAATACGGTTGCCTTCGCCGGGGCTGGTCGCGGGGATGACGACCGTGATGG

ProLysProCysGlyIleValProAlaLysSerValCysGlyProValTyrCysPheThr
121  CCCCAAAACCTTGCGGTATTGTGCCCGCGAAGAGTGTGTGTGGTCCGGTATATTGCTTCA
       GGGGTTTTGGAACGCCATAACACGGGCGCTTCTCACACACACCAGGCCATATAACGAAGT

ProSerProValValValGlyThrThrAspArgSerGlyAlaProThrTyrSerTrpGly
181  CTCCCAGCCCGTGGTGGTGGGAACGACCGACAGGTCGGGCGCGCCCACCTACAGCTGGG
       GAGGGTCGGGGCACCACCACCCTTGCTGGCTGTCCAGCCCGCGCGGGTGGATGTCGACCC

GluAsnAspThrAspValPheValLeuAsnAsnThrArgProProLeuGlyAsnTrpPhe
241  GTGAAAATGATACGGACGTCTTCGTCCTTAACAATACCAGGCCACCGCTGGGCAATTGGT
       CACTTTTACTATGCCTGCAGAAGCAGGAATTGTTATGGTCCGGTGGCGACCCGTTAACCA

GlyCysThrTrpMetAsnSerThrGlyPheThrLysValCysGlyAlaProProCysVal
301  TCGGTTGTACCTGGATGAACTCAACTGGATTCACCAAAGTGTGCGGAGCGCCTCCTTGTG
       AGCCAACATGGACCTACTTGAGTTGACCTAAGTGGTTTCACACGCCTCGCGGAGGAACAC

IleGlyGlyAlaGlyAsnAsnThrLeuHisCysProThrAspCysPheArgLysHisPro
361  TCATCGGAGGGGCGGGCAACAACACCCTGCACTGCCCCACTGATTGCTTCCGCAAGCATC
       AGTAGCCTCCCCGCCCGTTGTTGTGGGACGTGACGGGGTGACTAACGAAGGCGTTCGTAG

AspAlaThrTyrSerArgCysGlySerGlyProTrpIleThrProArgCysLeuValAsp
421  CGGACGCCACATACTCTCGGTGCGGCTCCGGTCCCTGGATCACACCCAGGTGCCTGGTCG
       GCCTGCGGTGTATGAGAGCCACGCCGAGGCCAGGGACCTAGTGTGGGTCCACGGACCAGC

TyrProTyrArgLeuTrpHisTyrProCysThrIleAsnTyrThrIlePheLysIleArg
481  ACTACCCGTATAGGCTTTGGCATTATCCTTGTACCATCAACTACACCATATTTAAAATCA
       TGATGGGCATATCCGAAACCGTAATAGGAACATGGTAGTTGATGTGGTATAAATTTTAGT

MetTyrValGlyGlyValGluHisArgLeuGluAlaAlaCysAsnTrpThrArgGlyGlu
541  GGATGTACGTGGGAGGGGTCGAACACAGGCTGGAAGCTGCCTGCAACTGGACGCGGGGCG
       CCTACATGCACCCTCCCCAGCTTGTGTCCGACCTTCGACGGACGTTGACCTGCGCCCCGC

ArgCysAspLeuGluAspArgAspArgSerGluLeuSerProLeuLeuLeuThrThrThr
601  AACGTTGCGATCTGGAAGACAGGGACAGGTCCGAGCTCAGCCCGTTACTGCTGACCACTA
       TTGCAACGCTAGACCTTCTGTCCCTGTCCAGGCTCGAGTCGGGCAATGACGACTGGTGAT

GlnTrpGlnValLeuProCysSerPheThrThrLeuProAlaLeuSerThrGlyLeuIle
661  CACAGTGGCAGGTCCTCCCGTGTTCCTTCACAACCCTACCAGCCTTGTCCACCGGCCTCA
       GTGTCACCGTCCAGGAGGGCACAAGGAAGTGTTGGGATGGTCGGAACAGGTGGCCGGAGT

HisLeuHisGlnAsnIleValAspValGlnTyrLeuTyrGlyValGlySerSerIleAla
721  TCCACCTCCACCAGAACATTGTGGACGTGCAGTACTTGTACGGGGTGGGGTCAAGCATCG
       AGGTGGAGGTGGTCTTGTAACACCTGCACGTCATGAACATGCCCCACCCCAGTTCGTAGC

SerTrpAlaIleLysTrpGluTyrValValLeuLeuPheLeuLeuLeuAlaAspAlaArg
781  CGTCCTGGGCCATTAAGTGGGAGTACGTCGTTCTCCTGTTCCTTCTGCTTGCAGACGCGC
       GCAGGACCCGGTAATTCACCCTCATGCAGCAAGAGGACAAGGAAGACGAACGTCTGCGCG

ValCysSerCysLeuTrpMetMetLeuLeuIleSerGlnAlaGluAlaAlaLeuGluAsn
841  GCGTCTGCTCCTGCTTGTGGATGATGCTACTCATATCCCAAGCGGAGGCGGCTTTGGAGA
       CGCAGACGAGGACGAACACCTACTACGATGAGTATAGGGTTCGCCTCCGCCGAAACCTCT

LeuValIleLeuAsnAlaAlaSerLeuAlaGlyThrHisGlyLeuValSerPheLeuVal
901  ACCTCGTAATACTTAATGCAGCATCCCTGGCCGGGACGCACGGTCTTGTATCCTTCCTCG
       TGGAGCATTATGAATTACGTCGTAGGGACCGGCCCTGCGTGCCAGAACATAGGAAGGAGC
```

FIG. 47B

```
          PhePheCysPheAlaTrpTyrLeuLysGlyLysTrpValProGlyAlaValTyrThrPhe
 961 TGTTCTTCTGCTTTGCATGGTATTTGAAGGGTAAGTGGGTGCCCGGAGCGGTCTACACCT
     ACAAGAAGACGAAACGTACCATAAACTTCCCATTCACCCACGGGCCTCGCCAGATGTGGA

TyrGlyMetTrpProLeuLeuLeuLeuLeuAlaLeuProGlnArgAlaTyrAlaLeu
1021 TCTACGGGATGTGGCCTCTCCTCCTGCTCCTGTTGGCGTTGCCCCAGCGGGCGTACGCGC
     AGATGCCCTACACCGGAGAGGAGGACGAGGACAACCGCAACGGGGTCGCCCGCATGCGCG

AspThrGluValAlaAlaSerCysGlyGlyValValLeuValGlyLeuMetAlaLeuThr
1081 TGGACACGGAGGTGGCCGCGTCGTGTGGCGGTGTTGTTCTCGTCGGGTTGATGGCGCTGA
     ACCTGTGCCTCCACCGGCGCAGCACACCGCCACAACAAGAGCAGCCCAACTACCGCGACT

LeuSerProTyrTyrLysArgTyrIleSerTrpCysLeuTrpTrpLeuGlnTyrPheLeu
1141 CTCTGTCACCATATTACAAGCGCTATATCAGCTGGTGCTTGTGGTGGCTTCAGTATTTTC
     GAGACAGTGGTATAATGTTCGCGATATAGTCGACCACGAACACCACCGAAGTCATAAAAG

ThrArgValGluAlaGlnLeuHisValTrpIleProProLeuAsnValArgGlyGlyArg
1201 TGACCAGAGTGGAAGCGCAACTGCACGTGTGGATTCCCCCCCTCAACGTCCGAGGGGGGC
     ACTGGTCTCACCTTCGCGTTGACGTGCACACCTAAGGGGGGGAGTTGCAGGCTCCCCCCG

AspAlaValIleLeuLeuMetCysAlaValHisProThrLeuValPheAspIleThrLys
1261 GCGACGCCGTCATCTTACTCATGTGTGCTGTACACCCGACTCTGGTATTTGACATCACCA
     CGCTGCGGCAGTAGAATGAGTACACACGACATGTGGGCTGAGACCATAAACTGTAGTGGT

LeuLeuLeuAlaValPheGlyProLeuTrpIleLeuGlnAlaSerLeuLeuLysValPro
1321 AATTGCTGCTGGCCGTCTTCGGACCCCTTTGGATTCTTCAAGCCAGTTTGCTTAAAGTAC
     TTAACGACGACCGGCAGAAGCCTGGGGAAACCTAAGAAGTTCGGTCAAACGAATTTCATG

TyrPheValArgValGlnGlyLeuLeuArgPheCysAlaLeuAlaArgLysMetIleGly
1381 CCTACTTTGTGCGCGTCCAAGGCCTTCTCCGGTTCTGCGCGTTAGCGCGGAAGATGATCG
     GGATGAAACACGCGCAGGTTCCGGAAGAGGCCAAGACGCGCAATCGCGCCTTCTACTAGC

GlyHisTyrValGlnMetValIleIleLysLeuGlyAlaLeuThrGlyThrTyrValTyr
1441 GAGGCCATTACGTGCAAATGGTCATCATTAAGTTAGGGGCGCTTACTGGCACCTATGTTT
     CTCCGGTAATGCACGTTTACCAGTAGTAATTCAATCCCCGCGAATGACCGTGGATACAAA

AsnHisLeuThrProLeuArgAspTrpAlaHisAsnGlyLeuArgAspLeuAlaValAla
1501 ATAACCATCTCACTCCTCTTCGGGACTGGGCGCACAACGGCTTGCGAGATCTGGCCGTGG
     TATTGGTAGAGTGAGGAGAAGCCCTGACCCGCGTGTTGCCGAACGCTCTAGACCGGCACC

ValGluProValValPheSerGlnMetGluThrLysLeuIleThrTrpGlyAlaAspThr
1561 CTGTAGAGCCAGTCGTCTTCTCCCAAATGGAGACCAAGCTCATCACGTGGGGGGCAGATA
     GACATCTCGGTCAGCAGAAGAGGGTTTACCTCTGGTTCGAGTAGTGCACCCCCCGTCTAT

AlaAlaCysGlyAspIleIleAsnGlyLeuProValSerAlaArgArgGlyArgGluIle
1621 CCGCCGCGTGCGGTGACATCATCAACGGCTTGCCTGTTTCCGCCCGCAGGGGCCGGGAGA
     GGCGGCGCACGCCACTGTAGTAGTTGCCGAACGGACAAAGGCGGGCGTCCCCGGCCCTCT

LeuLeuGlyProAlaAspGlyMetValSerLysGlyTrpArgLeuLeuAlaProIleThr
1681 TACTGCTCGGGCCAGCCGATGGAATGGTCTCCAAGGGGTGGAGGTTGCTGGCGCCCATCA
     ATGACGAGCCCGGTCGGCTACCTTACCAGAGGTTCCCCACCTCCAACGACCGCGGGTAGT

AlaTyrAlaGlnGlnThrArgGlyLeuLeuGlyCysIleIleThrSerLeuThrGlyArg
1741 CGGCGTACGCCCAGCAGACAAGGGGCCTCCTAGGGTGCATAATCACCAGCCTAACTGGCC
     GCCGCATGCGGGTCGTCTGTTCCCCGGAGGATCCCACGTATTAGTGGTCGGATTGACCGG

AspLysAsnGlnValGluGlyGluValGlnIleValSerThrAlaAlaGlnThrPheLeu
1801 GGGACAAAAACCAAGTGGAGGGTGAGGTCCAGATTGTGTCAACTGCTGCCCAAACCTTCC
     CCCTGTTTTTGGTTCACCTCCCACTCCAGGTCTAACACAGTTGACGACGGGTTTGGAAGG

AlaThrCysIleAsnGlyValCysTrpThrValTyrHisGlyAlaGlyThrArgThrIle
1861 TGGCAACGTGCATCAATGGGGTGTGCTGGACTGTCTACCACGGGGCCGGAACGAGGACCA
     ACCGTTGCACGTAGTTACCCCACACGACCTGACAGATGGTGCCCCGGCCTTGCTCCTGGT

AlaSerProLysGlyProValIleGlnMetTyrThrAsnValAspGlnAspLeuValGly
1921 TCGCGTCACCCAAGGGTCCTGTCATCCAGATGTATACCAATGTAGACCAAGACCTTGTGG
     AGCGCAGTGGGTTCCCAGGACAGTAGGTCTACATATGGTTACATCTGGTTCTGGAACACC
```

FIG. 47C

```
              TrpProAlaProGlnGlySerArgSerLeuThrProCysThrCysGlySerSerAspLeu
1981 GCTGGCCCGCTCCGCAAGGTAGCCGCTCATTGACACCCTGCACTTGCGGCTCCTCGGACC
     CGACCGGGCGAGGCGTTCCATCGGCGAGTAACTGTGGGACGTGAACGCCGAGGAGCCTGG

TyrLeuValThrArgHisAlaAspValIleProValArgArgArgGlyAspSerArgGly
2041 TTTACCTGGTCACGAGGCACGCCGATGTCATTCCCGTGCGCCGGCGGGGTGATAGCAGGG
     AAATGGACCAGTGCTCCGTGCGGCTACAGTAAGGGCACGCGGCCGCCCCACTATCGTCCC

SerLeuLeuSerProArgProIleSerTyrLeuLysGlySerSerGlyGlyProLeuLeu
2101 GCAGCCTGCTGTCGCCCCGGCCCATTTCCTACTTGAAAGGCTCCTCGGGGGGTCCGCTGT
     CGTCGGACGACAGCGGGGCCGGGTAAAGGATGAACTTTCCGAGGAGCCCCCCAGGCGACA

CysProAlaGlyHisAlaValGlyIlePheArgAlaAlaValCysThrArgGlyValAla
2161 TGTGCCCCGCGGGGCACGCCGTGGGCATATTTAGGGCCGCGGTGTGCACCCGTGGAGTGG
     ACACGGGGCGCCCCGTGCGGCACCCGTATAAATCCCGGCGCCACACGTGGGCACCTCACC

LysAlaValAspPheIleProValGluAsnLeuGluThrThrMetArgSerProValPhe
2221 CTAAGGCGGTGGACTTTATCCCTGTGGAGAACCTAGAGACAACCATGAGGTCCCCGGTGT
     GATTCCGCCACCTGAAATAGGGACACCTCTTGGATCTCTGTTGGTACTCCAGGGGCCACA

ThrAspAsnSerSerProProValValProGlnSerPheGlnValAlaHisLeuHisAla
2281 TCACGGATAACTCCTCTCCACCAGTAGTGCCCCAGAGCTTCCAGGTGGCTCACCTCCATG
     AGTGCCTATTGAGGAGAGGTGGTCATCACGGGGTCTCGAAGGTCCACCGAGTGGAGGTAC

ProThrGlySerGlyLysSerThrLysValProAlaAlaTyrAlaAlaGlnGlyTyrLys
2341 CTCCCACAGGCAGCGGCAAAAGCACCAAGGTCCCGGCTGCATATGCAGCTCAGGGCTATA
     GAGGGTGTCCGTCGCCGTTTTCGTGGTTCCAGGGCCGACGTATACGTCGAGTCCCGATAT

ValLeuValLeuAsnProSerValAlaAlaThrLeuGlyPheGlyAlaTyrMetSerLys
2401 AGGTGCTAGTACTCAACCCCTCTGTTGCTGCAACACTGGGCTTTGGTGCTTACATGTCCA
     TCCACGATCATGAGTTGGGGAGACAACGACGTTGTGACCCGAAACCACGAATGTACAGGT

AlaHisGlyIleAspProAsnIleArgThrGlyValArgThrIleThrThrGlySerPro
2461 AGGCTCATGGGATCGATCCTAACATCAGGACCGGGGTGAGAACAATTACCACTGGCAGCC
     TCCGAGTACCCTAGCTAGGATTGTAGTCCTGGCCCCACTCTTGTTAATGGTGACCGTCGG

IleThrTyrSerThrTyrGlyLysPheLeuAlaAspGlyGlyCysSerGlyGlyAlaTyr
2521 CCATCACGTACTCCACCTACGGCAAGTTCCTTGCCGACGGCGGGTGCTCGGGGGGCGCTT
     GGTAGTGCATGAGGTGGATGCCGTTCAAGGAACGGCTGCCGCCCACGAGCCCCCCGCGAA

AspIleIleIleCysAspGluCysHisSerThrAspAlaThrSerIleLeuGlyIleGly
2581 ATGACATAATAATTTGTGACGAGTGCCACTCCACGGATGCCACATCCATCTTGGGCATCG
     TACTGTATTATTAAACACTGCTCACGGTGAGGTGCCTACGGTGTAGGTAGAACCCGTAGC

ThrValLeuAspGlnAlaGluThrAlaGlyAlaArgLeuValValLeuAlaThrAlaThr
2641 GCACTGTCCTTGACCAAGCAGAGACTGCGGGGGCGAGACTGGTTGTGCTCGCCACCGCCA
     CGTGACAGGAACTGGTTCGTCTCTGACGCCCCCGCTCTGACCAACACGAGCGGTGGCGGT

ProProGlySerValThrValProHisProAsnIleGluGluValAlaLeuSerThrThr
2701 CCCCTCCGGGCTCCGTCACTGTGCCCCATCCCAACATCGAGGAGGTTGCTCTGTCCACCA
     GGGGAGGCCCGAGGCAGTGACACGGGGTAGGGTTGTAGCTCCTCCAACGAGACAGGTGGT

GlyGluIleProPheTyrGlyLysAlaIleProLeuGluValIleLysGlyGlyArgHis
2761 CCGGAGAGATCCCTTTTTACGGCAAGGCTATCCCCCTCGAAGTAATCAAGGGGGGAGAC
     GGCCTCTCTAGGGAAAAATGCCGTTCCGATAGGGGGAGCTTCATTAGTTCCCCCCCTCTG

LeuIlePheCysHisSerLysLysLysCysAspGluLeuAlaAlaLysLeuValAlaLeu
2821 ATCTCATCTTCTGTCATTCAAAGAAGAAGTGCGACGAACTCGCCGCAAAGCTGGTCGCAT
     TAGAGTAGAAGACAGTAAGTTTCTTCTTCACGCTGCTTGAGCGGCGTTTCGACCAGCGTA

GlyIleAsnAlaValAlaTyrTyrArgGlyLeuAspValSerValIleProThrSerGly
2881 TGGGCATCAATGCCGTGGCCTACTACCGCGGTCTTGACGTGTCCGTCATCCCGACCAGCG
     ACCCGTAGTTACGGCACCGGATGATGGCGCCAGAACTGCACAGGCAGTAGGGCTGGTCGC

AspValValValValAlaThrAspAlaLeuMetThrGlyTyrThrGlyAspPheAspSer
2941 GCGATGTTGTCGTCGTGGCAACCGATGCCCTCATGACCGGCTATACCGGCGACTTCGACT
     CGCTACAACAGCAGCACCGTTGGCTACGGGAGTACTGGCCGATATGGCCGCTGAAGCTGA
```

FIG. 47D

```
              ValIleAspCysAsnThrCysValThrGlnThrValAspPheSerLeuAspProThrPhe
3001 CGGTGATAGACTGCAATACGTGTGTCACCCAGACAGTCGATTTCAGCCTTGACCCTACCT
     GCCACTATCTGACGTTATGCACACAGTGGGTCTGTCAGCTAAAGTCGGAACTGGGATGGA

ThrIleGluThrIleThrLeuProGlnAspAlaValSerArgThrGlnArgArgGlyArg
3061 TCACCATTGAGACAATCACGCTCCCCCAGGATGCTGTCTCCCGCACTCAACGTCGGGGCA
     AGTGGTAACTCTGTTAGTGCGAGGGGGTCCTACGACAGAGGGCGTGAGTTGCAGCCCCGT

ThrGlyArgGlyLysProGlyIleTyrArgPheValAlaProGlyGluArgProSerGly
3121 GGACTGGCAGGGGGAAGCCAGGCATCTACAGATTTGTGGCACCGGGGGAGCGCCCCTCCG
     CCTGACCGTCCCCCTTCGGTCCGTAGATGTCTAAACACCGTGGCCCCCTCGCGGGGAGGC

MetPheAspSerSerValLeuCysGluCysTyrAspAlaGlyCysAlaTrpTyrGluLeu
3181 GCATGTTCGACTCGTCCGTCCTCTGTGAGTGCTATGACGCAGGCTGTGCTTGGTATGAGC
     CGTACAAGCTGAGCAGGCAGGAGACACTCACGATACTGCGTCCGACACGAACCATACTCG

ThrProAlaGluThrThrValArgLeuArgAlaTyrMetAsnThrProGlyLeuProVal
3241 TCACGCCCGCCGAGACTACAGTTAGGCTACGAGCGTACATGAACACCCCGGGGCTTCCCG
     AGTGCGGGCGGCTCTGATGTCAATCCGATGCTCGCATGTACTTGTGGGGCCCCGAAGGGC

CysGlnAspHisLeuGluPheTrpGluGlyValPheThrGlyLeuThrHisIleAspAla
3301 TGTGCCAGGACCATCTTGAATTTTGGGAGGGCGTCTTTACAGGCCTCACTCATATAGATG
     ACACGGTCCTGGTAGAACTTAAAACCCTCCCGCAGAAATGTCCGGAGTGAGTATATCTAC

HisPheLeuSerGlnThrLysGlnSerGlyGluAsnLeuProTyrLeuValAlaTyrGln
3361 CCCACTTTCTATCCCAGACAAAGCAGAGTGGGGAGAACCTTCCTTACCTGGTAGCGTACC
     GGGTGAAAGATAGGGTCTGTTTCGTCTCACCCCTCTTGGAAGGAATGGACCATCGCATGG

AlaThrValCysAlaArgAlaGlnAlaProProProSerTrpAspGlnMetTrpLysCys
3421 AAGCCACCGTGTGCGCTAGGGCTCAAGCCCCTCCCCCATCGTGGGACCAGATGTGGAAGT
     TTCGGTGGCACACGCGATCCCGAGTTCGGGGAGGGGGTAGCACCCTGGTCTACACCTTCA

LeuIleArgLeuLysProThrLeuHisGlyProThrProLeuLeuTyrArgLeuGlyAla
3481 GTTTGATTCGCCTCAAGCCCACCCTCCATGGGCCAACACCCCTGCTATACAGACTGGGCG
     CAAACTAAGCGGAGTTCGGGTGGGAGGTACCCGGTTGTGGGGACGATATGTCTGACCCGC

ValGlnAsnGluIleThrLeuThrHisProValThrLysTyrIleMetThrCysMetSer
3541 CTGTTCAGAATGAAATCACCCTGACGCACCCAGTCACCAAATACATCATGACATGCATGT
     GACAAGTCTTACTTTAGTGGGACTGCGTGGGTCAGTGGTTTATGTAGTACTGTACGTACA

AlaAspLeuGluValValThrSerThrTrpValLeuValGlyGlyValLeuAlaAlaLeu
3601 CGGCCGACCTGGAGGTCGTCACGAGCACCTGGGTGCTCGTTGGCGGCGTCCTGGCTGCTT
     GCCGGCTGGACCTCCAGCAGTGCTCGTGGACCCACGAGCAACCGCCGCAGGACCGACGAA

AlaAlaTyrCysLeuSerThrGlyCysValValIleValGlyArgValValLeuSerGly
3661 TGGCCGCGTATTGCCTGTCAACAGGCTGCGTGGTCATAGTGGGCAGGGTCGTCTTGTCCG
     ACCGGCGCATAACGGACAGTTGTCCGACGCACCAGTATCACCCGTCCCAGCAGAACAGGC

LysProAlaIleIleProAspArgGluValLeuTyrArgGluPheAspGluMetGluGlu
3721 GGAAGCCGGCAATCATACCTGACAGGGAAGTCCTCTACCGAGAGTTCGATGAGATGGAAG
     CCTTCGGCCGTTAGTATGGACTGTCCCTTCAGGAGATGGCTCTCAAGCTACTCTACCTTC

CysSerGlnHisLeuProTyrIleGluGlnGlyMetMetLeuAlaGluGlnPheLysGln
3781 AGTGCTCTCAGCACTTACCGTACATCGAGCAAGGGATGATGCTCGCCGAGCAGTTCAAGC
     TCACGAGAGTCGTGAATGGCATGTAGCTCGTTCCCTACTACGAGCGGCTCGTCAAGTTCG

LysAlaLeuGlyLeuLeuGlnThrAlaSerArgGlnAlaGluValIleAlaProAlaVal
3841 AGAAGGCCCTCGGCCTCCTGCAGACCGCGTCCCGTCAGGCAGAGGTTATCGCCCCTGCTG
     TCTTCCGGGAGCCGGAGGACGTCTGGCGCAGGGCAGTCCGTCTCCAATAGCGGGGACGAC

GlnThrAsnTrpGlnLysLeuGluThrPheTrpAlaLysHisMetTrpAsnPheIleSer
3901 TCCAGACCAACTGGCAAAAACTCGAGACCTTCTGGGCGAAGCATATGTGGAACTTCATCA
     AGGTCTGGTTGACCGTTTTTGAGCTCTGGAAGACCCGCTTCGTATACACCTTGAAGTAGT

GlyIleGlnTyrLeuAlaGlyLeuSerThrLeuProGlyAsnProAlaIleAlaSerLeu
3961 GTGGGATACAATACTTGGCGGGCTTGTCAACGCTGCCTGGTAACCCCGCCATTGCTTCAT
     CACCCTATGTTATGAACCGCCCGAACAGTTGCGACGGACCATTGGGGCGGTAACGAAGTA
```

FIG. 47E

```
          MetAlaPheThrAlaAlaValThrSerProLeuThrThrSerGlnThrLeuLeuPheAsn
4021 TGATGGCTTTTACAGCTGCTGTCACCAGCCCACTAACCACTAGCCAAACCCTCCTCTTCA
     ACTACCGAAAATGTCGACGACAGTGGTCGGGTGATTGGTGATCGGTTTGGGAGGAGAAGT

IleLeuGlyGlyTrpValAlaAlaGlnLeuAlaAlaProGlyAlaAlaThrAlaPheVal
4081 ACATATTGGGGGGGTGGGTGGCTGCCCAGCTCGCCGCCCCGGTGCCGCTACTGCCTTTG
     TGTATAACCCCCCCACCCACCGACGGGTCGAGCGGCGGGGGCCACGGCGATGACGGAAAC

GlyAlaGlyLeuAlaGlyAlaAlaIleGlySerValGlyLeuGlyLysValLeuIleAsp
4141 TGGGCGCTGGCTTAGCTGGCGCCGCCATCGGCAGTGTTGGACTGGGGAAGGTCCTCATAG
     ACCCGCGACCGAATCGACCGCGGCGGTAGCCGTCACAACCTGACCCCTTCCAGGAGTATC

IleLeuAlaGlyTyrGlyAlaGlyValAlaGlyAlaLeuValAlaPheLysIleMetSer
4201 ACATCCTTGCAGGGTATGGCGCGGGCGTGGCGGGAGCTCTTGTGGCATTCAAGATCATGA
     TGTAGGAACGTCCCATACCGCGCCCGCACCGCCCTCGAGAACACCGTAAGTTCTAGTACT

GlyGluValProSerThrGluAspLeuValAsnLeuLeuProAlaIleLeuSerProGly
4261 GCGGTGAGGTCCCCTCCACGGAGGACCTGGTCAATCTACTGCCCGCCATCCTCTCGCCCG
     CGCCACTCCAGGGGAGGTGCCTCCTGGACCAGTTAGATGACGGGCGGTAGGAGAGCGGGC

AlaLeuValValGlyValValCysAlaAlaIleLeuArgArgHisValGlyProGlyGlu
4321 GAGCCCTCGTAGTCGGCGTGGTCTGTGCAGCAATACTGCGCCGGCACGTTGGCCCGGGCG
     CTCGGGAGCATCAGCCGCACCAGACACGTCGTTATGACGCGGCCGTGCAACCGGGCCCGC

GlyAlaValGlnTrpMetAsnArgLeuIleAlaPheAlaSerArgGlyAsnHisValSer
4381 AGGGGGCAGTGCAGTGGATGAACCGGCTGATAGCCTTCGCCTCCCGGGGGAACCATGTTT
     TCCCCCGTCACGTCACCTACTTGGCCGACTATCGGAAGCGGAGGGCCCCCTTGGTACAAA

ProThrHisTyrValProGluSerAspAlaAlaAlaArgValThrAlaIleLeuSerSer
4441 CCCCCACGCACTACGTGCCGGAGAGCGATGCAGCTGCCCGCGTCACTGCCATACTCAGCA
     GGGGGTGCGTGATGCACGGCCTCTCGCTACGTCGACGGGCGCAGTGACGGTATGAGTCGT

LeuThrValThrGlnLeuLeuArgArgLeuHisGlnTrpIleSerSerGluCysThrThr
4501 GCCTCACTGTAACCCAGCTCCTGAGGCGACTGCACCAGTGGATAAGCTCGGAGTGTACCA
     CGGAGTGACATTGGGTCGAGGACTCCGCTGACGTGGTCACCTATTCGAGCCTCACATGGT

ProCysSerGlySerTrpLeuArgAspIleTrpAspTrpIleCysGluValLeuSerAsp
4561 CTCCATGCTCCGGTTCCTGGCTAAGGGACATCTGGGACTGGATATGCGAGGTGTTGAGCG
     GAGGTACGAGGCCAAGGACCGATTCCCTGTAGACCCTGACCTATACGCTCCACAACTCGC

PheLysThrTrpLeuLysAlaLysLeuMetProGlnLeuProGlyIleProPheValSer
4621 ACTTTAAGACCTGGCTAAAAGCTAAGCTCATGCCACAGCTGCCTGGGATCCCCTTTGTGT
     TGAAATTCTGGACCGATTTTCGATTCGAGTACGGTGTCGACGGACCCTAGGGGAAACACA

CysGlnArgGlyTyrLysGlyValTrpArgValAspGlyIleMetHisThrArgCysHis
4681 CCTGCCAGCGCGGGTATAAGGGGGTCTGGCGAGTGGACGGCATCATGCACACTCGCTGCC
     GGACGGTCGCGCCCATATTCCCCCAGACCGCTCACCTGCCGTAGTACGTGTGAGCGACGG

CysGlyAlaGluIleThrGlyHisValLysAsnGlyThrMetArgIleValGlyProArg
4741 ACTGTGGAGCTGAGATCACTGGACATGTCAAAAACGGGACGATGAGGATCGTCGGTCCTA
     TGACACCTCGACTCTAGTGACCTGTACAGTTTTTGCCCTGCTACTCCTAGCAGCCAGGAT

ThrCysArgAsnMetTrpSerGlyThrPheProIleAsnAlaTyrThrThrGlyProCys
4801 GGACCTGCAGGAACATGTGGAGTGGGACCTTCCCCATTAATGCCTACACCACGGGCCCCT
     CCTGGACGTCCTTGTACACCTCACCCTGGAAGGGGTAATTACGGATGTGGTGCCCGGGGA

ThrProLeuProAlaProAsnTyrThrPheAlaLeuTrpArgValSerAlaGluGluTyr
4861 GTACCCCCCTTCCTGCGCCGAACTACACGTTCGCGCTATGGAGGGTGTCTGCAGAGGAAT
     CATGGGGGGAAGGACGCGGCTTGATGTGCAAGCGCGATACCTCCCACAGACGTCTCCTTA

ValGluIleArgGlnValGlyAspPheHisTyrValThrGlyMetThrThrAspAsnLeu
4921 ATGTGGAGATAAGGCAGGTGGGGGACTTCCACTACGTGACGGGTATGACTACTGACAATC
     TACACCTCTATTCCGTCCACCCCCTGAAGGTGATGCACTGCCCATACTGATGACTGTTAG

LysCysProCysGlnValProSerProGluPhePheThrGluLeuAspGlyValArgLeu
4981 TCAAATGCCCGTGCCAGGTCCCATCGCCCGAATTTTTCACAGAATTGGACGGGGTGCGCC
     AGTTTACGGGCACGGTCCAGGGTAGCGGGCTTAAAAAGTGTCTTAACCTGCCCCACGCGG
```

FIG. 47F

```
           HisArgPheAlaProProCysLysProLeuLeuArgGluGluValSerPheArgValGly
5041 TACATAGGTTTGCGCCCCCCTGCAAGCCCTTGCTGCGGGAGGAGGTATCATTCAGAGTAG
     ATGTATCCAAACGCGGGGGGACGTTCGGGAACGACGCCCTCCTCCATAGTAAGTCTCATC

LeuHisGluTyrProValGlySerGlnLeuProCysGluProGluProAspValAlaVal
5101 GACTCCACGAATACCCGGTAGGGTCGCAATTACCTTGCGAGCCCGAACCGGACGTGGCCG
     CTGAGGTGCTTATGGGCCATCCCAGCGTTAATGGAACGCTCGGGCTTGGCCTGCACCGGC

LeuThrSerMetLeuThrAspProSerHisIleThrAlaGluAlaAlaGlyArgArgLeu
5161 TGTTGACGTCCATGCTCACTGATCCCTCCCATATAACAGCAGAGGCGGCCGGGCGAAGGT
     ACAACTGCAGGTACGAGTGACTAGGGAGGGTATATTGTCGTCTCCGCCGGCCCGCTTCCA

AlaArgGlySerProProSerValAlaSerSerSerAlaSerGlnLeuSerAlaProSer
5221 TGGCGAGGGGATCACCCCCCTCTGTGGCCAGCTCCTCGGCTAGCCAGCTATCCGCTCCAT
     ACCGCTCCCCTAGTGGGGGGAGACACCGGTCGAGGAGCCGATCGGTCGATAGGCGAGGTA

LeuLysAlaThrCysThrAlaAsnHisAspSerProAspAlaGluLeuIleGluAlaAsn
5281 CTCTCAAGGCAACTTGCACCGCTAACCATGACTCCCCTGATGCTGAGCTCATAGAGGCCA
     GAGAGTTCCGTTGAACGTGGCGATTGGTACTGAGGGGACTACGACTCGAGTATCTCCGGT

LeuLeuTrpArgGlnGluMetGlyGlyAsnIleThrArgValGluSerGluAsnLysVal
5341 ACCTCCTATGGAGGCAGGAGATGGGCGGCAACATCACCAGGGTTGAGTCAGAAAACAAAG
     TGGAGGATACCTCCGTCCTCTACCCGCCGTTGTAGTGGTCCCAACTCAGTCTTTTGTTTC

ValIleLeuAspSerPheAspProLeuValAlaGluGluAspGluArgGluIleSerVal
5401 TGGTGATTCTGGACTCCTTCGATCCGCTTGTGGCGGAGGAGGACGAGCGGGAGATCTCCG
     ACCACTAAGACCTGAGGAAGCTAGGCGAACACCGCCTCCTCCTGCTCGCCCTCTAGAGGC

ProAlaGluIleLeuArgLysSerArgArgPheAlaGlnAlaLeuProValTrpAlaArg
5461 TACCCGCAGAAATCCTGCGGAAGTCTCGGAGATTCGCCCAGGCCCTGCCCGTTTGGGCGC
     ATGGGCGTCTTTAGGACGCCTTCAGAGCCTCTAAGCGGGTCCGGGACGGGCAAACCCGCG

ProAspTyrAsnProProLeuValGluThrTrpLysLysProAspTyrGluProProVal
5521 GGCCGGACTATAACCCCCCGCTAGTGGAGACGTGGAAAAAGCCCGACTACGAACCACCTG
     CCGGCCTGATATTGGGGGGCGATCACCTCTGCACCTTTTTCGGGCTGATGCTTGGTGGAC

ValHisGlyCysProLeuProProProLysSerProProValProProProArgLysLys
5581 TGGTCCATGGCTGTCCGCTTCCACCTCCAAAGTCCCCTCCTGTGCCTCCGCCTCGGAAGA
     ACCAGGTACCGACAGGCGAAGGTGGAGGTTTCAGGGGAGGACACGGAGGCGGAGCCTTCT

ArgThrValValLeuThrGluSerThrLeuSerThrAlaLeuAlaGluLeuAlaThrArg
5641 AGCGGACGGTGGTCCTCACTGAATCAACCCTATCTACTGCCTTGGCCGAGCTCGCCACCA
     TCGCCTGCCACCAGGAGTGACTTAGTTGGGATAGATGACGGAACCGGCTCGAGCGGTGGT

SerPheGlySerSerSerThrSerGlyIleThrGlyAspAsnThrThrThrSerSerGlu
5701 GAAGCTTTGGCAGCTCCTCAACTTCCGGCATTACGGGCGACAATACGACAACATCCTCTG
     CTTCGAAACCGTCGAGGAGTTGAAGGCCGTAATGCCCGCTGTTATGCTGTTGTAGGAGAC

ProAlaProSerGlyCysProProAspSerAspAlaGluSerTyrSerSerMetProPro
5761 AGCCCGCCCCTTCTGGCTGCCCCCCCGACTCCGACGCTGAGTCCTATTCCTCCATGCCCC
     TCGGGCGGGGAAGACCGACGGGGGGGCTGAGGCTGCGACTCAGGATAAGGAGGTACGGGG

LeuGluGlyGluProGlyAspProAspLeuSerAspGlySerTrpSerThrValSerSer
5821 CCCTGGAGGGGGAGCCTGGGGATCCGGATCTTAGCGACGGGTCATGGTCAACGGTCAGTA
     GGGACCTCCCCCTCGGACCCCTAGGCCTAGAATCGCTGCCCAGTACCAGTTGCCAGTCAT

GluAlaAsnAlaGluAspValValCysCysSerMetSerTyrSerTrpThrGlyAlaLeu
5881 GTGAGGCCAACGCGGAGGATGTCGTGTGCTGCTCAATGTCTTACTCTTGGACAGGCGCAC
     CACTCCGGTTGCGCCTCCTACAGCACACGACGAGTTACAGAATGAGAACCTGTCCGCGTG

ValThrProCysAlaAlaGluGluGlnLysLeuProIleAsnAlaLeuSerAsnSerLeu
5941 TCGTCACCCCGTGCGCCGCGGAAGAACAGAAACTGCCCATCAATGCACTAAGCAACTCGT
     AGCAGTGGGGCACGCGGCGCCTTCTTGTCTTTGACGGGTAGTTACGTGATTCGTTGAGCA

LeuArgHisHisAsnLeuValTyrSerThrThrSerArgSerAlaCysGlnArgGlnLys
6001 TGCTACGTCACCACAATTTGGTGTATTCCACCACCTCACGCAGTGCTTGCCAAAGGCAGA
     ACGATGCAGTGGTGTTAAACCACATAAGGTGGTGGAGTGCGTCACGAACGGTTTCCGTCT
```

FIG. 47G

```
     LysValThrPheAspArgLeuGlnValLeuAspSerHisTyrGlnAspValLeuLysGlu
6061 AGAAAGTCACATTTGACAGACTGCAAGTTCTGGACAGCCATTACCAGGACGTACTCAAGG
     TCTTTCAGTGTAAACTGTCTGACGTTCAAGACCTGTCGGTAATGGTCCTGCATGAGTTCC

ValLysAlaAlaAlaSerLysValLysAlaAsnLeuLeuSerValGluGluAlaCysSer
6121 AGGTTAAAGCAGCGGCGTCAAAAGTGAAGGCTAACTTGCTATCCGTAGAGGAAGCTTGCA
     TCCAATTTCGTCGCCGCAGTTTTCACTTCCGATTGAACGATAGGCATCTCCTTCGAACGT

LeuThrProProHisSerAlaLysSerLysPheGlyTyrGlyAlaLysAspValArgCys
6181 GCCTGACGCCCCCACACTCAGCCAAATCCAAGTTTGGTTATGGGGCAAAAGACGTCCGTT
     CGGACTGCGGGGGTGTGAGTCGGTTTAGGTTCAAACCAATACCCCGTTTTCTGCAGGCAA

HisAlaArgLysAlaValThrHisIleAsnSerValTrpLysAspLeuLeuGluAspAsn
6241 GCCATGCCAGAAAGGCCGTAACCCACATCAACTCCGTGTGGAAAGACCTTCTGGAAGACA
     CGGTACGGTCTTTCCGGCATTGGGTGTAGTTGAGGCACACCTTTCTGGAAGACCTTCTGT

ValThrProIleAspThrThrIleMetAlaLysAsnGluValPheCysValGlnProGlu
6301 ATGTAACACCAATAGACACTACCATCATGGCTAAGAACGAGGTTTTCTGCGTTCAGCCTG
     TACATTGTGGTTATCTGTGATGGTAGTACCGATTCTTGCTCCAAAAGACGCAAGTCGGAC

LysGlyGlyArgLysProAlaArgLeuIleValPheProAspLeuGlyValArgValCys
6361 AGAAGGGGGGTCGTAAGCCAGCTCGTCTCATCGTGTTCCCCGATCTGGGCGTGCGCGTGT
     TCTTCCCCCCAGCATTCGGTCGAGCAGAGTAGCACAAGGGGCTAGACCCGCACGCGCACA

GluLysMetAlaLeuTyrAspValValThrLysLeuProLeuAlaValMetGlySerSer
6421 GCGAAAAGATGGCTTTGTACGACGTGGTTACAAAGCTCCCCTTGGCCGTGATGGGAAGCT
     CGCTTTTCTACCGAAACATGCTGCACCAATGTTTCGAGGGGAACCGGCACTACCCTTCGA

TyrGlyPheGlnTyrSerProGlyGlnArgValGluPheLeuValGlnAlaTrpLysSer
6481 CCTACGGATTCCAATACTCACCAGGACAGCGGGTTGAATTCCTCGTGCAAGCGTGGAAGT
     GGATGCCTAAGGTTATGAGTGGTCCTGTCGCCCAACTTAAGGAGCACGTTCGCACCTTCA

LysLysThrProMetGlyPheSerTyrAspThrArgCysPheAspSerThrValThrGlu
6541 CCAAGAAAACCCCAATGGGGTTCTCGTATGATACCCGCTGCTTTGACTCCACAGTCACTG
     GGTTCTTTTGGGGTTACCCCAAGAGCATACTATGGGCGACGAAACTGAGGTGTCAGTGAC

SerAspIleArgThrGluGluAlaIleTyrGlnCysCysAspLeuAspProGlnAlaArg
6601 AGAGCGACATCCGTACGGAGGAGGCAATCTACCAATGTTGTGACCTCGACCCCCAAGCCC
     TCTCGCTGTAGGCATGCCTCCTCCGTTAGATGGTTACAACACTGGAGCTGGGGGTTCGGG

ValAlaIleLysSerLeuThrGluArgLeuTyrValGlyGlyProLeuThrAsnSerArg
6661 GCGTGGCCATCAAGTCCCTCACCGAGAGGCTTTATGTTGGGGGCCCTCTTACCAATTCAA
     CGCACCGGTAGTTCAGGGAGTGGCTCTCCGAAATACAACCCCCGGGAGAATGGTTAAGTT

GlyGluAsnCysGlyTyrArgArgCysArgAlaSerGlyValLeuThrThrSerCysGly
6721 GGGGGGAGAACTGCGGCTATCGCAGGTGCCGCGCGAGCGGCGTACTGACAACTAGCTGTG
     CCCCCCTCTTGACGCCGATAGCGTCCACGGCGCGCTCGCCGCATGACTGTTGATCGACAC

AsnThrLeuThrCysTyrIleLysAlaArgAlaAlaCysArgAlaAlaGlyLeuGlnAsp
6781 GTAACACCCTCACTTGCTACATCAAGGCCCGGGCAGCCTGTCGAGCCGCAGGGCTCCAGG
     CATTGTGGGAGTGAACGATGTAGTTCCGGGCCCGTCGGACAGCTCGGCGTCCCGAGGTCC

CysThrMetLeuValCysGlyAspAspLeuValValIleCysGluSerAlaGlyValGln
6841 ACTGCACCATGCTCGTGTGTGGCGACGACTTAGTCGTTATCTGTGAAAGCGCGGGGGTCC
     TGACGTGGTACGAGCACACACCGCTGCTGAATCAGCAATAGACACTTTCGCGCCCCCAGG

GluAspAlaAlaSerLeuArgAlaPheThrGluAlaMetThrArgTyrSerAlaProPro
6901 AGGAGGACGCGGCGAGCCTGAGAGCCTTCACGGAGGCTATGACCAGGTACTCCGCCCCCC
     TCCTCCTGCGCCGCTCGGACTCTCGGAAGTGCCTCCGATACTGGTCCATGAGGCGGGGGG

GlyAspProProGlnProGluTyrAspLeuGluLeuIleThrSerCysSerSerAsnVal
6961 CTGGGGACCCCCCACAACCAGAATACGACTTGGAGCTCATAACATCATGCTCCTCCAACG
     GACCCCTGGGGGGTGTTGGTCTTATGCTGAACCTCGAGTATTGTAGTACGAGGAGGTTGC

SerValAlaHisAspGlyAlaGlyLysArgValTyrTyrLeuThrArgAspProThrThr
7021 TGTCAGTCGCCCACGACGGCGCTGGAAAGAGGGTCTACTACCTCACCCGTGACCCTACAA
     ACAGTCAGCGGGTGCTGCCGCGACCTTTCTCCCAGATGATGGAGTGGGCACTGGGATGTT
```

FIG. 47H

```
         ProLeuAlaArgAlaAlaTrpGluThrAlaArgHisThrProValAsnSerTrpLeuGly
7081 CCCCCCTCGCGAGAGCTGCGTGGGAGACAGCAAGACACACTCCAGTCAATTCCTGGCTAG
     GGGGGGAGCGCTCTCGACGCACCCTCTGTCGTTCTGTGTGAGGTCAGTTAAGGACCGATC

AsnIleIleMetPheAlaProThrLeuTrpAlaArgMetIleLeuMetThrHisPhePhe
7141 GCAACATAATCATGTTTGCCCCCACACTGTGGGCGAGGATGATACTGATGACCCATTTCT
     CGTTGTATTAGTACAAACGGGGGTGTGACACCCGCTCCTACTATGACTACTGGGTAAAGA

SerValLeuIleAlaArgAspGlnLeuGluGlnAlaLeuAspCysGluIleTyrGlyAla
7201 TTAGCGTCCTTATAGCCAGGGACCAGCTTGAACAGGCCCTCGATTGCGAGATCTACGGGG
     AATCGCAGGAATATCGGTCCCTGGTCGAACTTGTCCGGGAGCTAACGCTCTAGATGCCCC

CysTyrSerIleGluProLeuAspLeuProProIleIleGlnArgLeu
7261 CCTGCTACTCCATAGAACCACTTGATCTACCTCCAATCATTCAAAGACTC
     GGACGATGAGGTATCTTGGTGAACTAGATGGAGGTTAGTAAGTTTCTGAG
```

FIG. 48

```
                          ProSerProValValGlyThrThrAspArgSerGlyAlaProThrTyrSerTrpGly
  1 CTCCCAGCCCCGTGGTGGGAACGACCAGTCGGGCGCGCCTACTACAGCTGGG
    GAGGGTCGGGGCACCACCCTGCTGGTCAGCCCGCGCCCGGATGATGTCGACCC

GluAsnAspThrArgProLeuGlyAsnThrArgProPheThrValPhe
 61 GTGAAAATGATACGGACGTCTTCGTCCTTAACAATACCAGCCACCGCTGGGCAATTGT
    CACTTTTACTATGCCTGCAGAAGCAGGAATTGTTATGGTCGGTGGCGACCCGTTAACCA

GlyCysThrTrpMetAsnSerThrGlyPheThrLysValCysGlyAlaProProCysVal
121 TCGGTTGTACCTGGATGAACTCAACTGGATTCACCAAAGTGTGCGGAGCGCCTCCTGTG
    AGCCAACATGGACCTACTTGAGTTGACCTAAGTGGTTTCACACGCCTCGCGGAGAACAC

IleGlyGlyAlaGlyAsnAsnThrLeuHisCysProThrAspCysPheArgLysHisPro
181 TCATCGGAGGGGCAACACACCCTGCCCCACTGATTGCTTCCGCAAGCATC
    AGTAGCCTCCCGGTTGTGGACGTGACGGGGTGACTAACGAAGGCGTTCGTAG

AspAlaThrTyrSerArgCysGlySerGlyProTrpProArgCysLeuValAsp
241 CGGACGCCACATACTCTCGGTGCGGCTCCGGTCCCTGGCCTCACACCCAGTGCCTGGTCG
    GCCTGCGGTGTATGAGAGCCACGCCCAGGACCGAGTGTGGGTCCACGGACCAGC

TyrProTyrArgLeuTrpHisTyrProCysThrIleAsnTyrThrIlePheLysIleArg
301 ACTACCCGTATAGGCTTTGGCATTATCCTGTACCATCAACTACACCATATTAAAATCA
    TGATGGGCATATCCGAAACCGTAATAGGACATGGTAGTTGATGTGGTATAAATTTTAGT

MetTyrValGlyGlyValGlyHisArgLeuGluAlaAlaCysAsnTrpThrArgGlyGlu
361 GGATGTACGTGGGAGGGGTCGAGCACAGGCTGGAAGCTGCCTGCAACTGGACGCGGGG
    CCTACATGCACCCTCCCCAGCTCGTGTCCGACCTTCGACGGACGTTGACCTGCGCCCGC

-----------Overlap with 12f-------
              ArgCysAspLeuGluAspArgAspArgSerGlyGluLeuSerProLeuLeuThrThrThr
421 AACGTTGCGATCTGGAAGACAGGAGACAGGTCCGAGCTCCAGCCCGTTACTGCTGACCACTA
    TTGCAACGCTAGACCTTCTGTCCTCTGTCCAGGCTCGAGTCGGGCAATGACGACTGGTGAT GlnTrpGlnValLeuProCysSerPheThrThrLeuProAlaLeuSerThrGlyLeu
481 CACAGTGGCAGGTGCTCCCGTGTCCTTCACAACCCTGCCAGCCCTGTCCACCGGCCTCA
    GTGTCACCGTCCAGGCAGTCCAGGGCACACAAGGAAGTGTTGGACGTTGGAACAGGTGGCCGAGT
```

FIG. 49

```
    LeuPheTyrHisHisLysPheAsnSerSerGlyCysProGluArgLeuAlaSerCysArg
  1 GCTTTCTATCACCACAAGTTCAACTCTTCAGGCTGTCCTGAGAGGCTAGCCAGCTGCCG
    CGAAAAGATAGTGGTGTTCAAGTTGAGAAGTCCGACAGGACTCTCCGATCGGTCGACGGC
    ProLeuThrAspPheAspGlnGlyTrpGlyTyrProIleSerTyrAlaAsnGlySerGlyPro
 61 ACCCCTTACCGATTTGACCAGGGCTGGGGCCCTATCAGTTATGCCAACGGAAGCGGCCC
    TGGGGAATGGCTAAAACTGGTCCCGACCCCGGGATAGTCAATACGTTGCCTTCGCCGGG
    AspGlnArgProTyrCysTrpHisTyrProProLysProCysGlyIleValProAlaLys
121 CGACCAGCGCCCCTACTGCTGGCACTACCCCCCAAAACCTTGCGGTATTGTGCCGGCGAA
    GCTGGTCGCGGGGGATGACGACCGTGATGGGGTTTGGAACGCCATAACACGGGGCGCTT
                           ---Overlap with 131----
    SerValCysGlyProValTyrCysPheThrProSerProValVal
181 GAGTGTGTGTGGTCCGGTATATTGCTTCACTCCCAGCCCCGTGGTGGG
    CTCACACACACCAGGCCATATAACGAAGTGAGGGTCGGGGCACCACCC
```

FIG. 50

```
    LeuValMetAlaGlnLeuLeuArgIleProGlnAlaIleLeuLeuAspMetIleAlaGlyAla
  1 TTGGTAATGGCTCAGCTGCTCCGGATCCCACAAGCCATCTTGGACATGATCGCTGGTGCT
    AACCATTACCGAGTCGACGAGGCCTAGGGTGTTCGGTAGAACCTGTACTAGCGACCACGA

HisTrpGlyValLeuAlaGlyIleAlaTyrPheSerMetValGlyAsnTrpAlaLysVal
 61 CACTGGGGAGTCCTGGCGGGCATAGCGTATTCTCCATGTGGGGAACTGGGCGAAGGTC
    GTGACCCCTCAGGACCGCCCGTATCGCATAAGAGGTACCACCCCTTGACCCGCTTCCAG

LeuValValLeuLeuPheAlaGlyValAlaAspAlaGluThrHisValThrGlyGlySer
121 CTGGTAGTGCTGCTGCTATTTGCCGGCGTCGACGCGGAAACCCACGTCACCGGGGAAGT
    GACCATCACGACGACGATAAACGGCCGCAGCTGCGCCTTTGGGTGCAGTGGCCCCTTCA

AlaGlyHisThrValSerGlyPheValSerLeuLeuAlaProGlyAlaLysGlnAsnVal
181 GCCGGCCACACTGTCTGGATTTGTTAGCCTCCTGGCCAAGGCGCCAAGCAGAACGTC
    CGGCCGGTGTGACAGACCTAAACAATCGGAGGAGCCGGTTCCGCGGTTCGTCTTGCAG

GlnLeuIleAsnThrAsnGlySerTrpHisLeuAsnSerThrAlaLeuAsnCysAsnAsp
241 CAGCTGATCAACACCAACGGCAGTTGGCACCTCAATAGCACGGCCCTGAACTGCAATGAT
    GTCGACTAGTTGTGGTTGCCGTCAACCGTGGAGTTATCGTGCCGGGACTTGACGTTACTA
                                          -----Overlap with 26j-----

SerLeuAsnThrGlyTrpLeuAlaGlyLeuPheTyrHisHisLysPheAsnSerSerGly
301 AGCCTCAACACCGGCTGGTTGGCAGGCTTTTCTATCACCACAAGTTCAACTCTTCAGGC
    TCGGAGTTGTGGCCGACCAACCGTCCCGAAAAGATAGTGGTGTTCAAGTTGAGAAGTCCG

-----Overlap with K9-1-----
    CysProGluArgLeuAlaSerCysArgPro
361 TGTCCTGAGAGGCTAGCCAGCTGCCGACCCC
    ACAGGACTCTCCGATCGGTCGACGGCTGGGG
```

FIG. 51

```
              GlnGlyCysAsnCysSerIleTyrProGlyHisIleThrGlyHisArgMetAlaTrpAsp
  1 CGCAAGGTTGCAATTGCTCTATCTATCCCGGCCATATAACGGGTCACCGGCATGGCATGGG
    GCGTTCCAACGTTAACGAGATAGATAGGGCCGGTATATTGCCCAGTGGCCGTACCGTACCC

MetMetMetAsnTrpSerProThrThrAlaLeuValMetAlaGlnLeuLeuArgIlePro
 61 ATATGATGATGAACTGGTCCCCTACGACGGTTGGTAATGGCGTTCAGCTGCTCCGGATCC
    TATACTACTACTTGACCAGGGGATGCTGCCAACCATTACCGCAAGTCGACGAGGCCTAGG

GlnAlaIleLeuAspMetIleAlaGlyAlaHisTrpGlyValLeuAlaGlyIleAlaTyr
121 CACAAGCCATCTGGACATGATCGCTGGGAGTCGCTCACTGGGGAGTCCTGGCGGGCATAGCGT
    GTGTTCGGTAGAACCTGTACTAGCGACCCCTCAGGACGAGTGACCCCTGGCCGCCCGTATCGCA

----------Overlap with CA59a----------
              PheSerMetValGlyAsnTrpAlaLysValValLeuValValValLeuLeuPheAlaGlyVal
181 ATTTCTCCATGGTGGGGAACTGGGCGGAAGGTCCTGGTAGTGCTGCTGCTATTTGCCGGCG
    TAAAGAGGTACCACCCCCTTGACCCGCCTTCCAGGACCATCACGACGACGATAAACGGCCGC AspAlaGluThrHisValThrGly
241 TCGACGCGGGAAACCCACGTCACCGGGG
    AGCTGCGCCCTTTGGGTGCAGTGGCCCC
```

FIG. 52

```
    CysTrpValAlaMetThrProThrValAlaThrArgAspGlyLysLeuProAlaThrGln
  1 GTGTTGGGTGGCGATGACCCCGACGGTGGCCACCAGGGATGGCAAACTCCCCGCGACGCA
    CACAACCCACCGCTACTGGGGATGCCACCGGTGGTCCCTACCGTTTGAGGGGCGCTGCGT

LeuArgArgHisIleAspLeuLeuValGlySerAlaThrLeuCysSerAlaLeuTyrVal
 61 GCTTCGACGTCACATATCGATCTGCTTGTCGGGAGCGCCACCCTCTGTTCGGCCCTCTACGT
    CGAAGCTGCAGTGTAGCTAGACGAACAGCCCTCGCGGTGGGAGACAAGCCGGGAGATGCA

GlyAspLeuCysGlySerValPheLeuValGlyGlnLeuPheThrPheSerProArgArg
121 GGGGACCTATGCGGGGTCTGTCTTTCTTGTCGGCCAACTGTTCACCTTCTCCCCCAGGCG
    CCCCCTGGATACGCCCCAGACAGAAAGAACAGCCGGTTGACAAGTGGAAGAGGGTCCGC

HisTrpThrThrGlnGlyCysAsnCysSerIleTyrProGlyHisIleThrGlyHisArg
181 CCACTGACGACGCAAGGTTGCAATTGCTCTATCTATCCCGGCCATATAACGGGTCACCG
    GGTGACCTGCTGCGTTCCAACGTTAACGAGATAGATAGGGCCGGTATATTGCCAGTGGC

---------Overlap with CA84a---------
    MetAlaTrpAspMetMetAsnTrpSerProThrThrAlaLeuValValAlaGlnLeu
241 CATGGCATGGGATATGATGAACTGGTCCCCTACGACGGCGTTGGTAGTGGCTCAGCT
    GTACCGTACCCTATACTACTTGACCAGGGGATGCTGCCGCAACCATCACCGAGTCGA ------|
    LeuArgIleProGlnAla
301 GCTCCGGATCCCCACAAGCC
    CGAGGCCTAGGGGTGTTCGG
```

FIG. 53

```
    SerThrGlyLeuTyrHisValThrAsnAspCysProAsnSerSerIleValTyrGluAla
  1 CTCCACGGGGCTTTACCAGTCACCAGTGCCCTAACTCGAGTATTGTGTACGAGGC
    GAGGTGCCCCGAAATGGTGCAGTGGTTACTAACGGATTGAGCTCATAACACATGTCCG

AlaAspAlaIleLeuHisThrProGlyCysValProCysValArgGluGlyAsnAlaSer
 61 GGCCGATGCCATCCTGCACACTCCGGGGTGCGTCCCTTGCGTTCGTGAGGGCAACGCCTC
    CCGGCTACGGTAGGACGTGTGAGGCCCCACGCAGGGAACGCAAGCACTCCCGTTGCGGAG

ArgCysTrpValAlaMetThrProThrValAlaThrArgAspGlyLysLeuProAlaThr
121 GAGGTGTTGGGTGGCGATGACCCCTACGGTGGCCACCAGGATGGCAAACTCCCCGCGAC
    CTCCACAACCACCGCTACTGGGGATGCCACCGGTGGTCCTACCGTTTGAGGGGCGCTG
    ------------------Overlap with CA156e------------------

GlnLeuArgHisIleAspLeuLeuValGlySerAlaThrLeuCysSerAlaLeuTyr
181 GCAGCTTCGACGTCACACATCGATCTCTGTGTCGGGAGCGCTACCCTCTGTTCGGCCCCTA
    CGTCGAAGCTGCAGTGTAGCTAGACAGCCCTCGCGATGGGAGACAAGCCGGGAGAT

ValGlyAspLeuCysGlySerValPheLeu
241 CGTGGGGACTTGTGCGGGTCTGTCTTCTTG
    GCACCCCCTGAACACGCCCAGAGAAGAAC
```

FIG. 54A

```
    ArgSerArgAsnLeuGlyLysValIleAspThrLeuThrCysGlyPheAlaAspLeuMet
  1 AGGTCGCGCAATTTGGGTAAGGTCATCGATACCCTTACGTGCGGCTTCGCCGACCTCATG
    TCCAGCGCGTTAAACCCATTCCAGTAGCTATGGGAATGCACGCCGAAGCGGCTGGAGTAC

GlyTyrIleProLeuValGlyAlaProLeuGlyGlyAlaAlaArgAlaLeuAlaHisGly
 61 GGGTACATACCGCTCGTCGGCGCCCCTCTTGGAGGCGCTGCCAGGGCCCTGGCGCATGGC
    CCCATGTATGGCGAGCAGCCGCGGGGAGAACCTCCGCGACGGTCCCGGGACCGCGTACCG

ValArgValLeuGluAspGlyValAsnTyrAlaThrGlyAsnLeuProGlyCysSerPhe
121 GTCCGGGTTCTGGAAGACGGCGTGAACTATGCAACAGGGAACCTTCCTGGTTGCTCTTTC
    CAGGCCCAAGACCTTCTGCCGCACTTGATACGTTGTCCCTTGGAAGGACCAACGAGAAAG

SerIlePheLeuLeuAlaLeuLeuSerCysLeuThrValProAlaSerAlaTyrGlnVal
181 TCTATCTTCCTTCTGGCCCTGCTCTCTTGCTTGACTGTGCCCGCTTCGGCCTACCAAGTG
    AGATAGAAGGAAGACCGGGACGAGAGAACGAACTGACACGGGCGAAGCCGGATGGTTCAC

ArgAsnSerThrGlyLeuTyrHisValThrAsnAspCysProAsnSerSerIleValTyr
241 CGCAACTCCACGGGGCTTTACCACGTCACCAATGATTGCCCTAACTCGAGTATTGTGTAC
    GCGTTGAGGTGCCCCGAAATGGTGCAGTGGTTACTAACGGGATTGAGCTCATAACACATG

GluAlaAlaAspAlaIleLeuHisThrProGlyCysValProCysValArgGluGlyAsn
301 GAGGCGGCCGATGCCATCCTGCACACTCCGGGGTGCGTCCCTTGCGTTCGTGAGGGCAAC
    CTCCGCCGGCTACGGTAGGACGTGTGAGGCCCCACGCAGGGAACGCAAGCACTCCCGTTG

AlaSerArgCysTrpValAlaMetThrProThrValAlaThrArgAspGlyLysLeuPro
361 GCCTCGAGGTGTTGGGTGGCGATGACCCCTACGGTGGCCACCAGGGATGGCAAACTCCCC
    CGGAGCTCCACAACCCACCGCTACTGGGGATGCCACCGGTGGTCCCTACCGTTTGAGGGG

AlaThrGlnLeuArgArgHisIleAspLeuLeuValGlySerAlaThrLeuCysSerAla
421 GCGACGCAGCTTCGACGTCACATCGATCTGCTTGTCGGGAGCGCCACCCTCTGTTCGGCC
    CGCTGCGTCGAAGCTGCAGTGTAGCTAGACGAACAGCCCTCGCGGTGGGAGACAAGCCGG

LeuTyrValGlyAspLeuCysGlySerValPheLeuValGlyGlnLeuPheThrPheSer
481 CTCTACGTGGGGGACCTATGCGGGTCTGTCTTTCTTGTCGGCCAACTGTTCACCTTCTCT
    GAGATGCACCCCCTGGATACGCCCAGACAGAAAGAACAGCCGGTTGACAAGTGGAAGAGA

ProArgArgHisTrpThrThrGlnGlyCysAsnCysSerIleTyrProGlyHisIleThr
541 CCCAGGCGCCACTGGACGACGCAAGGTTGCAATTGCTCTATCTATCCCGGCCATATAACG
    GGGTCCGCGGTGACCTGCTGCGTTCCAACGTTAACGAGATAGATAGGGCCGGTATATTGC

GlyHisArgMetAlaTrpAspMetMetMetAsnTrpSerProThrThrAlaLeuValMet
601 GGTCACCGCATGGCATGGGATATGATGATGAACTGGTCCCCTACGACGGCGTTGGTAATG
    CCAGTGGCGTACCGTACCCTATACTACTACTTGACCAGGGGATGCTGCCGCAACCATTAC
```

FIG. 54B

```
         AlaGlnLeuLeuArgIleProGlnAlaIleLeuLeuAspMetIleAlaGlyAlaHisTrpGly
 661 GCTCAGCTGCTCCGGATCCCACAAGCCATCTTGGACATGATCGCTGGTGCTCACTGGGGA
     CGAGTCGACGAGGCCTAGGGTGTTCGGTAGAACCTGTACTAGCGACCACGAGTGACCCT

ValLeuAlaGlyIleAlaTyrPheSerMetValGlyAsnTrpAlaLysValLeuValVal
 721 GTCCTGGCGGGCATAGCGTATTTCTCCATGGTGGGGAACTGGGCGAAGGTCCTGGTAGTG
     CAGGACCGCCCGTATCGCATAAAGAGGTACCACCCCTTGACCCGCTTCCAGGACCATCAC

LeuLeuLeuPheAlaGlyValAspAlaGluThrHisValThrGlyGlySerAlaGlyHis
 781 CTGCTGCTATTTGCCGGCGTCGACGCGGAAACCCACGTCACCGGGGGAAGTGCCGGCCAC
     GACGACGATAAACGGCCGCAGCTGCGCCTTTGGGTGCAGTGGCCCCCTTCACGGCCGGTG

ThrValSerGlyPheValSerLeuLeuAlaProGlyAlaLysGlnAsnValGlnLeuIle
 841 ACTGTGTCTGGATTTGTTAGCCTCCTCGCACCAGGCGCCAAGCAGAACGTCCAGCTGATC
     TGACACAGACCTAAACAATCGGAGGAGCGTGGTCCGCGGTTCGTCTTGCAGGTCGACTAG

AsnThrAsnGlySerTrpHisLeuAsnSerThrAlaLeuAsnCysAsnAspSerLeuAsn
 901 AACACCAACGGCAGTTGGCACCTCAATAGCACGGCCCTGAACTGCAATGATAGCCTCAAC
     TTGTGGTTGCCGTCAACCGTGGAGTTATCGTGCCGGGACTTGACGTTACTATCGGAGTTG

ThrGlyTrpLeuAlaGlyLeuPheTyrHisHisLysPheAsnSerSerGlyCysProGlu
 961 ACCGGCTGGTTGGCAGGGCTTTTCTATCACCACAAGTTCAACTCTTCAGGCTGTCCTGAG
     TGGCCGACCAACCGTCCCGAAAAGATAGTGGTGTTCAAGTTGAGAAGTCCGACAGGACTC

ArgLeuAlaSerCysArgProLeuThrAspPheAspGlnGlyTrpGlyProIleSerTyr
1021 AGGCTAGCCAGCTGCCGACCCCTTACCGATTTTGACCAGGGCTGGGGCCCTATCAGTTAT
     TCCGATCGGTCGACGGCTGGGGAATGGCTAAAACTGGTCCCGACCCCGGGATAGTCAATA

AlaAsnGlySerGlyProAspGlnArgProTyrCysTrpHisTyrProProLysProCys
1081 GCCAACGGAAGCGGCCCCGACCAGCGCCCCTACTGCTGGCACTACCCCCCAAAACCTTGC
     CGGTTGCCTTCGCCGGGGCTGGTCGCGGGGATGACGACCGTGATGGGGGGTTTTGGAACG

GlyIleValProAlaLysSerValCysGlyProValTyrCysPheThrProSerProVal
1141 GGTATTGTGCCCGCGAAGAGTGTGTGTGGTCCGGTATATTGCTTCACTCCCAGCCCCGTG
     CCATAACACGGGCGCTTCTCACACACACCAGGCCATATAACGAAGTGAGGGTCGGGGCAC

ValValGlyThrThrAspArgSerGlyAlaProThrTyrSerTrpGlyGluAsnAspThr
1201 GTGGTGGGAACGACCGACAGGTCGGGCGCGCCCACCTACAGCTGGGGTGAAAATGATACG
     CACCACCCTTGCTGGCTGTCCAGCCCGCGCGGGTGGATGTCGACCCCACTTTTACTATGC

AspValPheValLeuAsnAsnThrArgProProLeuGlyAsnTrpPheGlyCysThrTrp
1261 GACGTCTTCGTCCTTAACAATACCAGGCCACCGCTGGGCAATTGGTTCGGTTGTACCTGG
     CTGCAGAAGCAGGAATTGTTATGGTCCGGTGGCGACCCGTTAACCAAGCCAACATGGACC

MetAsnSerThrGlyPheThrLysValCysGlyAlaProProCysValIleGlyGlyAla
1321 ATGAACTCAACTGGATTCACCAAAGTGTGCGGAGCGCCTCCTTGTGTCATCGGAGGGGCG
     TACTTGAGTTGACCTAAGTGGTTTCACACGCCTCGCGGAGGAACACAGTAGCCTCCCCGC

GlyAsnAsnThrLeuHisCysProThrAspCysPheArgLysHisProAspAlaThrTyr
1381 GGCAACAACACCCTGCACTGCCCCACTGATTGCTTCCGCAAGCATCCGGACGCCACATAC
     CCGTTGTTGTGGGACGTGACGGGGTGACTAACGAAGGCGTTCGTAGGCCTGCGGTGTATG

SerArgCysGlySerGlyProTrpIleThrProArgCysLeuValAspTyrProTyrArg
1441 TCTCGGTGCGGCTCCGGTCCCTGGATCACACCCAGGTGCCTGGTCGACTACCCGTATAGG
     AGAGCCACGCCGAGGCCAGGGACCTAGTGTGGGTCCACGGACCAGCTGATGGGCATATCC

LeuTrpHisTyrProCysThrIleAsnTyrThrIlePheLysIleArgMetTyrValGly
1501 CTTTGGCATTATCCTTGTACCATCAACTACACCATATATTTAAAATCAGGATGTACGTGGGA
     GAAACCGTAATAGGAACATGGTAGTTGATGTGGTATAAATTTTAGTCCTACATGCACCCT

GlyValGluHisArgLeuGluAlaAlaCysAsnTrpThrArgGlyGluArgCysAspLeu
1561 GGGGTCGAACACAGGCTGGAAGCTGCCTGCAACTGGACGCGGGGCGAACGTTGCGATCTG
     CCCCAGCTTGTGTCCGACCTTCGACGGACGTTGACCTGCGCCCCGCTTGCAACGCTAGAC

GluAspArgAspArgSerGluLeuSerProLeuLeuLeuThrThrThrGlnTrpGlnVal
1621 GAAGACAGGGACAGGTCCGAGCTCAGCCCGTTACTGCTGACCACTACACAGTGGCAGGTC
     CTTCTGTCCCTGTCCAGGCTCGAGTCGGGCAATGACGACTGGTGATGTGTCACCGTCCAG
```

FIG. 54C

```
          LeuProCysSerPheThrThrLeuProAlaLeuSerThrGlyLeuIleHisLeuHisGln
     1681 CTCCCGTGTTCCTTCACAACCCTACCAGCCTTGTCCACCGGCCTCATCCACCTCCACCAG
          GAGGGCACAAGGAAGTGTTGGGATGGTCGGAACAGGTGGCCGGAGTAGGTGGAGGTGGTC

AsnIleValAspValGlnTyrLeuTyrGlyValGlySerSerIleAlaSerTrpAlaIle
     1741 AACATTGTGGACGTGCAGTACTTGTACGGGGTGGGGTCAAGCATCGCGTCCTGGGCCATT
          TTGTAACACCTGCACGTCATGAACATGCCCCACCCCAGTTCGTAGCGCAGGACCCGGTAA

LysTrpGluTyrValValLeuLeuPheLeuLeuLeuAlaAspAlaArgValCysSerCys
     1801 AAGTGGGAGTACGTCGTTCTCCTGTTCCTTCTGCTTGCAGACGCGCGCGTCTGCTCCTGC
          TTCACCCTCATGCAGCAAGAGGACAAGGAAGACGAACGTCTGCGCGCGCAGACGAGGACG

LeuTrpMetMetLeuLeuIleSerGlnAlaGluAlaAlaLeuGluAsnLeuValIleLeu
     1861 TTGTGGATGATGCTACTCATATCCCAAGCGGAGGCGGCTTTGGAGAACCTCGTAATACTT
          AACACCTACTACGATGAGTATAGGGTTCGCCTCCGCCGAAACCTCTTGGAGCATTATGAA

AsnAlaAlaSerLeuAlaGlyThrHisGlyLeuValSerPheLeuValPhePheCysPhe
     1921 AATGCAGCATCCCTGGCCGGGACGCACGGTCTTGTATCCTTCCTCGTGTTCTTCTGCTTT
          TTACGTCGTAGGGACCGGCCCTGCGTGCCAGAACATAGGAAGGAGCACAAGAAGACGAAA

AlaTrpTyrLeuLysGlyLysTrpValProGlyAlaValTyrThrPheTyrGlyMetTrp
     1981 GCATGGTATTTGAAGGGTAAGTGGGTGCCCGGAGCGGTCTACACCTTCTACGGGATGTGG
          CGTACCATAAACTTCCCATTCACCCACGGGCCTCGCCAGATGTGGAAGATGCCCTACACC

ProLeuLeuLeuLeuLeuLeuAlaLeuProGlnArgAlaTyrAlaLeuAspThrGluVal
     2041 CCTCTCCTCCTGCTCCTGTTGGCGTTGCCCCAGCGGGCGTACGCGCTGGACACGGAGGTG
          GGAGAGGAGGACGAGGACAACCGCAACGGGGTCGCCCGCATGCGCGACCTGTGCCTCCAC

AlaAlaSerCysGlyGlyValValLeuValGlyLeuMetAlaLeuThrLeuSerProTyr
     2101 GCCGCGTCGTGTGGCGGTGTTGTTCTCGTCGGGTTGATGGCGCTGACTCTGTCACCATAT
          CGGCGCAGCACACCGCCACAACAAGAGCAGCCCAACTACCGCGACTGAGACAGTGGTATA

TyrLysArgTyrIleSerTrpCysLeuTrpTrpLeuGlnTyrPheLeuThrArgValGlu
     2161 TACAAGCGCTATATCAGCTGGTGCTTGTGGTGGCTTCAGTATTTTCTGACCAGAGTGGAA
          ATGTTCGCGATATAGTCGACCACGAACACCACCGAAGTCATAAAAGACTGGTCTCACCTT

AlaGlnLeuHisValTrpIleProProLeuAsnValArgGlyGlyArgAspAlaValIle
     2221 GCGCAACTGCACGTGTGGATTCCCCCCCTCAACGTCCGAGGGGGGCGCGACGCCGTCATC
          CGCGTTGACGTGCACACCTAAGGGGGGGAGTTGCAGGCTCCCCCCGCGCTGCGGCAGTAG

LeuLeuMetCysAlaValHisProThrLeuValPheAspIleThrLysLeuLeuLeuAla
     2281 TTACTCATGTGTGCTGTACACCCGACTCTGGTATTTGACATCACCAAATTGCTGCTGGCC
          AATGAGTACACACGACATGTGGGCTGAGACCATAAACTGTAGTGGTTTAACGACGACCGG

ValPheGlyProLeuTrpIleLeuGlnAlaSerLeuLeuLysValProTyrPheValArg
     2341 GTCTTCGGACCCCTTTGGATTCTTCAAGCCAGTTTGCTTAAAGTACCCTACTTTGTGCGC
          CAGAAGCCTGGGGAAACCTAAGAAGTTCGGTCAAACGAATTTCATGGGATGAAACACGCG

ValGlnGlyLeuLeuArgPheCysAlaLeuAlaArgLysMetIleGlyGlyHisTyrVal
     2401 GTCCAAGGCCTTCTCCGGTTCTGCGCGTTAGCGCGGAAGATGATCGGAGGCCATTACGTG
          CAGGTTCCGGAAGAGGCCAAGACGCGCAATCGCGCCTTCTACTAGCCTCCGGTAATGCAC

GlnMetValIleIleLysLeuGlyAlaLeuThrGlyThrTyrValTyrAsnHisLeuThr
     2461 CAAATGGTCATCATTAAGTTAGGGGCGCTTACTGGCACCTATGTTTATAACCATCTCACT
          GTTTACCAGTAGTAATTCAATCCCCGCGAATGACCGTGGATACAAATATTGGTAGAGTGA

ProLeuArgAspTrpAlaHisAsnGlyLeuArgAspLeuAlaValAlaValGluProVal
     2521 CCTCTTCGGGACTGGGCGCACAACCGCTTGCGAGATCTGGCCGTGGCTGTAGAGCCAGTC
          GGAGAAGCCCTGACCCGCGTGTTGCCGAACGCTCTAGACCGGCACCGACATCTCGGTCAG

ValPheSerGlnMetGluThrLysLeuIleThrTrpGlyAlaAspThrAlaAlaCysGly
     2581 GTCTTCTCCCAAATGGAGACCAAGCTCATCACGTGGGGGGCAGATACCGCCGCGTGCGGT
          CAGAAGAGGGTTTACCTCTGGTTCGAGTAGTGCACCCCCCGTCTATGGCGGCGCACGCCA

AspIleIleAsnGlyLeuProValSerAlaArgArgGlyArgGluIleLeuLeuGlyPro
     2641 GACATCATCAACGGCTTGCCTGTTTCCGCCCGCAGGGGCCGGGAGATACTGCTCGGGCCA
          CTGTAGTAGTTGCCGAACGGACAAAGGCGGGCGTCCCCGGCCCTCTATGACGAGCCCGGT
```

FIG. 54D

```
              AlaAspGlyMetValSerLysGlyTrpArgLeuLeuAlaProIleThrAlaTyrAlaGln
      2701  GCCGATGGAATGGTCTCCAAGGGGTGGAGGTTGCTGGCGCCCATCACGGCGTACGCCCAG
            CGGCTACCTTACCAGAGGTTCCCCACCTCCAACGACCGCGGGTAGTGCCGCATGCGGGTC

GlnThrArgGlyLeuLeuGlyCysIleIleThrSerLeuThrGlyArgAspLysAsnGln
      2761  CAGACAAGGGGCCTCCTAGGGTGCATAATCACCAGCCTAACTGGCCGGGACAAAAACCAA
            GTCTGTTCCCCGGAGGATCCCACGTATTAGTGGTCGGATTGACCGGCCCTGTTTTTGGTT

ValGluGlyGluValGlnIleValSerThrAlaAlaGlnThrPheLeuAlaThrCysIle
      2821  GTGGAGGGTGAGGTCCAGATTGTGTCAACTGCTGCCCAAACCTTCCTGGCAACGTGCATC
            CACCTCCCACTCCAGGTCTAACACAGTTGACGACGGGTTTGGAAGGACCGTTGCACGTAG

AsnGlyValCysTrpThrValTyrHisGlyAlaGlyThrArgThrIleAlaSerProLys
      2881  AATGGGGTGTGCTGGACTGTCTACCACGGGGCCGGAACGAGGACCATCGCGTCACCCAAG
            TTACCCCACACGACCTGACAGATGGTGCCCCGGCCTTGCTCCTGGTAGCGCAGTGGGTTC

GlyProValIleGlnMetTyrThrAsnValAspGlnAspLeuValGlyTrpProAlaPro
      2941  GGTCCTGTCATCCAGATGTATACCAATGTAGACCAAGACCTTGTGGGCTGGCCCGCTCCG
            CCAGGACAGTAGGTCTACATATGGTTACATCTGGTTCTGGAACACCCGACCGGGCGAGGC

GlnGlySerArgSerLeuThrProCysThrCysGlySerSerAspLeuTyrLeuValThr
      3001  CAAGGTAGCCGCTCATTGACACCCTGCACTTGCGGCTCCTCGGACCTTTACCTGGTCACG
            GTTCCATCGGCGAGTAACTGTGGGACGTGAACGCCGAGGAGCCTGGAAATGGACCAGTGC

ArgHisAlaAspValIleProValArgArgArgGlyAspSerArgGlySerLeuLeuSer
      3061  AGGCACGCCGATGTCATTCCCGTGCGCCGGCGGGTGATAGCAGGGGCAGCCTGCTGTCG
            TCCGTGCGGCTACAGTAAGGGCACGCGGCCGCCCCACTATCGTCCCCGTCGGACGACAGC

ProArgProIleSerTyrLeuLysGlySerSerGlyGlyProLeuLeuCysProAlaGly
      3121  CCCCGGCCCATTTCCTACTTGAAAGGCTCCTCGGGGGGTCCGCTGTTGTGCCCCGCGGGG
            GGGGCCGGGTAAAGGATGAACTTTCCGAGGAGCCCCCCAGGCGACAACACGGGGCGCCCC

HisAlaValGlyIlePheArgAlaAlaValCysThrArgGlyValAlaLysAlaValAsp
      3181  CACGCCGTGGGCATATTTAGGGCCGCGGTGTGCACCCGTGGAGTGGCTAAGGCGGTGGAC
            GTGCGGCACCCGTATAAATCCCGGCGCCACACGTGGGCACCTCACCGATTCCGCCACCTG

PheIleProValGluAsnLeuGluThrThrMetArgSerProValPheThrAspAsnSer
      3241  TTTATCCCTGTGGAGAACCTAGAGACAACCATGAGGTCCCCGGTGTTCACGGATAACTCC
            AAATAGGGACACCTCTTGGATCTCTGTTGGTACTCCAGGGGCCACAAGTGCCTATTGAGG

SerProProValValProGlnSerPheGlnValAlaHisLeuHisAlaProThrGlySer
      3301  TCTCCACCAGTAGTGCCCCAGAGCTTCCAGGTGGCTCACCTCCATGCTCCCACAGGCAGC
            AGAGGTGGTCATCACGGGGTCTCGAAGGTCCACCGAGTGGAGGTACGAGGGTGTCCGTCG

GlyLysSerThrLysValProAlaAlaTyrAlaAlaGlnGlyTyrLysValLeuValLeu
      3361  GGCAAAAGCACCAAGGTCCCGGCTGCATATGCAGCTCAGGGCTATAAGGTGCTAGTACTC
            CCGTTTTCGTGGTTCCAGGGCCGACGTATACGTCGAGTCCCGATATTCCACGATCATGAG

AsnProSerValAlaAlaThrLeuGlyPheGlyAlaTyrMetSerLysAlaHisGlyIle
      3421  AACCCCTCTGTTGCTGCAACACTGGGCTTTGGTGCTTACATGTCCAAGGCTCATGGGATC
            TTGGGGAGACAACGACGTTGTGACCCGAAACCACGAATGTACAGGTTCCGAGTACCCTAG

AspProAsnIleArgThrGlyValArgThrIleThrThrGlySerProIleThrTyrSer
      3481  GATCCTAACATCAGGACCGGGGTGAGAACAATTACCACTGGCAGCCCCATCACGTACTCC
            CTAGGATTGTAGTCCTGGCCCCACTCTTGTTAATGGTGACCGTCGGGGTAGTGCATGAGG

ThrTyrGlyLysPheLeuAlaAspGlyGlyCysSerGlyGlyAlaTyrAspIleIleIle
      3541  ACCTACGGCAAGTTCCTTGCCGACGGCGGGTGCTCGGGGGGCGCTTATGACATAATAATT
            TGGATGCCGTTCAAGGAACGGCTGCCGCCCACGAGCCCCCGCGAATACTGTATTATTAA

CysAspGluCysHisSerThrAspAlaThrSerIleLeuGlyIleGlyThrValLeuAsp
      3601  TGTGACGAGTGCCACTCCACGGATGCCACATCCATCTTGGGCATCGGCACTGTCCTTGAC
            ACACTGCTCACGGTGAGGTGCCTACGGTGTAGGTAGAACCCGTAGCCGTGACAGGAACTG
```

FIG. 54E

```
          GlnAlaGluThrAlaGlyAlaArgLeuValValLeuAlaThrAlaThrProProGlySer
3661 CAAGCAGAGACTGCGGGGGCGAGACTGGTTGTGCTCGCCACCGCCACCCCTCCGGGCTCC
     GTTCGTCTCTGACGCCCCCGCTCTGACCAACACGAGCGGTGGCGGTGGGGAGGCCCGAGG

ValThrValProHisProAsnIleGluGluValAlaLeuSerThrThrGlyGluIlePro
3721 GTCACTGTGCCCCATCCCAACATCGAGGAGGTTGCTCTGTCCACCACCGGAGAGATCCCT
     CAGTGACACGGGGTAGGGTTGTAGCTCCTCCAACGAGACAGGTGGTGGCCTCTCTAGGGA

PheTyrGlyLysAlaIleProLeuGluValIleLysGlyGlyArgHisLeuIlePheCys
3781 TTTTACGGCAAGGCTATCCCCCTCGAAGTAATCAAGGGGGGAGACATCTCATCTTCTGT
     AAAATGCCGTTCCGATAGGGGAGCTTCATTAGTTCCCCCCCTCTGTAGAGTAGAAGACA

HisSerLysLysLysCysAspGluLeuAlaAlaLysLeuValAlaLeuGlyIleAsnAla
3841 CATTCAAAGAAGAAGTGCGACGAACTCGCCGCAAAGCTGGTCGCATTGGGCATCAATGCC
     GTAAGTTTCTTCTTCACGCTGCTTGAGCGGCGTTTCGACCAGCGTAACCCGTAGTTACGG

ValAlaTyrTyrArgGlyLeuAspValSerValIleProThrSerGlyAspValValVal
3901 GTGGCCTACTACCGCGGTCTTGACGTGTCCGTCATCCCGACCAGCGGCGATGTTGTCGTC
     CACCGGATGATGGCGCCAGAACTGCACAGGCAGTAGGGCTGGTCGCCGCTACAACAGCAG

ValAlaThrAspAlaLeuMetThrGlyTyrThrGlyAspPheAspSerValIleAspCys
3961 GTGGCAACCGATGCCCTCATGACCGGCTATACCGGCGACTTCGACTCGGTGATAGACTGC
     CACCGTTGGCTACGGGAGTACTGGCCGATATGGCCGCTGAAGCTGAGCCACTATCTGACG

AsnThrCysValThrGlnThrValAspPheSerLeuAspProThrPheThrIleGluThr
4021 AATACGTGTGTCACCCAGACAGTCGATTTCAGCCTTGACCCTACCTTCACCATTGAGACA
     TTATGCACACAGTGGGTCTGTCAGCTAAAGTCGGAACTGGGATGGAAGTGGTAACTCTGT

IleThrLeuProGlnAspAlaValSerArgThrGlnArgArgGlyArgThrGlyArgGly
4081 ATCACGCTCCCCCAGGATGCTGTCTCCCGCACTCAACGTCGGGGCAGGACTGGCAGGGGG
     TAGTGCGAGGGGGTCCTACGACAGAGGGCGTGAGTTGCAGCCCCGTCCTGACCGTCCCCC

LysProGlyIleTyrArgPheValAlaProGlyGluArgProSerGlyMetPheAspSer
4141 AAGCCAGGCATCTACAGATTTGTGGCACCGGGGGAGCGCCCCTCCGGCATGTTCGACTCG
     TTCGGTCCGTAGATGTCTAAACACCGTGGCCCCCTCGCGGGGAGGCCGTACAAGCTGAGC

SerValLeuCysGluCysTyrAspAlaGlyCysAlaTrpTyrGluLeuThrProAlaGlu
4201 TCCGTCCTCTGTGAGTGCTATGACGCAGGCTGTGCTTGGTATGAGCTCACGCCCGCCGAG
     AGGCAGGAGACACTCACGATACTGCGTCCGACACGAACCATACTCGAGTGCGGGCGGCTC

ThrThrValArgLeuArgAlaTyrMetAsnThrProGlyLeuProValCysGlnAspHis
4261 ACTACAGTTAGGCTACGAGCGTACATGAACACCCCGGGGCTTCCCGTGTGCCAGGACCAT
     TGATGTCAATCCGATGCTCGCATGTACTTGTGGGGCCCCGAAGGGCACACGGTCCTGGTA

LeuGluPheTrpGluGlyValPheThrGlyLeuThrHisIleAspAlaHisPheLeuSer
4321 CTTGAATTTTGGGAGGGCGTCTTTACAGGCCTCACTCATATAGATGCCCACTTTCTATCC
     GAACTTAAAACCCTCCCGCAGAAATGTCCGGAGTGAGTATATCTACGGGTGAAAGATAGG

GlnThrLysGlnSerGlyGluAsnLeuProTyrLeuValAlaTyrGlnAlaThrValCys
4381 CAGACAAAGCAGAGTGGGGAGAACCTTCCTTACCTGGTAGCGTACCAAGCCACCGTGTGC
     GTCTGTTTCGTCTCACCCCTCTTGGAAGGAATGGACCATCGCATGGTTCGGTGGCACACG

AlaArgAlaGlnAlaProProProSerTrpAspGlnMetTrpLysCysLeuIleArgLeu
4441 GCTAGGGCTCAAGCCCCTCCCCCATCGTGGGACCAGATGTGGAAGTGTTTGATTCGCCTC
     CGATCCCGAGTTCGGGGAGGGGGTAGCACCCTGGTCTACACCTTCACAAACTAAGCGGAG

LysProThrLeuHisGlyProThrProLeuLeuTyrArgLeuGlyAlaValGlnAsnGlu
4501 AAGCCCACCCTCCATGGGCCAACACCCCTGCTATACAGACTGGGCGCTGTTCAGAATGAA
     TTCGGGTGGGAGGTACCCGGTTGTGGGGACGATATGTCTGACCCGCGACAAGTCTTACTT

IleThrLeuThrHisProValThrLysTyrIleMetThrCysMetSerAlaAspLeuGlu
4561 ATCACCCTGACGCACCCAGTCACCAAATACATCATGACATGCATGTCGGCCGACCTGGAG
     TAGTGGGACTGCGTGGGTCAGTGGTTTATGTAGTACTGTACGTACAGCCGGCTGGACCTC

ValValThrSerThrTrpValLeuValGlyGlyValLeuAlaAlaLeuAlaAlaTyrCys
4621 GTCGTCACGAGCACCTGGGTGCTCGTTGGCGGCGTCCTGGCTGCTTTGGCCGCGTATTGC
     CAGCAGTGCTCGTGGACCCACGAGCAACCGCCGCAGGACCGACGAAACCGGCGCATAACG
```

FIG. 54F

```
       LeuSerThrGlyCysValValIleValGlyArgValValLeuSerGlyLysProAlaIle
4681   CTGTCAACAGGCTGCGTGGTCATAGTGGGCAGGGTCGTCTTGTCCGGGAAGCCGGCAATC
       GACAGTTGTCCGACGCACCAGTATCACCCGTCCCAGCAGAACAGGCCCTTCGGCCGTTAG

IleProAspArgGluValLeuTyrArgGluPheAspGluMetGluGluCysSerGlnHis
4741   ATACCTGACAGGGAAGTCCTCTACCGAGAGTTCGATGAGATGGAAGAGTGCTCTCAGCAC
       TATGGACTGTCCCTTCAGGAGATGGCTCTCAAGCTACTCTACCTTCTCACGAGAGTCGTG

LeuProTyrIleGluGlnGlyMetMetLeuAlaGluGlnPheLysGlnLysAlaLeuGly
4801   TTACCGTACATCGAGCAAGGGATGATGCTCGCCGAGCAGTTCAAGCAGAAGGCCCTCGGC
       AATGGCATGTAGCTCGTTCCCTACTACGAGCGGCTCGTCAAGTTCGTCTTCCGGGAGCCG

LeuLeuGlnThrAlaSerArgGlnAlaGluValIleAlaProAlaValGlnThrAspTrp
4861   CTCCTGCAGACCGCGTCCCGTCAGGCAGAGGTTATCGCCCCTGCTGTCCAGACCAACTGG
       GAGGACGTCTGGCGCAGGGCAGTCCGTCTCCAATAGCGGGGACGACAGGTCTGGTTGACC

GlnLysLeuGluThrPheTrpAlaLysHisMetTrpAsnPheIleSerGlyIleGlnTyr
4921   CAAAAACTCGAGACCTTCTGGGCGAAGCATATGTGGAACTTCATCAGTGGGATACAATAC
       GTTTTTGAGCTCTGGAAGACCCGCTTCGTATACACCTTGAAGTAGTCACCCTATGTTATG

LeuAlaGlyLeuSerThrLeuProGlyAsnProAlaIleAlaSerLeuMetAlaPheThr
4981   TTGGCGGGCTTGTCAACGCTGCCTGGTAACCCCGCCATTGCTTCATTGATGGCTTTTACA
       AACCGCCCGAACAGTTGCGACGGACCATTGGGGCGGTAACGAAGTAACTACCGAAAATGT

AlaAlaValThrSerProLeuThrThrSerGlnThrLeuLeuPheAsnIleLeuGlyGly
5041   GCTGCTGTCACCAGCCCACTAACCACTAGCCAAACCCTCCTCTTCAACATATTGGGGGGG
       CGACGACAGTGGTCGGGTGATTGGTGATCGGTTTGGGAGGAGAAGTTGTATAACCCCCCC

TrpValAlaAlaGlnLeuAlaAlaProGlyAlaAlaThrAlaPheValGlyAlaGlyLeu
5101   TGGGTGGCTGCCCAGCTCGCCGCCCCCGGTGCCGCTACTGCCTTTGTGGGCGCTGGCTTA
       ACCCACCGACGGGTCGAGCGGCGGGGGCCACGGCGATGACGGAAACACCCGCGACCGAAT

AlaGlyAlaAlaIleGlySerValGlyLeuGlyLysValLeuIleAspIleLeuAlaGly
5161   GCTGGCGCCGCCATCGGCAGTGTTGGACTGGGGAAGGTCCTCATAGACATCCTTGCAGGG
       CGACCGCGGCGGTAGCCGTCACAACCTGACCCCTTCCAGGAGTATCTGTAGGAACGTCCC

TyrGlyAlaGlyValAlaGlyAlaLeuValAlaPheLysIleMetSerGlyGluValPro
5221   TATGGCGCGGGCGTGGCGGGAGCTCTTGTGGCATTCAAGATCATGAGCGGTGAGGTCCCC
       ATACCGCGCCCGCACCGCCCTCGAGAACACCGTAAGTTCTAGTACTCGCCACTCCAGGGG

SerThrGluAspLeuValAsnLeuLeuProAlaIleLeuSerProGlyAlaLeuValVal
5281   TCCACGGAGGACCTGGTCAATCTACTGCCCGCCATCCTCTCGCCCGGAGCCCTCGTAGTC
       AGGTGCCTCCTGGACCAGTTAGATGACGGGCGGTAGGAGAGCGGGCCTCGGGAGCATCAG

GlyValValCysAlaAlaIleLeuArgArgHisValGlyProGlyGluGlyAlaValGln
5341   GGCGTGGTCTGTGCAGCAATACTGCGCCGGCACGTTGGCCCGGGCGAGGGGGCAGTGCAG
       CCGCACCAGACACGTCGTTATGACGCGGCCGTGCAACCGGGCCCGCTCCCCCGTCACGTC

TrpMetAsnArgLeuIleAlaPheAlaSerArgGlyAsnHisValSerProThrHisTyr
5401   TGGATGAACCGGCTGATAGCCTTCGCCTCCCGGGGGAACCATGTTTCCCCCACGCACTAC
       ACCTACTTGGCCGACTATCGGAAGCGGAGGGCCCCCTTGGTACAAAGGGGGTGCGTGATG

ValProGluSerAspAlaAlaAlaArgValThrAlaIleLeuSerSerLeuThrValThr
5461   GTGCCGGAGAGCGATGCAGCTGCCCGCGTCACTGCCATACTCAGCAGCCTCACTGTAACC
       CACGGCCTCTCGCTACGTCGACGGGCGCAGTGACGGTATGAGTCGTCGGAGTGACATTGG

GlnLeuLeuArgArgLeuHisGlnTrpIleSerSerGluCysThrThrProCysSerGly
5521   CAGCTCCTGAGGCGACTGCACCAGTGGATAAGCTCGGAGTGTACCACTCCATGCTCCGGT
       GTCGAGGACTCCGCTGACGTGGTCACCTATTCGAGCCTCACATGGTGAGGTACGAGGCCA

SerTrpLeuArgAspIleTrpAspTrpIleCysGluValLeuSerAspPheLysThrTrp
5581   TCCTGGCTAAGGGACATCTGGGACTGGATATGCGAGGTGTTGAGCGACTTTAAGACCTGG
       AGGACCGATTCCCTGTAGACCCTGACCTATACGCTCCACAACTCGCTGAAATTCTGGACC

LeuLysAlaLysLeuMetProGlnLeuProGlyIleProPheValSerCysGlnArgGly
5641   CTAAAAGCTAAGCTCATGCCACAGCTGCCTGGGATCCCCTTTGTGTCCTGCCAGCGCGGG
       GATTTTCGATTCGAGTACGGTGTCGACGGACCCTAGGGGAAACACAGGACGGTCGCGCCC
```

FIG. 54G

```
     TyrLysGlyValTrpArgValAspGlyIleMetHisThrArgCysHisCysGlyAlaGlu
5701 TATAAGGGGGTCTGGCGAGTGGACGGCATCATGCACACTCGCTGCCACTGTGGAGCTGAG
     ATATTCCCCCAGACCGCTCACCTGCCGTAGTACGTGTGAGCGACGGTGACACCTCGACTC

IleThrGlyHisValLysAsnGlyThrMetArgIleValGlyPRoArgThrCysArgAsn
5761 ATCACTGGACATGTCAAAAACGGGACGATGAGGATCGTCGGTCCTAGGACCTGCAGGAAC
     TAGTGACCTGTACAGTTTTTGCCCTGCTACTCCTAGCAGCCAGGATCCTGGACGTCCTTG

MetTrpSerGlyThrPheProIleAsnAlaTyrThrThrGlyProCysThrProLeuPro
5821 ATGTGGAGTGGGACCTTCCCCATTAATGCCTACACCACGGGCCCCTGTACCCCCCTTCCT
     TACACCTCACCCTGGAAGGGGTAATTACGGATGTGGTGCCCGGGGACATGGGGGGAAGGA

AlaProAsnTyrThrPheAlaLeuTrpArgValSerAlaGluGluTyrValGluIleArg
5881 GCGCCGAACTACACGTTCGCGCTATGGAGGGTGTCTGCAGAGGAATATGTGGAGATAAGG
     CGCGGCTTGATGTGCAAGCGCGATACCTCCCACAGACGTCTCCTTATACACCTCTATTCC

GlnValGlyAspPheHisTyrValThrGlyMetThrThrAspAsnLeuLysCysProCys
5941 CAGGTGGGGGACTTCCACTACGTGACGGGTATGACTACTGACAATCTCAAATGCCCGTGC
     GTCCACCCCCTGAAGGTGATGCACTGCCCATACTGATGACTGTTAGAGTTTACGGGCACG

GlnValProSerProGluPhePheThrGluLeuAspGlyValArgLeuHisArgPheAla
6001 CAGGTCCCATCGCCCGAATTTTTCACAGAATTGGACGGGGTGCGCCTACATAGGTTTGCG
     GTCCAGGGTAGCGGGCTTAAAAAGTGTCTTAACCTGCCCCACGCGGATGTATCCAAACGC

ProProCysLysProLeuLeuArgGluGluValSerPheArgValGlyLeuHisGluTyr
6061 CCCCCCTGCAAGCCCTTGCTGCGGGAGGAGGTATCATTCAGAGTAGGACTCCACGAATAC
     GGGGGGACGTTCGGGAACGACGCCCTCCTCCATAGTAAGTCTCATCCTGAGGTGCTTATG

ProValGlySerGlnLeuProCysGluProGluProAspValAlaValLeuThrSerMet
6121 CCGGTAGGGTCGCAATTACCTTGCGAGCCCGAACCGGACGTGGCCGTGTTGACGTCCATG
     GGCCATCCCAGCGTTAATGGAACGCTCGGGCTTGGCCTGCACCGGCACAACTGCAGGTAC

LeuThrAspProSerHisIleThrAlaGluAlaAlaGlyArgArgLeuAlaArgGlySer
6181 CTCACTGATCCCTCCCATATAACAGCAGAGGCGGCCGGGCGAAGGTTGGCGAGGGGATCA
     GAGTGACTAGGGAGGGTATATTGTCGTCTCCGCCGGCCCGCTTCCAACCGCTCCCCTAGT

ProProSerValAlaSerSerSerAlaSerGlnLeuSerAlaProSerLeuLysAlaThr
6241 CCCCCCTCTGTGGCCAGCTCCTCGGCTAGCCAGCTATCCGCTCCATCTCTCAAGGCAACT
     GGGGGGAGACACCGGTCGAGGAGCCGATCGGTCGATAGGCGAGGTAGAGAGTTCCGTTGA

CysThrAlaAsnHisAspSerProAspAlaGluLeuIleGluAlaAsnLeuLeuTrpArg
6301 TGCACCGCTAACCATGACTCCCCTGATGCTGAGCTCATAGAGGCCAACCTCCTATGGAGG
     ACGTGGCGATTGGTACTGAGGGGACTACGACTCGAGTATCTCCGGTTGGAGGATACCTCC

GlnGluMetGlyGlyAsnIleThrArgValGluSerGluAsnLysValValIleLeuAsp
6361 CAGGAGATGGGCGGCAACATCACCAGGGTTGAGTCAGAAAACAAAGTGGTGATTCTGGAC
     GTCCTCTACCCGCCGTTGTAGTGGTCCCAACTCAGTCTTTTGTTTCACCACTAAGACCTG

SerPheAspProLeuValAlaGluGluAspGluArgGluIleSerValProAlaGluIle
6421 TCCTTCGATCCGCTTGTGGCGGAGGAGGACGAGCGGGAGATCTCCGTACCCGCAGAAATC
     AGGAAGCTAGGCGAACACCGCCTCCTCCTGCTCGCCCTCTAGAGGCATGGGCGTCTTTAG

LeuArgLysSerArgArgPheAlaGlnAlaLeuProValTrpAlaArgProAspTyrAsn
6481 CTGCGGAAGTCTCGGAGATTCGCCCAGGCCCTGCCCGTTTGGGCGCGGCCGGACTATAAC
     GACGCCTTCAGAGCCTCTAAGCGGGTCCGGGACGGGCAAACCCGCGCCGGCCTGATATTG

ProProLeuValGluThrTrpLysLysProAspTyrGluProProValValHisGlyCys
6541 CCCCCGCTAGTGGAGACGTGGAAAAAGCCCGACTACGAACCACCTGTGGTCCATGGCTGT
     GGGGGCGATCACCTCTGCACCTTTTTCGGGCTGATGCTTGGTGGACACCAGGTACCGACA

ProLeuProProProLysSerProProValProProProArgLysLysArgThrValVal
6601 CCGCTTCCACCTCCAAAGTCCCCTCCTGTGCCTCCGCCTCGGAAGAAGCGGACGGTGGTC
     GGCGAAGGTGGAGGTTTCAGGGGAGGACACGGAGGCGGAGCCTTCTTCGCCTGCCACCAG

LeuThrGluSerThrLeuSerThrAlaLeuAlaGluLeuAlaThrArgSerPheGlySer
6661 CTCACTGAATCAACCCTATCTACTGCCTTGGCCGAGCTCGCCACCAGAAGCTTTGGCAGC
     GAGTGACTTAGTTGGGATAGATGACGGAACCGGCTCGAGCGGTGGTCTTCGAAACCGTCG
```

FIG. 54H

```
     SerSerThrSerGlyIleThrGlyAspAsnThrThrThrSerSerGluProAlaProSer
6721 TCCTCAACTTCCGGCATTACGGGCGACAATACGACAACATCCTCTGAGCCCGCCCCTTCT
     AGGAGTTGAAGGCCGTAATGCCCGCTGTTATGCTGTTGTAGGAGACTCGGGCGGGGAAGA

GlyCysProProAspSerAspAlaGluSerTyrSerSerMetProProLeuGluGlyGlu
6781 GGCTGCCCCCCCGACTCCGACGCTGAGTCCTATTCCTCCATGCCCCCCCTGGAGGGGGAG
     CCGACGGGGGGGCTGAGGCTGCGACTCAGGATAAGGAGGTACGGGGGGGACCTCCCCCTC

ProGlyAspProAspLeuSerAspGlySerTrpSerThrValSerSerGluAlaAsnAla
6841 CCTGGGGATCCGGATCTTAGCGACGGGTCATGGTCAACGGTCAGTAGTGAGGCCAACGCG
     GGACCCCTAGGCCTAGAATCGCTGCCCAGTACCAGTTGCCAGTCATCACTCCGGTTGCGC

GluAspValValCysCysSerMetSerTyrSerTrpThrGlyAlaLeuValThrProCys
6901 GAGGATGTCGTGTGCTGCTCAATGTCTTACTCTTGGACAGGCGCACTCGTCACCCCGTGC
     CTCCTACAGCACACGACGAGTTACAGAATGAGAACCTGTCCGCGTGAGCAGTGGGGCACG

AlaAlaGluGluGlnLysLeuProIleAsnAlaLeuSerAsnSerLeuLeuArgHisHis
6961 GCCGCGGAAGAACAGAAACTGCCCATCAATGCACTAAGCAACTCGTTGCTACGTCACCAC
     CGGCGCCTTCTTGTCTTTGACGGGTAGTTACGTGATTCGTTGAGCAACGATGCAGTGGTG

AsnLeuValTyrSerThrThrSerArgSerAlaCysGlnArgGlnLysLysValThrPhe
7021 AATTTGGTGTATTCCACCACCTCACGCAGTGCTTGCCAAAGGCAGAAGAAAGTCACATTT
     TTAAACCACATAAGGTGGTGGAGTGCGTCACGAACGGTTTCCGTCTTCTTTCAGTGTAAA

AspARgLeuGlnValLeuAspSerHisTyrGlnAspValLeuLysGluValLysAlaAla
7081 GACAGACTGCAAGTTCTGGACAGCCATTACCAGGACGTACTCAAGGAGGTTAAAGCAGCG
     CTGTCTGACGTTCAAGACCTGTCGGTAATGGTCCTGCATGAGTTCCTCCAATTTCGTCGC

AlaSerLysValLysAlaAsnLeuLeuSerValGluGluAlaCysSerLeuThrProPro
7141 GCGTCAAAAGTGAAGGCTAACTTGCTATCCGTAGAGGAAGCTTGCAGCCTGACGCCCCCA
     CGCAGTTTTCACTTCCGATTGAACGATAGGCATCTCCTTCGAACGTCGGACTGCGGGGGT

HisSerAlaLysSerLysPheGlyTyrGlyAlaLysAspValArgCysHisAlaArgLys
7201 CACTCAGCCAAATCCAAGTTTGGTTATGGGGCAAAAGACGTCCGTTGCCATGCCAGAAAG
     GTGAGTCGGTTTAGGTTCAAACCAATACCCCGTTTTCTGCAGGCAACGGTACGGTCTTTC

AlaValThrHisIleAsnSerValTrpLysAspLeuLeuGluAspAsnValThrProIle
7261 GCCGTAACCCACATCAACTCCGTGTGGAAAGACCTTCTGGAAGACAATGTAACACCAATA
     CGGCATTGGGTGTAGTTGAGGCACACCTTTCTGGAAGACCTTCTGTTACATTGTGGTTAT

AspThrThrIleMetAlaLysAsnGluValPheCysValGlnProGluLysGlyGlyArg
7321 GACACTACCATCATGGCTAAGAACGAGGTTTTCTGCGTTCAGCCTGAGAAGGGGGGTCGT
     CTGTGATGGTAGTACCGATTCTTGCTCCAAAAGACGCAAGTCGGACTCTTCCCCCCAGCA

LysProAlaArgLeuIleValPheProAspLeuGlyValArgValCysGluLysMetAla
7381 AAGCCAGCTCGTCTCATCGTGTTCCCCGATCTGGGCGTGCGCGTGTGCGAAAAGATGGCT
     TTCGGTCGAGCAGAGTAGCACAAGGGGCTAGACCCGCACGCGCACACGCTTTTCTACCGA

LeuTyrAspValValThrLysLeuProLeuAlaValMetGlySerSerTyrGlyPheGln
7441 TTGTACGACGTGGTTACAAAGCTCCCCTTGGCCGTGATGGGAAGCTCCTACGGATTCCAA
     AACATGCTGCACCAATGTTTCGAGGGGAACCGGCACTACCCTTCGAGGATGCCTAAGGTT

TyrSerProGlyGlnArgValGluPheLeuValGlnAlaTrpLysSerLysLysThrPro
7501 TACTCACCAGGACAGCGGGTTGAATTCCTCGTGCAAGCGTGGAAGTCCAAGAAAACCCCA
     ATGAGTGGTCCTGTCGCCCAACTTAAGGAGCACGTTCGCACCTTCAGGTTCTTTTGGGGT

MetGlyPheSerTyrAspThrArgCysPheAspSerThrValThrGluSerAspIleArg
7561 ATGGGGTTCTCGTATGATACCCGCTGCTTTGACTCCACAGTCACTGAGAGCGACATCCGT
     TACCCCAAGAGCATACTATGGGCGACGAAACTGAGGTGTCAGTGACTCTCGCTGTAGGCA

ThrGluGluAlaIleTyrGlnCysCysAspLeuAspProGlnAlaArgValAlaIleLys
7621 ACGGAGGAGGCAATCTACCAATGTTGTGACCTCGACCCCCAAGCCCGCGTGGCCATCAAG
     TGCCTCCTCCGTTAGATGGTTACAACACTGGAGCTGGGGGTTCGGGCGCACCGGTAGTTC

SerLeuThrGluArgLeuTyrValGlyGlyProLeuThrAsnSerArgGlyGluAsnCys
7681 TCCCTCACCGAGAGGCTTTATGTTGGGGGCCCTCTTACCAATTCAAGGGGGGAGAACTGC
     AGGGAGTGGCTCTCCGAAATACAACCCCCGGGAGAATGGTTAAGTTCCCCCCTCTTGACG
```

FIG. 54I

```
         GlyTyrArgArgCysArgAlaSerGlyValLeuThrThrSerCysGlyAsnThrLeuThr
7741 GGCTATCGCAGGTGCCGCGCGAGCGGCGTACTGACAACTAGCTGTGGTAACACCCTCACT
     CCGATAGCGTCCACGGCGCGCTCGCCGCATGACTGTTGATCGACACCATTGTGGGAGTGA

CysTyrIleLysAlaArgAlaAlaCysArgAlaAlaGlyLeuGlnAspCysThrMetLeu
7801 TGCTACATCAAGGCCCGGGCAGCCTGTCGAGCCGCAGGGCTCCAGGACTGCACCATGCTC
     ACGATGTAGTTCCGGGCCCGTCGGACAGCTCGGCGTCCCGAGGTCCTGACGTGGTACGAG

ValCysGlyAspAspLeuValValIleCysGluSerAlaGlyValGlnGluAspAlaAla
7861 GTGTGTGGCGACGACTTAGTCGTTATCTGTGAAAGCGCGGGGGTCCAGGAGGACGCGGCG
     CACACACCGCTGCTGAATCAGCAATAGACACTTTCGCGCCCCCAGGTCCTCCTGCGCCGC

SerLeuArgAlaPheThrGluAlaMetThrArgTyrSerAlaProProGlyAspProPro
7921 AGCCTGAGAGCCTTCACGGAGGCTATGACCAGGTACTCCGCCCCCCTGGGGACCCCCCA
     TCGGACTCTCGGAAGTGCCTCCGATACTGGTCCATGAGGCGGGGGGGACCCCTGGGGGGT

GlnProGluTyrAspLeuGluLeuIleThrSerCysSerSerAsnValSerValAlaHis
7981 CAACCAGAATACGACTTGGAGCTCATAACATCATGCTCCTCCAACGTGTCAGTCGCCCAC
     GTTGGTCTTATGCTGAACCTCGAGTATTGTAGTACGAGGAGGTTGCACAGTCAGCGGGTG

AspGlyAlaGlyLysArgValTyrTyrLeuThrArgAspProThrThrProLeuAlaArg
8041 GACGGCGCTGGAAAGAGGGTCTACTACCTCACCCGTGACCCTACAACCCCCCTCGCGAGA
     CTGCCGCGACCTTTCTCCCAGATGATGGAGTGGGCACTGGGATGTTGGGGGGAGCGCTCT

AlaAlaTrpGluThrAlaArgHisThrProValAsnSerTrpLeuGlyAsnIleIleMet
8101 GCTGCGTGGGAGACAGCAAGACACACTCCAGTCAATTCCTGGCTAGGCAACATAATCATG
     CGACGCACCCTCTGTCGTTCTGTGTGAGGTCAGTTAAGGACCGATCCGTTGTATTAGTAC

PheAlaProThrLeuTrpAlaArgMetIleLeuMetThrHisPhePheSerValLeuIle
8161 TTTGCCCCCACACTGTGGGCGAGGATGATACTGATGACCCATTTCTTTAGCGTCCTTATA
     AAACGGGGGTGTGACACCCGCTCCTACTATGACTACTGGGTAAAGAAATCGCAGGAATAT

AlaArgAspGlnLeuGluGlnAlaLeuAspCysGluIleTyrGlyAlaCysTyrSerIle
8221 GCCAGGGACCAGCTTGAACAGGCCCTCGATTGCGAGATCTACGGGGCCTGCTACTCCATA
     CGGTCCCTGGTCGAACTTGTCCGGGAGCTAACGCTCTAGATGCCCCGGACGATGAGGTAT

GluProLeuAspLeuProProIleIleGlnArgLeu
8281 GAACCACTTGATCTACCTCCAATCATTCAAAGACTC
     CTTGGTGAACTAGATGGAGGTTAGTAAGTTTCTGAG
```

FIG. 56

```
     ArgArgSerArgAsnLeuGlyLysValIleAspThrLeuThrCysGlyPheAlaAsp
  1  CCCGGCGTAGGTCGCGCGCAATTTGGGTAAGGTCATCGATACCCTTACGTGCGGCTTCGCCG
     GGGCCGCATCCAGCGCGTTAAACCCATTCCAGTAGCTATGGGAATGCACGCCGAAGCGGC

LeuMetGlyTyrIleProLeuValGlyLeuGlyAlaProLeuGlyGlyAlaAlaArgAlaLeuAla
 61  ACCTCATGGGGTACATACCGCTCGTCGGCGCCCCTCTTGGAGGCGCTGCCAGGGCCCTGG
     TGGAGTACCCCATGTATGGCGAGCAGCCGCGGGGAGAACCTCCGACGGTCCCGGGACC

HisGlyValLeuArgValLeuGluAspGlyValAsnTyrAlaThrGlyAsnLeuProGlyCys
121  CGCATGGGCGTCCGGGTTCTGGAAGACGGGCGTGAACTATGCAACAGGAACCTTCCTGGTT
     GCGTACCCGCAGGCCCAAGACTTCGCCACTTGATACGTTGTCCTTGGAAGGACCAA

SerPheSerIlePheLeuLeuAlaLeuLeuSerCysLeuThrValProAlaSerAlaTyr
181  GCTCTTTCTCTATCTTTCCTTCTGGCCCTGCTCTCTTGCTGTCCCGCTTCGCCT
     CGAGAAAGAGATAGAAGGAAGACCGGGACGAGAGAACGAACTGACACGGCGAAGCCGGA

GlnValArgAsnSerThrGlyLeuTyrHisValThrAsnAspCysProAsnSerSerIle
241  ACCAAGTGCGCAACTCGCACGGGCTTTACCACGTCACCAATGATTGCCCTAACTCGAGTA
     TGGTTCACGCGTTGAGGTGCCCGAAATGGTGCAGTGGTTACTAACGGGATTGAGCTCAT

---------overlap with CA167b---------
     ValTyrGluAlaAlaAspAlaIleLeuHisThrProGlyCysValProCysValArgGlu
301  TTGTGTACGAAGCGGCCGATGCCATCCTGCACACTCCGGGGTGCGTCCCTTGCGTTCGTG
     AACACATGCTTCGCCGGCTACGGTAGGACGTGTGAGGCCCACGCAGGAACGCAAGCAC GlyAsnAlaSerArgCysTrpValAlaMetThrProThrValAla
361  AGGGCAACGCCTCGAGGTGTTGGGTGGCGATGACCCCTACGGTGCC
     TCCCGTTGCGGAGCTCCACAACCACCGCTACTGGGATGCCACCGG
```

```
      LysLysAsnLysArgAsnThrAsnArgArgProGlnAspValLysPheProGlyGlyGly
  1   AAAAAAAAACAAACGTAACACCAACCGTCGCCCACAGACGTCAAGTTCCCGGGTGCG
      TTTTTTTTTGTTTGCATTGTGGTTGGCAGCGGGTGTCCTGCAGTTCAAGGGCCACCGC

GlnIleValGlyGlyValTyrLeuLeuProArgArgGlyProArgLeuGlyValArgAla
 61   GTCAGATCGTTGGTGGAGTTTACTTGTTGCCCGCCAGGGCCCTAGATTGGGTGTGCGCG
      CAGTCTAGCAACCACCTCAAATGAACAACGGCGCTCCCGGGATCTAACCCACACGCGC

ThrArgLysThrSerGluArgGlnProArgGlyArgArgGlnIleProLysAla
121   CGACGAGAAAGACTTCCGAGCGTCGCCAACCTCGAGGTAGACGCCAGCCTATCCCAAGG
      GCTGCTCTTTCTGAAGGCTCGCAGCGGTTGGAGCTCCATCGCGGTCGGATAGGGTTCC

ArgArgProGluGlyArgThrTrpAlaGlnProGlyTyrProProLeuTyrGlyAsn
181   CTCGTCGGCCCGAGGCGCAGGACCTGGCTCAGCCCGGGTACCCCTTGGCCCTCTATGCA
      GAGCAGCCGGGCTCCCGTCCTGGACCGAGTCGGGCCCATGGGGAACCGGGAGATACCGT

GluGlyCysGlyTrpAlaGlyTrpLeuLeuSerProArgGlySerArgProSerTrpGly
241   ATGAGGGCTGCGGGTGGGGGGTGGCTCCTCCCCGTGCTCTCGGCCTAGCTGGG
      TACTCCCGACGCCCACCCCCGCCCTACCGAGGACAGAGGGCACCGAGAGCCGATCGACCC

ProThrAspProArgArgSerArgAsnLeuGlyLysValIleAspThrLeuThrCys
301   GCCCCACAGACCCCCGGCGTAGGTCGCGCAATTGGGTAAGGTCATCGATACCCTTACGT
      CGGGGTGTCTGGGGGCCGCATCCAGCGCGTTAACCATTCCAGTAGCTATGGAATGCA

GlyPheAlaAspLeuMetGlyTyrIleProLeuValGlyAlaProLeuGlyAlaAla
361   GCGGCTTCGCCGACCTCATGGGGTACATACCGCTCGTCGGCGCCCCTCTTGAGGCGCTG
      CGCCGAAGCGGCTGGAGTACCCCATGTATGCGAGCAGCCGCGGGGAGAACCTCCGCGAC

ArgAlaLeuAlaHisGlyLeuValArgValLeuAspValAlaAsnTyrAlaThrGlyAsn
421   CCAGGGCCCTGGCCGCATGGCCGTCCGGTTCGGAAGACGGCCGTGAACTATGCAACAGGGA
      GGTCCCCGGGACCGGCGTACCGGCAGCCCAAGACCTTCTGCCGCACTTGATACGTTGTCCCT

LeuProGlyCysSerPheSerThrPhe
481   ACCTTCCTGGTTGCTCTTTCTCTACCTTC
      TGGAAGGACCAACGAGAAGATGAAG
```

MetSerValValGlnProProGlyProProLeu

MetAlaLeuValOP

1  CGCAGAAAGCGTCTAGCCATGGCCGTTAGTATGAGTGTGCAGCCTCCAGACCCCCC
   GCGTCTTTCGCAGATCGGTACCGGCAATCATACTCACAGCACGTCGGAGGTCCTGGGGGG

ProGlyGluProAM

61 TCCCGGGAGAGCCATAGTGGTCTGCGGAACCGGTGAGTACACCGGAATTGCCAGGACGAC
   AGGGCCCTCTCGGTATCACCAGACGCCTTGGCCACTCATGTGGCCTTAACGGTCCTGCTG

MetProGlyAspLeuGlyValProProGlnAsp

121 CGGGTCCTTCTTTGGATCAACCCGCTCAATGCCTGGAGATTTGGGCGTGCCCCCGCAAGA
    GCCCAGGAAGAAACCTAGTTGGGCGAGTTACGGACCTCTAAACCCGCACGGGGCGTTCT

CysSAM                                  OP AM GlyAlaCys
                                                    *

181 CTGCTAGCCGAGTAGTGTTGGGTCGCGAAAGGCCTTGTGTACTGCCTGATAGGGTGCTT
    GACGATCGGCTCATCACAACCCAGCGCTTTCCGGAACACCATGACGGACTATCCCACGAA

GluCysProGlyArgSerArgArgProCysThrMetSerThrAsnProLysProGlnLys

FIG. 58B

```
241  GCGAGTGCCCCGGGAGGTCTCGTAGACCGTGCACCATGAGCACGAATCCTAAACCTCAAA
     CGCTCACGGGGCCCTCCAGAGCATCTGGCACGTGGTACTCGTGCTTAGGATTTGGAGTTT
        LysAsnLysArgAsnThrAsnArgArgProGlnAspValLysPheProGlyGlyGlyGln

301  AAAAAACAAACGTAACACCAACCGTCGCCCACAGGACGTCAAGTTCCCGGTGGCGGTC
     TTTTTTGTTTGCATTGTGGTTGGCAGCGGGTGTCCTGCAGTTCAAGGGCCACCGCCAG
        IleValGlyGlyValTyrLeuLeuProArgArgGlyProArgLeuGlyValArgAlaThr

361  AGATCGTTGGTGGAGTTTACTTGTGTGCCGCAGGGCCCTAGATTGGTGTGCCGCGA
     TCTAGCAACCACCTCAAATGAACACACGGCGTCCCCGGATCTAACCACACGGCGCT
        ArgLysThrSerGluArgSerGlnProArgGlyArgArgGlnProIleProLysAlaArg

421  CGAGAAAGACTTCCGAGCGGTCGCAACCTCGAGGTAGACGTCAGCCTATCCCCAAGGCTC
     GCTCTTTCTGAAGGCTCGCCAGCGTTGGAGCTCCATCTGCAGTCGGATAGGGGTTCCGAG
        ArgProGluGlyArgThrTrpAlaGlnProGlyTyrProTrpProLeuTyrGlyAsnGlu
```

```
        |------overlap with CA290a------|
481  GTCGGCCCGAGGGCAGGAGACCTGGCTCAGCCCCGGTACCCTTGCCCCTCTATGGCAATG
     CAGCCGGGCTCCCGTCCTGGACCCGAGTCGGGGCCCATGGGAACCGGGAGATACCGTTAC
            GlyCysGlyTrpAlaGlyTrpLeuLeuSerProArgGlySerArgProSerTrpGlyPro 541  AGGGCTGCGGGTGGGCGGGGATGGCTCCCCGTCTCCCCGTGGCTCTCGGCTTGGCTGGGCC
     TCCCGACGCCCACCCGCCCCTACCGAGGGGCACCGAGAGCCGAGAGCCGATCGACCCCGG
            ThrAspProArgArgSerArgAsnLeuGlyLysValIleAspThrLeuThrCysGly 601  CCACAGACCCCGGGCGTAGGTCGCGCAATTTGGTAAGGTCATCGATACCCTTACGTGCG
     GGTGTCTGGGGCCGCATCCAGCGCGTTAAACCCATTCCAGTAGCTATGGAATGCACGC
            Phe

661  GCTTC
     CGAAG
```

* = Start of long HCV ORF  
| = Putative first amino acid of large HCV polyprotein  
# = Putative small encoded peptides (that may play a translational regulatory role)

```
     ValLeuGlyArgGluArgProCysGlyThrAlaOP AM GlyAlaCysGluCysProGly
  1  GTCTTGGGTCGCGAAAGGCCTTGTGGTACTGCCTGATAGGGTGCTTGCGAGTGCCCGGG
     CAGAACCCAGCGCTTTCCGAACACCATGAGCGACTATCCCACGAACGCTCACGGACCCC
                              *

ArgSerArgArgProCysThrMetSerThrAsnProLysProGlnArgLysThrLysArg
 61  AGGTCTCGTAGACCGTGCACCATGAGCACGAATCCTAAACCTCAAAGAAAAACCAAACGT
     TCCAGAGCATCTGGCACGTGGTACTCGTGCTTAGGATTTGGAGTTTCTTTTTGGTTTGCA

AsnThrAsnArgArgProGlnAspValLysPheProGlyGlyGlyGlnIleValGlyGly
121  AACACCAACCGTCGCCCACAGGACGTCAAGTTCCCGGGTGGCGGTCAGATCGTTGGTGGA
     TTGTGGTTGGCAGCGGGTGTCCTGCAGTTCAAGGGCCCACCGCCAGTCTAGCAACCACCT

ValTyrLeuLeuProArgArgGlyProArgLeuGlyValArgAlaThrArgLysThrSer
181  GTTTACTTGTTGCCGCGAGGGGCCCTAGATTGGGTGCGCGCGACGAGAAAGACTTCC
     CAAATGAACAACGGCGCTCCCCGGGATCTAACCACACGCGCTGCTCTTTCTGAAGG
                  ──────overlap with CA290a──────

GluArgSerGlnProArgGlyArgArgGlnProIleProLysAlaArgArgProGluGly
241  GAGCGGTCGCAACCTCGAGGTAGACGTCAGCCTATCCCCAAGGCTCGTCGGCCCGAGGGC
     CTCGCCAGCGTTGGAGCTCCATCTGCAGTCGGATAGGGGTTCCGAGCAGCCGGGCTCCCG

ArgThrTrpAlaGlnProGlyTyrProTrpProLeuTyrGlyAsnGluGlyCys
301  AGGACCTGGGCTCAGCCCGGGCTACCCTGGCCCCTCTATGCCAATGAGGGCTGCG
     TCCTGGACCCGAGTCGGGCCCGATGGGAACCGGGGAGATACCGTTACTCCCGACGC
            * = putative initiator methionine codon
```

FIG. 60

```
    #ProProOP
    #SerThrMetAsnHisSerProValArgAsnTyrCysLeuHisAlaGluSerValAM
    #LeuHisHisGluSerLeuProCysGluLeuLeuSerSerArgArgLysArgLeuAla
    CTCCACCATGAATCACTCCCTGTGAGGAACTACTGTCTTCACGCAGAAAGCGTCTAGCC
  1 CTTCCACCATGAATCACTCCCTGTGAGGAACTACTGTCTTCACGCAGAAAGCGTCTAGCC
    GAGGTGGTACTTAGTGAGGGACACTCCTTGATGACAGAAGTGCGTCTTTCGCAGATCGG
                                          #MetSerValValGlnProProLeuProProGlyProAM
    MetAlaLeuValOP
 61 ATGGCGTTAGTAGTATGAGTGTCGTGCAGCCTCCAGGACCCCCCCTCCCGGGAGAGCCATAGT
    TACCGCAATCATATACTCACAGCACGTCGGAGGTCCTGGGGAGGCCCTCGTATCA
                      ------overlap with ag30a------
121 GGTCTGCGGAACCGGTGAGTACACCGGAATTGCCAGGACGACCGGTCCTTTCTTGGATC
    CCAGAGCGCCTTGGCCACTCATGTGGCCTTAACGGTCCTGCTGCCCAGGAAAGAACCTAG
                    #MetProGlyAspLeuGlyValProProGlnAspCysAM
181 AACCCGCTCAATGCCTGGAGATTTGGGCGTGCCCCCGCAAGACTGCTAGCCGAGTAGTGT
    TTGGGCGAGTTACGGACCTCTAAACCCGCACGGGGCGTTCTGACGATCGGCTCATCACA
                                                  OP AM GlyAlaCysGluCysProGlyArgSer
                                                        *
241 TGGGTCGCGGAAAGGCCTTGTGGTACTGCCTGATAGGTGCTTGCCGAGTGCCCCGGGAGGT
    ACCCAGCGCCTTTCCGGAACACCATGACGGACTATCCACGAACGCTCACGGGCCCTCCA
    ArgArg
301 CTCGTAGA
    GAGCATCT
```

\* = Start of long HCV ORF
\# = Putative small encoded peptides (that may play a translational regulatory role)

FIG. 61

```
-----Overlap with 15e -----
    GlyAlaCysTyrSerIleGluProLeuAspLeuProProIleIleGlnArgLeuHisGly
  1 GGGGCCTGCTACTCCATAGAACCACTGGATCTACCTCCAATCATTCAAAGACTTCCATGGC
    CCCCGGACGATGAGGTATCTTGGTGACCTAGATGGAGGTTAGTAAGTTTCTGAAGGTACCG LeuSerAlaPheSerLeuHisSerTyrSerProGlyGluIleAsnArgValAlaAlaCys
 61 CTCAGCGCATTTCACTCCACAGTTACTCTCCAGGTGAAATTAATAGGGTGCCGCATGC
    GAGTCGCGTAAAGTGAGGTGTCAATGAGAGGTCCACTTTAATTATCCCACGGCGTACG
                                                    Gly*
                                                      G LeuArgLysLeuGlyValProProLeuArgAlaTrpArgHisArgAlaArgSerValArg
121 CTCAGAAAACTTGGGGTACCGCCCCTTGCGAGCTTGGAGACACCGGGCCCGGAGCGTCCGC
    GAGTCTTTTGAACCCCATGGCGGGGAACGCTCGAACCTCTGTGGCCCGGGCCTCGCAGGCG AlaArgLeuLeuAlaArgGlyGlyArgAlaAlaIleCysGlyLysTyrLeuPheAsnTrp
181 GCTAGGCTTCTGGCCAGAGGAGGCAGGGCTGCCATATGTGGCAAGTACCTCTTCAACTGG
    CGATCCGAAGACCGGTCTCCTCCGTCCCGACGGTATACACCGTTCATGGAGAAGTTGACC AlaValArgThrLysLeuLys
241 GCAGTAAGAACAAAGCTCAAAC
    CGTCATTCTTGTTTCGAGTTTG
```

* = nucleotide heterogeneity

FIG. 62A

```
CACTCCACCATGAATCACTCCCCTGTGAGGAACTACTGTCTTCACGCAGAAAGCGTCTAG
CCATGGCGTTAGTATGAGTGTCGTGCAGCCTCCAGGACCCCCCCTCCCGGGAGAGCCATA
GTGGTCTGCGGAACCGGTGAGTACACCGGAATTGCCAGGACGACCGGGTCCTTTCTTGGA
TCAACCCGCTCAATGCCTGGAGATTTGGGCGTGCCCCGCAAGACTGCTAGCCGAGTAGT
GTTGGGTCGCGAAAGGCCTTGTGGTACTGCCTGATAGGGTGCTTGCGAGTGCCCCGGGAG-300
                    ---(Putative initiator methionine codon)
GTCTCGTAGACCGTGCACCATGAGCACGAATCCTAAACCTCAAAAAAAAAACAAACGTAA
CACCAACCGTCGCCCACAGGACGTCAAGTTCCCGGGTGGCGGTCAGATCGTTGGTGGAGT
TTACTTGTTGCCGCGCAGGGGCCCTAGATTGGGTGTGCGCGCGACGAGAAAGACTTCCGA
GCGGTCGCAACCTCGAGGTAGACGTCAGCCTATCCCCAAGGCTCGTCGGCCCGAGGGCAG
GACCTGGGCTCAGCCCGGGTACCCTTGGCCCCTCTATGGCAATGAGGGCTGCGGGTGGGC-600
GGGATGGCTCCTGTCTCCCCGTGGCTCTCGGCCTAGCTGGGGCCCCACAGACCCCCGGCG
TAGGTCGCGCAATTTGGGTAAGGTCATCGATACCCTTACGTGCGGCTTCGCCGACCTCAT
GGGGTACATACCGCTCGTCGGCGCCCCTCTTGGAGGCGCTGCCAGGGCCCTGGCGCATGG
CGTCCGGGTTCTGGAAGACGGCGTGAACTATGCAACAGGGAACCTTCCTGGTTGCTCTTT
CTCTATCTTCCTTCTGGCCCTGCTCTCTTGCTTGACTGTGCCCGCTTCGGCCTACCAAGT-900
GCGCAACTCCACGGGGCTTTACCACGTCACCAATGATTGCCCTAACTCGAGTATTGTGTA
CGAGGCGGCCGATGCCATCCTGCACACTCCGGGGTGCGTCCCTTGCGTTCGTGAGGGCAA
CGCCTCGAGGTGTTGGGTGGCGATGACCCCTACGGTGGCCACCAGGGATGGCAAACTCCC
CGCGACGCAGCTTCGACGTCACATCGATCTGCTTGTCGGGAGCGCCACCCTCTGTTCGGC
CCTCTACGTGGGGGACCTATGCGGGTCTGTCTTTCTTGTCGGCCAACTGTTCACCTTCTC-1200
TCCCAGGCGCCACTGGACGACGCAAGGTTGCAATTGCTCTATCTATCCCGGCCATATAAC
GGGTCACCGCATGGCATGGGATATGATGATGAACTGGTCCCCTACGACGGCGTTGGTAAT
GGCTCAGCTGCTCCGGATCCCACAAGCCATCTTGGACATGATCGCTGGTGCTCACTGGGG
AGTCCTGGCGGGCATAGCGTATTTCTCCATGGTGGGGAACTGGGCGAAGGTCCTGGTAGT
GCTGCTGCTATTTGCCGGCGTCGACGCGGAAACCCACGTCACCGGGGGAAGTGCCGGCCA-1500
CACTGTGTCTGGATTTGTTAGCCTCCTCGCACCAGGCGCCAAGCAGAACGTCCAGCTGAT
CAACACCAACGGCAGTTGGCACCTCAATAGCACGGCCCTGAACTGCAATGATAGCCTCAA
CACCGGCTGGTTGGCAGGGCTTTTCTATCACCACAAGTTCAACTCTTCAGGCTGTCCTGA
GAGGCTAGCCAGCTGCCGACCCCTTACCGATTTTGACCAGGGCTGGGGCCCTATCAGTTA
TGCCAACGGAAGCGGCCCCGACCAGCGCCCTACTGCTGGCACTACCCCCAAAACCTTG-1800
CGGTATTGTGCCCGCGAAGAGTGTGTGTGGTCCGGTATATTGCTTCACTCCCAGCCCCGT
GGTGGTGGGAACGACCGACAGGTCGGGCGCGCCCACCTACAGCTGGGGTGAAAATGATAC
GGACGTCTTCGTCCTTAACAATACCAGGCCACCGCTGGGCAATTGGTTCGGTTGTACCTG
GATGAACTCAACTGGATTCACCAAAGTGTGCGGAGCGCCTCCTTGTGTCATCGGAGGGGC
GGGCAACAACACCCTGCACTGCCCCACTGATTGCTTCCGCAAGCATCCGGACGCCACATA-2100
CTCTCGGTGCGGCTCCGGTCCCTGGATCACACCCAGGTGCCTGGTCGACTACCCGTATAG
GCTTTGGCATTATCCTTGTACCATCAACTACACCATATTTAAAATCAGGATGTACGTGGG
AGGGGTCGAACACAGGCTGGAAGCTGCCTGCAACTGGACGCGGGGCGAACGTTGCGATCT
GGAAGACAGGGACAGGTCCGAGCTCAGCCCGTTACTGCTGACCACTACACAGTGGCAGGT
CCTCCCGTGTTCCTTCACAACCCTACCAGCCTTGTCCACCGGCCTCATCCACCTCCACCA-2400
GAACATTGTGGACGTGCAGTACTTGTACGGGGTGGGGTCAAGCATCGCGTCCTGGGCCAT
TAACTGGGAGTACGTCGTTCTCCTGTTCCTTCTGCTTGCAGACGCGCCGCGTCTGCTCCTG
CTTGTGGATGATGCTACTCATATCCCAAGCGGAAGCGGCTTTGGAGAACCTCGTAATACT
TAATGCAGCATCCCTGGCCGGGACGCACGGTCTTGTATCCTTCCTCGTGTTCTTCTGCTT
TGCATGGTATTTGAAGGGTAAGTGGGTGCCCGGAGCGGTCTACACCTTCTACGGGATGTG-2700
GCCTCTCCTCCTGCTCCTGTTGGCGTTGCCCCAGCGGGCGTACGCGCTGGACACGGAGGT
GGCCGCGTCGTGTGGCGGTGTTGTTCTCGTCGGGTTGATGGCGCTGACTCTGTCACCATA
TTACAAGCGCTATATCAGCTGGTGCTTGTGGTGGCTTCAGTATTTTCTGACCAGAGTGGA
AGCGCAACTGCACGTGTGGATTCCCCCCCTCAACGTCCGAGGGGGGCGCGACGCCGTCAT
CTTACTCATGTGTGCTGTACACCCGACTCTGGTATTTGACATCACCAAATTGCTGCTGGC-3000
CGTCTTCGGACCCCTTTGGATTCTTCAAGCCAGTTTGCTTAAAGTACCCTACTTTGTGCG
CGTCCAAGGCCTTCTCCGGTTCTGCGCGTTAGCGCGGAAGATGATCGGAGGCCATTACGT
GCAAATGGTCATCATTAAGTTAGGGGCGCTTACTGGCACCTATGTTTATAACCATCTCAC
TCCTCTTCGGGACTGGGCGCACAACGGCTTGCGAGATCTGGCCGTGGCTGTAGAGCCAGT
CGTCTTCTCCCAAATGGAGACCAAGCTCATCACGTGGGGGGCAGATACCGCCGCGTGCGG-3300
TGACATCATCAACGGCTTGCCTGTTTCCGCCCGCAGGGGCCGGGAGATACTGCTCGGGCC
AGCCGATGGAATGGTCTCCAAGGGGTGGAGGTTGCTGGCGCCCATCACGGCGTACGCCCA
GCAGACAAGGGGCCTCCTAGGGTGCATAATCACCAGCCTAACTGGCCGGGACAAAAACCA
AGTGGAGGGTGAGGTCCAGATTGTGTCAACTGCTGCCCAAAACCTTCCTGGCAACGTGCAT
```

FIG. 62B

```
CAATGGGGTGTGCTGGACTGTCTACCACGGGGCCGGAACGAGGACCATCGCGTCACCCAA-3600
GGGTCCTGTCATCCAGATGTATACCAATGTAGACCAAGACCTTGTGGGCTGGCCCGCTCC
GCAAGGTAGCCGCTCATTGACACCCTGCACTTGCGGCTCCTCGGACCTTTACCTGGTCAC
GAGGCACGCCGATGTCATTCCCGTGCGCCGGCGGGGTGATAGCAGGGGCAGCCTGCTGTC
GCCCCGGCCCATTTCCTACTTGAAAGGCTCCTCGGGGGGTCCGCTGTTGTGCCCCGCGGG
GCACGCCGTGGGCATATTTAGGGCCGCGGTGTGCACCCGTGGAGTGGCTAAGGCGGTGGA-3900
CTTTATCCCTGTGGAGAACCTAGAGACAACCATGAGGTCCCCGGTGTTCACGGATAACTC
CTCTCCACCAGTAGTGCCCCAGAGCTTCCAGGTGGCTCACCTCCATGCTCCCACAGGCAG
CGGCAAAAGCACCAAGGTCCCGGCTGCATATGCAGCTCAGGGCTATAAGGTGCTAGTACT
CAACCCCTCTGTTGCTGCAACACTGGGCTTTGGTGCTTACATGTCCAAGGCTCATGGGAT
CGATCCTAACATCAGGACCGGGGTGAGAACAATTACCACTGGCAGCCCCATCACGTACTC-4200
CACCTACGGCAAGTTCCTTGCCGACGGCGGGTGCTCGGGGGGCGCTTATGACATAATAAT
TTGTGACGAGTGCCACTCCACGGATGCCACATCCATCTTGGGCATCGGCACTGTCCTTGA
CCAAGCAGAGACTGCGGGGGCGAGACTGGTTGTGCTCGCCACCGCCACCCCTCCGGGCTC
CGTCACTGTGCCCCATCCCAACATCGAGGAGGTTGCTCTGTCCACCACCGGAGAGATCCC
TTTTTACGGCAAGGCTATCCCCCTCGAAGTAATCAAGGGGGGGAGACATCTCATCTTCTG-4500
TCATTCAAAGAAGAAGTGCGACGAACTCGCCGCAAAGCTGGTCGCATTGGGCATCAATGC
CGTGGCCTACTACCGCGGTCTTGACGTGTCCGTCATCCCGACCAGCGGCGATGTTGTCGT
CGTGGCAACCGATGCCCTCATGACCGGCTATACCGGCGACTTCGACTCGGTGATAGACTG
CAATACGTGTGTCACCCAGACAGTCGATTTCAGCCTTGACCCTACCTTCACCATTGAGAC
AATCACGCTCCCCCAGGATGCTGTCTCCCGCACTCAACGTCGGGGCAGGACTGGCAGGGG-4800
GAAGCCAGGCATCTACAGATTTGTGGCACCGGGGGAGCGCCCCTCCGGCATGTTCGACTC
GTCCGTCCTCTGTGAGTGCTATGACGCAGGCTGTGCTTGGTATGAGCTCACGCCCGCCGA
GACTACAGTTAGGCTACGAGCGTACATGAACACCCCGGGGCTTCCCGTGTGCCAGGACCA
TCTTGAATTTTGGGAGGGCGTCTTTACAGGCCTCACTCATATAGATGCCCACTTTCTATC
CCAGACAAAGCAGAGTGGGGAGAACCTTCCTTACCTGGTAGCGTACCAAGCCACCGTGTG-5100
CGCTAGGGCTCAAGCCCCTCCCCCATCGTGGGACCAGATGTGGAAGTGTTTGATTCGCCT
CAAGCCCACCCTCCATGGGCCAACACCCCTGCTATACAGACTGGGCGCTGTTCAGAATGA
AATCACCCTGACGCACCCAGTCACCAAATACATCATGACATGCATGTCGGCCGACCTGGA
GGTCGTCACGAGCACCTGGGTGCTCGTTGGCGGCGTCCTGGCTGCTTTGGCCGCGTATTG
CCTGTCAACAGGCTGCGTGGTCATAGTGGGCAGGGTCGTCTTGTCCGGGAAGCCGGCAAT-5400
CATACCTGACAGGGAAGTCCTCTACCGAGAGTTCGATGAGATGGAAGAGTGCTCTCAGCA
CTTACCGTACATCGAGCAAGGGATGATGCTCGCCGAGCAGTTCAAGCAGAAGGCCCTCGG
CCTCCTGCAGACCGCGTCCCGTCAGGCAGAGGTTATCGCCCCTGCTGTCCAGACCAACTG
GCAAAAACTCGAGACCTTCTGGGCGAAGCATATGTGGAACTTCATCAGTGGGATACAATA
CTTGGCGGGCTTGTCAACGCTGCCTGGTAACCCCGCCATTGCTTCATTGATGGCTTTTAC-5700
AGCTGCTGTCACCAGCCCACTAACCACTAGCCAAACCCTCCTCTTCAACATATTGGGGGG
GTGGGTGGCTGCCCAGCTCGCCGCCCCGGTGCCGCTACTGCCTTTGTGGGCGCTGGCTT
AGCTGGCGCCGCCATCGGCAGTGTTGGACTGGGGAAGGTCCTCATAGACATCCTTGCAGG
GTATGGCGCGGGCGTGGCGGGAGCTCTTGTGGCATTCAAGATCATGAGCGGTGAGGTCCC
CTCCACGGAGGACCTGGTCAATCTACTGCCCGCCATCCTCTCGCCCGGAGCCCTCGTAGT-6000
CGGCGTGGTCTGTGCAGCAATACTGCGCCGGCACGTTGGCCCGGGCGAGGGGCAGTGCA
GTGGATGAACCGGCTGATAGCCTTCGCCTCCCGGGGGAACCATGTTTCCCCCACGCACTA
CGTGCCGGAGAGCGATGCAGCTGCCCGCGTCACTGCCATACTCAGCAGCCTCACTGTAAC
CCAGCTCCTGAGGCGACTGCACCAGTGGATAAGCTCGGAGTGTACCACTCCATGCTCCGG
TTCCTGGCTAAGGGACATCTGGGACTGGATATGCGAGGTGTTGAGCGACTTTAAGACCTG-6300
```

FIG. 62C

```
GCTAAAAGCTAAGCTCATGCCACAGCTGCCTGGGATCCCCTTTGTGTCCTGCCAGCGCGG
GTATAAGGGGGTCTGGCGAGTGGACGGCATCATGCACACTCGCTGCCACTGTGGAGCTGA
GATCACTGGACATGTCAAAAACGGGACGATGAGGATCGTCGGTCCTAGGACCTGCAGGAA
CATGTGGAGTGGGACCTTCCCCATTAATGCCTACACCACGGGCCCCTGTACCCCCTTCC
TGCGCCGAACTACACGTTCGCGCTATGGAGGGTGTCTGCAGAGGAATATGTGGAGATAAG-6600
GCAGGTGGGGGACTTCCACTACGTGACGGGTATGACTACTGACAATCTCAAATGCCCGTG
CCAGGTCCCATCGCCCGAATTTTTCACAGAATTGGACGGGGTGCGCCTACATAGGTTTGC
GCCCCCCTGCAAGCCCTTGCTGCGGGAGGAGGTATCATTCAGAGTAGGACTCCACGAATA
CCCGGTAGGGTCGCAATTACCTTGCGAGCCCGAACCGGACGTGGCCGTGTTGACGTCCAT
GCTCACTGATCCCTCCCATATAACAGCAGAGGCGGCCGGGCGAAGGTTGGCGAGGGGATC-6900
ACCCCCCTCTGTGGCCAGCTCCTCGGCTAGCCAGCTATCCGCTCCATCTCTCAAGGCAAC
TTGCACCGCTAACCATGACTCCCCTGATGCTGAGCTCATAGAGGCCAACCTCCTATGGAG
GCAGGAGATGGGCGGCAACATCACCAGGGTTGAGTCAGAAAACAAAGTGGTGATTCTGGA
CTCCTTCGATCCGCTTGTGGCGGAGGAGGACGAGCGGGAGATCTCCGTACCCGCAGAAAT
CCTGCGGAAGTCTCGGAGATTCGCCCAGGCCCTGCCCGTTTGGGCGCGGCCGGACTATAA-7200
CCCCCCGCTAGTGGAGACGTGGAAAAAGCCCGACTACGAACCACCTGTGGTCCATGGCTG
TCCGCTTCCACCTCCAAAGTCCCCTCCTGTGCCTCCGCCTCGGAAGAAGCGGACGGTGGT
CCTCACTGAATCAACCCTATCTACTGCCTTGGCCGAGCTCGCCACCAGAAGCTTTGGCAG
CTCCTCAACTTCCGGCATTACGGGCGACAATACGACAACATCCTCTGAGCCCGCCCCTTC
TGGCTGCCCCCCCGACTCCGACGCTGAGTCCTATTCCTCCATGCCCCCCCTGGAGGGGGA-7500
GCCTGGGGATCCGGATCTTAGCGACGGGTCATGGTCAACGGTCAGTAGTGAGGCCAACGC
GGAGGATGTCGTGTGCTGCTCAATGTCTTACTCTTGGACAGGCGCACTCGTCACCCCGTG
CGCCGCGGAAGAACAGAAACTGCCCATCAATGCACTAAGCAACTCGTTGCTACGTCACCA
CAATTTGGTGTATTCCACCACCTCACGCAGTGCTTGCCAAAGGCAGAAGAAAGTCACATT
TGACAGACTGCAAGTTCTGGACAGCCATTACCAGGACGTACTCAAGGAGGTTAAAGCAGC-7800
GGCGTCAAAAGTGAAGGCTAACTTGCTATCCGTAGAGGAAGCTTGCAGCCTGACGCCCCC
ACACTCAGCCAAATCCAAGTTTGGTTATGGGGCAAAAGACGTCCGTTGCCATGCCAGAAA
GGCCGTAACCCACATCAACTCCGTGTGGAAAGACCTTCTGGAAGACAATGTAACACCAAT
AGACACTACCATCATGGCTAAGAACGAGGTTTTCTGCGTTCAGCCTGAGAAGGGGGTCG
TAAGCCAGCTCGTCTCATCGTGTTCCCCGATCTGGGCGTGCGCGTGTGCGAAAAGATGGC-8100
TTTGTACGACGTGGTTACAAAGCTCCCCTTGGCCGTGATGGGAAGCTCCTACGGATTCCA
ATACTCACCAGGACAGCGGGTTGAATTCCTCGTGCAAGCGTGGAAGTCCAAGAAAACCCC
AATGGGGTTCTCGTATGATACCCGCTGCTTTGACTCCACAGTCACTGAGAGCGACATCCG
TACGGAGGAGGCAATCTACCAATGTTGTGACCTCGACCCCCAAGCCCGCGTGGCCATCAA
GTCCCTCACCGAGAGGCTTTATGTTGGGGCCCTCTTACCAATTCAAGGGGGAGAACTG-8400
CGGCTATCGCAGGTGCCGCGCGAGCGGCGTACTGACAACTAGCTGTGGTAACACCCTCAC
TTGCTACATCAAGGCCCGGGCAGCCTGTCGAGCCGCAGGGCTCCAGGACTGCACCATGCT
CGTGTGTGGCGACGACTTAGTCGTTATCTGTGAAAGCGCGGGGGTCCAGGAGGACGCGGC
GAGCCTGAGAGCCTTCACGGAGGCTATGACCAGGTACTCCGCCCCCCCTGGGGACCCCCC
ACAACCAGAATACGACTTGGAGCTCATAACATCATGCTCCTCCAACGTGTCAGTCGCCCA-8700
CGACGGCGCTGGAAAGAGGGTCTACTACCTCACCCGTGACCCTACAACCCCCCTCGCGAG
AGCTGCGTGGGAGACAGCAAGACACACTCCAGTCAATTCCTGGCTAGGCAACATAATCAT
GTTTGCCCCCACACTGTGGGCGAGGATGATACTGATGACCCATTTCTTTAGCGTCCTTAT
AGCCAGGGACCAGCTTGAACAGGCCCTCGATTGCGAGATCTACGGGGCCTGCTACTCCAT
AGAACCACTTGATCTACCTCCAATCATTCAAAGACTCCATGGCCTCAGCGCATTTTCACT-9000
CCACAGTTACTCTCCAGGTGAAATTAATAGGGTGGCCGCATGCCTCAGAAAACTTGGGGT
ACCGCCCTTGCGAGCTTGGAGACACCGGGCCCGGAGCGTCCGCGCTAGGCTTCTGGCCAG
AGGAGGCAGGGCTGCCATATGTGGCAAGTACCTCTTCAACTGGGCAGTAAGAACAAAGCT
CAAAC
```

FIG. 62D

```
   1 CACTCCACCATGAATCACTCCCCTGTGAGGAACTACTGTCTTCACGCAGAAAGCGTCTAG
     GTGAGGTGGTACTTAGTGAGGGGACACTCCTTGATGACAGAAGTGCGTCTTTCGCAGATC
  61 CCATGGCGTTAGTATGAGTGTCGTGCAGCCTCCAGGACCCCCCTCCCGGGAGAGCCATA
     GGTACCGCAATCATACTCACAGCACGTCGGAGGTCCTGGGGGGGAGGGCCCTCTCGGTAT
 121 GTGGTCTGCGGAACCGGTGAGTACACCGGAATTGCCAGGACGACCGGGTCCTTTCTTGGA
     CACCAGACGCCTTGGCCACTCATGTGGCCTTAACGGTCCTGCTGGCCCAGGAAAGAACCT
 181 TCAACCCGCTCAATGCCTGGAGATTTGGGCGTGCCCCCGCAAGACTGCTAGCCGAGTAGT
     AGTTGGGCGAGTTACGGACCTCTAAACCCGCACGGGGCGTTCTGACGATCGGCTCATCA
 241 GTTGGGTCGCGAAAGGCCTTGTGGTACTGCCTGATAGGGTGCTTGCGAGTGCCCCGGGAG
     CAACCCAGCGCTTTCCGGAACACCATGACGGACTATCCCACGAACGCTCACGGGGCCCTC
 301 GTCTCGTAGACCGTGCACCATGAGCACGAATCCTAAACCTCAAAAAAAAAACAAACGTAA
     CAGAGCATCTGGCACGTGGTACTCGTGCTTAGGATTTGGAGTTTTTTTTTTGTTTGCATT
 361 CACCAACCGTCGCCCACAGGACGTCAAGTTCCCGGGTGGCGGTCAGATCGTTGGTGGAGT
     GTGGTTGGCAGCGGGTGTCCTGCAGTTCAAGGGCCCACCGCCAGTCTAGCAACCACCTCA
 421 TTACTTGTTGCCGCGCAGGGGCCCTAGATTGGGTGTGCGCGCGACGAGAAAGACTTCCGA
     AATGAACAACGGCGCGTCCCCGGGATCTAACCCACACGCGCGCTGCTCTTTCTGAAGGCT
 481 GCGGTCGCAACCTCGAGGTAGACGTCAGCCTATCCCCAAGGCTCGTCGGCCCGAGGGCAG
     CGCCAGCGTTGGAGCTCCATCTGCAGTCGGATAGGGGTTCCGAGCAGCCGGGCTCCCGTC
 541 GACCTGGGCTCAGCCCGGGTACCCTTGGCCCCTCTATGGCAATGAGGGCTGCGGGTGGGC
     CTGGACCCGAGTCGGGCCCATGGGAACCGGGGAGATACCGTTACTCCCGACGCCCACCCG
 601 GGGATGGCTCCTGTCTCCCCGTGGCTCTCGGCCTAGCTGGGGCCCCACAGACCCCCGGCG
     CCCTACCGAGGACAGAGGGGCACCGAGAGCCGGATCGACCCCGGGGTGTCTGGGGGCCGC
 661 TAGGTCGCGCAATTTGGGTAAGGTCATCGATACCCTTACGTGCGGCTTCGCCGACCTCAT
     ATCCAGCGCGTTAAACCCATTCCAGTAGCTATGGGAATGCACGCCGAAGCGGCTGGAGTA
 721 GGGGTACATACCGCTCGTCGGCGCCCCTCTTGGAGGCGCTGCCAGGGCCCTGGCGCATGG
     CCCCATGTATGGCGAGCAGCCGCGGGGAGAACCTCCGCGACGGTCCCGGGACCGCGTACC
 781 CGTCCGGGTTCTGGAAGACGGCGTGAACTATGCAACAGGGAACCTTCCTGGTTGCTCTTT
     GCAGGCCCAAGACCTTCTGCCGCACTTGATACGTTGTCCCTTGGAAGGACCAACGAGAAA
 841 CTCTATCTTCCTTCTGGCCCTGCTCTCTTGCTTGACTGTGCCCGCTTCGGCCTACCAAGT
     GAGATAGAAGGAAGACCGGGACGAGAGAACGAACTGACACGGGCGAAGCCGGATGGTTCA
 901 GCGCAACTCCACGGGGCTTTACCACGTCACCAATGATTGCCCTAACTCGAGTATTGTGTA
     CGCGTTGAGGTGCCCCGAAATGGTGCAGTGGTTACTAACGGGATTGAGCTCATAACACAT
 961 CGAGGCGGCCGATGCCATCCTGCACACTCCGGGGTGCGTCCCTTGCGTTCGTGAGGGCAA
     GCTCCGCCGGCTACGGTAGGACGTGTGAGGCCCACGCAGGGAACGCAAGCACTCCCGTT
1021 CGCCTCGAGGTGTTGGGTGGCGATGACCCCTACGGTGGCCACCAGGGATGGCAAACTCCC
     GCGGAGCTCCACAACCCACCGCTACTGGGGATGCCACCGGTGGTCCCTACCGTTTGAGGG
1081 CGCGACGCAGCTTCGACGTCACATCGATCTGCTTGTCGGGAGCGCCACCCTCTGTTCGGC
     GCGCTGCGTCGAAGCTGCAGTGTAGCTAGACGAACAGCCCTCGCGGTGGGAGACAAGCCG
1141 CCTCTACGTGGGGGACCTATGCGGGTCTGTCTTTCTTGTCGGCCAACTGTTCACCTTCTC
     GGAGATGCACCCCCTGGATACGCCCAGACAGAAAGAACAGCCGGTTGACAAGTGGAAGAG
1201 TCCCAGGCGCCACTGGACGACGCAAGGTTGCAATTGCTCTATCTATCCCGGCCATATAAC
     AGGGTCCGCGGTGACCTGCTGCGTTCCAACGTTAACGAGATAGATAGGGCCGGTATATTG
1261 GGGTCACCGCATGGCATGGGATATGATGATGAACTGGTCCCCTACGACGGCGTTGGTAAT
     CCCAGTGGCGTACCGTACCCTATACTACTACTTGACCAGGGGATGCTGCCGCAACCATTA
```

FIG. 62E

```
1321 GGCTCAGCTGCTCCGGATCCCACAAGCCATCTTGGACATGATCGCTGGTGCTCACTGGGG
     CCGAGTCGACGAGGCCTAGGGTGTTCGGTAGAACCTGTACTAGCGACCACGAGTGACCCC
1381 AGTCCTGGCGGGCATAGCGTATTTCTCCATGGTGGGGAACTGGGCGAAGGTCCTGGTAGT
     TCAGGACCGCCCGTATCGCATAAAGAGGTACCACCCCTTGACCCGCTTCCAGGACCATCA
1441 GCTGCTGCTATTTGCCGGCGTCGACGCGGAAACCCACGTCACCGGGGGAAGTGCCGGCCA
     CGACGACGATAAACGGCCGCAGCTGCGCCTTTGGGTGCAGTGGCCCCCTTCACGGCCGGT
1501 CACTGTGTCTGGATTTGTTAGCCTCCTCGCACCAGGCGCCAAGCAGAACGTCCAGCTGAT
     GTGACACAGACCTAAACAATCGGAGGAGCGTGGTCCGCGGTTCGTCTTGCAGGTCGACTA
1561 CAACACCAACGGCAGTTGGCACCTCAATAGCACGGCCCTGAACTGCAATGATAGCCTCAA
     GTTGTGGTTGCCGTCAACCGTGGAGTTATCGTGCCGGGACTTGACGTTACTATCGGAGTT
1621 CACCGGCTGGTTGGCAGGGCTTTTCTATCACCACAAGTTCAACTCTTCAGGCTGTCCTGA
     GTGGCCGACCAACCGTCCCGAAAAGATAGTGGTGTTCAAGTTGAGAAGTCCGACAGGACT
1681 GAGGCTAGCCAGCTGCCGACCCCTTACCGATTTTGACCAGGGCTGGGGCCCTATCAGTTA
     CTCCGATCGGTCGACGGCTGGGGAATGGCTAAAACTGGTCCCGACCCCGGGATAGTCAAT
1741 TGCCAACGGAAGCGGCCCCGACCAGCGCCCCTACTGCTGGCACTACCCCCCAAAACCTTG
     ACGGTTGCCTTCGCCGGGGCTGGTCGCGGGGATGACGACCGTGATGGGGGGTTTTGGAAC
1801 CGGTATTGTGCCCGCGAAGAGTGTGTGTGGTCCGGTATATTGCTTCACTCCCAGCCCCGT
     GCCATAACACGGGCGCTTCTCACACACACCAGGCCATATAACGAAGTGAGGGTCGGGGCA
1861 GGTGGTGGGAACGACCGACAGGTCGGGCGCGCCCACCTACAGCTGGGGTGAAAATGATAC
     CCACCACCCTTGCTGGCTGTCCAGCCCGCGCGGGTGGATGTCGACCCCACTTTTACTATG
1921 GGACGTCTTCGTCCTTAACAATACCAGGCCACCGCTGGGCAATTGGTTCGGTTGTACCTG
     CCTGCAGAAGCAGGAATTGTTATGGTCCGGTGGCGACCCGTTAACCAAGCCAACATGGAC
1981 GATGAACTCAACTGGATTCACCAAAGTGTGCGGAGCGCCTCCTTGTGTCATCGGAGGGGC
     CTACTTGAGTTGACCTAAGTGGTTTCACACGCCTCGCGGAGGAACACAGTAGCCTCCCCG
2041 GGGCAACAACACCCTGCACTGCCCCACTGATTGCTTCCGCAAGCATCCGGACGCCACATA
     CCCGTTGTTGTGGGACGTGACGGGGTGACTAACGAAGGCGTTCGTAGGCCTGCGGTGTAT
2101 CTCTCGGTGCGGCTCCGGTCCCTGGATCACACCCAGGTGCCTGGTCGACTACCCGTATAG
     GAGAGCCACGCCGAGGCCAGGGACCTAGTGTGGGTCCACGGACCAGCTGATGGGCATATC
2161 GCTTTGGCATTATCCTTGTACCATCAACTACACCATATTTAAAATCAGGATGTACGTGGG
     CGAAACCGTAATAGGAACATGGTAGTTGATGTGGTATAAATTTTAGTCCTACATGCACCC
2221 AGGGGTCGAACACAGGCTGGAAGCTGCCTGCAACTGGACGCGGGGCGAACGTTGCGATCT
     TCCCCAGCTTGTGTCCGACCTTCGACGGACGTTGACCTGCGCCCCGCTTGCAACGCTAGA
2281 GGAAGACAGGGACAGGTCCGAGCTCAGCCCGTTACTGCTGACCACTACACAGTGGCAGGT
     CCTTCTGTCCCTGTCCAGGCTCGAGTCGGGCAATGACGACTGGTGATGTGTCACCGTCCA
2341 CCTCCCGTGTTCCTTCACAACCCTACCAGCCTTGTCCACCGGCCTCATCCACCTCCACCA
     GGAGGGCACAAGGAAGTGTTGGGATGGTCGGAACAGGTGGCCGGAGTAGGTGGAGGTGGT
2401 GAACATTGTGGACGTGCAGTACTTGTACGGGGTGGGGTCAAGCATCGCGTCCTGGGCCAT
     CTTGTAACACCTGCACGTCATGAACATGCCCCACCCCAGTTCGTAGCGCAGGACCCGGTA
2461 TAAGTGGGAGTACGTCGTTCTCCTGTTCCTTCTGCTTGCAGACGCGCGCGTCTGCTCCTG
     ATTCACCCTCATGCAGCAAGAGGACAAGGAAGACGAACGTCTGCGCGCGCAGACGAGGAC
2521 CTTGTGGATGATGCTACTCATATCCCAAGCGGAGGCGGCTTTGGAGAACCTCGTAATACT
     GAACACCTACTACGATGAGTATAGGGTTCGCCTCCGCCGAAACCTCTTGGAGCATTATGA
2581 TAATGCAGCATCCCTGGCCGGGACGCACGGTCTTGTATCCTTCCTCGTGTTCTTCTGCTT
     ATTACGTCGTAGGGACCGGCCCTGCGTGCCAGAACATAGGAAGGAGCACAAGAAGACGAA
```

FIG. 62F

```
2641 TGCATGGTATTTGAAGGGTAAGTGGGTGCCCGGAGCGGTCTACACCTTCTACGGGATGTG
     ACGTACCATAAACTTCCCATTCACCCACGGGCCTCGCCAGATGTGGAAGATGCCCTACAC

2701 GCCTCTCCTCCTGCTCCTGTTGGCGTTGCCCCAGCGGGCGTACGCGCTGGACACGGAGGT
     CGGAGAGGAGGACGAGGACAACCGCAACGGGGTCGCCCGCATGCGCGACCTGTGCCTCCA

2761 GGCCGCGTCGTGTGGCGGTGTTGTTCTCGTCGGGTTGATGGCGCTGACTCTGTCACCATA
     CCGGCGCAGCACACCGCCACAACAAGAGCAGCCCAACTACCGCGACTGAGACAGTGGTAT

2821 TTACAAGCGCTATATCAGCTGGTGCTTGTGGTGGCTTCAGTATTTTCTGACCAGAGTGGA
     AATGTTCGCGATATAGTCGACCACGAACACCACCGAAGTCATAAAAGACTGGTCTCACCT

2881 AGCGCAACTGCACGTGTGGATTCCCCCCCTCAACGTCCGAGGGGGGCGCGACGCCGTCAT
     TCGCGTTGACGTGCACACCTAAGGGGGGGAGTTGCAGGCTCCCCCCGCGCTGCGGCAGTA

2941 CTTACTCATGTGTGCTGTACACCCGACTCTGGTATTTGACATCACCAAATTGCTGCTGGC
     GAATGAGTACACACGACATGTGGGCTGAGACCATAAACTGTAGTGGTTTAACGACGACCG

3001 CGTCTTCGGACCCCTTTGGATTCTTCAAGCCAGTTTGCTTAAAGTACCCTACTTTGTGCG
     GCAGAAGCCTGGGGAAACCTAAGAAGTTCGGTCAAACGAATTTCATGGGATGAAACACGC

3061 CGTCCAAGGCCTTCTCCGGTTCTGCGCGTTAGCGCGGAAGATGATCGGAGGCCATTACGT
     GCAGGTTCCGGAAGAGGCCAAGACGCGCAATCGCGCCTTCTACTAGCCTCCGGTAATGCA

3121 GCAAATGGTCATCATTAAGTTAGGGGCGCTTACTGGCACCTATGTTTATAACCATCTCAC
     CGTTTACCAGTAGTAATTCAATCCCCGCGAATGACCGTGGATACAAATATTGGTAGAGTG

3181 TCCTCTTCGGGACTGGGCGCACAACGGCTTGCGAGATCTGGCCGTGGCTGTAGAGCCAGT
     AGGAGAAGCCCTGACCCGCGTGTTGCCGAACGCTCTAGACCGGCACCGACATCTCGGTCA

3241 CGTCTTCTCCCAAATGGAGACCAAGCTCATCACGTGGGGGGCAGATACCGCCGCGTGCGG
     GCAGAAGAGGGTTTACCTCTGGTTCGAGTAGTGCACCCCCCGTCTATGGCGGCGCACGCC

3301 TGACATCATCAACGGCTTGCCTGTTTCCGCCCGCAGGGGCCGGGAGATACTGCTCGGGCC
     ACTGTAGTAGTTGCCGAACGGACAAAGGCGGGCGTCCCCGGCCCTCTATGACGAGCCCGG

3361 AGCCGATGGAATGGTCTCCAAGGGGTGGAGGTTGCTGGCGCCCATCACGGCGTACGCCCA
     TCGGCTACCTTACCAGAGGTTCCCCACCTCCAACGACCGCGGGTAGTGCCGCATGCGGGT

3421 GCAGACAAGGGGCCTCCTAGGGTGCATAATCACCAGCCTAACTGGCCGGGACAAAAACCA
     CGTCTGTTCCCCGGAGGATCCCACGTATTAGTGGTCGGATTGACCGGCCCTGTTTTTGGT

3481 AGTGGAGGGTGAGGTCCAGATTGTGTCAACTGCTGCCCAAACCTTCCTGGCAACGTGCAT
     TCACCTCCCACTCCAGGTCTAACACAGTTGACGACGGGTTTGGAAGGACCGTTGCACGTA

3541 CAATGGGGTGTGCTGGACTGTCTACCACGGGGCCGGAACGAGGACCATCGCGTCACCCAA
     GTTACCCCACACGACCTGACAGATGGTGCCCCGGCCTTGCTCCTGGTAGCGCAGTGGGTT

3601 GGGTCCTGTCATCCAGATGTATACCAATGTAGACCAAGACCTTGTGGGCTGGCCCGCTCC
     CCCAGGACAGTAGGTCTACATATGGTTACATCTGGTTCTGGAACACCCGACCGGGCGAGG

3661 GCAAGGTAGCCGCTCATTGACACCCTGCACTTGCGGCTCCTCGGACCTTTACCTGGTCAC
     CGTTCCATCGGCGAGTAACTGTGGGACGTGAACGCCGAGGAGCCTGGAAATGGACCAGTG

3721 GAGGCACGCCGATGTCATTCCCGTGCGCCGGCGGGGTGATAGCAGGGGCAGCCTGCTGTC
     CTCCGTGCGGCTACAGTAAGGGCACGCGGCCGCCCCACTATCGTCCCCGTCGGACGACAG

3781 GCCCCGGCCCATTTCCTACTTGAAAGGCTCCTCGGGGGGTCCGCTGTTGTGCCCCGCGGG
     CGGGGCCGGGTAAAGGATGAACTTTCCGAGGAGCCCCCCAGGCGACAACACGGGGCGCCC

3841 GCACGCCGTGGGCATATTTAGGGCCGCGGTGTGCACCCGTGGAGTGGCTAAGGCGGTGGA
     CGTGCGGCACCCGTATAAATCCCGGCGCCACACGTGGGCACCTCACCGATTCCGCCACCT

3901 CTTTATCCCTGTGGAGAACCTAGAGACAACCATGAGGTCCCCGGTGTTCACGGATAACTC
     GAAATAGGGACACCTCTTGGATCTCTGTTGGTACTCCAGGGGCCACAAGTGCCTATTGAG
```

FIG. 62G

```
3961 CTCTCCACCAGTAGTGCCCCAGAGCTTCCAGGTGGCTCACCTCCATGCTCCCACAGGCAG
     GAGAGGTGGTCATCACGGGGTCTCGAAGGTCCACCGAGTGGAGGTACGAGGGTGTCCGTC

4021 CGGCAAAAGCACCAAGGTCCCGGCTGCATATGCAGCTCAGGGCTATAAGGTGCTAGTACT
     GCCGTTTTCGTGGTTCCAGGGCCGACGTATACGTCGAGTCCCGATATTCCACGATCATGA

4081 CAACCCCTCTGTTGCTGCAACACTGGGCTTTGGTGCTTACATGTCCAAGGCTCATGGGAT
     GTTGGGGAGACAACGACGTTGTGACCCGAAACCACGAATGTACAGGTTCCGAGTACCCTA

4141 CGATCCTAACATCAGGACCGGGGTGAGAACAATTACCACTGGCAGCCCCATCACGTACTC
     GCTAGGATTGTAGTCCTGGCCCCACTCTTGTTAATGGTGACCGTCGGGGTAGTGCATGAG

4201 CACCTACGGCAAGTTCCTTGCCGACGGCGGGTGCTCGGGGGGCGCTTATGACATAATAAT
     GTGGATGCCGTTCAAGGAACGGCTGCCGCCCACGAGCCCCCGCGAATACTGTATTATTA

4261 TTGTGACGAGTGCCACTCCACGGATGCCACATCCATCTTGGGCATCGGCACTGTCCTTGA
     AACACTGCTCACGGTGAGGTGCCTACGGTGTAGGTAGAACCCGTAGCCGTGACAGGAACT

4321 CCAAGCAGAGACTGCGGGGGCGAGACTGGTTGTGCTCGCCACCGCCACCCCTCCGGGCTC
     GGTTCGTCTCTGACGCCCCGCTCTGACCAACACGAGCGGTGGCGGTGGGGAGGCCCGAG

4381 CGTCACTGTGCCCCATCCCAACATCGAGGAGGTTGCTCTGTCCACCACCGGAGAGATCCC
     GCAGTGACACGGGGTAGGGTTGTAGCTCCTCCAACGAGACAGGTGGTGGCCTCTCTAGGG

4441 TTTTTACGGCAAGGCTATCCCCCTCGAAGTAATCAAGGGGGGGAGACATCTCATCTTCTG
     AAAAATGCCGTTCCGATAGGGGGAGCTTCATTAGTTCCCCCCCTCTGTAGAGTAGAAGAC

4501 TCATTCAAAGAAGAAGTGCGACGAACTCGCCGCAAAGCTGGTCGCATTGGGCATCAATGC
     AGTAAGTTTCTTCTTCACGCTGCTTGAGCGGCGTTTCGACCAGCGTAACCCGTAGTTACG

4561 CGTGGCCTACTACCGCGGTCTTGACGTGTCCGTCATCCCGACCAGCGGCGATGTTGTCGT
     GCACCGGATGATGGCGCCAGAACTGCACAGGCAGTAGGGCTGGTCGCCGCTACAACAGCA

4621 CGTGGCAACCGATGCCCTCATGACCGGCTATACCGGCGACTTCGACTCGGTGATAGACTG
     GCACCGTTGGCTACGGGAGTACTGGCCGATATGGCCGCTGAAGCTGAGCCACTATCTGAC

4681 CAATACGTGTGTCACCCAGACAGTCGATTTCAGCCTTGACCCTACCTTCACCATTGAGAC
     GTTATGCACACAGTGGGTCTGTCAGCTAAAGTCGGAACTGGGATGGAAGTGGTAACTCTG

4741 AATCACGCTCCCCCAGGATGCTGTCTCCCGCACTCAACGTCGGGGCAGGACTGGCAGGGG
     TTAGTGCGAGGGGGTCCTACGACAGAGGGCGTGAGTTGCAGCCCCGTCCTGACCGTCCCC

4801 GAAGCCAGGCATCTACAGATTTGTGGCACCGGGGGAGCGCCCCTCCGGCATGTTCGACTC
     CTTCGGTCCGTAGATGTCTAAACACCGTGGCCCCCTCGCGGGGAGGCCGTACAAGCTGAG

4861 GTCCGTCCTCTGTGAGTGCTATGACGCAGGCTGTGCTTGGTATGAGCTCACGCCCGCCGA
     CAGGCAGGAGACACTCACGATACTGCGTCCGACACGAACCATACTCGAGTGCGGGCGGCT

4921 GACTACAGTTAGGCTACGAGCGTACATGAACACCCCGGGGCTTCCCGTGTGCCAGGACCA
     CTGATGTCAATCCGATGCTCGCATGTACTTGTGGGCCCCGAAGGGCACACGGTCCTGGT

4981 TCTTGAATTTTGGGAGGGCGTCTTTACAGGCCTCACTCATATAGATGCCCACTTTCTATC
     AGAACTTAAAAACCCTCCCGCAGAAATGTCCGGAGTGAGTATATCTACGGGTGAAAGATAG

5041 CCAGACAAAGCAGAGTGGGGAGAACCTTCCTTACCTGGTAGCGTACCAAGCCACCGTGTG
     GGTCTGTTTCGTCTCACCCCTCTTGGAAGGAATGGACCATCGCATGGTTCGGTGGCACAC

5101 CGCTAGGGCTCAAGCCCCTCCCCCATCGTGGGACCAGATGTGGAAGTGTTTGATTCGCCT
     GCGATCCCGAGTTCGGGGAGGGGGTAGCACCCTGGTCTACACCTTCACAAACTAAGCGGA

5161 CAAGCCCACCCTCCATGGGCCAACACCCCTGCTATACAGACTGGGCGCTGTTCAGAATGA
     GTTCGGGTGGGAGGTACCCGGTTGTGGGGACGATATGTCTGACCCGCGACAAGTCTTACT

5221 AATCACCCTGACGCACCCAGTCACCAAATACATCATGACATGCATGTCGGCCGACCTGGA
     TTAGTGGGACTGCGTGGGTCAGTGGTTTATGTAGTACTGTACGTACAGCCGGCTGGACCT
```

FIG. 62H

```
5281 GGTCGTCACGAGCACCTGGGTGCTCGTTGGCGGCGTCCTGGCTGCTTTGGCCGCGTATTG
     CCAGCAGTGCTCGTGGACCCACGAGCAACCGCCGCAGGACCGACGAAACCGGCGCATAAC

5341 CCTGTCAACAGGCTGCGTGGTCATAGTGGGCAGGGTCGTCTTGTCCGGGAAGCCGGCAAT
     GGACAGTTGTCCGACGCACCAGTATCACCCGTCCCAGCAGAACAGGCCCTTCGGCCGTTA

5401 CATACCTGACAGGGAAGTCCTCTACCGAGAGTTCGATGAGATGGAAGAGTGCTCTCAGCA
     GTATGGACTGTCCCTTCAGGAGATGGCTCTCAAGCTACTCTACCTTCTCACGAGAGTCGT

5461 CTTACCGTACATCGAGCAAGGGATGATGCTCGCCGAGCAGTTCAAGCAGAAGGCCCTCGG
     GAATGGCATGTAGCTCGTTCCCTACTACGAGCGGCTCGTCAAGTTCGTCTTCCGGGAGCC

5521 CCTCCTGCAGACCGCGTCCCGTCAGGCAGAGGTTATCGCCCCTGCTGTCCAGACCAACTG
     GGAGGACGTCTGGCGCAGGGCAGTCCGTCTCCAATAGCGGGGACGACAGGTCTGGTTGAC

5581 GCAAAAACTCGAGACCTTCTGGGCGAAGCATATGTGGAACTTCATCAGTGGGATACAATA
     CGTTTTTGAGCTCTGGAAGACCCGCTTCGTATACACCTTGAAGTAGTCACCCTATGTTAT

5641 CTTGGCGGGCTTGTCAACGCTGCCTGGTAACCCCGCCATTGCTTCATTGATGGCTTTTAC
     GAACCGCCCGAACAGTTGCGACGGACCATTGGGGCGGTAACGAAGTAACTACCGAAAATG

5701 AGCTGCTGTCACCAGCCCACTAACCACTAGCCAAACCCTCCTCTTCAACATATTGGGGGG
     TCGACGACAGTGGTCGGGTGATTGGTGATCGGTTTGGGAGGAGAAGTTGTATAACCCCCC

5761 GTGGGTGGCTGCCCAGCTCGCCGCCCCGGTGCCGCTACTGCCTTTGTGGGCGCTGGCTT
     CACCCACCGACGGGTCGAGCGGCGGGGGCCACGGCGATGACGGAAACACCCGCGACCGAA

5821 AGCTGGCGCCGCCATCGGCAGTGTTGGACTGGGGAAGGTCCTCATAGACATCCTTGCAGG
     TCGACCGCGGCGGTAGCCGTCACAACCTGACCCCTTCCAGGAGTATCTGTAGGAACGTCC

5881 GTATGGCGCGGGCGTGGCGGGAGCTCTTGTGGCATTCAAGATCATGAGCGGTGAGGTCCC
     CATACCGCGCCCGCACCGCCCTCGAGAACACCGTAAGTTCTAGTACTCGCCACTCCAGGG

5941 CTCCACGGAGGACCTGGTCAATCTACTGCCCGCCATCCTCTCGCCCGGAGCCCTCGTAGT
     GAGGTGCCTCCTGGACCAGTTAGATGACGGGCGGTAGGAGAGCGGGCCTCGGGAGCATCA

6001 CGGCGTGGTCTGTGCAGCAATACTGCGCCGGCACGTTGGCCCGGGCGAGGGGGCAGTGCA
     GCCGCACCAGACACGTCGTTATGACGCGGCCGTGCAACCGGGCCCGCTCCCCCGTCACGT

6061 GTGGATGAACCGGCTGATAGCCTTCGCCTCCCGGGGGAACCATGTTTCCCCCACGCACTA
     CACCTACTTGGCCGACTATCGGAAGCGGAGGGCCCCCTTGGTACAAAGGGGGTGCGTGAT

6121 CGTGCCGGAGAGCGATGCAGCTGCCCGCGTCACTGCCATACTCAGCAGCCTCACTGTAAC
     GCACGGCCTCTCGCTACGTCGACGGGCGCAGTGACGGTATGAGTCGTCGGAGTGACATTG

6181 CCAGCTCCTGAGGCGACTGCACCAGTGGATAAGCTCGGAGTGTACCACTCCATGCTCCGG
     GGTCGAGGACTCCGCTGACGTGGTCACCTATTCGAGCCTCACATGGTGAGGTACGAGGCC

6241 TTCCTGGCTAAGGGACATCTGGGACTGGATATGCGAGGTGTTGAGCGACTTTAAGACCTG
     AAGGACCGATTCCCTGTAGACCCTGACCTATACGCTCCACAACTCGCTGAAATTCTGGAC

6301 GCTAAAAGCTAAGCTCATGCCACAGCTGCCTGGGATCCCCTTTGTGTCCTGCCAGCGCGG
     CGATTTTCGATTCGAGTACGGTGTCGACGGACCCTAGGGGAAACACAGGACGGTCGCGCC

6361 GTATAAGGGGGTCTGGCGAGTGGACGGCATCATGCACACTCGCTGCCACTGTGGAGCTGA
     CATATTCCCCCAGACCGCTCACCTGCCGTAGTACGTGTGAGCGACGGTGACACCTCGACT

6421 GATCACTGGACATGTCAAAAACGGGACGATGAGGATCGTCGGTCCTAGGACCTGCAGGAA
     CTAGTGACCTGTACAGTTTTTGCCCTGCTACTCCTAGCAGCCAGGATCCTGGACGTCCTT

6481 CATGTGGAGTGGGACCTTCCCCATTAATGCCTACACCACGGGCCCCTGTACCCCCCTTCC
     GTACACCTCACCCTGGAAGGGGTAATTACGGATGTGGTGCCCGGGGACATGGGGGGAAGG

6541 TGCGCCGAACTACACGTTCGCGCTATGGAGGGTGTCTGCAGAGGAATATGTGGAGATAAG
     ACGCGGCTTGATGTGCAAGCGCGATACCTCCCACAGACGTCTCCTTATACACCTCTATTC
```

FIG. 62I

```
6601 GCAGGTGGGGGACTTCCACTACGTGACGGGTATGACTACTGACAATCTCAAATGCCCGTG
     CGTCCACCCCCTGAAGGTGATGCACTGCCCATACTGATGACTGTTAGAGTTTACGGGCAC

6661 CCAGGTCCCATCGCCCGAATTTTTCACAGAATTGGACGGGGTGCGCCTACATAGGTTTGC
     GGTCCAGGGTAGCGGGCTTAAAAAGTGTCTTAACCTGCCCCACGCGGATGTATCCAAACG

6721 GCCCCCCTGCAAGCCCTTGCTGCGGGAGGAGGTATCATTCAGAGTAGGACTCCACGAATA
     CGGGGGGACGTTCGGGAACGACGCCCTCCTCCATAGTAAGTCTCATCCTGAGGTGCTTAT

6781 CCCGGTAGGGTCGCAATTACCTTGCGAGCCCGAACCGGACGTGGCCGTGTTGACGTCCAT
     GGGCCATCCCAGCGTTAATGGAACGCTCGGGCTTGGCCTGCACCGGCACAACTGCAGGTA

6841 GCTCACTGATCCCTCCCATATAACAGCAGAGGCGGCCGGGCGAAGGTTGGCGAGGGGATC
     CGAGTGACTAGGGAGGGTATATTGTCGTCTCCGCCGGCCCGCTTCCAACCGCTCCCCTAG

6901 ACCCCCCTCTGTGGCCAGCTCCTCGGCTAGCCAGCTATCCGCTCCATCTCTCAAGGCAAC
     TGGGGGGAGACACCGGTCGAGGAGCCGATCGGTCGATAGGCGAGGTAGAGAGTTCCGTTG

6961 TTGCACCGCTAACCATGACTCCCCTGATGCTGAGCTCATAGAGGCCAACCTCCTATGGAG
     AACGTGGCGATTGGTACTGAGGGGACTACGACTCGAGTATCTCCGGTTGGAGGATACCTC

7021 GCAGGAGATGGGCGGCAACATCACCAGGGTTGAGTCAGAAAACAAAGTGGTGATTCTGGA
     CGTCCTCTACCCGCCGTTGTAGTGGTCCCAACTCAGTCTTTTGTTTCACCACTAAGACCT

7081 CTCCTTCGATCCGCTTGTGGCGGAGGAGGACGAGCGGGAGATCTCCGTACCCGCAGAAAT
     GAGGAAGCTAGGCGAACACCGCCTCCTCCTGCTCGCCCTCTAGAGGCATGGGCGTCTTTA

7141 CCTGCGGAAGTCTCGGAGATTCGCCCAGGCCCTGCCCGTTTGGGCGCGGCCGGACTATAA
     GGACGCCTTCAGAGCCTCTAAGCGGGTCCGGGACGGGCAAACCCGCGCCGGCCTGATATT

7201 CCCCCCGCTAGTGGAGACGTGGAAAAAGCCCGACTACGAACCACCTGTGGTCCATGGCTG
     GGGGGGCGATCACCTCTGCACCTTTTTCGGGCTGATGCTTGGTGGACACCAGGTACCGAC

7261 TCCGCTTCCACCTCCAAAGTCCCCTCCTGTGCCTCCGCCTCGGAAGAAGCGGACGGTGGT
     AGGCGAAGGTGGAGGTTTCAGGGGAGGACACGGAGGCGGAGCCTTCTTCGCCTGCCACCA

7321 CCTCACTGAATCAACCCTATCTACTGCCTTGGCCGAGCTCGCCACCAGAAGCTTTGGCAG
     GGAGTGACTTAGTTGGGATAGATGACGGAACCGGCTCGAGCGGTGGTCTTCGAAACCGTC

7381 CTCCTCAACTTCCGGCATTACGGGCGACAATACGACAACATCCTCTGAGCCCGCCCCTTC
     GAGGAGTTGAAGGCCGTAATGCCCGCTGTTATGCTGTTGTAGGAGACTCGGGCGGGGAAG

7441 TGGCTGCCCCCCCGACTCCGACGCTGAGTCCTATTCCTCCATGCCCCCCTGGAGGGGGA
     ACCGACGGGGGGGCTGAGGCTGCGACTCAGGATAAGGAGGTACGGGGGGGACCTCCCCCT

7501 GCCTGGGGATCCGGATCTTAGCGACGGGTCATGGTCAACGGTCAGTAGTGAGGCCAACGC
     CGGACCCCTAGGCCTAGAATCGCTGCCCAGTACCAGTTGCCAGTCATCACTCCGGTTGCG

7561 GGAGGATGTCGTGTGCTGCTCAATGTCTTACTCTTGGACAGGCGCACTCGTCACCCCGTG
     CCTCCTACAGCACACGACGAGTTACAGAATGAGAACCTGTCCGCGTGAGCAGTGGGGCAC

7621 CGCCGCGGAAGAACAGAAACTGCCCATCAATGCACTAAGCAACTCGTTGCTACGTCACCA
     GCGGCGCCTTCTTGTCTTTGACGGGTAGTTACGTGATTCGTTGAGCAACGATGCAGTGGT

7681 CAATTTGGTGTATTCCACCACCTCACGCAGTGCTTGCCAAAGGCAGAAGAAAGTCACATT
     GTTAAACCACATAAGGTGGTGGAGTGCGTCACGAACGGTTTCCGTCTTCTTTCAGTGTAA

7741 TGACAGACTGCAAGTTCTGGACAGCCATTACCAGGACGTACTCAAGGAGGTTAAAGCAGC
     ACTGTCTGACGTTCAAGACCTGTCGGTAATGGTCCTGCATGAGTTCCTCCAATTTCGTCG

7801 GGCGTCAAAAGTGAAGGCTAACTTGCTATCCGTAGAGGAAGCTTGCAGCCTGACGCCCCC
     CCGCAGTTTTCACTTCCGATTGAACGATAGGCATCTCCTTCGAACGTCGGACTGCGGGGG

7861 ACACTCAGCCAAATCCAAGTTTGGTTATGGGGCAAAAGACGTCCGTTGCCATGCCAGAAA
     TGTGAGTCGGTTTAGGTTCAAACCAATACCCCGTTTTCTGCAGGCAACGGTACGGTCTTT
```

FIG. 62J

```
7921  GGCCGTAACCCACATCAACTCCGTGTGGAAAGACCTTCTGGAAGACAATGTAACACCAAT
      CCGGCATTGGGTGTAGTTGAGGCACACCTTTCTGGAAGACCTTCTGTTACATTGTGGTTA

7981  AGACACTACCATCATGGCTAAGAACGAGGTTTTCTGCGTTCAGCCTGAGAAGGGGGGTCG
      TCTGTGATGGTAGTACCGATTCTTGCTCCAAAAGACGCAAGTCGGACTCTTCCCCCCAGC

8041  TAAGCCAGCTCGTCTCATCGTGTTCCCCGATCTGGGCGTGCGCGTGTGCGAAAAGATGGC
      ATTCGGTCGAGCAGAGTAGCACAAGGGGCTAGACCCGCACGCGCACACGCTTTTCTACCG

8101  TTTGTACGACGTGGTTACAAAGCTCCCCTTGGCCGTGATGGGAAGCTCCTACGGATTCCA
      AAACATGCTGCACCAATGTTTCGAGGGGAACCGGCACTACCCTTCGAGGATGCCTAAGGT

8161  ATACTCACCAGGACAGCGGGTTGAATTCCTCGTGCAAGCGTGGAAGTCCAAGAAAACCCC
      TATGAGTGGTCCTGTCGCCCAACTTAAGGAGCACGTTCGCACCTTCAGGTTCTTTTGGGG

8221  AATGGGGTTCTCGTATGATACCCGCTGCTTTGACTCCACAGTCACTGAGAGCGACATCCG
      TTACCCCAAGAGCATACTATGGGCGACGAAACTGAGGTGTCAGTGACTCTCGCTGTAGGC

8281  TACGGAGGAGGCAATCTACCAATGTTGTGACCTCGACCCCCAAGCCCGCGTGGCCATCAA
      ATGCCTCCTCCGTTAGATGGTTACAACACTGGAGCTGGGGGTTCGGGCGCACCGGTAGTT

8341  GTCCCTCACCGAGAGGCTTTATGTTGGGGGCCCTCTTACCAATTCAAGGGGGGAGAACTG
      CAGGGAGTGGCTCTCCGAAATACAACCCCCGGGAGAATGGTTAAGTTCCCCCCTCTTGAC

8401  CGGCTATCGCAGGTGCCGCGCGAGCGGCGTACTGACAACTAGCTGTGGTAACACCCTCAC
      GCCGATAGCGTCCACGGCGCGCTCGCCGCATGACTGTTGATCGACACCATTGTGGGAGTG

8461  TTGCTACATCAAGGCCCGGGCAGCCTGTCGAGCCGCAGGGCTCCAGGACTGCACCATGCT
      AACGATGTAGTTCCGGGCCCGTCGGACAGCTCGGCGTCCCGAGGTCCTGACGTGGTACGA

8521  CGTGTGTGGCGACGACTTAGTCGTTATCTGTGAAAGCGCGGGGGTCCAGGAGGACGCGGC
      GCACACACCGCTGCTGAATCAGCAATAGACACTTTCGCGCCCCCAGGTCCTCCTGCGCCG

8581  GAGCCTGAGAGCCTTCACGGAGGCTATGACCAGGTACTCCGCCCCCCCTGGGGACCCCCC
      CTCGGACTCTCGGAAGTGCCTCCGATACTGGTCCATGAGGCGGGGGGGACCCCTGGGGGG

8641  ACAACCAGAATACGACTTGGAGCTCATAACATCATGCTCCTCCAACGTGTCAGTCGCCCA
      TGTTGGTCTTATGCTGAACCTCGAGTATTGTAGTACGAGGAGGTTGCACAGTCAGCGGGT

8701  CGACGGCGCTGGAAAGAGGGTCTACTACCTCACCCGTGACCCTACAACCCCCCTCGCGAG
      GCTGCCGCGACCTTTCTCCCAGATGATGGAGTGGGCACTGGGATGTTGGGGGAGCGCTC

8761  AGCTGCGTGGGAGACAGCAAGACACACTCCAGTCAATTCCTGGCTAGGCAACATAATCAT
      TCGACGCACCCTCTGTCGTTCTGTGTGAGGTCAGTTAAGGACCGATCCGTTGTATTAGTA

8821  GTTTGCCCCCACACTGTGGGCGAGGATGATACTGATGACCCATTTCTTTAGCGTCCTTAT
      CAAACGGGGGTGTGACACCCGCTCCTACTATGACTACTGGGTAAAGAAATCGCAGGAATA

8881  AGCCAGGGACCAGCTTGAACAGGCCCTCGATTGCGAGATCTACGGGGCCTGCTACTCCAT
      TCGGTCCCTGGTCGAACTTGTCCGGGAGCTAACGCTCTAGATGCCCCGGACGATGAGGTA

8941  AGAACCACTTGATCTACCTCCAATCATTCAAAGACTCCATGGCCTCAGCGCATTTTCACT
      TCTTGGTGAACTAGATGGAGGTTAGTAAGTTTCTGAGGTACCGGAGTCGCGTAAAAGTGA

9001  CCACAGTTACTCTCCAGGTGAAATTAATAGGGTGGCCGCATGCCTCAGAAAACTTGGGGT
      GGTGTCAATGAGAGGTCCACTTTAATTATCCCACCGGCGTACGGAGTCTTTTGAACCCCA

9061  ACCGCCCTTGCGAGCTTGGAGACACCGGGCCCGGAGCGTCCGCGCTAGGCTTCTGGCCAG
      TGGCGGGAACGCTCGAACCTCTGTGGCCCGGGCCTCGCAGGCGCGATCCGAAGACCGGTC

9121  AGGAGGCAGGGCTGCCATATGTGGCAAGTACCTCTTCAACTGGGCAGTAAGAACAAAGCT
      TCCTCCGTCCCGACGGTATACACCGTTCATGGAGAAGTTGACCCGTCATTCTTGTTTCGA

9181  CAAAC
      GTTTG
```

FIG. 64
TRANSFORM E coli WITH RECOMBINANT PLASMIDS
↓ (BLOT BACTERIA ON
↓ NITROCELLULOSE FILTER)
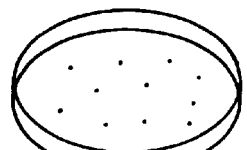 IPTG PLATE
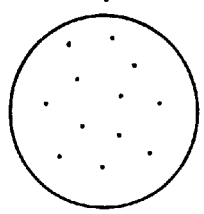 LYSE WITH CHLOROFORM
↓ BSA ABSORBTION/DNAse/LYSOZYME
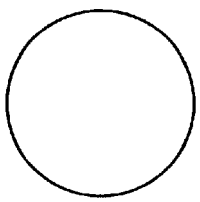 INCUBATE WITH PRIMARY ANTIBODY
↓ WASH
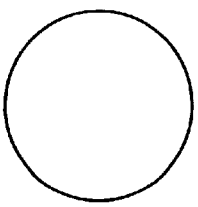 INCUBATE WITH $^{125}$I SECONDARY ANTIBODY
↓ WASH
 AUTORADIOGRAPH

| | EXPRESSION LEVEL | CHIMPS | | | CHRONIC HCV PATIENT C100 POSITIVE | | | | | | | | CHRONIC HCV PATIENT C100 NEGATIVE | | | | | | | | CONVALSCENT C100 NEGATIVE | COMMUNITY AC | | | | |
|---|---|---|---|---|---|---|---|---|---|---|---|---|---|---|---|---|---|---|---|---|---|---|---|---|---|---|
| | | 1. POST ACUTE | 2. POST ACUTE | 3. C100 CONVERSION | 1. | 2. | 3. | 4. | 5. | 6. | 7. | 8. | 1. | 2. | 3. | 4. | 5. | 6. | 7. | 8. | 1. C100(+) | 2. C100(±) | 3. C100(-) | 4. C100(-) | 5. C100(-) |
| SOD | + | − | − | − | − | − | − | − | − | − | − | − | − | − | − | − | − | − | − | − | − | − | − | − | − | − |
| CA259a | | − | − | | | | | + | + | + | + | | | | | | | | | | + | | | | | |
| CA290a | | − | − | | | | | + | + | + | + | | | | | | | | | | + | | | | | |
| CA202a | N.T. | − | − | | | | | − | − | | | | | | | | | | | | − | | | | | |
| CA167a | + | − | − | − | − | − | − | − | − | − | − | − | − | − | − | − | − | − | − | − | − | − | − | − | − | − |
| CA156C | + | − | − | − | − | − | − | − | − | − | − | − | − | − | − | − | − | − | − | − | − | − | − | − | − | − |
| π14a | − | − | − | − | − | − | − | − | − | − | − | − | − | − | − | − | − | − | − | − | − | − | − | − | − | − |
| CA84a | ± | − | − | − | − | − | − | − | − | − | − | − | − | − | − | − | − | − | − | − | − | − | − | − | − | − |
| CA59a | − | − | − | − | − | − | − | − | − | − | − | − | − | − | − | − | − | − | − | − | − | − | − | − | − | − |
| CA61C | − | − | − | − | − | − | − | − | − | − | − | − | − | − | − | − | − | − | − | − | − | − | − | − | − | − |
| CA74a | + | − | − | − | − | − | − | + | − | − | − | − | − | − | − | − | − | − | − | − | − | − | − | − | − | − |
| C26j | + | − | − | − | − | − | − | − | − | − | − | − | − | − | − | − | − | − | − | − | − | − | − | − | − | − |
| C13i | ± | − | − | − | − | − | − | + | − | − | − | − | − | − | − | − | − | − | − | − | − | − | − | − | − | − |
| C12f | + | − | − | − | − | − | − | − | − | − | − | − | − | − | − | − | − | − | − | − | − | − | − | − | − | − |
| C14i | − | − | − | − | − | − | − | − | − | − | − | − | − | − | − | − | − | − | − | − | − | − | − | − | − | − |
| C23g | + | − | − | − | − | − | − | − | − | − | − | − | − | − | − | − | − | − | − | − | − | − | − | − | − | − |
| C11b | − | − | − | − | − | − | − | − | − | − | − | − | − | − | − | − | − | − | − | − | − | − | − | − | − | − |
| C9h | ± | − | − | − | − | − | − | − | − | − | − | − | − | − | − | − | − | − | − | − | − | − | − | − | − | − |
| C7f | − | − | − | − | − | − | − | − | − | − | − | − | − | − | − | − | − | − | − | − | − | − | − | − | − | − |
| C7e | + | − | − | − | − | − | − | − | − | − | − | − | − | − | − | − | − | − | − | − | − | − | − | − | − | − |
| C8h | + | − | − | − | − | − | − | − | − | − | − | − | − | − | − | − | − | − | − | − | − | − | − | − | − | − |
| C33c | + | + | ± | + | + | + | + | + | + | + | +* | + | + | + | + | + | − | − | − | − | ± | + | + | − | ± | − |
| C40g | ± | − | − | − | − | − | − | − | − | − | +* | − | − | − | − | − | − | − | − | − | − | − | − | − | − | − |
| C37b | + | − | − | − | − | − | − | − | − | − | − | − | − | − | − | − | − | − | − | − | − | − | − | − | − | − |
| C35 | ± | − | − | − | − | − | − | − | − | − | − | − | − | − | − | − | − | − | − | − | − | − | − | − | − | − |
| C36 | − | − | − | − | − | − | − | − | − | − | − | − | − | − | − | − | − | − | − | − | − | − | − | − | − | − |
| 5-1-1 | + | − | − | + | ± | + | + | + | + | + | + | + | − | − | − | − | + | + | + | + | + | − | + | ± | + | + | − |
| C8l | + | − | − | − | − | − | − | − | − | − | + | − | − | − | − | − | − | − | − | − | − | − | + | − | − | − |
| C32 | − | − | − | − | − | − | − | − | − | − | − | − | − | − | − | − | − | − | − | − | − | − | − | − | − | − |
| C33b | | − | − | − | − | − | − | + | − | − | + | − | − | − | − | − | − | − | − | − | − | − | + | − | − | − |
| C25c | + | − | − | − | − | − | − | − | − | − | − | − | − | − | − | − | − | − | − | − | − | − | + | − | − | − |
| C14c | + | − | − | ± | − | − | − | − | − | − | − | − | + | − | + | − | − | − | − | − | + | − | + | − | − | − |
| C8f | ± | − | − | + | − | − | + | + | − | + | + | − | + | − | − | − | + | − | − | − | − | − | + | + | − | − |
| C33f | | − | − | − | − | + | + | − | − | − | + | − | + | − | − | − | − | − | − | + | − | + | − | − | − | − |
| C33g | ± | − | − | − | − | − | + | − | − | − | + | − | + | − | − | − | − | − | − | − | − | − | + | + | − | − |
| C39c | + | − | − | − | − | − | + | − | − | − | + | − | − | − | − | − | − | − | − | − | − | − | + | + | − | − |
| C35f | N.T. | − | − | − | − | − | − | − | − | − | − | − | − | − | − | − | − | − | − | − | − | − | − | − | − | − |
| C19g | + | − | − | − | − | − | − | − | − | − | − | − | − | − | − | − | − | − | − | − | − | − | − | − | − | − |
| C26g | + | − | − | − | − | − | − | − | − | − | − | − | − | − | − | − | − | − | − | − | − | − | − | − | − | − |
| C15e | ± | − | − | − | − | + | − | − | − | − | − | − | − | − | − | − | − | − | − | − | − | ± | − | − | − | − |

N.T. = EXPRESSION NOT TESTED
* THIS POLYPEPTIDE WAS NEGATIVE IN THIS COLONY SCREEN BUT POSITIVE BY WESTERN BLOT ANALYSIS

```
         R T
MSTNPKPQKKNKRNTNRRPQDVKFPGGGQIVGGVYLLPRRGPRLGVRATR
KTSERSQPRGRRQPIPKARRPEGRTWAQPGYPWPLYGNEGCGWAGWLLSP-100
RGSRPSWGPTDPRRRSRNLGKVIDTLTCGFADLMGYIPLVGAPLGGAARA

T
LAHGVRVLEDGVNYATGNLPGCSFSIFLLALLSCLTVPASAYQVRNSTGL-200
YHVTNDCPNSSIVYEAADAILHTPGCVPCVREGNASRCWVAMTPTVATRD
GKLPATQLRRHIDLLVGSATLCSALYVGDLCGSVFLVGQLFTFSPRRHWT-300

V
TQGCNCSIYPGHITGHRMAWDMMMNWSPTTALVMAQLLRIPQAILDMIAG
AHWGVLAGIAYFSMVGNWAKVLVVLLLFAGVDAETHVTGGSAGHTVSGFV-400
SLLAPGAKQNVQLINTNGSWHLNSTALNCNDSLNTGWLAGLFYHHKFNSS
GCPERLASCRPLTDFDQGWGPISYANGSGPDQRPYCWHYPPKPCGIVPAK-500
SVCGPVYCFTPSPVVVGTTDRSGAPTYSWGENDTDVFVLNNTRPPLGNWF
GCTWMNSTGFTKVCGAPPCVIGGAGNNTLHCPTDCFRKHPDATYSRCGSG-600

I
PWLTPRCLVDYPYRLWHYPCTINYTIFKIRMYVGGVEHRLEAACNWTRGE
RCDLEDRDRSELSPLLLTTTQWQVLPCSFTTLPALSTGLIHLHQNIVDVQ-700
YLYGVGSSIASWAIKWEYVVLLFLLLADARVCSCLWMMLLISQAEAALEN
LVILNAASLAGTHGLVSFLVFFCFAWYLKGKWVPGAVYTFYGMWPLLLLL-800

(N)
LALPQRAYALDTEVAASCGGVVLVGLMALTLSPYYKRYISWCLWWLQYFL
TRVEAQLHVWIPPLNVRGGRDAVILLMCAVHPTLVFDITKLLLAVFGPLN-900
ILQASLLKVPYFVRVQGLLRFCALARKMIGGHYVQMVIIKLGALTGTYVY
NHLTPLRDWAHNGLRDLAVAVEFVVFSQMETKLITWGADTAACGDIINGL-1000
PVSARRGREILLGPADGMVSKGWRLLAPITAYAQQTRGLLGCIITSLTGR
DKNQVEGEVQIVSTAAQTTFATCINGVCWTVYHGAGTRTIASPKGPVIQM-1100
YTNVDQDLVGWPAPQGSRSLTPCTCGSSDLYLVTRHADVIPVRRRGDSRG
SLLSPRPISYLKGSSGGPLLCPAGHAVGIFRAAVCTRGVAKAVDFIPVEN-1200
LETTMRSPVFTDNSSPPVVPQSFQVAHLHAPTGSGKSTKVPAAYAAQGYK

L
VLVLNPSVAATLGFGAYMSKAHGIDPNIRTGVRTITTGSPITYSTYGKFL-1300
ADGGCSGGAYDIIICDECHSTDATSILGIGTVLDQAETAGARLVVLATAT
PPGSVTVPHPNIEEVALSTTGEIPFYGKAIPLEVIKGGRHLIFCHSKKKC-1400
DELAAKLVALGINAVAYYRGLDVSVIPTSGDVVVVATDALMTGYTGDFDS

Y              (S)
VIDCNTCVTQTVDFSLDPTFTIETITLPQDAVSRTQRRGRTGRGKPGIYR-1500
FVAPGERPSGMFDSSVLCECYDAGCAWYELTPAETTVRLRAYMNTPGLPV
CQDHLEFWEGVFTGLTHIDAHFLSQTKQSGENLPYLVAYQATVCARAQAP-1600
PPSWDQMWKCLIRLKPTLHGPTPLLYRLGAVQNEITLTHPVTKYIMTCMS
ADLEVVTSTWVLVGGVLAALAAYCLSTGCVVIVGRVVLSGKPAIIPDREV-1700
LYREFDEMEECSQHLPYIEQGMMLAEQFKQKALGLLQTASRQAEVIAPAV
QTNWQKLETFWAKHMWNFISGIQYLAGLSTLPGNPAIASLMAFTAAVTSP-1800
LTTSQTLLFNILGGWVAAQLAAPGAATAFVGAGLAGAAIGSVGLGKVLID
```

FIG. 66B

```
                            (G)
ILAGYGAGVAGALVAFKIMSGEVPSTEDLVNLLPAILSPGALVVGVVCAA-1900

(HC)
ILRRHVGPGEGAVQWMNRLIAFASRGNHVSPTHYVPESDAAARVTAILSS
LTVTQLLRRLHQWISSECTTPCSGSWLRDIWDWICEVLSDFKTWLKAKLM-2000

(V)
PQLPGIPFVSCQRGYKGVWRGDGIMHTRCHCGAEITGHVKNGTMRIVGPR
TCRNMWSGTFPINAYTTGPCTPLPAPNYTFALWRVSAEEYVEIRQVGDFH-2100
YVTGMTTDNLKCPCQVPSPEFFTELDGVRLHRFAPPCKPLLREEVSFRVG
LHEYPVGSQLPCEPEPDVAVLTSMLTDPSHITAEAAGRRLARGSPPSVAS-2200
SSASQLSAPSLKATCTANHDSPDAELIEANLLWRQEMGGNITRVESENKV
VILDSFDPLVAEEDEREISVPAEILRKSRRFAQALPVWARPDYNPPLVET-2300

S
WKKPDYEPPVVHGCPLPPPKSPPVPPPRKKRTVVLTESTLSTALAELATR (FA)
SFGSSSTSGITGDNTTTSSEPAPSGCPPDSDAESYSSMPPLEGEPGDPDL-2400
SDGSWSTVSSEANAEDVVCCSMSYSWTGALVTPCAAEEQKLPINALSNSL
LRHHNLVYSTTSRSACQRQKKVTFDRLQVLDSHYQDVLKEVKAAASKVKA-2500

(F)
NLLSVEEACSLTPPHSAKSKFGYGAKDVRCHARKAVTHINSVWKDLLEDN
VTPIDTTIMAKNEVFCVQPEKGGRKPARLIVFPDLGVRVCEKMALYDVVT-2600
KLPLAVMGSSYGFQYSPGQRVEFLVQAWKSKKTPMGFSYDTRCFDSTVTE (G)
SDIRTEEAIYQCCDLDPQARVAIKSLTERLYVGGPLTNSRGENCGYRRCR-2700
ASGVLTTSCGNTLTCYIKARAACRAAGLQDCTMLVCGDDLVVICESAGVQ
EDAASLRAFTEAMTRYSAPPGDPPQPEYDLELITSCSSNVSVAHDGAGKR-2800
VYYLTRDPTTPLARAAWETARHTFVNSWLGNIIMFAPTLWARMILMTHFF
SVLIARDQLEQALDCEIYGACYSIEPLDLPPIIQRLHGLSAFSLHSYSPG-2900

G
EINRVAACLRKLGVPPLRAWRHRARSVRARLLARGGRAAICGKYLFNWAV
RTKLK--------------(Stop codon not yet reached)
```

( ) = Heterogeneity due to possible 5' or 3' terminal cloning artefacts.

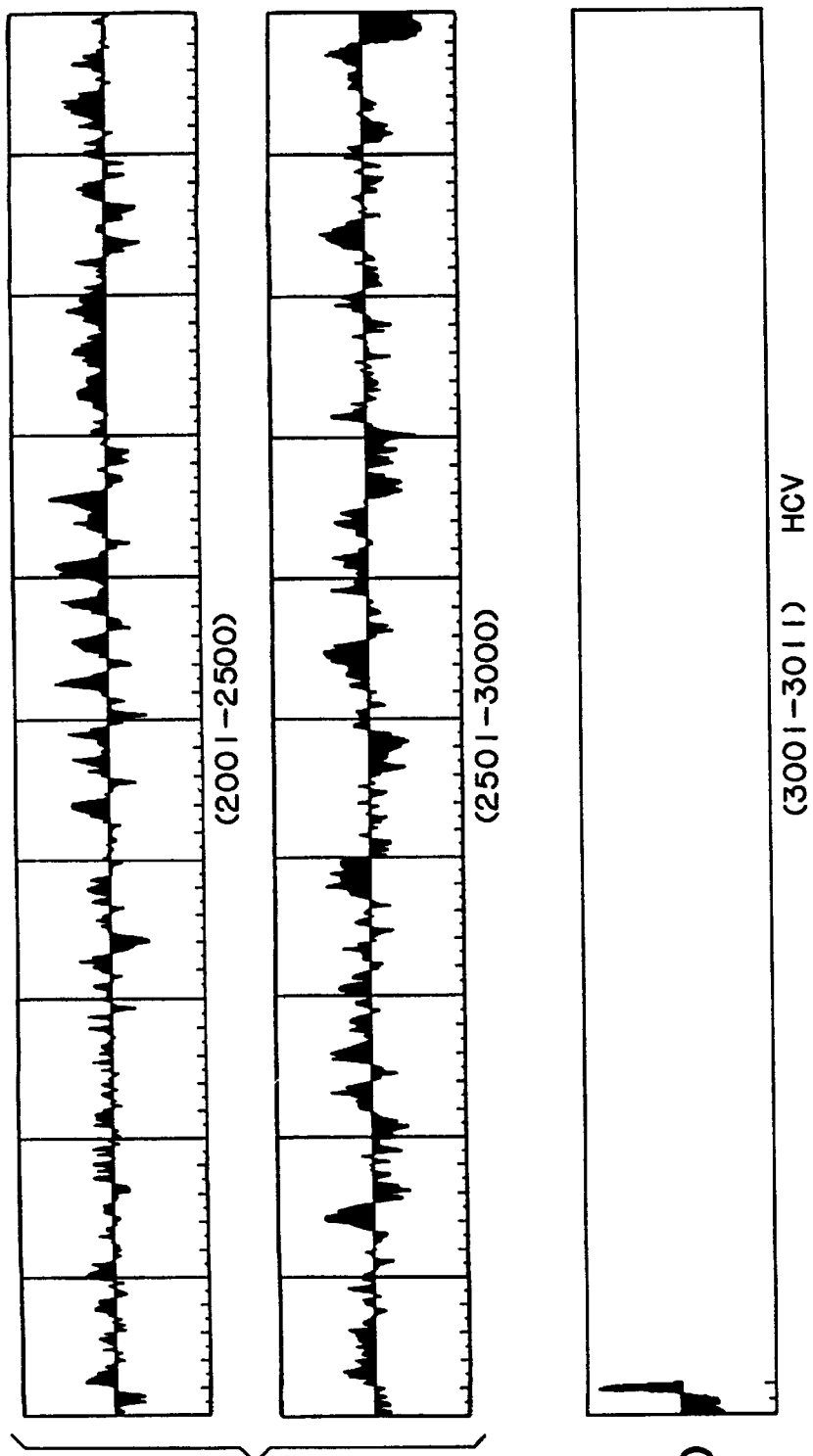
FIG. 67C (2001-2500) (2501-3000)
FIG. 67D (3001-3011) HCV

FIG. 68

```
                                                      NS5
                                                 Highly-conserved
                                                    Polymerase
                      NS3 region                      region Flaviviruses     TATPPG---------SAAQRRGRIGRNP----    ------------GDDCVV
(Yellow Fever,
West Nile,Dengue)
                 ******         *  ***** **                      *** **

HCV              TATPPG---------SRTQRRGRTGRGK----    ------------GDDLVV
                 |              |                                |
                 #1348          #1483                            #2737
```

FIG. 73

```
5'                                                                      3'
CCGGGCGAGGGGGCAGTGCAGTGGATGAACCGGCTGATAGCCTTCGCCTCCCGGGGGAAC
    CGCTCCCCCGTCACGTCACCTACTTGGCCGACTATCGGAAGCGGAGGGCCCCCTTG
3'                                                                      5'

5'                     3'
CATGTTTCCCCCTAATGAG
GTACAAAGGGGGATTACTCAGC
3'                         5'
```

FIG. 71

```
------------------Overlap with 16jh------------------
    GlyArgAlaAlaIleCysGlyLysTyrLeuPheAsnTrpAlaValArgThrLysLeuLys
1   GGCAGGGCTGCCATATGTGGCAAGTACCTCTTCAACTGGGCAGTAAGAACAAAGCTCAAA LeuThrProIleAlaAlaAlaGlyGlnLeuAspLeuSerGlyTrpPheThrAlaGlyTyr
61  CCGTCCCGACGGTATACACCGTTCATGGAGAAGTTGACCCGTCATTCTTGTTTGAGTTT
    -
    LeuThrProIleAlaAlaAlaGlyGlnLeuAspLeuSerGlyTrpPheThrAlaGlyTyr
    CTCACTCCAATAGCGGCCGCTGGCCAGCTGGACTTGTCCGGTTCACGGCTGGCTAC SerGlyGlyAspIleTyrHisSerValSerHisAlaArgProArgTrpIleTrpPheCys
121 AGCGGGGGAGACATTATCACACGCGTGTCTCATGCCCCGGCCCGCTGGATCTGGTTTTGC
    TCGCCCCTCTGTAAATAGTGTCGCACAGAGTACGGGGCCCGGGCGACCTAGACCAAAACG

```
    MetSerThrAsnProLysProGlnArgLysThrLysArgAsnThrArgArgProGln
1   ATGAGCACGAATCCTAAACCTCAAAAAAACAAGTAACACCAACCGTCGCCCACAG
    TACTCGTGCTTAGGATTTGGAGTTTTTTTGTTCATTGTGGTTGCAGCGGGTC

AspValLysPheProGlyGlyGlyGlnIleValGlyGlyValTyrLeuLeuProArgArg
61  GACGTCAAGTTCCCGGGCGGTGGCGGTCAGATCGTTGGTGGAGTTTACTTGTTGCCGCAGG
    CTGCAGTTCAAGGGCCCGCCACCGCCAGTCTAGCAACCACCTCAAATGAACAACGGCGTCC
```

FIG. 72B

```
       GlyProArgLeuGlyValArgAlaThrArgLysThrSerGluArgSerGlnProArgGly
121    GGCCCTAGATTGGGTGTGCGCGGCGACGAGAAAGACTTCCGAGCGGTCGCAACCTCGAGGT
       CCGGGATCTAACCCACACGCGCCGCTGCTCTTTCTGAAGGCTCGCCAGGTTGGAGCTCCA

ArgArgGlnProIleProLysAlaArgArgProGluGlyArgThrTrpAlaGlnProGly
181    AGACGTCAGCCTATCCCCAAGGCTCGTCGGCCCGAGGCAGGAACCTGGGCTCAGCCCGGG
       TCTGCAGTCGGATAGGGGTTCCGAGCAGCCGGGCTCCGTCCTTGGACCCGAGTCGGGCCC

TyrProTrpProLeuTyrGlyAsnGluGlyCysGlyTrpAlaGlyTrpLeuLeuSerPro
241    TACCCTTGGCCCTCTATGGCAATGAGGGCTGCGGGATGGCGGGATGGCTCCTGTCTCCC
       ATGGGAACCGGGAGATACCGTTACTCCCGACGCCCTACCGACGCCCTACCGAGGACAGAGGG

ArgGlySerArgProSerTrpGlyProThrAspProArgArgArgSerArgAsnLeuGly
301    CGTGGCTCTCGGCCTAGCTGGGGCCCCACAGACCCCGGCTAGGTCGCGCAATTTGGGT
       GCACCGAGAGCCGGATCGACCCCGGGGTGTCTGGGGCCGCATCCAGCGCGTTAAACCCA

LysValIleAspThrLeuThrCysGlyPheAlaAspLeuMetGlyTyrIleProLeuVal
361    AAGGTCATCGATACCCTTACGTGCGGCTTCGCCGACCTCATGGGCTACATACCGCTCGTC
       TTCCAGTAGCTATGGGAATGCACGCCGAAGCGGCTGGAGTACCCATGTATGGCGAGCAG

GlyAlaProLeuGlyGlyAlaAlaArgAlaLeuAlaHisGlyValArgValLeuGluAsp
421    GGCGCCCCTCTTGGAGGCGCTGCCAGGCGTGCCCGACGGCCTGGGCTGCTTGAAGAC
       CCGCGGGGAGAACCTCCGCGACGGTCCGCACGGGTACCCGGAGCCCAAGACTTCTG
```

FIG. 72C

```
     GlyValAsnTyrAlaThrGlyAsnLeuProGlyCysSerPheSerIlePheLeuLeuAla
481  GGGGTGAACTATGCAACAGGGAACCTTCCTGGTTGCTCTTTCTCTATCTTCCTTCTGGCC
     CCGCACTTGATACGTTGTCCCTTGGAAGGACCAACGAGAAAGAGATAGAAGGAAGACCGG

LeuLeuSerCysLeuThrValProAlaSerAlaTyrGlnValArgAsnSerThrGlyLeu
541  CTGCTCTCTTGCTTGACTGTGCCCGCTTCGGCCTACCAAGTGCGCAACTCCACGGGCTT
     GACGAGAGAACGAACTGACACGGGCGAAGCCGGATGGTTCACGCGTTGAGGTGCCCCGAA

TyrHisValThrAsnAspCysProAsnSerIleValTyrGluAlaAlaAspAlaIle
601  TACCACGTGACCAACAATGATTGCCCTAACTCGAGTATTGTGTACGAGGCGGCCGATGCCATC
     ATGGTGCAGTGGTTACTAACGGGATTGAGCTCATAACACATGCTCCGCCGGCTACGGTAG

LeuHisThrProGlyCysValProCysValArgGluGlyAsnAlaSerArgCysTrpVal
661  CTGCACACTCCGGGGTGCGTCCCTGCGTTCGTGAGGGCAACGCCTCGAGGTGTTGGGTG
     GACGTGTGAGGCCCCACGCAGGGACGCAAGCACTCCCGTTGCGGAGCTCCACAACCCAC

AlaMetThrProThrValAlaThrArgAspGlyLysLeuProAlaThrGlnLeuArgArg
721  GCGATGACCCCTACGGTGGCCACCCAGGGATGGCAAACTCCCGCGACGCAGCTTCGACGT
     CGCTACTGGGGATGCCACCGGTGGGTCCCTACCGTTTGAGGGCGCTGCGTCGAAGCTGCA

HisIleAspLeuLeuValGlySerAlaThrLeuCysSerAlaLeuTyrValGlyAspLeu
781  CACATCGATCTGCTTGTCGGGAGCGCCACCCTCTGTTCGGCCCTCTACGTGGGGGACCTG
     GTGTAGCTAGACGAACAGCCCTCGCGGTGGGAGACAAGCCGGGAGATGCACCCCCTGGAC

CysGlySerValPheLeuValGlyGlnLeuPheThrPheSerProArgArgHisTrpThr
841  TGCGGGTCTGTCTTTCTTGTGGGCCAACTGTTCACCTTCTCTCCCAGGCGCCACTGGACG
     ACGCCCAGACAGAACAGAAAGAACAGCCGGTTGACAAGTGAAGAGAGGGTCCGCGGTGACCTGC
```

FIG. 72D

```
     ThrGlnGlyAsnCysSerIleTyrProGlyHisIleThrGlyHisArgMetAlaTrp
901  ACGCAAGGTTGCAATTGCTCTATCTATCCCGGCCATATAACGGGTCACCGGCATGGCATGG
     TGCGTTCCAACGTTAACGAGATAGATAGGGCCGGTATATTGCCCAGTGGCCGTACCGTACC

AspMetMetAsnTrpSerProThrThrAlaLeuValMetAlaGlnLeuLeuArgIle
961  GATATGATGAATGAACTGGTCCCCTACGACGGCGTTGGTAATGGCGTCAGTGCTCCGGATC
     CTATACTACTTGACCAGGGGATGCTGCCGCAACCATTACCGAGTCGACGAGGCCTAG

ProGlnAlaIleLeuAspMetIleAlaGlyAlaAlaHisTrpGlyValLeuAlaGlyIleAla
1021 CCACAAGCCATCTTGGACATGATCGCTGGTGCTCACTGGGGAGTCCTGGCGGGCATAGCG
     GGTGTTCGGTAGAACCTGTACTAGCGACCACGAGTGACCCCCTCAGGACCGCCCGTATCGC

TyrPheSerMetValGlyAsnTrpAlaLysValValLeuValLeuLeuPheAlaGly
1081 TATTTCTCCATGGTGGGGAACTGGGCCAAGGTTCCTGGTAGTGCTGCTATTTGCCGGC
     ATAAAGAGGTACCACCCCTTGACCCGGTTCCAAGGACCATCACGACGATAAACGGCCG

ValAspAlaGluThrHisValThrGlyGlySerAlaGlyHisThrValSerGlyPheVal
1141 GTCGACGCGGGAAACCCACGTCACCGGGGAAGTGCCGGCCACACTGTGTCTGATTTGTT
     CAGCTGCGCCCTTTGGGTGCAGTGGCCCCCTTCACGGCCGGTGACACAGACTAAACAA

SerLeuLeuAlaProGlyAlaLysGlnAsnValGlnLeuIleAsnThrAsnGlySerTrp
1201 AGCCTCCTCGCACCAGGCGCCAAGCAGAACGTCCAGCTGATCAACACCAACGGCAGTTGG
     TCGGAGGAGCGTGGTCCGCGGTTCGTCTTGCAGGTCGACTAGTTGTGGTTGCCGTCAACC
```

FIG. 72E

```
     HisLeuAsnSerThrAlaLeuAsnCysAsnAspSerLeuAsnThrGlyTyrTrpLeuAlaGly
1261 CACCCTCAATAGCACGGGCCCTGAACTGCAATGATAGCCTCAACACCGGCTGGTTGGCAGGG
     GTGGAGTTATCGTGCCGGGACTTGACGTTACTATCGGAGTTGTGGCCGACCAACCGTCCC

LeuPheTyrHisHisLysPheAsnSerSerGlyCysProGluArgLeuAlaSerCysArg
1321 CTTTTCTATCACCACAAGTTCAACTCTTCAGGCTGTCCTGAGAGGCTAGCCAGCTGCCGA
     GAAAAGATAGTGGTGTTCAAGTTGAGAAGTCCGACAGGACTCTCCGATCGGTCGACGGCT

ProLeuThrAspPheAspGlnGlyTrpGlyProIleSerTyrAlaAsnGlySerGlyPro
1381 CCCCTTACCGATTTTGACCAGGGCTGGGGCCCTATCAGTTATGCCAACGGAAGCGGCCCC
     GGGGAATGGCTAAAACTGGTCCCGACCCCGGGATAGTCAATACGGTTGCCTTCGCCGGGG

AspGlnArgProTyrCysTrpHisTyrProProCysGlyIleValProAlaLys
1441 GACCAGCGCCCCTACTGCTGGCACTACCCCTGCGGTATTGTGCCCGCGAAG
     CTGGTCGCGGGGATGACGACCGTGATGGGGACGCCATAACACGGGCGCTTC

SerValCysGlyProValTyrCysPheThrProSerProValValValGlyThrThrAsp
1501 AGTGTGTGTGGTCCGGTATATTGCTTCACTCCCAGCCCCGTGGTGGTGGGAACGACCGAC
     TCACACACACCAGGCCATATAACGAAGTGAGGGTCGGGCACCACCCTTGCTGGCTG

ArgSerGlyAlaProThrTyrSerTrpGlyGluAsnAspThrAspValPheValLeuAsn
1561 AGGTCGGGCGCCCCTACAGCTGGGGTGAAAATGATACGGACGTCTTCGTCCTTAAC
     TCCAGCCCGCGGGGATGTCGACCCCACTTTTACTATGCCTGCAGAAGCAGGAATTG
```

FIG. 72F

```
     AsnThrArgProProLeuGlyAsnTrpPheGlyCysThrTrpMetAsnSerThrGlyPhe
1621 AATACCAGGCCACCGCTGGGCAATTGGTTCGGTTGTACCTGGATGAACTCAACTGGATTC
     TTATGGTCCGGTGGCGACCCGTTAACCAAGCCAACATGGACCTACTTGAGTTGACCTAAG

ThrLysValCysGlyAlaProProCysValIleGlyGlyAlaGlyAsnAsnThrLeuHis
1681 ACCAAAGTGTGCGGAGCGCCTCCTTGTGTCATCGGAGGGGCGGCAACAACACCCTGCAC
     TGGTTTCACACGCCTCGCGGAGGAACACAGTAGCCTCCCCGCCGTTGTTGTGGGACGTG

CysProThrAspCysPheArgLysHisProAspAlaThrTyrSerArgCysGlySerGly
1741 TGCCCCACTGATTGCTTCCGCAAGCATCCGGACGCCACATACTCTCGGTGCGGCTCCGGT
     ACGGGGTGACTAACGAAGGCGTTCGTAGGCCTGCGGTGTATGAGAGCCACGCCGAGGCCA

ProTrpLeuThrProArgCysLeuValAspTyrProTyrArgLeuTrpHisTyrProCys
1801 CCCTGGATCACACCCAGTGCCTGGTCGACTACCCGTATAGGCTTTGGCATTATCCTTGT
     GGGACCTAGTGTGGGTCACGGACCAGCTGATGGGCATATCCGAAACCGTAATAGGAACA

ThrIleAsnTyrThrIlePheLysIleArgMetTyrValGlyGlyValGluHisArgLeu
1861 ACCATCAACTACACCATATTTAAAATCAGGATGTACGTGGGAGGGGTCGAACACAGGCTG
     TGGTAGTTGATGTGGTATAAATTTTAGTCCTACATGCACCCCAGCTTGTGTCCGAC

GluAlaAlaCysAsnTrpThrArgGlyGluArgCysAspLeuGluAspArgArgSer
1921 GAAGCTGCCTGCAACTGGACGCGGGGCGAACGTTGCGATCTGGAAGACAGGGACAGGTCC
     CTTCGACGGACGTTGACCTGCGCCCCGCTTGCAACGCTAGACCTTCTGTCCCTGTCCAGG

GluLeuSerProLeuLeuThrThrThrGlnTrpGlnValLeuProCysSerPheThr
1981 GAGCTCAGCCCGTTACTGACCACTACACAGTGGCAGTCCTCCCCGTTCCTTCACA
     CTCGAGTCGGGCAATGACGACTGGTGATGTGTCACCGTCACCGTCAGGAGGGCACAAGAAGTGT
```

FIG. 72G

```
2041  ThrLeuProAlaLeuSerThrGlyLeuIleHisLeuHisGlnAsnIleValAspValGln
      ACCCTACCAGCCTTGTCCACCGGCCTCATCCACCTCCACCAGAACATTGTGGACGTGCAG
      TGGGATGGTCGGAACAGGTGGCCGGAGTAGGTGGAGGTGGTCTTGTAACACCTGCACGTC

2101  TyrLeuTyrGlyValGlySerSerIleAlaSerTrpAlaIleLysTrpGluTyrValVal
      TACTTGTACGGGGTGGGGTCAAGCATCGCGTCCTGGGCCATTAAGTGGGAGTACGTCGTT
      ATGAACATGCCCCACCCCAGTTCGTAGCGCAGGACCCGGTAATTCACCCTCATGCAGCAA

2161  LeuLeuPheLeuLeuLeuAlaAspAlaArgValCysSerCysLeuTrpMetMetLeuLeu
      CTCCTGTTCCTTCTCCTTGCTGCAGACGCGCGTGTCCTGCTCCTGTGGATGATGCTACTC
      GAGGACAAGGAAGAGACGACGTCTGCGCGCAGACGAGGACGAACACCTACGATGAG

2221  IleSerGlnAlaGluAlaAlaLeuGluAsnLeuValIleLeuAsnAlaAlaSerLeuAla
      ATATCCCAAGGCGGAGGCGGCGGCTTTGGAGAACCTCGTAATACTTAATGCAGCATCCGCC
      TATAGGGTTCGCCCTCCGCCGAAACCTCTTGGAGCATTATGAATTACGTCGTAGGACCGG

2281  GlyThrHisGlyLeuValSerPhePheLeuValPhePheCysPheAlaTrpTyrLeuLysGly
      GGGACGCACGGTCTTGTATCCTTCCTTCGTGTTCTTCTGCTTTGCATGGTATTTGAAGGGT
      CCCTGCGTGCCAGAACATAGGAAGGAAGCACAAGAGACGAAACGTACCATAAACTTCCCA

2341  LysTrpValProGlyAlaValTyrThrPheTyrGlyMetTrpProLeuLeuLeuLeuLeu
      AAGTGGGTGCCCGGAGCGGTCTACACCTTCTACGGGATGTGGCCTCTCCTGCTCCTG
      TTCACCCACGGGCCTCGCCAGATGTGGAAGATGCCCTACACCGGAGAGGAGGAGGAC
```

FIG. 72H

```
       LeuAlaLeuProGlnArgAlaTyrAlaLeuAspThrGluValAlaAlaSerCysGlyGly
2401   TTGGCGTTGCCCCAGCGCGGGCGTACGCGCTGGACACGGAGGTGGCCGCGTCGTGTGGCGGT
       AACCGCAACGGGGTCGCGCCCGCATGCGCGACCTGTGCCTCCACCGGCGCAGCACACCGCCA

ValValLeuValGlyLeuMetAlaLeuThrLeuSerProTyrTyrLysArgTyrIleSer
2461   GTTGTTCTCGTCGGGTTGATGGCGCTGACTCTGTCACCATATTACAAGCGCTATATCAGC
       CAACAAGAGCAGCCCAACTACCGCGACTGAGACAGTGGTATAATGTTCGCGATATAGTCG

TrpCysLeuTrpTrpLeuGlnTyrPheLeuThrArgValGluAlaGlnLeuHisValTrp
2521   TGGTGCTTGTGGTGGCTTCAGTATTTCTGACCAGAGTGGAAGCGCAACTGCACGTGTGG
       ACCACGAACACCACCGAAGTCATAAAGACTGGTCTCACCTTCGCGTTGACGTGCACACC

IleProProLeuAsnValArgGlyGlyArgAspAlaValIleLeuLeuMetCysAlaVal
2581   ATTCCCCCGCTCAACGTCCGAGGGGGCGCGACGCCGTCATCTTACTGTGTGCTGTA
       TAAGGGGGGAGTTGCAGGCTCCCCCGCGCTGCCAGTAGAATGAGTACACACGACAT

HisProThrLeuValPheAspIleThrLysLeuLeuLeuAlaValPheGlyProLeuTrp
2641   CACCCGACTCTGGTATTTGACATCACCAAATTGCTGCTGGCCGTCTTCGACCCCTTTGG
       GTGGGCTGAGACCATAAACTGTAGTGGTTTAACGACGACCGGCAGAAGCCTGGGAAACC

IleLeuGlnAlaSerLeuLeuLysValProTyrPheValArgValGlnGlyLeuLeuArg
2701   ATTCTTCAAGCCAGTTTGCTTAAAGTACCCTACTTTGTGCGCGTCCAAGGCCTTCTCCGG
       TAAGAAGTTCGGTCAAACGAATTTCATGGGATGAAACACGCGCAGGTTCCGAAGAGGCC
```

FIG. 72I

```
2761  PheCysAlaLeuAlaArgLysMetIleGlyGlyHisTyrValGlnMetValIleIleLys
      TTCTGCGCGTTAGCGCGGAAGATGATCGGCGGCCATTACGTGCAGAATGGTCATCATTAAG
      AAGACGCGCAATCGCGCCTTCTACTAGCCTCCGGTAATGCACGTTACCAGTAGTAATTC

2821  LeuGlyAlaLeuThrGlyThrTyrValTyrAsnHisLeuThrProLeuArgAspTrpAla
      TTAGGGGCGCTTACTGGCACCTATGTTTATAACCATCTCACTCCTCTTCGGGACTGGGCG
      AATCCCCGCGAATGACCGTGGATACAAATATTGGTAGAGTGAGGAGAAGCCCTGACCCGC

2881  HisAsnGlyLeuArgAspLeuAlaValAlaAlaValGluProValValPheSerGlnMetGlu
      CACAACGGCTTGCGAGATCTGGCCGTGTAGAGCCAGTCGTCTTCTCCCAAATGGAG
      GTGTTGCCGAACGCTCTAGACCGGCACCGACATCTCGGTCAGCAGAAGAGGGTTTACCTC

2941  ThrLysLeuIleThrTrpGlyAlaAspThrAlaAlaCysGlyAspIleIleAsnGlyLeu
      ACCAAGCTCATCACGTGGGGCGCAGATACCGCGTGCGGTGACATCATCAACGGCTTG
      TGGTTCGAGTAGTGCACCCCGTCTATGGCGGCACGCCACTGTAGTAGTTGCCGAAC

3001  ProValSerAlaArgArgGlyArgGluIleLeuLeuGlyProAlaAspGlyMetValSer
      CCTGTTTCCGCCCGCAGGGGCCGGGAGATACTGCTCGGGCCGATGGAATGGTCTCC
      GGACAAAGGCGGGGCGTCCCCGGCCCTCTATGACGAGCCCGGTCGGCTACCTTACCAGAGG

3061  LysGlyTrpArgLeuLeuAlaProIleThrAlaTyrAlaGlnGlnThrArgGlyLeuLeu
      AAGGGGTGGAGGTTGCTGGCGCCCATCACCGCGTACGCCCAGCAGACAAGGGGCCTCCTA
      TTCCCACCTCCAACGACCGCGGGTAGTGCCGCATGCGGGTCGTCGTTCCCGGAGGAT

3121  GlyCysIleIleThrSerLeuThrGlyArgAspLysAsnGlnValGlyValGln
      GGGTGCATAATCACCAGCTGGACCTAACTGGCCGGGACAAAACCAAGTGGAGGTGAGGTCCAG
      CCCACGTATTAGTGGTCGATTGACCGGCCCTGTTTTTGGTTCACTCCCACTCCAGGTC
```

FIG. 72J

```
3181  IleValSerThrAlaAlaGlnThrPheLeuAlaThrCysIleAsnGlyValCysTrpThr
      ATTGTGTCAACTGCTGCCAGCAGACCTTCCTGGCAACGTGCATCAATGGGGTGTGCTGACT
      TAACACAGTTGACGACGGTTTGGAAGGACCGTTGCACGTAGTTACCCACACGACCTGA

3241  ValTyrHisGlyAlaGlyThrIleAlaSerProLysGlyProValIleGlnMet
      GTCTACCACGGGGCCGGAACGATGGCGTCACCCAAGGGTCCTGTCATCCAGATG
      CAGATGGTGCCCCGGCCTTGCTACCGCAGTGGCAGTGGGTTCCCAGGACAGTAGGTCTAC

3301  TyrThrAsnValAspGlnGlySerArgSerLeu
      TATACCAATGTAGACCAAGACCTGTGGGCTGGCCCCGCTCCGCAAGGTAGCCGCTCATTG
      ATATGGTTACATCTGGTTCTGGACACCCGACCGGAGGCGTTCCATCGGCGAGTAAC

3361  ThrProCysThrGlySerSerAspLeuTyrLeuValThrArgHisAlaAspValIle
      ACACCCTGCACTTGCGGCTCCTCCTCGGACCTTTACCTGGTCACGAGGCACGCCGATGTCATT
      TGTGGGACGTGAACGCCGAGGAGGAGCCTGGAAATGACCAGTGCTCCGTGCGGCTACAGTAA

3421  ProValArgArgGlyAspSerArgGlySerLeuLeuSerProArgProIleSerTyr
      CCCGTGCGCCGGGGGGTGATAGCAGGGGCAGCCTGTCGCCCCGCCATTTCCTAC
      GGGCACGCGCCGCCCCCCACTATCGTCCCCGTCGACGACAGCGGGGCCGGGTAAAGGATG

3481  LeuLysGlySerSerGlyGlyProLeuLeuCysProAlaValGlyHisAlaValGlyIlePhe
      TTGAAAGGCTCCTCCGGGGGTCCGCTGTTGTGCCCCGGGGCACGCCGTGGGCATATTT
      AACTTTCCGAGGAGCCCCCAGGCGACAACACGGGGCGCCCCGTGCGGCACCGTATAAA

3541  ArgAlaAlaValCysThrArgGlyValAlaLysAlaValAspPheIleProValGluAsn
      AGGGCCGCCGTGTGCACCCGTGGAGTGGCTAAGGCGGTGGACTTATCCCCTGTGGAGAAC
      TCCCGGCGGCACACGTGGGCACCTCACCGATTCCGCCACCTGAAATAGGGACACCTCTTG
```

FIG. 72K

```
      LeuGluThrThrMetArgSerProValPheThrAspAsnSerSerProValPro
3601  CTAGAGACAACCATGAGGTCCCCGGTGTTCACGGATAACTCCTCTCCACCAGTAGTGCCC
      GATCTCTGTTGGTACTCCAGGGGCCACAAGTGCCTATTGAGGAGAGGTGGTCATCACGGG

GlnSerPheGlnValAlaAlaHisLeuHisAlaProThrGlySerGlyLysSerLysVal
3661  CAGAGCTTCCAGGTGGCTGCTCACCTCCATGCTCCCACAGCGGCAAAAGCACCAAGGTC
      GTCTCGAAGGTCCACCGAGTGGAGGTACGAGGGTGTCCGTCGCCGTTTCGTGGTTCCAG

ProAlaAlaTyrAlaAlaGlnGlyTyrLysValLeuValLeuAsnProSerValAlaAla
3721  CCGGCTGCATATGCAGCTCAGGGCTATAAGGTCCTAGTACTCAACCCCTCTGTTGCTGCA
      GGCCGACGTATACGTCGAGTCCCGATATTCCAGGATCATGAGTTGGGAGACAACGACGT

ThrLeuGlyPheGlyAlaTyrMetSerLysAlaHisGlyIleAspProAsnIleArgThr
3781  ACACTGGGCTTTGGTGCTTACATGTCCAAGGCTCATGGGATCGATCCTAACATCAGGACC
      TGTGACCCGAAACCACGAATGTACAGGTTCCGAGTACCCTAGGATTGTAGTCCTGG

GlyValArgThrIleThrThrGlySerProIleThrThrTyrSerThrTyrGlyLysPheLeu
3841  GGGTGAGAACAATTACCACTGGCAGCCCATCACCACGTACTCCACCTACGGCAAGTTCCTT
      CCCCACTCTTGTTAATGGTGACCGTCGGGTAGTGCATGAGGTGGATGCCGTTCAAGGAA

AlaAspGlyGlySerGlyGlyAlaTyrAspIleIleIleCysAspGluCysHisSer
3901  GCCGACGGCGGGTGCTCGGGGGCGCCTTATGACATAATAATTGTGACGAGTGCCACTCC
      CGGCTGCCGCCCACGAGCCCCGCGGAATACTGTATTATTAACACTGCTCACGGTGAGG
```

FIG. 72L

```
     ThrAspAlaThrSerIleLeuGlyIleGlyThrValLeuAspGlnAlaGluThrAlaGly
3961 ACGGATGCCACATCCATCTTGGGCATCGGCACTGTCCTTGACCAAGCAGAGACTGCGGGG
     TGCCTACGGTGTAGGTAGAACCCGTAGCCGTGACAGGAACTGGTTCGTCTCTGACGCCCC

AlaArgLeuValValLeuAlaThrAlaThrProProGlySerValThrValProHisPro
4021 GCGAGACTGGTTGTGCTCGCCACCGCCACCCCCTCCGGGTCCGTCACTGTGCCCCATCCC
     CGCTCTGACCAACACGAGCGGTGGCGGTGGGGAGGCCCAGGCAGTGACACGGGGTAGGG

AsnIleGluValAlaLeuSerThrThrGlyGluIleProPheTyrGlyLysAlaIle
4081 AACATCGAGGAGGTTGCTCTGTCCACCACCGGAGAGATCCCTTTTTACGGCAAGGCTATC
     TTGTAGCTCCTCCAACGAGACAGGTGGTGGCCTCTCTAGGGAAAAATGCCGTTCCGATAG

ProLeuGluValIleLysGlyGlyArgHisLeuIlePheCysHisSerLysLysLysCys
4141 CCCCTCGAAGTAATCAAGGGGGAGACATCTCATCTTCGTCATTCAAAGAAGAAGTGC
     GGGGAGCTTCATTAGTTCCCCCTCTGTAGAGTAGAAGCAGTAAGTTTCTTCTTCACG

AspGluLeuAlaAlaLysLeuValAlaAlaLeuGlyIleAsnAlaValAlaAlaTyrTyrArgGly
4201 GACGAACTCGCCGCCAAAGCTGGTCGCATTGGGCATCAATGCCGTGGCCTACTACCGCGGT
     CTGCTTGAGCGGCGGTTTCGACCAGCGTAACCCGTAGTTACGGCACCGGATGATGGCCA

LeuAspValSerValIleProThrSerGlyAspValValAlaThrAspAlaLeu
4261 CTTGACGTGTCCGTCATCCCGACCAGCGGGGATGTTGTCGTGGCAACCGATGCCCTC
     GAACTGCACAGGCAGTAGGGCTGGTCGCCCTACAACAGCAGCACCGTTGGCTACGGGAG
```

FIG. 72M

```
      MetThrGlyTyrThrGlyAspPheAspSerValIleAspCysAsnThrCysValThrGln
4321  ATGACCGGCTATACCGGCGACTTCGACTCGGTGATAGACTGCAATACGTGTGTCACCCAG
      TACTGGCCGATATGGCCGCTGAAGCTGAGCCACTATCTGACGTTATGCACACAGTGGGTC

ThrValAspPheSerLeuAspProThrPheThrIleGluThrIleThrLeuProGlnAsp
4381  ACAGTCGATTTCAGCCTTGACCCTACCTTCACCATTGAGACAATCACGCTCCCCAGGAT
      TGTCAGCTAAAGTCGGAATGGGATGGAAGTGGTAACTCTGTTAGTGCGAGGGGTCCTA

AlaValSerArgArgThrGlnArgArgGlyArgThrGlyLysLysProGlyIleTyrArg
4441  GCTGTCTCCGCACTCAACGTCGGGGCAGGACTGGGGAAGCCAGGCATCTACAGA
      CGACAGAGGGCGTGAGTTGCAGCCCCGTCCTGACCCCCCTTCGGTCCGTAGATGTCT

PheValAlaProGlyArgProSerGlyMetPheAspSerSerValLeuCysGluCys
4501  TTTGTGGCACCGGGGAGCCGCTCCGGCATGTTCGACTCGTCCGTCCTCTGTGAGTGC
      AAACACCGTGGCCCCCTCGGCGGAGCCGTACAAGCTGAGCAGGCAGGAGACACTCACG

TyrAspAlaGlyCysAlaTrpTyrGluLeuThrProAlaGluThrThrValArgLeuArg
4561  TATGACGCAGGCTGTGCTTGGTATGAGCTCACGCCCGCCGAGACTACAGTTAGGCTACGA
      ATACTGCGTCCGACACGAACCATACTCGAGTGCGGGCGGCTCTGATGTCAATCCGATGCT

AlaTyrMetAsnThrProGlyLeuProValCysGlnAspHisLeuGluPheTrpGluGly
4621  GCGTACATGAACACCCCGGGCCTTCCCGTGTGCCAGGACCATTTGAATTTTGGGAGGGC
      CGCATGTACTTGTGGGGCCCCGGAAGGGCACACGGTCCTGGTAGAACTTAAAACCCTCCCG

ValPheThrGlyLeuThrHisIleAspAlaHisPheLeuSerGlnThrLysGlnSerGly
4681  GTCTTTACAGGCCTCACTCATATAGATGCCCACTTTCTATCCCAGACAAAGCAGAGTGGG
      CAGAAATGTCCGGAGTGAGTATATCTACGGGTGAAAGATAGGTCTGTTTCGTCTCACCC
```

FIG. 72N

```
       GluAsnLeuProTyrLeuValAlaTyrGlnAlaThrValCysAlaArgAlaAlaGlnAlaPro
4741   GAGAACCTTCCTTACCTGGTAGCGTACCAAGCCACCGTGTGCGCTAGGGCTCAAGCCCCT
       CTCTTGGAAGGAATGGACCATCGCATGGTTCGGTGGCACACGGCGATCCCGAGTTCGGGA

ProProSerTrpAspGlnMetTrpLysCysLeuIleArgLeuLysProThrLeuHisGly
4801   CCCCCATCGTGGGACCAGATGTGGAAGTGTTTGATTCGCCTCAAGCCCACCCTCCATGGG
       GGGGTAGCACCCTGGTCTACACCTTCACAAACTAAGCGGAGTTCGGGTGGGAGTACCC

ProThrProLeuTyrArgLeuGlyAlaValGlnAsnGluIleThrLeuHisPro
4861   CCAACACCCCTGCTATACAGACTGGGCGCTGTTCAGAATGAAATCACCCTGACGCACCA
       GGTTGTGGGGACGATATGTCTGACCCGCGACAAGTCTTACTTTAGTGGGACTGCGTGGGT

ValThrLysTyrIleMetThrCysMetSerAlaAspLeuGluValValThrSerThrTrp
4921   GTCACCAAATACATCATGACATGCATGTCGGCCGACCTGGAGGTCGTCAGAGCACCTGG
       CAGTGGTTTATGTAGTACTGTACGTACAGCCGGCTGGACCTCCAGCAGTCGTCGTGGACC

ValLeuValGlyValGlyValLeuAlaAlaLeuAlaAlaTyrCysLeuSerThrGlyCysVal
4981   GTGCTCGTTGGCGTCGGCGTCCTGGCTGCTTTGGCCGCGTATTGCCTGTCAACAGGCTGCGTG
       CACGAGCAACCGCGCAGGACCGACGAAACCGGCGCATAACGGACAGTTGTCCGACGCAC

ValIleValGlyValValLeuSerGlyLysProAlaIleIleProAspArgGluVal
5041   GTCATAGTGGGCAGGGTCGTCTTGTCCGGAAGCCGGCAATCATACCTGACAGGGAAGTC
       CAGTATCACCCGTCCCAGACAGGTCTTCGGCCGTTAGTATGGACTGTCCCTTCAG

LeuTyrArgGluPheAspGluMetGluGluCysSerGlnHisLeuProTyrIleGluGln
5101   CTCTACCGAGAGTTCGATGAGATGGAAGAGTGCTCTCAGCACTTACCGTACATCGAGCAA
       GAGATGGCTCTCAAGCTACTCTACCTTCTCACGAGAGTCGTGAATGGCATGTAGCTCGTT
```

FIG. 72O

```
       GlyMetMetLeuAlaGluGlnPheLysGlnLysAlaLeuGlyLeuLeuGlnThrAlaSer
5161   GGGATGATGCTCGCCGAGCAGTTCAAGCAGAAGGCCCTCGGCCTCCTGCAGACCGCGTCC
       CCCTACTACGAGCGGCTCGTCAAGTTCGTCTTCCGGGAGCCGGAGGACGTCTGGGCAGG

ArgGlnAlaGluValIleAlaProAlaValGlnThrAsnTrpGlnLysLeuGluThrPhe
5221   CGTCAGGCAGAGGTTATCGCCCCTGCTGTCCAGACCAACTGGCAAAAACTCGAGACCTTC
       GCAGTCCGTCTCCAATAGCGGGGACGACAGGTCTGGTTGACCGTTTTGAGCTCTGGAAG

TrpAlaLysHisMetTrpAsnPheIleSerGlyIleGlnTyrLeuAlaGlyLeuSerThr
5281   TGGGCGAAGCATATGTGGAACTTCATCAGTGGGATACAATACTTGGCGGGCTTGTCAACG
       ACCCGCTTCGTATACACCTTGAAGTAGTCACCCTATGTTATGAACCGCCGAACAGTTGC

LeuProGlyAsnProAlaIleAlaSerLeuMetAlaPheThrAlaAlaValThrSerPro
5341   CTGCCTGGTAACCCGGCCATTGCTTCATTGATGGCTTTTACAGCTGCTGTCACCAGCCCA
       GACGGACCATTGGGCCGGTAACGAAGTAACTACCGAAAATGTCGACGACAGTGGTCGGGT

LeuThrThrSerGlnThrLeuLeuPheAsnIleLeuGlyGlyTrpValAlaAlaGlnLeu
5401   CTAACCACTAGCCAAACCCTCCTCTTCAACATATTGGGGGGTGGCTGCCAGCTC
       GATTGGTGATCGGTTTGGGAGGAGAAGTTGTATAACCCCACCGACGGGTCGAG

AlaAlaProGlyAlaAlaThrAlaPheValGlyAlaGlyLeuAlaAlaAlaIleGly
5461   GCCGCCCCCGGTGCCGCTACTGCCTTTGTGGGCGCTGGCTTAGCTGCGGCCATCGGC
       CGGCGGGGCCACGGCGATGACGGAAACACCCGCGACCGAATGACGACGCCGGTAGCCG
```

FIG. 72P

```
5521  SerValGlyLeuGlyLysLysValLeuIleAspIleLeuIleAlaGlyTyrGlyAlaGlyValAla
      AGTGTTGGACTGGGGAAGGTCCTCATAGACATCCTTGCAGGGTATGGCGGGGGCGTGGCG
      TCACAACCTGACCCCTTCCAGGAGTATCTGTAGGAACGTCCCATACCGCCCGCCACCGC

5581  GlyAlaLeuValAlaPheLysIleMetSerGlyGluValProSerThrGluAspLeuVal
      GGAGCTCTTGTGGCATTCAAGATCATGACCGGTGAGGTCCCCTCCACGGAGGACCTGGTC
      CCTCGAGAACACCGTAAGTTCTAGTACTGGCCACTCCAGGGAGGTGCCTCCTGGACCAG

5641  AsnLeuProAlaIleLeuSerProGlyAlaLeuValValGlyValValCysAlaAla
      AATCTACTGCCCGCCATCCTCTCGCCCGGAGCCCTCGTAGTCGGGGTGGTCTGTGCAGCA
      TTAGATGACGGGCGGTAGGAGAGCGGGCCTCGGGAGCATCAGCCCCACCAGACACGTCGT

5701  IleLeuArgArgHisValGlyProGlyGluGlyAlaValGlnTrpMetAsnArgLeuIle
      ATACTGCGCCGGCACGTTGGCCCGGAGGGGGCCAGTGCAGTGGATGAACCGGCTGATA
      TATGACGCGGCCGTGCAACCGGGCCCTCCCCCGGTCACGTCACCTACTTGGCCGACTAT

5761  AlaPheAlaSerArgGlyAsnHisValSerProThrHisTyrValProGluSerAspAla
      GCCTTCGCCTCCCGGGGGAACCATGTTTCCCCACGCACTACGTCCGGAGAGCGATGCA
      CGGAAGCGGAGGGCCCCCTTGGTACAAAGGGGTGCGTGATGCACGGCCCTCTCGCTACGT

5821  AlaAlaArgValThrAlaIleLeuSerSerLeuThrValThrGlnLeuLeuArgArgLeu
      GCTGCCCGCGTCACTGCCATCCTCAGCAGCCTGACCGTAACCCAGCTCCTGAGGCGACTG
      CGACGGGCGCAGTGACGGTAGGAGTCGTCGGACTGGCATTGGGTCGAGGACTCCGCTGAC
```

FIG. 72Q

```
5881  HisGlnTrpIleSerSerGluCysThrThrProCysSerGlySerTrpLeuArgAspIle
      CACCAGTGGATAAGCTCGGAGTGTACCACTCCATGCTCCGGTTCCTGCTAAGGGACATC
      GTGGTCACCTATTCGAGCCTCACATGGTGAGGTACGAGGCCAAGGACGATTCCCTGTAG

5941  TrpAspTrpIleCysGluValLeuSerAspPheLysThrTrpLeuLysAlaAlaLysLeuMet
      TGGGACTGGATATGCGAGGTGTTGAGCGACTTTAAGACCTGGCTAAAAGCTGCTAAGCTCATG
      ACCCTGACCTATACGCTCCACAACTCGCTGAAATTCTGGACCGATTTTCGACGATTCGAGTAC

6001  ProGlnLeuProGlyIleProPheValSerCysGlnArgGlyTyrLysGlyValTrpArg
      CCACAGCTGCCTGGGATCCCCTTTGTCCTGCCAGCGCGGCTATAAGGGGGTCTGGCGA
      GGTGTCGACGGACCCTAGGGGAAACACAGGACGGTCGCGCCGCCCATATTCCCCAGACCGCT

6061  ValAspGlyIleMetHisThrArgCysHisCysGlyAlaAlaGluIleThrGlyHisValLys
      GTGGACGGCATCATGCACACTCGCTGCCACTGTGGAGCTGAGATCACTGGACATGTCAAA
      CACCTGCCGTAGTACGTGTGAGCGACGGTGACACCTCGACTCTAGTGACCTGTACAGTTT

6121  AsnGlyThrArgMetArgIleValGlyProArgThrCysArgAsnMetTrpSerGlyThrPhe
      AACGGGACGAGGATGAGGATCGTCGGTCCTAGGACGTGCAGGAACATGTGGAGTGGGACCTTC
      TTGCCCTGCTACTCCTACTCCTAGCAGCCAGGATCCTGCACGTCCTTGTACACTCACCCTGAAG

6181  ProIleAsnAlaTyrThrThrGlyProCysThrProLeuProAlaProAsnTyrThrPhe
      CCCATTAATGCCTACACGACCGGGCCCTGTACCCCCTTCCTGCGCCACCTAACACGTTC
      GGGTAATTACGGATGTGCTGGCCCGGACATGGGGGAAGGACGCGGCTTGATGTGCAAG
```

FIG. 72R

```
       AlaLeuTrpArgValSerAlaGluGluTyrValGluIleArgGlnValGlyAspPheHis
6241   GCGCTATGGAGGGGTGTCTGCAGAGGAATATGTGGAGATAAGGCAGGTGGGGACTTCCAC
       CGCGATACCTCCCACAGACGTCTCCTTATACACCTCTATTCCGTCCACCCCTGAAGGTG

TyrValThrGlyMetThrThrAspAsnLeuLysCysProCysGlnValProSerProGlu
6301   TACGTGACGGGTATGACTACTGACAATCTCAAATGCCCGTGCCAGTCCCATGCCCGAA
       ATGCACTGCCCATACTGATGACTGTTAGAGTTTACGGGCACGGTCCAGGGTAGCGGCTT

PhePheThrGluLeuAspGlyValArgLeuHisArgPheAlaProProCysLysProLeu
6361   TTTTTCACAGAATTGGACGGGGTGCGCCTACATAGTTTGCGCCCCCTGCAAGCCCTTG
       AAAAAGTGTCTTAACCTGCCCCACGCGGATGTATCCAAACGCGGGGACGTTCGGGAAC

LeuArgGluGluValSerPheArgValGlyLeuHisGluTyrProValGlyLeuSerGlnLeu
6421   CTGCGGGAGGAGGTATCATTCAGAGTAGGACTCCACGAATACCCGGTAGGGTCGCAATTA
       GACGCCCTCCTCCATAGTAAGTCTCATCCTGAGGTGCTTATGGGCATCCCAGCGTTAAT

ProCysGluProAspValAlaValLeuThrSerMetLeuThrAspProSerHis
6481   CCTTGCGAGCCCGACGTTGCGGTTGACGTCCATGCTCACTGATCCCTCCCAT
       GGAACGCTCGGGCTGCACAACTGCAGGTACGAGTGACTAGGACTAGGGAGGGTA

IleThrAlaAlaAlaGlyArgArgLeuAlaArgGlySerProProSerValAlaSer
6541   ATAACAGCAGAGGCCGGGCGGGCCGAAGGTTGGCGCGAGGGGATCACCCCCTGTGGCCAGC
       TATTGTCGTCTCCGCCCCGGCCCCGGCTTCCAACCGCTCCCCTAGTGGGGAGACACCGGTCG
```

FIG. 72S

```
       SerSerAlaSerGlnLeuSerAlaProSerLeuLysAlaThrCysThrAlaAsnHisAsp
6601   TCCTCGGCTAGCCAGCTATCCGCTCCATCTCTCAAGGCAACTTGCACCGCTAACCATGAC
       AGGAGCCGATCGGTCGATAGGCGAGGTAGAGAGTTCCGTTGAACGTGGCGATTGGTACTG

SerProAspAlaGluLeuIleAlaAsnLeuLeuTrpArgGlnGluMetGlyGlyAsn
6661   TCCCCTGATGCTGAGCTCATAGAGCCAACCTCCTATGGAGGCAGGAGATGGGCGGCAAC
       AGGGACTACGACTCGAGTATCTCGGTTGGAGGATACCTCCGTCCTCTACCGCCGTTG

IleThrArgValGluSerGluAsnLysValValIleLeuAspSerPheAspProLeuVal
6721   ATCACCAGGGTTGAGTCAGAAAACAAAGTGTGATTCTGACTCCTTCGATCCGCTTGTG
       TAGTGGTCCCAACTCAGTCTTTTGTTTCACCACTAAGACTGAGGAAGCTAGGCGAACAC

AlaGluGluAspGluArgGluIleLeuArgLysSerArgArg
6781   GCGGAGGAGGAGGGGAGATCCTGCGTACCCGCAGAAATCCTGCGAAGTCTCGGAGA
       CGCCTCCTCCTCCTGCTCCGGGGCATGGGTCGTATTTAGGACGCCTTCAGAGCCTCT

PheAlaGlnAlaLeuProValTrpAlaArgProAspTyrAsnProProLeuValGluThr
6841   TTCGCCCAGGCCCTGCCCGTTGGGGCGGGGACTATAACCCCCGCTAGTGGAGACG
       AAGCGGGTCCGGGACGGGCAAACCCGGCGCCCTGATATTGGGGCGATCACCTCTGC

TrpLysLysProAspTyrGluProProValHisGlyCysProLeuProProProLys
6901   TGGAAAAAGCCCGACTACGAACCACCTGGTCCATGGCTGTCCGCTTCCACCTCCAAAG
       ACCTTTTTCGGGCTGATGCTTGGTGGACACCAGGTACCGACAGGCGAAGGTGGAGGTTTC

SerProProValProProArgLysLysArgThrValValLeuThrGluSerThrLeu
6961   TCCCCTCCTGTCCCTCCGCTCGGAAGAAGCGGACGGTGGTCCTCACTGAATCAACCCTA
       AGGGGAGGACACGAGGCGAGCCTTCTTCGCCTGCCACCAGGAGTGACTTAGTTGGGAT
```

FIG. 72T

```
           SerThrAlaLeuAlaGluLeuLeuAlaThrArgSerPheGlySerSerSerThrSerGlyIle
7021  TCTACTGCCCTTGCCGAGCTGCTCGCCACCAGAAGCTTTGGCAGCTCCTCAACTTCCGGCATT
      AGATGACGGGAACCGGCTCGAGGAGCGGTGGTCTTCGAAACCGTCGAGGAGTTGAAGGCCGTAA

ThrGlyAspAsnThrThrSerSerGluProAlaProSerGlyCysProProAspSer
7081  ACGGGCGACAATACGACAACATCCTCTGAGCCCGCCCCTTCTGGCTGCCCCCCCGACTCC
      TGCCCGCTGTTATGCTGTTGTAGGAGACTCGGGCGGGGAAGACCGACGGGGGGCTGAGG

AspAlaGluSerTyrSerSerMetProProLeuGluGlyGluProGlyAspProAspLeu
7141  GACGCTGAGTCCTATTCCTCCATGCCCCCCCTGGAGGGGGAGCCTGGGGATCCGGATCTT
      CTGCGACTCAGGATAAGGAGGTACGGGGGGGACCTCCCGACCCCTAGGCCTAGAA

SerAspGlySerTrpSerThrValSerSerGluAlaAsnAlaGluAspValValCysCys
7201  AGCGACGGGTCATGGTCAACGGTCAGTAGTGAGGCCAACGCCGAGGATGTCGTGTGCTGC
      TCGCTGCCCAGTACCAGTTGCCAGTCATCACTCCGGTTGCGCTCCTACAGCACGACG

SerMetSerTyrSerTrpThrGlyAlaAlaLeuValThrProCysAlaAlaGluGlnLys
7261  TCAATGTCTTACTCTTGGACAGGCGCACTCGTCACCCCGTGCGCCGCGGAAGAACAGAAA
      AGTTACAGAATGAGAACCTGTCCGCGTGAGCAGTGGGGCACGCGGCCTTCTTGTCTTT

LeuProIleAsnAlaLeuSerAsnSerLeuLeuArgHisHisAsnLeuValTyrSerThr
7321  CTGCCCATCAATGCACTAAGCAACTCGTTGCTACGTCACCACAATTTGGTGTATTCCACC
      GACGGGTAGTTACGTGATTCGTTGAGCAACGATGCAGTGGTGTTAAACCACATAAGGTGG
```

FIG. 72U

```
       ThrSerArgSerAlaCysGlnArgGlnLysLysValThrPheAspArgLeuGlnValLeu
7381   ACCTCACGCAGTGCTTGCCAAAGGCAGAAGAAAGTCACATTTGACAGACTGCAAGTTCTG
       TGGAGTGCGTCACGAACGGTTTCCGTCTTCTTTCAGTGTAAACTGTCTGACGTTCAAGAC

AspSerHisTyrGlnAspValLeuLysGluValLysAlaAlaAlaSerLysValLysAla
7441   GACAGCCATTACCAGGACGTACTCAAGGAGGTTAAAGCAGCGGCGTCAAAAGTGAAGCT
       CTGTCGGTAATGGTCCTGCATGAGTTCCTCCAATTCGTCGCCGCCAGTTTCACTTCCGA

AsnLeuSerValGluGluValAlaCysSerLeuThrProProHisSerAlaLysSerLys
7501   AACTTGCTATCCGTAGAGGAAGCTTGCAGCCTGACGCCCCACACTCAGCCAAATCCAAG
       TTGAACGATAGGCATCTCCTTCGAACGTCGGACTGCGGGGTGAGTCGGTTTAGGTTC

PheGlyTyrGlyAlaAlaLysAspValArgCysHisAlaArgLysAlaValThrHisIleAsn
7561   TTTGGTTATGGGCAAAAGACGTCCGTTGCCATGCCAGAAAGCCGTAACCCACATCAAC
       AAACCAATACCCCGTTTTCTGCAGGCAACGGTACGGTCTTTCCGGCATTGGGTGAGTTG

SerValTrpLysAspLeuLeuGluAspAsnValThrProIleAspThrThrIleMetAla
7621   TCCGTGTGGAAAGACCTTCTGGAAGACAATGTAACACCAATAGACACTACCATCATGGCT
       AGGCACACCTTTCTGGAAGACCTTCTGTTACATTGTGGTTATCTGTGATGGTAGTACCGA

LysAsnGluValPheCysValGlnProGluLysGlyGlyArgLysProAlaArgLeuIle
7681   AAGAACGAGGTTTTCTGCGTTCAGCCTGAGAAGGGGGTCGTAAGCCAGCTCGTCTCATC
       TTCTTGCTCCAAAGACGCAAGTCGGACTCTCCCCAGCATTCGGTCGAGCAGAGTAG

ValPheProAspLeuGlyValArgValCysGluLysMetAlaLeuTyrAspValValThr
7741   GTGTTCCCGATCTGGGCGTGCGCGTGTGCGAAAAGATGGCTTTGTACGACGTGGTTACA
       CACAAGGGCTAGACCCGCACGCGCACACGCTTTCTACCGAAACATGCTGCACCAATGT
```

FIG. 72V

```
      LysLeuProLeuAlaValMetGlySerSerTyrGlyPheGlnTyrSerProGlyGlnArg
7801  AAGCTCCCCTTGGCCGTGATGGGAAGCTCCTACGATTCCAATACTCCAGGACAGCGG
      TTCGAGGGGAACCGGCACTACCCTTCGAGGATGCTAAGGTTATGAGTGGTCCTGTCGCC

ValGluPheLeuValGlnAlaTrpLysSerLysThrProMetGlyPheSerTyrAsp
7861  GTTGAATTCCTCGTGCAAGCGTGGAAGTCCAAGAAAACCCAATGGGTTCTCGTATGAT
      CAACTTAAGGAGCACGTTCGCACCTTCAGGTTCTTTTGGGTTACCCAAGAGCATACTA

ThrArgCysPheAspSerThrValThrGluSerAspIleArgThrGluAlaIleTyr
7921  ACCCGCTGCTTTGACTCCACAGTCACTGAGAGCGACATCCGTACGGAGGAGCAATCTAC
      TGGGCGACGAAACTGAGGTGTCAGTGACTCTCGCTGTAGGCATGCCTCCTCCGTTAGATG

GlnCysCysAspLeuAspProGlnAlaArgValAlaIleLysSerLeuThrGluArgLeu
7981  CAATGTTGTGACCTTGACCCTCGAGCCCCGCGCTGGCCATCAAGTCCCTCACCGAGAGCTT
      GTTACAACACTGGAACTGGGAGCTCGGGGCGCGACCGGTAGTTCAGGGAGTGGCTCTCGAA

TyrValGlyGlyProLeuThrAsnSerArgGlyGluAsnCysGlyTyrArgArgCysArg
8041  TATGTTGGGGGCCCTCTTACCAATTCAAGGGGGGAGAACTGCGGCTATCGCAGGTGCCGC
      ATACAACCCCCGGGAGAATGGTTAAGTTCCCCCTCTTGACGCCGATAGCGTCCACGGCG

AlaSerGlyValLeuThrThrSerCysGlyAsnThrLeuThrCysTyrIleLysAlaArg
8101  GCGAGCGGCGTACTGACAACTAGCTGTGGTAACACCCTGACCTGCTACATCAAGGCCCGG
      CGCTCGCCGCATGACTGTTGATCGACACCATTGTGGGACTGGACGATGTAGTTCCGGCC
```

FIG. 72W

```
      AlaAlaCysArgAlaAlaAlaGlyLeuGlnAspCysThrMetLeuValCysGlyAspLeu
8161  GCAGCCTGTCGAGCCGCGCAGGCTCCAGGACTGCACCATGCTCGTGTGGGACGACTTA
      CGTCGGACAGCTCGGCGCGTCCCGAGGTCCTGACGTGGTACGAGCACACCCTGCTGAAT

ValValIleCysGluSerAlaGlyValGlnGluAspAlaAlaSerLeuArgAlaPheThr
8221  GTCGTTATCTGTGAAAGCGCGGGGGTCCAGGAGGACGCGGCGAGCCTGAGAGCCTTCACG
      CAGCAATAGACACTTTCGCGCCCCCAGGTCCTCCTGCGCCGCTCGGACTCTCGGAAGTGC

GluAlaMetThrArgTyrSerAlaProProGlyAspProProGlnProGluTyrAspLeu
8281  GAGGCTATGACCAGGTACTCCGCCCCCCCTGGGGACCCCCCACAACCAGAATACGACTTG
      CTCCGATACTGGTCCATGAGGCGGGGGGGACCCCTGGGGGTGTTGGTCTTATGCTGAAC

GluLeuIleThrSerCysSerSerAsnValSerAlaAlaHisAspGlyAlaGlyLysArg
8341  GAGCTCATAACATCATGCTCCTCCAACGTGTCAGTGCGCCAGTGACGGCGCTGGAAAGAGG
      CTCGAGTATTGTAGTACGAGGAGTTGCACAGTCACGCGGTCAGCGCGGCGACCTTTCTCC

ValTyrTyrLeuThrArgAspProThrThrProLeuAlaArgAlaAlaTrpGluThrAla
8401  GTCTACTACCTCACCCGTGACCCTACAACCCCTCGCGAGCTGCGTGGGAGACAGCA
      CAGATGATGGAGTGGGCACTGGGATGTTGGGGAGCGCTCTCGACGCACCCTCTGTGT

ArgHisThrProValAsnSerTrpLeuGlyAsnIleIleMetPheAlaProThrLeuTrp
8461  AGACACACTCCAGTCAATTCCTGGCTAGGCAACATAATCATGTTTGCCCCACACTGTGG
      TCTGTGTGAGGTCAGTTAAGGACCGATCCGTTGTATTAGTACAAACGGGGGTGTGACACC
```

FIG. 72X

```
           AlaArgMetIleLeuMetThrHisPhePheSerValLeuIleAlaArgAspGlnLeuGlu
     8521  GCGAGGATGATACTGATGACCCATTCTTTAGCGTCCTTATAGCCAGGACCAGCTTGAA
           CGCTCCTACTATGACTACTGGGTAAGAAATCGCAGGAATATCGGTCCCTGGTCGAACTT

GlnAlaLeuAspCysGluIleTyrGlyAlaCysTyrSerIleGluProLeuAspLeuPro
     8581  CAGGCCCTCGATTGCGAGATCTACGGGGCCTGCTACTCCATAGAACCACTGATCTACCT
           GTCCGGGAGCTAACGCTCTAGATGCCCCGGACGATGAGGTATCTTGGTGAACTAGATGA

ProIleGlnArgLeuHisGlyLeuSerAlaPheSerLeuHisSerTyrSerProGly
     8641  CCAATCATTCAAAGACTCCATGGCCTCAGCGCCATTTCACTCCACAGTTACTCTCCAGGT
           GGTTAGTAAGTTTCTGAGGTACCGGAGTCGCGGTAAAGTGAGGTGTCAATGAGAGGTCCA

GluIleAsnArgValAlaAlaCysLeuArgLysLeuGlyValProProLeuArgAlaTrp
     8701  GAAATTAATAGGGTGGCCGCATGCCTCAGAGCCTCAGAAAACTGGGTACCGCCCTTGCGAGCTGG
           CTTTAATTATCCCACCGGCGTACGGAGTCTCGGAGTCTTTGAACCCATGGCGGGAACGCTCGAACC

ArgHisArgAlaArgSerValArgAlaArgLeuLeuAlaArgGlyGlyArgAlaAlaIle
     8761  AGACACCGGGCCCGGAGCGTCCGCGCTAGGCTTCTGCCAGGAGGAGGCAGGCTGCCATA
           TCTGTGGCCCGGGCCTCGCAGGCGCGATCCGAAGACCGGTCTCCTCCGTCCGACGGTAT

CysGlyLysTyrLeuAsnTrpAlaValArgThrLysLeuThrProIleAla
     8821  TGTGGCAAGTACCTCTTCAACTGGGCAGTAAGAACAAAGCTCACTCCAATAGCG
           ACACCGTTCATGGAGAAGTTGACCCGTCATTCTTGTTTCGAGTTTGAGTTATCGC
```

FIG. 72Y

```
         AlaAlaGlyGlnLeuAspLeuSerGlyTrpPheThrAlaGlyTyrSerGlyGlyAspIle
8881     GCCGCTGGCCAGCTGGACTTGTCCGGCTGGTTCACGGCTGGCTACAGCGGGGGAGACATT
         CGGCGACCGGTCGACCTGAACAGGCCGACCAAGTGCCGACCGATGTCGCCCCCTCTGTAA

TyrHisSerValSerHisAlaArgProArgTrpIleTrpPheCys
8941     TATCACAGCGTGTCTCATGCCCCGCTGGATCTGGTTTTGCCC
         ATAGTGTCGCACAGAGTACGGGGCCGGGGGACCTAGAACCAAAACGGG
```

```
      GluPheGlySerValIleProThrSerGlyAspValValValValAlaThrAspAlaLeu
  1   GAATTCGGGTCCGTCATCCCGACCAGCGGCGATGTTGTCGTCGTGGCAACCGATGCCCTC
      CTTAAGCCCAGGCAGTAGGGCTGGTCGCCGCTACAACAGCAGCACCGTTGGCTACGGGAG

1 ECOR1, 7 NLA1V, 8 AVA2 SAU96, 15 FOK1, 24 NSPB11, 26 FNU4H
      1, 52 SFAN1, 57 MNL1, 60 NLA111,

MetThrGlyTyrThrGlyAspPheAspSerValIleAspCysAsnThrCysValThrGln
 61   ATGACCGGCTATACCGGCGACTTCGACTCGGTGATAGACTGCAATACGTGTGTCACCCAG
      TACTGGCCGATATGGCCGCTGAAGCTGAGCCACTATCTGACGTTATGCACACAGTGGGTC

65 HPA11, 74 HPA11, 83 TAQ1, 85 HINF1, 90 HPH, 106 AFL111 MA
      E2, 112 MAE3, 113 HPH,

ThrValAspPheSerLeuAspProThrPheThrIleGluThrIleThrLeuProGlnAsp
121   ACAGTCGATTTCAGCCTTGACCCTACCTTCACCATTGAGACAATCACGCTCCCCCAAGAT
      TGTCAGCTAAAGTCGGAACTGGGATGGAAGTGGTAACTCTGTTAGTGCGAGGGGGTTCTA

125 TAQ1, 149 HPH, 178 SFAN1,

AlaValSerArgThrGlnArgArgGlyArgThrGlyArgGlyLysProGlyIleTyrArg
181   GCTGTCTCCCGCACTCAACGTCGGGGCAGGACTGGCAGGGGGAAGCCAGGCATCTACAGA
      CGACAGAGGGCGTGAGTTGCAGCCCCGTCCTGACCGTCCCCCTTCGGTCCGTAGATGTCT

198 MAE2, 226 ECOR11 SCRF1, 230 SFAN1,

PheValAlaProGlyGluArgProProAlaCysSerThrArgProSerSerValSerAla
241   TTTGTGGCACCGGGGGAGCGCCCTCCGGCATGTTCGACTCGTCCGTCCTCTGTGAGTGCC
      AAACACCGTGGCCCCCTCGCGGGAGGCCGTACAAGCTGAGCAGGCAGGAGACACTCACGG

246 BAN1 NLA1V, 250 HPA11 NCI1 SCRF1, 257 HAE11, 258 HHA1, 2
      62 MNL1, 265 HPA11, 268 NSPC1, 269 NLA111, 274 TAQ1, 276 HIN
      F1, 287 MNL1, 296 BSP1286,

ArgIle
301   CGAATTC
      GCTTAAG

302 ECOR1,

```
         ------Overlap with 6k------
         TyrHisSerValSerHisAlaArgProArgTrpIleTrpPheCysLeuLeuLeuLeuAla
  1   TTATCACAGCGTGTCTCATGCCCGGCCCCGGCTGGATCTGGTTTGCCTACTCCTGCTTGC
      AATAGTGTCGCACAGAGTACGGGCCGGGGCCGACCTAGACCAAAACGGATGAGGACGAACG AlaGlyValGlyIleTyrLeuLeuProAsnArgOP
 61   TGCAGGGGTAGGCATCTACCTCCTCCCAACCGATGAAGGTTGGGTAAACACTCCGGCC
      ACGTCCCCATCCGTAGATGGAGGAGGGTTGGCTACTTCCAACCCCATTTGTGAGGCCGG

```
    AlaValAspPheIleProValGluAsnLeuGluThrThrMetArgSerProValPheThr
  2 GCGGTGGACTTTATCCCTGTGGAGAACCTAGAGACAACCATGAGGTCCCCGGTGTTCACG
    CGCCACCTGAAATAGGGACACCTCTTGGATCTCTGTTGGTACTCCAGGGGCCACAAGTGC
```

29 MAE1, 40 NLA111, 43 MNL1, 45 AVA2 NLA1V SAU96, 49 NCI1 SC RF1, 50 HPA11,

```
    AspAsnSerSerProProValValProGlnSerPheGlnValAlaHisLeuHisAlaPro
 62 GATAACTCCTCTCCACCAGTAGTGCCCCAGAGCTTCCAGGTGGCTCACCTCCATGCTCCC
    CTATTGAGGAGAGGTGGTCATCACGGGGTCTCGAAGGTCCACCGAGTGGAGGTACGAGGG
```

69 MNL1, 83 BSP1286, 92 ALU1, 97 ECOR11 SCRF1, 106 HPH, 109 MNL1, 113 NLA111,

```
    ThrGlySerGlyLysSerThrLysValProAlaAlaTyrAlaAlaGlnGlyTyrLysVal
122 ACAGGCAGCGGCAAAAGCACCAAGGTCCCGGCTGCATATGCAGCTCAGGGCTATAAGGTG
    TGTCCGTCGCCGTTTTCGTGGTTCCAGGGCCGACGTATACGTCGAGTCCCGATATTCCAC
```

126 BBV FNU4H1, 127 NSPB11, 129 FNU4H1, 145 AVA2 NLA1V SAU96 , 148 NCI1 SCRF1, 149 HPA11, 152 BBV FNU4H1, 156 NDE1, 161 B BV FNU4H1, 163 ALU1, 165 DDE1,

```
    LeuValLeuAsnProSerValAlaAlaThrLeuGlyPheGlyAlaTyrMetSerLysAla
182 CTAGTACTCAACCCCTCTGTTGCTGCAACACTGGGCTTTGGTGCTTACATGTCCAAGGCT
    GATCATGAGTTGGGGAGACAACGACGTTGTGACCCGAAACCACGAATGTACAGGTTCCGA
```

182 MAE1, 184 SCA1, 185 RSA1, 195 MNL1, 203 BBV FNU4H1, 228 AFL111 NSPC1, 229 NLA111,

```
    HisGlyIleAspProAsnIleArgThrGlyValArgThrIleThrThrGlySerProIle
242 CATGGGATCGATCCTAACATCAGGACCGGGGTGAGAACAATTACCACTGGCAGCCCCATC
    GTACCCTAGCTAGGATTGTAGTCCTGGCCCCACTCTTGTTAATGGTGACCGTCGGGGTAG
```

242 NLA111, 246 BIN1, 247 MBO1 SAU3A, 248 CLA1, 249 TAQ1, 25 1 BIN1 MBO1 SAU3A, 264 AVA2 SAU96, 267 HPA11 NCI1 SCRF1, 271 HPH, 291 BBV FNU4H1,

```
    ThrTyrSerThrTyrGlyLysPheLeuAlaAspGlyGlyCysSerGlyGlyAlaTyrAsp
302 ACGTACTCCACCTACGGCAAGTTCCTTGCCGACGGCGGGTGCTCGGGGGGCGCTTATGAC
    TGCATGAGGTGGATGCCGTTCAAGGAACGGCTGCCGCCCACGAGCCCCCGCGAATACTG
```

302 MAE2, 304 RSA1, 340 BSP1286 HGIA, 343 AVA1, 350 HAE11, 3 51 HHA1,

```
    IleIleIleCysAspGluCysHisSerThrAspAlaThrSerIleLeuGlyIleGlyThr
362 ATAATAATTTGTGACGAGTGCCACTCCACGGATGCCACATCCATCTTGGGCATTGGCACT
    TATTATTAAACACTGCTCACGGTGAGGTGCCTACGGTGTAGGTAGAACCCGTAACCGTGA
```

372 MAE3, 391 FOK1, 392 SFAN1, 399 FOK1,

```
    ValLeuAspGlnAlaGluThrAlaGlyAlaArgLeuValValLeuAlaThrAlaThrPro
422 GTCCTTGACCAAGCAGAGACTGCGGGGGCGAGACTGGTTGTGCTCGCCACCGCCACCCCT
    CAGGAACTGGTTCGTCTCTGACGCCCCGCTCTGACCAACACGAGCGGTGGCGGTGGGGA
```

431 TTHIII2, 435 ALWN1, 461 BSP1286 HGIA, 479 MNL1,

FIG. 79B

```
       ProGlySerValThrValProHisProAsnIleGluGluValAlaLeuSerThrThrGly
482    CCGGGCTCCGTCACTGTGCCCCATCCCAACATCGAGGAGGTTGCTCTGTCCACCACCGGA
       GGCCCGAGGCAGTGACACGGGGTAGGGTTGTAGCTCCTCCAACGAGACAGGTGGTGGCCT
```

482 HPAll NCIl SCRFl, 484 BANll BSP1286, 485 NLAlV, 491 MAE3
, 497 BSP1286, 503 FOKl, 513 TAQl, 515 MNLl, 518 MNLl, 537 H
PAll,

```
       GluIleProPheTyrGlyLysAlaIleProLeuGluValIleLysGlyGlyArgHisLeu
542    GAGATCCCTTTTTACGGCAAGGCTATCCCCCTCGAAGTAATCAAGGGGGGGAGACATCTC
       CTCTAGGGAAAAATGCCGTTCCGATAGGGGGAGCTTCATTAGTTCCCCCCCTCTGTAGAG
```

543 XHO2, 544 BINl MBOl SAU3A, 571 MNLl, 573 TAQl,

```
       IlePheCysHisSerLysLysLysCysAspGluLeuAlaAlaLysLeuValAlaLeuGly
602    ATCTTCTGTCATTCAAAGAAGAAGTGCGACGAACTCGCCGCAAAGCTGGTCGCATTGGGC
       TAGAAGACAGTAAGTTTCTTCTTCACGCTGCTTGAGCGGCGTTTCGACCAGCGTAACCCG.
```

603 MBOll, 619 MBOll, 638 FNU4Hl, 645 ALUl, 660 SFANl,

```
       IleAsnAlaValAlaTyrTyrArgGlyLeuAspValSerValIleProThrSerGlyAsp
662    ATCAATGCCGTGGCCTACTACCGCGGTCTTGACGTGTCCGTCATCCCGACCAGCGGCGAT
       TAGTTACGGCACCGGATGATGGCGCCAGAACTGCACAGGCAGTAGGGCTGGTCGCCGCTA
```

672 HAEl, 673 HAElll, 682 NSPBll SAC2, 683 THAl, 693 AFLlll
MAE2, 703 FOKl, 712 NSPBll, 714 FNU4Hl,

```
       ValValValValAlaThrAspAlaLeuMetThrGlyTyrThrGlyAspPheAspSerVal
722    GTTGTCGTCGTGGCAACCGATGCCCTCATGACCGGCTATACCGGCGACTTCGACTCGGTG
       CAACAGCAGCACCGTTGGCTACGGGAGTACTGGCCGATATGGCCGCTGAAGCTGAGCCAC
```

740 SFANl, 745 MNLl, 748 NLAlll, 753 HPAll, 762 HPAll, 771 T
AQl, 773 HINFl, 778 HPH,

```
       IleAspCysAsnThrCysValThrGlnThrValAspPheSerLeuAspProThrPheThr
782    ATAGACTGCAATACGTGTGTCACCCAGACAGTCGATTTCAGCCTTGACCCTACCTTCACC
       TATCTGACGTTATGCACACAGTGGGTCTGTCAGCTAAAGTCGGAACTGGGATGGAAGTGG
```

794 AFLlll MAE2, 800 MAE3, 801 HPH, 813 TAQl, 837 HPH,

```
       IleGluThrIleThrLeuProGlnAspAlaValSerArgThrGlnArgArgGlyArgThr
842    ATTGAGACAATCACGCTCCCCCAAGATGCTGTCTCCCGCACTCAACGTCGGGGCAGGACT
       TAACTCTGTTAGTGCGAGGGGGTTCTACGACAGAGGGCGTGAGTTGCAGCCCCGTCCTGA
```

866 SFANl, 886 MAE2,

```
       GlyArgGlyLysProGlyIleTyrArgPheValAlaProGlyGluArgProSerGlyMet
902    GGCAGGGGGAAGCCAGGCATCTACAGATTTGTGGCACCGGGGGAGCGCCCCTCCGGCATG
       CCGTCCCCCTTCGGTCCGTAGATGTCTAAACACCGTGGCCCCCTCGCGGGGAGGCCGTAC
```

914 ECORll SCRFl, 918 SFANl, 934 BANl NLAlV, 938 HPAll NCIl
SCRFl, 945 HAEll, 946 HHAl, 948 BGLl, 951 MNLl, 954 HPAll, 9
57 NSPCl, 958 NLAlll,

```
       PheAspSerSerValLeuCysGluCysTyrAspAlaGlyCysAlaTrpTyrGluLeuThr
962    TTCGACTCGTCCGTCCTCTGTGAGTGCTATGACGCAGGCTGTGCTTGGTATGAGCTCACG
       AAGCTGAGCAGGCAGGAGACACTCACGATACTGCGTCCGACACGAACCATACTCGAGTGC
```

963 TAQl, 965 HINFl, 976 MNLl, 992 HGAl, 1003 TTHIII2, 1013
BANll BSP1286 HGIA SACl, 1014 ALUl,

```
       ProAlaGluThrThrValArgLeuArgAlaTyrMetAsnThrProGlyLeuProValCys
1022   CCCGCCGAGACTACAGTTAGGCTACGAGCGTACATGAACACCCCGGGGCTTCCCGTGTGC
       GGGCGGCTCTGATGTCAATCCGATGCTCGCATGTACTTGTGGGGCCCCGAAGGGCACACG
```

FIG. 79C

1051 RSA1, 1054 NLA111, 1063 AVA1 NCI1 SCRF1 SMA1, 1064 HPA1
1 NCI1 SCRF1, 1081 ECOR11 SCRF1,

```
     GlnAspHisLeuGluPheTrpGluGlyValPheThrGlyLeuThrHisIleAspAlaHis
1082 CAGGACCATCTTGAATTTTGGGAGGGCGTCTTTACAGGCCTCACTCATATAGATGCCCAC
     GTCCTGGTAGAACTTAAAACCCTCCCGCAGAAATGTCCGGAGTGAGTATATCTACGGGTG
```

1084 AVA2 SAU96, 1103 MNL1, 1106 AHA11, 1107 HGA1, 1117 HAE1
   STU1, 1118 HAE111, 1120 MNL1, 1133 SFAN1,

```
     PheLeuSerGlnThrLysGlnSerGlyGluAsnLeuProTyrLeuValAlaTyrGlnAla
1142 TTTCTATCCCAGACAAAGCAGAGTGGGGAGAACCTTCCTTACCTGGTAGCGTACCAAGCC
     AAAGATAGGGTCTGTTTCGTCTCACCCCTCTTGGAAGGAATGGACCATCGCATGGTTCGG
```

1183 ECOR11 SCRF1, 1192 RSA1, 1201 DRA3,

```
     ThrValCysAlaArgAlaGlnAlaProProProSerTrpAspGlnMetTrpLysCysLeu
1202 ACCGTGTGCGCTAGGGCTCAAGCCCCTCCCCCATCGTGGGACCAGATGTGGAAGTGTTTG-
     TGGCACACGCGATCCCGAGTTCGGGGAGGGGGTAGCACCCTGGTCTACACCTTCACAAAC
```

1209 HHA1, 1212 MAE1, 1215 BAN11 BSP1286, 1226 MNL1, 1239 NL
   A1V, 1240 AVA2 SAU96, 1256 TTHIII2, 1261 HINF1,

```
     IleArgLeuLysProThrLeuHisGlyProThrProLeuLeuTyrArgLeuGlyAlaVal
1262 ATTCGCCTCAAGCCCACCCTCCATGGGCCAACACCCCTGCTATACAGACTGGGCGCTGTT
     TAAGCGGAGTTCGGGTGGGAGGTACCCGGTTGTGGGGACGATATGTCTGACCCGCGACAA
```

1267 MNL1, 1279 MNL1, 1282 NCO1, 1283 NLA111, 1286 SAU96, 12
87 HAE111, 1313 HAE11, 1314 HHA1,

```
     GlnAsnGluIleThrLeuThrHisProValThrLysTyrIleMetThrCysMetSerAla
1322 CAGAATGAAATCACCCTGACGCACCCAGTCACCAAATACATCATGACATGCATGTCGGCC
     GTCTTACTTTAGTGGGACTGCGTGGGTCAGTGGTTTATGTAGTACTGTACGTACAGCCGG
```

1332 HPH, 1339 HGA1, 1349 MAE3, 1350 HPH, 1363 NLA111, 1367
NSPC1, 1368 NLA111, 1369 AVA3 NSI1, 1371 NSPC1, 1372 NLA111,
   1377 CFR1 XMA3, 1378 HAE111,

```
     AspLeuGluValValThrSerThrTrpValLeuValGlyGlyValLeuAlaAlaLeuAla
1382 GACCTGGAGGTCGTCACGAGCACCTGGGTGCTCGTTGGCGGCGTCCTGGCTGCTTTGGCC
     CTGGACCTCCAGCAGTGCTCGTGGACCCACGAGCAACCGCCGCAGGACCGACGAAACCGG
```

1384 ECOR11 SCRF1, 1385 GSU1, 1388 MNL1, 1394 MAE3, 1399 BSP
1286 HGIA, 1404 ECOR11 SCRF1, 1409 BSP1286 HGIA, 1419 FNU4H1
, 1421 AHA11, 1422 HGA1, 1426 ECOR11 SCRF1, 1430 BBV FNU4H1,
   1437 CFR1, 1438 HAE111, 1439 FNU4H1, 1441 THA1,

```
     AlaTyrCysLeuSerThrGlyCysValValIleValGlyArgValValLeuSerGlyLys
1442 GCGTATTGCCTGTCAACAGGCTGCGTGGTCATAGTGGGCAGGGTCGTCTTGTCCGGGAAG
     CGCATAACGGACAGTTGTCCGACGCACCAGTATCACCCGTCCCAGCAGAACAGGCCCTTC
```

1453 HINC11, 1461 BBV FNU4H1, 1494 HPA11 NCI1 SCRF1, 1501 NA
E1,

```
     ProAlaIleIleProAspArgGluValLeuTyrArgGluPheAspGluMetGluGluCys
1502 CCGGCAATCATACCTGACAGGGAAGTCCTCTACCGAGAGTTCGATGAGATGGAAGAGTGC
     GGCCGTTAGTATGGACTGTCCCTTCAGGAGATGGCTCTCAAGCTACTCTACCTTCTCACG
```

1502 HPA11, 1528 MNL1, 1542 TAQ1, 1553 MBO11, 1558 BSP1286 H
GIA,

```
     SerGlnHisLeuProTyrIleGluGlnGlyMetMetLeuAlaGluGlnPheLysGlnLys
1562 TCTCAGCACTTACCGTACATCGAGCAAGGGATGATGCTCGCCGAGCAGTTCAAGCAGAAG
     AGAGTCGTGAATGGCATGTAGCTCGTTCCCTACTACGAGCGGCTCGTCAAGTTCGTCTTC
```

1563 DDE1, 1576 RSA1, 1581 TAQ1, 1590 FOK1, 1594 SFAN1, 1612

FIG. 79D

TTHIII2, 1621 HAEIII SAU96,

```
      AlaLeuGlyLeuLeuGlnThrAlaSerArgGlnAlaGluValIleAlaProAlaValGln
1622  GCCCTCGGCCTCCTGCAGACCGCGTCCCGTCAGGCAGAGGTTATCGCCCTGCTGTCCAG
      CGGGAGCCGGAGGACGTCTGGCGCAGGGCAGTCCGTCTCCAATAGCGGGACGACAGGTC
```

1624 MNL1, 1628 HAEIII, 1630 MNL1, 1634 PST1, 1639 TTHIII1, 1642 THA1, 1643 HGA1, 1658 MNL1,

```
      ThrAsnTrpGlnLysLeuGluThrPheTrpAlaLysHisMetTrpAsnPheIleSerGly
1682  ACCAACTGGCAAAAACTCGAGACCTTCTGGGCAAAGCATATGTGGAACTTCATCAGTGGG
      TGGTTGACCGTTTTTGAGCTCTGGAAGACCCGCTTCGTATACACCTTGAAGTAGTCACCC
```

1697 AVA1 XHO1, 1698 TAQ1, 1718 NDE1,

```
      IleGlnTyrLeuAlaGlyLeuSerThrLeuProGlyAsnProAlaIleAlaSerLeuMet
1742  ATACAATACTTGGCGGGCTTGTCAACGCTGCCTGGTAACCCCGCCATTGCTTCATTGATG
      TATGTTATGAACCGCCCGAACAGTTGCGACGGACCATTGGGGCGGTAACGAAGTAACTAC
```

1762 HINC11, 1768 BBV FNU4H1, 1772 ECOR11 SCRF1, 1775 BSTE2, 1776 MAE3,

```
      AlaPheThrAlaAlaValThrSerProLeuThrThrSerGlnThrLeuLeuPheAsnIle
1802  GCTTTTACAGCTGCTGTCACCAGCCCACTAACCACTAGCCAAACCCTCCTCTTCAACATA
      CGAAAATGTCGACGACAGTGGTCGGGTGATTGGTGATCGGTTTGGGAGGAGAAGTTGTAT
```

1809 ALWN1 NSPB11 PVU11, 1810 ALU1, 1811 BBV FNU4H1, 1817 MAE3, 1818 HPH, 1836 MAE1, 1846 MNL1, 1849 MNL1, 1851 MBO11,

```
      LeuGlyGlyTrpValAlaAlaGlnLeuAlaAlaProGlyAlaAlaThrAlaPheValGly
1862  TTGGGGGGGTGGGTGGCTGCCCAGCTCGCCGCCCCCGGTGCCGCTACTGCCTTTGTGGGC
      AACCCCCCCACCCACCGACGGGTCGAGCGGCGGGGGCCACGGCGATGACGGAAACACCCG
```

1877 BBV FNU4H1, 1884 ALU1, 1889 FNU4H1, 1895 NCI1 SCRF1, 1896 HPA11, 1898 BAN1 NLA1V, 1901 FNU4H1, 1919 HAE11, 1920 HHA1,

```
      AlaGlyLeuAlaGlyAlaAlaIleGlySerValGlyLeuGlyLysValLeuIleAspIle
1922  GCTGGCTTAGCTGGCGCCGCCATCGGCAGTGTTGGACTGGGGAAGGTCCTCATAGACATC
      CGACCGAATCGACCGCGGCGGTAGCCGTCACAACCTGACCCCTTCCAGGAGTATCTGTAG
```

1927 DDE1, 1930 ALU1, 1934 AHA11 BAN1 HAE11 NAR1 NLA1V, 1935 HHA1, 1937 FNU4H1, 1966 AVA2 SAU96, 1969 MNL1, 1978 FOK1,

```
      LeuAlaGlyTyrGlyAlaGlyValAlaGlyAlaLeuValAlaPheLysIleMetSerGly
1982  CTTGCAGGGTATGGCGCGGGCGTGGCGGGAGCTCTTGTGGCATTCAAGATCATGAGCGGT
      GAACGTCCCATACCGCGCCCGCACCGCCCTCGAGAACACCGTAAGTTCTAGTACTCGCCA
```

1995 HHA1, 1996 THA1, 2010 BAN11 BSP1286 HGIA SAC1, 2011 ALU1, 2021 BSM1, 2029 MBO1 SAU3A, 2032 NLA111, 2039 HPH,

```
      GluValProSerThrGluAspLeuValAsnLeuLeuProAlaIleLeuSerProGlyAla
2042  GAGGTCCCCTCCACGGAGGACCTGGTCAATCTACTGCCCGCCATCCTCTCGCCCGGAGCC
      CTCCAGGGGAGGTGCCTCCTGGACCAGTTAGATGACGGGCGGTAGGAGAGCGGGCCTCGG
```

2042 MNL1, 2044 AVA2 NLA1V SAU96, 2049 MNL1, 2057 MNL1, 2059 AVA2 SAU96, 2060 TTHIII1, 2062 ECOR11 SCRF1, 2083 FOK1, 2086 MNL1, 2093 NCI1 SCRF1, 2094 HPA11, 2096 NLA1V, 2097 BAN11 BSP1286, 2101 MNL1,

```
      LeuValValGlyValValCysAlaAlaIleLeuArgArgHisValGlyProGlyGluGly
2102  CTCGTAGTCGGCGTGGTCTGTGCAGCAATACTGCGCCGGCACGTTGGCCCGGGCGAGGGG
      GAGCATCAGCCGCACCAGACACGTCGTTATGACGCGGCCGTGCAACCGGGCCCGCTCCCC
```

2123 BBV FNU4H1, 2134 HHA1, 2136 NAE1, 2137 HPA11, 2142 MAE2, 2147 HAE111 SAU96, 2149 AVA1 NCI1 SCRF1 SMA1, 2150 HPA11 N

FIG. 79E

CI1 SCRF1, 2156 MNL1,

AlaValGlnTrpMetAsnArgLeuIleAlaPheAlaSerArgGlyAsnHisValSer
2162 GCAGTGCAGTGGATGAACCGGCTGATAGCCTTCGCCTCCCGGGGGAACCATGTTTCCCC
     CGTCACGTCACCTACTTGGCCGACTATCGGAAGCGGAGGGCCCCCTTGGTACAAAGGGG

2172 FOK1, 2179 HPA11, 2196 MNL1, 2199 AVA1 NCI1 SCRF1 SMA1,
  2200 HPA11 NCI1 SCRF1, 2205 NLA1V, 2210 NLA111,

Human 23

```
       GlyPheAlaAspLeuMetGlyTyrIleProLeuValGlyValGlyAlaProLeuGlyGlyGlyArgAla
  1    GGCTTCGCCGACCTCATGGGGTACATACCGCTCGTGGGCGTCGGCGCCCCTCTTGGAGCCGTGCC

ArgAlaLeuAlaHisGlyValArgValLeuGluAspValLeuAspGlyValAsnTyrAlaThrGlyAsn
  61   AGGGCCCTGGCGCACGGCGTCCGGGTTTTGGAAGACGTGCTGGACGGTGTGAACTATGCAACAGGAAAC
              CG        A

LeuProGlyCysSerPheLeuLeuAlaLeuLeuSerCysLeuThrValPro
 121   CTTCCTGGTTGCTCCTTCCTTCTATCTTCTGGCCCTACTCTCTTGCCTGACCGTGCCC
                                   GA                   T

AlaSerAlaTyrGlnValArgAsnSerThrGlyLeuTyrHisValThrAsnAspCysPro
 181   GCTTCAGCCTACCAAGTGCGCAACTCTACGGGGCTTTACCATGTCACCAATGATGCCCT

AsnSerSerIleValTyrGluAlaAlaAspAlaIleLeuHisAlaProGlyCysValPro
 241   AACTCGAGTATTGTGTACGAGGCGGCCGATGCCATCCTGCACGCTCCGGGTGTCCCT
                                                            C

CysValArgGluAspAsnValSerArgArgCysTrpValAlaValThrProThrValAlaThr
 301   TGCGTTCGCGAGGATAACGTCTCGAGACGTTGGGTGGCCGTGACCCCCACGGTGGCCACC
            G                                                      T

LysAspGlyLysLeuProThrThrGlnLeuArgArgHisIleAspLeuLeuValGlySer
 361   AAGGACGGCAAACTCCCACAACTCCAGCTTCGAGTCACATCGATCTGCTGGTGGGAGC
                                                                 A

AlaThrLeuCysSerAlaLeuTyrValGlyAspLeuCysGlySerIlePheLeuValGly
 421   GCCACCCTCTGCTCGGCCCTCTACGTGGGGGACCTTTGCGGGTCATCTTCTTGTCGGT
                                 T

GlnLeuPheThrPheSerProArgArgHisTrpThrThrGlnAspCysAsnCysSerIle
 481   CAACTGTTTACCTTCTCTCCCAGGCGCCACTGGACGACGCAGGACTGCAACTGTTCTATC
                                                               C
```

FIG. 80B

```
541  TyrProGlyHisIleThrGlyHisArgMetAlaTrpAspMetMetAsnTrpSerPro
     TATCCCGGCCATATAACGGGTCACCGGATGGCATGGGATATGATGAACTGGTCCCCT
                                                        G

601  ThrAlaAlaLeuValValAlaGlnLeuLeuArgIleProGlnAlaIleLeuAspMetIle
     ACGGCGGCATTGGTAGTAGCTCAGCTGCTCCGGATCCCACAAGCCATCTTGGACATGATC

661  AlaGlyAlaHisTrpGlyValLeuAlaGlyMetAlaTyrPheSerMetValGlyAsnTrp
     GCTGGTGCTCACTGGGGAGTCCTGGCGGGCATGGCGTATTTCTCCATGGTGGGGAACTGG
                  AG                                  G

721  AlaLysValLeuValValAlaLeuLeuPheAlaGlyValAspAlaGluThrHisArgThr
     GCGAAGGTCCTGGTAGTGGCTCTGCTTTTCGCGGGTGTCGACGCGGAAACCACGTACC
                                                   G

781  GlyGlySerAlaAlaArgSerThrAlaGlyLeuPheThrProGlyAlaArg
     GGGGGAAGTGCCGCCCGCAGCACCGCAGGGCTCTTCACCAGGGCTAGG
         C       T    A

841  GlnAsnIleGlnLeuIleIleAsnSerTrpHisIleAsnSerThrAlaLeuAsn
     CAGAACATCCAGCTGATCATCAACTCATGGCACATAATAGTACGGCCTTGAAC
                                                    AT

901  CysAsnAspSerLeuThrThrGlyTyrTrpLeuAlaGlyLeuPheTyrHisLysPheAsn
     TGCAATGACAGCCTTACCACCGGCTGGTTAGCGGGGCTTTTCTATCACCATAAATTCAAC
         A

961  SerSerGlyCysProGluArgLeuAlaSerCysArgProLeuThrAspPheAlaGln
     TCTTCAGGCTGTCCCGAGAGGTTGGCCAGCTGCGACCCTCACCGATTTTGCCCAGG
       G   A                                          G
```

FIG. 81A    Human 27

```
      GlyPheAlaAspLeuMetGlyTyrIleProLeuValGlyAlaProLeuGlyGlyAlaAla
  1   GGCTTCGCCGACCTCATGGGGTACATTCCGCTCGTTGGGGCTCCTCTTGGGGGCTGCC

ArgAlaLeuAlaHisGlyValArgValLeuGluAspGlyValAlaAsnTyrAlaThrGlyAsn
 61   AGGGCCCTGGCGCATGGGGTCCGGGTTCTGGAAGACGGGTGAACTATGCAACAGGGAAC

LeuProGlyCysSerPheSerIlePheLeuLeuLeuAlaLeuLeuSerCysLeuThrValPro
121   CTTCCTGGTTGCTCTTTCTCTATCTTCCTTCTGCTCTTGCTCTCTTGCCTGACCGTGCCC

AlaSerAlaTyrGlnValArgAsnSerSerGlyIleTyrHisValThrAsnAspCysPro
181   GCATCGGCCTACCAAGTACGCAACTCCTCGGGCATTTACCATGTCACCAATGATTGCCCT

AsnSerSerIleValTyrGluThrAlaAspThrIleLeuHisSerProGlyCysValPro
241   AATTCGAGTATTGTGTACGAGACGGCCGACACCATCCTACACTCTCCGGGGTGTCCCT
                    C

CysValArgGluGlyAsnAlaSerLysCysTrpValProValAlaProThrValAlaThr
301   TGCGTTCGCGAGGGTAACGCCTCGAAATGTTGGGTCCCCGTAGCCCCCACAGTGGCCACC
                                                  G

ArgAspGlyAsnLeuProAlaThrGlnLeuArgArgHisIleAspLeuLeuValGlySer
361   AGGGACGGCAACCTCCCCGCAACGCAGCTTCGACGTCACATGATCTGTGTGGGAGT
                                                  G

AlaThrLeuCysSerAlaLeuTyrValGlyAspLeuCysGlySerValPheLeuValGly
421   GCCACCCTTGCTCGGCCCTCTATGTGGGGACTTGTGGGGTCTGTCTTTGTCGGT
                                                  C

GlnLeuPheThrSerProArgArgHisTrpThrThrGlnAspCysAsnCysSerIle
481   CAACTGTTCACTTCTCCCCAGGCGCCACTGGACAACGCAAGATTGCAACTGTCTATC
                A
```

FIG. 81B

```
     TyrProGlyHisIleThrGlyHisArgMetAlaTrpAspMetMetAsnTrpSerPro
541  TACCCCGGCCATATAACGGGACACCGGCATGGCATGGGATATGATGATGAACTGGTCCCCT

ThrAlaAlaLeuValMetAlaGlnLeuLeuArgIleProGlnAlaIleLeuAspMetIle
601  ACAGCAGCGCTGGTAATGGCTCAGCTGCTCAGGATCCCGCAAGCCATCTTGGACATGATC
                                 G

AlaGlyAlaHisTrpGlyValLeuAlaGlyIleAlaTyrPheSerMetValGlyAsnTrp
661  GCTGGTGCTCACTGGGGAGTCCTAGCGGGCATAGCGTATTTCTCCATGGTGGGAACTGG

AlaLysValLeuValValLeuLeuPheAlaGlyValAspAlaThrThrTyrThrThr
721  GCGAAGGTCCTGGTGGTGCTGCTGTTTGCCGGTCGATGGACAACCTATACCACC

GlyGlyAsnAlaAlaArgThrThrSerPhePheSerProGlyAlaLys
781  GGGGGGAATGCTGCCAGGACCACCAGTTTTTTCAGCCCAGGCGCCAAG

GlnAspIleGlnLeuIleAsnThrAsnGlySerTrpHisIleAsnArgThrAlaLeuAsn
841  CAGGATATCCAGCTGATCAACACCAACGGCAGTTGGCACATCAATCGCACGGCCTTGAAC
         G                                  T

CysAsnAlaSerLeuAspThrGlyTrpValAlaGlyLeuPheTyrTyrHisLysPheAsn
901  TGTAATGCGAGCCTCGACACTGGCTGGGTAGCGGGGCTCTTCTATTACCACAAATTCAAC
                                           G

SerSerGlyCysProGluArgMetAlaSerCysArgProLeuAlaAspPheAspGln
961  TCTTCAGGCTGCCCCGAGAGGATGGCCAGCTGTAGGCCCTTGCCGATTTCGACCAGG
                                                          C
```

FIG. 82A

```
        1. human 27    2. HCV 1    3. human 23

1   CGGCTTCGCCGACCTCATGGCCGTCGCTCGTCGGCGCtCCTCTTGGgGGCGTGCCAGGCCCTGGC
      **********************************************************
  1   CGGCTTCGCCGACCTCATGGGGTACATACCGCTCGTCGTGCGCCCCCTCTTGGAGGCGCTGCCAGGCCCTGGC
      ***************************************    ****************
  1   CGGCTTGCCGACCTCATGGGGTACATACCGCTCGTCGGCGCCCCCTCTTGGAGGCgTGCCAGGGCCCTGGC

73   GCATGGCGTCCGGGTTCTGAAGACGGCGTGAACTATGCAACAGGGAACCTTCCTGGTTGCTCTTTCTAT
      ***********************************************************
 73   GCATGGCGTCCGGGTTCTGAAGACGGCGTGAACTATGCAACAGGGAACCTTCCTGGTTGCTCTTTCTAT
      ***                ***     ****     ***       **   **  *
 73   GCAcGGGCGTCCGGGTTtTGGAAGACGGCGTGAACTATGCAACAGGGAACCTTCCtTTtCTAT

145   CTTCCTTCTGCtCTGCTCTCTTGCCGTGCCCGAcCGTGACTGTGCCCGGCTTCgGCCAACTCCtCGGGcaT
      ***********************************************************
145   CTTCCTTCTGCCCTGCTCTCTTGCtCTGACtGTGCtCCGGCTTCGGCCAACTCCACGGGCT
      ******                 ***   ***  ****
145   CTTCCTTCTGCCCTGCTCTCTTGCCTGACTGTGCCCGGCTTCAGCCAACTCCtACGGGCT

217   TTACCAtGTCACCAATGATTGCCCTAAtTCGAGTATTGTACGAGaCGGCCGAcaCCATCCTaCACtCTCC
      ***********************************************************
217   TTACCAcGTCACCAATGATTGCCCTAACTCGAGTATTGTACGAGGCGGCCGATGCCATCCTGCACaCTCC
      *****  *                ***                  ***        **  *
217   TTACCATGTCACCAATGATTGCCCTAACTCGAGTATTGTACGAGGCGGCCGATGCCATCCTGCACgCTCC

289   GGGGTGTGTCCCTTGCGTTCGCGAGGGTAACGCCCTGAAaTGTTGGGTGCCGgTagCCCcACaGTGGCCAC
      ***********************************************************
289   GGGGTGCGTCCCTTGCGTTCGTGAGGGCAACGCCCTGAGTGTTGGGTGGCGATGACCCCtACGGTGGCCAC
      *****                  ***  *             **        **  *
289   GGGGTGTGTCCCTTGCGTTCGCGAGGATAACGtCTCGAGATGTTGGGTGGCGtGACCCCACGGTGGCCAC
```

FIG. 82B

```
361  CAGGGAcGGCAAcCTCCCCGCaaGCAGCTTCGACATGATCGCTTGTCGGGAGtGCCACCCTtTG
     *****  *****   ***** ***** ***** ******** ******** ********* **
361  CAGGGAtGGCAAACTCCCCGCgACGCAGCTTCGACATGATCGCTTGTCGGGAGCGCCACCCTCTG
     **  ***  ***** *****   *********************************** *****
361  CAaGGAcGGCAAACTCCCCaCaACGCAGCTTCGACGTCACATGATCGCTTGTCGGGAGCGCCACCCTCTG 433  cTCGGCCCTCTAtGTGGGGGACCTTGTGCGGGTCTCGTCTTTCTTGTGCGGtCAACTGTTCACtTTCTCCCCAG
     *  ***************    *   *   * ****** ***********  *********
433  tTCGGCCCTCTACGTGGGGGACCTTGTGCGGGTCTCTGTCTTTCTTGTCGGCCAACTGTTCACCTTCTCTCCAG
     *   **********************   *****  *****************  *****************
433  cTCGGCCCTCTACGTGGGGGACCTTGCGGGTCCaTCTTTCTTGTGCGGtCAACTGTTtACCTTCTCTCCAG

505  GCGCCACTGGACAaCGCAAGaTTGCAACTGCTCTATCTACCCCGGCCATATAACGGGaCACCGCATGGCATG
     ***********   ****** ******** * ********************** ******* ******
505  GCGCCACTGGACGACGCAAGgTTGCAATGCTCTATCTATCCCGGCCATATAACGGGTCACCGCATGGCATG
     ***********   ***** *  ***** ************************************
505  GCGCCACTGGACGACGCAgGacTGCAACTGtCTCTATCTATCCCGGCCATATAACGGGTCACCGCATGGCATG

577  GGATATGATGATGAACTGGTCCCCTACaGCAGCGCTGGTAATGCTCAGCTGCTCaGGATCCgCAAGCCAT
     ***********************  ********  *  ***  *   ********* ******  **
577  GGATATGATGATGAACTGTCCCCTACGaCGGCGTTGGTAAtGCTCAGCTGCTCCGGATCCACAAGCCAT
     *******************  *  ****** ** * ***********************
577  GGATATGATGATGAACTGTCCCCTACGGCGGCATTGGTAgTAgCTCAGCTGCTCCGGATCCACAAGCCAT

649  CTTGGACATGATCGCTGGTGTGCTGGGGAGTCCTaGCGGCATAGCGGCGTATTCTCCATGGTGGGAACTG
     *********************************  *********  ***********************
649  CTTGGACATGATCGCTGGTGTGCTGGGGAGTCACTGGGGCATAGCCGTATTCTCCATGGTGGGAACTG
     *********************************   ** ******* *  ***************
649  CTTGGACATGATCGCTGGTGTGCTGGGGAGTCCTGGGGCATgGCGTATTCTCCATGGTGGGAACTG

721  GGCGAAGGTCCTGGTgTGCTgTTGCCGGTCGAtGCGACAACCtAtACCACGGGGaAtGC
     *****************  ***  *** *    ***  *** *  *** *****  ***
721  GGCGAAGGTCCTGGTAGTGCTGCTATTTGCCGGCGTCGACGCGGAAACCCACgtCACCGGGGAAGTGC
     **************   *** ****      *    ****************************
721  GGCGAAGGTCCTGGTAGTGCTtCTATTGCCGGCGTCGACGCGAAACCCACCgtACCGGGGAAGTGC
```

```
793  tGcCaggACcacGcagGcgcTcaccAGtTTtTCagcCCAGGCGCCAAGCAGgAtaTCCAGCTGATCAACAC
            *   **        *          *   **   *************************
793  CGgCCaCACtgtGCTGGAtTTGtTAGCCTCcTCgCACCAGGCGCCAAGCAGAACgTCCAGCTGATCAACAC
     **  **  *   * *******  **      *****************************************
793  CGcCCgCAgcacGgCTGGAgTTGcTAGtCTCtTCaCACCAGGCGCtAgGCAGAACaTCCAGCTGATCAACAC
     *   *    *     ****    **  *** *  *************** ********************

865  CAACGGCAGTTGGCACAtCAATCGCACGGCCtTGAACTGtAATGcGAGCCTGaCACACtGGCTGGgTaGCgGG
     ****************  **  *********  ******  *** ********  ****** ***  ** **
865  CAACGGCAGTTGGCACCTGCACCTCAATAGCACGGCCCtCAATGATAGCCTCAACACCGGCTGGTTgGCaGG
     ****************    *    ****  ******  *  ***  *****  ***  ****** ** **
865  CAACGGCAGTTGGACACATCAATAGTCAATAGtACGGCCTtAcCACAGCCTTACCACCGGCTGGTTaGCgGG
     ************* ******* * ****** ****** **   ***  *** * **********  ** **

937  GCTcTCTATtACCACACAAaTTCAACTCTTCAGGCTGcCCCGAGAGGAtGcCCAGCTGtaGgCCCCTtGCCGA
     *** ***** ****** ****  ***********  *** *****   *   ***** ** *******  **
937  GCTTTTCTATCACCACAAgTTCAACTCTTCAGGCTGTCtGAGAGGCTaGCCAGCTGCCCGACCCCTTACCGA
         **  ** ****   * **************   *****     ******   ***  ****  ****
937  GCTTTTCTATCACCATAAaTTCAACTCTTCAGGCTGTCCCGAGAGGTTGGCCAGCTGCCGACCCCTcACCGA
         **  ** ****  * * ****************    ******   ******    ****** ****

1009 TTTCGACCAGG
     *** *******
1009 TTTTGACCAGG
     **** ******
1009 TTTTGCCCAGG
```

```
  1 GFADLMGYIPLVGAPLGGAARALAHGVRVLEDGVNYATGNLPGCSFSIFLLALLSCLTVPASAYQVRNSsGi    1. human 27
    ********************************************************************* *
  1 GFADLMGYIPLVGAPLGGAARALAHGVRVLEDGVNYATGNLPGCSFSIFLLALLSCLTVPASAYQVRNSTGL    2. HCV 1
    ********************************************************************* *
  1 GFADLMGYIPLVGAPLGGIARALAHGVRVLEDGVNYATGNLPGCSFSIFLLALLSCLTVPASAYQVRNSTGL    3. human 23

73 YHVTNDCPNSSIVYEtAdtILHsPGCVPCVREGNAsKcWVpvaPTVATRDGnLPATQLRRHIDLLVGSATLC
    *** ***  *                     *          *
 73 YHVTNDCPNSSIVYEAADAILHtPGCVPCVREGNAsRCWAmTPTVATRDGKLPATQLRRHIDLLVGSATLC
    ***                                *
 73 YHVTNDCPNSSIVYEAADAILHaPGCVPCVREdNvSRCWAvTPTVATkDGKLPtTQLRRHIDLLVGSATLC 145 SALYVGDLCGSVFLVGQLFTFSPRRHWTTQdCNCSIYPGHITGHRMAWDMMMNWSPTaALVMAQLLRIPQAI
    ***                              *          *     *
145 SALYVGDLCGSVFLVGQLFTFSPRRHWTTQgCNCSIYPGHITGHRMAWDMMMNWSPTtALVMAQLLRIPQAI
    ***
145 SALYVGDLCGSiFLVGQLFTFSPRRHWTTQdCNCSIYPGHITGHRMAWDMMMNWSPTaALVvAQLLRIPQAI 217 LDMIAGAHWGVLAGIAYFSMVGNWAKVLVVLLLFAGVDAtTytTGGnAarTtgaltSffsPGaKQdiQLINT
    ***                              *   *     *
217 LDMIAGAHWGVLAGIAYFSMVGNWAKVLVVLLLFAGVDAETHvTGGSAghTvsGfvSLlaPGAKQNvQLINT
    ***                                *       *
217 LDMIAGAHWGVLAGmAYFSMVGNWAKVLVVLLLFAGVDAETHrTGGSAarstaGvaSLftPGArQNiQLINT 289 NGSWHinrTALNCNaSLdTGWvAGLFYHKFNSSGCPERmASCRPLaDFDQ
    *      * **
289 NGSWHiNSTALNCNDSLnTGWLAGLFYHHKFNSSGCPERLASCRPLTDFDQ
    ***   *                 *
289 NGSWHiNSTALNCNDSLtTGWLAGLFYHHKFNSSGCPERLASCRPLTDFaQ
```

FIG. 85A

```
1.  ssThorn#8.r  (1-587)
2.  ssEC1#2.r    (1-587)
3.  ssHCT18#7.r  (1-587)
4.  env1.hcv     (1-1657)
```

```
  1                                                                                                                                    
  1                                                                                                                                  GA
  1                                                                                                                                  —
  1                                                                                                                                  GA
                                                                                                                                     —
289 gggtggcggatggctcctgtctcccgtgctctcggctagctgggcccacagacccccggcgtaGg                                                                 GA
                                                                                                                                     —
  3 ATTCGCAATTTGGGTAAGGTCATCGATACCCTTACGTGCGGCTTCGCCGACCTCATGGGTACATACCGCTC                                                           
  3 ATTCGCAATTTGGGTAAGGTCATCGATACCCTTACGTGCGGCTTCGCCGACCTCATGGGTACATACCGCTC                                                           
  3 ATTCGCAATTTGGGTAAGGTCATCGATACCCTTACGTGCGGCTTCGCCGACCTCATGGGTAtATACCGCTC                                                           
361 tcgCGCAATTTGGGTAAGGTCATCGATACCCTTACGTGCGGCTTCGCCGACCTCATGGGTACATACCGCTC 75 GTCGGCGCCCCCTCTTGGgGCGCCCTGCCAGGGCCCCTGCCATGGCGTTCGGGTTCTGGAAGACGGCGTGAAC                                                         
 75 GTCGGCGCCCCCTCTTGGAGGGCCCTGCCAGGGCCCCTGCCATGGCGTTCGGGTTCTGGAAGACGGCGTGAAC                                                         
 75 GTCGGCGCCCCCTCTTGGAGGGCCCTGCCAGGGCCCCTGCCATGGCGTTCGGGTTCTGGAAGACGGCGTGAAC                                                         
433 GTCGGCGCCCCCTCTTGGAGGGCCCTGCCAGGGCCCCTGCCATGGCGTTCGGGTTCTGGAAGACGGCGTGAAC                                                         
```

FIG. 85B

```
147  TATGCAACAGGGAACCTTCCTGGTTGCTCTTCTcTcTCTTCCTTCTGGCCCTGCTCTCTTGtcTGACCGTG
147  TATGCAACAGGGAACCTTCCTGGTTGCTGCTCTTGCTCTTTCTtTATCTTCCTTCTGCCTGCTCTCTTGCtTGACTGTG
147  TATGC   CAGGGAACCTTCCTGGTTGCTGCTCTTTGCTCTCTTCTCTTCTTCCTTCTGGCCCTGCTCTCTTGCcTGACTGTG
505  TATGCAACAGGGAACCTTCCTGGTTGCTGCTCTGTGCTCTTGCTCTTTCTCTTCTTCCTTCTGGCCCTGCTCTCTTGCtTGACTGTG
219  CCCGCTTCAGCCTTACCAAGTGCGCAACTCCaCGGGGCTTTACCATGTCACCAACGATTGCCCcAACTCGAGt
219  CCCGCTTCAGCCTACCAAGTGCGCAACTCCtCGGGGCTTTACCATGTCACCAATGATTGCCCtAACTCGAGc
219  CCCGCTTCAGCCTACCAAGTGCGCAACTCCGCGGGGCTTTACCATGTCACCAATGATTGCCCcAACTCGAGT
577  CCCGCTTCgGCCtACCAAGTGCGCAACTCCACGGGGCTTTACCAGTCACCAATGATTGCCCtAACTCGAGT
291  ATTGTGTACGAGGCGGCCGATGCtATCCTGCACgCTCCGCACACTCCTGCgCGTTCgCGAGGGtAACGCC
291  ATTGTGTACGAGGCGGCCGATGCCGCCGATGCCCATCCGCACACTCCTGCACACTCCGCGTTCgCGAGGGCAACGTC
291  ATTGTGTACGAGGCGGCCGACGCCGCCGACGCGCCATCCGCACACTCCTGCACACTCCGCGTTCgCGAGGGCAACGTC
649  ATTGTaTACGAaGCGGCCGACGCGCCGAtGCCATCCGCACACTCCTGCACACTCCGCGTTCgtGAGGGCAACGCC
363  TCGAGGTGTTGGGGTGGCGAGGCGGGCCGATGACCCCCACGGTGGCCgCCAGGGaCGGACAgACTCCCCACAACGCAGCTgCGA
363  TCGAGGTGTGGGGTGGCGAGGCGGGCCGATGACCCCACGGTGGCCACCAGGGgCGGCAAACTCCCACAACGCAGCTTCGA
363  TCGAGGTGTGGGTGGCGAGGCGGGCCGATGACCCCACGGTGACCCCACGGTGGCCACCAGGGATGCCAAACTCCCCACAACGCAGCTTCGA
721  TCGAGGTGTTGGGTGGCGAtGACCCCtACGGTGACCCCGCgCGTGGCCACCAGGGATGGCAAACTCCCCgCGACGCAGCTTCGA
```

```
435  CGTCACATCGATCTGCTTGTCGGGAGCGCCcACCCCTCTGCTCGGCCCCTCTACGTGGGGACCTGTGCGGGTCc
435  CGTCACATCGATCTGCTTGTCGGGAGCGCCtACCCCTCTGCTCGGCCCCTCTACGTGGGGACCTGTGCGGGTCT
435  CGTCACATCGATCTGCTTGTCGGGAGCGCCACCCCTCTGCTCGGCCCCTCTAtGTGGGGACtTGTGCGGGTCT
793  CGTCACATCGATCTGCTTGTCGGGAGCGCCACCCCTCTGtTCGGCCCCTCTACGTGGGGACCTaTGCGGGTCT 507  aTCTTtCTTGTCGGTCAACTGTTcACCTTCTCTCTCCCCAGGCGCCACTGGACGACGCAAGGTTGCAATTGCTCT
507  GTCTTcCTTGTCGGTCAACTGTTTACCTTCTCTCTCCCCAGGCGCCACTGGACGACGCAAGGTTGCAATTGCTCT
507  GTCTTTCTTGTCGGCCAACTGTTTACCTTCTCTCTCCCCAGGCGCCACTGGACGACGCAAGGTTGCAATTGCTCT
865  GTCTTTCTTGTCGGCCAACTGTTcACCTTCTCTCTCCCCAGGCGCCACTGGACGACGCAAGGTTGCAATTGCTCT

579  ATCGAATTC
579  ATCGAATTC
579  ATCGAATTC
937  ATCtAtccC
```

FIG. 85C

```
                       10        20        30        40
             GAATTCGGACGACGCAAGGTTGCAATTGCTCTATCTATCCCGGCCATAT
                  X:::::::::::::::::::::::::::::::::::::::::::
/SSp  CTCTCCCAGGCGCCACTGGACGACGCAAGGTTGCAATTGCTCTATCTATCCCGGCCATAT
           550       560       570       580       590       600

50        60        70        80   A    90       100
    AACAGGTCACCGCATGGCATGGGATATGATGATGAACTGGTCCCCTACGACGGCGTTAGT
    : : :  ::::::::::::::::::::::::::::::::::::::::::::::::: ::
    AACGGGTCACCGCATGGCATGGGATATGATGATGAACTGGTCCCCTACGACGGCGTTGGT
           610       620       630       640       650       660

110       120       130       140       150       160
     GGTAGCTCAGCTGCTCCGGATCCCACAAGCCATCTTGGACATGATCGCTGGTGCTCACTG
     :  ::::::::::::::::::::::::::::::::::::::::::::::::::::::::
     AATGGCTCAGCTGCTCCGGATCCCACAAGCCATCTTGGACATGATCGCTGGTGCTCACTG
           670       680       690       700       710       720

170       180       190       200       210       220
     GGGAGTCCTGGCGGGCATAGCGTATTTCTCCATGGTGGGGAACTGGGCGAAGGTCTTGGC
     ::::::::::::::::::::::::::::::::::::::::::::::::::::::::: ::
     GGGAGTCCTGGCGGGCATAGCGTATTTCTCCATGGTGGGGAACTGGGCGAAGGTCCTGGT
           730       740       750       760       770       780

230       240       250       260       270       280
     AGTGCTGCTGCTATTTGCCGGCGTCGACGCGGAAACCCACGTCACTGGGGGGATCGCCGC
     :::::::::::::::::::::::::::::::::::::::::::::: ::::: : ::::
     AGTGCTGCTGCTATTTGCCGGCGTCGACGCGGAAACCCACGTCACCGGGGGAAGTGCCGG
           790       800       810       820       830       840

290       300       310       320       330       340
     CAAAACTACGGCTAGCCTTACTGGTCTCTTCAATTTAGGTGCCAAGCAGAACATCCAGCT
     :  :  :::   :  ::   ::   :  :::  ::   ::: :::::::::::: :::::::
     CCACACTGTGTCTGGATTTGTTAGCCTCCTCGCACCAGGCGCCAAGCAGAACGTCCAGCT
           850       860       870       880       890       900

350       360       370       380       390       400
     GATCAACACCAACGGCAGTTGGCACATCAACAGGACGGCCTTGAACTGCAATGATAGCCT
     :::::::::::::::::::::::::::: :::: :: :::::: ::::::::::::::::
     GATCAACACCAACGGCAGTTGGCACCTCAATAGCACGGCCCTGAACTGCAATGATAGCCT
           910       920       930       940       950       960

410       420
     CAACACCGGCTGGAATTC
     ::::::::::::X
     CAACACCGGCTGGTTGGCAGGGCTTTTCTATCACCACAAGTTCAACTCTTCAGGCTGTCC
           970       980       990      1000      1010      1020
```

AA #117-308 (putative envelope region)

1) HCT #18 (USA)         3 clones sequenced
2) JH23 (USA)            ?
3) JH 27 (USA)           ?
4) PBL-Th (USA)          2 clones sequenced
5) EC1 (Italy)           3 clones sequenced
6) HCV-1 (chimpanzee)    multiple

```
     C/M←─┬─→S
1)           (P)
2)
3)
4)
5)
6)RNLGKVIDTLTCGFADLMGYIPLVGAPLGGAARALAHGVRVLEDGVNYATGNL

1)                  H
2)
3)                          S                    T  T
4)       L
5)    (F)                   S
6)PGCSFSIFLLALLSCLTVPASAYQVRNSTGLYHVTNDCPNSSIVYEAADAILH

Y
1)        (H)    V      V           T
2)A              D V    V      K    T
3)S                     PVA         N
4)A                            A R  T
5)        H V                       T
6)TPGCVPCVREGNASRCWVAMTPTVATRDGKLPATQLRRHIDLLVGSATLCS 1)
2)         I              D
3)                        D
4)
5)         I
6)ALYVGDLCGSVFLVGQLFTFSPRRHWTTQGCNCSI
```

SUMMARY: "S" AA117-308 (93%)

HCT#18, PBL-Th, EC1(Italy) have 97% homology with HCV-1

JH23 and JH 27 have 96% and 95% homology with HCV-1, respectively

AA#300-438 ( C-terminal region of the putative envelope region and amino ~1/3 of NS1)

1) JH23                             ?
2) JH27                             ?
3) Japanese isolate (T. Miyamura)   ?
4) EC10 (Italy)                     2 clones sequenced
                                    (one nt difference, which did not
                                    result in an amino acid change)
5) HCV-1 (chimpanzee)               multiple S ←┬→ NS I
1)   D                              A   V
2)   D                              A
3)                                  V S       VM  V
4)
5) TTQGCNCSIYPGHITGHRMAWDMMMNWSPTTALVMAQLLRIPQAILDMIAGA 1)        M                              R        A RST A  VA
2)                                 T YT           N A R TQALT  F
3)     L  Y              I M        GH R          VQ  VT  TLT
4)                         A                       I AK  TASLTA
5) HWGVLAGIAYFSMVGNWAKVLVVLLLFAGVDAETHVTGGSAGHTVSGFVSL 1)FS   R  I           I              T    V
2)FT   D I            I R      A D
3)FR   S KI  V        I R              Q  F
4)FNL     I           I R                 N
5) LAPGAKQNVQLINTNGSWHLNSTALNCNDSLNTGWL

SUMMARY: NS 1 AA 330-660

| "Isolate" | %Homology (AA330-438) | %Homology (AA383-405) |
|---|---|---|
| JH23 | 83 | 57 |
| JH27 | 80 | 39 |
| Japanese | 73 | 48 |
| EC10 (Italy) | 84 | 48 |

```
                              5'terminus------------------------
CACTCCACCATGAATCACTCCCCTGTGAGGAACTACTGTCTTCACGCAGAAAGCGTCTAG
CCATGGCGTTAGTATGAGTGTCGTGCAGCCTCCAGGACCCCCCCTCCCGGGAGAGCCATA
GTGGTCTGCGGAACCGGTGAGTACACCGGAATTGCCAGGACGACCGGGTCCTTTCTTGGA
TCAACCCGCTCAATGCCTGGAGATTTGGGCGTGCCCCCGCAAGACTGCTAGCCGAGTAGT
GTTGGGTCGCGAAAGGCCTTGTGGTACTGCCTGATAGGGTGCTTGCGAGTGCCCCGGGAG-300
```

(Putative initiator methionine codon)

```
                                        G        C
GTCTCGTAGACCGTGCACCATGAGCACGAATCCTAAACCTCAAAAAAAAAACAAACGTAA
CACCAACCGTCGCCCACAGGACGTCAAGTTCCCGGGTGGCGGTCAGATCGTTGGTGGAGT
TTACTTGTTGCCGCGCAGGGGCCCTAGATTGGGTGTGCGCGCGACGAGAAAGACTTCCGA
GCGGTCGCAACCTCGAGGTAGACGTCAGCCTATCCCCAAGGCTCGTCGGCCCGAGGGCAG
GACCTGGGCTCAGCCCGGGTACCCTTGGCCCCTCTATGGCAATGAGGGCTGCGGGTGGGC-600
GGGATGGCTCCTGTCTCCCCGTGGCTCTCGGCCTAGCTGGGGCCCCACAGACCCCCGGCG
TAGGTCGCGCAATTTGGGTAAGGTCATCGATACCCTTACGTGCGGCTTCGCCGACCTCAT
GGGGTACATACCGCTCGTCGGCGCCCCTCTTGGAGGCGCTGCCAGGGCCCTGGCGCATGG
CGTCCGGGTTCTGGAAGACGGCGTGAACTATGCAACAGGGAACCTTCCTGGTTGCTCTTT

C
CTCTATCTTCCTTCTGGCCCTGCTCTCTTGCTTGACTGTGCCCGCTTCGGCCTACCAAGT-900
GCGCAACTCCACGGGGCTTTACCACGTCACCAATGATTGCCCTAACTCGAGTATTGTGTA
CGAGGCGGCCGATGCCATCCTGCACACTCCGGGGTGCGTCCCTTGCGTTCGTGAGGGCAA
CGCCTCGAGGTGTTGGGTGGCGATGACCCCTACGGTGGCCACCAGGGATGGCAAACTCCC
CGCGACGCAGCTTCGACGTCACATCGATCTGCTTGTCGGGAGCGCCACCCTCTGTTCGGC
CCTCTACGTGGGGGACCTATGCGGGTCTGTCTTTCTTGTCGGCCAACTGTTCACCTTCTC-1200
TCCCAGGCGCCACTGGACGACGCAAGGTTGCAATTGCTCTATCTATCCCGGCCATATAAC

G
GGGTCACCGCATGGCATGGGATATGATGATGAACTGGTCCCCTACGACGGCGTTGGTAAT
GGCTCAGCTGCTCCGGATCCCACAAGCCATCTTGGACATGATCGCTGGTGCTCACTGGGG
AGTCCTGGCGGGCATAGCGTATTTCTCCATGGTGGGGAACTGGGCGAAGGTCCTGGTAGT
GCTGCTGCTATTTGCCGGCGTCGACGCGGAAACCCACGTCACCGGGGGAAGTGCCGGCCA-1500
CACTGTGTCTGGATTTGTTAGCCTCCTCGCACCAGGCGCCAAGCAGAACGTCCAGCTGAT
CAACACCAACGGCAGTTGGCACCTCAATAGCACGGCCCTGAACTGCAATGATAGCCTCAA
CACCGGCTGGTTGGCAGGGCTTTTCTATCACCACAAGTTCAACTCTTCAGGCTGTCCTGA
GAGGCTAGCCAGCTGCCGACCCCTTACCGATTTTGACCAGGGCTGGGGCCCTATCAGTTA
TGCCAACGGAAGCGGCCCCGACCAGCGCCCCTACTGCTGGCACTACCCCCAAAACCTTG-1800
CGGTATTGTGCCCGCGAAGAGTGTGTGTGGTCCGGTATATTGCTTCACTCCCAGCCCCGT
GGTGGTGGGAACGACCGACAGGTCGGGCGCGCCCACCTACAGCTGGGGTGAAAATGATAC
GGACGTCTTCGTCCTTAACAATACCAGGCCACCGCTGGGCAATTGGTTCGGTTGTACCTG
GATGAACTCAACTGGATTCACCAAAGTGTGCGGAGCGCCTCCTTGTGTCATCGGAGGGGC
GGGCAACAACACCCTGCACTGCCCCACTGATTGCTTCCGCAAGCATCCGGACGCCACATA-2100

C
CTCTCGGTGCGGCTCCGGTCCCTGGATCACACCCAGGTGCCTGGTCGACTACCCGTATAG
GCTTTGGCATTATCCTTGTACCATCAACTACACCATATTTAAAATCAGGATGTACGTGGG
AGGGGTCGAACACAGGCTGGAAGCTGCCTGCAACTGGACGCGGGGCGAACGTTGCGATCT
GGAAGACAGGGACAGGTCCGAGCTCAGCCCGTTACTGCTGACCACTACACAGTGGCAGGT
CCTCCCGTGTTCCTTCACAACCCTACCAGCCTTGTCCACCGGCCTCATCCACCTCCACCA-2400
GAACATTGTGGACGTGCAGTACTTGTACGGGGTGGGGTCAAGCATCGCGTCCTGGGCCAT
TAAGTGGGAGTACGTCGTTCTCCTGTTCCTTCTGCTTGCAGACGCGCGCGTCTGCTCCTG
CTTGTGGATGATGCTACTCATATCCCAAGCGGAGGCGGCTTTGGAGAACCTCGTAATACT
TAATGCAGCATCCCTGGCCGGGACGCACGGTCTTGTATCCTTCCTCGTGTTCTTCTGCTT
TGCATGGTATTTGAAGGGTAAGTGGGTGCCCGGAGCGGTCTACACCTTCTACGGGATGTG-2700
GCCTCTCCTCCTGCTCCTGTTGGCGTTGCCCCAGCGGGCGTACGCGCTGGACACGGAGGT
GGCCGCGTCGTGTGGCGGTGTTGTTCTCGTCGGGTTGATGGCGCTGACTCTGTCACCATA
TTACAAGCGCTATATCAGCTGGTGCTTGTGGTGGCTTCAGTATTTTCTGACCAGAGTGGA
AGCGCAACTGCACGTGTGGATTCCCCCCCTCAACGTCCGAGGGGGGCGCGACGCCGTCAT
```

FIG. 89B

```
CTTACTCATGTGTGCTGTACACCCGACTCTGGTATTTGACATCACCAAATTGCTGCTGGC-3000
CGTCTTCGGACCCCTTTGGATTCTTCAAGCCAGTTTGCTTAAAGTACCCTACTTTGTGCG
CGTCCAAGGCCTTCTCCGGTTCTGCGCGTTAGCGCGGAAGATGATCGGAGGCCATTACGT
GCAAATGGTCATCATTAAGTTAGGGGCGCTTACTGCACCTATGTTTTATAACCATCTCAC
TCCTCTTCGGGACTGGGCGCACAACGGCTTGCGAGATCTGGCCGTGGCTGTAGAGCCAGT
CGTCTTCTCCCAAATGGAGACCAAGCTCATCACGTGGGGGGCAGATACCGCCGCGTGCGG-3300
TGACATCATCAACGGCTTGCCTGTTTCCGCCCGCAGGGGCCGGGAGATACTGCTCGGGCC
AGCCGATGGAATGGTCTCCAAGGGGTGGAGGTTGCTGGCGCCCATCACGGCGTACGCCCA
GCAGACAAGGGGCCTCCTAGGGTGCATAATCACCAGCCTAACTGGCCGGGACAAAAACCA
AGTGGAGGGTGAGGTCCAGATTGTGTCAACTGCTGCCCAAACCTTCCTGGCAACGTGCAT
CAATGGGGTGTGCTGGACTGTCTACCACGGGGCCGGAACGAGGACCATCGCGTCACCCAA-3600
                                                         T
GGGTCCTGTCATCCAGATGTATACCAATGTAGACCAAGACCTTGTGGGCTGGCCCGCTCC
         C
GCAAGGTAGCCGCTCATTGACACCCTGCACTTGCGGCTCCTCGGACCTTTACCTGGTCAC
GAGGCACGCCGATGTCATTCCCGTGCGCCGGCGGGGTGATAGCAGGGGCAGCCTGCTGTC
GCCCCGGCCCATTTCCTACTTGAAAGGCTCCTCGGGGGGTCCGCTGTTGTGCCCCGCGGG
GCACGCCGTGGGCATATTTAGGGCCGCGGTGTGCACCCGTGGAGTGGCTAAGGCGGTGGA-3900
CTTTATCCCTGTGGAGAACCTAGAGACAACCATGAGGTCCCCGGTGTTCACGGATAACTC
CTCTCCACCAGTAGTGCCCCAGAGCTTCCAGGTGGCTCACCTCCATGCTCCCACAGGCAG
CGGCAAAAGCACCAAGGTCCCGGCTGCATATGCAGCTCAGGGCTATAAGGTGCTAGTACT
CAACCCCTCTGTTGCTGCAACACTGGGCTTTGGTGCTTACATGTCCAAGGCTCATGGGAT
     T
CGATCCTAACATCAGGACCGGGGTGAGAACAATTACCACTGGCAGCCCCATCACGTACTC-4200
CACCTACGGCAAGTTCCTTGCCGACGGCGGGTGCTCGGGGGGCGCTTATGACATAATAAT
TTGTGACGAGTGCCACTCCACGGATGCCACATCCATCTTGGGCATCGGCACTGTCCTTGA
CCAAGCAGAGACTGCGGGGGCGAGACTGGTTGTGCTCGCCACCGCCACCCCTCCGGGCTC
CGTCACTGTGCCCCATCCCAACATCGAGGAGGTTGCTCTGTCCACCACCGGAGAGATCCC
TTTTTACGGCAAGGCTATCCCCCTCGAAGTAATCAAGGGGGGGAGACATCTCATCTTCTG-4500
TCATTCAAAGAAGAAGTGCGACGAACTCGCCGCAAAGCTGGTCGCATTGGGCATCAATGC
CGTGGCCTACTACCGCGGTCTTGACGTGTCCGTCATCCCGACCAGCGGCGATGTTGTCGT
                                                              A
CGTGGCAACCGATGCCCTCATGACCGGCTATACCGGCGACTTCGACTCGGTGATAGACTG
CAATACGTGTGTCACCCAGACAGTCGATTTCAGCCTTGACCCTACCTTCACCATTGAGAC
AATCACGCTCCCCCAGGATGCTGTCTCCCGCACTCAACGTCGGGGCAGGACTGGCAGGGG-4800
GAAGCCAGGCATCTACAGATTTGTGGCACCGGGGGAGCGCCCCTCCGGCATGTTCGACTC
GTCCGTCCTCTGTGAGTGCTATGACGCAGGCTGTGCTTGGTATGAGCTCACGCCCGCCGA
GACTACAGTTAGGCTACGAGCGTACATGACACCCCGGGGCTTCCCGTGTGCCAGGACCA
TCTTGAATTTTGGGAGGGCGTCTTTACAGGCCTCACTCATATAGATGCCCACTTTCTATC
CCAGACAAAGCAGAGTGGGGAGAACCTTCCTTACCTGGTAGCGTACCAAGCCACCGTGTG-5100
CGCTAGGGCTCAAGCCCCTCCCCCATCGTGGGACCAGATGTGGAAGTGTTTGATTCGCCT
CAAGCCCACCCTCCATGGGCCAACACCCCTGCTATACAGACTGGGCGCTGTTCAGAATGA
AATCACCCTGACGCACCCAGTCACCAAATACATCATGACATGCATGTCGGCCGACCTGGA
GGTCGTCACGAGCACCTGGGTGCTCGTTGGCGGCGTCCTGGCTGCTTTGGCCGCGTATTG
CCTGTCAACAGGCTGCGTGGTCATAGTGGGCAGGGTCGTCTTGTCCGGGAAGCCGGCAAT-5400
CATACCTGACAGGGAAGTCCTCTACCGAGAGTTCGATGAGATGGAAGAGTGCTCTCAGCA
CTTACCGTACATCGAGCAAGGGATGATGCTCGCCGAGCAGTTCAAGCAGAAGGCCCTCGG
CCTCCTGCAGACCGCGTCCCGTCAGGCAGAGGTTATCGCCCCTGCTGTCCAGACCAACTG
GCAAAAACTCGAGACCTTCTGGGCGAAGCATATGTGGAACTTCATCAGTGGGATACAATA
CTTGGCGGGCTTGTCAACGCTGCCTGGTAACCCCGCCATTGCTTCATTGATGGCTTTTAC-5700
AGCTGCTGTCACCCACCTAACCACTAGCCAAACCCTCCTCTTCAACATATTGGGGGG
GTGGGTGGCTGCCCAGCTCGCCGCCCCCGGTGCCGCTACTGCCTTTGTGGGCGCTGGCTT
AGCTGGCGCCGCCATCGGCAGTGTTGGACTGGGGAAGGTCCTCATAGACATCCTTGCAGG
GTATGGCGCGGGCGTGGCGGGAGCTCTTGTGGCATTCAAGATCATGAGCGGTGAGGTCCC-6000
CTCCACGGAGGACCTGGTCAATCTACTGCCCGCCATCCTCTCGCCCGGAGCCCTCGTAGT
CGGCGTGGTCTGTGCAGCAATACTGCGCCGGCACGTTGGCCCGGGCGAGGGGCAGTGCA
GTGGATGAACCGGCTGATAGCCTTCGCCTCCCGGGGAACCATGTTTCCCCCACGCACTA
CGTGCCGGAGAGCGATGCAGCTGCCCGCGTCACTGCCATACTCAGCAGCCTCACTGTAAC
CCAGCTCCTGAGGCGACTGCACCAGTGGATAAGCTCGGAGTGTACCACTCCATGCTCCGG
```

FIG. 89C

```
TTCCTGGCTAAGGGACATCTGGGACTGGATATGCGAGGTGTTGAGCGACTTTAAGACCTG-6300
GCTAAAAGCTAAGCTCATGCCACAGCTGCCTGGGATCCCCTTTGTGTCCTGCCAGCGCGG
GTATAAGGGGGTCTGGCGAGTGGACGGCATCATGCACACTCGCTGCCACTGTGGAGCTGA
GATCACTGGACATGTCAAAAACGGGACGATGAGGATCGTCGGTCCTAGGACCTGCAGGAA
CATGTGGAGTGGGACCTTCCCCATTAATGCCTACACCACGGGCCCCTGTACCCCCCTTCC
TGCGCCGAACTACACGTTCGCGCTATGGAGGGTGTCTGCAGAGGAATATGTGGAGATAAG-6600
GCAGGTGGGGGACTTCCACTACGTGACGGGTATGACTACTGACAATCTCAAATGCCCGTG
CCAGGTCCCATCGCCCGAATTTTTCACAGAATTGGACGGGGTGCGCCTACATAGGTTTGC
GCCCCCCTGCAAGCCCTTGCTGCGGGAGGAGGTATCATTCAGAGTAGGACTCCACGAATA
CCCGGTAGGGTCGCAATTACCTTGCGAGCCCGAACCGGACGTGGCCGTGTTGACGTCCAT
GCTCACTGATCCCTCCCATATAACAGCAGAGGCGGCCGGGCGAAGGTTGGCGAGGGGATC-6900
ACCCCCCTCTGTGGCCAGCTCCTCGGCTAGCCAGCTATCCGCTCCATCTCTCAAGGCAAC
TTGCACCGCTAACCATGACTCCCCTGATGCTGAGCTCATAGAGGCCAACCTCCTATGGAG
GCAGGAGATGGGCGGCAACATCACCAGGGTTGAGTCAGAAAACAAAGTGGTGATTCTGGA
CTCCTTCGATCCGCTTGTGGCGGAGGAGGACGAGCGGGAGATCTCCGTACCCGCAGAAAT
CCTGCGGAAGTCTCGGAGATTCGCCCAGGCCCTGCCCGTTTGGGCGCGGCCGGACTATAA-7200
CCCCCCGCTAGTGGAGACGTGGAAAAAGCCCGACTACGAACCACCTGTGGTCCATGGCTG
TCCGCTTCCACCTCCAAAGTCCCCTCCTGTGCCTCCGCCTCGGAAGAAGCGGACGGTGGT
CCTCACTGAATCAACCCTATCTACTGCCTTGGCCGAGCTCGCCACCAGAAGCTTTGGCAG
CTCCTCAACTTCCGGCATTACGGGCGACAATACGACAACATCCTCTGAGCCCGCCCCTTC
TGGCTGCCCCCCCGACTCCGACGCTGAGTCCTATTCCTCCATGCCCCCCCTGGAGGGGGA-7500
GCCTGGGGATCCGGATCTTAGCGACGGGTCATGGTCAACGGTCAGTAGTGAGGCCAACGC
GGAGGATGTCGTGTGCTGCTCAATGTCTTACTCTTGGACAGGCGCACTCGTCACCCCGTG
CGCCGCGGAAGAACAGAAACTGCCCATCAATGCACTAAGCAACTCGTTGCTACGTCACCA
CAATTTGGTGTATTCCACCACCTCACGCAGTGCTTGCCAAAGGCAGAAGAAAGTCACATT
TGACAGACTGCAAGTTCTGGACAGCCATTACCAGGACGTACTCAAGGAGGTTAAAGCAGC-7800
GGCGTCAAAAGTGAAGGCTAACTTGCTATCCGTAGAGGAAGCTTGCAGCCTGACGCCCCC
ACACTCAGCCAAATCCAAGTTTGGTTATGGGGCAAAAGACGTCCGTTGCCATGCCAGAAA
GGCCGTAACCCACATCAACTCCGTGTGGAAAGACCTTCTGGAAGACAATGTAACACCAAT
AGACACTACCATCATGGCTAAGAACGAGGTTTTCTGCGTTCAGCCTGAGAAGGGGGGTCG
TAAGCCAGCTCGTCTCATCGTGTTCCCCGATCTGGGCGTGCGCGTGTGCGAAAAGATGGC-8100
TTTGTACGACGTGGTTACAAAGCTCCCCTTGGCCGTGATGGGAAGCTCCTACGGATTCCA
ATACTCACCAGGACAGCGGGTTGAATTCCTCGTGCAAGCGTGGAAGTCCAAGAAAACCCC
AATGGGGTTCTCGTATGATACCCGCTGCTTTGACTCCACAGTCACTGAGAGCGACATCCG
TACGGAGGAGGCAATCTACCAATGTTGTGACCTCGACCCCCAAGCCCGCGTGGCCATCAA
GTCCCTCACCGAGAGGCTTTATGTTGGGGGCCCTCTTACCAATTCAAGGGGGGAGAACTG-8400
CGGCTATCGCAGGTGCCGCCGAGCGGCGTACTGACAACTAGCTGTGGTAACACCCTCAC
TTGCTACATCAAGGCCCGGGCAGCCTGTCGAGCCGCAGGGCTCCAGGACTGCACCATGCT
CGTGTGTGGCGACGACTTAGTCGTTATCTGTGAAAGCGCGGGGGTCCAGGAGGACGCGGC
GAGCCTGAGAGCCTTCACGGAGGCTATGACCAGGTACTCCGCCCCCCCTGGGGACCCCCC
ACAACCAGAATACGACTTGGAGCTCATAACATCATGCTCCTCCAACGTGTCAGTCGCCCA-8700
CGACGGCGCTGGAAAGAGGGTCTACTACCTCACCCGTGACCCTACAACCCCCCTCGCGAG
AGCTGCGTGGGAGACAGCAAGACACACTCCAGTCAATTCCTGGCTAGGCAACATAATCAT
GTTTGCCCCCACACTGTGGGCGAGGATGATACTGATGACCCATTTCTTTAGCGTCCTTAT
AGCCAGGGACCAGCTTGAACAGGCCCTCGATTGCGAGATCTACGGGGCCTGCTACTCCAT
AGAACCACTGGATCTACCTCCAATCATTCAAAGACTCCATGGCCTCAGCGCATTTTCACT-9000
CCACAGTTACTCTCCAGGTGAAATTAATAGGGTGGCCGCATGCCTCAGAAAACTTGGGGT
                                G
ACCGCCCTTGCGAGCTTGGAGACACCGGGCCCGGAGCGTCCGCGCTAGGCTTCTGGCCAG
AGGAGGCAGGGCTGCCATATGTGGCAAGTACCTCTTCAACTGGGCAGTAAGAACAAAGCT
CAAACTCACTCCAATAGCGGCCGCTGGCCAGCTGGACTTGTCCGGCTGGTTCACGGCTGG
CTACAGCGGGGGAGACATTTATCACAGCGTGTCTCATGCCCGGCCCCGCTGGATCTGGTT-9300
TTGCCTACTCCTGCTTGCTGCAGGGGTAGGCATCTACCTCCTCCCCAACCGATGAAGGTT
GGGGTAAACACTCCGGCCT----------------------3'terminus
```

Some clonal heterogeneities producing amino acid substitutions are shown. There are many other "silent mutations (not shown).

FIG. 90A

```
            R T
MSTNPKPQKKNKRNTNRRPQDVKFPGGGQIVGGVYLLPRRGPRLGVRATR
KTSERSQPRGRRQPIPKARRPEGRTWAQPGYPWPLYGNEGCGWAGWLLSP-100
RGSRPSWGPTDPRRRSRNLGKVIDTLTCGFADLMGYIPLVGAPLGGAARA

T
LAHGVRVLEDGVNYATGNLPGCSFSIFLLALLSCLTVPASAYQVRNSTGL-200
YHVTNDCPNSSIVYEAADAILHTPGCVPCVREGNASRCWVAMTPTVATRD
GKLPATQLRRHIDLLVGSATLCSALYVGDLCGSVFLVGQLFTFSPRRHWT-300

V
TQGCNCSIYPGHITGHRMAWDMMMNWSPTTALVMAQLLRIPQAILDMIAG
AHWGVLAGIAYFSMVGNWAKVLVVLLLFAGVDAETHVTGGSAGHTVSGFV-400
SLLAPGAKQNVQLINTNGSWHLNSTALNCNDSLNTGWLAGLFYHHKFNSS
GCPERLASCRPLTDFDQGWGPISYANGSGPDQRPYCWHYPPKPCGIVPAK-500
SVCGPVYCFTPSPVVVGTTDRSGAPTYSWGENDTDVFVLNNTRPPLGNWF
GCTWMNSTGFTKVCGAPPCVIGGAGNNTLHCPTDCFRKHPDATYSRCGSG-600

I
PWLTPRCLVDYPYRLWHYPCTINYTIFKIRMYVGGVEHRLEAACNWTRGE
RCDLEDRDRSELSPLLLTTTQWQVLPCSFTTLPALSTGLIHLHQNIVDVQ-700
YLYGVGSSIASWAIKWEYVVLLFLLLADARVCSCLWMMLLISQAEAALEN
LVILNAASLAGTHGLVSFLVFFCFAWYLKGKWVPGAVYTFYGMWPLLLLL-800

(N)
LALPQRAYALDTEVAASCGGVVLVGLMALTLSPYYKRYISWCLWWLQYFL
TRVEAQLHVWIPPLNVRGGRDAVILLMCAVHPTLVFDITKLLLAVFGPLW-900
ILQASLLKVPYFVRVQGLLRFCALARKMIGGHYVQMVIIKLGALTGTYVY
NHLTPLRDWAHNGLRDLAVAVEPVVFSQMETKLITWGADTAACGDIINGL-1000
PVSARRGREILLGPADGMVSKGWRLLAPITAYAQQTRGLLGCIITSLTGR
DKNQVEGEVQIVSTAAQTFLATCINGVCWTVYHGAGTRTIASPKGPVIQM-1100

S T
YTNVDQDLVGWPAPQGSRSLTPCTCGSSDLYLVTRHADVIPVRRRGDSRG
SLLSPRPISYLKGSSGGPLLCPAGHAVGIFRAAVCTRGVAKAVDFIPVEN-1200
LETTMRSPVFTDNSSPPVVPQSFQVAHLHAPTGSGKSTKVPAAYAAQGYK

L
VLVLNPSVAATLGFGAYMSKAHGIDPNIRTGVRTITTGSPITYSTYGKFL-1300

ADGGCSGGAYDIIICDECHSTDATSILGIGTVLDQAETAGARLVVLATAT
PPGSVTVPHPNIEEVALSTTGEIPFYGKAIPLEVIKGGRHLIFCHSKKKC-1400
DELAAKLVALGINAVAYYRGLDVSVIPTSGDVVVVATDALMTGYTGDFDS

Y               (S)
VIDCNTCVTQTVDFSLDPTFTIETITLPQDAVSRTQRRGRTGRGKPGIYR-1500
FVAPGERPSGMFDSSVLCECYDAGCAWYELTPAETTVRLRAYMNTPGLPV
CQDHLEFWEGVFTGLTHIDAHFLSQTKQSGENLPYLVAYQATVCARAQAP-1600
PPSWDQMWKCLIRLKPTLHGPTPLLYRLGAVQNEITLTHPVTKYIMTCMS
ADLEVVTSTWVLVGGVLAALAAYCLSTGCVVIVGRVVLSGKPAIIPDREV-1700
LYREFDEMEECSQHLPYIEQGMMLAEQFKQKALGLLQTASRQAEVIAPAV
QTNWQKLETFWAKHMWNFISGIQYLAGLSTLPGNPAIASLMAFTAAVTSP-1800
LTTSQTLLFNILGGWVAAQLAAPGAATAFVGAGLAGAAIGSVGLGKVLID
```

FIG. 90B

```
                                     (G)
ILAGYGAGVAGALVAFKIMSGEVPSTEDLVNLLPAILSPGALVVGVVCAA-1900

(HC)
ILRRHVGPGEGAVQWMNRLIAFASRGNHVSPTHYVPESDAAARVTAILSS
LTVTQLLRRLHQWISSECTTPCSGSWLRDIWDWICEVLSDFKTWLKAKLM-2000

(V)
PQLPGIPFVSCQRGYKGVWRGDGIMHTRCHCGAEITGHVKNGTMRIVGPR
TCRNMWSGTFPINAYTTGPCTPLPAPNYTFALWRVSAEEYVEIRQVGDFH-2100
YVTGMTTDNLKCPCQVPSPEFFTELDGVRLHRFAPPCKPLLREEVSFRVG
LHEYPVGSQLPCEPEPDVAVLTSMLTDPSHITAEAAGRRLARGSPPSVAS-2200
SSASQLSAPSLKATCTANHDSPDAELIEANLLWRQEMGGNITRVESENKV
VILDSFDPLVAEEDEREISVPAEILRKSRRFAQALPVWARPDYNPPLVET-2300

(S)
WKKPDYEPPVVHGCPLPPPKSPPVPPPRKKRTVVLTESTLSTALAELATR
                        (FA)
SFGSSSTSGITGDNTTTSSEPAPSGCPPDSDAESYSSMPPLEGEPGDPDL-2400
SDGSWSTVSSEANAEDVVCCSMSYSWTGALVTPCAAEEQKLPINALSNSL
LRHHNLVYSTTSRSACQRQKKVTFDRLQVLDSHYQDVLKEVKAAASKVKA-2500

(F)
NLLSVEEACSLTPPHSAKSKFGYGAKDVRCHARKAVTHINSVWKDLLEDN
VTPIDTTIMAKNEVFCVQPEKGGRKPARLIVFPDLGVRVCEKMALYDVVT-2600
KLPLAVMGSSYGFQYSPGQRVEFLVQAWKSKKTPMGFSYDTRCFDSTVTE (G)
SDIRTEEAIYQCCDLDPQARVAIKSLTERLYVGGPLTNSRGENCGYRRCR-2700
ASGVLTTSCGNTLTCYIKARAACRAAGLQDCTMLVCGDDLVVICESAGVQ
EDAASLRAFTEAMTRYSAPPGDPPQPEYDLELITSCSSNVSVAHDGAGKR-2800
VYYLTRDPTTPLARAAWETARHTFVNSWLGNIIMFAPTLWARMILMTHFF
SVLIARDQLEQALDCEIYGACYSIEPLDLPPIIQRLHGLSAFSLHSYSPG-2900

G
EINRVAACLRKLGVPPLRAWRHRARSVRARLLARGGRAAICGKYLFNWAV (P)
RTKLKLTPIAAAGQLDLSGWFTAGYSGGDIYHSVSHARPRWIWFCLLLLA-3000
AGVGIYLLPNRO-3011
```

Stop codon ( ) = Heterogeneity due possibly
     to 5' or 3' terminal cloning
     artefact.

NANBV DIAGNOSTICS AND VACCINES

This application is a divisional, of application Ser. No. 08/403,590, filed Mar. 14, 1995, which is a continuation of application Ser. No. 07/722,489, filed Jun. 24, 1991.

TECHNICAL FIELD

The invention relates to materials and methodologies for managing the spread of non-A, non-B hepatitis virus (NANBV) infection. More specifically, it relates to diagnostic DNA fragments, diagnostic proteins, diagnostic antibodies and protective antigens and antibodies for an etiologic agent of NANB hepatitis, i.e., hepatitis C virus.

References Cited in the Application

Barr et al., *Biotechniques* (1986) 4:428.
Bradley et al., *Gastroenterolopy* (1985) 88:773.
Botstein, *Gene* (1979) 8:17.
M. A. Brinton, (1986) in "The Viruses: The Togaviridae and Flaviviridae" (Series eds. Fraenkel-Conrat and Wagner, vol. eds. Schlesinger and Schlesinger, Plenum Press), p.327–374.
Broach (1981) in: "Molecular Biology of the Yeast—Saccharomyces, Vol. 1, p.445, Cold Spring Harbor Press.
Broach et al., *Meth Enzymol* (1983) 101:307.
Catty (1988), "Antibodies, Volume 1: A Practical Approach" (IRL Press).
Chaney et al., *Cell Mol Genet* (1986) 12:237.
Chakrabarti et al., *Mol Cell Biol* (1985) 5:3403.
Chang et al., *Nature* (1977) 198:1056.
Chen and Seeburg, *DNA* (1985) 4:165.
Chirgwin et al., *Biochemistry* (1979) 18:5294.
Chomczynski and Sacchi, *Anal Biochem* (1987) 162:156.
Choo et al., *Science* (1989) 244:359.
Clewell et al., *Proc Natl Acad Sci USA* (1969) 62:1159.
Clewell, *J Bacteriol* (1972) 110:667.
Cohen, *Proc Natl Acad Sci USA* (1972) 69:2110.
Cousens et al., *Gene* (1987) 61:265.
De Boer et al., *Proc Natl Acad Sci USA* (1983) 292:128.
Dreesman et al., *J Infect Dis* (1985) 151:761.
S. M. Feinstone and J. H. Hoofnagle, *New Engl J Med* (1984) 311:185.
Felgner et al., *Proc Natl Acad Sci USA* (1987) 84:7413.
Fields & Knipe (1986), "Fundamental Virology" (Raven Press, N.Y.).
Fiers et al., *Nature* (1978) 273:113.
R. J. Gerety et al., in "Viral Hepatitis and Liver Disease" (B. N. Vyas, J. L. Dienstag, and J. H. Hoofnagle, eds)
Glennie et al., *Nature* (1982) 295:712.
Gluzman, *Cell* (1981) 23:175.
Goeddel et al., *Nuc Acids Res* (1980) 8:4057.
Graham and Van der Eb, *Virology* (1978) 52:546.
Grunstein and Hogness, *Proc Natl Acad Sci USA* (1975) 73:3961.
Grych et al., *Nature* (1985) 316:74.
Gubler and Hoffman *Gene* (1983) 25:263.
Hahn, *Virology* (1988) 162:167.
Hammerling et al., (1981), "Monoclonal Antibodies and T-Cell Hybridomas".
Han, *Biochemistry* (1987) 26:1617.
Helfman, *Proc Natl Acad Sci USA* (1983) 80:31.
Hess et al., *J Adv Enzyme Reg* (1968) 7:149.
Hinnen et al., *Proc Natl Acad Sci USA* (1978) 75:1929.
Hitzeman et al., *J Biol Chem* (1980) 255:2073.
Holland et al, *Biochemistry* (1978) 17:4900.
Holland, *J Biol Chem* (1981) 256:1385.
Holland and Holland, *J Biol Chem* (1980) 255:2596.
Hoopes et al., *Nuc Acids Res* (1981) 2:5493.
Houghton et al., *Nuc Acids Res* (1981) 9:247
T. V. Hunyh et al., (1985) in "DNA Cloning Techniques; A Practical Approach" (D. Glover, Ed., IRL Press, Oxford, U.K.) pp. 49–78.
*Immun Rev* (1982) 62:185.
Ito et al., *Agric Biol Chem* (1984) 48:341.
Iwarson, *British Medical J* (1987) 295:946.
Kennett et al. (1980) "Monoclonal Antibodies".
Kniskem et al., *Gene* (1986) 46:135.
Kyte and Doolittle, *J Mol Bio* (1982) 157:105–132.
Laemmli, *Nature* (1970) 227:680.
Lee et al., *Science* (1988) 239:1288.
Luckow and Summers, *Virol* (1989) 17:31.
Mackett et al., *J Virol* (1984) 49:857.
T. Maniatis et al. (1982) "Molecular Cloning; A Laboratory Manual" (Cold Spring Harbor Press, Cold Spring Harbor, N.Y.).
Sambrook et al. (1989), "Molecular Cloning; A Laboratory Manual", Second Edition (Cold Spring Harbor Press, Cold Spring Harbor, N.Y.).
Manning and Mocarski, *Virol* (1988) 167:477.
Mayer and Walker, eds. (1987), "Immunochemical Methods In Cell And Molecular Biology" (Academic Press, London).
Maxam et al, *Meth Enzymol* (1980) 65:499.
MacNamara et al., *Science* (1984) 226:1325.
Messing et al., *Nuc Acids Res* (1981) 9:309.
Messing, *Meth Enzymol* (1983) 101:20–37.
Michelle et al., Int. Symposium on Viral Hepatitis.
Monath (1986) in "The Viruses: The Togaviradae And Flaviviridae" (Series eds. Fraenkel Conrat and Wagner, vol. eds. Schlesinger and Schlesinger, Plenum Press), pp. 375–440.
Moss (1987) in "Gene Transfer Vectors For Mammalian Cells" (Miller and Calos, eds., Cold Spring Harbor Laboratory, Cold Spring Harbor, N.Y.), p. 10.
Nagahurna et al., *Anal Biochem* (1984) 141:74.
Neurath et al., *Science* (1984) 224:392.
Nisonoff et al., *Clin Immunol Immunopathol* (1981) 21:397–406.
L. R. Overby, *Curr Hepatol* (1985) 5:49.
L. R. Overby, *Curr Hepatol* (1986) 6:65.
L. R. Overby, *Curr Hepatol* (1987) 7:35.
Pachl et al., *J Virol* (1987) 61:315.
Peleg, *Nature* (1969) 221:193.
Pfefferkorn and Shapiro (1974), in "Comprehensive Virology", Vol. 2 (Fraenkel-Conrat & Wagner, eds., Plenum, N.Y.) pp. 171–230.
A. M. Prince, *Ann Rev Microbiol* (1983) 37:217.
Rice et al., *Science* (1985) 229:726.
Rice et al. (1986) in "The Viruses: The Togaviridae And Flaviviridae" (Series eds. Fraenkel-Conrat and Wagner, vol. eds. Schlesinger and Schlesinger, Plenum Press), p.279–328. Roehrig (1986) in "The Viruses: The Togaviridae And Flaviviridae" (Series eds. Fraenkel-Conrat and Wagner, vol. eds. Schlesinger and Schlesinger, Plenum Press)
Sadler et al., *Gene* (1980) 8:279.
Saiki et al., *Nature* (1986) 324:163.
Saiki et al., *Science* (1988) 239:487.
Sanger et al., *Proc Natl Acad Sci USA* (1977) 74:5463.
Setlow, ed. (1988), "Genetic Engineering" Vol. 10, pp. 195–219 (Plenum Publishing Co., N.Y.
Schlesinger et al., *J Virol* (1986) 60:1153.
M. Schreier et al., (1980) "Hybridoma Techniques"
Scopes (1984), "Protein Purification, Principles and Practice", 2nd Ed., (Springer-Verlag, N.Y.).

Shimatake et al., *Nature* (1981) 292:128.
Singh et al., *Nuc Acids Res* (1983) 11:4049.
Sippel, *Eur J Biochem* (1973) 37:31.
Smith et al., *Mol Cell Biol* (1983) 3:2156–2165.
Steimer et al., *J Virol* (1986) 58:9.
Stollar (1980), in "The Togaviruses" (R. W. Schlesinger, ed., Academic Press, N.Y.), pp. 584–622.
Stuve et al., *J Virol* (1987) 61:326.
Sumiyoshi et al., *Virol* (1987) 161:497.
Taylor et al., *Biochim Biophys Acta* (1976) 442:324.
Towbin et al., *Proc Natl Acad Sci USA* (1979) 76:4350.
Tsu and Herzenberg (1980), in "Selected Methods In Cellular Immunology" (W. H. Freeman and Co.) pp. 373–391.
Vytdehaag et al., *J Immunol* (1985) 134:1225.
P. Valenzuela et al., *Nature* (1982) 298:344.
P. Valenzuela et al., (1984), in "Hepatitis B" (I. Millman et al., ed, Plenum Press) pp. 225–236.
Warner, *DNA* (1984) 3:401.
Ward et al., *Nature* (1989) 341:544.
Wu and Grossman, *Meth Enzymol* (1987), 154 "Recombinant DNA", Part E.
Wu, *Meth Enzymol* (1987), 155, "Recombinant DNA", part F.
Zoller, *Nuc Acids Res* (1982) 10:6487.
Cited Patents
  U.S. Pat. No. 4,341,761
  U.S. Pat. No. 4,399,121
  U.S. Pat. No. 4,427,783
  U.S. Pat. No. 4,444,887
  U.S. Pat. No. 4,466,917
  U.S. Pat. No. 4,472,500
  U.S. Pat. No. 4,491,632
  U.S. Pat. No. 4,493,890
  U.S. Pat. No. 4,816,467

BACKGROUND ART

Non-A, Non-B hepatitis (NANBH) is a transmissible disease or family of diseases that are believed to be viral-induced, and that are distinguishable from other forms of viral-associated liver diseases, including that caused by the known hepatitis viruses, i.e., hepatitis A virus (HAV), hepatitis B virus (HBV), and delta hepatitis virus (HDV), as well as the hepatitis induced by cytomegalovirus (CMV) or Epstein-Barr virus (EBV). NANBH was first identified in transfused individuals. Transmission from man to chimpanzee and serial passage in chimpanzees provided evidence that NANBH is due to a transmissible infectious agent or agents. However, the transmissible agent responsible for NANBH is still unidentified and the number of agents which are causative of the disease are unknown.

Epidemiologic evidence is suggestive that there may be three types of NANBH: the water-borne epidemic type; the blood or needle associated type; and the sporadically occurring (community acquired) type. However, the number of agents which may be the causative of NANBH are unknown.

Clinical diagnosis and identification of NANBH has been accomplished primarily by exclusion of other viral markers. Among the methods used to detect putative NANBV antigens and antibodies are agar-gel diffusion, counterimmunoelectrophoresis, immunofluorescence microscopy, immune electron microscopy, radioimmunoassay, and enzyme-linked immunosorbent assay. However, none of these assays has proved to be sufficiently sensitive, specific, and reproducible to be used as a diagnostic test for NANBH.

Until now there has been neither clarity nor agreement as to the identity or specificity of the antigen antibody systems associated with agents of NANBH. This is due, at least in part, to the prior or co-infection of HBV with NANBV in individuals, and to the known complexity of the soluble and particulate antigens associated with HBV, as well as to the integration of HBV DNA into the genome of liver cells. In addition, there is the possibility that NANBH is caused by more than one infectious agent, as well as the possibility that NANBH has been misdiagnosed. Moreover, it is unclear what the serological assays detect in the serum of patients with NANBH. It has been postulated that the agar-gel diffusion and counterimmunoelectrophoresis assays detect autoimmune responses or nonspecific protein interactions that sometimes occur between serum specimens, and that they do not represent specific NANBV antigen-antibody reactions. The immunofluorescence, and enzyme-linked immunosorbent, and radioimmunoassays appear to detect low levels of a rheumatoid-factor-like material that is frequently present in the serum of patients with NANBH as well as in patients with other hepatic and non-hepatic diseases. Some of the reactivity detected may represent antibody to host-determined cytoplasmic antigens.

There are a number of alleged candidate NANBV. See, for example the reviews by Prince (1983), Feinstone and Hoofnagle (1984), and Overby (1985, 1986, 1987) and the article by Iwarson (1987). However, the field has not accepted that any of these candidates represent the etiological agent of NANBH.

The demand for sensitive, specific methods for screening and identifying carriers of NANBV and NANBV contaminated blood or blood products is significant. Post-transfusion hepatitis (PTH) occurs in approximately 10% of transfused patients, and NANBH accounts for up to 90% of these cases. The major problem in this disease is the frequent progression to chronic liver damage (25–55%).

Patient care as well as the prevention of transmission of NANBH by blood and blood products or by close personal contact require reliable diagnostic and prognostic tools to detect nucleic acids, antigens and antibodies related to NANBV. In addition, there is also a need for effective vaccines and immunotherapeutic therapeutic agents for the prevention and/or treatment of the disease.

DISCLOSURE OF THE INVENTION

The invention pertains to the isolation and characterization of a newly discovered etiologic agent of NANBH, hepatitis C virus (HCV), its nucleotide sequences, its protein sequences and resulting polynucleotides, polypeptides and antibodies derived therefrom. The inventions described herein were made possible by the discovery of cDNA replicas isolated by a technique which included a novel step of screening expression products from cDNA libraries created from a particulate agent in infected tissue with sera from patients with NANBH to detect newly synthesized antigens derived from the genome of the heretofore unisolated and uncharacterized viral agent, and of selecting clones which produced products which reacted immunologically only with sera from infected individuals as compared to non-infected individuals.

Studies of the nature of the genome of the HCV, utilizing probes derived from the HCV cDNA, as well as sequence information contained within the HCV cDNA, are suggestive that HCV is a positive-stranded RNA virus which appears to be distantly related to the flaviviridae family, and to the pestiviruses.

Portions of the cDNA sequences derived from HCV are useful as probes to diagnose the presence of virus in samples, and to isolate naturally occurring variants of the virus. These cDNAs also make available polypeptide sequences of HCV antigens encoded within the HCV genome(s) and permits the production of polypeptides which are useful as standards or reagents in diagnostic tests and/or as components of vaccines. Antibodies, including for example both polyclonal and monoclonal, directed against HCV epitopes contained within these polypeptide sequences are also useful for diagnostic tests, as therapeutic agents, for screening of antiviral agents, and for the isolation of the NANBV agent from which these cDNAs derive. In addition, by utilizing probes derived from these cDNAs it is possible to isolate and sequence other portions of the HCV genome, thus giving rise to additional probes and polypeptides which are useful in the diagnosis and/or treatment, both prophylactic and therapeutic, of NANBH.

Accordingly with respect to polynucleotides, some aspects of the invention are: a purified HCV polynucleotide; a recombinant HCV polynucleotide; a recombinant polynucleotide comprising a sequence derived from an HCV genome or from HCV cDNA; a recombinant polynucleotide encoding an epitope of HCV; a recombinant vector containing any of the above recombinant polynucleotides, and a host cell transformed with any of these vectors.

Other aspects of the invention are: a recombinant expression system comprising an open reading frame (ORF) of DNA derived from an HCV genome or from HCV cDNA, wherein the ORF is operably linked to a control sequence compatible with a desired host, a cell transformed with the recombinant expression system, and a polypeptide produced by the transformed cell.

Still other aspects of the invention are: purified HCV, a preparation of polypeptides from the purified HCV; a purified HCV polypeptide; a purified polypeptide comprising an epitope which is immunologically identifiable with an epitope contained in HCV.

Included aspects of the invention are a recombinant HCV polypeptide; a recombinant polypeptide comprised of a sequence derived from an HCV genome or from HCV cDNA; a recombinant polypeptide comprised of an HCV epitope; and a fusion polypeptide comprised of an HCV polypeptide.

Also included in the invention are a monoclonal antibody directed against an HCV epitope; and a purified preparation of polyclonal antibodies directed against an HCV epitope; and an anti-idiotype antibody comprising a region which mimics an HCV epitope.

Another aspect of the invention is a particle which is immunogenic against HCV infection comprising a non-HCV polypeptide having an amino acid sequence capable of forming a particle when said sequence is produced in a eukaryotic host, and an HCV epitope.

Still another aspect of the invention is a polynucleotide probe for HCV.

Aspects of the invention which pertain to kits are those for: analyzing samples for the presence of polynucleotides derived from HCV comprising a polynucleotide probe containing a nucleotide sequence from HCV of about 8 or more nucleotides, in a suitable container; analyzing samples for the presence of an HCV antigen comprising an antibody directed against the HCV antigen to be detected, in a suitable container; analyzing samples for the presence of an antibodies directed against an HCV antigen comprising a polypeptide containing an HCV epitope present in the HCV antigen, in a suitable container.

Other aspects of the invention are: a polypeptide comprising an HCV epitope, attached to a solid substrate; and an antibody to an HCV epitope, attached to a solid substrate.

Still other aspects of the invention are: a method for producing a polypeptide containing an HCV epitope comprising incubating host cells transformed with an expression vector containing a sequence encoding a polypeptide containing an HCV epitope under conditions which allow expression of said polypeptide; and a polypeptide containing an HCV epitope produced by this method.

The invention also includes a method for detecting HCV nucleic acids in a sample comprising reacting nucleic acids of the sample with a probe for an HCV polynucleotide under conditions which allow the formation of a polynucleotide duplex between the probe and the HCV nucleic acid from the sample; and detecting a polynucleotide duplex which contains the probe.

Still other aspects are also included in the invention. These include an immunoassay for detecting an HCV antigen comprising incubating a sample suspected of containing an HCV antigen with a probe antibody directed against the HCV antigen to be detected under conditions which allow the formation of an antigen-antibody complex; and detecting an antigen-antibody complex containing the probe antibody. An immunoassay for detecting antibodies directed against an HCV antigen comprising incubating a sample suspected of containing anti-HCV antibodies with a probe polypeptide which contains an epitope of the HCV, under conditions which allow the formation of an antibody-antigen complex; and detecting the antibody-antigen complex containing the probe antigen.

Also included in the invention are vaccines for treatment of HCV infection comprising an immunogenic peptide containing an HCV epitope, or an inactivated preparation of HCV, or an attenuated preparation of HCV.

Another aspect of the invention is a tissue culture grown cell infected with HCV.

Yet another aspect of the invention is a method for producing antibodies to HCV comprising administering to an individual an isolated immunogenic polypeptide containing an HCV epitope in an amount sufficient to produce an immune response.

BRIEF DESCRIPTION OF THE DRAWINGS

FIG. 1 (SEQ ID NO: 1 and SEQ ID NO:2) shows the double-stranded nucleotide sequence of the HCV cDNA insert in clone 5-1-1, and the putative amino acid sequence of the polypeptide encoded therein.

FIG. 2 (SEQ ID NO:3, SEQ ID NO:4, SEQ ID NO:5 and SEQ ID NO:6) shows the homologies of the overlapping HCV cDNA sequences in clones 5-1-1, 81, 1-2, and 9l.

FIG. 3 (SEQ ID NO:7 and SEQ ID NO:8) shows a composite sequence of HCV cDNA derived from overlapping clones 81, 1-2, and 91, and the amino acid sequence encoded therein.

FIG. 4 (SEQ ID NO:9 and SEQ ID NO: 10) shows the double-stranded nucleotide sequence of the HCV cDNA insert in clone 81, and the putative amino acid sequence of the polypeptide encoded therein.

FIG. 5 (SEQ ID NO: 11 and SEQ ID NO: 12) shows the HCV cDNA sequence in clone 36, the segment which overlaps the NANBV cDNA of clone 81, and the polypeptide sequence encoded within clone 36.

FIG. 6 (SEQ ID NO:13 and SEQ ID NO:14) shows the combined ORF of HCV cDNAs in clones 36 and 81, and the polypeptide encoded therein.

FIG. 7 (SEQ ID NO: 15 and SEQ ID NO: 16) shows the HCV cDNA sequence in clone 32, the segment which overlaps clone 81, and the polypeptide encoded therein.

FIG. 8 (SEQ ID NO:17 and SEQ ID NO:18) shows the HCV cDNA sequence in clone 35, the segment which overlaps clone 36, and the polypeptide encoded therein.

FIG. 9 (SEQ ID NO:19 and SEQ ID NO:20) shows the combined ORF of HCV cDNAs in clones 35, 36, 81, and 32, and the polypeptide encoded therein.

FIG. 10 (SEQ ID NO:21 and SEQ ID NO:22) shows the HCV cDNA sequence in clone 37b, the segment which overlaps clone 35, and the polypeptide encoded therein.

FIG. 11 (SEQ ID NO:23 and SEQ ID NO:24) shows the HCV cDNA sequence in clone 33b, the segment which overlaps clone 32, and the polypeptide encoded therein.

FIG. 12 (SEQ ID NO:25 and SEQ ID NO:26) shows the HCV cDNA sequence in clone 40b, the segment which overlaps clone 37b, and the polypeptide encoded therein.

FIG. 13 (SEQ ID NO:27 and SEQ ID NO:28) shows the HCV cDNA sequence in clone 25c, the segment which overlaps clone 33b, and the polypeptide encoded therein.

FIG. 14 (SEQ ID NO:29 and SEQ ID NO:30) shows the nucleotide sequence and polypeptide encoded therein of the ORF which extends through the HCV cDNAs in clones 40b, 37b, 35, 36, 81, 32, 33b, and 25c.

FIG. 15 (SEQ ID NO:31 and SEQ ID NO:32) shows the HCV cDNA sequence in clone 33c, the segment which overlaps clones 40b and 33c, and the amino acids encoded therein.

FIG. 16 (SEQ ID NO:33 and SEQ ID NO:34) shows the HCV cDNA sequence in clone 8h, the segment which overlaps clone 33c, and the amino acids encoded therein.

FIG. 17 (SEQ ID NO:35 and SEQ ID NO:36) shows the HCV cDNA sequence in clone 7e, the segment which overlaps clone 8h, and the amino acids encoded therein.

FIG. 18 (SEQ ID NO:37 and SEQ ID NO:38) shows the HCV cDNA sequence in clone 14c, the segment which overlaps clone 25c, and the amino acids encoded therein.

FIG. 19 (SEQ ID NO:39 and SEQ ID NO:40) shows the HCV cDNA sequence in clone 8f, the segment which overlaps clone 14c, and the amino acids encoded therein.

FIG. 20 (SEQ ID NO:41 and SEQ ID NO:42) shows the HCV cDNA sequence in clone 33f, the segment which overlaps clone 8f, and the amino acids encoded therein.

FIG. 21 (SEQ ID NO:43 and SEQ ID NO:44) shows the HCV cDNA sequence in clone 33g, the segment which overlaps clone 33f, and the amino acids encoded therein.

FIG. 22 (SEQ ID NO:45 and SEQ ID NO:46) shows the HCV cDNA sequence in clone 7f, the segment which overlaps the sequence in clone 7e, and the amino acids encoded therein.

FIG. 23 (SEQ ID NO:47 and SEQ ID NO:48) shows the HCV cDNA sequence in clone 11b, the segment which overlaps the sequence in clone 7f, and the amino acids encoded therein.

FIG. 24 (SEQ ID NO:49 and SEQ ID NO:50) shows the HCV cDNA sequence in clone 14i, the segment which overlaps the sequence in clone 11b, and the amino acids encoded therein.

FIG. 25 (SEQ ID NO:51 and SEQ ID NO:52) shows the HCV cDNA sequence in clone 39c, the segment which overlaps the sequence in clone 33g, and the amino acids encoded therein.

FIG. 26 (SEQ ID NO:53 and SEQ ID NO:54) shows a composite HCV cDNA sequence derived from the aligned cDNAs in clones 14i, 11b, 7f, 7e, 8h, 33c 40b 37b 35 36, 81, 32, 33b, 25c, 14c, 8f, 33f, and 33g; also shown is the amino acid sequence of the polypeptide encoded in the extended ORF in the derived sequence.

FIG. 27 (SEQ ID NO:55 and SEQ ID NO:56) shows the sequence of the HCV cDNA in clone 12f, the segment which overlaps clone 14i, and the amino acids encoded therein.

FIG. 28 (SEQ ID NO:57 and SEQ ID NO:58) shows the sequence of the HCV cDNA in clone 35f, the segment which overlaps clone 39c, and the amino acids encoded therein.

FIG. 29 (SEQ ID NO:59 and SEQ ID NO:60) shows the sequence of the HCV cDNA in clone 19g, the segment which overlaps clone 35f, and the amino acids encoded therein.

FIG. 30 (SEQ ID NO:61 and SEQ ID NO:62) shows the sequence of clone 26g, the segment which overlaps clone 19g, and the amino acids encoded therein.

FIG. 31 (SEQ ID NO:63 and SEQ ID NO:64) shows the sequence of clone 15e, the segment which overlaps clone 26g, and the amino acids encoded therein.

FIG. 32 (SEQ ID NO:65 and SEQ ID NO:66) shows the sequence in a composite cDNA, which was derived by aligning clones 12f through 15e in the 5' to 3' direction; it also shows the amino acids encoded in the continuous ORF.

FIG. 36 (SEQ ID NO:67 and SEQ ID NO:68) shows the putative amino acid sequence of the carboxy-terminus of the fusion polypeptide C100-3 and the nucleotide sequence encoding it.

FIG. 42 (SEQ ID NO:69 and SEQ ID NO:70) shows the homologies between a polypeptide encoded in HCV cDNA and an NS protein from Dengue flavivirus.

FIG. 45 (SEQ ID NO:7 1) shows the sequences in a primer mix, derived from a conserved sequence in NS1 of flaviviruses.

FIG. 46 (SEQ ID NO:72 and SEQ ID NO:73) shows the HCV cDNA sequence in clone k9-1, the segment which overlaps the cDNA in FIG. 26, and the amino acids encoded therein.

FIG. 47 (SEQ ID NO:74 and SEQ ID NO:75) shows the sequence in a composite cDNA which was derived by aligning clones k9-1 through 15e in the 5' to 3' direction; it also shows the amino acids encoded in the continuous ORF.

FIG. 48 (SEQ ID NO:76 and SEQ ID NO:77) shows the nucleotide sequence of HCV cDNA in clone 13i, the amino acids encoded therein, and the sequences which overlap with clone 12f.

FIG. 49 (SEQ ID NO:78 and SEQ ID NO:79) shows the nucleotide sequence of HCV cDNA in clone 26j, the amino acids encoded therein, and the sequences which overlap clone 13i.

FIG. 50 (SEQ ID NO:80 and SEQ ID NO:81) shows the nucleotide sequence of HCV cDNA in clone CA59a, the amino acids encoded therein, and the sequences which overlap with clones 26j and K9-1.

FIG. 51 (SEQ ID NO:82 and SEQ ID NO:83) shows the nucleotide sequence of HCV cDNA in clone CA84a, the amino acids encoded therein, and the sequences which overlap with clone CA59a.

FIG. 52 (SEQ ID NO:84 and SEQ ID NO:85) shows the nucleotide sequence of HCV cDNA in clone CA156e, the amino acids encoded therein, and the sequences which overlap with CA84a.

FIG. 53 (SEQ ID NO:86 and SEQ ID NO:87) shows the nucleotide sequence of HCV cDNA in clone CA167b, the amino acids encoded therein, and the sequences which overlap CA156e.

FIG. 54 (SEQ ID NO:88 and SEQ ID NO:89) shows the ORF of HCV cDNA derived from clones pi14a, CA167b, CA156e, CA84a, CA59a, K9-1, 12f, 14i, 11b, 7f, 7e, 8h, 33c, 40b, 37b, 35, 36, 81, 32, 33b, 25c, 14c, 8f, 33f, 33g, 39c, 35f, 19g, 26g, and 15e.

FIG. 56 (SEQ ID NO:90 and SEQ ID NO:91) shows the nucleotide sequence of HCV cDNA in clone CA216a, the amino acids encoded therein, and the overlap with clone CA167b.

FIG. 57 (SEQ ID NO:92 and SEQ ID NO:93) shows the nucleotide sequence of HCV cDNA in clone CA290a, the amino acids encoded therein, and the overlap with clone CA216a.

FIG. 58 (SEQ ID NO:94, SEQ ID NO:95, SEQ ID NO:96, SEQ ID NO:97, SEQ ID NO:98, SEQ ID NO:99, SEQ ID NO:100, SEQ ID NO:101, SEQ ID NO:102 and SEQ ID NO: 103) shows the nucleotide sequence of HCV cDNA in clone ag30a and the overlap with clone CA290a.

FIG. 59 (SEQ ID NO:104, SEQ ID NO:105, SEQ ID NO:106 and SEQ ID NO:107) shows the nucleotide sequence of HCV cDNA in clone CA205a, and the overlap with the HCV cDNA sequence in clone CA290a.

FIG. 60 (SEQ ID NO: 108, SEQ ID NO: 109, SEQ ID NO: 110, SEQ ID NO:111, SEQ ID NO: 112, SEQ ID NO: 113, SEQ ID NO: 114, SEQ ID NO: 115, SEQ ID NO:116, SEQ ID NO:117, SEQ ID NO: 118 and SEQ ID NO:119) shows the nucleotide sequence of HCV cDNA in clone 18g, and the overlap with the HCV cDNA sequence in clone ag30a.

FIG. 61 (SEQ ID NO:120 and SEQ ID NO:121) shows the nucleotide sequence of HCV cDNA in clone 16jh, the amino acids encoded therein, and the overlap of nucleotides with the HCV cDNA sequence in clone 15e.

FIG. 62 (SEQ ID NO: 122) shows the composite sequence of the HCV cDNA sense strand deduced from overlapping clones b114a, 18g, ag30a, CA205a, CA290a, CA216a, pi14a, CA167b, CA156e, CA84a, CA59a, K9-1 (also called k9-1), 26j, 13i, 12f, 14i, 11b, 7f, 7e, 8h, 33c, 40b, 37b, 35, 36, 81, 32, 33b, 25c, 14c, 8f, 33f, 33g, 39c, 35f, 19g, 26g, 15e, b5a, and 16jh.

FIG. 62A (SEQ ID NO: 123) shows the sequence of FIG. 62, but includes the complementary cDNA strand.

FIG. 64 is a diagram of the immunological colony screening method used in antigenic mapping studies.

FIG. 65 presents the antigenicity of polypeptides expressed from HCV cDNA clones used in an antigenic mapping study of the putative HCV polyprotein.

FIG. 66 (SEQ ID NO:124) presents the amino acid sequence of the putative polyprotein encoded in a composite HCV cDNA sequence shown in FIG. 62.

FIG. 68 (SEQ ID NO:125, SEQ ID NO:126, SEQ ID NO:127, SEQ ID NO:128, SEQ ID NO:129 and SEQ ID NO:130) shows the conserved co-linear peptides in HCV and Flaviviruses.

FIG. 71 (SEQ ID NO:135 and SEQ ID NO:136) shows the nucleotide sequence of clone 6k, the part of the sequence which overlaps clone 16jh, and the amino acids encoded therein.

FIG. 72 (SEQ ID NO:137 and SEQ ID NO:138) shows a composite cDNA sequence derived from overlapping clones b114a, 18g, ag30a, CA205a, CA290a, CA216a, pi14a, CA167b, CA156e, CA84a, CA59a, K9-1 (also called k9-1), 26j, 13i, 12f, 14i, 11b, 7f, 7e, 8h, 33c, 40b, 37b, 35, 36, 81, 32, 33b, 25c, 14c, 8f, 33f, 33g, 39c, 35f, 19g, 26g, 15e, b5a, 16jh and 6k; also shown are the amino acids encoded in the positive strand of the cDNA (which is the equivalent of the HCV RNA).

FIG. 73 (SEQ ID NO:139, SEQ ID NO:140, SEQ ID NO:141 and SEQ ID NO:142) shows the linkers used in the construction of $pS3\text{-}56_{c100m}$.

FIG. 74 (SEQ ID NO:143 and SEQ ID NO:144) shows the nucleotide sequence of the HCV cDNA in clone 31, the amino acids encoded therein, and putative restriction enzyme sites encoded therein.

FIG. 75 (SEQ ID NO:145 and SEQ ID NO:146) shows the nucleotide sequence of the HCV cDNA in clone p131jh, and its overlap with the nucleotide sequence in clone 6k.

FIG. 79 (SEQ ID NO:147 and SEQ ID NO:148) shows the nucleotide sequence of HCV cDNA in the C200-C100 construct, the amino acids encoded therein, and putative restriction enzyme sites encoded therein.

FIG. 80 (SEQ ID NO:149 and SEQ ID NO:150) shows the nucleotide consensus sequence of human isolate 23, variant sequences are shown below the sequence line. The amino acids encoded in the consensus sequence are also shown.

FIG. 81 (SEQ ID NO:151 and SEQ ID NO:152) shows the nucleotide consensus sequence of human isolate 27, variant sequences are shown below the sequence line. The amino acids encoded in the consensus sequence are also shown.

FIG. 82 (SEQ ID NO:153, SEQ ID NO:154 and SEQ ID NO:155) shows the aligned nucleotide sequences of human isolates 23 and 27 and of HCV1. Homologous sequences are indicated by the symbol (*). Non-homologous sequences are in small letters.

FIG. 83 (SEQ ID NO:156, SEQ ID NO:157 and SEQ ID NO:158) shows the aligned amino acid sequences of human isolates 23 and 27 and of HCV1. Homologous sequences are indicated by the symbol (*). Non-homologous sequences are in small letters.

FIG. 84 is a graph showing the relationship of the EnvL and EnvR primers to the model flavivirus polyprotein and putative HCV polyprotein.

FIG. 85 (SEQ ID NO:159, SEQ ID NO:160, SEQ ID NO:161 and SEQ ID NO:162) shows a comparison of the composite aligned nucleotide sequences of isolates Thorn, EC1, HCT #18, and HCV1.

FIG. 86 (SEQ ID NO:163 and SEQ ID NO:164) shows a comparison of the nucleotide sequences of EC10 and a composite of the HCV1 sequence; the EC10 sequence is on the line above the dots, and the HCV1 sequence is on the line below the dots.

FIG. 87 (SEQ ID NO:165, SEQ ID NO:166, SEQ ID NO:167, SEQ ID NO:168, SEQ ID NO:169 and SEQ ID NO:170) shows a comparison of the amino acid sequences 117–308 (relative to HCV1) encoded in the "EnvL" regions of the consensus sequences of human isolates HCT #18, JH23, JH 27, Thorne, EC1, and of HCV1.

FIG. 88 (SEQ ID NO:171, SEQ ID NO:172, SEQ ID NO:173, SEQ ID NO:174 and SEQ ID NO: 175) shows a comparison of the amino acid sequences 330–360 (relative to HCV1) encoded in the "EnvR" regions of the consensus sequences of human isolates HCT #18, JH23, JH 27, Thorne, EC1, and of HCV1.

FIG. 89 (SEQ ID NO: 176) shows a composite cDNA sequence for HCV1, deduced from overlapping clones b 114a, 18g, ag3 Oa, CA205a, CA290a, CA216a, pi14a, CA167b, CA156e, CA84a, CA59a, K9-1 (also called k9-1), 26j, 13i, 12f, 14i, 11b, 7f, 7e, 8h, 33c, 40b, 37b, 35, 36, 81, 32, 33b, 25c, 14c, 8f, 33f, 33g, 39c. 35f, 19g, 26g, 15e, b5a, 16jh, 6k, and 131jh.

FIG. 90 (SEQ ID NO: 177) shows a putative polyprotein encoded in the HCV cDNA shown in FIG. 89.

FIG. 91 is a flow chart for the preparation of expression vector pC22.

MODES FOR CARRYING OUT THE INVENTION

I. Definitions

The term "hepatitis C virus" has been reserved by workers in the field for an heretofore unknown etiologic agent of NANBH. Accordingly, as used herein, "hepatitis C virus" (HCV) refers to an agent causative of NANBH, which was formerly referred to as NANBV and/or BB-NANBV. The terms HCV, NANBV, and BB-NANBV are used interchangeably herein. As an extension of this terminology, the disease caused by HCV, formerly called NANB hepatitis (NANBH), is called hepatitis C. The terms NANBH and hepatitis C may be used interchangeably herein.

HCV is a viral species of which pathogenic strains cause NANBH, and attenuated strains or defective interfering particles derived therefrom. As shown infra, the HCV genome is comprised of RNA. It is known that RNA containing viruses have relatively high rates of spontaneous mutation, i.e., reportedly on the order of $10^{-3}$ to $10^{-4}$ per incorporated nucleotide (Fields & Knipe (1986)). Therefore, since heterogeneity and fluidity of genotype are inherent in RNA viruses, there are multiple strains/isolates, which may be virulent or avirulent, within the HCV species. The compositions and methods described herein, enable the propagation, identification, detection, and isolation of the various HCV strains or isolates. Moreover, the disclosure herein allows the preparation of diagnostics and vaccines for the various strains/isolates, as well as compositions and methods that have utility in screening procedures for anti-viral agents for pharmacologic use, such as agents that inhibit replication of HCV.

Information on several different strains/isolates of HCV is disclosed herein, particularly strain or isolate CDC/HCVI (also called HCV1). Information from one strain or isolate, such as a partial genomic sequence, is sufficient to allow those skilled in the art using standard techniques to isolate new strains/isolates and to identify whether such new strains/isolates are HCV. For example, several different strains/isolates are described in Section IV.H.7., infra. These strains, which were obtained from a number of human sera (and from different geographical areas), were isolated utilizing the information from the genomic sequence of HCV1.

The information provided herein is indicative that HCV may be distantly related to the flaviviridae. The Flavivirus family contains a large number of viruses which are small, enveloped pathogens of man. The morphology and composition of Flavivirus particles are known, and are discussed in Brinton (1986). Generally, with respect to morphology, Flaviviruses contain a central nucleocapsid surrounded by a lipid bilayer. Virions are spherical and have a diameter of about 40–50 nm. Their cores are about 25–30 nm in diameter. Along the outer surface of the virion envelope are projections that are about 5–10 nm long with terminal knobs about 2 nm in diameter. Typical examples of the family include Yellow Fever virus, West Nile virus, and Dengue Fever virus. They possess positive-stranded RNA genomes (~11,000 nucleotides) that are slightly larger than that of HCV and encode a polyprotein precursor of about 3500 amino acids. Individual viral proteins are cleaved from this precursor polypeptide.

Using the techniques derived infra, the genomic structure and the nucleotide sequence of HCV1 genomic RNA has been deduced. The genome appears to be single-stranded RNA containing ~10,000 nucleotides. The genome is positive-stranded, and possesses a continuous, translational open reading frame (ORF) that encodes a polyprotein of about 3,000 amino acids. In the ORF, the structural protein (s) appear to be encoded in approximately the first quarter of the N-terminus region, with the majority of the polyprotein responsible for nonstructural proteins. When compared with all known viral sequences, small but significant co-linear homologies are observed with the non-structural proteins of the flavivirus family, and with the pestiviruses (which are now also considered to be part of the Flavivirus family).

Figure 69:
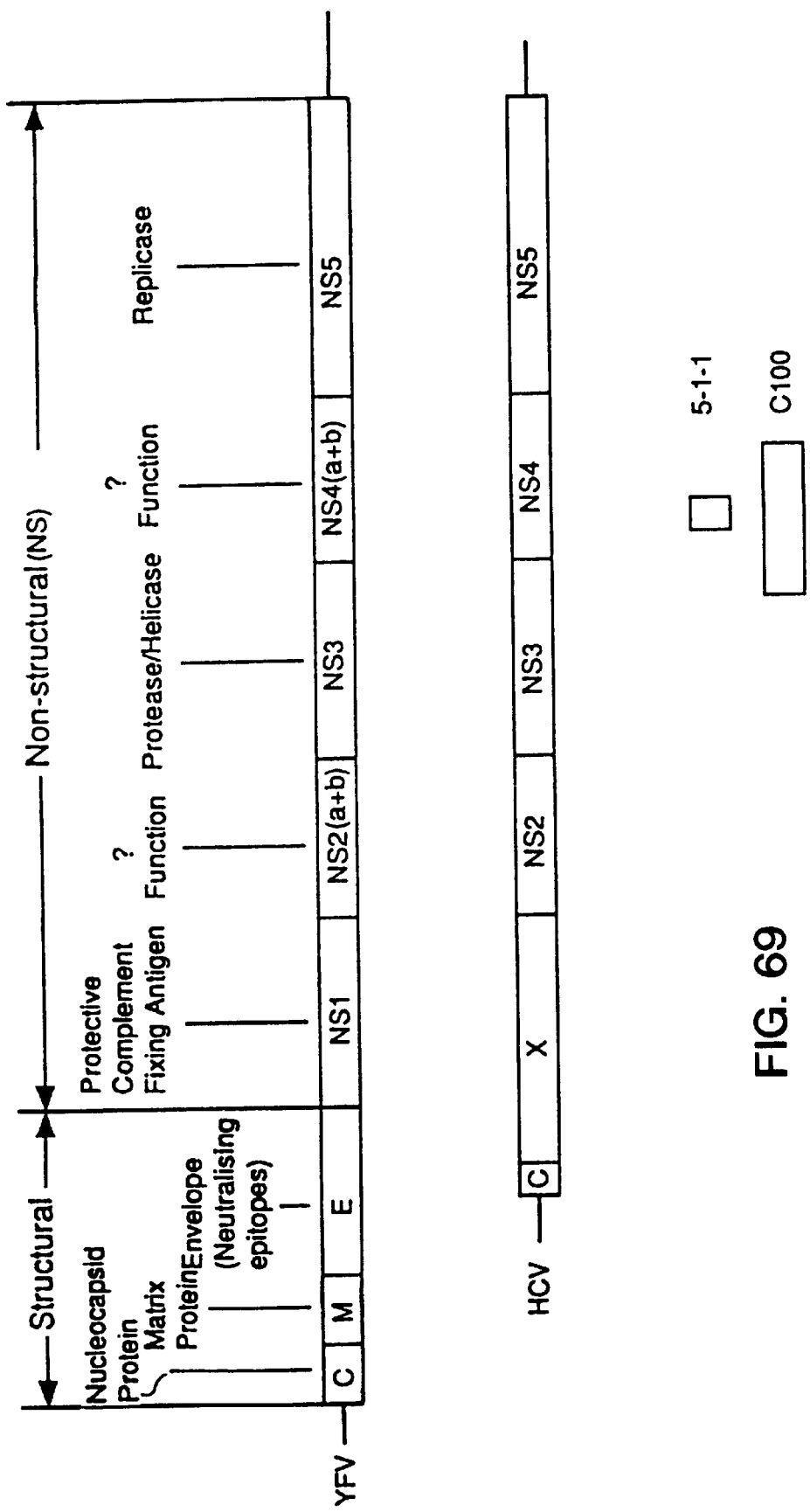
FIG. 69 shows schematic alignment of a flaviviral polyprotein and a putative HCV polyprotein encoded in the major ORF of the HCV genome. Also indicated in the figure are the possible functions of the flaviviral polypeptides cleaved from the flaviviral polyprotein. In addition, the relative placements of the HCV polypeptides, $NANB_{5\text{-}1\text{-}1}$ and C100, with respect to the putative HCV polyprotein are indicated.
Figure 70:
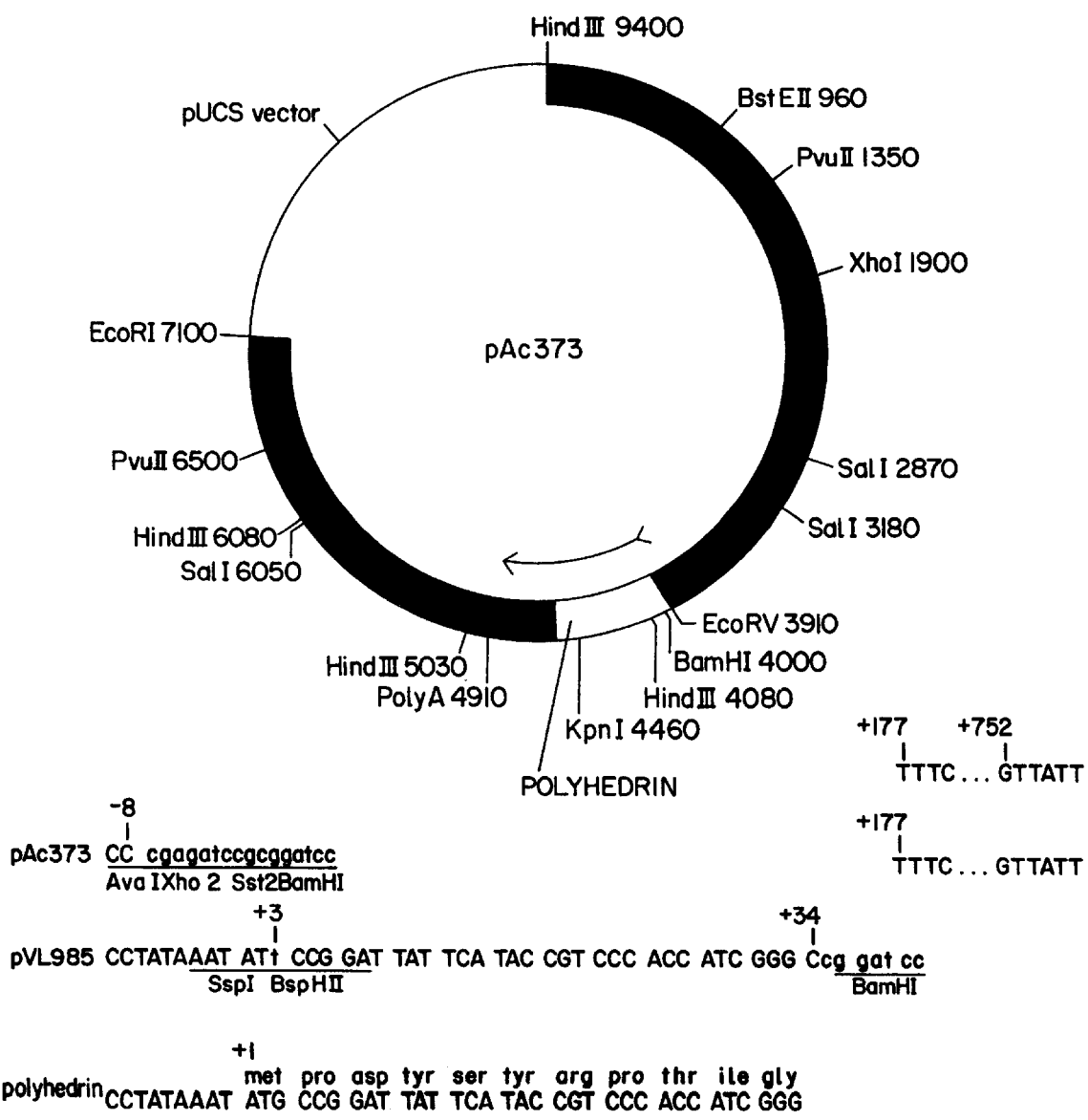
FIG. 70 (SEQ ID NO:131, SEQ ID NO:132, SEQ ID NO:133 and SEQ ID NO:134) shows relevant characteristics of AcNPV transfer vectors used for high level expression of nonfused foreign proteins. It also shows a restriction endonuclease map of the transfer vector pAc373.

A schematic alignment of possible regions of a flaviviral polyprotein (using Yellow Fever Virus as an example), and of a putative polyprotein encoded in the major ORF of the HCV genome, is shown in Fig. FIG. 69. In the figure the possible domains of the HCV polyprotein are indicated. The flavivirus polyprotein contains, from the amino terminus to the carboxy terminus, the nucleocapsid protein (C), the matrix protein (M), the envelope protein (E), and the nonstructural proteins 1, 2 (a+b), 3, 4 (a+b), and 5 (NS1, NS2, NS3, NS4, and NS5). Based upon the putative amino acids encoded in the nucleotide sequence of HCV1, a small domain at the extreme N-terminus of the HCV polyprotein appears similar both in size and high content of basic residues to the nucleocapsid protein (C) found at the N-terminus of flaviviral polyproteins. The nonstructural proteins 2,3,4, and 5 (NS2-5) of HCV and of yellow fever virus (YFV) appear to have counter parts of similar size and hydropathicity, although there is divergence of the amino acid sequences. However, the region of HCV which would correspond to the regions of YFV polyprotein which contains the M, E, and NS1 protein not only differs in sequence, but also appears to be quite different both in size and hydropathicity. Thus, while certain domains of the HCV genome may be referred to herein as, for example, NS1, or NS2, it should be borne in mind that these designations are speculative; there may be considerable differences between the HCV family and flaviviruses that have yet to be appreciated.

Based upon the nucleotide sequences encoding the polypeptides $NANB_{5-1-1}$ and HCV C100, and the sequence of the ORF, the relative placements of the 5-1-1 polypeptide and the C100 polypeptide with respect to the putative HCV polyprotein have been calculated. These are also shown in FIG. 69.

Different strains, isolates or subtypes of HCV are expected to contain variations at the amino acid and nucleic acids compared with HCV1. Many isolates are expected to show much (i.e., more than about 40%) homology in the total amino acid sequence compared with HCV1. However, it may also be found that there are other less homologous HCV isolates. These would be defined as HCV according to various criteria such as, for example, an ORF of approximately 9,000 nucleotides to approximately 12,000 nucleotides, encoding a polyprotein similar in size to that of HCV1, an encoded polyprotein of similar hydrophobic and/or antigenic character to that of HCV1, and the presence of co-linear peptide sequences that are conserved with HCV1. In addition, the genome would be a positive-stranded RNA.

HCV encodes at least one epitope which is immunologically identifiable with an epitope in the HCV genome from which the cDNAs described herein are derived; preferably the epitope is contained in an amino acid sequence described herein. The epitope is unique to HCV when compared to previously known Flaviviruses. The uniqueness of the epitope may be determined by its immunological reactivity with anti-HCV antibodies and lack of immunological reactivity with antibodies to known Flavivirus species. Methods for determining immunological reactivity are known in the art, for example, by radioimmunoassay, by ELISA assay, by hemagglutination, and several examples of suitable techniques for assays are provided herein.

In addition to the above, the following parameters of nucleic acid homology and amino acid homology are applicable, either alone or in combination, in identifying a strain/isolate as HCV. Since HCV strains and isolates are evolutionarily related, it is expected that the overall homology of the genomes at the nucleotide level may be about 10% or greater, probably will be about 40% or greater, probably about 60% or greater, and even more probably about 80% or greater; and in addition that there will be corresponding contiguous sequences of at least about 13 nucleotides. It should be noted, as shown infra, that there are variable and hypervariable regions within the HCV genome; therefore, the homology in these regions is expected to be significantly less than that in the overall genome. The correspondence between the putative HCV strain genomic sequence and, for example, the CDC/HCV1 cDNA sequence can be determined by techniques known in the art. For example, they can be determined by a direct comparison of the sequence information of the polynucleotide from the putative HCV, and the HCV cDNA sequence(s) described herein. For example, also, they can be determined by hybridization of the polynucleotides under conditions which form stable duplexes between homologous regions (for example, those which would be used prior to $S_1$ digestion), followed by digestion with single stranded specific nuclease(s), followed by size determination of the digested fragments.

Because of the evolutionary relationship of the strains or isolates of HCV, putative HCV strains or isolates are identifiable by their homology at the polypeptide level. Generally, HCV strains or isolates are expected to be at least 10% homologous, more than about 40% homologous, probably more than about 70% homologous, and even more probably more than about 80% homologous, and some may even be more than about 90% homologous at the polypeptide level. The techniques for determining amino acid sequence homology are known in the art. For example, the amino acid sequence may be determined directly and compared to the sequences provided herein. Alternatively the nucleotide sequence of the genomic material of the putative HCV may be determined (usually via a cDNA intermediate), the amino acid sequence encoded therein can be determined, and the corresponding regions compared.

As used herein, a polynucleotide "derived from" a designated sequence refers to a polynucleotide sequence which is comprised of a sequence of approximately at least about 6 nucleotides, preferably at least about 8 nucleotides, more preferably at least about 10–12 nucleotides, and even more preferably at least about 15–20 nucleotides corresponding to a region of the designated nucleotide sequence. "Corresponding" means homologous to or complementary to the designated sequence. Preferably, the sequence of the region from which the polynucleotide is derived is homologous to or complementary to a sequence which is unique to an HCV genome. Whether or not a sequence is unique to the HCV genome can be determined by techniques known to those of skill in the art. For example, the sequence can be compared to sequences in databanks, e.g., Genebank, to determine whether it is present in the uninfected host or other organisms. The sequence can also be compared to the known sequences of other viral agents, including those which are known to induce hepatitis, e.g., HAV, HBV, and HDV, and to members of the Flaviviridae. The correspondence or non-correspondence of the derived sequence to other sequences can also be determined by hybridization under the appropriate stringency conditions. Hybridization techniques for determining the complementarity of nucleic acid sequences are known in the art, and are discussed infra. See also, for example, Maniatis et al. (1982). In addition, mismatches of duplex polynucleotides formed by hybridization can be determined by known techniques, including for example, digestion with a nuclease such as S1 that specifically digests single-stranded areas in duplex polynucleotides. Regions from which typical DNA sequences may be "derived" include but are not limited to, for example, regions encoding specific epitopes, as well as non-transcribed and/or non-translated regions.

The derived polynucleotide is not necessarily physically derived from the nucleotide sequence shown, but may be generated in any manner, including for example, chemical synthesis or DNA replication or reverse transcription or transcription. In addition, combinations of regions corresponding to that of the designated sequence may be modified in ways known in the art to be formulated with an intended use.

Similarly, a polypeptide or amino acid sequence "derived from" a designated nucleic acid sequence refers to a polypeptide having an amino acid sequence identical to that of a polypeptide encoded in the sequence, or a portion thereof wherein the portion consists of at least 3–5 amino acids, and more preferably at least 8–10 amino acids, and even more preferably at least 11–15 amino acids, or which is immunologically identifiable with a polypeptide encoded in the sequence. This terminology also includes a polypeptide expressed from a designated nucleic acid sequence.

A recombinant or derived polypeptide is not necessarily translated from a designated nucleic acid sequence, for example, the sequences in Section IV.A, or from an HCV genome; it may be generated in any manner, including for example, chemical synthesis, or expression of a recombinant expression system, or isolation from HCV, including mutated HCV. A recombinant or derived polypeptide may include one or more analogs of amino acids or unnatural amino acids in its sequence. Methods of inserting analogs of amino acids into a sequence are known in the art. It also may include one or more labels, which are known to those of skill in the art.

The term "recombinant polynucleotide" as used herein intends a polynucleotide of genomic, cDNA, semisynthetic, or synthetic origin which, by virtue of its origin or manipulation: (1) is not associated with all or a portion of a polynucleotide with which it is associated in nature, (2) is linked to a polynucleotide other than that to which it is linked in nature, or (3) does not occur in nature.

The term "polynucleotide" as used herein refers to a polymeric form of nucleotides of any length, either ribonucleotides or deoxyribonucleotides. This term refers only to the primary structure of the molecule. Thus, this term includes double- and single-stranded DNA and RNA. It also includes known types of modifications, for example, labels which are known in the art, methylation, "caps", substitution of one or more of the naturally occurring nucleotides with an analog, internucleotide modifications such as, for example, those with uncharged linkages (e.g., methyl phosphonates, phosphotriesters, phosphoramidates, carbamates, etc.) and with charged linkages (e.g., phosphorothioates, phosphorodithioates, etc.), those containing pendant moieties, such as, for example proteins (including for e.g., nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide.

The term "purified viral polynucleotide" refers to an HCV genome or fragment thereof which is essentially free, i.e., contains less than about 50%, preferably less than about 70%, and even more preferably less than about 90% of polypeptides with which the viral polynucleotide is naturally associated. Techniques for purifying viral polynucleotides from viral particles are known in the art, and include for example, disruption of the particle with a chaotropic agent, differential extraction and separation of the polynucleotide (s) and polypeptides by ion-exchange chromatography, affinity chromatography, and sedimentation according to density.

The term "purified viral polypeptide" refers to an HCV polypeptide or fragment thereof which is essentially free, i.e., contains less than about 50%, preferably less than about 70%, and even more preferably less than about 90%, of cellular components with which the viral polypeptide is naturally associated. Techniques for purifying viral polypeptides are known in the art, and examples of these techniques are discussed infra.

"Recombinant host cells", "host cells", "cells", "cell lines", "cell cultures", and other such terms denoting microorganisms or higher eukaryotic cell lines cultured as unicellular entities refer to cells which can be, or have been, used as recipients for recombinant vector or other transfer DNA, and include the progeny of the original cell which has been transfected. It is understood that the progeny of a single parental cell may not necessarily be completely identical in morphology or in genomic or total DNA complement as the original parent, due to natural, accidental, or deliberate mutation.

A "replicon" is any genetic element, e.g., a plasmid, a chromosome, a virus, a cosmid, etc. that behaves as an autonomous unit of polynucleotide replication within a cell; i.e., capable of replication under its own control.

A "vector" is a replicon in which another polynucleotide segment is attached, so as to bring about the replication and/or expression of the attached segment.

"Control sequence" refers to polynucleotide sequences which are necessary to effect the expression of coding sequences to which they are ligated. The nature of such control sequences differs depending upon the host organism; in prokaryotes, such control sequences generally include promoter, ribosomal binding site, and terminators; in eukaryotes, generally, such control sequences include promoters, terminators and, in some instances, enhancers. The term "control sequences" is intended to include, at a minimum, all components whose presence is necessary for expression, and may also include additional components whose presence is advantageous, for example, leader sequences.

"Operably linked" refers to a juxtaposition wherein the components so described are in a relationship permitting them to function in their intended manner. A control sequence "operably linked" to a coding sequence is ligated in such a way that expression of the coding sequence is achieved under conditions compatible with the control sequences.

An "open reading frame" (ORF) is a region of a polynucleotide sequence which encodes a polypeptide; this region may represent a portion of a coding sequence or a total coding sequence.

A "coding sequence" is a polynucleotide sequence which is transcribed into mRNA and/or translated into a polypeptide when placed under the control of appropriate regulatory sequences. The boundaries of the coding sequence are determined by a translation start codon at the 5'-terminus and a translation stop codon at the 3'-terminus. A coding sequence can include, but is not limited to mRNA, cDNA, and recombinant polynucleotide sequences.

"Immunologically identifiable with/as" refers to the presence of epitope(s) and polypeptides(s) which are also present in the designated polypeptide(s), usually HCV proteins. Immunological identity may be determined by antibody binding and/or competition in binding; these techniques are known to those of average skill in the art, and are also illustrated infra.

As used herein, "epitope" refers to an antigenic determinant of a polypeptide. An epitope could comprise 3 amino acids in a spatial conformation which is unique to the epitope. Generally an epitope consists of at least 5 such amino acids, and more usually, consists of at least 8–10 such amino acids. Methods of determining the spatial conformation of amino acids are known in the art, and include, for example, x-ray crystallography and 2-dimensional nuclear magnetic resonance.

A polypeptide is "immunologically reactive" with an antibody when it binds to an antibody due to antibody recognition of a specific epitope contained within the polypeptide. Immunological reactivity may be determined by antibody binding, more particularly by the kinetics of antibody binding, and/or by competition in binding using as competitor(s) a known polypeptide(s) containing an epitope against which the antibody is directed. The techniques for determining whether a polypeptide is immunologically reactive with an antibody are known in the art.

As used herein, the term "antibody" refers to a polypeptide or group of polypeptides which are comprised of at least one antibody combining site. An "antibody combining site" or "binding domain" is formed from the folding of variable domains of an antibody molecule(s) to form three-dimensional binding spaces with an internal surface shape and charge distribution complementary to the features of an epitope of an antigen, which allows an immunological reaction with the antigen. An antibody combining site may be formed from a heavy and/or a light chain domain ($V_H$ and $V_L$, respectively), which form hypervariable loops which contribute to antigen binding. The term "antibody" includes, for example, vertebrate antibodies, hybrid antibodies, chimeric antibodies, altered antibodies, univalent antibodies, the Fab proteins, and single domain antibodies.

As used herein, a "single domain antibody" (dAb) is an antibody which is comprised of an VH domain, which reacts immunologically with a designated antigen. A dAb does not contain a $V_L$ domain, but may contain other antigen binding domains known to exist in antibodies, for example, the kappa and lambda domains. Methods for preparing dAbs are known in the art. See, for example, Ward et al. (1989). Antibodies may also be comprised of $V_H$ and $V_L$ domains, as well as other known antigen binding domains. Examples of these types of antibodies and methods for their preparation are known in the art (see, e.g., U.S. Pat. No. 4,816,467, which is incorporated herein by reference), and include the following. For example, "vertebrate antibodies" refers to antibodies which are tetramers or aggregates thereof, comprising light and heavy chains which are usually aggregated in a "Y" configuration and which may or may not have covalent linkages between the chains. In vertebrate antibodies, the amino acid sequences of all the chains of a particular antibody are homologous with the chains found in one antibody produced by the lymphocyte which produces that antibody in situ, or in vitro (for example, in hybridomas). Vertebrate antibodies typically include native antibodies, for example, purified polyclonal antibodies and monoclonal antibodies. Examples of the methods for the preparation of these antibodies are described infra.

"Hybrid antibodies" are antibodies wherein one pair of heavy and light chains is homologous to those in a first antibody, while the other pair of heavy and light chains is homologous to those in a different second antibody. Typically, each of these two pairs will bind different epitopes, particularly on different antigens. This results in the property of "divalence", i.e., the ability to bind two antigens simultaneously. Such hybrids may also be formed using chimeric chains, as set forth below.

"Chimeric antibodies", are antibodies in which the heavy and/or light chains are fusion proteins. Typically the constant domain of the chains is from one particular species and/or class, and the variable domains are from a different species and/or class. Also included is any antibody in which either or both of the heavy or light chains are composed of combinations of sequences mimicking the sequences in antibodies of different sources, whether these sources be differing classes, or different species of origin, and whether or not the fusion point is at the variable/constant boundary. Thus, it is possible to produce antibodies in which neither the constant nor the variable region mimic known antibody sequences. It then becomes possible, for example, to construct antibodies whose variable region has a higher specific affinity for a particular antigen, or whose constant region can elicit enhanced complement fixation, or to make other improvements in properties possessed by a particular constant region.

Another example is "altered antibodies", which refers to antibodies in which the naturally occurring amino acid sequence in a vertebrate antibody has been varied. Utilizing recombinant DNA techniques, antibodies can be redesigned to obtain desired characteristics. The possible variations are many, and range from the changing of one or more amino acids to the complete redesign of a region, for example, the constant region. Changes in the constant region, in general, to attain desired cellular process characteristics, e.g., changes in complement fixation, interaction with membranes, and other effector functions. Changes in the variable region may be made to alter antigen binding characteristics. The antibody may also be engineered to aid the specific delivery of a molecule or substance to a specific cell or tissue site. The desired alterations may be made by known techniques in molecular biology, e.g., recombinant techniques, site directed mutagenesis, etc.

Yet another example are "univalent antibodies", which are aggregates comprised of a heavy chain/light chain dimer bound to the Fc (i.e., constant) region of a second heavy chain. This type of antibody escapes antigenic modulation. See, e.g., Glennie et al. (1982).

Included also within the definition of antibodies are "Fab" fragments of antibodies. The "Fab" region refers to those portions of the heavy and light chains which are roughly equivalent, or analogous, to the sequences which comprise the branch portion of the heavy and light chains, and which have been shown to exhibit immunological binding to a specified antigen, but which lack the effector Fc portion. "Fab" includes aggregates of one heavy and one light chain (commonly known as Fab'), as well as tetramers containing the 2H and 2L chains (referred to as F(ab)$_2$), which are capable of selectively reacting with a designated antigen or antigen family. "Fab" antibodies may be divided into subsets analogous to those described above, i.e, "vertebrate Fab", "hybrid Fab", "chimeric Fab", and "altered Fab". Methods of producing "Fab" fragments of antibodies are known within the art and include, for example, proteolysis, and synthesis by recombinant techniques.

As used herein, the term "immunogenic polypeptide" is a polypeptide that elicits a cellular and/or humoral immune response, whether alone or linked to a carrier in the presence or absence of an adjuvant.

The term "polypeptide" refers to a polymer of amino acids and does not refer to a specific length of the product; thus, peptides, oligopeptides, and proteins are included within the definition of polypeptide. This term also does not refer to or exclude post-expression modifications of the polypeptide, for example, glycosylation, acetylation, phosphorylation and the like. Included within the definition are, for example, polypeptides containing one or more analogs of an amino acid (including, for example, unnatural amino acids, etc.), polypeptides with substituted linkages, as well as other modifications known in the art, both naturally occurring and non-naturally occurring.

"Transformation", as used herein, refers to the insertion of an exogenous polynucleotide into a host cell, irrespective of the method used for the insertion, for example, direct uptake, transduction, f-mating or electroporation. The exogenous polynucleotide may be maintained as a non-integrated vector, for example, a plasmid, or alternatively, may be integrated into the host genome.

"Treatment" as used herein refers to prophylaxis and/or therapy.

An "individual", as used herein, refers to vertebrates, particularly members of the mammalian species, and includes but is not limited to domestic animals, sports animals, and primates, including humans.

As used herein, the "sense strand" of a nucleic acid contains the sequence that has sequence homology to that of mRNA. The "anti-sense strand" contains a sequence which is complementary to that of the "sense strand".

As used herein, a "positive stranded genome" of a virus is one in which the genome, whether RNA or DNA, is single-stranded and which encodes a viral polypeptide(s). Examples of positive stranded RNA viruses include Togaviridae, Coronaviridae, Retroviridae, Picornaviridae, and Caliciviridae. Included also, are the Flaviviridae, which were formerly classified as Togaviradae. See Fields & Knipe (1986).

As used herein, "antibody containing body component" refers to a component of an individual's body which is a source of the antibodies of interest. Antibody containing body components are known in the art, and include but are not limited to, for example, plasma, serum, spinal fluid, lymph fluid, the external sections of the respiratory, intestinal, and genitourinary tracts, tears, saliva, milk, white blood cells, and myelomas.

As used herein, "purified HCV" refers to a preparation of HCV which has been isolated from the cellular constituents with which the virus is normally associated, and from other types of viruses which may be present in the infected tissue. The techniques for isolating viruses are known to those of skill in the art, and include, for example, centrifugation and affinity chromatography; a method of preparing purified HCV is discussed infra.

The term "HCV particles" as used herein include entire virion as well as particles which are intermediates in virion formation. HCV particles generally have one or more HCV proteins associated with the HCV nucleic acid.

As used herein, the term "probe" refers to a polynucleotide which forms a hybrid structure with a sequence in a target region, due to complementarity of at least one sequence in the probe with a sequence in the target region.

As used herein, the term "target region" refers to a region of the nucleic acid which is to be amplified and/or detected.

As used herein, the term "viral RNA", which includes HCV RNA, refers to RNA from the viral genome, fragments thereof, transcripts thereof, and mutant sequences derived therefrom.

As used herein, a "biological sample" refers to a sample of tissue or fluid isolated from an individual, including but not limited to, for example, plasma, serum, spinal fluid, lymph fluid, the external sections of the skin, respiratory, intestinal, and genitourinary tracts, tears, saliva, milk, blood cells, tumors, organs, and also samples of in vitro cell culture constituents (including but not limited to conditioned medium resulting from the growth of cells in cell culture medium, putatively virally infected cells, recombinant cells, and cell components).

II. Description of the Invention

The practice of the present invention will employ, unless otherwise indicated, conventional techniques of molecular biology, microbiology, recombinant DNA, and immunology, which are within the skill of the art. Such techniques are explained fully in the literature. See e.g., Maniatis, Fitsch & Sambrook, "Molecular Cloning; A Laboratory Manual" (1982); "DNA Cloning, Volumes I and II" (D. N Glover ed. 1985); "Oligonucleotide Synthesis" (M. J. Gait ed, 1984); "Nucleic Acid Hybridization" (B. D. Hames & S. J. Higgins eds. 1984); "Transcription and Translation" (B. D. Hames & S. J. Higgins eds. 1984); "Animal Cell Culture" (R. I. Freshney ed. 1986); "Immobilized Cells And Enzymes" (IRL Press, 1986); B. Perbal, "A Practical Guide To Molecular Cloning" (1984); the series, "Methods in Enzymology" (Academic Press, Inc.); "Gene Transfer Vectors For Mammalian Cells" (J. H. Miller and M. P. Calos eds. 1987, Cold Spring Harbor Laboratory), Meth Enzymol Vol. 154 and Vol. 155 (Wu and Grossman, and Wu, eds., respectively), Mayer and Walker, eds. (1987), "Immunochemical Methods In Cell And Molecular Biology" (Academic Press, London); Scopes, (1987) "Protein Purification: Principles and Practice", Second Edition (Springer-Verlag, N.Y.); and "Handbook of Experimental Immunology", Volumes I-IV (D. M. Weir and C. C. Blackwell eds 1986). All patents, patent applications, and publications mentioned herein, both supra and infra, are hereby incorporated herein by reference.

The useful materials and processes of the present invention are made possible by the provision of a family of closely homologous nucleotide sequences isolated from a cDNA library derived from nucleic acid sequences present in the plasma of an HCV infected chimpanzee. This family of nucleotide sequences is not of human or chimpanzee origin, since it hybridizes to neither human nor chimpanzee genomic DNA from uninfected individuals, since nucleotides of this family of sequences are present only in liver and plasma of chimpanzees with HCV infection, and since the sequence is not present in Genebank. In addition, the family of sequences shows no significant homology to sequences contained within the HBV genome.

The sequence of one member of the family, contained within clone 5-1-1, has one continuous open reading frame (ORF) which encodes a polypeptide of approximately 50 amino acids. Sera from HCV infected humans contain antibodies which bind to this polypeptide, whereas sera from non-infected humans do not contain antibodies to this polypeptide. Moreover, whereas the sera from uninfected chimpanzees do not contain antibodies to this polypeptide, the antibodies are induced in chimpanzees following acute NANBH infection. In addition, antibodies to this polypeptide are not detected in chimps and humans infected with HAV and HBV. By these criteria the sequence is a cDNA to a viral sequence, wherein the virus causes or is associated with NANBH; this cDNA sequence is shown in FIG. 1. As discussed infra, the cDNA sequence in clone 5-1-1 differs from that of the other isolated cDNAs in that it contains 28 extra base pairs.

A composite of other identified members of the cDNA family, which were isolated using as a probe a synthetic sequence equivalent to a fragment of the cDNA in clone 5-1-1, is shown in FIG. 3. A member of the cDNA family which was isolated using a synthetic sequence derived from the cDNA in clone 81 is shown in FIG. 5, and the composite of this sequence with that of clone 81 is shown in FIG. 6. Other members of the cDNA family are described in Section IV.A. A composite of the cDNAs in these clones is shown in FIG. 62. The composite cDNA shows that it contains one continuous ORF, and thus encodes a polyprotein. This data is consistent with the suggestion, discussed infra, that HCV is a flavi-like virus.

The availability of the family of cDNAs shown herein in Section IV.A permits the construction of DNA probes and polypeptides useful in diagnosing NANBH due to HCV infection and in screening blood donors as well as donated blood and blood products for infection. For example, from the sequences it is possible to synthesize DNA oligomers of about 8–10 nucleotides, or larger, which are useful as hybridization probes to detect the presence of HCV RNA in, for example, sera of subjects suspected of harboring the virus, or for screening donated blood for the presence of the virus. The family of cDNA sequences also allows the design and production of HCV specific polypeptides which are useful as diagnostic reagents for the presence of antibodies raised during NANBH. Antibodies to purified polypeptides derived from the cDNAs may also be used to detect viral antigens in infected individuals and in blood.

Knowledge of these cDNA sequences also enables the design and production of polypeptides which may be used as vaccines against HCV and also for the production of antibodies, which in turn may be used for protection against the disease, and/or for therapy of HCV infected individuals.

Moreover, the family of cDNA sequences enables further characterization of the HCV genome. Polynucleotide probes derived from these sequences may be used to screen cDNA libraries for additional overlapping cDNA sequences, which, in turn, may be used to obtain more overlapping sequences. Unless the genome is segmented and the segments lack common sequences, this technique may be used to gain the sequence of the entire genome. However, if the genome is segmented, other segments of the genome can be obtained by repeating the λgt11 serological screening procedure used to isolate the cDNA clones described herein, or alternatively by isolating the genome from purified HCV particles.

The family of cDNA sequences and the polypeptides derived from these sequences, as well as antibodies directed against these polypeptides are also useful in the isolation and identification of the BB-NANBV agent(s). For example, antibodies directed against HCV epitopes contained in polypeptides derived from the cDNAs may be used in processes based upon affinity chromatography to isolate the virus. Alternatively, the antibodies may be used to identify viral particles isolated by other techniques. The viral antigens and the genomic material within the isolated viral particles may then be further characterized.

The information obtained from further sequencing of the HCV genome(s), as well as from further characterization of the HCV antigens and characterization of the genome enables the design and synthesis of additional probes and polypeptides and antibodies which may be used for diagnosis, for prevention, and for therapy of HCV induced NANBH, and for screening for infected blood and blood-related products.

The availability of probes for HCV, including antigens and antibodies, and polynucleotides derived from the genome from which the family of cDNAs is derived also allows for the development of tissue culture systems which will be of major use in elucidating the biology of HCV. This in turn, may lead to the development of new treatment regimens based upon antiviral compounds which preferentially inhibit the replication of, or infection by HCV.

In addition to the above, the information provided infra allows the identification of additional HCV strains or isolates. The isolation and characterization of the additional HCV strains or isolates may be accomplished by isolating the nucleic acids from body components which contain viral particles and/or viral RNA, creating cDNA libraries using polynucleotide probes based on the HCV cDNA probes described infra, screening the libraries for clones containing HCV cDNA sequences described infra, and comparing the HCV cDNAs from the new isolates with the cDNAs described infra. The polypeptides encoded therein, or in the viral genome, may be monitored for immunological cross-reactivity utilizing the polypeptides and antibodies described supra. Strains or isolates which fit within the parameters of HCV, as described in the Definitions section, supra, are readily identifiable. Other methods for identifying HCV strains will be obvious to those of skill in the art, based upon the information provided herein.

The method used to identify and isolate the etiologic agent for NANBH may be applicable to the identification and/or isolation of heretofore uncharacterized agents which contain a genome, and which are associated with a variety of diseases, including those induced by viruses, viroids, bacteria, fungi and parasites. In this method, a cDNA library was created from the nucleic acids present in infected tissue from an infected individual. The library was created in a vector which allowed the expression of polypeptides encoded in the cDNA. Clones of host cells containing the vector, which expressed an immunologically reactive fragment of a polypeptide of the etiologic agent, were selected by immunological screening of the expression products of the library with an antibody-containing body component from another individual previously infected with the putative agent. The steps in the immunological screening technique included interacting the expression products of the cDNA containing vectors with the antibody-containing body component of a second infected individual, and detecting the formation of antibody-antigen complexes between the expression product(s) and antibodies of the second infected individual. The isolated clones are screened further immunologically by interacting their expression products with the antibody-containing body components of other individuals infected with the putative agent and with control individuals uninfected with the putative agent, and detecting the formation of antigen-antibody complexes with antibodies from the infected individuals; and the cDNA containing vectors which encode polypeptides which react immunologically with antibodies from infected individuals and individuals suspected of being infected with the agent, but not with control individuals are isolated. The infected individuals used for the construction of the cDNA library, and for the immunological screening need not be of the same species.

The cDNAs isolated as a result of this method, and their expression products, and antibodies directed against the expression products, are useful in characterizing and/or capturing the etiologic agent. As described in more detail infra, this method has been used successfully to isolate a family of cDNAs derived from the HCV genome.

II.A. Preparation of the cDNA Sequences

Pooled serum from a chimpanzee with chronic HCV infection and containing a high titer of the virus, i.e., at least $10^6$ chimp infectious doses/mL (CID/mL) was used to isolate viral particles; nucleic acids isolated from these particles was used as the template in the construction of a cDNA library to the viral genome. The procedures for isolation of putative HCV particles and for constructing the cDNA library in λgt11 is discussed in Section IV.A. 1. λgt11 is a vector that has been developed specifically to express inserted cDNAs as fusion polypeptides with b-galactosidase and to screen large numbers of recombinant phage with specific antisera raised against a defined antigen. T. V. Huynh et al. (1985). The λgt11 cDNA library generated from a cDNA pool containing cDNA of approximate mean size of 200 base pairs was screened for encoded epitopes that could bind specifically with sera derived from patients who had previously experienced NANB hepatitis. Approximately $10^6$ phages were screened, and five positive phages were identified, purified, and then further tested for specificity of binding to sera from different humans and chimpanzees previously infected with the HCV agent. One of the phages, 5-1-1, bound 5 of the 8 human sera tested. This binding appeared selective for sera derived from patients with prior NANB hepatitis infections since 7 normal blood donor sera did not exhibit such binding.

The sequence of the cDNA in recombinant phage 5-1-1 was determined, and is shown in FIG. 1. The polypeptide encoded by this cloned cDNA, which is in the same translational frame as the N-terminal b-galactosidase moiety of the fusion polypeptide is shown above the nucleotide sequence. This translational ORF, therefore, encodes an epitope(s) specifically recognized by sera from patients with NANB hepatitis infections.

The availability of the cDNA in recombinant phage 5-1-1 has allowed for the isolation of other clones containing additional segments and/or alternative segments of cDNA to the viral genome. The λgt11 cDNA library described supra, was screened using a synthetic polynucleotide derived from the sequence of the cloned 5-1-1 cDNA. This screening yielded three other clones, which were identified as 81, 1-2 and 91; the cDNAs contained within these clones were sequenced. See Sections IV.A.3. and IV.A.4. The homologies between the four independent clones are shown in FIG. 2, where the homologies are indicated by the vertical lines. Sequences of nucleotides present uniquely in clones 5-1-1, 81, and 91 are indicated by small letters.

The cloned cDNAs present in recombinant phages in clones 5-1- 1, 81, 1-2, and 91 are highly homologous, and differ in only two regions. First, nucleotide number 67 in clone 1–2 is a thymidine, whereas the other three clones contain a cytidine residue in this position. This substitution, however, does not alter the nature of the encoded amino acid.

The second difference between the clones is that clone 5-1-1 contains base pairs at its 5'-terminus which are not present in the other clones. The extra sequence may be a 5'-terminal cloning artifact; 5'-terminal cloning artifacts are commonly observed in the products of cDNA methods.

Synthetic sequences derived from the 5'-region and the 3'-region of the HCV cDNA in clone 81 were used to screen and isolate cDNAs from the λgt11 NANBV cDNA library, which overlapped clone 81 cDNA (Section IV.A.5.). The sequences of the resulting cDNAs, which are in clone 36 and clone 32, respectively, are shown in FIG. 5 and FIG. 7.

Similarly, a synthetic polynucleotide based on the 5'-region of clone 36 was used to screen and isolate cDNAs from the λgt-11 NANBV cDNA library which overlapped clone 36 cDNA (Section IV.A.8.). A purified clone of recombinant phage-containing cDNA which hybridized to the synthetic polynucleotide probe was named clone 35 and the NANBV cDNA sequence contained within this clone is shown in FIG. 8.

By utilizing the technique of isolating overlapping cDNA sequences, clones containing additional upstream and downstream HCV cDNA sequences have been obtained. The isolation of these clones, is described infra in Section IV.A.

Analysis of the nucleotide sequences of the HCV cDNAs encoded within the isolated clones show that the composite cDNA contains one long continuous ORF. FIG. 62 shows the sequence of the composite cDNA from these clones, along with the putative HCV polypeptide encoded therein.

The description of the method to retrieve the cDNA sequences is mostly of historical interest. The resultant sequences (and their complements) are provided herein, and the sequences, or any portion thereof, could be prepared using synthetic methods, or by a combination of synthetic methods with retrieval of partial sequences using methods similar to those described herein.

The description above, of "walking" the genome by isolating overlapping CDNA sequences from the HCV λgt11 library provides one method by which cDNAs corresponding to the entire HCV genome may be isolated. However, given the information provided herein, other methods for isolating these cDNAs are obvious to one of skill in the art. Some of these methods are described in Section IV.A., infra.

II.B. Preparation of Viral Polypeptides and Fragments

The availability of cDNA sequences, either those isolated by utilizing the cDNA sequences described in Section IV.A, as discussed infra, or nucleotide sequences derived therefrom (including segments and modifications of the sequence), permits the construction of expression vectors encoding antigenically active regions of the polypeptide encoded in either strand. These antigenically active regions may be derived from coat or envelope antigens or from core antigens, or from antigens which are non-structural including, for example, polynucleotide binding proteins, polynucleotide polymerase(s), and other viral proteins required for the replication and/or assembly of the virus particle. Fragments encoding the desired polypeptides are derived from the cDNA clones using conventional restriction digestion or by synthetic methods, and are ligated into vectors which may, for example, contain portions of fusion sequences such as b-Galactosidase or superoxide dismutase (SOD), preferably SOD. Methods and vectors which are useful for the production of polypeptides which contain fusion sequences of SOD are described in European Patent Office Publication number 0196056, published Oct. 1, 1986. Vectors encoding fusion polypeptides of SOD and HCV polypeptides, i.e., $NANB_{5-1-1}$, $NANB_{81}$, and C100-3, which is encoded in a composite of HCV cDNAs, are described in Sections IV.B.1, IV.B.2, and IV.B.4, respectively. Any desired portion of the HCV cDNA containing an open reading frame, in either sense strand, can be obtained as a recombinant polypeptide, such as a mature or fusion protein; alternatively, a polypeptide encoded in the cDNA can be provided by chemical synthesis.

The DNA encoding the desired polypeptide, whether in fused or mature form, and whether or not containing a signal sequence to permit secretion, may be ligated into expression vectors suitable for any convenient host. Both eukaryotic and prokaryotic host systems are presently used in forming recombinant polypeptides, and a summary of some of the more common control systems and host cell lines is given in Section III.A., infra. The polypeptide is then isolated from lysed cells or from the culture medium and purified to the extent needed for its intended use. Purification may be by techniques known in the art, for example, differential extraction, salt fractionation, chromatography on ion exchange resins, affinity chromatography, centrifugation, and the like. See, for example, Methods in Enzymology for a variety of methods for purifying proteins. Such polypeptides can be used as diagnostics, or those which give rise to neutralizing antibodies may be formulated into vaccines. Antibodies raised against these polypeptides can also be used as diagnostics, or for passive immunotherapy. In addition, as discussed in Section II.J. herein below, antibodies to these polypeptides are useful for isolating and identifying HCV particles.

The HCV antigens may also be isolated from HCV virions. The virions may be grown in HCV infected cells in tissue culture, or in an infected host.

II.C. Preparation of Antigenic Polypeptides and Conjugation with Carrier

An antigenic region of a polypeptide is generally relatively small--typically 8 to 10 amino acids or less in length. Fragments of as few as 5 amino acids may characterize an antigenic region. These segments may correspond to regions of HCV antigen. Accordingly, using the cDNAs of HCV as a basis, DNAs encoding short segments of HCV polypeptides can be expressed recombinantly either as fusion proteins, or as isolated polypeptides. In addition, short amino acid sequences can be conveniently obtained by chemical synthesis. In instances wherein the synthesized polypeptide is correctly configured so as to provide the correct epitope, but is too small to be immunogenic, the polypeptide may be linked to a suitable carrier.

A number of techniques for obtaining such linkage are known in the art, including the formation of disulfide linkages using N-succinimidyl-3-(2-pyridylthio)propionate (SPDP) and succinimidyl 4-(N-maleimido-methyl) cyclohexane-1-carboxylate (SMCC) obtained from Pierce Company, Rockford, Ill,, (if the peptide lacks a sulfhydryl group, this can be provided by addition of a cysteine residue.) These reagents create a disulfide linkage between themselves and peptide cysteine residues on one protein and an amide linkage through the epsilon-amino on a lysine, or other free amino group in the other. A variety of such disulfide/amide-forming agents are known. See, for example, *Immun Rev* (1982) 62:185. Other bifunctional coupling agents form a thioether rather than a disulfide linkage. Many of these thio-ether-forming agents are commercially available and include reactive esters of 6-maleimidocaproic acid, 2-bromoacetic acid, 2-iodoacetic acid, 4-(N-maleimido-methyl)cyclohexane-1-carboxylic acid, and the like. The carboxyl groups can be activated by combining them with succinimide or 1-hydroxyl-2 nitro-4-sulfonic acid, sodium salt. Additional methods of coupling antigens employs the rotavirus/"binding peptide" system described in EPO Pub. No. 259,149, the disclosure of which is incorporated herein by reference. The foregoing list is not meant to be exhaustive, and modifications of the named compounds can clearly be used.

Any carrier may be used which does not itself induce the production of antibodies harmful to the host. Suitable carriers are typically large, slowly metabolized macromolecules such as proteins; polysaccharides, such as latex functionalized Sepharose®, agarose, cellulose, cellulose beads and the like; polymeric amino acids, such as polyglutamic acid, polylysine, and the like; amino acid copolymers; and inactive virus particles, see, for example, Section II.D. Especially useful protein substrates are serum albumins, keyhole limpet hemocyanin, immunoglobulin molecules, thyroglobulin, ovalbumin, tetanus toxoid, and other proteins well known to those skilled in the art.

In addition to full-length viral proteins, polypeptides comprising truncated HCV amino acid sequences encoding at least one viral epitope are useful immunological reagents. For example, polypeptides comprising such truncated sequences can be used as reagents in an immunoassay. These polypeptides also are candidate subunit antigens in compositions for antiserum production or vaccines. While these truncated sequences can be produced by various known treatments of native viral protein, it is generally preferred to make synthetic or recombinant polypeptides comprising an HCV sequence. Polypeptides comprising these truncated HCV sequences can be made up entirely of HCV sequences (one or more epitopes, either contiguous or noncontiguous), or HCV sequences and heterologous sequences in a fusion protein. Useful heterologous sequences include sequences that provide for secretion from a recombinant host, enhance the immunological reactivity of the HCV epitope(s), or facilitate the coupling of the polypeptide to an immunoassay support or a vaccine carrier. See, e.g., EPO Pub. No. 116,201; U.S. Pat. No. 4,722,840; EPO Pub. No. 259,149; U.S. Pat. No. 4,629,783, the disclosures of which are incorporated herein by reference.

The size of polypeptides comprising the truncated HCV sequences can vary widely, the minimum size being a sequence of sufficient size to provide an HCV epitope, while the maximum size is not critical. For convenience, the maximum size usually is not substantially greater than that required to provide the desired HCV epitopes and function (s) of the heterologous sequence, if any. Typically, the truncated HCV amino acid sequence will range from about 5 to about 100 amino acids in length. More typically, however, the HCV sequence will be a maximum of about 50 amino acids in length, preferably a maximum of about 30 amino acids. It is usually desirable to select HCV sequences of at least about 10, 12 or 15 amino acids, up to a maximum of about 20 or 25 amino acids.

Figures 67A, 67B:
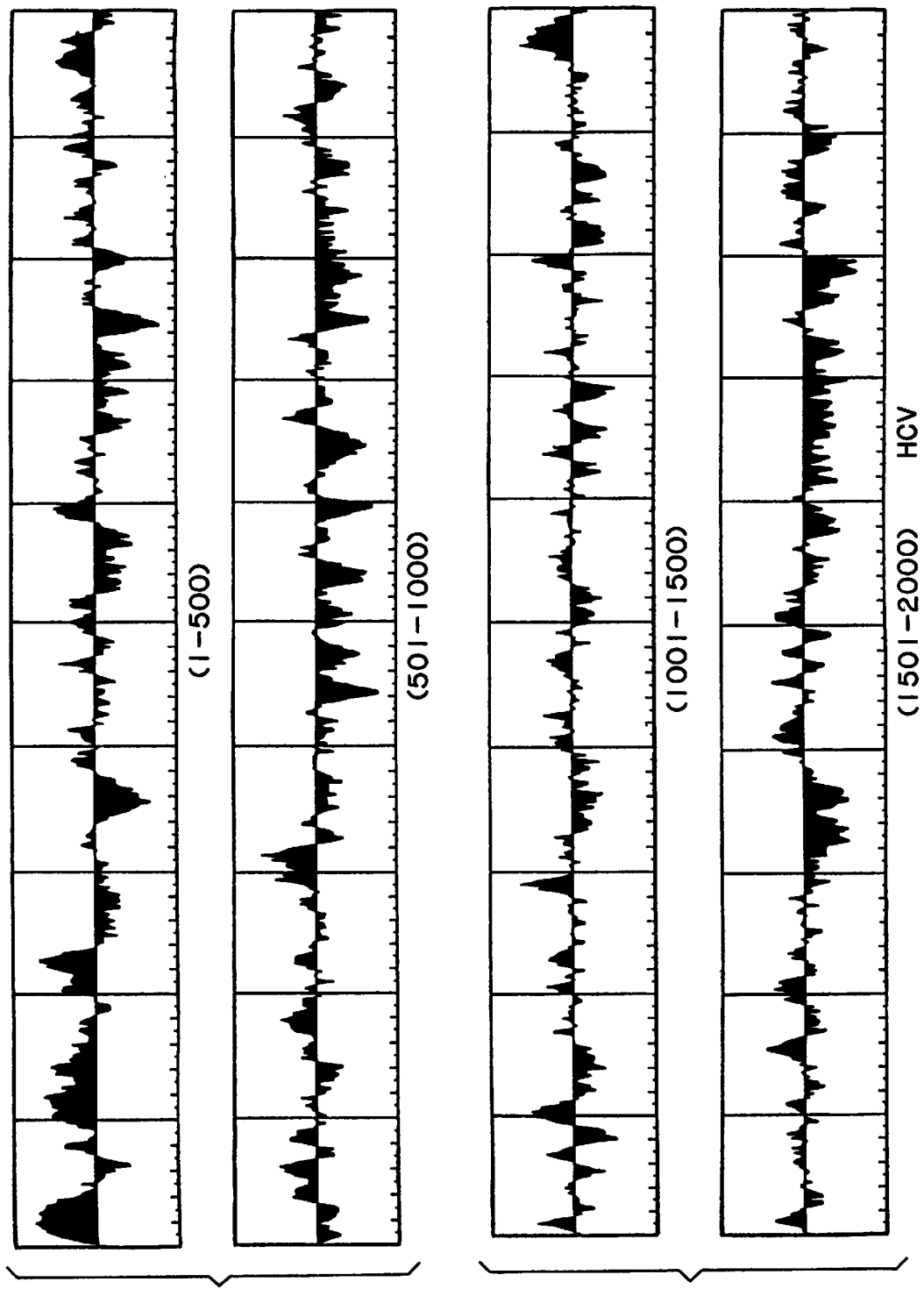
FIG. 67 is a tracing of the hydrophilicity/hydrophobicity profile and of the antigenic index of the putative HCV polyprotein.

Truncated HCV amino acid sequences comprising epitopes can be identified in a number of ways. For example, the entire viral protein sequence can be screened by preparing a series of short peptides that together span the entire protein sequence. By starting with, for example, 100mer polypeptides, it would be routine to test each polypeptide for the presence of epitope(s) showing a desired reactivity, and then testing progressively smaller and overlapping fragments from an identified 100mer to map the epitope of interest. Screening such peptides in an immunoassay is within the skill of the art. It is also known to carry out a computer analysis of a protein sequence to identify potential epitopes, and then prepare oligopeptides comprising the identified regions for screening. Such a computer analysis of the HCV amino acid sequence is shown in FIG. 67, where the hydrophilic/hydrophobic character is displayed above the antigen index. The amino acids are numbered from the starting MET (position 1) as shown in FIG. 66. It is appreciated by those of skill in the art that such computer analysis of antigenicity does not always identify an epitope that actually exists, and can also incorrectly identify a region of the protein as containing an epitope.

Examples of HCV amino acid sequences that may be useful as described herein are set forth below. It is to be understood that these peptides do not necessarily precisely map one epitope, but may also contain HCV sequence that is not immunogenic. These non-immunogenic portions of the sequence can be defined as described above using conventional techniques and deleted from the described sequences. Further, additional truncated HCV amino acid sequences that comprise an epitope or are immunogenic can be identified as described above. The following sequences are given by amino acid number (i.e., "AAn") where n is the amino acid number as shown in FIG. 66:

AA1-AA25; AA1-AA50; AA1-AA84; AA9-AA177; AA1-AA10; AA5-AA20; AA20-AA25; AA35-AA45; AA50-AA100; AA40-AA90; AA45-AA65; AA65-AA75; AA80-90; AA99-AA120; AA95-AA110; AA105-AA120; AA100-AA150; AA150-AA200; AA155-AA170; AA190-AA210; AA200-AA250; AA220-AA240; AA245-AA265; AA250-AA300; AA290-AA330; AA290-305; AA300-AA350; AA310-AA330; AA350-AA400; AA380-AA395; AA405-AA495; AA400-AA450; AA405-AA415; AA415-AA425; AA425-AA435; AA437-AA582; AA450-AA500; AA440-AA460; AA460-AA470; AA475-AA495; AA500-AA550; AA511-AA690; AA515-AA550; AA550-AA600; AA550-AA625; AA575-AA605; AA585-AA600; AA600-AA650; AA600-AA625; AA635-AA665; AA650-AA700; AA645-AA680; AA700-AA750; AA700-AA725; AA700-AA750; AA725-AA775; AA770-AA790; AA750-AA800; AA800-AA815; AA825-AA850; AA850-AA875; AA800-AA850; AA920-AA990; AA850-AA900; AA920-AA945; AA940-AA965; AA970-AA990; AA950-AA1000; AA1000-AA1060; AA1000-AA1025; AA1000-AA1050; AA1025-AA1040; AA1040-AA1055; AA1075-AA1175; AA1050-AA1200; AA1070-AA1100; AA1100-AA1130; AA1140-AA1165; AA1192-AA1457; AA1195-AA1250; AA1200-AA1225; AA1225-AA1250; AA1250-AA1300; AA1260-AA1310; AA1260-AA1280; AA1266-AA1428; AA1300-AA1350; AA1290-AA1310; AA1310-AA1340; AA1345-AA1405; AA1345-AA1365; AA1350-AA1400; AA1365-AA1380; AA1380-AA1405; AA1400-AA1450; AA1450-AA1500; AA1460-AA1475; AA1475-AA1515; AA1475-AA1500; AA1500-AA1550; AA1500-AA1515; AA1515-AA1550; AA1550-AA1600; AA1545-AA1560; AA1569-AA1931; AA1570-AA1590; AA1595-AA1610; AA1590-AA1650; AA1610-AA1645; AA1650-AA1690; AA1685-AA1770; AA1689-AA1805; AA1690-AA1720; AA1694-AA1735; AA1720-AA1745; AA1745-AA1770; AA1750-AA1800; AA1775-AA1810; AA1795-AA1850; AA1850-AA1900; AA1900-AA1950; AA1900-AA1920; AA1916-AA2021; AA1920-AA 1940; AA1949-AA2124; AA1950-AA2000; AA1950-AA1985; AA1980-AA2000; AA2000-AA2050; AA2005-AA2025; AA2020-AA2045; AA2045-AA2100; AA2045-AA2070; AA2054-AA2223; AA2070-AA2100; AA2100-AA2150; AA2150-AA2200; AA2200-AA2250; AA2200-AA2325; AA2250-AA2330; AA2255-AA2270; AA2265-AA2280; AA2280-AA2290; AA2287-AA2385; AA2300-AA2350; AA2290-AA2310; AA2310-AA2330; AA2330-AA2350; AA2350-AA2400; AA2348-AA2464; AA2345-AA2415; AA2345-AA2375; AA2370-AA2410; AA2371-AA2502; AA2400-AA2450; AA2400-AA2425; AA2415-AA2450; AA2445-AA2500; AA2445-AA2475; AA2470-AA2490; AA2500-AA2550; AA2505-AA2540; AA2535-AA2560; AA2550-AA2600; AA2560-AA2580; AA2600-AA2650; AA2605-AA2620; AA2620-AA2650; AA2640-AA2660; AA2650-AA2700; AA2655-AA2670; AA2670-AA2700; AA2700-AA2750; AA2740-AA2760; AA2750-AA2800; AA2755-AA2780; AA2780-AA2830; AA2785-AA2810; AA2796-AA2886; AA2810-AA2825; AA2800-AA2850; AA2850-AA2900; AA2850-AA2865; AA2885-AA2905; AA2900-AA2950; AA2910-AA2930; AA2925-AA2950; AA2945-end(C' terminal).

The above HCV amino acid sequences can be prepared as discrete peptides or incorporated into a larger polypeptide, and may find use as described herein. Additional polypeptides comprising truncated HCV sequences are described in the examples.

The observed relationship of the putative polyproteins of HCV and the Flaviviruses allows a prediction of the putative domains of the HCV "non-structural" (NS) proteins. The locations of the individual NS proteins in the putative Flavivirus precursor polyprotein are fairly well-known. Moreover, these also coincide with observed gross fluctuations in the hydrophobicity profile of the polyprotein. It is established that NS5 of Flaviviruses encodes the virion polymerase, and that NS1 corresponds with a complement fixation antigen which has been shown to be an effective vaccine in animals. Recently, it has been shown that a flaviviral protease function resides in NS3. Due to the observed similarities between HCV and the Flaviviruses, deductions concerning the approximate locations of the corresponding protein domains and functions in the HCV polyprotein are possible (see Section IV.H.6.). The expression of polypeptides containing these domains in a variety of recombinant host cells, including, for example, bacteria, yeast, insect, and vertebrate cells, should give rise to important immunological reagents which can be used for diagnosis, detection, and vaccines.

Although the non-structural protein region of the putative polyproteins of the HCV isolate described herein and of Flaviviruses appears to be generally similar, there is less similarity between the putative structural regions which are towards the N-terminus. In this region, there is a greater divergence in sequence, and in addition, the hydrophobic profile of the two regions show less similarity. This "divergence" begins in the N-terminal region of the putative NS1 domain in HCV, and extends to the presumed N-terminus. Nevertheless, it is still possible to predict the approximate locations of the putative nucleocapsid (N-terminal basic domain) and E (generally hydrophobic) domains within the HCV polyprotein. In Section IV.H.6., the predictions are based on the changes observed in the hydrophobic profile of the HCV polyprotein, and on a knowledge of the location and character of the flaviviral proteins. From these predictions it may be possible to identify approximate regions of the HCV polyprotein that could correspond with useful immunological reagents. For example, the E and NS1 proteins of Flaviviruses are known to have efficacy as protective vaccines. These regions, as well as some which are shown to be antigenic in the HCV isolate described herein, for example those within putative NS3, C, and NS5, etc., should also provide diagnostic reagents. Moreover, the location and expression of viral-encoded enzymes may also allow the evaluation of anti-viral enzyme inhibitors, i.e., for example, inhibitors which prevent enzyme activity by virtue of an interaction with the enzyme itself, or substances which may prevent expression of the enzyme, (for example, anti-sense RNA, or other drugs which interfere with expression).

II.D. Preparation of Hybrid Particle Immunogens Containing HCV Epitopes

The immunogenicity of the epitopes of HCV may also be enhanced by preparing them in mammalian or yeast systems fused with or assembled with particle-forming proteins such as, for example, that associated with hepatitis B surface antigen. See, e.g., U.S. Pat. No. 4,722,840. Constructs wherein the NANBV epitope is linked directly to the particle-forming protein coding sequences produce hybrids which are immunogenic with respect to the HCV epitope. In addition, all of the vectors prepared include epitopes specific to HBV, having various degrees of immunogenicity, such as, for example, the pre-S peptide. Thus, particles constructed from particle forming protein which include HCV sequences are immunogenic with respect to HCV and HBV.

Hepatitis surface antigen (HBSAg) has been shown to be formed and assembled into particles in *S. cerevisiae* (P. Valenzuela et al. (1982)), as well as in, for example, mammalian cells (P. Valenzuela et al. (1984)). The formation of such particles has been shown to enhance the immunogenicity of the monomer subunit. The constructs may also include the immunodominant epitope of HBSAg, comprising the 55 amino acids of the presurface (pre-S) region. Neurath et al. (1984). Constructs of the pre-S-HBSAg particle expressible in yeast are disclosed in EPO 174,444, published Mar. 19, 1986; hybrids including heterologous viral sequences for yeast expression are disclosed in EPO 175,261, published Mar. 26, 1966. These constructs may also be expressed in mammalian cells such as Chinese hamster ovary (CHO) cells using an SV40-dihydrofolate reductase vector (Michelle et al. (1984)).

In addition, portions of the particle-forming protein coding sequence may be replaced with codons encoding an HCV epitope. In this replacement, regions which are not required to mediate the aggregation of the units to form immunogenic particles in yeast or mammals can be deleted, thus eliminating additional HBV antigenic sites from competition with the HCV epitope.

II.E. Preparation of Vaccines

Vaccines may be prepared from one or more immunogenic polypeptides derived from HCV. The observed homology between HCV and Flaviviruses provides information concerning the polypeptides which are likely to be most effective as vaccines, as well as the regions of the genome in which they are encoded. The general structure of the Flavivirus genome is discussed in Rice et al (1986). The flavivirus genomic RNA is believed to be the only virus-specific mRNA species, and it is translated into the three viral structural proteins, i.e., C, M, and E, as well as two large nonstructural proteins, NS4 and NS5, and a complex set of smaller nonstructural proteins. It is known that major neutralizing epitopes for Flaviviruses reside in the E (envelope) protein (Roehrig (1986)). The corresponding HCV E gene and polypeptide encoding region may be predicted, based upon the homology to Flaviviruses. Thus, vaccines may be comprised of recombinant polypeptides containing epitopes of HCV E. These polypeptides may be expressed in various host cells (e.g., bacteria, yeast, insect, or mammalian cells), or alternatively may be isolated from viral preparations. It is also anticipated that the other structural proteins may also contain epitopes which give rise to protective anti-HCV antibodies. Thus, polypeptides containing the epitopes of E, C, and M may also be used, whether singly or in combination, in HCV vaccines.

In addition to the above, it has been shown that immunization with NS1 (nonstructural protein 1), results in protection against yellow fever (Schlesinger et al (1986)). This is true even though the immunization does not give rise to neutralizing antibodies. Thus, particularly since this protein appears to be highly conserved among Flaviviruses, it is likely that HCV NS1 will also be protective against HCV infection. Moreover, it also shows that nonstructural proteins may provide protection against viral pathogenicity, even if they do not cause the production of neutralizing antibodies.

In view of the above, multivalent vaccines against HCV may be comprised of one or more epitopes from one or more structural proteins, and/or one or more epitopes from one or more nonstructural proteins. These vaccines may be comprised of, for example, recombinant HCV polypeptides and/or polypeptides isolated from the virions. In particular, vaccines are contemplated comprising one or more of the following HCV proteins, or subunit antigens derived therefrom: E, NS1, C, NS2, NS3, NS4 and NS5. Particularly preferred are vaccines comprising E and/or NS1, or subunits thereof. In addition, it may be possible to use inactivated HCV in vaccines; inactivation may be by the preparation of viral lysates, or by other means known in the art to cause inactivation of Flaviviruses, for example, treatment with organic solvents or detergents, or treatment with formalin. Moreover, vaccines may also be prepared from attenuated HCV strains. The preparation of attenuated HCV strains is described infra.

It is known that some of the proteins in Flaviviruses contain highly conserved regions. Thus, some immunological cross-reactivity is possible between HCV and other Flaviviruses. It is possible that shared epitopes between the Flaviviruses and HCV will give rise to protective antibodies against one or more of the disorders caused by these pathogenic agents. Thus, it may be possible to design multipurpose vaccines based upon this knowledge.

In addition to the above, it is also possible to prepare live vaccines of attenuated microorganisms which express one or more recombinant HCV polypeptides. Suitable attenuated microorganisms are known in the art and include, for example, viruses (e.g., vaccinia virus (see Brown et al (1986)), as well as bacteria.

The preparation of vaccines which contain an immunogenic polypeptide(s) as active ingredients, is known to one skilled in the art. Typically, such vaccines are prepared as injectables, either as liquid solutions or suspensions; solid forms suitable for solution in, or suspension in, liquid prior to injection may also be prepared. The preparation may also be emulsified, or the protein encapsulated in liposomes. The active immunogenic ingredients are often mixed with excipients which are pharmaceutically acceptable and compatible with the active ingredient. Suitable excipients are, for example, water, saline, dextrose, glycerol, ethanol, or the like and combinations thereof. In addition, if desired, the vaccine may contain minor amounts of auxiliary substances such as wetting or emulsifying agents, pH buffering agents, and/or adjuvants which enhance the effectiveness of the vaccine. Examples of adjuvants which may be effective include but are not limited to: aluminum hydroxide, N-acetyl-muramyl-L-threonyl-D-isoglutamine (thr-MDP), N-acetyl-nor-muramyl-L-alanyl-D-isoglutamine (CGP 11637, referred to as nor-MDP), N-acetylmuramyl-L-alanyl-D-isoglutaminyl-L-alanine-2-(1'-2'-dipalmitoyl-sn-glycero-3-hydroxyphosphoryloxy)-ethylamine (CGP 19835A, referred to as MTP-PE), and RIBI, which contains three components extracted from bacteria, monophosphoryl lipid A, trehalose dimycolate and cell wall skeleton (MPL+ TDM+CWS) in a 2% squalene/Tween® 80 emulsion. The effectiveness of an adjuvant may be determined by measuring the amount of antibodies directed against an immunogenic polypeptide containing an HCV antigenic sequence resulting from administration of this polypeptide in vaccines which are also comprised of the various adjuvants.

The vaccines are conventionally administered parenterally, by injection, for example, either subcutaneously or intramuscularly. Additional formulations which are suitable for other modes of administration include suppositories and, in some cases, oral formulations. For suppositories, traditional binders and carriers may include, for example, polyalkylene glycols or triglycerides; such suppositories may be formed from mixtures containing the active ingredient in the range of 0.5% to 10%, preferably 1%–2%. Oral formulations include such normally employed excipients as, for example, pharmaceutical grades of mannitol, lactose, starch, magnesium stearate, sodium saccharine, cellulose, magnesium carbonate, and the like. These compositions take the form of solutions, suspensions, tablets, pills, capsules, sustained release formulations or powders and contain 10%–95% of active ingredient, preferably 25%–70%.

The proteins may be formulated into the vaccine as neutral or salt forms. Pharmaceutically acceptable salts include the acid addition salts (formed with free amino groups of the peptide) and which are formed with inorganic acids such as, for example, hydrochloric or phosphoric acids, or such organic acids such as acetic, oxalic, tartaric, maleic, and the like. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

II.F. Dosage and Administration of Vaccines

The vaccines are administered in a manner compatible with the dosage formulation, and in such amount as will be prophylactically and/or therapeutically effective. The quantity to be administered, which is generally in the range of 5 mg to 250 mg of antigen per dose, depends on the subject to be treated, capacity of the subject's immune system to synthesize antibodies, and the degree of protection desired. Precise amounts of active ingredient required to be administered may depend on the judgment of the practitioner and may be peculiar to each subject.

The vaccine may be given in a single dose schedule, or preferably in a multiple dose schedule. A multiple dose schedule is one in which a primary course of vaccination may be with 1–10 separate doses, followed by other doses given at subsequent time intervals required to maintain and or reinforce the immune response, for example, at 1–4 months for a second dose, and if needed, a subsequent dose(s) after several months. The dosage regimen will also, at least in part, be determined by the need of the individual and be dependent upon the judgment of the practitioner.

In addition, the vaccine containing the immunogenic HCV antigen(s) may be administered in conjunction with other immunoregulatory agents, for example, immune globulins.

II.G. Preparation of Antibodies Against HCV Epitopes

The immunogenic polypeptides prepared as described above are used to produce antibodies, including polyclonal and monoclonal. If polyclonal antibodies are desired, a selected mammal (e.g., mouse, rabbit, goat, horse, etc.) is immunized with an immunogenic polypeptide bearing an HCV epitope(s). Serum from the immunized animal is collected and treated according to known procedures. If serum containing polyclonal antibodies to an HCV epitope contains antibodies to other antigens, the polyclonal antibodies can be purified by immunoaffinity chromatography. Techniques for producing and processing polyclonal antisera are known in the art, see for example, Mayer and Walker (1987).

Alternatively, polyclonal antibodies may be isolated from a mammal which has been previously infected with HCV. An example of a method for purifying antibodies to HCV epitopes from serum from an infected individual, based upon affinity chromatography and utilizing a fusion polypeptide of SOD and a polypeptide encoded within cDNA clone 5-1-1, is presented in Section V.E.

Monoclonal antibodies directed against HCV epitopes can also be readily produced by one skilled in the art. The general methodology for making monoclonal antibodies by hybridomas is well known. Immortal antibody-producing cell lines can be created by cell fusion, and also by other techniques such as direct transformation of B lymphocytes with oncogenic DNA, or transfection with Epstein-Barr virus. See, e.g., M. Schreier et al (1980); Hammerling et al. (1981); Kennett et al. (1980); see also, U.S. Pat. Nos. 4,341,761; 4,399,121; 4,427,783; 4,444,887; 4,466,917; 4,472,500; 4,491,632; and 4,493,890. Panels of monoclonal antibodies produced against HCV epitopes can be screened for various properties; i.e., for isotype, epitope affinity, etc.

Antibodies, both monoclonal and polyclonal, which are directed against HCV epitopes are particularly useful in diagnosis, and those which are neutralizing are useful in passive immunotherapy. Monoclonal antibodies, in particular, may be used to raise anti-idiotype antibodies.

Anti-idiotype antibodies are immunoglobulins which carry an "internal image" of the antigen of the infectious agent against which protection is desired. See, for example, Nisonoff, A., et al. (1981) and Dreesman et al. (1985). Techniques for raising anti-idiotype antibodies are known in the art. See, for example, Grzych (1985), MacNamara et al. (1984), and Vytdehaag et al. (1985). These anti-idiotype antibodies may also be useful for treatment, vaccination and/or diagnosis of NANBH, as well as for an elucidation of the immunogenic regions of HCV antigens.

II.H. Diagnostic Oligonucleotide Probes and Kits

Using the disclosed portions of the isolated HCV cDNAs as a basis, including those described in Section IV.A, oligomers of approximately 8 nucleotides or more can be prepared, either by excision from recombinant polynucleotides or synthetically, which hybridize with the HCV genome and are useful in identification of the viral agent(s), further characterization of the viral genome(s), as well as in detection of the virus(es) in diseased individuals. The probes for HCV polynucleotides (natural or derived) are a length which allows the detection of unique viral sequences by hybridization. While 6–8 nucleotides may be a workable length, sequences of 10–12 nucleotides are preferred, and about 20 nucleotides appears optimal. Preferably, these sequences will derive from regions which lack heterogeneity. These probes can be prepared using routine methods, including automated oligonucleotide synthetic methods. Among useful probes, for example, are the clone 5-1-1 and the additional clones disclosed herein, as well as the various oligomers useful in probing cDNA libraries, set forth below. A complement to any unique portion of the HCV genome will be satisfactory. For use as probes, complete complementarity is desirable, though it may be unnecessary as the length of the fragment is increased.

For use of such probes as diagnostics, the biological sample to be analyzed, such as blood or serum, may be treated, if desired, to extract the nucleic acids contained therein. The resulting nucleic acid from the sample may be subjected to gel electrophoresis or other size separation techniques; alternatively, the nucleic acid sample may be dot blotted without size separation. The probes are usually labeled. Suitable labels, and methods for labeling probes are known in the art, and include, for example, radioactive labels incorporated by nick translation or kinasing, biotin, fluorescent probes, and chemiluminescent probes. The nucleic acids extracted from the sample are then treated with the labeled probe under hybridization conditions of suitable stringencies.

The probes can be made completely complementary to the HCV genome. Therefore, usually high stringency conditions are desirable in order to prevent false positives. However, as shown infra, portions of the HCV genome are variable. Therefore, conditions of high stringency should only be used if the probes are complementary to regions of the viral genome which lack heterogeneity. The stringency of hybridization is determined by a number of factors during hybridization and during the washing procedure, including temperature, ionic strength, length of time, and concentration of formamide. These factors are outlined in, for example, Maniatis, T. (1982).

Generally, it is expected that the HCV genome sequences will be present in serum of infected individuals at relatively low levels, i.e., at approximately $10^2$–$10^3$ chimp infectious doses (CID) per mL. This level may require that amplification techniques be used in hybridization assays. Such techniques are known in the art. For example, the Enzo Biochemical Corporation "Bio-Bridge" system uses terminal deoxynucleotide transferase to add unmodified 3'-poly-dT-tails to a DNA probe. The poly dT-tailed probe is hybridized to the target nucleotide sequence, and then to a biotin-modified poly-A. PCT application 84/03520 and EPA124221 describe a DNA hybridization assay in which: (1) analyte is annealed to a single-stranded DNA probe that is complementary to an enzyme-labeled oligonucleotide; and (2) the resulting tailed duplex is hybridized to an enzyme-labeled oligonucleotide. EPA 204510 describes a DNA hybridization assay in which analyte DNA is contacted with a probe that has a tail, such as a poly-dT tail, an amplifier strand that has a sequence that hybridizes to the tail of the probe, such as a poly-A sequence, and which is capable of binding a plurality of labeled strands. A particularly desirable technique may first involve amplification of the target HCV sequences in sera approximately 10,000 fold, i.e., to approximately $10^6$ sequences/mL. This may be accomplished, for example, by the polymerase chain reactions (PCR) technique described which is by Saiki et al. (1986), by Mullis, U.S. Pat. No. 4,683,195, and by Mullis et al. U.S. Pat. No. 4,683,202. The amplified sequence(s) may then be detected using a hybridization assay which is described in co-pending U.S. Ser. No. 109,282 (Attorney Docket No. 2300-0171), which was filed 15 Oct. 1987, U.S. Ser. No. 185,201 (filed 22 Apr. 1988), and U.S. Ser. No. 252,638 (filed 30 Sep. 1988), which are assigned to the herein assignee, and are hereby incorporated herein by reference. These hybridization assays, which should detect sequences at the level of $10^6$/mL, utilize nucleic acid multimers which bind to single-stranded analyte nucleic acid, and which also bind to a multiplicity of single-stranded labeled oligonucleotides. A suitable solution phase sandwich assay which may be used with labeled polynucleotide probes, and the methods for the preparation of probes is described in EPO 225,807, published June 16, 1987, which is assigned to the herein assignee, and which is hereby incorporated herein by reference.

The probes can be packaged into diagnostic kits. Diagnostic kits include the probe DNA, which may be labeled; alternatively, the probe DNA may be unlabeled and the ingredients for labeling may be included in the kit in separate containers. The kit may also contain other suitably packaged reagents and materials needed for the particular hybridization protocol, for example, standards, as well as instructions for conducting the test.

II.I. Immunoassay and Diagnostic Kits

Both the polypeptides which react immunologically with serum containing HCV antibodies, for example, those derived from, expressed from, or encoded within the clones described in Section IV.A., and composites thereof, (see section IV.A.) and the antibodies raised against the HCV specific epitopes in these polypeptides, see for example Section IV.E, are usefull in immunoassays to detect presence of HCV antibodies, or the presence of the virus and/or viral antigens, in biological samples. Design of the immunoassays is subject to a great deal of variation, and many formats are known in the art. The immunoassay will utilize at least one viral epitope derived from HCV. In one embodiment, the immunoassay uses a combination of viral epitopes derived from HCV. These epitopes may be derived from the same or from different viral polypeptides, and may be in separate recombinant or natural polypeptides, or together in the same recombinant polypeptides. An immunoassay may use, for example, a monoclonal antibody directed towards a viral epitope(s), a combination of monoclonal antibodies directed towards epitopes of one viral antigen, monoclonal antibodies directed towards epitopes of different viral antigens, polyclonal antibodies directed towards the same viral antigen, or polyclonal antibodies directed towards different viral antigens. Protocols may be based, for example, upon competition, or direct reaction, or sandwich type assays. Protocols may also, for example, use solid supports, or may be by immunoprecipitation. Most assays involve the use of labeled antibody or polypeptide; the labels may be, for example, enzymatic, fluorescent, chemiluminescent, radioactive, or dye molecules. Assays which amplify the signals from the probe are also known; examples of which are assays which utilize biotin and avidin, and enzyme-labeled and mediated immunoassays, such as ELISA assays.

Typically, an immunoassay for an anti-HCV antibody(s) will involve selecting and preparing the test sample suspected of containing the antibodies, such as a biological sample, then incubating it with an antigenic (i.e., epitope-containing) HCV polypeptide(s) under conditions that allow antigen-antibody complexes to form, and then detecting the formation of such complexes. Suitable incubation conditions are well known in the art. The immunoassay may be, without limitations, in a heterogeneous or in a homogeneous format, and of a standard or competitive type.

In a heterogeneous format, the polypeptide is typically bound to a solid support to facilitate separation of the sample from the polypeptide after incubation. Examples of solid supports that can be used are nitrocellulose (e.g., in membrane or microtiter well form), polyvinyl chloride (e.g., in sheets or microtiter wells), polystyrene latex (e.g., in beads or microtiter plates, polyvinylidine fluoride (known as Immulon®), diazotized paper, nylon membranes, activated beads, and Protein A beads. For example, Dynatech Immulon® 1 or Immulon® 2 microtiter plates or 0.25 inch polystyrene beads (Precision Plastic Ball) can be used in the heterogeneous format. The solid support containing the antigenic polypeptide is typically washed after separating it from the test sample, and prior to detection of bound antibodies. Both standard and competitive formats are known in the art.

In a homogeneous format, the test sample is incubated with antigen in solution. For example, it may be under conditions that will precipitate any antigen-antibody complexes which are formed. Both standard and competitive formats for these assays are known in the art.

In a standard format, the amount of HCV antibodies forming the antibody-antigen complex is directly monitored. This may be accomplished by determining whether labeled anti-xenogenic (e.g., anti-human) antibodies which recognize an epitope on anti-HCV antibodies will bind due to complex formation. In a competitive format, the amount of HCV antibodies in the sample is deduced by monitoring the competitive effect on the binding of a known amount of labeled antibody (or other competing ligand) in the complex.

Complexes formed comprising anti-HCV antibody (or, in the case of competitive assays, the amount of competing antibody) are detected by any of a number of known techniques, depending on the format. For example, unlabeled HCV antibodies in the complex may be detected using a conjugate of antixenogeneic Ig complexed with a label, (e.g., an enzyme label).

In immunoassays where HCV polypeptides are the analyte, the test sample, typically a biological sample, is incubated with anti-HCV antibodies under conditions that allow the formation of antigen-antibody complexes. Various formats can be employed. For example, a "sandwich assay" may be employed, where antibody bound to a solid support is incubated with the test sample; washed; incubated with a second, labeled antibody to the analyte, and the support is washed again. Analyte is detected by determining if the second antibody is bound to the support. In a competitive format, which can be either heterogeneous or homogeneous, a test sample is usually incubated with antibody and a labeled, competing antigen is also incubated, either sequentially or simultaneously. These and other formats are well known in the art.

The Flavivirus model for HCV allows predictions regarding the likely location of diagnostic epitopes for the virion structural proteins. The C, pre-M, M, and E domains are all likely to contain epitopes of significant potential for detecting viral antigens, and particularly for diagnosis. Similarly, domains of the nonstructural proteins are expected to contain important diagnostic epitopes (e.g., NS5 encoding a putative polymerase; and NS1 encoding a putative complement-binding antigen). Recombinant polypeptides, or viral polypeptides, which include epitopes from these specific domains may be useful for the detection of viral antibodies in infections blood donors and infected patients.

In addition, antibodies directed against the E and/or M proteins can be used in immunoassays for the detection of viral antigens in patients with HCV caused NANBH, and in infectious blood donors. Moreover, these antibodies may be extremely useful in detecting acute-phase donors and patients.

Some of the antigenic regions of the putative polyprotein have been mapped and identified by screening the antigenicity of bacterial expression products of HCV cDNAs which encode portions of the polyprotein. See Section IV.B.8. Other antigenic regions of HCV may be detected by expressing the portions of the HCV cDNAs in other expression systems, including yeast systems and cellular systems derived from insects and vertebrates. In addition, studies giving rise to an antigenicity index and hydrophobicity/hydrophilicity profile give rise to information concerning the probability of a region's antigenicity.

The studies on antigenic mapping by expression of HCV cDNAs showed that a number of clones containing these cDNAs expressed polypeptides which were immunologically reactive with serum from individuals with NANBH. No single polypeptide was immunologically reactive with all sera. Five of these polypeptides were very immunogenic in that antibodies to the HCV epitopes in these polypeptides were detected in many different patient sera, although the overlap in detection was not complete. Thus, the results on the immunogenicity of the polypeptides encoded in the various clones suggest that efficient detection systems for HCV infection may include the use of panels of epitopes. The epitopes in the panel may be constructed into one or multiple polypeptides. The assays for the varying epitopes may be sequential or simultaneous.

Kits suitable for immunodiagnosis and containing the appropriate labeled reagents are constructed by packaging the appropriate materials, including the polypeptides of the invention containing HCV epitopes or antibodies directed against HCV epitopes in suitable containers, along with the remaining reagents and materials required for the conduct of the assay, as well as a suitable set of assay instructions.

II.J. Further Characterization of the HCV Genome, Virions and Viral Antigens Using Probes Derived From cDNA to the Viral Genome The HCV cDNA sequence information in the clones described in Section IV.A may be used to gain further information on the sequence of the HCV genome, and for identification and isolation of the HCV agent, and thus will aid in its characterization including the nature of the genome, the structure of the viral particle, and the nature of the antigens of which it is composed. This information, in turn, can lead to additional polynucleotide probes, polypeptides derived from the HCV genome, and antibodies directed against HCV epitopes which would be useful for the diagnosis and/or treatment of HCV caused NANBH.

The cDNA sequence information in the above-mentioned clones is useful for the design of probes for the isolation of additional cDNA sequences which are derived from as yet undefined regions of the HCV genome(s) from which the cDNAs in clones described in Section IV.A. are derived. For example, labeled probes containing a sequence of approximately 8 or more nucleotides, and preferably 20 or more nucleotides, which are derived from regions close to the 5'-termini or 3'-termini of the family of HCV cDNA sequences shown in FIGS. 1, 3, 6, 9, 14 and 62 may be used to isolate overlapping cDNA sequences from HCV cDNA libraries. These sequences which overlap the cDNAs in the above-mentioned clones, but which also contain sequences derived from regions of the genome from which the cDNA in the above mentioned clones are not derived, may then be used to synthesize probes for identification of other overlapping fragments which do not necessarily overlap the cDNAs in the clones described in Section IV.A. Unless the HCV genome is segmented and the segments lack common sequences, it is possible to sequence the entire viral genome (s) utilizing the technique of isolation of overlapping cDNAs derived from the viral genome(s). Although it is unlikely, if the genome is a segmented genome which lacks common sequences, the sequence of the genome can be determined by serologically screening λgt11 HCV cDNA libraries, as used to isolate clone 5-1-1, sequencing cDNA isolates, and using the isolated cDNAs to isolate overlapping fragments, using the technique described for the isolation and sequencing of the clones described in Section IV.A. Alternatively, characterization of the genomic segments could be from the viral genome(s) isolated from purified HCV particles. Methods for purifying HCV particles and for detecting them during the purification procedure are described herein, infra. Procedures for isolating polynucleotide genomes from viral particles are known in the art, and one procedure which may be used is shown in Example IV.A.1. The isolated genomic segments could then be cloned and sequenced. Thus, with the information provided herein, it is possible to clone and sequence the HCV genome(s) irrespective of their nature.

Methods for constructing cDNA libraries are known in the art, and are discussed supra and infra; a method for the construction of HCV cDNA libraries in λgt11 is discussed infra in Section IV.A. However, cDNA libraries which are useful for screening with nucleic acid probes may also be constructed in other vectors known in the art, for example, λgt10 (Huynh et al. (1985)). The HCV derived cDNA detected by the probes derived from the cDNAs described in Section IV.A, and from the probes synthesized from polynucleotides derived from these cDNAs, may be isolated from the clone by digestion of the isolated polynucleotide with the appropriate restriction enzyme(s), and sequenced. See, for example, Section IV.A.3. and IV.A.4. for the techniques used for the isolation and sequencing of HCV cDNA which overlaps HCV cDNA in clone 5-1-1, Sections IV.A.5-IV.A.7 for the isolation and sequencing of HCV cDNA which overlaps that in clone 81, and Section IV.A.8 and IV.A.9 for the isolation and sequencing of a clone which overlaps another clone (clone 36), which overlaps clone 81.

The sequence information derived from these overlapping HCV cDNAs is useful for determining areas of homology and heterogeneity within the viral genome(s), which could indicate the presence of different strains of the genome, and/or of populations of defective particles. It is also useful for the design of hybridization probes to detect HCV or HCV antigens or HCV nucleic acids in biological samples, and during the isolation of HCV (discussed infra), utilizing the techniques described in Section II.G. Moreover, the overlapping cDNAs may be used to create expression vectors for polypeptides derived from the HCV genome(s) which also encode the polypeptides encoded in clones 5-1-1, 36, 81, 91, and 1-2, and in the other clones described in Section IV.A. The techniques for the creation of these polypeptides containing HCV epitopes, and for antibodies directed against HCV epitopes contained within them, as well as their uses, are analogous to those described for polypeptides derived from NANBV CDNA sequences contained within the HCV cDNA clones described in Section IV.A, discussed supra and infra.

Encoded within the family of cDNA sequences contained within clones 5-1-1, 32, 35, 36, 81, 91, 1-2, and the other clones described in Section IV.A. are antigen(s) containing epitopes which appear to be unique to HCV; i.e., antibodies directed against these antigens are absent from individuals infected with HAV or HBV, and from individuals not infected with HCV (see the serological data presented in Section IV.B.). Moreover, a comparison of the sequence information of these cDNAs with the sequences of HAV, HBV, HDV, and with the genomic sequences in Genebank indicates that minimal homology exists between these cDNAs and the polynucleotide sequences of those sources. Thus, antibodies directed against the antigens encoded within the cDNAs of these clones may be used to identify BB-NANBV particles isolated from infected individuals. In addition, they are also useful for the isolation of NANBH agent(s).

HCV particles may be isolated from the sera from individuals with NANBH or from cell cultures by any of the methods known in the art, including for example, techniques based on size discrimination such as sedimentation or exclusion methods, or techniques based on density such as ultracentrifugation in density gradients, or precipitation with agents such as polyethylene glycol, or chromatography on a variety of materials such as anionic or cationic exchange materials, and materials which bind due to hydrophobicity, as well as affinity columns. During the isolation procedure the presence of HCV may be detected by hybridization analysis of the extracted genome, using probes derived from the HCV cDNAs described supra, or by immunoassay (see Section II.I.) utilizing as probes antibodies directed against HCV antigens encoded within the family of cDNA sequences described in Section IV.A, and also directed against HCV antigens encoded within the overlapping HCV cDNA sequences discussed supra. The antibodies may be monoclonal, or polyclonal, and it may be desirable to purify the antibodies before their use in the immunoassay. A purification procedure for polyclonal antibodies directed against antigen(s) encoded within clone 5-1-1 is described in Section IV.E; analogous purification procedures may be utilized for antibodies directed against other HCV antigens.

Antibodies directed against HCV antigens encoded within the family of cDNAs described in Section IV.A, as well as those encoded within overlapping HCV cDNAs, which are affixed to solid supports are useful for the isolation of HCV by immunoaffinity chromatography. Techniques for immunoaffinity chromatography are known in the art, including techniques for affixing antibodies to solid supports so that they retain their immunoselective activity; the techniques may be those in which the antibodies are adsorbed to the support (see, for example, Kurstak in "Enzyme Immunodiagnosis", pp. 31–37), as well as those in which the antibodies are covalently linked to the support. Generally, the techniques are similar to those used for covalent linking of antigens to a solid support, which are generally described in Section II.C.; however, spacer groups may be included in the bifunctional coupling agents so that the antigen binding site of the antibody remains accessible.

During the purification procedure the presence of HCV may be detected and/or verified by nucleic acid hybridization, utilizing as probes polynucleotides derived from the family of HCV cDNA sequences described in Section IV.A, as well as from overlapping HCV cDNA sequences, described supra. In this case, the fractions are treated under conditions which would cause the disruption of viral particles, for example, with detergents in the presence of chelating agents, and the presence of viral nucleic acid determined by hybridization techniques described in Section II.H. Further confirmation that the isolated particles are the agents which induce HCV may be obtained by infecting chimpanzees with the isolated virus particles, followed by a determination of whether the symptoms of NANBH result from the infection.

Viral particles from the purified preparations may then be further characterized. The genomic nucleic acid has been purified. Based upon its sensitivity to RNase, and not DNase I, it appears that the virus is composed of an RNA genome. See Example IV.C.2., infra. The strandedness and circularity or non-circularity can determined by techniques known in the art, including, for example, its visualization by electron microscopy, its migration in density gradients, and its sedimentation characteristics. Based upon the hybridization of the captured HCV genome to the negative strands of HCV cDNAs, it appears that HCV may be comprised of a positive stranded RNA genome (see Section IV.H.1). Techniques such as these are described in, for example, *Meth Enzymol.* In addition, the purified nucleic acid can be cloned and sequenced by known techniques, including reverse transcription since the genomic material is RNA. See, for example, Maniatis (1982), and Glover (1985). Utilizing the nucleic acid derived from the viral particles, it is possible to sequence the entire genome, whether or not it is segmented.

Examination of the homology of the polypeptide encoded within the continuous ORF of combined clones 14i through 39c (the ORF is shown in FIG. 26), suggests that a portion of the HCV polypeptide contains regions of homology with the corresponding proteins in conserved regions of flaviviruses. An example of this is described in Section IV.H.3. This evidence, in conjunction with the results which show that HCV contains a positive-stranded genome, the size of which is approximately 10,000 nucleotides, is consistent with the suggestion that HCV is distantly related to the flaviviridae. Generally, flavivirus virions and their genomes have a relatively consistent structure and organization, which are known. See Rice et al. (1986), and Brinton, M. A. (1988). Using the comparison with flaviviruses, predictions as to the location of the sequences encoding some of the HCV proteins may be made.

The structure of the HCV may also be determined and its components isolated. The morphology and size may be determined by, for example, electron microscopy. The identification and localization of specific viral polypeptide antigens such as coat or envelope antigens, or internal antigens, such as nucleic acid binding proteins, core antigens, and polynucleotide polymerase(s) may also be determined by, for example, determining whether the antigens are present as major or minor viral components, as well as by utilizing antibodies directed against the specific antigens encoded within isolated cDNAs as probes. This information is useful in the design of vaccines; for example, it may be preferable to include an exterior antigen in a vaccine preparation. Multivalent vaccines may be comprised of, for example, an epitope derived from the genome encoding a structural protein, for example, E, as well as an epitope from another portion of the genome, for example, a nonstructural or structural polypeptide.

II.K. Cell Culture Systems and Animal Model Systems for HCV Replication

The suggestion that HCV is a flavi-like virus also provides information on methods for growing HCV. The virus is thought to be "Flavi-like" for several reasons. Based upon the HCV cDNA sequence, the genome appears to contain a large ORF which encodes a putative polyprotein. The HCV genome is positive-stranded with respect to translation of this polyprotein. The hydrophobicity profile of the HCV polyprotein resembles in particular that of putative polyproteins from known Flaviviruses. The apparent size of the genome, approximately 10,000 nucleotides in size, may be smaller than, but is close to that of known Flaviviruses. Although there is only a slight amount of amino acid homology between the HCV putative polyprotein and that of Flaviviruses, the homology is probably significant because there appear to be at three conserved motifs that have similar spacing in HCV and the Flaviviruses. Two of these conserved motifs, which are of larger size, are in the putative NS3 region. A third conserved motif is in putative NS5; the conserved sequence in this region, GDD, is usually associated with a Flavivirus polymerase. Other regions which are conserved between the Flaviviruses are also partially conserved in HCV. Methods for culturing flaviviruses are known to those of skill in the art (see, for example, the reviews by Brinton (1986) and Stollar, V. (1980)). Generally, suitable cells or cell lines for culturing HCV may include those known to support Flavivirus replication, for example, the following: monkey kidney cell lines (e.g. $MK_2$, VERO); porcine kidney cell lines (e.g. PS); baby hamster kidney cell lines (e.g. BHK); murine macrophage cell lines (e.g., P388D1, MK1, Mml); human macrophage cell lines (e.g., U-937); human peripheral blood leukocytes; human adherent monocytes; hepatocytes or hepatocyte cell lines (e.g., HUH7, HEPG2); embryos or embryonic cells (e.g., chick embryo fibroblasts); or cell lines derived from invertebrates, preferably from insects (e.g. drosophila cell lines), or more preferably from arthropods, for example, mosquito cell lines (e.g., A. Albopictus, Aedes aegypti, Cutex tritaeniorhynchus) or tick cell lines (e.g. RML-14 Dermacentor parumapertus).

It is possible that primary hepatocytes can be cultured, and then infected with HCV; or alternatively, the hepatocyte cultures could be derived from the livers of infected individuals (e.g., humans or chimpanzees). The latter case is an example of a cell which is infected in vivo being passaged in vitro. In addition, various immortalization methods can be used to obtain cell-lines derived from hepatocyte cultures. For example, primary liver cultures (before and after enrichment of the hepatocyte population) may be fused to a variety of cells to maintain stability. For example, also, cultures may be infected with transforming viruses, or transfected with transforming genes in order to create permanent or semi-permanent cell lines. In addition, for example, cells in liver cultures may be fused to established cell lines (e.g., HepG2). Methods for cell fusion are known in the art, and include, for example, the use of fusion agents such as polyethylene glycol, Sendai Virus, and Epstein-Barr virus.

As discussed above, HCV is a Flavi-like virus. Therefore, it is probable that HCV infection of cell lines may be accomplished by techniques known in the art for infecting cells with Flaviviruses. These include, for example, incubating the cells with viral preparations under conditions which allow viral entry into the cell. In addition, it may be possible to obtain viral production by transfecting the cells with isolated viral polynucleotides. It is known that Togavirus and Flavivirus RNAs are infectious in a variety of vertebrate cell lines (Pfefferkorn and Shapiro (1974)), and in a mosquito cell line (Peleg (1969)). Methods for transfecting tissue culture cells with RNA duplexes, positive stranded RNAs, and DNAs (including cDNAs) are known in the art, and include, for example, techniques which use electroporation, and precipitation with DEAE-Dextran or calcium phosphate. An abundant source of HCV RNA can be obtained by performing in vitro transcription of an HCV cDNA corresponding to the complete genome. Transfection with this material, or with cloned HCV cDNA should result in viral replication and the in vitro propagation of the virus.

In addition to cultured cells, animal model systems may be used for viral replication; animal systems in which flaviviruses are known to those of skill in the art (see, for example, the review by Monath (1986)). Thus, HCV replication may occur not only in chimpanzees, but also in, for example, marmosets and suckling mice.

II.L. Screening for Anti-Viral Agents for HCV

The availability of cell culture and animal model systems for HCV also makes possible screening for anti-viral agents which inhibit HCV replication, and particularly for those agents which preferentially allow cell growth and multiplication while inhibiting viral replication. These screening methods are known by those of skill in the art. Generally, the anti-viral agents are tested at a variety of concentrations, for their effect on preventing viral replication in cell culture systems which support viral replication, and then for an inhibition of infectivity or of viral pathogenicity (and a low level of toxicity) in an animal model system.

The methods and compositions provided herein for detecting HCV antigens and HCV polynucleotides are useful for screening of anti-viral agents in that they provide an alternative, and perhaps more sensitive means, for detecting the agent's effect on viral replication than the cell plaque assay or $ID_{50}$ assay. For example, the HCV-polynucleotide probes described herein may be used to quantitate the amount of viral nucleic acid produced in a cell culture. This could be accomplished, for example, by hybridization or competition hybridization of the infected cell nucleic acids with a labeled HCV-polynucleotide probe. For example, also, anti-HCV antibodies may be used to identify and quantitate HCV antigen(s) in the cell culture utilizing the immunoassays described herein. In addition, since it may be desirable to quantitate HCV antigens in the infected cell culture by a competition assay, the polypeptides encoded within the HCV cDNAs described herein are useful in these competition assays. Generally, a recombinant HCV polypeptide derived from the HCV cDNA would be labeled, and the inhibition of binding of this labeled polypeptide to an HCV polypeptide due to the antigen produced in the cell culture system would be monitored. Moreover, these techniques are particularly useful in cases where the HCV may be able to replicate in a cell line without causing cell death.

The anti-viral agents which may be tested for efficacy by these methods are known in the art, and include, for example, those which interact with virion components and/or cellular components which are necessary for the binding and/or replication of the virus. Typical anti-viral agents may include, for example, inhibitors of virion polymerase and/or protease(s) necessary for cleavage of the precursor polypeptides. Other anti-viral agents may include those which act with nucleic acids to prevent viral replication, for example, anti-sense polynucleotides, etc.

Antisense polynucleotides molecules are comprised of a complementary nucleotide sequence which allows them to hybridize specifically to designated regions of genomes or RNAs. Antisense polynucleotides may include, for example, molecules that will block protein translation by binding to mRNA, or may be molecules which prevent replication of viral RNA by transcriptase. They may also include molecules which carry agents (non-covalently attached or covalently bound) which cause the viral RNA to be inactive by causing, for example, scissions in the viral RNA. They may also bind to cellular polynucleotides which enhance and/or are required for viral infectivity, replicative ability, or chronicity. Antisense molecules which are to hybridize to HCV derived RNAs may be designed based upon the sequence information of the HCV cDNAs provided herein. The antiviral agents based upon anti-sense polynucleotides for HCV may be designed to bind with high specificity, to be of increased solubility, to be stable, and to have low toxicity. Hence, they may be delivered in specialized systems, for example, liposomes, or by gene therapy. In addition, they may include analogs, attached proteins, substituted or altered bonding between bases, etc.

Other types of drugs may be based upon polynucleotides which "mimic" important control regions of the HCV genome, and which may be therapeutic due to their interactions with key components of the system responsible for viral infectivity or replication.

II.M. Preparation of Attenuated Strains of HCV

In addition to the above, utilizing the tissue culture systems and/or animal model systems, it may be possible to isolate attenuated strains of HCV. These strains would be suitable for vaccines, or for the isolation of viral antigens. Attenuated strains are isolatable after multiple passages in cell culture and/or an animal model. Detection of an attenuated strain in an infected cell or individual is achievable by techniques known in the art, and could include, for example, the use of antibodies to one or more epitopes encoded in HCV as a probe or the use of a polynucleotide containing an HCV sequence of at least about 8 nucleotides as a probe. Alternatively, or in addition, an attenuated strain may be constructed utilizing the genomic information of HCV provided herein, and utilizing recombinant techniques. Generally, one would attempt to delete a region of the genome encoding, for example, a polypeptide related to pathogenicity, but which allows viral replication. In addition, the genome construction would allow the expression of an epitope which gives rise to neutralizing antibodies for HCV. The altered genome could then be utilized to transform cells which allow HCV replication, and the cells grown under conditions to allow viral replication. Attenuated HCV strains are useful not only for vaccine purposes, but also as sources for the commercial production of viral antigens, since the processing of these viruses would require less stringent protection measures for the employees involved in viral production and/or the production of viral products.

III. General Methods

The general techniques used in extracting the genome from a virus, preparing and probing a cDNA library, sequencing clones, constructing expression vectors, transforming cells, performing immunological assays such as radioimmunoassays and ELISA assays, for growing cells in culture, and the like are known in the art and laboratory manuals are available describing these techniques. However, as a general guide, the following sets forth some sources currently available for such procedures, and for materials useful in carrying them out.

III.A. Hosts and Expression Control Sequences

Both prokaryotic and eukaryotic host cells may be used for expression of desired coding sequences when appropriate control sequences which are compatible with the designated host are used. Among prokaryotic hosts, *E. coli* is most frequently used. Expression control sequences for prokaryotes include promoters, optionally containing operator portions, and ribosome binding sites. Transfer vectors compatible with prokaryotic hosts are commonly derived from, for example, pBR322, a plasmid containing operons conferring ampicillin and tetracycline resistance, and the various pUC vectors, which also contain sequences conferring antibiotic resistance markers. These markers may be used to obtain successful transformants by selection. Commonly used prokaryotic control sequences include the B-lactamase (penicillinase) and lactose promoter systems (Chang et al. (1977)), the tryptophan (trp) promoter system (Goeddel et al. (1980)) and the lambda-derived $P_L$ promoter and N gene ribosome binding site (Shimatake et al. (1981)) and the hybrid tac promoter (De Boer et al. (1983)) derived from sequences of the trp and lac UV5 promoters. The foregoing systems are particularly compatible with *E. coli;* if desired, other prokaryotic hosts such as strains of Bacillus or Pseudomonas may be used, with corresponding control sequences.

Eukaryotic hosts include yeast and mammalian cells in culture systems. *Saccharomyces cerevisiae* and *Saccharomyces carlsbergensis* are the most commonly used yeast hosts, and are convenient fungal hosts. Yeast compatible vectors carry markers which permit selection of successful transformants by conferring prototrophy to auxotrophic mutants or resistance to heavy metals on wild-type strains. Yeast compatible vectors may employ the 2m origin of replication (Broach et al. (1983)), the combination of CEN3 and ARSI or other means for assuring replication, such as sequences which will result in incorporation of an appropriate fragment into the host cell genome. Control sequences for yeast vectors are known in the art and include promoters for the synthesis of glycolytic enzymes (Hess et al. (1968); Holland et al. (1978)), including the promoter for 3 phosphoglycerate kinase (Hitzeman (1980)). Terminators may also be included, such as those derived from the enolase gene (Holland (1981)). Particularly useful control systems are those which comprise the glyceraldehyde-3 phosphate dehydrogenase (GAPDH) promoter or alcohol dehydrogenase (ADH) regulatable promoter, terminators also derived from GAPDH, and if secretion is desired, leader sequence from yeast α-factor. In addition, the transcriptional regulatory region and the transcriptional initiation region which are operably linked may be such that they are not naturally associated in the wild-type organism. These systems are described in detail in EPO 120,551, published Oct. 3, 1984; EPO 116,201, published Aug. 22, 1984; and EPO 164,556, published Dec. 18, 1985, all of which are assigned to the herein assignee, and are hereby incorporated herein by reference.

Mammalian cell lines available as hosts for expression are known in the art and include many immortalized cell lines available from the American Type Culture Collection (ATCC), including HeLa cells, Chinese hamster ovary (CHO) cells, baby hamster kidney (BHK) cells, and a number of other cell lines. Suitable promoters for mammalian cells are also known in the art and include viral promoters such as that from Simian Virus 40 (SV40) (Fiers (1978)), Rous sarcoma virus (RSV), adenovirus (ADV), and bovine papilloma virus (BPV). Mammalian cells may also require terminator sequences and poly A addition sequences; enhancer sequences which increase expression may also be included, and sequences which cause amplification of the gene may also be desirable. These sequences are known in the art.

Vectors suitable for replication in mammalian cells are known in the art, and may include viral replicons, or sequences which insure integration of the appropriate sequences encoding NANBV epitopes into the host genome.

A vector which is used to express foreign DNA, and which may be used in vaccine preparation is Vaccinia virus. In this case the heterologous DNA is inserted into the Vaccinia genome. Techniques for the insertion of foreign DNA into the vaccinia virus genome are known in the art, and utilize, for example, homologous recombination. The insertion of the heterologous DNA is generally into a gene which is non-essential in nature, for example, the thymidine kinase gene (tk), which also provides a selectable marker. Plasmid vectors that greatly facilitate the construction of recombinant viruses have been described (see, for example, Mackett et al. (1984), Chakrabarti et al. (1985); Moss (1987)). Expression of the HCV polypeptide then occurs in cells or individuals which are immunized with the live recombinant vaccinia virus.

The segment of HCV cDNA which is inserted into a Vaccinia vector may be derived from the "x" region of the HCV genome (see FIG. 69); for example, it may encode a polypeptide comprised of amino acid numbers 406–661. The polypeptide encoding sequence may be attached to a leader sequence. The leader sequence may be that for tissue plasminogen activator (tPA), or from another source, e.g., that for β-globin. The heterologous polynucleotide may be inserted into a vaccinia vector which is a modified version of pSC11, due to the addition of a polylinker sequence which contains a cloning site.

The segment of HCV cDNA which is inserted into the Vaccinia vector may also be derived from the "x" region of the HCV genome, but it may encode a larger polypeptide, i.e., one comprised of amino acid numbers 347–906. The polypeptide encoding sequence, which may or may not be attached to an upstream heterologous leader sequence, may be inserted into the modified pSC11 vaccinia vector described above.

In order to detect whether or not the HCV polypeptide is expressed from the vaccinia vector, BSC 1 cells may be infected with the recombinant vector and grown on microscope slides under conditions which allow expression. The cells may then be acetone-fixed, and immunofluorescence assays performed using serum which is known to contain anti-HCV antibodies to a polypeptide(s) encoded in the region of the HCV genome from which the HCV segment in the recombinant expression vector was derived.

Other systems for expression of eukaryotic or viral genomes include insect cells and vectors suitable for use in these cells. These systems are known in the art, and include, for example, insect expression transfer vectors derived from the baculovirus *Autographa californica* nuclear polyhedrosis virus (AcNPV), which is a helper-independent, viral expression vector. Expression vectors derived from this system usually use the strong viral polyhedron gene promoter to drive expression of heterologous genes. Currently the most commonly used transfer vector for introducing foreign genes into AcNPV is pAc373 (FIG. 70). Many other vectors, known to those of skill in the art, have also been designed for improved expression. These include, for example, pVL985 (which alters the polyhedron start codon from ATG to ATT, and which introduces a BamHI cloning site 32 basepairs downstream from the ATT; See Luckow and Summers (1989)). AcNPV transfer vectors for high level expression of nonfused foreign proteins are shown in FIG. 70. In the figure, the numbers shown refer to positions within the native gene, where the A of the ATG codon is +1. FIG. 70 also shows a restriction endonuclease map of the transfer vector pAc373. The map shows that a unique BamHI site is located following position 8 with respect to the translation initiation codon ATG of the polyhedron gene. There are no cleavage sites for SmaI, PstI, BglII, XbaI or SstI. Good expression of nonfused foreign proteins usually requires foreign genes that ideally have a short leader sequence containing suitable translation initiation signals preceding an ATG start signal. The plasmid also contains the polyhedron polyadenylation signal and the ampicillin-resistance (amp) gene and origin of replication for selection and propagation in *E. coli.*

Methods for the introduction of heterologous DNA into the desired site in the baculovirus virus are known in the art. (See Summer and Smith, Texas Agricultural Experiment Station Bulletin No. 1555; Ju et al. (1987); Smith et al. (1983); and Luckow and Summers (1989)). For example, the insertion can be into a gene such as the polyhedron gene, by homologous recombination; insertion can also be into a restriction enzyme site engineered into the desired baculovirus gene. The inserted sequences may be those which encode all or varying segments of the polyprotein, or other orfs which encode viral polypeptides. For example, the insert could encode the following numbers of amino acid segments from the polyprotein: amino acids 1–1078; amino acids 332–662; amino acids 406–662; amino acids 156–328, and amino acids 199–328.

The signals for posttranslational modifications, such as signal peptide cleavage, proteolytic cleavage, and phosphorylation, appear to be recognized by insect cells. The signals required for secretion and nuclear accumulation also appear to be conserved between the invertebrate cells and vertebrate cells. Examples of the signal sequences from vertebrate cells which are effective in invertebrate cells are known in the art, for example, the human interleukin 2 signal (IL2s) which is a signal for transport out of the cell, is recognized and properly removed in insect cells.

III.B. Transformations

Transformation may be by any known method for introducing polynucleotides into a host cell, including, for example packaging the polynucleotide in a virus and transducing a host cell with the virus, and by direct uptake of the polynucleotide. The transformation procedure used depends upon the host to be transformed. For example, transformation of the E. coli host cells with λgt11 containing BB-NANBV sequences is discussed in the Example section, infra. Bacterial transformation by direct uptake generally employs treatment with calcium or rubidium chloride (Cohen (1972); Maniatis (1982)). Yeast transformation by direct uptake may be carried out using the method of Hinnen et al. (1978). Mammalian transformations by direct uptake may be conducted using the calcium phosphate precipitation method of Graham and Van der Eb (1978), or the various known modifications thereof. Other methods for the introduction of recombinant polynucleotides into cells, particularly into mammalian cells, which are known in the art include dextran-mediated transfection, calcium phosphate mediated transfection, polybrene mediated transfection, protoplast fusion, electroporation, encapsulation of the polynucleotide(s) in liposomes, and direct microinjection of the polynucleotides into nuclei.

III.C. Vector Construction

Vector construction employs techniques which are known in the art. Site-specific DNA cleavage is performed by treating with suitable restriction enzymes under conditions which generally are specified by the manufacturer of these commercially available enzymes. In general, about 1 mg of plasmid or DNA sequence is cleaved by 1 unit of enzyme in about 20 mL buffer solution by incubation of 1–2 hr at 37° C. After incubation with the restriction enzyme, protein is removed by phenol/chloroform extraction and the DNA recovered by precipitation with ethanol. The cleaved fragments may be separated using polyacrylamide or agarose gel electrophoresis techniques, according to the general procedures found in Methods in Enzymology (1980) 65:499–560.

Sticky ended cleavage fragments may be blunt ended using E. coli DNA polymerase I (Klenow) in the presence of the appropriate deoxynucleotide triphosphates (dNTPs) present in the mixture. Treatment with S1 nuclease may also be used, resulting in the hydrolysis of any single stranded DNA portions.

Ligations are carried out using standard buffer and temperature conditions using T4 DNA ligase and ATP; sticky end ligations require less ATP and less ligase than blunt end ligations. When vector fragments are used as part of a ligation mixture, the vector fragment is often treated with bacterial alkaline phosphatase (BAP) or calf intestinal alkaline phosphatase to remove the 5'-phosphate and thus prevent religation of the vector; alternatively, restriction enzyme digestion of unwanted fragments can be used to prevent ligation.

Ligation mixtures are transformed into suitable cloning hosts, such as E. coli, and successful transformants selected by, for example, antibiotic resistance, and screened for the correct construction.

III.D. Construction of Desired DNA Sequences

Synthetic oligonucleotides may be prepared using an automated oligonucleotide synthesizer as described by Warner (1984). If desired the synthetic strands may be labeled with $^{32}P$ by treatment with polynucleotide kinase in the presence of $^{32}P$-ATP, using standard conditions for the reaction.

DNA sequences, including those isolated from cDNA libraries, may be modified by known techniques, including, for example site directed mutagenesis, as described by Zoller (1982). Briefly, the DNA to be modified is packaged into phage as a single stranded sequence, and converted to a double stranded DNA with DNA polymerase using, as a primer, a synthetic oligonucleotide complementary to the portion of the DNA to be modified, and having the desired modification included in its own sequence. The resulting double stranded DNA is transformed into a phage supporting host bacterium. Cultures of the transformed bacteria, which contain replications of each strand of the phage, are plated in agar to obtain plaques. Theoretically, 50% of the new plaques contain phage having the mutated sequence, and the remaining 50% have the original sequence. Replicates of the plaques are hybridized to labeled synthetic probe at temperatures and conditions which permit hybridization with the correct strand, but not with the unmodified sequence. The sequences which have been identified by hybridization are recovered and cloned.

III.E. Hybridization with Probe

DNA libraries may be probed using the procedure of Grunstein and Hogness (1975). Briefly, in this procedure, the DNA to be probed is immobilized on nitrocellulose filters, denatured, and prehybridized with a buffer containing 0–50% formamide, 0.75 M NaCl, 75 mM Na citrate, 0.02% (wt/v) each of bovine serum albumin, polyvinyl pyrollidone, and Ficoll, 50 mM Na Phosphate (pH 6.5), 0.1% SDS, and 100 mg/mL carrier denatured DNA. The percentage of formamide in the buffer, as well as the time and temperature conditions of the prehybridization and subsequent hybridization steps depends on the stringency required. Oligomeric probes which require lower stringency conditions are generally used with low percentages of formamide, lower temperatures, and longer hybridization times. Probes containing more than 30 or 40 nucleotides such as those derived from cDNA or genomic sequences generally employ higher temperatures, e.g., about 40–42° C., and a high percentage, e.g., 50%, formamide. Following prehybridization, 5'-$^{32}P$-labeled oligonucleotide probe is added to the buffer, and the filters are incubated in this mixture under hybridization conditions. After washing, the treated filters are subjected to autoradiography to show the location of the hybridized probe; DNA in corresponding locations on the original agar plates is used as the source of the desired DNA.

III.F. Verification of Construction and Sequencing

For routine vector constructions, ligation mixtures are transformed into E. coli strain HB101 or other suitable host, and successful transformants selected by antibiotic resistance or other markers. Plasmids from the transformants are then prepared according to the method of Clewell et al.

(1969), usually following chloramphenicol amplification (Clewell (1972)). The DNA is isolated and analyzed, usually by restriction enzyme analysis and/or sequencing. Sequencing may be by the dideoxy method of Sanger et al. (1977) as further described by Messing et al. (1981), or by the method of Maxam et al. (1980). Problems with band compression, which are sometimes observed in GC rich regions, were overcome by use of T-deazoguanosine according to Barr et al. (1986).

III.G. Enzyme Linked Immunosorbent Assay

The enzyme-linked immunosorbent assay (ELISA) can be used to measure either antigen or antibody concentrations. This method depends upon conjugation of an enzyme to either an antigen or an antibody, and uses the bound enzyme activity as a quantitative label. To measure antibody, the known antigen is fixed to a solid phase (e.g., a microplate or plastic cup), incubated with test serum dilutions, washed, incubated with anti-immunoglobulin labeled with an enzyme, and washed again. Enzymes suitable for labeling are known in the art, and include, for example, horseradish peroxidase. Enzyme activity bound to the solid phase is measured by adding the specific substrate, and determining product formation or substrate utilization calorimetrically. The enzyme activity bound is a direct function of the amount of antibody bound.

To measure antigen, a known specific antibody is fixed to the solid phase, the test material containing antigen is added, after an incubation the solid phase is washed, and a second enzyme-labeled antibody is added. After washing, substrate is added, and enzyme activity is estimated calorimetrically, and related to antigen concentration.

IV. Examples

Described below are examples of the present invention which are provided only for illustrative purposes, and not to limit the scope of the present invention. In light of the present disclosure, numerous embodiments within the scope of the claims will be apparent to those of ordinary skill in the art. The procedures set forth, for example, in Sections IV.A. may, if desired, be repeated but need not be, as techniques are available for construction of the desired nucleotide sequences based on the information provided by the invention. Expression is exemplified in *E. coli;* however, other systems are available as set forth more fully in Section III.A. Additional epitopes derived from the genomic structure may also be produced, and used to generate antibodies as set forth below.

IV.A. Preparation, Isolation and Sequencing of HCV cDNA

IV.A.1. Preparation of HCV cDNA

The source of NANB agent was a plasma pool derived from a chimpanzee with chronic NANBH. The chimpanzee had been experimentally infected with blood from another chimpanzee with chronic NANBH resulting from infection with HCV in a contaminated batch of factor 8 concentrate derived from pooled human sera. The chimpanzee plasma pool was made by combining many individual plasma samples containing high levels of alanine aminotransferase activity; this activity results from hepatic injury due to the HCV infection. Since 1 mL of a $10^{-6}$ dilution of this pooled serum given i.v. caused NANBH in another chimpanzee, its CID was at least $10^6$/mL, i.e., it had a high infectious virus titer.

A cDNA library from the high titer plasma pool was generated as follows. First, viral particles were isolated from the plasma; a 90 mL aliquot was diluted with 310 mL of a solution containing 50 mM Tris-HCl, pH 8.0, 1 mM EDTA, 100 mM NaCl. Debris was removed by centrifugation for 20 min at 15,000 x g at 20° C. Viral particles in the resulting supernatant were then pelleted by centrifugation in a Beckman SW28 rotor at 28,000 rpm for 5 hours at 20° C. To release the viral genome, the particles were disrupted by suspending the pellets in 15 mL solution containing 1% sodium dodecyl sulfate (SDS), 10 mM EDTA, 10 mM Tris-HCl, pH 7.5, also containing 2 mg/mL proteinase k, followed by incubation at 45° C. for 90 min. Nucleic acids were isolated by adding 0.8 mg MS2 bacteriophage RNA as carrier, and extracting the mixture four times with a 1:1 mixture of phenol:chloroform (phenol saturated with 0.05 M Tris-HCl, pH 7.5, 0.1% (v/v) b-mercaptoethanol, 0.1% (w/v) hydroxyquinolone, followed by extraction twice with chloroform. The aqueous phase was concentrated with 1-butanol prior to precipitation with 2.5 volumes absolute ethanol overnight at –20° C. Nucleic acid was recovered by centrifugation in a Beckman SW41 rotor at 40,000 rpm for 90 min at 4° C., and dissolved in water that had been treated with 0.05% (v/v) diethylpyrocarbonate and autoclaved.

Nucleic acid obtained by the above procedure (<2 mg) was denatured with 17.5 mM $CH_3HgOH$; cDNA was synthesized using this denatured nucleic acid as template, and was cloned into the EcoRI site of phage λgt11 using methods described by Huynh (1985), except that random primers replaced oligo(dT) 12–18 during the synthesis of the first cDNA strand by reverse transcriptase (Taylor et al. (1976)). The resulting double stranded cDNAs were fractionated according to size on a Sepharose® CL-4B column; eluted material of approximate mean size 400, 300, 200, and 100 base-pairs were pooled into cDNA pools 1, 2, 3, and 4, respectively. The λgt11 cDNA library was generated from the cDNA in pool 3.

The λgt11 cDNA library generated from pool 3 was screened for epitopes that could bind specifically with serum derived from a patient who had previously experienced NANBH. About $10^6$ phage were screened with patient sera using the methods of Huynh et al. (1985), except that bound human antibody was detected with sheep anti-human Ig antisera that had been radio-labeled with $^{125}I$. Five positive phages were identified and purified. The five positive phages were then tested for specificity of binding to sera from 8 different humans previously infected with the NANBH agent, using the same method. Four of the phage encoded a polypeptide that reacted immunologically with only one human serum, i.e., the one that was used for primary screening of the phage library. The fifth phage (5-1-1) encoded a polypeptide that reacted immunologically with 5 of 8 of the sera tested. Moreover, this polypeptide did not react immunologically with sera from 7 normal blood donors. Therefore, it appears that clone 5-1-1 encodes a polypeptide which is specifically recognized immunologically by sera from NANB patients.

IV.A.2. Sequences of the HCV cDNA in Recombinant Phage 5-1-1, and of the Polypeptide Encoded Within the Sequence.

The cDNA in recombinant phage 5-1-1 was sequenced by the method of Sanger et al. (1977). Essentially, the cDNA was excised with EcoRI, isolated by size fractionation using gel electrophoresis. The EcoRI restriction fragments were subcloned into the M13 vectors, mp 18 and mp 19 (Messing (1983)) and sequenced using the dideoxy chain termination method of Sanger et al. (1977). The sequence obtained is shown in FIG. 1.

The polypeptide encoded in FIG. 1 that is encoded in the HCV cDNA is in the same translational frame as the N-terminal b-galactosidase moiety to which it is fused. As shown in Section IV.A., the translational open reading frame (ORF) of 5-1-1 encodes epitope(s) specifically recognized by sera from patients and chimpanzees with NANBH infections.

IV.A.3. Isolation of Overlapping HCV cDNA to cDNA in Clone 5-1-1.

Overlapping HCV cDNA to the cDNA in clone 5-1-1 was obtained by screening the same λgt11 library, created as described in Section IV.A.1., with a synthetic polynucleotide derived from the sequence of the HCV cDNA in clones 5-1-1, as shown in FIG. 1. The sequence of the polynucleotide used for screening was:

5'-TCC CTT GCT CGA TGT ACG GTA AGT GCT GAG AGC
ACT CTT CCA TCT CAT CGA ACT CTC GGT AGA GGA
CTT CCC TGT CAG GT-3'   (SEQ ID NO:178).

The λgt11 library was screened with this probe, using the method described in Huynh (1985). Approximately 1 in 50,000 clones hybridized with the probe. Three clones which contained cDNAs which hybridized with the synthetic probe have been numbered 81, 1-2, and 91.

IV.A.4. Nucleotide Sequences of Overlapping HCV cDNAs to cDNA in Clone 5-1-1.

The nucleotide sequences of the three cDNAs in clones 81, 1-2, and 91 were determined essentially as in Section IV.A.2. The sequences of these clones relative to the HCV cDNA sequence in phage 5-1-1 is shown in FIG. 2, which shows the strand encoding the detected HCV epitope, and where the homologies in the nucleotide sequences are indicated by vertical lines between the sequences.

The sequences of the cloned HCV cDNAs are highly homologous in the overlapping regions (see FIG. 2). However, there are differences in two regions. Nucleotide 67 in clone 1-2 is a thymidine, whereas the other three clones contain a cytidine residue in this position. It should be noted, however, that the same amino acid is encoded when either C or T occupies this position.

The second difference is that clone 5-1-1 contains 28 base pairs which are not present in the other three clones. These base pairs occur at the start of the cDNA sequence in 5-1-1, and are indicated by small letters. The 28 bp region is probably a terminal artifact in clone 5-1 -1 which enhances its antigenicity.

The sequences of small letters in the nucleotide sequence of clones 81 and 91 simply indicate that these sequences have not been found in other cDNAs because cDNAs overlapping these regions were not yet isolated.

A composite HCV cDNA sequence derived from overlapping cDNAs in clones 5-1-1, 81, 1-2 and 91 is shown in FIG. 3. However, in this figure the unique 28 base pairs of clone 5-1-1 are omitted. The figure also shows the sequence of the polypeptide encoded within the ORF of the composite HCV cDNA.

IV.A.5. Isolation of Overlapping HCV cDNAs to cDNA in Clone 81.

The isolation of HCV cDNA sequences upstream of, and which overlap those in clone 81 cDNA was accomplished as follows. The λgt11 cDNA library prepared as described in Section IV.A.1. was screened by hybridization with a synthetic polynucleotide probe which was homologous to a 5'-terminal sequence of clone 81. The sequence of clone 81 is presented in FIG. 4. The sequence of the synthetic polynucleotide used for screening was:

5' CTG TCA GGT ATG ATT GCC GGC TTC CCG
GAC 3'   (SEQ ID NO:179).

The methods were essentially as described in Huynh (1985), except that the library filters were given two washes under stringent conditions, i.e., the washes were in 5' SSC, 0.1% SDS at 55° C. for 30 minutes each. Approximately 1 in 50,000 clones hybridized with the probe. A positive recombinant phage which contained cDNA which hybridized with the sequence was isolated and purified. This phage has been numbered clone 36.

Downstream cDNA sequences, which overlaps the carboxyl-end sequences in clone 81 cDNA were isolated using a procedure similar to that for the isolation of upstream cDNA sequences, except that a synthetic oligonucleotide probe was prepared which is homologous to a 3' terminal sequence of clone 81. The sequence of the synthetic polynucleotide used for screening was:

5' TTT GGC TAG TGG TTA GTG GGC TGG TGA
CAG 3'   (SEQ ID NO:180).

A positive recombinant phage, which contained cDNA which hybridized with this latter sequence was isolated and purified, and has been numbered clone 32.

IV.A.6. Nucleotide Sequence of HCV cDNA in Clone 36.

The nucleotide sequence of the cDNA in clone 36 was determined essentially as described in Section IV.A.2. The double-stranded sequence of this cDNA, its region of overlap with the HCV cDNA in clone 81, and the polypeptide encoded by the ORF are shown in FIG. 5.

The ORF in clone 36 is in the same translational frame as the HCV antigen encoded in clone 81. Thus, in combination, the ORFs in clones 36 and 81 encode a polypeptide that represents part of a large HCV antigen. The sequence of this putative HCV polypeptide and the double stranded DNA sequence encoding it, which is derived from the combined ORFs of the HCV cDNAs of clones 36 and 81, is shown in FIG. 6.

IV.A.7 Nucleotide Sequences of HCV cDNA in Clone 32

The nucleotide sequence of the cDNA in clone 32 was determined essentially as was that described in Section IV.A.2 for the sequence of clone 5-1-1. The sequence data indicated that the cDNA in clone 32 recombinant phage was derived from two different sources. One fragment of the cDNA was comprised of 418 nucleotides derived from the HCV genome; the other fragment was comprised of 172 nucleotides derived from the bacteriophage MS2 genome, which had been used as a carrier during the preparation of the λgt11 plasma cDNA library.

The sequence of the cDNA in clone 32 corresponding to that of the HCV genome is shown in FIG. 7. The region of the sequences that overlaps that of clone 81, and the polypeptide encoded by the ORF are also indicated in the figure. This sequence contains one continuous ORF that is in the same translational frame as the HCV antigen encoded by clone 81.

IV.A.8 Isolation of Overlapping HCV cDNA to cDNA in Clone 36

The isolation of HCV cDNA sequences upstream of, and which overlap those in clone 36 cDNA was accomplished as described in Section IV.A.5, for those which overlap clone 81 cDNA, except that the synthetic polynucleotide was based on the 5'-region of clone 36. The sequence of the synthetic polynucleotide used for screening was:

5' AAG CCA CCG TGT GCG CTA GGG CTC AAG
CCC 3'   (SEQ ID NO:181).

Approximately 1 in 50,000 clones hybridized with the probe. The isolated, purified clone of recombinant phage which contained cDNA which hybridized to this sequence was named clone 35.

IV.A.9 Nucleotide Sequence of HCV cDNA in Clone 35

The nucleotide sequence of the cDNA in clone 35 was determined essentially as described in Section IV.A.2. The sequence, its region of overlap with that of the cDNA in clone 36, and the putative polypeptide encoded therein, are shown in FIG. 8.

Clone 35 apparently contains a single, continuous ORF that encodes a polypeptide in the same translational frame as that encoded by clone 36, clone 81, and clone 32. FIG. 9 shows the sequence of the long continuous ORF that extends through clones 35, 36, 81, and 32, along with the putative HCV polypeptide encoded therein. This combined sequence has been confirmed using other independent cDNA clones derived from the same λgt11 cDNA library.

IV.A.10. Isolation of Overlapping HCV cDNA to cDNA in Clone 35

The isolation of HCV cDNA sequences upstream of, and which overlap those in clone 35 cDNA was accomplished as described in Section IV.A.8, for those which overlap clone 36 cDNA, except that the synthetic polynucleotide was based on the 5'-region of clone 35. The sequence of the synthetic polynucleotide used for screening was:

5' CAG GAT GCT GTC TCC CGC ACT CAA
    CGT 3'                              (SEQ ID NO:182).

Approximately 1 in 50,000 clones hybridized with the probe. The isolated, purified clone of recombinant phage which contained cDNA which hybridized to this sequence was named clone 37b.

IV.A.11. Nucleotide Sequence of HCV in Clone 37b

The nucleotide sequence of the cDNA in clone 37b was determined essentially as described in Section IV.A.2. The sequence, its region of overlap with that of the cDNA in clone 35, and the putative polypeptide encoded therein, are shown in FIG. 10.

The 5'-terminal nucleotide of clone 35 is a T, whereas the corresponding nucleotide in clone 37b is an A. The cDNAs from three other independent clones which were isolated during the procedure in which clone 37b was isolated, described in Section IV.A.10, have also been sequenced. The cDNAs from these clones also contain an A in this position. Thus, the 5'-terminal T in clone 35 may be an artifact of the cloning procedure. It is known that artifacts often arise at the 5'-termini of cDNA molecules.

Clone 37b apparently contains one continuous ORF which encodes a polypeptide which is a continuation of the polypeptide encoded in the ORF which extends through the overlapping clones 35, 36, 81 and 32.

IV.A.12. Isolation of Overlapping HCV cDNA to cDNA in Clone 32

The isolation of HCV cDNA sequences downstream of clone 32 was accomplished as follows. First, clone cla was isolated utilizing a synthetic hybridization probe which was based on the nucleotide sequence of the HCV cDNA sequence in clone 32. The method was essentially that described in Section IV.A.5, except that the sequence of the synthetic probe was:

5' AGT GCA GTG GAT GAA CCG GCT GAT AGC
    CTT 3'                              SEQ ID NO:183).

Utilizing the nucleotide sequence from clone cla, another synthetic nucleotide was synthesized which had the sequence:

5' TCC TGA GGC GAC TGC ACC AGT GGA TAA
    GCT 3'                              SEQ ID NO:184).

Screening of the λgt11 library using the clone cla derived sequence as probe yielded approximately 1 in 50,000 positive colonies. An isolated, purified clone which hybridized with this probe was named clone 33b.

IV.A.13. Nucleotide Sequence of HCV cDNA in Clone 33b

The nucleotide sequence of the cDNA in clone 33b was determined essentially as described in Section IV.A.2. The sequence, its region of overlap with that of the cDNA in clone 32, and the putative polypeptide encoded therein, are shown in FIG. 11.

Clone 33b apparently contains one continuous ORF which is an extension of the ORFs in overlapping clones 37b, 35, 36, 81 and 32. The polypeptide encoded in clone 33b is in the same translational frame as that encoded in the extended ORF of these overlapping clones.

IV.A. 14. Isolation of Overlapping HCV cDNAs to cDNA Clone 37b and to cDNA in Clone 33b In order to isolate HCV cDNAs which overlap the cDNAs in clone 37b and in clone 33b, the following synthetic oligonucleotide probes, which were derived from the cDNAs in those clones, were used to screen the λgt11 library, using essentially the method described in Section IV.A.3. The probes used were:

5° CAG GAT GCT GTC TCC CGC ACT CAA CGT
    C 3'                                (SEQ ID NO:185)

and

5' TCC TGA GGC GAC TGC ACC ACT GGA TAA
    GCT 3'                              (SEQ ID NO: 186)

to detect colonies containing HCV cDNA sequences which overlap those in clones 37b and 33b, respectively. Approximately 1 in 50,000 colonies were detected with each probe. A clone which contained cDNA which was upstream of, and which overlapped the cDNA in clone 37b, was named clone 40b. A clone which contained cDNA which was downstream of, and which overlapped the cDNA in clone 33b was named clone 25c.

IV.A.15 Nucleotide Sequences of HCV cDNA in clone 40b and in clone 25c

The nucleotide sequences of the cDNAs in clone 40b and in clone 25c were determined essentially as described in Section IV.A.2. The sequences of 40b and 25c, their regions of overlap with the cDNAs in clones 37b and 33b, and the putative polypeptides encoded therein, are shown in FIG. 12 (clone 40b) and FIG. 13 (clone 25c).

The 5'-terminal nucleotide of clone 40b is a G. However, the cDNAs from five other independent clones which were isolated during the procedure in which clone 40b was isolated, described in Section IV.A.14, have also been sequenced. The cDNAs from these clones also contain a T in this position. Thus, the G may represent a cloning artifact (see the discussion in Section IV.A.11).

The 5'-terminus of clone 25c is ACT, but the sequence of this region in clone cla (sequence not shown), and in clone 33b is TCA. This difference may also represent a cloning artifact, as may the 28 extra 5'-terminal nucleotides in clone 5-1-1.

Clones 40b and 25c each apparently contain an ORF which is an extension of the continuous ORF in the previously sequenced clones. The nucleotide sequence of the ORF extending through clones 40b, 37b, 35, 36, 81, 32, 33b, and 25c, and the amino acid sequence of the putative polypeptide encoded therein, are shown in FIG. 14. In the figure, the potential artifacts have been omitted from the sequence, and instead, the corresponding sequences in non-5'-terminal regions of multiple overlapping clones are shown.

IV.A.16. Preparation of a Composite HCV cDNA from the cDNAs in Clones 36 81. and 32

The composite HCV cDNA, C100, was constructed as follows. First the cDNAs from the clones 36, 81, and 32 were excised with EcoRI. The EcoRI fragment of cDNA from each clone was cloned individually into the EcoRI site of the vector pGEM3 -blue (Promega Biotec). The resulting recombinant vectors which contained the cDNAs from clones 36, 81, and 32 were named pGEM3-blue/36, pGEM3-blue/81, and pGEM3-blue/32, respectively. The appropriately oriented recombinant of pGEM3-blue/81 was digested with NaeI and NarI, and the large (~2850 bp) fragment was purified and ligated with the small (~570bp) NaeI/NarI purified restriction fragment from pGEM3-blue/36. This composite of the cDNAs from clones 36 and 81 was used to generate another pGEM3-blue vector containing the continuous HCV ORF contained within the overlapping cDNA within these clones. This new plasmid was then digested with PvuII and EcoRi to release a fragment of approximately 680bp, which was then ligated with the small (580 bp) PvuII/EcoRI fragment isolated from the appropriately oriented pGEM3-blue/32 plasmid, and the composite cDNA from clones 36, 81, and 32 was ligated into the EcoRI linearized vector pSODcf1, which is described in Section IV.B.1, and which was used to express clone 5-1-1 in bacteria. Recombinants containing the 1270 bp EcoRI fragment of composite HCV cDNA (C100) were selected, and the cDNA from the plasmids was excised with EcoRI and purified.

IV.A.17. Isolation and Nucleotide Sequences of HCV cDNAs in Clones 14i, 11b, 7f. 7e, 8h 33c, 14c, 8f 33f 33g, and 39c The HCV cDNAs in clones 14i, 11b, 7f, 7e, 8h, 33c, 14c, 8f, 33f, 33g, and 39c were isolated by the technique of isolating overlapping cDNA fragments from the λgt11 library of HCV cDNAs described in Section IV.A.1. The technique used was essentially as described in Section IV.A.3., except that the probes used were designed from the nucleotide sequence of the last isolated clones from the 5' and the 3' end of the combined HCV sequences. The frequency of clones which hybridized with the probes described below was approximately 1 in 50,000 in each case.

The nucleotide sequences of the HCV cDNAs in clones 14i, 7f, 7e, 8h, 33c, 14c, 8f, 33f, 33g, and 39c were determined essentially as described in Section IV.A.2., except that the cDNA excised from these phages were substituted for the cDNA isolated from clone 5-1-1.

Clone 33c was isolated using a hybridization probe based on the sequence of nucleotides in clone 40b. The nucleotide sequence of clone 40b is presented in FIG. 12. The nucleotide sequence of the probe used to isolate 33c was:

5' ATC AGG ACC GGG GTG AGA ACA ATT ACC
    ACT 3'    (SEQ ID NO:187).

The sequence of the HCV cDNA in clone 33c, and the overlap with that in clone 40b, is shown in FIG. 15, which also shows the amino acids encoded therein.

Clone 8h was isolated using a probe based on the sequence of nucleotides in clone 33c. The nucleotide sequence of the probe was

5' AGA GAC AAC CAT GAG GTC CCC GGT
    GTT C 3'    (SEQ ID NO: 188).

The sequence of the HCV cDNA in clone 8h, and the overlap with that in clone 33c, and the amino acids encoded therein, are shown in FIG. 16.

Clone 7e was isolated using a probe based on the sequence of nucleotides in clone 8h. The nucleotide sequence of the probe was

5' TCG GAC CTT TAC CTG GTC ACG AGG
    CAC 3'    (SEQ ID NO: 189).

The sequence of HCV cDNA in clone 7e, the overlap with clone 8h, and the amino acids encoded therein, are shown in FIG. 17.

Clone 14c was isolated with a probe based on the sequence of nucleotides in clone 25c. The sequence of clone 25c is shown in FIG. 13. The probe in the isolation of clone 14c had the sequence

5' ACC TTC CCC ATT AAT GCC TAC ACC ACG
    GGC 3'    (SEQ ID NO:190).

The sequence of HCV cDNA in clone 14c, its overlap with that in clone 25c, and the amino acids encoded therein are shown in FIG. 18.

Clone 8f was isolated using a probe based on the sequence of nucleotides in clone 14c. The nucleotide sequence of the probe was

5' TCC ATC TCT CAA GGC AAC TTG CAC CGC
    TAA 3'    (SEQ ID NO: 191).

The sequence of HCV cDNA in clone 8f, its overlap with that in clone 14c, and the amino acids encoded therein are shown in FIG. 19.

Clone 33f was isolated using a probe based on the nucleotide sequence present in clone 8f. The nucleotide sequence of the probe was

5' TCC ATG GCT GTC CGC TTC CAC CTC CAA
    AGT 3'    (SEQ ID NO:192).

The sequence of HCV cDNA in clone 33f, its overlap with that in clone 8f, and the amino acids encoded therein are shown in FIG. 20.

Clone 33g was isolated using a probe based on the sequence of nucleotides in clone 33f. The nucleotide sequence of the probe was

5' GCG ACA ATA CGA CAA CAT CCT CTG AGC
    CCG 3'    (SEQ ID NO:193).

The sequence of HCV cDNA in clone 33g, its overlap with that in clone 33f, and the amino acids encoded therein are shown in FIG. 21.

Clone 7f was isolated using a probe based on the sequence of nucleotides in clone 7e. The nucleotide sequence of the probe was

5' AGC AGA CAA GGG GCC TCC TAG GGT GCA
    TAA T 3'    (SEQ ID NO:194).

The sequence of HCV cDNA in clone 7f, its overlap with clone 7e, and the amino acids encoded therein are shown in FIG. 22.

Clone 11b was isolated using a probe based on the sequence of clone 7f. The nucleotide sequence of the probe was

5' CAC CTA TGT TTA TAA CCA TCT CAC TCC
    TCT 3'    (SEQ ID NO:195).

The sequence of HCV cDNA in clone 11b, its overlap with clone 7f, and the amino acids encoded therein are shown in FIG. 23.

Clone 14i was isolated using a probe based on the sequence of nucleotides in clone 11b. The nucleotide sequence of the probe was

5' CTC TGT CAC CAT ATT ACA AGC GCT ATA
    TCA 3'    (SEQ ID NO:196).

The sequence of HCV cDNA in clone 14i, its overlap with 11b, and the amino acids encoded therein are shown in FIG. 24.

Clone 39c was isolated using a probe based on the sequence of nucleotides in clone 33g. The nucleotide sequence of the probe was

5' CTC GTT GCT ACG TCA CCA CAA TTT GGT
GTA 3' (SEQ ID NO:197).

The sequence of HCV cDNA in clone 39c, its overlap with clone 33g, and the amino acids encoded therein are shown in FIG. 25.

IV.A.18. The Composite HCV cDNA Sequence Derived from Isolated Clones Containing HCV cDNA The HCV cDNA sequences in the isolated clones described supra have been aligned to create a composite HCV cDNA sequence. The isolated clones, aligned in the 5' to 3' direction are: 14i, 7f, 7e, 8h, 33c, 40b, 37b, 35, 36, 81, 32, 33b, 25c, 14c, 8f, 33f, 33g, and 39c.

A composite HCV cDNA sequence derived from the isolated clones, and the amino acids encoded therein, is shown in FIG. 26.

In creating the composite sequence the following sequence heterogeneities have been considered. Clone 33c contains an HCV cDNA of 800 base pairs, which overlaps the cDNAs in clones 40b and 37c. In clone 33c, as well as in 5 other overlapping clones, nucleotide #789 is a G. However, in clone 37b (see Section IV.A. 11), the corresponding nucleotide is an A. This sequence difference creates an apparent heterogeneity in the amino acids encoded therein, which would be either CYS or TYR, for G or A, respectively. This heterogeneity may have important ramifications in terms of protein folding.

Nucleotide residue #2 in clone 8h HCV cDNA is a T. However, as shown infra, the corresponding residue in clone 7e is an A; moreover, an A in this position is also found in 3 other isolated overlapping clones. Thus, the T residue in clone 8h may represent a cloning artifact. Therefore, in FIG. 26, the residue in this position is designated as an A.

The 3'-terminal nucleotide in clone 8f HCV cDNA is a G. However, the corresponding residue in clone 33f, and in 2 other overlapping clones is a T. Therefore, in FIG. 26, the residue in this position is designated as a T.

The 3'-terminal sequence in clone 33f HCV cDNA is TTGC. However, the corresponding sequence in clone 33g and in 2 other overlapping clones is ATTC. Therefore, in FIG. 26, the corresponding region is represented as ATTC.

Nucleotide residue #4 in clone 33g HCV cDNA is a T. However, in clone 33f and in 2 other overlapping clones the corresponding residue is an A. Therefore, in FIG. 26, the corresponding residue is designated as an A.

The 3'-terminus of clone 14i is an AA, whereas the corresponding dinucleotide in clone 11b, and in three other clones, is TA. Therefore, in FIG. 26, the TA residue is depicted.

The resolution of other sequence heterogeneities is discussed supra.

An examination of the composite HCV cDNA indicates that it contains one large ORF. This suggests that the viral genome is translated into a large polypeptide which is processed concomitant with, or subsequent to translation.

IV.A.19. Isolation and Nucleotide Sequences of HCV cDNAs in Clones 12f, 35f 19g. 26g, and 15e The HCV cDNAs in clones 12f, 35f, 19g, 26g, and 15e were isolated essentially by the technique described in Section IV.A.17, except that the probes were as indicated below. The frequency of clones which hybridized with the probes was approximately 1 in 50,000 in each case. The nucleotide sequences of the HCV cDNAs in these clones were determined essentially as described in Section IV.A.2., except that the cDNA from the indicated clones were substituted for the cDNA isolated from clone 5-1-1.

The isolation of clone 12f, which contains cDNA upstream of the HCV cDNA in FIG. 26, was accomplished using a hybridization probe based on the sequence of nucleotides in clone 14i. The nucleotide sequence of the probe was

5' TGC TTG TGG ATG ATG CTA CTC ATA TCC
CAA 3' (SEQ ID NO:198).

The HCV cDNA sequence of clone 12f, its overlap with clone 14i, and the amino acids encoded therein are shown in FIG. 27.

The isolation of clone 35f, which contains cDNA downstream of the HCV cDNA in FIG. 26, was accomplished using a hybridization probe based on the sequence of nucleotides in clone 39c. The nucleotide sequence of the probe was

5' AGC AGC GGC GTC AAA AGT GAA GGC TAA
CTT 3' (SEQ ID NO:199).

The sequence of clone 35f, its overlap with the sequence in clone 39c, and the amino acids encoded therein are shown in FIG. 28.

The isolation of clone 19g was accomplished using a hybridization probe based on the 3' sequence of clone 35f. The nucleotide sequence of the probe was

5' TTC TCG TAT GAT ACC CGC TGC TTT GAC
TCC 3' (SEQ ID NO:200).

The HCV cDNA sequence of clone 19g, its overlap with the sequence in clone 35f, and the amino acids encoded therein are shown in FIG. 29.

The isolation of clone 26g was accomplished using a hybridization probe based on the 3' sequence of clone 19g. The nucleotide sequence of the probe was

5' TGT GTG GCG ACG ACT TAG TCG TTA TCT
GTG 3' (SEQ ID NO:201).

The HCV cDNA sequence of clone 26g, its overlap with the sequence in clone 19g, and the amino acids encoded therein are shown in FIG. 30.

Clone 15e was isolated using a hybridization probe based on the 3' sequence of clone 26g. The nucleotide sequence of the probe was

5' CAC ACT CCA GTC AAT TCC TGG CTA GGC
AAC 3' (SEQ ID NO:202).

The HCV cDNA sequence of clone 15e, its overlap with the sequence in clone 26g, and the amino acids encoded therein are shown in FIG. 31.

The HCV cDNA sequences in the isolated clones described supra. have been aligned to create a composite HCV cDNA sequence. The isolated clones, aligned in the 5' to 3' direction are: 12f, 14i, 7f, 7e, 8h, 33c, 40b, 37b, 35, 36, 81, 32, 33b, 25c, 14c, 8f 33f, 33g, 39c, 35f, 19g, 26g, and 15e.

A composite HCV cDNA sequence derived from the isolated clones, and the amino acids encoded therein, is shown in FIG. 32.

IV.A.20. Alternative Method of Isolating cDNA Sequences Upstream of the HCV cDNA Sequence in Clone 12f Based on the most 5' HCV sequence in FIG. 32, which is derived from the HCV cDNA in clone 12f, small synthetic oligonucleotide primers of reverse transcriptase are synthesized and used to bind to the corresponding sequence in HCV genomic RNA, to prime reverse transcription of the upstream sequences. The primer sequences are proximal to the known 5'-terminal sequence of clone 12f, but sufficiently downstream to allow the design of probe sequences upstream of the primer sequences. Known standard methods of priming and cloning are used. The resulting cDNA libraries are screened with sequences upstream of the priming sites (as deduced from the elucidated sequence in clone 12f). The HCV genomic RNA is obtained from either plasma or liver samples from chimpanzees with NANBH, or from analogous samples from humans with NANBH.

IV.A.21. Alternative Method Utilizing Tailing to Isolate Sequences from the 5'-Terminal Region of the HCV Genome In order to isolate the extreme 5'-terminal sequences of the HCV RNA genome, the cDNA product of the first round of reverse transcription, which is duplexed with the template RNA, is tailed with oligo C. This is accomplished by incubating the product with terminal transferase in the presence of CTP. The second round of cDNA synthesis, which yields the complement of the first strand of cDNA, is accomplished utilizing oligo G as a primer for the reverse transcriptase reaction. The sources of genomic HCV RNA are as described in Section IV.A.20. The methods for tailing with terminal transferase, and for the reverse transcriptase reactions are as in Maniatis et al (1982). The cDNA products are then cloned, screened, and sequenced.

IV.A.22. Alternative Method Utilizing Tailing, to Isolate Sequences from the 3'-Terminal Region of the HCV Genome This method is based on previously used methods for cloning cDNAs of Flavivirus RNA. In this method, the RNA is subjected to denaturing conditions to remove secondary structures at the 3'-terminus, and is then tailed with Poly A polymerase using rATP as a substrate. Reverse transcription of the poly A tailed RNA is catalyzed by reverse transcriptase, utilizing oligo dT as a primer. The second strands of cDNA are synthesized, the cDNA products are cloned, screened, and sequenced.

IV.A.23. Creation of λgt11 HCV cDNA Libraries Containing Larger cDNA Inserts

The method used to create and screen the λgt11 libraries are essentially as described in Section IV.A.1., except that the library is generated from a pool of larger size cDNAs eluted from the ion exchange column Sepharose® (Pharmacia) CL-4B column.

IV.A.24. Creation of HCV cDNA Libraries Using Synthetic Oligomers as Primers

New HCV CDNA libraries have been prepared from the RNA derived from the infectious chimpanzee plasma pool described in Section IV.A.1., and from the poly $A^+$ RNA fraction derived from the liver of this infected animal. The cDNA was constructed essentially as described by Gubler and Hoffman (1983), except that the primers for the first cDNA strand synthesis were two synthetic oligomers based on the sequence of the HCV genome described supra. Primers based on the sequence of clone 11 b and 7e were, respectively,

5' CTG GCT TGA AGA ATC 3'  (SEQ ID NO:203)

and

5' AGT TAG GCT GGT GAT TAT GC 3'  (SEQ ID NO:204).

The resulting cDNAs were cloned into X bacteriophage vectors, and screened with various other synthetic oligomers, whose sequences were based on the HCV sequence in FIG. 32.

IV.A.25. Creation of HCV cDNA Library From Liver of a Chimpanzee with Infectious NANBH An HCV CDNA library was created from liver from the chimpanzee from which the HCV cDNA library in Section IV.A.1. was created. The technique for creating the library was similar to that in Section IV.A.24, except for this different source of the RNA, and that a primer based on the sequence of HCV cDNA in clone 11b was used. The sequence of the primer was

5' CTG GCT TGA AGA ATC 3'.  (SEQ ID NO:203)

IV.A.26. Isolation and Nucleotide Sequence of Overlapping HCV cDNA in Clone k9-1 to cDNA in Clone 11b Clone k9- 1 was isolated from the HCV cDNA library created from the liver of an NANBH infected chimpanzee, as described in Section IV.A.25. The library was screened for clones which overlap the sequence in clone 11b, by using a clone which overlaps clone 1 b at the 5'-terminus, clone 1 e. The sequence of clone 11b is shown in FIG. 23. Positive clones were isolated with a frequency of 1 in 500,000. One isolated clone, k9-1, was subjected to further study. The overlapping nature of the HCV cDNA in clone k9-1 to the 5'-end of the HCV-cDNA sequence in FIG. 26 was confirmed by probing the clone with clone Alex46; this latter clone contains an HCV cDNA sequence of 30 base pairs which corresponds to those base pairs at the 5'-terminus of the HCV cDNA in clone 14i, described supra.

The nucleotide sequence of the HCV cDNA isolated from clone k9-1 was determined using the techniques described supra. The sequence of the HCV cDNA in clone k9-1, the overlap with the HCV cDNA in FIG. 26 (indicated by the dotted line), and the amino acids encoded therein are shown in FIG. 46.

The HCV cDNA sequence in clone k9-1 has been aligned with those of the clones described in Section IV.A.19. to create a composite HCV cDNA sequence, with the k9-1 sequence being placed upstream of the sequence shown in FIG. 32. The composite HCV cDNA which includes the k9-1 sequence, and the amino acids encoded therein, is shown in FIG. 47.

IV.A.27. Isolation and Sequence of Overlapping HCV cDNA Clones 13i, 26j CA59a, CA84a, CA156e and CA167b The clones 13i, 26j, CA59a, CA84a, CA156e and CA167b were isolated from the λgt11 library described in Section IV.A.I. The frequencies with which positive clones appeared with the respective probes was about 1 in 50,000.

The isolation of clone 13i was accomplished using a synthetic probe derived from the sequence of clone 12f. The sequence of the probe was:

5'GAA CGT TGC GAT CTG GAA GAC AGG GAC
    AGG 3'                              (SEQ ID NO:205).

The isolation of clone 26j was accomplished using a probe derived from the 5'-region of clone k9-1. The sequence of the probe was:

5' TAT CAG TTA TGC CAA CGG AAG CGG CCC
    CGA 3'                              (SEQ ID NO:206).

The HCV cDNA sequences of clones 13i and 26j, are shown in FIGS. 48 and 49, respectively. Also shown are the amino acids encoded therein, as well as the overlap of clone 13i with clone 12f, and the overlap of clone 26j with clone 13i. The sequences for these clones confirmed the sequence of clone k9- 1, which had been isolated from a different HCV cDNA library (see Section IV.A.26).

Clone CA59a was isolated utilizing a probe based upon the sequence of the 5'-region of clone 26j. The sequence of this probe was:

5° CTG GTT AGC AGG GCT TTT CTA TCA CCA
    CAA 3'                              (SEQ ID NO:207).

A probe derived from the sequence of clone CA59a was used to isolate clone CA84a. The sequence of the probe used for this isolation was:

5' AAG GTC CTG GTA GTG CTG CTG CTA TTT
    GCC 3'                              (SEQ ID NO:208).

Clone CA156e was isolated using a probe derived from the sequence of clone CA84a. The sequence of the probe was:

5' ACT GGA CGA CGC AAG GTT GCA ATT GCT
CTA 3' (SEQ ID NO:209).

Clone CA167b was isolated using a probe derived from the sequence of clone CA 156e. The sequence of the probe was:

5' TTC GAC GTC ACA TCG ATC TGC TTG TCG
GGA 3' (SEQ ID NO:210).

The nucleotide sequences of the HCV cDNAs in clones CA59a, CA84a, CA156e, and CA167b, are shown FIGS. 50, 51, 52, and 53, respectively. The amino acids encoded therein, as well as the overlap with the sequences of relevant clones, are also shown in the Figs.

IV.A.28. Creation of "pi" HCV cDNA Library

A library of HCV cDNA, the "pi" library, was constructed from the same batch of infectious chimpanzee plasma used to construct the λgt11 described in Section IV.A.1, and utilizing essentially the same techniques. However, construction of the pi library utilized a primer-extension method, in which the primer for reverse transcriptase was based on the sequence of clone CA59A. The sequence of the primer was:

5' GGT GAC GTG GGT TTC 3' (SEQ ID NO:211).

IV.A.29. Isolation and Sequence of Clone pi14a

Screening of the "pi" HCV cDNA library described in Section IV.A.28 with the probe used to isolate clone CA167b (see Section IV.A.27.) yielded clone pi14a. The clone contains about 800 base pairs of cDNA which overlaps clones CA16i7b, CA156e, CA84a and CA59a (which were isolated from the HCV cDNA library described in Section IV.A.1.). In addition, pi14a also contains about 250 base pairs of DNA which are upstream of the HCV cDNA in clone CA167b.

The combined ORF derived from the HCV cDNA sequences in clones pi14a, CA167b, CA156e, CA84a, CA59a, k9-1, 12f, 14i, 11b, 7f, 7e, 8h, 33c, 40b, 37b, 35, 36, 81, 32, 33b, 25c, 14c, 8f, 33f, 33g, 39c, 35f, 19g, 26g, and 15e is shown in FIG. 54; also shown are the amino acids encoded therein.

IV.A.30. Isolation and Sequence of Clones CA216a CA290a and ag30a

Based on the sequence of clone CA167b (see Section IV.A.27 and FIG. 53), a synthetic probe was made having the following sequence:

5' GGC TTT ACC ACG TCA CCA ATG ATT GCC
CTA 3' (SEQ ID NO:212).

The above probe was used to screen the λgt11 library described in Section IV.A. 1, which yielded clone CA216a, whose HCV sequences are shown in FIG. 56.

Another probe was made based on the sequence of clone CA216a having the following sequence:

5' TTT GGG TAA GGT CAT CGA TAC CCT TAC
GTG 3' (SEQ ID NO:213).

Screening the above library with this probe yielded clone CA290a, the HCV sequences therein being shown in FIG. 57.

In a parallel approach, a primer-extension cDNA library was made using nucleic acid extracted from the same infectious plasma used in the original λgt11 cDNA library described above. The primer used was based on the sequence of clones CA216a and CA290a:

5' GAA GCC GCA CGT AAG 3' (SEQ ID NO:214).

The cDNA library was made using methods similar to those described previously for libraries used in the isolation of clones pi14a and k9-1 (see Sections IV.A.26 and IV.A.29).

The probe used to screen this library was based on the sequence of clone CA290a:

5' CCG GCG TAG GTC GCG CAA TTT GGG
TAA 3' (SEQ ID NO:215).

Clone ag30a was isolated from the new library with the above probe, and contained about 670 basepairs of HCV sequence. See FIG. 58. Part of this sequence overlaps the HCV sequence of clones CA216a and CA290a. About 300 base-pairs of the ag3oa sequence, however, is upstream of the sequence from clone CA290a. The non-overlapping sequence shows a start codon (*) and stop codons that may indicate the start of the HCV ORF. Also indicated in FIG. 58 are putative small encoded peptides (#) which may play a role in regulating translation, as well as the putative first amino acid of the putative polypeptide (/), and downstream amino acids encoded therein.

IV.A.31. Isolation and Sequence of Clone CA205a

Clone CA205a was isolated from the original λgt11 library, using a synthetic probe derived from the HCV sequence in clone CA290a (FIG. 57). The sequence of the probe was:

5' TCA GAT COT TGG TGG AGT TTA CTT GTT
GCC 3' (SEQ ID NO:216).

The sequence of the HCV cDNA in CA205a, shown in FIG. 59, overlaps with the cDNA sequences in both clones ag3oa and CA290a. The overlap of the sequence with that of CA290a is shown by the dotted line above the sequence (the figure also shows the putative amino acids encoded in this fragment).

As observed from the HCV cDNA sequences in clones CA205a and ag30a, the putative HCV polyprotein appears to begin at the ATG start codon; the HCV sequences in both clones contain an in-frame, contiguous double stop codon (TGATAG) forty two nucleotides upstream from this ATG. The HCV ORF appears to begin after these stop codons, and to extend for at least 8907 nucleotides (see the composite HCV cDNA shown in FIG. 62).

IV.A.32. Isolation and Sequence of Clone 18g

Based on the sequence of clone ag3oa (see IV.A.30 and FIG. 58) and of an overlapping clone from the original λgt11 library, CA230a, a synthetic probe was made having the following sequence:

5' CCA TAG TOG TCT GCG GAA CCG GTG AGT
ACA 3' (SEQ ID NO:217).

Screening of the original λgt11 HCV cDNA library (described in Section IV.A.1.) with the probe yielded clone 18g, the HCV cDNA sequence of which is shown in FIG. 60. Also shown in the figure are the overlap with clone ag30a, and putative polypeptides encoded within the HCV cDNA.

The cDNA in clone 18 g (C18 g or 18 g) overlaps that in clones ag30a and CA205a, described in Section IV.A.32. The sequence of C18g also contains the double stop codon region observed in clone ag3oa. The polynucleotide region upstream of these stop codons presumably represents part of the 5'-region of the HCV genome, which may contain short ORFs, and which can be confirmed by direct sequencing of the purified HCV genome. These putative small encoded peptides may play a regulatory role in translation. The region of the HCV genome upstream of that represented by C18g can be isolated for sequence analysis using essentially the technique described in Section IC.A.20., except that the primers of reverse transcriptase are based upon the sequence of C18g. Since HCV appears to be a Flavi-like virus, it is probable that the 5'-terminus of the genome will be modified with a "cap" structure. It is known that Flavivirus genomes contain 5'-terminal "cap" structures. (Yellow Fever virus, Rice et al. (1988); Dengue virus, Hahn et al (1988); Japanese Encephalitis Virus (1987)).

IV.A.33. Isolation and Sequence of Clones from the b-HCV cDNA library

Clones containing cDNA representative of the 3'-terminal region of the HCV genome were isolated from a cDNA library constructed from the original infectious chimpanzee plasma pool which was used for the creation of the HCV cDNA λgt11 library described in Section IV.A.1. In order to create the DNA library, RNA extracted from the plasma was "tailed" with poly rA using poly (rA) polymerase, and cDNA was synthesized using oligo(dT)$_{12-18}$ as a primer for reverse transcriptase. The resulting RNA:cDNA hybrid was digested with RNAase H, and converted to double stranded HCV cDNA. The resulting HCV cDNA was cloned into λgt10, using essentially the technique described in Huynh (1985), yielding the beta (or b) HCV cDNA library. The procedures used were as follows.

An aliquot (12 mL) of the plasma was treated with proteinase K, and extracted with an equal volume of phenol saturated with 0.05M Tris-Cl, pH 7.5, 0.05% (v/v) b-mercaptoethanol, 0.1% (w/v) hydroxyquinolone, 1 mM EDTA. The resulting aqueous phase was re-extracted with the phenol mixture, followed by 3 extractions with a 1:1 mixture containing phenol and chloroform:isoamyl alcohol (24:1), followed by 2 extractions with a mixture of chloroform and isoamyl alcohol (1:1). Subsequent to adjustment of the aqueous phase to 200 mM with respect to NaCl, nucleic acids in the aqueous phase were precipitated overnight at −20° C., with 2.5 volumes of cold absolute ethanol. The precipitates were collected by centrifugation at 10,000 RPM for 40 min., washed with 70% ethanol containing 20 mM NaCl, and with 100% cold ethanol, dried for 5 min. in a desiccator, and dissolved in water.

The isolated nucleic acids from the infectious chimpanzee plasma pool were tailed with poly rA utilizing poly-A polymerase in the presence of human placenta ribonuclease inhibitor (HPRI) (purchased from Amersham Corp.), utilizing MS2 RNA as carrier. Isolated nucleic acids equivalent to that in 2 mL of plasma were incubated in a solution containing TMN (50 mM Tris HCl, pH 7.9, 10 mM MgCl$_2$, 250 mM NaCl, 2.5 mM MnCl$_2$, 2 mM dithiothreitol (DTT)), 40 mM a-[$^{32}$P] ATP, 20 units HPRI (Amersham Corp.), and about 9 to 10 units of RNase free poly-A polymerase (BRL). Incubation was for 10 min. at 37° C., and the reactions were stopped with EDTA (final concentration about 250 mM). The solution was extracted with an equal volume of phenol-chloroform, and with an equal volume of chloroform, and nucleic acids were precipitated overnight at −20° C. with 2.5 volumes of ethanol in the presence of 200 mM NaCl.

IV.A.33.a. Isolation of Clone b5a

The b HCV cDNA library was screened by hybridization using a synthetic probe, which had a sequence based upon the HCV cDNA sequence in clone 15e. The sequence of the probe was:

5' ATT GCG AGA TCT ACG GGG CCT GCT ACT CCA 3' (SEQ ID NO:218).

Screening of the library yielded clone b-5a (b5a), which contains an HCV cDNA region of approximately 1000 base pairs. The 5'-region of this cDNA overlaps clones 35f, 19g, 26g, and 15e (these clones are described supra). The region between the 3'-terminal poly-A sequence and the 3'-sequence which overlaps clone 15e, contains approximately 200 base pairs. This clone allows the identification of a region of the 3'-terminal sequence the HCV genome.

The sequence of b5a is contained within the sequence of the HCV cDNA in clone 16jh (described infra). Moreover, the sequence is also present in CC34a, isolated from the original λgt11 library. (The original λgt11 library is referred to herein as the "C" library).

IV.A.34. Isolation and Sequence of Clones Generated by PCR Amplification of the 3'-Region of the HCV Genome Multiple cDNA clones have been generated which contain nucleotide sequences derived from the 3'-region of the HCV genome. This was accomplished by amplifying a targeted region of the genome by a polymerase chain reaction technique described in Saiki et al. (1986), and in Saiki et al. (1988), which was modified as described below. The HCV RNA which was amplified was obtained from the original infectious chimpanzee plasma pool which was used for the creation of the HCV cDNA λgt11 library described in Section IV.A.1. Isolation of the HCV RNA was as described in Section IV.A.33. The isolated RNA was tailed at the 3'-end with ATP by E. coli poly-A polymerase as described in Sippel (1973), except that the nucleic acids isolated from chimp serum were substituted for the nucleic acid substrate. The tailed RNA was then reverse transcribed into cDNA by reverse transcriptase, using an oligo dT-primer adapter, essentially as described by Han (1987), except that the components and sequence of the primer-adapter were:

| Stuffer | NotI | SP6 Promoter | Primer |
|---|---|---|---|
| AATTC | GCGGCCGC | CATACGATTTAGGTGACACTA-TAGAA | T$_{15}$ |
| (SEQ ID NO: 219). | | | |

The resultant cDNA was subjected to amplification by PCR using two primers:

| Primer | Sequence |
|---|---|
| JH32 (30 mer) (SEQ ID NO: 220) | ATAGCGGCCGCCCTCGATTGCGAGATCTAC |
| JH11 (20 mer) (SEQ ID NO: 221). | AATTCGGGCGGCCGCCATACGA |

The JH32 primer contained 20 nucleotide sequences hybridizable to the 5'-end of the target region in the cDNA, with an estimated T$_m$ of 66° C. The JH11 was derived from a portion of the oligo dT-primer adapter; thus, it is specific to the 3'-end of the cDNA with a T$_m$ of 64° C. Both primers were designed to have a recognition site for the restriction enzyme, NotI, at the 5'-end, for use in subsequent cloning of the amplified HCV cDNA.

The PCR reaction was carried out by suspending the cDNA and the primers in 100 mL of reaction mixture containing the four deoxynucleoside triphosphates, buffer salts and metal ions, and a thermostable DNA polymerase isolated from *Thermus aquaticus* (Taq polymerase), which are in a Perkin Elmer Cetus PCR kit (N801-0043 or N801-0055). The PCR reaction was performed for 35 cycles in a Perkin Elmer Cetus DNA thermal cycler. Each cycle consisted of a 1.5 min denaturation step at 94° C., an annealing step at 60° C. for 2 min, and a primer extension step at 72° C. for 3 min. The PCR products were subjected to Southern blot analysis using a 30 nucleotide probe, JH34, the sequence of which was based upon that of the 3'-terminal region of clone 15e. The sequence of JH34 is:

5' CTT GAT CTA CCT CCA ATC ATT CAA AGA CTC 3' (SEQ ID NO:222).

The PCR products detected by the HCV cDNA probe ranged in size from about 50 to about 400 base pairs.

In order to clone the amplified HCV cDNA, the PCR products were cleaved with NotI and size selected by polyacrylamide gel electrophoresis. DNA larger than 300 base pairs was cloned into the NotI site of pUC18S The vector pUC18S is constructed by including a NotI polylinker cloned between the EcoRI and SalI sites of pUC18. The clones were screened for HCV cDNA using the JH34 probe. A number of positive clones were obtained and sequenced. The nucleotide sequence of the HCV cDNA insert in one of these clones, 16jh, and the amino acids encoded therein, are shown in FIG. 61. A nucleotide heterogeneity, detected in the sequence of the HCV cDNA in clone 16jh as compared to another clone of this region, is indicated in the figure.

IV.A.35. Compiled HCV cDNA Sequence

The HCV cDNA sequence compiled from a series of overlapping clones derived from the various HCV cDNA libraries described supra and infra is shown in FIG. 62. The clones from which the sequence was derived are b114a, 18g, ag3oa, CA205a, CA290a, CA216a, pi14a, CA167b, CA156e, CA84a, CA59a, K9-1 (also called k9-1), 26j, 13i, 12f, 14i, 11b, 7f, 7e, 8h, 33c, 40b, 37b, 35, 36, 81, 32, 33b, 25c, 14c, 8f, 33f, 33g, 39c, 35f, 19g, 26g, 15e, b5a, and 16jh. In the figure the three dashes above the sequence indicate the position of the putative initiator methionine codon.

Clone b114a was obtained using the cloning procedure described for clone b5a, supra, except that the probe was the synthetic probe used to detect clone 18g, supra. Clone b114a overlaps with clones 18g, ag3oa, and CA205a, except that clone b114a contains an extra two nucleotides upstream of the sequence in clone 18g (i.e., 5'-CA). These extra two nucleotides have been included in the HCV genomic sequence shown in FIG. 62.

It should be noted that although several of the clones described supra have been obtained from libraries other than the original HCV cDNA λgt11 library described in Section IV.A. 1., these clones contain HCV cDNA sequences which overlap HCV cDNA sequences in the original library. Thus, essentially all of the HCV sequence is derivable from the original λgt11 library which was used to isolate the first clone (5-1-1).

IV.A.36. Isolation and Sequence of Clone 6k

Based on the sequence of clone 16jh and clone b5a (see IV.A.34. and FIG. 61), a synthetic probe was made having the following sequence:

5' TCT TCA ACT GGG CAG TAA GAA CAA AGC
       TCA 3'                              (SEQ ID NO:223).

Screening of the original λgt11 HCV cDNA library (described in Section IV.A.1.) with the probe yielded clones with a frequency of approximately I in 106; one of these was called clone 6k (also called C6k), the HCV cDNA sequence of which is shown in FIG. 71. Also shown in the figure are the overlap with clone 16jh, and putative polypeptides encoded within the HCV cDNA. Sequence information on the HCV cDNA in clone 6k was obtained from only one strand. Information on the deposit of this clone is provided infra, wherein the clone is listed as λgt11 C6k. Confirmation of the C6K sequence as part of an ORF encoding HCV1 polypeptide has been obtained by sequencing other overlapping clones.

A composite of the HCV cDNA sequence derived from overlapping clones b114a, 18g, ag3oa, CA205a, CA290a, CA216a, pi14a, CA167b, CA156e, CA84a, CA59a, K9-1 (also called k9-1), 26j, 13i, 12f, 14i, 11b, 7f, 7e, 8h, 33c, 40b, 37b, 35, 36, 81, 32, 33b, 25c, 14c, 8f, 33f, 33g, 39c, 35f, 19g, 26g, 15e, b5a, 16jh, and 16k is shown in FIG. 72. The figure also shows the amino acids encoded in the sense strand of the cDNA, which is the equivalent of the genomic RNA.

IV.A.36. Construction of S3-56$_{C100m}$

The vector pS$^3$-56$_{C100}$ contains a construct which encodes the fusion polypeptide SOD-C100 (see Section IV.B.4.). In addition, this vector contains an ms2 phage sequence, which was removed from the HCV C100 encoding sequence by digestion of pS$^3$-56$_{c100}$ with XmaI and SalI, followed by isolation of the large fragment. The aforementioned digestion, however, removes some of the HCV sequence. The latter was recreated by ligation of the fragment with the following linkers, which also introduced a SalI site and a stop codon. The linker sequences, annealed to each other, are shown in FIG. 73. The resulting vector is called pS3-56$_{c100m}$ (also called pS356$_{c100m}$).

IV.A.37. Construction of Composite Sequence C200

An HCV-cDNA sequence, C200, which is a composite of HCV sequences derived from clones 33c, 31, and 35, was constructed. Clones 33c and 35 are described in Section IV.A.17. and IV.A.8., respectively. Clone 31 is from the C library, and has one difference from the confirmed sequence of HCV- 1 in FIG. 62. The sequence of clone 31 is shown in FIG. 74, which also shows the amino acids encoded therein, and the location of restriction enzyme sites within the HCV cDNA. A C200 cassette was constructed by ligating together a 718 bp fragment obtained by digestion of clone 33c DNA with EcoRI and HinfI, a 179 bp fragment obtained by digestion of clone 31 DNA with HinfI and BgII, and a 377 bp fragment obtained by digestion of clone 35 DNA with BgII and EcoRI. The construct of ligated fragments were inserted into the EcoRI site of pBR322, yielding the plasmid pBR322-C200.

IV.A.38. Isolation and Sequence of Clone 131jh

A clone containing sequence from the 3'-region of the HCV genome, and which contains an in-frame stop codon, was isolated essentially as described in Section IV.A.34, except that HCV 1 RNA was converted to cDNA using the oligonucleotide 5' AAT TCG CGG CCG CCA TAC GAT TTA GGT GAC ACT
       ATA GAA T 3'                        (SEQ ID NO:224).

The cDNA was then amplified by the PCR reaction using the primers:

5' TTC GCG GCC GCT ACA GCG GGG GAG
       ACA T 3'                            (SEQ ID NO:225)

and

5' AAT TCG CGG CCG CCA TAC GA 3'       (SEQ ID NO:226).

After amplification, the PCR products were precipitated with spermine, digested with NotI, and extracted with phenol. The purified products were cloned into the NotI site of pUC18S, and HCV positive clones were selected using the oligonucleotide:

5' CGA TGA AGG TTG GGG TAA ACA CTC CGG
       CCT 3'                              (SEQ ID NO:227).

The HCV cDNA in one clone, designated p131jh, is shown in FIG. 75. This clone contains an in-frame stop codon for the large ORF contained in the HCV genome.

IV.B. Expression and Purification of Polypeptides Encoded Within HCV cDNAs and Identification of the Expressed Products as HCV Induced Antigens.

IV.B.1. Expression of the Polypeptide Encoded in Clone 5-1-1.

The HCV polypeptide encoded within clone 5-1-1 (see Section IV.A.2., supra) was expressed as a fusion polypeptide with superoxide dismutase (SOD). This was accomplished by subcloning the clone 5-1-1 cDNA insert into the expression vector pSODcf1 (Steimer et al. (1986)) as follows.

First, DNA isolated from pSODcf1 was treated with BamHI and EcoRI, and the following linker was ligated into the linear DNA created by the restriction enzymes:

5' GAT CCT GGA ATT CTG ATA AGA CCT TAA GAC TAT TTT AA 3' (SEQ ID NO:228)

After cloning, the plasmid containing the insert was isolated.

Plasmid containing the insert was restricted with EcoRI. The HCV cDNA insert in clone 5-1-1 was excised with EcoRi, and ligated into this EcoRi linearized plasmid DNA. The DNA mixture was used to transform *E. coli* strain D1210 (Sadler et al. (1980)). Recombinants with the 5-1-1 cDNA in the correct orientation for expression of the ORF shown in FIG. 1 were identified by restriction mapping and nucleotide sequencing.

Recombinant bacteria from one clone were induced to express the SOD-NANB$_{5-1-1}$ polypeptide by growing the bacteria in the presence of IPTG.

IV.B.2. Expression of the Polypeptide Encoded in Clone 81.

The HCV cDNA contained within clone 81 was expressed as a SOD-NANB$_{81}$, fusion polypeptide. The method for preparing the vector encoding this fusion polypeptide was analogous to that used for the creation of the vector encoding SOD-NANB$_{5-1-1}$, except that the source of the HCV cDNA was clone 81, which was isolated as described in Section IV.A.3, and for which the cDNA sequence was determined as described in Section IV.A.4. The nucleotide sequence of the HCV cDNA in clone 81, and the putative amino acid sequence of the polypeptide encoded therein are shown in FIG. 4.

The HCV cDNA insert in clone 81 was excised with EcoRI, and ligated into the pSODcf1 which contained the linker (see IV.B.1.) and which was linearized by treatment with EcoRI. The DNA mixture was used to transform *E. coli* strain D1210. Recombinants with the clone 81 HCV cDNA in the correct orientation for expression of the ORF shown in FIG. 4 were identified by restriction mapping and nucleotide sequencing.

Recombinant bacteria from one clone were induced to express the SOD-NANB$_{81}$ polypeptide by growing the bacteria in the presence of IPTG.

IV.B.3. Identification of the Polypeptide Encoded Within Clone 5-1-1 as an HCV and NANBH Associated Antigen.

The polypeptide encoded within the HCV cDNA of clone 5-1-1 was identified as a NANBH associated antigen by demonstrating that sera of chimpanzees and humans infected with NANBH reacted immunologically with the fusion polypeptide, SOD-NANB$_{5-1-1}$, which is comprised of superoxide dismutase at its N-terminus and the in-frame 5-1-1 antigen at its C-terminus. This was accomplished by "Western" blotting (Towbin et al. (1979)) as follows.

A recombinant strain of bacteria transformed with an expression vector encoding the SOD-NANB$_{5-1-1}$ polypeptide, described in Section IV.B.1., was induced to express the fusion polypeptide by growth in the presence of IPTG. Total bacterial lysate was subjected to electrophoresis through polyacrylamide gels in the presence of SDS according to Laemmli (1970). The separated polypeptides were transferred onto nitrocellulose filters (Towbin et al. (1979)). The filters were then cut into thin strips, and the strips were incubated individually with the different chimpanzee and human sera. Bound antibodies were detected by further incubation with $^{125}$I-labeled sheep anti-human Ig, as described in Section IV.A.1.

Figure 33A:
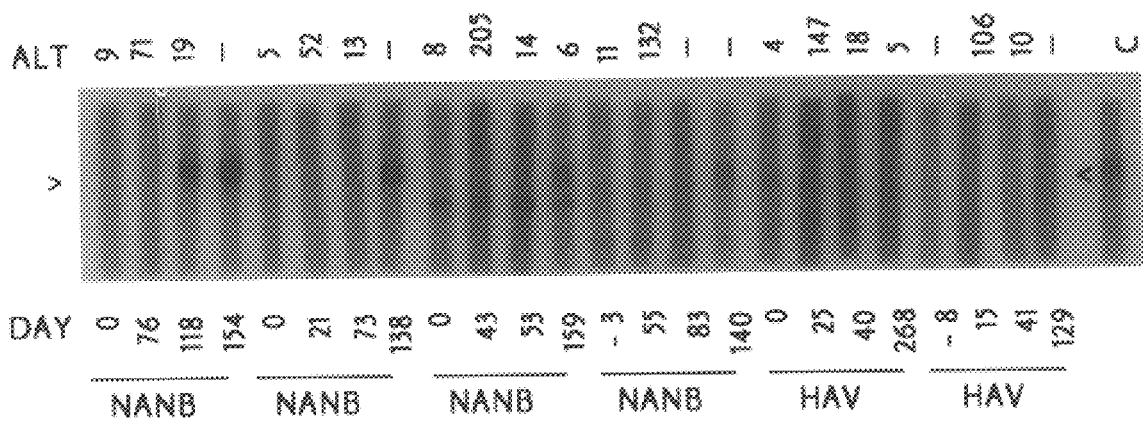
FIG. 33 shows a photograph of Western blots of a fusion protein, SOD-NANB$_{5-1-1}$, with chimpanzee serum from chimpanzees infected with BB-NANB, HAV, and HBV.
Figure 33B:
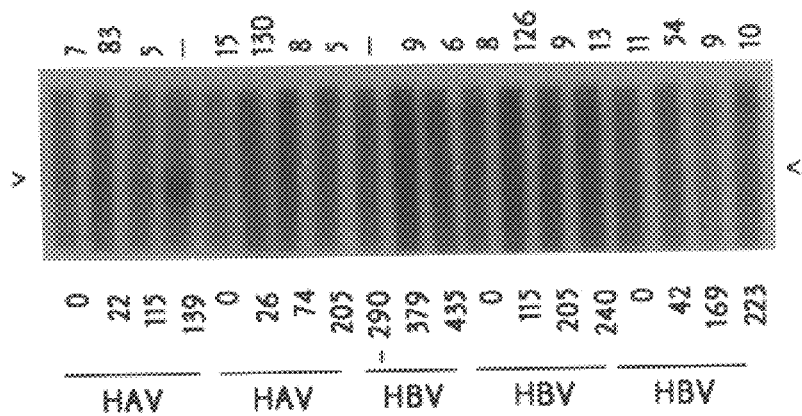

The characterization of the chimpanzee sera used for the Western blots and the results, shown in the photograph of the autoradiographed strips, are presented in FIG. 33. Nitrocellulose strips containing polypeptides were incubated with sera derived from chimpanzees at different times during acute NANBH (Hutchinson strain) infections (lanes 1–16), hepatitis A infections (lanes 17–24, and 26–33), and hepatitis B infections (lanes 34–44). Lanes 25 and 45 show positive controls in which the immunoblots were incubated with serum from the patient used to identify the recombinant clone 5-1 -1 in the original screening of the λgt11 cDNA library (see Section IV.A.1.).

The band visible in the control lanes, 25 and 45, in FIG. 23 reflects the binding of antibodies to the NANB$_{5-1-1}$ moiety of the SOD fusion polypeptide. These antibodies do not exhibit binding to SOD alone, since this has also been included as a negative control in these samples, and would have appeared as a band migrating significantly faster than the SOD-NANB$_{5-1-1}$ fusion polypeptide.

Lanes 1–16 of FIG. 33 show the binding of antibodies in sera samples of 4 chimpanzees; the sera were obtained just prior to infection with NANBH, and sequentially during acute infection. As seen from the figure, whereas antibodies which reacted immunologically with the SOD-NANB$_{5-1-1}$ polypeptide were absent in sera samples obtained before administration of infectious HCV inoculum and during the early acute phase of infection, all 4 animals eventually induced circulating antibodies to this polypeptide during the late part of, or following the acute phase. Additional bands observed on the immunoblots in the cases of chimps numbers 3 and 4 were due to background binding to host bacterial proteins.

In contrast to the results obtained with sera from chimps infected with NANBH, the development of antibodies to the NANB$_{5-1-1}$ moiety of the fusion polypeptide was not observed in 4 chimpanzees infected with HAV or 3 chimpanzees infected with HBV. The only binding in these cases was background binding to the host bacterial proteins, which also occurred in the HCV infected samples.

Figure 34A:
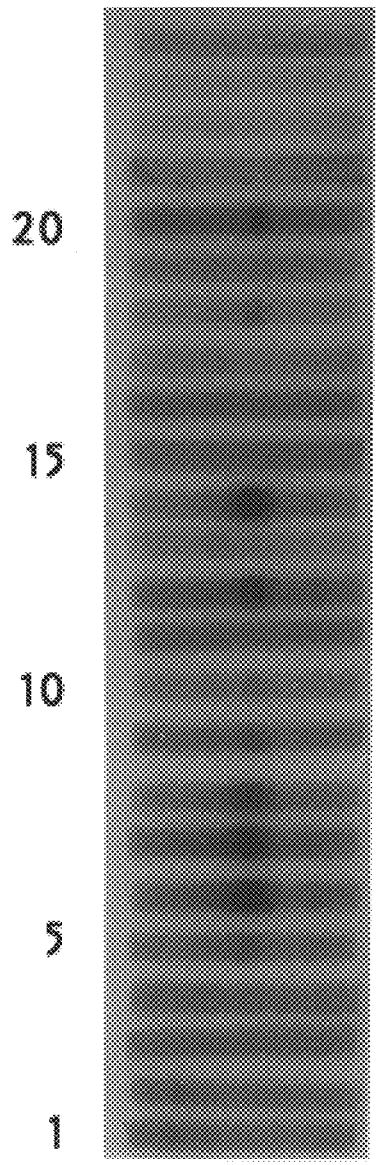
FIG. 34 shows a photograph of Western blots of a fusion protein, SOD-NANB$_{5-1-1}$, with serum from humans infected with NANBV, HAV, HBV, and from control humans.
Figure 34B:
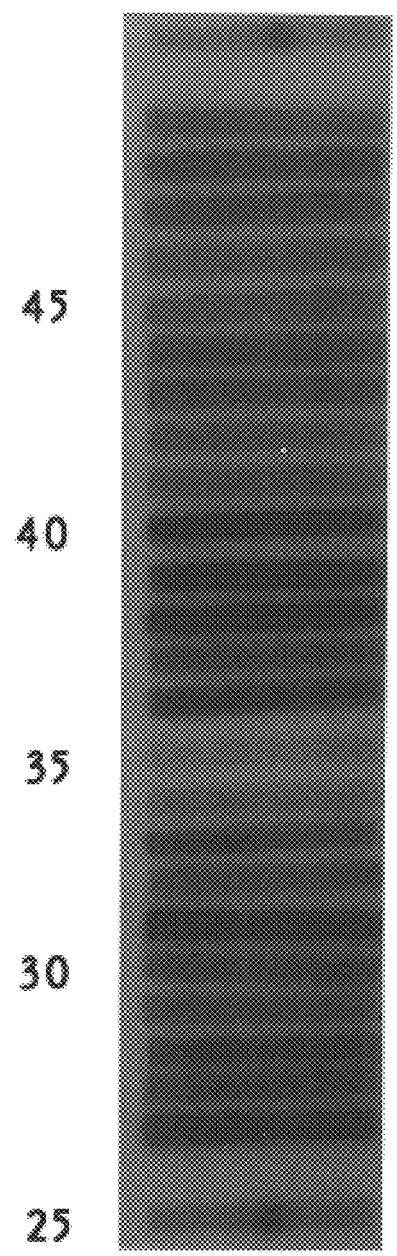

The characterization of the human sera used for the Western blots, and the results, which are shown in the photograph of the autoradiographed strips, are presented in FIG. 34. Nitrocellulose strips containing polypeptides were incubated with sera derived from humans at different times during infections with NANBH (lanes 1–21), HAV (lanes 33–40), and HBV (lanes 41–49). Lanes 25 and 50 show positive controls in which the immunoblots were incubated with serum from patient used in the original screening of the λgt11 library, described supra. Lanes 22–24 and 26–32 show "non-infected" controls in which the sera was from "normal" blood donors.

As seen in FIG. 34, sera from nine NANBH patients, including the serum used for screening the λgt11 library, contained antibodies to the NANB$_{5-1-1}$ moiety of the fusion polypeptide. Sera from three patients with NANBH did not contain these antibodies. It is possible that the anti-NANB$_{5-1-1}$ antibodies will develop at a future date in these patients. It is also possible that this lack of reaction resulted from a different NANBV agent being causative of the disease in the individuals from which the non-responding serum was taken.

FIG. 34 also shows that sera from many patients infected with HAV and HBV did not contain anti-NANB$_{5-1-1}$ antibodies, and that these antibodies were also not present in the sera from "normal" controls. Although one HAV patient (lane 36) appears to contain anti-NANB$_{5-1-1}$ antibodies, it is possible that this patient had been previously infected with HCV, since the incidence of NANBH is very high and since it is often subclinical.

These serological studies indicate that the cDNA in clone 5-1-1 encodes epitopes which are recognized specifically by sera from patients and animals infected with BB-NANBV. In addition, the cDNA does not appear to be derived from the primate genome. A hybridization probe made from clone 5-1-1 or from clone 81 did not hybridize to "Southern" blots of control human and chimpanzee genomic DNA from uninfected individuals under conditions where unique, single-copy genes are detectable. These probes also did not hybridize to Southern blots of control bovine genomic DNA.

V.B.4. Expression of the Polypeptide Encoded in a Composite of the HCV cDNAs in Clones 36, 81 and 32

The HCV polypeptide which is encoded in the ORF which extends through clones 36, 81 and 32 was expressed as a fusion polypeptide with SOD. This was accomplished by inserting the composite cDNA, C100, into an expression cassette which contains the human superoxide dismutase gene, inserting the expression cassette into a yeast expression vector, and expressing the polypeptide in yeast.

An expression cassette containing the composite C100 cDNA derived from clones 36, 81, and 32, was constructed by inserting the ~1270bp EcoRI fragment into the EcoRI site of the vector pS3-56 (also called pS356), yielding the plasmid pS3-56$_{C100}$. The construction of C100 is described in Section IV.A.16, supra.

The vector pS3-56, which is a pBR322 derivative, contains an expression cassette which is comprised of the ADH2/GAPDH hybrid yeast promoter upstream of the human superoxide dismutase gene, and a downstream a-factor transcription terminator. A similar cassette, which contains these control elements and the superoxide dismutase gene has been described in Cousens et al. (1987), and in copending application EPO 196,056, published Oct. 1, 1986, which is commonly owned by the herein assignee. The cassette in pS3-56, however, differs from that in Cousens et al. (1987) in that the heterologous proinsulin gene and the immunoglobulin hinge are deleted, and in that the gln$_{154}$ of the superoxide dismutase is followed by an adaptor sequence which contains an EcoRi site. The sequence of the adaptor is:

5'-AAT TTG GGA ATT CCA TAA TGA GAC CCT TAA GGT
ATT ACT CAG CT 3'           (SEQ ID NO:229).

The EcoRI site allows the insertion of heterologous sequences which, when expressed from a vector containing the cassette, yield polypeptides which are fused to superoxide dismutase via an oligopeptide linker containing the amino acid sequence:

-Asn-Leu-Gly-Ile-Arg-           (SEQ ID NO:230).

After recombinants containing the C100 cDNA insert in the correct orientation were isolated, the expression cassette containing the C100 cDNA was excised from pS$^3$-56$_{c100}$ with BamHI, and a fragment of 3400bp which contains the cassette was isolated and purified. This fragment was then inserted into the BamHI site of the yeast vector pAB24.

Figure 35:
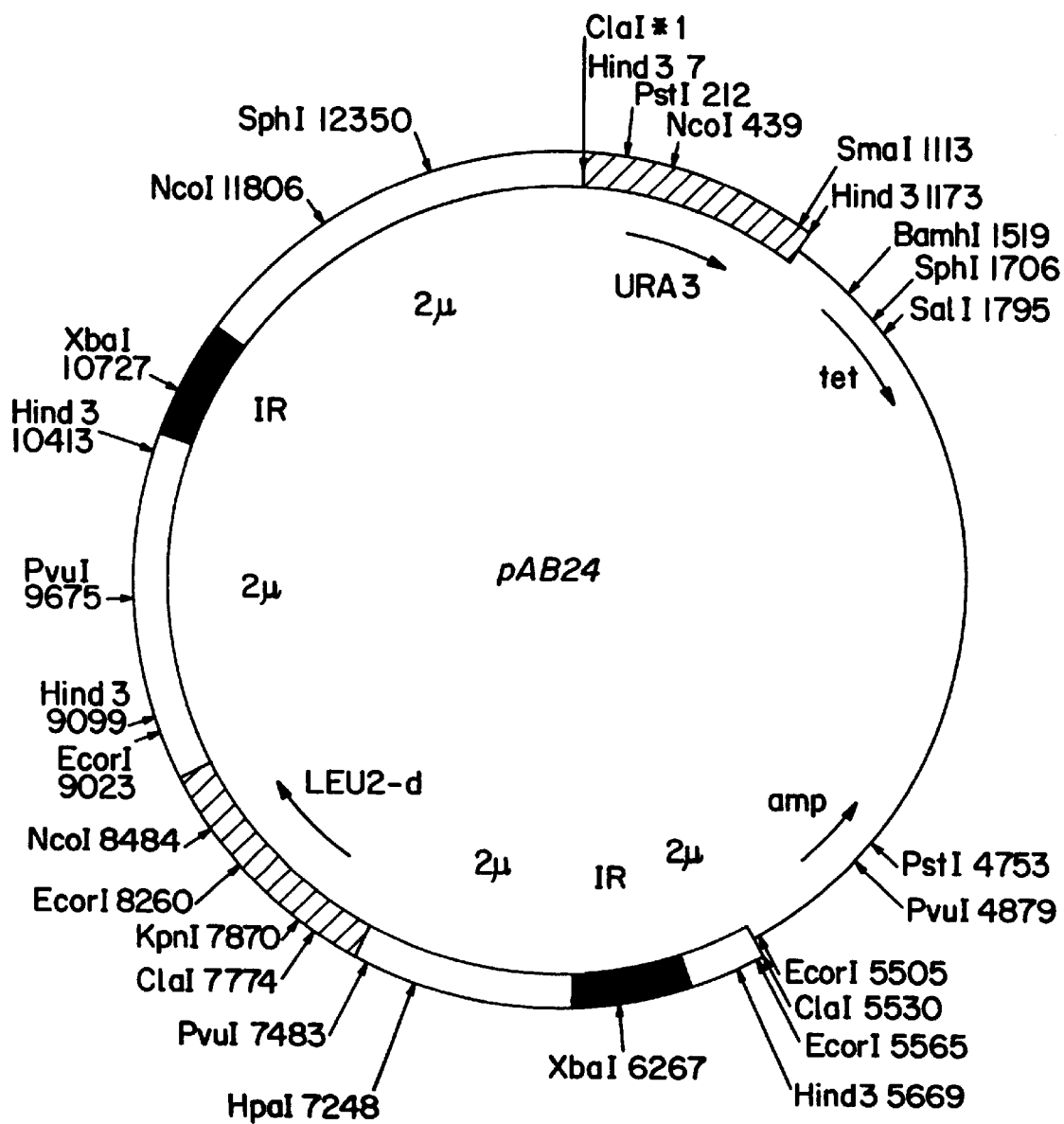
FIG. 35 is a map showing the significant features of the vector pAB24.

Plasmid pAB24, the significant features of which are shown in FIG. 35, is a yeast shuttle vector which contains the complete 2m sequence for replication [Broach (1981)] and pBR322 sequences. It also contains the yeast URA3 gene derived from plasmid YEp24 [Botstein et al. (1979)], and the yeast LEU$_2$d gene derived from plasmid pC1/1. EPO Pub. No. 116,201. Plasmid pAB24 was constructed by digesting YEp24 with EcoRI and religating the vector to remove the partial 2m sequences. The resulting plasmid, YEP24DRI, was linearized by digestion with Clal and ligated with the complete 2m plasmid which had been linearized with Clal. The resulting plasmid, pCBou, was then digested with XbaI and the 8605 bp vector fragment was gel isolated. This isolated XbaI fragment was ligated with a 4460 bp XbaI fragment containing the LEU$_{2d}$ gene isolated from pC1/1; the orientation of the LEU$_{2d}$ gene is in the same direction as the URA3 gene. Insertion of the expression was in the unique BamHI site of the pBR322 sequence, thus interrupting the gene for bacterial resistance to tetracycline.

The recombinant plasmid which contained the SOD-C100 expression cassette, pAB24C100-3, was transformed into yeast strain JSC 308, as well as into other yeast strains. The cells were transformed as described by Hinnen et al. (1978), and plated onto ura-selective plates. Single colonies were inoculated into leu-selective media and grown to saturation. The culture was induced to express the SOD-C100 polypeptide (called C100-3) by growth in YEP containing 1% glucose.

Strain JSC 308 is of the genotype MAT @, leu2, ura3(del) DM15 (GAP/ADR1) integrated at the ADR1 locus. In JSC 308, over-expression of the positive activator gene product, ADR1, results in hyperderepression (relative to an ADR1 wild type control) and significantly higher yields of expressed heterologous proteins when such proteins are synthesized via an ADH2 UAS regulatory system. The construction of the yeast strain JSC 308 is disclosed in copending application, U.S. Ser. No. 190,868, filed concurrently herewith, and which is hereby incorporated herein by reference.

The complete C100-3 fusion polypeptide encoded in pAB24C100-3 should contain 154 amino acids of human SOD at the amino-terminus, 5 amino acid residues derived from the synthetic adaptor containing the EcoRI site, 363 amino acid residues derived from C100 cDNA, and 5 carboxy-terminal amino acids derived from the MS2 nucleotide sequence adjoining the HCV cDNA sequence in clone 32. (see Section IV.A.7.) The putative amino acid sequence of the carboxy-terminus of this polypeptide, beginning at the penultimate Ala residue of SOD, is shown in FIG. 36; also shown is the nucleotide sequence encoding this portion of the polypeptide.

IV.B.4.b. Contents of Selective Media For Yeast Auxotrophs Leu- Medium

| | |
|---|---|
| Yeast Minimal Media | 850 mL |
| Leu- Supplements (10×) | 100 mL |
| 50% Glucose (in MILLI-Q) | 40 mL |

(If the Leu- medium is to be used for growth of yeast in flasks, Ura- supplements are also included in the medium.

Yeast Minimal Medium

| | |
|---|---|
| Yeast Nitrogen Base w/o amino acids | 6.7 g |
| MILLI Q water | q.s. to 850 mL |

Leu- Supplements

| | |
|---|---|
| Adenine | 0.8 g |
| Uridine | 0.6 g |

-continued

|   |   |
|---|---|
| L-Tryptophan | 0.4 g |
| L-Histidine | 0.4 g |
| L-Arginine | 0.4 g |
| L-Methionine | 0.4 g |
| L-Tyrosine | 0.6 g |
| L-Lysine | 0.6 g |
| L-Phenylalanine | 0.96 g |

Add all components to a coffee grinder and grind until the powder is homogenous. The powder may be added to a solution or the mix can be autoclaved as a 10x concentrated solution by adding 2L of MILLI-Q water.

Ura-/Sorbitol Plates

|   |   |
|---|---|
| Ura-/Sorbitol Medium for Plates | 500 mL |
| 50% Glucose | 20 mL |
| 20% Casamino acids | 12.5 mL |
| 1% Adenine | 2.5 mL |
| 1% Tryptophan | 2.5 mL |

Stir gently and pour into plates. Flame plates.
Ura-Sorbitol Medium

|   |   |
|---|---|
| D-Sorbitol | 91. g |
| Agar | 10. g |
| Yeast Nitrogen Base w/o amino acids | 3.35 g |
| Water | q.s. to 450. mL |

Autoclave for 30 minutes
YEP

|   |   |
|---|---|
| Peptone | 20 g |
| Yeast Extract | 10 g |
| MILLI Q Water | q.s. to 1000 mL |

Autoclave at 121° C. for 30 minutes. The solution is good for six months when stored at 15 to 30° C.

Leu- Plates

|   |   |
|---|---|
| Leu-Plate Medium | 950 mL |
| 50% Glucose | 40 mL |
| 5% Threonine | 4 mL |
| 1% Adenine | 1 mL |

Leu- Medium for Plates

|   |   |
|---|---|
| Agar | 20 g |
| Leu- Supplements | 0.25 g |
| 10x Basal Salts w/o amino acids | 100 mL |
| MILLI Q | q.s to 950 mL |

10x Basal Salts

|   |   |
|---|---|
| Yeast Nitrogen Base w/o Amino Acids | 66.8 g |
| Succinic Acid | 100. g |

-continued

|   |   |
|---|---|
| NaOH | 60. g |
| MILLI Q Water | q.s to 1000. mL |

Filter Sterilize.
Leu-, Ura-plate

|   |   |
|---|---|
| Leu-, Ura- Plate media | 840 mL |
| 50% Glucose | 160 mL |
| 5% Threonine | 8 mL |

Leu-, Ura- Plate Medium

|   |   |
|---|---|
| Yeast Nitrogen Base w/o amino acids | 6.7 g |
| Bacto Agar | 20 g |
| Leu-, Ura- supplements | 0.5 g |

(Note: the Leu-, Ura- supplement recipe is the same as the Leu- supplement recipe, except that uridine is not added.)

IV.B.5. Identification of the Polypeptide Encoded within C100 as an NANBH Associated Antigen The C100-3 fusion polypeptide expressed from plasmid pAB24C100-3 in yeast strain JSC 308 was characterized with respect to size, and the polypeptide encoded within C100 was identified as an NANBH-associated antigen by its immunological reactivity with serum from a human with chronic NANBH.

The C100-3 polypeptide, which was expressed as described in Section IV.B.4., was analyzed as follows. Yeast JSC 308 cells were transformed with pAB24, or with pAB24C100-3, and were induced to express the heterologous plasmid encoded polypeptide. The induced yeast cells in 1 mL of culture ($OD_{650nm}$ ~20) were pelleted by centrifugation at 10,000 rpm for 1 minute, and were lysed by vortexing them vigorously (10×1 min) with 2 volumes of solution and 1 volume of glass beads (0.2 mm diameter). The solution contained 50 mM Tris-HCl, pH 8.0, 1 mM EDTA, 1 mM phenylmethylsulfonyl fluoride (PMSF), and 1 mg/mL pepstatin. Insoluble material in the lysate, which includes the C100-3 polypeptide, was collected by centrifugation (10,000 rpm for 5 minutes), and was dissolved by boiling for 5 minutes in Laemmli SDS sample buffer. (See Laemmli (1970)). An amount of polypeptides equivalent to that in 0.3 mL of the induced yeast culture was subjected to electrophoresis through 10% polyacrylamide gels in the presence of SDS according to Laemmli (1970). Protein standards were co-electrophoresed on the gels. Gels containing the expressed polypeptides were either stained with Coomassie brilliant blue, or were subjected to "Western" blotting as described in Section IV.B.2., using serum from a patient with chronic NANBH to determine the immunological reactivity of the polypeptides expressed from pAB24 and from pAB24C100-3.

Figure 37A:
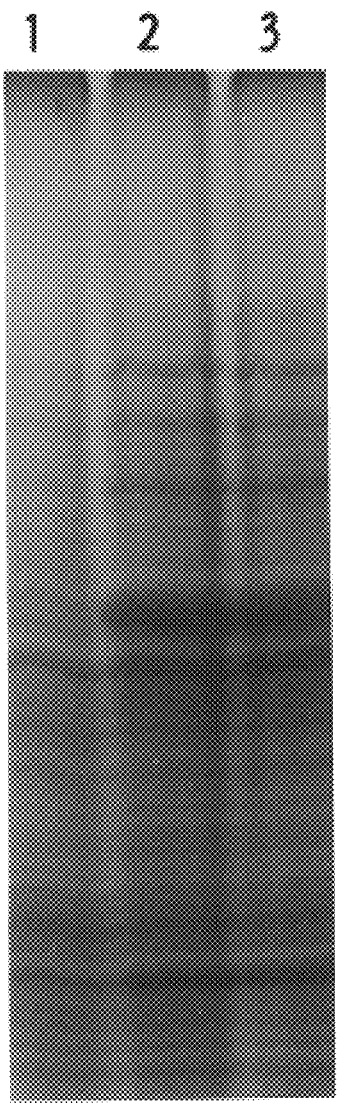
FIG. 37A is a photograph of a coomassie blue stained polyacrylamide gel which identifies C100-3 expressed in yeast.

The results are shown in FIG. 37. In FIG. 37A the polypeptides were stained with Coomassie brilliant blue. The insoluble polypeptide(s) from JSC 308 transformed with pAB24 and from two different colonies of JSC transformed with pAB24C100-3 are shown in lane 1 (pAB24), and lanes 2 and 3, respectively. A comparison of lanes 2 and 3 with lane 1 shows the induced expression of a polypeptide corresponding to a molecular weight of ~54,000 daltons from JSC 308 transformed with pAB24C100-3, which is not induced in JSC 308 transformed with pAB24. This polypeptide is indicated by the arrow.

Figure 37B:
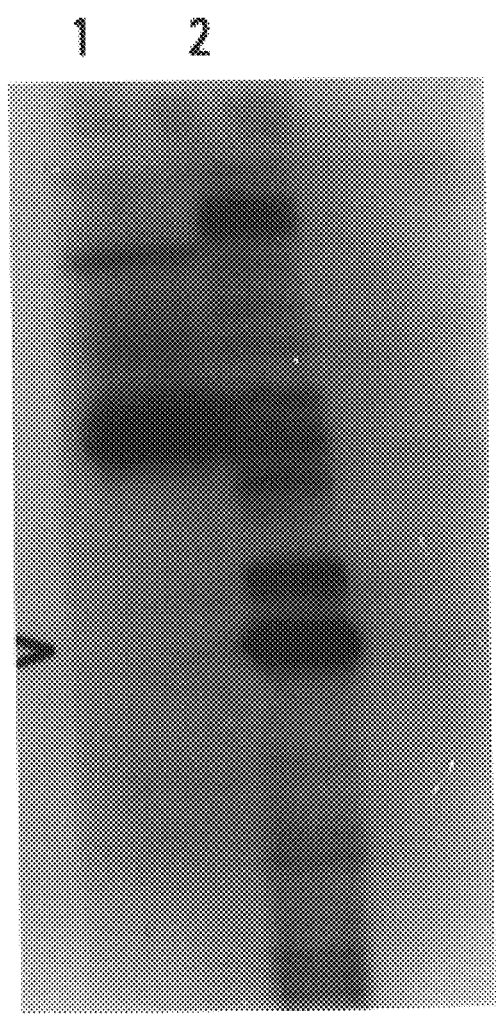
FIG. 37B shows a Western blot of C100-3 with serum from a NANBV infected human.

FIG. 37B shows the results of the Western blots of the insoluble polypeptides expressed in JSC 308 transformed with pAB24 (lane 1), or with pAB24C100-3 (lane 2). The polypeptides expressed from pAB24 were not immunologically reactive with serum from a human with NANBH. However, as indicated by the arrow, JSC 308 transformed with pAB24C100-3 expressed a polypeptide of ~54,000 dalton molecular weight which did react immunologically with the human NANBH serum. The other immunologically reactive polypeptides in lane 2 may be degradation and/or aggregation products of this ~54,000 dalton polypeptide.

IV.B.6. Purification of Fusion Polypeptide C100-3

The fusion polypeptide, C100-3, comprised of SOD at the N-terminus and in-frame C100 HCV-polypeptide at the C-terminus was purified by differential extraction of the insoluble fraction of the extracted host yeast cells in which the polypeptide was expressed.

The fusion polypeptide, C100-3, was expressed in yeast strain JSC 308 transformed with pAB24C100-3, as described in Section IV.B.4. The yeast cells were then lysed by homogenization, the insoluble material in the lysate was extracted at pH 12.0, and C100-3 in the remaining insoluble fraction was solubilized in buffer containing SDS.

The yeast lysate was prepared essentially according to Nagahuma et al. (1984). A yeast cell suspension was prepared which was 33% cells (v/v) suspended in a solution (Buffer A) containing 20 mM Tris HCl, pH 8.0, 1 mM dithiothreitol, and 1 mM phenylmethylsulfonylfluoride (PMSF). An aliquot of the suspension (15 mL) was mixed with an equal volume of glass beads (0.45–0.50 mm diameter), and the mixture was vortexed at top speed on a Super Mixer (Lab Line Instruments, Inc.) for 8 min. The homogenate and glass beads were separated, and the glass beads were washed 3 times with the same volume of Buffer A as the original packed cells. After combining the washes and homogenate, the insoluble material in the lysate was obtained by centrifuging the homogenate at 7,000 xg for 15 minutes at 4° C., resuspending the pellets in Buffer A equal to twice the volume of original packed cells, and repelleting the material by centrifugation at 7,000 xg for 15 min. This washing procedure was repeated 3 times.

The insoluble material from the lysate was extracted at pH 12.0 as follows. The pellet was suspended in buffer containing 0.5 M NaCl, 1 mM EDTA, where the suspending volume was equal to 1.8 times the of the original packed cells. The pH of the suspension was adjusted by adding 0.2 volumes of 0.4 M Na phosphate buffer, pH 12.0. After mixing, the suspension was centrifuged at 7,000 xg for 15 min at 4° C., and the supernatant removed. The extraction was repeated 2 times. The extracted pellets were washed by suspending them in 0.5 M NaCl, 1 mM EDTA, using a suspension volume equal to two volumes of the original packed cells, followed by centrifugation at 7,000 xg for 15 min at 4° C.

The C100-3 polypeptide in the extracted pellet was solubilized by treatment with SDS. The pellets were suspended in Buffer A equal to 0.9 volumes of the original packed cell volume, and 0.1 volumes of 2% SDS was added. After the suspension was mixed, it was centrifuged at 7,000 xg for 15 min at 4° C. The resulting pellet was extracted 3 more times with SDS. The resulting supernatants, which contained C100-3 were pooled.

This procedure purifies C100-3 more than 10-fold from the insoluble fraction of the yeast homogenate, and the recovery of the polypeptide is greater than 50%.

The purified preparation of fusion polypeptide was analyzed by polyacrylamide gel electrophoresis according to Laemmli (1970). Based upon this analysis, the polypeptide was greater than 80% pure, and had an apparent molecular weight of ~54,000 daltons.

IV.B.7.a. Purification of Fusion Polypeptide C100-3 (Alternate method 1)

The fusion polypeptide, C100-3 (HCV c100-3), expressed in yeast strain JSC 308 transformed with pAB24C100-3, may be purified by an alternative method. In this method the antigen is precipitated from the crude cell lysate with acetone; the acetone precipitated antigen is then subjected to ion-exchange chromatography, and further purified by gel filtration.

The transformed yeast are grown under conditions which allow expression (see Section IV.B.4). A cell lysate is prepared by suspending the cells in Buffer A (20 mM Tris HCl, pH 8.0, 1 mM EDTA, 1 mM PMSF. The cells are broken by grinding with glass beads in a Dynomill type homogenizer or its equivalent. The extent of cell breakage is monitored by counting cells under a microscope with phase optics. Broken cells appear dark, while viable cells are light-colored. The percentage of broken cells is determined.

When the percentage of broken cells is approximately 90% or greater, the broken cell debris is separated from the glass beads by centrifugation, and the glass beads are washed with Buffer A. After combining the washes and homogenate, the insoluble material in the lysate is obtained by centrifugation. The material in the pellet is washed to remove soluble proteins by suspension in Buffer B (50 mM glycine, pH 12.0, 1 mM DTT, 500 mM NaCl), followed by Buffer C (50 mM glycine, pH 10.0, 1 mM DTT). The insoluble material is recovered by centrifugation, and solubilized by suspension in Buffer C containing SDS. The extract solution may be heated in the presence of b-mercaptoethanol and concentrated by ultrafiltration. The HCV c100-3 in the extract is precipitated with cold acetone. If desired, the precipitate may be stored at temperatures at about or below −15° C.

Prior to ion exchange chromatography, the acetone precipitated material is recovered by centrifugation, and may be dried under nitrogen. The precipitate is suspended in Buffer D (50 mM glycine, pH 10.0, 1 mM DTT, 7 M urea), and centrifuged to pellet insoluble material. The supernatant material is applied to an anion exchange column previously equilibrated with Buffer D. Fractions are collected and analyzed by ultraviolet absorbance or gel electrophoresis on SDS polyacrylamide gels. Those fractions containing the HCV c100-3 polypeptide are pooled.

In order to purify the HCV c100-3 polypeptide by gel filtration, the pooled fractions from the ion-exchange column are heated in the presence of b-mercaptoethanol and SDS, and the eluate is concentrated by ultrafiltration. The concentrate is applied to a gel filtration column previously equilibrated with Buffer E (20 mM Tris HCl, pH 7.0, 1 mM DTT, 0.1% SDS). The presence of HCV c100-3 in the eluted fractions, as well as the presence of impurities, are determined by gel electrophoresis on polyacrylamide gels in the presence of SDS and visualization of the polypeptides. Those fractions containing purified HCV c100-3 are pooled. Fractions high in HCV c100-3 may be further purified by repeating the gel filtration process. If the removal of particulate material is desired, the HCV c100-3 containing material may be filtered through a 0.22 mm filter.

IV.B.7.b. Expression and Purification of Fusion Polypeptide C100-3 (Alternate Method 2)

The fusion polypeptide C100-3 (also called HCV c100-3), is expressed in yeast strain JSC308 transformed with pAB24C100-3. The expression of the C100-3 coding region is under control of the ADH2 upstream activator sequences (UAS) and GAP promoter sequences. This system is repressed when glucose is present in the medium. In the fermentation process, the inocula cultures (Inoculum 1 and 2) are prepared in selective medium containing a high amount of glucose to repress synthesis of the C100-3 polypeptide. Inoculum 2 is then diluted into complete medium containing an initial concentration of glucose sufficient to allow substantial mass increase before being metabolically exhausted by fermentation growth of the culture. After the glucose has been exhausted from this expression medium, the cells derepress the ADH-2 regulated system as they begin to grow by respiration. In this method, the majority of the mass increase of the cell culture is functionally uncoupled from the production of the HCV C100-3 polypeptide. The expressed C100-3 polypeptide thus expressed is purified by isolation of an insoluble cell fraction, extraction of this fraction with SDS followed by acetone precipitation, solubilization of the acetone precipitate, followed by chromatography on an ion exchange column, Q-Sepharose® (Pharmacia), and on gel filtration columns.

Preparation and isolation of transformants is as follows. Yeast strain JSC308 (MATa, ura3-delta 1, leu2-04 [cir$^0$],:: DM15 (G418$^R$) is transformed with plasmid pAB24-c100-3, using the lithium transformation procedure described by Ito et al. (1984). The transformation mix is plated onto selective ura$^-$ agar plates, and the plates are incubated at 30° C. for 2 to 4 days. Next, transformants having high plasmid copy numbers are selected by streaking ura$^+$ colonies to leucine selective plates. Transformants are selected on their ability to express the C100-3 polypeptide, as described below.

In order to test expression of C100-3, single transformant colonies are transferred into leu$^-$, 2% glucose medium and grown at 30° C. until saturation. Under these conditions, expression of C100-3 is repressed due to the high glucose concentration in the medium. Expression is induced by a ⅟25 dilution of the saturated culture into YEP/1% glucose; the diluted cells are grown to saturation. The cells are harvested, lysed by grinding with glass beads in TE buffer containing NaCl. The insoluble fractions are collected by centrifugation, and solubilized by resuspension in SDS sample buffer and boiling. The solubilized fraction is examined by fractionation on standard 10% denaturing acrylamide gels (Laemmli (1970)). The polypeptides on the gel are visualized by staining with Coomassie blue. Evidence of expression is initially determined by appearance of a new polypeptide in extracts of transformants harboring pAB24-c100-3 as compared with control extracts (cells transformed with pAB24 vector lacking the C100-3 coding region). A protein band of about 53 Kd was clearly seen in extracts of cells harboring the C100-3 expression plasmid; this band was absent from the control extract.

A stock is prepared from a single transformant colony by streaking onto a leu$^-$ selective agar plate, and incubating at 30° C. for 1–4 days. Single colonies are picked, and individually inoculated into about 5 mL of leu$^-$, 2% glucose medium, and grown to saturation at 30° C. One mL is aseptically removed from each tube, and is transferred to a flask containing 500 mL of leu$^-$ medium, 2% glucose. The flask is incubated at 30° C. with agitation, for approximately 29 hours, after which time the flask is removed from incubation, an O.D. 650 value is determined, and the viability of the sample is determined. If the sample is viable, glycerol is added to a final concentration of 15%, and the sample is stored in 1 mL aliquots at $\leq$60° C.

A working seed stock is prepared. An aliquot of the frozen stock is plated onto leu$^-$ selective plates. An isolated small colony is picked, inoculated into 1–5 mL of selective culture (described above), and incubated at 30° C. for one day. One mL from this culture is used to inoculate a larger leu$^-$ selective media culture (500–1000 mL). After 30–60 hours of incubation, the OD$_{650}$ value and viability is determined. Glycerol is added to a final concentration of 15% to the viable culture. The culture is stored at $\leq$60° C. in 1 mL aliquots.

The stocks of transformed cells are analyzed. Viability of the stocks is equal to or greater than 5×10$^5$ viable cells per mL of culture. Phenotypic analysis is for the chromosomal markers MATa and ::DM15(G418$^R$). MATa is tested by a plate assay that detects secretion of mating factor when the test cells are patched onto a lawn of cells carrying the opposite mating type. Opposite mating types of the lawn and patched cells produce a clear halo around the patch. DM15 (G418$^R$) is tested by patching cells onto YEPD plates with and without geneticin. The presence of the latter marker allows for growth of the cells in geneticin plates.

The plasmids from the cells are also analyzed by restriction map and nucleotide sequence confirmation for the expression cassette.

In order to prepare inoculum 1, the transformed yeast cells from the working stock are incubated in sterile selective medium (leu$^-$, 2% glucose); incubation is at 30±2° C. at 250–350 rpm for 30 to 36 hours.

In order to prepare inoculum 2, sterile selective medium at pH 5.9±0.1 containing approximately 10 g of yeast nitrogen base without amino acids (DIFCO) per liter, 0.5 g of Leu$^-$ supplements per liter, antifoam (approximately 0.1 mL/L), and 200 g of dextrose per liter, is prepared in a fermentor. Inoculum 1 is transferred aseptically to the fermentor, and is incubated at 30±2° C. at an agitation speed of 400±50 rpm with an air flow of 10±2 liters per minute. Incubation is for 24±6 hours.

Expression of C100-3 is accomplished by transferring inoculum 2 to a fresh batch of sterile YEP medium with 2% dextrose, and incubating the cells in a fermentor for 53±7 hours at 30±2° C., with an agitation speed of 200±20 rpm and an air flow 200±20 liters per minute. After the incubation, the fermentor culture is cooled to <20° C., and harvested by continuous flow centrifugation. The supernatant is discarded, and the yeast slurry is collected.

The C100-3 polypeptide is partially purified by removal of the soluble yeast fraction. The yeast slurry is adjusted to 50 mM Tris HCl (using 1.0 M Tris HCl, pH 8.0), 0.15 M NaCl, 2 mM EDTA, and 1 mM PMSF. The yeast is mechanically disrupted using a continuous flow Dynomill glass bead mill with 0.5 mm nominal diameter glass beads. Breakage is continued until >90% of the yeast cells are broken. The resulting lysate is then diluted to achieve a 10% (v/v) solids concentration based on pre-lysis volume and packed cell volume by adding the same lysis buffer containing PMSF. Gross cellular debris is removed by continuous flow centrifugation in a Westfalia Model SA-1 centrifuge, and is discarded. The partially clarified, diluted lysate is further centrifuged at a higher relative G-force to recover the C100-3 polypeptide. This step is accomplished by continuous centrifugation of the lysate in a CEPA LE centrifuge at full speed (flow rate, 100 to 200±20 mL/minute). The supernatant is discarded, and the CEPA pellets are collected and stored at $\leq$60° C.

Further purification of the C100-3 polypeptide from the CEPA pelleted material is accomplished by acetone precipitation of an SDS solubilized fraction, followed by ion-exchange chromatography of the precipitated material, and then by gel filtration chromatography of the eluate from the ion-exchange column.

The CEPA pelleted material is resuspended in a Tris/EDTA buffer (20 mM Tris HCL, pH 8.0, 1.0 mM EDTA, 1.0 mM PMSF), and insoluble material is collected by centrifugation at 17,000 x G for 60 minutes at approximately 4° C. The pellet is washed twice with a glycine/DTT/NaCl buffer (50 mM glycine, 1.0 mM DTT, 50 mM NaCl, pH 12) and once with glycine/DTT buffer (50 mM glycine, 1.0 mM DTT, pH 10.0) before it is extracted by suspension in the same buffer containing 0.5% SDS (w/v). The pellet is recovered by centrifugation (17,000 xg, 30 min, about 4° C.), and the SDS extraction is repeated. The two extracts are combined, and heated to 80–85° C. to solubilize the C100-3 polypeptide. After solubilization, the extract is cooled and BME is added to a concentration of 1% (w/v), and the extract solution is precipitated with cold acetone to remove excess SDS; this material may be stored at <−15° C. for up to five weeks. The acetone precipitate is recovered by centrifugation (5,000 xg).

In order to further purify the material in the acetone precipitate by chromatography, the precipitate is suspended in glycine/urea buffer (50 mM glycine, pH 10, 7 mM urea, 10 mM DTT), is heated to 80–85° C., then cooled. The extract is then applied to a Q-Sepharose® anion exchange column (2.5 L Q Sepharose®, 25 cm diameter column) which was previously equilibrated against the glycine/urea buffer; the flow rate is ~50 mL per minute, and the temperature is 2 to 8° C. The fractions are collected, and those containing C100-3 polypeptide, as determined by absorbance at 280 nm, are pooled.

The material which passes through the ion exchange column is further purified by gel filtration. The pool of fractions from the ion-exchange column is adjusted to 0.5% (w/v) SDS, and is concentrated two-fold with an ultrafiltration unit using a 30K molecular weight cut-off membrane. The concentrated fraction is then adjusted to 2% (v/v) BME, heated, the protein concentration is measured, and the fraction is cooled. The cooled eluate is then applied to Sephacryl® S-300 HR gel filtration columns which were previously equilibrated with an SDS/Tris buffer (0.1% SDS (w/v), 20 mM Tris HCl, pH 7.0, 10 mM DTT). The gel filtration columns are 55 cm high by 25 cm diameter; the filtration is over two of these units in series; the operating flow is 100 mL per minute. Fraction collection is started immediately after loading. The eluted fractions are analyzed by electrophoresis on polyacrylamide gels containing SDS, in order to determine which of the fractions should be pooled. Prior to electrophoresis, the test samples and a reference sample are prepared by boiling in a buffer containing BME and SDS. Following electrophoresis, the gels are stained with Coomassie blue for visualization of the protein bands. The determination of which fractions to pool is based on the following analysis. The fraction containing the highest and purest amount of polypeptide is called "peak fraction". This fraction together with fractions which elute earlier are pooled up to, and including the first fraction exhibiting a decrease of approximately ⅓ the amount of C100-3 polypeptide band relative to the adjacent fraction, and a decrease of approximately ⅔ relative to the peak fraction. The decrease is observed in the relative thickness of the C100-3 bands. Fractions which elute later than the C100-3 peak are pooled up to, but not including the first fraction exhibiting a visible band at the molecular weight of about 18,000 relative to a molecular weight marker, and including the last fraction exhibiting a decrease of approximately ⅔ of the polypeptide band relative to the peak fraction.

The pooled fractions are further purified by repeating the gel filtration process. The fractions from the second gel filtration column are analyzed as described above, and are further analyzed by HPLC to determine pooling. Analysis by HPLC uses a TSK-400 gel filtration HPLC column, equipped with a computerized integrator. All samples are prepared in a buffer containing 20 mM DTT to prevent oxidation of the C100-3 polypeptide. Pooling based on HPLC analysis is as follows. Using the HPLC chromatograms, the ratio of peak height to peak area for the C100-3 peak in each of the fractions is calculated. The ratio values follow a trend, increasing to a maximum value and then decreasing. Those fractions with a ratio equal to or greater than 85% of the maximum value and which meet the criteria in gel electrophoresis are pooled. The total volume of the pool of fractions is measured, the protein concentration is determined by the Lowry method, and the concentration of the final pool is adjusted to 0.5 to 1.0 mg/mL with the same buffer used for the gel filtration columns.

IV.B.8. Expression and Antigenicity of Polypeptides Encoded in HCV cDNA

IV.B.8.a. Polypeptides Expressed in *E. coli*

Figure 63:
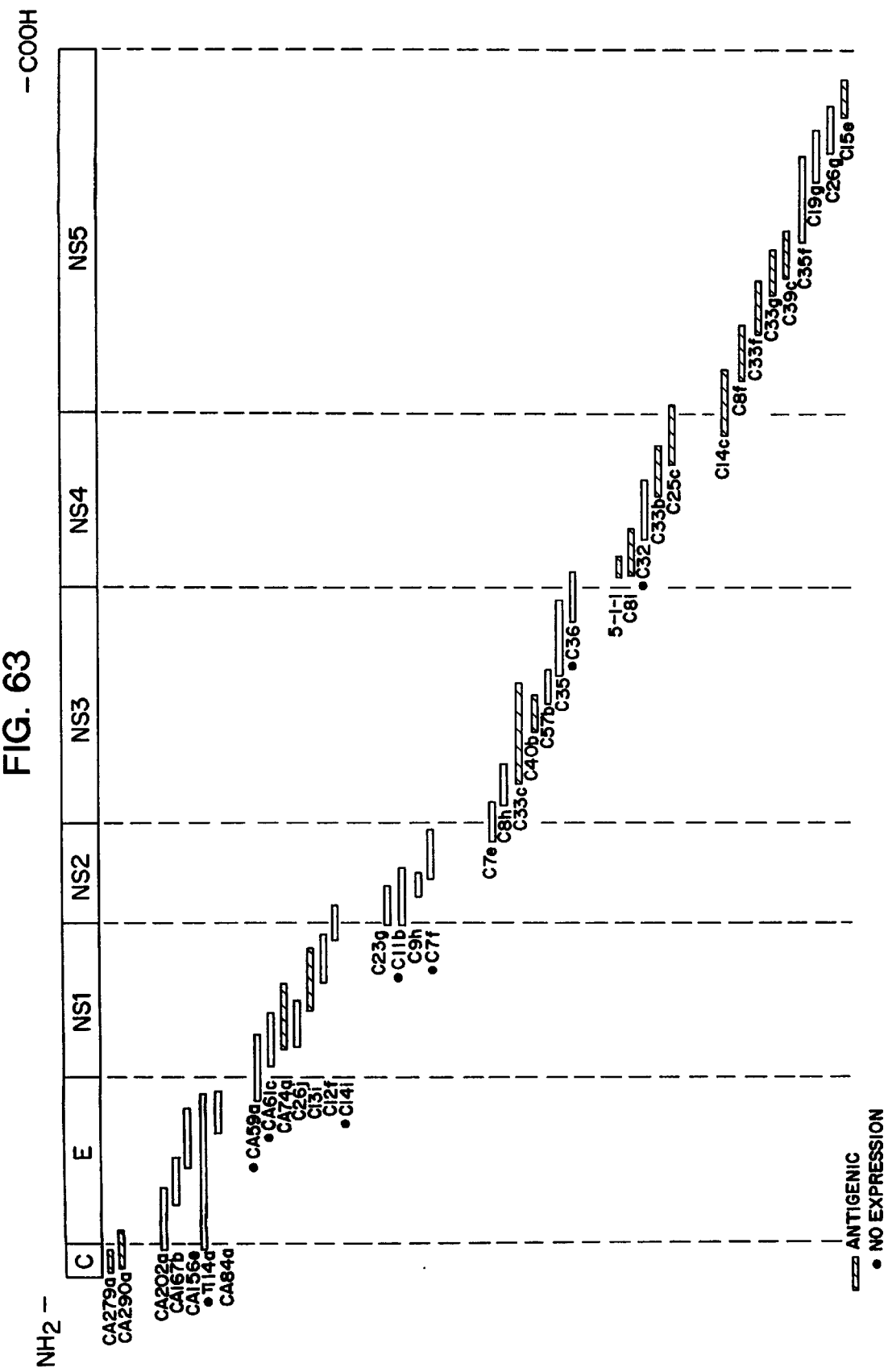
FIG. 63 shows the relative positions of the clones from which HCV cDNA was isolated for expression and antigenic mapping of the putative HCV polyprotein.

The polypeptides encoded in a number of HCV cDNAs which span the HCV genomic ORF were expressed in *E. coli*, and tested for their antigenicity using serum obtained from a variety of individuals with NANBH. The clones from which the HCV cDNAs were isolated, as well as their relative relationships, and antigenicity, are shown in FIG. 63. Also indicated in the figure are the putative polypeptides encoded in the ORF of the HCV genome, based upon the Flavivirus model and the hydropathic character of the putative encoded polypeptides. However, the hydrophobicity profiles (described infra), indicate that HCV diverges from the Flavivirus model, particularly with respect to the region upstream of NS2. Moreover, the boundaries indicated are not intended to show firm demarcations between the putative polypeptides.

Possible protein domains of the encoded HCV polyprotein, as well as the approximate boundaries, are the following:

| Putative Domain | Approximate Boundary (amino acid nos.) |
|---|---|
| C (nucleocapsid protein) | 1–120 |
| E (Virion envelope protein(s) and possibly matrix (M) proteins | 120–400 |
| NS1 (complement fixation antigen?) | 400–660 |
| NS2 (unknown function) | 660–1050 |
| NS3 (protease?) | 1050–1640 |
| NS4 (unknown function) | 1640–2000 |
| NS5 (polymerase) | 2000-? end |

These domains are, however, extremely tentative, since they are based upon the Flavivirus model, and recent evidence suggests that the relationship between HCV and the flaviviridae may be distant.

The expression vectors containing the cloned HCV cDNAs were constructed from pSODcf1, which is described in Section IV.B. 1. In order to be certain that a correct reading frame would be achieved, three separate expression vectors, pcf1AB, pcf1 CD, and pcf1EF were created by ligating three new linkers, AB, CD, and EF to a BamHI-EcoRI fragment derived by digesting to completion the vector pSODcf1 with EcoRI and BamHI, followed by treatment with alkaline phosphatase. The linkers were created from six oligomers, A, B, C, D, E, and F. Each oligomer was phosphorylated by treatment with kinase in the presence of ATP prior to annealing to its complementary oligomer. The sequences of the synthetic linkers were the following.

| Name | DNA Sequence (5' to 3') | |
|------|-------------------------|---|
| A | GATC CTG AAT TCC TGA TAA | (SEQ ID NO: 231) |
| B | GAC TTA AGG ACT ATT TTA A | (SEQ ID NO: 232) |
| C | GATC CGA ATT CTG TGA TAA | (SEQ ID NO: 233) |
| D | GCT TAA GAC ACT ATT TTA A | (SEQ ID NO: 234) |
| E | GATC CTG GAA TTC TGA TAA | (SEQ ID NO: 235) |
| F | GAC CTT AAG ACT ATT TTA A | (SEQ ID NO: 236) |

Each of the three linkers destroys the original EcoRI site, and creates a new EcoRI site within the linker, but within a different reading frame. Hence, the HCV cDNA EcoRI fragments isolated from the clones when inserted into the expression vector, were in three different reading frames.

The HCV cDNA fragments in the designated λgt11 clones (indicated in FIG. 63) were excised by digestion with EcoRI; each fragment was inserted into pcf1AB, pcf1CD, and pcf1EF. These expression constructs were then transformed into D1210 *E. coli* cells, the transformants were cloned, and polypeptides were expressed as described in Section IV.B.2.

Expression products of the indicated HCV cDNAs were tested for antigenicity by direct immunological screening of the colonies, using a modification of the method described in Helfman et al. (1983). Briefly, as shown in FIG. 64, the bacteria were plated onto nitrocellulose filters overlaid on ampicillin plates to give approximately 1,000 colonies per filter. Colonies were replica plated onto nitrocellulose filters, and the replicas were regrown overnight in the presence of 2 mM IPTG and ampicillin. The bacterial colonies were lysed by suspending the nitrocellulose filters for about 15 to 20 min in an atmosphere saturated with $CHCl_3$ vapor. Each filter then was placed in an individual 100 mm Petri dish containing 10 mL of 50 mM Tris HCl, pH 7.5, 150 mM NaCl, 5 mM $MgCl_2$, 3% (w/v) BSA, 40 mg/mL lysozyme, and 0.1 mg/mL DNase. The plates were agitated gently for at least 8 hours at room temperature. The filters were rinsed in TBST (50 mM Tris HCl, pH8.0, 150 mM NaCl, 0.005% Tween® 20). After incubation, the cell residues were rinsed and incubated in TBS (TBST without Tween®) containing 10% sheep serum; incubation was for 1 hour. The filters were then incubated with pretreated sera in TBS from individuals with NANBH, which included: 3 chimpanzees; 8 patients with chronic NANBH whose sera were positive with respect to antibodies to HCV C100-3 polypeptide (described in Sections IV.B.6. and IV.B.7.) (also called C100); 8 patients with chronic NANBH whose sera were negative for anti-C100 antibodies; a convalescent patient whose serum was negative for anti-C100 antibodies; and 6 patients with community acquired NANBH, including one whose sera was strongly positive with respect to anti-C100 antibodies, and one whose sera was marginally positive with respect to anti-C100 antibodies. The sera, diluted in TBS, was pretreated by preabsorption with hSOD. Incubation of the filters with the sera was for at least two hours. After incubation, the filters were washed two times for 30 min with TBST. Labeling of expressed proteins to which antibodies in the sera bound was accomplished by incubation for 2 hours with $^{125}$I-labeled sheep anti-human antibody. After washing, the filters were washed twice for 30 min with TBST, dried, and autoradiographed.

As seen from the results shown in FIG. 65, a number of clones expressed polypeptides containing HCV epitopes which were immunologically reactive with serum from individuals with NANBH. Five of these polypeptides were very immunogenic in that antibodies to HCV epitopes in these polypeptides were detected in many different patient sera. The clones encoding these polypeptides, and the location of the polypeptide in the putative HCV polyprotein (wherein the amino acid numbers begin with the putative initiator codon) are the following: clone 5-1-1, amino acids 1694–1735; clone C100, amino acids 1569–1931; clone 33c, amino acids 1192–1457; clone CA279a, amino acids 1–84; and clone CA290a amino acids 9–177. The location of the immunogenic polypeptides within the putative HCV polyprotein are shown immediately below.

| Clones encoding polypeptides of proven reactivity with sera from NANBH patients. | |
|---|---|
| Clone | Location within the HCV polyprotein (amino acid no. beginning with putative initiator methionine) |
| CA279a | 1–84 |
| CA74a | 437–582 |
| 13i | 511–690 |
| CA290a | 9–177 |
| 33c | 1192–1457 |
| 40b | 1266–1428 |
| 5-1-1 | 1694–1735 |
| 81 | 1689–1805 |
| 33b | 1916–2021 |
| 25c | 1949–2124 |
| 14c | 2054–2223 |
| 8f | 2200–3325 |
| 33f | 2287–2385 |
| 33g | 2348–2464 |
| 39c | 2371–2502 |
| 15e | 2796–2886 |
| C100 | 1569–1931 |

The results on the immunogenicity of the polypeptides encoded in the various clones examined suggest efficient detection and immunization systems may include panels of HCV polypeptides/epitopes.

IV.B.8.b. Expression of HCV Epitopes in Yeast

Three different yeast expression vectors which allow the insertion of HCV cDNA into three different reading frames are constructed. The construction of one of the vectors is described in Section IV.B.4., except that HCV cDNA from the clones listed in Section IV.B.8.a. are substituted for the C100 HCV cDNA. The construction of the other vectors replaces the adaptor described in Section IV.B.4. with one of the following adapters:

| | Adaptor 1 |
|---|---|
| (SEQ ID NO: 237) | ATT TTG AAT TCC TAA TGA G<br>AC TTA AGG ATT ACT CAG CT |
| | Adaptor 2 |
| (SEQ ID NO: 238) | AAT TTG GAA TTC TAA TGA G<br>AC CTT AAG ATT ACT CAG CT. |

The inserted HCV cDNA is expressed in yeast transformed with the vectors, using the expression conditions described in Section IV.B.4. The resulting polypeptides are screened using the sera from individuals with NANBH, described in Section IV.B.8.a.

IV.B.9. Expression and Purification of Fusion Polypeptide SOD-C33c

A fusion polypeptide comprised of SOD at the N-terminus and in-frame C33c HCV-polypeptide at the C-terminus (SOD-C33c), is encoded in clone pCF1EF/C33c (see Section IV.B.8.). This polypeptide was expressed in *E. coli*, and purified therefrom.

Expression was accomplished by inoculating 1500 mL of Luria broth containing ampicillin (100 mg/mL) with 15 mL of an overnight culture of *E. coli* D1210 transformed with clone pCF1EF/C33c. The cells were grown to an O.D. of 0.3, IPTG was added to yield a final concentration of 2 mM, and growth continued until the cells attained a density of 1 O.D., at which time they were harvested by centrifugation at 3,000 xg at 4° C. for 20 minutes. The packed cells can be stored at −80° C. for several months.

In order to purify the SOD-C33c polypeptide the bacterial cells in which the polypeptide was expressed were subjected to osmotic shock and mechanical disruption, the insoluble fraction containing SOD-C33c was isolated and subjected to differential extraction with an alkaline-NaCl solution, and the fusion polypeptide in the extract purified by chromatography on a cation exchange column, S-Sepharose® (Pharmacia) and an anion exchange column, Q-Sepharose® (Pharmacia).

The crude extract resulting from osmotic shock and mechanical disruption was prepared by the following procedure. One gram of the packed cells were suspended in 10 mL of a solution containing 0.02 M Tris HCl, pH 7.5, 10 mM EDTA, 20% sucrose, and incubated for 10 minutes on ice. The cells were then pelleted by centrifugation at 4,000 xg for 15 min at 4° C. After the supernatant was removed, the cell pellets were resuspended in 10 mL of Buffer A1 (0.01M Tris HCl, pH 7.5, 1 mM EDTA, 14 mM b-mercaptoethanol [BME]), and incubated on ice for 10 minutes. The cells were again pelleted at 4,000 xg for 15 minutes at 4° C. After removal of the clear supernatant (periplasmic fraction I), the cell pellets were resuspended in Buffer A1, incubated on ice for 10 minutes, and again centrifuged at 4,000 xg for 15 minutes at 4° C. The clear supernatant (periplasmic fraction II) was removed, and the cell pellet resuspended in 5 mL of Buffer A2 (0.02 M Tris HCl, pH 7.5, 14 mM BME, 1 mM EDTA, 1 mM PMSF). In order to disrupt the cells, the suspension (5 mL) and 7.5 mL of Dyno-mill lead-free acid washed glass beads (0.10–0.15 mm diameter)(obtained from Glen-Mills, Inc.) were placed in a Falcon tube, and vortexed at top speed for two minutes, followed by cooling for at least 2 min on ice; the vortexing-cooling procedure was repeated another four times. After vortexing, the slurry was filtered through a scintered glass funnel using low suction; the glass beads were washed two times with Buffer A2, and the filtrate and washes combined.

The insoluble fraction of the crude extract was collected by centrifugation at 20,000 xg for 15 min at 4° C., washed twice with 10 mL Buffer A2, and resuspended in 5 mL of MILLI-Q water.

A fraction containing SOD-C33c was isolated from the insoluble material by adding to the suspension NaOH (2 M) and NaCl (2 M) to yield a final concentration of 20 mM each, vortexing the mixture for 1 minute, centrifuging it 20,000 xg for 20 min at 4° C., and retaining the supernatant.

In order to purify SOD-C33c on a cation exchange column, S-Sepharose® (Pharmacia), the supernatant fraction was adjusted to a final concentration of 6M urea, 0.05M Tris HCl, pH 7.5, 14 mM BME, 1 mM EDTA. This fraction was then applied to a cation exchange column, S-Sepharose Fast Flow® (Pharmacia) (1.5×10 cm) which had been equilibrated with Buffer B (0.05M Tris HCl, pH 7.5, 14 mM BME, 1 mM EDTA). After application, the column was washed with two column volumes of Buffer B. The flow through and wash fractions were collected. The flow rate of application and wash, was 1 mL/min; and collected fractions were 1 mL. In order to identify fractions containing SOD-C33c, aliquots of the fractions were analyzed by electrophoresis on 10% polyacrylamide gels containing SDS followed by staining with Coomassie blue. The fractions are also analyzable by Western blots using an antibody directed against SOD. Fractions containing SOD-C33c were pooled.

Further purification of SOD-C33c was on an anion exchange column, Q-Sepharose column(® (Pharmacia) (1.5×5 cm) which was equilibrated with Buffer B. The pooled fractions containing SOD-C33c obtained from chromatography on a cation exchange column, S-Sepharose® (Pharmacia) was applied to the column. The column was then washed with Buffer B, and eluted with 60 mL of a gradient of 0.0 to 0.4 M NaCl in Buffer B. The flow rate for application, wash, and elution was 1 mL/min; collected fractions were 1 mL. All fractions from the anion exchange column, Q-Sepharose® (Pharmacia) were analyzed as described for the cation exchange column, S-Sepharose® (Pharmacia). The peak of SOD-C33c eluted from the column at about 0.2 M NaCl.

The SOD-C33c obtained from the anion exchange column, Q-Sepharose® (Pharmacia) was greater than about 90% pure, as judged by analysis on the polyacrylamide SDS gels and immunoblot using a monoclonal antibody directed against human SOD.

IV.B.10. Expression in Yeast of Fusion Polypeptide SOD-C200-C100

IV.B.10.a. Construction of an Expression Vector Comprised of Expression Cassette C200-C100

An expression cassette containing the ADH2/GAP promoter, a sequence encoding SOD, the composite HCV sequences C200 and C100, and the a-factor terminator was constructed. The C200 sequence overlaps the C100 sequence. Thus, the C200-C100 construct was designed to express the segment of the continuous ORF contained in clones 33c/31135/36/81/32. FIG. 79 shows the sequence of the HCV cDNA in the construct, the polypeptides encoded therein, and the putative restriction enzyme sites encoded therein.

The C200-C100 construct was formed by ligating together a ~1.29 Kbp fragment obtained by digestion of plasmid pBR322-C200 with EcoRI and NcoI, and a ~950 bp fragment obtained by digestion of plasmid pS3-56$_{C100m}$ with NcoI and SalI. The construction of plasmids pBR322-C200 and of pS3-56$_{C100m}$ described in Sections IV.A.37 and IV.A.36, respectively.

In order to join the ADH2/GAP promoter, and the sequence encoding SOD to the 5'-terminus of the construct, and the α-factor terminator to the 3'-terminus of the construct, the C200-C100 construct was inserted into the vector pS3-34, which had been digested with EcoRI and SalI.

The vector pS3-34 was created from the vector pYS13 by deletion of the insulin sequences encoded therein, and by insertion of two linkers, C and D. These linkers allow the SOD encoding sequence and the HCV C200-C100 sequences to be in correct reading frame. Deletion of the insulin sequences was accomplished by digestion with EcoRI and SalI, followed by purification of the large vector fragment. The sequences of the inserted linkers are:

Linker C: 5' AAT TTG GAA TTC TAA TTA ATT AAG 3'Linker
D: AC CTT AAG ATT AAT TAA
    TTCAGCT           (SEQ ID NO:239 and SEQ ID NO:240)

The underlined sequences, CTTAAG and CAGCT, indicate an EcoRI site and a SalI site, respectively.

The plasmid pYSI3, described briefly in Table 1 of the U.S. Pat. No. 4,751,180, was used as a convenient way to attach the C100 and C200-C100m sequences to the ADH2/GAP hybrid promoter, the α-factor terminator and the SOD sequences. Previously, pYSI3 was used to express insulin; therefore, the vector contains a BamHI cassette (2.4 Kbp) which comprises the ADH2/GAP hybrid yeast promoter upstream of the hSOD gene (see U.S. Pat. No. 4,751,180) which in turn is fused to a hinge region and an insulin gene. Downstream of the insulin sequence is the yeast α-factor transcription terminator which is a 270 bp, SalI to EcoRI fragment, from the *Saccharomyces cerevisiae* α-factor gene described in Singh et al., *Nuc Acids Res* (1983) 11(12) :4049–4063. The insulin and hinge sequences were removed from the vector by digestion with EcoRI and SalI and the appropriate synthetic adapters were inserted between these two restriction sites to yield plasmid pS3-56 and pS3-34.

An expression vector containing the C200-C100 expression cassette was constructed by insertion of the cassette into the yeast expression vector pAB24; the vector pAB24 is described in Section IV.B.4.. The insertion was accomplished by excising a 4349 bp BamHI/BamHI cassette from the pS3-34/C200-C100 cloning vector and inserting the fragment into the BamHI site of the expression vector pAB24. The resulting vector, which is called pAB24/C200-C100, was transformed into yeast strain JSC308. Yeast strain JSC308 is described in commonly owned U.S. Ser. No. 190,868, and is on deposit with the American Type Culture Collection under Accession No. 20879.

IV.B.10.b. Expression of Fusion Polypeptide SOD/C200-C100

Expression of fusion polypeptide SOD/C200-C100 encoded in pAB24/C200-C100 was in yeast strain JSC308, which had been transformed with the isolated expression vector. The yeast transformants were grown in an inoculum culture for 24 to 30 hours in Leu⁻ medium containing 2% glucose; growth was at 30° C. at an agitation rate of 300 rpm. Expression of the fusion polypeptide was obtained by inoculating 500 mL of YEP containing 2% glucose with 25 mL of the inoculum culture, followed by incubation at 30° C. for 48 hours at an agitation rate of about 300 rpm. Growth was in a 2.8 L Fernbach flask.

Alternatively, 500 mL of inoculum was added to 10 L of YEP containing 4% glucose, and growth was in a Braun Biotech Model Biostat E fermentor at an agitation rate of about 400±20 rpm at a temperature of about 30° C.±2° C. and an air flow rate of 10±slpm; the cells were harvested 50 hours after inoculation.

IV.B.11. Expression of HCV Polypeptide C100 in Yeast

The composite HCV cDNA C100 (see Section IV.A. 16) was fused directly to the ADH2/GAP promoter, and expressed in yeast.

IV.B.11.a. Construction of Yeast Expression Vector pC100-d#3

Figure 76:
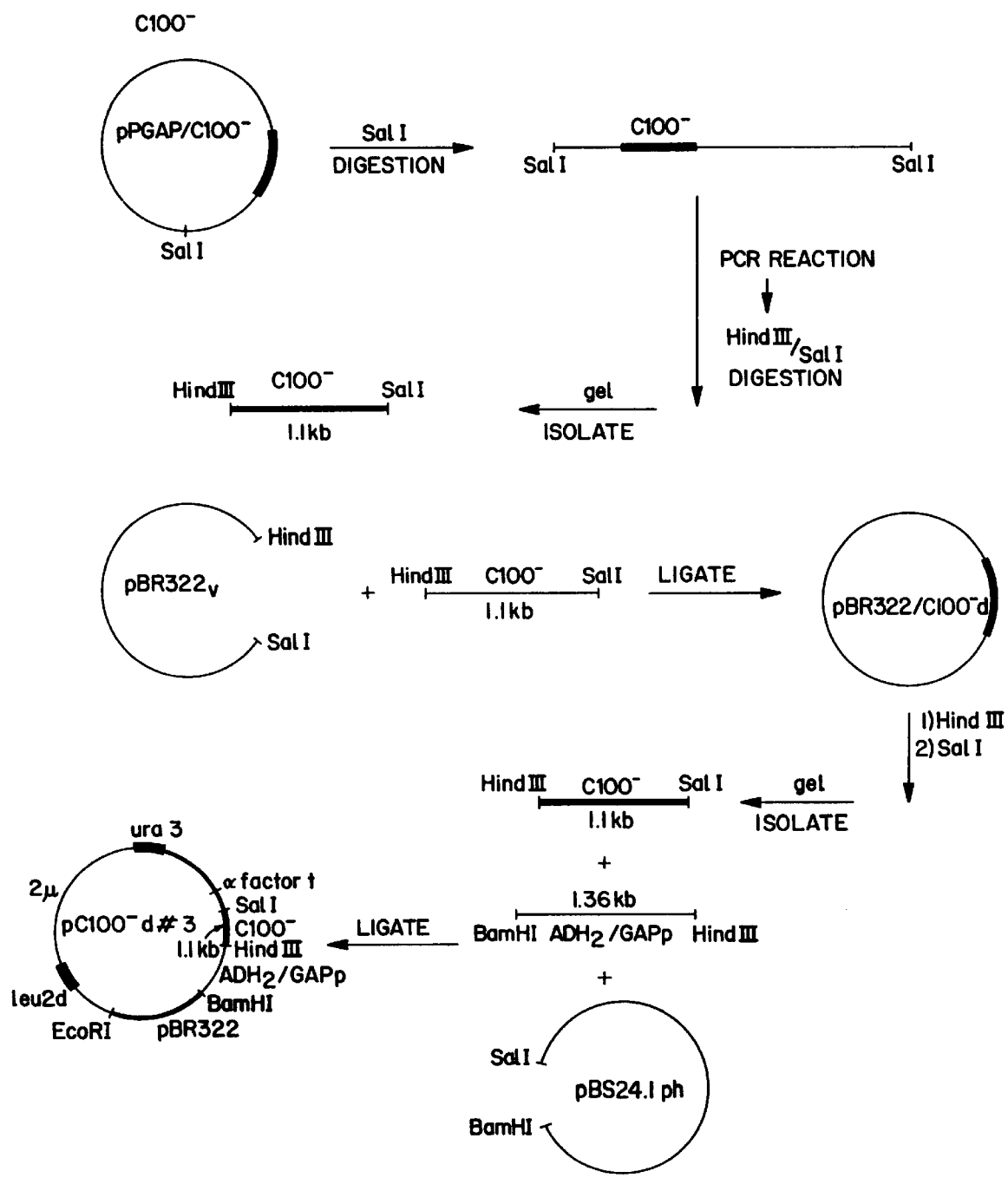
FIG. 76 shows a flow chart for construction of the expression vector pC100-d#3.

The construction of a yeast expression vector in which the HCV cDNA C100 sequence (described in Sections IV.A.16.) was fused directly to the ADH2/GAP promoter was accomplished by a protocol which included amplification of the C100 sequence using a PCR method, followed by ligation of the amplified sequence into a cloning vector. After cloning, the C100 sequence was excised, and with a sequence which contained the ADH2/GAP promoter, was ligated to a large fragment of a yeast vector to yield a yeast expression vector. A flow chart of the construction of the yeast expression vector is shown in FIG. 76.

The PCR amplification of C100 was performed using as template the vector pS3-56$_{C100m}$ (see Section IV.A.36.), which had been linearized by digestion with SalI.

The oligonucleotide primers used for the amplification were designed to facilitate cloning into the expression vector, and to introduce a translation termination codon. Specifically, novel 5'-HindIII and 3'-SalI sites were generated with the PCR oligonucleotides. The oligonucleotide containing the SalI site also encodes the double termination codons, TAA and TGA. The oligonucleotide containing the HindIII site also contains an untranslated leader sequence derived from the pgap63 gene, situated immediately upstream of the AUG codon. The pEco63GAPDH gene is described by Holland and Holland (1980) and by Kniskem et al. (1986). The PCR primer sequences used for the direct expression of C100m were:

5' GAG TGC TCA AGC TTC AAA ACA AAA TGG CTC ACT
       TTC TAT CCC AGA CAA AGC AGA GT 3' (SEQ ID NO:241)

and

5' GAG TGC TCG TCG ACT CAT TAG GGG GAA ACA TGG
       TTC CCC CGG GAG GCG AA 3'       (SEQ ID NO:242).

Amplification by PCR, utilizing the primers, and template, was with a Cetus-Perkin-Elmer PCR kit, and was performed according to the manufacturer's directions. The PCR conditions were 29 cycles of 94° C. for a minute, 37° C. for 2 minutes, 72° C. for 3 minutes; and the final incubation was at 72° C. for 10 minutes. The DNA can be stored at 4° C. or −20° C. overnight.

After amplification, the PCR products were digested with HindIII and SalI. The major product of 1.1 kb was purified by electrophoresis on a gel, and the eluted purified product was ligated with a large SalI-HindIII fragment of pBR322. In order to isolate correct recombinants, competent HB101 cells were transformed with the recombinant vectors, and after cloning, the desired recombinants were identified on the basis of the predicted size of HindIII-SalI fragments excised from the clones. One of the clones which contained the a HindIII-SalI fragment of the correct size was named pBR322/C100-d. Confirmation that this clone contained amplified C100 was by direct sequence analysis of the HindIII-SalI fragment.

The expression vector containing C100 was constructed by ligating the HindIII-SalI fragment from pBR322/C100-d to a 13.1 kb BamHI-SalI fragment of pBS24.1, and a 1369 bm BamHI-HindIII fragment containing the ADH2/GAP promoter. (The latter fragment is described in EPO 164, 556). The pBS24.1 vector is described in commonly owned U.S. Ser. No. 382,805 filed 19 Jul. 1989. The ADH2/GAP promoter fragment was obtained by digestion of the vector pPGAP/AG/HindIII with HindIII and BamHI, followed by purification of the 1369 bp fragment on a gel.

Competent HB 101 cells were transformed with the recombinant vectors; and correct recombinants were identified by the generation of a 2464 bp fragment and a 13.1 kb fragment generated by BamHI and SalI digestion of the cloned vectors. One of the cloned correct recombinant vectors was named pC 100-d#3.

IV.B.11.b. Expression of C100 from pC100-d#3

In order to express C100, competent cells of Saccharomyces cerevisiae strain AB122 (MATa leu2 ura3-53 prb 1-1122 pep4-3 prc1-407[cir-0]) were transformed with the expression vector pC100-d#3. The transformed cells were plated on URA-sorbitol, and individual transformants were then streaked on Leu-plates.

Individual clones were cultured in Leu⁻, ura⁻ medium with 2% glucose at 30° C. for 24–36 hours. One liter of Yeast Extract Peptone Medium (YEP) containing 2% glucose was inoculated with 10 mL of the overnight culture, and the resulting culture was grown at 30° C. at an agitation rate of 400 rpm and an aeration rate of 1 L of air per 1 L of medium per minute (i.e., 1 vvm) for 48 hours. The pH of the medium was not controlled. The culture was grown in a BioFlo II fermentor manufactured by New Brunswick Science Corp. Following fermentation, the cells were isolated and analyzed for C100 expression.

Analysis for expressed C100 polypeptide by the transformed cells was performed on total cell lysates and crude extracts prepared from single yeast colonies obtained from the Leu⁻ plates. The cell lysates and crude extracts were analyzed by electrophoresis on SDS polyacrylamide gels, and by Western blots. The Western blots were probed with rabbit polyclonal antibodies directed against the SOD-C100 polypeptide expressed in yeast. The expected size of the C100 polypeptide is 364 amino acids. By gel analysis the expressed polypeptide has a $MW_r$ of 39.9K.

Both analytical methods demonstrated that the expressed C100 polypeptide was present in total cell lysates, but was absent from crude extracts. These results suggest that the expressed C100 polypeptide may be insoluble.

IV.B.12 Expression of HCV Polypeptide S2 in Yeast

An S2 polypeptide encoded in the HCV cDNA shown in FIG. 72 contains amino acids 199 to 328 encoded in the ORF. The clone, pi14a, described supra, contains an HCV cDNA which encodes these amino acids.

Figure 77:
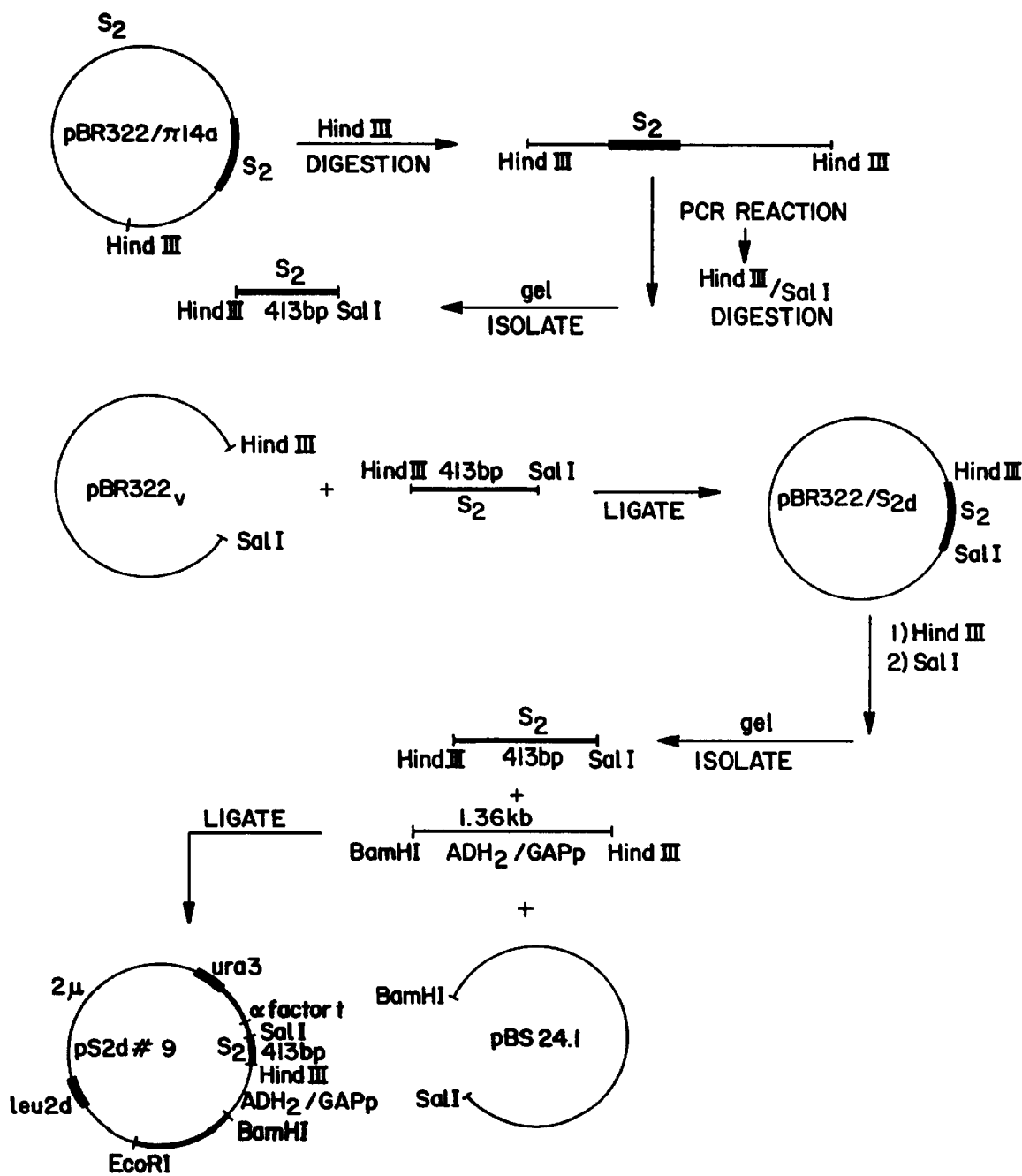
FIG. 77 shows a flow chart for construction of the expression vector pS2d#9.

The protocol for the construction of the expression vector encoding the S2 polypeptide and for its expression in yeast was analogous to that used for the expression of the C100 polypeptide, described in Sections IV.B.11, IV.B.11a and IV.B.11b, except for the following. (A flow chart of the construction of the yeast expression vector encoding S2 is shown in FIG. 77.)

The template for the PCR reaction was the vector pBR322/Pi14a, which had been linearized by digestion with HindIII.

The oligonucleotides used as primers for the amplification by PCR of the S2 encoding sequence were the following.

For the 5'-region of the S2 sequence:

5' GAG TGC TCA AGC TTC AAA ACA AAA TGG GGC TCT ACC ACG TCA CCA ATG ATT GCC CTA
AC 3'  (SEQ ID NO:243)

and for the 3'-region of the S2 sequence:

5' GAG TGC TCG TCG ACT CAT TAA GGG GAC CAG TTC ATC ATC ATA TCC CAT GCC AT 3'  (SEQ ID NO:244).

The primer for the 5'-region introduces a HindIII site and an ATG start codon into the amplified product. The primer for the 3'-region introduces translation stop codons and a SalI site into the amplified product.

The PCR conditions were 29 cycles of 94° C. for a minute, 37° C. for 2 minutes, 72° C. for 3 minutes, and the final incubation was at 72° C. for 10 minutes.

The main product of the PCR reaction was a 413 bp fragment, which was gel purified. The purified fragment was ligated to the large fragment obtained from pBR322 digested with HindIII and SalI fragment, yielding the plasmid pBR322/S2d. 15 Ligation of the 413 bp HindIII-SalI S2 fragment with the 1.36 kb BamHI-HindIII fragment containing the ADH2/GAP promoter, and with the large BamHI-SalI fragment of the yeast vector pBS24.1 yielded recombinant vectors, which were cloned. Correct recombinant vectors were identified by the presence of a 1.77 kb fragment after digestion with BamHI and SalI. An expression vector constructed from the amplified sequence, and containing the sequence encoding S2 fused directly to the ADH2/GAP promoter is identified as pS2d#9.

Analysis for expressed S2 polypeptide by the transformed cells was performed on total cell lysates and crude extracts prepared from single yeast colonies obtained from the Leu⁻ plates. The cell lysates and crude extracts were analyzed by electrophoresis on SDS polyacrylamide gels. The expected size of the S2 polypeptide is 130 amino acids. By gel analysis, the expressed polypeptide has a $MW_r$ of 16 Kd. The expressed S2 was detected in the total lysates, and not in the crude extracts, suggesting that the expressed S2 may be insoluble.

IV.B.13. Expression of HCV C Polypeptide in Yeast

A polypeptide encoded in the HCV cDNA shown in FIG. 72, and which contains amino acids numbers 1 to 122 encoded in the ORF, is named herein the C polypeptide.

The protocol for the construction of the expression vector encoding the C polypeptide and for its expression in yeast was analogous to that used for the expression of the C100 polypeptide, described in Sections IV.B.11, IV.B.11.a and IV.B.11.b, except for the following. (A flow chart of the construction of the yeast expression vector encoding the C polypeptide is shown in FIG. 92.)

The template for the PCR reaction was pBR322/Ag30a which had been linearized with HindIII. The HCV cDNA in clone Ag30a is described in Section IV.A.30. The oligonucleotides used as primers for the amplification by PCR of the C encoding sequence were the following.

For the 5'-region of the C sequence:

5' GAG TGC AGC TTC AAA ACA AAA TGA GCA CGA ATC CTA AAC CTC AAA AAA AAA AC 3'  (SEQ ID NO:245)

and for the 3'-region of the C sequence:

5' GAG TGC TCG TCG ACT CAT TAA CCC AAA TTG CGC GAC CTA CGC CGG GGG TCT GT 3'  (SEQ ID NO:246).

The primer for the 5'-region introduces a HindIII site into the amplified product, and the primer for the 3'-region introduces translation stop codons and a SalI site. The PCR was run for 29 cycles of 94° C. for a minute, 37° C. for 2 minutes, 72° C. for 3 minutes, and the final incubation was at 72° C. for 10 minutes.

The major product of PCR amplification is a 381 bp polynucleotide. Ligation of this fragment with the SalI-HindIII large SalI-HindIII fragment of pBR322 yielded the plasmid pBR322/C2.

Ligation of the 381 bp HindIII-SalI C coding fragment excised from pBR322/C2 with the 1.36 kb BamHI-HindIII fragment containing the ADH2/GAP promoter, and with the large BamHI-SalI fragment of the yeast vector pBS24.1 yielded recombinant vectors, which were cloned. Correct recombinant vectors were identified by the presence of a 1.74 kb fragment after digestion with BamHI and SalI. An expression vector constructed from the amplified sequence, and containing the sequence encoding C fused directly to the ADH2/GAP promoter is identified as pC22.

Analysis for expressed C polypeptide by the transformed cells was performed on total cell lysates and crude extracts prepared from single yeast colonies obtained from the Leu⁻ plates. The cell lysates and crude extracts were analyzed by electrophoresis on SDS polyacrylamide gels. The C polypeptide is expected to have 122 amino acids and by gel analysis the expressed polypeptide has a $MW_r$ of approximately 13.6 Kd.

IV.B.14. Expression of a Polypeptide Which Contains Amino Acid Numbers 404–661 of the HCV Polyprotein A polypeptide encoded in the HCV cDNA shown in FIG. 72, and which contains amino acids numbers 404 to 661 encoded in a region of the HCV ORF designated as "x" is named herein the NS1 polypeptide. It should be noted that this designation is not meant to connote that the characteristics of this polypeptide are equivalent to that of the NS1 polypeptide of the flaviviruses, for the reasons discussed supra.

IV.B.14.a. Expression of NS1 in Yeast

Figure 78:
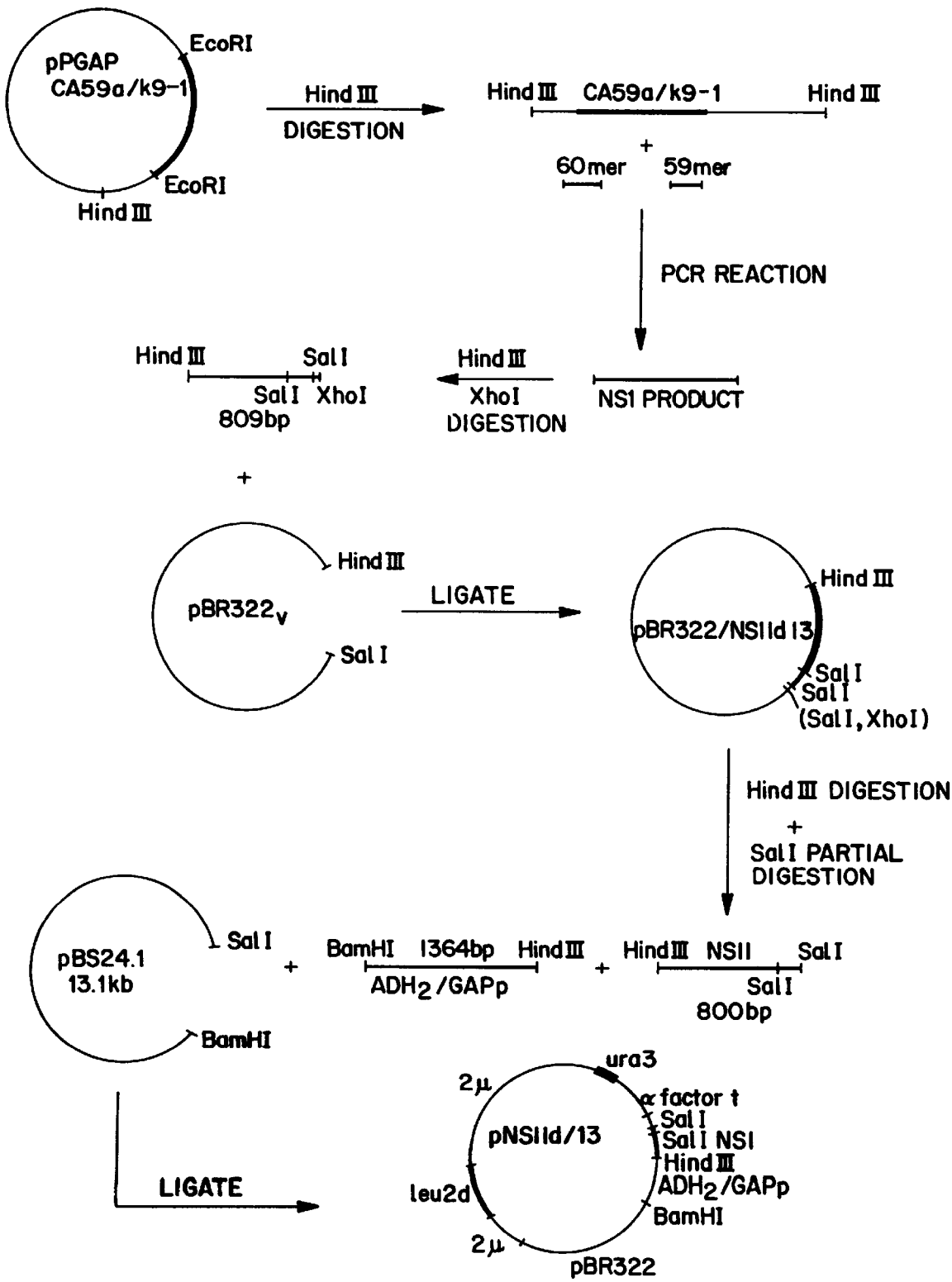
FIG. 78 shows a flow chart for construction of the expression vector pNS11d/13.

The protocol for the construction of the expression vector encoding the NS1 polypeptide and for its expression in yeast was analogous to that used for the expression of the C100 polypeptide, described in Sections IV.B.11, IV.B.11.a, and IV.B.11.b, except for the following. (A flow chart of the construction of the yeast expression vector encoding NS1 is shown in FIG. 78).

The template for the PCR amplification of the NS1 encoding sequence was pBR K-9-1/59a (also called pBR K/9-1/59a), which had been linearized by digestion with HindIII. The clone CA59a, described in Example IV.A.27, was inserted into the EcoRI site of pBR322 and the clone K-9-1, described in Example IV.A.26, was inserted into the BglII site of pPGAP. A PstI to NheI fragment from the pBR322/CA59a vector was ligated to a PstI to NheI fragment from the pPGAP3/K-9-1 to create the vector pBR K-9-1/59a, from which the HCV cDNA can be released by digestion with BglII and EcoRI. The vector pPGAP3 is a PBR322 derivative with the GAP promoter and terminator, described in U.S. patent application Ser. No. 468,589, filed on 22 Feb. 1983.

The oligonucleotides used as primers for PCR amplification of the NS1 coding sequence were designed to not only to generate novel 5' HindIII site, and a 3'-SalI site and double termination codons; in addition, the 3'-oligonucleotide primer also included an XhoI restriction site. The sequences of the oligonucleotide primers is the following.

For the 5'-region of the NS1 sequence:

5' GAG TGC TCA AGC TTA CAA AAC AAA ATG GCA CCA
GGC GCC AAG CAG AAC GTC CAG CTG
ATC 3'                                (SEQ ID NO:247)

and for the 3'-region of the NS1 sequence:

5' GAG TGC TCC TCG AGG TCG ACT CAT TAC TCG GAC
CTG TCC CTA TCT TCC AGA TCG CAA
CG 3'                                 (SEQ ID NO:248).

For cloning NS1 into a yeast expression vector, the PCR conditions were 15 cycles of 94° C. for 1.5 minutes, 60° C. for 2 minutes, and 72° C. for 3 minutes. After 15 cycles, the last incubation was at 72° C. for 10 minutes.

After amplification by PCR, the products were digested with HindIII and XhoI, and an 809 bp product isolated after gel electrophoresis. This product was ligated with the large HindIII-SalI fragment of pBR322. (This construction results in the loss of 3'-XhoI site from the NS1 coding sequence, and the SalI site of pBR322). After cloning in HB 101, plasmids containing the correct insert were identified by the presence of an 800 bp HindIII-SalI fragment, after digestion of the DNA with HindIII and partial digestion with SalI. A plasmid containing the correct insert was named pBR322/NS11d/13.

An 800 bp fragment which encodes NS1 was excised from pBR322/NS11d/13 by digestion with HindIII and partial digestion with SalI, and was isolated by gel electrophoresis. Ligation of this fragment with the 1.36 kb BamHI-HindIII fragment containing the ADH2/GAP promoter, and with the large BamHI-SalI fragment of the yeast vector pBS24.1 yielded recombinant vectors, which were cloned. Correct recombinant vectors were identified by the liberation of 2008 bp and 165 bp fragments in addition to a 13.1 kb fragment after digestion with HindIII and SalI. A recombinant vector containing the desired insert is named pNS11d/13 (also named pNS11/13-15).

Analysis for expressed NS1 polypeptide by the pNS11d/13 transformed cells was performed on total cell lysates and crude extracts prepared from single yeast colonies obtained from the Leu⁻ plates. The cell lysates and crude extracts were analyzed by electrophoresis on SDS polyacrylamide gels and by Western blots. A human serum sample was identified by the experiment described in Section IV.B.8.a to contain antibodies against the NS1 region. This serum was used as a primary antibody in the Western blotting. The NS1 polypeptide is expected to have 258 amino acids, and by gel analysis the expressed polypeptide has a $MW_r$ of approximately 29 K. Both methods of analysis indicated the presence of expressed NS1 polypeptide in the total cell lysates, but not in crude extracts. These results suggest that the expressed NS1 polypeptide is insoluble.

IV.B.14.b. Expression of NS1 in Mammalian Cells

A vector for expression of NS 1 in mammalian cells was constructed using a 795 bp fragment obtained by PCR amplification of the NS1 ORF which is contained in plasmid pPGAT/K9-1/59a, described in Section IV.B.14.a. The PCR reaction was performed using the following oligonucleotide sequences as primers.

The primer for the 5'-region of NS1 was:

5' GGA TCC GCT AGC GGC GCC AAG CAG AAC GTC CAG
CTG ATC AAC ACC 3'                    (SEQ ID NO:249)

where the underlined sequence encodes an NheI site.

The primer for the 3'-region of NS1 was:

5' GGA TCC AAG CTT TTA CTC GGA CCT GTC CCT ATC
TTC CAG ATC GCA ACG 3'                (SEQ ID NO:250)

where the first and second underlined sequences encode a HindIII site and a stop codon, respectively.

A polyacrylamide gel purified 795 bp fragment was digested with NheI and HindIII. The resulting 777bp NheI-HindIII fragment, which encodes NS1, was ligated to the 3.98 Kbp fragment obtained by digestion of pCMV6a120 with NheI, and partial digestion with HindIII. A resulting plasmid containing the correct insert was designated ptpa-NS1.

The vector pCMV6a120, which is described in U.S. Ser. No. 138,894 filed 24 Dec. 1987 (which is incorporated by reference, along with any foreign filed counterparts), is a mammalian cell expression vector which encodes gp 120 of human immunodeficiency virus (HIV). The gp120 encoding sequence was excised by the digestion with NheI and the partial digestion with HindIII.

Transient expression studies were performed in COS-7 cells (Gluzman (1981)), which had been transfected with ptpa-NS1. Transfection was accomplished using Lipofectin® using techniques described by Felgner et al. (1987). In order to perform immunofluorescence studies, the transfected cells were subcultured into 2-chamber plastic slide wells (Lab-Tek). The COS-7 cells were fixed with acetone at 72 hours following transfection, and cells producing NS1 were identified using indirect immunofluorescence methods (Pachl et al. (1987)). In the immunofluorescence studies, the source of primary antibodies was an HCV positive human antiserum which was immunoreactive with bacterially expressed NS1. The secondary antibody was FITC-conjugated goat anti-human IgG (Tago, Inc., Burlingame, Calif.), which had been diluted 1:200. Immunofluorescence on the slides was observed using a Leitz Dialux 20 EB fluorescent microscope. The cells which were transfected with ptpa-NS1 exhibited a diffuse cytoplasmic immunofluorescent staining pattern. Mock controls were also run. Positive controls included cells transfected with plasmids expressing CMV glycoprotein B, including plasmids pXgB8, the pXgB23 clv1 -4 series, and the pXgB24clv1-3 series.

IV.B.14.c. Expression of NS1 in Mammalian Cells Using a Vector with a Selectable Marker In order to physically link the NS1 encoding sequence to a sequence encoding a selectable marker, i.e., the DHFR gene, the NS1 ORF DNA sequence was subcloned into two mammalian cell expression vectors, pCMVAdhfr and pMCMVAdhfr. The vector pCMVAdhfr contains the human CMV major immediate early (MIE) promoter, and also contains the mouse dhfr gene linked to the adenovirus major late promoter (Stuve et al. (1987)). The vector pMCMVAdhfr is collinear to pCMVAdhfr, except that murine CMV (MCMV) MIE promoter is substituted for the human CMV MIE promoter. The MCMV MIE promoter is a HpaI-PstI fragment, which was cloned from pON402 (Manning and Mocarski (1988)).

In order to subclone the NS1 ORF DNA, it was excised from ptpa-NS1 by partial digestion with SalI. The 962 bp fragment was then ligated to SalI digested pCMVAdhfr, or to SalI digested pMCMVAdhfr. Each of these vectors contains a unique SalI site.

The recombinant dhfr vectors comprised of the NS1 sequence were used to transfect dhfr⁻ CHO cells in order to generate stable cell lines expressing this ORF. Transfection was by the polybrene transfection procedure of Chaney et al. (1986).

IV.B.15 Epitope Mapping of HCV Genome

IV.B.15.a Synthesis of Overlapping Peptides

Polyethylene pins arranged on a block in an 8'12 array (Coselco Mimetopes, Victoria, Australia) were prepared by placing the pins in a bath (20% v/v piperidine in dimethylformamide (DMF)) for 30 minutes at room temperature. The pins were then removed, washed in DMF for 5 min, then washed in methanol four times (2 min/wash). The pins were allowed to air dry for at least 10 min, then washed a final time in DMF (5 min). 1-Hydroxybenzotriazole (HOBt, 367 mg) was dissolved in DMF (80 mL) for use in coupling Fmoc-protected amino acids: Fmoc-L-Ala-OPfp, Fmoc-L-Cys(Trt)-OPfp, Fmoc-L-Asp(O-tBu)-OPfp, Fmoc-L-Glu(O-tBu)-OPfp, Fmoc-L-Phe-OPfp, Fmoc-Gly-OPfp, Fmoc-L-His(Boc)-OPfp, Fmoc-L-Ile-OPfp, Fmoc-L-Lys(Boc)-OPfp, Fmoc-L-Leu-OPfp, Fmoc-L-Met-OPfp, Fmoc-L-Asn-OPfp, Fmoc-L-Pro-OPfp, Fmoc-L-Gln-OPfp, Fmoc-L-Arg(Mtr)-OPfp, Fmoc-L-Ser(t-Bu)-ODhbt, Fmoc-L-Thr(t-Bu)-ODhbt, Fmoc-L-Val-OPfp, and Fmoc-L-Tyr-OPfp.

The protected amino acids were placed in microtiter plate wells with HOBt, and the pin block placed over the plate, immersing the pins in the wells. The assembly was then sealed in a plastic bag and allowed to react at 25° C. for 18 hours to couple the first amino acids to the pins. The block was then removed, and the pins washed with DMF (2 min), MeOH (4×2 min), and again with DMF (2 min) to clean and deprotect the bound amino acids. The procedure was repeated for each additional amino acid coupled, until all octamers had been prepared.

The free N-termini were then acetylated to compensate for the free amide, as most of the epitopes are not found at the N-terminus and thus would not have the associated positive charge. Acetylation was accomplished by filling the wells of a microtiter plate with DMF/acetic anhydride/triethylamine (5:2:1 v/v/v) and allowing the pins to react in the wells for 90 min at 20° C. The pins were then washed with DMF (2 min) and MeOH (4×2 min), and air dried for at least 10 min.

The side chain protecting groups were removed by treating the pins with trifluoroacetic acid/phenol/dithioethane (95:2.5:2.5, v/v/v) in polypropylene bags for 4 hours at room temperature. The pins were then washed in dichloromethane (2× 2 min), 5% di-isopropylethylamine/dichloromethane (2×5 min), dichloromethane (5 min), and air-dried for at least 10 min. The pins were then washed in water (2 min), MeOH (18 hours), dried in vacuo, and stored in sealed plastic bags over silica gel.

IV.B .15.b Assay of Peptides (A) Procedure:

Octamer-bearing pins prepared according to Section IV.B.15.a were first treated by sonicating for 30 min in a disruption buffer (1% sodium dodecylsulfate, 0.1% 2-mercaptoethanol, 0.1 M NaH$_2$PO$_4$) at 60° C. The pins were then immersed several times in water (60° C.), followed by boiling MeOH (2 min), and allowed to air dry.

The pins were then precoated for 1 hour at 25° C. in microtiter wells containing 200 mL blocking buffer (1% ovalbumin, 1% BSA, 0.1% Tween®, and 0.05% NaN$_3$ in PBS), with agitation. The pins were then immersed in microtiter wells containing 175 mL antisera obtained from human patients diagnosed as having HCV and allowed to incubate at 4° C. overnight. The pins were assayed against antisera from three individual patients. Specimen #PAA 3663-s ("A") exhibited strong reaction to HCV Western blots, HCV competitive ELISA, HCV ELISA to clone C100-3 (at 1:1000 dilution), and RIBA responses of>4+ to C100, 5-1-1, and C33c (C22 not done). Neat plasma was diluted 1:500 in blocking buffer. Specimen #PAA 33028 ("B") exhibited strong reaction to HCV Western blots, HCV competitive ELISA, HCV ELISA to clone C100-3 (at 1:500 dilution), and RIBA responses of >4+ to C100, 5-1-1, C33C and C22. Polyclonal antisera was partially purified by passage through a protein A column, and was used at a dilution of 1:200 in blocking buffer. Specimen #PAA s32931 ("C") exhibited moderate reaction to HCV Western blots (3+), HCV competitive ELISA, HCV ELISA to clone C100-3 (at 1:64 dilution), and RIBA responses of 3+ and 4+ to C100 and 5-1-1, respectively (C33c and C22 not done). Polyclonal antisera was partially purified by passage through a protein A column, and was used at a dilution of 1:500 in blocking buffer.

The pins were washed in PBS/Tween® 20 (4×10 min) at room temperature, then incubated in microtiter wells containing horseradish peroxidase-labeled goat anti-Human Ig antisera (175 mL, 1:2000 dilution in blocking buffer without NaN$_3$) for 1 hour at 25° C. with agitation. The antihuman antisera is specific for human Ig light and heavy chains, and reacts with both IgG and IgM classes. The pins were again washed in PBS/Tween® 20 (4×10 min) at room temperature.

Substrate solution was prepared by diluting NaH$_2$PO$_4$ (1 M, 200 mL) and citric acid (1 M, 160 mL) to 2 L with distilled water, adjusting the pH to 4.0. Azino-di-3-ethylbenzthiazodinsulfonate (ABTS, 50 mg) and hydrogen peroxide (0.3 mL/mL) was added to 100 mL of buffer immediately prior to use to complete the subtrate solution. The substrate solution (150 mL) was added to each well of a microtiter plate, and the pins immersed in the wells and incubated at 25° C. in the dark. After color developed, the reactions were halted by removing the pins, and absorbance of the solutions read at 405 nm.

(B) Results:

The octamers listed below were immunoreactive with anti-HCV antisera. Peptides reacting with all three antisera are listed as epitopes, while peptides reacting with only one or two antisera are listed as weak epitopes (indicated by "~").

Particularly strong epitopes are labeled with letters rather than numbers (e.g., EpAA).

| C22 | | | |
|---|---|---|---|
| 23 | KEPGGGQA | | (SEQ ID NO: 251) |
| 24 | EPGGGQAV | | (SEQ ID NO: 252) |
| 25 | PGGGQAVG | | (SEQ ID NO: 253) |
| 26 | GGGQAVGG | | (SEQ ID NO: 254) |
| 27 | GGQAVGGV | | (SEQ ID NO: 255) |
| 28 | GQAVGGVY | | (SEQ ID NO: 256) |
| 29 | QAVGGVYL~ | | (SEQ ID NO: 257) |
| 30 | AVGGVYLL | | (SEQ ID NO: 258) |
| 31 | VGGVYLLP | | (SEQ ID NO: 259) |
| 32 | GGVYLLPR | | (SEQ ID NO: 260) |
| 33 | GVYLLPRR | | (SEQ ID NO: 261) |
| 34 | VYLLPRRG | | (SEQ ID NO: 262) |
| 35 | YLLPRRGP | | (SEQ ID NO: 263) |
| 36 | LLPRRGPR | | (SEQ ID NO: 264) |
| C22 | | | |
| 66 | PKARRPEG | Ep1 | (SEQ ID NO: 265) |
| 67 | KARRPEGR | | (SEQ ID NO: 266) |
| 68 | ARRPEGRT | | (SEQ ID NO: 267) |
| 69 | RRPEGRTW | | (SEQ ID NO: 268) |
| 70 | RPEGRTWA | | (SEQ ID NO: 269) |
| 71 | PEGRTWAQ | | (SEQ ID NO: 270) |
| 72 | EGRTWAQP | | (SEQ ID NO: 271) |
| 73 | GRTWAQPG | EpA | (SEQ ID NO: 272) |
| 74 | RTWAQPGY | | (SEQ ID NO: 273) |
| 75 | TWAQPGYP | | (SEQ ID NO: 274) |
| 76 | WAQPGYPW | | (SEQ ID NO: 275) |
| 77 | AQPGYPWP | | (SEQ ID NO: 276) |
| 78 | QPGYPWPL | | (SEQ ID NO: 277) |
| 79 | PGYPWPLG | | (SEQ ID NO: 278) |
| 80 | GYPWPLYG | | (SEQ ID NO: 279) |
| 81 | YPWPLYGN | | (SEQ ID NO: 280) |
| 82 | PWPLYGNE | | (SEQ ID NO: 281) |
| 83 | WPLYGNEG | | (SEQ ID NO: 282) |
| 84 | PLYGNEGC | | (SEQ ID NO: 283) |
| 85 | LYGNEGCG | | (SEQ ID NO: 284) |
| 86 | YGNEGCGW | | (SEQ ID NO: 285) |
| 87 | GNEGCGWA | Ep2 | (SEQ ID NO: 286) |
| 88 | NEGCGWAG | | (SEQ ID NO: 287) |
| 89 | EGCGWAGW | | (SEQ ID NO: 288) |
| 90 | GCGWAGWL | | (SEQ ID NO: 289) |
| 91 | CGWAGWLL | | (SEQ ID NO: 290) |
| 92 | GWAGWLLS | | (SEQ ID NO: 291) |
| 93 | WAGWLLSP | | (SEQ ID NO: 292) |
| 94 | AGWLLSPR | | (SEQ ID NO: 293) |
| 95 | GWLLSPRG | | (SEQ ID NO: 294) |
| 96 | WLLSPRGS | | (SEQ ID NO: 295) |
| 97 | LLSPRGSR | | (SEQ ID NO: 296) |
| 98 | LSPRGSRP | | (SEQ ID NO: 297) |
| 99 | SPRGSRPS | | (SEQ ID NO: 298) |
| 100 | PRGSRPSW | Ep3 | (SEQ ID NO: 299) |
| 101 | RGSRPSWG | | (SEQ ID NO: 300) |
| 102 | GSRPSWGP | | (SEQ ID NO: 301) |
| 103 | SRPSWGPT | | (SEQ ID NO: 302) |
| 186 | TVPASAYQ | Ep4 | (SEQ ID NO: 303) |
| 187 | VPASAYQV | | (SEQ ID NO: 304) |
| 188 | PASAYQVR | | (SEQ ID NO: 305) |
| 189 | ASAYQVRN | | (SEQ ID NO: 306) |
| 190 | SAYQVRNS | | (SEQ ID NO: 307) |
| 191 | AYQVRNST | | (SEQ ID NO: 308) |
| 206 | DCPNSSIV~ | | (SEQ ID NO: 309) |
| 223 | TPGCVPCV~ | | (SEQ ID NO: 310) |
| 232 | EGNASRCW | Ep5 | (SEQ ID NO: 311) |
| 256 | TQLRRHID~ | | (SEQ ID NO: 312) |
| 286 | LVGQLFTF~ | | (SEQ ID NO: 313) |
| 297 | RHWTTQGC | Ep6 | (SEQ ID NO: 314) |
| 298 | HWTTQGCN | | (SEQ ID NO: 315) |
| 299 | WTTQGCNC | | (SEQ ID NO: 316) |
| 321 | MMMNWSPI~ | | (SEQ ID NO: 317) |
| 347 | DMIAGAHW | Ep7 | (SEQ ID NO: 318) |
| 357 | LAGIAYFS | Ep8 | (SEQ ID NO: 319) |
| 413 | LINTNGSW | EpB | (SEQ ID NO: 320) |
| 414 | INTNGSWH | | (SEQ ID NO: 321) |
| 432 | SLNTGWLA~ | | (SEQ ID NO: 322) |

-continued

| 465 | FDQGWGPI | EpC | (SEQ ID NO: 323) |
|---|---|---|---|
| 466 | DQGWGPIS | | (SEQ ID NO: 324) |
| 467 | QGWGPISY | | (SEQ ID NO: 325) |
| 468 | GWGPISYA | | (SEQ ID NO: 326) |
| 469 | WGPISYAN | | (SEQ ID NO: 327) |
| 470 | GPISYANG | | (SEQ ID NO: 328) |
| 471 | PISYANGS | | (SEQ ID NO: 329) |
| 480 | PDQRPYCW | EpD | (SEQ ID NO: 330) |
| 481 | DQRPYCWH | | (SEQ ID NO: 331) |
| 482 | QRPYCWHY | | (SEQ ID NO: 332) |
| 483 | RPYCWHYP | | (SEQ ID NO: 333) |
| 484 | PYCWHYPP | | (SEQ ID NO: 334) |
| 500 | KSVCGPVY | Ep9 | (SEQ ID NO: 335) |
| 501 | SVCGPVYC | | (SEQ ID NO: 336) |
| 502 | VCGPVYCE | | (SEQ ID NO: 337) |
| 521 | RSGAPTYS | Ep10 | (SEQ ID NO: 338) |
| 540 | NNTRPPLG | EpE | (SEQ ID NO: 339) |
| 541 | NTRPPLGN | | (SEQ ID NO: 340) |
| 542 | TRPPLGNW | | (SEQ ID NO: 341) |
| 543 | RPPLGNWF | | (SEQ ID NO: 342) |
| 544 | PPLGNWFG | | (SEQ ID NO: 343) |
| 545 | PLGNWFGC | | (SEQ ID NO: 344) |
| 546 | LGNWFGCT | | (SEQ ID NO: 345) |
| 547 | GNWFGCTW | | (SEQ ID NO: 346) |
| 548 | NWFGCTWM | | (SEQ ID NO: 347) |
| 549 | WFGCTWMN | | (SEQ ID NO: 348) |
| 579 | LHCPTDCF~ | | (SEQ ID NO: 349) |
| 594 | YSRCGSGP | $F_A$ | (SEQ ID NO: 350) |
| 595 | SRCGSGPW | | (SEQ ID NO: 351) |
| 596 | RCGSGPWL | | (SEQ ID NO: 352) |
| 597 | CGSGPWLT | | (SEQ ID NO: 353) |
| 598 | GSGPWLTP | | (SEQ ID NO: 354) |
| 599 | SGPWLTPR | | (SEQ ID NO: 355) |
| 600 | GPWLTPRC | | (SEQ ID NO: 356) |
| 601 | PWLTPRCL | | (SEQ ID NO: 357) |
| 602 | WLTPRCLV | | (SEQ ID NO: 358) |
| 603 | LTPRCLVD | EpF | (SEQ ID NO: 359) |
| 604 | TPRCLVDY | | (SEQ ID NO: 360) |
| 605 | PRCLVDYP | | (SEQ ID NO: 361) |
| 606 | RCLVDYPY | | (SEQ ID NO: 362) |
| 607 | CLVDYPYR | | (SEQ ID NO: 363) |
| 608 | LVDYPYRL | | (SEQ ID NO: 364) |
| 609 | VDYPYRLW | | (SEQ ID NO: 365) |
| 610 | DYPYRLWH | | (SEQ ID NO: 366) |
| 611 | YPYRLWHY | $F_B$ | (SEQ ID NO: 367) |
| 612 | PYRLWHYP | | (SEQ ID NO: 368) |
| 613 | YRLWHYPC | | (SEQ ID NO: 369) |
| 641 | EAACNWTR | Ep12 | (SEQ ID NO: 370) |
| 662 | LSPLLLII | Ep13 | (SEQ ID NO: 371) |
| 663 | SPLLLIII | | (SEQ ID NO: 372) |
| 664 | PLLLIIIQ | | (SEQ ID NO: 373) |
| 665 | LLLIIIQW | | (SEQ ID NO: 374) |
| 685 | LSTGLIHL~ | | (SEQ ID NO: 375) |
| 705 | VGSSIASW~ | | (SEQ ID NO: 376) |
| 706 | GSSIASWA | | (SEQ ID NO: 377) |
| 729 | ARVCSCIW | Ep14 | (SEQ ID NO: 378) |
| 782 | WVPGAVYT | EpG | (SEQ ID NO: 379) |
| 783 | VPGAVYTF | | (SEQ ID NO: 380) |
| 784 | PGAVYTFY | | (SEQ ID NO: 381) |
| 785 | GAVYTFYG | | (SEQ ID NO: 382) |
| 786 | AVYTFYGM | | (SEQ ID NO: 383) |
| 787 | VYTFYGMW | | (SEQ ID NO: 384) |
| 788 | YTFYGMWP | | (SEQ ID NO: 385) |
| 789 | TFYGMWPL | | (SEQ ID NO: 386) |
| 801 | LALPQRAY~ | | (SEQ ID NO: 387) |
| 851 | RVEAQLHV | EpH | (SEQ ID NO: 388) |
| 852 | VEAQLHVW | | (SEQ ID NO: 389) |
| 853 | EAQLHVWI | | (SEQ ID NO: 390) |
| 854 | AQLHVWIP | | (SEQ ID NO: 391) |
| 855 | QLHVWIPP | | (SEQ ID NO: 392) |
| 893 | LAVFGPLW~ | | (SEQ ID NO: 393) |
| 916 | QGLLRFCA~ | | (SEQ ID NO: 394) |
| 928 | MIGGHYVQ | Ep15 | (SEQ ID NO: 395) |
| 946 | TGTYVYNH | EpI | (SEQ ID NO: 396) |
| 952 | NHLTPLRD | EpJ | (SEQ ID NO: 397) |
| 953 | HLTPLRDW | | (SEQ ID NO: 398) |
| 954 | LTPLRDWA | | (SEQ ID NO: 399) |
| 1026 | LAPITAYA~ | | (SEQ ID NO: 400) |
| 1072 | TCINGVCW | EpK | (SEQ ID NO: 401) |

| | | | |
|---|---|---|---|
| 1109 | LVGWPAPQ | Ep16 | (SEQ ID NO: 402) |
| 1112 | CPAGHAVG | Ep17 | (SEQ ID NO: 403) |
| 1113 | PAGHAVGI | | (SEQ ID NO: 404) |
| 1114 | AGHAVGIF | | (SEQ ID NO: 405) |
| 1115 | GHAVGIFR | | (SEQ ID NO: 406) |
| 1116 | HAVGIFRA | | (SEQ ID NO: 407) |
| 1117 C33 | AVGIFRAA | | (SEQ ID NO: 408) |
| 1218 C33 | VVPQSEQV | EpL | (SEQ ID NO: 409) |
| 1240 C33 | VPAAYAAQ~ | | (SEQ ID NO: 410) |
| 1260 C33 | ATLGFGAY~ | | (SEQ ID NO: 411) |
| 1280 | GVRITTGS | Ep18 | (SEQ ID NO: 412) |
| 1281 | VRITTGSP | | (SEQ ID NO: 413) |
| 1282 | RITTGSPI | | (SEQ ID NO: 414) |
| 1283 | ITTGSPIT | | (SEQ ID NO: 415) |
| 1284 | TTGSPITY | | (SEQ ID NO: 416) |
| 1285 C33 | TGSPITYG | | (SEQ ID NO: 417) |
| 1322 C33 | DATSILGI~ | | (SEQ ID NO: 418) |
| 1338 C33 | TAGARLVV~ | | (SEQ ID NO: 419) |
| 1371 C33 | GEIPFYGK | Ep19 | (SEQ ID NO: 420) |
| 1384 C33 | VIKGGRHL | Ep20 | (SEQ ID NO: 421) |
| 1410 | LGINAVAY | Ep21 | (SEQ ID NO: 422) |
| 1411 C33 | GINAVAYY | | (SEQ ID NO: 423) |
| 1454 | CNTCVIQT~ | | (SEQ ID NO: 424) |
| 1492 | GRGKPGIY | Ep22 | (SEQ ID NO: 425) |
| 1493 | RGKPGIYR | | (SEQ ID NO: 426) |
| 1532 | PAETTVRL | Ep23 | (SEQ ID NO: 427) |
| 1533 | AETTVRLR | | (SEQ ID NO: 428) |
| 1534 | ETTVRLRA | | (SEQ ID NO: 429) |
| 1535 | TTVRLRAY | | (SEQ ID NO: 430) |
| 1560 | GVFIGLIH | Ep24 | (SEQ ID NO: 431) |
| 1561 C100-3 | VFIGLIHI | | (SEQ ID NO: 432) |
| 1566 | ENLPYLVA | Ep25 | (SEQ ID NO: 433) |
| 1567 | NLPYLVAY | | (SEQ ID NO: 434) |
| 1568 | LPYLVAYQ | | (SEQ ID NO: 435) |
| 1569 | PYLVAYQA | | (SEQ ID NO: 436) |
| 1570 | YLVAYQAT | | (SEQ ID NO: 437) |
| 1571 | LVAYQATV | | (SEQ ID NO: 438) |
| 1572 | VAYQATVC | | (SEQ ID NO: 439) |
| 1573 | AYQATVCA | | (SEQ ID NO: 440) |
| 1574 | YQATVCAR | | (SEQ ID NO: 441) |
| 1575 | QATVCARQ | | (SEQ ID NO: 442) |
| 1576 | ATVCARQA | | (SEQ ID NO: 443) |
| 1577 C100-3 | TVCARQAP | | (SEQ ID NO: 444) |
| 1601 | PPSWDQMW | Ep26 | (SEQ ID NO: 445) |
| 1602 | PSWDQMWK | | (SEQ ID NO: 446) |
| 1603 | SWDQMWKC | | (SEQ ID NO: 447) |
| 1604 | WDQMWKCL | | (SEQ ID NO: 448) |
| 1605 | DQMWKCLI | | (SEQ ID NO: 449) |
| 1606 | QMWKCLIR | | (SEQ ID NO: 450) |
| 1607 C100-3 | MWKCLIRL | | (SEQ ID NO: 451) |
| 1615 | KPTLHGPI | Ep27 | (SEQ ID NO: 452) |
| 1616 | PTLHGPIP | | (SEQ ID NO: 453) |
| 1617 | TLHGPIPL | | (SEQ ID NO: 454) |
| 1618 | LHGPIPLL | | (SEQ ID NO: 455) |
| 1619 | HGPIPLLY | | (SEQ ID NO: 456) |
| 1620 C100-3 | GPIPLLYR | | (SEQ ID NO: 457) |
| 1655 5-1-1 | VVTSTWVL~ | | (SEQ ID NO: 458) |
| 1694 | IIPDREVL | EpM | (SEQ ID NO: 459) |
| 1695 5-1-1 | IPDREVLY | | (SEQ ID NO: 460) |
| 1710 | ECSQHLPY | EpN | (SEQ ID NO: 461) |
| 1711 | CSQHLPYI | | (SEQ ID NO: 462) |
| 1712 5-1-1 | SQHLPYIE | | (SEQ ID NO: 463) |
| 1728 | EKQKALGL | EpO | (SEQ ID NO: 464) |
| 1729 C100-3 | KQKALGLL | | (SEQ ID NO: 465) |
| 1758 | EIEWAKLM | EpP | (SEQ ID NO: 466) |
| 1759 | IEWAKLMW | | (SEQ ID NO: 467) |
| 1760 | EWAKLMWN | | (SEQ ID NO: 468) |
| 1761 | WAKLMWNE | | (SEQ ID NO: 469) |
| 1762 C100-3 | AKLMWNEI | | (SEQ ID NO: 470) |
| 1781 C100-3 | LPGNPAIA~ | | (SEQ ID NO: 471) |
| 1808 C100-3 | LFNILGGW | Ep28 | (SEQ ID NO: 472) |
| 1821 C100-3 | AAPGAATA~ | | (SEQ ID NO: 473) |
| 1851 C100-3 | ILAGYGAG | Ep29 | (SEQ ID NO: 474) |
| 1880 C100-3 | VNLLPAIL~ | | (SEQ ID NO: 475) |
| 1908 | PGEGAVQW | EpG | (SEQ ID NO: 476) |
| 1909 | GEGAVQWM | | (SEQ ID NO: 477) |
| 1910 | EGAVQWMN | | (SEQ ID NO: 478) |
| 1911 | GAVQWMNR | | (SEQ ID NO: 479) |
| 1912 | AVQWMNRL | | (SEQ ID NO: 480) |
| 1913 C100-3 | VQWMNRLI | | (SEQ ID NO: 481) |
| 1925 C100-3 | RGNHVSPI | EpR | (SEQ ID NO: 482) |
| 1940 | AAARVTAI | Ep30 | (SEQ ID NO: 483) |
| 1941 | AARVTAIL | | (SEQ ID NO: 484) |
| 1942 | ARVTAILS | | (SEQ ID NO: 485) |
| 1943 | RVTAILSS | | (SEQ ID NO: 486) |
| 1944 | VTAILSSL | | (SEQ ID NO: 487) |
| 1945 | TAILSSLV | | (SEQ ID NO: 488) |
| 1946 | AILSSLVT | | (SEQ ID NO: 489) |
| 1947 | ILSSLVTQ | | (SEQ ID NO: 490) |
| 1948 | LSSLVTQL | | (SEQ ID NO: 491) |
| 1949 | SSLVTQLL | | (SEQ ID NO: 492) |
| 1950 | SLVTQLLR | | (SEQ ID NO: 493) |
| 1951 C100-3 | LVTQLLRR | | (SEQ ID NO: 494) |
| 1966 | SECTIPCS | EpS | (SEQ ID NO: 495) |
| 1967 | ECTIPCSG | | (SEQ ID NO: 496) |
| 1968 | CTIPCSGS | | (SEQ ID NO: 497) |
| 1969 C100-3 | TIPCSGSW | | (SEQ ID NO: 498) |
| 1999 | LMPQLPGI | EpT | (SEQ ID NO: 499) |
| 2000 | MPQLPGIP | | (SEQ ID NO: 500) |
| 2001 | PQLPGIPE | | (SEQ ID NO: 501) |
| 2002 | QLPGIPEV | | (SEQ ID NO: 502) |
| 2003 | LPGIPEVS | | (SEQ ID NO: 503) |

| | | | |
|---|---|---|---|
| 2004 | PGIPEVSC | | (SEQ ID NO: 504) |
| 2005 | GIPEVSCQ | | (SEQ ID NO: 505) |
| 2006 | IPEVSCQR | | (SEQ ID NO: 506) |
| 2007 | PEVSCQRG | | (SEQ ID NO: 507) |
| 2008 | EVSCQRGY | | (SEQ ID NO: 508) |
| 2009 | VSCQRGYK | | (SEQ ID NO: 509) |
| 2010 | SCQRGYKG | | (SEQ ID NO: 510) |
| 2011 | CQRGYKGV | | (SEQ ID NO: 511) |
| 2012 | QRGYKGVW | | (SEQ ID NO: 512) |
| 2013 | RGYKGVWR | | (SEQ ID NO: 513) |
| 2014 | GYKGVWRG | | (SEQ ID NO: 514) |
| C100-3 | | | |
| 2024 | IMHTRCHC | Ep31 | (SEQ ID NO: 515) |
| C100-3 | | | |
| 2048 | VGPRICRN | EpU | (SEQ ID NO: 516) |
| 2049 | GPRICRNY | | (SEQ ID NO: 517) |
| 2050 | PRICRNYW | | (SEQ ID NO: 518) |
| 2051 | RICRNYWS | | (SEQ ID NO: 519) |
| 2052 | ICRNYWSG | | (SEQ ID NO: 520) |
| 2053 | CRNYWSGT | | (SEQ ID NO: 521) |
| 2054 | RNYWSGTE | | (SEQ ID NO: 522) |
| 2055 | NYWSGTEP | | (SEQ ID NO: 523) |
| 2056 | YWSGTEPI | | (SEQ ID NO: 524) |
| 2057 | WSGTEPIN | | (SEQ ID NO: 525) |
| C100-3 | | | |
| 2071 | TPLPAPNY | Ep32 | (SEQ ID NO: 526) |
| C100-3 | | | |
| 2088 | EEYVIRQV | EpV | (SEQ ID NO: 527) |
| 2089 | EYVIRQVG | | (SEQ ID NO: 528) |
| 2090 | YVIRQVGD | | (SEQ ID NO: 529) |
| 2091 | VIRQVGDF | | (SEQ ID NO: 530) |
| 2092 | IRQVGDFH | | (SEQ ID NO: 531) |
| 2093 | RQVGDFHY | | (SEQ ID NO: 532) |
| C100-3 | | | |
| 2108 | DNLKCPCQ~ | | (SEQ ID NO: 533) |
| C100-3 | | | |
| 2122 | EIELDGVR | EpW | (SEQ ID NO: 534) |
| 2123 | IELDGVRL | | (SEQ ID NO: 535) |
| 2124 | ELDGVRLH | | (SEQ ID NO: 536) |
| 2125 | LDGVRLHR | | (SEQ ID NO: 537) |
| 2126 | DGVRLHRF | | (SEQ ID NO: 538) |
| 2127 | GVRLHRFA | | (SEQ ID NO: 539) |
| 2128 | VRLHRFAP | | (SEQ ID NO: 540) |
| 2129 | RLHRFAPP | | (SEQ ID NO: 541) |
| 2130 | LHRFAPPC | | (SEQ ID NO: 542) |
| 2131 | HRFAPPCK | | (SEQ ID NO: 543) |
| 2132 | RFAPPCKP | | (SEQ ID NO: 544) |
| 2133 | FAPPCKPL | | (SEQ ID NO: 545) |
| 2134 | APPCKPLL | | (SEQ ID NO: 546) |
| 2135 | PPCKPLLR | | (SEQ ID NO: 547) |
| 2136 | PCKPLLRE | | (SEQ ID NO: 548) |
| 2137 | CKPLLREE | | (SEQ ID NO: 549) |
| 2138 | KPLLREEV | | (SEQ ID NO: 550) |
| 2139 | PLLREEVS | | (SEQ ID NO: 551) |
| 2140 | LLREEVSF | EpX | (SEQ ID NO: 552) |
| 2141 | LREEVSFR | | (SEQ ID NO: 553) |
| 2142 | REEVSFRV | | (SEQ ID NO: 554) |
| 2143 | EEVSFRVG | | (SEQ ID NO: 555) |
| 2144 | EVSFRVGL | | (SEQ ID NO: 556) |
| 2145 | VSFRVGLH | | (SEQ ID NO: 557) |
| 2146 | SFRVGLHE | | (SEQ ID NO: 558) |
| 2147 | FRVGLHEY | | (SEQ ID NO: 559) |
| 2148 | RVGLHEYP | | (SEQ ID NO: 560) |
| C100-3 | | | |
| 2165 | EPEPDVAV~ | | (SEQ ID NO: 561) |
| C100-3 | | | |
| 2187 | GRRLARGS~ | | (SEQ ID NO: 562) |
| C100-3 | | | |
| 2226 | LIEANLLW | EpY | (SEQ ID NO: 563) |
| 2227 | IEANLLWR | | (SEQ ID NO: 564) |
| 2228 | EANLLWRQ | | (SEQ ID NO: 565) |
| 2229 | ANLLWRQE | | (SEQ ID NO: 566) |
| 2230 | NLLWRQEM | | (SEQ ID NO: 567) |
| 2231 | LLWRQEMG | | (SEQ ID NO: 568) |
| 2232 | LWRQEMGG | | (SEQ ID NO: 569) |
| C100-3 | | | |
| 2244 | VESENKVV | Ep33 | (SEQ ID NO: 570) |
| 2245 | ESENKVVI | | (SEQ ID NO: 571) |
| 2246 | SENKVVIL | | (SEQ ID NO: 572) |
| 2247 | ENKVVILD | | (SEQ ID NO: 573) |
| 2248 | NKVVILDS | | (SEQ ID NO: 574) |
| 2249 | KVVILDSF | | (SEQ ID NO: 575) |
| 2250 | VVILDSFD | | (SEQ ID NO: 576) |
| C100-3 | | | |
| 2267 | EISVPAEI | Ep34 | (SEQ ID NO: 577) |
| C100-3 | | | |
| 2280 | REAQALPV | EpZ | (SEQ ID NO: 578) |
| 2281 | EAQALPVW | | (SEQ ID NO: 579) |
| 2282 | AQALPVWA | | (SEQ ID NO: 580) |
| 2283 | QALPVWAR | | (SEQ ID NO: 581) |
| 2284 | ALPVWARP | | (SEQ ID NO: 582) |
| 2285 | LPVWARPD | | (SEQ ID NO: 583) |
| 2286 | PVWARPDY | | (SEQ ID NO: 584) |
| 2287 | VWARPDYN | | (SEQ ID NO: 585) |
| 2288 | WARPDYNP | | (SEQ ID NO: 586) |
| 2289 | ARPDYNPP | | (SEQ ID NO: 587) |
| 2290 | RPDYNPPL | | (SEQ ID NO: 588) |
| C100-3 | | | |
| 2325 | PPPRKKRT | Ep35 | (SEQ ID NO: 589) |
| 2326 | PPRKKRTV | | (SEQ ID NO: 590) |
| 2327 | PRKKRTVV | | (SEQ ID NO: 591) |
| C100-3 | | | |
| 2345 | AELASRSE | Ep36 | (SEQ ID NO: 592) |
| 2346 | ELASRSEG | | (SEQ ID NO: 593) |
| 2347 | LASRSEGS | | (SEQ ID NO: 594) |
| 2348 | ASRSEGSS | | (SEQ ID NO: 595) |
| 2349 | SRSEGSSS | | (SEQ ID NO: 596) |
| C100-3 | | | |
| 2382 | AESYSSMP | Ep37 | (SEQ ID NO: 597) |
| C100-3 | | | |
| 2401 | SDGSWSTV | Ep38 | (SEQ ID NO: 598) |
| C100-3 | | | |
| 2417 | VVCCSMSY | EpAA | (SEQ ID NO: 599) |
| 2418 | VCCSMSYW | | (SEQ ID NO: 600) |
| 2419 | CCSMSYWI | | (SEQ ID NO: 601) |
| 2420 | CSMSYWIG | | (SEQ ID NO: 602) |
| 2421 | SMSYWIGA | | (SEQ ID NO: 603) |
| 2422 | MSYWIGAL | | (SEQ ID NO: 604) |
| C100-3 | | | |
| 2439 | QKLPINAL | EpBB | (SEQ ID NO: 605) |
| 2440 | KLPINALS | | (SEQ ID NO: 606) |
| 2441 | LPINALSN | | (SEQ ID NO: 607) |
| 2442 | PINALSNS | | (SEQ ID NO: 608) |
| 2443 | INALSNSL | | (SEQ ID NO: 609) |
| 2444 | NALSNSLL | | (SEQ ID NO: 610) |
| 2445 | ALSNSLLR | | (SEQ ID NO: 611) |
| 2446 | LSNSLLRH | | (SEQ ID NO: 612) |
| 2447 | SNSLLRHH | | (SEQ ID NO: 613) |
| 2448 | NSLLRHHN | | (SEQ ID NO: 614) |
| 2449 | SLLRHHNL | | (SEQ ID NO: 615) |
| 2450 | LLRHHNLV | | (SEQ ID NO: 616) |
| 2451 | LRHHNLVY | | (SEQ ID NO: 617) |
| 2452 | RHHNLVYS | | (SEQ ID NO: 618) |
| 2453 | HHNLVYST | | (SEQ ID NO: 619) |
| 2454 | HNLVYSTI | | (SEQ ID NO: 620) |
| 2455 | NLVYSTIS | | (SEQ ID NO: 621) |
| 2456 | LVYSTISR | | (SEQ ID NO: 622) |
| C100-3 | | | |
| 2469 | QKKVTFDR | Ep39 | (SEQ ID NO: 623) |

| | | | |
|---|---|---|---|
| 2470 | KKVTFDRL | | (SEQ ID NO: 624) |
| 2471 | KVTFDRLQ | | (SEQ ID NO: 625) |
| 2472 | VTFDRLQV | | (SEQ ID NO: 626) |
| 2473 | TFDRLQVL | | (SEQ ID NO: 627) |
| 2474 | FDRLQVLD | | (SEQ ID NO: 628) |
| 2475 | DRLQVLDS | | (SEQ ID NO: 629) |
| 2476 | RLQVLDSH | | (SEQ ID NO: 630) |
| C100-3 | | | |
| 2495 | ASKVKANL~ | | (SEQ ID NO: 631) |
| C100-3 | | | |
| 2533 | RKAVTHIN | EpCC | (SEQ ID NO: 632) |
| 2534 | KAVTHINS | | (SEQ ID NO: 633) |
| C100-3 | | | |
| 2573 | GRKPARLI | Ep40 | (SEQ ID NO: 634) |
| 2574 | RKPARLIV | | (SEQ ID NO: 635) |
| 2575 | KPARLIVF | | (SEQ ID NO: 636) |
| 2576 | PARLIVFP | | (SEQ ID NO: 637) |
| 2577 | ARLIVFPD | | (SEQ ID NO: 638) |
| 2578 | RLIVFPDL | | (SEQ ID NO: 639) |
| C100-3 | | | |
| 2602 | LPLAVMGS | EpDD | (SEQ ID NO: 640) |
| 2603 | PLAVMGSS | | (SEQ ID NO: 641) |
| 2604 | LAVMGSSY | | (SEQ ID NO: 642) |
| 2605 | AVMGSSYG | | (SEQ ID NO: 643) |
| 2606 | VMGSSYGE | | (SEQ ID NO: 644) |
| 2607 | MGSSYGEQ | | (SEQ ID NO: 645) |
| 2608 | GSSYGEQR | | (SEQ ID NO: 646) |
| 2609 | SSYGEQRV | | (SEQ ID NO: 647) |
| 2610 | SYGEQRVE | | (SEQ ID NO: 648) |
| 2611 | YGEQRVEE | | (SEQ ID NO: 649) |
| 2612 | GEQRVEEL | | (SEQ ID NO: 650) |
| C100-3 | | | |
| 2632 | KTPMGFSY | Ep41 | (SEQ ID NO: 651) |
| 2633 | TPMGFSYD | | (SEQ ID NO: 652) |
| 2634 | PMGFSYDT | | (SEQ ID NO: 653) |
| 2635 | MGFSYDTR | | (SEQ ID NO: 654) |
| 2636 | GFSYDTRC | | (SEQ ID NO: 655) |
| 2637 | FSYDTRCE | | (SEQ ID NO: 656) |
| 2638 | SYDTRCED | | (SEQ ID NO: 657) |
| C100-3 | | | |
| 2660 | YQCCDLDP~ | | (SEQ ID NO: 658) |
| C100-3 | | | |
| 2676 | LTERLYVG | EpEE | (SEQ ID NO: 659) |
| 2677 | TERLYVGG | | (SEQ ID NO: 660) |
| 2678 | ERLYVGGP | | (SEQ ID NO: 661) |
| 2679 | RLYVGGPL | | (SEQ ID NO: 662) |
| C100-3 | | | |
| 2688 | NSRGENCG | EpFF | (SEQ ID NO: 663) |
| 2689 | SRGENCGY | | (SEQ ID NO: 664) |
| 2690 | RGENCGYR | | (SEQ ID NO: 665) |
| 2691 | GENCGYRR | | (SEQ ID NO: 666) |
| 2692 | ENCGYRRC | | (SEQ ID NO: 667) |
| 2693 | NCGYRRCR | | (SEQ ID NO: 668) |
| C100-3 | | | |
| 2707 | TSCGNTLI | Ep42 | (SEQ ID NO: 669) |
| C100-3 | | | |
| 2721 | AACRAAGL~ | | (SEQ ID NO: 670) |
| C100-3 | | | |
| 2757 | AFTEAMTR | Ep43 | (SEQ ID NO: 671) |
| 2758 | FTEAMTRY | | (SEQ ID NO: 672) |
| 2759 | TEAMTRYS | | (SEQ ID NO: 673) |
| 2760 | EAMTRYSA | | (SEQ ID NO: 674) |
| 2761 | AMTRYSAP | | (SEQ ID NO: 675) |
| 2762 | MTRYSAPP | | (SEQ ID NO: 676) |
| C100-3 | | | |
| 2779 | DLELIISC | Ep44 | (SEQ ID NO: 677) |
| 2780 | LELIISCS | | (SEQ ID NO: 678) |
| C100-3 | | | |
| 2794 | HDGAGKRV | Ep45 | (SEQ ID NO: 679) |
| 2795 | DGAGKRVY | | (SEQ ID NO: 680) |
| 2796 | GAGKRVYY | | (SEQ ID NO: 681) |
| 2797 | AGKRVYYL | | (SEQ ID NO: 682) |
| 2798 | GKRVYYLT | | (SEQ ID NO: 683) |
| 2799 | KRVYYLTR | | (SEQ ID NO: 684) |
| 2800 | RVYYLTRD | | (SEQ ID NO: 685) |
| 2801 | VYYLTRDP | | (SEQ ID NO: 686) |
| 2802 | YYLTRDPT | | (SEQ ID NO: 687) |
| C100-3 | | | |
| 2817 | WETARHTP | EpGG | (SEQ ID NO: 688) |
| 2818 | ETARHTPV | | (SEQ ID NO: 689) |
| 2819 | TARHTPVN | | (SEQ ID NO: 690) |
| 2820 | ARHTPVNS | | (SEQ ID NO: 691) |
| 2821 | RHTPVNSW | | (SEQ ID NO: 692) |
| 2822 | HTPVNSWL | | (SEQ ID NO: 693) |
| 2823 | TPVNSWLG | | (SEQ ID NO: 694) |
| 2824 | PVNSWLGN | | (SEQ ID NO: 695) |
| 2825 | VNSWLGNI | | (SEQ ID NO: 696) |
| 2826 | NSWLGNII | | (SEQ ID NO: 697) |
| 2827 | SWLGNIIM | | (SEQ ID NO: 698) |
| 2828 | WLGNIIME | | (SEQ ID NO: 699) |
| 2829 | LGNIIMEA | | (SEQ ID NO: 700) |
| 2830 | GNIIMEAP | | (SEQ ID NO: 701) |
| 2831 | NIIMEAPT | | (SEQ ID NO: 702) |
| 2832 | IIMEAPTL | | (SEQ ID NO: 703) |
| 2833 | IMEAPTLW | | (SEQ ID NO: 704) |
| 2834 | MEAPTLWA | | (SEQ ID NO: 705) |
| 2835 | EAPTLWAR | | (SEQ ID NO: 706) |
| 2836 | APTLWARM | | (SEQ ID NO: 707) |
| 2837 | PTLWARMI | | (SEQ ID NO: 708) |
| 2838 | TLWARMIL | | (SEQ ID NO: 709) |
| 2839 | LWARMILM | | (SEQ ID NO: 710) |
| 2840 | WARMILMT | | (SEQ ID NO: 711) |
| 2841 | ARMILMTH | | (SEQ ID NO: 712) |
| 2842 | RMILMTHF | | (SEQ ID NO: 713) |
| 2843 | MILMTHFE | | (SEQ ID NO: 714) |
| C100-3 | | | |
| 2863 | LDCEIYGA | Ep46 | (SEQ ID NO: 715) |
| 2864 | DCEIYGAC | | (SEQ ID NO: 716) |
| 2865 | CEIYGACY | | (SEQ ID NO: 717) |
| 2866 | EIYGACYS | | (SEQ ID NO: 718) |
| 2867 | IYGACYSI | | (SEQ ID NO: 719) |
| C100-3 | | | |
| 2878 | DLPPIIQR | Ep47 | (SEQ ID NO: 720) |
| 2879 | LPPIIQRL | | (SEQ ID NO: 721) |
| 2880 | PPIIQRLH | | (SEQ ID NO: 722) |
| 2881 | PIIQRLHG | | (SEQ ID NO: 723) |
| 2882 | IIQRLHGL | | (SEQ ID NO: 724) |
| 2883 | IQRLHGLS | | (SEQ ID NO: 725) |
| 2884 | QRLHGLSA | | (SEQ ID NO: 726) |
| 2885 | RLHGLSAF | | (SEQ ID NO: 727) |
| 2886 | LHGLSAFS | | (SEQ ID NO: 728) |
| 2887 | HGLSAFSL | | (SEQ ID NO: 729) |
| 2888 | GLSAFSLH | | (SEQ ID NO: 730) |
| 2889 | LSAFSLHS | | (SEQ ID NO: 731) |
| 2890 | SAFSLHSY | | (SEQ ID NO: 732) |
| 2891 | AFSLHSYS | | (SEQ ID NO: 733) |
| 2892 | FSLHSYSP | | (SEQ ID NO: 734) |
| 2893 | SLHSYSPG | | (SEQ ID NO: 735) |
| 2894 | LHSYSPGE | | (SEQ ID NO: 736) |
| 2895 | HSYSPGEI | | (SEQ ID NO: 737) |
| C100-3 | | | |
| 2912 | LGVPPLRA | Ep48 | (SEQ ID NO: 738) |
| 2913 | GVPPLRAW | | (SEQ ID NO: 739) |
| 2914 | VPPLRAWR | | (SEQ ID NO: 740) |
| C100-3 | | | |
| 2938 | AAICGKYL | Ep49 | (SEQ ID NO: 741) |
| 2939 | AICGKYLE | | (SEQ ID NO: 742) |
| 2940 | ICGKYLEN | | (SEQ ID NO: 743) |

-continued

| | C100-3 | | | |
|---|---|---|---|---|
| 2966 | DLSGWETA | EpHH | (SEQ ID NO: 744) |
| | C100-3 | | | |
| 2984 | VSHARPRW | EpII | (SEQ ID NO: 745) |

IV.B.15.c Differential Assay

The following assay was performed to distinguish early antigens from later antigens. Antibodies to the early antigens may be detected, and used to diagnose HCV infection more quickly.

Serial bleeds were obtained from a human patient presenting with elevated ALT, but negative for anti-C100-3 antibody. The five bleeds obtained prior to complete seroconversion (C100-3 positive) were pooled and used in the assay at a dilution of 1:2000. The assay was conducted as described in Section IV.B.15.b above. However, one duplicate set of pins was incubated with horseradish peroxidase-labeled goat anti-Human IgG specific antisera, while the other set was incubated with horseradish peroxidase-labeled goat anti-Human IgM specific antisera. Epitopes immunoreactive with IgM antibodies are early epitopes.

The results indicated that most early epitopes are found in the region extending from about amino acid 480 to about amino acid 650. Particularly strong IgM epitopes were octamers beginning with amino acid nos. 506, 510, 523, 553, 562, 580, and the region from 590 to 620. Assays which employ antigens bearing epitopes from this region will permit diagnosis of HCV infection at an early point than assays employing other antigens.

We have additionally tested serial plasma specimens taken from five patients with open heart post-transfusion NANB hepatitis, with studies followed for 3–12 years. Initial bleed dates were less than one week apart. Each specimen was tested for IgG and IgM by EIA against one core antigen (C22), two envelope antigens (E1 and E2), and three nonstructural region antigens (C33c, C100, and NS5). We found that the IgM response to C22 and C33c preceded the IgG response for those antigens. NS-5 also induced an IgM response, but this response did not precede the IgG response for that antigen. Thus, one can prepare assays capable of determining very early stages of infection by utilizing epitopes derived from the C22 and C33c regions and assaying for IgM binding. Antibodies to the C33c region persisted for the longest period of time, suggesting that diagnostic assays directed toward C33c should be the most reliable.

IV.C. Identification of RNA in Infected Individuals Which Hybridizes to HCV cDNA.

IV.C.1. Identification of RNA in the Liver of a Chimipanzee With NANBH Which Hybridizes to HCV cDNA.

RNA from the liver of a chimpanzee which had NANBH was shown to contain a species of RNA which hybridized to the HCV cDNA contained within clone 81 by Northern blotting, as follows.

RNA was isolated from a liver biopsy of the chimpanzee from which the high titer plasma was derived (see Section IV.A. 1.) using techniques described in Maniatis et al. (1982) for the isolation of total RNA from mammalian cells, and for its separation into poly A⁺ and poly A⁻ fractions. These RNA fractions were subjected to electrophoresis on a formaldehyde/agarose gel (1% w/v), and transferred to nitrocellulose. (Maniatis et al. (1982)). The nitrocellulose filters were hybridized with radiolabeled HCV cDNA from clone 81 (see FIG. 4 for the nucleotide sequence of the insert.) To prepare the radio-labeled probe, the HCV cDNA insert isolated from clone 81 was radiolabeled with $^{32}$P by nick translation using DNA Polymerase I (Maniatis et al. (1982)). Hybridization was for 18 hours at 42° C. in a solution containing 10% (w/v) Dextran sulphate, 50% (w/v) deionized formamide, 750 mM NaCl, 75 mM Na citrate, 20 mM Na$_2$HPO$_4$, pH 6.5, 0.1% SDS, 0.02% (w/v) bovine serum albumin (BSA), 0.02% (w/v) Ficoll-400, 0.02% (w/v) polyvinylpyrrolidone, 100 mg/mL salmon sperm DNA which had been sheared by sonication and denatured, and 10$^6$ CPM/mL of the nick-translated cDNA probe.

Figure 38:
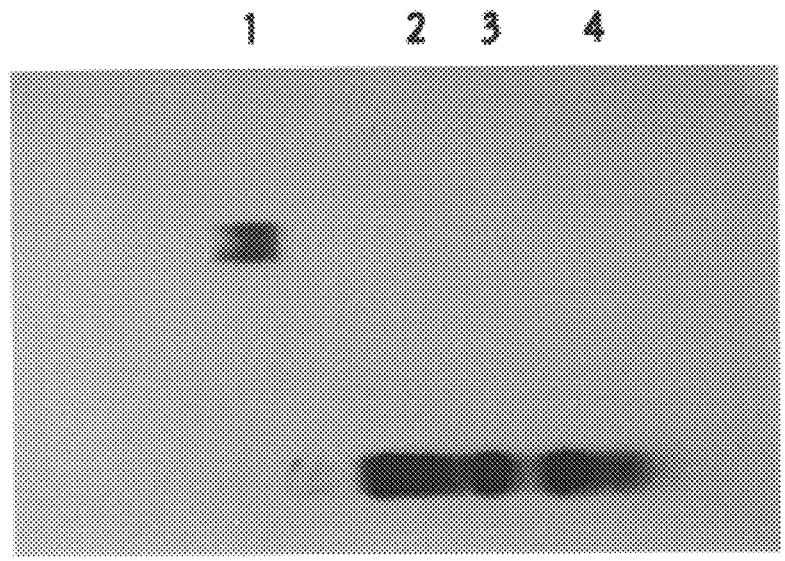
FIG. 38 shows an autoradiograph of a Northern blot of RNA isolated from the liver of a BB-NANBV infected chimpanzee, probed with BB-NANBV cDNA of clone 81.

An autoradiograph of the probed filter is shown in FIG. 38. Lane 1 contains $^{32}$P-labeled restriction fragment markers. Lanes 2–4 contain chimpanzee liver RNA as follows: lane 2 contains 30 mg of total RNA; lane 3 contains 30 mg of poly A–RNA; and lane 4 contains 20 mg of poly A+RNA. As shown in FIG. 38, the liver of the chimpanzee with NANBH contains a heterogeneous population of related poly A+RNA molecules which hybridizes to the HCV cDNA probe, and which appears to be from about 5000 nucleotides to about 1,000 nucleotides in size. This RNA, which hybridizes to the HCV cDNA, could represent viral genomes and/or specific transcripts of the viral genome.

The experiment described in Section IV.C.2., infra, is consistent with the suggestion that HCV contains an RNA genome.

IV.C.2. Identification of HCV Derived RNA in Serum from Infected Individuals.

Figure 39:
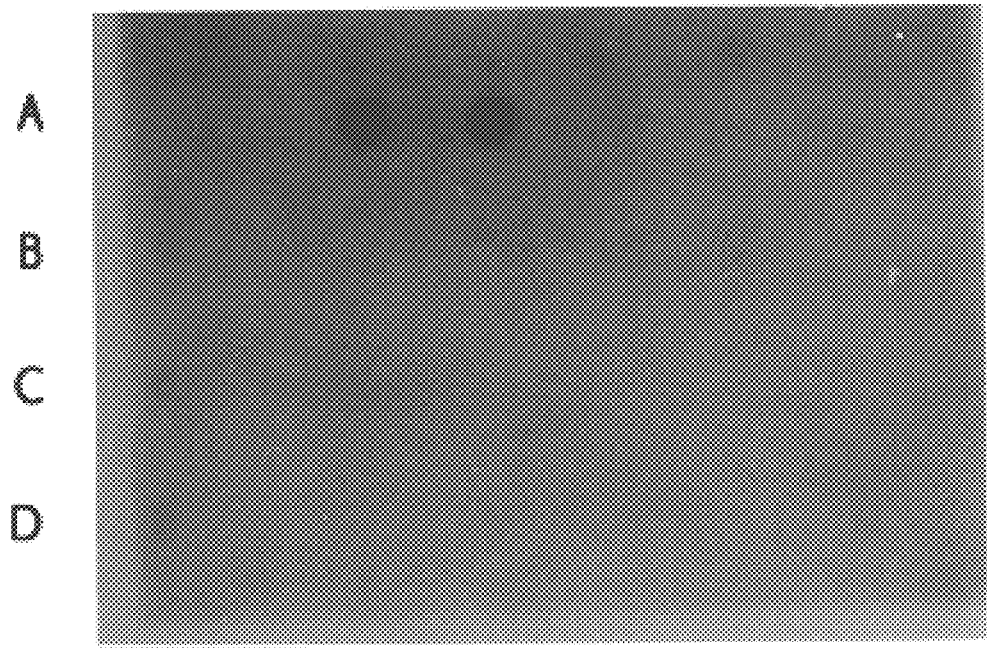
FIG. 39 shows an autoradiograph of NANBV nucleic acid treated with RNase A or DNase I, and probed with BB-NANBV cDNA of clone 81.

Nucleic acids were extracted from particles isolated from high titer chimpanzee NANBH plasma as described in Section IV.A.1.. Aliquots (equivalent to 1 mL of original plasma) of the isolated nucleic acids were resuspended in 20 mL 50 mM Hepes, pH 7.5, 1 mm EDTA and 16 mg/mL yeast soluble RNA. The samples were denatured by boiling for 5 minutes followed by immediate freezing, and were treated with RNase A (5 mL containing 0.1 mg/mL RNase A in 25 mM EDTA, 40 mM Hepes, pH 7.5) or with DNase 1 (5 mL containing 1 unit DNase I in 10 mM MgCl$_2$, 25 mM Hepes, pH 7.5); control samples were incubated without enzyme. Following incubation, 230 mL of ice-cold 2'SSC containing 2 mg/mL yeast soluble RNA was added, and the samples were filtered on a nitrocellulose filter. The filters were hybridized with a cDNA probe from clone 81, which had been $^{32}$P-labeled by nick-translation. FIG. 39 shows an autoradiograph of the filter. Hybridization signals were detected in the DNase treated and control samples (lanes 2 and 1, respectively), but were not detected in the RNase treated sample (lane 3). Thus, since RNase A treatment destroyed the nucleic acids isolated from the particles, and DNase I treatment had no effect, the evidence strongly suggests that the HCV genome is composed of RNA.

IV.C.3. Detection of Amplified HCV Nucleic Acid Sequences derived from HCV Nucleic Acid Sequences in Liver and Plasma Specimens from Chimpanzees with NANBH HCV nucleic acids present in liver and plasma of chimpanzees with NANBH, and in control chimpanzees, were amplified using essentially the polymerase chain reaction (PCR) technique described by Saiki et al. (1986). The primer oligonucleotides were derived from the HCV cDNA sequences in clone 81, or clones 36 and 37. The amplified sequences were detected by gel electrophoresis and Southern blotting, using as probes the appropriate cDNA oligomer with a sequence from the region between, but not including, the two primers.

Samples of RNA containing HCV sequences to be examined by the amplification system were isolated from liver biopsies of three chimpanzees with NANBH, and from two control chimpanzees. The isolation of the RNA fraction was by the guanidinium thiocyanate procedure described in Section IV.C.1.

Samples of RNA which were to be examined by the amplification system were also isolated from the plasmas of two chimpanzees with NANBH, and from one control chimpanzee, as well as from a pool of plasmas from control chimpanzees. One infected chimpanzee had a CID/mL equal to or greater than $10^6$, and the other infected chimpanzee had a CID/mL equal to or greater than $10^5$.

The nucleic acids were extracted from the plasma as follows. Either 0.1 mL or 0.01 mL of plasma was diluted to a final volume of 1.0 mL, with a TENB/proteinase K/SDS solution (0.05 M Tris-HCL, pH 8.0, 0.001 M EDTA, 0.1 M NaCl, 1 mg/mL Proteinase K, and 0.5% SDS) containing 10 mg/mL polyadenylic acid, and incubated at 37° C. for 60 minutes. After this proteinase K digestion, the resultant plasma fractions were deproteinized by extraction with TE (10.0 mM Tris-HCl, pH 8.0, 1 mM EDTA) saturated phenol. The phenol phase was separated by centrifugation, and was reextracted with TENB containing 0.1% SDS. The resulting aqueous phases from each extraction were pooled, and extracted twice with an equal volume of phenol/chloroform/isoamyl alcohol [1:1(99:2)], and then twice with an equal volume of a 99:1 mixture of chloroform/isoamyl alcohol. Following phase separation by centrifugation, the aqueous phase was brought to a final concentration of 0.2 M Na acetate, and the nucleic acids were precipitated by the addition of two volumes of ethanol. The precipitated nucleic acids were recovered by ultracentrifugation in a SW 41 rotor at 38 K, for 60 minutes at 4° C.

In addition to the above, the high titer chimpanzee plasma and the pooled control plasma alternatively were extracted with 50 mg of poly-A carrier by the procedure of Chomcyzski and Sacchi (1987). This procedure uses an acid guanidinium thiocyanate extraction. RNA was recovered by centrifugation at 10,000 RPM for 10 minutes at 4° C. in an Eppendorf microfuge.

On two occasions, prior to the synthesis of cDNA in the PCR reaction, the nucleic acids extracted from plasma by the proteinase K/SDS/phenol method were further purified by binding to and elution from S and S Elutip-R Columns. The procedure followed was according to the manufacturer's directions.

The cDNA used as a template for the PCR reaction was derived from the nucleic acids (either total nucleic acids or RNA) prepared as described above. Following ethanol precipitation, the precipitated nucleic acids were dried, and resuspended in DEPC treated distilled water. Secondary structures in the nucleic acids were disrupted by heating at 65° C. for 10 minutes, and the samples were immediately cooled on ice. cDNA was synthesized using 1 to 3 mg of total chimpanzee RNA from liver, or from nucleic acids (or RNA) extracted from 10 to 100 mL of plasma. The synthesis utilized reverse transcriptase, and was in a 25 mL reaction, using the protocol specified by the manufacturer, BRL. The primers for cDNA synthesis were those also utilized in the PCR reaction, described below. All reaction mixtures for cDNA synthesis contained 23 units of the RNAase inhibitor, Rnasin® (Fisher/Promega). Following cDNA synthesis, the reaction mixtures were diluted with water, boiled for 10 minutes, and quickly chilled on ice.

The PCR reactions were performed essentially according to the manufacturer's directions (Cetus/Perkin-Elmer), except for the addition of 1 mg of RNase A. The reactions were carried out in a final volume of 100 mL. The PCR was performed for 35 cycles, utilizing a regimen of 37° C., 72° C., and 94° C.

The primers for cDNA synthesis and for the PCR reactions were derived from the HCV cDNA sequences in either clone 81, clone 36, or clone 37b. (The HCV cDNA sequences of clones 81, 36, and 37b are shown in FIGS. 4, 5, and 10, respectively.) The sequences of the two 16-mer primers derived from clone 81 were:

5' CAA TCA TAC CTG ACA G 3'   (SEQ ID NO:746)

and

5' GAT AAC CTC TGC CTG A 3'   (SEQ ID NO:747).

The sequence of the primer from clone 36 was:

5' GCA TGT CAT GAT GTA T 3'   (SEQ ID NO:748).

The sequence of the primer from clone 37b was:

5' ACA ATA CGT GTG TCA C3'   (SEQ ID NO:749).

In the PCR reactions, the primer pairs consisted of either the two 16-mers derived from clone 81, or the 16-mer from clone 36 and the 16-mer from clone 37b.

The PCR reaction products were analyzed by separation of the products by alkaline gel electrophoresis, followed by Southern blotting, and detection of the amplified HCV-cDNA sequences with a $^{32}$P-labeled internal oligonucleotide probe derived from a region of the HCV cDNA which does not overlap the primers. The PCR reaction mixtures were extracted with phenol/chloroform, and the nucleic acids precipitated from the aqueous phase with salt and ethanol. The precipitated nucleic acids were collected by centrifugation, and dissolved in distilled water. Aliquots of the samples were subjected to electrophoresis on 1.8% alkaline agarose gels. Single stranded DNA of 60, 108, and 161 nucleotide lengths were co-electrophoresed on the gels as molecular weight markers. After electrophoresis, the DNAs in the gel were transferred onto nucleic acid paper, Biorad Zeta Probe(D (Biorad, Hercules, Calif.). Prehybridization and hybridization, and wash conditions were those specified by the manufacturer (Biorad).

The probes used for the hybridization-detection of amplified HCV cDNA sequences were the following. When the pair of PCR primers were derived from clone 81, the probe was an 108-mer with a sequence corresponding to that which is located in the region between the sequences of the two primers. When the pair of PCR primers were derived from clones 36 and 37b, the probe was the nick-translated HCV cDNA insert derived from clone 35. The primers are derived from nucleotides 155–170 of the clone 37b insert, and 206–268 of the clone 36 insert. The 3'-end of the HCV cDNA insert in clone 35 overlaps nucleotides 1–186 of the insert in clone 36; and the 5'-end of clone 35 insert overlaps nucleotides 207–269 of the insert in clone 37b. (Compare FIGS. 5, 8 and 10.) Thus, the cDNA insert in clone 35 spans part of the region between the sequences of the clone 36 and 37b derived primers, and is useful as a probe for the amplified sequences which include these primers.

Analysis of the RNA from the liver specimens was according to the above procedure utilizing both sets of primers and probes. The RNA from the liver of the three chimpanzees with NANBH yielded positive hybridization results for amplification sequences of the expected size (161 and 586 nucleotides for 81 and 36 and 37b, respectively), while the control chimpanzees yielded negative hybridization results. The same results were achieved when the experiment was repeated three times.

Analysis of the nucleic acids and RNA from plasma was also according to the above procedure utilizing the primers and probe from clone 81. The plasmas were from two chimpanzees with NANBH, from a control chimpanzee, and pooled plasmas from control chimpanzees. Both of the NANBH plasmas contained nucleic acids/RNA which yielded positive results in the PCR amplified assay, while both of the control plasmas yielded negative results. These results have been repeatedly obtained several times.

Defective viruses have been known to occur in RNA viruses. By using PCR technology it is possible to design primers to amplify sequences of the HCV genome. By analysis of the amplified products, it is expected to be able to identify both defective versions of the viral genome as well as wild-type viral species. Accordingly, using two primers based on known HCV sequence, one can predict accurately the expected size of the PCR product. Any larger species observed by gel electrophoresis and hybridization analysis could represent potential wild-type genomes. Alternatively, any smaller species observed in this fashion might represent defective agents. Analyses of these types would be useful in confirming the exact origin of the known HCV sequence, whether it is indeed a wild-type viral sequence or a defective genome. Techniques and methods for these analyses are well known in the art and have been previously described. This methodology will enable one skilled in the art to obtain related (wild-type or defective) forms of the viral genome.

IV.D. Radioimmunoassay for Detecting HCV Antibodies in Serum from Infected Individuals Solid phase radioimmunoassays to detect antibodies to HCV antigens were developed based upon Tsu and Herzenberg (1980). Generally, microtiter plates (Immulon 2, Removawell strips) are coated with purified polypeptides containing HCV epitopes. The coated plates are incubated with either human serum samples suspected of containing antibodies to the HCV epitopes, or to appropriate controls. During incubation, antibody, if present, is immunologically bound to the solid phase antigen. After removal of the unbound material and washing of the microtiter plates, complexes of human antibody-NANBV antigen are detected by incubation with $^{125}$I-labeled sheep anti-human immunoglobulin. Unbound labeled antibody is removed by aspiration, and the plates are washed. The radioactivity in individual wells is determined; the amount of bound human anti-HCV antibody is proportional to the radioactivity in the well.

The detection in serum of antibodies to HCV epitopes present in fusion polypeptides of SOD with $NANB_{5-1-1}$, with $NANB_{81}$, with $NANB_{C100}$, and with $NANB_{C33}$c (these polypeptides are also called SOD-5-1-1, SOD-81, C100-3, and SOD-C33c, respectively), was accomplished by solid phase radioimmunoassay.

Microtiter plates were coated with any of the aforementioned antigens, which had been purified as described herein in Section IV.D. 1. (SOD-$NANB_{5-1-1}$), Section IV.D.2. (SOD-$NANB_{81}$), Section IV.B.7. (C100-3), and Section IV.B.9. (SOD-33c). The assays were conducted as follows.

One hundred microliter aliquots containing 0.1 to 0.5 mg of the designated SOD-NANB fusion polypeptide in 0.125 M Na borate buffer, pH 8.3, 0.075 M NaCl (BBS) was added to each well of a microtiter plate (Dynatech Immulon 2 Removawell Strips). The plate was incubated at 4° C. overnight in a humid chamber, after which, the protein solution was removed and the wells washed 3 times with BBS containing 0.02% Triton® X-100 (BBST). To prevent nonspecific binding, the wells were coated with bovine serum albumin (BSA) by addition of 100 mL of a 5 mg/mL solution of BSA in BBS followed by incubation at room temperature for 1 hour; after this incubation the BSA solution was removed. The polypeptides in the coated wells were reacted with serum by adding 100 mL of serum samples diluted 1:100 in 0.01M Na phosphate buffer, pH 7.2, 0.15 M NaCl (PBS) containing 10 mg/mL BSA, and incubating the serum containing wells for 1 hr at 37° C. After incubation, the serum samples were removed by aspiration, and the wells were washed 5 times with BBST. Anti-$NANB_{5-1-1}$ and Anti-$NANB_{81}$ bound to the fusion polypeptides was determined by the binding of $^{125}$I-labeled F'(ab)$_2$ sheep anti-human IgG to the coated wells. Aliquots of 100 mL of the labeled probe (specific activity 5–20 mCi/mg) were added to each well, and the plates were incubated at 37° C. for 1 hour, followed by removal of excess probe by aspiration, and 5 washes with BBST. The amount of radioactivity bound in each well was determined by counting in a counter which detects gamma radiation.

IV.D.1. Purification of Fusion Polypeptide SOD-$NANB_{5-1-1}$.

The fusion polypeptide SOD-$NANB_{5-1-1}$, expressed in recombinant bacteria as described in Section IV.B.1., was purified from the recombinant *E. coli* by differential extraction of the cell extracts with urea, followed by chromatography on anion and cation exchange columns as follows.

Thawed cells from 1 liter of culture were resuspended in 10 mL of 20% (w/v) sucrose containing 0.01M Tris HCl, pH 8.0, and 0.4 mL of 0.5M EDTA, pH 8.0 was added. After 5 minutes at 0° C., the mixture was centrifuged at 4,000 ' g for 10 minutes. The resulting pellet was suspended in 10 mL of 25% (w/v) sucrose containing 0.05 M Tris HCl, pH 8.0, 1 mM phenylmethylsulfonylfluoride (PMSF) and 1 mg/mL pepstatin A, followed by addition of 0.5 mL lysozyme (10 mg/mL) and incubation at 0° C. for 10 minutes. After the addition of 10 mL 1% (v/v) Triton® X-100 in 0.05 M Tris HCl, pH 8.0, 1 mM EDTA, the mixture was incubated an additional 10 min at 0° C. with occasional shaking. The resulting viscous solution was homogenized by passage 6 times through a sterile 20-gauge hypodermic needle, and centrifuged at 13,000 x g for 25 minutes. The pelleted material was suspended in 5 mL of 0.01 M Tris HCl pH 8.0, and the suspension centrifuged at 4,000 x g for 10 minutes. The pellet, which contained SOD-$NANB_{5-1-1}$ fusion protein, was dissolved in 5 mL of 6 M urea in 0.02 M Tris HCl, pH 8.0, 1 mM dithiothreitol (Buffer A), and was applied to a column of Q-Sepharose® Fast Flow equilibrated with Buffer A. Polypeptides were eluted with a linear gradient of 0.0 to 0.3 M NaCl in Buffer A. After elution, fractions were analyzed by polyacrylamide gel electrophoresis in the presence of SDS to determine their content of SOD-$NANB_{5-1-1}$. Fractions containing this polypeptide were pooled, and dialyzed against 6 M urea in 0.02 M sodium phosphate buffer, pH 6.0, 1 mM dithiothreitol (Buffer B). The dialyzed sample was applied on a column of S-Sepharose® Fast Flow equilibrated with Buffer B, and polypeptides eluted with a linear gradient of 0.0 to 0.3 M NaCl in Buffer B. The fractions were analyzed by polyacrylamide gel electrophoresis for the presence of SOD-$NANB_{5-1-1}$, and the appropriate fractions were pooled.

The final preparation of SOD-$NANB_{5-1-1}$ polypeptide was examined by electrophoresis on polyacrylamide gels in the presence of SDS. Based upon this analysis, the preparation was more than 80% pure.

IV.D.2. Purification of Fusion Polypeptide SOD-$NANB_{81}$.

The fusion polypeptide SOD-$NANB_{81}$, expressed in recombinant bacteria as described in Section IV.B.2., was purified from recombinant *E. coli* by differential extraction of the cell extracts with urea, followed by chromatography on anion and cation exchange columns utilizing the procedure described for the isolation of fusion polypeptide SOD-NANB$_{5-1-1}$ (see Section IV.D. 1.).

The final preparation of SOD-NANB81 polypeptide was examined by electrophoresis on polyacrylamide gels in the presence of SDS. Based upon this analysis, the preparation was more than 50% pure.

IV.D.3. Detection of Antibodies to HCV Epitopes by Solid Phase Radioimmunoassay.

Serum samples from 32 patients who were diagnosed as having NANBH were analyzed by radioimmunoassay (RIA) to determine whether antibodies to HCV epitopes present in fusion polypeptides SOD-$NANB_{5-1-1}$ and SOD-$NANB_{81}$ were detected.

Microtiter plates were coated with SOD-$NANB_{5-1-1}$ or SOD-$NANB_{81}$, which had been partially purified according to Sections IV.D.1. and IV.D.2., respectively. The assays were conducted as described supra.

The results of the detection of anti-$NANB_{5-1-1}$ and anti-$NANB_{81}$ in individuals with NANBH is presented in Table 1.

TABLE 1

Detection of Anti-5-1-1 and Anti-81 in Sera of NANB, HAV and HBV Hepatitis Patients

| Patient Reference Number | Diagnosis | S/N Anti-5-1-1 | S/N Anti-81 |
|---|---|---|---|
| 1. 28[1] | Chronic NANB, IVD[2] | 0.77 | 4.20 |
| | Chronic NANB, IVD | 1.14 | 5.14 |
| | Chronic NANB, IVD | 2.11 | 4.05 |
| 2. 29[1] | AVH[3], NANB, Sporadic | 1.09 | 1.05 |
| | Chronic, NANB | 33.89 | 11.39 |
| | Chronic, NANB | 36.22 | 13.67 |
| 3. 30[1] | AVH, NANB, IVD | 1.90 | 1.54 |
| | Chronic NANB, IVD | 34.17 | 30.28 |
| | Chronic NANB, IVD | 32.45 | 30.84 |
| 4. 31 | Chronic NANB, PT[4] | 16.09 | 8.05 |
| 5. 32[1] | Late AVH NANB, IVD | 0.69 | 0.94 |
| | Late AVH NANB, IVD | 0.73 | 0.68 |
| 6. 33[1] | AVH, NANB, IVD | 1.66 | 1.96 |
| | AVH, NANB, IVD | 1.53 | 0.56 |
| 7. 34[1] | Chronic NANB, PT | 34.40 | 7.55 |
| | Chronic NANB, PT | 45.55 | 13.11 |
| | Chronic NANB, PT | 41.58 | 13.45 |
| | Chronic NANB, PT | 44.20 | 15.48 |
| 8. 35[1] | AVH NANB, IVD | 31.92 | 31.95 |
| | "Healed" recent NANB, AVH | 6.87 | 4.45 |
| 9. 36 | Late AVH NANB PT | 11.84 | 5.79 |
| 10. 37 | AVH NANB, IVD | 6.52 | 1.33 |
| 11. 38 | Late AVH NANB, PT | 39.44 | 39.18 |
| 12. 39 | Chronic NANB, PT | 42.22 | 37.54 |
| 13. 40 | AVH, NANB, PT | 1.35 | 1.17 |
| 14. 41 | Chronic NANB? PT | 0.35 | 0.28 |
| 15. 42 | AVH, NANB, IVD | 6.25 | 2.34 |
| 16. 43 | Chronic NANB, PT | 0.74 | 0.61 |
| 17. 44 | AVH, NANB, PT | 5.40 | 1.83 |
| 18. 45 | Chronic, NANB, PT | 0.52 | 0.32 |
| 19. 46 | AVH, NANB | 23.25 | 4.45 |
| 20. 47 | AVH, Type A | 1.60 | 1.35 |
| 21. 48 | AVH, Type A | 1.30 | 0.66 |
| 22. 49 | AVH, Type A | 1.44 | 0.74 |
| 23. 50 | Resolved Recent AVH, Type A | 0.48 | 0.56 |
| 24. 51 | AVH, Type A | 0.68 | 0.64 |
| | Resolved AVH, Type A | 0.80 | 0.65 |
| 25. 52 | Resolved Recent AVH, Type A | 1.38 | 1.04 |
| | Resolved Recent AVH, Type A | 0.80 | 0.65 |
| 26. 53 | AVH, Type A | 1.85 | 1.16 |
| | Resolved Recent AVH Type A | 1.02 | 0.88 |
| 27. 54 | AVH, Type A | 1.35 | 0.74 |
| 28. 55 | Late AVH, HBV | 0.58 | 0.55 |
| 29. 56 | Chronic HBV | 0.84 | 1.06 |
| 30. 57 | Late AVH, HBV | 3.20 | 1.60 |
| 31. 58 | Chronic HBV | 0.47 | 0.46 |
| 32. 59[1] | AVH, HBV | 0.73 | 0.60 |
| | Healed AVH, HBV | 0.43 | 0.44 |
| 33. 60[1] | AVH, HBV | 1.06 | 0.92 |
| | Healed AVH, HBV | 0.75 | 0.68 |
| 34. 61[1] | AVH, HBV | 1.66 | 0.61 |
| | Healed AVH, HBV | 0.63 | 0.36 |
| 35. 62[1] | AVH, HBV | 1.02 | 0.73 |
| | Healed AVH, HBV | 0.41 | 0.42 |
| 36. 63[1] | AVH, HBV | 1.24 | 1.31 |
| | Healed AVH, HBV | 1.55 | 0.45 |
| 37. 64[1] | AVH, HBV | 0.82 | 0.79 |
| | Healed AVH, HBV | 0.53 | 0.37 |
| 38. 65[1] | AVH, HBV | 0.95 | 0.92 |
| | Healed AVH, HBV | 0.70 | 0.50 |
| 39. 66[1] | AVH, HBV | 1.03 | 0.68 |
| | Healed AVH, HBV | 1.71 | 1.39 |

[1]Sequential serum samples available from these patients
[2]IVD = Intravenous Drug User
[3]AVH = Acute viral hepatitis
[4]PT = Post transfusion As seen in Table 1, 19 of 32 sera from patients diagnosed as having NANBH were positive with respect to antibodies directed against HCV epitopes present in SOD-$NANB_{5-1-1}$ and SOD-$NANB_{81}$.

However, the serum samples which were positive were not equally immunologically reactive with SOD-$NANB_{5-1-1}$ and SOD-$NANB_{81}$. Serum samples from patient No. 1 were positive to SOD-$NANB_{81}$ but not to SOD-$NANB_{5-1-1}$. Serum samples from patients number 10, 15, and 17 were positive to SOD-$NANB_{5-1-1}$ but not to SOD-$NANB_{81}$. Serum samples from patients No. 3, 8, 11, and 12 reacted equally with both fusion polypeptides, whereas serum samples from patients No. 2, 4, 7, and 9 were 2–3 fold higher in the reaction to SOD-$NANB_{5-1-1}$, than to SOD-$NANB_{81}$. These results suggest that $NANB_{5-1-1}$ and $NANB_{81}$ may contain at least 3 different epitopes; i.e., it is possible that each polypeptide contains at least 1 unique epitope, and that the two polypeptides share at least 1 epitope.

IV.D.4. Specificity of the Solid Phase RIA for NANBH

The specificity of the solid phase RIAs for NANBH was tested by using the assay on serum from patients infected with HAV or with HBV and on sera from control individuals. The assays utilizing partially purified SOD-$NANB_{5-1-1}$ and SOD-$NANB_{81}$ were conducted essentially as described in Section IV.D.3, except that the sera was from patients previously diagnosed as having HAV or HBV, or from individuals who were blood bank donors. The results for sera from HAV and HBV infected patients are presented in table 1. The RIA was tested using 11 serum specimens from HAV infected patients, and 20 serum specimens from HBV infected patients. As shown in table 1, none of these sera yielded a positive immunological reaction with the fusion polypeptides containing BB-NANBV epitopes.

The RIA using the $NANB_{5-1-1}$ antigen was used to determine immunological reactivity of serum from control individuals. Out of 230 serum samples obtained from the normal blood donor population, only 2 yielded positive reactions in the RIA (data not shown). It is possible that the two blood donors from whom these serum samples originated had previously been exposed to HCV.

IV.D.5. Reactivity of $NANB_{5-1-1}$ During the Course of NANBH Infection.

The presence of anti-$NANB_{5-1-1}$ antibodies during the course of NANBH infection of 2 patients and 4 chimpanzees was followed using RIA as described in Section IV.D.3. In addition the RIA was used to determine the presence or absence of anti-$NANB_{5-1-1}$ antibodies during the course of infection of HAV and HBV in infected chimpanzees.

The results, which are presented in Table 2, show that with chimpanzees and with humans, anti-$NANB_{5-1-1}$ antibodies were detected following the onset of the acute phase of NANBH infection. Anti-$NANB_{5-1-1}$ antibodies were not detected in serum samples from chimpanzees infected with either HAV or HBV.

Thus anti-$NANB_{5-1-1}$ antibodies serve as a marker for an individual's exposure to HCV.

TABLE 2

Seroconversion in Sequential Serum Samples from Hepatitis patients and Chimpanzees Using 5-1-1 Antigen

| Patient/ Chimp | Sample Date (Days) (0 = inoculation day) | Hepatitis Viruses | Anti-5-1-1 (S/N) | ALT (mu/mL) |
|---|---|---|---|---|
| Patient 29 | T[a] | NANB | 1.09 | 1180 |
|  | T + 180 |  | 33.89 | 425 |
|  | T + 208 |  | 36.22 | — |
| Patient 30 | T | NANB | 1.90 | 1830 |
|  | T + 307 |  | 34.17 | 290 |
|  | T + 799 |  | 32.45 | 276 |
| Chimp 1 | 0 | NANB | 0.87 | 9 |
|  | 76 |  | 0.93 | 71 |
|  | 118 |  | 23.67 | 19 |
|  | 154 |  | 32.41 | — |
| Chimp 2 | 0 | NANB | 1.00 | 5 |
|  | 21 |  | 1.08 | 52 |
|  | 73 |  | 4.64 | 13 |
|  | 138 |  | 23.01 | — |
| Chimp 3 | 0 | NANB | 1.08 | 8 |
|  | 43 |  | 1.44 | 205 |
|  | 53 |  | 1.82 | 14 |
|  | 159 |  | 11.87 | 6 |
| Chimp 4 | −3 | NANB | 1.12 | 11 |
|  | 55 |  | 1.25 | 132 |
|  | 83 |  | 6.60 | — |
|  | 140 |  | 17.51 | — |
| Chimp 5 | 0 | HAV | 1.50 | 4 |
|  | 25 |  | 2.39 | 147 |
|  | 40 |  | 1.92 | 18 |
|  | 268 |  | 1.53 | 5 |
| Chimp 6 | −8 | HAV | 0.85 | — |
|  | 15 |  | — | 106 |
|  | 41 |  | 0.81 | 10 |
|  | 129 |  | 1.33 | — |
| Chimp 7 | 0 | HAV | 1.17 | 7 |
|  | 22 |  | 1.60 | 83 |
|  | 115 |  | 1.55 | 5 |
|  | 139 |  | 1.60 | — |
| Chimp 8 | 0 | HAV | 0.77 | 15 |
|  | 26 |  | 1.98 | 130 |
|  | 74 |  | 1.77 | 8 |
|  | 205 |  | 1.27 | 5 |
| Chimp 9 | −290 | HBV | 1.74 | — |
|  | 379 |  | 3.29 | 9 |
|  | 435 |  | 2.77 | 6 |
| Chimp 10 | 0 | HBV | 2.35 | 8 |
|  | 111–118 (pool) |  | 2.74 | 96–155 (pool) |
|  | 205 |  | 2.05 | 9 |
|  | 240 |  | 1.78 | 13 |
| Chimp 11 | 0 | HBV | 1.82 | 11 |
|  | 28–56 (pool) |  | 1.26 | 8–100 (pool) |
|  | 169 |  | — | 9 |
|  | 223 |  | 0.52 | 10 |

[a]T = day of initial sampling

IV.E. Purification of Polyclonal Serum Antibodies to $NANB_{5-1-1}$

On the basis of the specific immunological reactivity of the SOD-$NANB_{5-1-1}$ polypeptide with the antibodies in serum samples from patients with NANBH, a method was developed to purify serum antibodies which react immunologically with the epitope(s) in $NANB_{5-1-1}$. This method utilizes affinity chromatography. Purified SOD-$NANB_{5-1-1}$ polypeptide (see Section IV.D.1) was attached to an insoluble support; the attachment is such that the immobilized polypeptide retains its affinity for antibody to $NANB_{5-1-1}$. Antibody in serum samples is absorbed to the matrix-bound polypeptide. After washing to remove non-specifically bound materials and unbound materials, the bound antibody is released from the bound SOD-HCV polypeptide by change in pH, and/or by chaotropic reagents, for example, urea.

Nitrocellulose membranes containing bound SOD-$NANB_{5-1-1}$ were prepared as follows. A nitrocellulose membrane, 2.1 cm Sartorius of 0.2 mm pore size, was washed for 3 minutes three times with BBS. SOD-$NANB_{5-1-1}$ was bound to the membrane by incubation of the purified preparation in BBS at room temperature for 2 hours; alternatively it was incubated at 4° C. overnight. The solution containing unbound antigen was removed, and the filter was washed three times with BBS for three minutes per wash. The remaining active sites on the membrane were blocked with BSA by incubation with a 5 mg/mL BSA solution for 30 minutes. Excess BSA was removed by washing the membrane with 5 times with BBS and 3 times with distilled water. The membrane containing the viral antigen and BSA was then treated with 0.05 M glycine hydrochloride, pH 2.5, 0. 0 M NaCl (GlyHCl) for 15 minutes, followed by 3 three minute washes with PBS.

Polyclonal anti-$NANB_{5-1-1}$ antibodies were isolated by incubating the membranes containing the fusion polypeptide with serum from an individual with NANBH for 2 hours. After the incubation, the filters were washed 5 times with BBS, and twice with distilled water. Bound antibodies were then eluted from each filter with 5 elutions of GlyHCl, at 3 minutes per elution. The pH of the eluates was adjusted to pH 8.0 by collecting each eluate in a test tube containing 2.0 M Tris HCl, pH 8.0. Recovery of the anti-$NANB_{5-1-1}$ antibody after affinity chromatography is approximately 50%.

The nitrocellulose membranes containing the bound viral antigen can be used several times without appreciable decrease in binding capacity. To reuse the membranes, after the antibodies have been eluted the membranes are washed with BBS three times for 3 minutes. They are then stored in BBS at 4° C.

IV.F. The Capture of HCV Particles from Infected Plasma Using Purified Human Polyclonal Anti-HCV Antibodies, Hybridization of the Nucleic Acid in the Captured Particles to HCV cDNA

IV.F.1. The Capture of HCV Particles from Infected Plasma Using Human Polyclonal Anti-HCV Antibodies Protein-nucleic acid complexes present in infectious plasma of a chimpanzee with NANBH were isolated using purified human polyclonal anti-HCV antibodies which were bound to polystyrene beads.

Polyclonal anti-$NANB_{5-1-1}$ antibodies were purified from serum from a human with NANBH using the SOD-HCV polypeptide encoded in clone 5-1-1. The method for purification was that described in Section IV.E.

The purified anti-$NANB_{5-1-1}$ antibodies were bound to polystyrene beads (¼" diameter, specular finish, Precision Plastic Ball Co., Chicago, Ill.) by incubating each at room temperature overnight with 1 mL of antibodies (1 mg/mL in borate buffered saline, pH 8.5). Following the overnight incubation, the beads were washed once with TBST [50 mM Tris HCl, pH 8.0, 150 mM NaCl, 0.05% (v/v) Tween® 20], and then with phosphate buffered saline (PBS) containing 10 mg/mL BSA.

Control beads were prepared in an identical fashion, except that the purified anti-$NANB_{5-1-1}$ antibodies were replaced with total human immunoglobulin.

Capture of HCV from NANBH infected chimpanzee plasma using the anti-$NANB_{5-1-1}$ antibodies bound to beads was accomplished as follows. The plasma from a chimpanzee with NANBH used is described in Section IV.A. 1. An aliquot (1 mL) of the NANBV infected chimpanzee plasma was incubated for 3 hours at 37° C with each of 5 beads coated with either anti-$NANB_{5-1-1}$ antibodies, or with control immunoglobulins. The beads were washed 3 times with TBST.

IV.F.2. Hybridization of the Nucleic Acid in the Captured Particles to NANBV-cDNA The nucleic acid component released from the particles captured with anti-$NANB_{5-1-1}$ antibodies was analyzed for hybridization to HCV cDNA derived from clone 81.

Figure 40:
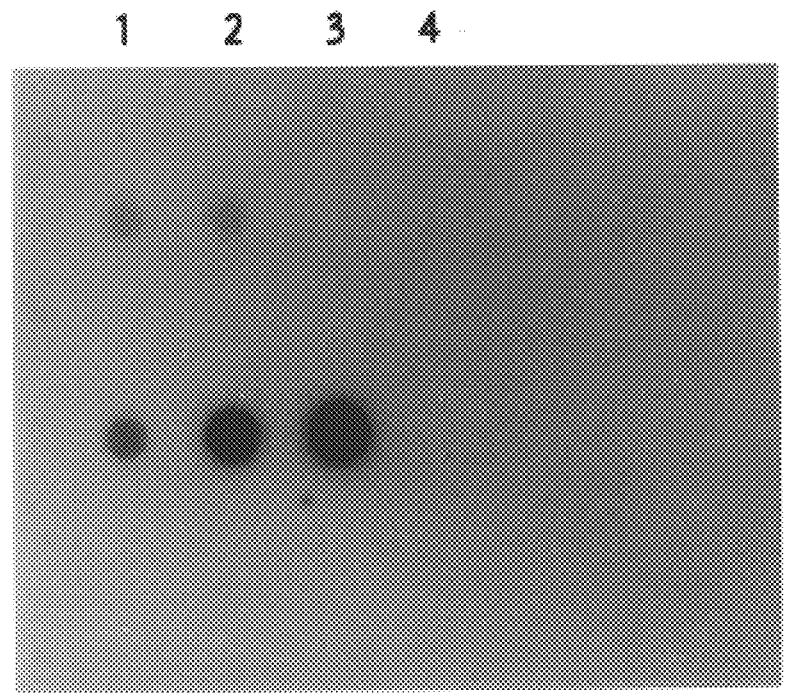
FIG. 40 shows an autoradiograph of nucleic acids extracted from NANBV particles captured from infected plasma with anti-NANB$_{5-1-1}$, and probed with $^{32}$P-labeled NANBV cDNA from clone 81.

HCV particles were captured from NANBH infected chimpanzee plasma, as described in IV.F.1. To release the nucleic acids from the particles, the washed beads were incubated for 60 min. at 37° C. with 0.2 mL per bead of a solution containing proteinase K (1 mg/mL), 10 mM Tris HCl, pH 7.5, 10 mM EDTA, 0.25% (w/v) SDS, 10 mg/mL soluble yeast RNA, and the supernatant solution was removed. The supernatant was extracted with phenol and chloroform, and the nucleic acids precipitated with ethanol overnight at −20° C. The nucleic acid precipitate was collected by centrifugation, dried, and dissolved in 50 mM Hepes, pH 7.5. Duplicate aliquots of the soluble nucleic acids from the samples obtained from beads coated with anti-$NANB_{5-1-1}$ antibodies and with control beads containing total human immunoglobulin were filtered onto to nitrocellulose filters. The filters were hybridized with a $^{32}P$-labeled, nick-translated probe made from the purified HCV cDNA fragment in clone 81. The methods for preparing the probe and for the hybridization are described in Section IV.C.1. Autoradiographs of a probed filter containing the nucleic acids from particles captured by beads containing anti-$NANB_{5-1-1}$ antibodies are shown in FIG. 40. The extract obtained using the anti-$NANB_{5-1-1}$ antibody ($A_1, A_2$) gave clear hybridization signals relative to the control antibody extract ($A_3, A_4$) and to control yeast RNA ($B_1, B_2$). Standards consisting of 1 pg, 5 pg, and 10 pg of the purified, clone 81 cDNA fragment are shown in C1-3, respectively.

These results demonstrate that the particles captured from NANBH plasma by anti-$NANB_{5-1-1}$-antibodies contain nucleic acids which hybridize with HCV cDNA in clone 81, and thus provide further evidence that the cDNAs in these clones are derived from the etiologic agent for NANBH.

IV.G. Immunological Reactivity of C100-3 with Purified Anti-$NANB_{5-1-1}$ Antibodies The immunological reactivity of C100-3 fusion polypeptide with anti-$NANB_{5-1-1}$ antibodies was determined by a radioimmunoassay, in which the antigens which were bound to a solid phase were challenged with purified anti-$NANB_{5-1-1}$ antibodies, and the antigen-antibody complex detected with $^{125}I$-labeled sheep anti-human antibodies. The immunological reactivity of C100-3 polypeptide was compared with that of SOD-$NANB_{5-1-1}$ antigen.

The fusion polypeptide C100-3 was synthesized and purified as described in Section IV.B.5. and in Section IV.B.6., respectively. The fusion polypeptide SOD-$NANB_{5-1-1}$ was synthesized and purified as described in Section IV.B. 1. and in Section IV.D.1., respectively. Purified anti-$NANB_{5-1-1}$ antibodies were obtained as described in Section IV.E.

One hundred mL aliquots containing varying amounts of purified C100-3 antigen in 0.125 M Na borate buffer, pH 8.3, 0.075 M NaCl (BBS) was added to each well of a microtiter plate (Dynatech Immulon 2 Removawell Strips). The plate was incubated at 4° C. overnight in a humid chamber, after which, the protein solution was removed and the wells washed 3 times with BBS containing 0.02% Triton® X-100 (BBST). To prevent non-specific binding, the wells were coated with BSA by addition of 100 mL of a 5 mg/mL solution of BSA in BBS followed by incubation at room temperature for 1 hour, after which the excess BSA solution was removed. The polypeptides in the coated wells were reacted with purified anti-$NANB_{5-1-1}$ antibodies by adding 1 mg antibody/well, and incubating the samples for 1 hr at 37° C. After incubation, the excess solution was removed by aspiration, and the wells were washed 5 times with BBST. Anti-$NANB_{5-1-1}$ bound to the fusion polypeptides was determined by the binding of $^{125}I$-labeled $F'(ab)_2$ sheep anti-human IgG to the coated wells. Aliquots of 100 mL of the labeled probe (specific activity 5–20 mCi/mg) were added to each well, and the plates were incubated at 37° C. for 1 hour, followed by removal of excess probe by aspiration, and 5 washes with BBST. The amount of radioactivity bound in each well was determined by counting in a counter which detects gamma radiation.

The results of the immunological reactivity of C100 with purified anti-$NANB_{5-1-1}$ as compared to that of $NANB_{5-1-1}$ with the purified antibodies are shown in Table 3.

TABLE 3

Immunological Reactivity of C100-3 compared to $NANB_{5-1-1}$ by Radioimmunoassay

| | RIA (cpm/assay) | | | | | |
|---|---|---|---|---|---|---|
| AG(ng) | 400 | 320 | 240 | 160 | 60 | 0 |
| $NANB_{5-1-1}$ | 7332 | 6732 | 4954 | 4050 | 3051 | 57 |
| C100-3 | 7450 | 6985 | 5920 | 5593 | 4096 | 67 |

The results in Table 3 show that anti-$NANB_{5-1-1}$ recognizes an epitope(s) in the C100 moiety of the C100-3 polypeptide. Thus $NANB_{5-1-1}$ and C100 share a common epitope(s). The results suggest that the cDNA sequence encoding this NANBV epitope(s) is one which is present in both clone 5-1-1 and in clone 81.

IV.H. Characterization of HCV

IV.H. 1. Characterization of the Strandedness of the HCV Genome.

The HCV genome was characterized with respect to its strandedness by isolating the nucleic acid fraction from particles captured on anti-NANB$_{5-1-1}$ antibody coated polystyrene beads, and determining whether the isolated nucleic acid hybridized with plus and/or minus strands of HCV cDNA.

Particles were captured from HCV infected chimpanzee plasma using polystyrene beads coated with immunopurified anti-NANB$_{5-1-1}$ antibody as described in Section IV.F.1. The nucleic acid component of the particles was released using the method described in Section IV.F.2. Aliquots of the isolated genomic nucleic acid equivalent to 3 mLs of high titer plasma were blotted onto nitrocellulose filters. As controls, aliquots of denatured HCV cDNA from clone 81 (2 pg) was also blotted onto the same filters. The filters were probed with $^{32}$P-labeled mixture of plus or mixture of minus strands of single stranded DNA cloned from HCV cDNAs; the cDNAs were excised from clones 40b, 81, and 25c.

The single stranded probes were obtained by excising the HCV cDNAs from clones 81, 40b, and 25c with EcoRi, and cloning the cDNA fragments in M13 vectors, mp18 and mp19 [Messing (1983)]. The M13 clones were sequenced to determine whether they contained the plus or minus strands of DNA derived from the HCV cDNAs. Sequencing was by the dideoxy chain termination method of Sanger et al. (1977).

Figure 41A:
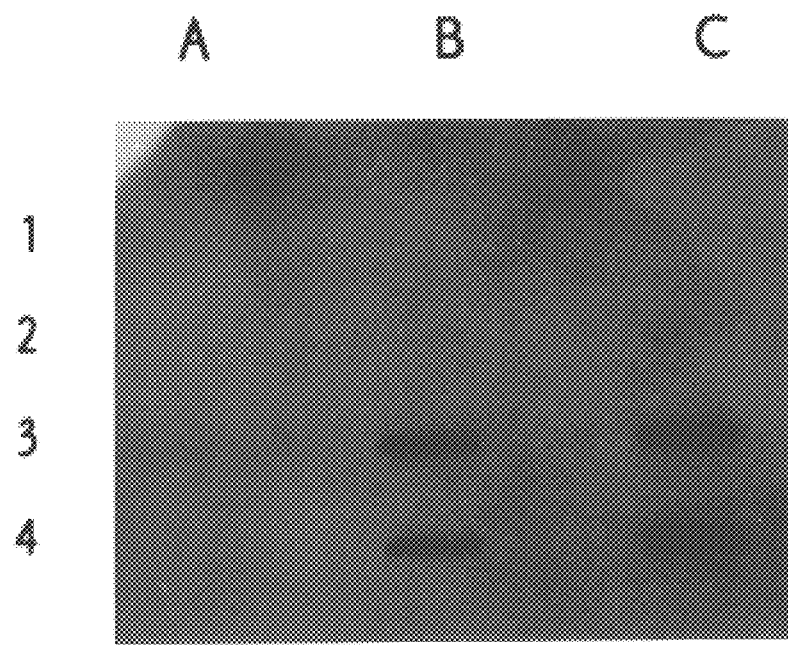
FIG. 41 shows autoradiographs of filters containing isolated NANBV nucleic acids, probed with $^{32}$P-labeled plus and minus strand DNA probes derived from NANBV cDNA in clone 81.
Figure 41B:
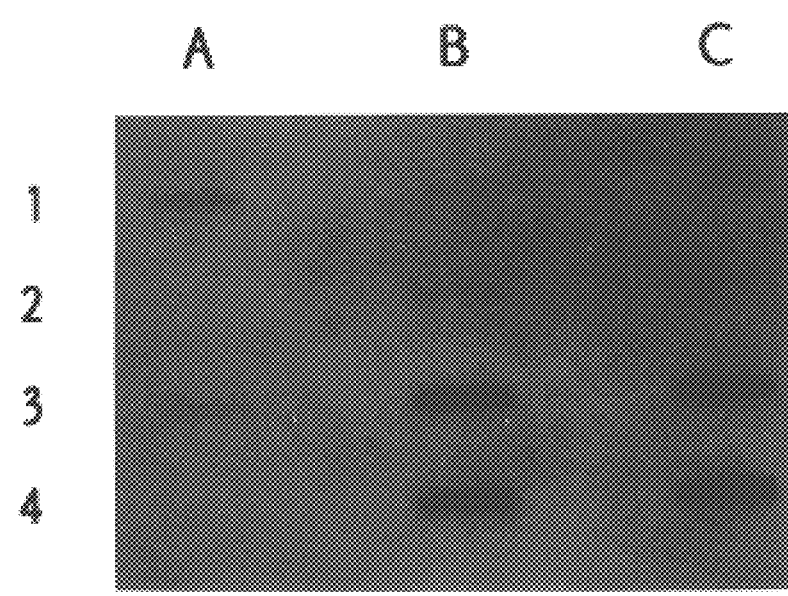

Each of a set of duplicate filters containing aliquots of the HCV genome isolated from the captured particles was hybridized with either plus or minus strand probes derived from the HCV cDNAs. FIG. 41 shows the autoradiographs obtained from probing the NANBV genome with the mixture of probes derived from clones 81, 40b, and 25c. This mixture was used to increase the sensitivity of the hybridization assay. The samples in panel I were hybridized with the plus strand probe mixture. The samples in panel II were probed by hybridization with the minus strand probe mixture. The composition of the samples in the panels of the immunoblot are presented in Table 4.

TABLE 4

| lane | A | B |
|---|---|---|
| 1 | HCV genome | * |
| 2 | — | * |
| 3 | * | cDNA 81 |
| 4 | — | cDNA 81 |

* is an undescribed sample.

As seen from the results in FIG. 41, only the minus strand DNA probe hybridizes with the isolated HCV genome. This result, in combination with the result showing that the genome is sensitive to RNase and not DNase (see Section IV.C.2.), suggests that the genome of NANBV is positive stranded RNA.

These data, and data from other laboratories concerning the physicochemical properties of a putative NANBV(s), are consistent with the possibility that HCV is Flavi-like.

IV.H.2. Detection of Sequences in Captured Particles Which When Amplified by PCR Hybridize to HCV cDNA Derived from Clone 81

The RNA in captured particles was obtained as described in Section IV.H.1. The analysis for sequences which hybridize to the HCV cDNA derived from clone 81 was carried out utilizing the PCR amplification procedure, as described in Section IV.C.3, except that the hybridization probe was a kinased oligonucleotide derived from the clone 81 cDNA sequence. The results showed that the amplified sequences hybridized with the clone 81 derived HCV cDNA probe.

IV.H.3. Homology Between the Non-Structural Protein of Dengue Flavivirus (MNWWVD1) and the HCV Polypeptides Encoded by the Combined ORF of Clones 14i Through 39c The combined HCV cDNAs of clones 14i through 39c contain one continuous ORF, as shown in FIG. 26. The polypeptide encoded therein was analyzed for sequence homology with the region of the non-structural polypeptide (s) in Dengue flavivirus (MNWVD1). The analysis used the Dayhoff protein data base, and was performed on a computer. The results are shown in FIG. 42, where the symbol (:) indicates an exact homology, and the symbol (.) indicates a conservative replacement in the sequence; the dashes indicate spaces inserted into the sequence to achieve the greatest homologies. As seen from the figure, there is significant homology between the sequence encoded in the HCV cDNA, and the non-structural polypeptide(s) of Dengue virus. In addition to the homology shown in FIG. 42, analysis of the polypeptide segment encoded in a region towards the 3'-end of the cDNA also contained sequences which are homologous to sequences in the Dengue polymerase. Of consequence is the finding that the canonical Gly-Asp-Asp (GDD) sequence thought to be essential for RNA-dependent RNA polymerases is contained in the polypeptide encoded in HCV cDNA, in a location which is consistent with that in Dengue 2 virus. (Data not shown.)

IV.H.4. HCV-DNA is Not Detectable in NANBH Infected Tissue

Two types of studies provide results suggesting that HCV-DNA is not detectable in tissue from an individual with NANBH. These results, in conjunction with those described in IV.C. and IV.H.1. and IV.H.2. provide evidence that HCV is not a DNA containing virus, and that its replication does not involve cDNA.

IV.H.4.a. Southern Blotting Procedure

In order to determine whether NANBH infected chimpanzee liver contains detectable HCV-DNA (or HCV-cDNA), restriction enzyme fragments of DNA isolated from this source was Southern blotted, and the blots probed with $^{32}$P-labeled HCV cDNA. The results showed that the labeled HCV cDNA did not hybridize to the blotted DNA from the infected chimpanzee liver. It also did not hybridize to control blotted DNA from normal chimpanzee liver. In contrast, in a positive control, a labeled probe of the b-interferon gene hybridized strongly to Southern blots of restriction enzyme digested human placental DNA. These systems were designed to detect a single copy of the gene which was to be detected with the labeled probe.

DNAs were isolated from the livers of two chimpanzees with NANBH. Control DNAs were isolated from uninfected chimpanzee liver, and from human placentas. The procedure for extracting DNA was essentially according to Maniatis et al. (1982), and the DNA samples were treated with RNase during the isolation procedure.

Each DNA sample was treated with either EcoRI, MboI, or HincII (12 mg), according to the manufacturer's directions. The digested DNAs were electrophoresed on 1% neutral agarose gels, Southern blotted onto nitrocellulose, and the blotted material hybridized with the appropriate nick-translated probe cDNA ($3 \times 10^6$ cpm/mL of hybridization mix). The DNA from infected chimpanzee liver and normal liver were hybridized with $^{32}$P-labeled HCV cDNA from clones 36 plus 81; the DNA from human placenta was hybridized with $^{32}$P-labeled DNA from the β-interferon gene. After hybridization, the blots were washed under stringent conditions, i.e., with a solution containing 0.1x SSC, 0.1% SDS, at 65° C. The β-interferon gene DNA was prepared as described by Houghton et al (1981).

IV.H.4.b. Amplification by the PCR Technique

In order to determine whether HCV-DNA could be detected in liver from chimpanzees with NANBH, DNA was isolated from the tissue, and subjected to the PCR amplification-detection technique using primers and probe polynucleotides derived from HCV cDNA from clone 81. Negative controls were DNA samples isolated from uninfected HepG2 tissue culture cells, and from presumably uninfected human placenta. Positive controls were samples of the negative control DNAs to which a known relatively small amount (250 molecules) of the HCV cDNA insert from clone 81 was added.

In addition, to confirm that RNA fractions isolated from the same livers of chimpanzees with NANBH contained sequences complementary to the HCV-cDNA probe, the PCR amplification-detection system was also used on the isolated RNA samples.

In the studies, the DNAs were isolated by the procedure described in Section IV.H.4.a, and RNAs were extracted essentially as described by Chirgwin et al. (1981).

Samples of DNA were isolated from 2 infected chimpanzee livers, from uninfected HepG2 cells, and from human placenta. One mg of each DNA was digested with HindIII according to the manufacturer's directions. The digested samples were subjected to PCR amplification and detection for amplified HCV cDNA essentially as described in Section IV.C.3., except that the reverse transcriptase step was omitted. The PCR primers and probe were from HCV cDNA clone 81, and are described in Section IV.C.3. Prior to the amplification, for positive controls, a 1 mg sample of each DNA was "spiked" by the addition of 250 molecules of HCV cDNA insert isolated from clone 81.

In order to determine whether HCV sequences were present in RNA isolated from the livers of chimpanzees with NANBH, samples containing 0.4 mg of total RNA were subjected to the amplification procedure essentially as described in Section IV.C.3., except that the reverse transcriptase was omitted from some of the samples as a negative control. The PCR primers and probe were from HCV cDNA clone 81, as described supra.

The results showed that amplified sequences complementary to the HCV cDNA probe were not detectable in the DNAs from infected chimpanzee liver, nor were they detectable in the negative controls. In contrast, when the samples, including the DNA from infected chimpanzee liver, was spiked with the HCV cDNA prior to amplification, the clone 81 sequences were detected in all positive control samples. In addition, in the RNA studies, amplified HCV cDNA clone 81 sequences were detected only when reverse transcriptase was used, suggesting strongly that the results were not due to a DNA contamination.

These results show that hepatocytes from chimpanzees with NANBH contain no HCV DNA, or undetectable levels thereof. Based upon the spiking study, if HCV DNA is present, it is at a level far below 0.06 copies per hepatocyte. In contrast, the HCV RNA sequences in total RNA from the same liver samples was readily detected with the PCR technique.

IV.H.5 Comparison of the Hydrophobic Profiles of HCV Polyproteins with West Nile Virus Polyprotein and with Dengue Virus NS1

The hydrophobicity profile of an HCV polyprotein segment was compared with that of a typical flavivirus, West Nile virus. The polypeptide sequence of the West Nile virus polyprotein was deduced from the known polynucleotide sequences encoding the non-structural proteins of that virus. The HCV polyprotein sequence was deduced from the sequence of overlapping cDNA clones. The profiles were determined using an antigen program which uses a window of 7 amino acid width (the amino acid in question, and 3 residues on each side) to report the average hydrophobicity about a given amino acid residue. The parameters giving the reactive hydrophobicity for each amino acid residue are from Kyte and Doolittle (1982). FIG. 55 shows the hydrophobic profiles of the two polyproteins; the areas corresponding to the non-structural proteins of West Nile virus, NS1 through NS5, are indicated in the figure. As seen in the figure, there is a general similarity in the profiles of the HCV polyprotein and the West Nile virus polyprotein.

The sequence of the amino acids encoded in the 5'-region of HCV cDNA shown in FIG. 47 has been compared with the corresponding region of one of the strains of Dengue virus, described supra, with respect to the profile of regions of hydrophobicity and hydrophilicity (data not shown). This comparison indicated that the polypeptides from HCV and Dengue encoded in this region, which corresponds to the region encoding NS1 (or a portion thereof), have a similar hydrophobic/hydrophilic profile.

The similarity in hydrophobicity profiles, in combination with the previously identified homologies in the amino acid sequences of HCV and Dengue Flavivirus in Section IV.H.3., suggests that HCV is related to these members of the Flavivirus family.

IV.H.6. Characterization of the Putative Polypeptides Encoded Within the HCV ORF The sequence of the HCV cDNA sense strand, shown in FIG. 62, was deduced from the overlapping HCV cDNAs in the various clones described in Section IV.A. It may be deduced from the sequence that the HCV genome contains primarily one long continuous ORF, which encodes a polyprotein. The amino acid sequence of the putative HCV polyprotein deduced from the HCV cDNA sense strand sequence is shown in FIG. 66, where position 1 begins with the putative initiator methionine, and the amino acids are indicated by the one-letter code. In the figure, the numbers of the amino acids are at the right of the sequence. The letters above the sequence indicate heterogeneities which have been detected by sequencing a number of clones which overlap the same region; the letters in parentheses indicates that the heterogeneity is possibly due to 5' or 3' terminal cloning artifacts.

IV.H.6.a. The Hydrophilic and Antigenic Profile of the Polypeptide

Profiles of the hydrophilicity/hydrophobicity and the antigenic index of the putative polyprotein encoded in the HCV cDNA sequence shown in FIG. 89 were determined by computer analysis. The program for hydrophilicity/hydrophobicity was as described in Section IV.H.5. The antigenic index results from a computer program which relies on the following criteria: 1)surface probability, 2) prediction of α-helicity by two different methods; 3) prediction of β-sheet regions by two different methods; 4) prediction of U-turns by two different methods; 5) hydrophilicity/hydrophobicity; and flexibility. The traces of the profiles generated by the computer analyses are shown in FIG. 67. In the hydrophilicity profile, deflection above the abscissa indicates hydrophilicity, and below the abscissa indicates hydrophobicity. The probability that a polypeptide region is antigenic is usually considered to increase when there is a deflection upward from the abscissa in the hydrophilic and/or antigenic profile. It should be noted, however, that these profiles are not necessarily indicators of the strength of the immunogenicity of a polypeptide.

IV.H.6.c. Identification of Co-linear Peptides in HCV and Flaviviruses

The amino acid sequence of the putative polyprotein encoded in the HCV cDNA sense strand was compared with the known amino acid sequences of several members of Flaviviruses. The comparison shows that homology is slight, but due to the regions in which it is found, it is probably significant. The conserved colinear regions are shown in FIG. 68. The amino acid numbers listed below the sequences represent the number in the putative HCV polyprotein (see FIG. 66.)

The spacing of these conserved motifs is similar between the Flaviviruses and HCV, and implies that there is some similarity between HCV and these flaviviral agents.

IV.H.7. Sequence Variations in HCV Isolates from Different Individuals

Isolates of HCV which contain sequences which deviate from CDC/HCV1 were identified in human individuals, some of whom were serologically positive for anti-C100-3 antibodies (EC10 was antibody negative). Identification of these new isolates was accomplished by cloning and sequencing segments of the HCV genome which had been amplified by the PCR technique using CDC/HCl sequences. Amplification was accomplished essentially based on an HCV/cPCR method described in U.S. Ser. No. 398,667 filed 25 Aug. 1989, which is commonly owned by the herein assignee, and which is hereby incorporated herein by reference. The method utilizes primers and probes based upon the HCV cDNA sequences described herein. The first step in the method is the synthesis of a cDNA to either the HCV genome, or its replicative intermediate, using reverse transcriptase. After synthesis of the HCV cDNA, and prior to amplification, the RNA in the sample is degraded by techniques known in the art. A designated segment of the HCV cDNA is then amplified by the use of the appropriate primers. The amplified sequences are cloned, and clones containing the amplified sequences are detected by a probe which is complementary to a sequence lying between the primers, but which does not overlap the primers.

IV.H.7.a. HCV Isolates Isolated from Humans in the U.S.

Blood samples which were used as a source of HCV virions were obtained from the American Red Cross in Charlotte, North Carolina, and from the Community Blood Center of Kansas, Kansas City, Mo. The samples were screened for antibodies to the HCV C100-3 antigen using an ELISA assay as described in Section IV.I.1, and subjected to supplemental Western blot analysis using a polyclonal goat anti-human HRP to measure anti-HCV antibodies. Two samples, #23 and #27, from the American Red Cross and from the Community Blood Center of Kansas, respectively, were determined to be HCV positive by these assays.

Viral particles present in the serum of these samples were isolated by ultracentrifugation under the conditions described by Bradley et al. (1985). RNA was extracted from the particles by digestion with proteinase K and SDS at final concentrations of 10 mg/mL proteinase K, and 0.1% SDS; digestion was for 1 hour at 37° C. Viral RNA was further purified by extraction with chloroform-phenol, as described in Section IV.A.1.

HCV RNA in the preparation of RNA was reverse transcribed into cDNA essentially as described in Section IV.A.1., except that the oligonucleotide JHC 7, which corresponds to the cDNA sequence 1958–1939, and which has the following sequence, was used as primer for the reverse transcriptase reaction.

JHC 7: CCA GCG GTG GCC TGG TAT TG (SEQ ID NO:750).

After both strands of the cDNA were synthesized, the resulting cDNA was then amplified by the PCR method, essentially as described in Section IV.A.34, except that the oligonucleotide primers used, i.e., JHC 6 and ALX 80, were designed to amplify a 1080 nucleotide segment of the HCV genome from CDC/HCV1 nucleotides 673 to 1751. The primers, in addition, are designed to incorporate a NOT I restriction site at the 3'-end of the PCR product, and a blunt end at the 5'-terminus. The sequences of the primers is:

ALX 80: TTT GGG TAA GGT CAT CGA TAC CCT
TAC GTG; (SEQ ID NO:751)

and

JHC 6: ATA TGC GGCCCGC CTT CCG TTG GCA
TAA (SEQ ID NO:752).

ALX 80 corresponds to nucleotides 673–702 of the CDC/HCV1 sequence; JHC 6 corresponds to nucleotides 1752–1738 of the HCV1 (in addition there are 12 extra nucleotides which encode a NotI site). The designation of nucleotides in JHC 6, i.e., a declining number, indicates the placement in the anti-sense strand.

After PCR amplification with the above described primers, the blunt end terminus was converted into a NotI site as follows. A homopolymer tail of 15 dGs was attached to the PCR product using terminal deoxynucleotide transferase, and the products were again subjected to amplification by PCR using as primers JHC 6 and JHC 13. The latter primer, JHC 13, the sequence of which follows, is designed to contain a NotI site in addition to an SP6 phage promoter. (The SP6 promoter is described in GENETIC ENGINEERING, J. Setlow Ed. (1988)

JHC 13: AAT TCG CGG CCG CCA TAC GAT TTA GGT GAC
ACT ATA GAA CCC CCC CCC CCC CCC (SEQ IDNO:753).

In order to clone the amplified HCV cDNA, the PCR products were cleaved with NotI, precipitated with spermine to remove free oligonucleotides (Hoopes et al. (1981)), and cloned into the NotI site of pUC1 8S (see Section IV.A.34.). The HCV cDNAs in three clones derived from each HCV isolate, were subjected to sequence analysis. Analysis was essentially by the method described in Chen and Seeburg (1985).

Consensus sequences of the clones derived from HCV in samples 23 and 27 are shown in FIG. 80 and FIG. 81, respectively. The variable sequences are also shown in these figures, as are the amino acids encoded in the consensus sequences.

FIGS. 82 and 83 show comparisons of the aligned positive strand nucleotide sequences (FIG. 82) and putative amino acid sequences (FIG. 83) of samples 23, 27, and HCV1. The amino acid sequence of HCV1 in FIG. 83 represents amino acid numbers 129–467 of the HCV polyprotein encoded by the large ORF in the HCV genomic RNA. An examination of FIGS. 82 and 83 show that there are variations in the sequences of the three isolated clones. The sequence variations at the nucleotide level and the amino acid level are summarized in the table immediately below. In the table, the polypeptides designated S and NS1 represent amino acid numbers 130 to ~380, and 380 to ~470, respectively. The numbering is from the putative initiator methionine. The terminology S and NS1 is based upon the positioning of the sequences encoding the polypeptides using the Flavivirus model. As discussed above, however, recent evidence suggests that there is not total correlation between HCV and the Flaviviruses with regard to viral polypeptide domains, particularly in the putative E/NS1 domains. Indeed, HCV polypeptides and their coding domains may exhibit substantial deviation from the Flavivirus model.

TABLE

Sequence Homology

| | Necleotide Encoding | | | Amino Acid Encoded | | |
|---|---|---|---|---|---|---|
| | overall % | S % | NSI % | overall % | S % | NSI % |
| HCV1/HCV23 | 93 | 95 | 91 | 92 | 95 | 87 |
| HCV1/HCV27 | 89 | 93 | 84 | 89 | 95 | 82 |
| HCV23/HCV27 | 89 | 93 | 85 | 90 | 93 | 84 |

Although there are variations in the newly isolated HCV sequences, the cloned sequences from samples 23 and 27 (called HCV23 and HCV27) each contain 1019 nucleotides, indicating a lack of deletion and addition mutants in this region in the selected clones. The sequences in FIGS. 82 and 83 also show that the isolated sequences are not rearranged in this region.

A comparison of the consensus sequences for HCV1 and for the other isolates of HCV is summarized in the Table, supra. The sequence variations between the chimpanzee isolate HCV1, and the HCVs isolated from humans are about the same as that seen between the HCVs of human origin.

It is of interest that the sequence variations in two of the putative domains is not uniform. The sequence in a putative S region appears to be relatively constant, and randomly scattered throughout the region. In contrast, a putative NS1 region has a higher degree of variability than the overall sequence, and the variation appears to be in a hypervariable pocket of about 28 amino acids which is located about 70 amino acids downstream from the putative N-terminus of the putative polyprotein.

Although it may be argued that the detected variations were introduced during the amplification process, it is unlikely that all of the variations are from this result. It has been estimated that Taq polymerase introduces errors into a sequence at approximately one base per 10 kilobases of DNA template per cycle (Saiki et al. (1988)). Based upon this estimate, up to 7 errors may have been introduced during the PCR amplification of the 1019 bp DNA fragment. However, the three subclones of HCV-23 and HCV-27 yielded 29 and 14 base variations, respectively. The following suggest that these variations are naturally occurring. About 60% of the base changes are silent mutations which do not change the amino acid sequence. Variations introduced by the Taq polymerase during PCR amplification would be expected to occur randomly; however, the results show that the variant sequences are clustered in at least one specific region.

Moreover, a consensus sequence was derived by sequencing multiple different clones derived from the PCR amplified products.

IV.H.7.b. HCV Isolates from Humans in Italy and in the U.S.

Segments of HCV RNA present in different isolates were amplified by the HCV/cPCR method. These segments span a region of ~0.6 Kb to ~1.6 Kb downstream from the methionine encoding start codon of the putative HCV polyprotein. The isolates are from biological specimens obtained from HCV infected individuals. More specifically, isolate HCT #18 is from human plasma from an individual in the USA, EC1 and EC10 are from a liver biopsy of an Italian patient, and Th is from a peripheral blood mononucleocyte fraction of an American patient. Comparable segments of HCV RNA have been isolated from a chimpanzee.

RNA was extracted from the human plasma specimens using phenol:$CHCl_3$:isoamyl alcohol extraction. Either 0.1 mL or 0.01 mL of plasma was diluted to a final volume of 1.0 mL, with a TENB/proteinase K/SDS solution (0.05 M Tris-HCL, pH 8.0, 0.001 M EDTA, 0.1 M NaCl, 1 mg/mL Proteinase K, and 0.5% SDS) containing 10 to 40 mg/mL polyadenylic acid, and incubated at 37° C. for 60 minutes. After this proteinase K digestion, the resultant plasma fractions were deproteinized by extraction with TE (50 mM Tris-HCl, pH 8.0, 1 mM EDTA) saturated phenol, pH 6.5. The phenol phase was separated by centrifugation, and was reextracted with TENB containing 0.1% SDS. The resulting aqueous phases from each extraction were pooled, and extracted twice with an equal volume of phenol/chloroform/ isoamyl alcohol [1:1(99:1)], and then twice with an equal volume of a 99:1 mixture of chloroform/isoamyl alcohol. Following phase separation by centrifugation, the aqueous phase was brought to a final concentration of 0.2 M Na acetate, and the nucleic acids were precipitated by the addition of two volumes of ethanol. The precipitated nucleic acids were recovered by ultracentrifugation in a SW 41 rotor at 38 K, for 60 minutes at 4° C. or in a microfuge for 10 minutes at 10 K, 4° C.

RNA extracted from the liver biopsy was provided by Dr. F. Bonino, Ospedale Maggiore di S. Giovanni Battista, Torino, Italy.

The mononucleocyte fraction was obtained by sedimentation of the individual's aliquot of blood through Ficoll-Paque® (Pharmacia Corp), using the manufacturer's directions. Total RNA was extracted from the fraction using the guanidinium thiocyanate procedure described in Section IV.C.1 (see also Section IV.C.1; See also Choo et al (1989)).

Synthesis of HCV cDNA from the samples was accomplished using reverse transcriptase, and primers derived from clone 156e and from clone K91. These primers, which are anti-sense relative to the genomic RNA, have the following sequences.

156e16B: 5' CGA CAA GAA AGA CAG A 3'  (SEQ ID NO:754), and

K91/16B 5' CGT TGG CAT AAC TGA T 3'  (SEQ ID NO:755).

Following ethanol precipitation, the precipitated RNA or nucleic acid fraction was dried, and resuspended in DEPC treated distilled water. Secondary structures in the nucleic acids were disrupted by heating at 65° C. for 10 minutes, and the samples were immediately cooled on ice. cDNA was synthesized using 1 to 3 mg of total RNA from liver, or from nucleic acids (or RNA) extracted from 10 to 100 mL of plasma. The synthesis utilized reverse transcriptase, and was in a 25 mL reaction, using the protocol specified by the manufacturer, BRL. All reaction mixtures for cDNA synthesis contained 23 units of the RNAase inhibitor, Rnasin® (Fisher/Promega). Following cDNA synthesis, the reaction mixtures were diluted with water, boiled for 10 minutes, and quickly chilled on ice.

Figure 84:
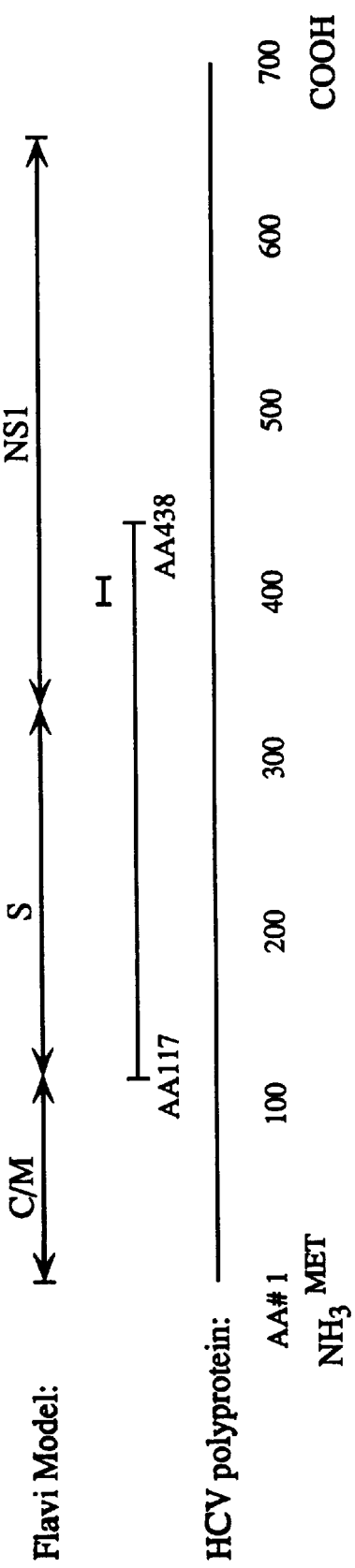
Figure 91:
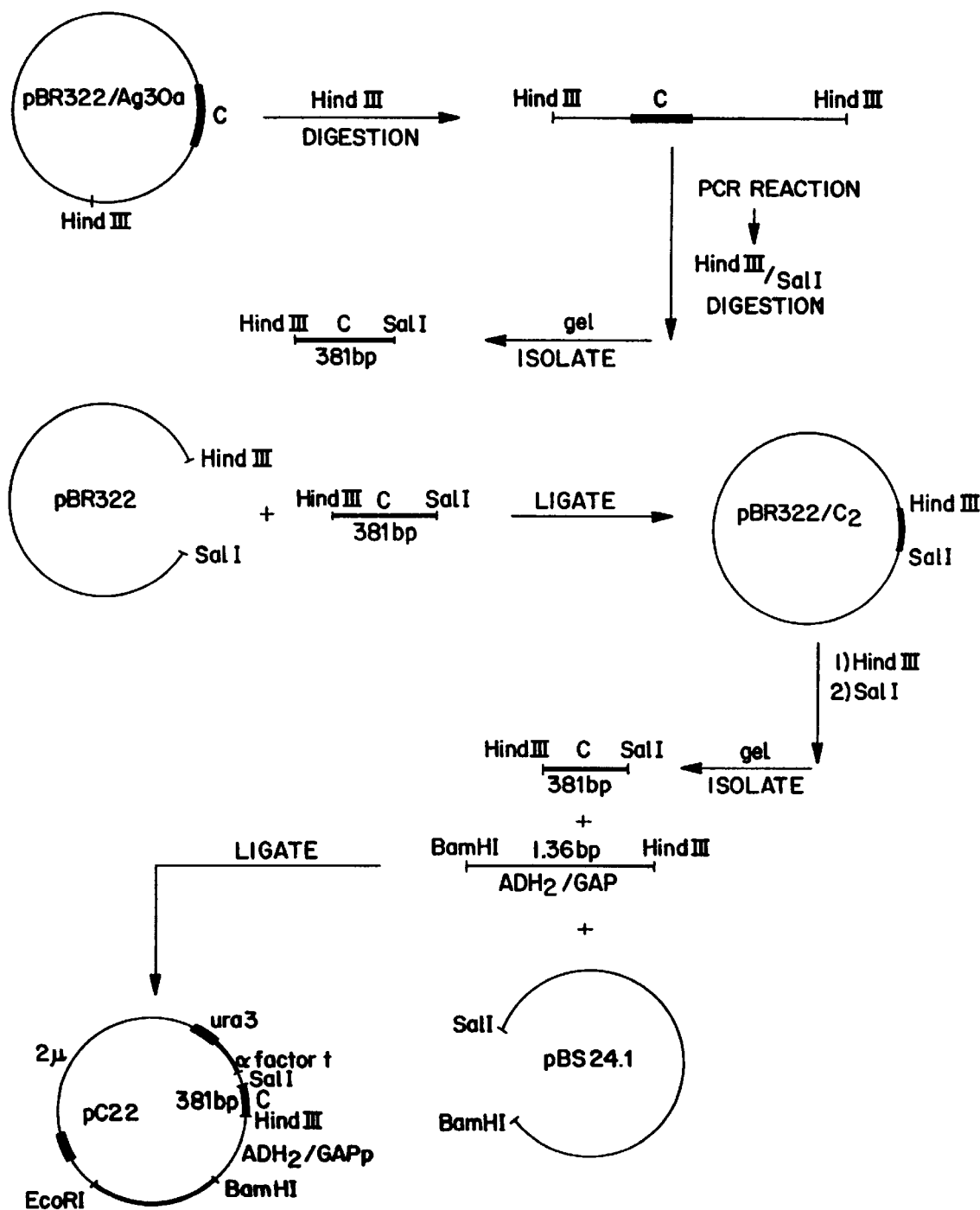

Each set of samples was subjected to two rounds of PCR amplification. The primers for the reactions were selected to amplify regions designated "EnvL" and EnvR". The "EnvL" region encompasses nucleotides 669–1243, and putative amino acids 117 to 308; the "EnvR" region encompasses nucleotides 1215–1629, and encodes putative amino acids 300–408 (the putative amino acids are numbered starting from the putative methionine initiation codon). The relationship of these regions relative to the putative polyprotein encoded in the HCV cDNA, and to the polypeptides encoded in the Flavivirus model is shown in FIG. 84.

The primers for the first round of PCR reactions were derived from the HCV cDNA sequences in either clone ag30a, clone 156e, or clone k9-1. The primers used for the amplification of the EnvL region were 156e16B (shown supra), and ag30a16A for the sense strand; the amplification of the EnvR region utilized the primer K91/16B (shown supra), and 156e16a for the sense strand. The sequences of he sense strand primers are the following.

For EnvL, ag30a16A: 5' CTC TAT GGC AAT GAG G 3', (SEQ ID NO:756)

and

For EnvR, 156e16A: 5' AGC TTC GAC GTC ACA T 3' (SEQ ID NO:757).

The PCR reactions were performed essentially according to the manufacturer's directions (Cetus-Perkin-Elmer), except for the addition of 1 mg of RNase A. The reactions were carried out in a final volume of 100 mL. The PCR was performed for 30 cycles, utilizing a regimen of 94° C. (1 min), 37° C. (2 min), and 72° C. (3 min), with a 7 minute extension at 72° C. for the last cycle. The samples were then extracted with phenol:CHCl$_3$, ethanol precipitated two times, resuspended in 10 mM Tris HCl, pH 8.0, and concentrated using Centricon-30 (Amicon) filtration. This procedure efficiently removes oligonucleotides less than 30 nucleotides in size; thus, the primers from the first round of PCR amplification are removed.

The Centricon-30 concentrated samples were then subjected to a second round of PCR amplification using probes designed from clones 202a and 156e for the EnvL region, and from 156e and 59a for the EnvR region. The primers for amplification of the EnvL region have the following sequences.

202aEnv41a: 5' CTT GAA TTC GCA ATT TGG GTA AGG TCA TCG ATA CCC TTA CG 3' (SEQ ID NO:758)

and

156e38B': 5' CTT GAA TTC GAT AGA GCA ATT GCA ACC TTG CGT CGT CC 3' (SEQ ID NO:759).

The primers for amplification of the EnvR region in RNAs derived from humans have the following sequences.

156e38A': 5' CTT GAA TTC GGA CGA CGC AAG GTT GCA ATT GCT CTA TC 3' (SEQ ID NO:760)

and

59aEnv39C: 5' CTT GAA TTC CAG CCG GTG TTG AGG CTA TCA TTG CAG TTC 3' (SEQ ID NO:761).

Amplification by PCR was for 35 cycles utilizing a regimen of 94° C. (1 min), 60° C. (1 min), and 72° C. (2 min), with a 7 minute extension at 72° C. for the last cycle. The samples were then extracted with phenol:CHCl$_3$, precipitated two times, and digested with EcoRi. The PCR reaction products were analyzed by separation of the products by electrophoresis on 6% polyacrylamide gels. DNA of approximately the estimated size of the expected PCR product was electroeluted from the gels, and subcloned into either a pGEM-4 plasmid vector or into λgt11. The expected product sizes for the EnvL and EnvR after the first round of amplification are 615 bp and 683 bp, respectively; after the second round of amplification the expected product sizes for EnvL and EnvR are 414 bp and 575 bp, respectively. The plasmids containing the amplified products were used to transform host cells; the pGEM-4 plasmid was used to transform DH5-alpha, and λgt11 was used to transform C600 delta-HFL. Clones of the transformed cells which either hybridized to the appropriate HCV probes (described below), or those which had inserts of the correct size were selected. The inserts were then cloned in M13 and sequenced.

The probes for all of the HCV/cPCR products consisted of $^{32}$P labeled sections of HCV cDNA which had been prepared by PCR amplification of a region of clone 216 (using CA216a16A and 216a16B as primers), and of clone 84 (using CA84a16A and CA84a16B or CA84a16C as primers); $^{32}$P was introduced into the PCR products by nick translation. The probes for the first and second round of EnvL amplification were from clone 216. Those for the first round of EnvR amplification were from 84 (i.e., CA84a16A and CA84a16B), for the second round of EnvL amplification were CA84a16A and CA84a16C. These probes did not overlap the primers used in the HCV/cPCR reactions. The sequence of the primers for the PCR amplification of the probes is in the following table.

TABLE

| Primer | Clone | Sequence |
| --- | --- | --- |
| CA216a16A | 216 | 5' TGA ACT ATG CAA CAG G 3' (SEQ ID NO: 762) |
| CA216a16B | 216 | 5' GGA GTG TGC AGG ATG G 3' (SEQ ID NO: 763) |
| CA84a16A | 84 | 5' AAG GTT GCA ATT GCT C 3' (SEQ ID NO: 764) |
| CA84a16B | 84 | 5' ACT AAC AGG ACC TTC G 3' (SEQ ID NO: 765) |
| CA84a16C | 84 | 5' TAA CGG GTC ACC GCA T 3' (SEQ ID NO: 766) |

Sequence information on variants in the EnvL region was obtained from 3 clones from HCT #18, 2 clones from TH, 3 clones from EC 1, and from the HCV1 clones described in Section IV.A. A comparison of the composite nucleotide sequence of each isolate derived from these clones is shown in FIG. 85. In the figure, each sequence is shown 5' to 3' for the sense strand for the EnvL region, and the sequences have been aligned. The vertical lines and capital letters indicate sequence homology, the absence of a line and an uncapitalized letter indicates a lack of homology. The sequences shown in the lines are as follows: line 1, Thorn; line 2, EC1; line 3, HCT#18; line 4, HCV1.

Sequence information on variants in the EnvR region was obtained from two clones of EC10, and from the HCV1 clones described in Section IV.A.. The two EC10 clones differed by only one nucleotide. A comparison of the nucleotide sequences of EC10 (clone 2) and a composite of the HCV1 sequences is shown in FIG. 86; each sequence is shown 5' to 3' for the sense strand of the EnvR region, and the sequences have been aligned. The double dots between the sequences indicate sequence homology.

A comparison of the amino acid sequences encoded in the EnvL (amino acids #117–308) and EnvR region (amino acids #300–438) for each of the isolates is shown in FIG. 87 and FIG. 88, respectively. Included in the Figures are sequences for the isolates JH23 and JH27, described in Section IV.H.7.a. Also indicated are sequences from a Japanese isolate; these sequences were provided by Dr. T. Miyamura, Japan. In the figures, the amino acid sequence for the region is given in its entirety for HCV1, and the non-homologous amino acids in the various isolates are indicated.

As seen in FIG. 87, In the EnvL region there is overall about a 93% homology between HCV1 and the other isolates. HCT18, Th, and EC1 have about a 97% homology with HCV1; JH23 and JH27 have about 96% and about 95% homology, respectively, with HCV1. FIG. 88 shows that the homologies in the EnvR region are significantly less than in the EnvL region; moreover, one subregion appears to be hypervariable (i.e., from amino acid 383–405). This data is summarized in the Table immediately below.

TABLE

Homology of EnvR Region

| Isolate | Percent Homology with HCV 1 | |
| --- | --- | --- |
|  | AA330–AA438 | AA383–AA405 |
| JH23(U.S.) | 83 | 57 |
| JH27(U.S.) | 80 | 39 |
| Japanese | 73 | 48 |
| EC10 (Italy) | 84 | 48 |

IV.H.8. Composite cDNA Sequence of HCV1

As described supra, in Section IV.A., overlapping clones of HCV cDNA from a λgt11 library have been isolated and sequenced. A composite cDNA sequence for HCV1, deduced from overlapping clones b114a, 18g, ag3oa, CA205a, CA290a, CA216a, pi14a, CA167b, CA156e, CA84a, CA59a, K9-1 (also called k9-1),26j, 13i, 12f, 14i, 11b, 7f, 7e, 8h, 33c, 40b, 37b, 35, 36, 81, 32, 33b, 25c, 14c, 8f, 33f, 33g, 39c, 35f, 19g, 26g, 15e, b5a, 16jh, 6k, and 131jh is shown in FIG. 89. Shown above the sequence are the position of the putative initiator methionine codon, and nucleotides which vary from the sequence, which produce changes in encoded amino acids. These variant nucleotides were detected by the sequencing of overlapping clones, isolated from the same λgt11 library, described in Section IV.A.1. Clonal heterogeneities which cause many "silent" mutations were detected also, but are not shown in the Figure.

The putative sequence of the major HCV polyprotein encoded in the composite of HCV1 cDNA is shown in FIG. 90. The first amino acid in the sequence is the putative initiator methionine. The variant amino acids, due to the clonal heterogeneities, are indicated above the sequence. Since the λgt11 library was created from serum obtained from one individual (see Section IV.A.1.), the results suggest that variant viral sequences (both nucleotide and amino acid) are present in that individual.

An examination of the composite HCV cDNA sequence in FIG. 89 shows that besides the large ORF, there are a number or ORFs upstream of that encoding the polyprotein, and within the sequence encoding the polyprotein there are a large number of smaller ORFs in the other two translational frames. The ORFs upstream of the HCV polyprotein are shown in the Table immediately below.

TABLE

ORFs Upstream of that Encoding the Large HCV Polyprotein

| Nucl. # | Translation Frame | Amino Acid Sequence |
| --- | --- | --- |
| 10 | 1 | MNHSPVRNYCLHAESV (SEQ ID NO: 767) |
| 63 | 3 | MALV (SEQ ID NO: 768) |
| 74 | 2 | MSVVQPPGPPLPGEP (SEQ ID NO: 769) |

TABLE-continued

ORFs Upstream of that Encoding the Large HCV Polyprotein

| Nucl. # | Translation Frame | Amino Acid Sequence |
| --- | --- | --- |
| 193 | 1 | MPGDLGVPPQDC (SEQ ID NO: 770) |

The reading frame, position, and size of the ORFs downstream of the sequence encoding the putative initiator MET of the polyprotein are shown in the Table below. The major polyprotein is that translated from reading frame 2.

TABLE

ORFs Downstream of the Putative Initiator MET Encoding Sequence

| Reading Frame | Size (aa) | Position (bp) |
| --- | --- | --- |
| 1 | 168 | 1015 |
| 1 | 105 | 2662 |
| 1 | 119 | 5935 |
| 2 | 3025 | 278 |
| 3 | 160 | 324 |
| 3 | 111 | 1986 |
| 3 | 148 | 7212 |

In addition to the above, an examination of the sequence which is complementary to the genomic strand of HCV RNA also contains several small ORFs. One of these ORFs encodes a polypeptide of 385 amino acids.

IV.1. ELISA Assays Using HCV Polypeptides

IV.1.1. ELISA Determinations for HCV Infection Using HCV c100-3 As Test Antigen

All samples were assayed using the HCV c100-3 ELISA. This assay utilizes the HCV c 100-3 antigen (which was synthesized and purified as described in Section IV.B.5), and a horseradish peroxidase (HRP) conjugate of mouse monoclonal anti-human IgG.

Plates coated with the HCV c100-3 antigen were prepared as follows. A solution containing Coating buffer (50 mM Na Borate, pH 9.0), 21 mL/plate, BSA (25 mg/mL) c100-3 (2.50 mg/mL) was prepared just prior to addition to the Removeawell Immulon I plates (Dynatech Corp.). After mixing for 5 minutes, 0.2 mL/well of the solution was added to the plates, they were covered and incubated for 2 hours at 37° C., after which the solution was removed by aspiration. The wells were washed once with 400 mL Wash Buffer (100 mM sodium phosphate, pH 7.4, 140 mM sodium chloride, 0.1% (W/V) casein, 1% (W/V) Triton X-100, 0.01% (W/V) Thimerosal). After removal of the wash solution, 200 mL/well of Postcoat solution (10 mM sodium phosphate, pH 7.2, 150 mM sodium chloride, 0.1% (w/v) casein, 3% sucrose and 2 mM phenylmethylsulfonylfluoride (PMSF)) was added, the plates were loosely covered to prevent evaporation, and were allowed to stand at room temperature for 30 minutes. The wells were then aspirated to remove the solution, and lyophilized dry overnight, without shelf heating. The prepared plates may be stored at 2–8° C. in sealed aluminum pouches with desiccant (3 g Sorb-it® packs).

In order to perform the ELISA determination, 20 mL of serum sample or control sample was added to a well containing 200 mL of sample diluent (100 mM sodium phosphate, pH 7.4, 500 mM sodium chloride, 1 mM EDTA, 0. 1% (w/v) Casein, 0.01% (w/v) Thimerosal, 1% (w/v) Triton® X-100, 100 mg/mL yeast extract). The plates were sealed, and incubated at 37° C. for two hours, after which the solution was removed by aspiration, and the wells were washed three times with 400 mL of wash buffer (phosphate buffered saline (PBS) containing 0.05% Tween® 20). The washed wells were treated with 200 mL of mouse anti-human IgG-HRP conjugate contained in a solution of Ortho conjugate diluent (10 mM sodium phosphate, pH 7.2, 150 mM sodium chloride, 50% (v/v) fetal bovine serum, 1% (v/v) heat treated horse serum, 1 mM $K_3Fe(CN)_6$, 0.05% (w/v) Tween(® 20, 0.02% (W/V) Thimerosal). Treatment was for 1 hour at 37° C., the solution was removed by aspiration, and the wells were washed three times with 400 mL wash buffer, which was also removed by aspiration. To determine the amount of bound enzyme conjugate, 200 mL of substrate solution (10 mg 0-phenylenediamine dihydrochloride per 5 mL of Developer solution) was added. Developer solution contains 50 mM sodium citrate adjusted to pH 5.1 with phosphoric acid, and 0.6 mg/mL of 30% $H_2O_2$. The plates containing the substrate solution were incubated in the dark for 30 minutes at room temperature, the reactions were stopped by the addition of 50 mg/mL 4N sulfuric acid, and the ODs determined.

The examples provided below show that the microtiter plate screening ELISA which utilizes HCV c100-3 antigen has a high degree of specificity, as evidenced by an initial rate of reactivity of about 1%, with a repeat reactive rate of about 0.5% on random donors. The assay is capable of detecting an immune response in both the post acute phase of the infection, and during the chronic phase of the disease. In addition, the assay is capable of detecting some samples which score negative in the surrogate tests for NANBH; these samples come from individuals with a history of NANBH, or from donors implicated in NANBH transmission.

In the examples described below, the following abbreviations are used:

| | |
|---|---|
| ALT | Alanine amino transferase |
| Anti-HBc | Antibody against HBc |
| Anti-HBsAg | Antibody against HBsAg |
| HBc | Hepatitis B core antigen |
| ABsAg | Hepatitis B surface antigen |
| IgG | Immunoglobulin G |
| IgM | Immunoglobulin M |
| IU/L | International units/Liter |
| NA | Not available |
| NT | Not tested |
| N | Sample size |
| Neg | Negative |
| OD | Optical density |
| Pos | Positive |
| S/CO | Signal/cutoff |
| SD | Standard deviation |
| x | Average or mean |
| WNL | Within normal limits |

IV.I.1.a. HCV Infection in a Population of Random Blood Donors

Figure 43:
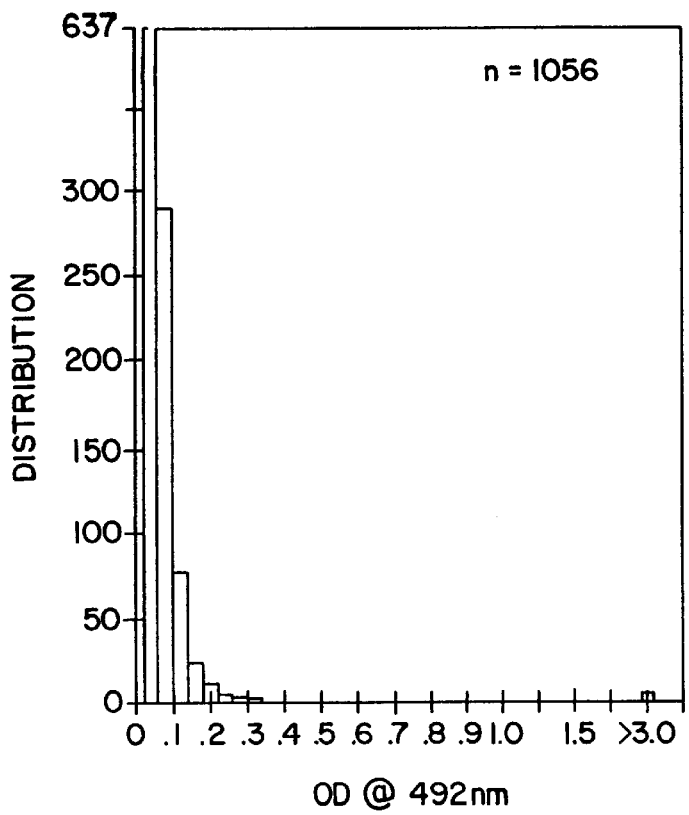
FIG. 43 shows a histogram of the distribution of HCV infection in random samples, as determined by an ELISA screening.

A group of 1,056 samples (fresh sera) from random blood donors were obtained from Irwin Memorial Blood Bank, San Francisco, Calif. The test results obtained with these samples are summarized in a histogram showing the distribution of the OD values (FIG. 43). As seen in FIG. 43, 4 samples read >3, 1 sample reads between 1 and 3, 5 samples read between 0.4 and 1, and the remaining 1,046 samples read <0.4, with over 90% of these samples reading <0.1.

The results on the reactive random samples are presented in Table 5. Using a cut-off value equal to the mean plus 5 standard deviations, ten samples out of the 1,056 (0.95%) were initially reactive. Of these, five samples (0.47%) repeated as reactive when they were assayed a second time using the ELISA. Table 5 also shows the ALT and Anti-HBc status for each of the repeatedly reactive samples. Of particular interest is the fact that all five repeat reactive samples were negative in both surrogate tests for NANBH, while scoring positive in the HCV ELISA.

TABLE 5

Results on Reactive Random Samples
N = 1051, x = 0.049*, SD = ± 0.074
Cut-off: x + 5SD = 0.419 (0.400 + Negative Control)

| Samples | Initial Reactives OD | Repeat Reactives OD | ALT** | Anti HBc*** |
|---|---|---|---|---|
| 4227 | 0.462 | 0.084 | NA | (OD) |
| 6292 | 0.569 | 0.294 | NA | NA |
| 6188 | 0.699 | 0.326 | NA | NA |
| 6157 | 0.735 | 0.187 | NA | NA |
| 6277 | 0.883 | 0.152 | NA | NA |
| 6397 | 1.567 | 1.392 | 30.14 | 1.433 |
| 6019 | >3.000 | >3.000 | 46.48 | 1.057 |
| 6651 | >3.000 | >3.000 | 48.53 | 1.343 |
| 6669 | >3.000 | >3.000 | 60.53 | 1.165 |
| 4003 | >3.000 | >3.000 | WNL**** | Neg. |
| 10/1056 = 0.95% | | | 5/1056 = 0.47% | |

*Samples reading >1.5 were not included in calculating the Mean and SD
**ALT ≧ 68 IU/L is above normal limits.
***Anti-HBc ≦0.535 (competition assay) is considered positive.
****WNL: Within normal limits IV.I.1b. Chimpanzee Serum Samples Serum samples from eleven chimpanzees were tested with the HCV c100-3 ELISA. Four of these chimpanzees were infected with NANBH from a contaminated batch of Factor VIII (presumably Hutchinson strain), following an established procedure in a collaboration with Dr. Daniel Bradley at the Centers for Disease Control. As controls, four other chimpanzees were infected with HAV and three with HBV. Serum samples were obtained at different times after infection.

The results, which are summarized in Table 6, show documented antibody seroconversion in all chimpanzees infected with the Hutchinson strain of NANBH. Following the acute phase of infection (as evidenced by the significant rise and subsequent return to normal of ALT levels), antibodies to HCV e100-3 became detectable in the sera of the 4/4 NANBH infected chimpanzees. These samples had previously been shown, as discussed in Section IV.B.3., to be positive by a Western analysis, and an RIA. In contrast, none of the control chimpanzees which had been infected with HAV or HBV showed evidence of reactivity in the ELISA.

TABLE 6

Chimpanzee Serum Samples

| | OD | S/CO | Inoculation Date | Bleed Date | ALT (IU/L) | Transfused |
|---|---|---|---|---|---|---|
| Neg. Control | 0.001 | | | | | |
| Pos. Control | 1.504 | | | | | |
| Cutoff | 0.401 | | | | | |
| Chimp 1 | -0.007 | 0.00 | 5/24/84 | 5/24/84 | 9 | NANB |
| | 0.003 | 0.01 | | 8/07/84 | 71 | |
| | >3.000 | >7.48 | | 09/18/84 | 19 | |
| | >3.000 | >7.48 | | 10/24/84 | — | |
| Chimp 2 | — | — | 6/07/84 | — | — | NANB |
| | -0.003 | 0.00 | | 5/31/84 | 5 | |
| | -0.005 | 0.00 | | 6/28/84 | 52 | |

TABLE 6-continued

Chimpanzee Serum Samples

|  | OD | S/CO | Inoculation Date | Bleed Date | ALT (IU/L) | Transfused |
|---|---|---|---|---|---|---|
|  | 0.945 | 2.36 |  | 8/20/84 | 13 |  |
|  | >3.000 | >7.48 |  | 10/24/84 | — |  |
| Chimp 3 | 0.005 | 0.01 | 3/14/85 | 3/14/85 | 8 | NANB |
|  | 0.017 | 0.04 |  | 4/26/85 | 205 |  |
|  | 0.006 | 0.01 |  | 5/06/85 | 14 |  |
|  | 1.010 | 2.52 |  | 8/20/85 | 6 |  |
| Chimp 4 | −0.006 | 0.00 | 3/11/85 | 3/11/85 | 11 | NANB |
|  | 0.003 | 0.01 |  | 5/09/85 | 132 |  |
|  | 0.523 | 1.31 |  | 6/06/85 | — |  |
|  | 1.574 | 3.93 |  | 8/01/85 | — |  |
| Chimp 5 | −0.006 | 0.00 | 11/21/80 | 11/21/80 | 4 | HAV |
|  | 0.001 | 0.00 |  | 12/16/80 | 147 |  |
|  | 0.003 | 0.01 |  | 12/30/80 | 18 |  |
|  | 0.006 | 0.01 |  | 7/29–8/21/81 | 5 |  |
| Chimp 6 | — | — | 5/25/82 | — | — | HAV |
|  | −0.005 | 0.00 |  | 5/17/82 | — |  |
|  | 0.001 | 0.00 |  | 6/10/82 | 106 |  |
|  | −0.004 | 0.00 |  | 7/06/82 | 10 |  |
|  | 0.290 | 0.72 |  | 10/01/82 | — |  |
| Chimp 7 | −0.008 | 0.00 | 5/25/82 | 5/25/82 | 7 | HAV |
|  | −0.004 | 0.00 |  | 6/17/82 | 83 |  |
|  | −0.006 | 0.00 |  | 9/16/82 | 5 |  |
|  | 0.005 | 0.01 |  | 10/09/82 | — |  |
| Chimp 8 | −0.007 | 0.00 | 11/21/80 | 11/21/80 | 15 | HAV |
|  | 0.000 | 0.00 |  | 12/16/80 | 130 |  |
|  | 0.004 | 0.01 |  | 2/03/81 | 8 |  |
|  | 0.000 | 0.00 |  | 6/03–6/10/81 | 4.5 |  |
| Chimp 9 | — | — | 7/24/80 | — | — | HBV |
|  | 0.019 | 0.050 |  | 8/22–10/10/79 | — |  |
|  | — | — |  | 3/11/81 | 57 |  |
|  | 0.015 | 0.04 |  | 7/01–8/05/81 | 9 |  |
|  | 0.008 | 0.02 |  | 10/01/81 | 6 |  |
| Chimp 10 | — | — | 5/12/82 | — | — | HBV |
|  | 0.011 | 0.03 |  | 4/21–5/12/82 | 9 |  |
|  | 0.015 | 0.04 |  | 9/01–9/08/82 | 126 |  |
|  | 0.008 | 0.02 |  | 12/02/82 | 9 |  |
|  | 0.010 | 0.02 |  | 1/06/83 | 13 |  |
| Chimp 11 | — | — | 5/12/82 | — | — | HBV |
|  | 0.000 | 0.00 |  | 1/06–5/12/82 | 11 |  |
|  | — | — |  | 6/23/82 | 100 |  |
|  | −0.003 | 0.00 |  | 6/09–7/07/82 | — |  |
|  | −0.003 | 0.00 |  | 10/28/82 | 9 |  |
|  | −0.003 | 0.00 |  | 12/20/82 | 10 |  |

IV.I.1.c. Panel 1: Proven Infectious Sera from Chronic Human NANBH Carriers

A coded panel consisted of 22 unique samples, each one in duplicate, for a total of 44 samples. The samples were from proven infectious sera from chronic NANBH carriers, infectious sera from implicated donors, and infectious sera from acute phase NANBH patients. In addition, the samples were from highly pedigreed negative controls, and other disease controls. This panel was provided by Dr. H. Alter of the Department of Health and Human Services, National Institutes of Health, Bethesda, Md. The panel was constructed by Dr. Alter several years ago, and has been used by Dr. Alter as a qualifying panel for putative NANBH assays.

The entire panel was assayed twice with the ELISA assay, and the results were sent to Dr. Alter to be scored. The results of the scoring are shown in Table 7. Although the Table reports the results of only one set of duplicates, the same values were obtained for each of the duplicate samples.

As shown in Table 7, 6 sera which were proven infectious in a chimpanzee model were strongly positive. The seventh infectious serum corresponded to a sample for an acute NANBH case, and was not reactive in this ELISA. A sample from an implicated donor with both normal ALT levels and equivocal results in the chimpanzee studies was non-reactive in the assay. Three other serial samples from one individual with acute NANBH were also non-reactive. All samples coming from the highly pedigreed negative controls, obtained from donors who had at least 10 blood donations without hepatitis implication, were non-reactive in the ELISA. Finally, four of the samples tested had previously scored as positive in putative NANBH assays developed by others, but these assays were not confirmable. These four samples scored negatively with the HCV ELISA.

TABLE 7

H. Alter's Panel 1:

| Panel | 1st Result | 2nd Result |
|---|---|---|
| 1) Proven Infectious by Chimpanzee Transmission | | |
| A. Chronic NANB; Post-Tx | | |
| JF | + | + |
| EB | + | + |
| PG | + | + |
| B. Implicated Donors with Elevated ALT | | |
| BC | + | + |
| JJ | + | + |
| BB | + | + |
| C. Acute NANB; Post-Tx | | |
| WH | − | − |
| 2) Equivocally Infectious by Chimpanzee Transmission | | |
| A. Implicated Donor with Normal ALT | | |
| CC | − | − |
| 3) Acute NANB; Post-Tx | | |
| JL Week 1 | − | − |
| JL Week 2 | − | − |
| JL Week 3 | − | − |
| 4) Disease Controls | | |
| A. Primary Biliary Cirrhosis | | |
| EK | − | − |
| B. Alcoholic Hepatitis in Recovery | | |
| HB | − | − |
| 5) Pedigreed Negative Controls | | |
| DH | − | − |
| DC | − | − |
| LV | − | − |
| ML | − | − |
| AH | − | − |
| 6) Potential NANB "Antigens" | | |
| JS-80-01T-0 (Ishida) | − | − |
| Asterix (Trepo) | − | − |
| Zurtz (Amold) | − | − |
| Becassdine (Trepo) | − | − |

IV.I.1.d. Panel 2: Donor/Recipient NANBH

The coded panel consisted of 10 unequivocal donor-recipient cases of transfusion associated NANBH, with a total of 188 samples. Each case consisted of samples of some or all the donors to the recipient, and of serial samples (drawn 3, 6, and 12 months after transfusion) from the recipient. Also included was a pre-bleed, drawn from the recipient before transfusion. The coded panel was provided by Dr. H. Alter, from the NIH, and the results were sent to him for scoring.

The results, which are summarized in Table 8, show that the ELISA detected antibody seroconversion in 9 of 10 cases of transfusion associated NANBH. Samples from case 4 (where no seroconversion was detected), consistently reacted poorly in the ELISA. Two of the 10 recipient samples were reactive at 3 months post transfusion. At six months, 8 recipient samples were reactive; and at twelve months, with the exception of case 4, all samples were reactive. In addition, at least one antibody positive donor was found in 7 out of the 10 cases, with case 10 having two positive donors. Also, in case 10, the recipient's pre-bleed was positive for HCV antibodies. The one month bleed from this recipient dropped to borderline reactive levels, while it was elevated to positive at 4 and 10 month bleeds. Generally, a S/CO of 0.4 is considered positive. Thus, this case may represent a prior infection of the individual with HCV.

The ALT and HBc status for all the reactive, i.e., positive, samples are summarized in Table 9. As seen in the table, ⅛ donor samples was negative for the surrogate markers and reactive in the HCV antibody ELISA. On the other hand, the recipient samples (followed up to 12 months after transfusion) had either elevated ALT, positive Anti-HBc, or both.

TABLE 8

H. Alter Donor/Recipient NANB Panel

| Case | Donor | | Recipient Prebleed | | 3 Months | | Post-TX 6 Months | | 12 Months | |
|---|---|---|---|---|---|---|---|---|---|---|
| | OD | S/CO | OD | S/CO | OD | S/CO | OD | S/CO | OD | S/CO |
| 1. | — | — | .032 | 0.07 | .112 | 0.26 | >3.000 | >6.96 | >3.000 | >6.96 |
| 2. | — | — | .059 | 0.14 | .050 | 0.12 | 1.681 | 3.90 | >3.000 | >6.96 |
| 3. | .403 | 0.94 | .049 | 0.11 | .057 | 0.13 | >3.000 | >6.96 | >3.000 | >6.96 |
| 4. | — | — | .065 | 0.15 | .073 | 0.17 | .067 | 0.16 | .217 | 0.50 |
| 5. | >3.000 | >6.96 | .034 | 0.08 | .096 | 0.22 | >3.000 | >6.96 | >3.000 | >6.96 |
| 6. | >3.000 | >6.96 | .056 | 0.13 | 1.475 | 3.44 | >3.000 | >6.96 | >3.000 | >6.96 |
| 7. | >3.000 | >6.96 | .034 | 0.08 | .056 | 0.13 | >3.000 | >6.96 | >3.000 | >6.96 |
| 8. | >3.000 | >6.96 | .061 | 0.14 | .078 | 0.18 | 2.262 | 5.28 | >3.000 | >6.96 |
| 9. | >3.000 | >6.96 | .080 | 0.19 | .127 | 0.30 | .055 | 0.13 | >3.000 | >6.96 |
| 10. | >3.000 | >6.96 | >3.000 | >6.96 | .317* | 0.74 | >3.000** | >6.96 | >3.000*** | >6.96 |
| | >3.000 | >6.96 | | | | | | | | |

*1 Month,  4 Months, * 10 Months

TABLE 9

ALT AND HBc STATUS FOR REACTIVE SAMPLES IN H. ALTER PANEL 1

| | Samples | Anti-ALT* | HBc** |
|---|---|---|---|
| Donors | | | |
| Case 3 | | Normal | Negative |
| Case 5 | | Elevated | Positive |
| Case 6 | | Elevated | Positive |
| Case 7 | | Not Available | Negative |
| Case 8 | | Normal | Positive |
| Case 9 | | Elevated | Not Available |
| Case 10 | | Normal | Positive |
| Case 10 | | Normal | Positive |
| Recipients | | | |
| Case 1 | 6 mo | Elevated | Positive |
| | 12 mo | Elevated | Not tested |
| Case 2 | 6 mo | Elevated | Negative |

TABLE 9-continued

ALT AND HBc STATUS FOR REACTIVE SAMPLES IN H. ALTER PANEL 1

| | Samples | Anti-ALT* | HBc** |
|---|---|---|---|
| | 12 mo | Elevated | Not tested |
| Case 3 | 6 mo | Normal | Not tested*** |
| | 12 mo | Elevated | Not tested*** |
| Case 5 | 6 mo | Elevated | Not tested |
| | 12 mo | Elevated | Not tested |
| Case 6 | 3 mo | Elevated | Negative |
| | 6 mo | Elevated | Negative |
| | 12 mo | Elevated | Not tested |
| Case 7 | 6 mo | Elevated | Negative |
| | 12 mo | Elevated | Negative |
| Case 8 | 6 mo | Normal | Positive |
| | 12 mo | Elevated | Not tested |
| Case 9 | 12 mo | Elevated | Not tested |
| Case 10 | 4 mo | Elevated | Not tested |
| | 10 mo | Elevated | Not tested |

*ALT ≧45 IU/L is above normal limits
**Anti-HBc ≦50% (competition assay) is considered positive.
***Prebleed and 3 mo samples were negative for HBc.

IV.I.1.e.. Determination of HCV Infection in High Risk Group Samples

Samples from high risk groups were monitored using the ELISA to determine reactivity to HCV c100-3 antigen. These samples were obtained from Dr. Gary Tegtmeier, Community Blood Bank, Kansas City. The results are summarized in Table 10.

As shown in the table, the samples with the highest reactivity are obtained from hemophiliacs (76%). In addition, samples from individuals with elevated ALT and positive for Anti-HBc, scored 51% reactive, a value which is consistent with the value expected from clinical data and NANBH prevalence in this group. The incidence of antibody to HCV was also higher in blood donors with elevated ALT alone, blood donors positive for antibodies to Hepatitis B core alone, and in blood donors rejected for reasons other than high ALT or anti-core antibody when compared to random volunteer donors.

TABLE 10

NANBH HIGH RISK GROUP SAMPLES

| | | Distribution | | |
|---|---|---|---|---|
| Group | N | N | OD | % Reactive |
| Elevated ALT | 35 | 3 | >3.000 | 11.4% |
| | | 1 | 0.728 | |
| Anti-HBc | 24 | 5 | >3.000 | 20.8% |
| Elevated ALT, Anti-HBc | 33 | 12 | >3.000 | 51.5% |
| | | 1 | 2.768 | |
| | | 1 | 2.324 | |
| | | 1 | 0.939 | |
| | | 1 | 0.951 | |
| | | 1 | 0.906 | |
| Rejected Donors | 25 | 5 | >3.000 | 20.0% |
| Donors with History of Hepatitis | 150 | 19 | >3.000 | 14.7% |
| | | 1 | 1.837 | |
| | | 1 | 0.714 | |
| | | 1 | 0.469 | |
| Hemophiliacs | 50 | 31 | >3.000 | 76.0% |
| | | 1 | 2.568 | |
| | | 1 | 2.483 | |
| | | 1 | 2.000 | |
| | | 1 | 1.979 | |
| | | 1 | 1.495 | |
| | | 1 | 1.209 | |
| | | 1 | 0.819 | |

IV.I.1.f.(1) Comparative Studies Using Anti-IgG or Anti-IgM Monoclonal Antibodies, or Polyclonal Antibodies as a Second Antibody in the HCV c100-3 ELISA The sensitivity of the ELISA determination which uses the anti-IgG monoclonal conjugate was compared to that obtained by using either an anti-IgM monoclonal conjugate, or by replacing both with a polyclonal antiserum reported to be both heavy and light chain specific. The following studies were performed.

IV.I.6.a. Serial Samples from Seroconverters

Serial samples from three cases of NANB seroconverters were studied in the HCV c100-3 ELISA assay using in the enzyme conjugate either the anti-IgG monoclonal alone, or in combination with an anti-IgM monoclonal, or using a polyclonal antiserum. The samples were provided by Dr. Cladd Stevens, N.Y. Blood Center, N.Y.C., N.Y.. The sample histories are shown in Table 11.

The results obtained using an anti-IgG monoclonal antibody-enzyme conjugate are shown in Table 12. The data shows that strong reactivity is initially detected in samples 1–4, 2–8, and 3–5, of cases 1, 2, and 3, respectively.

The results obtained using a combination of an anti-IgG monoclonal conjugate and an anti-IgM conjugate are shown in Table 13. Three different ratios of anti-IgG to anti-IgM were tested; the 1: 10,000 dilution of anti-IgG was constant throughout. Dilutions tested for the anti-IgM monoclonal conjugate were 1:30,000, 1:60,000, and 1:120,000. The data shows that, in agreement with the studies with anti-IgG alone, initial strong reactivity is detected in samples 1–4, 2–8, and 3–5.

The results obtained with the ELISA using anti-IgG monoclonal conjugate (1:10,000 dilution), or Tago polyclonal conjugate (1:80,000 dilution), or Jackson polyclonal conjugate (1:80,000 dilution) are shown in Table 14. The data indicates that initial strong reactivity is detected in samples 1–4, 2–8, and 3–5 using all three configurations; the Tago polyclonal antibodies yielded the lowest signals.

The results presented above show that all three configurations detect reactive samples at the same time after the acute phase of the disease (as evidenced by the ALT elevation). Moreover, the results indicate that the sensitivity of the HCV c100-3 ELISA using anti-IgG monoclonal-enzyme conjugate is equal to or better than that obtained using the other tested configurations for the enzyme conjugate.

TABLE 11

DESCRIPTION OF SAMPLES FROM CLADD STEVENS PANEL

| | Date | HBsAg | Anti-HBs | Anti-HBc | ALT | Bilirubin |
|---|---|---|---|---|---|---|
| Case 1 | | | | | | |
| 1-1 | 8/5/81 | 1.0 | 91.7 | 12.9 | 40.0 | −1.0 |
| 1-2 | 9/2/81 | 1.0 | 121.0 | 15.1 | 274.0 | 1.4 |
| 1-3 | 10/7/81 | 1.0 | 64.0 | 23.8 | 261.0 | 0.9 |
| 1-4 | 11/19/81 | 1.0 | 67.3 | 33.8 | 75.0 | 0.9 |
| 1-5 | 12/15/81 | 1.0 | 50.5 | 27.6 | 71.0 | 1.0 |
| Case 2 | | | | | | |
| 2-1 | 10/19/81 | 1.0 | 1.0 | 116.2 | 17.0 | −1.0 |
| 2-2 | 11/17/81 | 1.0 | 0.8 | 89.5 | 46.0 | 1.1 |
| 2-3 | 12/02/81 | 1.0 | 1.2 | 78.3 | 63.0 | 1.4 |
| 2-4 | 12/14/81 | 1.0 | 0.9 | 90.6 | 152.0 | 1.4 |
| 2-5 | 12/23/81 | 1.0 | 0.8 | 93.6 | 624.0 | 1.7 |
| 2-6 | 1/20/82 | 1.0 | 0.8 | 92.9 | 66.0 | 1.5 |
| 2-7 | 2/15/82 | 1.0 | 0.8 | 86.7 | 70.0 | 1.3 |
| 2-8 | 3/17/82 | 1.0 | 0.9 | 69.8 | 24.0 | −1.0 |
| 2-9 | 4/21/82 | 1.0 | 0.9 | 67.1 | 53.0 | 1.5 |
| 2-10 | 5/19/82 | 1.0 | 0.5 | 74.8 | 95.0 | 1.6 |
| 2-11 | 6/14/82 | 1.0 | 0.8 | 82.9 | 37.0 | −1.0 |
| Case 3 | | | | | | |
| 3-1 | 4/7/81 | 1.0 | 1.2 | 88.4 | 13.0 | −1.0 |
| 3-2 | 5/12/81 | 1.0 | 1.1 | 126.2 | 236.0 | 0.4 |
| 3-3 | 5/30/81 | 1.0 | 0.7 | 99.9 | 471.0 | 0.2 |
| 3-4 | 6/9/81 | 1.0 | 1.2 | 110.8 | 315.0 | 0.4 |
| 3-5 | 7/6/81 | 1.0 | 1.1 | 89.9 | 273.0 | 0.4 |
| 3-6 | 8/10/81 | 1.0 | 1.0 | 118.2 | 158.0 | 0.4 |
| 3-7 | 9/8/81 | 1.0 | 1.0 | 112.3 | 84.0 | 0.3 |
| 3-8 | 10/14/81 | 1.0 | 0.9 | 102.5 | 180.0 | 0.5 |
| 3-9 | 11/1/81 | 1.0 | 1.0 | 84.6 | 154.0 | 0.3 |

TABLE 12

ELISA RESULTS OBTAINED USING AN ANTI-IgG MONOCLONAL CONJUGATE

| SAMPLE | DATE | ALT | OD | S/CO |
|---|---|---|---|---|
| Neg Control | | | .076 | |
| Cutoff | | | .476 | |
| PC (1:128) | | | 1.390 | |
| Case #1 | | | | |
| 1-1 | 08/05/81 | 40.0 | .178 | .37 |
| 1-2 | 09/02/81 | 274.0 | .154 | .32 |
| 1-3 | 10/07/81 | 261.0 | .129 | .27 |
| 1-4 | 11/19/81 | 75.0 | .937 | 1.97 |
| 1-5 | 12/15/81 | 71.0 | >3.000 | >6.30 |
| Case #2 | | | | |
| 2-1 | 10/19/81 | 17.0 | .058 | 0.12 |
| 2-2 | 11/17/81 | 46.0 | .050 | 0.11 |
| 2-3 | 12/02/81 | 63.0 | .047 | 0.10 |
| 2-4 | 12/14/81 | 152.0 | .059 | 0.12 |
| 2-5 | 12/23/81 | 624.0 | .070 | 0.15 |
| 2-6 | 01/20/82 | 66.0 | .051 | 0.11 |
| 2-7 | 02/15/82 | 70.0 | .139 | 0.29 |
| 2-8 | 03/17/82 | 24.0 | 1.867 | 3.92 |
| 2-9 | 04/21/82 | 53.0 | >3.000 | >6.30 |
| 2-10 | 05/19/82 | 95.0 | >3.000 | >6.30 |
| 2-11 | 06/14/82 | 37.0 | >3.000 | >6.30 |
| Case #3 | | | | |
| 3-1 | 04/07/81 | 13.0 | .090 | .19 |
| 3-2 | 05/12/81 | 236.0 | .064 | .13 |

TABLE 12-continued

ELISA RESULTS OBTAINED USING AN ANTI-IgG MONOCLONAL CONJUGATE

| SAMPLE | DATE | ALT | OD | S/CO |
|---|---|---|---|---|
| 3-3 | 05/30/81 | 471.0 | .079 | .17 |
| 3-4 | 06/09/81 | 315.0 | .211 | .44 |
| 3-5 | 07/06/81 | 273.0 | 1.707 | 3.59 |
| 3-6 | 08/10/81 | 158.0 | >3.000 | >6.30 |
| 3-7 | 09/08/81 | 84.0 | >3.000 | >6.30 |
| 3-8 | 10/14/81 | 180.0 | >3.000 | >6.30 |
| 3-9 | 11/11/81 | 154.0 | >3.000 | >6.30 |

TABLE 13

ELISA RESULTS OBTAINED USING ANTI-IgG and ANTI-IgM MONOCLONAL CONJUGATE NANB ELISAs

| | | | Monoclonals IgG 1:10K IgM 1:30K | | Monoclonals IgG 1:10K IgM 1:60K | | Monoclonals IgG 1:10K IgM 1:120K | |
|---|---|---|---|---|---|---|---|---|
| SAMPLE | DATE | ALT | OD | S/CO | OD | S/CO | OD | S/CO |
| Neg Control Cutoff | | | .100 | | .080 | | .079 | |
| PC (1:128) | | | 1.083 | | 1.328 | | 1.197 | |
| Case #1 | | | | | | | | |
| 1-1 | 08/05/81 | 40 | .173 | | .162 | | .070 | |
| 1-2 | 09/02/81 | 274 | .194 | | .141 | | .079 | |
| 1-3 | 10/07/81 | 261 | .162 | | .129 | | .063 | |
| 1-4 | 11/19/81 | 75 | .812 | | .85 | | .709 | |
| 1-5 | 12/15/81 | 71 | >3.00 | | >3.00 | | >3.00 | |
| Case #2 | | | | | | | | |
| 2-1 | 10/19/81 | 17 | .442 | | .045 | | .085 | |
| 2-2 | 11/17/82 | 46 | .102 | | .029 | | .030 | |
| 2-3 | 12/02/81 | 63 | .059 | | .036 | | .027 | |
| 2-4 | 12/14/81 | 152 | .065 | | .041 | | .025 | |
| 2-5 | 12/23/81 | 624 | .082 | | .033 | | .032 | |
| 2-6 | 01/20/82 | 66 | .102 | | .042 | | .027 | |
| 2-7 | 02/15/82 | 70 | .188 | | .068 | | .096 | |
| 2-8 | 03/17/82 | 24 | 1.728 | | 1.668 | | 1.541 | |
| 2-9 | 04/21/82 | 53 | >3.00 | | 2.443 | | >3.00 | |
| 2-10 | 05/19/82 | 95 | >3.00 | | >3.00 | | >3.00 | |
| 2-11 | 06/14/82 | 37 | >3.00 | | >3.00 | | >3.00 | |
| Case #3 | | | | | | | | |
| 3-1 | 04/07/81 | 13 | .193 | | .076 | | .049 | |
| 3-2 | 05/12/81 | 236 | .201 | | .051 | | .038 | |
| 3-3 | 05/30/81 | 471 | .132 | | .067 | | .052 | |
| 3-4 | 06/09/81 | 315 | .175 | | .155 | | .140 | |
| 3-5 | 07/06/81 | 273 | 1.335 | | 1.238 | | 1.260 | |
| 3-6 | 08/10/81 | 158 | >3.00 | | >3.00 | | >3.00 | |
| 3-7 | 09/08/81 | 84 | >3.00 | | >3.00 | | >3.00 | |
| 3-8 | 10/14/81 | 180 | >3.00 | | >3.00 | | >3.00 | |
| 3-9 | 11/11/81 | 154 | >3.00 | | >3.00 | | >3.00 | |

TABLE 14

ELISA RESULTS OBTAINED USING POLYCLONAL CONJUGATES NANB ELISAs

| | | | Monoclonal 1:10K | | Tago 1:80K | | Jackson 1:80K | |
|---|---|---|---|---|---|---|---|---|
| SAMPLE | DATE | ALT | OD | S/CO | OD | S/CO | OD | S/CO |
| Neg Control | | | .076 | | .045 | | .154 | |
| Cutoff | | | .476 | | .545 | | .654 | |

TABLE 14-continued

ELISA RESULTS OBTAINED USING POLYCLONAL CONJUGATES NANB ELISAs

| | | | Monoclonal 1:10K | | Tago 1:80K | | Jackson 1:80K | |
|---|---|---|---|---|---|---|---|---|
| SAMPLE | DATE | ALT | OD | S/CO | OD | S/CO | OD | S/CO |
| PC (1:128) | | | 1.390 | | .727 | | 2.154 | |
| Case #1 | | | | | | | | |
| 1-1 | 08/05/81 | 40 | .178 | .37 | .067 | .12 | .153 | .23 |
| 1-2 | 09/02/81 | 274 | .154 | .32 | .097 | .18 | .225 | .34 |
| 1-3 | 10/07/81 | 261 | .129 | .27 | .026 | .05 | .167 | .26 |
| 1-4 | 11/19/81 | 75 | .937 | 1.97 | .324 | .60 | .793 | 1.21 |
| 1-5 | 12/15/81 | 71 | >3.00 | >6.30 | 1.778 | 3.27 | >3.00 | >4.29 |
| Case #2 | | | | | | | | |
| 2-1 | 10/19/81 | 17 | .058 | .12 | .023 | .04 | .052 | .08 |
| 2-2 | 11/17/81 | 46 | .050 | .11 | .018 | .03 | .058 | .09 |
| 2-3 | 12/02/81 | 63 | .047 | .10 | .020 | .04 | .060 | .09 |
| 2-4 | 12/14/81 | 152 | .059 | .12 | .025 | .05 | .054 | .08 |
| 2-5 | 12/23/81 | 624 | .070 | .15 | .026 | .05 | .074 | .11 |
| 2-6 | 01/20/82 | 66 | .051 | .11 | .018 | .03 | .058 | .09 |
| 2-7 | 02/15/82 | 70 | .139 | .29 | .37 | .07 | .146 | .22 |
| 2-8 | 03/17/82 | 24 | 1.867 | 3.92 | .355 | .65 | 1.429 | 2.19 |
| 2-9 | 04/21/82 | 53 | >3.00 | >6.30 | .748 | 1.37 | >3.00 | >4.59 |
| 2-10 | 05/19/82 | 95 | >3.00 | >6.30 | 1.025 | 1.88 | >3.00 | >4.59 |
| 2-11 | 06/14/82 | 37 | >3.00 | >6.30 | .971 | 1.68 | >3.00 | >4.59 |
| Case #3 | | | | | | | | |
| 3-1 | 04/07/81 | 13 | .090 | .19 | .049 | .09 | .138 | .21 |
| 3-2 | 05/12/81 | 236 | .064 | .13 | .040 | .07 | .094 | .14 |
| 3-3 | 05/30/81 | 471 | .079 | .17 | .045 | .08 | .144 | .22 |
| 3-4 | 06/09/81 | 315 | .211 | .44 | .085 | .16 | .275 | .42 |
| 3-5 | 07/06/81 | 273 | 1.707 | 3.59 | .272 | .50 | 1.773 | 2.71 |
| 3-6 | 08/10/81 | 158 | >3.00 | >6.30 | 1.347 | 2.47 | >3.00 | >4.59 |
| 3-7 | 09/08/81 | 84 | >3.00 | >6.30 | 2.294 | 4.21 | >3.00 | >4.59 |
| 3-8 | 10/14/81 | 180 | >3.00 | >6.30 | >3.00 | >5.50 | >3.00 | >4.59 |
| 3-9 | 11/11/81 | 154 | >3.00 | >6.30 | >3.00 | >5.50 | >3.00 | >4.59 |

IV.I.1.f.(2). Samples from Random Blood Donors

Figure 44:
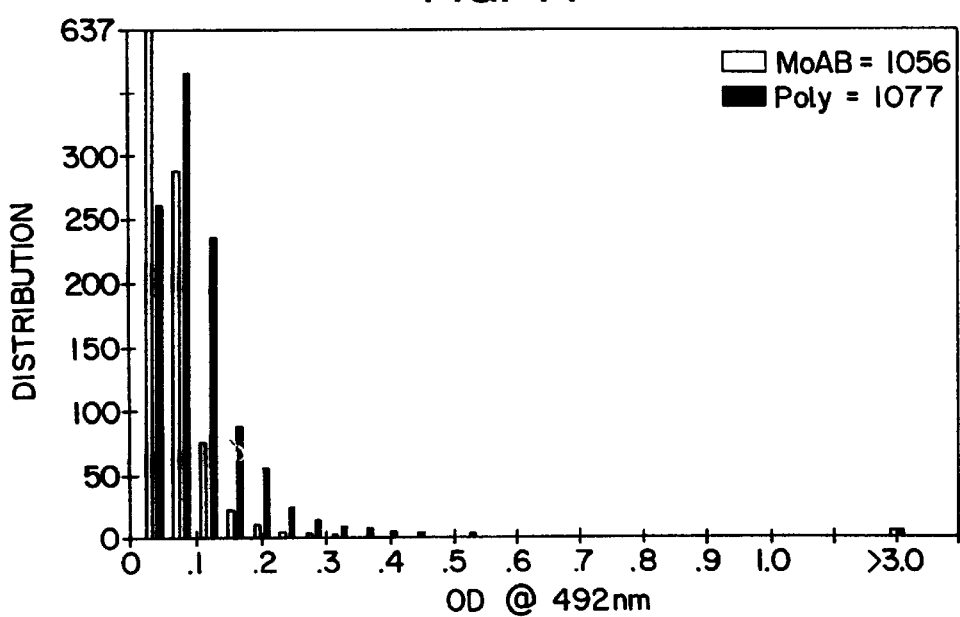
FIG. 44 shows a histogram of the distribution of HCV infection in random samples using two configurations of immunoglobulin-enzyme conjugate in an ELISA assay.
Figure 55A:
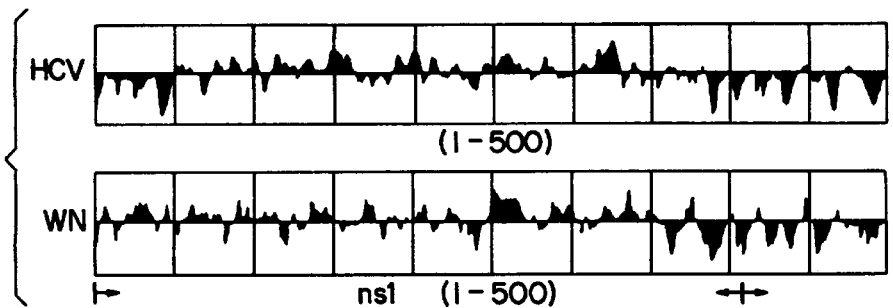
FIG. 55 shows the hydrophobicity profiles of polyproteins encoded in HCV and in West Nile virus.
Figure 55B:
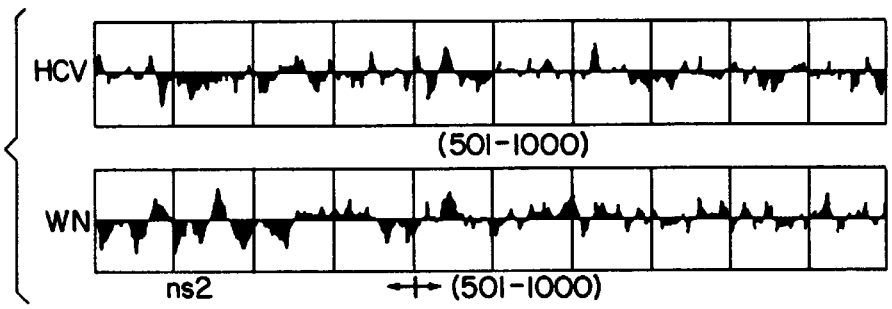
Figure 55C:
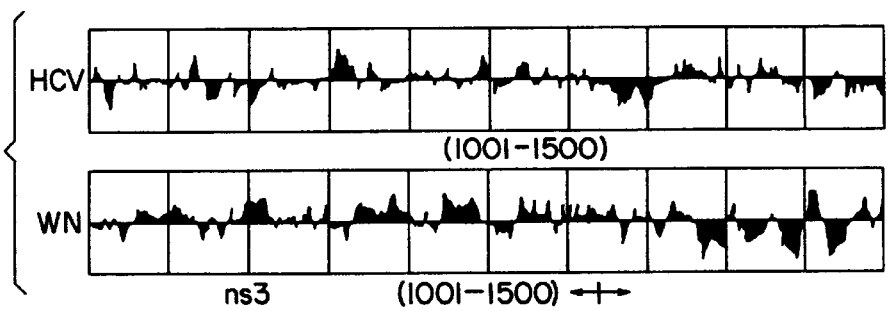
Figure 55D:
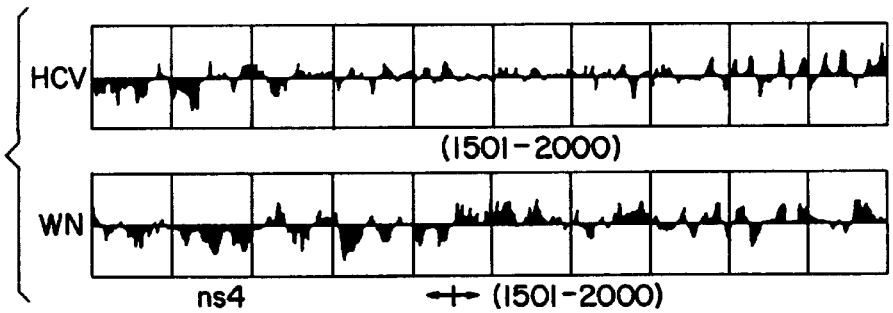
Figure 55E:
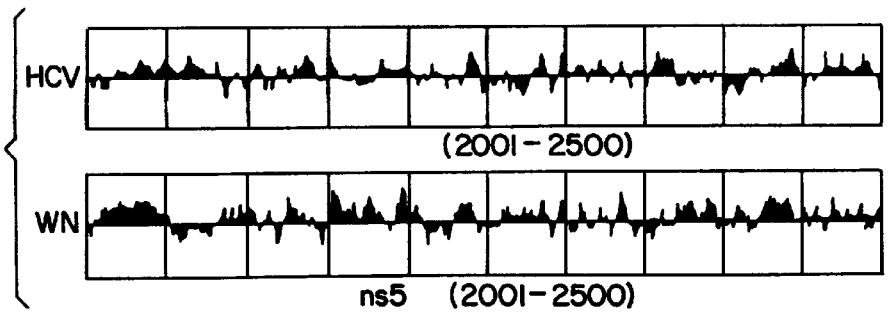

Samples from random blood donors (see Section IV.I.1.) were screened for HCV infection using the HCV c100-3 ELISA, in which the antibody-enzyme conjugate was either an anti-IgG monoclonal conjugate, or a polyclonal conjugate. The total number of samples screened were 1077 and 1056, for the polyclonal conjugate and the monoclonal conjugate, respectively. A summary of the results of the screening is shown in Table 15, and the sample distributions are shown in the histogram in FIG. 44.

The calculation of the average and standard deviation was performed excluding samples that gave a signal over 1.5, i.e., 1073 OD values were used for the calculations utilizing the polyclonal conjugate, and 1051 for the anti-IgG monoclonal conjugate. As seen in Table 15, when the polyclonal conjugate was used, the average was shifted from 0.0493 to 0.0931, and the standard deviation was increased from 0.074 to 0.0933. Moreover, the results also show that if the criteria of x +5SD is employed to define the assay cutoff, the polyclonal-enzyme conjugate configuration in the ELISA requires a higher cutoff value. This indicates a reduced assay specificity as compared to the monoclonal system. In addition, as depicted in the histogram in FIG. 44, a greater separation of results between negative and positive distributions occurs when random blood donors are screened in an ELISA using the anti-IgG monoclonal conjugate as compared to the assay using a commercial polyclonal label.

TABLE 15

COMPARISON OF TWO ELISA CONFIGURATIONS IN
TESTING SAMPLES FROM RANDOM BLOOD DONORS

| CONJUGATE | POLYCLONAL (Jackson) | ANTI-IgG MONOCLONAL |
|---|---|---|
| Number of samples | 1073 | 1051 |
| Average (x) | 0.0931 | 0.04926 |
| Standard deviation (SD) | 0.0933 | 0.07427 |
| 5 SD | 0.4666 | 0.3714 |
| CUT-OFF (5 SD + x) | 0.5596 | 0.4206 |

IV.I.2. ELISA Assay Using Recombinant SOD-NANB$_{5-1-1}$

This assay utilizes the SOD-NANB$_{5-1-1}$ antigen, and is similar to the assay utilizing the c100-3 antigen (see Section IV.1.1.) except for the following.

The HCV polypeptide used in the assay is SOD-NANB$_{5-1-1}$ which is purified as described in Section IV.N.1.b., infra.

In the preparation of the plates, Immulon 2 plates replace Immulon 1 plates. In addition, BSA is omitted from the coating solution, and the coating solution contains 3.75 mg/mL of SOD-NANB$_{5-1-1}$ instead of c100-3.

The assay is also changed in that the sample diluent contains 1 mg/mL yeast extract, and also contains 500 mg/mL of the second E. coli extract (which comprised proteins in the soluble fraction of the lysozyme treated bacteria), and 100 mg/mL SOD. The extracts are prepared as described in Section IV.N.1.a., infra.

IV.1.3. ELISA Assay Using Recombinant C33c

This assay utilizes the SOD-C33c antigen, and is similar to the assay utilizing the SOD-NANB$_{5-1-1}$ antigen (see Section IV.I.2.) except for the following.

The HCV polypeptide used in the assay is SOD-C33c, which is prepared as described in Section IV.B.9., supra. The plates coated are Immulon 1 plates instead of Immulon 2 plates, and the coating solution 1.25 mg/mL of SOD-C33c instead of c100-3. The assay is also changed in that the sample diluent contains 1 mg/mL yeast extract instead of 100 mg/mL of the second E. coli extract and 100 mg/mL of SOD.

IV.I.4. ELISA Assay Using a Synthetic Polypeptide Containing NANB Sequences

This assay utilizes a synthetic peptide containing 42 amino acids encoded in HCV which are in the NANB$_{5-1-1}$ polypeptide, and which are also in the c100-3 polypeptide. The polypeptide, which was prepared by Peninsula Laboratory using chemical synthesis, has the following sequence.

NH$_2$-Ile-Ile-Pro-Asp-Arg-Glu-Val-Leu-Tyr-Arg-Glu-Phe-Asp-Glu-Met-Glu-Glu-Cys-Ser-Gln-His-Leu-Pro-Tyr-Ile-Glu-Gln-Met-Met-Leu-Ala-Glu-Gln-Phe-Lys-Gln-Lys-Ala-Leu-Gly-Leu-COOH. (SEQ ID NO:771)

The assay is essentially as described in Section IV.I.1., except that the synthetic 5-1-1 polypeptide replaces the c100-3 polypeptide in the coating solution at a concentration of 2.5 mg/mL. Also, Immulon 2 plates replace Immulon 1 plates, and the BSA is omitted from the coating solution.

IV.J. Detection of HCV Seroconversion in NANBH Patients from a Variety of Geographical Locations Sera from patients who were suspected to have NANBH based upon elevated ALT levels, and who were negative in HAV and HBV tests were screened using the RIA essentially as described in Section IV.D., except that the HCV C100-3 antigen was used as the screening antigen in the microtiter plates. As seen from the results presented in Table 16, the RIA detected positive samples in a high percentage of the cases.

TABLE 16

Seroconversion Frequencies for Anti-c100-3
Among NANBH Patients in Different Countries

| Country | The Netherlands | Italy | Japan |
|---|---|---|---|
| No. Examined | 5 | 36 | 26 |
| No. Positive | 3 | 29 | 19 |
| % Positive | 60 | 80 | 73 |

IV.K. Detection of HCV Seroconversion in Patients with "Community Acquired" NANBH Sera which was obtained from 100 patients with NANBH, for whom there was no obvious transmission route (i.e., no transfusions, i.v. drug use, promiscuity, etc. were identified as risk factors), was provided by Dr. M. Alter of the Center for Disease Control, and Dr. J. Dienstag of Harvard University. These samples were screened using an RIA essentially as described in Section IV.D., except that the HCV c100-3 antigen was used as the screening antigen attached to the microtiter plates. The results showed that of the 100 serum samples, 55 contained antibodies that reacted immunologically with the HCV c100-3 antigen.

The results described above suggest that "Community Acquired" NANBH is also caused by HCV. Moreover, since it has been demonstrated herein that HCV is related to Flaviviruses, most of which are transmitted by arthropods, it is suggestive that HCV transmission in the "Community Acquired" cases also results from arthropod transmission.

IV.L. Comparison of Incidence of HCV Antibodies and Surrogate Markers in Donors Implicated in NANBH Transmission A prospective study was carried out to determine whether recipients of blood from suspected NANBH positive donors, who developed NANBH, seroconverted to anti-HCV-antibody positive. The blood donors were tested for the surrogate marker abnormalities which are currently used as markers for NANBH infection, i.e., elevated ALT levels, and the presence of anti-core antibody. In addition, the donors were also tested for the presence of anti-HCV antibodies. The determination of the presence of anti-HCV antibodies was determined using a radioimmunoassay as described in Section IV.K. The results of the study are presented in Table 17, which shows: the patient number (column 1); the presence of anti-HCV antibodies in patient serum (column 2); the number of donations received by the patient, with each donation being from a different donor (column 3); the presence of anti-HCV antibodies in donor serum (column 4); and the surrogate abnormality of the donor (column 5) (NT or—means not tested) (ALT is elevated transaminase, and ANTI-HBc is anti-core antibody).

The results in Table 17 demonstrate that the HCV antibody test is more accurate in detecting infected blood donors than are the surrogate marker tests. Nine out of ten patients who developed NANBH symptoms tested positive for anti-HCV antibody seroconversion. Of the 11 suspected donors, (patient 6 received donations from two different individuals suspected of being NANBH carriers), 9 were positive for anti-HCV antibodies, and 1 was borderline positive, and therefore equivocal (donor for patient 1). In contrast, using the elevated ALT test 6 of the ten donors tested negative, and using the anticore-antibody test 5 of the ten donors tested negative. Of greater consequence, though, in three cases (donors to patients 8, 9, and 10) the ALT test and the ANTI-HBc test yielded inconsistent results.

TABLE 17

Development of Anti-HCV Antibodies in Patients Receiving Blood
From Donors Suspected of Being NANBH Carriers

| Patient | Anti-HCV Seroconversion in Patients | No. of Donations/ Donors | Anti-HCV Positive Donor | Surrogate Abnormality* | |
|---|---|---|---|---|---|
| | | | | Alt | Anti-HBc |
| 1 | yes | 18 | equiv | no | no |
| 2 | yes | 18 | yes | NT | yes |
| 3 | yes | 13 | yes | no | no |
| 4 | no | 18 | no | — | — |
| 5 | yes | 16 | yes | yes | yes |
| 6 | yes | 11 | yes(2) | no | no |
| | | | | yes | yes |
| 7 | yes | 15 | yes | NT | no |
| 8 | yes | 20 | yes | no | yes |
| 9 | yes | 5 | yes | yes | no |
| 10 | yes | 15 | yes | no | yes |

*Same donor as anti-NANBV Positive

IV.M. Amplification for Cloning of HCV cDNA Sequences Utilizing the PCR and Primers Derived from Conserved Regions of Flavivirus Genomic Sequences The results presented supra, which suggest that HCV is a flavivirus or flavi-like virus, allows a strategy for cloning uncharacterized HCV cDNA sequences utilizing the PCR technique, and primers derived from the regions encoding conserved amino acid sequences in flaviviruses. Generally, one of the primers is derived from a defined HCV genomic sequence, and the other primer which flanks a region of unsequenced HCV polynucleotide is derived from a conserved region of the flavivirus genome. The flavivirus genomes are known to contain conserved sequences within the NS1, and E polypeptides, which are encoded in the 5'-region of the flavivirus genome. Corresponding sequences encoding these regions lie upstream of the HCV cDNA sequence shown in FIG. 26. Thus, to isolate cDNA sequences derived from this region of the HCV genome, upstream primers are designed which are derived from the conserved sequences within these flavivirus polypeptides. The downstream primers are derived from an upstream end of the known portion of the HCV cDNA.

Because of the degeneracy of the code, it is probable that there will be mismatches between the flavivirus probes and the corresponding HCV genomic sequence. Therefore a strategy which is similar to the one described by Lee (1988) is used. The Lee procedure utilizes mixed oligonucleotide primers complementary to the reverse translation products of an amino acid sequence; the sequences in the mixed primers takes into account every codon degeneracy for the conserved amino acid sequence.

Three sets of primer mixes are generated, based on the amino acid homologies found in several flaviviruses, including Dengue-2,4 (D-2,4), Japanese Encephalitis Virus (JEV), Yellow Fever (YF), and West Nile Virus (WN). The primer mixture derived from the most upstream conserved sequence (5'-1), is based upon the amino acid sequence Gly-Trp-Gly, which is part of the conserved sequence Asp-Arg-Gly-Trp-Gly-AspN (SEQ ID NO:772) found in the E protein of D-2, JEV, YF, and WN. The next primer mixture (5'-2) is based upon a downstream conserved sequence in E protein, Phe-Asp-Gly-Asp-Ser-Tyr-Ile-Phe-Gly-Asp-Ser-Tyr-Ile, (SEQ ID NO:773) and is derived from Phe-Gly-Asp; the conserved sequence is present in D-2, JEV, YF, and WN. The third primer mixture (5'-3), is based on the amino acid sequence Arg-Ser-Cys, which is part of the conserved sequence Cys-Cys-Arg-Ser-Cys (SEQ ID NO:774) in the NS1 protein of D-2, D-4, JEV, YF, and WN. The individual primers which form the mixture in 5'-3 are shown in FIG. 45. In addition to the varied sequences derived from conserved region, each primer in each mixture also contains a constant region at the 5'-end which contains a sequence encoding sites for restriction enzymes, HindIII, MboI, and EcoRI.

The downstream primer, ssc5h2OA, is derived from a nucleotide sequence in clone 5h, which contains HCV cDNA with sequences with overlap those in clones 14i and 1 lb. The sequence of ssc5h2OA is

5'GTA ATA TGG TGA CAG AGT CA 3'    (SEQ ID NO:775).

An alternative primer, ssc5h34A, may also be used. This primer is derived from a sequence in clone 5h, and in addition contains nucleotides at the 5'-end which create a restriction enzyme site, thus facilitating cloning. The sequence of ssc5h34A is

5' GAT CTC TAG AGA AAT CAA TAT GGT
       GAC AGAGTCA3'    (SEQ ID NO:776).

The PCR reaction, which was initially described by Saiki et al. (1986), is carried out essentially as described in Lee et al. (1988), except that the template for the cDNA is RNA isolated from HCV infected chimpanzee liver, as described in Section IV.C.2., or from viral particles isolated from HCV infected chimpanzee serum, as described in Section IV.A.1. In addition, the annealing conditions are less stringent in the first round of amplification (0.6M NaCl, and 25° C), since the part of the primer which will anneal to the HCV sequence is only 9 nucleotides, and there could be mismatches. Moreover, if ssc5h34A is used, the additional sequences not derived from the HCV genome tend to destabilize the primer-template hybrid. After the first round of amplification, the annealing conditions can be more stringent (0.066M NaCl, and 32° C.–37° C.), since the amplified sequences now contain regions which are complementary to, or duplicates of the primers. In addition, the first 10 cycles of amplification are run with Klenow enzyme I, under appropriate PCR conditions for that enzyme. After the completion of these cycles, the samples are extracted, and run with Taq polymerase, according to kit directions, as furnished by Cetus/Perkin-Elmer.

After the amplification, the amplified HCV cDNA sequences are detected by hybridization using a probe derived from clone 5h. This probe is derived from sequences upstream of those used to derive the primer, and does not overlap the sequences of the clone 5h derived primers. The sequence of the probe is 5' CCC AGC GGC GTA CGC GCT GGA CAC GGA GGT GGC
       CGC GTC GTG TGG COG TGT TGT TCT COT CGG GTT
       GAT GGC GC 3'    (SEQ ID NO:777).

IV.N.1. Immunoblot Assay for HCV Antibodies Using HCV Antigens

The immunoblot assay for HCV employs an immunoblot ELISA technique for the qualitative detection of antibodies to HCV in biological specimens. The assay uses three purified recombinant antigens: the fusion polypeptide, SOD-NANB$_{5-1-1}$ (also called 5-1-1); the fusion polypeptide SOD-C33c; the fusion polypeptide HCV C100-3; and human superoxide dismutase (hSOD). The latter antigen is included as a control to detect the presence of antibodies against SOD. The purification procedure for SOD-NANB$_{5-1-1}$ is described below in Section IV.N.1.b.; that for the fusion C100-3 polypeptide is described in Section IV.B.7.b; and that for the C33c polypeptide is described in Section IV.B.9.

IV.N.1.a. The Immunoblot Assay System for HCV

In the immunoblot assay system for HCV, the above described individual recombinant derived HCV antigens are immobilized in discreet bands on nitrocellulose strips (0.45 mm) by vacuum blotting solutions of individual antigens. During the incubation of the strips with the biological specimens, antibodies to HCV, if present, react with the corresponding antigens coated in bands on the nitrocellulose strips. After the removal of nonspecific antibodies by aspiration and washing, the strip is then reacted with goat anti-human IgG (heavy and light chain specific) labeled with horseradish peroxidase (HRP). Following incubation, decantation, and washing to remove excess conjugate, 4-chloro-1-naphthol solution containing hydrogen peroxide is added. The corresponding intensities of the blue-black colored bands which develop are proportional to the amount of specific antibody bound to each of the recombinant proteins on the strips. After the precipitation reaction is stopped by decantation and washing, the reactivity of specimens towards each antigen is determined by visually comparing the intensity of the individual antigen band with that of the low and high IgG internal controls included on each strip.

The reagents utilized in the test are the following. The conjugate is goat anti-human IgG (heavy and light chain specific) labeled with HRP in sodium phosphate buffer containing sodium chloride and protein stabilizers. The stock substrate is 4-chloro-1-naphthol (3 g/L) in methanol. The developer buffer is sodium monobasic phosphate (1.3 g) containing sodium chloride (1.17 g/L) and hydrogen peroxide (1 mL/L). The developer buffer contains sodium monobasic phosphate (13.8 g/L), NaCl (29.2 g/L), casein (1 g/L), EDTA disodium salt (0.34 g/L), Triton X-100 (10 g/L), 10% thimerosal (1 mL/L), yeast extract (1 g/L), BSA (10 g/L), the first *E. coli* extract (20 mg/L) and the second *E. coli* extract (0.5 g/L). The HCV antibody positive control is inactivated human serum containing antibodies to HCV; the serum is inactivated by heat and psoralen treatment. The HCV antibody negative control is human serum which does not demonstrate antibodies to HCV. A working sample diluent for the assay is prepared by weighing out 0.5 gm nonfat dry milk powder into each 10 mL sample diluent, and mixing well before use. The working substrate for the assay is prepared by combining 1 part of the stock substrate with 5 parts of developer buffer.

The yeast extract used in the sample diluent is prepared as follows. Red Star baker's yeast (Universal Foods) is slurried with an approximately equal amount (weight to volume) of 64 mM Tris HCl, and the pH is adjusted to 7.0. The yeast is mechanically disrupted using a glass bead mill (Dynomill) using 0.5 mm nominal diameter beads, until 95% of the cells are broken. Concentrated sodium dodecylsulfate (SDS) is added to the lysate to yield a final concentration of SDS of ~2.14 %. The lysate is then agitated and heated to 70° C.±5° C. for 10 minutes. The heated lysate is diluted with 3 volumes of buffer containing 67M Tris HCl, pH 7.0, 2.25% SDS, and is cooled to 20–25° C. Gross debris is removed from the diluted lysate by centrifugation using a Westphalia SA1 continuous flow desludging centrifuge at a feed rate of about 1.5 liters per minute and back pressure of 20–23 psig. The desludge interval is about 3.5 minutes.

One of the *E. coli* extracts used in the diluent is comprised of bacterial proteins which are solubilized during urea treatment of an insoluble protein fraction. This extract is prepared from a lysate of strain D1210 cells transformed with the expression vector pSODcf1 (see Section IV.B.1.). The cells are cultured and pelleted as described in Section IV.N.7.b., except that the pSODcf1 transformants replace the transformants which harbor pSODcf1 containing the HCV sequence from clone 5-1-1. In order to prepare the extract, 40 g of pelleted cells are placed into a 500 mL Beckman bottle, and resuspended in 14.4 mL of TE buffer (10 mM Tris, pH8.0, 1 mM EDTA). Next, 18 mL of distilled water, 6.8 mL of lysozyme solution, 0.8 mL of 0.1M PMSF (in ethanol) are added to the suspension, and it is incubated on ice for 1 hour. After the incubation, a solution containing 120 mL sterile water, 240 mL 0.5 M $MgCl_2$, 180 mL DNAse I (20,000 U/mL in distilled water) and 1.2 mL of 0.1M PMSF is added for each 40 g of cells. The suspension is then sonicated in a Branson Sonifier 450 at setting 1 for 30 seconds and placed on ice for 1 minute; this cycle is repeated five more times, after which the sonicate is incubated at room temperature for 15 minutes. The solution is then sonicated at setting 5 for 30 seconds and placed on ice for 1 minute; this cycle is repeated 3 more times, after which the sonicate is incubated at room temperature for 15 minutes. This last cycle of sonication is repeated. After sonication, the sonicate is centrifuged at 10,000 rpm for 25 minutes. The supernatant is decanted, and the remaining pellet is extracted with urea as follows. Using an Omni mixer, the pellet is resuspended in 120 mL of 6 M urea, 50 mM Tris HCl, pH 8.0, 0.1% b-mercaptoethanol (BME). The bottle is attached to a tilt shaker and rocked at 4° C. for four hours. The suspension is then centrifuged at 10,000 rpm for 25 minutes at 4° C. The supernatant containing urea is dialyzed against a 400-fold volume of buffer containing 50 mM sodium borate, 0.5 M NaCl, pH 8.4. Dialysis is for 1.5 hours at room temperature, using Spectrapor® dialysis tubing with a molecular weight cut-off of 12,000–14,000. Precipitate in the dialysate is removed by centrifugation at 10,000 rpm for 15 minutes, and the supernatant is subjected to a repeated round of dialysis and centrifugation, yielding a supernatant which is used as the bacterial extract.

The second *E. coli* extract used in the diluent is prepared from non-transformed *E. coli* cells, and is comprised of proteins in the soluble fraction of the lysozyme treated bacteria. The extract is prepared by adding to 15 mL of packed cells the following: 3 mL of lysozyme (5 mg/mL) in 0.25 M Tris HCl, H 8.0, 150 mL 0.1M PMSF in ethanol, 3.3 mL 0.25 M EDTA, pH 8.0, and 12.5 mL of a solution containing 1% Triton and 0.4% deoxycholate. The cells are suspended using an Omnimixer, and are broken by mixing for 15–25 minutes at 2–8° C; if breakage is incomplete (i.e., the material is not viscous), an additional 150 mL 0.1 M PMSF is added, and the mixing is continued for an additional 15 to 25 minutes. After cell breakage, 20,000 units of DNAse I in 1 mL water and 15 mL 0.5 M $MgCl_2$ are added, and the mixing is continued for 15 to 25 minutes at room temperature, until the DNA is digested (i.e., the mixture approaches the viscosity of water. The mixture is then centrifuged at 17,000 x G for 20 minutes at 2° C. to 8° C., and the supernatant is decanted. The supernatant is then dialyzed against 1 liter of phosphate buffered saline (PBS) from 8 to 72 hours, using Spectropor tubing with a molecular weight cutoff of 6,000 to 8,000. The protein concentration of the dialysate is adjusted to 5 to 15 mg/mL.

The immunoblot assay is performed by setting up one tube per sample, each containing a nitrocellulose assay strip. Each strip is banded with the three aforementioned HCV antigens, with hSOD, and with two levels of human IgG (internal controls), one of which yields a weak positive reaction, and one of which yields a moderate positive reaction. Sufficient working sample diluent is added to each tube to cover the strip with liquid. An aliquot of the appropriate specimen or control sample is added to each tube. The tubes are covered, and inverted to mix, the tubes are placed in a rocker, and agitated for 4 hours at room temperature. (The motion of the sample solution over the strips, generated by the rocker, is important in achieving even band staining and maximum sensitivity). After the 4 hour incubation, the tubes are uncapped, the liquid aspirated, and the strips are washed with distilled water, and transferred to a wash vessel. Following another three washes with excess distilled water, and removal of the wash by decantation, the strips are reacted with conjugate (the aliquot added is in excess of that which is sufficient to cover all of the strips). During the reaction with conjugate, the vessel containing the strip and conjugate is agitated on a rotary shaker at approximately 110 rpm for 30 minutes at room temperature. Excess conjugate is removed by washing the strips three times with an excess of distilled water, and the final wash is decanted. An aliquot of working substrate is added to the wash vessel, and the vessel is agitated on a rotary shaker at approximately 110 rpm for 15 minutes at room temperature. After the reaction, the working substrate is decanted off, and the strips are washed twice with excess distilled water. The strips are transferred to absorbent paper to blot off the excess water, air dried for at least twenty minutes at room temperature (protected from the light), and read within three hours after completion of the assay.

IV.N.1.b. Purification of SOD-NANB$_{5-1-1}$

The HCV fusion polypeptide, SOD-NANB$_{5-1-1}$ (also called the 5-1-1 polypeptide), used in the immunoblot assay system for HCV is purified according to the following procedure.

The 5-1-1 polypeptide is expressed in recombinant bacteria D1210 transformed with the vector described in Section IV.B.1.. In order to prepare an overnight culture of the transformed bacteria, the cells (about 150 mL of glycerol stock) were grown in 35 mL of L broth containing 160±15 mL of 2% ampicillin); growth is overnight at 37° C. with shaking at 300 rpm. For expression, each 1.5 liters of culture (L broth containing 6.5±0.25 mL 2% ampicillin) is inoculated with 15 mL of the overnight culture, and grown at 37° C. in a Fernbach flask with shaking for 2½ to 3 hours, until an OD$_{650}$ of 0.80±0.5 is attained; at this time expression is induced by the addition of 15 mL 200 mM IPTG. After induction, the cells are grown for 3 hours at 37° C. with shaking. The cells are then harvested by pelleting in a J6-B centrifuge in a JS5.2 rotor at 3.5K rpm for 15 minutes.

A 6 M urea extract of the cell pellet is prepared. Five grams of cell pellet is resuspended in 1.8 mL of TE, and then 2.25 mL sterile water, 0.85 mL lysozyme solution (5 mg/mL in 0.25 M Tris HCl, pH 8.0), and 100 mL of 0.1M PMSF in ethanol are added. The resuspended pellet is incubated on ice for one hour. After the incubation, 15 mL of distilled water, 30 mL of 0.5 M MgCl$_2$, 22.5 mL DNAse I (20,000 units/mL in water), and 150 mL of PMSF are added. The mixture is sonicated and the insoluble material pelleted using the procedure for the preparation of the E. coli extract described supra, except that sonication at setting 1 is repeated for a total of four times, and sonication at setting 5 is repeated for a total of two times. The pellet, which has a volume of about 1.5 mL is suspended in 15 mL of solution containing 6 M urea, 50 mM Tris HCl, pH 8.0, and 0.1% BME, using a pipetter and with vortexing. The suspension is then rocked in a tilt shaker at 4° C. for 4 hours, and centrifuged at 12,000 rpm for 15 minutes at 4° C.

The 5-1-1 polypeptide contained in the supernatant from the above described centrifugation is purified from the urea extract by passage through a Q Sepharose® Fast Flow ion exchange column (Pharmacia Corp.). A 30 mL column is equilibrated by pumping through approximately 80 mL of running buffer (6 M urea in 20 mM Tris HCl, pH 8.0, 1 mM dithiothreitol (DTT)), or RB, at a speed of about 2 mL per minute. After the column is equilibrated, the entire 6 M urea extract is loaded onto the column, and is washed in with approximately 80 mL of running buffer; fractions of 2 mL are collected during the loading and the washing steps. After the load is washed into the column, the 5-1-1 polypeptide is eluted using a 0.0 to 0.5 M NaCl gradient in RB. The gradient solution is pumped over the column at 2 mL per minute; 1 mL fractions are collected; and the OD$_{280}$ is monitored throughout the load, wash, and elution. The 5-1-1 polypeptide is expected to elute from the column approximately two-thirds of the way through the gradient. The column fractions are analyzed by electrophoresis on 12.5% polyacrylamide gels containing SDS, and by Western blot using positive polyclonal antibodies to SOD and/or the 5-1-1 polypeptide and/or serum samples. The purity of the 5-1-1 polypeptide is estimated based upon the O.D.$_{280}$, the Western blot, and the polyacrylamide gel analysis. Based upon this, appropriate fractions are pooled, yielding a total volume of ~30 mL. Each 10 mL of the pooled material is dialyzed at room temperature against 2 liters of buffer containing 50 mM sodium borate, pH 8.4, 0.5 M NaCl, 10 mM BME, and 2 mM EDTA for 1.5 hours, with 1 change of buffer after 1.5 hours; total dialysis time is approximately 3 hours. Protein concentration in the dialysate is determined by the Lowry method. The purified, dialyzed material is stored at −70° C.

IV.O Preparation of HCV Vaccines

IV.O.1 Preparation of Hybrid Particle Immunogens

The immunogenicity of the epitopes of HCV may also be enhanced by preparing them in mammalian or yeast systems fused with or assembled with particle-forming proteins such as, for example, that associated with hepatitis B surface antigen. See, e.g., U.S. Pat. No. 4,722,840, incorporated herein by reference. Constructs wherein the NANBV epitope is linked directly to the particle-forming protein coding sequences produce hybrids which are immunogenic with respect to the HCV epitope. In addition, all of the vectors prepared include epitopes specific to HBV, having various degrees of immunogenicity, such as, for example, the pre-S peptide. Thus, particles constructed from particle forming protein which include HCV sequences are immunogenic with respect to HCV and HBV.

Hepatitis surface antigen (HBSAg) has been shown to be formed and assembled into particles in *S. cerevisiae* (P. Valenzuela et al., *Nature* (1982) 298:344), as well as in, for example, mammalian cells (P. Valenzuela et al. in "Hepatitis B" (I. Millman et al., ed, Plenum Press, 1984) pp. 225–236). The formation of such particles has been shown to enhance the immunogenicity of the monomer subunit. The constructs may also include the immunodominant epitope of HBsAg, comprising the 55 amino acids of the presurface (pre-S) region (Neurath et al, *Science* (1984) 224:392). Constructs of the pre-S-HBsAg particle expressible in yeast are disclosed in EPO 174,444, published Mar. 19, 1986; hybrids including heterologous viral sequences for yeast expression are disclosed in EPO 175,261, published Mar. 26, 1966. These constructs may also be expressed in mammalian cells such as Chinese hamster ovary (CHO) cells using an SV40-dihydrofolate reductase vector (Michelle et al., *Int Symposium on Viral Hepatitis* (1984)).

In addition, portions of the particle-forming protein coding sequence may be replaced with codons encoding an HCV epitope. In this replacement, regions which are not required to mediate the aggregation of the units to form immunogenic particles in yeast or mammals can be deleted, thus eliminating additional HBV antigenic sites from competition with the HCV epitope.

IV.O.2 Preparation of Vaccines

Vaccines may be prepared from one or more immunogenic polypeptides derived from HCV. The observed homology between HCV and Flaviviruses provides information concerning the polypeptides which are likely to be most effective as vaccines, as well as the regions of the genome in which they are encoded. The general structure of the Flavivirus genome is discussed in Rice et al., in "The Viruses" supra p.279–328. The flavivirus genomic RNA is believed to be the only virus-specific mRNA species, and is translated into the three viral structural proteins (C, M, and E) as well as two large nonstructural proteins, NS4 and NS5, and a complex set of smaller nonstructural proteins. It is known that major neutralizing epitopes for Flaviviruses reside in the E (envelope) protein (Roehrig in "The Viruses" supra). The corresponding HCV E gene and polypeptide encoding region may be predicted, based upon the homology to Flaviviruses. Thus, vaccines may comprise recombinant polypeptides containing epitopes of HCV E. These polypeptides may be expressed in various host cells (e.g., bacteria, yeast, insect, or mammalian cells), or alternatively may be isolated from viral preparations. It is also anticipated that the other structural proteins may also contain epitopes which give rise to protective anti-HCV antibodies. Thus, polypeptides containing the epitopes of E, C, and M may also be used, whether singly or in combination, in HCV vaccines.

In addition to the above, it has been shown that immunization with NS1 (nonstructural protein 1), results in protection against yellow fever (Schlesinger et al, *J Virol* (1986) 60:1153). This is true even though the immunization does not give rise to neutralizing antibodies. Thus, particularly since this protein appears to be highly conserved among Flaviviruses, it is likely that HCV NS1 will also be protective against HCV infection. Moreover, it also shows that nonstructural proteins may provide protection against viral pathogenicity, even if they do not cause the production of neutralizing antibodies.

In view of the above, multivalent vaccines against HCV may comprise one or more epitopes from one or more structural proteins, and/or one or more epitopes from one or more nonstructural proteins. These vaccines may comprise, for example, recombinant HCV polypeptides and/or polypeptides isolated from the virions. In particular, vaccines are contemplated comprising one or more of the following HCV proteins, or subunit antigens derived therefrom: E, NS1, C, NS2, NS3, NS4 and NS5. Particularly preferred are vaccines comprising E and/or NS1, or subunits thereof. In addition, it may be possible to use inactivated HCV in vaccines; inactivation may be by the preparation of viral lysates, or by other means known in the art to cause inactivation of Flaviviruses, for example, treatment with organic solvents or detergents, or treatment with formalin. Moreover, vaccines may also be prepared from attenuated HCV strains.

It is known that some of the proteins in Flaviviruses contain highly conserved regions. Thus, some immunological cross-reactivity is possible between HCV and other Flaviviruses. It is possible that shared epitopes between the Flaviviruses and HCV will give rise to protective antibodies against one or more of the disorders caused by these pathogenic agents. Thus, it may be possible to design multipurpose vaccines based upon this knowledge.

In addition to the above, it is also possible to prepare live vaccines of attenuated microorganisms which express one or more recombinant HCV polypeptides. Suitable attenuated microorganisms are known in the art and include, without limitation, viruses and bacteria. See for example Dulbecco, U.S. Pat. No. 4,593,002, incorporated herein by reference.

The preparation of vaccines which contain an immunogenic polypeptide(s) as active ingredients, is known to one skilled in the art. Typically, such vaccines are prepared as injectables, either as liquid solutions or suspensions; solid forms suitable for solution in, or suspension in, liquid prior to injection may also be prepared. The preparation may also be emulsified, or the protein encapsulated in liposomes. The active immunogenic ingredients are often mixed with excipients which are pharmaceutically acceptable and compatible with the active ingredient. Suitable excipients are, for example, water, saline, dextrose, glycerol, ethanol, or the like and combinations thereof. In addition, if desired, the vaccine may contain minor amounts of auxiliary substances such as wetting or emulsifying agents, pH buffering agents, and/or adjuvants which enhance the effectiveness of the vaccine. Examples of adjuvants which may be effective include but are not limited to: aluminum hydroxide, N-acetyl-muramyl-L-threonyl-D-isoglutamine (thr-MDP), N-acetyl-nor-muramyl-L-alanyl-D-isoglutamine (CGP11637, referred to as nor-MDP), N-acetylmuramyl-L-alanyl-D-isoglutaminyl-L-alanine-2-(1'-2'-dipalmitoyl-sn-glycero-3-hydroxyphosphoryloxy)-ethylamine (CGP 19835A, referred to as MTP-PE), and RIBI, which contains three components extracted from bacteria, monophosphoryl lipid A, trehalose dimycolate and cell wall skeleton (MPL+ TDM+CWS) in a 2% squalene/Tween® 80 emulsion. The effectiveness of an adjuvant may be determined by measuring the amount of antibodies directed against an immunogenic polypeptide containing an HCV antigenic sequence resulting from administration of this polypeptide in vaccines which also comprise the various adjuvants.

The vaccines are conventionally administered parenterally, by injection; for example, either subcutaneously or intramuscularly. Additional formulations which are suitable for other modes of administration include suppositories and, in some cases, oral formulations. For suppositories, traditional binders and carriers may include, for example, polyalkylene glycols or triglycerides; such suppositories may be formed from mixtures containing the active ingredient in the range of 0.5% to 10%, preferably 1%–2%. Oral formulations include such normally employed excipients as, for example, pharmaceutical grades of mannitol, lactose, starch, magnesium stearate, sodium saccharine, cellulose, magnesium carbonate, and the like. These compositions take the form of solutions, suspensions, tablets, pills, capsules, sustained release formulations or powders and contain 10%–95% of active ingredient, preferably 25%–70%.

The proteins may be formulated into the vaccine as neutral or salt forms. Pharmaceutically acceptable salts include the acid addition salts (formed with free amino groups of the peptide) and which are formed with inorganic acids such as, for example, hydrochloric or phosphoric acids, or such organic acids such as acetic, oxalic, tartaric, maleic, and the like. Salts formed with the free carboxyl groups may also be derived from inorganic bases such as, for example, sodium, potassium, ammonium, calcium, or ferric hydroxides, and such organic bases as isopropylamine, trimethylamine, 2-ethylaminoethanol, histidine, procaine, and the like.

Vaccines are administered in a manner compatible with the dosage formulation, and in such amount as will be prophylactically and/or therapeutically effective. The quantity to be administered, which is generally in the range of 5 mg to 250 mg of antigen per dose, depends on the subject to be treated, capacity of the subject's immune system to express antibodies, and the degree of protection desired. Precise amounts of active ingredient required to be administered may depend on the judgment of the practitioner and may be peculiar to each subject.

The vaccine may be given in a single dose schedule, or preferably in a multiple dose schedule. A multiple dose schedule is one in which a primary course of vaccination may be with 1–10 separate doses, followed by other doses given at subsequent time intervals required to maintain and or reinforce the immune response, for example, at 1–4 months for a second dose, and if needed, a subsequent dose(s) after several months. The dosage regimen will also, at least in part, be determined by the need of the individual and be dependent upon the judgment of the practitioner.

In addition, the vaccine containing the immunogenic HCV antigen(s) may be administered in conjunction with other immunoregulatory agents, for example, immune globulins.

V. Deposit Information

The following listed materials are on deposit under the terms of the Budapest Treaty with the American Type Culture Collection (ATCC), 12301 Parklawn Dr., Rockville, Md. 20852, and have been assigned the following Accession Numbers.

| λgt11 | ATCC No. | Deposit Date |
|---|---|---|
| HCV cDNA library | 40394 | Dec. 1, 1987 |
| clone 81 | 40388 | Nov. 17, 1987 |
| clone 91 | 40389 | Nov. 17, 1987 |
| clone 1-2 | 40390 | Nov. 17, 1987 |
| clone 5-1-1 | 40391 | Nov. 18, 1987 |
| clone 12f | 40514 | Nov. 10, 1988 |
| clone 35f | 40511 | Nov. 10, 1988 |
| clone 15e | 40513 | Nov. 10, 1988 |
| clone K9-1 | 40512 | Nov. 10, 1988 |
| JSC 308 | 20879 | May 5, 1988 |
| pS356 | 67683 | April 29, 1988 |

In addition, the following deposits were made on 11 May 1989.

| Strain | Linkers | ATCC No. |
|---|---|---|
| D1210 (Cfl/5-1-1) | EF | 67967 |
| D1210 (Cfl/81) | EF | 67968 |
| D1210 (Cfl/CA74a) | EF | 67969 |
| D1210 (Cfl/35f) | AB | 67970 |
| D1210 (Cfl/279a) | EF | 67971 |
| D1210 (Cfl/C36) | CD | 67972 |
| D1210 (Cfl/13i) | AB | 67973 |
| D1210 (Cfl/C33b) | EF | 67974 |
| D1210 (Cfl/CA290a) | AB | 67975 |
| HB101 (AB24/C100 #3R) | | 67976 |

The following derivatives of strain D1210 were deposited on 3 May 1989.

| Strain Derivatives | ATCC No. |
|---|---|
| pCF1CS/C8f | 67956 |
| pCF1AB/C12f | 67952 |

-continued

| Strain Derivatives | ATCC No. |
|---|---|
| pCF1EF/14c | 67949 |
| pCF1EF/15e | 67954 |
| pCF1AB/C25c | 67958 |
| pCF1EF/C33c | 67953 |
| pCF1EF/C33f | 67050 |
| pCF1CD/33g | 67951 |
| pCF1CD/C39c | 67955 |
| pCF1EF/C40b | 67957 |
| pCF1EF/CA167b | 67959 |

The following biological materials were deposited on May 12, 1989.

| Material | ATCC No. |
|---|---|
| λgt11(C35) | 40603 |
| λgt10(b-5a) | 40602 |
| D1210 (C40b) | 67980 |
| D1210 (M16) | 67981 |

The following biological materials were deposited on Oct. 13, 1989.

| Material | ATCC No. |
|---|---|
| AB122 | 20961 |
| λgt11 | 40678 |
| pAB24/C200–C100 | 40679 |
| pNS11d- 13–15 | 40680 |
| pC100-d #3 | 68113 |
| pC22 | 68114 |
| pS2d #9 | 68115 |

The following biological materials were deposited on Oct. 17, 1989.

| Material | ATCC No. |
|---|---|
| pCMV-NS1 | 68125 |
| pMCMV-NS1 | 68126 |

Upon allowance and issuance of this application as a United States Patent, all restriction on availability of these deposits will be irrevocably removed; and access to the designated deposits will be available during pendency of the above-named application to one determined by the Commissioner to be entitled thereto under 37 CFR 1.14 and 35 USC 1.22. Moreover, the designated deposits will be maintained for a period of thirty (30) years from the date of deposit, or for five (5) years after the last request for the deposit; or for the enforceable life of the U.S. patent, whichever is longer. The deposited materials mentioned herein are intended for convenience only, and are not required to practice the present invention in view of the descriptions herein, and in addition these materials are incorporated herein by reference.

VI. Industrial Applicability

The invention, in the various manifestations disclosed herein, has many industrial uses, some of which are the following. The HCV cDNAs may be used for the design of probes for the detection of HCV nucleic acids in samples.

The probes derived from the cDNAs may be used to detect HCV nucleic acids in, for example, chemical synthetic reactions. They may also be used in screening programs for anti-viral agents, to determine the effect of the agents in inhibiting viral replication in cell culture systems, and animal model systems. The HCV polynucleotide probes are also useful in detecting viral nucleic acids in humans, and thus, may serve as a basis for diagnosis of HCV infections in humans.

In addition to the above, the cDNAs provided herein provide information and a means for synthesizing polypeptides containing epitopes of HCV. These polypeptides are useful in detecting antibodies to HCV antigens. A series of immunoassays for HCV infection, based on recombinant polypeptides containing HCV epitopes are described herein, and will find commercial use in diagnosing HCV induced NANBH, in screening blood bank donors for HCV-caused infectious hepatitis, and also for detecting contaminated blood from infectious blood donors. The viral antigens will also have utility in monitoring the efficacy of anti-viral agents in animal model systems. In addition, the polypeptides derived from the HCV cDNAs disclosed herein will have utility as vaccines for treatment of HCV infections.

The polypeptides derived from the HCV cDNAs, besides the above stated uses, are also useful for raising anti-HCV antibodies. Thus, they may be used in anti-HCV vaccines. However, the antibodies produced as a result of immunization with the HCV polypeptides are also useful in detecting the presence of viral antigens in samples. Thus, they may be used to assay the production of HCV polypeptides in chemical systems. The anti-HCV antibodies may also be used to monitor the efficacy of anti-viral agents in screening programs where these agents are tested in tissue culture systems. They may also be used for passive immunotherapy, and to diagnose HCV caused NANBH by allowing the detection of viral antigen(s) in both blood donors and recipients. Another important use for anti-HCV antibodies is in affinity chromatography for the purification of virus and viral polypeptides. The purified virus and viral polypeptide preparations may be used in vaccines. However, the purified virus may also be useful for the development of cell culture systems in which HCV replicates.

Cell culture systems containing HCV infected cells will have many uses. They can be used for the relatively large scale production of HCV, which is normally a low titer virus. These systems will also be useful for an elucidation of the molecular biology of the virus, and lead to the development of anti-viral agents. The cell culture systems will also be useful in screening for the efficacy of antiviral agents. In addition, HCV permissive cell culture systems are useful for the production of attenuated strains of HCV.

For convenience, the anti-HCV antibodies and HCV polypeptides, whether natural or recombinant, may be packaged into kits.

The method used for isolating HCV cDNA, which is comprised of preparing a cDNA library derived from infected tissue of an individual, in an expression vector, and selecting clones which produce the expression products which react immunologically with antibodies in antibody-containing body components from other infected individuals and not from non-infected individuals, may also be applicable to the isolation of cDNAs derived from other heretofore uncharacterized disease-associated agents which are comprised of a genomic component. This, in turn, could lead to isolation and characterization of these agents, and to diagnostic reagents and vaccines for these other disease-associated agents.

SEQUENCE LISTING (1) GENERAL INFORMATION:

(iii) NUMBER OF SEQUENCES: 777

(2) INFORMATION FOR SEQ ID NO:1:

(i) SEQUENCE CHARACTERISTICS:
      (A) LENGTH: 155 base pairs
      (B) TYPE: nucleic acid
      (C) STRANDEDNESS: single
      (D) TOPOLOGY: linear (ii) MOLECULE TYPE: cDNA (vii) IMMEDIATE SOURCE:
      (B) CLONE: 5-1-1

(ix) FEATURE:
      (A) NAME/KEY: CDS
      (B) LOCATION: 2..154

(xi) SEQUENCE DESCRIPTION: SEQ ID NO:1:

```
G GCC TCC TGC TTG AAC TGC TCG GCG AGC ATC ATA CCT GAC AGG GAA         46
  Ala Ser Cys Leu Asn Cys Ser Ala Ser Ile Ile Pro Asp Arg Glu
   1               5                  10                  15

GTC CTC TAC CGA GAG TTC GAT GAG ATG GAA GAG TGC TCT CAG CAC TTA       94
Val Leu Tyr Arg Glu Phe Asp Glu Met Glu Glu Cys Ser Gln His Leu
             20                  25                  30
```

```
CCG TAC ATC GAG CAA GGG ATG ATG CTC GCC GAG CAG TTC AAG CAG AAG     142
Pro Tyr Ile Glu Gln Gly Met Met Leu Ala Glu Gln Phe Lys Gln Lys
             35                  40                  45

GCC CTC GGC CTC C                                                   155
Ala Leu Gly Leu
        50

(2) INFORMATION FOR SEQ ID NO:2:

(i) SEQUENCE CHARACTERISTICS:
        (A) LENGTH: 51 amino acids
        (B) TYPE: amino acid
        (D) TOPOLOGY: linear (ii) MOLECULE TYPE: protein (xi) SEQUENCE DESCRIPTION: SEQ ID NO:2:

Ala Ser Cys Leu Asn Cys Ser Ala Ser Ile Ile Pro Asp Arg Glu Val
 1               5                  10                  15

Leu Tyr Arg Glu Phe Asp Glu Met Glu Glu Cys Ser Gln His Leu Pro
             20                  25                  30

Tyr Ile Glu Gln Gly Met Met Leu Ala Glu Gln Phe Lys Gln Lys Ala
             35                  40                  45

Leu Gly Leu
     50

(2) INFORMATION FOR SEQ ID NO:3:

(i) SEQUENCE CHARACTERISTICS:
        (A) LENGTH: 155 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (B) CLONE: 5-1-1

(xi) SEQUENCE DESCRIPTION: SEQ ID NO:3:

GGCCTCCTGC TTGAACTGCT CGGCGAGCAT CATACCTGAC AGGGAAGTCC TCTACCGAGA     60

GTTCGATGAG ATGGAAGAGT GCTCTCAGCA CTTACCGTAC ATCGAGCAAG GGATGATGCT    120

CGCCGAGCAG TTCAAGCAGA AGGCCCTCGG CCTCC                               155

(2) INFORMATION FOR SEQ ID NO:4:

(i) SEQUENCE CHARACTERISTICS:
        (A) LENGTH: 353 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (B) CLONE: 81

(xi) SEQUENCE DESCRIPTION: SEQ ID NO:4:

GTCCGGGAAG CCGGCAATCA TACCTGACAG GGAAGTCCTC TACCGAGAGT TCGATGAGAT     60

GGAAGAGTGC TCTCAGCACT TACCGTACAT CGAGCAAGGG ATGATGCTCG CCGAGCAGTT    120

CAAGCAGAAG GCCCTCGGCC TCCTGCAGAC CGCGTCCCGT CAGGCAGAGG TTATCGCCCC    180

TGCTGTCCAG ACCAACTGGC AAAAACTCGA GACCTTCTGG CGAAGCATA TGTGGAACTT     240

CATCAGTGGG ATACAATACT TGGCGGGCTT GTCAACGCTG CCTGGTAACC CCGCCATTGC    300
```

TTCATTGATG GCTTTTACAG CTGCTGTCAC CAGCCCACTA ACCACTAGCC AAA                353

(2) INFORMATION FOR SEQ ID NO:5:

(i) SEQUENCE CHARACTERISTICS:
        (A) LENGTH: 318 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (B) CLONE: 91

(xi) SEQUENCE DESCRIPTION: SEQ ID NO:5:

CTGGCTGCGT GGTCATAGTG GGCAGGGTCG TCTTGTCCGG GAAGCCGGCA ATCATACCTG           60

ACAGGGAAGT CCTCTACGAG AGTTCGATGA GATGGAAGAG TGCTCTCAGC ACTTACCGTA          120

CATCGAGCAA GGGATGATGC TCGCCGAGCA GTTCAAGCAG AAGGCCCTCG GCCTCCTGCA          180

GACCGCGTCC CGTCAGGCAG AGGTTATCGC CCCTGCTGTC CAGACCAACT GGCAAAAACT          240

CGAGACCTTC TGGGCGAAGC ATATGTGGAA CTTCATCAGT GGGATACAAT ACTTGGCGGG          300

CTTGTCAACG CTGCCTGG                                                       318

(2) INFORMATION FOR SEQ ID NO:6:

(i) SEQUENCE CHARACTERISTICS:
        (A) LENGTH: 164 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (B) CLONE: 1-2

(xi) SEQUENCE DESCRIPTION: SEQ ID NO:6:

GGTCATAGTG GGCAGGGTCG TCTTGTCCGG GAAGCCGGCA ATCATACCTG ACAGGGAAGT           60

CCTCTATCGA GAGTTCGATG AGATGGAAGA GTGCTCTCAG CACTTACCGT ACATCGAGCA          120

AGGGATGATG CTCGCCGAGC AGTTCAAGCA GAAGGCCCTC GGCC                          164

(2) INFORMATION FOR SEQ ID NO:7:

(i) SEQUENCE CHARACTERISTICS:
        (A) LENGTH: 387 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 3..386

(ix) FEATURE:
        (A) NAME/KEY: misc_feature
        (B) LOCATION: 77
        (D) OTHER INFORMATION: /note= "A heterogeneity may exist
            nucleotide 77 = C or T and amino acid Xaa = Tyr"

(xi) SEQUENCE DESCRIPTION: SEQ ID NO:7:

CT GGC TGC GTG GTC ATA GTG GGC AGG GTC GTC TTG TCC GGG AAG CCG              47
   Gly Cys Val Val Ile Val Gly Arg Val Val Leu Ser Gly Lys Pro
    1          5             10            15

```
GCA ATC ATA CCT GAC AGG GAA GTC CTC TAY CGA GAG TTC GAT GAG ATG       95
Ala Ile Ile Pro Asp Arg Glu Val Leu Xaa Arg Glu Phe Asp Glu Met
             20                  25                  30

GAA GAG TGC TCT CAG CAC TTA CCG TAC ATC GAG CAA GGG ATG ATG CTC      143
Glu Glu Cys Ser Gln His Leu Pro Tyr Ile Glu Gln Gly Met Met Leu
         35                  40                  45

GCC GAG CAG TTC AAG CAG AAG GCC CTC GGC CTC CTG CAG ACC GCG TCC      191
Ala Glu Gln Phe Lys Gln Lys Ala Leu Gly Leu Leu Gln Thr Ala Ser
         50                  55                  60

CGT CAG GCA GAG GTT ATC GCC CCT GCT GTC CAG ACC AAC TGG CAA AAA      239
Arg Gln Ala Glu Val Ile Ala Pro Ala Val Gln Thr Asn Trp Gln Lys
     65                  70                  75

CTC GAG ACC TTC TGG GCG AAG CAT ATG TGG AAC TTC ATC AGT GGG ATA      287
Leu Glu Thr Phe Trp Ala Lys His Met Trp Asn Phe Ile Ser Gly Ile
 80                  85                  90                  95

CAA TAC TTG GCG GGC TTG TCA ACG CTG CCT GGT AAC CCC GCC ATT GCT      335
Gln Tyr Leu Ala Gly Leu Ser Thr Leu Pro Gly Asn Pro Ala Ile Ala
                100                 105                 110

TCA TTG ATG GCT TTT ACA GCT GCT GTC ACC AGC CCA CTA ACC ACT AGC      383
Ser Leu Met Ala Phe Thr Ala Ala Val Thr Ser Pro Leu Thr Thr Ser
             115                 120                 125

CAA A                                                                387
Gln
```

(2) INFORMATION FOR SEQ ID NO:8:

(i) SEQUENCE CHARACTERISTICS:
        (A) LENGTH: 128 amino acids
        (B) TYPE: amino acid
        (D) TOPOLOGY: linear (ii) MOLECULE TYPE: protein (xi) SEQUENCE DESCRIPTION: SEQ ID NO:8:

```
Gly Cys Val Val Ile Val Gly Arg Val Val Leu Ser Gly Lys Pro Ala
 1               5                  10                  15

Ile Ile Pro Asp Arg Glu Val Leu Xaa Arg Glu Phe Asp Glu Met Glu
             20                  25                  30

Glu Cys Ser Gln His Leu Pro Tyr Ile Glu Gln Gly Met Met Leu Ala
         35                  40                  45

Glu Gln Phe Lys Gln Lys Ala Leu Gly Leu Leu Gln Thr Ala Ser Arg
     50                  55                  60

Gln Ala Glu Val Ile Ala Pro Ala Val Gln Thr Asn Trp Gln Lys Leu
 65                  70                  75                  80

Glu Thr Phe Trp Ala Lys His Met Trp Asn Phe Ile Ser Gly Ile Gln
                 85                  90                  95

Tyr Leu Ala Gly Leu Ser Thr Leu Pro Gly Asn Pro Ala Ile Ala Ser
                100                 105                 110

Leu Met Ala Phe Thr Ala Ala Val Thr Ser Pro Leu Thr Thr Ser Gln
             115                 120                 125
```

(2) INFORMATION FOR SEQ ID NO:9:

(i) SEQUENCE CHARACTERISTICS:
        (A) LENGTH: 353 base pairs
        (B) TYPE: nucleic acid
        (C) STRANDEDNESS: single
        (D) TOPOLOGY: linear (ii) MOLECULE TYPE: cDNA (ix) FEATURE:
              (A) NAME/KEY: CDS
              (B) LOCATION: 2..352

(xi) SEQUENCE DESCRIPTION: SEQ ID NO:9:

```
G TCC GGG AAG CCG GCA ATC ATA CCT GAC AGG GAA GTC CTC TAC CGA          46
  Ser Gly Lys Pro Ala Ile Ile Pro Asp Arg Glu Val Leu Tyr Arg
  1               5                  10                  15

GAG TTC GAT GAG ATG GAA GAG TGC TCT CAG CAC TTA CCG TAC ATC GAG        94
Glu Phe Asp Glu Met Glu Glu Cys Ser Gln His Leu Pro Tyr Ile Glu
                20                  25                  30

CAA GGG ATG ATG CTC GCC GAG CAG TTC AAG CAG AAG GCC CTC GGC CTC       142
Gln Gly Met Met Leu Ala Glu Gln Phe Lys Gln Lys Ala Leu Gly Leu
            35                  40                  45

CTG CAG ACC GCG TCC CGT CAG GCA GAG GTT ATC GCC CCT GCT GTC CAG       190
Leu Gln Thr Ala Ser Arg Gln Ala Glu Val Ile Ala Pro Ala Val Gln
        50                  55                  60

ACC AAC TGG CAA AAA CTC GAG ACC TTC TGG GCG AAG CAT ATG TGG AAC       238
Thr Asn Trp Gln Lys Leu Glu Thr Phe Trp Ala Lys His Met Trp Asn
    65                  70                  75

TTC ATC AGT GGG ATA CAA TAC TTG GCG GGC TTG TCA ACG CTG CCT GGT       286
Phe Ile Ser Gly Ile Gln Tyr Leu Ala Gly Leu Ser Thr Leu Pro Gly
80                  85                  90                  95

AAC CCC GCC ATT GCT TCA TTG ATG GCT TTT ACA GCT GCT GTC ACC AGC       334
Asn Pro Ala Ile Ala Ser Leu Met Ala Phe Thr Ala Ala Val Thr Ser
                100                 105                 110

CCA CTA ACC ACT AGC CAA A                                             353
Pro Leu Thr Thr Ser Gln
            115
```

(2) INFORMATION FOR SEQ ID NO:10:

(i) SEQUENCE CHARACTERISTICS:
              (A) LENGTH: 117 amino acids
              (B) TYPE: amino acid
              (D) TOPOLOGY: linear (ii) MOLECULE TYPE: protein (xi) SEQUENCE DESCRIPTION: SEQ ID NO:10:

```
Ser Gly Lys Pro Ala Ile Ile Pro Asp Arg Glu Val Leu Tyr Arg Glu
1               5                   10                  15

Phe Asp Glu Met Glu Glu Cys Ser Gln His Leu Pro Tyr Ile Glu Gln
                20                  25                  30

Gly Met Met Leu Ala Glu Gln Phe Lys Gln Lys Ala Leu Gly Leu Leu
            35                  40                  45

Gln Thr Ala Ser Arg Gln Ala Glu Val Ile Ala Pro Ala Val Gln Thr
        50                  55                  60

Asn Trp Gln Lys Leu Glu Thr Phe Trp Ala Lys His Met Trp Asn Phe
65                  70                  75                  80

Ile Ser Gly Ile Gln Tyr Leu Ala Gly Leu Ser Thr Leu Pro Gly Asn
                85                  90                  95

Pro Ala Ile Ala Ser Leu Met Ala Phe Thr Ala Ala Val Thr Ser Pro
            100                 105                 110

Leu Thr Thr Ser Gln
        115
```

(2) INFORMATION FOR SEQ ID NO:11:

(i) SEQUENCE CHARACTERISTICS:
              (A) LENGTH: 406 base pairs (B) TYPE: nucleic acid
    (C) STRANDEDNESS: single
    (D) TOPOLOGY: linear (ii) MOLECULE TYPE: cDNA (ix) FEATURE:
    (A) NAME/KEY: CDS
    (B) LOCATION: 1..405

(xi) SEQUENCE DESCRIPTION: SEQ ID NO:11:

```
GAT GCC CAC TTT GTA TCC CAG ACA AAG CAG AGT GGG GAG AAC CTT CCT      48
Asp Ala His Phe Val Ser Gln Thr Lys Gln Ser Gly Glu Asn Leu Pro
 1               5                  10                  15

TAC CTG GTA GCG TAC CAA GCC ACC GTG TGC GCT AGG GCT CAA GCC CCT      96
Tyr Leu Val Ala Tyr Gln Ala Thr Val Cys Ala Arg Ala Gln Ala Pro
            20                  25                  30

CCC CCA TCG TGG GAC CAG ATG TGG AAG TGT TTG ATT CGC CTC AAG CCC     144
Pro Pro Ser Trp Asp Gln Met Trp Lys Cys Leu Ile Arg Leu Lys Pro
        35                  40                  45

ACC CTC CAT GGG CCA ACA CCC CTG CTA TAC AGA CTG GGC GCT GTT CAG     192
Thr Leu His Gly Pro Thr Pro Leu Leu Tyr Arg Leu Gly Ala Val Gln
    50                  55                  60

AAT GAA ATC ACC CTG ACG CAC CCA GTC ACC AAA TAC ATC ATG ACA TGC     240
Asn Glu Ile Thr Leu Thr His Pro Val Thr Lys Tyr Ile Met Thr Cys
65                  70                  75                  80

ATG TCG GCC GAC CTG GAG GTC GTC ACG AGC ACC TGG GTG CTC GTT GGC     288
Met Ser Ala Asp Leu Glu Val Val Thr Ser Thr Trp Val Leu Val Gly
                85                  90                  95

GGC GTC CTG GCT GCT TTG GCC GCG TAT TGC CTG TCA ACA GGC TGC GTG     336
Gly Val Leu Ala Ala Leu Ala Ala Tyr Cys Leu Ser Thr Gly Cys Val
            100                 105                 110

GTC ATA GTG GGC AGG GTC GTC TTG TCC GGG AAG CCG GCA ATC ATA CCT     384
Val Ile Val Gly Arg Val Val Leu Ser Gly Lys Pro Ala Ile Ile Pro
        115                 120                 125

GAC AGG GAA GTC CTC TAC CGA G                                       406
Asp Arg Glu Val Leu Tyr Arg
    130                 135
```

(2) INFORMATION FOR SEQ ID NO:12:

(i) SEQUENCE CHARACTERISTICS:
        (A) LENGTH: 135 amino acids
        (B) TYPE: amino acid
        (D) TOPOLOGY: linear (ii) MOLECULE TYPE: protein (xi) SEQUENCE DESCRIPTION: SEQ ID NO:12:

```
Asp Ala His Phe Val Ser Gln Thr Lys Gln Ser Gly Glu Asn Leu Pro
 1               5                  10                  15

Tyr Leu Val Ala Tyr Gln Ala Thr Val Cys Ala Arg Ala Gln Ala Pro
            20                  25                  30

Pro Pro Ser Trp Asp Gln Met Trp Lys Cys Leu Ile Arg Leu Lys Pro
        35                  40                  45

Thr Leu His Gly Pro Thr Pro Leu Leu Tyr Arg Leu Gly Ala Val Gln
    50                  55                  60

Asn Glu Ile Thr Leu Thr His Pro Val Thr Lys Tyr Ile Met Thr Cys
65                  70                  75                  80

Met Ser Ala Asp Leu Glu Val Val Thr Ser Thr Trp Val Leu Val Gly
                85                  90                  95

Gly Val Leu Ala Ala Leu Ala Ala Tyr Cys Leu Ser Thr Gly Cys Val
```

```
                         100                 105                 110
Val Ile Val Gly Arg Val Val Leu Ser Gly Lys Pro Ala Ile Ile Pro
            115                 120                 125

Asp Arg Glu Val Leu Tyr Arg
        130                 135
```

(2) INFORMATION FOR SEQ ID NO:13:

(i) SEQUENCE CHARACTERISTICS:
        (A) LENGTH: 712 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..711

(xi) SEQUENCE DESCRIPTION: SEQ ID NO:13:

```
GAT GCC CAC TTT CTA TCC CAG ACA AAG CAG AGT GGG GAG AAC CTT CCT     48
Asp Ala His Phe Leu Ser Gln Thr Lys Gln Ser Gly Glu Asn Leu Pro
 1               5                  10                  15

TAC CTG GTA GCG TAC CAA GCC ACC GTG TGC GCT AGG GCT CAA GCC CCT     96
Tyr Leu Val Ala Tyr Gln Ala Thr Val Cys Ala Arg Ala Gln Ala Pro
            20                  25                  30

CCC CCA TCG TGG GAC CAG ATG TGG AAG TGT TTG ATT CGC CTC AAG CCC    144
Pro Pro Ser Trp Asp Gln Met Trp Lys Cys Leu Ile Arg Leu Lys Pro
        35                  40                  45

ACC CTC CAT GGG CCA ACA CCC CTG CTA TAC AGA CTG GGC GCT GTT CAG    192
Thr Leu His Gly Pro Thr Pro Leu Leu Tyr Arg Leu Gly Ala Val Gln
    50                  55                  60

AAT GAA ATC ACC CTG ACG CAC CCA GTC ACC AAA TAC ATC ATG ACA TGC    240
Asn Glu Ile Thr Leu Thr His Pro Val Thr Lys Tyr Ile Met Thr Cys
65                  70                  75                  80

ATG TCG GCC GAC CTG GAG GTC GTC ACG AGC ACC TGG GTG CTC GTT GGC    288
Met Ser Ala Asp Leu Glu Val Val Thr Ser Thr Trp Val Leu Val Gly
                85                  90                  95

GGC GTC CTG GCT GCT TTG GCC GCG TAT TGC CTG TCA ACA GGC TGC GTG    336
Gly Val Leu Ala Ala Leu Ala Ala Tyr Cys Leu Ser Thr Gly Cys Val
            100                 105                 110

GTC ATA GTG GGC AGG GTC GTC TTG TCC GGG AAG CCG GCA ATC ATA CCT    384
Val Ile Val Gly Arg Val Val Leu Ser Gly Lys Pro Ala Ile Ile Pro
        115                 120                 125

GAC AGG GAA GTC CTC TAC CGA GAG TTC GAT GAG ATG GAA GAG TGC TCT    432
Asp Arg Glu Val Leu Tyr Arg Glu Phe Asp Glu Met Glu Glu Cys Ser
    130                 135                 140

CAG CAC TTA CCG TAC ATC GAG CAA GGG ATG ATG CTC GCC GAG CAG TTC    480
Gln His Leu Pro Tyr Ile Glu Gln Gly Met Met Leu Ala Glu Gln Phe
145                 150                 155                 160

AAG CAG AAG GCC CTC GGC CTC CTG CAG ACC GCG TCC CGT CAG GCA GAG    528
Lys Gln Lys Ala Leu Gly Leu Leu Gln Thr Ala Ser Arg Gln Ala Glu
                165                 170                 175

GTT ATC GGC CCT GCT GTC CAG ACC AAC TGG CAA AAA CTC GAG ACC TTC    576
Val Ile Gly Pro Ala Val Gln Thr Asn Trp Gln Lys Leu Glu Thr Phe
            180                 185                 190

TGG GCA AAG CAT ATG TGG AAC TTC ATC AGT GGG ATA CAA TAC TTG GCG    624
Trp Ala Lys His Met Trp Asn Phe Ile Ser Gly Ile Gln Tyr Leu Ala
        195                 200                 205

GGC TTG TCA ACG CTG CCT GGT AAC CCC GCC ATT GCT TCA TTG ATG GCT    672
Gly Leu Ser Thr Leu Pro Gly Asn Pro Ala Ile Ala Ser Leu Met Ala
```

```
                210                 215                 220
TTT ACA GCT GCT GTC ACC AGC CCA CTA ACC ACT AGC CAA A                    712
Phe Thr Ala Ala Val Thr Ser Pro Leu Thr Thr Ser Gln
225                 230                 235
```

(2) INFORMATION FOR SEQ ID NO:14:

(i) SEQUENCE CHARACTERISTICS:
  (A) LENGTH: 237 amino acids
  (B) TYPE: amino acid
  (D) TOPOLOGY: linear (ii) MOLECULE TYPE: protein (xi) SEQUENCE DESCRIPTION: SEQ ID NO:14:

```
Asp Ala His Phe Leu Ser Gln Thr Lys Gln Ser Gly Glu Asn Leu Pro
1               5                   10                  15

Tyr Leu Val Ala Tyr Gln Ala Thr Val Cys Ala Arg Ala Gln Ala Pro
            20                  25                  30

Pro Pro Ser Trp Asp Gln Met Trp Lys Cys Leu Ile Arg Leu Lys Pro
        35                  40                  45

Thr Leu His Gly Pro Thr Pro Leu Leu Tyr Arg Leu Gly Ala Val Gln
    50                  55                  60

Asn Glu Ile Thr Leu Thr His Pro Val Thr Lys Tyr Ile Met Thr Cys
65                  70                  75                  80

Met Ser Ala Asp Leu Glu Val Val Thr Ser Thr Trp Val Leu Val Gly
                85                  90                  95

Gly Val Leu Ala Ala Leu Ala Ala Tyr Cys Leu Ser Thr Gly Cys Val
            100                 105                 110

Val Ile Val Gly Arg Val Val Leu Ser Gly Lys Pro Ala Ile Ile Pro
        115                 120                 125

Asp Arg Glu Val Leu Tyr Arg Glu Phe Asp Glu Met Glu Glu Cys Ser
    130                 135                 140

Gln His Leu Pro Tyr Ile Glu Gln Gly Met Met Leu Ala Glu Gln Phe
145                 150                 155                 160

Lys Gln Lys Ala Leu Gly Leu Leu Gln Thr Ala Ser Arg Gln Ala Glu
                165                 170                 175

Val Ile Gly Pro Ala Val Gln Thr Asn Trp Gln Lys Leu Glu Thr Phe
            180                 185                 190

Trp Ala Lys His Met Trp Asn Phe Ile Ser Gly Ile Gln Tyr Leu Ala
        195                 200                 205

Gly Leu Ser Thr Leu Pro Gly Asn Pro Ala Ile Ala Ser Leu Met Ala
    210                 215                 220

Phe Thr Ala Ala Val Thr Ser Pro Leu Thr Thr Ser Gln
225                 230                 235
```

(2) INFORMATION FOR SEQ ID NO:15:

(i) SEQUENCE CHARACTERISTICS:
  (A) LENGTH: 418 base pairs
  (B) TYPE: nucleic acid
  (C) STRANDEDNESS: single
  (D) TOPOLOGY: linear (ii) MOLECULE TYPE: cDNA (ix) FEATURE:
  (A) NAME/KEY: CDS
  (B) LOCATION: 3..416

(xi) SEQUENCE DESCRIPTION: SEQ ID NO:15:

```
CT TTT ACA GCT GCT GTC ACC AGC CCA CTA ACC ACT AGC CAA ACC CTC        47
   Phe Thr Ala Ala Val Thr Ser Pro Leu Thr Thr Ser Gln Thr Leu
    1               5                  10                  15

CTC TTC AAC ATA TTG GGG GGG TGG GTG GCT GCC CAG CTC GCC GCC CCC        95
Leu Phe Asn Ile Leu Gly Gly Trp Val Ala Ala Gln Leu Ala Ala Pro
                20                  25                  30

GGT GCC GCT ACT GCC TTT GTG GGC GCT GGC TTA GCT GGC GCC GCC ATC       143
Gly Ala Ala Thr Ala Phe Val Gly Ala Gly Leu Ala Gly Ala Ala Ile
                    35                  40                  45

GGC AGT GTT GGA CTG GGG AAG GTC CTC ATA GAC ATC CTT GCA GGG TAT       191
Gly Ser Val Gly Leu Gly Lys Val Leu Ile Asp Ile Leu Ala Gly Tyr
                50                  55                  60

GGC GCG GGC GTG GCG GGA GCT CTT GTG GCA TTC AAG ATC ATG AGC GGT       239
Gly Ala Gly Val Ala Gly Ala Leu Val Ala Phe Lys Ile Met Ser Gly
                65                  70                  75

GAG GTC CCC TCC ACG GAG GAC CTG GTC AAT CTA CTG CCC GCC ATC CTC       287
Glu Val Pro Ser Thr Glu Asp Leu Val Asn Leu Leu Pro Ala Ile Leu
 80                  85                  90                  95

TCG CCC GGA GCC CTC GTA GTC GGC GTG GTC TGT GCA GCA ATA CTG CGC       335
Ser Pro Gly Ala Leu Val Val Gly Val Val Cys Ala Ala Ile Leu Arg
                100                 105                 110

CGG CAC GTT GGC CCG GGC GAG GGG GCA GTG CAG TGG ATG AAC CGG CTG       383
Arg His Val Gly Pro Gly Glu Gly Ala Val Gln Trp Met Asn Arg Leu
                115                 120                 125

ATA GCC TTC GCC TCC CGG GGG AAC CAT GTT TCC CC                        418
Ile Ala Phe Ala Ser Arg Gly Asn His Val Ser
                130                 135

(2) INFORMATION FOR SEQ ID NO:16:

(i) SEQUENCE CHARACTERISTICS:
        (A) LENGTH: 138 amino acids
        (B) TYPE: amino acid
        (D) TOPOLOGY: linear (ii) MOLECULE TYPE: protein (xi) SEQUENCE DESCRIPTION: SEQ ID NO:16:

Phe Thr Ala Ala Val Thr Ser Pro Leu Thr Thr Ser Gln Thr Leu Leu
 1               5                  10                  15

Phe Asn Ile Leu Gly Gly Trp Val Ala Ala Gln Leu Ala Ala Pro Gly
            20                  25                  30

Ala Ala Thr Ala Phe Val Gly Ala Gly Leu Ala Gly Ala Ala Ile Gly
                35                  40                  45

Ser Val Gly Leu Gly Lys Val Leu Ile Asp Ile Leu Ala Gly Tyr Gly
            50                  55                  60

Ala Gly Val Ala Gly Ala Leu Val Ala Phe Lys Ile Met Ser Gly Glu
65                  70                  75                  80

Val Pro Ser Thr Glu Asp Leu Val Asn Leu Leu Pro Ala Ile Leu Ser
                85                  90                  95

Pro Gly Ala Leu Val Val Gly Val Val Cys Ala Ala Ile Leu Arg Arg
                100                 105                 110

His Val Gly Pro Gly Glu Gly Ala Val Gln Trp Met Asn Arg Leu Ile
            115                 120                 125

Ala Phe Ala Ser Arg Gly Asn His Val Ser
            130                 135

(2) INFORMATION FOR SEQ ID NO:17:
```

(i) SEQUENCE CHARACTERISTICS:
    (A) LENGTH: 480 base pairs
    (B) TYPE: nucleic acid
    (C) STRANDEDNESS: single
    (D) TOPOLOGY: linear (ii) MOLECULE TYPE: cDNA (ix) FEATURE:
    (A) NAME/KEY: CDS
    (B) LOCATION: 1..480

(xi) SEQUENCE DESCRIPTION: SEQ ID NO:17:

| | | | | | | | | | | | | | | | | |
|---|---|---|---|---|---|---|---|---|---|---|---|---|---|---|---|---|
| TCC | ATT | GAG | ACA | ATC | ACG | CTC | CCC | CAG | GAT | GCT | GTC | TCC | CGC | ACT | CAA | 48 |
| Ser | Ile | Glu | Thr | Ile | Thr | Leu | Pro | Gln | Asp | Ala | Val | Ser | Arg | Thr | Gln | |
| 1 | | | | 5 | | | | | 10 | | | | | 15 | | |
| CGT | CGG | GGC | AGG | ACT | GGC | AGG | GGG | AAG | CCA | GGC | ATC | TAC | AGA | TTT | GTG | 96 |
| Arg | Arg | Gly | Arg | Thr | Gly | Arg | Gly | Lys | Pro | Gly | Ile | Tyr | Arg | Phe | Val | |
| | | | 20 | | | | | 25 | | | | | 30 | | | |
| GCA | CCG | GGG | GAG | CGC | CCC | TCC | GGC | ATG | TTC | GAC | TCG | TCC | GTC | CTC | TGT | 144 |
| Ala | Pro | Gly | Glu | Arg | Pro | Ser | Gly | Met | Phe | Asp | Ser | Ser | Val | Leu | Cys | |
| | | 35 | | | | | 40 | | | | | 45 | | | | |
| GAG | TGC | TAT | GAC | GCA | GGC | TGT | GCT | TGG | TAT | GAG | CTC | ACG | CCC | GCC | GAG | 192 |
| Glu | Cys | Tyr | Asp | Ala | Gly | Cys | Ala | Trp | Tyr | Glu | Leu | Thr | Pro | Ala | Glu | |
| | 50 | | | | | 55 | | | | | 60 | | | | | |
| ACT | ACA | GTT | AGG | CTA | CGA | GCG | TAC | ATG | AAC | ACC | GCG | GGG | CTT | CCC | GTG | 240 |
| Thr | Thr | Val | Arg | Leu | Arg | Ala | Tyr | Met | Asn | Thr | Ala | Gly | Leu | Pro | Val | |
| 65 | | | | | 70 | | | | | 75 | | | | | 80 | |
| TGC | CAG | GAC | CAT | CTT | GAA | TTT | TGG | GAG | GGC | GTC | TTT | ACA | GGC | CTC | ACT | 288 |
| Cys | Gln | Asp | His | Leu | Glu | Phe | Trp | Glu | Gly | Val | Phe | Thr | Gly | Leu | Thr | |
| | | | | 85 | | | | | 90 | | | | | 95 | | |
| CAT | ATA | GAT | GCC | CAC | TTT | CTA | TCC | CAG | ACA | AAG | CAG | AGT | GGG | GAG | AAC | 336 |
| His | Ile | Asp | Ala | His | Phe | Leu | Ser | Gln | Thr | Lys | Gln | Ser | Gly | Glu | Asn | |
| | | | 100 | | | | | 105 | | | | | 110 | | | |
| CTT | CCT | TAC | CTG | GTA | GCG | TAC | CAA | GCC | ACC | GTG | TGC | GCT | AGG | GCT | CAA | 384 |
| Leu | Pro | Tyr | Leu | Val | Ala | Tyr | Gln | Ala | Thr | Val | Cys | Ala | Arg | Ala | Gln | |
| | | 115 | | | | | 120 | | | | | 125 | | | | |
| GCC | CCT | CCC | CCA | TCG | TGG | GAC | CAG | ATG | TGG | AAG | TGT | TTG | ATT | CGC | CTC | 432 |
| Ala | Pro | Pro | Pro | Ser | Trp | Asp | Gln | Met | Trp | Lys | Cys | Leu | Ile | Arg | Leu | |
| | 130 | | | | | 135 | | | | | 140 | | | | | |
| AAG | CCC | ACC | CTC | CAT | GGG | CCA | ACA | CCC | CTG | CTA | TAC | AGA | CTG | GGC | GCT | 480 |
| Lys | Pro | Thr | Leu | His | Gly | Pro | Thr | Pro | Leu | Leu | Tyr | Arg | Leu | Gly | Ala | |
| 145 | | | | 150 | | | | | 155 | | | | | 160 | | |

(2) INFORMATION FOR SEQ ID NO:18:

(i) SEQUENCE CHARACTERISTICS:
    (A) LENGTH: 160 amino acids
    (B) TYPE: amino acid
    (D) TOPOLOGY: linear (ii) MOLECULE TYPE: protein (xi) SEQUENCE DESCRIPTION: SEQ ID NO:18:

Ser Ile Glu Thr Ile Thr Leu Pro Gln Asp Ala Val Ser Arg Thr Gln
 1               5                  10                  15

Arg Arg Gly Arg Thr Gly Arg Gly Lys Pro Gly Ile Tyr Arg Phe Val
            20                  25                  30

Ala Pro Gly Glu Arg Pro Ser Gly Met Phe Asp Ser Ser Val Leu Cys
        35                  40                  45

Glu Cys Tyr Asp Ala Gly Cys Ala Trp Tyr Glu Leu Thr Pro Ala Glu
    50                  55                  60

Thr Thr Val Arg Leu Arg Ala Tyr Met Asn Thr Ala Gly Leu Pro Val

```
                    65                  70                  75                  80
        Cys Gln Asp His Leu Glu Phe Trp Glu Gly Val Phe Thr Gly Leu Thr
                                85                  90                  95

His Ile Asp Ala His Phe Leu Ser Gln Thr Lys Gln Ser Gly Glu Asn
                            100                 105                 110

Leu Pro Tyr Leu Val Ala Tyr Gln Ala Thr Val Cys Ala Arg Ala Gln
                        115                 120                 125

Ala Pro Pro Ser Trp Asp Gln Met Trp Lys Cys Leu Ile Arg Leu
                    130                 135                 140

Lys Pro Thr Leu His Gly Pro Thr Pro Leu Leu Tyr Arg Leu Gly Ala
        145                 150                 155                 160

(2) INFORMATION FOR SEQ ID NO:19:

(i) SEQUENCE CHARACTERISTICS:
        (A) LENGTH: 1382 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..1380

(xi) SEQUENCE DESCRIPTION: SEQ ID NO:19:

TCC ATT GAG ACA ATC ACG CTC CCC CAG GAT GCT GTC TCC CGC ACT CAA        48
Ser Ile Glu Thr Ile Thr Leu Pro Gln Asp Ala Val Ser Arg Thr Gln
 1               5                  10                  15

CGT CGG GGC AGG ACT GGC AGG GGG AAG CCA GGC ATC TAC AGA TTT GTG        96
Arg Arg Gly Arg Thr Gly Arg Gly Lys Pro Gly Ile Tyr Arg Phe Val
                20                  25                  30

GCA CCG GGG GAG CGC CCC TCC GGC ATG TTC GAC TCG TCC GTC CTC TGT       144
Ala Pro Gly Glu Arg Pro Ser Gly Met Phe Asp Ser Ser Val Leu Cys
            35                  40                  45

GAG TGC TAT GAC GCA GGC TGT GCT TGG TAT GAG CTC ACG CCC GCC GAG       192
Glu Cys Tyr Asp Ala Gly Cys Ala Trp Tyr Glu Leu Thr Pro Ala Glu
        50                  55                  60

ACT ACA GTT AGG CTA CGA GCG TAC ATG AAC ACC CCG GGG CTT CCC GTG       240
Thr Thr Val Arg Leu Arg Ala Tyr Met Asn Thr Pro Gly Leu Pro Val
 65                 70                  75                  80

TGC CAG GAC CAT CTT GAA TTT TGG GAG CGC GTC TTT ACA GGC CTC ACT       288
Cys Gln Asp His Leu Glu Phe Trp Glu Arg Val Phe Thr Gly Leu Thr
                85                  90                  95

CAT ATA GAT GCC CAC TTT CTA TCC CAG ACA AAG CAG AGT GGG GAG AAC       336
His Ile Asp Ala His Phe Leu Ser Gln Thr Lys Gln Ser Gly Glu Asn
            100                 105                 110

CTT CCT TAC CTG GTA GCG TAC CAA GCC ACC GTG TGC GCT AGG GCT CAA       384
Leu Pro Tyr Leu Val Ala Tyr Gln Ala Thr Val Cys Ala Arg Ala Gln
        115                 120                 125

GCC CCT CCC CCA TCG TGG GAC CAG ATG TGG AAG TGT TTG ATT CGC CTC       432
Ala Pro Pro Pro Ser Trp Asp Gln Met Trp Lys Cys Leu Ile Arg Leu
    130                 135                 140

AAG CCC ACC CTC CAT GGG CCA ACA CCC CTG CTA TAC AGA CTG GGC GCT       480
Lys Pro Thr Leu His Gly Pro Thr Pro Leu Leu Tyr Arg Leu Gly Ala
145                 150                 155                 160

GTT CAG AAT GAA ATC ACC CTG ACG CAC CCA GTC ACC AAA TAC ATC ATG       528
Val Gln Asn Glu Ile Thr Leu Thr His Pro Val Thr Lys Tyr Ile Met
                165                 170                 175

ACA TGC ATG TCG GCC GAC CTG GAG GTC GTC ACG AGC ACC TGG GTG CTC       576
```

```
                Thr Cys Met Ser Ala Asp Leu Glu Val Val Thr Ser Thr Trp Val Leu
                            180                 185                 190

GTT GGC GGC GTC CTG GCT GCT TTG GCC GCG TAT TGC CTG TCA ACA GGC            624
Val Gly Gly Val Leu Ala Ala Leu Ala Ala Tyr Cys Leu Ser Thr Gly
            195                 200                 205

TGC GTG GTC ATA GTG GGC AGG GTC GTC TTG TCC GGG AAG CCG GCA ATC            672
Cys Val Val Ile Val Gly Arg Val Val Leu Ser Gly Lys Pro Ala Ile
210                 215                 220

ATA CCT GAC AGG GAA GTC CTC TAC CGA GAG TTC GAT GAG ATG GAA GAG            720
Ile Pro Asp Arg Glu Val Leu Tyr Arg Glu Phe Asp Glu Met Glu Glu
225                 230                 235                 240

TGC TCT CAG CAC TTA CCG TAC ATC GAG CAA GGG ATG ATG CTC GCC GAG            768
Cys Ser Gln His Leu Pro Tyr Ile Glu Gln Gly Met Met Leu Ala Glu
                245                 250                 255

CAG TTC AAG CAG AAG GCC CTC GGC CTC CTG CAG ACC GCG TCC CGT CAG            816
Gln Phe Lys Gln Lys Ala Leu Gly Leu Leu Gln Thr Ala Ser Arg Gln
            260                 265                 270

GCA GAG GTT ATC GCC CCT GCT GTC CAG ACC AAC TGG CAA AAA CTC GAG            864
Ala Glu Val Ile Ala Pro Ala Val Gln Thr Asn Trp Gln Lys Leu Glu
        275                 280                 285

ACC TTC TGG GCG AAG CAT ATG TGG AAC TTC ATC AGT GGG ATA CAA TAC            912
Thr Phe Trp Ala Lys His Met Trp Asn Phe Ile Ser Gly Ile Gln Tyr
    290                 295                 300

TTG GCG GGC TTG TCA ACG CTG CCT GGT AAC CCC GCC ATT GCT TCA TTG            960
Leu Ala Gly Leu Ser Thr Leu Pro Gly Asn Pro Ala Ile Ala Ser Leu
305                 310                 315                 320

ATG GCT TTT ACA GCT GCT GTC ACC AGC CCA CTA ACC ACT AGC CAA ACC           1008
Met Ala Phe Thr Ala Ala Val Thr Ser Pro Leu Thr Thr Ser Gln Thr
                325                 330                 335

CTC CTC TTC AAC ATA TTG GGG GGG TGG GTG GCT GCC CAG CTC GCC GCC           1056
Leu Leu Phe Asn Ile Leu Gly Gly Trp Val Ala Ala Gln Leu Ala Ala
            340                 345                 350

CCC GGT GCC GCT ACT GCC TTT GTG GGC GCT GGC TTA GCT GGC GCC GCC           1104
Pro Gly Ala Ala Thr Ala Phe Val Gly Ala Gly Leu Ala Gly Ala Ala
        355                 360                 365

ATC GGC AGT GTT GGA CTG GGG AAG GTC CTC ATA GAC ATC CTT GCA GGG           1152
Ile Gly Ser Val Gly Leu Gly Lys Val Leu Ile Asp Ile Leu Ala Gly
    370                 375                 380

TAT GGC GCG GGC GTG GCG GGA GCT CTT GTG GCA TTC AAG ATC ATG AGC           1200
Tyr Gly Ala Gly Val Ala Gly Ala Leu Val Ala Phe Lys Ile Met Ser
385                 390                 395                 400

GGT GAG GTC CCC TCC ACG GAG GAC CTG GTC AAT CTA CTG CCC GCC ATC           1248
Gly Glu Val Pro Ser Thr Glu Asp Leu Val Asn Leu Leu Pro Ala Ile
                405                 410                 415

CTC TCG CCC GGA GCC CTC GTA GTC GGC GTG GTC TGT GCA GCA ATA CTG           1296
Leu Ser Pro Gly Ala Leu Val Val Gly Val Val Cys Ala Ala Ile Leu
            420                 425                 430

CGC CGG CAC GTT GGC CCG GGC GAG GGG GCA GTG CAG TGG ATG AAC CGG           1344
Arg Arg His Val Gly Pro Gly Glu Gly Ala Val Gln Trp Met Asn Arg
        435                 440                 445

CTG ATA GCC TTC GCC TCC CGG GGG AAC CAT GTT TCC CC                        1382
Leu Ile Ala Phe Ala Ser Arg Gly Asn His Val Ser
    450                 455                 460

(2) INFORMATION FOR SEQ ID NO:20:

(i) SEQUENCE CHARACTERISTICS:
            (A) LENGTH: 460 amino acids
            (B) TYPE: amino acid
            (D) TOPOLOGY: linear
```

(ii) MOLECULE TYPE: protein (xi) SEQUENCE DESCRIPTION: SEQ ID NO:20:

```
Ser Ile Glu Thr Ile Thr Leu Pro Gln Asp Ala Val Ser Arg Thr Gln
 1               5                  10                  15

Arg Arg Gly Arg Thr Gly Arg Gly Lys Pro Gly Ile Tyr Arg Phe Val
                20                  25                  30

Ala Pro Gly Glu Arg Pro Ser Gly Met Phe Asp Ser Ser Val Leu Cys
                35                  40                  45

Glu Cys Tyr Asp Ala Gly Cys Ala Trp Tyr Glu Leu Thr Pro Ala Glu
        50                  55                  60

Thr Thr Val Arg Leu Arg Ala Tyr Met Asn Thr Pro Gly Leu Pro Val
 65                 70                  75                  80

Cys Gln Asp His Leu Glu Phe Trp Glu Arg Val Phe Thr Gly Leu Thr
                85                  90                  95

His Ile Asp Ala His Phe Leu Ser Gln Thr Lys Gln Ser Gly Glu Asn
                100                 105                 110

Leu Pro Tyr Leu Val Ala Tyr Gln Ala Thr Val Cys Ala Arg Ala Gln
            115                 120                 125

Ala Pro Pro Pro Ser Trp Asp Gln Met Trp Lys Cys Leu Ile Arg Leu
130                 135                 140

Lys Pro Thr Leu His Gly Pro Thr Pro Leu Leu Tyr Arg Leu Gly Ala
145                 150                 155                 160

Val Gln Asn Glu Ile Thr Leu Thr His Pro Val Thr Lys Tyr Ile Met
                165                 170                 175

Thr Cys Met Ser Ala Asp Leu Glu Val Val Thr Ser Thr Trp Val Leu
                180                 185                 190

Val Gly Gly Val Leu Ala Ala Leu Ala Ala Tyr Cys Leu Ser Thr Gly
            195                 200                 205

Cys Val Val Ile Val Gly Arg Val Val Leu Ser Gly Lys Pro Ala Ile
            210                 215                 220

Ile Pro Asp Arg Glu Val Leu Tyr Arg Glu Phe Asp Glu Met Glu Glu
225                 230                 235                 240

Cys Ser Gln His Leu Pro Tyr Ile Glu Gln Gly Met Met Leu Ala Glu
                245                 250                 255

Gln Phe Lys Gln Lys Ala Leu Gly Leu Leu Gln Thr Ala Ser Arg Gln
                260                 265                 270

Ala Glu Val Ile Ala Pro Ala Val Gln Thr Asn Trp Gln Lys Leu Glu
            275                 280                 285

Thr Phe Trp Ala Lys His Met Trp Asn Phe Ile Ser Gly Ile Gln Tyr
290                 295                 300

Leu Ala Gly Leu Ser Thr Leu Pro Gly Asn Pro Ala Ile Ala Ser Leu
305                 310                 315                 320

Met Ala Phe Thr Ala Ala Val Thr Ser Pro Leu Thr Thr Ser Gln Thr
                325                 330                 335

Leu Leu Phe Asn Ile Leu Gly Gly Trp Val Ala Ala Gln Leu Ala Ala
                340                 345                 350

Pro Gly Ala Ala Thr Ala Phe Val Gly Ala Gly Leu Ala Gly Ala Ala
            355                 360                 365

Ile Gly Ser Val Gly Leu Gly Lys Val Leu Ile Asp Ile Leu Ala Gly
            370                 375                 380

Tyr Gly Ala Gly Val Ala Gly Ala Leu Val Ala Phe Lys Ile Met Ser
385                 390                 395                 400
```

```
Gly Glu Val Pro Ser Thr Glu Asp Leu Val Asn Leu Leu Pro Ala Ile
            405                 410                 415

Leu Ser Pro Gly Ala Leu Val Gly Val Val Cys Ala Ala Ile Leu
            420                 425                 430

Arg Arg His Val Gly Pro Gly Glu Gly Ala Val Gln Trp Met Asn Arg
            435                 440                 445

Leu Ile Ala Phe Ala Ser Arg Gly Asn His Val Ser
            450                 455                 460
```

(2) INFORMATION FOR SEQ ID NO:21:

(i) SEQUENCE CHARACTERISTICS:
        (A) LENGTH: 268 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..267

(xi) SEQUENCE DESCRIPTION: SEQ ID NO:21:

```
CTC GCC GCA AAG CTG GTC GCA TTG GGC ATC AAT GCC GTG GCC TAC TAC     48
Leu Ala Ala Lys Leu Val Ala Leu Gly Ile Asn Ala Val Ala Tyr Tyr
 1               5                  10                  15

CGC GGT CTT GAC GTG TCC GTC ATC CCG ACC AGC GGC GAT GTT GTC GTC     96
Arg Gly Leu Asp Val Ser Val Ile Pro Thr Ser Gly Asp Val Val Val
                20                  25                  30

GTG GCA ACC GAT GCC CTC ATG ACC GGC TAT ACC GGC GAC TTC GAC TCG    144
Val Ala Thr Asp Ala Leu Met Thr Gly Tyr Thr Gly Asp Phe Asp Ser
            35                  40                  45

GTG ATA GAC TAC AAT ACG TGT GTC ACC CAG ACA GTC GAT TTC AGC CTT    192
Val Ile Asp Tyr Asn Thr Cys Val Thr Gln Thr Val Asp Phe Ser Leu
    50                  55                  60

GAC CCT ACC TTC ACC ATT GAG ACA ATC ACG CTC CCC CAG GAT GCT GTC    240
Asp Pro Thr Phe Thr Ile Glu Thr Ile Thr Leu Pro Gln Asp Ala Val
65                  70                  75                  80

TCC CGC ACT CAA CGT CGG GGC AGG ACT G                              268
Ser Arg Thr Gln Arg Arg Gly Arg Thr
                85
```

(2) INFORMATION FOR SEQ ID NO:22:

(i) SEQUENCE CHARACTERISTICS:
        (A) LENGTH: 89 amino acids
        (B) TYPE: amino acid
        (D) TOPOLOGY: linear (ii) MOLECULE TYPE: protein (xi) SEQUENCE DESCRIPTION: SEQ ID NO:22:

```
Leu Ala Ala Lys Leu Val Ala Leu Gly Ile Asn Ala Val Ala Tyr Tyr
 1               5                  10                  15

Arg Gly Leu Asp Val Ser Val Ile Pro Thr Ser Gly Asp Val Val Val
                20                  25                  30

Val Ala Thr Asp Ala Leu Met Thr Gly Tyr Thr Gly Asp Phe Asp Ser
            35                  40                  45

Val Ile Asp Tyr Asn Thr Cys Val Thr Gln Thr Val Asp Phe Ser Leu
    50                  55                  60

Asp Pro Thr Phe Thr Ile Glu Thr Ile Thr Leu Pro Gln Asp Ala Val
65                  70                  75                  80
```

```
Ser Arg Thr Gln Arg Arg Gly Arg Thr
            85
```

(2) INFORMATION FOR SEQ ID NO:23:

(i) SEQUENCE CHARACTERISTICS:
        (A) LENGTH: 319 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 2..319

(xi) SEQUENCE DESCRIPTION: SEQ ID NO:23:

```
G ATG AAC CGG CTG ATA GCC TTC GCC TCC CGG GGG AAC CAT GTT TCC        46
  Met Asn Arg Leu Ile Ala Phe Ala Ser Arg Gly Asn His Val Ser
    1               5                  10                  15

CCC ACG CAC TAC GTG CCG GAG AGC GAT GCA GCT GCC CGC GTC ACT GCC      94
Pro Thr His Tyr Val Pro Glu Ser Asp Ala Ala Ala Arg Val Thr Ala
             20                  25                  30

ATA CTC AGC AGC CTC ACT GTA ACC CAG CTC CTG AGG CGA CTG CAC CAG      142
Ile Leu Ser Ser Leu Thr Val Thr Gln Leu Leu Arg Arg Leu His Gln
         35                  40                  45

TGG ATA AGC TCG GAG TGT ACC ACT CCA TGC TCC GGT TCC TGG CTA AGG      190
Trp Ile Ser Ser Glu Cys Thr Thr Pro Cys Ser Gly Ser Trp Leu Arg
     50                  55                  60

GAC ATC TGG GAC TGG ATA TGC GAG GTG TTG AGC GAC TTT AAG ACC TGG      238
Asp Ile Trp Asp Trp Ile Cys Glu Val Leu Ser Asp Phe Lys Thr Trp
 65                  70                  75

CTA AAA GCT AAG CTC ATG CCA CAG CTG CCT GGG ATC CCC TTT GTG TCC      286
Leu Lys Ala Lys Leu Met Pro Gln Leu Pro Gly Ile Pro Phe Val Ser
 80                  85                  90                  95

TGC CAG CGC GGG TAT AAG GGG GTC TGG CGA GTG                          319
Cys Gln Arg Gly Tyr Lys Gly Val Trp Arg Val
                 100                 105
```

(2) INFORMATION FOR SEQ ID NO:24:

(i) SEQUENCE CHARACTERISTICS:
        (A) LENGTH: 106 amino acids
        (B) TYPE: amino acid
        (D) TOPOLOGY: linear (ii) MOLECULE TYPE: protein (xi) SEQUENCE DESCRIPTION: SEQ ID NO:24:

```
Met Asn Arg Leu Ile Ala Phe Ala Ser Arg Gly Asn His Val Ser Pro
  1               5                  10                  15

Thr His Tyr Val Pro Glu Ser Asp Ala Ala Ala Arg Val Thr Ala Ile
             20                  25                  30

Leu Ser Ser Leu Thr Val Thr Gln Leu Leu Arg Arg Leu His Gln Trp
         35                  40                  45

Ile Ser Ser Glu Cys Thr Thr Pro Cys Ser Gly Ser Trp Leu Arg Asp
     50                  55                  60

Ile Trp Asp Trp Ile Cys Glu Val Leu Ser Asp Phe Lys Thr Trp Leu
 65                  70                  75                  80

Lys Ala Lys Leu Met Pro Gln Leu Pro Gly Ile Pro Phe Val Ser Cys
                 85                  90                  95
```

```
Gln Arg Gly Tyr Lys Gly Val Trp Arg Val
            100                 105
```

(2) INFORMATION FOR SEQ ID NO:25:

(i) SEQUENCE CHARACTERISTICS:
        (A) LENGTH: 492 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 2..490

(xi) SEQUENCE DESCRIPTION: SEQ ID NO:25:

```
G GCT TAC ATG TCC AAG GCT CAT GGG ATC GAT CCT AAC ATC AGG ACC        46
  Ala Tyr Met Ser Lys Ala His Gly Ile Asp Pro Asn Ile Arg Thr
   1               5                  10                  15

GGG GTG AGA ACA ATT ACC ACT GGC AGC CCC ATC ACG TAC TCC ACC TAC      94
Gly Val Arg Thr Ile Thr Thr Gly Ser Pro Ile Thr Tyr Ser Thr Tyr
                 20                  25                  30

GGC AAG TTC CTT GCC GAC GGC GGG TGC TCG GGG GGC GCT TAT GAC ATA     142
Gly Lys Phe Leu Ala Asp Gly Gly Cys Ser Gly Gly Ala Tyr Asp Ile
             35                  40                  45

ATA ATT TGT GAC GAG TGC CAC TCC ACG GAT GCC ACA TCC ATC TTG GGC     190
Ile Ile Cys Asp Glu Cys His Ser Thr Asp Ala Thr Ser Ile Leu Gly
     50                  55                  60

ATC GGC ACT GTC CTT GAC CAA GCA GAG ACT GCG GGG GCG AGA CTG GTT     238
Ile Gly Thr Val Leu Asp Gln Ala Glu Thr Ala Gly Ala Arg Leu Val
 65                  70                  75

GTG CTC GCC ACC GCC ACC CCT CCG GGC TCC GTC ACT GTG CCC CAT CCC     286
Val Leu Ala Thr Ala Thr Pro Pro Gly Ser Val Thr Val Pro His Pro
 80                  85                  90                  95

AAC ATC GAG GAG GTT GCT CTG TCC ACC ACC GGA GAG ATC CCT TTT TAC     334
Asn Ile Glu Glu Val Ala Leu Ser Thr Thr Gly Glu Ile Pro Phe Tyr
                100                 105                 110

GGC AAG GCT ATC CCC CTC GAA GTA ATC AAG GGG GGG AGA CAT CTC ATC     382
Gly Lys Ala Ile Pro Leu Glu Val Ile Lys Gly Gly Arg His Leu Ile
            115                 120                 125

TTC TGT CAT TCA AAG AAG AAG TGC GAC GAA CTC GCC GCA AAG CTG GTC     430
Phe Cys His Ser Lys Lys Lys Cys Asp Glu Leu Ala Ala Lys Leu Val
        130                 135                 140

GCA TTG GGC ATC AAT GCC GTG GCC TAC TAC CGC GGT CTT GAC GTG TCC     478
Ala Leu Gly Ile Asn Ala Val Ala Tyr Tyr Arg Gly Leu Asp Val Ser
    145                 150                 155

GTC ATC CCG ACC AG                                                   492
Val Ile Pro Thr
160
```

(2) INFORMATION FOR SEQ ID NO:26:

(i) SEQUENCE CHARACTERISTICS:
        (A) LENGTH: 163 amino acids
        (B) TYPE: amino acid
        (D) TOPOLOGY: linear (ii) MOLECULE TYPE: protein (xi) SEQUENCE DESCRIPTION: SEQ ID NO:26:

```
Ala Tyr Met Ser Lys Ala His Gly Ile Asp Pro Asn Ile Arg Thr Gly
 1               5                  10                  15
```

-continued

```
Val Arg Thr Ile Thr Thr Gly Ser Pro Ile Thr Tyr Ser Thr Tyr Gly
             20                  25                  30

Lys Phe Leu Ala Asp Gly Gly Cys Ser Gly Gly Ala Tyr Asp Ile Ile
         35                  40                  45

Ile Cys Asp Glu Cys His Ser Thr Asp Ala Thr Ser Ile Leu Gly Ile
     50                  55                  60

Gly Thr Val Leu Asp Gln Ala Glu Thr Ala Gly Ala Arg Leu Val Val
 65                  70                  75                  80

Leu Ala Thr Ala Thr Pro Pro Gly Ser Val Thr Val Pro His Pro Asn
                 85                  90                  95

Ile Glu Glu Val Ala Leu Ser Thr Thr Gly Glu Ile Pro Phe Tyr Gly
             100                 105                 110

Lys Ala Ile Pro Leu Glu Val Ile Lys Gly Gly Arg His Leu Ile Phe
         115                 120                 125

Cys His Ser Lys Lys Lys Cys Asp Glu Leu Ala Ala Lys Leu Val Ala
     130                 135                 140

Leu Gly Ile Asn Ala Val Ala Tyr Tyr Arg Gly Leu Asp Val Ser Val
145                 150                 155                 160

Ile Pro Thr
```

(2) INFORMATION FOR SEQ ID NO:27:

(i) SEQUENCE CHARACTERISTICS:
        (A) LENGTH: 531 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 3..530

(xi) SEQUENCE DESCRIPTION: SEQ ID NO:27:

```
AC TGC AGC CTC ACT GTA ACC CAG CTC CTG AGG CGA CTG CAC CAG TGG        47
   Cys Ser Leu Thr Val Thr Gln Leu Leu Arg Arg Leu His Gln Trp
    1               5                  10                  15

ATA AGC TCG GAG TGT ACC ACT CCA TGC TCC GGT TCC TGG CTA AGG GAC       95
Ile Ser Ser Glu Cys Thr Thr Pro Cys Ser Gly Ser Trp Leu Arg Asp
                 20                  25                  30

ATC TGG GAC TGG ATA TGC GAG GTG TTG AGC GAC TTT AAG ACC TGG CTA      143
Ile Trp Asp Trp Ile Cys Glu Val Leu Ser Asp Phe Lys Thr Trp Leu
             35                  40                  45

AAA GCT AAG CTC ATG CCA CAG CTG CCT GGG ATC CCC TTT GTG TCC TGC      191
Lys Ala Lys Leu Met Pro Gln Leu Pro Gly Ile Pro Phe Val Ser Cys
         50                  55                  60

CAG CGC GGG TAT AAG GGG GTC TGG CGA GGG GAC GGC ATC ATG CAC ACT      239
Gln Arg Gly Tyr Lys Gly Val Trp Arg Gly Asp Gly Ile Met His Thr
 65                  70                  75

CGC TGC CAC TGT GGA GCT GAG ATC ACT GGA CAT GTC AAA AAC GGG ACG      287
Arg Cys His Cys Gly Ala Glu Ile Thr Gly His Val Lys Asn Gly Thr
 80                  85                  90                  95

ATG AGG ATC GTC GGT CCT AGG ACC TGC AGG AAC ATG TGG AGT GGG ACC      335
Met Arg Ile Val Gly Pro Arg Thr Cys Arg Asn Met Trp Ser Gly Thr
             100                 105                 110

TTC CCC ATT AAT GCC TAC ACC ACG GGC CCC TGT ACC CCC CTT CCT GCG      383
Phe Pro Ile Asn Ala Tyr Thr Thr Gly Pro Cys Thr Pro Leu Pro Ala
         115                 120                 125

CCG AAC TAC ACG TTC GCG CTA TGG AGG GTG TCT GCA GAG GAA TAT GTG      431
```

```
Pro Asn Tyr Thr Phe Ala Leu Trp Arg Val Ser Ala Glu Glu Tyr Val
            130                 135                 140

GAG ATA AGG CAG GTG GGG GAC TTC CAC TAC GTG ACG GGT ATG ACT ACT        479
Glu Ile Arg Gln Val Gly Asp Phe His Tyr Val Thr Gly Met Thr Thr
145                 150                 155

GAC AAT CTC AAA TGC CCG TGC CAG GTC CCA TCG CCC GAA TTT TTC ACA        527
Asp Asn Leu Lys Cys Pro Cys Gln Val Pro Ser Pro Glu Phe Phe Thr
160                 165                 170                 175

GAA T                                                                  531
Glu (2) INFORMATION FOR SEQ ID NO:28:

(i) SEQUENCE CHARACTERISTICS:
        (A) LENGTH: 176 amino acids
        (B) TYPE: amino acid
        (D) TOPOLOGY: linear (ii) MOLECULE TYPE: protein (xi) SEQUENCE DESCRIPTION: SEQ ID NO:28:

Cys Ser Leu Thr Val Thr Gln Leu Leu Arg Arg Leu His Gln Trp Ile
1               5                   10                  15

Ser Ser Glu Cys Thr Thr Pro Cys Ser Gly Ser Trp Leu Arg Asp Ile
            20                  25                  30

Trp Asp Trp Ile Cys Glu Val Leu Ser Asp Phe Lys Thr Trp Leu Lys
        35                  40                  45

Ala Lys Leu Met Pro Gln Leu Pro Gly Ile Pro Phe Val Ser Cys Gln
    50                  55                  60

Arg Gly Tyr Lys Gly Val Trp Arg Gly Asp Gly Ile Met His Thr Arg
65                  70                  75                  80

Cys His Cys Gly Ala Glu Ile Thr Gly His Val Lys Asn Gly Thr Met
                85                  90                  95

Arg Ile Val Gly Pro Arg Thr Cys Arg Asn Met Trp Ser Gly Thr Phe
            100                 105                 110

Pro Ile Asn Ala Tyr Thr Thr Gly Pro Cys Thr Pro Leu Pro Ala Pro
        115                 120                 125

Asn Tyr Thr Phe Ala Leu Trp Arg Val Ser Ala Glu Glu Tyr Val Glu
    130                 135                 140

Ile Arg Gln Val Gly Asp Phe His Tyr Val Thr Gly Met Thr Thr Asp
145                 150                 155                 160

Asn Leu Lys Cys Pro Cys Gln Val Pro Ser Pro Glu Phe Phe Thr Glu
                165                 170                 175

(2) INFORMATION FOR SEQ ID NO:29:

(i) SEQUENCE CHARACTERISTICS:
        (A) LENGTH: 2579 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 2..2578

(xi) SEQUENCE DESCRIPTION: SEQ ID NO:29:

T GCT TAC ATG TCC AAG GCT CAT GGG ATC GAT CCT AAC ATC AGG ACC          46
  Ala Tyr Met Ser Lys Ala His Gly Ile Asp Pro Asn Ile Arg Thr
  1               5                   10                  15
```

-continued

| | |
|---|---|
| GGG GTG AGA ACA ATT ACC ACT GGC AGC CCC ATC ACG TAC TCC ACC TAC<br>Gly Val Arg Thr Ile Thr Thr Gly Ser Pro Ile Thr Tyr Ser Thr Tyr<br>20                        25                  30 | 94 |
| GGC AAG TTC CTT GCC GAC GGC GGG TGC TCG GGG GGC GCT TAT GAC ATA<br>Gly Lys Phe Leu Ala Asp Gly Gly Cys Ser Gly Gly Ala Tyr Asp Ile<br>35                        40                  45 | 142 |
| ATA ATT TGT GAC GAG TGC CAC TCC ACG GAT GCC ACA TCC ATC TTG GGC<br>Ile Ile Cys Asp Glu Cys His Ser Thr Asp Ala Thr Ser Ile Leu Gly<br>50                        55                  60 | 190 |
| ATC GGC ACT GTC CTT GAC CAA GCA GAG ACT GCG GGG GCG AGA CTG GTT<br>Ile Gly Thr Val Leu Asp Gln Ala Glu Thr Ala Gly Ala Arg Leu Val<br>65                        70                  75 | 238 |
| GTG CTC GCC ACC GCC ACC CCT CCG GGC TCC GTC ACT GTG CCC CAT CCC<br>Val Leu Ala Thr Ala Thr Pro Pro Gly Ser Val Thr Val Pro His Pro<br>80                        85                  90                  95 | 286 |
| AAC ATC GAG GAG GTT GCT CTG TCC ACC ACC GGA GAG ATC CCT TTT TAC<br>Asn Ile Glu Glu Val Ala Leu Ser Thr Thr Gly Glu Ile Pro Phe Tyr<br>                    100                   105                  110 | 334 |
| GGC AAG GCT ATC CCC CTC GAA GTA ATC AAG GGG GGA AGA CAT CTC ATC<br>Gly Lys Ala Ile Pro Leu Glu Val Ile Lys Gly Gly Arg His Leu Ile<br>                    115                   120                  125 | 382 |
| TTC TGT CAT TCA AAG AAG AAG TGC GAC GAA CTC GCC GCA AAG CTG GTC<br>Phe Cys His Ser Lys Lys Lys Cys Asp Glu Leu Ala Ala Lys Leu Val<br>         130                   135                   140 | 430 |
| GCA TTG GGC ATC AAT GCC GTG GCC TAC TAC CGC GGT CTT GAC GTG TCC<br>Ala Leu Gly Ile Asn Ala Val Ala Tyr Tyr Arg Gly Leu Asp Val Ser<br>145                     150                   155 | 478 |
| GTC ATC CCG ACC AGC GGC GAT GTT GTC GTC GTG GCA ACC GAT GCC CTC<br>Val Ile Pro Thr Ser Gly Asp Val Val Val Val Ala Thr Asp Ala Leu<br>160                     165                   170                  175 | 526 |
| ATG ACC GGC TAT ACC GGC GAC TTC GAC TCG GTG ATA GAC TAC AAT ACG<br>Met Thr Gly Tyr Thr Gly Asp Phe Asp Ser Val Ile Asp Tyr Asn Thr<br>                    180                   185                  190 | 574 |
| TGT GTC ACC CAG ACA GTC GAT TTC AGC CTT GAC CCT ACC TTC ACC ATT<br>Cys Val Thr Gln Thr Val Asp Phe Ser Leu Asp Pro Thr Phe Thr Ile<br>         195                   200                   205 | 622 |
| GAG ACA ATC ACG CTC CCC CAG GAT GCT GTC TCC CGC ACT CAA CGT CGG<br>Glu Thr Ile Thr Leu Pro Gln Asp Ala Val Ser Arg Thr Gln Arg Arg<br>210                     215                   220 | 670 |
| GGC AGG ACT GGC AGG GGG AAG CCA GGC ATC TAC AGA TTT GTG GCA CCG<br>Gly Arg Thr Gly Arg Gly Lys Pro Gly Ile Tyr Arg Phe Val Ala Pro<br>225                     230                   235 | 718 |
| GGG CAG CGC CCC TCC GGC ATG TTC GAC TCG TCC GTC CTC TGT GAG TGC<br>Gly Gln Arg Pro Ser Gly Met Phe Asp Ser Ser Val Leu Cys Glu Cys<br>240                     245                   250                  255 | 766 |
| TAT GAC GCA GGC TGT GCT TGG TAT GAG CTC ACG CCC GCC GAG ACT ACA<br>Tyr Asp Ala Gly Cys Ala Trp Tyr Glu Leu Thr Pro Ala Glu Thr Thr<br>                    260                   265                  270 | 814 |
| GTT AGG CTA CGA GCG TAC ATG AAC ACC CCG GGG CTT CCC GTG TGC CAG<br>Val Arg Leu Arg Ala Tyr Met Asn Thr Pro Gly Leu Pro Val Cys Gln<br>         275                   280                   285 | 862 |
| GAC CAT CTT GAA TTT TGG GAG GGC GTC TTT ACA GGC CTC ACT CAT ATA<br>Asp His Leu Glu Phe Trp Glu Gly Val Phe Thr Gly Leu Thr His Ile<br>         290                   295                   300 | 910 |
| GAT GCC CAC TTT CTA TCC CAG ACA AAG CAG AGT GGG GAG AAC TTT CCT<br>Asp Ala His Phe Leu Ser Gln Thr Lys Gln Ser Gly Glu Asn Leu Pro<br>305                     310                   315 | 958 |
| TAC CTG GTA GCG TAC CAA GCC ACC GTG TGC GCT AGG GCT CAA GCC CCT<br>Tyr Leu Val Ala Tyr Gln Ala Thr Val Cys Ala Arg Ala Gln Ala Pro | 1006 |

-continued

| | | | | | | | | | | | | | | | | |
|---|---|---|---|---|---|---|---|---|---|---|---|---|---|---|---|---|
| 320 | | | | 325 | | | | 330 | | | | 335 | | | | |
| CCC | CCA | TCG | TGG | GAC | CAG | ATG | TGG | AAG | TGT | TTG | ATT | CGC | CTC | AAG | CCC | 1054 |
| Pro | Pro | Ser | Trp | Asp | Gln | Met | Trp | Lys | Cys | Leu | Ile | Arg | Leu | Lys | Pro | |
| | | | 340 | | | | | 345 | | | | | 350 | | | |
| ACC | CTC | CAT | GGG | CCA | ACA | CCC | CTG | CTA | TAC | AGA | CTG | GGC | GCT | GTT | CAG | 1102 |
| Thr | Leu | His | Gly | Pro | Thr | Pro | Leu | Leu | Tyr | Arg | Leu | Gly | Ala | Val | Gln | |
| | | | 355 | | | | | 360 | | | | | 365 | | | |
| AAT | GAA | ATC | ACC | CTG | ACG | CAC | CCA | GTC | ACC | AAA | TAC | ATC | ATG | ACA | TGC | 1150 |
| Asn | Glu | Ile | Thr | Leu | Thr | His | Pro | Val | Thr | Lys | Tyr | Ile | Met | Thr | Cys | |
| | | 370 | | | | | 375 | | | | | 380 | | | | |
| ATG | TCG | GCC | GAC | CTG | GAG | GTC | GTC | ACG | AGC | ACC | TGG | GTG | CTC | GTT | GGC | 1198 |
| Met | Ser | Ala | Asp | Leu | Glu | Val | Val | Thr | Ser | Thr | Trp | Val | Leu | Val | Gly | |
| | 385 | | | | | 390 | | | | | 395 | | | | | |
| GGC | GTC | CTG | GCT | GCT | TTG | GCC | GCG | TAT | TGC | CTG | TCA | ACA | GGC | TGC | GTG | 1246 |
| Gly | Val | Leu | Ala | Ala | Leu | Ala | Ala | Tyr | Cys | Leu | Ser | Thr | Gly | Cys | Val | |
| 400 | | | | | 405 | | | | | 410 | | | | | 415 | |
| GTC | ATA | GTG | GGC | AGG | GTC | GTC | TTG | TCC | GGG | AAG | CCG | GCA | ATC | ATA | CCT | 1294 |
| Val | Ile | Val | Gly | Arg | Val | Val | Leu | Ser | Gly | Lys | Pro | Ala | Ile | Ile | Pro | |
| | | | | 420 | | | | | 425 | | | | | 430 | | |
| GAC | AGG | GAA | GTC | CTC | TAC | CGA | GAG | TTC | GAT | GAG | ATG | GAA | GAG | TGC | TCT | 1342 |
| Asp | Arg | Glu | Val | Leu | Tyr | Arg | Glu | Phe | Asp | Glu | Met | Glu | Glu | Cys | Ser | |
| | | | | 435 | | | | | 440 | | | | | 445 | | |
| CAG | CAC | TTA | CCG | TAC | ATC | GAG | CAA | GGG | ATG | ATG | CTC | GCC | GAG | CAG | TTC | 1390 |
| Gln | His | Leu | Pro | Tyr | Ile | Glu | Gln | Gly | Met | Met | Leu | Ala | Glu | Gln | Phe | |
| | | | 450 | | | | | 455 | | | | | 460 | | | |
| AAG | CAG | AAG | GCC | CTC | GGC | CTC | CTG | CAG | ACC | GCG | TCC | CGT | CAG | GCA | GAG | 1438 |
| Lys | Gln | Lys | Ala | Leu | Gly | Leu | Leu | Gln | Thr | Ala | Ser | Arg | Gln | Ala | Glu | |
| | 465 | | | | | 470 | | | | | 475 | | | | | |
| GTT | ATC | GCC | CCT | GCT | GTC | CAG | ACC | AAC | TGG | CAA | AAA | CTC | GAG | ACC | TTC | 1486 |
| Val | Ile | Ala | Pro | Ala | Val | Gln | Thr | Asn | Trp | Gln | Lys | Leu | Glu | Thr | Phe | |
| 480 | | | | | 485 | | | | | 490 | | | | | 495 | |
| TGG | GCG | AAG | CAT | ATG | TGG | AAC | TTC | ATC | AGT | GGG | ATA | CAA | TAC | TTG | GCG | 1534 |
| Trp | Ala | Lys | His | Met | Trp | Asn | Phe | Ile | Ser | Gly | Ile | Gln | Tyr | Leu | Ala | |
| | | | | 500 | | | | | 505 | | | | | 510 | | |
| GGC | TTG | TCA | ACG | CTG | CCT | GGT | AAC | CCC | GCC | ATT | GCT | TCA | TTG | ATG | GCT | 1582 |
| Gly | Leu | Ser | Thr | Leu | Pro | Gly | Asn | Pro | Ala | Ile | Ala | Ser | Leu | Met | Ala | |
| | | | 515 | | | | | 520 | | | | | 525 | | | |
| TTT | ACA | GCT | GCT | GTC | ACC | AGC | CCA | CTA | ACC | ACT | AGC | CAA | ACC | CTC | CTC | 1630 |
| Phe | Thr | Ala | Ala | Val | Thr | Ser | Pro | Leu | Thr | Thr | Ser | Gln | Thr | Leu | Leu | |
| | | 530 | | | | | 535 | | | | | 540 | | | | |
| TTC | AAC | ATA | TTG | GGG | GGG | TGG | GTG | GCT | GCC | CAG | CTC | GCC | GCC | CCC | GGT | 1678 |
| Phe | Asn | Ile | Leu | Gly | Gly | Trp | Val | Ala | Ala | Gln | Leu | Ala | Ala | Pro | Gly | |
| | | 545 | | | | | 550 | | | | | 555 | | | | |
| GCC | GCT | ACT | GCC | TTT | GTG | GGC | GCT | GGC | TTA | GCT | GGC | GCC | GCC | ATC | GGC | 1726 |
| Ala | Ala | Thr | Ala | Phe | Val | Gly | Ala | Gly | Leu | Ala | Gly | Ala | Ala | Ile | Gly | |
| 560 | | | | | 565 | | | | | 570 | | | | | 575 | |
| AGT | GTT | GGA | CTG | GGG | AAG | GTC | CTC | ATA | GAC | ATC | CTT | GCA | GGG | TAT | GGC | 1774 |
| Ser | Val | Gly | Leu | Gly | Lys | Val | Leu | Ile | Asp | Ile | Leu | Ala | Gly | Tyr | Gly | |
| | | | 580 | | | | | 585 | | | | | 590 | | | |
| GCG | GGC | GTG | GCG | GGA | GCT | CTT | GTG | GCA | TTC | AAG | ATC | ATG | AGC | GGT | GAG | 1822 |
| Ala | Gly | Val | Ala | Gly | Ala | Leu | Val | Ala | Phe | Lys | Ile | Met | Ser | Gly | Glu | |
| | | | 595 | | | | | 600 | | | | | 605 | | | |
| GTC | CCC | TCC | ACG | GAG | GAC | CTG | GTC | AAT | CTA | CTG | CCC | GCC | ATC | CTC | TCG | 1870 |
| Val | Pro | Ser | Thr | Glu | Asp | Leu | Val | Asn | Leu | Leu | Pro | Ala | Ile | Leu | Ser | |
| | | 610 | | | | | 615 | | | | | 620 | | | | |
| CCC | GGA | GCC | CTC | GTA | GTC | GGC | GTG | GTC | TGT | GCA | GCA | ATA | CTG | CGC | CGG | 1918 |
| Pro | Gly | Ala | Leu | Val | Val | Gly | Val | Val | Cys | Ala | Ala | Ile | Leu | Arg | Arg | |
| | 625 | | | | | 630 | | | | | 635 | | | | | |
| CAC | GTT | GGC | CCG | GGC | GAG | GGG | GCA | GTG | CAG | TGG | ATG | AAC | CGG | CTG | ATA | 1966 |

```
His Val Gly Pro Gly Glu Gly Ala Val Gln Trp Met Asn Arg Leu Ile
640                 645                 650                 655

GCC TTC GCC TCC CGG GGG AAC CAT GTT TCC CCC ACG CAC TAC GTG CCG      2014
Ala Phe Ala Ser Arg Gly Asn His Val Ser Pro Thr His Tyr Val Pro
                660                 665                 670

GAG AGC GAT GCA GCT GCC CGC GTC ACT GCC ATA CTC AGC AGC CTC ACT      2062
Glu Ser Asp Ala Ala Ala Arg Val Thr Ala Ile Leu Ser Ser Leu Thr
            675                 680                 685

GTA ACC CAG CTC CTG AGG CGA CTG CAC CAG TGG ATA AGC TCG GAG TGT      2110
Val Thr Gln Leu Leu Arg Arg Leu His Gln Trp Ile Ser Ser Glu Cys
        690                 695                 700

ACC ACT CCA TGC TCC GGT TCC TGG CTA AGG GAC ATC TGG GAC TGG ATA      2158
Thr Thr Pro Cys Ser Gly Ser Trp Leu Arg Asp Ile Trp Asp Trp Ile
    705                 710                 715

TGC GAG GTG TTG AGC GAC TTT AAG ACC TGG CTA AAA GCT AAG CTC ATG      2206
Cys Glu Val Leu Ser Asp Phe Lys Thr Trp Leu Lys Ala Lys Leu Met
720                 725                 730                 735

CCA CAG CTG CCT GGG ATC CCC TTT GTG TCC TGC CAG CGC GGG TAT AAG      2254
Pro Gln Leu Pro Gly Ile Pro Phe Val Ser Cys Gln Arg Gly Tyr Lys
                740                 745                 750

GGG GTC TGG CGA GTG GAC GGC ATC ATG CAC ACT CGC TGC CAC TGT GGA      2302
Gly Val Trp Arg Val Asp Gly Ile Met His Thr Arg Cys His Cys Gly
            755                 760                 765

GCT GAG ATC ACT GGA CAT GTC AAA AAC GGG ACG ATG AGG ATC GTC GGT      2350
Ala Glu Ile Thr Gly His Val Lys Asn Gly Thr Met Arg Ile Val Gly
        770                 775                 780

CCT AGG ACC TGC AGG AAC ATG TGG AGT GGG ACC TTC CCC ATT AAT GCC      2398
Pro Arg Thr Cys Arg Asn Met Trp Ser Gly Thr Phe Pro Ile Asn Ala
    785                 790                 795

TAC ACC ACG GGC CCC TGT ACC CCC CTT CCT GCG CCG AAC TAC ACG TTC      2446
Tyr Thr Thr Gly Pro Cys Thr Pro Leu Pro Ala Pro Asn Tyr Thr Phe
800                 805                 810                 815

GCG CTA TGG AGG GTG TCT GCA GAG GAA TAT GTG GAG ATA AGG CAG GTG      2494
Ala Leu Trp Arg Val Ser Ala Glu Glu Tyr Val Glu Ile Arg Gln Val
                820                 825                 830

GGG GAC TTC CAC TAC GTG ACG GGT ATG ACT ACT GAC AAT CTC AAA TGC      2542
Gly Asp Phe His Tyr Val Thr Gly Met Thr Thr Asp Asn Leu Lys Cys
            835                 840                 845

CCG TGC CAG GTC CCA TCG CCC GAA TTT TTC ACA GAA T                    2579
Pro Cys Gln Val Pro Ser Pro Glu Phe Phe Thr Glu
        850                 855

(2) INFORMATION FOR SEQ ID NO:30:

(i) SEQUENCE CHARACTERISTICS:
        (A) LENGTH: 859 amino acids
        (B) TYPE: amino acid
        (D) TOPOLOGY: linear (ii) MOLECULE TYPE: protein (xi) SEQUENCE DESCRIPTION: SEQ ID NO:30:

Ala Tyr Met Ser Lys Ala His Gly Ile Asp Pro Asn Ile Arg Thr Gly
  1               5                  10                  15

Val Arg Thr Ile Thr Thr Gly Ser Pro Ile Thr Tyr Ser Thr Tyr Gly
                 20                  25                  30

Lys Phe Leu Ala Asp Gly Gly Cys Ser Gly Gly Ala Tyr Asp Ile Ile
             35                  40                  45

Ile Cys Asp Glu Cys His Ser Thr Asp Ala Thr Ser Ile Leu Gly Ile
         50                  55                  60
```

```
Gly Thr Val Leu Asp Gln Ala Glu Thr Ala Gly Ala Arg Leu Val Val
 65                  70                  75                  80

Leu Ala Thr Ala Thr Pro Pro Gly Ser Val Thr Val Pro His Pro Asn
                 85                  90                  95

Ile Glu Glu Val Ala Leu Ser Thr Thr Gly Glu Ile Pro Phe Tyr Gly
            100                 105                 110

Lys Ala Ile Pro Leu Glu Val Ile Lys Gly Gly Arg His Leu Ile Phe
            115                 120                 125

Cys His Ser Lys Lys Cys Asp Glu Leu Ala Ala Lys Leu Val Ala
130                 135                 140

Leu Gly Ile Asn Ala Val Ala Tyr Arg Gly Leu Asp Val Ser Val
145                 150                 155                 160

Ile Pro Thr Ser Gly Asp Val Val Val Ala Thr Asp Ala Leu Met
                165                 170                 175

Thr Gly Tyr Thr Gly Asp Phe Asp Ser Val Ile Asp Tyr Asn Thr Cys
                180                 185                 190

Val Thr Gln Thr Val Asp Phe Ser Leu Asp Pro Thr Phe Thr Ile Glu
                195                 200                 205

Thr Ile Thr Leu Pro Gln Asp Ala Val Ser Arg Thr Gln Arg Gly
            210                 215                 220

Arg Thr Gly Arg Gly Lys Pro Gly Ile Tyr Arg Phe Val Ala Pro Gly
225                 230                 235                 240

Gln Arg Pro Ser Gly Met Phe Asp Ser Ser Val Leu Cys Glu Cys Tyr
                245                 250                 255

Asp Ala Gly Cys Ala Trp Tyr Glu Leu Thr Pro Ala Glu Thr Thr Val
                260                 265                 270

Arg Leu Arg Ala Tyr Met Asn Thr Pro Gly Leu Pro Val Cys Gln Asp
            275                 280                 285

His Leu Glu Phe Trp Glu Gly Val Phe Thr Gly Leu Thr His Ile Asp
            290                 295                 300

Ala His Phe Leu Ser Gln Thr Lys Gln Ser Gly Glu Asn Leu Pro Tyr
305                 310                 315                 320

Leu Val Ala Tyr Gln Ala Thr Val Cys Ala Arg Ala Gln Ala Pro Pro
                325                 330                 335

Pro Ser Trp Asp Gln Met Trp Lys Cys Leu Ile Arg Leu Lys Pro Thr
                340                 345                 350

Leu His Gly Pro Thr Pro Leu Leu Tyr Arg Leu Gly Ala Val Gln Asn
            355                 360                 365

Glu Ile Thr Leu Thr His Pro Val Thr Lys Tyr Ile Met Thr Cys Met
    370                 375                 380

Ser Ala Asp Leu Glu Val Val Thr Ser Thr Trp Val Leu Val Gly Gly
385                 390                 395                 400

Val Leu Ala Ala Leu Ala Ala Tyr Cys Leu Ser Thr Gly Cys Val Val
                405                 410                 415

Ile Val Gly Arg Val Val Leu Ser Gly Lys Pro Ala Ile Ile Pro Asp
                420                 425                 430

Arg Glu Val Leu Tyr Arg Glu Phe Asp Glu Met Glu Glu Cys Ser Gln
            435                 440                 445

His Leu Pro Tyr Ile Glu Gln Gly Met Met Leu Ala Glu Gln Phe Lys
            450                 455                 460

Gln Lys Ala Leu Gly Leu Leu Gln Thr Ala Ser Arg Gln Ala Glu Val
465                 470                 475                 480

Ile Ala Pro Ala Val Gln Thr Asn Trp Gln Lys Leu Glu Thr Phe Trp
```

-continued

```
                       485                 490                 495
Ala Lys His Met Trp Asn Phe Ile Ser Gly Ile Gln Tyr Leu Ala Gly
                500                 505                 510
Leu Ser Thr Leu Pro Gly Asn Pro Ala Ile Ala Ser Leu Met Ala Phe
            515                 520                 525
Thr Ala Ala Val Thr Ser Pro Leu Thr Thr Ser Gln Thr Leu Leu Phe
        530                 535                 540
Asn Ile Leu Gly Gly Trp Val Ala Ala Gln Leu Ala Ala Pro Gly Ala
545                 550                 555                 560
Ala Thr Ala Phe Val Gly Ala Gly Leu Ala Gly Ala Ile Gly Ser
                565                 570                 575
Val Gly Leu Gly Lys Val Leu Ile Asp Ile Leu Ala Gly Tyr Gly Ala
                580                 585                 590
Gly Val Ala Gly Ala Leu Val Ala Phe Lys Ile Met Ser Gly Glu Val
                595                 600                 605
Pro Ser Thr Glu Asp Leu Val Asn Leu Leu Pro Ala Ile Leu Ser Pro
            610                 615                 620
Gly Ala Leu Val Val Gly Val Val Cys Ala Ala Ile Leu Arg Arg His
625                 630                 635                 640
Val Gly Pro Gly Glu Gly Ala Val Gln Trp Met Asn Arg Leu Ile Ala
                645                 650                 655
Phe Ala Ser Arg Gly Asn His Val Ser Pro Thr His Tyr Val Pro Glu
                660                 665                 670
Ser Asp Ala Ala Ala Arg Val Thr Ala Ile Leu Ser Ser Leu Thr Val
            675                 680                 685
Thr Gln Leu Leu Arg Arg Leu His Gln Trp Ile Ser Ser Glu Cys Thr
        690                 695                 700
Thr Pro Cys Ser Gly Ser Trp Leu Arg Asp Ile Trp Asp Trp Ile Cys
705                 710                 715                 720
Glu Val Leu Ser Asp Phe Lys Thr Trp Leu Lys Ala Lys Leu Met Pro
                725                 730                 735
Gln Leu Pro Gly Ile Pro Phe Val Ser Cys Gln Arg Gly Tyr Lys Gly
            740                 745                 750
Val Trp Arg Val Asp Gly Ile Met His Thr Arg Cys His Cys Gly Ala
        755                 760                 765
Glu Ile Thr Gly His Val Lys Asn Gly Thr Met Arg Ile Val Gly Pro
770                 775                 780
Arg Thr Cys Arg Asn Met Trp Ser Gly Thr Phe Pro Ile Asn Ala Tyr
785                 790                 795                 800
Thr Thr Gly Pro Cys Thr Pro Leu Pro Ala Pro Asn Tyr Thr Phe Ala
                805                 810                 815
Leu Trp Arg Val Ser Ala Glu Glu Tyr Val Glu Ile Arg Gln Val Gly
            820                 825                 830
Asp Phe His Tyr Val Thr Gly Met Thr Thr Asp Asn Leu Lys Cys Pro
        835                 840                 845
Cys Gln Val Pro Ser Pro Glu Phe Phe Thr Glu
    850                 855
```

(2) INFORMATION FOR SEQ ID NO:31:

(i) SEQUENCE CHARACTERISTICS:
        (A) LENGTH: 800 base pairs
        (B) TYPE: nucleic acid
        (C) STRANDEDNESS: single
        (D) TOPOLOGY: linear (ii) MOLECULE TYPE: cDNA (ix) FEATURE:
    (A) NAME/KEY: CDS
    (B) LOCATION: 2..799

(xi) SEQUENCE DESCRIPTION: SEQ ID NO:31:

```
G GCG GTG GAC TTT ATC CCT GTG GAG AAC CTA GAG ACA ACC ATG AGG        46
  Ala Val Asp Phe Ile Pro Val Glu Asn Leu Glu Thr Thr Met Arg
   1               5                  10                  15

TCC CCG GTG TTC ACG GAT AAC TCC TCT CCA CCA GTA GTG CCC CAG AGC      94
Ser Pro Val Phe Thr Asp Asn Ser Ser Pro Pro Val Val Pro Gln Ser
                 20                  25                  30

TTC CAG GTG GCT CAC CTC CAT GCT CCC ACA GGC AGC GGC AAA AGC ACC     142
Phe Gln Val Ala His Leu His Ala Pro Thr Gly Ser Gly Lys Ser Thr
                 35                  40                  45

AAG GTC CCG GCT GCA TAT GCA GCT CAG GGC TAT AAG GTG CTA GTA CTC     190
Lys Val Pro Ala Ala Tyr Ala Ala Gln Gly Tyr Lys Val Leu Val Leu
                 50                  55                  60

AAC CCC TCT GTT GCT GCA ACA CTG GGC TTT GGT GCT TAC ATG TCC AAG     238
Asn Pro Ser Val Ala Ala Thr Leu Gly Phe Gly Ala Tyr Met Ser Lys
 65                  70                  75

GCT CAT GGG ATC GAT CCT AAC ATC AGG ACC GGG GTG AGA ACA ATT ACC     286
Ala His Gly Ile Asp Pro Asn Ile Arg Thr Gly Val Arg Thr Ile Thr
 80                  85                  90                  95

ACT GGC AGC CCC ATC ACG TAC TCC ACC TAC GGC AAG TTC CTT GCC GAC     334
Thr Gly Ser Pro Ile Thr Tyr Ser Thr Tyr Gly Lys Phe Leu Ala Asp
                100                 105                 110

GGC GGG TGC TCG GGG GGC GCT TAT GAC ATA ATA ATT TGT GAC GAG TGC     382
Gly Gly Cys Ser Gly Gly Ala Tyr Asp Ile Ile Ile Cys Asp Glu Cys
                115                 120                 125

CAC TCC ACG GAT GCC ACA TCC ATC TTG GGC ATT GGC ACT GTC CTT GAC     430
His Ser Thr Asp Ala Thr Ser Ile Leu Gly Ile Gly Thr Val Leu Asp
                130                 135                 140

CAA GCA GAG ACT GCG GGG GCG AGA CTG GTT GTG CTC GCC ACC GCC ACC     478
Gln Ala Glu Thr Ala Gly Ala Arg Leu Val Val Leu Ala Thr Ala Thr
145                 150                 155

CCT CCG GGC TCC GTC ACT GTG CCC CAT CCC AAC ATC GAG GAG GTT GCT     526
Pro Pro Gly Ser Val Thr Val Pro His Pro Asn Ile Glu Glu Val Ala
160                 165                 170                 175

CTG TCC ACC ACC GGA GAG ATC CCT TTT TAC GGC AAG GCT ATC CCC CTC     574
Leu Ser Thr Thr Gly Glu Ile Pro Phe Tyr Gly Lys Ala Ile Pro Leu
                180                 185                 190

GAA GTA ATC AAG GGG GGG AGA CAT CTC ATC TTC TGT CAT TCA AAG AAG     622
Glu Val Ile Lys Gly Gly Arg His Leu Ile Phe Cys His Ser Lys Lys
                195                 200                 205

AAG TGC GAC GAA CTC GCC GCA AAG CTG GTC GCA TTG GGC ATC AAT GCC     670
Lys Cys Asp Glu Leu Ala Ala Lys Leu Val Ala Leu Gly Ile Asn Ala
                210                 215                 220

GTG GCC TAC TAC CGC GGT CTT GAC GTG TCC GTC ATC CCG ACC AGC GGC     718
Val Ala Tyr Tyr Arg Gly Leu Asp Val Ser Val Ile Pro Thr Ser Gly
225                 230                 235

GAT GTT GTC GTC GTG GCA ACC GAT GCC CTC ATG ACC GGC TAT ACC GGC     766
Asp Val Val Val Val Ala Thr Asp Ala Leu Met Thr Gly Tyr Thr Gly
240                 245                 250                 255

GAC TTC GAC TCG GTG ATA GAC TGC AAT ACG TGT G                       800
Asp Phe Asp Ser Val Ile Asp Cys Asn Thr Cys
                260                 265
```

(2) INFORMATION FOR SEQ ID NO:32:

(i) SEQUENCE CHARACTERISTICS:
    (A) LENGTH: 266 amino acids
    (B) TYPE: amino acid
    (D) TOPOLOGY: linear (ii) MOLECULE TYPE: protein (xi) SEQUENCE DESCRIPTION: SEQ ID NO:32:

Ala Val Asp Phe Ile Pro Val Glu Asn Leu Glu Thr Thr Met Arg Ser
 1               5                  10                  15

Pro Val Phe Thr Asp Asn Ser Ser Pro Val Pro Gln Ser Phe
             20                  25                  30

Gln Val Ala His Leu His Ala Pro Thr Gly Ser Gly Lys Ser Thr Lys
         35                  40                  45

Val Pro Ala Ala Tyr Ala Ala Gln Gly Tyr Lys Val Leu Val Leu Asn
     50                  55                  60

Pro Ser Val Ala Ala Thr Leu Gly Phe Gly Ala Tyr Met Ser Lys Ala
65                  70                  75                  80

His Gly Ile Asp Pro Asn Ile Arg Thr Gly Val Arg Thr Ile Thr Thr
             85                  90                  95

Gly Ser Pro Ile Thr Tyr Ser Thr Tyr Gly Lys Phe Leu Ala Asp Gly
            100                 105                 110

Gly Cys Ser Gly Gly Ala Tyr Asp Ile Ile Ile Cys Asp Glu Cys His
        115                 120                 125

Ser Thr Asp Ala Thr Ser Ile Leu Gly Ile Gly Thr Val Leu Asp Gln
    130                 135                 140

Ala Glu Thr Ala Gly Ala Arg Leu Val Val Leu Ala Thr Ala Thr Pro
145                 150                 155                 160

Pro Gly Ser Val Thr Val Pro His Pro Asn Ile Glu Glu Val Ala Leu
                165                 170                 175

Ser Thr Thr Gly Glu Ile Pro Phe Tyr Gly Lys Ala Ile Pro Leu Glu
            180                 185                 190

Val Ile Lys Gly Gly Arg His Leu Ile Phe Cys His Ser Lys Lys Lys
        195                 200                 205

Cys Asp Glu Leu Ala Ala Lys Leu Val Ala Leu Gly Ile Asn Ala Val
    210                 215                 220

Ala Tyr Tyr Arg Gly Leu Asp Val Ser Val Ile Pro Thr Ser Gly Asp
225                 230                 235                 240

Val Val Val Val Ala Thr Asp Ala Leu Met Thr Gly Tyr Thr Gly Asp
                245                 250                 255

Phe Asp Ser Val Ile Asp Cys Asn Thr Cys
            260                 265

(2) INFORMATION FOR SEQ ID NO:33:

(i) SEQUENCE CHARACTERISTICS:
        (A) LENGTH: 283 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 3..281

(xi) SEQUENCE DESCRIPTION: SEQ ID NO:33:

CT CCC TGC ACT TGC GGC TCC TCG GAC CTT TAC CTG GTC ACG AGG CAC         47

```
    Pro Cys Thr Cys Gly Ser Ser Asp Leu Tyr Leu Val Thr Arg His
    1               5                   10                  15

GCC GAT GTC ATT CCC GTG CGC CGG CGG GGT GAT AGC AGG GGC AGC CTG              95
Ala Asp Val Ile Pro Val Arg Arg Arg Gly Asp Ser Arg Gly Ser Leu
            20                  25                  30

CTG TCG CCC CGG CCC ATT TCC TAC TTG AAA GGC TCC TCG GGG GGT CCG             143
Leu Ser Pro Arg Pro Ile Ser Tyr Leu Lys Gly Ser Ser Gly Gly Pro
        35                  40                  45

CTG TTG TGC CCC GCG GGG CAC GCC GTG GGC ATA TTT AGG GCC GCG GTG             191
Leu Leu Cys Pro Ala Gly His Ala Val Gly Ile Phe Arg Ala Ala Val
    50                  55                  60

TGC ACC CGT GGA GTG GCT AAG GCG GTG GAC TTT ATC CCT GTG GAG AAC             239
Cys Thr Arg Gly Val Ala Lys Ala Val Asp Phe Ile Pro Val Glu Asn
65                  70                  75

CTA GAG ACA ACC ATG AGG TCC CCG GTG TTC ACG GAT AAC TCC                     281
Leu Glu Thr Thr Met Arg Ser Pro Val Phe Thr Asp Asn Ser
80                  85                  90

TC                                                                          283

(2) INFORMATION FOR SEQ ID NO:34:

(i) SEQUENCE CHARACTERISTICS:
        (A) LENGTH: 93 amino acids
        (B) TYPE: amino acid
        (D) TOPOLOGY: linear (ii) MOLECULE TYPE: protein (xi) SEQUENCE DESCRIPTION: SEQ ID NO:34:

Pro Cys Thr Cys Gly Ser Ser Asp Leu Tyr Leu Val Thr Arg His Ala
1               5                   10                  15

Asp Val Ile Pro Val Arg Arg Arg Gly Asp Ser Arg Gly Ser Leu Leu
            20                  25                  30

Ser Pro Arg Pro Ile Ser Tyr Leu Lys Gly Ser Ser Gly Gly Pro Leu
        35                  40                  45

Leu Cys Pro Ala Gly His Ala Val Gly Ile Phe Arg Ala Ala Val Cys
    50                  55                  60

Thr Arg Gly Val Ala Lys Ala Val Asp Phe Ile Pro Val Glu Asn Leu
65                  70                  75                  80

Glu Thr Thr Met Arg Ser Pro Val Phe Thr Asp Asn Ser
                85                  90

(2) INFORMATION FOR SEQ ID NO:35:

(i) SEQUENCE CHARACTERISTICS:
        (A) LENGTH: 347 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 2..346

(xi) SEQUENCE DESCRIPTION: SEQ ID NO:35:

G GGG TGG AGG TTG CTG GCG CCC ATC ACG GCG TAC GCC CAG CAG ACA                46
  Gly Trp Arg Leu Leu Ala Pro Ile Thr Ala Tyr Ala Gln Gln Thr
  1               5                   10                  15

AGG GGC CTC CTA GGG TGC ATA ATC ACC AGC CTA ACT GGC CGG GAC AAA              94
Arg Gly Leu Leu Gly Cys Ile Ile Thr Ser Leu Thr Gly Arg Asp Lys
            20                  25                  30
```

```
AAC CAA GTG GAG GGT GAG GTC CAG ATT GTG TCA ACT GCT GCC CAA ACC         142
Asn Gln Val Glu Gly Glu Val Gln Ile Val Ser Thr Ala Ala Gln Thr
             35                  40                  45

TTC CTG GCA ACG TGC ATC AAT GGG GTG TGC TGG ACT GTC TAC CAC GGG         190
Phe Leu Ala Thr Cys Ile Asn Gly Val Cys Trp Thr Val Tyr His Gly
         50                  55                  60

GCC GGA ACG AGG ACC ATC GCG TCA CCC AAG GGT CCT GTC ATC CAG ATG         238
Ala Gly Thr Arg Thr Ile Ala Ser Pro Lys Gly Pro Val Ile Gln Met
     65                  70                  75

TAT ACC AAT GTA GAC CAA GAC CTT GTG GGC TGG CCC GCT CCG CAA GGT         286
Tyr Thr Asn Val Asp Gln Asp Leu Val Gly Trp Pro Ala Pro Gln Gly
 80                  85                  90                  95

AGC CGC TCA TTG ACA CCC TGC ACT TGC GGC TCC TCG GAC CTT TAC CTG         334
Ser Arg Ser Leu Thr Pro Cys Thr Cys Gly Ser Ser Asp Leu Tyr Leu
                100                 105                 110

GTC ACG AGG CAC G                                                       347
Val Thr Arg His
        115

(2) INFORMATION FOR SEQ ID NO:36:

(i) SEQUENCE CHARACTERISTICS:
        (A) LENGTH: 115 amino acids
        (B) TYPE: amino acid
        (D) TOPOLOGY: linear (ii) MOLECULE TYPE: protein (xi) SEQUENCE DESCRIPTION: SEQ ID NO:36:

Gly Trp Arg Leu Leu Ala Pro Ile Thr Ala Tyr Ala Gln Gln Thr Arg
 1               5                  10                  15

Gly Leu Leu Gly Cys Ile Ile Thr Ser Leu Thr Gly Arg Asp Lys Asn
             20                  25                  30

Gln Val Glu Gly Glu Val Gln Ile Val Ser Thr Ala Ala Gln Thr Phe
         35                  40                  45

Leu Ala Thr Cys Ile Asn Gly Val Cys Trp Thr Val Tyr His Gly Ala
     50                  55                  60

Gly Thr Arg Thr Ile Ala Ser Pro Lys Gly Pro Val Ile Gln Met Tyr
 65                  70                  75                  80

Thr Asn Val Asp Gln Asp Leu Val Gly Trp Pro Ala Pro Gln Gly Ser
             85                  90                  95

Arg Ser Leu Thr Pro Cys Thr Cys Gly Ser Ser Asp Leu Tyr Leu Val
            100                 105                 110

Thr Arg His
        115

(2) INFORMATION FOR SEQ ID NO:37:

(i) SEQUENCE CHARACTERISTICS:
        (A) LENGTH: 511 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 2..511

(xi) SEQUENCE DESCRIPTION: SEQ ID NO:37:

G AAC ATG TGG AGT GGG ACC TTC CCC ATT AAT GCC TAC ACC ACG GGC           46
```

-continued

```
    Asn Met Trp Ser Gly Thr Phe Pro Ile Asn Ala Tyr Thr Thr Gly
    1               5                   10                  15

CCC TGT ACC CCC CTT CCT GCG CCG AAC TAC ACG TTC GCG CTA TGG AGG          94
Pro Cys Thr Pro Leu Pro Ala Pro Asn Tyr Thr Phe Ala Leu Trp Arg
                20                  25                  30

GTG TCT GCA GAG GAA TAC GTG GAG ATA AGG CAG GTG GGG GAC TTC CAC         142
Val Ser Ala Glu Glu Tyr Val Glu Ile Arg Gln Val Gly Asp Phe His
            35                  40                  45

TAC GTG ACG GGT ATG ACT ACT GAC AAT CTT AAA TGC CCG TGC CAG GTC         190
Tyr Val Thr Gly Met Thr Thr Asp Asn Leu Lys Cys Pro Cys Gln Val
        50                  55                  60

CCA TCG CCC GAA TTT TTC ACA GAA TTG GAC GGG GTG CGC CTA CAT AGG         238
Pro Ser Pro Glu Phe Phe Thr Glu Leu Asp Gly Val Arg Leu His Arg
    65                  70                  75

TTT GCG CCC CCC TGC AAG CCC TTG CTG CGG GAG GAG GTA TCA TTC AGA         286
Phe Ala Pro Pro Cys Lys Pro Leu Leu Arg Glu Glu Val Ser Phe Arg
80                  85                  90                  95

GTA GGA CTC CAC GAA TAC CCG GTA GGG TCG CAA TTA CCT TGC GAG CCC         334
Val Gly Leu His Glu Tyr Pro Val Gly Ser Gln Leu Pro Cys Glu Pro
                100                 105                 110

GAA CCG GAC GTG GCC GTG TTG ACG TCC ATG CTC ACT GAT CCC TCC CAT         382
Glu Pro Asp Val Ala Val Leu Thr Ser Met Leu Thr Asp Pro Ser His
            115                 120                 125

ATA ACA GCA GAG GCG GCC GGG CGA AGG TTG GCG AGG GGA TCA CCC CCC         430
Ile Thr Ala Glu Ala Ala Gly Arg Arg Leu Ala Arg Gly Ser Pro Pro
        130                 135                 140

TCT GTG GCC AGC TCC TCG GCT AGC CAG CTA TCC GCT CCA TCT CTC AAG         478
Ser Val Ala Ser Ser Ser Ala Ser Gln Leu Ser Ala Pro Ser Leu Lys
    145                 150                 155

GCA ACT TGC ACC GCT AAC CAT GAC TCC CCT GAT                             511
Ala Thr Cys Thr Ala Asn His Asp Ser Pro Asp
160                 165                 170
```

(2) INFORMATION FOR SEQ ID NO:38:

(i) SEQUENCE CHARACTERISTICS:
        (A) LENGTH: 170 amino acids
        (B) TYPE: amino acid
        (D) TOPOLOGY: linear (ii) MOLECULE TYPE: protein (xi) SEQUENCE DESCRIPTION: SEQ ID NO:38:

```
Asn Met Trp Ser Gly Thr Phe Pro Ile Asn Ala Tyr Thr Thr Gly Pro
1               5                   10                  15

Cys Thr Pro Leu Pro Ala Pro Asn Tyr Thr Phe Ala Leu Trp Arg Val
                20                  25                  30

Ser Ala Glu Glu Tyr Val Glu Ile Arg Gln Val Gly Asp Phe His Tyr
            35                  40                  45

Val Thr Gly Met Thr Thr Asp Asn Leu Lys Cys Pro Cys Gln Val Pro
        50                  55                  60

Ser Pro Glu Phe Phe Thr Glu Leu Asp Gly Val Arg Leu His Arg Phe
65                  70                  75                  80

Ala Pro Pro Cys Lys Pro Leu Leu Arg Glu Glu Val Ser Phe Arg Val
                85                  90                  95

Gly Leu His Glu Tyr Pro Val Gly Ser Gln Leu Pro Cys Glu Pro Glu
            100                 105                 110

Pro Asp Val Ala Val Leu Thr Ser Met Leu Thr Asp Pro Ser His Ile
        115                 120                 125
```

```
Thr Ala Glu Ala Ala Gly Arg Arg Leu Ala Arg Gly Ser Pro Pro Ser
    130                 135                 140

Val Ala Ser Ser Ala Ser Gln Leu Ser Ala Pro Ser Leu Lys Ala
145                 150                 155                 160

Thr Cys Thr Ala Asn His Asp Ser Pro Asp
                165                 170

(2) INFORMATION FOR SEQ ID NO:39:

(i) SEQUENCE CHARACTERISTICS:
        (A) LENGTH: 378 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..378

(xi) SEQUENCE DESCRIPTION: SEQ ID NO:39:

AGC TCC TCG GCT AGC CAG CTA TCC GCT CCA TCT CTC AAG GCA ACT TGC        48
Ser Ser Ser Ala Ser Gln Leu Ser Ala Pro Ser Leu Lys Ala Thr Cys
  1               5                  10                  15

ACC GCT AAC CAT GAC TCC CCT GAT GCT GAG CTC ATA GAG GCC AAC CTC        96
Thr Ala Asn His Asp Ser Pro Asp Ala Glu Leu Ile Glu Ala Asn Leu
                 20                  25                  30

CTA TGG AGG CAG GAG ATG GGC GGC AAC ATC ACC AGG GTT GAG TCA GAA       144
Leu Trp Arg Gln Glu Met Gly Gly Asn Ile Thr Arg Val Glu Ser Glu
         35                  40                  45

AAC AAA GTG GTG ATT CTG GAC TCC TTC GAT CCG CTT GTG GCG GAG GAG       192
Asn Lys Val Val Ile Leu Asp Ser Phe Asp Pro Leu Val Ala Glu Glu
     50                  55                  60

GAC GAG CGG GAG ATC TCC GTA CCC GCA GAA ATC CTG CGG AAG TCT CGG       240
Asp Glu Arg Glu Ile Ser Val Pro Ala Glu Ile Leu Arg Lys Ser Arg
 65                  70                  75                  80

AGA TTC GCC CAG GCC CTG CCC GTT TGG GCG CGG CCG GAC TAT AAC CCC       288
Arg Phe Ala Gln Ala Leu Pro Val Trp Ala Arg Pro Asp Tyr Asn Pro
                 85                  90                  95

CCG CTA GTG GAG ACG TGG AAA AAG CCC GAC TAC GAA CCA CCT GTG GTC       336
Pro Leu Val Glu Thr Trp Lys Lys Pro Asp Tyr Glu Pro Pro Val Val
            100                 105                 110

CAT GGC TGT CCG CTT CCA CCT CCA AAG TCC CCT CCT GTG CCG               378
His Gly Cys Pro Leu Pro Pro Pro Lys Ser Pro Pro Val Pro
            115                 120                 125

(2) INFORMATION FOR SEQ ID NO:40:

(i) SEQUENCE CHARACTERISTICS:
        (A) LENGTH: 126 amino acids
        (B) TYPE: amino acid
        (D) TOPOLOGY: linear (ii) MOLECULE TYPE: protein (xi) SEQUENCE DESCRIPTION: SEQ ID NO:40:

Ser Ser Ser Ala Ser Gln Leu Ser Ala Pro Ser Leu Lys Ala Thr Cys
  1               5                  10                  15

Thr Ala Asn His Asp Ser Pro Asp Ala Glu Leu Ile Glu Ala Asn Leu
                 20                  25                  30

Leu Trp Arg Gln Glu Met Gly Gly Asn Ile Thr Arg Val Glu Ser Glu
         35                  40                  45
```

```
Asn Lys Val Val Ile Leu Asp Ser Phe Asp Pro Leu Val Ala Glu Glu
 50                  55                  60

Asp Glu Arg Glu Ile Ser Val Pro Ala Glu Ile Leu Arg Lys Ser Arg
 65                  70                  75                  80

Arg Phe Ala Gln Ala Leu Pro Val Trp Ala Arg Pro Asp Tyr Asn Pro
                 85                  90                  95

Pro Leu Val Glu Thr Trp Lys Lys Pro Asp Tyr Glu Pro Pro Val Val
            100                 105                 110

His Gly Cys Pro Leu Pro Pro Pro Lys Ser Pro Pro Val Pro
        115                 120                 125
```

(2) INFORMATION FOR SEQ ID NO:41:

(i) SEQUENCE CHARACTERISTICS:
        (A) LENGTH: 300 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 2..298

(xi) SEQUENCE DESCRIPTION: SEQ ID NO:41:

```
C GTT TGG GCG CGG CCG GAC TAT AAC CCC CCG CTA GTG GAG ACG TGG        46
  Val Trp Ala Arg Pro Asp Tyr Asn Pro Pro Leu Val Glu Thr Trp
   1               5                  10                  15

AAA AAA CCC GAC TAC GAA CCA CCT GTG GTC CAT GGC TGC CCG CTT CCA      94
Lys Lys Pro Asp Tyr Glu Pro Pro Val Val His Gly Cys Pro Leu Pro
                 20                  25                  30

CCT CCA AAG TCC CCT CCT GTG CCT CCG CCT CGG AAG AAG CGG ACG GTG     142
Pro Pro Lys Ser Pro Pro Val Pro Pro Pro Arg Lys Lys Arg Thr Val
             35                  40                  45

GTC CTC ACT GAA TCA ACC CTA TCT ACT GCC TTG GCC GAG CTC GCC ACC     190
Val Leu Thr Glu Ser Thr Leu Ser Thr Ala Leu Ala Glu Leu Ala Thr
         50                  55                  60

AGA AGC TTT GGC AGC TCC TCA ACT TCC GGC ATT ACG GGC GAC AAT ACG     238
Arg Ser Phe Gly Ser Ser Ser Thr Ser Gly Ile Thr Gly Asp Asn Thr
 65                  70                  75

ACA ACA TCC TCT GAG CCC GCC CCT TCT GGC TGC CCC CCC GAC TCC GAC     286
Thr Thr Ser Ser Glu Pro Ala Pro Ser Gly Cys Pro Pro Asp Ser Asp
 80                  85                  90                  95

GCT GAG TCC TTT GC                                                  300
Ala Glu Ser Phe
```

(2) INFORMATION FOR SEQ ID NO:42:

(i) SEQUENCE CHARACTERISTICS:
        (A) LENGTH: 99 amino acids
        (B) TYPE: amino acid
        (D) TOPOLOGY: linear (ii) MOLECULE TYPE: protein (xi) SEQUENCE DESCRIPTION: SEQ ID NO:42:

```
Val Trp Ala Arg Pro Asp Tyr Asn Pro Pro Leu Val Glu Thr Trp Lys
 1                5                  10                  15

Lys Pro Asp Tyr Glu Pro Pro Val Val His Gly Cys Pro Leu Pro Pro
                 20                  25                  30

Pro Lys Ser Pro Pro Val Pro Pro Pro Arg Lys Lys Arg Thr Val Val
             35                  40                  45
```

```
Leu Thr Glu Ser Thr Leu Ser Thr Ala Leu Ala Glu Leu Ala Thr Arg
     50                  55                  60

Ser Phe Gly Ser Ser Thr Ser Gly Ile Thr Gly Asp Asn Thr Thr
 65              70                  75                  80

Thr Ser Ser Glu Pro Ala Pro Ser Gly Cys Pro Pro Asp Ser Asp Ala
                 85                  90                  95

Glu Ser Phe
```

(2) INFORMATION FOR SEQ ID NO:43:

(i) SEQUENCE CHARACTERISTICS:
        (A) LENGTH: 352 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..351

(xi) SEQUENCE DESCRIPTION: SEQ ID NO:43:

```
GCC TCC AGA AGC TTT GGC AGC TCC TCA ACT TCC GGC ATT ACG GGC GAC      48
Ala Ser Arg Ser Phe Gly Ser Ser Ser Thr Ser Gly Ile Thr Gly Asp
 1               5                  10                  15

AAT ACG ACA ACA TCC TCT GAG CCC GCC CCT TCT GGC TGC CCC CCC GAC      96
Asn Thr Thr Thr Ser Ser Glu Pro Ala Pro Ser Gly Cys Pro Pro Asp
                 20                  25                  30

TCC GAC GCT GAG TCC TAT TCC TCC ATG CCC CCC CTG GAG GGG GAG CCT     144
Ser Asp Ala Glu Ser Tyr Ser Ser Met Pro Pro Leu Glu Gly Glu Pro
             35                  40                  45

GGG GAT CCG GAT CTT AGC GAC GGG TCA TGG TCA ACG GTC AGT AGT GAG     192
Gly Asp Pro Asp Leu Ser Asp Gly Ser Trp Ser Thr Val Ser Ser Glu
         50                  55                  60

GCC AAC GCG GAG GAT GTC GTG TGC TGC TCA ATG TCT TAC TCT TGG ACA     240
Ala Asn Ala Glu Asp Val Val Cys Cys Ser Met Ser Tyr Ser Trp Thr
 65                  70                  75                  80

GGC GCA CTC GTC ACC CCG TGC GCC GCG GAA GAA CAG AAA CTG CCC ATC     288
Gly Ala Leu Val Thr Pro Cys Ala Ala Glu Glu Gln Lys Leu Pro Ile
                 85                  90                  95

AAT GCA CTA AGC AAC TCG TTG CTA CGT CAC CAC AAT TTG GTG TAT TCC     336
Asn Ala Leu Ser Asn Ser Leu Leu Arg His His Asn Leu Val Tyr Ser
             100                 105                 110

ACC ACC TCA CGC AGT G                                                352
Thr Thr Ser Arg Ser
         115
```

(2) INFORMATION FOR SEQ ID NO:44:

(i) SEQUENCE CHARACTERISTICS:
        (A) LENGTH: 117 amino acids
        (B) TYPE: amino acid
        (D) TOPOLOGY: linear (ii) MOLECULE TYPE: protein (xi) SEQUENCE DESCRIPTION: SEQ ID NO:44:

```
Ala Ser Arg Ser Phe Gly Ser Ser Ser Thr Ser Gly Ile Thr Gly Asp
 1               5                  10                  15

Asn Thr Thr Thr Ser Ser Glu Pro Ala Pro Ser Gly Cys Pro Pro Asp
                 20                  25                  30
```

```
Ser Asp Ala Glu Ser Tyr Ser Ser Met Pro Pro Leu Glu Gly Glu Pro
        35                  40                  45

Gly Asp Pro Asp Leu Ser Asp Gly Ser Trp Ser Thr Val Ser Ser Glu
    50                  55                  60

Ala Asn Ala Glu Asp Val Val Cys Cys Ser Met Ser Tyr Ser Trp Thr
65                  70                  75                  80

Gly Ala Leu Val Thr Pro Cys Ala Ala Glu Gln Lys Leu Pro Ile
                85                  90                  95

Asn Ala Leu Ser Asn Ser Leu Leu Arg His His Asn Leu Val Tyr Ser
            100                 105                 110

Thr Thr Ser Arg Ser
        115
```

(2) INFORMATION FOR SEQ ID NO:45:

(i) SEQUENCE CHARACTERISTICS:
        (A) LENGTH: 402 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..402

(xi) SEQUENCE DESCRIPTION: SEQ ID NO:45:

```
GGC ACC TAT GTT TAT AAC CAT CTC ACT CCT CTT CGG GAC TGG GCG CAC      48
Gly Thr Tyr Val Tyr Asn His Leu Thr Pro Leu Arg Asp Trp Ala His
 1               5                  10                  15

AAC GGC TTG CGA GAT CTG GCC GTG GCT GTA GAG CCA GTC GTC TTC TCC      96
Asn Gly Leu Arg Asp Leu Ala Val Ala Val Glu Pro Val Val Phe Ser
                20                  25                  30

CAA ATG GAG ACC AAG CTC ATC ACG TGG GGG GCA GAT ACC GCC GCG TGC     144
Gln Met Glu Thr Lys Leu Ile Thr Trp Gly Ala Asp Thr Ala Ala Cys
            35                  40                  45

GGT GAC ATC ATC AAC GGC TTG CCT GTT TCC GCC CGC AGG GGC CGG GAG     192
Gly Asp Ile Ile Asn Gly Leu Pro Val Ser Ala Arg Arg Gly Arg Glu
        50                  55                  60

ATA CTG CTC GGG CCA GCC GAT GGA ATG GTC TCC AAG GGT TGG AGG TTG     240
Ile Leu Leu Gly Pro Ala Asp Gly Met Val Ser Lys Gly Trp Arg Leu
65                  70                  75                  80

CTG GCG CCC ATC ACG GCG TAC GCC CAG CAG ACA AGG GGC CTC CTA GGG     288
Leu Ala Pro Ile Thr Ala Tyr Ala Gln Gln Thr Arg Gly Leu Leu Gly
                85                  90                  95

TGC ATA ATC ACC AGC CTA ACT GGC CGG GAC AAA AAC CAA GTG GAG GGT     336
Cys Ile Ile Thr Ser Leu Thr Gly Arg Asp Lys Asn Gln Val Glu Gly
            100                 105                 110

GAG GTC CAG ATT GTG TCA ACT GCT GCC CAA ACC TTC CTG GCA ACG TGC     384
Glu Val Gln Ile Val Ser Thr Ala Ala Gln Thr Phe Leu Ala Thr Cys
        115                 120                 125

ATC AAT GGG GTG TGC TGG                                             402
Ile Asn Gly Val Cys Trp
        130
```

(2) INFORMATION FOR SEQ ID NO:46:

(i) SEQUENCE CHARACTERISTICS:
        (A) LENGTH: 134 amino acids
        (B) TYPE: amino acid
        (D) TOPOLOGY: linear (ii) MOLECULE TYPE: protein (xi) SEQUENCE DESCRIPTION: SEQ ID NO:46:

```
Gly Thr Tyr Val Tyr Asn His Leu Thr Pro Leu Arg Asp Trp Ala His
 1               5                  10                  15

Asn Gly Leu Arg Asp Leu Ala Val Ala Val Glu Pro Val Val Phe Ser
                20                  25                  30

Gln Met Glu Thr Lys Leu Ile Thr Trp Gly Ala Asp Thr Ala Ala Cys
            35                  40                  45

Gly Asp Ile Ile Asn Gly Leu Pro Val Ser Ala Arg Arg Gly Arg Glu
         50                  55                  60

Ile Leu Leu Gly Pro Ala Asp Gly Met Val Ser Lys Gly Trp Arg Leu
 65                  70                  75                  80

Leu Ala Pro Ile Thr Ala Tyr Ala Gln Gln Thr Arg Gly Leu Leu Gly
                 85                  90                  95

Cys Ile Ile Thr Ser Leu Thr Gly Arg Asp Lys Asn Gln Val Glu Gly
                100                 105                 110

Glu Val Gln Ile Val Ser Thr Ala Ala Gln Thr Phe Leu Ala Thr Cys
            115                 120                 125

Ile Asn Gly Val Cys Trp
        130
```

(2) INFORMATION FOR SEQ ID NO:47:

(i) SEQUENCE CHARACTERISTICS:
        (A) LENGTH: 509 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..507

(xi) SEQUENCE DESCRIPTION: SEQ ID NO:47:

```
GGC GGT GTT GTT CTC GTC GGG TTG ATG GCG CTG ACT CTG TCA CCA TAT    48
Gly Gly Val Val Leu Val Gly Leu Met Ala Leu Thr Leu Ser Pro Tyr
 1               5                  10                  15

TAC AAG CGC TAT ATC AGC TGG TGC TTG TGG TGG CTT CAG TAT TTT CTG    96
Tyr Lys Arg Tyr Ile Ser Trp Cys Leu Trp Trp Leu Gln Tyr Phe Leu
                20                  25                  30

ACC AGA GTG GAA GCG CAA CTG CAC GTG TGG ATT CCC CCC CTC AAC GTC   144
Thr Arg Val Glu Ala Gln Leu His Val Trp Ile Pro Pro Leu Asn Val
            35                  40                  45

CGA GGG GGC CGC GAC GCC GTC ATC TTA CTC ATG TGT GCT GTA CAC CCG   192
Arg Gly Gly Arg Asp Ala Val Ile Leu Leu Met Cys Ala Val His Pro
         50                  55                  60

ACT CTG GTA TTT GAC ATC ACC AAA TTG CTG CTG GCC GTC TTC GGA CCC   240
Thr Leu Val Phe Asp Ile Thr Lys Leu Leu Leu Ala Val Phe Gly Pro
 65                  70                  75                  80

CTT TGG ATT CTT CAA GCC AGT TTG CTT AAA GTA CCC TAC TTT GTG CGC   288
Leu Trp Ile Leu Gln Ala Ser Leu Leu Lys Val Pro Tyr Phe Val Arg
                85                  90                  95

GTC CAA GGC CTT CTC CGG TTC TGC GCG TTA GCG CGG AAG ATG ATC GGA   336
Val Gln Gly Leu Leu Arg Phe Cys Ala Leu Ala Arg Lys Met Ile Gly
                100                 105                 110

GGC CAT TAC GTG CAA ATG GTC ATC ATT AAG TTA GGG GCG CTT ACT GGC   384
Gly His Tyr Val Gln Met Val Ile Ile Lys Leu Gly Ala Leu Thr Gly
            115                 120                 125
```

```
ACC TAT GTT TAT AAC CAT CTC ACT CCT CTT CGG GAC TGG GCG CAC AAC      432
Thr Tyr Val Tyr Asn His Leu Thr Pro Leu Arg Asp Trp Ala His Asn
    130                 135                 140

GGC TTG CGA GAT CTG GCC GTG GCT GTA GAG CCA GTC GTC TTC TCC CAA      480
Gly Leu Arg Asp Leu Ala Val Ala Val Glu Pro Val Val Phe Ser Gln
145                 150                 155                 160

ATG GAG ACC AAG CTC ATC ACG TGG GGG GC                               509
Met Glu Thr Lys Leu Ile Thr Trp Gly
                165
```

(2) INFORMATION FOR SEQ ID NO:48:

(i) SEQUENCE CHARACTERISTICS:
        (A) LENGTH: 169 amino acids
        (B) TYPE: amino acid
        (D) TOPOLOGY: linear (ii) MOLECULE TYPE: protein (xi) SEQUENCE DESCRIPTION: SEQ ID NO:48:

```
Gly Gly Val Val Leu Val Gly Leu Met Ala Leu Thr Leu Ser Pro Tyr
 1               5                  10                  15

Tyr Lys Arg Tyr Ile Ser Trp Cys Leu Trp Trp Leu Gln Tyr Phe Leu
                20                  25                  30

Thr Arg Val Glu Ala Gln Leu His Val Trp Ile Pro Pro Leu Asn Val
            35                  40                  45

Arg Gly Gly Arg Asp Ala Val Ile Leu Leu Met Cys Ala Val His Pro
        50                  55                  60

Thr Leu Val Phe Asp Ile Thr Lys Leu Leu Leu Ala Val Phe Gly Pro
65                  70                  75                  80

Leu Trp Ile Leu Gln Ala Ser Leu Leu Lys Val Pro Tyr Phe Val Arg
                85                  90                  95

Val Gln Gly Leu Leu Arg Phe Cys Ala Leu Ala Arg Lys Met Ile Gly
                100                 105                 110

Gly His Tyr Val Gln Met Val Ile Ile Lys Leu Gly Ala Leu Thr Gly
            115                 120                 125

Thr Tyr Val Tyr Asn His Leu Thr Pro Leu Arg Asp Trp Ala His Asn
130                 135                 140

Gly Leu Arg Asp Leu Ala Val Ala Val Glu Pro Val Val Phe Ser Gln
145                 150                 155                 160

Met Glu Thr Lys Leu Ile Thr Trp Gly
                165
```

(2) INFORMATION FOR SEQ ID NO:49:

(i) SEQUENCE CHARACTERISTICS:
        (A) LENGTH: 397 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 3..395

(xi) SEQUENCE DESCRIPTION: SEQ ID NO:49:

```
GG GAG TAC GTC GTT CTC CTG TTC CTT CTG CTT GCA GAC GCG CGC GTC       47
   Glu Tyr Val Val Leu Leu Phe Leu Leu Leu Ala Asp Ala Arg Val
    1               5                  10                  15
```

```
TGC TCC TGC TTG TGG ATG ATG CTA CTC ATA TCC CAA GCG GAG GCG GCT     95
Cys Ser Cys Leu Trp Met Met Leu Leu Ile Ser Gln Ala Glu Ala Ala
            20                  25                  30

TTG GAG AAC CTC GTA ATA CTT AAT GCA GCA TCC CTG GCC GGG ACG CAC    143
Leu Glu Asn Leu Val Ile Leu Asn Ala Ala Ser Leu Ala Gly Thr His
                35                  40                  45

GGT CTT GTA TCC TTC CTC GTG TTC TTC TGC TTT GCA TGG TAT TTG AAG    191
Gly Leu Val Ser Phe Leu Val Phe Phe Cys Phe Ala Trp Tyr Leu Lys
                50                  55                  60

GGT AAG TGG GTG CCC GGA GCG GTC TAC ACC TTC TAC GGG ATG TGG CCT    239
Gly Lys Trp Val Pro Gly Ala Val Tyr Thr Phe Tyr Gly Met Trp Pro
        65                  70                  75

CTC CTC CTG CTC CTG TTG GCG TTG CCC CAG CGG GCG TAC GCG CTG GAC    287
Leu Leu Leu Leu Leu Leu Ala Leu Pro Gln Arg Ala Tyr Ala Leu Asp
80                  85                  90                  95

ACG GAG GTG GCC GCG TCG TGT GGC GGT GTT GTT CTC GTC GGG TTG ATG    335
Thr Glu Val Ala Ala Ser Cys Gly Gly Val Val Leu Val Gly Leu Met
                    100                 105                 110

GCG CTG ACT CTG TCA CCA TAT TAC AAG CGC TAT ATC AGC TGG TGC TTG    383
Ala Leu Thr Leu Ser Pro Tyr Tyr Lys Arg Tyr Ile Ser Trp Cys Leu
                115                 120                 125

TGG TGG CTT CAG AA                                                  397
Trp Trp Leu Gln
        130
```

(2) INFORMATION FOR SEQ ID NO:50:

(i) SEQUENCE CHARACTERISTICS:
        (A) LENGTH: 131 amino acids
        (B) TYPE: amino acid
        (D) TOPOLOGY: linear (ii) MOLECULE TYPE: protein (xi) SEQUENCE DESCRIPTION: SEQ ID NO:50:

```
Glu Tyr Val Val Leu Leu Phe Leu Leu Leu Ala Asp Ala Arg Val Cys
 1               5                  10                  15

Ser Cys Leu Trp Met Met Leu Leu Ile Ser Gln Ala Glu Ala Ala Leu
            20                  25                  30

Glu Asn Leu Val Ile Leu Asn Ala Ala Ser Leu Ala Gly Thr His Gly
        35                  40                  45

Leu Val Ser Phe Leu Val Phe Phe Cys Phe Ala Trp Tyr Leu Lys Gly
    50                  55                  60

Lys Trp Val Pro Gly Ala Val Tyr Thr Phe Tyr Gly Met Trp Pro Leu
65                  70                  75                  80

Leu Leu Leu Leu Leu Ala Leu Pro Gln Arg Ala Tyr Ala Leu Asp Thr
                85                  90                  95

Glu Val Ala Ala Ser Cys Gly Gly Val Val Leu Val Gly Leu Met Ala
                100                 105                 110

Leu Thr Leu Ser Pro Tyr Tyr Lys Arg Tyr Ile Ser Trp Cys Leu Trp
        115                 120                 125

Trp Leu Gln
        130
```

(2) INFORMATION FOR SEQ ID NO:51:

(i) SEQUENCE CHARACTERISTICS:
        (A) LENGTH: 396 base pairs
        (B) TYPE: nucleic acid
        (C) STRANDEDNESS: single
        (D) TOPOLOGY: linear (ii) MOLECULE TYPE: cDNA (ix) FEATURE:
             (A) NAME/KEY: CDS
             (B) LOCATION: 1..396

(xi) SEQUENCE DESCRIPTION: SEQ ID NO:51:

| CCA | GCC | CCT | TCT | GGC | TGC | CCC | CCC | GAC | TCC | GAC | GCT | GAG | TCC | TAT | TCC | 48 |
|---|---|---|---|---|---|---|---|---|---|---|---|---|---|---|---|---|
| Pro | Ala | Pro | Ser | Gly | Cys | Pro | Pro | Asp | Ser | Asp | Ala | Glu | Ser | Tyr | Ser | |
| 1 | | | | 5 | | | | | 10 | | | | | 15 | | |

| TCC | ATG | CCC | CCC | CTG | GAG | GGG | GAG | CCT | GGG | GAT | CCG | GAT | CTT | AGC | GAC | 96 |
|---|---|---|---|---|---|---|---|---|---|---|---|---|---|---|---|---|
| Ser | Met | Pro | Pro | Leu | Glu | Gly | Glu | Pro | Gly | Asp | Pro | Asp | Leu | Ser | Asp | |
| | | | 20 | | | | | 25 | | | | | 30 | | | |

| GGG | TCA | TGG | TCA | ACA | GTC | AGT | AGT | GAG | GCC | AAC | GCG | GAG | GAT | GTC | GTG | 144 |
|---|---|---|---|---|---|---|---|---|---|---|---|---|---|---|---|---|
| Gly | Ser | Trp | Ser | Thr | Val | Ser | Ser | Glu | Ala | Asn | Ala | Glu | Asp | Val | Val | |
| | | 35 | | | | | 40 | | | | | 45 | | | | |

| TGC | TGC | TCA | ATG | TCC | TAC | TCT | TGG | ACA | GGC | GCA | CTC | GTC | ACC | CCG | TGC | 192 |
|---|---|---|---|---|---|---|---|---|---|---|---|---|---|---|---|---|
| Cys | Cys | Ser | Met | Ser | Tyr | Ser | Trp | Thr | Gly | Ala | Leu | Val | Thr | Pro | Cys | |
| 50 | | | | | 55 | | | | | 60 | | | | | | |

| GCC | GCG | GAA | GAA | CAG | AAA | CTG | CCC | ATC | AAT | GCA | CTG | AGC | AAC | TCG | TTG | 240 |
|---|---|---|---|---|---|---|---|---|---|---|---|---|---|---|---|---|
| Ala | Ala | Glu | Glu | Gln | Lys | Leu | Pro | Ile | Asn | Ala | Leu | Ser | Asn | Ser | Leu | |
| 65 | | | | | 70 | | | | | 75 | | | | | 80 | |

| CTA | CGT | CAC | CAC | AAT | TTG | GTG | TAT | TCC | ACC | ACC | TCA | CGC | AGT | GCT | TGC | 288 |
|---|---|---|---|---|---|---|---|---|---|---|---|---|---|---|---|---|
| Leu | Arg | His | His | Asn | Leu | Val | Tyr | Ser | Thr | Thr | Ser | Arg | Ser | Ala | Cys | |
| | | | | 85 | | | | | 90 | | | | | 95 | | |

| CAA | AGG | CAG | AAG | AAA | GTC | ACA | TTT | GAC | AGA | CTG | CAA | GTT | CTG | GAC | AGC | 336 |
|---|---|---|---|---|---|---|---|---|---|---|---|---|---|---|---|---|
| Gln | Arg | Gln | Lys | Lys | Val | Thr | Phe | Asp | Arg | Leu | Gln | Val | Leu | Asp | Ser | |
| | | | 100 | | | | | 105 | | | | | 110 | | | |

| CAT | TAC | CAG | GAC | GTA | CTC | AAG | GAG | GTT | AAA | GCA | GCG | GCG | TCA | AAA | GTG | 384 |
|---|---|---|---|---|---|---|---|---|---|---|---|---|---|---|---|---|
| His | Tyr | Gln | Asp | Val | Leu | Lys | Glu | Val | Lys | Ala | Ala | Ala | Ser | Lys | Val | |
| | | 115 | | | | | 120 | | | | | 125 | | | | |

| AAG | GCT | AAC | TTC | | | | | | | | | | | | | 396 |
|---|---|---|---|---|---|---|---|---|---|---|---|---|---|---|---|---|
| Lys | Ala | Asn | Phe | | | | | | | | | | | | | |
| 130 | | | | | | | | | | | | | | | | |

(2) INFORMATION FOR SEQ ID NO:52:

(i) SEQUENCE CHARACTERISTICS:
            (A) LENGTH: 132 amino acids
            (B) TYPE: amino acid
            (D) TOPOLOGY: linear (ii) MOLECULE TYPE: protein (xi) SEQUENCE DESCRIPTION: SEQ ID NO:52:

Pro Ala Pro Ser Gly Cys Pro Pro Asp Ser Asp Ala Glu Ser Tyr Ser
  1               5                  10                  15

Ser Met Pro Pro Leu Glu Gly Glu Pro Gly Asp Pro Asp Leu Ser Asp
             20                  25                  30

Gly Ser Trp Ser Thr Val Ser Ser Glu Ala Asn Ala Glu Asp Val Val
         35                  40                  45

Cys Cys Ser Met Ser Tyr Ser Trp Thr Gly Ala Leu Val Thr Pro Cys
 50                  55                  60

Ala Ala Glu Glu Gln Lys Leu Pro Ile Asn Ala Leu Ser Asn Ser Leu
 65                  70                  75                  80

Leu Arg His His Asn Leu Val Tyr Ser Thr Thr Ser Arg Ser Ala Cys
                 85                  90                  95

Gln Arg Gln Lys Lys Val Thr Phe Asp Arg Leu Gln Val Leu Asp Ser
            100                 105                 110

His Tyr Gln Asp Val Leu Lys Glu Val Lys Ala Ala Ala Ser Lys Val

-continued

```
                115                 120                 125
Lys Ala Asn Phe
    130

(2) INFORMATION FOR SEQ ID NO:53:

(i) SEQUENCE CHARACTERISTICS:
         (A) LENGTH: 5360 base pairs
         (B) TYPE: nucleic acid
         (C) STRANDEDNESS: single
         (D) TOPOLOGY: linear (ii) MOLECULE TYPE: cDNA (ix) FEATURE:
         (A) NAME/KEY: CDS
         (B) LOCATION: 3..5360

(xi) SEQUENCE DESCRIPTION: SEQ ID NO:53:

GG GAG TAC GTC GTT CTC CTG TTC CTT CTG CTT GCA GAC GCG CGC GTC            47
   Glu Tyr Val Val Leu Leu Phe Leu Leu Leu Ala Asp Ala Arg Val
   1               5                   10                  15

TGC TCC TGC TTG TGG ATG ATG CTA CTC ATA TCC CAA GCG GAG GCG GCT           95
Cys Ser Cys Leu Trp Met Met Leu Leu Ile Ser Gln Ala Glu Ala Ala
                20                  25                  30

TTG GAG AAC CTC GTA ATA CTT AAT GCA GCA TCC CTG GCC GGG ACG CAC          143
Leu Glu Asn Leu Val Ile Leu Asn Ala Ala Ser Leu Ala Gly Thr His
            35                  40                  45

GGT CTT GTA TCC TTC CTC GTG TTC TTC TGC TTT GCA TGG TAT TTG AAG          191
Gly Leu Val Ser Phe Leu Val Phe Phe Cys Phe Ala Trp Tyr Leu Lys
        50                  55                  60

GGT AAG TGG GTG CCC GGA GCG GTC TAC ACC TTC TAC GGG ATG TGG CCT          239
Gly Lys Trp Val Pro Gly Ala Val Tyr Thr Phe Tyr Gly Met Trp Pro
65                  70                  75

CTC CTC CTG CTC CTG TTG GCG TTG CCC CAG CGG GCG TAC GCG CTG GAC          287
Leu Leu Leu Leu Leu Leu Ala Leu Pro Gln Arg Ala Tyr Ala Leu Asp
80                  85                  90                  95

ACG GAG GTG GCC GCG TCG TGT GGC GGT GTT GTT CTC GTC GGG TTG ATG          335
Thr Glu Val Ala Ala Ser Cys Gly Gly Val Val Leu Val Gly Leu Met
                100                 105                 110

GCG CTG ACT CTG TCA CCA TAT TAC AAG CGC TAT ATC AGC TGG TGC TTG          383
Ala Leu Thr Leu Ser Pro Tyr Tyr Lys Arg Tyr Ile Ser Trp Cys Leu
            115                 120                 125

TGG TGG CTT CAG TAT TTT CTG ACC AGA GTG GAA GCG CAA CTG CAC GTG          431
Trp Trp Leu Gln Tyr Phe Leu Thr Arg Val Glu Ala Gln Leu His Val
        130                 135                 140

TGG ATT CCC CCC CTC AAC GTC CGA GGG GGG CGC GAC GCC GTC ATC TTA          479
Trp Ile Pro Pro Leu Asn Val Arg Gly Gly Arg Asp Ala Val Ile Leu
    145                 150                 155

CTC ATG TGT GCT GTA CAC CCG ACT CTG GTA TTT GAC ATC ACC AAA TTG          527
Leu Met Cys Ala Val His Pro Thr Leu Val Phe Asp Ile Thr Lys Leu
160                 165                 170                 175

CTG CTG GCC GTC TTC GGA CCC CTT TGG ATT CTT CAA GCC AGT TTG CTT          575
Leu Leu Ala Val Phe Gly Pro Leu Trp Ile Leu Gln Ala Ser Leu Leu
                180                 185                 190

AAA GTA CCC TAC TTT GTG CGC GTC CAA GGC CTT CTC CGG TTC TGC GCG          623
Lys Val Pro Tyr Phe Val Arg Val Gln Gly Leu Leu Arg Phe Cys Ala
            195                 200                 205

TTA GCG CGG AAG ATG ATC GGA GGC CAT TAC GTG CAA ATG GTC ATC ATT          671
Leu Ala Arg Lys Met Ile Gly Gly His Tyr Val Gln Met Val Ile Ile
        210                 215                 220

AAG TTA GGG GCG CTT ACT GGC ACC TAT GTT TAT AAC CAT CTC ACT CCT          719
```

```
                                              -continued

Lys Leu Gly Ala Leu Thr Gly Thr Tyr Val Tyr Asn His Leu Thr Pro
    225                 230                 235

CTT CGG GAC TGG GCG CAC AAC GGC TTG CGA GAT CTG GCC GTG GCT GTA      767
Leu Arg Asp Trp Ala His Asn Gly Leu Arg Asp Leu Ala Val Ala Val
240                 245                 250                 255

GAG CCA GTC GTC TTC TCC CAA ATG GAG ACC AAG CTC ATC ACG TGG GGG      815
Glu Pro Val Val Phe Ser Gln Met Glu Thr Lys Leu Ile Thr Trp Gly
                260                 265                 270

GCA GAT ACC GCC GCG TGC GGT GAC ATC ATC AAC GGC TTG CCT GTT TCC      863
Ala Asp Thr Ala Ala Cys Gly Asp Ile Ile Asn Gly Leu Pro Val Ser
                275                 280                 285

GCC CGC AGG GGC CGG GAG ATA CTG CTC GGG CCA GCC GAT GGA ATG GTC      911
Ala Arg Arg Gly Arg Glu Ile Leu Leu Gly Pro Ala Asp Gly Met Val
                290                 295                 300

TCC AAG GGG TGG AGG TTG CTG GCG CCC ATC ACG GCG TAC GCC CAG CAG      959
Ser Lys Gly Trp Arg Leu Leu Ala Pro Ile Thr Ala Tyr Ala Gln Gln
                305                 310                 315

ACA AGG GGC CTC CTA GGG TGC ATA ATC ACC AGC CTA ACT GGC CGG GAC     1007
Thr Arg Gly Leu Leu Gly Cys Ile Ile Thr Ser Leu Thr Gly Arg Asp
320                 325                 330                 335

AAA AAC CAA GTG GAG GGT GAG GTC CAG ATT GTG TCA ACT GCT GCC CAA     1055
Lys Asn Gln Val Glu Gly Glu Val Gln Ile Val Ser Thr Ala Ala Gln
                340                 345                 350

ACC TTC CTG GCA ACG TGC ATC AAT GGG GTG TGC TGG ACT GTC TAC CAC     1103
Thr Phe Leu Ala Thr Cys Ile Asn Gly Val Cys Trp Thr Val Tyr His
                355                 360                 365

GGG GCC GGA ACG AGG ACC ATC GCG TCA CCC AAG GGT CCT GTC ATC CAG     1151
Gly Ala Gly Thr Arg Thr Ile Ala Ser Pro Lys Gly Pro Val Ile Gln
                370                 375                 380

ATG TAT ACC AAT GTA GAC CAA GAC CTT GTG GGC TGG CCC GCT CCG CAA     1199
Met Tyr Thr Asn Val Asp Gln Asp Leu Val Gly Trp Pro Ala Pro Gln
385                 390                 395

GGT AGC CGC TCA TTG ACA CCC TGC ACT TGC GGC TCC TCG GAC CTT TAC     1247
Gly Ser Arg Ser Leu Thr Pro Cys Thr Cys Gly Ser Ser Asp Leu Tyr
400                 405                 410                 415

CTG GTC ACG AGG CAC GCC GAT GTC ATT CCC GTG CGC CGG CGG GGT GAT     1295
Leu Val Thr Arg His Ala Asp Val Ile Pro Val Arg Arg Arg Gly Asp
                420                 425                 430

AGC AGG GGC AGC CTG CTG TCG CCC CGG CCC ATT TCC TAC TTG AAA GGC     1343
Ser Arg Gly Ser Leu Leu Ser Pro Arg Pro Ile Ser Tyr Leu Lys Gly
                435                 440                 445

TCC TCG GGG GGT CCG CTG TTG TGC CCC GCG GGG CAC GCC GTG GGC ATA     1391
Ser Ser Gly Gly Pro Leu Leu Cys Pro Ala Gly His Ala Val Gly Ile
                450                 455                 460

TTT AGG GCC GCG GTG TGC ACC CGT GGA GTG GCT AAG GCG GTG GAC TTT     1439
Phe Arg Ala Ala Val Cys Thr Arg Gly Val Ala Lys Ala Val Asp Phe
465                 470                 475

ATC CCT GTG GAG AAC CTA GAG ACA ACC ATG AGG TCC CCG GTG TTC ACG     1487
Ile Pro Val Glu Asn Leu Glu Thr Thr Met Arg Ser Pro Val Phe Thr
480                 485                 490                 495

GAT AAC TCC TCT CCA CCA GTA GTG CCC CAG AGC TTC CAG GTG GCT CAC     1535
Asp Asn Ser Ser Pro Pro Val Val Pro Gln Ser Phe Gln Val Ala His
                500                 505                 510

CTC CAT GCT CCC ACA GGC AGC GGC AAA AGC ACC AAG GTC CCG GCT GCA     1583
Leu His Ala Pro Thr Gly Ser Gly Lys Ser Thr Lys Val Pro Ala Ala
                515                 520                 525

TAT GCA GCT CAG GGC TAT AAG GTG CTA GTA CTC AAC CCC TCT GTT GCT     1631
Tyr Ala Ala Gln Gly Tyr Lys Val Leu Val Leu Asn Pro Ser Val Ala
                530                 535                 540
```

```
GCA ACA CTG GGC TTT GGT GCT TAC ATG TCC AAG GCT CAT GGG ATC GAT       1679
Ala Thr Leu Gly Phe Gly Ala Tyr Met Ser Lys Ala His Gly Ile Asp
        545                 550                 555

CCT AAC ATC AGG ACC GGG GTG AGA ACA ATT ACC ACT GGC AGC CCC ATC       1727
Pro Asn Ile Arg Thr Gly Val Arg Thr Ile Thr Thr Gly Ser Pro Ile
560                 565                 570                 575

ACG TAC TCC ACC TAC GGC AAG TTC CTT GCC GAC GGC GGG TGC TCG GGG       1775
Thr Tyr Ser Thr Tyr Gly Lys Phe Leu Ala Asp Gly Gly Cys Ser Gly
                580                 585                 590

GGC GCT TAT GAC ATA ATA ATT TGT GAC GAG TGC CAC TCC ACG GAT GCC       1823
Gly Ala Tyr Asp Ile Ile Ile Cys Asp Glu Cys His Ser Thr Asp Ala
            595                 600                 605

ACA TCC ATC TTG GGC ATC GGC ACT GTC CTT GAC CAA GCA GAG ACT GCG       1871
Thr Ser Ile Leu Gly Ile Gly Thr Val Leu Asp Gln Ala Glu Thr Ala
        610                 615                 620

GGG GCG AGA CTG GTT GTG CTC GCC ACC GCC ACC CCT CCG GGC TCC GTC       1919
Gly Ala Arg Leu Val Val Leu Ala Thr Ala Thr Pro Pro Gly Ser Val
625                 630                 635

ACT GTG CCC CAT CCC AAC ATC GAG GAG GTT GCT CTG TCC ACC ACC GGA       1967
Thr Val Pro His Pro Asn Ile Glu Glu Val Ala Leu Ser Thr Thr Gly
640                 645                 650                 655

GAG ATC CCT TTT TAC GGC AAG GCT ATC CCC CTC GAA GTA ATC AAG GGG       2015
Glu Ile Pro Phe Tyr Gly Lys Ala Ile Pro Leu Glu Val Ile Lys Gly
                660                 665                 670

GGG AGA CAT CTC ATC TTC TGT CAT TCA AAG AAG AAG TGC GAC GAA CTC       2063
Gly Arg His Leu Ile Phe Cys His Ser Lys Lys Lys Cys Asp Glu Leu
            675                 680                 685

GCC GCA AAG CTG GTC GCA TTG GGC ATC AAT GCC GTG GCC TAC TAC CGC       2111
Ala Ala Lys Leu Val Ala Leu Gly Ile Asn Ala Val Ala Tyr Tyr Arg
        690                 695                 700

GGT CTT GAG CTG TCC GTC ATC CCG ACC AGC GGC GAT GTT GTC GTC GTG       2159
Gly Leu Glu Leu Ser Val Ile Pro Thr Ser Gly Asp Val Val Val Val
705                 710                 715

GCA ACC GAT GCC CTC ATG ACC GGC TAT ACC GGC GAC TTC GAC TCG GTG       2207
Ala Thr Asp Ala Leu Met Thr Gly Tyr Thr Gly Asp Phe Asp Ser Val
720                 725                 730                 735

ATA GAC TGC AAT ACG TGT GTC ACC CAG ACA GTC GAT TTC AGC CTT GAC       2255
Ile Asp Cys Asn Thr Cys Val Thr Gln Thr Val Asp Phe Ser Leu Asp
                740                 745                 750

CCT ACC TTC ACC ATT GAG ACA ATC ACG CTC CCC CAG GAT GCT GTC TCC       2303
Pro Thr Phe Thr Ile Glu Thr Ile Thr Leu Pro Gln Asp Ala Val Ser
            755                 760                 765

CGC ACT CAA CGT CGG GGC AGG ACT GGC AGG GGG AAG CCA GGC ATC TAC       2351
Arg Thr Gln Arg Arg Gly Arg Thr Gly Arg Gly Lys Pro Gly Ile Tyr
        770                 775                 780

AGA TTT GTG GCA CCG GGG GAG CGC CCC TCC GGC ATG TTC GAC TCG TCC       2399
Arg Phe Val Ala Pro Gly Glu Arg Pro Ser Gly Met Phe Asp Ser Ser
785                 790                 795

GTC CTC TGT GAG TGC TAT GAC GCA GGC TGT GCT TGG TAT GAG CTC ACG       2447
Val Leu Cys Glu Cys Tyr Asp Ala Gly Cys Ala Trp Tyr Glu Leu Thr
800                 805                 810                 815

CCC GCC GAG ACT ACA GTT AGG CTA CGA GCG TAC ATG AAC ACC CCG GGG       2495
Pro Ala Glu Thr Thr Val Arg Leu Arg Ala Tyr Met Asn Thr Pro Gly
                820                 825                 830

CTT CCC GTG TGC CAG GAC CAT CTT GAA TTT TGG GAG GGC GTC TTT ACA       2543
Leu Pro Val Cys Gln Asp His Leu Glu Phe Trp Glu Gly Val Phe Thr
            835                 840                 845

GGC CTC ACT CAT ATA GAT GCC CAC TTT CTA TCC CAG ACA AAG CAG AGT       2591
Gly Leu Thr His Ile Asp Ala His Phe Leu Ser Gln Thr Lys Gln Ser
        850                 855                 860
```

-continued

```
GGG GAG AAC CTT CCT TAC CTG GTA GCG TAC CAA GCC ACC GTG TGC GCT      2639
Gly Glu Asn Leu Pro Tyr Leu Val Ala Tyr Gln Ala Thr Val Cys Ala
    865                 870                 875

AGG GCT CAA GCC CCT CCC CCA TCG TGG GAC CAG ATG TGG AAG TGT TTG      2687
Arg Ala Gln Ala Pro Pro Pro Ser Trp Asp Gln Met Trp Lys Cys Leu
880                 885                 890                 895

ATT CGC CTC AAG CCC ACC CTC CAT GGG CCA ACA CCC CTG CTA TAC AGA      2735
Ile Arg Leu Lys Pro Thr Leu His Gly Pro Thr Pro Leu Leu Tyr Arg
                900                 905                 910

CTG GGC GCT GTT CAG AAT GAA ATC ACC CTG ACG CAC CCA GTC ACC AAA      2783
Leu Gly Ala Val Gln Asn Glu Ile Thr Leu Thr His Pro Val Thr Lys
                915                 920                 925

TAC ATC ATG ACA TGC ATG TCG GCC GAC CTG GAG GTC GTC ACG AGC ACC      2831
Tyr Ile Met Thr Cys Met Ser Ala Asp Leu Glu Val Val Thr Ser Thr
            930                 935                 940

TGG GTG CTC GTT GGC GGC GTC CTG TCT GCT TTG GCC GCG TAT TGC CTG      2879
Trp Val Leu Val Gly Gly Val Leu Ser Ala Leu Ala Ala Tyr Cys Leu
        945                 950                 955

TCA ACA GGC TGC GTG GTC ATA GTG GGC AGG GTC GTC TTG TCC GGG AAG      2927
Ser Thr Gly Cys Val Val Ile Val Gly Arg Val Val Leu Ser Gly Lys
960                 965                 970                 975

CCG GCA ATC ATA CCT GAC AGG GAA GTC CTC TAC CGA GAG TTC GAT GAG      2975
Pro Ala Ile Ile Pro Asp Arg Glu Val Leu Tyr Arg Glu Phe Asp Glu
                980                 985                 990

ATG GAA GAG TCC TCT CAG CAC TTA CCG TAC ATC GAG CAA GGG ATG ATG      3023
Met Glu Glu Ser Ser Gln His Leu Pro Tyr Ile Glu Gln Gly Met Met
                995                 1000                1005

CTC GCC GAG CAG TTC AAG CAG AAG GCC CTC GGC CTG CTG CAG ACC GCG      3071
Leu Ala Glu Gln Phe Lys Gln Lys Ala Leu Gly Leu Leu Gln Thr Ala
            1010                1015                1020

TCC CGT CAG GCA GAG GTT ATC GCC CCG TGC TGT CCA ACC AAC TGG CAA      3119
Ser Arg Gln Ala Glu Val Ile Ala Pro Cys Cys Pro Thr Asn Trp Gln
        1025                1030                1035

AAA CTC GAG ACC TTC TGG GCG AAG CAT ATG TGG AAC TTC ATC AGT GGG      3167
Lys Leu Glu Thr Phe Trp Ala Lys His Met Trp Asn Phe Ile Ser Gly
1040                1045                1050                1055

ATA CAA TAC TTG GCG GGC TTG TCA ACG CTG CCT GGT AAC CCC GCC ATT      3215
Ile Gln Tyr Leu Ala Gly Leu Ser Thr Leu Pro Gly Asn Pro Ala Ile
                1060                1065                1070

GCT TCA TTG ATG GCT TTT ACA GCT GCT GTC ACC AGC CCA CTA ACC ACT      3263
Ala Ser Leu Met Ala Phe Thr Ala Ala Val Thr Ser Pro Leu Thr Thr
                1075                1080                1085

AGC CAA ACC CTC CTC TTC AAC ATA TTG GGG GGG TGG GTG GCT GCC CAG      3311
Ser Gln Thr Leu Leu Phe Asn Ile Leu Gly Gly Trp Val Ala Ala Gln
            1090                1095                1100

CTC GCC GCC CCC GGT GCC GCT ACT GCC TTT GTG GGC GCT GGC TTA GCT      3359
Leu Ala Ala Pro Gly Ala Ala Thr Ala Phe Val Gly Ala Gly Leu Ala
        1105                1110                1115

GGC GCC GCC ATC GGC AGT GTT GGA CTG GGG AAG GTC CTC ATA GAC ATC      3407
Gly Ala Ala Ile Gly Ser Val Gly Leu Gly Lys Val Leu Ile Asp Ile
1120                1125                1130                1135

CTT GCA GGG TAT GGC GCG GGC GTG GCG GGA GCT CTT GTG GCA TTC AAG      3455
Leu Ala Gly Tyr Gly Ala Gly Val Ala Gly Ala Leu Val Ala Phe Lys
                1140                1145                1150

ATC ATG AGC GGT GAG GTC CCC TCC ACG GAG GAC CTG GTC AAT CTA CTG      3503
Ile Met Ser Gly Glu Val Pro Ser Thr Glu Asp Leu Val Asn Leu Leu
                1155                1160                1165

CCC GCC ATC CTC TCG CCC GGA GCC CTC GTA GTC GGC GTG GTC TGT GCA      3551
Pro Ala Ile Leu Ser Pro Gly Ala Leu Val Val Gly Val Val Cys Ala
```

```
                 1170             1175              1180
GCA ATA CTG CGC CGG CAC GTT GGC CCG GGC GAG GGG GCA GTG CAG TGG           3599
Ala Ile Leu Arg Arg His Val Gly Pro Gly Glu Gly Ala Val Gln Trp
        1185             1190              1195

ATG AAC CGG CTG ATA GCC TTC GCC TCC CGG GGG AAC CAT GTT TCC CCC           3647
Met Asn Arg Leu Ile Ala Phe Ala Ser Arg Gly Asn His Val Ser Pro
1200             1205             1210              1215

ACG CAC TAC GTG CCG GAG AGC GAT GCA GCT GCC CGC GTC ACT GCC ATA           3695
Thr His Tyr Val Pro Glu Ser Asp Ala Ala Ala Arg Val Thr Ala Ile
                1220             1225              1230

CTC AGC AGC CTC ACT GTA ACC CAG CTC CTG AGG CGA CTG CAC CAG TGG           3743
Leu Ser Ser Leu Thr Val Thr Gln Leu Leu Arg Arg Leu His Gln Trp
            1235             1240              1245

ATA AGC TCG GAG TGT ACC ACT CCA TGC TCC GGT TCC TGG CTA AGG GAC           3791
Ile Ser Ser Glu Cys Thr Thr Pro Cys Ser Gly Ser Trp Leu Arg Asp
        1250             1255              1260

ATC TGG GAC TGG ATA TGC GAG GTG TTG AGC GAC TTT AAG ACC TGG CTA           3839
Ile Trp Asp Trp Ile Cys Glu Val Leu Ser Asp Phe Lys Thr Trp Leu
    1265             1270              1275

AAA GCT AAG CTC ATG CCA CAG CTG CCT GGG ATC CCC TTT GTG TCC TGC           3887
Lys Ala Lys Leu Met Pro Gln Leu Pro Gly Ile Pro Phe Val Ser Cys
1280             1285             1290              1295

CAG CGC GGG TAT AAG GGG GTC TGG CGA GTG GAC GGC ATC ATG CAC ACT           3935
Gln Arg Gly Tyr Lys Gly Val Trp Arg Val Asp Gly Ile Met His Thr
                1300             1305              1310

CGC TGC CAC TGT GGA GCT GAG ATC ACT GGA CAT GTC AAA AAC GGG ACG           3983
Arg Cys His Cys Gly Ala Glu Ile Thr Gly His Val Lys Asn Gly Thr
            1315             1320              1325

ATG AGG ATC GTC GGT CCT AGG ACC TGC AGG AAC ATG TGG AGT GGG ACC           4031
Met Arg Ile Val Gly Pro Arg Thr Cys Arg Asn Met Trp Ser Gly Thr
        1330             1335              1340

TTC CCC ATT AAT GCC TAC ACC ACG GGC CCC TGT ACC CCC CTT CCT GCG           4079
Phe Pro Ile Asn Ala Tyr Thr Thr Gly Pro Cys Thr Pro Leu Pro Ala
    1345             1350              1355

CCG AAC TAC ACG TTC GCG CTA TGG AGG GTG TCT GCA GAG GAA TAT GTG           4127
Pro Asn Tyr Thr Phe Ala Leu Trp Arg Val Ser Ala Glu Glu Tyr Val
1360             1365             1370              1375

GAG ATA AGG CAG GTG GGG GAC TTC CAC TAC GTG ACG GGT ATG ACT ACT           4175
Glu Ile Arg Gln Val Gly Asp Phe His Tyr Val Thr Gly Met Thr Thr
                1380             1385              1390

GAC AAT CTC AAA TGC CCG TGC CAG GTC CCA TCG CCC GAA TTT TTC ACA           4223
Asp Asn Leu Lys Cys Pro Cys Gln Val Pro Ser Pro Glu Phe Phe Thr
            1395             1400              1405

GAA TTG GAC GGG GTG CGC CTA CAT AGG TTT GCG CCC CCC TGC AAG CCC           4271
Glu Leu Asp Gly Val Arg Leu His Arg Phe Ala Pro Pro Cys Lys Pro
        1410             1415              1420

TTG CTG CGG GAG GAG GTA TCA TTC AGA GTA GGA CTC CAC GAA TAC CCG           4319
Leu Leu Arg Glu Glu Val Ser Phe Arg Val Gly Leu His Glu Tyr Pro
    1425             1430              1435

GTA GGG TCG CAA TTA CCT TGC GAG CCC GAA CCG GAC GTG GCC GTG TTG           4367
Val Gly Ser Gln Leu Pro Cys Glu Pro Glu Pro Asp Val Ala Val Leu
1440             1445             1450              1455

ACG TCC ATG CTC ACT GAT CCC TCC CAT ATA ACA GCA GAG GCG GCC GGG           4415
Thr Ser Met Leu Thr Asp Pro Ser His Ile Thr Ala Glu Ala Ala Gly
                1460             1465              1470

CGA AGG TTG GCG AGG GGA TCA CCC CCC TCT GTG GCC AGC TCC TCG GCT           4463
Arg Arg Leu Ala Arg Gly Ser Pro Pro Ser Val Ala Ser Ser Ser Ala
            1475             1480              1485

AGC CAG CTA TCC GCT CCA TCT CTC AAG GCA ACT TGC ACC GCT AAC CAT           4511
```

```
Ser Gln Leu Ser Ala Pro Ser Leu Lys Ala Thr Cys Thr Ala Asn His
        1490                1495                1500

GAC TCC CCT GAT GCT GAG CTC ATA GAG GCC AAC CTC CTA TGG AGG CAG          4559
Asp Ser Pro Asp Ala Glu Leu Ile Glu Ala Asn Leu Leu Trp Arg Gln
1505                1510                1515

GAG ATG GGC GGC AAC ATC ACC AGG GTT GAG TCA GAA AAC AAA GTG GTG          4607
Glu Met Gly Gly Asn Ile Thr Arg Val Glu Ser Glu Asn Lys Val Val
1520                1525                1530                1535

ATT CTG GAC TCC TTC GAT CCG CTT GTG GCG GAG GAG GAC GAG CGG GAG          4655
Ile Leu Asp Ser Phe Asp Pro Leu Val Ala Glu Glu Asp Glu Arg Glu
                1540                1545                1550

ATC TCC GTA CCC GCA GAA ATC CTG CGG AAG TCT CGG AGA TTC GCC CAG          4703
Ile Ser Val Pro Ala Glu Ile Leu Arg Lys Ser Arg Arg Phe Ala Gln
                1555                1560                1565

GCC CTG CCC GTT TGG GCG CGG CCG GAC TAT AAC CCC CCG CTA GTG GAG          4751
Ala Leu Pro Val Trp Ala Arg Pro Asp Tyr Asn Pro Pro Leu Val Glu
        1570                1575                1580

ACG TGG AAA AAG CCC GAC TAC GAA CCA CCT GTG GTC CAT GGC TGT CCG          4799
Thr Trp Lys Lys Pro Asp Tyr Glu Pro Pro Val Val His Gly Cys Pro
1585                1590                1595

CTT CCA CCT CCA AAG TCC CCT CCT GTG CCT CCG CCT CGG AAG AAG CGG          4847
Leu Pro Pro Pro Lys Ser Pro Pro Val Pro Pro Pro Arg Lys Lys Arg
1600                1605                1610                1615

ACG GTG GTC CTC ACT GAA TCA ACC CTA TCT ACT GCC TTG GCC GAG CTC          4895
Thr Val Val Leu Thr Glu Ser Thr Leu Ser Thr Ala Leu Ala Glu Leu
                1620                1625                1630

GCC ACC AGA AGC TTT GGC AGC TCC TCA ACT TCC GGC ATT ACG GGC GAC          4943
Ala Thr Arg Ser Phe Gly Ser Ser Ser Thr Ser Gly Ile Thr Gly Asp
                1635                1640                1645

AAT ACG ACA ACA TCC TCT GAG CCC GCC CCT TCT GGC TGC CCC CCC GAC          4991
Asn Thr Thr Thr Ser Ser Glu Pro Ala Pro Ser Gly Cys Pro Pro Asp
                1650                1655                1660

TCC GAC GCT GAG TCC TAT TCC TCC ATG CCC CCC CTG GAG GGG GAG CCT          5039
Ser Asp Ala Glu Ser Tyr Ser Ser Met Pro Pro Leu Glu Gly Glu Pro
        1665                1670                1675

GGG GAT CCG GAT CTT AGC GAC GGG TCA TGG TCA ACG GTC AGT AGT GTG          5087
Gly Asp Pro Asp Leu Ser Asp Gly Ser Trp Ser Thr Val Ser Ser Val
1680                1685                1690                1695

GCC AAC GCG GAG GAT GTC GTG TGC TGC TCA ATG TCT TAC TCT TGG ACA          5135
Ala Asn Ala Glu Asp Val Val Cys Cys Ser Met Ser Tyr Ser Trp Thr
                1700                1705                1710

GGC GCA CTC GTC ACC CCG TGC GCC GCG GAA GAA CAG AAA CTG CCC ATC          5183
Gly Ala Leu Val Thr Pro Cys Ala Ala Glu Glu Gln Lys Leu Pro Ile
                1715                1720                1725

AAT GCA CTA AGC AAC TCG TTG CTA CGT CAC CAC AAT TTG GTG TAT TCC          5231
Asn Ala Leu Ser Asn Ser Leu Leu Arg His His Asn Leu Val Tyr Ser
        1730                1735                1740

ACC ACC TCA CGC AGT GCT TGC CAA AGG CAG AAG AAA GTC ACA TTT GAC          5279
Thr Thr Ser Arg Ser Ala Cys Gln Arg Gln Lys Lys Val Thr Phe Asp
1745                1750                1755

AGA CTG CAA GTT CTG GAC AGC CAT TAC CAG GAC GTA CTC AAG GAG GTT          5327
Arg Leu Gln Val Leu Asp Ser His Tyr Gln Asp Val Leu Lys Glu Val
1760                1765                1770                1775

AAA GCA GCG GCG TCA AAA GTG AAG GCT AAC TTG                              5360
Lys Ala Ala Ala Ser Lys Val Lys Ala Asn Leu
                1780                1785
```

(2) INFORMATION FOR SEQ ID NO:54:

(i) SEQUENCE CHARACTERISTICS:

(A) LENGTH: 1786 amino acids
(B) TYPE: amino acid
(D) TOPOLOGY: linear (ii) MOLECULE TYPE: protein (xi) SEQUENCE DESCRIPTION: SEQ ID NO:54:

```
Glu Tyr Val Val Leu Leu Phe Leu Leu Leu Ala Asp Ala Arg Val Cys
  1               5                  10                  15

Ser Cys Leu Trp Met Met Leu Leu Ile Ser Gln Ala Glu Ala Ala Leu
                 20                  25                  30

Glu Asn Leu Val Ile Leu Asn Ala Ala Ser Leu Ala Gly Thr His Gly
             35                  40                  45

Leu Val Ser Phe Leu Val Phe Phe Cys Phe Ala Trp Tyr Leu Lys Gly
 50                  55                  60

Lys Trp Val Pro Gly Ala Val Tyr Thr Phe Tyr Gly Met Trp Pro Leu
 65                  70                  75                  80

Leu Leu Leu Leu Leu Ala Leu Pro Gln Arg Ala Tyr Ala Leu Asp Thr
                 85                  90                  95

Glu Val Ala Ala Ser Cys Gly Gly Val Val Leu Val Gly Leu Met Ala
            100                 105                 110

Leu Thr Leu Ser Pro Tyr Tyr Lys Arg Tyr Ile Ser Trp Cys Leu Trp
            115                 120                 125

Trp Leu Gln Tyr Phe Leu Thr Arg Val Glu Ala Gln Leu His Val Trp
130                 135                 140

Ile Pro Pro Leu Asn Val Arg Gly Gly Arg Asp Ala Val Ile Leu Leu
145                 150                 155                 160

Met Cys Ala Val His Pro Thr Leu Val Phe Asp Ile Thr Lys Leu Leu
                165                 170                 175

Leu Ala Val Phe Gly Pro Leu Trp Ile Leu Gln Ala Ser Leu Leu Lys
            180                 185                 190

Val Pro Tyr Phe Val Arg Val Gln Gly Leu Leu Arg Phe Cys Ala Leu
            195                 200                 205

Ala Arg Lys Met Ile Gly Gly His Tyr Val Gln Met Val Ile Ile Lys
210                 215                 220

Leu Gly Ala Leu Thr Gly Thr Tyr Val Tyr Asn His Leu Thr Pro Leu
225                 230                 235                 240

Arg Asp Trp Ala His Asn Gly Leu Arg Asp Leu Ala Val Ala Val Glu
                245                 250                 255

Pro Val Val Phe Ser Gln Met Glu Thr Lys Leu Ile Thr Trp Gly Ala
            260                 265                 270

Asp Thr Ala Ala Cys Gly Asp Ile Ile Asn Gly Leu Pro Val Ser Ala
            275                 280                 285

Arg Arg Gly Arg Glu Ile Leu Leu Gly Pro Ala Asp Gly Met Val Ser
290                 295                 300

Lys Gly Trp Arg Leu Leu Ala Pro Ile Thr Ala Tyr Ala Gln Gln Thr
305                 310                 315                 320

Arg Gly Leu Leu Gly Cys Ile Ile Thr Ser Leu Thr Gly Arg Asp Lys
                325                 330                 335

Asn Gln Val Glu Gly Glu Val Gln Ile Val Ser Thr Ala Ala Gln Thr
            340                 345                 350

Phe Leu Ala Thr Cys Ile Asn Gly Val Cys Trp Thr Val Tyr His Gly
            355                 360                 365

Ala Gly Thr Arg Thr Ile Ala Ser Pro Lys Gly Pro Val Ile Gln Met
370                 375                 380
```

-continued

```
Tyr Thr Asn Val Asp Gln Asp Leu Val Gly Trp Pro Ala Pro Gln Gly
385                 390                 395                 400

Ser Arg Ser Leu Thr Pro Cys Thr Cys Gly Ser Ser Asp Leu Tyr Leu
                405                 410                 415

Val Thr Arg His Ala Asp Val Ile Pro Val Arg Arg Arg Gly Asp Ser
                420                 425                 430

Arg Gly Ser Leu Leu Ser Pro Arg Pro Ile Ser Tyr Leu Lys Gly Ser
                435                 440                 445

Ser Gly Gly Pro Leu Leu Cys Pro Ala Gly His Ala Val Gly Ile Phe
450                 455                 460

Arg Ala Ala Val Cys Thr Arg Gly Val Ala Lys Ala Val Asp Phe Ile
465                 470                 475                 480

Pro Val Glu Asn Leu Glu Thr Thr Met Arg Ser Pro Val Phe Thr Asp
                485                 490                 495

Asn Ser Ser Pro Pro Val Val Pro Gln Ser Phe Gln Val Ala His Leu
                500                 505                 510

His Ala Pro Thr Gly Ser Gly Lys Ser Thr Lys Val Pro Ala Ala Tyr
                515                 520                 525

Ala Ala Gln Gly Tyr Lys Val Leu Val Leu Asn Pro Ser Val Ala Ala
                530                 535                 540

Thr Leu Gly Phe Gly Ala Tyr Met Ser Lys Ala His Gly Ile Asp Pro
545                 550                 555                 560

Asn Ile Arg Thr Gly Val Arg Thr Ile Thr Thr Gly Ser Pro Ile Thr
                565                 570                 575

Tyr Ser Thr Tyr Gly Lys Phe Leu Ala Asp Gly Gly Cys Ser Gly Gly
                580                 585                 590

Ala Tyr Asp Ile Ile Ile Cys Asp Glu Cys His Ser Thr Asp Ala Thr
                595                 600                 605

Ser Ile Leu Gly Ile Gly Thr Val Leu Asp Gln Ala Glu Thr Ala Gly
                610                 615                 620

Ala Arg Leu Val Val Leu Ala Thr Ala Thr Pro Pro Gly Ser Val Thr
625                 630                 635                 640

Val Pro His Pro Asn Ile Glu Glu Val Ala Leu Ser Thr Thr Gly Glu
                645                 650                 655

Ile Pro Phe Tyr Gly Lys Ala Ile Pro Leu Glu Val Ile Lys Gly Gly
                660                 665                 670

Arg His Leu Ile Phe Cys His Ser Lys Lys Lys Cys Asp Glu Leu Ala
                675                 680                 685

Ala Lys Leu Val Ala Leu Gly Ile Asn Ala Val Ala Tyr Tyr Arg Gly
                690                 695                 700

Leu Glu Leu Ser Val Ile Pro Thr Ser Gly Asp Val Val Val Val Ala
705                 710                 715                 720

Thr Asp Ala Leu Met Thr Gly Tyr Thr Gly Asp Phe Asp Ser Val Ile
                725                 730                 735

Asp Cys Asn Thr Cys Val Thr Gln Thr Val Asp Phe Ser Leu Asp Pro
                740                 745                 750

Thr Phe Thr Ile Glu Thr Ile Thr Leu Pro Gln Asp Ala Val Ser Arg
                755                 760                 765

Thr Gln Arg Arg Gly Arg Thr Gly Arg Gly Lys Pro Gly Ile Tyr Arg
                770                 775                 780

Phe Val Ala Pro Gly Glu Arg Pro Ser Gly Met Phe Asp Ser Ser Val
785                 790                 795                 800
```

-continued

```
Leu Cys Glu Cys Tyr Asp Ala Gly Cys Ala Trp Tyr Glu Leu Thr Pro
                805                 810                 815

Ala Glu Thr Thr Val Arg Leu Arg Ala Tyr Met Asn Thr Pro Gly Leu
            820                 825                 830

Pro Val Cys Gln Asp His Leu Glu Phe Trp Glu Gly Val Phe Thr Gly
        835                 840                 845

Leu Thr His Ile Asp Ala His Phe Leu Ser Gln Thr Lys Gln Ser Gly
    850                 855                 860

Glu Asn Leu Pro Tyr Leu Val Ala Tyr Gln Ala Thr Val Cys Ala Arg
865                 870                 875                 880

Ala Gln Ala Pro Pro Ser Trp Asp Gln Met Trp Lys Cys Leu Ile
            885                 890                 895

Arg Leu Lys Pro Thr Leu His Gly Pro Thr Pro Leu Leu Tyr Arg Leu
            900                 905                 910

Gly Ala Val Gln Asn Glu Ile Thr Leu Thr His Pro Val Thr Lys Tyr
        915                 920                 925

Ile Met Thr Cys Met Ser Ala Asp Leu Glu Val Val Thr Ser Thr Trp
    930                 935                 940

Val Leu Val Gly Gly Val Leu Ser Ala Leu Ala Ala Tyr Cys Leu Ser
945                 950                 955                 960

Thr Gly Cys Val Val Ile Val Gly Arg Val Val Leu Ser Gly Lys Pro
            965                 970                 975

Ala Ile Ile Pro Asp Arg Glu Val Leu Tyr Arg Glu Phe Asp Glu Met
            980                 985                 990

Glu Glu Ser Ser Gln His Leu Pro Tyr Ile Glu Gln Gly Met Met Leu
            995                 1000                1005

Ala Glu Gln Phe Lys Gln Lys Ala Leu Gly Leu Leu Gln Thr Ala Ser
        1010                1015                1020

Arg Gln Ala Glu Val Ile Ala Pro Cys Cys Pro Thr Asn Trp Gln Lys
1025                1030                1035                1040

Leu Glu Thr Phe Trp Ala Lys His Met Trp Asn Phe Ile Ser Gly Ile
            1045                1050                1055

Gln Tyr Leu Ala Gly Leu Ser Thr Leu Pro Gly Asn Pro Ala Ile Ala
            1060                1065                1070

Ser Leu Met Ala Phe Thr Ala Ala Val Thr Ser Pro Leu Thr Thr Ser
        1075                1080                1085

Gln Thr Leu Leu Phe Asn Ile Leu Gly Gly Trp Val Ala Ala Gln Leu
    1090                1095                1100

Ala Ala Pro Gly Ala Ala Thr Ala Phe Val Gly Ala Gly Leu Ala Gly
1105                1110                1115                1120

Ala Ala Ile Gly Ser Val Gly Leu Gly Lys Val Leu Ile Asp Ile Leu
            1125                1130                1135

Ala Gly Tyr Gly Ala Gly Val Ala Gly Ala Leu Val Ala Phe Lys Ile
            1140                1145                1150

Met Ser Gly Glu Val Pro Ser Thr Glu Asp Leu Val Asn Leu Leu Pro
        1155                1160                1165

Ala Ile Leu Ser Pro Gly Ala Leu Val Val Gly Val Val Cys Ala Ala
    1170                1175                1180

Ile Leu Arg Arg His Val Gly Pro Gly Glu Gly Ala Val Gln Trp Met
1185                1190                1195                1200

Asn Arg Leu Ile Ala Phe Ala Ser Arg Gly Asn His Val Ser Pro Thr
            1205                1210                1215

His Tyr Val Pro Glu Ser Asp Ala Ala Ala Arg Val Thr Ala Ile Leu
```

```
                    1220              1225              1230
Ser Ser Leu Thr Val Thr Gln Leu Leu Arg Arg Leu His Gln Trp Ile
            1235              1240              1245

Ser Ser Glu Cys Thr Thr Pro Cys Ser Gly Ser Trp Leu Arg Asp Ile
1250              1255              1260

Trp Asp Trp Ile Cys Glu Val Leu Ser Asp Phe Lys Thr Trp Leu Lys
1265              1270              1275              1280

Ala Lys Leu Met Pro Gln Leu Pro Gly Ile Pro Phe Val Ser Cys Gln
            1285              1290              1295

Arg Gly Tyr Lys Gly Val Trp Arg Val Asp Gly Ile Met His Thr Arg
            1300              1305              1310

Cys His Cys Gly Ala Glu Ile Thr Gly His Val Lys Asn Gly Thr Met
            1315              1320              1325

Arg Ile Val Gly Pro Arg Thr Cys Arg Asn Met Trp Ser Gly Thr Phe
            1330              1335              1340

Pro Ile Asn Ala Tyr Thr Thr Gly Pro Cys Thr Pro Leu Pro Ala Pro
1345              1350              1355              1360

Asn Tyr Thr Phe Ala Leu Trp Arg Val Ser Ala Glu Glu Tyr Val Glu
            1365              1370              1375

Ile Arg Gln Val Gly Asp Phe His Tyr Val Thr Gly Met Thr Thr Asp
            1380              1385              1390

Asn Leu Lys Cys Pro Cys Gln Val Pro Ser Pro Glu Phe Phe Thr Glu
            1395              1400              1405

Leu Asp Gly Val Arg Leu His Arg Phe Ala Pro Pro Cys Lys Pro Leu
            1410              1415              1420

Leu Arg Glu Glu Val Ser Phe Arg Val Gly Leu His Glu Tyr Pro Val
1425              1430              1435              1440

Gly Ser Gln Leu Pro Cys Glu Pro Glu Pro Asp Val Ala Val Leu Thr
            1445              1450              1455

Ser Met Leu Thr Asp Pro Ser His Ile Thr Ala Glu Ala Ala Gly Arg
            1460              1465              1470

Arg Leu Ala Arg Gly Ser Pro Pro Ser Val Ala Ser Ser Ser Ala Ser
            1475              1480              1485

Gln Leu Ser Ala Pro Ser Leu Lys Ala Thr Cys Thr Ala Asn His Asp
            1490              1495              1500

Ser Pro Asp Ala Glu Leu Ile Glu Ala Asn Leu Leu Trp Arg Gln Glu
1505              1510              1515              1520

Met Gly Gly Asn Ile Thr Arg Val Glu Ser Glu Asn Lys Val Val Ile
            1525              1530              1535

Leu Asp Ser Phe Asp Pro Leu Val Ala Glu Glu Asp Glu Arg Glu Ile
            1540              1545              1550

Ser Val Pro Ala Glu Ile Leu Arg Lys Ser Arg Arg Phe Ala Gln Ala
            1555              1560              1565

Leu Pro Val Trp Ala Arg Pro Asp Tyr Asn Pro Pro Leu Val Glu Thr
            1570              1575              1580

Trp Lys Lys Pro Asp Tyr Glu Pro Pro Val Val His Gly Cys Pro Leu
1585              1590              1595              1600

Pro Pro Pro Lys Ser Pro Pro Val Pro Pro Pro Arg Lys Lys Arg Thr
            1605              1610              1615

Val Val Leu Thr Glu Ser Thr Leu Ser Thr Ala Leu Ala Glu Leu Ala
            1620              1625              1630

Thr Arg Ser Phe Gly Ser Ser Ser Thr Ser Gly Ile Thr Gly Asp Asn
            1635              1640              1645
```

```
Thr Thr Thr Ser Ser Glu Pro Ala Pro Ser Gly Cys Pro Pro Asp Ser
        1650                1655                1660

Asp Ala Glu Ser Tyr Ser Ser Met Pro Pro Leu Glu Gly Glu Pro Gly
1665                1670                1675                1680

Asp Pro Asp Leu Ser Asp Gly Ser Trp Ser Thr Val Ser Ser Val Ala
            1685                1690                1695

Asn Ala Glu Asp Val Val Cys Cys Ser Met Ser Tyr Ser Trp Thr Gly
            1700                1705                1710

Ala Leu Val Thr Pro Cys Ala Ala Glu Glu Gln Lys Leu Pro Ile Asn
            1715                1720                1725

Ala Leu Ser Asn Ser Leu Leu Arg His His Asn Leu Val Tyr Ser Thr
            1730                1735                1740

Thr Ser Arg Ser Ala Cys Gln Arg Gln Lys Lys Val Thr Phe Asp Arg
1745                1750                1755                1760

Leu Gln Val Leu Asp Ser His Tyr Gln Asp Val Leu Lys Glu Val Lys
            1765                1770                1775

Ala Ala Ala Ser Lys Val Lys Ala Asn Leu
            1780                1785

(2) INFORMATION FOR SEQ ID NO:55:

(i) SEQUENCE CHARACTERISTICS:
        (A) LENGTH: 427 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 3..425

(xi) SEQUENCE DESCRIPTION: SEQ ID NO:55:

CC ATA TTT AAA ATC AGG ATG TAC GTG GGA GGG GTC GAA CAC AGG CTG         47
   Ile Phe Lys Ile Arg Met Tyr Val Gly Gly Val Glu His Arg Leu
    1               5                  10                  15

GAA GCT GCC TGC AAC TGG ACG CGG GGC GAA CGT TGC GAT CTG GAA GAC        95
Glu Ala Ala Cys Asn Trp Thr Arg Gly Glu Arg Cys Asp Leu Glu Asp
                20                  25                  30

AGG GAC AGG TCC GAG CTC AGC CCG TTA CTG CTG ACC ACT ACA CAG TGG       143
Arg Asp Arg Ser Glu Leu Ser Pro Leu Leu Leu Thr Thr Thr Gln Trp
            35                  40                  45

CAG GTC CTC CCG TGT TCC TTC ACA ACC CTA CCA GCC TTG TCC ACC GGC       191
Gln Val Leu Pro Cys Ser Phe Thr Thr Leu Pro Ala Leu Ser Thr Gly
        50                  55                  60

CTC ATC CAC CTC CAC CAG AAC ATT GTG GAC GTG CAG TAC TTG TAC GGG       239
Leu Ile His Leu His Gln Asn Ile Val Asp Val Gln Tyr Leu Tyr Gly
    65                  70                  75

GTG GGG TCA AGC ATC GCG TCC TGG GCC ATT AAG TGG GAG TAC GTC GTT       287
Val Gly Ser Ser Ile Ala Ser Trp Ala Ile Lys Trp Glu Tyr Val Val
 80                  85                  90                  95

CTC CTG TTC CTT CTG CTT GCA GAC GCG CGC GTC TGC TCC TGC TTG TGG       335
Leu Leu Phe Leu Leu Leu Ala Asp Ala Arg Val Cys Ser Cys Leu Trp
                100                 105                 110

ATG ATG CTA CTC ATA TCC CAA GCG GAG GCG GCT TTG GAG AAC CTC GTA       383
Met Met Leu Leu Ile Ser Gln Ala Glu Ala Ala Leu Glu Asn Leu Val
            115                 120                 125

ATA CTT AAT GCA GCA TCC CTG GCC GGG ACG CAC GGT CTT GTA               425
Ile Leu Asn Ala Ala Ser Leu Ala Gly Thr His Gly Leu Val
```

```
              130             135             140
TC                                                                      427

(2) INFORMATION FOR SEQ ID NO:56:

(i) SEQUENCE CHARACTERISTICS:
        (A) LENGTH: 141 amino acids
        (B) TYPE: amino acid
        (D) TOPOLOGY: linear (ii) MOLECULE TYPE: protein (xi) SEQUENCE DESCRIPTION: SEQ ID NO:56:

Ile Phe Lys Ile Arg Met Tyr Val Gly Gly Val Glu His Arg Leu Glu
  1               5                  10                  15

Ala Ala Cys Asn Trp Thr Arg Gly Glu Arg Cys Asp Leu Glu Asp Arg
             20                  25                  30

Asp Arg Ser Glu Leu Ser Pro Leu Leu Thr Thr Thr Gln Trp Gln
         35                  40                  45

Val Leu Pro Cys Ser Phe Thr Thr Leu Pro Ala Leu Ser Thr Gly Leu
     50                  55                  60

Ile His Leu His Gln Asn Ile Val Asp Val Gln Tyr Leu Tyr Gly Val
 65                  70                  75                  80

Gly Ser Ser Ile Ala Ser Trp Ala Ile Lys Trp Glu Tyr Val Val Leu
                 85                  90                  95

Leu Phe Leu Leu Leu Ala Asp Ala Arg Val Cys Ser Cys Leu Trp Met
             100                 105                 110

Met Leu Leu Ile Ser Gln Ala Glu Ala Ala Leu Glu Asn Leu Val Ile
         115                 120                 125

Leu Asn Ala Ala Ser Leu Ala Gly Thr His Gly Leu Val
     130                 135                 140

(2) INFORMATION FOR SEQ ID NO:57:

(i) SEQUENCE CHARACTERISTICS:
        (A) LENGTH: 515 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 3..515

(xi) SEQUENCE DESCRIPTION: SEQ ID NO:57:

TG CTC AAG GAG GTT AAA GCA GCG GCG TCA AAA GTG AAG GCT AAC TTG         47
   Leu Lys Glu Val Lys Ala Ala Ala Ser Lys Val Lys Ala Asn Leu
    1               5                  10                  15

CTA TCC GTA GAG GAA GCT TGC AGC CTG ACG CCC CCA CAC TCA GCC AAA        95
Leu Ser Val Glu Glu Ala Cys Ser Leu Thr Pro Pro His Ser Ala Lys
             20                  25                  30

TCC AAG TTT GGT TAT GGG GCA AAA GAC GTC CGT TGC CAT GCC AGA AAG       143
Ser Lys Phe Gly Tyr Gly Ala Lys Asp Val Arg Cys His Ala Arg Lys
         35                  40                  45

GCC GTA ACC CAC ATC AAC TCC GTG TGG AAA GAC CTT CTG GAA GAC AAT       191
Ala Val Thr His Ile Asn Ser Val Trp Lys Asp Leu Leu Glu Asp Asn
     50                  55                  60

GTA ACA CCA CTA GAC ACT ACC ATC ATG GCT AAG AAC GAG GTT TTC TGC       239
Val Thr Pro Leu Asp Thr Thr Ile Met Ala Lys Asn Glu Val Phe Cys
 65                  70                  75
```

```
GTT CAG CCT GAG AAG GGG GGT CGT AAG CCA GCT CGT CTC ATC GTG TTC          287
Val Gln Pro Glu Lys Gly Gly Arg Lys Pro Ala Arg Leu Ile Val Phe
 80              85                  90                  95

CCC GAT CTG GGC GTG CGC GTG TGC GAA AAG ATG GCT TTG TAC GAC GTG          335
Pro Asp Leu Gly Val Arg Val Cys Glu Lys Met Ala Leu Tyr Asp Val
                100                 105                 110

GTT ACA AAG CTC CCC TTG GCC GTG ATG GGA AGC TCC TAC GGA TTC CAA          383
Val Thr Lys Leu Pro Leu Ala Val Met Gly Ser Ser Tyr Gly Phe Gln
            115                 120                 125

TAC TCA CCA GGA CAG CGG GTT GAA TTC CTC GTG CAA GCG TGG AAG TCC          431
Tyr Ser Pro Gly Gln Arg Val Glu Phe Leu Val Gln Ala Trp Lys Ser
        130                 135                 140

AAG AAA ACC CCA ATG GGG TTC TCG TAT GAT ACC CGC TGC TTT GAC TCC          479
Lys Lys Thr Pro Met Gly Phe Ser Tyr Asp Thr Arg Cys Phe Asp Ser
145                 150                 155

ACA GTC ACT GAG AGC GAC ATC CGT ACG GAG GAG GCA                          515
Thr Val Thr Glu Ser Asp Ile Arg Thr Glu Glu Ala
160                 165                 170
```

(2) INFORMATION FOR SEQ ID NO:58:

(i) SEQUENCE CHARACTERISTICS:
        (A) LENGTH: 171 amino acids
        (B) TYPE: amino acid
        (D) TOPOLOGY: linear (ii) MOLECULE TYPE: protein (xi) SEQUENCE DESCRIPTION: SEQ ID NO:58:

```
Leu Lys Glu Val Lys Ala Ala Ser Lys Val Lys Ala Asn Leu Leu
 1               5                  10                  15

Ser Val Glu Glu Ala Cys Ser Leu Thr Pro Pro His Ser Ala Lys Ser
                20                  25                  30

Lys Phe Gly Tyr Gly Ala Lys Asp Val Arg Cys His Ala Arg Lys Ala
            35                  40                  45

Val Thr His Ile Asn Ser Val Trp Lys Asp Leu Leu Glu Asp Asn Val
        50                  55                  60

Thr Pro Leu Asp Thr Thr Ile Met Ala Lys Asn Glu Val Phe Cys Val
 65                 70                  75                  80

Gln Pro Glu Lys Gly Gly Arg Lys Pro Ala Arg Leu Ile Val Phe Pro
                85                  90                  95

Asp Leu Gly Val Arg Val Cys Glu Lys Met Ala Leu Tyr Asp Val Val
            100                 105                 110

Thr Lys Leu Pro Leu Ala Val Met Gly Ser Ser Tyr Gly Phe Gln Tyr
        115                 120                 125

Ser Pro Gly Gln Arg Val Glu Phe Leu Val Gln Ala Trp Lys Ser Lys
    130                 135                 140

Lys Thr Pro Met Gly Phe Ser Tyr Asp Thr Arg Cys Phe Asp Ser Thr
145                 150                 155                 160

Val Thr Glu Ser Asp Ile Arg Thr Glu Glu Ala
                165                 170
```

(2) INFORMATION FOR SEQ ID NO:59:

(i) SEQUENCE CHARACTERISTICS:
        (A) LENGTH: 401 base pairs
        (B) TYPE: nucleic acid
        (C) STRANDEDNESS: single
        (D) TOPOLOGY: linear (ii) MOLECULE TYPE: cDNA (ix) FEATURE:
 (A) NAME/KEY: CDS
 (B) LOCATION: 1..399

(xi) SEQUENCE DESCRIPTION: SEQ ID NO:59:

```
GAA TTC CTC GTG CAA GCG TGG AAG TCC AAG AAA ACC CCA ATG GGG TTC      48
Glu Phe Leu Val Gln Ala Trp Lys Ser Lys Lys Thr Pro Met Gly Phe
  1               5                  10                  15

TCG TAT GAT ACC CGC TGC TTT GAC TCC ACA GTC ACT GAG AGC GAC ATC      96
Ser Tyr Asp Thr Arg Cys Phe Asp Ser Thr Val Thr Glu Ser Asp Ile
                 20                  25                  30

CGT ACG GAG GAG GCA ATC TAC CAA TGT TGT GAC CTC GAC CCC CAA GCC     144
Arg Thr Glu Glu Ala Ile Tyr Gln Cys Cys Asp Leu Asp Pro Gln Ala
             35                  40                  45

CGC GTG GCC ATC AAG TCC CTC ACC GAG AGG CTT TAT GTT GGG GGC CCT     192
Arg Val Ala Ile Lys Ser Leu Thr Glu Arg Leu Tyr Val Gly Gly Pro
     50                  55                  60

CTT ACC AAT TCA AGG GGG GAG AAC TGC GGC TAT CGC AGG TGC CGC GCG     240
Leu Thr Asn Ser Arg Gly Glu Asn Cys Gly Tyr Arg Arg Cys Arg Ala
 65                  70                  75                  80

AGC GGC GTA CTG ACA ACT AGC TGT GGT AAC ACC CTC ACT TGC TAC ATC     288
Ser Gly Val Leu Thr Thr Ser Cys Gly Asn Thr Leu Thr Cys Tyr Ile
                 85                  90                  95

AAG GCC CCG GCA GCC TGT CGA GCC GCA GGG CTC CAG GAC TGC ACC ATG     336
Lys Ala Pro Ala Ala Cys Arg Ala Ala Gly Leu Gln Asp Cys Thr Met
            100                 105                 110

CTC GTG TGT GGC GAC GAC TTA GTC GTT ATC TGT GAA AGC GCG GGG GTC     384
Leu Val Cys Gly Asp Asp Leu Val Val Ile Cys Glu Ser Ala Gly Val
            115                 120                 125

CAG GAG GAC GCG GCG AG                                              401
Gln Glu Asp Ala Ala
        130
```

(2) INFORMATION FOR SEQ ID NO:60:

(i) SEQUENCE CHARACTERISTICS:
  (A) LENGTH: 133 amino acids
  (B) TYPE: amino acid
  (D) TOPOLOGY: linear (ii) MOLECULE TYPE: protein (xi) SEQUENCE DESCRIPTION: SEQ ID NO:60:

```
Glu Phe Leu Val Gln Ala Trp Lys Ser Lys Lys Thr Pro Met Gly Phe
  1               5                  10                  15

Ser Tyr Asp Thr Arg Cys Phe Asp Ser Thr Val Thr Glu Ser Asp Ile
                 20                  25                  30

Arg Thr Glu Glu Ala Ile Tyr Gln Cys Cys Asp Leu Asp Pro Gln Ala
             35                  40                  45

Arg Val Ala Ile Lys Ser Leu Thr Glu Arg Leu Tyr Val Gly Gly Pro
     50                  55                  60

Leu Thr Asn Ser Arg Gly Glu Asn Cys Gly Tyr Arg Arg Cys Arg Ala
 65                  70                  75                  80

Ser Gly Val Leu Thr Thr Ser Cys Gly Asn Thr Leu Thr Cys Tyr Ile
                 85                  90                  95

Lys Ala Pro Ala Ala Cys Arg Ala Ala Gly Leu Gln Asp Cys Thr Met
            100                 105                 110

Leu Val Cys Gly Asp Asp Leu Val Val Ile Cys Glu Ser Ala Gly Val
            115                 120                 125
```

Gln Glu Asp Ala Ala
    130

(2) INFORMATION FOR SEQ ID NO:61:

(i) SEQUENCE CHARACTERISTICS:
       (A) LENGTH: 456 base pairs
       (B) TYPE: nucleic acid
       (C) STRANDEDNESS: single
       (D) TOPOLOGY: linear (ii) MOLECULE TYPE: cDNA (ix) FEATURE:
       (A) NAME/KEY: CDS
       (B) LOCATION: 1..456

(xi) SEQUENCE DESCRIPTION: SEQ ID NO:61:

```
GGG GGG GAG AAC TGC GGC TAT CGC AGG TGC CGC GCA AGC GGC GTA CTG       48
Gly Gly Glu Asn Cys Gly Tyr Arg Arg Cys Arg Ala Ser Gly Val Leu
  1               5                  10                  15

ACA ACT AGC TGT GGT AAC ACC CTC ACT TGT TAC ATC AAG GCC CGA GCA       96
Thr Thr Ser Cys Gly Asn Thr Leu Thr Cys Tyr Ile Lys Ala Arg Ala
                 20                  25                  30

GCC TGT CGA GCC GCA GGG CTC CAG GAC TGC ACC ATG CTC GTG TGT GGC      144
Ala Cys Arg Ala Ala Gly Leu Gln Asp Cys Thr Met Leu Val Cys Gly
             35                  40                  45

GAC GAC TTA GTC GTT ATC TGT GAA AGC GCG GGG GTC CAG GAG GAC GCG      192
Asp Asp Leu Val Val Ile Cys Glu Ser Ala Gly Val Gln Glu Asp Ala
 50                  55                  60

GCG AGC CTG AGA GCC TTC ACG GAG GCT ATG ACC AGG TAC TCC GCC CCC      240
Ala Ser Leu Arg Ala Phe Thr Glu Ala Met Thr Arg Tyr Ser Ala Pro
 65                  70                  75                  80

CCT GGG GAC CCC CCA CAA CCA GAA TAC GAC TTG GAG CTC ATA ACA TCA      288
Pro Gly Asp Pro Pro Gln Pro Glu Tyr Asp Leu Glu Leu Ile Thr Ser
                 85                  90                  95

TGC TCC TCC AAC GTG TCA GTC GCC CAC GAC GGC GCT GGA AAG AGG GTC      336
Cys Ser Ser Asn Val Ser Val Ala His Asp Gly Ala Gly Lys Arg Val
             100                 105                 110

TAC TAC CTC ACC CGT GAC CCT ACA ACC CCC CTC GCG AGA GCT GCG TGG      384
Tyr Tyr Leu Thr Arg Asp Pro Thr Thr Pro Leu Ala Arg Ala Ala Trp
         115                 120                 125

GAG ACA GCA AGA CAC ACT CCA GTC AAT TCC TGG CTA GGC AAC ATA ATC      432
Glu Thr Ala Arg His Thr Pro Val Asn Ser Trp Leu Gly Asn Ile Ile
 130                 135                 140

ATG TTT GCC CCC ACA CTG TGG GCG                                      456
Met Phe Ala Pro Thr Leu Trp Ala
145                 150
```

(2) INFORMATION FOR SEQ ID NO:62:

(i) SEQUENCE CHARACTERISTICS:
       (A) LENGTH: 152 amino acids
       (B) TYPE: amino acid
       (D) TOPOLOGY: linear (ii) MOLECULE TYPE: protein (xi) SEQUENCE DESCRIPTION: SEQ ID NO:62:

```
Gly Gly Glu Asn Cys Gly Tyr Arg Arg Cys Arg Ala Ser Gly Val Leu
  1               5                  10                  15

Thr Thr Ser Cys Gly Asn Thr Leu Thr Cys Tyr Ile Lys Ala Arg Ala
                 20                  25                  30
```

```
Ala Cys Arg Ala Ala Gly Leu Gln Asp Cys Thr Met Leu Val Cys Gly
        35                  40                  45

Asp Asp Leu Val Val Ile Cys Glu Ser Ala Gly Val Gln Glu Asp Ala
    50                  55                  60

Ala Ser Leu Arg Ala Phe Thr Glu Ala Met Thr Arg Tyr Ser Ala Pro
65                  70                  75                  80

Pro Gly Asp Pro Pro Gln Pro Gly Tyr Asp Leu Glu Leu Ile Thr Ser
                85                  90                  95

Cys Ser Ser Asn Val Ser Val Ala His Asp Gly Ala Gly Lys Arg Val
                100                 105                 110

Tyr Tyr Leu Thr Arg Asp Pro Thr Thr Pro Leu Ala Arg Ala Ala Trp
        115                 120                 125

Glu Thr Ala Arg His Thr Pro Val Asn Ser Trp Leu Gly Asn Ile Ile
130                 135                 140

Met Phe Ala Pro Thr Leu Trp Ala
145                 150
```

(2) INFORMATION FOR SEQ ID NO:63:

(i) SEQUENCE CHARACTERISTICS:
        (A) LENGTH: 274 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 2..274

(xi) SEQUENCE DESCRIPTION: SEQ ID NO:63:

```
C GGC GCT GGA AAG AGG GTC TAC TAC CTC ACC CGT GAC CCT ACA ACC      46
  Gly Ala Gly Lys Arg Val Tyr Tyr Leu Thr Arg Asp Pro Thr Thr
  1               5                   10                  15

CCC CTC GCG AGA GCT GCG TGG GAG ACA GCA AGA CAC ACT CCA GTC AAT    94
Pro Leu Ala Arg Ala Ala Trp Glu Thr Ala Arg His Thr Pro Val Asn
                20                  25                  30

TCC TGG CTA GGC AAC ATA ATC ATG TTT GCC CCC ACA CTG TGG GCG AGG   142
Ser Trp Leu Gly Asn Ile Ile Met Phe Ala Pro Thr Leu Trp Ala Arg
                35                  40                  45

ATG ATA CTG ATG ACC CAT TTC TTT AGC GTC CTT ATA GCC AGG GAC CAG   190
Met Ile Leu Met Thr His Phe Phe Ser Val Leu Ile Ala Arg Asp Gln
            50                  55                  60

CTT GAA CAG GCC CTC GAT TGC GAG ATC TAC GGG GCC TGC TAC TCC ATA   238
Leu Glu Gln Ala Leu Asp Cys Glu Ile Tyr Gly Ala Cys Tyr Ser Ile
        65                  70                  75

GAA CCA CTT GAT CTA CCT CCA ATC ATT CAA AGA CTC                   274
Glu Pro Leu Asp Leu Pro Pro Ile Ile Gln Arg Leu
80                  85                  90
```

(2) INFORMATION FOR SEQ ID NO:64:

(i) SEQUENCE CHARACTERISTICS:
        (A) LENGTH: 91 amino acids
        (B) TYPE: amino acid
        (D) TOPOLOGY: linear (ii) MOLECULE TYPE: protein (xi) SEQUENCE DESCRIPTION: SEQ ID NO:64:

```
Gly Ala Gly Lys Arg Val Tyr Tyr Leu Thr Arg Asp Pro Thr Thr Pro
1               5                   10                  15
```

```
Leu Ala Arg Ala Ala Trp Glu Thr Ala Arg His Thr Pro Val Asn Ser
            20                  25                  30

Trp Leu Gly Asn Ile Ile Met Phe Ala Pro Thr Leu Trp Ala Arg Met
        35                  40                  45

Ile Leu Met Thr His Phe Phe Ser Val Leu Ile Ala Arg Asp Gln Leu
    50                  55                  60

Glu Gln Ala Leu Asp Cys Glu Ile Tyr Gly Ala Cys Tyr Ser Ile Glu
65                  70                  75                  80

Pro Leu Asp Leu Pro Pro Ile Ile Gln Arg Leu
                85                  90

(2) INFORMATION FOR SEQ ID NO:65:

(i) SEQUENCE CHARACTERISTICS:
        (A) LENGTH: 6785 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 3..6785

(xi) SEQUENCE DESCRIPTION: SEQ ID NO:65:
```

| | |
|---|---:|
| CC ATA TTT AAA ATC AGG ATG TAC GTG GGA GGG GTC GAA CAC AGG CTG<br>   Ile Phe Lys Ile Arg Met Tyr Val Gly Gly Val Glu His Arg Leu<br>    1           5                  10                15 | 47 |
| GAA GCT GCC TGC AAC TGG ACG CGG GGC GAA CGT TGC GAT CTG GAA GAC<br>Glu Ala Ala Cys Asn Trp Thr Arg Gly Glu Arg Cys Asp Leu Glu Asp<br>                20                  25                30 | 95 |
| AGG GAC AGG TCC GAG CTC AGC CCG TTA CTG CTG ACC ACT ACA CAG TGG<br>Arg Asp Arg Ser Glu Leu Ser Pro Leu Leu Leu Thr Thr Thr Gln Trp<br>        35                  40                  45 | 143 |
| CAG GTC CTC CCG TGT TCC TTC ACA ACC CTA CCA GCC TTG TCC ACC GGC<br>Gln Val Leu Pro Cys Ser Phe Thr Thr Leu Pro Ala Leu Ser Thr Gly<br>            50                  55                60 | 191 |
| CTC ATC CAC CTC CAC CAG AAC ATT GTG GAC GTG CAG TAC TTG TAC GGG<br>Leu Ile His Leu His Gln Asn Ile Val Asp Val Gln Tyr Leu Tyr Gly<br>      65                  70                  75 | 239 |
| GTG GGG TCA AGC ATC GCG TCC TGG GCC ATT AAG TGG GAG TAC GTC GTT<br>Val Gly Ser Ser Ile Ala Ser Trp Ala Ile Lys Trp Glu Tyr Val Val<br>80                  85                  90                95 | 287 |
| CTC CTG TTC CTT CTG CTT GCA GAC GCG CGC GTC TGC TCC TGC TTG TGG<br>Leu Leu Phe Leu Leu Leu Ala Asp Ala Arg Val Cys Ser Cys Leu Trp<br>            100               105             110 | 335 |
| ATG ATG CTA CTC ATA TCC CAA GCG GAG GCG GCT TTG GAG AAC CTC GTA<br>Met Met Leu Leu Ile Ser Gln Ala Glu Ala Ala Leu Glu Asn Leu Val<br>              115               120             125 | 383 |
| ATA CTT AAT GCA GCA TCC CTG GCC GGG ACG CAC GGT CTT GTA TCC TTC<br>Ile Leu Asn Ala Ala Ser Leu Ala Gly Thr His Gly Leu Val Ser Phe<br>    130                  135               140 | 431 |
| CTC GTG TTC TTC TGC TTT GCA TGG TAT TTG AAG GGT AAG TGG GTG CCC<br>Leu Val Phe Phe Cys Phe Ala Trp Tyr Leu Lys Gly Lys Trp Val Pro<br>145                 150               155 | 479 |
| GGA GCG GTC TAC ACC TTC TAC GGG ATG TGG CCT CTC CTG CTG CTC CTG<br>Gly Ala Val Tyr Thr Phe Tyr Gly Met Trp Pro Leu Leu Leu Leu Leu<br>160                 165              170             175 | 527 |
| TTG GCG TTG CCC CAG CGG GCG TAC GCG CTG GAC ACG GAG GTG GCC GCG<br>Leu Ala Leu Pro Gln Arg Ala Tyr Ala Leu Asp Thr Glu Val Ala Ala | 575 |

-continued

|  | 180 | | | | 185 | | | | 190 | | | | |
|---|---|---|---|---|---|---|---|---|---|---|---|---|---|
| TCG | TGT | GGC | GGT | GTT | GTT | CTC | GTC | GGG | TTG | ATG | GCG | CTG | ACT | CTG | TCA | 623 |
| Ser | Cys | Gly | Gly | Val | Val | Leu | Val | Gly | Leu | Met | Ala | Leu | Thr | Leu | Ser | |
| | | 195 | | | | 200 | | | | 205 | | | | | | |

| CCA | TAT | TAC | AAG | CGC | TAT | ATC | AGC | TGG | TGC | TTG | TGG | TGG | CTT | CAG | TAT | 671 |
| Pro | Tyr | Tyr | Lys | Arg | Tyr | Ile | Ser | Trp | Cys | Leu | Trp | Trp | Leu | Gln | Tyr | |
| | | 210 | | | | 215 | | | | 220 | | | | | | |

| TTT | CTG | ACC | AGA | GTG | GAA | GCG | CAA | CTG | CAC | GTG | TGG | ATT | CCC | CCC | CTC | 719 |
| Phe | Leu | Thr | Arg | Val | Glu | Ala | Gln | Leu | His | Val | Trp | Ile | Pro | Pro | Leu | |
| | 225 | | | | 230 | | | | 235 | | | | | | | |

| AAC | GTC | CGA | GGG | GGG | CGC | GAC | GCC | GTC | ATC | TTA | CTC | ATG | TGT | GCT | GTA | 767 |
| Asn | Val | Arg | Gly | Gly | Arg | Asp | Ala | Val | Ile | Leu | Leu | Met | Cys | Ala | Val | |
| 240 | | | | 245 | | | | 250 | | | | 255 | | | | |

| CAC | CCG | ACT | CTG | GTA | TTT | GAC | ATC | ACC | AAA | TTG | CTG | CTG | GCC | GTC | TTC | 815 |
| His | Pro | Thr | Leu | Val | Phe | Asp | Ile | Thr | Lys | Leu | Leu | Leu | Ala | Val | Phe | |
| | | | 260 | | | | 265 | | | | 270 | | | | | |

| GGA | CCC | CTT | TGG | ATT | CTT | CAA | GCC | AGT | TTG | CTT | AAA | GTA | CCC | TAC | TTT | 863 |
| Gly | Pro | Leu | Trp | Ile | Leu | Gln | Ala | Ser | Leu | Leu | Lys | Val | Pro | Tyr | Phe | |
| | | 275 | | | | 280 | | | | 285 | | | | | | |

| GTG | CGC | GTC | CAA | GGC | CTT | CTC | CGG | TTC | TGC | GCG | TTA | GCG | CGG | AAG | ATG | 911 |
| Val | Arg | Val | Gln | Gly | Leu | Leu | Arg | Phe | Cys | Ala | Leu | Ala | Arg | Lys | Met | |
| | 290 | | | | 295 | | | | 300 | | | | | | | |

| ATC | GGA | GGC | CAT | TAC | GTG | CAA | ATG | GTC | ATC | ATT | AAG | TTA | GGG | GCG | CTT | 959 |
| Ile | Gly | Gly | His | Tyr | Val | Gln | Met | Val | Ile | Ile | Lys | Leu | Gly | Ala | Leu | |
| 305 | | | | 310 | | | | 315 | | | | | | | | |

| ACT | GGC | ACC | TAT | GTT | TAT | AAC | CAT | CTC | ACT | CCT | CTT | CGG | GAC | TGG | GCG | 1007 |
| Thr | Gly | Thr | Tyr | Val | Tyr | Asn | His | Leu | Thr | Pro | Leu | Arg | Asp | Trp | Ala | |
| 320 | | | | 325 | | | | 330 | | | | 335 | | | | |

| CAC | AAC | GGC | TTG | CGA | GAT | CTG | GCC | GTG | GCT | GTA | GAG | CCA | GTC | GTC | TTC | 1055 |
| His | Asn | Gly | Leu | Arg | Asp | Leu | Ala | Val | Ala | Val | Glu | Pro | Val | Val | Phe | |
| | | | 340 | | | | 345 | | | | 350 | | | | | |

| TCC | CAA | ATG | GAG | ACC | AAG | CTC | ATC | ACG | TGG | GGG | GCA | GAT | ACC | GCC | GCG | 1103 |
| Ser | Gln | Met | Glu | Thr | Lys | Leu | Ile | Thr | Trp | Gly | Ala | Asp | Thr | Ala | Ala | |
| | | 355 | | | | 360 | | | | 365 | | | | | | |

| TGC | GGT | GAC | ATC | ATC | AAC | GGC | TTG | CCT | GTT | TCC | GCC | CGC | AGG | GGC | CGG | 1151 |
| Cys | Gly | Asp | Ile | Ile | Asn | Gly | Leu | Pro | Val | Ser | Ala | Arg | Arg | Gly | Arg | |
| | 370 | | | | 375 | | | | 380 | | | | | | | |

| GAG | ATA | CTG | CTC | GGG | CCA | GCC | GAT | GGA | ATG | GTC | TCC | AAG | GGG | TGG | AGG | 1199 |
| Glu | Ile | Leu | Leu | Gly | Pro | Ala | Asp | Gly | Met | Val | Ser | Lys | Gly | Trp | Arg | |
| 385 | | | | 390 | | | | 395 | | | | | | | | |

| TTG | CTG | GCG | CCC | ATC | ACG | GCG | TAC | GCC | CAG | CAG | ACA | AGG | GGC | CTC | CTA | 1247 |
| Leu | Leu | Ala | Pro | Ile | Thr | Ala | Tyr | Ala | Gln | Gln | Thr | Arg | Gly | Leu | Leu | |
| 400 | | | | 405 | | | | 410 | | | | 415 | | | | |

| GGG | TGC | ATA | ATC | ACC | AGC | CTA | ACT | GGC | CGG | GAC | AAA | AAC | CAA | GTG | GAG | 1295 |
| Gly | Cys | Ile | Ile | Thr | Ser | Leu | Thr | Gly | Arg | Asp | Lys | Asn | Gln | Val | Glu | |
| | | | 420 | | | | 425 | | | | 430 | | | | | |

| GGT | GAG | GTC | CAG | ATT | GTG | TCA | ACT | GCT | GCC | CAA | ACC | TTC | CTG | GCA | ACG | 1343 |
| Gly | Glu | Val | Gln | Ile | Val | Ser | Thr | Ala | Ala | Gln | Thr | Phe | Leu | Ala | Thr | |
| | | 435 | | | | 440 | | | | 445 | | | | | | |

| TGC | ATC | AAT | GGG | GTG | TGC | TGG | ACT | GTC | TAC | CAC | GGG | GCC | GGA | ACG | AGG | 1391 |
| Cys | Ile | Asn | Gly | Val | Cys | Trp | Thr | Val | Tyr | His | Gly | Ala | Gly | Thr | Arg | |
| | | 450 | | | | 455 | | | | 460 | | | | | | |

| ACC | ATC | GCG | TCA | CCC | AAG | GGT | CCT | GTC | ATC | CAG | ATG | TAT | ACC | AAT | GTA | 1439 |
| Thr | Ile | Ala | Ser | Pro | Lys | Gly | Pro | Val | Ile | Gln | Met | Tyr | Thr | Asn | Val | |
| | 465 | | | | 470 | | | | 475 | | | | | | | |

| GAC | CAA | GAC | CTT | GTG | GGC | TGG | CCC | GCT | CCG | CAA | GGT | AGC | CGC | TCA | TTG | 1487 |
| Asp | Gln | Asp | Leu | Val | Gly | Trp | Pro | Ala | Pro | Gln | Gly | Ser | Arg | Ser | Leu | |
| 480 | | | | 485 | | | | 490 | | | | 495 | | | | |

| ACA | CCC | TGC | ACT | TGC | GGC | TCC | TCG | GAC | CTT | TAC | CTG | GTC | ACG | AGG | CAC | 1535 |

-continued

```
Thr Pro Cys Thr Cys Gly Ser Ser Asp Leu Tyr Leu Val Thr Arg His
            500                 505                 510

GCC GAT GTC ATT CCC GTG CGC CGG CGG GGT GAT AGC AGG GGC AGC CTG      1583
Ala Asp Val Ile Pro Val Arg Arg Arg Gly Asp Ser Arg Gly Ser Leu
            515                 520                 525

CTG TCG CCC CGG CCC ATT TCC TAC TTG AAA GGC TCC TCG GGG GGT CCG      1631
Leu Ser Pro Arg Pro Ile Ser Tyr Leu Lys Gly Ser Ser Gly Gly Pro
            530                 535                 540

CTG TTG TGC CCC GCG GGG CAC GCC GTG GGC ATA TTT AGG GCC GCG GTG      1679
Leu Leu Cys Pro Ala Gly His Ala Val Gly Ile Phe Arg Ala Ala Val
        545                 550                 555

TGC ACC CGT GGA GTG GCT AAG GCG GTG GAC TTT ATC CCT GTG GAG AAC      1727
Cys Thr Arg Gly Val Ala Lys Ala Val Asp Phe Ile Pro Val Glu Asn
560                 565                 570                 575

CTA GAG ACA ACC ATG AGG TCC CCG GTG TTC ACG GAT AAC TCC TCT CCA      1775
Leu Glu Thr Thr Met Arg Ser Pro Val Phe Thr Asp Asn Ser Ser Pro
                580                 585                 590

CCA GTA GTG CCC CAG AGC TTC CAG GTG GCT CAC CTC CAT GCT CCC ACA      1823
Pro Val Val Pro Gln Ser Phe Gln Val Ala His Leu His Ala Pro Thr
            595                 600                 605

GGC AGC GGC AAA AGC ACC AAG GTC CCG GCT GCA TAT GCA GCT CAG GGC      1871
Gly Ser Gly Lys Ser Thr Lys Val Pro Ala Ala Tyr Ala Ala Gln Gly
            610                 615                 620

TAT AAG GTG CTA GTA CTC AAC CCC TCT GTT GCT GCA ACA CTG GGC TTT      1919
Tyr Lys Val Leu Val Leu Asn Pro Ser Val Ala Ala Thr Leu Gly Phe
        625                 630                 635

GGT GCT TAC ATG TCC AAG GCT CAT GGG ATC GAT CCT AAC ATC AGG ACC      1967
Gly Ala Tyr Met Ser Lys Ala His Gly Ile Asp Pro Asn Ile Arg Thr
640                 645                 650                 655

GGG GTG AGA ACA ATT ACC ACT GGC AGC CCC ATC ACG TAC TCC ACC TAC      2015
Gly Val Arg Thr Ile Thr Thr Gly Ser Pro Ile Thr Tyr Ser Thr Tyr
                660                 665                 670

GGC AAG TTC CTT GCC GAC GGC GGG TGC TCG GGG GGC GCT TAT GAC ATA      2063
Gly Lys Phe Leu Ala Asp Gly Gly Cys Ser Gly Gly Ala Tyr Asp Ile
            675                 680                 685

ATA ATT TGT GAC GAC TGC CAC TCC ACG GAT GCC ACA TCC ATC TTG GGC      2111
Ile Ile Cys Asp Asp Cys His Ser Thr Asp Ala Thr Ser Ile Leu Gly
            690                 695                 700

ATC GGC ACT GTC CTT GAC CAA GCA GAG ACT GCG GGG GCG AGA CTG GTT      2159
Ile Gly Thr Val Leu Asp Gln Ala Glu Thr Ala Gly Ala Arg Leu Val
        705                 710                 715

GTG CTC GCC ACC GCC ACC CCT CCG GGC TCC GTC ACT GTG CCC CAT CCC      2207
Val Leu Ala Thr Ala Thr Pro Pro Gly Ser Val Thr Val Pro His Pro
720                 725                 730                 735

AAC ATC GAG GAG GTT GCT CTG TCC ACC ACC GGA GAG ATC CCT TTT TAC      2255
Asn Ile Glu Glu Val Ala Leu Ser Thr Thr Gly Glu Ile Pro Phe Tyr
                740                 745                 750

GGC AAG GCT ATC CCC CTC GAA GTA ATC AAG GGG GGG AGA CAT CTC ATC      2303
Gly Lys Ala Ile Pro Leu Glu Val Ile Lys Gly Gly Arg His Leu Ile
            755                 760                 765

TTC TGT CAT TCA AAG AAG AAG TGC GAC GAA CTC GCC GCA AAG CTG GTC      2351
Phe Cys His Ser Lys Lys Lys Cys Asp Glu Leu Ala Ala Lys Leu Val
            770                 775                 780

GCA TTG GGC ATC AAT GCC GTG GCC TAC TAC CGC GGT CTT GAC GTG TCC      2399
Ala Leu Gly Ile Asn Ala Val Ala Tyr Tyr Arg Gly Leu Asp Val Ser
        785                 790                 795

GTC ATC CCG ACC AGC GGC GAT GTT GTC GTC GTG GCA ACC GAT GCC CTC      2447
Val Ile Pro Thr Ser Gly Asp Val Val Val Val Ala Thr Asp Ala Leu
800                 805                 810                 815
```

```
ATG ACC GGC TAT ACC GGC GAC TTC GAC TCG GTG ATA GAC TGC AAT ACG   2495
Met Thr Gly Tyr Thr Gly Asp Phe Asp Ser Val Ile Asp Cys Asn Thr
                    820                 825                 830

TGT GTC ACC CAG ACA GTC GAT TTC AGC CTT GAC CCT ACC TTC ACC ATT   2543
Cys Val Thr Gln Thr Val Asp Phe Ser Leu Asp Pro Thr Phe Thr Ile
                835                 840                 845

GAG ACA ATC ACG CTC CCC CAG GAT GCT GTC TCC CGC ACT CAA CGT CGG   2591
Glu Thr Ile Thr Leu Pro Gln Asp Ala Val Ser Arg Thr Gln Arg Arg
            850                 855                 860

GGC AGG ACT GGC AGG GGG AAG CCA GGC ATC TAC AGA TTT GTG GCA CCG   2639
Gly Arg Thr Gly Arg Gly Lys Pro Gly Ile Tyr Arg Phe Val Ala Pro
865                 870                 875

GGG GAG CGC CCC TCC GGC ATG TTC GAC TCG TCC GTC CTC TGT GAG TGC   2687
Gly Glu Arg Pro Ser Gly Met Phe Asp Ser Ser Val Leu Cys Glu Cys
880                 885                 890                 895

TAT GAC GCA GGC TGT GCT TGG TAT GAG CTC ACG CCC GCC GAG ACT ACA   2735
Tyr Asp Ala Gly Cys Ala Trp Tyr Glu Leu Thr Pro Ala Glu Thr Thr
                    900                 905                 910

GTT AGG CTA CGA GCG TAC ATG AAC ACC CCG GGG CTT CCC GTG TGC CAG   2783
Val Arg Leu Arg Ala Tyr Met Asn Thr Pro Gly Leu Pro Val Cys Gln
                915                 920                 925

GAC CAT CTT GAA TTT TGG GAG GGC GTC TTT ACA GGC CTC ACT CAT ATA   2831
Asp His Leu Glu Phe Trp Glu Gly Val Phe Thr Gly Leu Thr His Ile
            930                 935                 940

GAT GCC CAC TTT CTA TCC CAG ACA AAG CAG AGT GGG GAG AAC CTT CCT   2879
Asp Ala His Phe Leu Ser Gln Thr Lys Gln Ser Gly Glu Asn Leu Pro
945                 950                 955

TAC CTG GTA GCG TAC CAA GCC ACC GTG TGC GCT AGG GCT CAA GCC CCT   2927
Tyr Leu Val Ala Tyr Gln Ala Thr Val Cys Ala Arg Ala Gln Ala Pro
960                 965                 970                 975

CCC CCA TCG TGG GAC CAG ATG TGG AAG TGT TTG ATT CGC CTC AAG CCC   2975
Pro Pro Ser Trp Asp Gln Met Trp Lys Cys Leu Ile Arg Leu Lys Pro
                    980                 985                 990

ACC CTC CAT GGG CCA ACA CCC CTG CTA TAC AGA CTG GGC GCT GTT CAG   3023
Thr Leu His Gly Pro Thr Pro Leu Leu Tyr Arg Leu Gly Ala Val Gln
                995                 1000                1005

AAT GAA ATC ACC CTG ACG CAC CCA GTC ACC AAA TAC ATC ATG ACA TGC   3071
Asn Glu Ile Thr Leu Thr His Pro Val Thr Lys Tyr Ile Met Thr Cys
            1010                1015                1020

ATG TCG GCC GAC CTG GAG GTC GTC ACG AGC ACC TGG GTG CTC GTT GGC   3119
Met Ser Ala Asp Leu Glu Val Val Thr Ser Thr Trp Val Leu Val Gly
1025                1030                1035

GGC GTC CTG GCT GCT TTG GCC GCG TAT TGC CTG TCA ACA GGC TGC GTG   3167
Gly Val Leu Ala Ala Leu Ala Ala Tyr Cys Leu Ser Thr Gly Cys Val
1040                1045                1050                1055

GTC ATA GTG GGC AGG GTC GTC TTG TCC GGG AAG CCG GCA ATC ATA CCT   3215
Val Ile Val Gly Arg Val Val Leu Ser Gly Lys Pro Ala Ile Ile Pro
                    1060                1065                1070

GAC AGG GAA GTC CTC TAC CGA GAG TTC GAT GAG ATG GAA GAG TGC TCT   3263
Asp Arg Glu Val Leu Tyr Arg Glu Phe Asp Glu Met Glu Glu Cys Ser
                1075                1080                1085

CAG CAC TTA CCG TAC ATC GAG CAA GGG ATG ATG CTC GCC GAG CAG TTC   3311
Gln His Leu Pro Tyr Ile Glu Gln Gly Met Met Leu Ala Glu Gln Phe
            1090                1095                1100

AAG CAG AAG GCC CTC GGC CTC CTG CAG ACC GCG TCC CGT CAG GCA GAG   3359
Lys Gln Lys Ala Leu Gly Leu Leu Gln Thr Ala Ser Arg Gln Ala Glu
1105                1110                1115

GTT ATC GCC CCT GCT GTC CAG ACC AAC TGG CAA AAA CTC GAG ACC TTC   3407
Val Ile Ala Pro Ala Val Gln Thr Asn Trp Gln Lys Leu Glu Thr Phe
1120                1125                1130                1135
```

```
TGG GCG AAG CAT ATG TGG AAC TTC ATC AGT GGG ATA CAA TAC TTG GCG        3455
Trp Ala Lys His Met Trp Asn Phe Ile Ser Gly Ile Gln Tyr Leu Ala
                1140            1145                1150

GGC TTG TCA ACG CTG CCT GGT AAC CCC GCC ATT GCT TCA TTG ATG GCT        3503
Gly Leu Ser Thr Leu Pro Gly Asn Pro Ala Ile Ala Ser Leu Met Ala
            1155                1160                1165

TTT ACA GCT GCT GTC ACC AGC CCA CTA ACC ACT AGC CAA ACC CTC CTC        3551
Phe Thr Ala Ala Val Thr Ser Pro Leu Thr Thr Ser Gln Thr Leu Leu
            1170                1175                1180

TTC AAC ATA TTG GGG GGG TGG GTG GCT GCC CAG CTC GCC GCC CCC GGT        3599
Phe Asn Ile Leu Gly Gly Trp Val Ala Ala Gln Leu Ala Ala Pro Gly
        1185                1190                1195

GCC GCT ACT GCC TTT GTG GGC GCT GGC TTA GCT GGC GCC GCC ATC GGC        3647
Ala Ala Thr Ala Phe Val Gly Ala Gly Leu Ala Gly Ala Ala Ile Gly
1200                1205                1210                1215

AGT GTT GGA CTG GGG AAG GTC CTC ATA GAC ATC CTT GCA GGG TAT GGC        3695
Ser Val Gly Leu Gly Lys Val Leu Ile Asp Ile Leu Ala Gly Tyr Gly
                1220                1225                1230

GCG GGC GTG GCG GGA GCT CTT GTG GCA TTC AAG ATC ATG AGC GGT GAG        3743
Ala Gly Val Ala Gly Ala Leu Val Ala Phe Lys Ile Met Ser Gly Glu
            1235                1240                1245

GTC CCC TCC ACG GAG GAC CTG GTC AAT CTA CTG CCC GCC ATC CTC TCG        3791
Val Pro Ser Thr Glu Asp Leu Val Asn Leu Leu Pro Ala Ile Leu Ser
            1250                1255                1260

CCC GGA GCC CTC GTA GTC GGC GTG GTC TGT GCA GCA ATA CTG CGC CGG        3839
Pro Gly Ala Leu Val Val Gly Val Val Cys Ala Ala Ile Leu Arg Arg
        1265                1270                1275

CAC GTT GGC CCG GGC GAG GGG GCA GTG CAG TGG ATG AAC CGG CTG ATA        3887
His Val Gly Pro Gly Glu Gly Ala Val Gln Trp Met Asn Arg Leu Ile
1280                1285                1290                1295

GCC TTC GCC TCC CGG GGG AAC CAT GTT TCC CCC ACG CAC TAC GTG CCG        3935
Ala Phe Ala Ser Arg Gly Asn His Val Ser Pro Thr His Tyr Val Pro
                1300                1305                1310

GAG AGC GAT GCA GCT GCC CGC GTC ACT GCC ATA CTC AGC AGC CTC ACT        3983
Glu Ser Asp Ala Ala Ala Arg Val Thr Ala Ile Leu Ser Ser Leu Thr
            1315                1320                1325

GTA ACC CAG CTC CTG AGG CGA CTG CAC CAG TGG ATA AGC TCG GAG TGT        4031
Val Thr Gln Leu Leu Arg Arg Leu His Gln Trp Ile Ser Ser Glu Cys
            1330                1335                1340

ACC ACT CCA TGC TCC GGT TCC TGG CTA AGG GAC ATC TGG GAC TGG ATA        4079
Thr Thr Pro Cys Ser Gly Ser Trp Leu Arg Asp Ile Trp Asp Trp Ile
        1345                1350                1355

TGC GAG GTG TTG AGC GAC TTT AAG ACC TGG CTA AAA GCT AAG CTC ATG        4127
Cys Glu Val Leu Ser Asp Phe Lys Thr Trp Leu Lys Ala Lys Leu Met
1360                1365                1370                1375

CCA CAG CTG CCT GGG ATC CCC TTT GTG TCC TGC CAG CGC GGG TAT AAG        4175
Pro Gln Leu Pro Gly Ile Pro Phe Val Ser Cys Gln Arg Gly Tyr Lys
                1380                1385                1390

GGG GTC TGG CGA GTG GAC GGC ATC ATG CAC ACT CGC TGC CAC TGT GGA        4223
Gly Val Trp Arg Val Asp Gly Ile Met His Thr Arg Cys His Cys Gly
            1395                1400                1405

GCT GAG ATC ACT GGA CAT GTC AAA AAC GGG ACG ATG AGG ATC GTC GGT        4271
Ala Glu Ile Thr Gly His Val Lys Asn Gly Thr Met Arg Ile Val Gly
            1410                1415                1420

CCT AGG ACC TGC AGG AAC ATG TGG AGT GGG ACC TTC CCC ATT AAT GCC        4319
Pro Arg Thr Cys Arg Asn Met Trp Ser Gly Thr Phe Pro Ile Asn Ala
        1425                1430                1435

TAC ACC ACG GGC CCC TGT ACC CCC CTT CCT GCG CCG AAC TAC ACG TTC        4367
Tyr Thr Thr Gly Pro Cys Thr Pro Leu Pro Ala Pro Asn Tyr Thr Phe
```

```
                   1440              1445              1450              1455

GCG CTA TGG AGG GTG TCT GCA GAG GAA TAT GTG GAG ATA AGG CAG GTG                 4415
Ala Leu Trp Arg Val Ser Ala Glu Glu Tyr Val Glu Ile Arg Gln Val
                    1460              1465              1470

GGG GAC TTC CAC TAC GTG ACG GGT ATG ACT ACT GAC AAT CTC AAA TGC                 4463
Gly Asp Phe His Tyr Val Thr Gly Met Thr Thr Asp Asn Leu Lys Cys
                1475              1480              1485

CCG TGC CAG GTC CCA TCG CCC GAA TTT TTC ACA GAA TTG GAC GGG GTG                 4511
Pro Cys Gln Val Pro Ser Pro Glu Phe Phe Thr Glu Leu Asp Gly Val
            1490              1495              1500

CGC CTA CAT AGG TTT GCG CCC CCC TGC AAG CCC TTG CTG CGG GAG GAG                 4559
Arg Leu His Arg Phe Ala Pro Pro Cys Lys Pro Leu Leu Arg Glu Glu
        1505              1510              1515

GTA TCA TTC AGA GTA GGA CTC CAC GAA TAC CCG GTA GGG TCG CAA TTA                 4607
Val Ser Phe Arg Val Gly Leu His Glu Tyr Pro Val Gly Ser Gln Leu
1520              1525              1530              1535

CCT TGC GAG CCC GAA CCG GAC GTG GCC GTG TTG ACG TCC ATG CTC ACT                 4655
Pro Cys Glu Pro Glu Pro Asp Val Ala Val Leu Thr Ser Met Leu Thr
                1540              1545              1550

GAT CCC TCC CAT ATA ACA GCA GAG GCG GCC GGG CGA AGG TTG GCG AGG                 4703
Asp Pro Ser His Ile Thr Ala Glu Ala Ala Gly Arg Arg Leu Ala Arg
            1555              1560              1565

GGA TCA CCC CCC TCT GTG GCC AGC TCC TCG GCT AGC CAG CTA TCC GCT                 4751
Gly Ser Pro Pro Ser Val Ala Ser Ser Ser Ala Ser Gln Leu Ser Ala
        1570              1575              1580

CCA TCT CTC AAG GCA ACT TGC ACC GCT AAC CAT GAC TCC CCT GAT GCT                 4799
Pro Ser Leu Lys Ala Thr Cys Thr Ala Asn His Asp Ser Pro Asp Ala
    1585              1590              1595

GAG CTC ATA GAG GCC AAC CTC CTA TGG AGG CAG GAG ATG GGC GGC AAC                 4847
Glu Leu Ile Glu Ala Asn Leu Leu Trp Arg Gln Glu Met Gly Gly Asn
1600              1605              1610              1615

ATC ACC AGG GTT GAG TCA GAA AAC AAA GTG GTG ATT CTG GAC TCC TTC                 4895
Ile Thr Arg Val Glu Ser Glu Asn Lys Val Val Ile Leu Asp Ser Phe
                1620              1625              1630

GAT CCG CTT GTG GCG GAG GAG GAC GAG CGG GAG ATC TCC GTA CCC GCA                 4943
Asp Pro Leu Val Ala Glu Glu Asp Glu Arg Glu Ile Ser Val Pro Ala
            1635              1640              1645

GAA ATC CTG CGG AAG TCT CGG AGA TTC GCC CAG GCC CTG CCC GTT TGG                 4991
Glu Ile Leu Arg Lys Ser Arg Arg Phe Ala Gln Ala Leu Pro Val Trp
        1650              1655              1660

GCG CGG CCG GAC TAT AAC CCC CCG CTA GTG GAG ACG TGG AAA AAG CCC                 5039
Ala Arg Pro Asp Tyr Asn Pro Pro Leu Val Glu Thr Trp Lys Lys Pro
    1665              1670              1675

GAC TAC GAA CCA CCT GTG GTC CAT GGC TGT CCG CTT CCA CCT CCA AAG                 5087
Asp Tyr Glu Pro Pro Val Val His Gly Cys Pro Leu Pro Pro Pro Lys
1680              1685              1690              1695

TCC CCT CCT GTG CCT CCG CCT CGG AAG AAG CGG ACG GTG GTC CTC ACT                 5135
Ser Pro Pro Val Pro Pro Pro Arg Lys Lys Arg Thr Val Val Leu Thr
                1700              1705              1710

GAA TCA ACC CTA TCT ACT GCC TTG GCC GAG CTC GCC ACC AGA AGC TTT                 5183
Glu Ser Thr Leu Ser Thr Ala Leu Ala Glu Leu Ala Thr Arg Ser Phe
            1715              1720              1725

GGC AGC TCC TCA ACT TCC GGC ATT ACG GGC GAC AAT ACG ACA ACA TCC                 5231
Gly Ser Ser Ser Thr Ser Gly Ile Thr Gly Asp Asn Thr Thr Thr Ser
        1730              1735              1740

TCT GAG CCC GCC CCT TCT GGC TGC CCC CCC GAC TCC GAC GCT GAG TCC                 5279
Ser Glu Pro Ala Pro Ser Gly Cys Pro Pro Asp Ser Asp Ala Glu Ser
    1745              1750              1755

TAT TCC TCC ATG CCC CCC CTG GAG GGG GAG CCT GGG GAT CCG GAT CTT                 5327
```

```
Tyr Ser Ser Met Pro Pro Leu Glu Gly Glu Pro Gly Asp Pro Asp Leu
1760                1765                1770                1775

AGC GAC GGG TCA TGG TCA ACG GTC AGT AGT GAG GCC AAC GCG GAG GAT        5375
Ser Asp Gly Ser Trp Ser Thr Val Ser Ser Glu Ala Asn Ala Glu Asp
                1780                1785                1790

GTC GTG TGC TGC TCA ATG TCT TAC TCT TGG ACA GGC GCA CTC GTC ACC        5423
Val Val Cys Cys Ser Met Ser Tyr Ser Trp Thr Gly Ala Leu Val Thr
            1795                1800                1805

CCG TGC GCC GCG GAA GAA CAG AAA CTG CCC ATC AAT GCA CTA AGC AAC        5471
Pro Cys Ala Ala Glu Glu Gln Lys Leu Pro Ile Asn Ala Leu Ser Asn
        1810                1815                1820

TCG TTG CTA CGT CAC CAC AAT TTG GTG TAT TCC ACC ACC TCA CGC AGT        5519
Ser Leu Leu Arg His His Asn Leu Val Tyr Ser Thr Thr Ser Arg Ser
    1825                1830                1835

GCT TGC CAA AGG CAG AAG AAA GTC ACA TTT GAC AGA CTG CAA GTT CTG        5567
Ala Cys Gln Arg Gln Lys Lys Val Thr Phe Asp Arg Leu Gln Val Leu
1840                1845                1850                1855

GAC AGC CAT TAC CAG GAC GTA CTC AAG GAG GTT AAA GCA GCG GCG TCA        5615
Asp Ser His Tyr Gln Asp Val Leu Lys Glu Val Lys Ala Ala Ala Ser
                1860                1865                1870

AAA GTG AAG GCT AAC TTG CTA TCC GTA GAG GAA GCT TGC AGC CTG ACG        5663
Lys Val Lys Ala Asn Leu Leu Ser Val Glu Glu Ala Cys Ser Leu Thr
            1875                1880                1885

CCC CCA CAC TCA GCC AAA TCC AAG TTT GGT TAT GGG GCA AAA GAC GTC        5711
Pro Pro His Ser Ala Lys Ser Lys Phe Gly Tyr Gly Ala Lys Asp Val
        1890                1895                1900

CGT TGC CAT GCC AGA AAG GCC GTA ACC CAC ATC AAC TCC GTG TGG AAA        5759
Arg Cys His Ala Arg Lys Ala Val Thr His Ile Asn Ser Val Trp Lys
    1905                1910                1915

GAC CTT CTG GAA GAC AAT GTA ACA CCA ATA GAC ACT ACC ATC ATG GCT        5807
Asp Leu Leu Glu Asp Asn Val Thr Pro Ile Asp Thr Thr Ile Met Ala
1920                1925                1930                1935

AAG AAC GAG GTT TTC TGC GTT CAG CCT GAG AAG GGG GGT CGT AAG CCA        5855
Lys Asn Glu Val Phe Cys Val Gln Pro Glu Lys Gly Gly Arg Lys Pro
                1940                1945                1950

GCT CGT CTC ATC GTG TTC CCC GAT CTG GGC GTG CGC GTG TGC GAA AAG        5903
Ala Arg Leu Ile Val Phe Pro Asp Leu Gly Val Arg Val Cys Glu Lys
            1955                1960                1965

ATG GCT TTG TAC GAC GTG GTT ACA AAG CTC CCC TTG GCC GTG ATG GGA        5951
Met Ala Leu Tyr Asp Val Val Thr Lys Leu Pro Leu Ala Val Met Gly
        1970                1975                1980

AGC TCC TAC GGA TTC CAA TAC TCA CCA GGA CAG CGG GTT GAA TTC CTC        5999
Ser Ser Tyr Gly Phe Gln Tyr Ser Pro Gly Gln Arg Val Glu Phe Leu
    1985                1990                1995

GTG CAA GCG TGG AAG TCC AAG AAA ACC CCA ATG GGG TTC TCG TAT GAT        6047
Val Gln Ala Trp Lys Ser Lys Lys Thr Pro Met Gly Phe Ser Tyr Asp
2000                2005                2010                2015

ACC CGC TGC TTT GAC TCC ACA GTC ACT GAG AGC GAC ATC CGT ACG GAG        6095
Thr Arg Cys Phe Asp Ser Thr Val Thr Glu Ser Asp Ile Arg Thr Glu
                2020                2025                2030

GAG GCA ATC TAC CAA TGT TGT GAC CTC GAC CCC CAA GCC CGC GTG GCC        6143
Glu Ala Ile Tyr Gln Cys Cys Asp Leu Asp Pro Gln Ala Arg Val Ala
            2035                2040                2045

ATC AAG TCC CTC ACC GAG AGG CTT TAT GTT GGG GGC CCT CTT ACC AAT        6191
Ile Lys Ser Leu Thr Glu Arg Leu Tyr Val Gly Gly Pro Leu Thr Asn
        2050                2055                2060

TCA AGG GGG GAG AAC TGC GGC TAT CGC AGG TGC CGC GCG AGC GGC GTA        6239
Ser Arg Gly Glu Asn Cys Gly Tyr Arg Arg Cys Arg Ala Ser Gly Val
    2065                2070                2075
```

```
CTG ACA ACT AGC TGT GGT AAC ACC CTC ACT TGC TAC ATC AAG GCC CGG       6287
Leu Thr Thr Ser Cys Gly Asn Thr Leu Thr Cys Tyr Ile Lys Ala Arg
2080                2085                2090                2095

GCA GCC TGT CGA GCC GCA GGG CTC CAG GAC TGC ACC ATG CTC GTG TGT       6335
Ala Ala Cys Arg Ala Ala Gly Leu Gln Asp Cys Thr Met Leu Val Cys
            2100                2105                2110

GGC GAC GAC TTA GTC GTT ATC TGT GAA AGC GCG GGG GTC CAG GAG GAC       6383
Gly Asp Asp Leu Val Val Ile Cys Glu Ser Ala Gly Val Gln Glu Asp
        2115                2120                2125

GCG GCG AGC CTG AGA GCC TTC ACG GAG GCT ATG ACC AGG TAC TCC GCC       6431
Ala Ala Ser Leu Arg Ala Phe Thr Glu Ala Met Thr Arg Tyr Ser Ala
    2130                2135                2140

CCC CCT GGG GAC CCC CCA CAA CCA GAA TAC GAC TTG GAG CTC ATA ACA       6479
Pro Pro Gly Asp Pro Pro Gln Pro Glu Tyr Asp Leu Glu Leu Ile Thr
2145                2150                2155

TCA TGC TCC TCC AAC GTG TCA GTC GCC CAC GAC GGC GCT GGA AAG AGG       6527
Ser Cys Ser Ser Asn Val Ser Val Ala His Asp Gly Ala Gly Lys Arg
2160                2165                2170                2175

GTC TAC TAC CTC ACC CGT GAC CCT ACA ACC CCC CTC GCG AGA GCT GCG       6575
Val Tyr Tyr Leu Thr Arg Asp Pro Thr Thr Pro Leu Ala Arg Ala Ala
            2180                2185                2190

TGG GAG ACA GCA AGA CAC ACT CCA GTC AAT TCC TGG CTA GGC AAC ATA       6623
Trp Glu Thr Ala Arg His Thr Pro Val Asn Ser Trp Leu Gly Asn Ile
        2195                2200                2205

ATC ATG TTT GCC CCC ACA CTG TGG GCG AGG ATG ATA CTG ATG ACC CAT       6671
Ile Met Phe Ala Pro Thr Leu Trp Ala Arg Met Ile Leu Met Thr His
    2210                2215                2220

TTC TTT AGC GTC CTT ATA GCC AGG GAC CAG CTT GAA CAG GCC CTC GAT       6719
Phe Phe Ser Val Leu Ile Ala Arg Asp Gln Leu Glu Gln Ala Leu Asp
2225                2230                2235

TGC GAG ATC TAC GGG GCC TGC TAC TCC ATA GAA CCA CTT GAT CTA CCT       6767
Cys Glu Ile Tyr Gly Ala Cys Tyr Ser Ile Glu Pro Leu Asp Leu Pro
2240                2245                2250                2255

CCA ATC ATT CAA AGA CTC                                                6785
Pro Ile Ile Gln Arg Leu
            2260

(2) INFORMATION FOR SEQ ID NO:66:

(i) SEQUENCE CHARACTERISTICS:
        (A) LENGTH: 2261 amino acids
        (B) TYPE: amino acid
        (D) TOPOLOGY: linear (ii) MOLECULE TYPE: protein (xi) SEQUENCE DESCRIPTION: SEQ ID NO:66:

Ile Phe Lys Ile Arg Met Tyr Val Gly Gly Val Glu His Arg Leu Glu
1               5                   10                  15

Ala Ala Cys Asn Trp Thr Arg Gly Glu Arg Cys Asp Leu Glu Asp Arg
            20                  25                  30

Asp Arg Ser Glu Leu Ser Pro Leu Leu Leu Thr Thr Thr Gln Trp Gln
        35                  40                  45

Val Leu Pro Cys Ser Phe Thr Thr Leu Pro Ala Leu Ser Thr Gly Leu
    50                  55                  60

Ile His Leu His Gln Asn Ile Val Asp Val Gln Tyr Leu Tyr Gly Val
65                  70                  75                  80

Gly Ser Ser Ile Ala Ser Trp Ala Ile Lys Trp Glu Tyr Val Val Leu
                85                  90                  95

Leu Phe Leu Leu Leu Ala Asp Ala Arg Val Cys Ser Cys Leu Trp Met
```

```
                    100                 105                 110
Met Leu Leu Ile Ser Gln Ala Glu Ala Ala Leu Glu Asn Leu Val Ile
                115                 120                 125

Leu Asn Ala Ala Ser Leu Ala Gly Thr His Gly Leu Val Ser Phe Leu
130                 135                 140

Val Phe Phe Cys Phe Ala Trp Tyr Leu Lys Gly Lys Trp Val Pro Gly
145                 150                 155                 160

Ala Val Tyr Thr Phe Tyr Gly Met Trp Pro Leu Leu Leu Leu Leu Leu
                165                 170                 175

Ala Leu Pro Gln Arg Ala Tyr Ala Leu Asp Thr Glu Val Ala Ala Ser
                180                 185                 190

Cys Gly Gly Val Val Leu Val Gly Leu Met Ala Leu Thr Leu Ser Pro
                195                 200                 205

Tyr Tyr Lys Arg Tyr Ile Ser Trp Cys Leu Trp Trp Leu Gln Tyr Phe
                210                 215                 220

Leu Thr Arg Val Glu Ala Gln Leu His Val Trp Ile Pro Pro Leu Asn
225                 230                 235                 240

Val Arg Gly Gly Arg Asp Ala Val Ile Leu Leu Met Cys Ala Val His
                245                 250                 255

Pro Thr Leu Val Phe Asp Ile Thr Lys Leu Leu Leu Ala Val Phe Gly
                260                 265                 270

Pro Leu Trp Ile Leu Gln Ala Ser Leu Leu Lys Val Pro Tyr Phe Val
                275                 280                 285

Arg Val Gln Gly Leu Leu Arg Phe Cys Ala Leu Ala Arg Lys Met Ile
                290                 295                 300

Gly Gly His Tyr Val Gln Met Val Ile Ile Lys Leu Gly Ala Leu Thr
305                 310                 315                 320

Gly Thr Tyr Val Tyr Asn His Leu Thr Pro Leu Arg Asp Trp Ala His
                325                 330                 335

Asn Gly Leu Arg Asp Leu Ala Val Ala Val Glu Pro Val Val Phe Ser
                340                 345                 350

Gln Met Glu Thr Lys Leu Ile Thr Trp Gly Ala Asp Thr Ala Ala Cys
                355                 360                 365

Gly Asp Ile Ile Asn Gly Leu Pro Val Ser Ala Arg Gly Arg Glu
370                 375                 380

Ile Leu Leu Gly Pro Ala Asp Gly Met Val Ser Lys Gly Trp Arg Leu
385                 390                 395                 400

Leu Ala Pro Ile Thr Ala Tyr Ala Gln Gln Thr Arg Gly Leu Leu Gly
                405                 410                 415

Cys Ile Ile Thr Ser Leu Thr Gly Arg Asp Lys Asn Gln Val Glu Gly
                420                 425                 430

Glu Val Gln Ile Val Ser Thr Ala Ala Gln Thr Phe Leu Ala Thr Cys
                435                 440                 445

Ile Asn Gly Val Cys Trp Thr Val Tyr His Gly Ala Gly Thr Arg Thr
450                 455                 460

Ile Ala Ser Pro Lys Gly Pro Val Ile Gln Met Tyr Thr Asn Val Asp
465                 470                 475                 480

Gln Asp Leu Val Gly Trp Pro Ala Pro Gln Gly Ser Arg Ser Leu Thr
                485                 490                 495

Pro Cys Thr Cys Gly Ser Ser Asp Leu Tyr Leu Val Thr Arg His Ala
                500                 505                 510

Asp Val Ile Pro Val Arg Arg Arg Gly Asp Ser Arg Gly Ser Leu Leu
                515                 520                 525
```

-continued

```
Ser Pro Arg Pro Ile Ser Tyr Leu Lys Gly Ser Ser Gly Gly Pro Leu
    530                 535                 540

Leu Cys Pro Ala Gly His Ala Val Gly Ile Phe Arg Ala Ala Val Cys
545                 550                 555                 560

Thr Arg Gly Val Ala Lys Ala Val Asp Phe Ile Pro Val Glu Asn Leu
                565                 570                 575

Glu Thr Thr Met Arg Ser Pro Val Phe Thr Asp Asn Ser Ser Pro Pro
                580                 585                 590

Val Val Pro Gln Ser Phe Gln Val Ala His Leu His Ala Pro Thr Gly
                595                 600                 605

Ser Gly Lys Ser Thr Lys Val Pro Ala Ala Tyr Ala Ala Gln Gly Tyr
    610                 615                 620

Lys Val Leu Val Leu Asn Pro Ser Val Ala Ala Thr Leu Gly Phe Gly
625                 630                 635                 640

Ala Tyr Met Ser Lys Ala His Gly Ile Asp Pro Asn Ile Arg Thr Gly
                645                 650                 655

Val Arg Thr Ile Thr Thr Gly Ser Pro Ile Thr Tyr Ser Thr Tyr Gly
                660                 665                 670

Lys Phe Leu Ala Asp Gly Gly Cys Ser Gly Gly Ala Tyr Asp Ile Ile
    675                 680                 685

Ile Cys Asp Asp Cys His Ser Thr Asp Ala Thr Ser Ile Leu Gly Ile
690                 695                 700

Gly Thr Val Leu Asp Gln Ala Glu Thr Ala Gly Ala Arg Leu Val Val
705                 710                 715                 720

Leu Ala Thr Ala Thr Pro Pro Gly Ser Val Thr Val Pro His Pro Asn
                725                 730                 735

Ile Glu Glu Val Ala Leu Ser Thr Thr Gly Glu Ile Pro Phe Tyr Gly
                740                 745                 750

Lys Ala Ile Pro Leu Glu Val Ile Lys Gly Gly Arg His Leu Ile Phe
    755                 760                 765

Cys His Ser Lys Lys Lys Cys Asp Glu Leu Ala Ala Lys Leu Val Ala
    770                 775                 780

Leu Gly Ile Asn Ala Val Ala Tyr Tyr Arg Gly Leu Asp Val Ser Val
785                 790                 795                 800

Ile Pro Thr Ser Gly Asp Val Val Val Ala Thr Asp Ala Leu Met
                805                 810                 815

Thr Gly Tyr Thr Gly Asp Phe Asp Ser Val Ile Asp Cys Asn Thr Cys
                820                 825                 830

Val Thr Gln Thr Val Asp Phe Ser Leu Asp Pro Thr Phe Thr Ile Glu
                835                 840                 845

Thr Ile Thr Leu Pro Gln Asp Ala Val Ser Arg Thr Gln Arg Arg Gly
    850                 855                 860

Arg Thr Gly Arg Gly Lys Pro Gly Ile Tyr Arg Phe Val Ala Pro Gly
865                 870                 875                 880

Glu Arg Pro Ser Gly Met Phe Asp Ser Ser Val Leu Cys Glu Cys Tyr
                885                 890                 895

Asp Ala Gly Cys Ala Trp Tyr Glu Leu Thr Pro Ala Glu Thr Thr Val
                900                 905                 910

Arg Leu Arg Ala Tyr Met Asn Thr Pro Gly Leu Pro Val Cys Gln Asp
    915                 920                 925

His Leu Glu Phe Trp Glu Gly Val Phe Thr Gly Leu Thr His Ile Asp
    930                 935                 940
```

```
Ala His Phe Leu Ser Gln Thr Lys Gln Ser Gly Glu Asn Leu Pro Tyr
945                 950                 955                 960

Leu Val Ala Tyr Gln Ala Thr Val Cys Ala Arg Ala Gln Ala Pro Pro
            965                 970                 975

Pro Ser Trp Asp Gln Met Trp Lys Cys Leu Ile Arg Leu Lys Pro Thr
        980                 985                 990

Leu His Gly Pro Thr Pro Leu Leu Tyr Arg Leu Gly Ala Val Gln Asn
    995                 1000                1005

Glu Ile Thr Leu Thr His Pro Val Thr Lys Tyr Ile Met Thr Cys Met
1010                1015                1020

Ser Ala Asp Leu Glu Val Val Thr Ser Thr Trp Val Leu Val Gly Gly
1025                1030                1035                1040

Val Leu Ala Ala Leu Ala Ala Tyr Cys Leu Ser Thr Gly Cys Val Val
            1045                1050                1055

Ile Val Gly Arg Val Val Leu Ser Gly Lys Pro Ala Ile Ile Pro Asp
            1060                1065                1070

Arg Glu Val Leu Tyr Arg Glu Phe Asp Glu Met Glu Glu Cys Ser Gln
            1075                1080                1085

His Leu Pro Tyr Ile Glu Gln Gly Met Met Leu Ala Glu Gln Phe Lys
    1090                1095                1100

Gln Lys Ala Leu Gly Leu Leu Gln Thr Ala Ser Arg Gln Ala Glu Val
1105                1110                1115                1120

Ile Ala Pro Ala Val Gln Thr Asn Trp Gln Lys Leu Glu Thr Phe Trp
            1125                1130                1135

Ala Lys His Met Trp Asn Phe Ile Ser Gly Ile Gln Tyr Leu Ala Gly
            1140                1145                1150

Leu Ser Thr Leu Pro Gly Asn Pro Ala Ile Ala Ser Leu Met Ala Phe
            1155                1160                1165

Thr Ala Ala Val Thr Ser Pro Leu Thr Thr Ser Gln Thr Leu Leu Phe
            1170                1175                1180

Asn Ile Leu Gly Gly Trp Val Ala Ala Gln Leu Ala Ala Pro Gly Ala
1185                1190                1195                1200

Ala Thr Ala Phe Val Gly Ala Gly Leu Ala Gly Ala Ala Ile Gly Ser
            1205                1210                1215

Val Gly Leu Gly Lys Val Leu Ile Asp Ile Leu Ala Gly Tyr Gly Ala
            1220                1225                1230

Gly Val Ala Gly Ala Leu Val Ala Phe Lys Ile Met Ser Gly Glu Val
            1235                1240                1245

Pro Ser Thr Glu Asp Leu Val Asn Leu Leu Pro Ala Ile Leu Ser Pro
            1250                1255                1260

Gly Ala Leu Val Val Gly Val Val Cys Ala Ala Ile Leu Arg Arg His
1265                1270                1275                1280

Val Gly Pro Gly Glu Gly Ala Val Gln Trp Met Asn Arg Leu Ile Ala
            1285                1290                1295

Phe Ala Ser Arg Gly Asn His Val Ser Pro Thr His Tyr Val Pro Glu
            1300                1305                1310

Ser Asp Ala Ala Ala Arg Val Thr Ala Ile Leu Ser Ser Leu Thr Val
            1315                1320                1325

Thr Gln Leu Leu Arg Arg Leu His Gln Trp Ile Ser Ser Glu Cys Thr
            1330                1335                1340

Thr Pro Cys Ser Gly Ser Trp Leu Arg Asp Ile Trp Asp Trp Ile Cys
1345                1350                1355                1360

Glu Val Leu Ser Asp Phe Lys Thr Trp Leu Lys Ala Lys Leu Met Pro
```

```
                    1365                1370                1375
Gln Leu Pro Gly Ile Pro Phe Val Ser Cys Gln Arg Gly Tyr Lys Gly
                1380                1385                1390
Val Trp Arg Val Asp Gly Ile Met His Thr Arg Cys His Cys Gly Ala
            1395                1400                1405
Glu Ile Thr Gly His Val Lys Asn Gly Thr Met Arg Ile Val Gly Pro
        1410                1415                1420
Arg Thr Cys Arg Asn Met Trp Ser Gly Thr Phe Pro Ile Asn Ala Tyr
1425                1430                1435                1440
Thr Thr Gly Pro Cys Thr Pro Leu Pro Ala Pro Asn Tyr Thr Phe Ala
                1445                1450                1455
Leu Trp Arg Val Ser Ala Glu Glu Tyr Val Glu Ile Arg Gln Val Gly
            1460                1465                1470
Asp Phe His Tyr Val Thr Gly Met Thr Thr Asp Asn Leu Lys Cys Pro
        1475                1480                1485
Cys Gln Val Pro Ser Pro Glu Phe Phe Thr Glu Leu Asp Gly Val Arg
    1490                1495                1500
Leu His Arg Phe Ala Pro Pro Cys Lys Pro Leu Leu Arg Glu Glu Val
1505                1510                1515                1520
Ser Phe Arg Val Gly Leu His Glu Tyr Pro Val Gly Ser Gln Leu Pro
                1525                1530                1535
Cys Glu Pro Glu Pro Asp Val Ala Val Leu Thr Ser Met Leu Thr Asp
            1540                1545                1550
Pro Ser His Ile Thr Ala Glu Ala Ala Gly Arg Arg Leu Ala Arg Gly
        1555                1560                1565
Ser Pro Pro Ser Val Ala Ser Ser Ser Ala Ser Gln Leu Ser Ala Pro
    1570                1575                1580
Ser Leu Lys Ala Thr Cys Thr Ala Asn His Asp Ser Pro Asp Ala Glu
1585                1590                1595                1600
Leu Ile Glu Ala Asn Leu Leu Trp Arg Gln Glu Met Gly Gly Asn Ile
                1605                1610                1615
Thr Arg Val Glu Ser Glu Asn Lys Val Val Ile Leu Asp Ser Phe Asp
            1620                1625                1630
Pro Leu Val Ala Glu Glu Asp Glu Arg Glu Ile Ser Val Pro Ala Glu
        1635                1640                1645
Ile Leu Arg Lys Ser Arg Arg Phe Ala Gln Ala Leu Pro Val Trp Ala
1650                1655                1660
Arg Pro Asp Tyr Asn Pro Pro Leu Val Glu Thr Trp Lys Lys Pro Asp
1665                1670                1675                1680
Tyr Glu Pro Pro Val Val His Gly Cys Pro Leu Pro Pro Pro Lys Ser
                1685                1690                1695
Pro Pro Val Pro Pro Pro Arg Lys Lys Arg Thr Val Val Leu Thr Glu
            1700                1705                1710
Ser Thr Leu Ser Thr Ala Leu Ala Glu Leu Ala Thr Arg Ser Phe Gly
        1715                1720                1725
Ser Ser Ser Thr Ser Gly Ile Thr Gly Asp Asn Thr Thr Thr Ser Ser
    1730                1735                1740
Glu Pro Ala Pro Ser Gly Cys Pro Pro Asp Ser Asp Ala Glu Ser Tyr
1745                1750                1755                1760
Ser Ser Met Pro Pro Leu Glu Gly Glu Pro Gly Asp Pro Asp Leu Ser
                1765                1770                1775
Asp Gly Ser Trp Ser Thr Val Ser Ser Glu Ala Asn Ala Glu Asp Val
            1780                1785                1790
```

```
Val Cys Cys Ser Met Ser Tyr Ser Trp Thr Gly Ala Leu Val Thr Pro
        1795            1800                1805

Cys Ala Ala Glu Glu Gln Lys Leu Pro Ile Asn Ala Leu Ser Asn Ser
1810            1815                1820

Leu Leu Arg His His Asn Leu Val Tyr Ser Thr Thr Ser Arg Ser Ala
1825            1830                1835                1840

Cys Gln Arg Gln Lys Lys Val Thr Phe Asp Arg Leu Gln Val Leu Asp
                1845                1850                1855

Ser His Tyr Gln Asp Val Leu Lys Glu Val Lys Ala Ala Ser Lys
                1860            1865                1870

Val Lys Ala Asn Leu Leu Ser Val Glu Glu Ala Cys Ser Leu Thr Pro
        1875            1880                1885

Pro His Ser Ala Lys Ser Lys Phe Gly Tyr Gly Ala Lys Asp Val Arg
        1890            1895                1900

Cys His Ala Arg Lys Ala Val Thr His Ile Asn Ser Val Trp Lys Asp
1905            1910                1915                1920

Leu Leu Glu Asp Asn Val Thr Pro Ile Asp Thr Thr Ile Met Ala Lys
                1925                1930                1935

Asn Glu Val Phe Cys Val Gln Pro Glu Lys Gly Gly Arg Lys Pro Ala
        1940            1945                1950

Arg Leu Ile Val Phe Pro Asp Leu Gly Val Arg Val Cys Glu Lys Met
        1955            1960                1965

Ala Leu Tyr Asp Val Val Thr Lys Leu Pro Leu Ala Val Met Gly Ser
        1970            1975                1980

Ser Tyr Gly Phe Gln Tyr Ser Pro Gly Gln Arg Val Glu Phe Leu Val
1985            1990                1995                2000

Gln Ala Trp Lys Ser Lys Lys Thr Pro Met Gly Phe Ser Tyr Asp Thr
        2005            2010                2015

Arg Cys Phe Asp Ser Thr Val Thr Glu Ser Asp Ile Arg Thr Glu Glu
        2020            2025                2030

Ala Ile Tyr Gln Cys Cys Asp Leu Asp Pro Gln Ala Arg Val Ala Ile
        2035            2040                2045

Lys Ser Leu Thr Glu Arg Leu Tyr Val Gly Gly Pro Leu Thr Asn Ser
2050            2055                2060

Arg Gly Glu Asn Cys Gly Tyr Arg Arg Cys Arg Ala Ser Gly Val Leu
2065            2070                2075                2080

Thr Thr Ser Cys Gly Asn Thr Leu Thr Cys Tyr Ile Lys Ala Arg Ala
                2085            2090                2095

Ala Cys Arg Ala Ala Gly Leu Gln Asp Cys Thr Met Leu Val Cys Gly
        2100            2105                2110

Asp Asp Leu Val Val Ile Cys Glu Ser Ala Gly Val Gln Glu Asp Ala
        2115            2120                2125

Ala Ser Leu Arg Ala Phe Thr Glu Ala Met Thr Arg Tyr Ser Ala Pro
        2130            2135                2140

Pro Gly Asp Pro Pro Gln Pro Glu Tyr Asp Leu Glu Leu Ile Thr Ser
2145            2150                2155                2160

Cys Ser Ser Asn Val Ser Val Ala His Asp Gly Ala Gly Lys Arg Val
                2165            2170                2175

Tyr Tyr Leu Thr Arg Asp Pro Thr Thr Pro Leu Ala Arg Ala Ala Trp
        2180            2185                2190

Glu Thr Ala Arg His Thr Pro Val Asn Ser Trp Leu Gly Asn Ile Ile
        2195            2200                2205
```

```
                                    -continued

Met Phe Ala Pro Thr Leu Trp Ala Arg Met Ile Leu Met Thr His Phe
    2210                2215                2220

Phe Ser Val Leu Ile Ala Arg Asp Gln Leu Glu Gln Ala Leu Asp Cys
2225            2230                2235                2240

Glu Ile Tyr Gly Ala Cys Tyr Ser Ile Glu Pro Leu Asp Leu Pro Pro
                2245                2250                2255

Ile Ile Gln Arg Leu
        2260

(2) INFORMATION FOR SEQ ID NO:67:

(i) SEQUENCE CHARACTERISTICS:
        (A) LENGTH: 1310 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (B) CLONE: composite of clones 36, 81, and 32

(ix) FEATURE:
        (A) NAME/KEY: CDS
        (B) LOCATION: 1..1146

(xi) SEQUENCE DESCRIPTION: SEQ ID NO:67:

GCT TGT GGT GTA ATT GGG ATC GCC CAG AAT TTG GGA ATT CGG GAT GCC      48
Ala Cys Gly Val Ile Gly Ile Ala Gln Asn Leu Gly Ile Arg Asp Ala
 1               5                  10                  15

CAC TTT CTA TCC CAG ACA AAG CAG AGT GGG GAG AAC CTT CCT TAC CTG      96
His Phe Leu Ser Gln Thr Lys Gln Ser Gly Glu Asn Leu Pro Tyr Leu
                 20                  25                  30

GTA GCG TAC CAA GCC ACC GTG TGC GCT AGG GCT CAA GCC CCT CCC CCA     144
Val Ala Tyr Gln Ala Thr Val Cys Ala Arg Ala Gln Ala Pro Pro Pro
             35                  40                  45

TCG TGG GAC CAG ATG TGG AAG TGT TTG ATT CGC CTC AAG CCC ACC CTC     192
Ser Trp Asp Gln Met Trp Lys Cys Leu Ile Arg Leu Lys Pro Thr Leu
 50                  55                  60

CAT GGG CCA ACA CCC CTG CTA TAC AGA CTG GGC GCT GTT CAG AAT GAA     240
His Gly Pro Thr Pro Leu Leu Tyr Arg Leu Gly Ala Val Gln Asn Glu
 65                  70                  75                  80

ATC ACC CTG ACG CAC CCA GTC ACC AAA TAC ATC ATG ACA TGC ATG TCG     288
Ile Thr Leu Thr His Pro Val Thr Lys Tyr Ile Met Thr Cys Met Ser
                 85                  90                  95

GCC GAC CTG GAG GTC GTC ACG AGC ACC TGG GTG CTC GTT GGC GGC GTC     336
Ala Asp Leu Glu Val Val Thr Ser Thr Trp Val Leu Val Gly Gly Val
                100                 105                 110

CTG GCT GCT TTG GCC GCG TAT TGC CTG TCA ACA GGC TGC GTG GTC ATA     384
Leu Ala Ala Leu Ala Ala Tyr Cys Leu Ser Thr Gly Cys Val Val Ile
            115                 120                 125

GTG GGC AGG GTC GTC TTG TCC GGG AAG CCG GCA ATC ATA CCT GAC AGG     432
Val Gly Arg Val Val Leu Ser Gly Lys Pro Ala Ile Ile Pro Asp Arg
130                 135                 140

GAA GTC CTC TAC CGA GAG TTC GAT GAG ATG GAA GAG TGC TCT CAG CAC     480
Glu Val Leu Tyr Arg Glu Phe Asp Glu Met Glu Glu Cys Ser Gln His
145                 150                 155                 160

TTA CCG TAC ATC GAG CAA GGG ATG ATG CTC GCC GAG CAG TTC AAG CAG     528
Leu Pro Tyr Ile Glu Gln Gly Met Met Leu Ala Glu Gln Phe Lys Gln
                165                 170                 175

AAG GCC CTC GGC CTC CTG CAG ACC GCG TCC CGT CAG GCA GAG GTT ATC     576
Lys Ala Leu Gly Leu Leu Gln Thr Ala Ser Arg Gln Ala Glu Val Ile
            180                 185                 190
```

```
GCC CCT GCT GTC CAG ACC AAC TGG CAA AAA CTC GAG ACC TTC TGG GCG         624
Ala Pro Ala Val Gln Thr Asn Trp Gln Lys Leu Glu Thr Phe Trp Ala
        195                 200                 205

AAG CAT ATG TGG AAC TTC ATC AGT GGG ATA CAA TAC TTG GCG GGC TTG         672
Lys His Met Trp Asn Phe Ile Ser Gly Ile Gln Tyr Leu Ala Gly Leu
    210                 215                 220

TCA ACG CTG CCT GGT AAC CCC GCC ATT GCT TCA TTG ATG GCT TTT ACA         720
Ser Thr Leu Pro Gly Asn Pro Ala Ile Ala Ser Leu Met Ala Phe Thr
225                 230                 235                 240

GCT GCT GTC ACC AGC CCA CTA ACC ACT AGC CAA ACC CTC CTC TTC AAC         768
Ala Ala Val Thr Ser Pro Leu Thr Thr Ser Gln Thr Leu Leu Phe Asn
                245                 250                 255

ATA TTG GGG GGG TGG GTG GCT GCC CAG CTC GCC GCC CCC GGT GCC GCT         816
Ile Leu Gly Gly Trp Val Ala Ala Gln Leu Ala Ala Pro Gly Ala Ala
            260                 265                 270

ACT GCC TTT GTG GGC GCT GGC TTA GCT GGC GCC GCC ATC GGC AGT GTT         864
Thr Ala Phe Val Gly Ala Gly Leu Ala Gly Ala Ala Ile Gly Ser Val
        275                 280                 285

GGA CTG GGG AAG GTC CTC ATA GAC ATC CTT GCA GGG TAT GGC GCG GGC         912
Gly Leu Gly Lys Val Leu Ile Asp Ile Leu Ala Gly Tyr Gly Ala Gly
    290                 295                 300

GTG GCG GGA GCT CTT GTG GCA TTC AAG ATC ATG AGC GGT GAG GTC CCC         960
Val Ala Gly Ala Leu Val Ala Phe Lys Ile Met Ser Gly Glu Val Pro
305                 310                 315                 320

TCC ACG GAG GAC CTG GTC AAT CTA CTG CCC GCC ATC CTC TCG CCC GGA        1008
Ser Thr Glu Asp Leu Val Asn Leu Leu Pro Ala Ile Leu Ser Pro Gly
                325                 330                 335

GCC CTC GTA GTC GGC GTG GTC TGT GCA GCA ATA CTG CGC CGG CAC GTT        1056
Ala Leu Val Val Gly Val Val Cys Ala Ala Ile Leu Arg Arg His Val
            340                 345                 350

GGC CCG GGC GAG GGG GCA GTG CAG TGG ATG AAC CGG CTG ATA GCC TTC        1104
Gly Pro Gly Glu Gly Ala Val Gln Trp Met Asn Arg Leu Ile Ala Phe
        355                 360                 365

GCC TCC CGG GGG AAC CAT GTT TCC CCA GTC CAT CAT AAG CGT                1146
Ala Ser Arg Gly Asn His Val Ser Pro Val His His Lys Arg
    370                 375                 380

TGACGCTCCC TACGGGTGGA CTGTGGAGAG ACAGGGCACT GCTAAGGCCC AAATCTCAGC      1206

CATGCATCGA GGGGTACAAT CCGTATGGCC AACAACTAGC GCGTACGTAA AGTCTCCTTT      1266

CTCGATGGTC CATACCTTAG ATGCGTTAGC ATTAATCCGA ATTC                       1310

(2) INFORMATION FOR SEQ ID NO:68:

(i) SEQUENCE CHARACTERISTICS:
        (A) LENGTH: 382 amino acids
        (B) TYPE: amino acid
        (D) TOPOLOGY: linear (ii) MOLECULE TYPE: protein (xi) SEQUENCE DESCRIPTION: SEQ ID NO:68:

Ala Cys Gly Val Ile Gly Ile Ala Gln Asn Leu Gly Ile Arg Asp Ala
1               5                   10                  15

His Phe Leu Ser Gln Thr Lys Gln Ser Gly Glu Asn Leu Pro Tyr Leu
                20                  25                  30

Val Ala Tyr Gln Ala Thr Val Cys Ala Arg Ala Gln Ala Pro Pro Pro
            35                  40                  45

Ser Trp Asp Gln Met Trp Lys Cys Leu Ile Arg Leu Lys Pro Thr Leu
        50                  55                  60
```

```
His Gly Pro Thr Pro Leu Leu Tyr Arg Leu Gly Ala Val Gln Asn Glu
 65                  70                  75                  80

Ile Thr Leu Thr His Pro Val Thr Lys Tyr Ile Met Thr Cys Met Ser
                 85                  90                  95

Ala Asp Leu Glu Val Val Thr Ser Thr Trp Val Leu Val Gly Gly Val
            100                 105                 110

Leu Ala Ala Leu Ala Ala Tyr Cys Leu Ser Thr Gly Cys Val Val Ile
        115                 120                 125

Val Gly Arg Val Val Leu Ser Gly Lys Pro Ala Ile Ile Pro Asp Arg
    130                 135                 140

Glu Val Leu Tyr Arg Glu Phe Asp Glu Met Glu Glu Cys Ser Gln His
145                 150                 155                 160

Leu Pro Tyr Ile Glu Gln Gly Met Met Leu Ala Glu Gln Phe Lys Gln
                165                 170                 175

Lys Ala Leu Gly Leu Leu Gln Thr Ala Ser Arg Gln Ala Glu Val Ile
            180                 185                 190

Ala Pro Ala Val Gln Thr Asn Trp Gln Lys Leu Glu Thr Phe Trp Ala
        195                 200                 205

Lys His Met Trp Asn Phe Ile Ser Gly Ile Gln Tyr Leu Ala Gly Leu
    210                 215                 220

Ser Thr Leu Pro Gly Asn Pro Ala Ile Ala Ser Leu Met Ala Phe Thr
225                 230                 235                 240

Ala Ala Val Thr Ser Pro Leu Thr Thr Ser Gln Thr Leu Leu Phe Asn
                245                 250                 255

Ile Leu Gly Gly Trp Val Ala Ala Gln Leu Ala Ala Pro Gly Ala Ala
            260                 265                 270

Thr Ala Phe Val Gly Ala Gly Leu Ala Gly Ala Ala Ile Gly Ser Val
        275                 280                 285

Gly Leu Gly Lys Val Leu Ile Asp Ile Leu Ala Gly Tyr Gly Ala Gly
    290                 295                 300

Val Ala Gly Ala Leu Val Ala Phe Lys Ile Met Ser Gly Glu Val Pro
305                 310                 315                 320

Ser Thr Glu Asp Leu Val Asn Leu Leu Pro Ala Ile Leu Ser Pro Gly
                325                 330                 335

Ala Leu Val Val Gly Val Val Cys Ala Ala Ile Leu Arg Arg His Val
            340                 345                 350

Gly Pro Gly Glu Gly Ala Val Gln Trp Met Asn Arg Leu Ile Ala Phe
        355                 360                 365

Ala Ser Arg Gly Asn His Val Ser Pro Val His His Lys Arg
    370                 375                 380

(2) INFORMATION FOR SEQ ID NO:69:

(i) SEQUENCE CHARACTERISTICS:
        (A) LENGTH: 829 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:69:

Glu Tyr Val Val Leu Leu Phe Leu Leu Leu Ala Asp Ala Arg Val Cys
1                5                  10                  15

Ser Cys Leu Trp Met Met Leu Leu Ile Ser Gln Ala Glu Ala Ala Leu
            20                  25                  30
```

-continued

```
Glu Asn Leu Val Ile Leu Asn Ala Ala Ser Leu Ala Gly Thr His Gly
         35                  40                  45

Leu Val Ser Phe Leu Val Phe Phe Cys Phe Ala Trp Tyr Leu Lys Gly
 50                  55                  60

Lys Trp Val Pro Gly Ala Val Tyr Thr Phe Tyr Gly Met Trp Pro Leu
 65              70                  75                  80

Leu Leu Leu Leu Leu Ala Leu Pro Gln Arg Ala Tyr Ala Leu Asp Thr
                     85                  90                  95

Glu Val Ala Ala Ser Cys Gly Gly Val Val Leu Val Gly Leu Met Ala
                100                 105                 110

Leu Thr Leu Ser Pro Tyr Tyr Lys Arg Tyr Ile Ser Trp Cys Leu Trp
            115                 120                 125

Trp Leu Gln Tyr Phe Leu Thr Arg Val Glu Ala Gln Leu His Val Trp
        130                 135                 140

Ile Pro Pro Leu Asn Val Arg Gly Gly Arg Asp Ala Val Ile Leu Leu
145                 150                 155                 160

Met Cys Ala Val His Pro Thr Leu Val Phe Asp Ile Thr Lys Leu Leu
                165                 170                 175

Leu Ala Val Phe Gly Pro Leu Trp Ile Leu Gln Ala Ser Leu Leu Lys
            180                 185                 190

Val Pro Tyr Phe Val Arg Val Gln Gly Leu Leu Arg Phe Cys Ala Leu
        195                 200                 205

Ala Arg Lys Met Ile Gly Gly His Tyr Val Gln Met Val Ile Ile Lys
    210                 215                 220

Leu Gly Ala Leu Thr Gly Thr Tyr Val Tyr Asn His Leu Thr Pro Leu
225                 230                 235                 240

Arg Asp Trp Ala His Asn Gly Leu Arg Asp Leu Ala Val Ala Val Glu
                245                 250                 255

Pro Val Val Phe Ser Gln Met Glu Thr Lys Leu Ile Thr Trp Gly Ala
            260                 265                 270

Asp Thr Ala Ala Cys Gly Asp Ile Ile Asn Gly Leu Pro Val Ser Ala
        275                 280                 285

Arg Arg Gly Arg Glu Ile Leu Leu Gly Pro Ala Asp Gly Met Val Ser
    290                 295                 300

Lys Gly Trp Arg Leu Leu Ala Pro Ile Thr Ala Tyr Ala Gln Gln Thr
305                 310                 315                 320

Arg Gly Leu Leu Gly Cys Ile Ile Thr Ser Leu Thr Gly Arg Asp Lys
                325                 330                 335

Asn Gln Val Glu Gly Glu Val Gln Ile Val Ser Thr Ala Ala Gln Thr
            340                 345                 350

Phe Leu Ala Thr Cys Ile Asn Gly Val Cys Trp Thr Val Tyr His Gly
        355                 360                 365

Ala Gly Thr Arg Thr Ile Ala Ser Pro Lys Gly Pro Val Ile Gln Met
    370                 375                 380

Tyr Thr Asn Val Asp Gln Asp Leu Val Gly Trp Pro Ala Pro Gln Gly
385                 390                 395                 400

Ser Arg Ser Leu Thr Pro Cys Thr Cys Gly Ser Ser Asp Leu Tyr Leu
                405                 410                 415

Val Thr Arg His Ala Asp Val Ile Pro Val Arg Arg Arg Gly Asp Ser
            420                 425                 430

Arg Gly Ser Leu Leu Ser Pro Arg Pro Ile Ser Tyr Leu Lys Gly Ser
        435                 440                 445

Ser Gly Gly Pro Leu Leu Cys Pro Ala Gly His Ala Val Gly Ile Phe
```

```
            450                 455                 460
Arg Ala Ala Val Cys Thr Arg Gly Val Ala Lys Ala Val Asp Phe Ile
465                 470                 475                 480

Pro Val Glu Asn Leu Glu Thr Thr Met Arg Ser Pro Val Phe Thr Asp
                485                 490                 495

Asn Ser Ser Pro Pro Val Val Pro Gln Ser Phe Gln Val Ala His Leu
                500                 505                 510

His Ala Pro Thr Gly Ser Gly Lys Ser Thr Lys Val Pro Ala Ala Tyr
                515                 520                 525

Ala Ala Gln Gly Tyr Lys Val Leu Val Leu Asn Pro Ser Val Ala Ala
                530                 535                 540

Thr Leu Gly Phe Gly Ala Tyr Met Ser Lys Ala His Gly Ile Asp Pro
545                 550                 555                 560

Asn Ile Arg Thr Gly Val Arg Thr Ile Thr Thr Gly Ser Pro Ile Thr
                565                 570                 575

Tyr Ser Thr Tyr Gly Lys Phe Leu Ala Asp Gly Gly Cys Ser Gly Gly
                580                 585                 590

Ala Tyr Asp Ile Ile Ile Cys Asp Glu Cys His Ser Thr Asp Ala Thr
                595                 600                 605

Ser Ile Leu Gly Ile Gly Thr Val Leu Asp Gln Ala Glu Thr Ala Gly
610                 615                 620

Ala Arg Leu Val Val Leu Ala Thr Ala Thr Pro Pro Gly Ser Val Thr
625                 630                 635                 640

Val Pro His Pro Asn Ile Glu Glu Val Ala Leu Ser Thr Thr Gly Glu
                645                 650                 655

Ile Pro Phe Tyr Gly Lys Ala Ile Pro Leu Glu Val Ile Lys Gly Gly
                660                 665                 670

Arg His Leu Ile Phe Cys His Ser Lys Lys Cys Asp Glu Leu Ala
                675                 680                 685

Ala Lys Leu Val Ala Leu Gly Ile Asn Ala Val Ala Tyr Tyr Arg Gly
                690                 695                 700

Leu Glu Leu Ser Val Ile Pro Thr Ser Gly Asp Val Val Val Val Ala
705                 710                 715                 720

Thr Asp Ala Leu Met Thr Gly Tyr Thr Gly Asp Phe Asp Ser Val Ile
                725                 730                 735

Asp Cys Asn Thr Cys Val Thr Gln Thr Val Asp Phe Ser Leu Asp Pro
                740                 745                 750

Thr Phe Thr Ile Glu Thr Ile Thr Leu Pro Gln Asp Ala Val Ser Arg
                755                 760                 765

Thr Gln Arg Arg Gly Arg Thr Gly Arg Gly Lys Pro Gly Ile Tyr Arg
                770                 775                 780

Phe Val Ala Pro Gly Glu Arg Pro Ser Gly Met Phe Asp Ser Ser Val
785                 790                 795                 800

Leu Cys Glu Cys Tyr Asp Ala Gly Cys Ala Trp Tyr Glu Leu Thr Pro
                805                 810                 815

Ala Glu Thr Thr Val Arg Leu Arg Ala Tyr Met Asn Thr
                820                 825

(2) INFORMATION FOR SEQ ID NO:70:

(i) SEQUENCE CHARACTERISTICS:
        (A) LENGTH: 765 amino acids
        (B) TYPE: amino acid
        (C) STRANDEDNESS: single
        (D) TOPOLOGY: linear
```

(ii) MOLECULE TYPE: peptide (vi) ORIGINAL SOURCE:
         (A) ORGANISM: Dengue flavivirus(MNWVD1)

(xi) SEQUENCE DESCRIPTION: SEQ ID NO:70:

Ala Val Ser Phe Val Thr Leu Ile Thr Gly Asn Met Ser Phe Arg Asp
1               5                   10                  15

Leu Gly Arg Val Met Val Met Val Gly Ala Thr Met Thr Asp Asp Ile
            20                  25                  30

Gly Met Gly Val Thr Tyr Leu Ala Leu Leu Ala Ala Phe Lys Val Arg
            35                  40                  45

Pro Thr Phe Ala Ala Gly Leu Leu Leu Arg Lys Leu Thr Ser Lys Glu
50                      55                  60

Leu Met Met Thr Thr Ile Gly Ile Val Leu Leu Ser Gln Ser Thr Ile
65                      70                  75                  80

Pro Glu Thr Ile Leu Glu Leu Thr Asp Ala Leu Ala Leu Gly Met Met
                85                  90                  95

Val Leu Lys Met Val Arg Lys Met Glu Lys Tyr Gln Leu Ala Val Thr
            100                 105                 110

Ile Met Ala Ile Leu Cys Val Pro Asn Ala Val Ile Leu Gln Asn Ala
            115                 120                 125

Trp Lys Val Ser Cys Thr Ile Leu Ala Val Val Ser Val Ser Pro Leu
130                 135                 140

Phe Leu Thr Ser Ser Gln Gln Lys Ala Asp Trp Ile Pro Leu Ala Leu
145                 150                 155                 160

Thr Ile Lys Gly Leu Asn Pro Thr Ala Ile Phe Leu Thr Thr Leu Ser
                165                 170                 175

Arg Thr Asn Lys Lys Arg Ser Trp Pro Leu Asn Glu Ala Ile Met Ala
            180                 185                 190

Val Gly Met Val Ser Ile Leu Ala Ser Ser Leu Leu Lys Asn Asp Ile
            195                 200                 205

Pro Met Thr Gly Pro Leu Val Ala Gly Gly Leu Leu Thr Val Cys Tyr
210                 215                 220

Val Leu Thr Gly Arg Ser Ala Asp Leu Glu Leu Glu Arg Ala Ala Asp
225                 230                 235                 240

Val Lys Trp Glu Asp Gln Ala Glu Ile Ser Gly Ser Ser Pro Ile Leu
                245                 250                 255

Ser Ile Thr Ile Ser Glu Asp Gly Ser Met Ser Ile Lys Asn Glu Glu
            260                 265                 270

Glu Glu Gln Thr Leu Thr Ile Leu Ile Arg Thr Gly Leu Leu Val Ile
            275                 280                 285

Ser Gly Leu Phe Pro Val Ser Ile Pro Ile Thr Ala Ala Ala Trp Tyr
290                 295                 300

Leu Trp Glu Val Lys Lys Gln Arg Ala Gly Val Leu Trp Asp Val Pro
305                 310                 315                 320

Ser Pro Pro Pro Val Gly Lys Ala Glu Leu Glu Asp Gly Ala Tyr Arg
                325                 330                 335

Ile Lys Gln Lys Gly Ile Leu Gly Tyr Ser Gln Ile Gly Ala Gly Val
            340                 345                 350

Tyr Lys Glu Gly Thr Phe His Thr Met Trp His Val Thr Arg Gly Ala
            355                 360                 365

Val Leu Met His Lys Gly Lys Arg Ile Glu Pro Ser Trp Ala Asp Val
370                 375                 380

```
Lys Lys Asp Leu Val Ser Cys Gly Gly Trp Lys Leu Glu Gly Glu
385                 390                 395                 400

Trp Lys Glu Gly Glu Val Gln Val Leu Ala Leu Glu Pro Gly Lys
            405                 410                 415

Asn Pro Arg Ala Val Gln Thr Lys Pro Gly Leu Phe Lys Thr Asn Ala
            420                 425                 430

Gly Thr Ile Gly Ala Val Ser Leu Asp Phe Ser Pro Gly Thr Ser Gly
            435                 440                 445

Ser Pro Ile Ile Asp Lys Lys Gly Lys Val Val Gly Leu Tyr Gly Asn
    450                 455                 460

Gly Val Val Thr Arg Ser Gly Ala Tyr Val Ser Ala Ile Ala Gln Thr
465                 470                 475                 480

Glu Lys Ser Ile Glu Asp Asn Pro Glu Ile Glu Asp Ile Phe Arg
                485                 490                 495

Lys Arg Lys Leu Thr Ile Met Asp Leu His Pro Gly Ala Gly Lys Thr
                500                 505                 510

Lys Arg Tyr Leu Pro Ala Ile Val Arg Gly Ala Ile Lys Arg Gly Leu
            515                 520                 525

Arg Thr Leu Ile Leu Ala Pro Thr Arg Val Val Ala Ala Glu Met Glu
530                 535                 540

Glu Ala Leu Arg Gly Leu Pro Ile Arg Tyr Gln Thr Pro Ala Ile Arg
545                 550                 555                 560

Ala Glu His Thr Gly Arg Glu Ile Val Asp Leu Met Cys His Ala Thr
                565                 570                 575

Phe Thr Met Arg Leu Leu Ser Pro Val Arg Val Pro Asn Tyr Asn Leu
                580                 585                 590

Ile Ile Met Asp Glu Ala His Phe Thr Asp Pro Ala Ser Ile Ala Ala
            595                 600                 605

Arg Gly Tyr Ile Ser Thr Arg Val Glu Met Gly Glu Ala Ala Gly Ile
            610                 615                 620

Phe Met Thr Ala Thr Pro Pro Gly Ser Arg Asp Pro Phe Pro Gln Ser
625                 630                 635                 640

Asn Ala Pro Ile Met Asp Glu Glu Arg Glu Ile Pro Glu Arg Ser Trp
            645                 650                 655

Ser Ser Gly His Glu Trp Val Thr Asp Phe Lys Gly Lys Thr Val Trp
            660                 665                 670

Phe Val Pro Ser Ile Lys Ala Gly Asn Asp Thr Ala Ala Cys Leu Arg
            675                 680                 685

Lys Asn Gly Lys Lys Val Thr Gln Leu Ser Arg Lys Thr Phe Asp Ser
690                 695                 700

Glu Tyr Val Lys Thr Arg Thr Asn Asp Trp Asn Phe Val Val Thr Thr
705                 710                 715                 720

Asp Ile Ser Glu Met Gly Ala Asn Phe Lys Ala Glu Arg Val Ile Asp
                725                 730                 735

Pro Arg Arg Cys Met Lys Pro Val Ile Leu Thr Asp Gly Glu Glu Arg
            740                 745                 750

Val Ile Leu Ala Gly Pro Met Pro Val Thr His Ser Ser
            755                 760                 765

(2) INFORMATION FOR SEQ ID NO:71:

(i) SEQUENCE CHARACTERISTICS:
        (A) LENGTH: 16 base pairs
        (B) TYPE: nucleic acid
```

(C) STRANDEDNESS: single
                    (D) TOPOLOGY: linear (ii) MOLECULE TYPE: DNA (genomic)

(xi) SEQUENCE DESCRIPTION: SEQ ID NO:71:

AAGCTTGATC GAATTC                                                          16

(2) INFORMATION FOR SEQ ID NO:72:

(i) SEQUENCE CHARACTERISTICS:
                (A) LENGTH: 1366 base pairs
                (B) TYPE: nucleic acid
                (C) STRANDEDNESS: single
                (D) TOPOLOGY: linear (ii) MOLECULE TYPE: cDNA (vii) IMMEDIATE SOURCE:
                (B) CLONE: k9-1

(ix) FEATURE:
                (A) NAME/KEY: CDS
                (B) LOCATION: 3..1364

(xi) SEQUENCE DESCRIPTION: SEQ ID NO:72:

```
CA GGC TGT CCT GAG AGG CTA GCC AGC TGC CGA CCC CTT ACC GAT TTT          47
   Gly Cys Pro Glu Arg Leu Ala Ser Cys Arg Pro Leu Thr Asp Phe
    1               5                  10                  15

GAC CAG GGC TGG GGC CCT ATC AGT TAT GCC AAC GGA AGC GGC CCC GAC          95
Asp Gln Gly Trp Gly Pro Ile Ser Tyr Ala Asn Gly Ser Gly Pro Asp
                20                  25                  30

CAG CGC CCC TAC TGC TGG CAC TAC CCC CCA AAA CCT TGC GGT ATT GTG         143
Gln Arg Pro Tyr Cys Trp His Tyr Pro Pro Lys Pro Cys Gly Ile Val
            35                  40                  45

CCC GCG AAG AGT GTG TGT GGT CCG GTA TAT TGC TTC ACT CCC AGC CCC         191
Pro Ala Lys Ser Val Cys Gly Pro Val Tyr Cys Phe Thr Pro Ser Pro
        50                  55                  60

GTG GTG GTG GGA ACG ACC GAC AGG TCG GGC GCG CCC ACC TAC AGC TGG         239
Val Val Val Gly Thr Thr Asp Arg Ser Gly Ala Pro Thr Tyr Ser Trp
    65                  70                  75

GGT GAA ATA GAT ACG GAC GTC TTC GTC CTT AAC AAT ACC AGG CCA CCG         287
Gly Glu Ile Asp Thr Asp Val Phe Val Leu Asn Asn Thr Arg Pro Pro
 80                  85                  90                  95

CTG GGC AAT TGG TTC GGT TGT ACC TGG ATG AAC TCA ACT GGA TTC ACC         335
Leu Gly Asn Trp Phe Gly Cys Thr Trp Met Asn Ser Thr Gly Phe Thr
                100                 105                 110

AAA GTG TGC GGA GCG CCT CCT TGT GTC ATC GGA GGG GCG GGC AAC AAC         383
Lys Val Cys Gly Ala Pro Pro Cys Val Ile Gly Gly Ala Gly Asn Asn
            115                 120                 125

ACC CTG CAC TGC CCC ACT GAT TGC TTC CGC AAG CAT CCG GAC GCC ACA         431
Thr Leu His Cys Pro Thr Asp Cys Phe Arg Lys His Pro Asp Ala Thr
        130                 135                 140

TAC TCT CGG TGC GGC TCC GGT CCC TGG ATC ACA CCC AGG TGC CTG GTC         479
Tyr Ser Arg Cys Gly Ser Gly Pro Trp Ile Thr Pro Arg Cys Leu Val
    145                 150                 155

GAC TAC CCG TAT AGG CTT TGG CAT TAT CCT TGT ACC ATC AAC TAC ACT         527
Asp Tyr Pro Tyr Arg Leu Trp His Tyr Pro Cys Thr Ile Asn Tyr Thr
160                 165                 170                 175

ATA TTT AAA ATC AGG ATG TAC GTG GGA GGG GTC GAG CAC AGG CTG GAA         575
Ile Phe Lys Ile Arg Met Tyr Val Gly Gly Val Glu His Arg Leu Glu
                180                 185                 190

GCT GCC TGC AAC TGG ACG CGG GGC GAA CGT TGC GAT CTG GAA GAT AGG         623
Ala Ala Cys Asn Trp Thr Arg Gly Glu Arg Cys Asp Leu Glu Asp Arg
```

```
GAC AGG TCC GAG CTC AGC CCG TTA CTG CTG ACC ACT ACA CAG TGG CAG       671
Asp Arg Ser Glu Leu Ser Pro Leu Leu Leu Thr Thr Thr Gln Trp Gln
        210                 215                 220

GTC CTC CCG TGT TCC TTC ACA ACC CTG CCA GCC TTG TCC ACC GGC CTC       719
Val Leu Pro Cys Ser Phe Thr Thr Leu Pro Ala Leu Ser Thr Gly Leu
        225                 230                 235

ATC CAC CTC CAC CAG AAC ATT GTG GAC GTG CAG TAC TTG TAC GGG GTG       767
Ile His Leu His Gln Asn Ile Val Asp Val Gln Tyr Leu Tyr Gly Val
240                 245                 250                 255

GGG TCA AGC ATC GCG TCC TGG GCC ATT AAG TGG GAG TAC GTC GTC CTC       815
Gly Ser Ser Ile Ala Ser Trp Ala Ile Lys Trp Glu Tyr Val Val Leu
                260                 265                 270

CTG TTC CTT CTG CTT GCA GAC GCG CGC GTC TGC TCC TGC TTG TGG ATG       863
Leu Phe Leu Leu Leu Ala Asp Ala Arg Val Cys Ser Cys Leu Trp Met
                275                 280                 285

ATG CTA CTC ATA TCC CAA GCG GAA GCG GCT TTG GAG AAC CTC GTA ATA       911
Met Leu Leu Ile Ser Gln Ala Glu Ala Ala Leu Glu Asn Leu Val Ile
            290                 295                 300

CTT AAT GCA GCA TCC CTG GCC GGG ACG CAC GGT CTT GTA TCC TTC CTC       959
Leu Asn Ala Ala Ser Leu Ala Gly Thr His Gly Leu Val Ser Phe Leu
        305                 310                 315

GTG TTC TTC TGC TTT GCA TGG TAT CTG AAG GGT AAG TGG GTG CCC GGA      1007
Val Phe Phe Cys Phe Ala Trp Tyr Leu Lys Gly Lys Trp Val Pro Gly
320                 325                 330                 335

GCG GTC TAC ACC TTC TAC GGG ATG TGG CCT CTC CTC CTG CTC CTG TTG      1055
Ala Val Tyr Thr Phe Tyr Gly Met Trp Pro Leu Leu Leu Leu Leu Leu
                340                 345                 350

GCG TTG CCC CAG CGG GCG TAC GCG CTG GAC ACG GAG GTG GCC GCG TCG      1103
Ala Leu Pro Gln Arg Ala Tyr Ala Leu Asp Thr Glu Val Ala Ala Ser
                355                 360                 365

TGT GGC GGT GTT GTT CTC GTC GGG TTG ATG GCG CTA ACT CTG TCA CCA      1151
Cys Gly Gly Val Val Leu Val Gly Leu Met Ala Leu Thr Leu Ser Pro
        370                 375                 380

TAT TAC AAG CGC TAT ATC AGC TGG TGC TTG TGG TGG CTT CAG TAT TTT      1199
Tyr Tyr Lys Arg Tyr Ile Ser Trp Cys Leu Trp Trp Leu Gln Tyr Phe
        385                 390                 395

CTG ACC AGA GTG GAA GCG CAA CTG CAC GTG TGG ATT CCC CCC CTC AAC      1247
Leu Thr Arg Val Glu Ala Gln Leu His Val Trp Ile Pro Pro Leu Asn
400                 405                 410                 415

GTC CGA GGG GGG CGC GAC GCT GTC ATC TTA CTC ATG TGT GCT GTA CAC      1295
Val Arg Gly Gly Arg Asp Ala Val Ile Leu Leu Met Cys Ala Val His
                420                 425                 430

CCG ACT CTG GTA TTT GAC ATC ACC AAA TTG CTG CTG GCC GTC TTC GGA      1343
Pro Thr Leu Val Phe Asp Ile Thr Lys Leu Leu Leu Ala Val Phe Gly
                435                 440                 445

CCC CTT TGG ATT CTT CAA GCC AG                                       1366
Pro Leu Trp Ile Leu Gln Ala
            450

(2) INFORMATION FOR SEQ ID NO:73:

(i) SEQUENCE CHARACTERISTICS:
        (A) LENGTH: 454 amino acids
        (B) TYPE: amino acid
        (D) TOPOLOGY: linear (ii) MOLECULE TYPE: protein (xi) SEQUENCE DESCRIPTION: SEQ ID NO:73:

Gly Cys Pro Glu Arg Leu Ala Ser Cys Arg Pro Leu Thr Asp Phe Asp
```

-continued

```
  1               5                   10                  15
Gln Gly Trp Gly Pro Ile Ser Tyr Ala Asn Gly Ser Gly Pro Asp Gln
                 20                  25                  30

Arg Pro Tyr Cys Trp His Tyr Pro Pro Lys Pro Cys Gly Ile Val Pro
             35                  40                  45

Ala Lys Ser Val Cys Gly Pro Val Tyr Cys Phe Thr Pro Ser Pro Val
         50                  55                  60

Val Val Gly Thr Thr Asp Arg Ser Gly Ala Pro Thr Tyr Ser Trp Gly
 65                  70                  75                  80

Glu Ile Asp Thr Asp Val Phe Val Leu Asn Asn Thr Arg Pro Pro Leu
                 85                  90                  95

Gly Asn Trp Phe Gly Cys Thr Trp Met Asn Ser Thr Gly Phe Thr Lys
                100                 105                 110

Val Cys Gly Ala Pro Pro Cys Val Ile Gly Gly Ala Gly Asn Asn Thr
            115                 120                 125

Leu His Cys Pro Thr Asp Cys Phe Arg Lys His Pro Asp Ala Thr Tyr
        130                 135                 140

Ser Arg Cys Gly Ser Gly Pro Trp Ile Thr Pro Arg Cys Leu Val Asp
145                 150                 155                 160

Tyr Pro Tyr Arg Leu Trp His Tyr Pro Cys Thr Ile Asn Tyr Thr Ile
                165                 170                 175

Phe Lys Ile Arg Met Tyr Val Gly Gly Val Glu His Arg Leu Glu Ala
                180                 185                 190

Ala Cys Asn Trp Thr Arg Gly Glu Arg Cys Asp Leu Glu Asp Arg Asp
            195                 200                 205

Arg Ser Glu Leu Ser Pro Leu Leu Leu Thr Thr Thr Gln Trp Gln Val
210                 215                 220

Leu Pro Cys Ser Phe Thr Thr Leu Pro Ala Leu Ser Thr Gly Leu Ile
225                 230                 235                 240

His Leu His Gln Asn Ile Val Asp Val Gln Tyr Leu Tyr Gly Val Gly
                245                 250                 255

Ser Ser Ile Ala Ser Trp Ala Ile Lys Trp Glu Tyr Val Val Leu Leu
            260                 265                 270

Phe Leu Leu Leu Ala Asp Ala Arg Val Cys Ser Cys Leu Trp Met Met
        275                 280                 285

Leu Leu Ile Ser Gln Ala Glu Ala Ala Leu Glu Asn Leu Val Ile Leu
    290                 295                 300

Asn Ala Ala Ser Leu Ala Gly Thr His Gly Leu Val Ser Phe Leu Val
305                 310                 315                 320

Phe Phe Cys Phe Ala Trp Tyr Leu Lys Gly Lys Trp Val Pro Gly Ala
                325                 330                 335

Val Tyr Thr Phe Tyr Gly Met Trp Pro Leu Leu Leu Leu Leu Leu Ala
            340                 345                 350

Leu Pro Gln Arg Ala Tyr Ala Leu Asp Thr Glu Val Ala Ala Ser Cys
        355                 360                 365

Gly Gly Val Val Leu Val Gly Leu Met Ala Leu Thr Leu Ser Pro Tyr
    370                 375                 380

Tyr Lys Arg Tyr Ile Ser Trp Cys Leu Trp Trp Leu Gln Tyr Phe Leu
385                 390                 395                 400

Thr Arg Val Glu Ala Gln Leu His Val Trp Ile Pro Pro Leu Asn Val
                405                 410                 415

Arg Gly Gly Arg Asp Ala Val Ile Leu Leu Met Cys Ala Val His Pro
            420                 425                 430
```

-continued

```
Thr Leu Val Phe Asp Ile Thr Lys Leu Leu Ala Val Phe Gly Pro
        435                 440                 445

Leu Trp Ile Leu Gln Ala
    450

(2) INFORMATION FOR SEQ ID NO:74:

(i) SEQUENCE CHARACTERISTICS:
        (A) LENGTH: 7310 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 3..7310

(xi) SEQUENCE DESCRIPTION: SEQ ID NO:74:

CA GGC TGT CCT GAG AGG CTA GCC AGC TGC CGA CCC CTT ACC GAT TTT        47
   Gly Cys Pro Glu Arg Leu Ala Ser Cys Arg Pro Leu Thr Asp Phe
   1               5                  10                  15

GAC CAG GGC TGG GGC CCT ATC AGT TAT GCC AAC GGA AGC GGC CCC GAC       95
Asp Gln Gly Trp Gly Pro Ile Ser Tyr Ala Asn Gly Ser Gly Pro Asp
            20                  25                  30

CAG CGC CCC TAC TGC TGG CAC TAC CCC CCA AAA CCT TGC GGT ATT GTG      143
Gln Arg Pro Tyr Cys Trp His Tyr Pro Pro Lys Pro Cys Gly Ile Val
        35                  40                  45

CCC GCG AAG AGT GTG TGT GGT CCG GTA TAT TGC TTC ACT CCC AGC CCC      191
Pro Ala Lys Ser Val Cys Gly Pro Val Tyr Cys Phe Thr Pro Ser Pro
    50                  55                  60

GTG GTG GTG GGA ACG ACC GAC AGG TCG GGC GCG CCC ACC TAC AGC TGG      239
Val Val Val Gly Thr Thr Asp Arg Ser Gly Ala Pro Thr Tyr Ser Trp
65                  70                  75

GGT GAA AAT GAT ACG GAC GTC TTC GTC CTT AAC AAT ACC AGG CCA CCG      287
Gly Glu Asn Asp Thr Asp Val Phe Val Leu Asn Asn Thr Arg Pro Pro
80                  85                  90                  95

CTG GGC AAT TGG TTC GGT TGT ACC TGG ATG AAC TCA ACT GGA TTC ACC      335
Leu Gly Asn Trp Phe Gly Cys Thr Trp Met Asn Ser Thr Gly Phe Thr
                100                 105                 110

AAA GTG TGC GGA GCG CCT CCT TGT GTC ATC GGA GGG GCG GGC AAC AAC      383
Lys Val Cys Gly Ala Pro Pro Cys Val Ile Gly Gly Ala Gly Asn Asn
            115                 120                 125

ACC CTG CAC TGC CCC ACT GAT TGC TTC CGC AAG CAT CCG GAC GCC ACA      431
Thr Leu His Cys Pro Thr Asp Cys Phe Arg Lys His Pro Asp Ala Thr
        130                 135                 140

TAC TCT CGG TGC GGC TCC GGT CCC TGG ATC ACA CCC AGG TGC CTG GTC      479
Tyr Ser Arg Cys Gly Ser Gly Pro Trp Ile Thr Pro Arg Cys Leu Val
    145                 150                 155

GAC TAC CCG TAT AGG CTT TGG CAT TAT CCT TGT ACC ATC AAC TAC ACC      527
Asp Tyr Pro Tyr Arg Leu Trp His Tyr Pro Cys Thr Ile Asn Tyr Thr
160                 165                 170                 175

ATA TTT AAA ATC AGG ATG TAC GTG GGA GGG GTC GAA CAC AGG CTG GAA      575
Ile Phe Lys Ile Arg Met Tyr Val Gly Gly Val Glu His Arg Leu Glu
                180                 185                 190

GCT GCC TGC AAC TGG ACG CGG GGC GAA CGT TGC GAT CTG GAA GAC AGG      623
Ala Ala Cys Asn Trp Thr Arg Gly Glu Arg Cys Asp Leu Glu Asp Arg
            195                 200                 205

GAC ACG TCC GAG CTC AGC CCG TTA CTG CTG ACC ACT ACA CAG TGG CAG      671
Asp Thr Ser Glu Leu Ser Pro Leu Leu Leu Thr Thr Thr Gln Trp Gln
        210                 215                 220
```

-continued

| | | |
|---|---|---|
| GTC CTC CCG TGT TCC TTC ACA ACC CTA CCA GCC TTG TCC ACC GGC CTC<br>Val Leu Pro Cys Ser Phe Thr Thr Leu Pro Ala Leu Ser Thr Gly Leu<br>225                        230                              235 | 719 |

```
GTC CTC CCG TGT TCC TTC ACA ACC CTA CCA GCC TTG TCC ACC GGC CTC         719
Val Leu Pro Cys Ser Phe Thr Thr Leu Pro Ala Leu Ser Thr Gly Leu
    225                 230                 235

ATC CAC CTC CAC CAG AAC ATT GTG GAC GTG CAG TAC TTG TAC GGG GTG         767
Ile His Leu His Gln Asn Ile Val Asp Val Gln Tyr Leu Tyr Gly Val
240                 245                 250                 255

GGG TCA AGC ATC GCG TCC TGG GCC ATT AAG TGG GAG TAC GTC GTT CTC         815
Gly Ser Ser Ile Ala Ser Trp Ala Ile Lys Trp Glu Tyr Val Val Leu
                260                 265                 270

CTG TTC CTT CTG CTT GCA GAC GCG CGC GTC TGC TCC TGC TTG TGG ATG         863
Leu Phe Leu Leu Leu Ala Asp Ala Arg Val Cys Ser Cys Leu Trp Met
            275                 280                 285

ATG CTA CTC ATA TCC CAA GCG GAG GCG GCT TTG GAG AAC CTC GTA ATA         911
Met Leu Leu Ile Ser Gln Ala Glu Ala Ala Leu Glu Asn Leu Val Ile
        290                 295                 300

CTT AAT GCA GCA TCC CTG GCC GGG ACG CAC GGT CTT GTA TCC TTC CTC         959
Leu Asn Ala Ala Ser Leu Ala Gly Thr His Gly Leu Val Ser Phe Leu
    305                 310                 315

GTG TTC TTC TGC TTT GCA TGG TAT TTG AAG GGT AAG TGG GTG CCC GGA        1007
Val Phe Phe Cys Phe Ala Trp Tyr Leu Lys Gly Lys Trp Val Pro Gly
320                 325                 330                 335

GCG GTC TAC ACC TTC TAC GGG ATG TGG CCT CTC CTC CTG CTC CTG TTG        1055
Ala Val Tyr Thr Phe Tyr Gly Met Trp Pro Leu Leu Leu Leu Leu Leu
                340                 345                 350

GCG TTG CCC CAG CGG GCG TAC GCG CTG GAC ACG GAG GTG GCC GCG TCG        1103
Ala Leu Pro Gln Arg Ala Tyr Ala Leu Asp Thr Glu Val Ala Ala Ser
            355                 360                 365

TGT GGC GGT GTT GTT CTC GTC GGG TTG ATG GCG CTG ACT CTG TCA CCA        1151
Cys Gly Gly Val Val Leu Val Gly Leu Met Ala Leu Thr Leu Ser Pro
        370                 375                 380

TAT TAC AAG CGC TAT ATC AGC TGG TGC TTG TGG TGG CTT CAG TAT TTT        1199
Tyr Tyr Lys Arg Tyr Ile Ser Trp Cys Leu Trp Trp Leu Gln Tyr Phe
    385                 390                 395

CTG ACC AGA GTG GAA GCG CAA CTG CAC GTG TGG ATT CCC CCC CTC AAC        1247
Leu Thr Arg Val Glu Ala Gln Leu His Val Trp Ile Pro Pro Leu Asn
400                 405                 410                 415

GTC CGA GGG GGG CGC GAC GCC GTC ATC TTA CTC ATG TGT GCT GTA CAC        1295
Val Arg Gly Gly Arg Asp Ala Val Ile Leu Leu Met Cys Ala Val His
                420                 425                 430

CCG ACT CTG GTA TTT GAC ATC ACC AAA TTG CTG CTG GCC GTC TTC GGA        1343
Pro Thr Leu Val Phe Asp Ile Thr Lys Leu Leu Leu Ala Val Phe Gly
            435                 440                 445

CCC CTT TGG ATT CTT CAA GCC AGT TTG CTT AAA GTA CCC TAC TTT GTG        1391
Pro Leu Trp Ile Leu Gln Ala Ser Leu Leu Lys Val Pro Tyr Phe Val
        450                 455                 460

CGC GTC CAA GGC CTT CTC CGG TTC TGC GCG TTA GCG CGG AAG ATG ATC        1439
Arg Val Gln Gly Leu Leu Arg Phe Cys Ala Leu Ala Arg Lys Met Ile
    465                 470                 475

GGA GGC CAT TAC GTG CAA ATG GTC ATC ATT AAG TTA GGG GCG CTT ACT        1487
Gly Gly His Tyr Val Gln Met Val Ile Ile Lys Leu Gly Ala Leu Thr
480                 485                 490                 495

GGC ACC TAT GTT TAT AAC CAT CTC ACT CCT CTT CGG GAC TGG GCG CAC        1535
Gly Thr Tyr Val Tyr Asn His Leu Thr Pro Leu Arg Asp Trp Ala His
                500                 505                 510

AAC GGC TTG CGA GAT CTG GCC GTG GCT GTA GAG CCA GTC GTC TTC TCC        1583
Asn Gly Leu Arg Asp Leu Ala Val Ala Val Glu Pro Val Val Phe Ser
            515                 520                 525

CAA ATG GAG ACC AAG CTC ATC ACG TGG GGG GCA GAT ACC GCC GCG TGC        1631
Gln Met Glu Thr Lys Leu Ile Thr Trp Gly Ala Asp Thr Ala Ala Cys
```

-continued

```
           530                       535                       540
GGT GAC ATC ATC AAC GGC TTG CCT GTT TCC GCC CGC AGG GGC CGG GAG    1679
Gly Asp Ile Ile Asn Gly Leu Pro Val Ser Ala Arg Arg Gly Arg Glu
545                     550                     555

ATA CTG CTC GGG CCA GCC GAT GGA ATG GTC TCC AAG GGG TGG AGG TTG    1727
Ile Leu Leu Gly Pro Ala Asp Gly Met Val Ser Lys Gly Trp Arg Leu
560                 565                     570                 575

CTG GCG CCC ATC ACG GCG TAC GCC CAG CAG ACA AGG GGC CTC CTA GGG    1775
Leu Ala Pro Ile Thr Ala Tyr Ala Gln Gln Thr Arg Gly Leu Leu Gly
                580                     585                 590

TGC ATA ATC ACC AGC CTA ACT GGC CGG GAC AAA AAC CAA GTG GAG GGT    1823
Cys Ile Ile Thr Ser Leu Thr Gly Arg Asp Lys Asn Gln Val Glu Gly
                    595                     600                 605

GAG GTC CAG ATT GTG TCA ACT GCT GCC CAA ACC TTC CTG GCA ACG TGC    1871
Glu Val Gln Ile Val Ser Thr Ala Ala Gln Thr Phe Leu Ala Thr Cys
            610                     615                     620

ATC AAT GGG GTG TGC TGG ACT GTC TAC CAC GGG GCC GGA ACG AGG ACC    1919
Ile Asn Gly Val Cys Trp Thr Val Tyr His Gly Ala Gly Thr Arg Thr
625                     630                     635

ATC GCG TCA CCC AAG GGT CCT GTC ATC CAG ATG TAT ACC AAT GTA GAC    1967
Ile Ala Ser Pro Lys Gly Pro Val Ile Gln Met Tyr Thr Asn Val Asp
640                 645                     650                 655

CAA GAC CTT GTG GGC TGG CCC GCT CCG CAA GGT AGC CGC TCA TTG ACA    2015
Gln Asp Leu Val Gly Trp Pro Ala Pro Gln Gly Ser Arg Ser Leu Thr
                660                     665                 670

CCC TGC ACT TGC GGC TCC TCG GAC CTT TAC CTG GTC ACG AGG CAC GCC    2063
Pro Cys Thr Cys Gly Ser Ser Asp Leu Tyr Leu Val Thr Arg His Ala
                    675                     680                 685

GAT GTC ATT CCC GTG CGC CGG CGG GGT GAT AGC AGG GGC AGC CTG CTG    2111
Asp Val Ile Pro Val Arg Arg Arg Gly Asp Ser Arg Gly Ser Leu Leu
            690                     695                     700

TCG CCC CGG CCC ATT TCC TAC TTG AAA GGC TCC TCG GGG GGT CCG CTG    2159
Ser Pro Arg Pro Ile Ser Tyr Leu Lys Gly Ser Ser Gly Gly Pro Leu
705                     710                     715

TTG TGC CCC GCG GGG CAC GCC GTG GGC ATA TTT AGG GCC GCG GTG TGC    2207
Leu Cys Pro Ala Gly His Ala Val Gly Ile Phe Arg Ala Ala Val Cys
720                 725                     730                 735

ACC CGT GGA GTG GCT AAG GCG GTG GAC TTT ATC CCT GTG GAG AAC CTA    2255
Thr Arg Gly Val Ala Lys Ala Val Asp Phe Ile Pro Val Glu Asn Leu
                740                     745                 750

GAG ACA ACC ATG AGG TCC CCG GTG TTC ACG GAT AAC TCC TCT CCA CCA    2303
Glu Thr Thr Met Arg Ser Pro Val Phe Thr Asp Asn Ser Ser Pro Pro
                    755                     760                 765

GTA GTG CCC CAG AGC TTC CAG GTG GCT CAC CTC CAT GCT CCC ACA GGC    2351
Val Val Pro Gln Ser Phe Gln Val Ala His Leu His Ala Pro Thr Gly
            770                     775                     780

AGC GGC AAA AGC ACC AAG GTC CCG GCT GCA TAT GCA GCT CAG GGC TAT    2399
Ser Gly Lys Ser Thr Lys Val Pro Ala Ala Tyr Ala Ala Gln Gly Tyr
785                     790                     795

AAG GTG CTA GTA CTC AAC CCC TCT GTT GCT GCA ACA CTG GGC TTT GGT    2447
Lys Val Leu Val Leu Asn Pro Ser Val Ala Ala Thr Leu Gly Phe Gly
800                 805                     810                 815

GCT TAC ATG TCC AAG GCT CAT GGG ATC GAT CCT AAC ATC AGG ACC GGG    2495
Ala Tyr Met Ser Lys Ala His Gly Ile Asp Pro Asn Ile Arg Thr Gly
                820                     825                 830

GTG AGA ACA ATT ACC ACT GGC AGC CCC ATC ACG TAC TCC ACC TAC GGC    2543
Val Arg Thr Ile Thr Thr Gly Ser Pro Ile Thr Tyr Ser Thr Tyr Gly
            835                     840                     845

AAG TTC CTT GCC GAC GGC GGG TGC TCG GGG GGC GCT TAT GAC ATA ATA    2591
```

-continued

```
Lys Phe Leu Ala Asp Gly Gly Cys Ser Gly Gly Ala Tyr Asp Ile Ile
            850                 855                 860

ATT TGT GAC GAG TGC CAC TCC ACG GAT GCC ACA TCC ATC TTG GGC ATC      2639
Ile Cys Asp Glu Cys His Ser Thr Asp Ala Thr Ser Ile Leu Gly Ile
865                 870                 875

GGC ACT GTC CTT GAC CAA GCA GAG ACT GCG GGG GCG AGA CTG GTT GTG      2687
Gly Thr Val Leu Asp Gln Ala Glu Thr Ala Gly Ala Arg Leu Val Val
880                 885                 890                 895

CTC GCC ACC GCC ACC CCT CCG GGC TCC GTC ACT GTG CCC CAT CCC AAC      2735
Leu Ala Thr Ala Thr Pro Pro Gly Ser Val Thr Val Pro His Pro Asn
                900                 905                 910

ATC GAG GAG GTT GCT CTG TCC ACC ACC GGA GAG ATC CCT TTT TAC GGC      2783
Ile Glu Glu Val Ala Leu Ser Thr Thr Gly Glu Ile Pro Phe Tyr Gly
            915                 920                 925

AAG GCT ATC CCC CTC GAA GTA ATC AAG GGG GGG AGA CAT CTC ATC TTC      2831
Lys Ala Ile Pro Leu Glu Val Ile Lys Gly Gly Arg His Leu Ile Phe
                930                 935                 940

TGT CAT TCA AAG AAG AAG TGC GAC GAA CTC GCC GCA AAG CTG GTC GCA      2879
Cys His Ser Lys Lys Lys Cys Asp Glu Leu Ala Ala Lys Leu Val Ala
945                 950                 955

TTG GGC ATC AAT GCC GTG GCC TAC TAC CGC GGT CTT GAC GTG TCC GTC      2927
Leu Gly Ile Asn Ala Val Ala Tyr Tyr Arg Gly Leu Asp Val Ser Val
960                 965                 970                 975

ATC CCG ACC AGC GGC GAT GTT GTC GTC GTG GCA ACC GAT GCC CTC ATG      2975
Ile Pro Thr Ser Gly Asp Val Val Val Val Ala Thr Asp Ala Leu Met
                980                 985                 990

ACC GGC TAT ACC GGC GAC TTC GAC TCG GTG ATA GAC TGC AAT ACG TGT      3023
Thr Gly Tyr Thr Gly Asp Phe Asp Ser Val Ile Asp Cys Asn Thr Cys
            995                 1000                1005

GTC ACC CAG ACA GTC GAT TTC AGC CTT GAC CCT ACC TTC ACC ATT GAG      3071
Val Thr Gln Thr Val Asp Phe Ser Leu Asp Pro Thr Phe Thr Ile Glu
                1010                1015                1020

ACA ATC ACG CTC CCC CAG GAT GCT GTC TCC CGC ACT CAA CGT CGG GGC      3119
Thr Ile Thr Leu Pro Gln Asp Ala Val Ser Arg Thr Gln Arg Arg Gly
1025                1030                1035

AGG ACT GGC AGG GGG AAG CCA GGC ATC TAC AGA TTT GTG GCA CCG GGG      3167
Arg Thr Gly Arg Gly Lys Pro Gly Ile Tyr Arg Phe Val Ala Pro Gly
1040                1045                1050                1055

GAG CGC CCC TCC GGC ATG TTC GAC TCG TCC GTC CTC TGT GAG TGC TAT      3215
Glu Arg Pro Ser Gly Met Phe Asp Ser Ser Val Leu Cys Glu Cys Tyr
                1060                1065                1070

GAC GCA GGC TGT GCT TGG TAT GAG CTC ACG CCC GCC GAG ACT ACA GTT      3263
Asp Ala Gly Cys Ala Trp Tyr Glu Leu Thr Pro Ala Glu Thr Thr Val
            1075                1080                1085

AGG CTA CGA GCG TAC ATG AAC ACC CCG GGG CTT CCC GTG TGC CAG GAC      3311
Arg Leu Arg Ala Tyr Met Asn Thr Pro Gly Leu Pro Val Cys Gln Asp
                1090                1095                1100

CAT CTT GAA TTT TGG GAG GGC GTC TTT ACA GGC CTC ACT CAT ATA GAT      3359
His Leu Glu Phe Trp Glu Gly Val Phe Thr Gly Leu Thr His Ile Asp
1105                1110                1115

GCC CAC TTT CTA TCC CAG ACA AAG CAG AGT GGG GAG AAC CTT CCT TAC      3407
Ala His Phe Leu Ser Gln Thr Lys Gln Ser Gly Glu Asn Leu Pro Tyr
1120                1125                1130                1135

CTG GTA GCG TAC CAA GCC ACC GTG TGC GCT AGG GCT CAA GCC CCT CCC      3455
Leu Val Ala Tyr Gln Ala Thr Val Cys Ala Arg Ala Gln Ala Pro Pro
                1140                1145                1150

CCA TCG TGG GAC CAG ATG TGG AAG TGT TTG ATT CGC CTC AAG CCC ACC      3503
Pro Ser Trp Asp Gln Met Trp Lys Cys Leu Ile Arg Leu Lys Pro Thr
            1155                1160                1165
```

```
CTC CAT GGG CCA ACA CCC CTG CTA TAC AGA CTG GGC GCT GTT CAG AAT         3551
Leu His Gly Pro Thr Pro Leu Leu Tyr Arg Leu Gly Ala Val Gln Asn
        1170            1175            1180

GAA ATC ACC CTG ACG CAC CCA GTC ACC AAA TAC ATC ATG ACA TGC ATG         3599
Glu Ile Thr Leu Thr His Pro Val Thr Lys Tyr Ile Met Thr Cys Met
        1185            1190            1195

TCG GCC GAC CTG GAG GTC GTC ACG AGC ACC TGG GTG CTC GTT GGC GGC         3647
Ser Ala Asp Leu Glu Val Val Thr Ser Thr Trp Val Leu Val Gly Gly
1200            1205            1210            1215

GTC CTG GCT GCT TTG GCC GCG TAT TGC CTG TCA ACA GGC TGC GTG GTC         3695
Val Leu Ala Ala Leu Ala Ala Tyr Cys Leu Ser Thr Gly Cys Val Val
                1220            1225            1230

ATA GTG GGC AGG GTC GTC TTG TCC GGG AAG CCG GCA ATC ATA CCT GAC         3743
Ile Val Gly Arg Val Val Leu Ser Gly Lys Pro Ala Ile Ile Pro Asp
        1235            1240            1245

AGG GAA GTC CTC TAC CGA GAG TTC GAT GAG ATG GAA GAG TGC TCT CAG         3791
Arg Glu Val Leu Tyr Arg Glu Phe Asp Glu Met Glu Glu Cys Ser Gln
        1250            1255            1260

CAC TTA CCG TAC ATC GAG CAA GGG ATG ATG CTC GCC GAG CAG TTC AAG         3839
His Leu Pro Tyr Ile Glu Gln Gly Met Met Leu Ala Glu Gln Phe Lys
        1265            1270            1275

CAG AAG GCC CTC GGC CTC CTG CAG ACC GCG TCC CGT CAG GCA GAG GTT         3887
Gln Lys Ala Leu Gly Leu Leu Gln Thr Ala Ser Arg Gln Ala Glu Val
1280            1285            1290            1295

ATC GCC CCT GCT GTC CAG ACC AAC TGG CAA AAA CTC GAG ACC TTC TGG         3935
Ile Ala Pro Ala Val Gln Thr Asn Trp Gln Lys Leu Glu Thr Phe Trp
                1300            1305            1310

GCG AAG CAT ATG TGG AAC TTC ATC AGT GGG ATA CAA TAC TTG GCG GGC         3983
Ala Lys His Met Trp Asn Phe Ile Ser Gly Ile Gln Tyr Leu Ala Gly
        1315            1320            1325

TTG TCA ACG CTG CCT GGT AAC CCC GCC ATT GCT TCA TTG ATG GCT TTT         4031
Leu Ser Thr Leu Pro Gly Asn Pro Ala Ile Ala Ser Leu Met Ala Phe
        1330            1335            1340

ACA GCT GCT GTC ACC AGC CCA CTA ACC ACT AGC CAA ACC CTC CTC TTC         4079
Thr Ala Ala Val Thr Ser Pro Leu Thr Thr Ser Gln Thr Leu Leu Phe
        1345            1350            1355

AAC ATA TTG GGG GGG TGG GTG GCT GCC CAG CTC GCC GCC CCC GGT GCC         4127
Asn Ile Leu Gly Gly Trp Val Ala Ala Gln Leu Ala Ala Pro Gly Ala
1360            1365            1370            1375

GCT ACT GCC TTT GTG GGC GCT GGC TTA GCT GGC GCC GCC ATC GGC AGT         4175
Ala Thr Ala Phe Val Gly Ala Gly Leu Ala Gly Ala Ala Ile Gly Ser
                1380            1385            1390

GTT GGA CTG GGG AAG GTC CTC ATA GAC ATC CTT GCA GGG TAT GGC GCG         4223
Val Gly Leu Gly Lys Val Leu Ile Asp Ile Leu Ala Gly Tyr Gly Ala
        1395            1400            1405

GGC GTG GCG GGA GCT CTT CTG GCA TTC AAG ATC ATG AGC GGT GAG GTC         4271
Gly Val Ala Gly Ala Leu Leu Ala Phe Lys Ile Met Ser Gly Glu Val
        1410            1415            1420

CCC TCC ACG GAG GAC CTG GTC AAT CTA CTG CCC GCC ATC CTC TCG CCC         4319
Pro Ser Thr Glu Asp Leu Val Asn Leu Leu Pro Ala Ile Leu Ser Pro
        1425            1430            1435

GGA GCC CTC GTA GTC GGC GTG GTC TGT GCA GCA ATA CTG CGC CGG CAC         4367
Gly Ala Leu Val Val Gly Val Val Cys Ala Ala Ile Leu Arg Arg His
1440            1445            1450            1455

GTT GGC CCG GGC GAG GGG GCA GTG CAG TGG ATG AAC CGG CTG ATA GCC         4415
Val Gly Pro Gly Glu Gly Ala Val Gln Trp Met Asn Arg Leu Ile Ala
                1460            1465            1470

TTC GCC TCC CGG GGG AAC CAT GTT TCC CCC ACG CAC TAC GTG CCG GAG         4463
Phe Ala Ser Arg Gly Asn His Val Ser Pro Thr His Tyr Val Pro Glu
        1475            1480            1485
```

```
AGC GAT GCA GCT GCC CGC GTC ACT GCC ATA CTC AGC AGC CTC ACT GTA         4511
Ser Asp Ala Ala Ala Arg Val Thr Ala Ile Leu Ser Ser Leu Thr Val
            1490                1495                1500

ACC CAG CTC CTG AGG CGA CTG CAC CAG TGG ATA AGC TCG GAG TGT ACC         4559
Thr Gln Leu Leu Arg Arg Leu His Gln Trp Ile Ser Ser Glu Cys Thr
        1505                1510                1515

ACT CCA TGC TCC GGT TCC TGG CTA AGG GAC ATC TGG GAC TGG ATA TGC         4607
Thr Pro Cys Ser Gly Ser Trp Leu Arg Asp Ile Trp Asp Trp Ile Cys
1520                1525                1530                1535

GAG GTG TTG AGC GAC TTT AAG ACC TGG CTA AAA GCT AAG CTC ATG CCA         4655
Glu Val Leu Ser Asp Phe Lys Thr Trp Leu Lys Ala Lys Leu Met Pro
                1540                1545                1550

CAG CTG CCT GGG ATC CCC TTT GTG TCC TGC CAG CGC GGG TAT AAG GGG         4703
Gln Leu Pro Gly Ile Pro Phe Val Ser Cys Gln Arg Gly Tyr Lys Gly
            1555                1560                1565

GTC TGG CGA GTG GAC GGC ATC ATG CAC ACT CGC TGC CAC TGT GGA GCT         4751
Val Trp Arg Val Asp Gly Ile Met His Thr Arg Cys His Cys Gly Ala
        1570                1575                1580

GAG ATC ACT GGA CAT GTC AAA AAC GGG ACG ATG AGG ATC GTC GGT CCT         4799
Glu Ile Thr Gly His Val Lys Asn Gly Thr Met Arg Ile Val Gly Pro
    1585                1590                1595

AGG ACC TGC AGG AAC ATG TGG AGT GGG ACC TTC CCC ATT AAT GCC TAC         4847
Arg Thr Cys Arg Asn Met Trp Ser Gly Thr Phe Pro Ile Asn Ala Tyr
1600                1605                1610                1615

ACC ACG GGC CCC TGT ACC CCC CTT CCT GCG CCG AAC TAC ACG TTC GCG         4895
Thr Thr Gly Pro Cys Thr Pro Leu Pro Ala Pro Asn Tyr Thr Phe Ala
                1620                1625                1630

CTA TGG AGG GTG TCT GCA GAG GAA TAT GTG GAG ATA AGG CAG GTG GGG         4943
Leu Trp Arg Val Ser Ala Glu Glu Tyr Val Glu Ile Arg Gln Val Gly
            1635                1640                1645

GAC TTC CAC TAC GTG ACG GGT ATG ACT ACT GAC AAT CTC AAA TGC CCG         4991
Asp Phe His Tyr Val Thr Gly Met Thr Thr Asp Asn Leu Lys Cys Pro
        1650                1655                1660

TGC CAG GTC CCA TCG CCC GAA TTT TTC ACA GAA TTG GAC GGG GTG CGC         5039
Cys Gln Val Pro Ser Pro Glu Phe Phe Thr Glu Leu Asp Gly Val Arg
    1665                1670                1675

CTA CAT AGG TTT GCG CCC CCC TGC AAG CCC TTG CTG CGG GAG GAG GTA         5087
Leu His Arg Phe Ala Pro Pro Cys Lys Pro Leu Leu Arg Glu Glu Val
1680                1685                1690                1695

TCA TTC AGA GTA GGA CTC CAC GAA TAC CCG GTA GGG TCG CAA TTA CCT         5135
Ser Phe Arg Val Gly Leu His Glu Tyr Pro Val Gly Ser Gln Leu Pro
                1700                1705                1710

TGC GAG CCC GAA CCG GAC GTG GCC GTG TTG ACG TCC ATG CTC ACT GAT         5183
Cys Glu Pro Glu Pro Asp Val Ala Val Leu Thr Ser Met Leu Thr Asp
            1715                1720                1725

CCC TCC CAT ATA ACA GCA GAG GCG GCC GGG CGA AGG TTG GCG AGG GGA         5231
Pro Ser His Ile Thr Ala Glu Ala Ala Gly Arg Arg Leu Ala Arg Gly
        1730                1735                1740

TCA CCC CCC TCT GTG GCC AGC TCC TCG GCT AGC CAG CTA TCC GCT CCA         5279
Ser Pro Pro Ser Val Ala Ser Ser Ser Ala Ser Gln Leu Ser Ala Pro
    1745                1750                1755

TCT CTC AAG GCA ACT TGC ACC GCT AAC CAT GAC TCC CCT GAT GCT GAG         5327
Ser Leu Lys Ala Thr Cys Thr Ala Asn His Asp Ser Pro Asp Ala Glu
1760                1765                1770                1775

CTC ATA GAG GCC AAC CTC CTA TGG AGG CAG GAG ATG GGC GGC AAC ATC         5375
Leu Ile Glu Ala Asn Leu Leu Trp Arg Gln Glu Met Gly Gly Asn Ile
                1780                1785                1790

ACC AGG GTT GAG TCA GAA AAC AAA GTG GTG ATT CTG GAC TCC TTC GAT         5423
Thr Arg Val Glu Ser Glu Asn Lys Val Val Ile Leu Asp Ser Phe Asp
```

```
                    1795                1800                1805
CCG CTT GTG GCG GAG GAG GAC GAG CGG GAG ATC TCC GTA CCC GCA GAA          5471
Pro Leu Val Ala Glu Glu Asp Glu Arg Glu Ile Ser Val Pro Ala Glu
        1810                1815                1820

ATC CTG CGG AAG TCT CGG AGA TTC GCC CAG GCC CTG CCC GTT TGG GCG          5519
Ile Leu Arg Lys Ser Arg Arg Phe Ala Gln Ala Leu Pro Val Trp Ala
    1825                1830                1835

CGG CCG GAC TAT AAC CCC CCG CTA GTG GAG ACG TGG AAA AAG CCC GAC          5567
Arg Pro Asp Tyr Asn Pro Pro Leu Val Glu Thr Trp Lys Lys Pro Asp
1840                1845                1850                1855

TAC GAA CCA CCT GTG GTC CAT GGC TGT CCG CTT CCA CCT CCA AAG TCC          5615
Tyr Glu Pro Pro Val Val His Gly Cys Pro Leu Pro Pro Pro Lys Ser
            1860                1865                1870

CCT CCT GTG CCT CCG CCT CGG AAG AAG CGG ACG GTG GTC CTC ACT GAA          5663
Pro Pro Val Pro Pro Pro Arg Lys Lys Arg Thr Val Val Leu Thr Glu
        1875                1880                1885

TCA ACC CTA TCT ACT GCC TTG GCC GAG CTC GCC ACC AGA AGC TTT GGC          5711
Ser Thr Leu Ser Thr Ala Leu Ala Glu Leu Ala Thr Arg Ser Phe Gly
        1890                1895                1900

AGC TCC TCA ACT TCC GGC ATT ACG GGC GAC AAT ACG ACA ACA TCC TCT          5759
Ser Ser Ser Thr Ser Gly Ile Thr Gly Asp Asn Thr Thr Thr Ser Ser
        1905                1910                1915

GAG CCC GCC CCT TCT GGC TGC CCC CCC GAC TCC GAC GCT GAG TCC TAT          5807
Glu Pro Ala Pro Ser Gly Cys Pro Pro Asp Ser Asp Ala Glu Ser Tyr
1920                1925                1930                1935

TCC TCC ATG CCC CCC CTG GAG GGG GAG CCT GGG GAT CCG GAT CTT AGC          5855
Ser Ser Met Pro Pro Leu Glu Gly Glu Pro Gly Asp Pro Asp Leu Ser
                1940                1945                1950

GAC GGG TCA TGG TCA ACG GTC AGT AGT GAG GCC AAC GCG GAG GAT GTC          5903
Asp Gly Ser Trp Ser Thr Val Ser Ser Glu Ala Asn Ala Glu Asp Val
            1955                1960                1965

GTG TGC TGC TCA ATG TCT TAC TCT TGG ACA GGC GCA CTC GTC ACC CCG          5951
Val Cys Cys Ser Met Ser Tyr Ser Trp Thr Gly Ala Leu Val Thr Pro
        1970                1975                1980

TGC GCC GCG GAA GAA CAG AAA CTG CCC ATC AAT GCA CTA AGC AAC TCG          5999
Cys Ala Ala Glu Glu Gln Lys Leu Pro Ile Asn Ala Leu Ser Asn Ser
        1985                1990                1995

TTG CTA CGT CAC CAC AAT TTG GTG TAT TCC ACC ACC TCA CGC AGT GCT          6047
Leu Leu Arg His His Asn Leu Val Tyr Ser Thr Thr Ser Arg Ser Ala
2000                2005                2010                2015

TGC CAA AGG CAG AAG AAA GTC ACA TTT GAC AGA CTG CAA GTT CTG GAC          6095
Cys Gln Arg Gln Lys Lys Val Thr Phe Asp Arg Leu Gln Val Leu Asp
                2020                2025                2030

AGC CAT TAC CAG GAC GTA CTC AAG GAG GTT AAA GCA GCG GCG TCA AAA          6143
Ser His Tyr Gln Asp Val Leu Lys Glu Val Lys Ala Ala Ala Ser Lys
            2035                2040                2045

GTG AAG GCT AAC TTG CTA TCC GTA GAG GAA GCT TGC AGC CTG ACG CCC          6191
Val Lys Ala Asn Leu Leu Ser Val Glu Glu Ala Cys Ser Leu Thr Pro
        2050                2055                2060

CCA CAC TCA GCC AAA TCC AAG TTT GGT TAT GGG GCA AAA GAC GTC CGT          6239
Pro His Ser Ala Lys Ser Lys Phe Gly Tyr Gly Ala Lys Asp Val Arg
        2065                2070                2075

TGC CAT GCC AGA AAG GCC GTA ACC CAC ATC AAC TCC GTG TGG AAA GAC          6287
Cys His Ala Arg Lys Ala Val Thr His Ile Asn Ser Val Trp Lys Asp
2080                2085                2090                2095

CTT CTG GAA GAC AAT GTA ACA CCA ATA GAC ACT ACC ATC ATG GCT AAG          6335
Leu Leu Glu Asp Asn Val Thr Pro Ile Asp Thr Thr Ile Met Ala Lys
                2100                2105                2110

AAC GAG GTT TTC TGC GTT CAG CCT GAG AAG GGG GGT CGT AAG CCA GCT          6383
```

```
Asn Glu Val Phe Cys Val Gln Pro Glu Lys Gly Gly Arg Lys Pro Ala
            2115                2120                2125

CGT CTC ATC GTG TTC CCC GAT CTG GGC GTG CGC GTG TGC GAA AAG ATG    6431
Arg Leu Ile Val Phe Pro Asp Leu Gly Val Arg Val Cys Glu Lys Met
        2130                2135                2140

GCT TTG TAC GAC GTG GTT ACA AAG CTC CCC TTG GCC GTG ATG GGA AGC    6479
Ala Leu Tyr Asp Val Val Thr Lys Leu Pro Leu Ala Val Met Gly Ser
    2145                2150                2155

TCC TAC GGA TTC CAA TAC TCA CCA GGA CAG CGG GTT GAA TTC CTC GTG    6527
Ser Tyr Gly Phe Gln Tyr Ser Pro Gly Gln Arg Val Glu Phe Leu Val
2160                2165                2170                2175

CAA GCG TGG AAG TCC AAG AAA ACC CCA ATG GGG TTC TCG TAT GAT ACC    6575
Gln Ala Trp Lys Ser Lys Lys Thr Pro Met Gly Phe Ser Tyr Asp Thr
            2180                2185                2190

CGC TGC TTT GAC TCC ACA GTC ACT GAG AGC GAC ATC CGT ACG GAG GAG    6623
Arg Cys Phe Asp Ser Thr Val Thr Glu Ser Asp Ile Arg Thr Glu Glu
        2195                2200                2205

GCA ATC TAC CAA TGT TGT GAC CTC GAC CCC CAA GCC CGC GTG GCC ATC    6671
Ala Ile Tyr Gln Cys Cys Asp Leu Asp Pro Gln Ala Arg Val Ala Ile
    2210                2215                2220

AAG TCC CTC ACC GAG AGG CTT TAT GTT GGG GGC CCT CTT ACC AAT TCA    6719
Lys Ser Leu Thr Glu Arg Leu Tyr Val Gly Gly Pro Leu Thr Asn Ser
2225                2230                2235

AGG GGG GAG AAC TGC GGC TAT CGC AGG TGC CGC GCG AGC GGC GTA CTG    6767
Arg Gly Glu Asn Cys Gly Tyr Arg Arg Cys Arg Ala Ser Gly Val Leu
2240                2245                2250                2255

ACA ACT AGC TGT GGT AAC ACC CTC ACT TGC TAC ATC AAG GCC CGG GCA    6815
Thr Thr Ser Cys Gly Asn Thr Leu Thr Cys Tyr Ile Lys Ala Arg Ala
            2260                2265                2270

GCC TGT CGA GCC GCA GGG CTC CAG GAC TGC ACC ATG CTC GTG TGT GGC    6863
Ala Cys Arg Ala Ala Gly Leu Gln Asp Cys Thr Met Leu Val Cys Gly
        2275                2280                2285

GAC GAC TTA GTC GTT ATC TGT GAA AGC GCG GGG GTC CAG GAG GAC GCG    6911
Asp Asp Leu Val Val Ile Cys Glu Ser Ala Gly Val Gln Glu Asp Ala
    2290                2295                2300

GCG AGC CTG AGA GCC TTC ACG GAG GCT ATG ACC AGG TAC TCC GCC CCC    6959
Ala Ser Leu Arg Ala Phe Thr Glu Ala Met Thr Arg Tyr Ser Ala Pro
2305                2310                2315

CCT GGG GAC CCC CCA CAA CCA GAA TAC GAC TTG GAG CTC ATA ACA TCA    7007
Pro Gly Asp Pro Pro Gln Pro Glu Tyr Asp Leu Glu Leu Ile Thr Ser
2320                2325                2330                2335

TGC TCC TCC AAC GTG TCA GTC GCC CAC GAC GGC GCT GGA AAG AGG GTC    7055
Cys Ser Ser Asn Val Ser Val Ala His Asp Gly Ala Gly Lys Arg Val
            2340                2345                2350

TAC TAC CTC ACC CGT GAC CCT ACA ACC CCC CTC GCG AGA GCT GCG TGG    7103
Tyr Tyr Leu Thr Arg Asp Pro Thr Thr Pro Leu Ala Arg Ala Ala Trp
        2355                2360                2365

GAG ACA GCA AGA CAC ACT CCA GTC AAT TCC TGG CTA GGC AAC ATA ATC    7151
Glu Thr Ala Arg His Thr Pro Val Asn Ser Trp Leu Gly Asn Ile Ile
    2370                2375                2380

ATG TTT GCC CCC ACA CTG TGG GCG AGG ATG ATA CTG ATG ACC CAT TTC    7199
Met Phe Ala Pro Thr Leu Trp Ala Arg Met Ile Leu Met Thr His Phe
2385                2390                2395

TTT AGC GTC CTT ATA GCC AGG GAC CAG CTT GAA CAG GCC CTC GAT TGC    7247
Phe Ser Val Leu Ile Ala Arg Asp Gln Leu Glu Gln Ala Leu Asp Cys
2400                2405                2410                2415

GAG ATC TAC GGG GCC TGC TAC TCC ATA GAA CCA CTT GAT CTA CCT CCA    7295
Glu Ile Tyr Gly Ala Cys Tyr Ser Ile Glu Pro Leu Asp Leu Pro Pro
            2420                2425                2430
```

```
ATC ATT CAA AGA CTC                                          7310
Ile Ile Gln Arg Leu
        2435
```

(2) INFORMATION FOR SEQ ID NO:75:

(i) SEQUENCE CHARACTERISTICS:
        (A) LENGTH: 2436 amino acids
        (B) TYPE: amino acid
        (D) TOPOLOGY: linear (ii) MOLECULE TYPE: protein (xi) SEQUENCE DESCRIPTION: SEQ ID NO:75:

```
Gly Cys Pro Glu Arg Leu Ala Ser Cys Arg Pro Leu Thr Asp Phe Asp
 1               5                  10                  15

Gln Gly Trp Gly Pro Ile Ser Tyr Ala Asn Gly Ser Gly Pro Asp Gln
                20                  25                  30

Arg Pro Tyr Cys Trp His Tyr Pro Pro Lys Pro Cys Gly Ile Val Pro
            35                  40                  45

Ala Lys Ser Val Cys Gly Pro Val Tyr Cys Phe Thr Pro Ser Pro Val
        50                  55                  60

Val Val Gly Thr Thr Asp Arg Ser Gly Ala Pro Thr Tyr Ser Trp Gly
 65                  70                  75                  80

Glu Asn Asp Thr Asp Val Phe Val Leu Asn Asn Thr Arg Pro Pro Leu
                85                  90                  95

Gly Asn Trp Phe Gly Cys Thr Trp Met Asn Ser Thr Gly Phe Thr Lys
               100                 105                 110

Val Cys Gly Ala Pro Pro Cys Val Ile Gly Gly Ala Gly Asn Asn Thr
            115                 120                 125

Leu His Cys Pro Thr Asp Cys Phe Arg Lys His Pro Asp Ala Thr Tyr
        130                 135                 140

Ser Arg Cys Gly Ser Gly Pro Trp Ile Thr Pro Arg Cys Leu Val Asp
145                 150                 155                 160

Tyr Pro Tyr Arg Leu Trp His Tyr Pro Cys Thr Ile Asn Tyr Thr Ile
                165                 170                 175

Phe Lys Ile Arg Met Tyr Val Gly Gly Val Glu His Arg Leu Glu Ala
            180                 185                 190

Ala Cys Asn Trp Thr Arg Gly Glu Arg Cys Asp Leu Glu Asp Arg Asp
        195                 200                 205

Thr Ser Glu Leu Ser Pro Leu Leu Thr Thr Thr Gln Trp Gln Val
    210                 215                 220

Leu Pro Cys Ser Phe Thr Thr Leu Pro Ala Leu Ser Thr Gly Leu Ile
225                 230                 235                 240

His Leu His Gln Asn Ile Val Asp Val Gln Tyr Leu Tyr Gly Val Gly
                245                 250                 255

Ser Ser Ile Ala Ser Trp Ala Ile Lys Trp Glu Tyr Val Val Leu Leu
            260                 265                 270

Phe Leu Leu Leu Ala Asp Ala Arg Val Cys Ser Cys Leu Trp Met Met
        275                 280                 285

Leu Leu Ile Ser Gln Ala Glu Ala Ala Leu Glu Asn Leu Val Ile Leu
        290                 295                 300

Asn Ala Ala Ser Leu Ala Gly Thr His Gly Leu Val Ser Phe Leu Val
305                 310                 315                 320

Phe Phe Cys Phe Ala Trp Tyr Leu Lys Gly Lys Trp Val Pro Gly Ala
                325                 330                 335
```

-continued

```
Val Tyr Thr Phe Tyr Gly Met Trp Pro Leu Leu Leu Leu Leu Ala
            340                 345                 350

Leu Pro Gln Arg Ala Tyr Ala Leu Asp Thr Glu Val Ala Ala Ser Cys
            355                 360                 365

Gly Gly Val Val Leu Val Gly Leu Met Ala Leu Thr Leu Ser Pro Tyr
            370                 375                 380

Tyr Lys Arg Tyr Ile Ser Trp Cys Leu Trp Trp Leu Gln Tyr Phe Leu
385                 390                 395                 400

Thr Arg Val Glu Ala Gln Leu His Val Trp Ile Pro Pro Leu Asn Val
            405                 410                 415

Arg Gly Gly Arg Asp Ala Val Ile Leu Leu Met Cys Ala Val His Pro
            420                 425                 430

Thr Leu Val Phe Asp Ile Thr Lys Leu Leu Leu Ala Val Phe Gly Pro
            435                 440                 445

Leu Trp Ile Leu Gln Ala Ser Leu Leu Lys Val Pro Tyr Phe Val Arg
        450                 455                 460

Val Gln Gly Leu Leu Arg Phe Cys Ala Leu Ala Arg Lys Met Ile Gly
465                 470                 475                 480

Gly His Tyr Val Gln Met Val Ile Ile Lys Leu Gly Ala Leu Thr Gly
                485                 490                 495

Thr Tyr Val Tyr Asn His Leu Thr Pro Leu Arg Asp Trp Ala His Asn
            500                 505                 510

Gly Leu Arg Asp Leu Ala Val Ala Val Glu Pro Val Val Phe Ser Gln
            515                 520                 525

Met Glu Thr Lys Leu Ile Thr Trp Gly Ala Asp Thr Ala Ala Cys Gly
            530                 535                 540

Asp Ile Ile Asn Gly Leu Pro Val Ser Ala Arg Arg Gly Arg Glu Ile
545                 550                 555                 560

Leu Leu Gly Pro Ala Asp Gly Met Val Ser Lys Gly Trp Arg Leu Leu
                565                 570                 575

Ala Pro Ile Thr Ala Tyr Ala Gln Gln Thr Arg Gly Leu Leu Gly Cys
            580                 585                 590

Ile Ile Thr Ser Leu Thr Gly Arg Asp Lys Asn Gln Val Glu Gly Glu
            595                 600                 605

Val Gln Ile Val Ser Thr Ala Ala Gln Thr Phe Leu Ala Thr Cys Ile
    610                 615                 620

Asn Gly Val Cys Trp Thr Val Tyr His Gly Ala Gly Thr Arg Thr Ile
625                 630                 635                 640

Ala Ser Pro Lys Gly Pro Val Ile Gln Met Tyr Thr Asn Val Asp Gln
            645                 650                 655

Asp Leu Val Gly Trp Pro Ala Pro Gln Gly Ser Arg Ser Leu Thr Pro
            660                 665                 670

Cys Thr Cys Gly Ser Ser Asp Leu Tyr Leu Val Thr Arg His Ala Asp
            675                 680                 685

Val Ile Pro Val Arg Arg Arg Gly Asp Ser Arg Gly Ser Leu Leu Ser
            690                 695                 700

Pro Arg Pro Ile Ser Tyr Leu Lys Gly Ser Ser Gly Gly Pro Leu Leu
705                 710                 715                 720

Cys Pro Ala Gly His Ala Val Gly Ile Phe Arg Ala Ala Val Cys Thr
                725                 730                 735

Arg Gly Val Ala Lys Ala Val Asp Phe Ile Pro Val Glu Asn Leu Glu
            740                 745                 750

Thr Thr Met Arg Ser Pro Val Phe Thr Asp Asn Ser Ser Pro Pro Val
```

-continued

```
              755                 760                 765
Val Pro Gln Ser Phe Gln Val Ala His Leu His Ala Pro Thr Gly Ser
    770                 775                 780

Gly Lys Ser Thr Lys Val Pro Ala Ala Tyr Ala Ala Gln Gly Tyr Lys
785                 790                 795                 800

Val Leu Val Leu Asn Pro Ser Val Ala Ala Thr Leu Gly Phe Gly Ala
                805                 810                 815

Tyr Met Ser Lys Ala His Gly Ile Asp Pro Asn Ile Arg Thr Gly Val
                820                 825                 830

Arg Thr Ile Thr Thr Gly Ser Pro Ile Thr Tyr Ser Thr Tyr Gly Lys
                835                 840                 845

Phe Leu Ala Asp Gly Gly Cys Ser Gly Gly Ala Tyr Asp Ile Ile Ile
    850                 855                 860

Cys Asp Glu Cys His Ser Thr Asp Ala Thr Ser Ile Leu Gly Ile Gly
865                 870                 875                 880

Thr Val Leu Asp Gln Ala Glu Thr Ala Gly Ala Arg Leu Val Val Leu
                885                 890                 895

Ala Thr Ala Thr Pro Pro Gly Ser Val Thr Val Pro His Pro Asn Ile
                900                 905                 910

Glu Glu Val Ala Leu Ser Thr Thr Gly Glu Ile Pro Phe Tyr Gly Lys
                915                 920                 925

Ala Ile Pro Leu Glu Val Ile Lys Gly Gly Arg His Leu Ile Phe Cys
    930                 935                 940

His Ser Lys Lys Lys Cys Asp Glu Leu Ala Ala Lys Leu Val Ala Leu
945                 950                 955                 960

Gly Ile Asn Ala Val Ala Tyr Tyr Arg Gly Leu Asp Val Ser Val Ile
                965                 970                 975

Pro Thr Ser Gly Asp Val Val Val Ala Thr Asp Ala Leu Met Thr
                980                 985                 990

Gly Tyr Thr Gly Asp Phe Asp Ser Val Ile Asp Cys Asn Thr Cys Val
                995                 1000                1005

Thr Gln Thr Val Asp Phe Ser Leu Asp Pro Thr Phe Thr Ile Glu Thr
    1010                1015                1020

Ile Thr Leu Pro Gln Asp Ala Val Ser Arg Thr Gln Arg Arg Gly Arg
1025                1030                1035                1040

Thr Gly Arg Gly Lys Pro Gly Ile Tyr Arg Phe Val Ala Pro Gly Glu
                1045                1050                1055

Arg Pro Ser Gly Met Phe Asp Ser Ser Val Leu Cys Glu Cys Tyr Asp
                1060                1065                1070

Ala Gly Cys Ala Trp Tyr Glu Leu Thr Pro Ala Glu Thr Thr Val Arg
                1075                1080                1085

Leu Arg Ala Tyr Met Asn Thr Pro Gly Leu Pro Val Cys Gln Asp His
    1090                1095                1100

Leu Glu Phe Trp Glu Gly Val Phe Thr Gly Leu Thr His Ile Asp Ala
1105                1110                1115                1120

His Phe Leu Ser Gln Thr Lys Gln Ser Gly Glu Asn Leu Pro Tyr Leu
                1125                1130                1135

Val Ala Tyr Gln Ala Thr Val Cys Ala Arg Ala Gln Ala Pro Pro Pro
                1140                1145                1150

Ser Trp Asp Gln Met Trp Lys Cys Leu Ile Arg Leu Lys Pro Thr Leu
                1155                1160                1165

His Gly Pro Thr Pro Leu Leu Tyr Arg Leu Gly Ala Val Gln Asn Glu
    1170                1175                1180
```

-continued

```
Ile Thr Leu Thr His Pro Val Thr Lys Tyr Ile Met Thr Cys Met Ser
1185                1190                1195                1200

Ala Asp Leu Glu Val Val Thr Ser Thr Trp Val Leu Val Gly Gly Val
            1205                1210                1215

Leu Ala Ala Leu Ala Ala Tyr Cys Leu Ser Thr Gly Cys Val Val Ile
        1220                1225                1230

Val Gly Arg Val Val Leu Ser Gly Lys Pro Ala Ile Ile Pro Asp Arg
            1235                1240                1245

Glu Val Leu Tyr Arg Glu Phe Asp Glu Met Glu Glu Cys Ser Gln His
        1250                1255                1260

Leu Pro Tyr Ile Glu Gln Gly Met Met Leu Ala Glu Gln Phe Lys Gln
1265                1270                1275                1280

Lys Ala Leu Gly Leu Leu Gln Thr Ala Ser Arg Gln Ala Glu Val Ile
            1285                1290                1295

Ala Pro Ala Val Gln Thr Asn Trp Gln Lys Leu Glu Thr Phe Trp Ala
        1300                1305                1310

Lys His Met Trp Asn Phe Ile Ser Gly Ile Gln Tyr Leu Ala Gly Leu
            1315                1320                1325

Ser Thr Leu Pro Gly Asn Pro Ala Ile Ala Ser Leu Met Ala Phe Thr
        1330                1335                1340

Ala Ala Val Thr Ser Pro Leu Thr Thr Ser Gln Thr Leu Leu Phe Asn
1345                1350                1355                1360

Ile Leu Gly Gly Trp Val Ala Ala Gln Leu Ala Ala Pro Gly Ala Ala
            1365                1370                1375

Thr Ala Phe Val Gly Ala Gly Leu Ala Gly Ala Ala Ile Gly Ser Val
            1380                1385                1390

Gly Leu Gly Lys Val Leu Ile Asp Ile Leu Ala Gly Tyr Gly Ala Gly
        1395                1400                1405

Val Ala Gly Ala Leu Leu Ala Phe Lys Ile Met Ser Gly Glu Val Pro
            1410                1415                1420

Ser Thr Glu Asp Leu Val Asn Leu Leu Pro Ala Ile Leu Ser Pro Gly
1425                1430                1435                1440

Ala Leu Val Val Gly Val Val Cys Ala Ala Ile Leu Arg Arg His Val
            1445                1450                1455

Gly Pro Gly Glu Gly Ala Val Gln Trp Met Asn Arg Leu Ile Ala Phe
        1460                1465                1470

Ala Ser Arg Gly Asn His Val Ser Pro Thr His Tyr Val Pro Glu Ser
        1475                1480                1485

Asp Ala Ala Ala Arg Val Thr Ala Ile Leu Ser Ser Leu Thr Val Thr
        1490                1495                1500

Gln Leu Leu Arg Arg Leu His Gln Trp Ile Ser Ser Glu Cys Thr Thr
1505                1510                1515                1520

Pro Cys Ser Gly Ser Trp Leu Arg Asp Ile Trp Asp Trp Ile Cys Glu
            1525                1530                1535

Val Leu Ser Asp Phe Lys Thr Trp Leu Lys Ala Lys Leu Met Pro Gln
            1540                1545                1550

Leu Pro Gly Ile Pro Phe Val Ser Cys Gln Arg Gly Tyr Lys Gly Val
        1555                1560                1565

Trp Arg Val Asp Gly Ile Met His Thr Arg Cys His Cys Gly Ala Glu
        1570                1575                1580

Ile Thr Gly His Val Lys Asn Gly Thr Met Arg Ile Val Gly Pro Arg
1585                1590                1595                1600
```

-continued

```
Thr Cys Arg Asn Met Trp Ser Gly Thr Phe Pro Ile Asn Ala Tyr Thr
                1605                1610                1615
Thr Gly Pro Cys Thr Pro Leu Pro Ala Pro Asn Tyr Thr Phe Ala Leu
            1620                1625                1630
Trp Arg Val Ser Ala Glu Glu Tyr Val Glu Ile Arg Gln Val Gly Asp
        1635                1640                1645
Phe His Tyr Val Thr Gly Met Thr Thr Asp Asn Leu Lys Cys Pro Cys
    1650                1655                1660
Gln Val Pro Ser Pro Glu Phe Phe Thr Glu Leu Asp Gly Val Arg Leu
1665                1670                1675                1680
His Arg Phe Ala Pro Pro Cys Lys Pro Leu Leu Arg Glu Glu Val Ser
                1685                1690                1695
Phe Arg Val Gly Leu His Glu Tyr Pro Val Gly Ser Gln Leu Pro Cys
            1700                1705                1710
Glu Pro Glu Pro Asp Val Ala Val Leu Thr Ser Met Leu Thr Asp Pro
        1715                1720                1725
Ser His Ile Thr Ala Glu Ala Ala Gly Arg Arg Leu Ala Arg Gly Ser
    1730                1735                1740
Pro Pro Ser Val Ala Ser Ser Ala Ser Gln Leu Ser Ala Pro Ser
1745                1750                1755                1760
Leu Lys Ala Thr Cys Thr Ala Asn His Asp Ser Pro Asp Ala Glu Leu
                1765                1770                1775
Ile Glu Ala Asn Leu Leu Trp Arg Gln Glu Met Gly Gly Asn Ile Thr
            1780                1785                1790
Arg Val Glu Ser Glu Asn Lys Val Val Ile Leu Asp Ser Phe Asp Pro
        1795                1800                1805
Leu Val Ala Glu Glu Asp Glu Arg Glu Ile Ser Val Pro Ala Glu Ile
    1810                1815                1820
Leu Arg Lys Ser Arg Arg Phe Ala Gln Ala Leu Pro Val Trp Ala Arg
1825                1830                1835                1840
Pro Asp Tyr Asn Pro Pro Leu Val Glu Thr Trp Lys Lys Pro Asp Tyr
                1845                1850                1855
Glu Pro Pro Val Val His Gly Cys Pro Leu Pro Pro Lys Ser Pro
            1860                1865                1870
Pro Val Pro Pro Pro Arg Lys Lys Arg Thr Val Val Leu Thr Glu Ser
        1875                1880                1885
Thr Leu Ser Thr Ala Leu Ala Glu Leu Ala Thr Arg Ser Phe Gly Ser
    1890                1895                1900
Ser Ser Thr Ser Gly Ile Thr Gly Asp Asn Thr Thr Thr Ser Ser Glu
1905                1910                1915                1920
Pro Ala Pro Ser Gly Cys Pro Pro Asp Ser Asp Ala Glu Ser Tyr Ser
                1925                1930                1935
Ser Met Pro Pro Leu Glu Gly Glu Pro Gly Asp Pro Asp Leu Ser Asp
            1940                1945                1950
Gly Ser Trp Ser Thr Val Ser Ser Glu Ala Asn Ala Glu Asp Val Val
        1955                1960                1965
Cys Cys Ser Met Ser Tyr Ser Trp Thr Gly Ala Leu Val Thr Pro Cys
    1970                1975                1980
Ala Ala Glu Glu Gln Lys Leu Pro Ile Asn Ala Leu Ser Asn Ser Leu
1985                1990                1995                2000
Leu Arg His His Asn Leu Val Tyr Ser Thr Thr Ser Arg Ser Ala Cys
                2005                2010                2015
Gln Arg Gln Lys Lys Val Thr Phe Asp Arg Leu Gln Val Leu Asp Ser
```

-continued

```
                 2020                2025                2030
His Tyr Gln Asp Val Leu Lys Glu Val Lys Ala Ala Ala Ser Lys Val
                 2035                2040            2045
Lys Ala Asn Leu Leu Ser Val Glu Glu Ala Cys Ser Leu Thr Pro Pro
2050                 2055                2060
His Ser Ala Lys Ser Lys Phe Gly Tyr Gly Ala Lys Asp Val Arg Cys
2065                 2070                2075                2080
His Ala Arg Lys Ala Val Thr His Ile Asn Ser Val Trp Lys Asp Leu
                 2085                2090            2095
Leu Glu Asp Asn Val Thr Pro Ile Asp Thr Thr Ile Met Ala Lys Asn
                 2100                2105            2110
Glu Val Phe Cys Val Gln Pro Glu Lys Gly Gly Arg Lys Pro Ala Arg
                 2115                2120            2125
Leu Ile Val Phe Pro Asp Leu Gly Val Arg Val Cys Glu Lys Met Ala
                 2130                2135            2140
Leu Tyr Asp Val Val Thr Lys Leu Pro Leu Ala Val Met Gly Ser Ser
2145                 2150                2155                2160
Tyr Gly Phe Gln Tyr Ser Pro Gly Gln Arg Val Glu Phe Leu Val Gln
                 2165                2170            2175
Ala Trp Lys Ser Lys Lys Thr Pro Met Gly Phe Ser Tyr Asp Thr Arg
                 2180                2185            2190
Cys Phe Asp Ser Thr Val Thr Glu Ser Asp Ile Arg Thr Glu Glu Ala
                 2195                2200            2205
Ile Tyr Gln Cys Cys Asp Leu Asp Pro Gln Ala Arg Val Ala Ile Lys
                 2210                2215            2220
Ser Leu Thr Glu Arg Leu Tyr Val Gly Gly Pro Leu Thr Asn Ser Arg
2225                 2230                2235                2240
Gly Glu Asn Cys Gly Tyr Arg Arg Cys Arg Ala Ser Gly Val Leu Thr
                 2245                2250            2255
Thr Ser Cys Gly Asn Thr Leu Thr Cys Tyr Ile Lys Ala Arg Ala Ala
                 2260                2265            2270
Cys Arg Ala Ala Gly Leu Gln Asp Cys Thr Met Leu Val Cys Gly Asp
                 2275                2280            2285
Asp Leu Val Val Ile Cys Glu Ser Ala Gly Val Gln Glu Asp Ala Ala
                 2290                2295            2300
Ser Leu Arg Ala Phe Thr Glu Ala Met Thr Arg Tyr Ser Ala Pro Pro
2305                 2310                2315                2320
Gly Asp Pro Pro Gln Pro Glu Tyr Asp Leu Glu Leu Ile Thr Ser Cys
                 2325                2330            2335
Ser Ser Asn Val Ser Val Ala His Asp Gly Ala Gly Lys Arg Val Tyr
                 2340                2345            2350
Tyr Leu Thr Arg Asp Pro Thr Thr Pro Leu Ala Arg Ala Ala Trp Glu
                 2355                2360            2365
Thr Ala Arg His Thr Pro Val Asn Ser Trp Leu Gly Asn Ile Ile Met
                 2370                2375            2380
Phe Ala Pro Thr Leu Trp Ala Arg Met Ile Leu Met Thr His Phe Phe
2385                 2390                2395                2400
Ser Val Leu Ile Ala Arg Asp Gln Leu Glu Gln Ala Leu Asp Cys Glu
                 2405                2410            2415
Ile Tyr Gly Ala Cys Tyr Ser Ile Glu Pro Leu Asp Leu Pro Pro Ile
                 2420                2425            2430
Ile Gln Arg Leu
                 2435
```

(2) INFORMATION FOR SEQ ID NO:76:

(i) SEQUENCE CHARACTERISTICS:
        (A) LENGTH: 540 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (B) CLONE: 13i (ix) FEATURE:
        (A) NAME/KEY: CDS
        (B) LOCATION: 3..539

(xi) SEQUENCE DESCRIPTION: SEQ ID NO:76:

```
CT CCC AGC CCC GTG GTG GTG GGA ACG ACC GAC AGG TCG GGC GCG CCC        47
   Pro Ser Pro Val Val Val Gly Thr Thr Asp Arg Ser Gly Ala Pro
    1               5                  10                  15

ACC TAC AGC TGG GGT GAA AAT GAT ACG GAC GTC TTC GTC CTT AAC AAT       95
Thr Tyr Ser Trp Gly Glu Asn Asp Thr Asp Val Phe Val Leu Asn Asn
                20                  25                  30

ACC AGG CCA CCG CTG GGC AAT TGG TTC GGT TGT ACC TGG ATG AAC TCA      143
Thr Arg Pro Pro Leu Gly Asn Trp Phe Gly Cys Thr Trp Met Asn Ser
            35                  40                  45

ACT GGA TTC ACC AAA GTG TGC GGA GCG CCT CCT TGT GTC ATC GGA GGG      191
Thr Gly Phe Thr Lys Val Cys Gly Ala Pro Pro Cys Val Ile Gly Gly
        50                  55                  60

GCG GGC AAC AAC ACC CTG CAC TGC CCC ACT GAT TGC TTC CGC AAG CAT      239
Ala Gly Asn Asn Thr Leu His Cys Pro Thr Asp Cys Phe Arg Lys His
     65                  70                  75

CCG GAC GCC ACA TAC TCT CGG TGC GGC TCC GGT CCC TGG ATC ACA CCC      287
Pro Asp Ala Thr Tyr Ser Arg Cys Gly Ser Gly Pro Trp Ile Thr Pro
 80                  85                  90                  95

AGG TGC CTG GTC GAC TAC CCG TAT AGG CTT TGG CAT TAT CCT TGT ACC      335
Arg Cys Leu Val Asp Tyr Pro Tyr Arg Leu Trp His Tyr Pro Cys Thr
                100                 105                 110

ATC AAC TAC ACC ATA TTT AAA ATC AGG ATG TAC GTG GGA GGG GTC GAA      383
Ile Asn Tyr Thr Ile Phe Lys Ile Arg Met Tyr Val Gly Gly Val Glu
            115                 120                 125

CAC AGG CTG GAA GCT GCC TGC AAC TGG ACG CGG GGC GAA CGT TGC GAT      431
His Arg Leu Glu Ala Ala Cys Asn Trp Thr Arg Gly Glu Arg Cys Asp
        130                 135                 140

CTG GAA GAC AGG GAC AGG TCC GAG CTC ACC CCG TTA CTG CTG ACC ACT      479
Leu Glu Asp Arg Asp Arg Ser Glu Leu Thr Pro Leu Leu Leu Thr Thr
    145                 150                 155

ACA CAG TGG CAG GTC CTC CCG TGT TCC TTC ACA ACC CTA CCA GCC TTG      527
Thr Gln Trp Gln Val Leu Pro Cys Ser Phe Thr Thr Leu Pro Ala Leu
160                 165                 170                 175

TCC ACC GGC CTC A                                                    540
Ser Thr Gly Leu
```

(2) INFORMATION FOR SEQ ID NO:77:

(i) SEQUENCE CHARACTERISTICS:
        (A) LENGTH: 179 amino acids
        (B) TYPE: amino acid
        (D) TOPOLOGY: linear (ii) MOLECULE TYPE: protein (xi) SEQUENCE DESCRIPTION: SEQ ID NO:77:

```
Pro Ser Pro Val Val Gly Thr Thr Asp Arg Ser Gly Ala Pro Thr
 1               5                  10                 15

Tyr Ser Trp Gly Glu Asn Asp Thr Asp Val Phe Val Leu Asn Asn Thr
             20                  25                  30

Arg Pro Pro Leu Gly Asn Trp Phe Gly Cys Thr Trp Met Asn Ser Thr
         35                  40                  45

Gly Phe Thr Lys Val Cys Gly Ala Pro Cys Val Ile Gly Gly Ala
     50                  55                  60

Gly Asn Asn Thr Leu His Cys Pro Thr Asp Cys Phe Arg Lys His Pro
 65                  70                  75                  80

Asp Ala Thr Tyr Ser Arg Cys Gly Ser Gly Pro Trp Ile Thr Pro Arg
                 85                  90                  95

Cys Leu Val Asp Tyr Pro Tyr Arg Leu Trp His Tyr Pro Cys Thr Ile
                100                 105                 110

Asn Tyr Thr Ile Phe Lys Ile Arg Met Tyr Val Gly Gly Val Glu His
            115                 120                 125

Arg Leu Glu Ala Ala Cys Asn Trp Thr Arg Gly Glu Arg Cys Asp Leu
        130                 135                 140

Glu Asp Arg Asp Arg Ser Glu Leu Thr Pro Leu Leu Leu Thr Thr Thr
145                 150                 155                 160

Gln Trp Gln Val Leu Pro Cys Ser Phe Thr Thr Leu Pro Ala Leu Ser
                165                 170                 175

Thr Gly Leu (2) INFORMATION FOR SEQ ID NO:78:

(i) SEQUENCE CHARACTERISTICS:
        (A) LENGTH: 231 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
         (B) CLONE: 26j (ix) FEATURE:
         (A) NAME/KEY: CDS
         (B) LOCATION: 2..229

(xi) SEQUENCE DESCRIPTION: SEQ ID NO:78:

G CTT TTC TAT CAC CAC AAG TTC AAC TCT TCA GGC TGT CCT GAG AGG        46
  Leu Phe Tyr His His Lys Phe Asn Ser Ser Gly Cys Pro Glu Arg
   1               5                  10                 15

CTA GCC AGC TGC CGA CCC CTT ACC GAT TTT GAC CAG GGC TGG GGC CCT      94
Leu Ala Ser Cys Arg Pro Leu Thr Asp Phe Asp Gln Gly Trp Gly Pro
             20                  25                  30

ATC AGT TAT GCC AAC GGA AGC GGC CCC GAC CAG CGC CCC TAC TGC TGG     142
Ile Ser Tyr Ala Asn Gly Ser Gly Pro Asp Gln Arg Pro Tyr Cys Trp
         35                  40                  45

CAC TAC CCC CCA AAA CCT TGC GGT ATT GTG CCC GCG AAG AGT GTG TGT     190
His Tyr Pro Pro Lys Pro Cys Gly Ile Val Pro Ala Lys Ser Val Cys
     50                  55                  60

GGT CCG GTA TAT TGC TTC ACT CCC AGC CCC GTG GTG GTG GG             231
Gly Pro Val Tyr Cys Phe Thr Pro Ser Pro Val Val Val
 65                  70                  75

(2) INFORMATION FOR SEQ ID NO:79:
```

(i) SEQUENCE CHARACTERISTICS:
     (A) LENGTH: 76 amino acids
     (B) TYPE: amino acid
     (D) TOPOLOGY: linear (ii) MOLECULE TYPE: protein (xi) SEQUENCE DESCRIPTION: SEQ ID NO:79:

```
Leu Phe Tyr His His Lys Phe Asn Ser Ser Gly Cys Pro Glu Arg Leu
 1               5                  10                  15

Ala Ser Cys Arg Pro Leu Thr Asp Phe Asp Gln Gly Trp Gly Pro Ile
            20                  25                  30

Ser Tyr Ala Asn Gly Ser Gly Pro Asp Gln Arg Pro Tyr Cys Trp His
         35                  40                  45

Tyr Pro Pro Lys Pro Cys Gly Ile Val Pro Ala Lys Ser Val Cys Gly
     50                  55                  60

Pro Val Tyr Cys Phe Thr Pro Ser Pro Val Val Val
 65                  70                  75
```

(2) INFORMATION FOR SEQ ID NO:80:

(i) SEQUENCE CHARACTERISTICS:
       (A) LENGTH: 391 base pairs
       (B) TYPE: nucleic acid
       (C) STRANDEDNESS: single
       (D) TOPOLOGY: linear (ii) MOLECULE TYPE: cDNA (vii) IMMEDIATE SOURCE:
        (B) CLONE: CA59a (ix) FEATURE:
       (A) NAME/KEY: CDS
       (B) LOCATION: 1..390

(xi) SEQUENCE DESCRIPTION: SEQ ID NO:80:

```
TTG GTA ATG GCT CAG CTG CTC CGG ATC CCA CAA GCC ATC TTG GAC ATG      48
Leu Val Met Ala Gln Leu Leu Arg Ile Pro Gln Ala Ile Leu Asp Met
 1               5                  10                  15

ATC GCT GGT GCT CAC TGG GGA GTC CTG GCG GGC ATA GCG TAT TTC TCC      96
Ile Ala Gly Ala His Trp Gly Val Leu Ala Gly Ile Ala Tyr Phe Ser
            20                  25                  30

ATG GTG GGG AAC TGG GCG AAG GTC CTG GTA GTG CTG CTG CTA TTT GCC     144
Met Val Gly Asn Trp Ala Lys Val Leu Val Val Leu Leu Leu Phe Ala
         35                  40                  45

GGC GTC GAC GCG GAA ACC CAC GTC ACC GGG GGA AGT GCC GGC CAC ACT     192
Gly Val Asp Ala Glu Thr His Val Thr Gly Gly Ser Ala Gly His Thr
     50                  55                  60

GTG TCT GGA TTT GTT AGC CTC CTC GCA CCA GGC GCC AAG CAG AAC GTC     240
Val Ser Gly Phe Val Ser Leu Leu Ala Pro Gly Ala Lys Gln Asn Val
 65                  70                  75                  80

CAG CTG ATC AAC ACC AAC GGC AGT TGG CAC CTC AAT AGC ACG GCC CTG     288
Gln Leu Ile Asn Thr Asn Gly Ser Trp His Leu Asn Ser Thr Ala Leu
                 85                  90                  95

AAC TGC AAT GAT AGC CTC AAC ACC GGC TGG TTG GCA GGG CTT TTC TAT     336
Asn Cys Asn Asp Ser Leu Asn Thr Gly Trp Leu Ala Gly Leu Phe Tyr
            100                 105                 110

CAC CAC AAG TTC AAC TCT TCA GGC TGT CCT GAG AGG CTA GCC AGC TGC     384
His His Lys Phe Asn Ser Ser Gly Cys Pro Glu Arg Leu Ala Ser Cys
        115                 120                 125

CGA CCC C                                                            391
Arg Pro
    130
```

(2) INFORMATION FOR SEQ ID NO:81:

(i) SEQUENCE CHARACTERISTICS:
        (A) LENGTH: 130 amino acids
        (B) TYPE: amino acid
        (D) TOPOLOGY: linear (ii) MOLECULE TYPE: protein (xi) SEQUENCE DESCRIPTION: SEQ ID NO:81:

```
Leu Val Met Ala Gln Leu Leu Arg Ile Pro Gln Ala Ile Leu Asp Met
  1               5                  10                  15

Ile Ala Gly Ala His Trp Gly Val Leu Ala Gly Ile Ala Tyr Phe Ser
                 20                  25                  30

Met Val Gly Asn Trp Ala Lys Val Leu Val Val Leu Leu Leu Phe Ala
             35                  40                  45

Gly Val Asp Ala Glu Thr His Val Thr Gly Gly Ser Ala Gly His Thr
     50                  55                  60

Val Ser Gly Phe Val Ser Leu Leu Ala Pro Gly Ala Lys Gln Asn Val
 65                  70                  75                  80

Gln Leu Ile Asn Thr Asn Gly Ser Trp His Leu Asn Ser Thr Ala Leu
                 85                  90                  95

Asn Cys Asn Asp Ser Leu Asn Thr Gly Trp Leu Ala Gly Leu Phe Tyr
            100                 105                 110

His His Lys Phe Asn Ser Ser Gly Cys Pro Glu Arg Leu Ala Ser Cys
        115                 120                 125

Arg Pro
    130
```

(2) INFORMATION FOR SEQ ID NO:82:

(i) SEQUENCE CHARACTERISTICS:
        (A) LENGTH: 267 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (B) CLONE: CA84a (ix) FEATURE:
        (A) NAME/KEY: CDS
        (B) LOCATION: 3..266

(xi) SEQUENCE DESCRIPTION: SEQ ID NO:82:

```
CG CAA GGT TGC AAT TGC TCT ATC TAT CCC GGC CAT ATA ACG GGT CAC         47
   Gln Gly Cys Asn Cys Ser Ile Tyr Pro Gly His Ile Thr Gly His
    1               5                  10                  15

CGC ATG GCA TGG GAT ATG ATG ATG AAC TGG TCC CCT ACG ACG GCG TTG        95
Arg Met Ala Trp Asp Met Met Met Asn Trp Ser Pro Thr Thr Ala Leu
             20                  25                  30

GTA ATG GCT CAG CTG CTC CGG ATC CCA CAA GCC ATC TTG GAC ATG ATC       143
Val Met Ala Gln Leu Leu Arg Ile Pro Gln Ala Ile Leu Asp Met Ile
         35                  40                  45

GCT GGT GCT CAC TGG GGA GTC CTG GCG GGC ATA GCG TAT TTC TCC ATG       191
Ala Gly Ala His Trp Gly Val Leu Ala Gly Ile Ala Tyr Phe Ser Met
     50                  55                  60

GTG GGG AAC TGG GCG AAG GTC CTG GTA GTG CTG CTA TTT GCC GGC           239
Val Gly Asn Trp Ala Lys Val Leu Val Val Leu Leu Phe Ala Gly
 65                  70                  75
```

```
GTC GAC GCG GAA ACC CAC GTC ACC GGG G                                      267
Val Asp Ala Glu Thr His Val Thr Gly
 80                  85

(2) INFORMATION FOR SEQ ID NO:83:

(i) SEQUENCE CHARACTERISTICS:
        (A) LENGTH: 88 amino acids
        (B) TYPE: amino acid
        (D) TOPOLOGY: linear (ii) MOLECULE TYPE: protein (xi) SEQUENCE DESCRIPTION: SEQ ID NO:83:

Gln Gly Cys Asn Cys Ser Ile Tyr Pro Gly His Ile Thr Gly His Arg
 1               5                  10                  15

Met Ala Trp Asp Met Met Met Asn Trp Ser Pro Thr Thr Ala Leu Val
                20                  25                  30

Met Ala Gln Leu Leu Arg Ile Pro Gln Ala Ile Leu Asp Met Ile Ala
            35                  40                  45

Gly Ala His Trp Gly Val Leu Ala Gly Ile Ala Tyr Phe Ser Met Val
        50                  55                  60

Gly Asn Trp Ala Lys Val Leu Val Val Leu Leu Phe Ala Gly Val
 65                  70                  75                  80

Asp Ala Glu Thr His Val Thr Gly
                85

(2) INFORMATION FOR SEQ ID NO:84:

(i) SEQUENCE CHARACTERISTICS:
        (A) LENGTH: 319 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (B) CLONE: CA156e (ix) FEATURE:
        (A) NAME/KEY: CDS
        (B) LOCATION: 2..319

(xi) SEQUENCE DESCRIPTION: SEQ ID NO:84:

G TGT TGG GTG GCG ATG ACC CCT ACG GTG GCC ACC AGG GAT GGC AAA             46
  Cys Trp Val Ala Met Thr Pro Thr Val Ala Thr Arg Asp Gly Lys
   1               5                  10                  15

CTC CCC GCG ACG CAG CTT CGA CGT CAC ATC GAT CTG CTT GTC GGG AGC           94
Leu Pro Ala Thr Gln Leu Arg Arg His Ile Asp Leu Leu Val Gly Ser
                20                  25                  30

GCC ACC CTC TGT TCG GCC CTC TAC GTG GGG GAC CTA TGC GGG TCT GTC          142
Ala Thr Leu Cys Ser Ala Leu Tyr Val Gly Asp Leu Cys Gly Ser Val
            35                  40                  45

TTT CTT GTC GGC CAA CTG TTC ACC TTC TCT CCC AGG CGC CAC TGG ACG          190
Phe Leu Val Gly Gln Leu Phe Thr Phe Ser Pro Arg Arg His Trp Thr
        50                  55                  60

ACG CAA GGT TGC AAT TGC TCT ATC TAT CCC GGC CAT ATA ACG GGT CAC          238
Thr Gln Gly Cys Asn Cys Ser Ile Tyr Pro Gly His Ile Thr Gly His
 65                  70                  75

CGC ATG GCA TGG GAT ATG ATG ATG AAC TGG TCC CCT ACG ACG GCG TTG          286
Arg Met Ala Trp Asp Met Met Met Asn Trp Ser Pro Thr Thr Ala Leu
 80                  85                  90                  95
```

```
GTA ATG GCT CAG CTG CTC CGG ATC CCA CAA GCC                              319
Val Met Ala Gln Leu Leu Arg Ile Pro Gln Ala
            100                 105
```

(2) INFORMATION FOR SEQ ID NO:85:

(i) SEQUENCE CHARACTERISTICS:
        (A) LENGTH: 106 amino acids
        (B) TYPE: amino acid
        (D) TOPOLOGY: linear (ii) MOLECULE TYPE: protein (xi) SEQUENCE DESCRIPTION: SEQ ID NO:85:

```
Cys Trp Val Ala Met Thr Pro Thr Val Ala Thr Arg Asp Gly Lys Leu
 1               5                  10                  15

Pro Ala Thr Gln Leu Arg Arg His Ile Asp Leu Leu Val Gly Ser Ala
            20                  25                  30

Thr Leu Cys Ser Ala Leu Tyr Val Gly Asp Leu Cys Gly Ser Val Phe
        35                  40                  45

Leu Val Gly Gln Leu Phe Thr Phe Ser Pro Arg Arg His Trp Thr Thr
    50                  55                  60

Gln Gly Cys Asn Cys Ser Ile Tyr Pro Gly His Ile Thr Gly His Arg
65                  70                  75                  80

Met Ala Trp Asp Met Met Asn Trp Ser Pro Thr Thr Ala Leu Val
                85                  90                  95

Met Ala Gln Leu Leu Arg Ile Pro Gln Ala
            100                 105
```

(2) INFORMATION FOR SEQ ID NO:86:

(i) SEQUENCE CHARACTERISTICS:
        (A) LENGTH: 272 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (B) CLONE: CA167b (ix) FEATURE:
        (A) NAME/KEY: CDS
        (B) LOCATION: 2..271

(xi) SEQUENCE DESCRIPTION: SEQ ID NO:86:

```
C TCC ACG GGG CTT TAC CAC GTC ACC AAT GAT TGC CCT AAC TCG AGT           46
  Ser Thr Gly Leu Tyr His Val Thr Asn Asp Cys Pro Asn Ser Ser
   1               5                  10                  15

ATT GTG TAC GAG GCG GCC GAT GCC ATC CTG CAC ACT CCG GGG TGC GTC         94
Ile Val Tyr Glu Ala Ala Asp Ala Ile Leu His Thr Pro Gly Cys Val
            20                  25                  30

CCT TGC GTT CGT GAG GGC AAC GCC TCG AGG TGT TGG GTG GCG ATG ACC        142
Pro Cys Val Arg Glu Gly Asn Ala Ser Arg Cys Trp Val Ala Met Thr
        35                  40                  45

CCT ACG GTG GCC ACC AGG GAT GGC AAA CTC CCC GCG ACG CAG CTT CGA        190
Pro Thr Val Ala Thr Arg Asp Gly Lys Leu Pro Ala Thr Gln Leu Arg
    50                  55                  60

CGT CAC ATC GAT CTG CTT GTC GGG AGC GCC ACC CTC TGT TCG GCC CTC        238
Arg His Ile Asp Leu Leu Val Gly Ser Ala Thr Leu Cys Ser Ala Leu
65                  70                  75

TAC GTG GGG GAC CTA TGC GGG TCT GTC TTT CTT G                          272
Tyr Val Gly Asp Leu Cys Gly Ser Val Phe Leu
```

(2) INFORMATION FOR SEQ ID NO:87:

(i) SEQUENCE CHARACTERISTICS:
        (A) LENGTH: 90 amino acids
        (B) TYPE: amino acid
        (D) TOPOLOGY: linear (ii) MOLECULE TYPE: protein (xi) SEQUENCE DESCRIPTION: SEQ ID NO:87:

```
Ser Thr Gly Leu Tyr His Val Thr Asn Asp Cys Pro Asn Ser Ser Ile
 1               5                  10                  15

Val Tyr Glu Ala Ala Asp Ala Ile Leu His Thr Pro Gly Cys Val Pro
             20                  25                  30

Cys Val Arg Glu Gly Asn Ala Ser Arg Cys Trp Val Ala Met Thr Pro
         35                  40                  45

Thr Val Ala Thr Arg Asp Gly Lys Leu Pro Ala Thr Gln Leu Arg Arg
     50                  55                  60

His Ile Asp Leu Leu Val Gly Ser Ala Thr Leu Cys Ser Ala Leu Tyr
 65                  70                  75                  80

Val Gly Asp Leu Cys Gly Ser Val Phe Leu
                 85                  90
```

(2) INFORMATION FOR SEQ ID NO:88:

(i) SEQUENCE CHARACTERISTICS:
        (A) LENGTH: 8316 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..8316

(xi) SEQUENCE DESCRIPTION: SEQ ID NO:88:

```
AGG TCG CGC AAT TTG GGT AAG GTC ATC GAT ACC CTT ACG TGC GGC TTC      48
Arg Ser Arg Asn Leu Gly Lys Val Ile Asp Thr Leu Thr Cys Gly Phe
 1               5                  10                  15

GCC GAC CTC ATG GGG TAC ATA CCG CTC GTC GGC GCC CCT CTT GGA GGC      96
Ala Asp Leu Met Gly Tyr Ile Pro Leu Val Gly Ala Pro Leu Gly Gly
             20                  25                  30

GCT GCC AGG GCC CTG GCG CAT GGC GTC CGG GTT CTG GAA GAC GGC GTG     144
Ala Ala Arg Ala Leu Ala His Gly Val Arg Val Leu Glu Asp Gly Val
         35                  40                  45

AAC TAT GCA ACA GGG AAC CTT CCT GGT TGC TCT TTC TCT ATC TTC CTT     192
Asn Tyr Ala Thr Gly Asn Leu Pro Gly Cys Ser Phe Ser Ile Phe Leu
     50                  55                  60

CTG GCC CTG CTC TCT TGC TTG ACT GTG CCC GCT TCG GCC TAC CAA GTG     240
Leu Ala Leu Leu Ser Cys Leu Thr Val Pro Ala Ser Ala Tyr Gln Val
 65                  70                  75                  80

CGC AAC TCC ACG GGG CTT TAC CAC GTC ACC AAT GAT TGC CCT AAC TCG     288
Arg Asn Ser Thr Gly Leu Tyr His Val Thr Asn Asp Cys Pro Asn Ser
                 85                  90                  95

AGT ATT GTG TAC GAG GCG GCC GAT GCC ATC CTG CAC ACT CCG GGG TGC     336
Ser Ile Val Tyr Glu Ala Ala Asp Ala Ile Leu His Thr Pro Gly Cys
                100                 105                 110

GTC CCT TGC GTT CGT GAG GGC AAC GCC TCG AGG TGT TGG GTG GCG ATG     384
Val Pro Cys Val Arg Glu Gly Asn Ala Ser Arg Cys Trp Val Ala Met
```

```
                115                      120                      125
ACC CCT ACG GTG GCC ACC AGG GAT GGC AAA CTC CCC GCG ACG CAG CTT          432
Thr Pro Thr Val Ala Thr Arg Asp Gly Lys Leu Pro Ala Thr Gln Leu
        130                      135                      140

CGA CGT CAC ATC GAT CTG CTT GTC GGG AGC GCC ACC CTC TGT TCG GCC          480
Arg Arg His Ile Asp Leu Leu Val Gly Ser Ala Thr Leu Cys Ser Ala
145                      150                      155                      160

CTC TAC GTG GGG GAC CTA TGC GGG TCT GTC TTT CTT GTC GGC CAA CTG          528
Leu Tyr Val Gly Asp Leu Cys Gly Ser Val Phe Leu Val Gly Gln Leu
                165                      170                      175

TTC ACC TTC TCT CCC AGG CGC CAC TGG ACG ACG CAA GGT TGC AAT TGC          576
Phe Thr Phe Ser Pro Arg Arg His Trp Thr Thr Gln Gly Cys Asn Cys
        180                      185                      190

TCT ATC TAT CCC GGC CAT ATA ACG GGT CAC CGC ATG GCA TGG GAT ATG          624
Ser Ile Tyr Pro Gly His Ile Thr Gly His Arg Met Ala Trp Asp Met
                195                      200                      205

ATG ATG AAC TGG TCC CCT ACG ACG GCG TTG GTA ATG GCT CAG CTG CTC          672
Met Met Asn Trp Ser Pro Thr Thr Ala Leu Val Met Ala Gln Leu Leu
        210                      215                      220

CGG ATC CCA CAA GCC ATC TTG GAC ATG ATC GCT GGT GCT CAC TGG GGA          720
Arg Ile Pro Gln Ala Ile Leu Asp Met Ile Ala Gly Ala His Trp Gly
225                      230                      235                      240

GTC CTG GCG GGC ATA GCG TAT TTC TCC ATG GTG GGG AAC TGG GCG AAG          768
Val Leu Ala Gly Ile Ala Tyr Phe Ser Met Val Gly Asn Trp Ala Lys
                245                      250                      255

GTC CTG GTA GTG CTG CTG CTA TTT GCC GGC GTC GAC GCG GAA ACC CAC          816
Val Leu Val Val Leu Leu Leu Phe Ala Gly Val Asp Ala Glu Thr His
        260                      265                      270

GTC ACC GGG GGA AGT GCC GGC CAC ACT GTG TCT GGA TTT GTT AGC CTC          864
Val Thr Gly Gly Ser Ala Gly His Thr Val Ser Gly Phe Val Ser Leu
        275                      280                      285

CTC GCA CCA GGC GCC AAG CAG AAC GTC CAG CTG ATC AAC ACC AAC GGC          912
Leu Ala Pro Gly Ala Lys Gln Asn Val Gln Leu Ile Asn Thr Asn Gly
        290                      295                      300

AGT TGG CAC CTC AAT AGC ACG GCC CTG AAC TGC AAT GAT AGC CTC AAC          960
Ser Trp His Leu Asn Ser Thr Ala Leu Asn Cys Asn Asp Ser Leu Asn
305                      310                      315                      320

ACC GGC TGG TTG GCA GGG CTT TTC TAT CAC CAC AAG TTC AAC TCT TCA         1008
Thr Gly Trp Leu Ala Gly Leu Phe Tyr His His Lys Phe Asn Ser Ser
                325                      330                      335

GGC TGT CCT GAG AGG CTA GCC AGC TGC CGA CCC CTT ACC GAT TTT GAC         1056
Gly Cys Pro Glu Arg Leu Ala Ser Cys Arg Pro Leu Thr Asp Phe Asp
        340                      345                      350

CAG GGC TGG GGC CCT ATC AGT TAT GCC AAC GGA AGC GGC CCC GAC CAG         1104
Gln Gly Trp Gly Pro Ile Ser Tyr Ala Asn Gly Ser Gly Pro Asp Gln
        355                      360                      365

CGC CCC TAC TGC TGG CAC TAC CCC CCA AAA CCT TGC GGT ATT GTG CCC         1152
Arg Pro Tyr Cys Trp His Tyr Pro Pro Lys Pro Cys Gly Ile Val Pro
        370                      375                      380

GCG AAG AGT GTG TGT GGT CCG GTA TAT TGC TTC ACT CCC AGC CCC GTG         1200
Ala Lys Ser Val Cys Gly Pro Val Tyr Cys Phe Thr Pro Ser Pro Val
385                      390                      395                      400

GTG GTG GGA ACG ACC GAC AGG TCG GGC GCG CCC ACC TAC AGC TGG GGT         1248
Val Val Gly Thr Thr Asp Arg Ser Gly Ala Pro Thr Tyr Ser Trp Gly
                405                      410                      415

GAA AAT GAT ACG GAC GTC TTC GTC CTT AAC AAT ACC AGG CCA CCG CTG         1296
Glu Asn Asp Thr Asp Val Phe Val Leu Asn Asn Thr Arg Pro Pro Leu
        420                      425                      430

GGC AAT TGG TTC GGT TGT ACC TGG ATG AAC TCA ACT GGA TTC ACC AAA         1344
```

-continued

```
Gly Asn Trp Phe Gly Cys Thr Trp Met Asn Ser Thr Gly Phe Thr Lys
        435                 440                 445

GTG TGC GGA GCG CCT CCT TGT GTC ATC GGA GGG GCG GGC AAC AAC ACC       1392
Val Cys Gly Ala Pro Pro Cys Val Ile Gly Gly Ala Gly Asn Asn Thr
450                 455                 460

CTG CAC TGC CCC ACT GAT TGC TTC CGC AAG CAT CCG GAC GCC ACA TAC       1440
Leu His Cys Pro Thr Asp Cys Phe Arg Lys His Pro Asp Ala Thr Tyr
465                 470                 475                 480

TCT CGG TGC GGC TCC GGT CCC TGG ATC ACA CCC AGG TGC CTG GTC GAC       1488
Ser Arg Cys Gly Ser Gly Pro Trp Ile Thr Pro Arg Cys Leu Val Asp
                485                 490                 495

TAC CCG TAT AGG CTT TGG CAT TAT CCT TGT ACC ATC AAC TAC ACC ATA       1536
Tyr Pro Tyr Arg Leu Trp His Tyr Pro Cys Thr Ile Asn Tyr Thr Ile
                500                 505                 510

TTT AAA ATC AGG ATG TAC GTG GGA GGG GTC GAA CAC AGG CTG GAA GCT       1584
Phe Lys Ile Arg Met Tyr Val Gly Gly Val Glu His Arg Leu Glu Ala
            515                 520                 525

GCC TGC AAC TGG ACG CGG GGC GAA CGT TGC GAT CTG GAA GAC AGG GAC       1632
Ala Cys Asn Trp Thr Arg Gly Glu Arg Cys Asp Leu Glu Asp Arg Asp
530                 535                 540

AGG TCC GAG CTC ACC CCG TTA CTG CTG ACC ACT ACA CAG TGG CAG GTC       1680
Arg Ser Glu Leu Thr Pro Leu Leu Leu Thr Thr Thr Gln Trp Gln Val
545                 550                 555                 560

CTC CCG TGT TCC TTC ACA ACC CTA CCA GCC TTG TCC ACC GGC CTC ATC       1728
Leu Pro Cys Ser Phe Thr Thr Leu Pro Ala Leu Ser Thr Gly Leu Ile
                565                 570                 575

CAC CTC CAC CAG AAC ATT GTG GAC GTG CAG TAC TTG TAC GGG GTG GGG       1776
His Leu His Gln Asn Ile Val Asp Val Gln Tyr Leu Tyr Gly Val Gly
                580                 585                 590

TCA AGC ATC GCG TCC TGG GCC ATT AAG TGG GAG TAC GTC GTT CTC CTG       1824
Ser Ser Ile Ala Ser Trp Ala Ile Lys Trp Glu Tyr Val Val Leu Leu
            595                 600                 605

TTC CTT CTG CTT GCA GAC GCG CGC GTC TGC TCC TGC TTG TGG ATG ATG       1872
Phe Leu Leu Leu Ala Asp Ala Arg Val Cys Ser Cys Leu Trp Met Met
610                 615                 620

CTA CTC ATA TCC CAA GCG GAG GCG GCT TTG GAG AAC CTC GTA ATA CTT       1920
Leu Leu Ile Ser Gln Ala Glu Ala Ala Leu Glu Asn Leu Val Ile Leu
625                 630                 635                 640

AAT GCA GCA TCC CTG GCC GGG ACG CAC GGT CTT GTA TCC TTC CTC GTG       1968
Asn Ala Ala Ser Leu Ala Gly Thr His Gly Leu Val Ser Phe Leu Val
                645                 650                 655

TTC TTC TGC TTT GCA TGG TAT TTG AAG GGT AAG TGG GTG CCC GGA GCG       2016
Phe Phe Cys Phe Ala Trp Tyr Leu Lys Gly Lys Trp Val Pro Gly Ala
                660                 665                 670

GTC TAC ACC TTC TAC GGG ATG TGG CCT CTC CTG CTC CTG TTG GCG       2064
Val Tyr Thr Phe Tyr Gly Met Trp Pro Leu Leu Leu Leu Leu Leu Ala
            675                 680                 685

TTG CCC CAG CGG GCG TAC GCG CTG GAC ACG GAG GTG GCC GCG TCG TGT       2112
Leu Pro Gln Arg Ala Tyr Ala Leu Asp Thr Glu Val Ala Ala Ser Cys
690                 695                 700

GGC GGT GTT GTT CTC GTC GGG TTG ATG GCG CTG ACT CTG TCA CCA TAT       2160
Gly Gly Val Val Leu Val Gly Leu Met Ala Leu Thr Leu Ser Pro Tyr
705                 710                 715                 720

TAC AAG CGC TAT ATC AGC TGG TGC TTG TGG TGG CTT CAG TAT TTT CTG       2208
Tyr Lys Arg Tyr Ile Ser Trp Cys Leu Trp Trp Leu Gln Tyr Phe Leu
                725                 730                 735

ACC AGA GTG GAA GCG CAA CTG CAC GTG TGG ATT CCC CCC CTC AAC GTC       2256
Thr Arg Val Glu Ala Gln Leu His Val Trp Ile Pro Pro Leu Asn Val
                740                 745                 750
```

```
CGA GGG GGG CGC GAC GCC GTC ATC TTA CTC ATG TGT GCT GTA CAC CCG      2304
Arg Gly Gly Arg Asp Ala Val Ile Leu Leu Met Cys Ala Val His Pro
        755                 760                 765

ACT CTG GTA TTT GAC ATC ACC AAA TTG CTG CTG GCC GTC TTC GGA CCC      2352
Thr Leu Val Phe Asp Ile Thr Lys Leu Leu Leu Ala Val Phe Gly Pro
770                 775                 780

CTT TGG ATT CTT CAA GCC AGT TTG CTT AAA GTA CCC TAC TTT GTG CGC      2400
Leu Trp Ile Leu Gln Ala Ser Leu Leu Lys Val Pro Tyr Phe Val Arg
785                 790                 795                 800

GTC CAA GGC CTT CTC CGG TTC TGC GCG TTA GCG CGG AAG ATG ATC GGA      2448
Val Gln Gly Leu Leu Arg Phe Cys Ala Leu Ala Arg Lys Met Ile Gly
        805                 810                 815

GGC CAT TAC GTG CAA ATG GTC ATC ATT AAG TTA GGG GCG CTT ACT GGC      2496
Gly His Tyr Val Gln Met Val Ile Ile Lys Leu Gly Ala Leu Thr Gly
        820                 825                 830

ACC TAT GTT TAT AAC CAT CTC ACT CCT CTT CGG GAC TGG GCG CAC AAC      2544
Thr Tyr Val Tyr Asn His Leu Thr Pro Leu Arg Asp Trp Ala His Asn
        835                 840                 845

GGC TTG CGA GAT CTG GCC GTG GCT GTA GAG CCA GTC GTC TTC TCC CAA      2592
Gly Leu Arg Asp Leu Ala Val Ala Val Glu Pro Val Val Phe Ser Gln
850                 855                 860

ATG GAG ACC AAG CTC ATC ACG TGG GGG GCA GAT ACC GCC GCG TGC GGT      2640
Met Glu Thr Lys Leu Ile Thr Trp Gly Ala Asp Thr Ala Ala Cys Gly
865                 870                 875                 880

GAC ATC ATC AAC GGC TTG CCT GTT TCC GCC CGC AGG GGC CGG GAG ATA      2688
Asp Ile Ile Asn Gly Leu Pro Val Ser Ala Arg Arg Gly Arg Glu Ile
                885                 890                 895

CTG CTC GGG CCA GCC GAT GGA ATG GTC TCC AAG GGG TGG AGG TTG CTG      2736
Leu Leu Gly Pro Ala Asp Gly Met Val Ser Lys Gly Trp Arg Leu Leu
                900                 905                 910

GCG CCC ATC ACG GCG TAC GCC CAG CAG ACA AGG GGC CTC CTA GGG TGC      2784
Ala Pro Ile Thr Ala Tyr Ala Gln Gln Thr Arg Gly Leu Leu Gly Cys
        915                 920                 925

ATA ATC ACC AGC CTA ACT GGC CGG GAC AAA AAC CAA GTG GAG GGT GAG      2832
Ile Ile Thr Ser Leu Thr Gly Arg Asp Lys Asn Gln Val Glu Gly Glu
930                 935                 940

GTC CAG ATT GTG TCA ACT GCT GCC CAA ACC TTC CTG GCA ACG TGC ATC      2880
Val Gln Ile Val Ser Thr Ala Ala Gln Thr Phe Leu Ala Thr Cys Ile
945                 950                 955                 960

AAT GGG GTG TGC TGG ACT GTC TAC CAC GGG GCC GGA ACG AGG ACC ATC      2928
Asn Gly Val Cys Trp Thr Val Tyr His Gly Ala Gly Thr Arg Thr Ile
                965                 970                 975

GCG TCA CCC AAG GGT CCT GTC ATC CAG ATG TAT ACC AAT GTA GAC CAA      2976
Ala Ser Pro Lys Gly Pro Val Ile Gln Met Tyr Thr Asn Val Asp Gln
        980                 985                 990

GAC CTT GTG GGC TGG CCC GCT CCG CAA GGT AGC CGC TCA TTG ACA CCC      3024
Asp Leu Val Gly Trp Pro Ala Pro Gln Gly Ser Arg Ser Leu Thr Pro
                995                 1000                1005

TGC ACT TGC GGC TCC TCG GAC CTT TAC CTG GTC ACG AGG CAC GCC GAT      3072
Cys Thr Cys Gly Ser Ser Asp Leu Tyr Leu Val Thr Arg His Ala Asp
        1010                1015                1020

GTC ATT CCC GTG CGC CGG CGG GGT GAT AGC AGG GGC AGC CTG CTG TCG      3120
Val Ile Pro Val Arg Arg Arg Gly Asp Ser Arg Gly Ser Leu Leu Ser
1025                1030                1035                1040

CCC CGG CCC ATT TCC TAC TTG AAA GGC TCC TCG GGG GGT CCG CTG TTG      3168
Pro Arg Pro Ile Ser Tyr Leu Lys Gly Ser Ser Gly Gly Pro Leu Leu
                1045                1050                1055

TGC CCC GCG GGG CAC GCC GTG GGC ATA TTT AGG GCC GCG GTG TGC ACC      3216
Cys Pro Ala Gly His Ala Val Gly Ile Phe Arg Ala Ala Val Cys Thr
                1060                1065                1070
```

| | | |
|---|---|---|
| CGT GGA GTG GCT AAG GCG GTG GAC TTT ATC CCT GTG GAG AAC CTA GAG<br>Arg Gly Val Ala Lys Ala Val Asp Phe Ile Pro Val Glu Asn Leu Glu<br>　　　　1075　　　　　　　　1080　　　　　　　　1085 | | 3264 |
| ACA ACC ATG AGG TCC CCG GTG TTC ACG GAT AAC TCC TCT CCA CCA GTA<br>Thr Thr Met Arg Ser Pro Val Phe Thr Asp Asn Ser Ser Pro Pro Val<br>1090　　　　　　　　1095　　　　　　　　1100 | | 3312 |
| GTG CCC CAG AGC TTC CAG GTG GCT CAC CTC CAT GCT CCC ACA GGC AGC<br>Val Pro Gln Ser Phe Gln Val Ala His Leu His Ala Pro Thr Gly Ser<br>1105　　　　　　　　1110　　　　　　　　1115　　　　　　　　1120 | | 3360 |
| GGC AAA AGC ACC AAG GTC CCG GCT GCA TAT GCA GCT CAG GGC TAT AAG<br>Gly Lys Ser Thr Lys Val Pro Ala Ala Tyr Ala Ala Gln Gly Tyr Lys<br>　　　　　　　　1125　　　　　　　　1130　　　　　　　　1135 | | 3408 |
| GTG CTA GTA CTC AAC CCC TCT GTT GCT GCA ACA CTG GGC TTT GGT GCT<br>Val Leu Val Leu Asn Pro Ser Val Ala Ala Thr Leu Gly Phe Gly Ala<br>　　　　1140　　　　　　　　1145　　　　　　　　1150 | | 3456 |
| TAC ATG TCC AAG GCT CAT GGG ATC GAT CCT AAC ATC AGG ACC GGG GTG<br>Tyr Met Ser Lys Ala His Gly Ile Asp Pro Asn Ile Arg Thr Gly Val<br>1155　　　　　　　　1160　　　　　　　　1165 | | 3504 |
| AGA ACA ATT ACC ACT GGC AGC CCC ATC ACG TAC TCC ACC TAC GGC AAG<br>Arg Thr Ile Thr Thr Gly Ser Pro Ile Thr Tyr Ser Thr Tyr Gly Lys<br>1170　　　　　　　　1175　　　　　　　　1180 | | 3552 |
| TTC CTT GCC GAC GGC GGG TGC TCG GGG GGC GGT TAT GAC ATA ATA ATT<br>Phe Leu Ala Asp Gly Gly Cys Ser Gly Gly Gly Tyr Asp Ile Ile Ile<br>1185　　　　　　　　1190　　　　　　　　1195　　　　　　　　1200 | | 3600 |
| TGT GAC GAG TGC CAC TCC ACG GAT GCC ACA TCC ATC TTG GGC ATC GGC<br>Cys Asp Glu Cys His Ser Thr Asp Ala Thr Ser Ile Leu Gly Ile Gly<br>　　　　　　　　1205　　　　　　　　1210　　　　　　　　1215 | | 3648 |
| ACT GTC CTT GAC CAA GCA GAG ACT GCG GGG GCG AGA CTG GTT GTG CTC<br>Thr Val Leu Asp Gln Ala Glu Thr Ala Gly Ala Arg Leu Val Val Leu<br>　　　　1220　　　　　　　　1225　　　　　　　　1230 | | 3696 |
| GCC ACC GCC ACC CCT CCG GGC TCC GTC ACT GTG CCC CAT CCC AAC ATC<br>Ala Thr Ala Thr Pro Pro Gly Ser Val Thr Val Pro His Pro Asn Ile<br>　　　　　　　　1235　　　　　　　　1240　　　　　　　　1245 | | 3744 |
| GAG GAG GTT GCT CTG TCC ACC ACC GGA GAG ATC CCT TTT TAC GGC AAG<br>Glu Glu Val Ala Leu Ser Thr Thr Gly Glu Ile Pro Phe Tyr Gly Lys<br>1250　　　　　　　　1255　　　　　　　　1260 | | 3792 |
| GCT ATC CCC CTC GAA GTA ATC AAG GGG GGG AGA CAT CTC ATC TTC TGT<br>Ala Ile Pro Leu Glu Val Ile Lys Gly Gly Arg His Leu Ile Phe Cys<br>1265　　　　　　　　1270　　　　　　　　1275　　　　　　　　1280 | | 3840 |
| CAT TCA AAG AAG AAG TGC GAC GAA CTC GCC GCA AAG CTG GTC GCA TTG<br>His Ser Lys Lys Lys Cys Asp Glu Leu Ala Ala Lys Leu Val Ala Leu<br>　　　　　　　　1285　　　　　　　　1290　　　　　　　　1295 | | 3888 |
| GGC ATC AAT GCC GTG GCC TAC TAC CGC GGT CTT GAC GTG TCC GTC ATC<br>Gly Ile Asn Ala Val Ala Tyr Tyr Arg Gly Leu Asp Val Ser Val Ile<br>　　　　1300　　　　　　　　1305　　　　　　　　1310 | | 3936 |
| CCG ACC AGC GGC GAT GTT GTC GTC GTG GCA ACC GAT GCC CTC ATG ACC<br>Pro Thr Ser Gly Asp Val Val Val Val Ala Thr Asp Ala Leu Met Thr<br>1315　　　　　　　　1320　　　　　　　　1325 | | 3984 |
| GGC TAT ACC GGC GAC TTC GAC TCG GTG ATA GAC TGC AAT ACG TGT GTC<br>Gly Tyr Thr Gly Asp Phe Asp Ser Val Ile Asp Cys Asn Thr Cys Val<br>1330　　　　　　　　1335　　　　　　　　1340 | | 4032 |
| ACC CAG ACA GTC GAT TTC AGC CTT GAC CCT ACC TTC ACC ATT GAG ACA<br>Thr Gln Thr Val Asp Phe Ser Leu Asp Pro Thr Phe Thr Ile Glu Thr<br>1345　　　　　　　　1350　　　　　　　　1355　　　　　　　　1360 | | 4080 |
| ATC ACG CTC CCC CAG GAT GCT GTC TCC CGC ACT CAA CGT CGG GGC AGG<br>Ile Thr Leu Pro Gln Asp Ala Val Ser Arg Thr Gln Arg Arg Gly Arg<br>　　　　　　　　1365　　　　　　　　1370　　　　　　　　1375 | | 4128 |
| ACT GGC AGG GGG AAG CCA GGC ATC TAC AGA TTT GTG GCA CCG GGG GAG<br>Thr Gly Arg Gly Lys Pro Gly Ile Tyr Arg Phe Val Ala Pro Gly Glu | | 4176 |

-continued

```
               1380              1385              1390
CGC CCC TCC GGC ATG TTC GAC TCG TCC GTC CTC TGT GAG TGC TAT GAC         4224
Arg Pro Ser Gly Met Phe Asp Ser Ser Val Leu Cys Glu Cys Tyr Asp
        1395              1400              1405

GCA GGC TGT GCT TGG TAT GAG CTC ACG CCC GCC GAG ACT ACA GTT AGG         4272
Ala Gly Cys Ala Trp Tyr Glu Leu Thr Pro Ala Glu Thr Thr Val Arg
    1410              1415              1420

CTA CGA GCG TAC ATG AAC ACC CCG GGG CTT CCC GTG TGC CAG GAC CAT         4320
Leu Arg Ala Tyr Met Asn Thr Pro Gly Leu Pro Val Cys Gln Asp His
1425              1430              1435              1440

CTT GAA TTT TGG GAG GGC GTC TTT ACA GGC CTC ACT CAT ATA GAT GCC         4368
Leu Glu Phe Trp Glu Gly Val Phe Thr Gly Leu Thr His Ile Asp Ala
                1445              1450              1455

CAC TTT CTA TCC CAG ACA AAG CAG AGT GGG GAG AAC CTT CCT TAC CTG         4416
His Phe Leu Ser Gln Thr Lys Gln Ser Gly Glu Asn Leu Pro Tyr Leu
            1460              1465              1470

GTA GCG TAC CAA GCC ACC GTG TGC GCT AGG GCT CAA GCC CCT CCC CCA         4464
Val Ala Tyr Gln Ala Thr Val Cys Ala Arg Ala Gln Ala Pro Pro Pro
        1475              1480              1485

TCG TGG GAC CAG ATG TGG AAG TGT TTG ATT CGC CTC AAG CCC ACC CTC         4512
Ser Trp Asp Gln Met Trp Lys Cys Leu Ile Arg Leu Lys Pro Thr Leu
    1490              1495              1500

CAT GGG CCA ACA CCC CTG CTA TAC AGA CTG GGC GCT GTT CAG AAT GAA         4560
His Gly Pro Thr Pro Leu Leu Tyr Arg Leu Gly Ala Val Gln Asn Glu
1505              1510              1515              1520

ATC ACC CTG ACG CAC CCA GTC ACC AAA TAC ATC ATG ACA TGC ATG TCG         4608
Ile Thr Leu Thr His Pro Val Thr Lys Tyr Ile Met Thr Cys Met Ser
                1525              1530              1535

GCC GAC CTG GAG GTC GTC ACG AGC ACC TGG GTG CTC GTT GGC GGC GTC         4656
Ala Asp Leu Glu Val Val Thr Ser Thr Trp Val Leu Val Gly Gly Val
            1540              1545              1550

CTG GCT GCT TTG GCC GCG TAT TGC CTG TCA ACA GGC TGC GTG GTC ATA         4704
Leu Ala Ala Leu Ala Ala Tyr Cys Leu Ser Thr Gly Cys Val Val Ile
        1555              1560              1565

GTG GGC AGG GTC GTC TTG TCC GGG AAG CCG GCA ATC ATA CCT GAC AGG         4752
Val Gly Arg Val Val Leu Ser Gly Lys Pro Ala Ile Ile Pro Asp Arg
    1570              1575              1580

GAA GTC CTC TAC CGA GAG TTC GAT GAG ATG GAA GAG TGC TCT CAG CAC         4800
Glu Val Leu Tyr Arg Glu Phe Asp Glu Met Glu Glu Cys Ser Gln His
1585              1590              1595              1600

TTA CCG TAC ATC GAG CAA GGG ATG ATG CTC GCC GAG CAG TTC AAG CAG         4848
Leu Pro Tyr Ile Glu Gln Gly Met Met Leu Ala Glu Gln Phe Lys Gln
                1605              1610              1615

AAG GCC CTC GGC CTC CTG CAG ACC GCG TCC CGT CAG GCA GAG GTT ATC         4896
Lys Ala Leu Gly Leu Leu Gln Thr Ala Ser Arg Gln Ala Glu Val Ile
            1620              1625              1630

GCC CCT GCT GTC CAG ACC AAC TGG CAA AAA CTC GAG ACC TTC TGG GCG         4944
Ala Pro Ala Val Gln Thr Asn Trp Gln Lys Leu Glu Thr Phe Trp Ala
        1635              1640              1645

AAG CAT ATG TGG AAC TTC ATC AGT GGG ATA CAA TAC TTG GCG GGC TTG         4992
Lys His Met Trp Asn Phe Ile Ser Gly Ile Gln Tyr Leu Ala Gly Leu
    1650              1655              1660

TCA ACG CTG CCT GGT AAC CCC GCC ATT GCT TCA TTG ATG GCT TTT ACA         5040
Ser Thr Leu Pro Gly Asn Pro Ala Ile Ala Ser Leu Met Ala Phe Thr
1665              1670              1675              1680

GCT GCT GTC ACC AGC CCA CTA ACC ACT AGC CAA ACC CTC CTC TTC AAC         5088
Ala Ala Val Thr Ser Pro Leu Thr Thr Ser Gln Thr Leu Leu Phe Asn
                1685              1690              1695

ATA TTG GGG GGG TGG GTG GCT GCC CAG CTC GCC GCC CCC GGT GCC GCT         5136
```

-continued

```
Ile Leu Gly Gly Trp Val Ala Ala Gln Leu Ala Ala Pro Gly Ala Ala
            1700                1705                1710
ACT GCC TTT GTG GGC GCT GGC TTA GCT GGC GCC GCC ATC GGC AGT GTT       5184
Thr Ala Phe Val Gly Ala Gly Leu Ala Gly Ala Ala Ile Gly Ser Val
            1715                1720                1725
GGA CTG GGG AAG GTC CTC ATA GAC ATC CTT GCA GGG TAT GGC GCG GGC       5232
Gly Leu Gly Lys Val Leu Ile Asp Ile Leu Ala Gly Tyr Gly Ala Gly
            1730                1735                1740
GTG GCG GGA GCT CTT GTG GCA TTC AAG ATC ATG AGC GGT GAG GTC CCC       5280
Val Ala Gly Ala Leu Val Ala Phe Lys Ile Met Ser Gly Glu Val Pro
1745                1750                1755                1760
TCC ACG GAG GAC CTG GTC AAT CTA CTG CCC GCC ATC CTC TCG CCC GGA       5328
Ser Thr Glu Asp Leu Val Asn Leu Leu Pro Ala Ile Leu Ser Pro Gly
            1765                1770                1775
GCC CTC GTA GTC GGC GTG GTC TGT GCA GCA ATA CTG CGC CGG CAC GTT       5376
Ala Leu Val Val Gly Val Val Cys Ala Ala Ile Leu Arg Arg His Val
            1780                1785                1790
GGC CCG GGC GAG GGG GCA GTG CAG TGG ATG AAC CGG CTG ATA GCC TTC       5424
Gly Pro Gly Glu Gly Ala Val Gln Trp Met Asn Arg Leu Ile Ala Phe
            1795                1800                1805
GCC TCC CGG GGG AAC CAT GTT TCC CCC ACG CAC TAC GTG CCG GAG AGC       5472
Ala Ser Arg Gly Asn His Val Ser Pro Thr His Tyr Val Pro Glu Ser
            1810                1815                1820
GAT GCA GCT GCC CGC GTC ACT GCC ATA CTC AGC AGC CTC ACT GTA ACC       5520
Asp Ala Ala Ala Arg Val Thr Ala Ile Leu Ser Ser Leu Thr Val Thr
1825                1830                1835                1840
CAG CTC CTG AGG CGA CTG CAC CAG TGG ATA AGC TCG GAG TGT ACC ACT       5568
Gln Leu Leu Arg Arg Leu His Gln Trp Ile Ser Ser Glu Cys Thr Thr
            1845                1850                1855
CCA TGC TCC GGT TCC TGG CTA AGG GAC ATC TGG GAC TGG ATA TGC GAG       5616
Pro Cys Ser Gly Ser Trp Leu Arg Asp Ile Trp Asp Trp Ile Cys Glu
            1860                1865                1870
GTG TTG AGC GAC TTT AAG ACC TGG CTA AAA GCT AAG CTC ATG CCA CAG       5664
Val Leu Ser Asp Phe Lys Thr Trp Leu Lys Ala Lys Leu Met Pro Gln
            1875                1880                1885
CTG CCT GGG ATC CCC TTT GTG TCC TGC CAG CGC GGG TAT AAG GGG GTC       5712
Leu Pro Gly Ile Pro Phe Val Ser Cys Gln Arg Gly Tyr Lys Gly Val
            1890                1895                1900
TGG CGA GTG GAC GGC ATC ATG CAC ACT CGC TGC CAC TGT GGA GCT GAG       5760
Trp Arg Val Asp Gly Ile Met His Thr Arg Cys His Cys Gly Ala Glu
1905                1910                1915                1920
ATC ACT GGA CAT GTC AAA AAC GGG ACG ATG AGG ATC GTC GGT CCT AGG       5808
Ile Thr Gly His Val Lys Asn Gly Thr Met Arg Ile Val Gly Pro Arg
            1925                1930                1935
ACC TGC AGG AAC ATG TGG AGT GGG ACC TTC CCC ATT AAT GCC TAC ACC       5856
Thr Cys Arg Asn Met Trp Ser Gly Thr Phe Pro Ile Asn Ala Tyr Thr
            1940                1945                1950
ACG GGC CCC TGT ACC CCC CTT CCT GCG CCG AAC TAC ACG TTC GCG CTA       5904
Thr Gly Pro Cys Thr Pro Leu Pro Ala Pro Asn Tyr Thr Phe Ala Leu
            1955                1960                1965
TGG AGG GTG TCT GCA GAG GAA TAT GTG GAG ATA AGG CAG GTG GGG GAC       5952
Trp Arg Val Ser Ala Glu Glu Tyr Val Glu Ile Arg Gln Val Gly Asp
            1970                1975                1980
TTC CAC TAC GTG ACG GGT ATG ACT ACT GAC AAT CTC AAA TGC CCG TGC       6000
Phe His Tyr Val Thr Gly Met Thr Thr Asp Asn Leu Lys Cys Pro Cys
1985                1990                1995                2000
CAG GTC CCA TCG CCC GAA TTT TTC ACA GAA TTG GAC GGG GTG CGC CTA       6048
Gln Val Pro Ser Pro Glu Phe Phe Thr Glu Leu Asp Gly Val Arg Leu
            2005                2010                2015
```

```
CAT AGG TTT GCG CCC CCC TGC AAG CCC TTG CTG CGG GAG GAG GTA TCA    6096
His Arg Phe Ala Pro Pro Cys Lys Pro Leu Leu Arg Glu Glu Val Ser
            2020                2025                2030

TTC AGA GTA GGA CTC CAC GAA TAC CCG GTA GGG TCG CAA TTA CCT TGC    6144
Phe Arg Val Gly Leu His Glu Tyr Pro Val Gly Ser Gln Leu Pro Cys
            2035                2040                2045

GAG CCC GAA CCG GAC GTG GCC GTG TTG ACG TCC ATG CTC ACT GAT CCC    6192
Glu Pro Glu Pro Asp Val Ala Val Leu Thr Ser Met Leu Thr Asp Pro
            2050                2055                2060

TCC CAT ATA ACA GCA GAG GCG GCC GGG CGA AGG TTG GCG AGG GGA TCA    6240
Ser His Ile Thr Ala Glu Ala Ala Gly Arg Arg Leu Ala Arg Gly Ser
2065                2070                2075                2080

CCC CCC TCT GTG GCC AGC TCC TCG GCT AGC CAG CTA TCC GCT CCA TCT    6288
Pro Pro Ser Val Ala Ser Ser Ser Ala Ser Gln Leu Ser Ala Pro Ser
                2085                2090                2095

CTC AAG GCA ACT TGC ACC GCT AAC CAT GAC TCC CCT GAT GCT GAG CTC    6336
Leu Lys Ala Thr Cys Thr Ala Asn His Asp Ser Pro Asp Ala Glu Leu
            2100                2105                2110

ATA GAG GCC AAC CTC CTA TGG AGG CAG GAG ATG GGC GGC AAC ATC ACC    6384
Ile Glu Ala Asn Leu Leu Trp Arg Gln Glu Met Gly Gly Asn Ile Thr
            2115                2120                2125

AGG GTT GAG TCA GAA AAC AAA GTG GTG ATT CTG GAC TCC TTC GAT CCG    6432
Arg Val Glu Ser Glu Asn Lys Val Val Ile Leu Asp Ser Phe Asp Pro
            2130                2135                2140

CTT GTG GCG GAG GAG GAC GAG CGG GAG ATC TCC GTA CCC GCA GAA ATC    6480
Leu Val Ala Glu Glu Asp Glu Arg Glu Ile Ser Val Pro Ala Glu Ile
2145                2150                2155                2160

CTG CGG AAG TCT CGG AGA TTC GCC CAG GCC CTG CCC GTT TGG GCG CGG    6528
Leu Arg Lys Ser Arg Arg Phe Ala Gln Ala Leu Pro Val Trp Ala Arg
                2165                2170                2175

CCG GAC TAT AAC CCC CCG CTA GTG GAG ACG TGG AAA AAG CCC GAC TAC    6576
Pro Asp Tyr Asn Pro Pro Leu Val Glu Thr Trp Lys Lys Pro Asp Tyr
            2180                2185                2190

GAA CCA CCT GTG GTC CAT GGC TGT CCG CTT CCA CCT CCA AAG TCC CCT    6624
Glu Pro Pro Val Val His Gly Cys Pro Leu Pro Pro Pro Lys Ser Pro
            2195                2200                2205

CCT GTG CCT CCG CCT CGG AAG AAG CGG ACG GTG GTC CTC ACT GAA TCA    6672
Pro Val Pro Pro Pro Arg Lys Lys Arg Thr Val Val Leu Thr Glu Ser
            2210                2215                2220

ACC CTA TCT ACT GCC TTG GCC GAG CTC GCC ACC AGA AGC TTT GGC AGC    6720
Thr Leu Ser Thr Ala Leu Ala Glu Leu Ala Thr Arg Ser Phe Gly Ser
2225                2230                2235                2240

TCC TCA ACT TCC GGC ATT ACG GGC GAC AAT ACG ACA ACA TCC TCT GAG    6768
Ser Ser Thr Ser Gly Ile Thr Gly Asp Asn Thr Thr Thr Ser Ser Glu
                2245                2250                2255

CCC GCC CCT TCT GGC TGC CCC CCC GAC TCC GAC GCT GAG TCC TAT TCC    6816
Pro Ala Pro Ser Gly Cys Pro Pro Asp Ser Asp Ala Glu Ser Tyr Ser
            2260                2265                2270

TCC ATG CCC CCC CTG GAG GGG GAG CCT GGG GAT CCG GAT CTT AGC GAC    6864
Ser Met Pro Pro Leu Glu Gly Glu Pro Gly Asp Pro Asp Leu Ser Asp
            2275                2280                2285

GGG TCA TGG TCA ACG GTC AGT AGT GAG GCC AAC GCG GAG GAT GTC GTG    6912
Gly Ser Trp Ser Thr Val Ser Ser Glu Ala Asn Ala Glu Asp Val Val
            2290                2295                2300

TGC TGC TCA ATG TCT TAC TCT TGG ACA GGC GCA CTC GTC ACC CCG TGC    6960
Cys Cys Ser Met Ser Tyr Ser Trp Thr Gly Ala Leu Val Thr Pro Cys
2305                2310                2315                2320

GCC GCG GAA GAA CAG AAA CTG CCC ATC AAT GCA CTA AGC AAC TCG TTG    7008
Ala Ala Glu Glu Gln Lys Leu Pro Ile Asn Ala Leu Ser Asn Ser Leu
                2325                2330                2335
```

```
CTA CGT CAC CAC AAT TTG GTG TAT TCC ACC ACC TCA CGC AGT GCT TGC      7056
Leu Arg His His Asn Leu Val Tyr Ser Thr Thr Ser Arg Ser Ala Cys
        2340                2345                2350

CAA AGG CAG AAG AAA GTC ACA TTT GAC AGA CTG CAA GTT CTG GAC AGC      7104
Gln Arg Gln Lys Lys Val Thr Phe Asp Arg Leu Gln Val Leu Asp Ser
            2355                2360                2365

CAT TAC CAG GAC GTA CTC AAG GAG GTT AAA GCA GCG GCG TCA AAA GTG      7152
His Tyr Gln Asp Val Leu Lys Glu Val Lys Ala Ala Ala Ser Lys Val
        2370                2375                2380

AAG GCT AAC TTG CTA TCC GTA GAG GAA GCT TGC AGC CTG ACG CCC CCA      7200
Lys Ala Asn Leu Leu Ser Val Glu Glu Ala Cys Ser Leu Thr Pro Pro
2385                2390                2395                2400

CAC TCA GCC AAA TCC AAG TTT GGT TAT GGG GCA AAA GAC GTC CGT TGC      7248
His Ser Ala Lys Ser Lys Phe Gly Tyr Gly Ala Lys Asp Val Arg Cys
            2405                2410                2415

CAT GCC AGA AAG GCC GTA ACC CAC ATC AAC TCC GTG TGG AAA GAC CTT      7296
His Ala Arg Lys Ala Val Thr His Ile Asn Ser Val Trp Lys Asp Leu
        2420                2425                2430

CTG GAA GAC AAT GTA ACA CCA ATA GAC ACT ACC ATC ATG GCT AAG AAC      7344
Leu Glu Asp Asn Val Thr Pro Ile Asp Thr Thr Ile Met Ala Lys Asn
        2435                2440                2445

GAG GTT TTC TGC GTT CAG CCT GAG AAG GGG GGT CGT AAG CCA GCT CGT      7392
Glu Val Phe Cys Val Gln Pro Glu Lys Gly Gly Arg Lys Pro Ala Arg
        2450                2455                2460

CTC ATC GTG TTC CCC GAT CTG GGC GTG CGC GTG TGC GAA AAG ATG GCT      7440
Leu Ile Val Phe Pro Asp Leu Gly Val Arg Val Cys Glu Lys Met Ala
2465                2470                2475                2480

TTG TAC GAC GTG GTT ACA AAG CTC CCC TTG GCC GTG ATG GGA AGC TCC      7488
Leu Tyr Asp Val Val Thr Lys Leu Pro Leu Ala Val Met Gly Ser Ser
            2485                2490                2495

TAC GGA TTC CAA TAC TCA CCA GGA CAG CGG GTT GAA TTC CTC GTG CAA      7536
Tyr Gly Phe Gln Tyr Ser Pro Gly Gln Arg Val Glu Phe Leu Val Gln
        2500                2505                2510

GCG TGG AAG TCC AAG AAA ACC CCA ATG GGG TTC TCG TAT GAT ACC CGC      7584
Ala Trp Lys Ser Lys Lys Thr Pro Met Gly Phe Ser Tyr Asp Thr Arg
        2515                2520                2525

TGC TTT GAC TCC ACA GTC ACT GAG AGC GAC ATC CGT ACG GAG GAG GCA      7632
Cys Phe Asp Ser Thr Val Thr Glu Ser Asp Ile Arg Thr Glu Glu Ala
        2530                2535                2540

ATC TAC CAA TGT TGT GAC CTC GAC CCC CAA GCC CGC GTG GCC ATC AAG      7680
Ile Tyr Gln Cys Cys Asp Leu Asp Pro Gln Ala Arg Val Ala Ile Lys
2545                2550                2555                2560

TCC CTC ACC GAG AGG CTT TAT GTT GGG GGC CCT CTT ACC AAT TCA AGG      7728
Ser Leu Thr Glu Arg Leu Tyr Val Gly Gly Pro Leu Thr Asn Ser Arg
            2565                2570                2575

GGG GAG AAC TGC GGC TAT CGC AGG TGC CGC GCG AGC GGC GTA CTG ACA      7776
Gly Glu Asn Cys Gly Tyr Arg Arg Cys Arg Ala Ser Gly Val Leu Thr
        2580                2585                2590

ACT AGC TGT GGT AAC ACC CTC ACT TGC TAC ATC AAG GCC CGG GCA GCC      7824
Thr Ser Cys Gly Asn Thr Leu Thr Cys Tyr Ile Lys Ala Arg Ala Ala
        2595                2600                2605

TGT CGA GCC GCA GGG CTC CAG GAC TGC ACC ATG CTC GTG TGT GGC GAC      7872
Cys Arg Ala Ala Gly Leu Gln Asp Cys Thr Met Leu Val Cys Gly Asp
        2610                2615                2620

GAC TTA GTC GTT ATC TGT GAA AGC GCG GGG GTC CAG GAG GAC GCG GCG      7920
Asp Leu Val Val Ile Cys Glu Ser Ala Gly Val Gln Glu Asp Ala Ala
2625                2630                2635                2640

AGC CTG AGA GCC TTC ACG GAG GCT ATG ACC AGG TAC TCC GCC CCC CCT      7968
Ser Leu Arg Ala Phe Thr Glu Ala Met Thr Arg Tyr Ser Ala Pro Pro
```

```
                    2645                2650                2655
GGG GAC CCC CCA CAA CCA GAA TAC GAC TTG GAG CTC ATA ACA TCA TGC         8016
Gly Asp Pro Pro Gln Pro Glu Tyr Asp Leu Glu Leu Ile Thr Ser Cys
                2660                2665                2670

TCC TCC AAC GTG TCA GTC GCC CAC GAC GGC GCT GGA AAG AGG GTC TAC         8064
Ser Ser Asn Val Ser Val Ala His Asp Gly Ala Gly Lys Arg Val Tyr
            2675                2680                2685

TAC CTC ACC CGT GAC CCT ACA ACC CCC CTC GCG AGA GCT GCG TGG GAG         8112
Tyr Leu Thr Arg Asp Pro Thr Thr Pro Leu Ala Arg Ala Ala Trp Glu
        2690                2695                2700

ACA GCA AGA CAC ACT CCA GTC AAT TCC TGG CTA GGC AAC ATA ATC ATG         8160
Thr Ala Arg His Thr Pro Val Asn Ser Trp Leu Gly Asn Ile Ile Met
2705                2710                2715                2720

TTT GCC CCC ACA CTG TGG GCG AGG ATG ATA CTG ATG ACC CAT TTC TTT         8208
Phe Ala Pro Thr Leu Trp Ala Arg Met Ile Leu Met Thr His Phe Phe
                2725                2730                2735

AGC GTC CTT ATA GCC AGG GAC CAG CTT GAA CAG GCC CTC GAT TGC GAG         8256
Ser Val Leu Ile Ala Arg Asp Gln Leu Glu Gln Ala Leu Asp Cys Glu
            2740                2745                2750

ATC TAC GGG GCC TGC TAC TCC ATA GAA CCA CTT GAT CTA CCT CCA ATC         8304
Ile Tyr Gly Ala Cys Tyr Ser Ile Glu Pro Leu Asp Leu Pro Pro Ile
        2755                2760                2765

ATT CAA AGA CTC                                                          8316
Ile Gln Arg Leu
    2770

(2) INFORMATION FOR SEQ ID NO:89:

(i) SEQUENCE CHARACTERISTICS:
        (A) LENGTH: 2772 amino acids
        (B) TYPE: amino acid
        (D) TOPOLOGY: linear (ii) MOLECULE TYPE: protein (xi) SEQUENCE DESCRIPTION: SEQ ID NO:89:

Arg Ser Arg Asn Leu Gly Lys Val Ile Asp Thr Leu Thr Cys Gly Phe
  1               5                  10                  15

Ala Asp Leu Met Gly Tyr Ile Pro Leu Val Gly Ala Pro Leu Gly Gly
             20                  25                  30

Ala Ala Arg Ala Leu Ala His Gly Val Arg Val Leu Glu Asp Gly Val
         35                  40                  45

Asn Tyr Ala Thr Gly Asn Leu Pro Gly Cys Ser Phe Ser Ile Phe Leu
     50                  55                  60

Leu Ala Leu Leu Ser Cys Leu Thr Val Pro Ala Ser Ala Tyr Gln Val
 65                  70                  75                  80

Arg Asn Ser Thr Gly Leu Tyr His Val Thr Asn Asp Cys Pro Asn Ser
                 85                  90                  95

Ser Ile Val Tyr Glu Ala Ala Asp Ala Ile Leu His Thr Pro Gly Cys
            100                 105                 110

Val Pro Cys Val Arg Glu Gly Asn Ala Ser Arg Cys Trp Val Ala Met
        115                 120                 125

Thr Pro Thr Val Ala Thr Arg Asp Gly Lys Leu Pro Ala Thr Gln Leu
    130                 135                 140

Arg Arg His Ile Asp Leu Leu Val Gly Ser Ala Thr Leu Cys Ser Ala
145                 150                 155                 160

Leu Tyr Val Gly Asp Leu Cys Gly Ser Val Phe Leu Val Gly Gln Leu
                165                 170                 175
```

-continued

```
Phe Thr Phe Ser Pro Arg Arg His Trp Thr Thr Gln Gly Cys Asn Cys
            180                 185                 190

Ser Ile Tyr Pro Gly His Ile Thr Gly His Arg Met Ala Trp Asp Met
        195                 200                 205

Met Met Asn Trp Ser Pro Thr Thr Ala Leu Val Met Ala Gln Leu Leu
    210                 215                 220

Arg Ile Pro Gln Ala Ile Leu Asp Met Ile Ala Gly Ala His Trp Gly
225                 230                 235                 240

Val Leu Ala Gly Ile Ala Tyr Phe Ser Met Val Gly Asn Trp Ala Lys
                245                 250                 255

Val Leu Val Val Leu Leu Phe Ala Gly Val Asp Ala Glu Thr His
            260                 265                 270

Val Thr Gly Gly Ser Ala Gly His Thr Val Ser Gly Phe Val Ser Leu
        275                 280                 285

Leu Ala Pro Gly Ala Lys Gln Asn Val Gln Leu Ile Asn Thr Asn Gly
    290                 295                 300

Ser Trp His Leu Asn Ser Thr Ala Leu Asn Cys Asn Asp Ser Leu Asn
305                 310                 315                 320

Thr Gly Trp Leu Ala Gly Leu Phe Tyr His His Lys Phe Asn Ser Ser
                325                 330                 335

Gly Cys Pro Glu Arg Leu Ala Ser Cys Arg Pro Leu Thr Asp Phe Asp
            340                 345                 350

Gln Gly Trp Gly Pro Ile Ser Tyr Ala Asn Gly Ser Gly Pro Asp Gln
        355                 360                 365

Arg Pro Tyr Cys Trp His Tyr Pro Pro Lys Pro Cys Gly Ile Val Pro
370                 375                 380

Ala Lys Ser Val Cys Gly Pro Val Tyr Cys Phe Thr Pro Ser Pro Val
385                 390                 395                 400

Val Val Gly Thr Thr Asp Arg Ser Gly Ala Pro Thr Tyr Ser Trp Gly
                405                 410                 415

Glu Asn Asp Thr Asp Val Phe Val Leu Asn Asn Thr Arg Pro Pro Leu
            420                 425                 430

Gly Asn Trp Phe Gly Cys Thr Trp Met Asn Ser Thr Gly Phe Thr Lys
        435                 440                 445

Val Cys Gly Ala Pro Pro Cys Val Ile Gly Gly Ala Gly Asn Asn Thr
    450                 455                 460

Leu His Cys Pro Thr Asp Cys Phe Arg Lys His Pro Asp Ala Thr Tyr
465                 470                 475                 480

Ser Arg Cys Gly Ser Gly Pro Trp Ile Thr Pro Arg Cys Leu Val Asp
                485                 490                 495

Tyr Pro Tyr Arg Leu Trp His Tyr Pro Cys Thr Ile Asn Tyr Thr Ile
            500                 505                 510

Phe Lys Ile Arg Met Tyr Val Gly Gly Val Glu His Arg Leu Glu Ala
        515                 520                 525

Ala Cys Asn Trp Thr Arg Gly Glu Arg Cys Asp Leu Glu Asp Arg Asp
    530                 535                 540

Arg Ser Glu Leu Thr Pro Leu Leu Thr Thr Thr Gln Trp Gln Val
545                 550                 555                 560

Leu Pro Cys Ser Phe Thr Thr Leu Pro Ala Leu Ser Thr Gly Leu Ile
                565                 570                 575

His Leu His Gln Asn Ile Val Asp Val Gln Tyr Leu Tyr Gly Val Gly
            580                 585                 590

Ser Ser Ile Ala Ser Trp Ala Ile Lys Trp Glu Tyr Val Val Leu Leu
```

-continued

```
                595                 600                 605
Phe Leu Leu Ala Asp Ala Arg Val Cys Ser Cys Leu Trp Met Met
            610                 615                 620
Leu Leu Ile Ser Gln Ala Glu Ala Leu Glu Asn Leu Val Ile Leu
625                 630                 635                 640
Asn Ala Ala Ser Leu Ala Gly Thr His Gly Leu Val Ser Phe Leu Val
                645                 650                 655
Phe Phe Cys Phe Ala Trp Tyr Leu Lys Gly Lys Trp Val Pro Gly Ala
            660                 665                 670
Val Tyr Thr Phe Tyr Gly Met Trp Pro Leu Leu Leu Leu Leu Ala
            675                 680                 685
Leu Pro Gln Arg Ala Tyr Ala Leu Asp Thr Glu Val Ala Ala Ser Cys
        690                 695                 700
Gly Gly Val Val Leu Val Gly Leu Met Ala Leu Thr Leu Ser Pro Tyr
705                 710                 715                 720
Tyr Lys Arg Tyr Ile Ser Trp Cys Leu Trp Trp Leu Gln Tyr Phe Leu
                725                 730                 735
Thr Arg Val Glu Ala Gln Leu His Val Trp Ile Pro Pro Leu Asn Val
            740                 745                 750
Arg Gly Gly Arg Asp Ala Val Ile Leu Leu Met Cys Ala Val His Pro
        755                 760                 765
Thr Leu Val Phe Asp Ile Thr Lys Leu Leu Leu Ala Val Phe Gly Pro
770                 775                 780
Leu Trp Ile Leu Gln Ala Ser Leu Leu Lys Val Pro Tyr Phe Val Arg
785                 790                 795                 800
Val Gln Gly Leu Leu Arg Phe Cys Ala Leu Ala Arg Lys Met Ile Gly
                805                 810                 815
Gly His Tyr Val Gln Met Val Ile Ile Lys Leu Gly Ala Leu Thr Gly
            820                 825                 830
Thr Tyr Val Tyr Asn His Leu Thr Pro Leu Arg Asp Trp Ala His Asn
        835                 840                 845
Gly Leu Arg Asp Leu Ala Val Ala Val Glu Pro Val Phe Ser Gln
        850                 855                 860
Met Glu Thr Lys Leu Ile Thr Trp Gly Ala Asp Thr Ala Ala Cys Gly
865                 870                 875                 880
Asp Ile Ile Asn Gly Leu Pro Val Ser Ala Arg Arg Gly Arg Glu Ile
                885                 890                 895
Leu Leu Gly Pro Ala Asp Gly Met Val Ser Lys Gly Trp Arg Leu Leu
            900                 905                 910
Ala Pro Ile Thr Ala Tyr Ala Gln Gln Thr Arg Gly Leu Leu Gly Cys
        915                 920                 925
Ile Ile Thr Ser Leu Thr Gly Arg Asp Lys Asn Gln Val Glu Gly Glu
        930                 935                 940
Val Gln Ile Val Ser Thr Ala Ala Gln Thr Phe Leu Ala Thr Cys Ile
945                 950                 955                 960
Asn Gly Val Cys Trp Thr Val Tyr His Gly Ala Gly Thr Arg Thr Ile
                965                 970                 975
Ala Ser Pro Lys Gly Pro Val Ile Gln Met Tyr Thr Asn Val Asp Gln
            980                 985                 990
Asp Leu Val Gly Trp Pro Ala Pro Gln Gly Ser Arg Ser Leu Thr Pro
        995                 1000                1005
Cys Thr Cys Gly Ser Ser Asp Leu Tyr Leu Val Thr Arg His Ala Asp
        1010                1015                1020
```

-continued

```
Val Ile Pro Val Arg Arg Arg Gly Asp Ser Arg Gly Ser Leu Leu Ser
1025                1030                1035                1040

Pro Arg Pro Ile Ser Tyr Leu Lys Gly Ser Ser Gly Pro Leu Leu
            1045                1050                1055

Cys Pro Ala Gly His Ala Val Gly Ile Phe Arg Ala Val Cys Thr
            1060                1065                1070

Arg Gly Val Ala Lys Ala Val Asp Phe Ile Pro Val Glu Asn Leu Glu
            1075                1080                1085

Thr Thr Met Arg Ser Pro Val Phe Thr Asp Asn Ser Ser Pro Pro Val
            1090                1095                1100

Val Pro Gln Ser Phe Gln Val Ala His Leu His Ala Pro Thr Gly Ser
1105                1110                1115                1120

Gly Lys Ser Thr Lys Val Pro Ala Ala Tyr Ala Ala Gln Gly Tyr Lys
            1125                1130                1135

Val Leu Val Leu Asn Pro Ser Val Ala Ala Thr Leu Gly Phe Gly Ala
            1140                1145                1150

Tyr Met Ser Lys Ala His Gly Ile Asp Pro Asn Ile Arg Thr Gly Val
            1155                1160                1165

Arg Thr Ile Thr Thr Gly Ser Pro Ile Thr Tyr Ser Thr Tyr Gly Lys
            1170                1175                1180

Phe Leu Ala Asp Gly Gly Cys Ser Gly Gly Gly Tyr Asp Ile Ile Ile
1185                1190                1195                1200

Cys Asp Glu Cys His Ser Thr Asp Ala Thr Ser Ile Leu Gly Ile Gly
            1205                1210                1215

Thr Val Leu Asp Gln Ala Glu Thr Ala Gly Ala Arg Leu Val Val Leu
            1220                1225                1230

Ala Thr Ala Thr Pro Pro Gly Ser Val Thr Val Pro His Pro Asn Ile
            1235                1240                1245

Glu Glu Val Ala Leu Ser Thr Thr Gly Glu Ile Pro Phe Tyr Gly Lys
            1250                1255                1260

Ala Ile Pro Leu Glu Val Ile Lys Gly Gly Arg His Leu Ile Phe Cys
1265                1270                1275                1280

His Ser Lys Lys Lys Cys Asp Glu Leu Ala Ala Lys Leu Val Ala Leu
            1285                1290                1295

Gly Ile Asn Ala Val Ala Tyr Tyr Arg Gly Leu Asp Val Ser Val Ile
            1300                1305                1310

Pro Thr Ser Gly Asp Val Val Val Ala Thr Asp Ala Leu Met Thr
            1315                1320                1325

Gly Tyr Thr Gly Asp Phe Asp Ser Val Ile Asp Cys Asn Thr Cys Val
            1330                1335                1340

Thr Gln Thr Val Asp Phe Ser Leu Asp Pro Thr Phe Thr Ile Glu Thr
1345                1350                1355                1360

Ile Thr Leu Pro Gln Asp Ala Val Ser Arg Thr Gln Arg Arg Gly Arg
            1365                1370                1375

Thr Gly Arg Gly Lys Pro Gly Ile Tyr Arg Phe Val Ala Pro Gly Glu
            1380                1385                1390

Arg Pro Ser Gly Met Phe Asp Ser Ser Val Leu Cys Glu Cys Tyr Asp
            1395                1400                1405

Ala Gly Cys Ala Trp Tyr Glu Leu Thr Pro Ala Glu Thr Thr Val Arg
            1410                1415                1420

Leu Arg Ala Tyr Met Asn Thr Pro Gly Leu Pro Val Cys Gln Asp His
1425                1430                1435                1440
```

-continued

```
Leu Glu Phe Trp Glu Gly Val Phe Thr Gly Leu Thr His Ile Asp Ala
            1445                1450                1455

His Phe Leu Ser Gln Thr Lys Gln Ser Gly Glu Asn Leu Pro Tyr Leu
            1460                1465                1470

Val Ala Tyr Gln Ala Thr Val Cys Ala Arg Ala Gln Ala Pro Pro Pro
            1475                1480                1485

Ser Trp Asp Gln Met Trp Lys Cys Leu Ile Arg Leu Lys Pro Thr Leu
            1490                1495                1500

His Gly Pro Thr Pro Leu Leu Tyr Arg Leu Gly Ala Val Gln Asn Glu
1505                1510                1515                1520

Ile Thr Leu Thr His Pro Val Thr Lys Tyr Ile Met Thr Cys Met Ser
            1525                1530                1535

Ala Asp Leu Glu Val Val Thr Ser Thr Trp Val Leu Val Gly Gly Val
            1540                1545                1550

Leu Ala Ala Leu Ala Ala Tyr Cys Leu Ser Thr Gly Cys Val Val Ile
            1555                1560                1565

Val Gly Arg Val Val Leu Ser Gly Lys Pro Ala Ile Ile Pro Asp Arg
            1570                1575                1580

Glu Val Leu Tyr Arg Glu Phe Asp Glu Met Glu Glu Cys Ser Gln His
1585                1590                1595                1600

Leu Pro Tyr Ile Glu Gln Gly Met Met Leu Ala Glu Gln Phe Lys Gln
            1605                1610                1615

Lys Ala Leu Gly Leu Leu Gln Thr Ala Ser Arg Gln Ala Glu Val Ile
            1620                1625                1630

Ala Pro Ala Val Gln Thr Asn Trp Gln Lys Leu Glu Thr Phe Trp Ala
            1635                1640                1645

Lys His Met Trp Asn Phe Ile Ser Gly Ile Gln Tyr Leu Ala Gly Leu
            1650                1655                1660

Ser Thr Leu Pro Gly Asn Pro Ala Ile Ala Ser Leu Met Ala Phe Thr
1665                1670                1675                1680

Ala Ala Val Thr Ser Pro Leu Thr Thr Ser Gln Thr Leu Leu Phe Asn
            1685                1690                1695

Ile Leu Gly Gly Trp Val Ala Ala Gln Leu Ala Ala Pro Gly Ala Ala
            1700                1705                1710

Thr Ala Phe Val Gly Ala Gly Leu Ala Gly Ala Ala Ile Gly Ser Val
            1715                1720                1725

Gly Leu Gly Lys Val Leu Ile Asp Ile Leu Ala Gly Tyr Gly Ala Gly
            1730                1735                1740

Val Ala Gly Ala Leu Val Ala Phe Lys Ile Met Ser Gly Glu Val Pro
1745                1750                1755                1760

Ser Thr Glu Asp Leu Val Asn Leu Leu Pro Ala Ile Leu Ser Pro Gly
            1765                1770                1775

Ala Leu Val Val Gly Val Val Cys Ala Ala Ile Leu Arg Arg His Val
            1780                1785                1790

Gly Pro Gly Glu Gly Ala Val Gln Trp Met Asn Arg Leu Ile Ala Phe
            1795                1800                1805

Ala Ser Arg Gly Asn His Val Ser Pro Thr His Tyr Val Pro Glu Ser
            1810                1815                1820

Asp Ala Ala Ala Arg Val Thr Ala Ile Leu Ser Ser Leu Thr Val Thr
1825                1830                1835                1840

Gln Leu Leu Arg Arg Leu His Gln Trp Ile Ser Ser Glu Cys Thr Thr
            1845                1850                1855

Pro Cys Ser Gly Ser Trp Leu Arg Asp Ile Trp Asp Trp Ile Cys Glu
```

```
            1860                1865                1870
Val Leu Ser Asp Phe Lys Thr Trp Leu Lys Ala Lys Leu Met Pro Gln
        1875                1880                1885
Leu Pro Gly Ile Pro Phe Val Ser Cys Gln Arg Gly Tyr Lys Gly Val
    1890                1895                1900
Trp Arg Val Asp Gly Ile Met His Thr Arg Cys His Cys Gly Ala Glu
1905                1910                1915                1920
Ile Thr Gly His Val Lys Asn Gly Thr Met Arg Ile Val Gly Pro Arg
            1925                1930                1935
Thr Cys Arg Asn Met Trp Ser Gly Thr Phe Pro Ile Asn Ala Tyr Thr
                1940                1945                1950
Thr Gly Pro Cys Thr Pro Leu Pro Ala Pro Asn Tyr Thr Phe Ala Leu
            1955                1960                1965
Trp Arg Val Ser Ala Glu Glu Tyr Val Glu Ile Arg Gln Val Gly Asp
    1970                1975                1980
Phe His Tyr Val Thr Gly Met Thr Thr Asp Asn Leu Lys Cys Pro Cys
1985                1990                1995                2000
Gln Val Pro Ser Pro Glu Phe Phe Thr Glu Leu Asp Gly Val Arg Leu
            2005                2010                2015
His Arg Phe Ala Pro Pro Cys Lys Pro Leu Leu Arg Glu Glu Val Ser
            2020                2025                2030
Phe Arg Val Gly Leu His Glu Tyr Pro Val Gly Ser Gln Leu Pro Cys
            2035                2040                2045
Glu Pro Glu Pro Asp Val Ala Val Leu Thr Ser Met Leu Thr Asp Pro
    2050                2055                2060
Ser His Ile Thr Ala Glu Ala Ala Gly Arg Arg Leu Ala Arg Gly Ser
2065                2070                2075                2080
Pro Pro Ser Val Ala Ser Ser Ser Ala Ser Gln Leu Ser Ala Pro Ser
            2085                2090                2095
Leu Lys Ala Thr Cys Thr Ala Asn His Asp Ser Pro Asp Ala Glu Leu
            2100                2105                2110
Ile Glu Ala Asn Leu Leu Trp Arg Gln Glu Met Gly Gly Asn Ile Thr
            2115                2120                2125
Arg Val Glu Ser Glu Asn Lys Val Val Ile Leu Asp Ser Phe Asp Pro
        2130                2135                2140
Leu Val Ala Glu Glu Asp Glu Arg Glu Ile Ser Val Pro Ala Glu Ile
2145                2150                2155                2160
Leu Arg Lys Ser Arg Arg Phe Ala Gln Ala Leu Pro Val Trp Ala Arg
            2165                2170                2175
Pro Asp Tyr Asn Pro Pro Leu Val Glu Thr Trp Lys Lys Pro Asp Tyr
            2180                2185                2190
Glu Pro Pro Val Val His Gly Cys Pro Leu Pro Pro Pro Lys Ser Pro
            2195                2200                2205
Pro Val Pro Pro Pro Arg Lys Lys Arg Thr Val Val Leu Thr Glu Ser
            2210                2215                2220
Thr Leu Ser Thr Ala Leu Ala Glu Leu Ala Thr Arg Ser Phe Gly Ser
2225                2230                2235                2240
Ser Ser Thr Ser Gly Ile Thr Gly Asp Asn Thr Thr Thr Ser Ser Glu
            2245                2250                2255
Pro Ala Pro Ser Gly Cys Pro Pro Asp Ser Asp Ala Glu Ser Tyr Ser
            2260                2265                2270
Ser Met Pro Pro Leu Glu Gly Glu Pro Gly Asp Pro Asp Leu Ser Asp
            2275                2280                2285
```

-continued

```
Gly Ser Trp Ser Thr Val Ser Ser Glu Ala Asn Ala Glu Asp Val Val
            2290                2295                2300

Cys Cys Ser Met Ser Tyr Ser Trp Thr Gly Ala Leu Val Thr Pro Cys
2305                2310                2315                2320

Ala Ala Glu Glu Gln Lys Leu Pro Ile Asn Ala Leu Ser Asn Ser Leu
            2325                2330                2335

Leu Arg His His Asn Leu Val Tyr Ser Thr Thr Ser Arg Ser Ala Cys
            2340                2345                2350

Gln Arg Gln Lys Lys Val Thr Phe Asp Arg Leu Gln Val Leu Asp Ser
            2355                2360                2365

His Tyr Gln Asp Val Leu Lys Glu Val Lys Ala Ala Ser Lys Val
            2370                2375                2380

Lys Ala Asn Leu Leu Ser Val Glu Glu Ala Cys Ser Leu Thr Pro Pro
2385                2390                2395                2400

His Ser Ala Lys Ser Lys Phe Gly Tyr Gly Ala Lys Asp Val Arg Cys
            2405                2410                2415

His Ala Arg Lys Ala Val Thr His Ile Asn Ser Val Trp Lys Asp Leu
            2420                2425                2430

Leu Glu Asp Asn Val Thr Pro Ile Asp Thr Thr Ile Met Ala Lys Asn
            2435                2440                2445

Glu Val Phe Cys Val Gln Pro Glu Lys Gly Gly Arg Lys Pro Ala Arg
            2450                2455                2460

Leu Ile Val Phe Pro Asp Leu Gly Val Arg Val Cys Glu Lys Met Ala
2465                2470                2475                2480

Leu Tyr Asp Val Val Thr Lys Leu Pro Leu Ala Val Met Gly Ser Ser
            2485                2490                2495

Tyr Gly Phe Gln Tyr Ser Pro Gly Gln Arg Val Glu Phe Leu Val Gln
            2500                2505                2510

Ala Trp Lys Ser Lys Lys Thr Pro Met Gly Phe Ser Tyr Asp Thr Arg
            2515                2520                2525

Cys Phe Asp Ser Thr Val Thr Glu Ser Asp Ile Arg Thr Glu Glu Ala
            2530                2535                2540

Ile Tyr Gln Cys Cys Asp Leu Asp Pro Gln Ala Arg Val Ala Ile Lys
2545                2550                2555                2560

Ser Leu Thr Glu Arg Leu Tyr Val Gly Gly Pro Leu Thr Asn Ser Arg
            2565                2570                2575

Gly Glu Asn Cys Gly Tyr Arg Arg Cys Arg Ala Ser Gly Val Leu Thr
            2580                2585                2590

Thr Ser Cys Gly Asn Thr Leu Thr Cys Tyr Ile Lys Ala Arg Ala Ala
            2595                2600                2605

Cys Arg Ala Ala Gly Leu Gln Asp Cys Thr Met Leu Val Cys Gly Asp
            2610                2615                2620

Asp Leu Val Val Ile Cys Glu Ser Ala Gly Val Gln Glu Asp Ala Ala
2625                2630                2635                2640

Ser Leu Arg Ala Phe Thr Glu Ala Met Thr Arg Tyr Ser Ala Pro Pro
            2645                2650                2655

Gly Asp Pro Pro Gln Pro Glu Tyr Asp Leu Glu Leu Ile Thr Ser Cys
            2660                2665                2670

Ser Ser Asn Val Ser Val Ala His Asp Gly Ala Gly Lys Arg Val Tyr
            2675                2680                2685

Tyr Leu Thr Arg Asp Pro Thr Thr Pro Leu Ala Arg Ala Ala Trp Glu
            2690                2695                2700
```

```
Thr Ala Arg His Thr Pro Val Asn Ser Trp Leu Gly Asn Ile Ile Met
2705                2710                2715                2720

Phe Ala Pro Thr Leu Trp Ala Arg Met Ile Leu Met Thr His Phe Phe
                2725                2730                2735

Ser Val Leu Ile Ala Arg Asp Gln Leu Glu Gln Ala Leu Asp Cys Glu
            2740                2745                2750

Ile Tyr Gly Ala Cys Tyr Ser Ile Glu Pro Leu Asp Leu Pro Pro Ile
        2755                2760                2765

Ile Gln Arg Leu
    2770
```

(2) INFORMATION FOR SEQ ID NO:90:

(i) SEQUENCE CHARACTERISTICS:
        (A) LENGTH: 407 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (B) CLONE: CA216a (ix) FEATURE:
        (A) NAME/KEY: CDS
        (B) LOCATION: 3..407

(xi) SEQUENCE DESCRIPTION: SEQ ID NO:90:

```
CC CGG CGT AGG TCG CGC AAT TTG GGT AAG GTC ATC GAT ACC CTT ACG        47
   Arg Arg Arg Ser Arg Asn Leu Gly Lys Val Ile Asp Thr Leu Thr
   1               5                   10                  15

TGC GGC TTC GCC GAC CTC ATG GGG TAC ATA CCG CTC GTC GGC GCC CCT       95
Cys Gly Phe Ala Asp Leu Met Gly Tyr Ile Pro Leu Val Gly Ala Pro
                20                  25                  30

CTT GGA GGC GCT GCC AGG GCC CTG GCG CAT GGC GTC CGG GTT CTG GAA      143
Leu Gly Gly Ala Ala Arg Ala Leu Ala His Gly Val Arg Val Leu Glu
            35                  40                  45

GAC GGC GTG AAC TAT GCA ACA GGG AAC CTT CCT GGT TGC TCT TTC TCT      191
Asp Gly Val Asn Tyr Ala Thr Gly Asn Leu Pro Gly Cys Ser Phe Ser
        50                  55                  60

ATC TTC CTT CTG GCC CTG CTC TCT TGC TTG ACT GTG CCC GCT TCG GCC      239
Ile Phe Leu Leu Ala Leu Leu Ser Cys Leu Thr Val Pro Ala Ser Ala
    65                  70                  75

TAC CAA GTG CGC AAC TCC ACG GGG CTT TAC CAC GTC ACC AAT GAT TGC      287
Tyr Gln Val Arg Asn Ser Thr Gly Leu Tyr His Val Thr Asn Asp Cys
80                  85                  90                  95

CCT AAC TCG AGT ATT GTG TAC GAG GCG GCC GAT GCC ATC CTG CAC ACT      335
Pro Asn Ser Ser Ile Val Tyr Glu Ala Ala Asp Ala Ile Leu His Thr
                100                 105                 110

CCG GGG TGC GTC CCT TGC GTT CGT GAG GGC AAC GCC TCG AGG TGT TGG      383
Pro Gly Cys Val Pro Cys Val Arg Glu Gly Asn Ala Ser Arg Cys Trp
            115                 120                 125

GTG GCG ATG ACC CCT ACG GTG GCC                                     407
Val Ala Met Thr Pro Thr Val Ala
        130                 135
```

(2) INFORMATION FOR SEQ ID NO:91:

(i) SEQUENCE CHARACTERISTICS:
        (A) LENGTH: 135 amino acids
        (B) TYPE: amino acid
        (D) TOPOLOGY: linear (ii) MOLECULE TYPE: protein (xi) SEQUENCE DESCRIPTION: SEQ ID NO:91:

```
Arg Arg Arg Ser Arg Asn Leu Gly Lys Val Ile Asp Thr Leu Thr Cys
  1               5                  10                  15

Gly Phe Ala Asp Leu Met Gly Tyr Ile Pro Leu Val Gly Ala Pro Leu
                 20                  25                  30

Gly Gly Ala Ala Arg Ala Leu Ala His Gly Val Arg Val Leu Glu Asp
             35                  40                  45

Gly Val Asn Tyr Ala Thr Gly Asn Leu Pro Gly Cys Ser Phe Ser Ile
         50                  55                  60

Phe Leu Leu Ala Leu Leu Ser Cys Leu Thr Val Pro Ala Ser Ala Tyr
 65                  70                  75                  80

Gln Val Arg Asn Ser Thr Gly Leu Tyr His Val Thr Asn Asp Cys Pro
                 85                  90                  95

Asn Ser Ser Ile Val Tyr Glu Ala Ala Asp Ala Ile Leu His Thr Pro
                100                 105                 110

Gly Cys Val Pro Cys Val Arg Glu Gly Asn Ala Ser Arg Cys Trp Val
            115                 120                 125

Ala Met Thr Pro Thr Val Ala
        130                 135
```

(2) INFORMATION FOR SEQ ID NO:92:

(i) SEQUENCE CHARACTERISTICS:
(A) LENGTH: 509 base pairs
(B) TYPE: nucleic acid
(C) STRANDEDNESS: single
(D) TOPOLOGY: linear (ii) MOLECULE TYPE: cDNA (vii) IMMEDIATE SOURCE:
(B) CLONE: CA290a (ix) FEATURE:
(A) NAME/KEY: CDS
(B) LOCATION: 3..509

(xi) SEQUENCE DESCRIPTION: SEQ ID NO:92:

```
AA AAA AAA AAC AAA CGT AAC ACC AAC CGT CGC CCA CAG GAC GTC AAG         47
   Lys Lys Asn Lys Arg Asn Thr Asn Arg Arg Pro Gln Asp Val Lys
     1               5                  10                  15

TTC CCG GGT GGC GGT CAG ATC GTT GGT GGA GTT TAC TTG TTG CCG CGC        95
Phe Pro Gly Gly Gly Gln Ile Val Gly Gly Val Tyr Leu Leu Pro Arg
                 20                  25                  30

AGG GGC CCT AGA TTG GGT GTG CGC GCG ACG AGA AAG ACT TCC GAG CGG       143
Arg Gly Pro Arg Leu Gly Val Arg Ala Thr Arg Lys Thr Ser Glu Arg
             35                  40                  45

TCG CAA CCT CGA GGT AGA CGT CAG CCT ATC CCC AAG GCT CGT CGG CCC       191
Ser Gln Pro Arg Gly Arg Arg Gln Pro Ile Pro Lys Ala Arg Arg Pro
         50                  55                  60

GAG GGC AGG ACC TGG GCT CAG CCC GGG TAC CCT TGG CCC CTC TAT GGC       239
Glu Gly Arg Thr Trp Ala Gln Pro Gly Tyr Pro Trp Pro Leu Tyr Gly
     65                  70                  75

AAT GAG GGC TGC GGG TGG GCG GGA TGG CTC CTG TCT CCC CGT GGC TCT       287
Asn Glu Gly Cys Gly Trp Ala Gly Trp Leu Leu Ser Pro Arg Gly Ser
 80                  85                  90                  95

CGG CCT AGC TGG GGC CCC ACA GAC CCC CGG CGT AGG TCG CGC AAT TTG       335
Arg Pro Ser Trp Gly Pro Thr Asp Pro Arg Arg Arg Ser Arg Asn Leu
                100                 105                 110
```

```
GGT AAG GTC ATC GAT ACC CTT ACG TGC GGC TTC GCC GAC CTC ATG GGG      383
Gly Lys Val Ile Asp Thr Leu Thr Cys Gly Phe Ala Asp Leu Met Gly
            115                 120                 125

TAC ATA CCG CTC GTC GGC GCC CCT CTT GGA GGC GCT GCC AGG GCC CTG      431
Tyr Ile Pro Leu Val Gly Ala Pro Leu Gly Gly Ala Ala Arg Ala Leu
            130                 135                 140

GCG CAT GGC GTC CGG GTT CTG GAA GAC GGC GTG AAC TAT GCA ACA GGG      479
Ala His Gly Val Arg Val Leu Glu Asp Gly Val Asn Tyr Ala Thr Gly
    145                 150                 155

AAC CTT CCT GGT TGC TCT TTC TCT ACC TTC                              509
Asn Leu Pro Gly Cys Ser Phe Ser Thr Phe
160             165
```

(2) INFORMATION FOR SEQ ID NO:93:

(i) SEQUENCE CHARACTERISTICS:
        (A) LENGTH: 169 amino acids
        (B) TYPE: amino acid
        (D) TOPOLOGY: linear (ii) MOLECULE TYPE: protein (xi) SEQUENCE DESCRIPTION: SEQ ID NO:93:

```
Lys Lys Asn Lys Arg Asn Thr Asn Arg Arg Pro Gln Asp Val Lys Phe
  1               5                  10                  15

Pro Gly Gly Gly Gln Ile Val Gly Gly Val Tyr Leu Leu Pro Arg Arg
                 20                  25                  30

Gly Pro Arg Leu Gly Val Arg Ala Thr Arg Lys Thr Ser Glu Arg Ser
            35                  40                  45

Gln Pro Arg Gly Arg Arg Gln Pro Ile Pro Lys Ala Arg Arg Pro Glu
    50                  55                  60

Gly Arg Thr Trp Ala Gln Pro Gly Tyr Pro Trp Pro Leu Tyr Gly Asn
65                  70                  75                  80

Glu Gly Cys Gly Trp Ala Gly Trp Leu Leu Ser Pro Arg Gly Ser Arg
                85                  90                  95

Pro Ser Trp Gly Pro Thr Asp Pro Arg Arg Arg Ser Arg Asn Leu Gly
                100                 105                 110

Lys Val Ile Asp Thr Leu Thr Cys Gly Phe Ala Asp Leu Met Gly Tyr
            115                 120                 125

Ile Pro Leu Val Gly Ala Pro Leu Gly Gly Ala Ala Arg Ala Leu Ala
            130                 135                 140

His Gly Val Arg Val Leu Glu Asp Gly Val Asn Tyr Ala Thr Gly Asn
145                 150                 155                 160

Leu Pro Gly Cys Ser Phe Ser Thr Phe
                165
```

(2) INFORMATION FOR SEQ ID NO:94:

(i) SEQUENCE CHARACTERISTICS:
        (A) LENGTH: 665 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (B) CLONE: ag30a (xi) SEQUENCE DESCRIPTION: SEQ ID NO:94:

```
CGCAGAAAGC GTCTAGCCAT GGCGTTAGTA TGAGTGTCGT GCAGCCTCCA GGACCCCCCC      60
```

-continued

```
TCCCGGGAGA GCCATAGTGG TCTGCGGAAC CGGTGAGTAC ACCGGAATTG CCAGGACGAC      120

CGGGTCCTTT CTTGGATCAA CCCGCTCAAT GCCTGGAGAT TTGGGCGTGC CCCCGCAAGA      180

CTGCTAGCCG AGTAGTGTTG GGTCGCGAAA GGCCTTGTGG TACTGCCTGA TAGGGTGCTT      240

GCGAGTGCCC CGGGAGGTCT CGTAGACCGT GCACCATGAG CACGAATCCT AAACCTCAAA      300

AAAAAAACAA ACGTAACACC AACCGTCGCC CACAGGACGT CAAGTTCCCG GGTGGCGGTC      360

AGATCGTTGG TGGAGTTTAC TTGTTGCCGC GCAGGGGCCC TAGATTGGGT GTGCGCGCGA      420

CGAGAAAGAC TTCCGAGCGG TCGCAACCTC GAGGTAGACG TCAGCCTATC CCAAGGCTC       480

GTCGGCCCGA GGGCAGGACC TGGGCTCAGC CCGGGTACCC TTGGCCCCTC TATGGCAATG      540

AGGGCTGCGG GTGGGCGGGA TGGCTCCTGT CTCCCCGTGG CTCTCGGCCT AGCTGGGGCC      600

CCACAGACCC CCGGCGTAGG TCGCGCAATT TGGGTAAGGT CATCGATACC CTTACGTGCG      660

GCTTC                                                                  665
```

(2) INFORMATION FOR SEQ ID NO:95:

(i) SEQUENCE CHARACTERISTICS:
        (A) LENGTH: 665 base pairs
        (B) TYPE: nucleic acid
        (C) STRANDEDNESS: single
        (D) TOPOLOGY: linear (ii) MOLECULE TYPE: cDNA (iv) ANTI-SENSE: YES (vii) IMMEDIATE SOURCE:
        (B) CLONE: ag30a (xi) SEQUENCE DESCRIPTION: SEQ ID NO:95:

```
GAAGCCGCAC GTAAGGGTAT CGATGACCTT ACCCAAATTG CGCGACCTAC GCCGGGGGTC      60

TGTGGGGCCC CAGCTAGGCC GAGAGCCACG GGGAGACAGG AGCCATCCCG CCCACCCGCA      120

GCCCTCATTG CCATAGAGGG GCCAAGGGTA CCCGGGCTGA GCCCAGGTCC TGCCCTCGGG      180

CCGACGAGCC TTGGGGATAG GCTGACGTCT ACCTCGAGGT TGCGACCGCT CGGAAGTCTT      240

TCTCGTCGCG CGCACACCCA ATCTAGGGCC CCTGCGCGGC AACAAGTAAA CTCCACCAAC      300

GATCTGACCG CCACCCGGGA ACTTGACGTC CTGTGGGCGA CGGTTGGTGT TACGTTTGTT      360

TTTTTTTTGA GGTTTAGGAT TCGTGCTCAT GGTGCACGGT CTACGAGACC TCCCGGGGCA      420

CTCGCAAGCA CCCTATCAGG CAGTACCACA AGGCCTTTCG CGACCCAACA CTACTCGGCT      480

AGCAGTCTTG CGGGGCACG CCCAAATCTC CAGGCATTGA GCGGGTTGAT CCAAGAAAGG       540

ACCCGGTCGT CCTGGCAATT CCGGTGTACT CACCGGTTCC GCAGACCACT ATGGCTCTCC      600

CGGGAGGGGG GGTCCTGGAG GCTGCACGAC ACTCATACTA ACGCCATGGC TAGACGCTTT      660

CTGCG                                                                  665
```

(2) INFORMATION FOR SEQ ID NO:96:

(i) SEQUENCE CHARACTERISTICS:
        (A) LENGTH: 665 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (B) CLONE: ag30a (ix) FEATURE:

(A) NAME/KEY: CDS
            (B) LOCATION: 19..30

(xi) SEQUENCE DESCRIPTION: SEQ ID NO:96:

CGCAGAAAGC GTCTAGCC ATG GCG TTA GTA TGAGTGTCGT GCAGCCTCCA            50
                    Met Ala Leu Val
                     1

GGACCCCCCC TCCCGGGAGA GCCATAGTGG TCTGCGGAAC CGGTGAGTAC ACCGGAATTG   110

CCAGGACGAC CGGGTCCTTT CTTGGATCAA CCCGCTCAAT GCCTGGAGAT TTGGGCGTGC   170

CCCCGCAAGA CTGCTAGCCG AGTAGTGTTG GGTCGCGAAA GGCCTTGTGG TACTGCCTGA   230

TAGGGTGCTT GCGAGTGCCC CGGGAGGTCT CGTAGACCGT GCACCATGAG CACGAATCCT   290

AAACCTCAAA AAAAAAACAA ACGTAACACC AACCGTCGCC CACAGGACGT CAAGTTCCCG   350

GGTGGCGGTC AGATCGTTGG TGGAGTTTAC TTGTTGCCGC GCAGGGGCCC TAGATTGGGT   410

GTGCGCGCGA CGAGAAAGAC TTCCGAGCGG TCGCAACCTC GAGGTAGACG TCAGCCTATC   470

CCCAAGGCTC GTCGGCCCGA GGGCAGGACC TGGGCTCAGC CCGGGTACCC TTGGCCCCTC   530

TATGGCAATG AGGGCTGCGG GTGGGCGGGA TGGCTCCTGT CTCCCCGTGG CTCTCGGCCT   590

AGCTGGGGCC CCACAGACCC CCGGCGTAGG TCGCGCAATT TGGGTAAGGT CATCGATACC   650

CTTACGTGCG GCTTC                                                    665

(2) INFORMATION FOR SEQ ID NO:97:

(i) SEQUENCE CHARACTERISTICS:
         (A) LENGTH: 4 amino acids
         (B) TYPE: amino acid
         (D) TOPOLOGY: linear (ii) MOLECULE TYPE: protein (xi) SEQUENCE DESCRIPTION: SEQ ID NO:97:

Met Ala Leu Val
 1

(2) INFORMATION FOR SEQ ID NO:98:

(i) SEQUENCE CHARACTERISTICS:
         (A) LENGTH: 665 base pairs
         (B) TYPE: nucleic acid
         (C) STRANDEDNESS: single
         (D) TOPOLOGY: linear (ii) MOLECULE TYPE: cDNA (vii) IMMEDIATE SOURCE:
         (B) CLONE: ag30a (ix) FEATURE:
         (A) NAME/KEY: CDS
         (B) LOCATION: 30..74

(xi) SEQUENCE DESCRIPTION: SEQ ID NO:98:

CGCAGAAAGC GTCTAGCCAT GGCGTTAGT ATG AGT GTC GTG CAG CCT CCA GGA    53
                                Met Ser Val Val Gln Pro Pro Gly
                                 1               5

CCC CCC CTC CCG GGA GAG CCA TAGTGGTCTG CGGAACCGGT GAGTACACCG       104
Pro Pro Leu Pro Gly Glu Pro
    10              15

GAATTGCCAG GACGACCGGG TCCTTTCTTG GATCAACCCG CTCAATGCCT GGAGATTTGG   164

GCGTGCCCCC GCAAGACTGC TAGCCGAGTA GTGTTGGGTC GCGAAAGGCC TTGTGGTACT   224

GCCTGATAGG GTGCTTGCGA GTGCCCCGGG AGGTCTCGTA GACCGTGCAC CATGAGCACG   284

```
AATCCTAAAC CTCAAAAAAA AAACAAACGT AACACCAACC GTCGCCCACA GGACGTCAAG        344

TTCCCGGGTG GCGGTCAGAT CGTTGGTGGA GTTTACTTGT TGCCGCGCAG GGGCCCTAGA        404

TTGGGTGTGC GCGCGACGAG AAAGACTTCC GAGCGGTCGC AACCTCGAGG TAGACGTCAG        464

CCTATCCCCA AGGCTCGTCG GCCCGAGGGC AGGACCTGGG CTCAGCCCGG GTACCCTTGG        524

CCCCTCTATG GCAATGAGGG CTGCGGGTGG GCGGGATGGC TCCTGTCTCC CCGTGGCTCT        584

CGGCCTAGCT GGGGCCCCAC AGACCCCCGG CGTAGGTCGC GCAATTTGGG TAAGGTCATC        644

GATACCCTTA CGTGCGGCTT C                                                  665

(2) INFORMATION FOR SEQ ID NO:99:

(i) SEQUENCE CHARACTERISTICS:
        (A) LENGTH: 15 amino acids
        (B) TYPE: amino acid
        (D) TOPOLOGY: linear (ii) MOLECULE TYPE: protein (xi) SEQUENCE DESCRIPTION: SEQ ID NO:99:

Met Ser Val Val Gln Pro Pro Gly Pro Pro Leu Pro Gly Glu Pro
 1               5                  10                  15

(2) INFORMATION FOR SEQ ID NO:100:

(i) SEQUENCE CHARACTERISTICS:
        (A) LENGTH: 665 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (B) CLONE: ag30a (ix) FEATURE:
        (A) NAME/KEY: CDS
        (B) LOCATION: 149..184

(xi) SEQUENCE DESCRIPTION: SEQ ID NO:100:

CGCAGAAAGC GTCTAGCCAT GGCGTTAGTA TGAGTGTCGT GCAGCCTCCA GGACCCCCCC         60

TCCCGGGAGA GCCATAGTGG TCTGCGGAAC CGGTGAGTAC ACCGGAATTG CCAGGACGAC        120

CGGGTCCTTT CTTGGATCAA CCCGCTCA ATG CCT GGA GAT TTG GGC GTG CCC          172
                                Met Pro Gly Asp Leu Gly Val Pro
                                  1               5

CCG CAA GAC TGC TAGCCGAGTA GTGTTGGGTC GCGAAAGGCC TTGTGGTACT              224
Pro Gln Asp Cys
    10

GCCTGATAGG GTGCTTGCGA GTGCCCCGGG AGGTCTCGTA GACCGTGCAC CATGAGCACG        284

AATCCTAAAC CTCAAAAAAA AAACAAACGT AACACCAACC GTCGCCCACA GGACGTCAAG        344

TTCCCGGGTG GCGGTCAGAT CGTTGGTGGA GTTTACTTGT TGCCGCGCAG GGGCCCTAGA        404

TTGGGTGTGC GCGCGACGAG AAAGACTTCC GAGCGGTCGC AACCTCGAGG TAGACGTCAG        464

CCTATCCCCA AGGCTCGTCG GCCCGAGGGC AGGACCTGGG CTCAGCCCGG GTACCCTTGG        524

CCCCTCTATG GCAATGAGGG CTGCGGGTGG GCGGGATGGC TCCTGTCTCC CCGTGGCTCT        584

CGGCCTAGCT GGGGCCCCAC AGACCCCCGG CGTAGGTCGC GCAATTTGGG TAAGGTCATC        644

GATACCCTTA CGTGCGGCTT C                                                  665
```

(2) INFORMATION FOR SEQ ID NO:101:

(i) SEQUENCE CHARACTERISTICS:
        (A) LENGTH: 12 amino acids
        (B) TYPE: amino acid
        (D) TOPOLOGY: linear (ii) MOLECULE TYPE: protein (xi) SEQUENCE DESCRIPTION: SEQ ID NO:101:

```
Met Pro Gly Asp Leu Gly Val Pro Pro Gln Asp Cys
 1               5                  10
```

(2) INFORMATION FOR SEQ ID NO:102:

(i) SEQUENCE CHARACTERISTICS:
        (A) LENGTH: 665 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (B) CLONE: ag30a (ix) FEATURE:
        (A) NAME/KEY: CDS
        (B) LOCATION: 234..665

(xi) SEQUENCE DESCRIPTION: SEQ ID NO:102:

```
CGCAGAAAGC GTCTAGCCAT GGCGTTAGTA TGAGTGTCGT GCAGCCTCCA GGACCCCCCC      60

TCCCGGGAGA GCCATAGTGG TCTGCGGAAC CGGTGAGTAC ACCGGAATTG CCAGGACGAC     120

CGGGTCCTTT CTTGGATCAA CCCGCTCAAT GCCTGGAGAT TTGGGCGTGC CCCCGCAAGA     180

CTGCTAGCCG AGTAGTGTTG GGTCGCGAAA GGCCTTGTGG TACTGCCTGA TAG GGT       236
                                                         Gly
                                                          1

GCT TGC GAG TGC CCC GGG AGG TCT CGT AGA CCG TGC ACC ATG AGC ACG       284
Ala Cys Glu Cys Pro Gly Arg Ser Arg Arg Pro Cys Thr Met Ser Thr
         5                  10                  15

AAT CCT AAA CCT CAA AAA AAA AAC AAA CGT AAC ACC AAC CGT CGC CCA       332
Asn Pro Lys Pro Gln Lys Lys Asn Lys Arg Asn Thr Asn Arg Arg Pro
         20                  25                  30

CAG GAC GTC AAG TTC CCG GGT GGC GGT CAG ATC GTT GGT GGA GTT TAC       380
Gln Asp Val Lys Phe Pro Gly Gly Gly Gln Ile Val Gly Gly Val Tyr
     35                  40                  45

TTG TTG CCG CGC AGG GGC CCT AGA TTG GGT GTG CGC GCG ACG AGA AAG       428
Leu Leu Pro Arg Arg Gly Pro Arg Leu Gly Val Arg Ala Thr Arg Lys
 50                  55                  60                  65

ACT TCC GAG CGG TCG CAA CCT CGA GGT AGA CGT CAG CCT ATC CCC AAG       476
Thr Ser Glu Arg Ser Gln Pro Arg Gly Arg Arg Gln Pro Ile Pro Lys
                 70                  75                  80

GCT CGT CGG CCC GAG GGC AGG ACC TGG GCT CAG CCC GGG TAC CCT TGG       524
Ala Arg Arg Pro Glu Gly Arg Thr Trp Ala Gln Pro Gly Tyr Pro Trp
             85                  90                  95

CCC CTC TAT GGC AAT GAG GGC TGC GGG TGG GCG GGA TGG CTC CTG TCT       572
Pro Leu Tyr Gly Asn Glu Gly Cys Gly Trp Ala Gly Trp Leu Leu Ser
         100                 105                 110

CCC CGT GGC TCT CGG CCT AGC TGG GGC CCC ACA GAC CCC CGG CGT AGG       620
Pro Arg Gly Ser Arg Pro Ser Trp Gly Pro Thr Asp Pro Arg Arg Arg
     115                 120                 125

TCG CGC AAT TTG GGT AAG GTC ATC GAT ACC CTT ACG TGC GGC TTC            665
Ser Arg Asn Leu Gly Lys Val Ile Asp Thr Leu Thr Cys Gly Phe
 130                 135                 140
```

(2) INFORMATION FOR SEQ ID NO:103:

(i) SEQUENCE CHARACTERISTICS:
        (A) LENGTH: 144 amino acids
        (B) TYPE: amino acid
        (D) TOPOLOGY: linear (ii) MOLECULE TYPE: protein (xi) SEQUENCE DESCRIPTION: SEQ ID NO:103:

```
Gly Ala Cys Glu Cys Pro Gly Arg Ser Arg Arg Pro Cys Thr Met Ser
  1               5                  10                  15

Thr Asn Pro Lys Pro Gln Lys Lys Asn Lys Arg Asn Thr Asn Arg Arg
             20                  25                  30

Pro Gln Asp Val Lys Phe Pro Gly Gly Gly Gln Ile Val Gly Gly Val
         35                  40                  45

Tyr Leu Leu Pro Arg Arg Gly Pro Arg Leu Gly Val Arg Ala Thr Arg
     50                  55                  60

Lys Thr Ser Glu Arg Ser Gln Pro Arg Gly Arg Arg Gln Pro Ile Pro
 65                  70                  75                  80

Lys Ala Arg Arg Pro Glu Gly Arg Thr Trp Ala Gln Pro Gly Tyr Pro
                 85                  90                  95

Trp Pro Leu Tyr Gly Asn Glu Gly Cys Gly Trp Ala Gly Trp Leu Leu
            100                 105                 110

Ser Pro Arg Gly Ser Arg Pro Ser Trp Gly Pro Thr Asp Pro Arg Arg
        115                 120                 125

Arg Ser Arg Asn Leu Gly Lys Val Ile Asp Thr Leu Thr Cys Gly Phe
    130                 135                 140
```

(2) INFORMATION FOR SEQ ID NO:104:

(i) SEQUENCE CHARACTERISTICS:
        (A) LENGTH: 355 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (B) CLONE: CA205a (ix) FEATURE:
        (A) NAME/KEY: CDS
        (B) LOCATION: 1..33

(xi) SEQUENCE DESCRIPTION: SEQ ID NO:104:

```
GTC TTG GGT CGC GAA AGG CCT TGT GGT ACT GCC TGATAGGGTG CTTGCGAGTG      53
Val Leu Gly Arg Glu Arg Pro Cys Gly Thr Ala
  1               5                  10

CCCCGGGAGG TCTCGTAGAC CGTGCACCAT GAGCACGAAT CCTAAACCTC AAAAAAAAAA     113

CAAACGTAAC ACCAACCGTC GCCCACAGGA CGTCAAGTTC CCGGGTGGCG GTCAGATCGT     173

TGGTGGAGTT TACTTGTTGC CGCGCAGGGG CCCTAGATTG GGTGTGCGCG CGACGAGAAA     233

GACTTCCGAG CGGTCGCAAC CTCGAGGTAG ACGTCAGCCT ATCCCCAAGG CTCGTCGGCC     293

CGAGGGCAGG ACCTGGGCTC AGCCCGGGTA CCCTTGGCCC CTCTATGGCA ATGAGGGCTG     353

CG                                                                    355
```

(2) INFORMATION FOR SEQ ID NO:105:

(i) SEQUENCE CHARACTERISTICS:
            (A) LENGTH: 11 amino acids
            (B) TYPE: amino acid
            (D) TOPOLOGY: linear (ii) MOLECULE TYPE: protein (xi) SEQUENCE DESCRIPTION: SEQ ID NO:105:

Val Leu Gly Arg Glu Arg Pro Cys Gly Thr Ala
 1               5                  10

(2) INFORMATION FOR SEQ ID NO:106:

(i) SEQUENCE CHARACTERISTICS:
            (A) LENGTH: 355 base pairs
            (B) TYPE: nucleic acid
            (C) STRANDEDNESS: single
            (D) TOPOLOGY: linear (ii) MOLECULE TYPE: cDNA (vii) IMMEDIATE SOURCE:
            (B) CLONE: CA205a (ix) FEATURE:
            (A) NAME/KEY: CDS
            (B) LOCATION: 40..354

(xi) SEQUENCE DESCRIPTION: SEQ ID NO:106:

GTCTTGGGTC GCGAAAGGCC TTGTGGTACT GCCTGATAG GGT GCT TGC GAG TGC         54
                                           Gly Ala Cys Glu Cys
                                             1               5

CCC GGG AGG TCT CGT AGA CCG TGC ACC ATG AGC ACG AAT CCT AAA CCT      102
Pro Gly Arg Ser Arg Arg Pro Cys Thr Met Ser Thr Asn Pro Lys Pro
             10                  15                  20

CAA AAA AAA AAC AAA CGT AAC ACC AAC CGT CGC CCA CAG GAC GTC AAG      150
Gln Lys Lys Asn Lys Arg Asn Thr Asn Arg Arg Pro Gln Asp Val Lys
             25                  30                  35

TTC CCG GGT GGC GGT CAG ATC GTT GGT GGA GTT TAC TTG TTG CCG CGC      198
Phe Pro Gly Gly Gly Gln Ile Val Gly Gly Val Tyr Leu Leu Pro Arg
         40                  45                  50

AGG GGC CCT AGA TTG GGT GTG CGC GCG ACG AGA AAG ACT TCC GAG CGG      246
Arg Gly Pro Arg Leu Gly Val Arg Ala Thr Arg Lys Thr Ser Glu Arg
 55                  60                  65

TCG CAA CCT CGA GGT AGA CGT CAG CCT ATC CCC AAG GCT CGT CGG CCC      294
Ser Gln Pro Arg Gly Arg Arg Gln Pro Ile Pro Lys Ala Arg Arg Pro
 70                  75                  80                  85

GAG GGC AGG ACC TGG GCT CAG CCC GGG TAC CCT TGG CCC CTC TAT GGC      342
Glu Gly Arg Thr Trp Ala Gln Pro Gly Tyr Pro Trp Pro Leu Tyr Gly
                 90                  95                 100

AAT GAG GGC TGC G                                                    355
Asn Glu Gly Cys
            105

(2) INFORMATION FOR SEQ ID NO:107:

(i) SEQUENCE CHARACTERISTICS:
            (A) LENGTH: 105 amino acids
            (B) TYPE: amino acid
            (D) TOPOLOGY: linear (ii) MOLECULE TYPE: protein (xi) SEQUENCE DESCRIPTION: SEQ ID NO:107:

Gly Ala Cys Glu Cys Pro Gly Arg Ser Arg Arg Pro Cys Thr Met Ser
 1               5                  10                  15

```
Thr Asn Pro Lys Pro Gln Lys Lys Asn Lys Arg Asn Thr Asn Arg Arg
         20                  25                  30

Pro Gln Asp Val Lys Phe Pro Gly Gly Gly Gln Ile Val Gly Gly Val
             35                  40                  45

Tyr Leu Leu Pro Arg Arg Gly Pro Arg Leu Gly Val Arg Ala Thr Arg
     50                  55                  60

Lys Thr Ser Glu Arg Ser Gln Pro Arg Gly Arg Arg Gln Pro Ile Pro
 65                  70                  75                  80

Lys Ala Arg Arg Pro Glu Gly Arg Thr Trp Ala Gln Pro Gly Tyr Pro
                 85                  90                  95

Trp Pro Leu Tyr Gly Asn Glu Gly Cys
            100                 105
```

(2) INFORMATION FOR SEQ ID NO:108:

(i) SEQUENCE CHARACTERISTICS:
        (A) LENGTH: 308 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (B) CLONE: 18g (xi) SEQUENCE DESCRIPTION: SEQ ID NO:108:

```
CTCCACCATG AATCACTCCC CTGTGAGGAA CTACTGTCTT CACGCAGAAA GCGTCTAGCC    60

ATGGCGTTAG TATGAGTGTC GTGCAGCCTC CAGGACCCCC CCTCCCGGGA GAGCCATAGT   120

GGTCTGCGGA ACCGGTGAGT ACACCGGAAT TGCCAGGACG ACCGGGTCCT TTCTTGGATC   180

AACCCGCTCA ATGCCTGGAG ATTTGGGCGT GCCCCCGCAA GACTGCTAGC CGAGTAGTGT   240

TGGGTCGCGA AAGGCCTTGT GGTACTGCCT GATAGGGTGC TTGCGAGTGC CCCGGGAGGT   300

CTCGTAGA                                                            308
```

(2) INFORMATION FOR SEQ ID NO:109:

(i) SEQUENCE CHARACTERISTICS:
        (A) LENGTH: 308 base pairs
        (B) TYPE: nucleic acid
        (C) STRANDEDNESS: single
        (D) TOPOLOGY: linear (ii) MOLECULE TYPE: cDNA (iv) ANTI-SENSE: YES (vii) IMMEDIATE SOURCE:
        (B) CLONE: 18g (xi) SEQUENCE DESCRIPTION: SEQ ID NO:109:

```
TCTACGAGAC CTCCCGGGGC ACTCGCAAGC ACCCTATCAG GCAGTACCAC AAGGCCTTTC    60

GCGACCCAAC ACTACTCGGC TAGCAGTCTT GCGGGGGCAC GCCCAAATCT CCAGGCATTG   120

AGCGGGTTGA TCCAAGAAAG GACCCGGTCG TCCTGGCAAT TCCGGTGTAC TCACCGGTTC   180

CGCAGACCAC TATGGCTCTC CCGGGAGGGG GGGTCCTGGA GGCTGCACGA CACTCATACT   240

AACGCCATGG CTAGACGCTT TCTGCGTGAA GACAGTAGTT CCTCACAGGG GAGTGATTCA   300

TGGTGGAG                                                            308
```

(2) INFORMATION FOR SEQ ID NO:110:

(i) SEQUENCE CHARACTERISTICS:
            (A) LENGTH: 308 base pairs
            (B) TYPE: nucleic acid
            (C) STRANDEDNESS: single
            (D) TOPOLOGY: linear (ii) MOLECULE TYPE: cDNA (vii) IMMEDIATE SOURCE:
            (B) CLONE: 18g (ix) FEATURE:
            (A) NAME/KEY: CDS
            (B) LOCATION: 1..72

(xi) SEQUENCE DESCRIPTION: SEQ ID NO:110:

```
CTC CAC CAT GAA TCA CTC CCC TGT GAG GAA CTA CTG TCT TCA CGC AGA        48
Leu His His Glu Ser Leu Pro Cys Glu Glu Leu Leu Ser Ser Arg Arg
  1               5                  10                  15

AAG CGT CTA GCC ATG GCG TTA GTA TGAGTGTCGT GCAGCCTCCA GGACCCCCCC      102
Lys Arg Leu Ala Met Ala Leu Val
            20

TCCCGGGAGA GCCATAGTGG TCTGCGGAAC CGGTGAGTAC ACCGGAATTG CCAGGACGAC     162

CGGGTCCTTT CTTGGATCAA CCCGCTCAAT GCCTGGAGAT TTGGGCGTGC CCCCGCAAGA     222

CTGCTAGCCG AGTAGTGTTG GGTCGCGAAA GGCCTTGTGG TACTGCCTGA TAGGGTGCTT     282

GCGAGTGCCC CGGGAGGTCT CGTAGA                                          308
```

(2) INFORMATION FOR SEQ ID NO:111:

(i) SEQUENCE CHARACTERISTICS:
            (A) LENGTH: 24 amino acids
            (B) TYPE: amino acid
            (D) TOPOLOGY: linear (ii) MOLECULE TYPE: protein (xi) SEQUENCE DESCRIPTION: SEQ ID NO:111:

```
Leu His His Glu Ser Leu Pro Cys Glu Glu Leu Leu Ser Ser Arg Arg
  1               5                  10                  15

Lys Arg Leu Ala Met Ala Leu Val
            20
```

(2) INFORMATION FOR SEQ ID NO:112:

(i) SEQUENCE CHARACTERISTICS:
            (A) LENGTH: 308 base pairs
            (B) TYPE: nucleic acid
            (C) STRANDEDNESS: single
            (D) TOPOLOGY: linear (ii) MOLECULE TYPE: cDNA (vii) IMMEDIATE SOURCE:
            (B) CLONE: 18g (ix) FEATURE:
            (A) NAME/KEY: CDS
            (B) LOCATION: 2..55

(xi) SEQUENCE DESCRIPTION: SEQ ID NO:112:

```
C TCC ACC ATG AAT CAC TCC CCT GTG AGG AAC TAC TGT CTT CAC GCA          46
  Ser Thr Met Asn His Ser Pro Val Arg Asn Tyr Cys Leu His Ala
    1               5                  10                  15

GAA AGC GTC TAGCCATGGC GTTAGTATGA GTGTCGTGCA GCCTCCAGGA                95
Glu Ser Val

CCCCCCCTCC CGGGAGAGCC ATAGTGGTCT GCGGAACCGG TGAGTACACC GGAATTGCCA     155
```

```
GGACGACCGG GTCCTTTCTT GGATCAACCC GCTCAATGCC TGGAGATTTG GGCGTGCCCC      215

CGCAAGACTG CTAGCCGAGT AGTGTTGGGT CGCGAAAGGC CTTGTGGTAC TGCCTGATAG      275

GGTGCTTGCG AGTGCCCCGG GAGGTCTCGT AGA                                  308
```

(2) INFORMATION FOR SEQ ID NO:113:

(i) SEQUENCE CHARACTERISTICS:
        (A) LENGTH: 18 amino acids
        (B) TYPE: amino acid
        (D) TOPOLOGY: linear (ii) MOLECULE TYPE: protein (xi) SEQUENCE DESCRIPTION: SEQ ID NO:113:

```
Ser Thr Met Asn His Ser Pro Val Arg Asn Tyr Cys Leu His Ala Glu
  1               5                  10                  15
Ser Val
```

(2) INFORMATION FOR SEQ ID NO:114:

(i) SEQUENCE CHARACTERISTICS:
        (A) LENGTH: 308 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (B) CLONE: 18g (ix) FEATURE:
        (A) NAME/KEY: CDS
        (B) LOCATION: 72..116

(xi) SEQUENCE DESCRIPTION: SEQ ID NO:114:

```
CTCCACCATG AATCACTCCC CTGTGAGGAA CTACTGTCTT CACGCAGAAA GCGTCTAGCC       60

ATGGCGTTAG T ATG AGT GTC GTG CAG CCT CCA GGA CCC CCC CTC CCG GGA      110
             Met Ser Val Val Gln Pro Pro Gly Pro Pro Leu Pro Gly
               1               5                  10

GAG CCA TAGTGGTCTG CGGAACCGGT GAGTACACCG GAATTGCCAG GACGACCGGG        166
Glu Pro
     15

TCCTTTCTTG GATCAACCCG CTCAATGCCT GGAGATTTGG GCGTGCCCCC GCAAGACTGC      226

TAGCCGAGTA GTGTTGGGTC GCGAAAGGCC TTGTGGTACT GCCTGATAGG GTGCTTGCGA      286

GTGCCCCGGG AGGTCTCGTA GA                                              308
```

(2) INFORMATION FOR SEQ ID NO:115:

(i) SEQUENCE CHARACTERISTICS:
        (A) LENGTH: 15 amino acids
        (B) TYPE: amino acid
        (D) TOPOLOGY: linear (ii) MOLECULE TYPE: protein (xi) SEQUENCE DESCRIPTION: SEQ ID NO:115:

```
Met Ser Val Val Gln Pro Pro Gly Pro Pro Leu Pro Gly Glu Pro
  1               5                  10                  15
```

(2) INFORMATION FOR SEQ ID NO:116:

(i) SEQUENCE CHARACTERISTICS:

(A) LENGTH: 308 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (B) CLONE: 18g (ix) FEATURE:
        (A) NAME/KEY: CDS
        (B) LOCATION: 191..226

(xi) SEQUENCE DESCRIPTION: SEQ ID NO:116:

CTCCACCATG AATCACTCCC CTGTGAGGAA CTACTGTCTT CACGCAGAAA GCGTCTAGCC      60

ATGGCGTTAG TATGAGTGTC GTGCAGCCTC CAGGACCCCC CCTCCCGGGA GAGCCATAGT     120

GGTCTGCGGA ACCGGTGAGT ACACCGGAAT TGCCAGGACG ACCGGGTCCT TTCTTGGATC     180

AACCCGCTCA ATG CCT GGA GAT TTG GGC GTG CCC CCG CAA GAC TGC           226
           Met Pro Gly Asp Leu Gly Val Pro Pro Gln Asp Cys
            1               5                  10

TAGCCGAGTA GTGTTGGGTC GCGAAAGGCC TTGTGGTACT GCCTGATAGG GTGCTTGCGA     286

GTGCCCCGGG AGGTCTCGTA GA                                             308

(2) INFORMATION FOR SEQ ID NO:117:

(i) SEQUENCE CHARACTERISTICS:
        (A) LENGTH: 12 amino acids
        (B) TYPE: amino acid
        (D) TOPOLOGY: linear (ii) MOLECULE TYPE: protein (xi) SEQUENCE DESCRIPTION: SEQ ID NO:117:

Met Pro Gly Asp Leu Gly Val Pro Pro Gln Asp Cys
 1               5                  10

(2) INFORMATION FOR SEQ ID NO:118:

(i) SEQUENCE CHARACTERISTICS:
        (A) LENGTH: 308 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (B) CLONE: 18g (ix) FEATURE:
        (A) NAME/KEY: CDS
        (B) LOCATION: 276..308

(xi) SEQUENCE DESCRIPTION: SEQ ID NO:118:

CTCCACCATG AATCACTCCC CTGTGAGGAA CTACTGTCTT CACGCAGAAA GCGTCTAGCC      60

ATGGCGTTAG TATGAGTGTC GTGCAGCCTC CAGGACCCCC CCTCCCGGGA GAGCCATAGT     120

GGTCTGCGGA ACCGGTGAGT ACACCGGAAT TGCCAGGACG ACCGGGTCCT TTCTTGGATC     180

AACCCGCTCA ATGCCTGGAG ATTTGGGCGT GCCCCCGCAA GACTGCTAGC CGAGTAGTGT     240

TGGGTCGCGA AAGGCCTTGT GGTACTGCCT GATAG GGT GCT TGC GAG TGC CCC       293
                                       Gly Ala Cys Glu Cys Pro
                                        1               5

GGG AGG TCT CGT AGA                                                  308
Gly Arg Ser Arg Arg (2) INFORMATION FOR SEQ ID NO:119:

(i) SEQUENCE CHARACTERISTICS:
        (A) LENGTH: 11 amino acids
        (B) TYPE: amino acid
        (D) TOPOLOGY: linear (ii) MOLECULE TYPE: protein (xi) SEQUENCE DESCRIPTION: SEQ ID NO:119:

```
Gly Ala Cys Glu Cys Pro Gly Arg Ser Arg Arg
 1               5                  10
```

(2) INFORMATION FOR SEQ ID NO:120:

(i) SEQUENCE CHARACTERISTICS:
        (A) LENGTH: 262 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (B) CLONE: 16jh (ix) FEATURE:
        (A) NAME/KEY: CDS
        (B) LOCATION: 1..261
        (D) OTHER INFORMATION: /codon= (seq: "rga", aa: OTR)
            /note= "There exists a heterogeneity at nucleotide 157
            "R" which is either A or G and corresponding amino acid
            residue 53 "Xaa" is either Arg or Gly"

(xi) SEQUENCE DESCRIPTION: SEQ ID NO:120:

```
GGG GCC TGC TAC TCC ATA GAA CCA CTT GAT CTA CCT CCA ATC ATT CAA       48
Gly Ala Cys Tyr Ser Ile Glu Pro Leu Asp Leu Pro Pro Ile Ile Gln
 1               5                  10                  15

AGA CTC CAT GGC CTC AGC GCA TTT TCA CTC CAC AGT TAC TCT CCA GGT       96
Arg Leu His Gly Leu Ser Ala Phe Ser Leu His Ser Tyr Ser Pro Gly
             20                  25                  30

GAA ATT AAT AGG GTG GCC GCA TGC CTC AGA AAA CTT GGG GTA CCG CCC      144
Glu Ile Asn Arg Val Ala Ala Cys Leu Arg Lys Leu Gly Val Pro Pro
         35                  40                  45

TTG CGA GCT TGG RGA CAC CGG GCC CGG AGC GTC CGC GCT AGG CTT CTG      192
Leu Arg Ala Trp Xaa His Arg Ala Arg Ser Val Arg Ala Arg Leu Leu
     50                  55                  60

GCC AGA GGA GGC AGG GCT GCC ATA TGT GGC AAG TAC CTC TTC AAC TGG      240
Ala Arg Gly Gly Arg Ala Ala Ile Cys Gly Lys Tyr Leu Phe Asn Trp
 65                  70                  75                  80

GCA GTA AGA ACA AAG CTC AAA C                                         262
Ala Val Arg Thr Lys Leu Lys
                 85
```

(2) INFORMATION FOR SEQ ID NO:121:

(i) SEQUENCE CHARACTERISTICS:
        (A) LENGTH: 87 amino acids
        (B) TYPE: amino acid
        (D) TOPOLOGY: linear (ii) MOLECULE TYPE: protein (xi) SEQUENCE DESCRIPTION: SEQ ID NO:121:

```
Gly Ala Cys Tyr Ser Ile Glu Pro Leu Asp Leu Pro Pro Ile Ile Gln
 1               5                  10                  15
```

-continued

```
Arg Leu His Gly Leu Ser Ala Phe Ser Leu His Ser Tyr Ser Pro Gly
             20                  25                  30

Glu Ile Asn Arg Val Ala Ala Cys Leu Arg Lys Leu Gly Val Pro Pro
         35                  40                  45

Leu Arg Ala Trp Xaa His Arg Ala Arg Ser Val Arg Ala Arg Leu Leu
     50                  55                  60

Ala Arg Gly Gly Arg Ala Ala Ile Cys Gly Lys Tyr Leu Phe Asn Trp
 65                  70                  75                  80

Ala Val Arg Thr Lys Leu Lys
                 85
```

(2) INFORMATION FOR SEQ ID NO:122:

(i) SEQUENCE CHARACTERISTICS:
        (A) LENGTH: 9185 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:122:

```
CACTCCACCA TGAATCACTC CCCTGTGAGG AACTACTGTC TTCACGCAGA AAGCGTCTAG      60

CCATGGCGTT AGTATGAGTG TCGTGCAGCC TCCAGGACCC CCCCTCCCGG GAGAGCCATA     120

GTGGTCTGCG GAACCGGTGA GTACACCGGA ATTGCCAGGA CGACCGGGTC CTTTCTTGGA     180

TCAACCCGCT CAATGCCTGG AGATTTGGGC GTGCCCCCGC AAGACTGCTA GCCGAGTAGT     240

GTTGGGTCGC GAAAGGCCTT GTGGTACTGC CTGATAGGGT GCTTGCGAGT GCCCCGGGAG     300

GTCTCGTAGA CCGTGCACCA TGAGCACGAA TCCTAAACCT CAAAAAAAAA ACAAACGTAA     360

CACCAACCGT CGCCCACAGG ACGTCAAGTT CCCGGGTGGC GGTCAGATCG TTGGTGGAGT     420

TTACTTGTTG CCGCGCAGGG GCCCTAGATT GGGTGTGCGC GCGACGAGAA AGACTTCCGA     480

GCGGTCGCAA CCTCGAGGTA GACGTCAGCC TATCCCCAAG GCTCGTCGGC CCGAGGGCAG     540

GACCTGGGCT CAGCCCGGGT ACCCTTGGCC CCTCTATGGC AATGAGGGCT GCGGGTGGGC     600

GGGATGGCTC CTGTCTCCCC GTGGCTCTCG GCCTAGCTGG GGCCCCACAG ACCCCCGGCG     660

TAGGTCGCGC AATTTGGGTA AGGTCATCGA TACCCTTACG TGCGGCTTCG CCGACCTCAT     720

GGGGTACATA CCGCTCGTCG GCGCCCCTCT TGGAGGCGCT GCCAGGGCCC TGGCGCATGG     780

CGTCCGGGTT CTGGAAGACG GCGTGAACTA TGCAACAGGG AACCTTCCTG GTTGCTCTTT     840

CTCTATCTTC CTTCTGGCCC TGCTCTCTTG CTTGACTGTG CCCGCTTCGG CCTACCAAGT     900

GCGCAACTCC ACGGGCTTT  ACCACGTCAC CAATGATTGC CCTAACTCGA GTATTGTGTA     960

CGAGGCGGCC GATGCCATCC TGCACACTCC GGGGTGCGTC CCTTGCGTTC GTGAGGGCAA    1020

CGCCTCGAGG TGTTGGGTGG CGATGACCCC TACGGTGGCC ACCAGGGATG GCAAACTCCC    1080

CGCGACGCAG CTTCGACGTC ACATCGATCT GCTTGTCGGG AGCGCCACCC TCTGTTCGGC    1140

CCTCTACGTG GGGGACCTAT GCGGGTCTGT CTTTCTTGTC GGCCAACTGT TCACCTTCTC    1200

TCCCAGGCGC CACTGGACGA CGCAAGGTTG CAATTGCTCT ATCTATCCCG GCCATATAAC    1260

GGGTCACCGC ATGGCATGGG ATATGATGAT GAACTGGTCC CCTACGACGG CGTTGGTAAT    1320

GGCTCAGCTG CTCCGGATCC CACAAGCCAT CTTGGACATG ATCGCTGGTG CTCACTGGGG    1380

AGTCCTGGCG GGCATAGCGT ATTTCTCCAT GGTGGGGAAC TGGGCGAAGG TCCTGGTAGT    1440

GCTGCTGCTA TTTGCCGGCG TCGACGCGGA AACCCACGTC ACCGGGGGAA GTGCCGGCCA    1500
```

```
CACTGTGTCT GGATTTGTTA GCCTCCTCGC ACCAGGCGCC AAGCAGAACG TCCAGCTGAT      1560

CAACACCAAC GGCAGTTGGC ACCTCAATAG CACGGCCCTG AACTGCAATG ATAGCCTCAA      1620

CACCGGCTGG TTGGCAGGGC TTTTCTATCA CCACAAGTTC AACTCTTCAG GCTGTCCTGA      1680

GAGGCTAGCC AGCTGCCGAC CCCTTACCGA TTTTGACCAG GGCTGGGGCC CTATCAGTTA      1740

TGCCAACGGA AGCGGCCCCG ACCAGCGCCC CTACTGCTGG CACTACCCCC CAAAACCTTG      1800

CGGTATTGTG CCCGCGAAGA GTGTGTGTGG TCCGGTATAT TGCTTCACTC CCAGCCCCGT      1860

GGTGGTGGGA ACGACCGACA GGTCGGGCGC GCCCACCTAC AGCTGGGGTG AAAATGATAC      1920

GGACGTCTTC GTCCTTAACA ATACCAGGCC ACCGCTGGGC AATTGGTTCG GTTGTACCTG      1980

GATGAACTCA ACTGGATTCA CCAAAGTGTG CGGAGCGCCT CCTTGTGTCA TCGGAGGGGC      2040

GGGCAACAAC ACCCTGCACT GCCCCACTGA TTGCTTCCGC AAGCATCCGG ACGCCACATA      2100

CTCTCGGTGC GGCTCCGGTC CCTGGATCAC ACCCAGGTGC CTGGTCGACT ACCCGTATAG      2160

GCTTTGGCAT TATCCTTGTA CCATCAACTA CACCATATTT AAAATCAGGA TGTACGTGGG      2220

AGGGGTCGAA CACAGGCTGG AAGCTGCCTG CAACTGACG CGGGGCGAAC GTTGCGATCT      2280

GGAAGACAGG GACAGGTCCG AGCTCACCCC GTTACTGCTG ACCACTACAC AGTGGCAGGT      2340

CCTCCCGTGT TCCTTCACAA CCCTACCAGC CTTGTCCACC GGCCTCATCC ACCTCCACCA      2400

GAACATTGTG GACGTGCAGT ACTTGTACGG GGTGGGGTCA AGCATCGCGT CCTGGGCCAT      2460

TAAGTGGGAG TACGTCGTTC TCCTGTTCCT TCTGCTTGCA GACGCGCGCG TCTGCTCCTG      2520

CTTGTGGATG ATGCTACTCA TATCCCAAGC GGAGGCGGCT TTGGAGAACC TCGTAATACT      2580

TAATGCAGCA TCCCTGGCCG GGACGCACGG TCTTGTATCC TTCCTCGTGT TCTTCTGCTT      2640

TGCATGGTAT TTGAAGGGTA AGTGGGTGCC CGGAGCGGTC TACACCTTCT ACGGGATGTG      2700

GCCTCTCCTC CTGCTCCTGT TGGCGTTGCC CCAGCGGGCG TACGCGCTGG ACACGGAGGT      2760

GGCCGCGTCG TGTGGCGGTG TTGTTCTCGT CGGGTTGATG GCGCTGACTC TGTCACCATA      2820

TTACAAGCGC TATATCAGCT GGTGCTTGTG GTGGCTTCAG TATTTTCTGA CCAGAGTGGA      2880

AGCGCAACTG CACGTGTGGA TTCCCCCCCT CAACGTCCGA GGGGGGCGCG ACGCCGTCAT      2940

CTTACTCATG TGTGCTGTAC ACCCGACTCT GGTATTTGAC ATCACCAAAT TGCTGCTGGC      3000

CGTCTTCGGA CCCCTTTGGA TTCTTCAAGC CAGTTTGCTT AAAGTACCCT ACTTTGTGCG      3060

CGTCCAAGGC CTTCTCCGGT TCTGCGCGTT AGCGCGGAAG ATGATCGGAG GCCATTACGT      3120

GCAAATGGTC ATCATTAAGT TAGGGGCGCT TACTGGCACC TATGTTTATA ACCATCTCAC      3180

TCCTCTTCGG GACTGGGCGC ACAACGGCTT GCGAGATCTG GCCGTGGCTG TAGAGCCAGT      3240

CGTCTTCTCC CAAATGGAGA CCAAGCTCAT CACGTGGGGG GCAGATACCG CCGCGTGCGG      3300

TGACATCATC AACGGCTTGC CTGTTTCCGC CCGCAGGGGC CGGGAGATAC TGCTCGGGCC      3360

AGCCGATGGA ATGGTCTCCA AGGGGTGGAG GTTGCTGGCG CCCATCACGG CGTACGCCCA      3420

GCAGACAAGG GGCCTCCTAG GGTGCATAAT CACCAGCCTA ACTGGCCGGG ACAAAAACCA      3480

AGTGGAGGGT GAGGTCCAGA TTGTGTCAAC TGCTGCCCAA ACCTTCCTGG CAACGTGCAT      3540

CAATGGGGTG TGCTGGACTG TCTACCACGG GGCCGGAACG AGGACCATCG CGTCACCCAA      3600

GGGTCCTGTC ATCCAGATGT ATACCAATGT AGACCAAGAC CTTGTGGGCT GGCCCGCTCC      3660

GCAAGGTAGC CGCTCATTGA CACCCTGCAC TTGCGGCTCC TCGGACCTTT ACCTGGTCAC      3720

GAGGCACGCC GATGTCATTC CCGTGCGCCG GCGGGGTGAT AGCAGGGCA GCCTGCTGTC      3780

GCCCCGGCCC ATTTCCTACT TGAAAGGCTC CTCGGGGGGT CCGCTGTTGT GCCCCGCGGG      3840

GCACGCCGTG GGCATATTTA GGGCCGCGGT GTGCACCCGT GGAGTGGCTA AGGCGGTGGA      3900
```

```
CTTTATCCCT GTGGAGAACC TAGAGACAAC CATGAGGTCC CCGGTGTTCA CGGATAACTC    3960

CTCTCCACCA GTAGTGCCCC AGAGCTTCCA GGTGGCTCAC CTCCATGCTC CCACAGGCAG    4020

CGGCAAAAGC ACCAAGGTCC CGGCTGCATA TGCAGCTCAG GGCTATAAGG TGCTAGTACT    4080

CAACCCCTCT GTTGCTGCAA CACTGGGCTT TGGTGCTTAC ATGTCCAAGG CTCATGGGAT    4140

CGATCCTAAC ATCAGGACCG GGGTGAGAAC AATTACCACT GGCAGCCCCA TCACGTACTC    4200

CACCTACGGC AAGTTCCTTG CCGACGGCGG GTGCTCGGGG GGCGGTTATG ACATAATAAT    4260

TTGTGACGAG TGCCACTCCA CGGATGCCAC ATCCATCTTG GGCATCGGCA CTGTCCTTGA    4320

CCAAGCAGAG ACTGCGGGGG CGAGACTGGT TGTGCTCGCC ACCGCCACCC CTCCGGGCTC    4380

CGTCACTGTG CCCCATCCCA ACATCGAGGA GGTTGCTCTG TCCACCACCG GAGAGATCCC    4440

TTTTTACGGC AAGGCTATCC CCCTCGAAGT AATCAAGGGG GGGAGACATC TCATCTTCTG    4500

TCATTCAAAG AAGAAGTGCG ACGAACTCGC CGCAAAGCTG GTCGCATTGG GCATCAATGC    4560

CGTGGCCTAC TACCGCGGTC TTGACGTGTC CGTCATCCCG ACCAGCGGCG ATGTTGTCGT    4620

CGTGGCAACC GATGCCCTCA TGACCGGCTA TACCGGCGAC TTCGACTCGG TGATAGACTG    4680

CAATACGTGT GTCACCCAGA CAGTCGATTT CAGCCTTGAC CCTACCTTCA CCATTGAGAC    4740

AATCACGCTC CCCCAGGATG CTGTCTCCCG CACTCAACGT CGGGGCAGGA CTGGCAGGGG    4800

GAAGCCAGGC ATCTACAGAT TTGTGGCACC GGGGGAGCGC CCCTCCGGCA TGTTCGACTC    4860

GTCCGTCCTC TGTGAGTGCT ATGACGCAGG CTGTGCTTGG TATGAGCTCA CGCCCGCCGA    4920

GACTACAGTT AGGCTACGAG CGTACATGAA CACCCCGGGG CTTCCCGTGT GCCAGGACCA    4980

TCTTGAATTT TGGGAGGGCG TCTTTACAGG CCTCACTCAT ATAGATGCCC ACTTTCTATC    5040

CCAGACAAAG CAGAGTGGGG AGAACCTTCC TTACCTGGTA GCGTACCAAG CCACCGTGTG    5100

CGCTAGGGCT CAAGCCCCTC CCCCATCGTG GGACCAGATG TGGAAGTGTT TGATTCGCCT    5160

CAAGCCCACC CTCCATGGGC AACACCCCT GCTATACAGA CTGGGCGCTG TTCAGAATGA    5220

AATCACCCTG ACGCACCCAG TCACCAAATA CATCATGACA TGCATGTCGG CCGACCTGGA    5280

GGTCGTCACG AGCACCTGGG TGCTCGTTGG CGGCGTCCTG GCTGCTTTGG CCGCGTATTG    5340

CCTGTCAACA GGCTGCGTGG TCATAGTGGG CAGGGTCGTC TTGTCCGGGA AGCCGGCAAT    5400

CATACCTGAC AGGGAAGTCC TCTACCGAGA GTTCGATGAG ATGGAAGAGT GCTCTCAGCA    5460

CTTACCGTAC ATCGAGCAAG GGATGATGCT CGCCGAGCAG TTCAAGCAGA AGGCCCTCGG    5520

CCTCCTGCAG ACCGCGTCCC GTCAGGCAGA GGTTATCGCC CCTGCTGTCC AGACCAACTG    5580

GCAAAAACTC GAGACCTTCT GGGCGAAGCA TATGTGGAAC TTCATCAGTG GATACAATA    5640

CTTGGCGGGC TTGTCAACGC TGCCTGGTAA CCCCGCCATT GCTTCATTGA TGGCTTTTAC    5700

AGCTGCTGTC ACCAGCCCAC TAACCACTAG CCAAACCCTC CTCTTCAACA TATTGGGGGG    5760

GTGGGTGGCT GCCCAGCTCG CCGCCCCCGG TGCCGCTACT GCCTTTGTGG GCGCTGGCTT    5820

AGCTGGCGCC GCCATCGGCA GTGTTGGACT GGGGAAGGTC CTCATAGACA TCCTTGCAGG    5880

GTATGGCGCG GGCGTGGCGG GAGCTCTTGT GGCATTCAAG ATCATGAGCG GTGAGGTCCC    5940

CTCCACGGAG GACCTGGTCA ATCTACTGCC CGCCATCCTC TCGCCCGGAG CCCTCGTAGT    6000

CGGCGTGGTC TGTGCAGCAA TACTGCGCCG GCACGTTGGC CCGGGCGAGG GGCAGTGCA    6060

GTGGATGAAC CGGCTGATAG CCTTCGCCTC CCGGGGGAAC CATGTTTCCC CCACGCACTA    6120

CGTGCCGGAG AGCGATGCAG CTGCCCGCGT CACTGCCATA CTCAGCAGCC TCACTGTAAC    6180

CCAGCTCCTG AGGCGACTGC ACCAGTGGAT AAGCTCGGAG TGTACCACTC CATGCTCCGG    6240
```

```
-continued

TTCCTGGCTA AGGGACATCT GGGACTGGAT ATGCGAGGTG TTGAGCGACT TTAAGACCTG    6300

GCTAAAAGCT AAGCTCATGC CACAGCTGCC TGGGATCCCC TTTGTGTCCT GCCAGCGCGG    6360

GTATAAGGGG GTCTGGCGAG TGGACGGCAT CATGCACACT CGCTGCCACT GTGGAGCTGA    6420

GATCACTGGA CATGTCAAAA ACGGGACGAT GAGGATCGTC GGTCCTAGGA CCTGCAGGAA    6480

CATGTGGAGT GGGACCTTCC CCATTAATGC CTACACCACG GGCCCCTGTA CCCCCCTTCC    6540

TGCGCCGAAC TACACGTTCG CGCTATGGAG GGTGTCTGCA GAGGAATATG TGGAGATAAG    6600

GCAGGTGGGG GACTTCCACT ACGTGACGGG TATGACTACT GACAATCTCA AATGCCCGTG    6660

CCAGGTCCCA TCGCCCGAAT TTTTCACAGA ATTGGACGGG GTGCGCCTAC ATAGGTTTGC    6720

GCCCCCCTGC AAGCCCTTGC TGCGGGAGGA GGTATCATTC AGAGTAGGAC TCCACGAATA    6780

CCCGGTAGGG TCGCAATTAC CTTGCGAGCC CGAACCGGAC GTGGCCGTGT TGACGTCCAT    6840

GCTCACTGAT CCCTCCCATA TAACAGCAGA GGCGGCCGGG CGAAGGTTGG CGAGGGGATC    6900

ACCCCCCTCT GTGGCCAGCT CCTCGGCTAG CCAGCTATCC GCTCCATCTC TCAAGGCAAC    6960

TTGCACCGCT AACCATGACT CCCCTGATGC TGAGCTCATA GAGGCCAACC TCCTATGGAG    7020

GCAGGAGATG GGCGGCAACA TCACCAGGGT TGAGTCAGAA AACAAAGTGG TGATTCTGGA    7080

CTCCTTCGAT CCGCTTGTGG CGGAGGAGGA CGAGCGGGAG ATCTCCGTAC CCGCAGAAAT    7140

CCTGCGGAAG TCTCGGAGAT TCGCCCAGGC CCTGCCCGTT TGGGCGCGGC CGGACTATAA    7200

CCCCCCGCTA GTGGAGACGT GGAAAAAGCC CGACTACGAA CCACCTGTGG TCCATGGCTG    7260

TCCGCTTCCA CCTCCAAAGT CCCCTCCTGT GCCTCCGCCT CGGAAGAAGC GGACGGTGGT    7320

CCTCACTGAA TCAACCCTAT CTACTGCCTT GGCCGAGCTC GCCACCAGAA GCTTTGGCAG    7380

CTCCTCAACT TCCGGCATTA CGGGCGACAA TACGACAACA TCCTCTGAGC CCGCCCCTTC    7440

TGGCTGCCCC CCCGACTCCG ACGCTGAGTC CTATTCCTCC ATGCCCCCCC TGGAGGGGGA    7500

GCCTGGGGAT CCGGATCTTA GCGACGGGTC ATGGTCAACG GTCAGTAGTG AGGCCAACGC    7560

GGAGGATGTC GTGTGCTGCT CAATGTCTTA CTCTTGGACA GGCGCACTCG TCACCCCGTG    7620

CGCCGCGGAA GAACAGAAAC TGCCCATCAA TGCACTAAGC AACTCGTTGC TACGTCACCA    7680

CAATTTGGTG TATTCCACCA CCTCACGCAG TGCTTGCCAA AGGCAGAAGA AAGTCACATT    7740

TGACAGACTG CAAGTTCTGG ACAGCCATTA CCAGGACGTA CTCAAGGAGG TTAAAGCAGC    7800

GGCGTCAAAA GTGAAGGCTA ACTTGCTATC CGTAGAGGAA GCTTGCAGCC TGACGCCCCC    7860

ACACTCAGCC AAATCCAAGT TTGGTTATGG GGCAAAAGAC GTCCGTTGCC ATGCCAGAAA    7920

GGCCGTAACC CACATCAACT CCGTGTGGAA AGACCTTCTG GAAGACAATG TAACACCAAT    7980

AGACACTACC ATCATGGCTA AGAACGAGGT TTTCTGCGTT CAGCCTGAGA AGGGGGGTCG    8040

TAAGCCAGCT CGTCTCATCG TGTTCCCCGA TCTGGGCGTG CGCGTGTGCG AAAAGATGGC    8100

TTTGTACGAC GTGGTTACAA AGCTCCCCTT GGCCGTGATG GGAAGCTCCT ACGGATTCCA    8160

ATACTCACCA GGACAGCGGG TTGAATTCCT CGTGCAAGCG TGGAAGTCCA AGAAAACCCC    8220

AATGGGGTTC TCGTATGATA CCCGCTGCTT TGACTCCACA GTCACTGAGA GCGACATCCG    8280

TACGGAGGAG GCAATCTACC AATGTTGTGA CCTCGACCCC CAAGCCCGCG TGGCCATCAA    8340

GTCCCTCACC GAGAGGCTTT ATGTTGGGGG CCCTCTTACC AATTCAAGGG GGGAGAACTG    8400

CGGCTATCGC AGGTGCCGCG CGAGCGGCGT ACTGACAACT AGCTGTGGTA ACACCCTCAC    8460

TTGCTACATC AAGGCCCGGG CAGCCTGTCG AGCCGCAGGG CTCCAGGACT GCACCATGCT    8520

CGTGTGTGGC GACGACTTAG TCGTTATCTG TGAAAGCGCG GGGGTCCAGG AGGACGCGGC    8580

GAGCCTGAGA GCCTTCACGG AGGCTATGAC CAGGTACTCC GCCCCCCCTG GGGACCCCCC    8640
```

```
ACAACCAGAA TACGACTTGG AGCTCATAAC ATCATGCTCC TCCAACGTGT CAGTCGCCCA    8700

CGACGGCGCT GGAAAGAGGG TCTACTACCT CACCCGTGAC CCTACAACCC CCCTCGCGAG    8760

AGCTGCGTGG GAGACAGCAA GACACACTCC AGTCAATTCC TGGCTAGGCA ACATAATCAT    8820

GTTTGCCCCC ACACTGTGGG CGAGGATGAT ACTGATGACC CATTTCTTTA GCGTCCTTAT    8880

AGCCAGGGAC CAGCTTGAAC AGGCCCTCGA TTGCGAGATC TACGGGGCCT GCTACTCCAT    8940

AGAACCACTT GATCTACCTC CAATCATTCA AAGACTCCAT GGCCTCAGCG CATTTTCACT    9000

CCACAGTTAC TCTCCAGGTG AAATTAATAG GGTGGCCGCA TGCCTCAGAA AACTTGGGGT    9060

ACCGCCCTTG CGAGCTTGGA GACACCGGGC CCGGAGCGTC CGCGCTAGGC TTCTGGCCAG    9120

AGGAGGCAGG GCTGCCATAT GTGGCAAGTA CCTCTTCAAC TGGGCAGTAA GAACAAAGCT    9180

CAAAC                                                               9185
```

(2) INFORMATION FOR SEQ ID NO:123:

(i) SEQUENCE CHARACTERISTICS:
        (A) LENGTH: 9185 base pairs
        (B) TYPE: nucleic acid
        (C) STRANDEDNESS: single
        (D) TOPOLOGY: linear (ii) MOLECULE TYPE: cDNA (iv) ANTI-SENSE: YES (xi) SEQUENCE DESCRIPTION: SEQ ID NO:123:

```
GTTTGAGCTT TGTTCTTACT GCCCAGTTGA AGAGGTACTT GCCACATATG GCAGCCCTGC      60

CTCCTCTGGC CAGAAGCCTA GCGCGGACGC TCCGGGCCCG GTGTCTCCAA GCTCGCAAGG     120

GCGGTACCCC AAGTTTTCTG AGGCATGCGG CCACCCTATT AATTTCACCT GGAGAGTAAC     180

TGTGGAGTGA AAATGCGCTG AGGCCATGGA GTCTTTGAAT GATTGGAGGT AGATCAAGTG     240

GTTCTATGGA GTAGCAGGCC CCGTAGATCT CGCAATCGAG GGCCTGTTCA AGCTGGTCCC     300

TGGCTATAAG GACGCTAAAG AAATGGGTCA TCAGTATCAT CCTCGCCCAC AGTGTGGGGG     360

CAAACATGAT TATGTTGCCT AGCCAGGAAT TGACTGGAGT GTGTCTTGCT GTCTCCCACG     420

CAGCTCTCGC GAGGGGGGTT GTAGGGTCAC GGGTGAGGTA GTAGACCCTC TTTCCAGCGC     480

CGTCGTGGGC GACTGACACG TTGGAGGAGC ATGATGTTAT GAGCTCCAAG TCGTATTCTG     540

GTTGTGGGGG GTCCCCAGGG GGGCGGAGT ACCTGGTCAT AGCCTCCGTG AAGGCTCTCA      600

GGCTCGCCGC GTCCTCCTGG ACCCCCGCGC TTTCACAGAT AACGACTAAG TCGTCGCCAC     660

ACACGAGCAT GGTGCAGTCC TGGAGCCCTG CGGCTCGACA GGCTGCCCGG GCCTTGATGT     720

AGCAAGTGAG GGTGTTACCA CAGCTAGTTG TCAGTACGCC GCTCGCGCGG CACCTGCGAT     780

AGCCGCAGTT CTCCCCCCTT GAATTGGTAA GAGGGCCCCC AACATAAAGC CTCTCGGTGA     840

GGGACTTGAT GGCCACGCGG GCTTGGGGGT CGAGGTCACA ACATTGGTAG ATTGCCTCCT     900

CCGTACGGAT GTCGCTCTCA GTGACTGTGG AGTCAAAGCA GCGGGTATCA TACGAGAACC     960

CCATTGGGGT TTTCTTGGAC TTCCACGCTT GCACGAGGAA TTCAACCCGC TGTCCTGGTG    1020

AGTATTGGAA TCCGTAGGAG CTTCCCATCA CGGCCAAGGG GAGCTTTGTA ACCACGTCGT    1080

ACAAAGCCAT CTTTTCGCAC ACGCGCACGC CCAGATCGGG GAACACGATG AGACGAGCTG    1140

GCTTACGACC CCCCTTCTCA GGCTGAACGC AGAAAACCTC GTTCTTAGCC ATGATGGTAG    1200

TGTCTATTGG TGTTACATTG TCTTCCAGAA GGTCTTTCCA CACGGAGTTG ATGTGGGTTA    1260

CGGCCTTTCT GGCATGGCAA CGGACGTCTT TTGCCCCATA ACCAAACTTG GATTTGGCTG    1320
```

-continued

| | |
|---|---|
| AGTGTGGGGG CGTCAGGCTG CAAGCTTCCT CTACGGATAG CAAGTTAGCC TTCACTTTTG | 1380 |
| ACGCCGCTGC TTTAACCTCC TTGAGTACGT CCTGGTAATG GCTGTCCAGA ACTTGCAGTC | 1440 |
| TGTCAAATGT GACTTTCTTC TGCCTTTGGC AAGCACTGCG TGAGGTGGTG GAATACACCA | 1500 |
| AATTGTGGTG ACGTAGCAAC GAGTTGCTTA GTGCATTGAT GGGCAGTTTC TGTTCTTCCG | 1560 |
| CGGCGCACGG GGTGACGAGT GCGCCTGTCC AAGAGTAAGA CATTGAGCAG CACACGACAT | 1620 |
| CCTCCGCGTT GGCCTCACTA CTGACCGTTG ACCATGACCC GTCGCTAAGA TCCGGATCCC | 1680 |
| CAGGCTCCCC CTCCAGGGGG GGCATGGAGG AATAGGACTC AGCGTCGGAG TCGGGGGGGC | 1740 |
| AGCCAGAAGG GGCGGGCTCA GAGGATGTTG TCGTATTGTC GCCCGTAATG CCGGAAGTTG | 1800 |
| AGGAGCTGCC AAAGCTTCTG GTGGCGAGCT CGGCCAAGGC AGTAGATAGG GTTGATTCAG | 1860 |
| TGAGGACCAC CGTCCGCTTC TTCCGAGGCG GAGGCACAGG AGGGGACTTT GGAGGTGGAA | 1920 |
| GCGGACAGCC ATGGACCACA GGTGGTTCGT AGTCGGGCTT TTTCCACGTC TCCACTAGCG | 1980 |
| GGGGGTTATA GTCCGGCCGC GCCCAAACGG GCAGGGCCTG GGCGAATCTC CGAGACTTCC | 2040 |
| GCAGGATTTC TGCGGGTACG GAGATCTCCC GCTCGTCCTC CTCCGCCACA AGCGGATCGA | 2100 |
| AGGAGTCCAG AATCACCACT TTGTTTTCTG ACTCAACCCT GGTGATGTTG CCGCCCATCT | 2160 |
| CCTGCCTCCA TAGGAGGTTG GCCTCTATGA GCTCAGCATC AGGGGAGTCA TGGTTAGCGG | 2220 |
| TGCAAGTTGC CTTGAGAGAT GGAGCGGATA GCTGGCTAGC CGAGGAGCTG GCCACAGAGG | 2280 |
| GGGGTGATCC CCTCGCCAAC CTTCGCCCGG CCGCCTCTGC TGTTATATGG GAGGGATCAG | 2340 |
| TGAGCATGGA CGTCAACACG GCCACGTCCG GTTCGGGCTC GCAAGGTAAT TGCGACCCTA | 2400 |
| CCGGGTATTC GTGGAGTCCT ACTCTGAATG ATACCTCCTC CCGCAGCAAG GGCTTGCAGG | 2460 |
| GGGGCGCAAA CCTATGTAGG CGCACCCCGT CCAATTCTGT GAAAAATTCG GGCGATGGGA | 2520 |
| CCTGGCACGG GCATTTGAGA TTGTCAGTAG TCATACCCGT CACGTAGTGG AAGTCCCCCA | 2580 |
| CCTGCCTTAT CTCCACATAT TCCTCTGCAG ACACCCTCCA TAGCGCGAAC GTGTAGTTCG | 2640 |
| GCGCAGGAAG GGGGGTACAG GGGCCCGTGG TGTAGGCATT AATGGGGAAG GTCCCACTCC | 2700 |
| ACATGTTCCT GCAGGTCCTA GGACCGACGA TCCTCATCGT CCCGTTTTTG ACATGTCCAG | 2760 |
| TGATCTCAGC TCCACAGTGG CAGCGAGTGT GCATGATGCC GTCCACTCGC CAGACCCCCT | 2820 |
| TATACCCGCG CTGGCAGGAC ACAAAGGGGA TCCCAGGCAG CTGTGGCATG AGCTTAGCTT | 2880 |
| TTAGCCAGGT CTTAAAGTCG CTCAACACCT CGCATATCCA GTCCCAGATG TCCCTTAGCC | 2940 |
| AGGAACCGGA GCATGGAGTG GTACACTCCG AGCTTATCCA CTGGTGCAGT CGCCTCAGGA | 3000 |
| GCTGGGTTAC AGTGAGGCTG CTGAGTATGG CAGTGACGCG GGCAGCTGCA TCGCTCTCCG | 3060 |
| GCACGTAGTG CGTGGGGGAA ACATGGTTCC CCCGGGAGGC GAAGGCTATC AGCCGGTTCA | 3120 |
| TCCACTGCAC TGCCCCCTCG CCCGGGCCAA CGTGCCGGCG CAGTATTGCT GCACAGACCA | 3180 |
| CGCCGACTAC GAGGGCTCCG GGCGAGAGGA TGGCGGGCAG TAGATTGACC AGGTCCTCCG | 3240 |
| TGGAGGGGAC CTCACCGCTC ATGATCTTGA ATGCCACAAG AGCTCCCGCC ACGCCCGCGC | 3300 |
| CATACCCTGC AAGGATGTCT ATGAGGACCT TCCCCAGTCC AACACTGCCG ATGGCGGCGC | 3360 |
| CAGCTAAGCC AGCGCCCACA AAGGCAGTAG CGGCACCGGG GGCGGCGAGC TGGGCAGCCA | 3420 |
| CCCACCCCCC CAATATGTTG AAGAGGAGGG TTTGGCTAGT GGTTAGTGGG CTGGTGACAG | 3480 |
| CAGCTGTAAA AGCCATCAAT GAAGCAATGG CGGGGTTACC AGGCAGCGTT GACAAGCCCG | 3540 |
| CCAAGTATTG TATCCCACTG ATGAAGTTCC ACATATGCTT CGCCCAGAAG GTCTCGAGTT | 3600 |
| TTTGCCAGTT GGTCTGGACA GCAGGGGCGA TAACCTCTGC CTGACGGGAC GCGGTCTGCA | 3660 |

-continued

```
GGAGGCCGAG GGCCTTCTGC TTGAACTGCT CGGCGAGCAT CATCCCTTGC TCGATGTACG    3720

GTAAGTGCTG AGAGCACTCT TCCATCTCAT CGAACTCTCG GTAGAGGACT TCCCTGTCAG    3780

GTATGATTGC CGGCTTCCCG GACAAGACGA CCCTGCCCAC TATGACCACG CAGCCTGTTG    3840

ACAGGCAATA CGCGGCCAAA GCAGCCAGGA CGCCGCCAAC GAGCACCCAG GTGCTCGTGA    3900

CGACCTCCAG GTCGGCCGAC ATGCATGTCA TGATGTATTT GGTGACTGGG TGCGTCAGGG    3960

TGATTTCATT CTGAACAGCG CCCAGTCTGT ATAGCAGGGG TGTTGGCCCA TGGAGGGTGG    4020

GCTTGAGGCG AATCAAACAC TTCCACATCT GGTCCCACGA TGGGGAGGG GCTTGAGCCC     4080

TAGCGCACAC GGTGGCTTGG TACGCTACCA GGTAAGGAAG GTTCTCCCCA CTCTGCTTTG    4140

TCTGGGATAG AAAGTGGGCA TCTATATGAG TGAGGCCTGT AAAGACGCCC TCCCAAAATT    4200

CAAGATGGTC CTGGCACACG GGAAGCCCCG GGGTGTTCAT GTACGCTCGT AGCCTAACTG    4260

TAGTCTCGGC GGGCGTGAGC TCATACCAAG CACAGCCTGC GTCATAGCAC TCACAGAGGA    4320

CGGACGAGTC GAACATGCCG GAGGGCGCT CCCCCGGTGC CACAAATCTG TAGATGCCTG     4380

GCTTCCCCCT GCCAGTCCTG CCCCGACGTT GAGTGCGGGA GACAGCATCC TGGGGGAGCG    4440

TGATTGTCTC AATGGTGAAG GTAGGGTCAA GGCTGAAATC GACTGTCTGG GTGACACACG    4500

TATTGCAGTC TATCACCGAG TCGAAGTCGC CGGTATAGCC GGTCATGAGG GCATCGGTTG    4560

CCACGACGAC AACATCGCCG CTGGTCGGGA TGACGGACAC GTCAAGACCG CGGTAGTAGG    4620

CCACGGCATT GATGCCCAAT GCGACCAGCT TTGCGGCGAG TTCGTCGCAC TTCTTCTTTG    4680

AATGACAGAA GATGAGATGT CTCCCCCCCT TGATTACTTC GAGGGGGATA GCCTTGCCGT    4740

AAAAAGGGAT CTCTCCGGTG GTGGACAGAG CAACCTCCTC GATGTTGGGA TGGGCACAG    4800

TGACGGAGCC CGGAGGGGTG GCGGTGGCGA GCACAACCAG TCTCGCCCCC GCAGTCTCTG    4860

CTTGGTCAAG GACAGTGCCG ATGCCCAAGA TGGATGTGGC ATCCGTGGAG TGGCACTCGT    4920

CACAAATTAT TATGTCATAA CCGCCCCCCG AGCACCCGCC GTCGGCAAGG AACTTGCCGT    4980

AGGTGGAGTA CGTGATGGGG CTGCCAGTGG TAATTGTTCT CACCCCGGTC CTGATGTTAG    5040

GATCGATCCC ATGAGCCTTG GACATGTAAG CACCAAAGCC CAGTGTTCA GCAACAGAGG     5100

GGTTGAGTAC TAGCACCTTA TAGCCCTGAG CTGCATATGC AGCCGGGACC TTGGTGCTTT    5160

TGCCGCTGCC TGTGGGAGCA TGGAGGTGAG CCACCTGGAA GCTCTGGGGC ACTACTGGTG    5220

GAGAGGAGTT ATCCGTGAAC ACCGGGGACC TCATGGTTGT CTCTAGGTTC TCCACAGGGA    5280

TAAAGTCCAC CGCCTTAGCC ACTCCACGGG TGCACACCGC GGCCCTAAAT ATGCCCACGG    5340

CGTGCCCCGC GGGGCACAAC AGCGGACCCC CCGAGGAGCC TTTCAAGTAG GAAATGGGCC    5400

GGGGCGACAG CAGGCTGCCC CTGCTATCAC CCCGCCGGCG CACGGGAATG ACATCGGCGT    5460

GCCTCGTGAC CAGGTAAAGG TCCGAGGAGC CGCAAGTGCA GGGTGTCAAT GAGCGGCTAC    5520

CTTGCGGAGC GGGCCAGCCC ACAAGGTCTT GGTCTACATT GGTATACATC TGGATGACAG    5580

GACCCTTGGG TGACGCGATG GTCCTCGTTC CGGCCCCGTG GTAGACAGTC CAGCACACCC    5640

CATTGATGCA CGTTGCCAGG AAGGTTTGGG CAGCAGTTGA CACAATCTGG ACCTCACCCT    5700

CCACTTGGTT TTTGTCCCGG CCAGTTAGGC TGGTGATTAT GCACCCTAGG AGGCCCCTTG    5760

TCTGCTGGGT GTACGCCGTG ATGGGCGCCA GCAACCTCCA CCCCTTGGAG ACCATTCCAT    5820

CGGCTGGCCC GAGCAGTATC TCCCGGCCCC TGCGGGCGGA AACAGGCAAG CCGTTGATGA    5880

TGTCACCGCA CGCGGCGGTA TCTGCCCCCC ACGTGATGAG CTTGGTCTCC ATTTGGGAGA    5940

AGACGACTGG CTCTACAGCC ACGGCCAGAT CTCGCAAGCC GTTGTGCGCC CAGTCCCGAA    6000

GAGGAGTGAG ATGGTTATAA ACATAGGTGC CAGTAAGCGC CCCTAACTTA ATGATGACCA    6060
```

-continued

```
TTTGCACGTA ATGGCCTCCG ATCATCTTCC GCGCTAACGC GCAGAACCGG AGAAGGCCTT    6120

GGACGCGCAC AAAGTAGGGT ACTTTAAGCA AACTGGCTTG AAGAATCCAA AGGGGTCCGA    6180

AGACGGCCAG CAGCAATTTG GTGATGTCAA ATACCAGAGT CGGGTGTACA GCACACATGA    6240

GTAAGATGAC GGCGTCGCGC CCCCCTCGGA CGTTGAGGGG GGGAATCCAC ACGTGCAGTT    6300

GCGCTTCCAC TCTGGTCAGA AAATACTGAA GCCACCACAA GCACCAGCTG ATATAGCGCT    6360

TGTAATATGG TGACAGAGTC AGCGCCATCA ACCCGACGAG AACAACACCG CCACACGACG    6420

CGGCCACCTC CGTGTCCAGC GCGTACGCCC GCTGGGCAA CGCCAACAGG AGCAGGAGGA    6480

GAGGCCACAT CCCGTAGAAG GTGTAGACCG CTCCGGGCAC CCACTTACCC TTCAAATACC    6540

ATGCAAAGCA GAAGAACACG AGGAAGGATA CAAGACCGTG CGTCCCGGCC AGGGATGCTG    6600

CATTAAGTAT TACGAGGTTC TCCAAAGCCG CCTCCGCTTG GGATATGAGT AGCATCATCC    6660

ACAAGCAGGA GCAGACGCGC GCGTCTGCAA GCAGAAGGAA CAGGAGAACG ACGTACTCCC    6720

ACTTAATGGC CCAGGACGCG ATGCTTGACC CCACCCCGTA CAAGTACTGC ACGTCCACAA    6780

TGTTCTGGTG GAGGTGGATG AGGCCGGTGG ACAAGGCTGG TAGGGTTGTG AAGGAACACG    6840

GGAGGACCTG CCACTGTGTA GTGGTCAGCA GTAACGGGGT GAGCTCGGAC CTGTCCCTGT    6900

CTTCCAGATC GCAACGTTCG CCCCGCGTCC AGTTGCAGGC AGCTTCCAGC CTGTGTTCGA    6960

CCCCTCCCAC GTACATCCTG ATTTTAAATA TGGTGTAGTT GATGGTACAA GGATAATGCC    7020

AAAGCCTATA CGGGTAGTCG ACCAGGCACC TGGGTGTGAT CCAGGGACCG GAGCCGCACC    7080

GAGAGTATGT GGCGTCCGGA TGCTTGCGGA AGCAATCAGT GGGGCAGTGC AGGGTGTTGT    7140

TGCCCGCCCC TCCGATGACA CAAGGAGGCG CTCCGCACAC TTTGGTGAAT CCAGTTGAGT    7200

TCATCCAGGT ACAACCGAAC CAATTGCCCA GCGGTGGCCT GGTATTGTTA AGGACGAAGA    7260

CGTCCGTATC ATTTTCACCC CAGCTGTAGG TGGGCGCGCC CGACCTGTCG GTCGTTCCCA    7320

CCACCACGGG GCTGGGAGTG AAGCAATATA CCGGACCACA CACACTCTTC GCGGGCACAA    7380

TACCGCAAGG TTTTGGGGGG TAGTGCCAGC AGTAGGGGCG CTGGTCGGGG CCGCTTCCGT    7440

TGGCATAACT GATAGGGCCC CAGCCCTGGT CAAAATCGGT AAGGGGTCGG CAGCTGGCTA    7500

GCCTCTCAGG ACAGCCTGAA GAGTTGAACT TGTGGTGATA GAAAAGCCCT GCCAACCAGC    7560

CGGTGTTGAG GCTATCATTG CAGTTCAGGG CCGTGCTATT GAGGTGCCAA CTGCCGTTGG    7620

TGTTGATCAG CTGGACGTTC TGCTTGGCGC CTGGTGCGAG GAGGCTAACA AATCCAGACA    7680

CAGTGTGGCC GGCACTTCCC CCGGTGACGT GGGTTTCCGC GTCGACGCCG GCAAATAGCA    7740

GCAGCACTAC CAGGACCTTC GCCCAGTTCC CCACCATGGA GAAATACGCT ATGCCCGCCA    7800

GGACTCCCCA GTGAGCACCA GCGATCATGT CCAAGATGGC TTGTGGGATC CGGAGCAGCT    7860

GAGCCATTAC CAACGCCGTC GTAGGGGACC AGTTCATCAT CATATCCCAT GCCATGCGGT    7920

GACCCGTTAT ATGGCCGGGA TAGATAGAGC AATTGCAACC TTGCGTCGTC CAGTGGCGCC    7980

TGGGAGAGAA GGTGAACAGT TGGCCGACAA GAAAGACAGA CCCGCATAGG TCCCCCACGT    8040

AGAGGGCCGA ACAGAGGGTG GCGCTCCCGA CAAGCAGATC GATGTGACGT CGAAGCTGCG    8100

TCGCGGGGAG TTTGCCATCC CTGGTGGCCA CCGTAGGGGT CATCGCCACC CAACACCTCG    8160

AGGCGTTGCC CTCACGAACG CAAGGGACGC ACCCCGGAGT GTGCAGGATG GCATCGGCCG    8220

CCTCGTACAC AATACTCGAG TTAGGGCAAT CATTGGTGAC GTGGTAAAGC CCCGTGGAGT    8280

TGCGCACTTG GTAGGCCGAA GCGGGCACAG TCAAGCAAGA GAGCAGGGCC AGAAGGAAGA    8340

TAGAGAAAGA GCAACCAGGA AGGTTCCCTG TTGCATAGTT CACGCCGTCT TCCAGAACCC    8400
```

```
GGACGCCATG CGCCAGGGCC CTGGCAGCGC CTCCAAGAGG GGCGCCGACG AGCGGTATGT    8460

ACCCCATGAG GTCGGCGAAG CCGCACGTAA GGGTATCGAT GACCTTACCC AAATTGCGCG    8520

ACCTACGCCG GGGGTCTGTG GGGCCCCAGC TAGGCCGAGA GCCACGGGGA GACAGGAGCC    8580

ATCCCGCCCA CCCGCAGCCC TCATTGCCAT AGAGGGGCCA AGGGTACCCG GGCTGAGCCC    8640

AGGTCCTGCC CTCGGGCCGA CGAGCCTTGG GGATAGGCTG ACGTCTACCT CGAGGTTGCG    8700

ACCGCTCGGA AGTCTTTCTC GTCGCGCGCA CACCCAATCT AGGGCCCCTG CGCGGCAACA    8760

AGTAAACTCC ACCAACGATC TGACCGCCAC CCGGGAACTT GACGTCCTGT GGGCGACGGT    8820

TGGTGTTACG TTTGTTTTTT TTTTGAGGTT TAGGATTCGT GCTCATGGTG CACGGTCTAC    8880

GAGACCTCCC GGGGCACTCG CAAGCACCCT ATCAGGCAGT ACCACAAGGC CTTTCGCGAC    8940

CCAACACTAC TCGGCTAGCA GTCTTGCGGG GGCACGCCCA AATCTCCAGG CATTGAGCGG    9000

GTTGATCCAA GAAAGGACCC GGTCGTCCTG GCAATTCCGG TGTACTCACC GGTTCCGCAG    9060

ACCACTATGG CTCTCCCGGG AGGGGGGGTC CTGGAGGCTG CACGACACTC ATACTAACGC    9120

CATGGCTAGA CGCTTTCTGC GTGAAGACAG TAGTTCCTCA CAGGGGAGTG ATTCATGGTG    9180

GAGTG                                                               9185
```

(2) INFORMATION FOR SEQ ID NO:124:

(i) SEQUENCE CHARACTERISTICS:
        (A) LENGTH: 2955 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Duplication
        (B) LOCATION: 9
        (D) OTHER INFORMATION: /note= "A heterogeneity exists at
           Xaa which is either Lys or Arg"

(ix) FEATURE:
        (A) NAME/KEY: Duplication
        (B) LOCATION: 11
        (D) OTHER INFORMATION: /note= "A heterogeneity exists at
           Xaa which is either Asn or Thr"

(ix) FEATURE:
        (A) NAME/KEY: Duplication
        (B) LOCATION: 176
        (D) OTHER INFORMATION: /note= "A heterogeneity exists at
           Xaa which is either Ile or Thr"

(ix) FEATURE:
        (A) NAME/KEY: Duplication
        (B) LOCATION: 334
        (D) OTHER INFORMATION: /note= "A heterogeneity exists at
           Xaa which is either Met or Val"

(ix) FEATURE:
        (A) NAME/KEY: Duplication
        (B) LOCATION: 603
        (D) OTHER INFORMATION: /note= "A heterogeneity exists at
           Xaa which is either Leu or Ile"

(ix) FEATURE:
        (A) NAME/KEY: Duplication
        (B) LOCATION: 848
        (D) OTHER INFORMATION: /note= "A heterogeneity exists at
           Xaa which is either Tyr or Asn"

(ix) FEATURE:
        (A) NAME/KEY: Duplication
        (B) LOCATION: 1276
        (D) OTHER INFORMATION: /note= "A heterogeneity exists at Xaa which is either Pro or Leu"

(ix) FEATURE:
        (A) NAME/KEY: Duplication
        (B) LOCATION: 1454
        (D) OTHER INFORMATION: /note= "A heterogeneity exists at
            Xaa which is either Cys or Tyr"

(ix) FEATURE:
        (A) NAME/KEY: Duplication
        (B) LOCATION: 1471
        (D) OTHER INFORMATION: /note= "A heterogeneity exists at
            Xaa which is either Thr or Ser"

(ix) FEATURE:
        (A) NAME/KEY: Duplication
        (B) LOCATION: 1877
        (D) OTHER INFORMATION: /note= "A heterogeneity exists at
            Xaa which is either Glu or Gly"

(ix) FEATURE:
        (A) NAME/KEY: Duplication
        (B) LOCATION: 1948
        (D) OTHER INFORMATION: /note= "A heterogeneity exists at
            Xaa which is either Leu or His"

(ix) FEATURE:
        (A) NAME/KEY: Duplication
        (B) LOCATION: 1949
        (D) OTHER INFORMATION: /note= "A heterogeneity exists at
            Xaa which is either Ser or Cys"

(ix) FEATURE:
        (A) NAME/KEY: Duplication
        (B) LOCATION: 2021
        (D) OTHER INFORMATION: /note= "A heterogeneity exists at
            Xaa which is either Gly or Val"

(ix) FEATURE:
        (A) NAME/KEY: Duplication
        (B) LOCATION: 2349
        (D) OTHER INFORMATION: /note= "A heterogeneity exists at
            Xaa which is either Thr or Ser"

(ix) FEATURE:
        (A) NAME/KEY: Duplication
        (B) LOCATION: 2385
        (D) OTHER INFORMATION: /note= "A heterogeneity exists at
            Xaa which is either Tyr or Phe"

(ix) FEATURE:
        (A) NAME/KEY: Duplication
        (B) LOCATION: 2386
        (D) OTHER INFORMATION: /note= "A heterogeneity exists at
            Xaa which is either Ser or Ala"

(ix) FEATURE:
        (A) NAME/KEY: Duplication
        (B) LOCATION: 2502
        (D) OTHER INFORMATION: /note= "A heterogeneity exists at
            Xaa which is either Leu or Phe"

(ix) FEATURE:
        (A) NAME/KEY: Duplication
        (B) LOCATION: 2690
        (D) OTHER INFORMATION: /note= "A heterogeneity exists at
            Xaa which is either Arg or Gly"

(ix) FEATURE:
        (A) NAME/KEY: Duplication
        (B) LOCATION: 2921
        (D) OTHER INFORMATION: /note= "A heterogeneity exists at
            Xaa which is either Arg or Gly"

(xi) SEQUENCE DESCRIPTION: SEQ ID NO:124:

Met Ser Thr Asn Pro Lys Pro Gln Xaa Lys Xaa Lys Arg Asn Thr Asn
1               5                   10                  15

-continued

```
Arg Arg Pro Gln Asp Val Lys Phe Pro Gly Gly Gln Ile Val Gly
             20                  25                  30

Gly Val Tyr Leu Leu Pro Arg Arg Gly Pro Arg Leu Gly Val Arg Ala
         35                  40                  45

Thr Arg Lys Thr Ser Glu Arg Ser Gln Pro Arg Gly Arg Arg Gln Pro
 50                  55                  60

Ile Pro Lys Ala Arg Arg Pro Glu Gly Arg Thr Trp Ala Gln Pro Gly
 65                  70                  75                  80

Tyr Pro Trp Pro Leu Tyr Gly Asn Glu Gly Cys Gly Trp Ala Gly
                 85                  90                  95

Leu Leu Ser Pro Arg Gly Ser Arg Pro Ser Trp Gly Pro Thr Asp Pro
                100                 105                 110

Arg Arg Arg Ser Arg Asn Leu Gly Lys Val Ile Asp Thr Leu Thr Cys
                115                 120                 125

Gly Phe Ala Asp Leu Met Gly Tyr Ile Pro Leu Val Gly Ala Pro Leu
                130                 135                 140

Gly Ser Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Xaa
                165                 170                 175

Phe Leu Leu Ala Leu Leu Ser Cys Leu Thr Val Pro Ala Ser Ala Tyr
                180                 185                 190

Gln Val Arg Asn Ser Thr Gly Leu Tyr His Val Thr Asn Asp Cys Pro
                195                 200                 205

Asn Ser Ser Ile Val Tyr Glu Ala Ala Asp Ala Ile Leu His Thr Pro
210                 215                 220

Gly Cys Val Pro Cys Val Arg Glu Gly Asn Ala Ser Arg Cys Trp Val
225                 230                 235                 240

Ala Met Thr Pro Thr Val Ala Thr Arg Asp Gly Lys Leu Pro Ala Thr
                245                 250                 255

Gln Leu Arg Arg His Ile Asp Leu Leu Val Gly Ser Ala Thr Leu Cys
                260                 265                 270

Ser Ala Leu Tyr Val Gly Asp Leu Cys Gly Ser Val Phe Leu Val Gly
                275                 280                 285

Gln Leu Phe Thr Phe Ser Pro Arg Arg His Trp Thr Thr Gln Gly Cys
                290                 295                 300

Asn Cys Ser Ile Tyr Pro Gly His Ile Thr Gly His Arg Met Ala Trp
305                 310                 315                 320

Asp Met Met Met Asn Trp Ser Pro Thr Thr Ala Leu Val Xaa Ala Gln
                325                 330                 335

Leu Leu Arg Ile Pro Gln Ala Ile Leu Asp Met Ile Ala Gly Ala His
                340                 345                 350

Trp Gly Val Leu Ala Gly Ile Ala Tyr Phe Ser Met Val Gly Asn Trp
                355                 360                 365

Ala Lys Val Leu Val Val Leu Leu Phe Ala Gly Val Asp Ala Glu
                370                 375                 380

Thr His Val Thr Gly Gly Ser Ala Gly His Thr Val Ser Gly Phe Val
385                 390                 395                 400

Ser Leu Leu Ala Pro Gly Ala Lys Gln Asn Val Gln Leu Ile Asn Thr
                405                 410                 415

Asn Gly Ser Trp His Leu Asn Ser Thr Ala Leu Asn Cys Asn Asp Ser
                420                 425                 430

Leu Asn Thr Gly Trp Leu Ala Gly Leu Phe Tyr His His Lys Phe Asn
```

-continued

```
              435                 440                 445

Ser Ser Gly Cys Pro Glu Arg Leu Ala Ser Cys Arg Pro Leu Thr Asp
        450                 455                 460

Phe Asp Gln Gly Trp Gly Pro Ile Ser Tyr Ala Asn Gly Ser Gly Pro
    465                 470                 475                 480

Asp Gln Arg Pro Tyr Cys Trp His Tyr Pro Pro Lys Pro Cys Gly Ile
                    485                 490                 495

Val Pro Ala Lys Ser Val Cys Gly Pro Val Tyr Cys Phe Thr Pro Ser
                500                 505                 510

Pro Val Val Gly Thr Thr Asp Arg Ser Gly Ala Pro Thr Tyr Ser
                515                 520                 525

Trp Gly Glu Asn Asp Thr Asp Val Phe Val Leu Asn Asn Thr Arg Pro
        530                 535                 540

Pro Leu Gly Asn Trp Phe Gly Cys Thr Trp Met Asn Ser Thr Gly Phe
    545                 550                 555                 560

Thr Lys Val Cys Gly Ala Pro Pro Cys Val Ile Gly Gly Ala Gly Asn
                    565                 570                 575

Asn Thr Leu His Cys Pro Thr Asp Cys Phe Arg Lys His Pro Asp Ala
                580                 585                 590

Thr Tyr Ser Arg Cys Gly Ser Gly Pro Trp Xaa Thr Pro Arg Cys Leu
                595                 600                 605

Val Asp Tyr Pro Tyr Arg Leu Trp His Tyr Pro Cys Thr Ile Asn Tyr
    610                 615                 620

Thr Ile Phe Lys Ile Arg Met Tyr Val Gly Gly Val Glu His Arg Leu
    625                 630                 635                 640

Glu Ala Ala Cys Asn Trp Thr Arg Gly Glu Arg Cys Asp Leu Glu Asp
                    645                 650                 655

Arg Asp Arg Ser Glu Leu Ser Pro Leu Leu Leu Thr Thr Thr Gln Trp
                660                 665                 670

Gln Val Leu Pro Cys Ser Phe Thr Thr Leu Pro Ala Leu Ser Thr Gly
                675                 680                 685

Leu Ile His Leu His Gln Asn Ile Val Asp Val Gln Tyr Leu Tyr Gly
        690                 695                 700

Val Gly Ser Ser Ile Ala Ser Trp Ala Ile Lys Trp Glu Tyr Val Val
    705                 710                 715                 720

Leu Leu Phe Leu Leu Leu Ala Asp Ala Arg Val Cys Ser Cys Leu Trp
                    725                 730                 735

Met Met Leu Leu Ile Ser Gln Ala Glu Ala Ala Leu Glu Asn Leu Val
                740                 745                 750

Ile Leu Asn Ala Ala Ser Leu Ala Gly Thr His Gly Leu Val Ser Phe
                755                 760                 765

Leu Val Phe Phe Cys Phe Ala Trp Tyr Leu Lys Gly Lys Trp Val Pro
    770                 775                 780

Gly Ala Val Tyr Thr Phe Tyr Gly Met Trp Pro Leu Leu Leu Leu Leu
    785                 790                 795                 800

Leu Ala Leu Pro Gln Arg Ala Tyr Ala Leu Asp Thr Glu Val Ala Ala
                    805                 810                 815

Ser Cys Gly Gly Val Val Leu Val Gly Leu Met Ala Leu Thr Leu Ser
                820                 825                 830

Pro Tyr Tyr Lys Arg Tyr Ile Ser Trp Cys Leu Trp Trp Leu Gln Xaa
                835                 840                 845

Phe Leu Thr Arg Val Glu Ala Gln Leu His Val Trp Ile Pro Pro Leu
    850                 855                 860
```

```
Asn Val Arg Gly Gly Arg Asp Ala Val Ile Leu Leu Met Cys Ala Val
865                 870                 875                 880

His Pro Thr Leu Val Phe Asp Ile Thr Lys Leu Leu Ala Val Phe
            885                 890                 895

Gly Pro Leu Trp Ile Leu Gln Ala Ser Leu Leu Lys Val Pro Tyr Phe
            900                 905                 910

Val Arg Val Gln Gly Leu Leu Arg Phe Cys Ala Leu Ala Arg Lys Met
            915                 920                 925

Ile Gly Gly His Tyr Val Gln Met Val Ile Lys Leu Gly Ala Leu
930                 935                 940

Thr Gly Thr Tyr Val Tyr Asn His Leu Thr Pro Leu Arg Asp Trp Ala
945                 950                 955                 960

His Asn Gly Leu Arg Asp Leu Ala Val Ala Val Glu Pro Val Val Phe
            965                 970                 975

Ser Gln Met Glu Thr Lys Leu Ile Thr Trp Gly Ala Asp Thr Ala Ala
            980                 985                 990

Cys Gly Asp Ile Ile Asn Gly Leu Pro Val Ser Ala Arg Arg Gly Arg
            995                 1000                1005

Glu Ile Leu Leu Gly Pro Ala Asp Gly Met Val Ser Lys Gly Trp Arg
    1010            1015                1020

Leu Leu Ala Pro Ile Thr Ala Tyr Ala Gln Gln Thr Arg Gly Leu Leu
1025                1030                1035                1040

Gly Cys Ile Ile Thr Ser Leu Thr Gly Arg Asp Lys Asn Gln Val Glu
                1045                1050                1055

Gly Glu Val Gln Ile Val Ser Thr Ala Ala Gln Thr Phe Leu Ala Thr
                1060                1065                1070

Cys Ile Asn Gly Val Cys Trp Thr Val Tyr His Gly Ala Gly Thr Arg
                1075                1080                1085

Thr Ile Ala Ser Pro Lys Gly Pro Val Ile Gln Met Tyr Thr Asn Val
                1090                1095                1100

Asp Gln Asp Leu Val Gly Trp Pro Ala Pro Gln Gly Ser Arg Ser Leu
1105                1110                1115                1120

Thr Pro Cys Thr Cys Gly Ser Ser Asp Leu Tyr Leu Val Thr Arg His
                1125                1130                1135

Ala Asp Val Ile Pro Val Arg Arg Arg Gly Asp Ser Arg Gly Ser Leu
                1140                1145                1150

Leu Ser Pro Arg Pro Ile Ser Tyr Leu Lys Gly Ser Ser Gly Gly Pro
                1155                1160                1165

Leu Leu Cys Pro Ala Gly His Ala Val Gly Ile Phe Arg Ala Ala Val
                1170                1175                1180

Cys Thr Arg Gly Val Ala Lys Ala Val Asp Phe Ile Pro Val Glu Asn
1185                1190                1195                1200

Leu Glu Thr Thr Met Arg Ser Pro Val Phe Thr Asp Asn Ser Ser Pro
                1205                1210                1215

Pro Val Val Pro Gln Ser Phe Gln Val Ala His Leu His Ala Pro Thr
                1220                1225                1230

Gly Ser Gly Lys Ser Thr Lys Val Pro Ala Ala Tyr Ala Ala Gln Gly
                1235                1240                1245

Tyr Lys Val Leu Val Leu Asn Pro Ser Val Ala Ala Thr Leu Gly Phe
    1250                1255                1260

Gly Ala Tyr Met Ser Lys Ala His Gly Ile Asp Xaa Asn Ile Arg Thr
1265                1270                1275                1280
```

```
Gly Val Arg Thr Ile Thr Thr Gly Ser Pro Ile Thr Tyr Ser Thr Tyr
            1285                1290                1295

Gly Lys Phe Leu Ala Asp Gly Gly Cys Ser Gly Gly Ala Tyr Asp Ile
        1300                1305                1310

Ile Ile Cys Asp Glu Cys His Ser Thr Asp Ala Thr Ser Ile Leu Gly
        1315                1320                1325

Ile Gly Thr Val Leu Asp Gln Ala Glu Thr Ala Gly Ala Arg Leu Val
        1330                1335                1340

Val Leu Ala Thr Ala Thr Pro Pro Gly Ser Val Thr Val Pro His Pro
1345                1350                1355                1360

Asn Ile Glu Glu Val Ala Leu Ser Thr Thr Gly Glu Ile Pro Phe Tyr
            1365                1370                1375

Gly Lys Ala Ile Pro Leu Glu Val Ile Lys Gly Gly Arg His Leu Ile
        1380                1385                1390

Phe Cys His Ser Lys Lys Lys Cys Asp Glu Leu Ala Ala Lys Leu Val
        1395                1400                1405

Ala Leu Gly Ile Asn Ala Val Ala Tyr Tyr Arg Gly Leu Asp Val Ser
        1410                1415                1420

Val Ile Pro Thr Ser Gly Asp Val Val Val Ala Thr Asp Ala Leu
1425                1430                1435                1440

Met Thr Gly Tyr Thr Gly Asp Phe Asp Ser Val Ile Asp Xaa Asn Thr
            1445                1450                1455

Cys Val Thr Gln Thr Val Asp Phe Ser Leu Asp Pro Thr Phe Xaa Ile
            1460                1465                1470

Glu Thr Ile Thr Leu Pro Gln Asp Ala Val Ser Arg Thr Gln Arg Arg
        1475                1480                1485

Gly Arg Thr Gly Arg Gly Lys Pro Gly Ile Asn Arg Phe Val Ala Pro
        1490                1495                1500

Gly Glu Arg Pro Ser Gly Met Phe Asp Ser Ser Val Leu Cys Glu Cys
1505                1510                1515                1520

Tyr Asp Ala Gly Cys Ala Trp Tyr Glu Leu Thr Pro Ala Glu Thr Thr
            1525                1530                1535

Val Arg Leu Arg Ala Tyr Met Asn Thr Pro Gly Leu Pro Val Cys Gln
            1540                1545                1550

Asp His Leu Glu Phe Trp Glu Gly Val Phe Thr Gly Leu Thr His Ile
            1555                1560                1565

Asp Ala His Phe Leu Ser Gln Thr Lys Gln Ser Gly Glu Asn Leu Pro
        1570                1575                1580

Tyr Leu Val Ala Tyr Gln Ala Thr Val Cys Ala Arg Ala Gln Ala Pro
1585                1590                1595                1600

Pro Pro Ser Trp Asp Gln Met Trp Lys Cys Leu Ile Arg Leu Lys Pro
            1605                1610                1615

Thr Leu His Gly Pro Thr Pro Leu Leu Tyr Arg Leu Gly Ala Val Gln
            1620                1625                1630

Asn Glu Ile Thr Leu Thr His Pro Val Thr Lys Tyr Ile Met Thr Cys
            1635                1640                1645

Met Ser Ala Asp Leu Glu Val Val Thr Ser Thr Trp Val Leu Val Gly
        1650                1655                1660

Gly Val Leu Ala Ala Leu Ala Ala Tyr Cys Leu Ser Thr Gly Cys Val
1665                1670                1675                1680

Val Ile Val Gly Arg Val Val Leu Ser Gly Lys Pro Ala Ile Ile Pro
            1685                1690                1695

Asp Arg Glu Val Leu Tyr Arg Glu Phe Asp Glu Met Glu Glu Cys Ser
```

```
                    1700              1705              1710
Gln His Leu Pro Tyr Ile Glu Gln Gly Met Met Leu Ala Glu Gln Phe
            1715              1720              1725
Lys Gln Lys Ala Leu Gly Leu Leu Gln Thr Ala Ser Arg Gln Ala Glu
        1730              1735              1740
Val Ile Ala Pro Ala Val Gln Thr Asn Trp Gln Lys Leu Glu Thr Phe
1745              1750              1755              1760
Trp Ala Lys His Met Trp Asn Phe Ile Ser Gly Ile Gln Tyr Leu Ala
            1765              1770              1775
Gly Leu Ser Thr Leu Pro Gly Asn Pro Ala Ile Ala Ser Leu Met Ala
                1780              1785              1790
Phe Thr Ala Ala Val Thr Ser Pro Leu Thr Thr Ser Gln Thr Leu Leu
            1795              1800              1805
Phe Asn Ile Leu Gly Gly Trp Val Ala Ala Gln Leu Ala Ala Pro Gly
        1810              1815              1820
Ala Ala Thr Ala Phe Val Gly Ala Gly Leu Ala Gly Ala Ala Ile Gly
1825              1830              1835              1840
Ser Val Gly Leu Gly Lys Val Leu Ile Asp Ile Leu Ala Gly Tyr Gly
            1845              1850              1855
Ala Gly Val Ala Gly Ala Leu Val Ala Phe Lys Ile Met Ser Gly Glu
        1860              1865              1870
Val Pro Ser Thr Xaa Asp Leu Val Asn Leu Leu Pro Ala Ile Leu Ser
    1875              1880              1885
Pro Gly Ala Leu Val Val Gly Val Val Cys Ala Ala Ile Leu Arg Arg
        1890              1895              1900
His Val Gly Pro Gly Glu Gly Ala Val Gln Trp Met Asn Arg Leu Ile
1905              1910              1915              1920
Ala Phe Ala Ser Arg Gly Asn His Val Ser Pro Thr His Tyr Val Pro
            1925              1930              1935
Glu Ser Asp Ala Ala Ala Arg Val Thr Ala Ile Xaa Xaa Ser Leu Thr
            1940              1945              1950
Val Thr Gln Leu Leu Arg Arg Leu His Gln Trp Ile Ser Ser Glu Cys
            1955              1960              1965
Thr Thr Pro Cys Ser Gly Ser Trp Leu Arg Asp Ile Trp Asp Trp Ile
    1970              1975              1980
Cys Glu Val Leu Ser Asp Phe Lys Thr Trp Leu Lys Ala Lys Leu Met
1985              1990              1995              2000
Pro Gln Leu Pro Gly Ile Pro Phe Val Ser Cys Gln Arg Gly Tyr Lys
                2005              2010              2015
Gly Val Trp Arg Xaa Asp Gly Ile Met His Thr Arg Cys His Cys Gly
            2020              2025              2030
Ala Glu Ile Thr Gly His Val Lys Asn Gly Thr Met Arg Ile Val Gly
            2035              2040              2045
Pro Arg Thr Cys Arg Asn Met Trp Ser Gly Thr Phe Pro Ile Asn Ala
    2050              2055              2060
Tyr Thr Thr Gly Pro Cys Thr Pro Leu Pro Ala Pro Asn Tyr Thr Phe
2065              2070              2075              2080
Ala Leu Trp Arg Val Ser Ala Glu Glu Tyr Val Glu Ile Arg Gln Val
            2085              2090              2095
Gly Asp Phe His Tyr Val Thr Gly Met Thr Thr Asp Asn Leu Lys Cys
            2100              2105              2110
Pro Cys Gln Val Pro Ser Pro Glu Phe Phe Thr Glu Leu Asp Gly Val
        2115              2120              2125
```

-continued

```
Arg Leu His Arg Phe Ala Pro Pro Cys Lys Pro Leu Leu Arg Glu Glu
    2130                2135                2140
Val Ser Phe Arg Val Gly Leu His Glu Tyr Pro Val Gly Ser Gln Leu
2145                2150                2155                2160
Pro Cys Glu Pro Glu Pro Asp Val Ala Val Leu Thr Ser Met Leu Thr
                2165                2170                2175
Asp Pro Ser His Ile Thr Ala Glu Ala Ala Gly Arg Arg Leu Ala Arg
            2180                2185                2190
Gly Ser Pro Pro Ser Val Ala Ser Ser Ala Ser Gln Leu Ser Ala
    2195                2200                2205
Pro Ser Leu Lys Ala Thr Cys Thr Ala Asn His Asp Ser Pro Asp Ala
    2210                2215                2220
Glu Leu Ile Glu Ala Asn Leu Leu Trp Arg Gln Glu Met Gly Gly Asn
2225                2230                2235                2240
Ile Thr Arg Val Glu Ser Glu Asn Lys Val Val Ile Leu Asp Ser Phe
                2245                2250                2255
Asp Pro Leu Val Ala Glu Glu Asp Glu Arg Glu Ile Ser Val Pro Ala
            2260                2265                2270
Glu Ile Leu Arg Lys Ser Arg Arg Phe Ala Gln Ala Leu Pro Val Trp
        2275                2280                2285
Ala Arg Pro Asp Tyr Asn Pro Pro Leu Val Glu Thr Trp Lys Lys Pro
    2290                2295                2300
Asp Tyr Glu Pro Pro Val Val His Gly Cys Pro Leu Pro Pro Pro Lys
2305                2310                2315                2320
Ser Pro Pro Val Pro Pro Pro Arg Lys Lys Arg Thr Val Val Leu Thr
                2325                2330                2335
Glu Ser Thr Leu Ser Thr Ala Leu Ala Glu Leu Ala Xaa Arg Ser Phe
            2340                2345                2350
Gly Ser Ser Ser Thr Ser Gly Ile Thr Gly Asp Asn Thr Thr Thr Ser
        2355                2360                2365
Ser Glu Pro Ala Pro Ser Gly Cys Pro Pro Asp Ser Asp Ala Glu Ser
    2370                2375                2380
Xaa Xaa Ser Met Pro Pro Leu Glu Gly Glu Pro Gly Asp Pro Asp Leu
2385                2390                2395                2400
Ser Asp Gly Ser Trp Ser Thr Val Ser Ser Glu Ala Asn Ala Glu Asp
                2405                2410                2415
Val Val Cys Cys Ser Met Ser Tyr Ser Trp Thr Gly Ala Leu Val Thr
            2420                2425                2430
Pro Cys Ala Ala Glu Glu Gln Lys Leu Pro Ile Asn Ala Leu Ser Asn
        2435                2440                2445
Ser Leu Leu Arg His His Asn Leu Val Tyr Ser Thr Thr Ser Arg Ser
    2450                2455                2460
Ala Cys Gln Arg Gln Lys Lys Val Thr Phe Asp Arg Leu Gln Val Leu
2465                2470                2475                2480
Asp Ser His Tyr Gln Asp Val Leu Lys Glu Val Lys Ala Ala Ala Ser
                2485                2490                2495
Lys Val Lys Ala Asn Xaa Leu Ser Val Glu Glu Ala Cys Ser Leu Thr
            2500                2505                2510
Pro Pro His Ser Ala Lys Ser Lys Phe Gly Tyr Gly Ala Lys Asp Val
        2515                2520                2525
Arg Cys His Ala Arg Lys Ala Val Thr His Ile Asn Ser Val Trp Lys
    2530                2535                2540
```

-continued

```
Asp Leu Leu Glu Asp Asn Val Thr Pro Ile Asp Thr Ile Met Ala
2545                2550                2555                2560

Lys Asn Glu Val Phe Cys Val Gln Pro Glu Lys Gly Arg Lys Pro
            2565                2570                2575

Ala Arg Leu Ile Val Phe Pro Asp Leu Gly Val Arg Val Cys Glu Lys
            2580                2585                2590

Met Ala Leu Tyr Asp Val Val Thr Lys Leu Pro Leu Ala Val Met Gly
            2595                2600                2605

Ser Ser Tyr Gly Phe Gln Tyr Ser Pro Gly Gln Arg Val Glu Phe Leu
            2610                2615                2620

Val Gln Ala Trp Lys Ser Lys Lys Thr Pro Met Gly Phe Ser Tyr Asp
2625                2630                2635                2640

Thr Arg Cys Phe Asp Ser Thr Val Thr Glu Ser Asp Ile Arg Thr Glu
            2645                2650                2655

Glu Ala Ile Tyr Gln Cys Cys Asp Leu Asp Pro Gln Ala Arg Val Ala
            2660                2665                2670

Ile Lys Ser Leu Thr Glu Arg Leu Tyr Val Gly Gly Pro Leu Thr Asn
            2675                2680                2685

Ser Xaa Gly Glu Asn Cys Gly Tyr Arg Arg Cys Arg Ala Ser Gly Val
            2690                2695                2700

Leu Thr Thr Ser Cys Gly Asn Thr Leu Thr Cys Tyr Ile Lys Ala Arg
2705                2710                2715                2720

Ala Ala Cys Arg Ala Ala Gly Leu Gln Asp Cys Thr Met Leu Val Cys
            2725                2730                2735

Gly Asp Asp Leu Val Val Ile Cys Glu Ser Ala Gly Val Gln Glu Asp
            2740                2745                2750

Ala Ala Ser Leu Arg Ala Phe Thr Glu Ala Met Thr Arg Tyr Ser Ala
            2755                2760                2765

Pro Pro Gly Asp Pro Pro Gln Pro Glu Tyr Asp Leu Glu Leu Ile Thr
            2770                2775                2780

Ser Cys Ser Ser Asn Val Ser Val Ala His Asp Gly Ala Gly Lys Arg
2785                2790                2795                2800

Val Tyr Tyr Leu Thr Arg Asp Pro Thr Thr Pro Leu Ala Arg Ala Ala
            2805                2810                2815

Trp Glu Thr Ala Arg His Thr Pro Val Asn Ser Trp Leu Gly Asn Ile
            2820                2825                2830

Ile Met Phe Ala Pro Thr Leu Trp Ala Arg Met Ile Leu Met Thr His
            2835                2840                2845

Phe Phe Ser Val Leu Ile Ala Arg Asp Gln Leu Glu Gln Ala Leu Asp
            2850                2855                2860

Cys Glu Ile Tyr Gly Ala Cys Tyr Ser Ile Glu Pro Leu Asp Leu Pro
2865                2870                2875                2880

Pro Ile Ile Gln Arg Leu His Gly Leu Ser Ala Phe Ser Leu His Ser
            2885                2890                2895

Tyr Ser Pro Gly Glu Ile Asn Arg Val Ala Ala Cys Leu Arg Lys Leu
            2900                2905                2910

Gly Val Pro Pro Leu Arg Ala Trp Xaa His Arg Ala Arg Ser Val Arg
            2915                2920                2925

Ala Arg Leu Leu Ala Arg Gly Gly Arg Ala Ala Ile Cys Gly Lys Tyr
            2930                2935                2940

Leu Phe Asn Trp Ala Val Arg Thr Lys Leu Lys
2945                2950                2955
```

```
(2) INFORMATION FOR SEQ ID NO:125:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:125:

Thr Ala Thr Pro Pro Gly
1               5

(2) INFORMATION FOR SEQ ID NO:126:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:126:

Ser Ala Ala Gln Arg Arg Gly Arg Ile Gly Arg Asn Pro
1               5                   10

(2) INFORMATION FOR SEQ ID NO:127:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:127:

Gly Asp Asp Cys Val Val
1               5

(2) INFORMATION FOR SEQ ID NO:128:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:128:

Thr Ala Thr Pro Pro Gly
1               5

(2) INFORMATION FOR SEQ ID NO:129:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:129:

Ser Arg Thr Gln Arg Arg Gly Arg Thr Gly Arg Gly Lys
1               5                   10
```

(2) INFORMATION FOR SEQ ID NO:130:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:130:

```
Gly Asp Asp Leu Val Val
 1               5
```

(2) INFORMATION FOR SEQ ID NO:131:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "transfer vector pAc373"

(xi) SEQUENCE DESCRIPTION: SEQ ID NO:131:

CCCGAGATCC GCGGATCC                                            18

(2) INFORMATION FOR SEQ ID NO:132:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "transfer vector pVL985"

(xi) SEQUENCE DESCRIPTION: SEQ ID NO:132:

CCTATAAATA TTCCGGATTA TTCATACCGT CCCACCATCG GGCCGGATCC         50

(2) INFORMATION FOR SEQ ID NO:133:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 10..42

(xi) SEQUENCE DESCRIPTION: SEQ ID NO:133:

```
CCTATAAAT ATG CCG GAT TAT TCA TAC CGT CCC ACC ATC GGG      42
          Met Pro Asp Tyr Ser Tyr Arg Pro Thr Ile Gly
           1               5                  10
```

(2) INFORMATION FOR SEQ ID NO:134:

(i) SEQUENCE CHARACTERISTICS:
        (A) LENGTH: 11 amino acids
        (B) TYPE: amino acid
        (D) TOPOLOGY: linear (ii) MOLECULE TYPE: protein (xi) SEQUENCE DESCRIPTION: SEQ ID NO:134:

Met Pro Asp Tyr Ser Tyr Arg Pro Thr Ile Gly
 1               5                  10

(2) INFORMATION FOR SEQ ID NO:135:

(i) SEQUENCE CHARACTERISTICS:
        (A) LENGTH: 182 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (B) CLONE: 6k (ix) FEATURE:
        (A) NAME/KEY: CDS
        (B) LOCATION: 1..180

(xi) SEQUENCE DESCRIPTION: SEQ ID NO:135:

GGC AGG GCT GCC ATA TGT GGC AAG TAC CTC TTC AAC TGG GCA GTA AGA      48
Gly Arg Ala Ala Ile Cys Gly Lys Tyr Leu Phe Asn Trp Ala Val Arg
 1               5                  10                  15

ACA AAG CTC AAA CTC ACT CCA ATA GCG GCC GCT GGC CAG CTG GAC TTG      96
Thr Lys Leu Lys Leu Thr Pro Ile Ala Ala Ala Gly Gln Leu Asp Leu
             20                  25                  30

TCC GGC TGG TTC ACG GCT GGC TAC AGC GGG GGA GAC ATT TAT CAC AGC     144
Ser Gly Trp Phe Thr Ala Gly Tyr Ser Gly Gly Asp Ile Tyr His Ser
         35                  40                  45

GTG TCT CAT GCC CGG CCC CGC TGG ATC TGG TTT TGC CC                  182
Val Ser His Ala Arg Pro Arg Trp Ile Trp Phe Cys
     50                  55                  60

(2) INFORMATION FOR SEQ ID NO:136:

(i) SEQUENCE CHARACTERISTICS:
        (A) LENGTH: 60 amino acids
        (B) TYPE: amino acid
        (D) TOPOLOGY: linear (ii) MOLECULE TYPE: protein (xi) SEQUENCE DESCRIPTION: SEQ ID NO:136:

Gly Arg Ala Ala Ile Cys Gly Lys Tyr Leu Phe Asn Trp Ala Val Arg
 1               5                  10                  15

Thr Lys Leu Lys Leu Thr Pro Ile Ala Ala Ala Gly Gln Leu Asp Leu
             20                  25                  30

Ser Gly Trp Phe Thr Ala Gly Tyr Ser Gly Gly Asp Ile Tyr His Ser
         35                  40                  45

Val Ser His Ala Arg Pro Arg Trp Ile Trp Phe Cys
     50                  55                  60

(2) INFORMATION FOR SEQ ID NO:137:

(i) SEQUENCE CHARACTERISTICS:
        (A) LENGTH: 8987 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..8985

(xi) SEQUENCE DESCRIPTION: SEQ ID NO:137:

| | | | | | | | | | | | | | | | | |
|---|---|---|---|---|---|---|---|---|---|---|---|---|---|---|---|---|
| ATG | AGC | ACG | AAT | CCT | AAA | CCT | CAA | AAA | AAA | AAC | AAA | CGT | AAC | ACC | AAC | 48 |
| Met | Ser | Thr | Asn | Pro | Lys | Pro | Gln | Lys | Lys | Asn | Lys | Arg | Asn | Thr | Asn | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| CGT | CGC | CCA | CAG | GAC | GTC | AAG | TTC | CCG | GGT | GGC | GGT | CAG | ATC | GTT | GGT | 96 |
| Arg | Arg | Pro | Gln | Asp | Val | Lys | Phe | Pro | Gly | Gly | Gly | Gln | Ile | Val | Gly | |
| | | | 20 | | | | | 25 | | | | | 30 | | | |

| | | | | | | | | | | | | | | | | |
|---|---|---|---|---|---|---|---|---|---|---|---|---|---|---|---|---|
| GGA | GTT | TAC | TTG | TTG | CCG | CGC | AGG | GGC | CCT | AGA | TTG | GGT | GTG | CGC | GCG | 144 |
| Gly | Val | Tyr | Leu | Leu | Pro | Arg | Arg | Gly | Pro | Arg | Leu | Gly | Val | Arg | Ala | |
| | | 35 | | | | | 40 | | | | | 45 | | | | |

| | | | | | | | | | | | | | | | | |
|---|---|---|---|---|---|---|---|---|---|---|---|---|---|---|---|---|
| ACG | AGA | AAG | ACT | TCC | GAG | CGG | TCG | CAA | CCT | CGA | GGT | AGA | CGT | CAG | CCT | 192 |
| Thr | Arg | Lys | Thr | Ser | Glu | Arg | Ser | Gln | Pro | Arg | Gly | Arg | Arg | Gln | Pro | |
| | 50 | | | | | 55 | | | | | 60 | | | | | |

| | | | | | | | | | | | | | | | | |
|---|---|---|---|---|---|---|---|---|---|---|---|---|---|---|---|---|
| ATC | CCC | AAG | GCT | CGT | CGG | CCC | GAG | GGC | AGG | ACC | TGG | GCT | CAG | CCC | GGG | 240 |
| Ile | Pro | Lys | Ala | Arg | Arg | Pro | Glu | Gly | Arg | Thr | Trp | Ala | Gln | Pro | Gly | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| TAC | CCT | TGG | CCC | CTC | TAT | GGC | AAT | GAG | GGC | TGC | GGG | TGG | GCG | GGA | TGG | 288 |
| Tyr | Pro | Trp | Pro | Leu | Tyr | Gly | Asn | Glu | Gly | Cys | Gly | Trp | Ala | Gly | Trp | |
| | | | | 85 | | | | | 90 | | | | | 95 | | |

| | | | | | | | | | | | | | | | | |
|---|---|---|---|---|---|---|---|---|---|---|---|---|---|---|---|---|
| CTC | CTG | TCT | CCC | CGT | GGC | TCT | CGG | CCT | AGC | TGG | GGC | CCC | ACA | GAC | CCC | 336 |
| Leu | Leu | Ser | Pro | Arg | Gly | Ser | Arg | Pro | Ser | Trp | Gly | Pro | Thr | Asp | Pro | |
| | | | 100 | | | | | 105 | | | | | 110 | | | |

| | | | | | | | | | | | | | | | | |
|---|---|---|---|---|---|---|---|---|---|---|---|---|---|---|---|---|
| CGG | CGT | AGG | TCG | CGC | AAT | TTG | GGT | AAG | GTC | ATC | GAT | ACC | CTT | ACG | TGC | 384 |
| Arg | Arg | Arg | Ser | Arg | Asn | Leu | Gly | Lys | Val | Ile | Asp | Thr | Leu | Thr | Cys | |
| | | 115 | | | | | 120 | | | | | 125 | | | | |

| | | | | | | | | | | | | | | | | |
|---|---|---|---|---|---|---|---|---|---|---|---|---|---|---|---|---|
| GGC | TTC | GCC | GAC | CTC | ATG | GGG | TAC | ATA | CCG | CTC | GTC | GGC | GCC | CCT | CTT | 432 |
| Gly | Phe | Ala | Asp | Leu | Met | Gly | Tyr | Ile | Pro | Leu | Val | Gly | Ala | Pro | Leu | |
| | 130 | | | | | 135 | | | | | 140 | | | | | |

| | | | | | | | | | | | | | | | | |
|---|---|---|---|---|---|---|---|---|---|---|---|---|---|---|---|---|
| GGA | AGC | GCT | GCC | AGG | GCC | CTG | GCG | CAT | GGC | GTC | CGG | GTT | CTG | GAA | GAC | 480 |
| Gly | Ser | Ala | Ala | Arg | Ala | Leu | Ala | His | Gly | Val | Arg | Val | Leu | Glu | Asp | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| GGC | GTG | AAC | TAT | GCA | ACA | GGG | AAC | CTT | CCT | GGT | TGC | TCT | TTC | TCT | ATC | 528 |
| Gly | Val | Asn | Tyr | Ala | Thr | Gly | Asn | Leu | Pro | Gly | Cys | Ser | Phe | Ser | Ile | |
| | | | | 165 | | | | | 170 | | | | | 175 | | |

| | | | | | | | | | | | | | | | | |
|---|---|---|---|---|---|---|---|---|---|---|---|---|---|---|---|---|
| TTC | CTT | CTG | GCC | CTG | CTC | TCT | TGC | TTG | ACT | GTG | CCC | GCT | TCG | GCC | TAC | 576 |
| Phe | Leu | Leu | Ala | Leu | Leu | Ser | Cys | Leu | Thr | Val | Pro | Ala | Ser | Ala | Tyr | |
| | | | 180 | | | | | 185 | | | | | 190 | | | |

| | | | | | | | | | | | | | | | | |
|---|---|---|---|---|---|---|---|---|---|---|---|---|---|---|---|---|
| CAA | GTG | CGC | AAC | TCC | ACG | GGG | CTT | TAC | CAC | GTC | ACC | AAT | GAT | TGC | CCT | 624 |
| Gln | Val | Arg | Asn | Ser | Thr | Gly | Leu | Tyr | His | Val | Thr | Asn | Asp | Cys | Pro | |
| | | 195 | | | | | 200 | | | | | 205 | | | | |

| | | | | | | | | | | | | | | | | |
|---|---|---|---|---|---|---|---|---|---|---|---|---|---|---|---|---|
| AAC | TCG | AGT | ATT | GTG | TAC | GAG | GCG | GCC | GAT | GCC | ATC | CTG | CAC | ACT | CCG | 672 |
| Asn | Ser | Ser | Ile | Val | Tyr | Glu | Ala | Ala | Asp | Ala | Ile | Leu | His | Thr | Pro | |
| | 210 | | | | | 215 | | | | | 220 | | | | | |

| | | | | | | | | | | | | | | | | |
|---|---|---|---|---|---|---|---|---|---|---|---|---|---|---|---|---|
| GGG | TGC | GTC | CCT | TGC | GTT | CGT | GAG | GGC | AAC | GCC | TCG | AGG | TGT | TGG | GTG | 720 |
| Gly | Cys | Val | Pro | Cys | Val | Arg | Glu | Gly | Asn | Ala | Ser | Arg | Cys | Trp | Val | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| GCG | ATG | ACC | CCT | ACG | GTG | GCC | ACC | AGG | GAT | GGC | AAA | CTC | CCC | GCG | ACG | 768 |
| Ala | Met | Thr | Pro | Thr | Val | Ala | Thr | Arg | Asp | Gly | Lys | Leu | Pro | Ala | Thr | |
| | | | | 245 | | | | | 250 | | | | | 255 | | |

| | | | | | | | | | | | | | | | | |
|---|---|---|---|---|---|---|---|---|---|---|---|---|---|---|---|---|
| CAG | CTT | CGA | CGT | CAC | ATC | GAT | CTG | CTT | GTC | GGG | AGC | GCC | ACC | CTC | TGT | 816 |
| Gln | Leu | Arg | Arg | His | Ile | Asp | Leu | Leu | Val | Gly | Ser | Ala | Thr | Leu | Cys | |
| | | | | 260 | | | | | 265 | | | | | 270 | | |

| | | | | | | | | | | | | | | | | |
|---|---|---|---|---|---|---|---|---|---|---|---|---|---|---|---|---|
| TCG | GCC | CTC | TAC | GTG | GGG | GAC | CTA | TGC | GGG | TCT | GTC | TTT | CTT | GTC | GGC | 864 |
| Ser | Ala | Leu | Tyr | Val | Gly | Asp | Leu | Cys | Gly | Ser | Val | Phe | Leu | Val | Gly | |
| | | | 275 | | | | | 280 | | | | | 285 | | | |

| | | | | | | | | | | | | | | | | |
|---|---|---|---|---|---|---|---|---|---|---|---|---|---|---|---|---|
| CAA | CTG | TTC | ACC | TTC | TCT | CCC | AGG | CGC | CAC | TGG | ACG | ACG | CAA | GGT | TGC | 912 |
| Gln | Leu | Phe | Thr | Phe | Ser | Pro | Arg | Arg | His | Trp | Thr | Thr | Gln | Gly | Cys | |
| | | 290 | | | | | 295 | | | | | 300 | | | | |

-continued

```
AAT TGC TCT ATC TAT CCC GGC CAT ATA ACG GGT CAC CGC ATG GCA TGG      960
Asn Cys Ser Ile Tyr Pro Gly His Ile Thr Gly His Arg Met Ala Trp
305                 310                 315                 320

GAT ATG ATG ATG AAC TGG TCC CCT ACG ACG GCG TTG GTA ATG GCT CAG     1008
Asp Met Met Met Asn Trp Ser Pro Thr Thr Ala Leu Val Met Ala Gln
                325                 330                 335

CTG CTC CGG ATC CCA CAA GCC ATC TTG GAC ATG ATC GCT GGT GCT CAC     1056
Leu Leu Arg Ile Pro Gln Ala Ile Leu Asp Met Ile Ala Gly Ala His
            340                 345                 350

TGG GGA GTC CTG GCG GGC ATA GCG TAT TTC TCC ATG GTG GGG AAC TGG     1104
Trp Gly Val Leu Ala Gly Ile Ala Tyr Phe Ser Met Val Gly Asn Trp
        355                 360                 365

GCG AAG GTC CTG GTA GTG CTG CTG CTA TTT GCC GGC GTC GAC GCG GAA     1152
Ala Lys Val Leu Val Val Leu Leu Leu Phe Ala Gly Val Asp Ala Glu
    370                 375                 380

ACC CAC GTC ACC GGG GGA AGT GCC GGC CAC ACT GTG TCT GGA TTT GTT     1200
Thr His Val Thr Gly Gly Ser Ala Gly His Thr Val Ser Gly Phe Val
385                 390                 395                 400

AGC CTC CTC GCA CCA GGC GCC AAG CAG AAC GTC CAG CTG ATC AAC ACC     1248
Ser Leu Leu Ala Pro Gly Ala Lys Gln Asn Val Gln Leu Ile Asn Thr
                405                 410                 415

AAC GGC AGT TGG CAC CTC AAT AGC ACG GCC CTG AAC TGC AAT GAT AGC     1296
Asn Gly Ser Trp His Leu Asn Ser Thr Ala Leu Asn Cys Asn Asp Ser
            420                 425                 430

CTC AAC ACC GGC TGG TTG GCA GGG CTT TTC TAT CAC CAC AAG TTC AAC     1344
Leu Asn Thr Gly Trp Leu Ala Gly Leu Phe Tyr His His Lys Phe Asn
        435                 440                 445

TCT TCA GGC TGT CCT GAG AGG CTA GCC AGC TGC CGA CCC CTT ACC GAT     1392
Ser Ser Gly Cys Pro Glu Arg Leu Ala Ser Cys Arg Pro Leu Thr Asp
    450                 455                 460

TTT GAC CAG GGC TGG GGC CCT ATC AGT TAT GCC AAC GGA AGC GGC CCC     1440
Phe Asp Gln Gly Trp Gly Pro Ile Ser Tyr Ala Asn Gly Ser Gly Pro
465                 470                 475                 480

GAC CAG CGC CCC TAC TGC TGG CAC TAC CCC CCA AAA CCT TGC GGT ATT     1488
Asp Gln Arg Pro Tyr Cys Trp His Tyr Pro Pro Lys Pro Cys Gly Ile
                485                 490                 495

GTG CCC GCG AAG AGT GTG TGT GGT CCG GTA TAT TGC TTC ACT CCC AGC     1536
Val Pro Ala Lys Ser Val Cys Gly Pro Val Tyr Cys Phe Thr Pro Ser
            500                 505                 510

CCC GTG GTG GTG GGA ACG ACC GAC AGG TCC GGC GCG CCC ACC TAC AGC     1584
Pro Val Val Val Gly Thr Thr Asp Arg Ser Gly Ala Pro Thr Tyr Ser
        515                 520                 525

TGG GGT GAA AAT GAT ACG GAC GTC TTC GTC CTT AAC AAT ACC AGG CCA     1632
Trp Gly Glu Asn Asp Thr Asp Val Phe Val Leu Asn Asn Thr Arg Pro
    530                 535                 540

CCG CTG GGC AAT TGG TTC GGT TGT ACC TGG ATG AAC TCA ACT GGA TTC     1680
Pro Leu Gly Asn Trp Phe Gly Cys Thr Trp Met Asn Ser Thr Gly Phe
545                 550                 555                 560

ACC AAA GTG TGC GGA GCG CCT CCT TGT GTC ATC GGA GGG GCG GGC AAC     1728
Thr Lys Val Cys Gly Ala Pro Pro Cys Val Ile Gly Gly Ala Gly Asn
                565                 570                 575

AAC ACC CTG CAC TGC CCC ACT GAT TGC TTC CGC AAG CAT CCG GAC GCC     1776
Asn Thr Leu His Cys Pro Thr Asp Cys Phe Arg Lys His Pro Asp Ala
            580                 585                 590

ACA TAC TCT CGG TGC GGC TCC GGT CCC TGG ATC ACA CCC AGG TGC CTG     1824
Thr Tyr Ser Arg Cys Gly Ser Gly Pro Trp Ile Thr Pro Arg Cys Leu
        595                 600                 605

GTC GAC TAC CCG TAT AGG CTT TGG CAT TAT CCT TGT ACC ATC AAC TAC     1872
Val Asp Tyr Pro Tyr Arg Leu Trp His Tyr Pro Cys Thr Ile Asn Tyr
    610                 615                 620
```

-continued

```
ACC ATA TTT AAA ATC AGG ATG TAC GTG GGA GGG GTC GAA CAC AGG CTG      1920
Thr Ile Phe Lys Ile Arg Met Tyr Val Gly Gly Val Glu His Arg Leu
625             630                 635                 640

GAA GCT GCC TGC AAC TGG ACG CGG GGC GAA CGT TGC GAT CTG GAA GAC      1968
Glu Ala Ala Cys Asn Trp Thr Arg Gly Glu Arg Cys Asp Leu Glu Asp
                645                 650                 655

AGG GAC AGG TCC GAG CTC AGC CCG TTA CTG CTG ACC ACT ACA CAG TGG      2016
Arg Asp Arg Ser Glu Leu Ser Pro Leu Leu Leu Thr Thr Thr Gln Trp
                660                 665                 670

CAG GTC CTC CCG TGT TCC TTC ACA ACC CTA CCA GCC TTG TCC ACC GGC      2064
Gln Val Leu Pro Cys Ser Phe Thr Thr Leu Pro Ala Leu Ser Thr Gly
            675                 680                 685

CTC ATC CAC CTC CAC CAG AAC ATT GTG GAC GTG CAG TAC TTG TAC GGG      2112
Leu Ile His Leu His Gln Asn Ile Val Asp Val Gln Tyr Leu Tyr Gly
        690                 695                 700

GTG GGG TCA AGC ATC GCG TCC TGG GCC ATT AAG TGG GAG TAC GTC GTT      2160
Val Gly Ser Ser Ile Ala Ser Trp Ala Ile Lys Trp Glu Tyr Val Val
705                 710                 715                 720

CTC CTG TTC CTT CTG CTT GCA GAC GCG CGC GTC TGC TCC TGC TTG TGG      2208
Leu Leu Phe Leu Leu Leu Ala Asp Ala Arg Val Cys Ser Cys Leu Trp
                725                 730                 735

ATG ATG CTA CTC ATA TCC CAA GCG GAG GCG GCT TTG GAG AAC CTC GTA      2256
Met Met Leu Leu Ile Ser Gln Ala Glu Ala Ala Leu Glu Asn Leu Val
                740                 745                 750

ATA CTT AAT GCA GCA TCC CTG GCC GGG ACG CAC GGT CTT GTA TCC TTC      2304
Ile Leu Asn Ala Ala Ser Leu Ala Gly Thr His Gly Leu Val Ser Phe
            755                 760                 765

CTC GTG TTC TTC TGC TTT GCA TGG TAT TTG AAG GGT AAG TGG GTG CCC      2352
Leu Val Phe Phe Cys Phe Ala Trp Tyr Leu Lys Gly Lys Trp Val Pro
        770                 775                 780

GGA GCG GTC TAC ACC TTC TAC GGG ATG TGG CCT CTC CTC CTG CTC CTG      2400
Gly Ala Val Tyr Thr Phe Tyr Gly Met Trp Pro Leu Leu Leu Leu Leu
785                 790                 795                 800

TTG GCG TTG CCC CAG CGG GCG TAC GCG CTG GAC ACG GAG GTG GCC GCG      2448
Leu Ala Leu Pro Gln Arg Ala Tyr Ala Leu Asp Thr Glu Val Ala Ala
                805                 810                 815

TCG TGT GGC GGT GTT GTT CTC GTC GGG TTG ATG GCG CTG ACT CTG TCA      2496
Ser Cys Gly Gly Val Val Leu Val Gly Leu Met Ala Leu Thr Leu Ser
                820                 825                 830

CCA TAT TAC AAG CGC TAT ATC AGC TGG TGC TTG TGG TGG CTT CAG TAT      2544
Pro Tyr Tyr Lys Arg Tyr Ile Ser Trp Cys Leu Trp Trp Leu Gln Tyr
            835                 840                 845

TTT CTG ACC AGA GTG GAA GCG CAA CTG CAC GTG TGG ATT CCC CCC CTC      2592
Phe Leu Thr Arg Val Glu Ala Gln Leu His Val Trp Ile Pro Pro Leu
850                 855                 860

AAC GTC CGA GGG GGG CGC GAC GCC GTC ATC TTA CTC ATG TGT GCT GTA      2640
Asn Val Arg Gly Gly Arg Asp Ala Val Ile Leu Leu Met Cys Ala Val
865                 870                 875                 880

CAC CCG ACT CTG GTA TTT GAC ATC ACC AAA TTG CTG CTG GCC GTC TTC      2688
His Pro Thr Leu Val Phe Asp Ile Thr Lys Leu Leu Leu Ala Val Phe
                885                 890                 895

GGA CCC CTT TGG ATT CTT CAA GCC AGT TTG CTT AAA GTA CCC TAC TTT      2736
Gly Pro Leu Trp Ile Leu Gln Ala Ser Leu Leu Lys Val Pro Tyr Phe
                900                 905                 910

GTG CGC GTC CAA GGC CTT CTC CGG TTC TGC GCG TTA GCG CGG AAG ATG      2784
Val Arg Val Gln Gly Leu Leu Arg Phe Cys Ala Leu Ala Arg Lys Met
            915                 920                 925

ATC GGA GGC CAT TAC GTG CAA ATG GTC ATC ATT AAG TTA GGG GCG CTT      2832
Ile Gly Gly His Tyr Val Gln Met Val Ile Ile Lys Leu Gly Ala Leu
```

```
        930                 935                 940
ACT GGC ACC TAT GTT TAT AAC CAT CTC ACT CCT CTT CGG GAC TGG GCG          2880
Thr Gly Thr Tyr Val Tyr Asn His Leu Thr Pro Leu Arg Asp Trp Ala
945                 950                 955                 960

CAC AAC GGC TTG CGA GAT CTG GCC GTG GCT GTA GAG CCA GTC GTC TTC          2928
His Asn Gly Leu Arg Asp Leu Ala Val Ala Val Glu Pro Val Val Phe
                965                 970                 975

TCC CAA ATG GAG ACC AAG CTC ATC ACG TGG GGG GCA GAT ACC GCC GCG          2976
Ser Gln Met Glu Thr Lys Leu Ile Thr Trp Gly Ala Asp Thr Ala Ala
            980                 985                 990

TGC GGT GAC ATC ATC AAC GGC TTG CCT GTT TCC GCC CGC AGG GGC CGG          3024
Cys Gly Asp Ile Ile Asn Gly Leu Pro Val Ser Ala Arg Arg Gly Arg
        995                 1000                1005

GAG ATA CTG CTC GGG CCA GCC GAT GGA ATG GTC TCC AAG GGG TGG AGG          3072
Glu Ile Leu Leu Gly Pro Ala Asp Gly Met Val Ser Lys Gly Trp Arg
    1010                1015                1020

TTG CTG GCG CCC ATC ACG GCG TAC GCC CAG CAG ACA AGG GGC CTC CTA          3120
Leu Leu Ala Pro Ile Thr Ala Tyr Ala Gln Gln Thr Arg Gly Leu Leu
1025                1030                1035                1040

GGG TGC ATA ATC ACC AGC CTA ACT GGC CGG GAC AAA AAC CAA GTG GAG          3168
Gly Cys Ile Ile Thr Ser Leu Thr Gly Arg Asp Lys Asn Gln Val Glu
                1045                1050                1055

GGT GAG GTC CAG ATT GTG TCA ACT GCT GCC CAA ACC TTC CTG GCA ACG          3216
Gly Glu Val Gln Ile Val Ser Thr Ala Ala Gln Thr Phe Leu Ala Thr
            1060                1065                1070

TGC ATC AAT GGG GTG TGC TGG ACT GTC TAC CAC GGG GCC GGA ACG AGG          3264
Cys Ile Asn Gly Val Cys Trp Thr Val Tyr His Gly Ala Gly Thr Arg
        1075                1080                1085

ACC ATC GCG TCA CCC AAG GGT CCT GTC ATC CAG ATG TAT ACC AAT GTA          3312
Thr Ile Ala Ser Pro Lys Gly Pro Val Ile Gln Met Tyr Thr Asn Val
    1090                1095                1100

GAC CAA GAC CTT GTG GGC TGG CCC GCT CCG CAA GGT AGC CGC TCA TTG          3360
Asp Gln Asp Leu Val Gly Trp Pro Ala Pro Gln Gly Ser Arg Ser Leu
1105                1110                1115                1120

ACA CCC TGC ACT TGC GGC TCC TCG GAC CTT TAC CTG GTC ACG AGG CAC          3408
Thr Pro Cys Thr Cys Gly Ser Ser Asp Leu Tyr Leu Val Thr Arg His
                1125                1130                1135

GCC GAT GTC ATT CCC GTG CGC CGG CGG GGT GAT AGC AGG GGC AGC CTG          3456
Ala Asp Val Ile Pro Val Arg Arg Arg Gly Asp Ser Arg Gly Ser Leu
            1140                1145                1150

CTG TCG CCC CGG CCC ATT TCC TAC TTG AAA GGC TCC TCG GGG GGT CCG          3504
Leu Ser Pro Arg Pro Ile Ser Tyr Leu Lys Gly Ser Ser Gly Gly Pro
        1155                1160                1165

CTG TTG TGC CCC GCG GGG CAC GCC GTG GGC ATA TTT AGG GCC GCG GTG          3552
Leu Leu Cys Pro Ala Gly His Ala Val Gly Ile Phe Arg Ala Ala Val
    1170                1175                1180

TGC ACC CGT GGA GTG GCT AAG GCG GTG GAC TTT ATC CCT GTG GAG AAC          3600
Cys Thr Arg Gly Val Ala Lys Ala Val Asp Phe Ile Pro Val Glu Asn
1185                1190                1195                1200

CTA GAG ACA ACC ATG AGG TCC CCG GTG TTC ACG GAT AAC TCC TCT CCA          3648
Leu Glu Thr Thr Met Arg Ser Pro Val Phe Thr Asp Asn Ser Ser Pro
                1205                1210                1215

CCA GTA GTG CCC CAG AGC TTC CAG GTG GCT CAC CTC CAT GCT CCC ACA          3696
Pro Val Val Pro Gln Ser Phe Gln Val Ala His Leu His Ala Pro Thr
            1220                1225                1230

GGC AGC GGC AAA AGC ACC AAG GTC CCG GCT GCA TAT GCA GCT CAG GGC          3744
Gly Ser Gly Lys Ser Thr Lys Val Pro Ala Ala Tyr Ala Ala Gln Gly
        1235                1240                1245

TAT AAG GTG CTA GTA CTC AAC CCC TCT GTT GCT GCA ACA CTG GGC TTT          3792
```

-continued

| | | |
|---|---|---|
| Tyr Lys Val Leu Val Leu Asn Pro Ser Val Ala Ala Thr Leu Gly Phe<br>    1250                1255                1260 | | |
| GGT GCT TAC ATG TCC AAG GCT CAT GGG ATC GAT CCT AAC ATC AGG ACC<br>Gly Ala Tyr Met Ser Lys Ala His Gly Ile Asp Pro Asn Ile Arg Thr<br>1265                1270                1275                1280 | | 3840 |
| GGG GTG AGA ACA ATT ACC ACT GGC AGC CCC ATC ACG TAC TCC ACC TAC<br>Gly Val Arg Thr Ile Thr Thr Gly Ser Pro Ile Thr Tyr Ser Thr Tyr<br>                1285                1290                1295 | | 3888 |
| GGC AAG TTC CTT GCC GAC GGG GGG TGC TCG GGG GGC GCT TAT GAC ATA<br>Gly Lys Phe Leu Ala Asp Gly Gly Cys Ser Gly Gly Ala Tyr Asp Ile<br>1300                1305                1310 | | 3936 |
| ATA ATT TGT GAC GAG TGC CAC TCC ACG GAT GCC ACA TCC ATC TTG GGC<br>Ile Ile Cys Asp Glu Cys His Ser Thr Asp Ala Thr Ser Ile Leu Gly<br>            1315                1320                1325 | | 3984 |
| ATC GGC ACT GTC CTT GAC CAA GCA GAG ACT GCG GGG GCG AGA CTG GTT<br>Ile Gly Thr Val Leu Asp Gln Ala Glu Thr Ala Gly Ala Arg Leu Val<br>1330                1335                1340 | | 4032 |
| GTG CTC GCC ACC GCC ACC CCT CCG GGC TCC GTC ACT GTG CCC CAT CCC<br>Val Leu Ala Thr Ala Thr Pro Pro Gly Ser Val Thr Val Pro His Pro<br>1345                1350                1355                1360 | | 4080 |
| AAC ATC GAG GAG GTT GCT CTG TCC ACC ACC GGA GAG ATC CCT TTT TAC<br>Asn Ile Glu Glu Val Ala Leu Ser Thr Thr Gly Glu Ile Pro Phe Tyr<br>                1365                1370                1375 | | 4128 |
| GGC AAG GCT ATC CCC CTC GAA GTA ATC AAG GGG GGG AGA CAT CTC ATC<br>Gly Lys Ala Ile Pro Leu Glu Val Ile Lys Gly Gly Arg His Leu Ile<br>            1380                1385                1390 | | 4176 |
| TTC TGT CAT TCA AAG AAG AAG TGC GAC GAA CTC GCC GCA AAG CTG GTC<br>Phe Cys His Ser Lys Lys Lys Cys Asp Glu Leu Ala Ala Lys Leu Val<br>            1395                1400                1405 | | 4224 |
| GCA TTG GGC ATC AAT GCC GTG GCC TAC TAC CGC GGT CTT GAC GTG TCC<br>Ala Leu Gly Ile Asn Ala Val Ala Tyr Tyr Arg Gly Leu Asp Val Ser<br>    1410                1415                1420 | | 4272 |
| GTC ATC CCG ACC AGC GGC GAT GTT GTC GTG GCA ACC GAT GCC CTC<br>Val Ile Pro Thr Ser Gly Asp Val Val Val Ala Thr Asp Ala Leu<br>1425                1430                1435                1440 | | 4320 |
| ATG ACC GGC TAT ACC GGC GAC TTC GAC TCG GTG ATA GAC TGC AAT ACG<br>Met Thr Gly Tyr Thr Gly Asp Phe Asp Ser Val Ile Asp Cys Asn Thr<br>                1445                1450                1455 | | 4368 |
| TGT GTC ACC CAG ACA GTC GAT TTC AGC CTT GAC CCT ACC TTC ACC ATT<br>Cys Val Thr Gln Thr Val Asp Phe Ser Leu Asp Pro Thr Phe Thr Ile<br>            1460                1465                1470 | | 4416 |
| GAG ACA ATC ACG CTC CCC CAG GAT GCT GTC TCC CGC ACT CAA CGT CGG<br>Glu Thr Ile Thr Leu Pro Gln Asp Ala Val Ser Arg Thr Gln Arg Arg<br>            1475                1480                1485 | | 4464 |
| GGC AGG ACT GGC AGG GGG AAG CCA GGC ATC AAC AGA TTT GTG GCA CCG<br>Gly Arg Thr Gly Arg Gly Lys Pro Gly Ile Asn Arg Phe Val Ala Pro<br>1490                1495                1500 | | 4512 |
| GGG GAG CGC CCC TCC GGC ATG TTC GAC TCG TCC GTC CTC TGT GAG TGC<br>Gly Glu Arg Pro Ser Gly Met Phe Asp Ser Ser Val Leu Cys Glu Cys<br>1505                1510                1515                1520 | | 4560 |
| TAT GAC GCA GGC TGT GCT TGG TAT GAG CTC ACG CCC GCC GAG ACT ACA<br>Tyr Asp Ala Gly Cys Ala Trp Tyr Glu Leu Thr Pro Ala Glu Thr Thr<br>                1525                1530                1535 | | 4608 |
| GTT AGG CTA CGA GCG TAC ATG AAC ACC CCG GGG CTT CCC GTG TGC CAG<br>Val Arg Leu Arg Ala Tyr Met Asn Thr Pro Gly Leu Pro Val Cys Gln<br>            1540                1545                1550 | | 4656 |
| GAC CAT CTT GAA TTT TGG GAG GGC GTC TTT ACA GGC CTC ACT CAT ATA<br>Asp His Leu Glu Phe Trp Glu Gly Val Phe Thr Gly Leu Thr His Ile<br>            1555                1560                1565 | | 4704 |

-continued

| | |
|---|---|
| GAT GCC CAC TTT CTA TCC CAG ACA AAG CAG AGT GGG GAG AAC CTT CCT<br>Asp Ala His Phe Leu Ser Gln Thr Lys Gln Ser Gly Glu Asn Leu Pro<br>1570                   1575                  1580 | 4752 |
| TAC CTG GTA GCG TAC CAA GCC ACC GTG TGC GCT AGG GCT CAA GCC CCT<br>Tyr Leu Val Ala Tyr Gln Ala Thr Val Cys Ala Arg Ala Gln Ala Pro<br>1585                     1590                   1595                  1600 | 4800 |
| CCC CCA TCG TGG GAC CAG ATG TGG AAG TGT TTG ATT CGC CTC AAG CCC<br>Pro Pro Ser Trp Asp Gln Met Trp Lys Cys Leu Ile Arg Leu Lys Pro<br>                 1605                   1610                  1615 | 4848 |
| ACC CTC CAT GGG CCA ACA CCC CTG CTA TAC AGA CTG GGC GCT GTT CAG<br>Thr Leu His Gly Pro Thr Pro Leu Leu Tyr Arg Leu Gly Ala Val Gln<br>1620                   1625                   1630 | 4896 |
| AAT GAA ATC ACC CTG ACG CAC CCA GTC ACC AAA TAC ATC ATG ACA TGC<br>Asn Glu Ile Thr Leu Thr His Pro Val Thr Lys Tyr Ile Met Thr Cys<br>                 1635                   1640                  1645 | 4944 |
| ATG TCG GCC GAC CTG GAG GTC GTC ACG AGC ACC TGG GTG CTC GTT GGC<br>Met Ser Ala Asp Leu Glu Val Val Thr Ser Thr Trp Val Leu Val Gly<br>1650                   1655                   1660 | 4992 |
| GGC GTC CTG GCT GCT TTG GCC GCG TAT TGC CTG TCA ACA GGC TGC GTG<br>Gly Val Leu Ala Ala Leu Ala Ala Tyr Cys Leu Ser Thr Gly Cys Val<br>1665                   1670                   1675                  1680 | 5040 |
| GTC ATA GTG GGC AGG GTC GTC TTG TCC GGG AAG CCG GCA ATA ATA CCT<br>Val Ile Val Gly Arg Val Val Leu Ser Gly Lys Pro Ala Ile Ile Pro<br>                 1685                   1690                  1695 | 5088 |
| GAC AGG GAA GTC CTC TAC CGA GAG TTC GAT GAG ATG GAA GAG TGC TCT<br>Asp Arg Glu Val Leu Tyr Arg Glu Phe Asp Glu Met Glu Glu Cys Ser<br>1700                   1705                   1710 | 5136 |
| CAG CAC TTA CCG TAC ATC GAG CAA GGG ATG ATG CTC GCC GAG CAG TTC<br>Gln His Leu Pro Tyr Ile Glu Gln Gly Met Met Leu Ala Glu Gln Phe<br>                 1715                   1720                  1725 | 5184 |
| AAG CAG AAG GCC CTC GGC CTC CTG CAG ACC GCG TCC CGT CAG GCA GAG<br>Lys Gln Lys Ala Leu Gly Leu Leu Gln Thr Ala Ser Arg Gln Ala Glu<br>1730                   1735                   1740 | 5232 |
| GTT ATC GCC CCT GCT GTC CAG ACC AAC TGG CAA AAA CTC GAG ACC TTC<br>Val Ile Ala Pro Ala Val Gln Thr Asn Trp Gln Lys Leu Glu Thr Phe<br>1745                   1750                   1755                  1760 | 5280 |
| TGG GCG AAG CAT ATG TGG AAC TTC ATC AGT GGG ATA CAA TAC TTG GCG<br>Trp Ala Lys His Met Trp Asn Phe Ile Ser Gly Ile Gln Tyr Leu Ala<br>                 1765                   1770                  1775 | 5328 |
| GGC TTG TCA ACG CTG CCT GGT AAC CCC GCC ATT GCT TCA TTG ATG GCT<br>Gly Leu Ser Thr Leu Pro Gly Asn Pro Ala Ile Ala Ser Leu Met Ala<br>1780                   1785                   1790 | 5376 |
| TTT ACA GCT GCT GTC ACC AGC CCA CTA ACC ACT AGC CAA ACC CTC CTC<br>Phe Thr Ala Ala Val Thr Ser Pro Leu Thr Thr Ser Gln Thr Leu Leu<br>                 1795                   1800                  1805 | 5424 |
| TTC AAC ATA TTG GGG GGG TGG GTG GCT GCC CAG CTC GCC GCC CCC GGT<br>Phe Asn Ile Leu Gly Gly Trp Val Ala Ala Gln Leu Ala Ala Pro Gly<br>1810                   1815                   1820 | 5472 |
| GCC GCT ACT GCC TTT GTG GGC GCT GGC TTA GCT GGC GCC GCC ATC GGC<br>Ala Ala Thr Ala Phe Val Gly Ala Gly Leu Ala Gly Ala Ala Ile Gly<br>1825                   1830                   1835                  1840 | 5520 |
| AGT GTT GGA CTG GGG AAG GTC CTC ATA GAC ATC CTT GCA GGG TAT GGC<br>Ser Val Gly Leu Gly Lys Val Leu Ile Asp Ile Leu Ala Gly Tyr Gly<br>                 1845                   1850                  1855 | 5568 |
| GCG GGC GTG GCG GGA GCT CTT GTG GCA TTC AAG ATC ATG AGC GGT GAG<br>Ala Gly Val Ala Gly Ala Leu Val Ala Phe Lys Ile Met Ser Gly Glu<br>1860                   1865                   1870 | 5616 |
| GTC CCC TCC ACG GAG GAC CTG GTC AAT CTA CTG CCC GCC ATC CTC TCG<br>Val Pro Ser Thr Glu Asp Leu Val Asn Leu Leu Pro Ala Ile Leu Ser<br>                 1875                   1880                  1885 | 5664 |

-continued

```
CCC GGA GCC CTC GTA GTC GGC GTG GTC TGT GCA GCA ATA CTG CGC CGG       5712
Pro Gly Ala Leu Val Val Gly Val Val Cys Ala Ala Ile Leu Arg Arg
    1890            1895                1900

CAC GTT GGC CCG GGC GAG GGG GCA GTG CAG TGG ATG AAC CGG CTG ATA       5760
His Val Gly Pro Gly Glu Gly Ala Val Gln Trp Met Asn Arg Leu Ile
1905            1910                1915                1920

GCC TTC GCC TCC CGG GGG AAC CAT GTT TCC CCC ACG CAC TAC GTG CCG       5808
Ala Phe Ala Ser Arg Gly Asn His Val Ser Pro Thr His Tyr Val Pro
                1925                1930                1935

GAG AGC GAT GCA GCT GCC CGC GTC ACT GCC ATA CTC AGC AGC CTC ACT       5856
Glu Ser Asp Ala Ala Ala Arg Val Thr Ala Ile Leu Ser Ser Leu Thr
            1940                1945                1950

GTA ACC CAG CTC CTG AGG CGA CTG CAC CAG TGG ATA AGC TCG GAG TGT       5904
Val Thr Gln Leu Leu Arg Arg Leu His Gln Trp Ile Ser Ser Glu Cys
        1955                1960                1965

ACC ACT CCA TGC TCC GGT TCC TGG CTA AGG GAC ATC TGG GAC TGG ATA       5952
Thr Thr Pro Cys Ser Gly Ser Trp Leu Arg Asp Ile Trp Asp Trp Ile
    1970                1975                1980

TGC GAG GTG TTG AGC GAC TTT AAG ACC TGG CTA AAA GCT AAG CTC ATG       6000
Cys Glu Val Leu Ser Asp Phe Lys Thr Trp Leu Lys Ala Lys Leu Met
1985            1990                1995                2000

CCA CAG CTG CCT GGG ATC CCC TTT GTG TCC TGC CAG CGC GGG TAT AAG       6048
Pro Gln Leu Pro Gly Ile Pro Phe Val Ser Cys Gln Arg Gly Tyr Lys
                2005                2010                2015

GGG GTC TGG CGA GTG GAC GGC ATC ATG CAC ACT CGC TGC CAC TGT GGA       6096
Gly Val Trp Arg Val Asp Gly Ile Met His Thr Arg Cys His Cys Gly
            2020                2025                2030

GCT GAG ATC ACT GGA CAT GTC AAA AAC GGG ACG ATG AGG ATC GTC GGT       6144
Ala Glu Ile Thr Gly His Val Lys Asn Gly Thr Met Arg Ile Val Gly
        2035                2040                2045

CCT AGG ACC TGC AGG AAC ATG TGG AGT GGG ACC TTC CCC ATT AAT GCC       6192
Pro Arg Thr Cys Arg Asn Met Trp Ser Gly Thr Phe Pro Ile Asn Ala
    2050                2055                2060

TAC ACC ACG GGC CCC TGT ACC CCC CTT CCT GCG CCG AAC TAC ACG TTC       6240
Tyr Thr Thr Gly Pro Cys Thr Pro Leu Pro Ala Pro Asn Tyr Thr Phe
2065            2070                2075                2080

GCG CTA TGG AGG GTG TCT GCA GAG GAA TAT GTG GAG ATA AGG CAG GTG       6288
Ala Leu Trp Arg Val Ser Ala Glu Glu Tyr Val Glu Ile Arg Gln Val
                2085                2090                2095

GGG GAC TTC CAC TAC GTG ACG GGT ATG ACT ACT GAC AAT CTC AAA TGC       6336
Gly Asp Phe His Tyr Val Thr Gly Met Thr Thr Asp Asn Leu Lys Cys
            2100                2105                2110

CCG TGC CAG GTC CCA TCG CCC GAA TTT TTC ACA GAA TTG GAC GGG GTG       6384
Pro Cys Gln Val Pro Ser Pro Glu Phe Phe Thr Glu Leu Asp Gly Val
        2115                2120                2125

CGC CTA CAT AGG TTT GCG CCC CCC TGC AAG CCC TTG CTG CGG GAG GAG       6432
Arg Leu His Arg Phe Ala Pro Pro Cys Lys Pro Leu Leu Arg Glu Glu
    2130                2135                2140

GTA TCA TTC AGA GTA GGA CTC CAC GAA TAC CCG GTA GGG TCG CAA TTA       6480
Val Ser Phe Arg Val Gly Leu His Glu Tyr Pro Val Gly Ser Gln Leu
2145            2150                2155                2160

CCT TGC GAG CCC GAA CCG GAC GTG GCC GTG TTG ACG TCC ATG CTC ACT       6528
Pro Cys Glu Pro Glu Pro Asp Val Ala Val Leu Thr Ser Met Leu Thr
                2165                2170                2175

GAT CCC TCC CAT ATA ACA GCA GAG GCG GCC GGG CGA AGG TTG GCG AGG       6576
Asp Pro Ser His Ile Thr Ala Glu Ala Ala Gly Arg Arg Leu Ala Arg
            2180                2185                2190

GGA TCA CCC CCC TCT GTG GCC AGC TCC TCG GCT AGC CAG CTA TCC GCT       6624
Gly Ser Pro Pro Ser Val Ala Ser Ser Ser Ala Ser Gln Leu Ser Ala
```

-continued

```
               2195                2200                2205
CCA TCT CTC AAG GCA ACT TGC ACC GCT AAC CAT GAC TCC CCT GAT GCT    6672
Pro Ser Leu Lys Ala Thr Cys Thr Ala Asn His Asp Ser Pro Asp Ala
        2210                2215                2220

GAG CTC ATA GAG GCC AAC CTC CTA TGG AGG CAG GAG ATG GGC GGC AAC    6720
Glu Leu Ile Glu Ala Asn Leu Leu Trp Arg Gln Glu Met Gly Gly Asn
2225                2230                2235                2240

ATC ACC AGG GTT GAG TCA GAA AAC AAA GTG GTG ATT CTG GAC TCC TTC    6768
Ile Thr Arg Val Glu Ser Glu Asn Lys Val Val Ile Leu Asp Ser Phe
            2245                2250                2255

GAT CCG CTT GTG GCG GAG GAG GAC GAG CGG GAG ATC TCC GTA CCC GCA    6816
Asp Pro Leu Val Ala Glu Glu Asp Glu Arg Glu Ile Ser Val Pro Ala
    2260                2265                2270

GAA ATC CTG CGG AAG TCT CGG AGA TTC GCC CAG GCC CTG CCC GTT TGG    6864
Glu Ile Leu Arg Lys Ser Arg Arg Phe Ala Gln Ala Leu Pro Val Trp
        2275                2280                2285

GCG CGG CCG GAC TAT AAC CCC CCG CTA GTG GAG ACG TGG AAA AAG CCC    6912
Ala Arg Pro Asp Tyr Asn Pro Pro Leu Val Glu Thr Trp Lys Lys Pro
2290                2295                2300

GAC TAC GAA CCA CCT GTG GTC CAT GGC TGT CCG CTT CCA CCT CCA AAG    6960
Asp Tyr Glu Pro Pro Val Val His Gly Cys Pro Leu Pro Pro Pro Lys
2305                2310                2315                2320

TCC CCT CCT GTG CCT CCG CCT CGG AAG AAG CGG ACG GTG GTC CTC ACT    7008
Ser Pro Pro Val Pro Pro Pro Arg Lys Lys Arg Thr Val Val Leu Thr
            2325                2330                2335

GAA TCA ACC CTA TCT ACT GCC TTG GCC GAG CTC GCC ACC AGA AGC TTT    7056
Glu Ser Thr Leu Ser Thr Ala Leu Ala Glu Leu Ala Thr Arg Ser Phe
        2340                2345                2350

GGC AGC TCC TCA ACT TCC GGC ATT ACG GGC GAC AAT ACG ACA ACA TCC    7104
Gly Ser Ser Ser Thr Ser Gly Ile Thr Gly Asp Asn Thr Thr Thr Ser
    2355                2360                2365

TCT GAG CCC GCC CCT TCT GGC TGC CCC CCC GAC TCC GAC GCT GAG TCC    7152
Ser Glu Pro Ala Pro Ser Gly Cys Pro Pro Asp Ser Asp Ala Glu Ser
2370                2375                2380

TAT TCC TCC ATG CCC CCC CTG GAG GGG GAG CCT GGG GAT CCG GAT CTT    7200
Tyr Ser Ser Met Pro Pro Leu Glu Gly Glu Pro Gly Asp Pro Asp Leu
2385                2390                2395                2400

AGC GAC GGG TCA TGG TCA ACG GTC AGT AGT GAG GCC AAC GCG GAG GAT    7248
Ser Asp Gly Ser Trp Ser Thr Val Ser Ser Glu Ala Asn Ala Glu Asp
            2405                2410                2415

GTC GTG TGC TGC TCA ATG TCT TAC TCT TGG ACA GGC GCA CTC GTC ACC    7296
Val Val Cys Cys Ser Met Ser Tyr Ser Trp Thr Gly Ala Leu Val Thr
        2420                2425                2430

CCG TGC GCC GCG GAA GAA CAG AAA CTG CCC ATC AAT GCA CTA AGC AAC    7344
Pro Cys Ala Ala Glu Glu Gln Lys Leu Pro Ile Asn Ala Leu Ser Asn
    2435                2440                2445

TCG TTG CTA CGT CAC CAC AAT TTG GTG TAT TCC ACC ACC TCA CGC AGT    7392
Ser Leu Leu Arg His His Asn Leu Val Tyr Ser Thr Thr Ser Arg Ser
2450                2455                2460

GCT TGC CAA AGG CAG AAG AAA GTC ACA TTT GAC AGA CTG CAA GTT CTG    7440
Ala Cys Gln Arg Gln Lys Lys Val Thr Phe Asp Arg Leu Gln Val Leu
2465                2470                2475                2480

GAC AGC CAT TAC CAG GAC GTA CTC AAG GAG GTT AAA GCA GCG GCG TCA    7488
Asp Ser His Tyr Gln Asp Val Leu Lys Glu Val Lys Ala Ala Ala Ser
            2485                2490                2495

AAA GTG AAG GCT AAC TTG CTA TCC GTA GAG GAA GCT TGC AGC CTG ACG    7536
Lys Val Lys Ala Asn Leu Leu Ser Val Glu Glu Ala Cys Ser Leu Thr
        2500                2505                2510

CCC CCA CAC TCA GCC AAA TCC AAG TTT GGT TAT GGG GCA AAA GAC GTC    7584
```

```
                                              -continued

Pro Pro His Ser Ala Lys Ser Lys Phe Gly Tyr Gly Ala Lys Asp Val
        2515                2520                2525

CGT TGC CAT GCC AGA AAG GCC GTA ACC CAC ATC AAC TCC GTG TGG AAA      7632
Arg Cys His Ala Arg Lys Ala Val Thr His Ile Asn Ser Val Trp Lys
        2530                2535                2540

GAC CTT CTG GAA GAC AAT GTA ACA CCA ATA GAC ACT ACC ATC ATG GCT      7680
Asp Leu Leu Glu Asp Asn Val Thr Pro Ile Asp Thr Thr Ile Met Ala
2545                2550                2555                2560

AAG AAC GAG GTT TTC TGC GTT CAG CCT GAG AAG GGG GGT CGT AAG CCA      7728
Lys Asn Glu Val Phe Cys Val Gln Pro Glu Lys Gly Gly Arg Lys Pro
                2565                2570                2575

GCT CGT CTC ATC GTG TTC CCC GAT CTG GGC GTG CGC GTG TGC GAA AAG      7776
Ala Arg Leu Ile Val Phe Pro Asp Leu Gly Val Arg Val Cys Glu Lys
            2580                2585                2590

ATG GCT TTG TAC GAC GTG GTT ACA AAG CTC CCC TTG GCC GTG ATG GGA      7824
Met Ala Leu Tyr Asp Val Val Thr Lys Leu Pro Leu Ala Val Met Gly
        2595                2600                2605

AGC TCC TAC GGA TTC CAA TAC TCA CCA GGA CAG CGG GTT GAA TTC CTC      7872
Ser Ser Tyr Gly Phe Gln Tyr Ser Pro Gly Gln Arg Val Glu Phe Leu
    2610                2615                2620

GTG CAA GCG TGG AAG TCC AAG AAA ACC CCA ATG GGG TTC TCG TAT GAT      7920
Val Gln Ala Trp Lys Ser Lys Lys Thr Pro Met Gly Phe Ser Tyr Asp
2625                2630                2635                2640

ACC CGC TGC TTT GAC TCC ACA GTC ACT GAG AGC GAC ATC CGT ACG GAG      7968
Thr Arg Cys Phe Asp Ser Thr Val Thr Glu Ser Asp Ile Arg Thr Glu
                2645                2650                2655

GAG GCA ATC TAC CAA TGT TGT GAC CTC GAC CCC CAA GCC CGC GTG GCC      8016
Glu Ala Ile Tyr Gln Cys Cys Asp Leu Asp Pro Gln Ala Arg Val Ala
            2660                2665                2670

ATC AAG TCC CTC ACC GAG AGG CTT TAT GTT GGG GGC CCT CTT ACC AAT      8064
Ile Lys Ser Leu Thr Glu Arg Leu Tyr Val Gly Gly Pro Leu Thr Asn
        2675                2680                2685

TCA AGG GGG GAG AAC TGC GGC TAT CGC AGG TGC CGC GCG AGC GGC GTA      8112
Ser Arg Gly Glu Asn Cys Gly Tyr Arg Arg Cys Arg Ala Ser Gly Val
    2690                2695                2700

CTG ACA ACT AGC TGT GGT AAC ACC CTC ACT TGC TAC ATC AAG GCC CGG      8160
Leu Thr Thr Ser Cys Gly Asn Thr Leu Thr Cys Tyr Ile Lys Ala Arg
2705                2710                2715                2720

GCA GCC TGT CGA GCC GCA GGG CTC CAG GAC TGC ACC ATG CTC GTG TGT      8208
Ala Ala Cys Arg Ala Ala Gly Leu Gln Asp Cys Thr Met Leu Val Cys
                2725                2730                2735

GGC GAC GAC TTA GTC GTT ATC TGT GAA AGC GCG GGG GTC CAG GAG GAC      8256
Gly Asp Asp Leu Val Val Ile Cys Glu Ser Ala Gly Val Gln Glu Asp
            2740                2745                2750

GCG GCG AGC CTG AGA GCC TTC ACG GAG GCT ATG ACC AGG TAC TCC GCC      8304
Ala Ala Ser Leu Arg Ala Phe Thr Glu Ala Met Thr Arg Tyr Ser Ala
        2755                2760                2765

CCC CCT GGG GAC CCC CCA CAA CCA GAA TAC GAC TTG GAG CTC ATA ACA      8352
Pro Pro Gly Asp Pro Pro Gln Pro Glu Tyr Asp Leu Glu Leu Ile Thr
    2770                2775                2780

TCA TGC TCC TCC AAC GTG TCA GTC GCC CAC GAC GGC GCT GGA AAG AGG      8400
Ser Cys Ser Ser Asn Val Ser Val Ala His Asp Gly Ala Gly Lys Arg
2785                2790                2795                2800

GTC TAC TAC CTC ACC CGT GAC CCT ACA ACC CCC CTC GCG AGA GCT GCG      8448
Val Tyr Tyr Leu Thr Arg Asp Pro Thr Thr Pro Leu Ala Arg Ala Ala
                2805                2810                2815

TGG GAG ACA GCA AGA CAC ACT CCA GTC AAT TCC TGG CTA GGC AAC ATA      8496
Trp Glu Thr Ala Arg His Thr Pro Val Asn Ser Trp Leu Gly Asn Ile
            2820                2825                2830
```

```
ATC ATG TTT GCC CCC ACA CTG TGG GCG AGG ATG ATA CTG ATG ACC CAT    8544
Ile Met Phe Ala Pro Thr Leu Trp Ala Arg Met Ile Leu Met Thr His
        2835                2840                2845

TTC TTT AGC GTC CTT ATA GCC AGG GAC CAG CTT GAA CAG GCC CTC GAT    8592
Phe Phe Ser Val Leu Ile Ala Arg Asp Gln Leu Glu Gln Ala Leu Asp
2850                2855                2860

TGC GAG ATC TAC GGG GCC TGC TAC TCC ATA GAA CCA CTT GAT CTA CCT    8640
Cys Glu Ile Tyr Gly Ala Cys Tyr Ser Ile Glu Pro Leu Asp Leu Pro
2865                2870                2875                2880

CCA ATC ATT CAA AGA CTC CAT GGC CTC AGC GCA TTT TCA CTC CAC AGT    8688
Pro Ile Ile Gln Arg Leu His Gly Leu Ser Ala Phe Ser Leu His Ser
            2885                2890                2895

TAC TCT CCA GGT GAA ATT AAT AGG GTG GCC GCA TGC CTC AGA AAA CTT    8736
Tyr Ser Pro Gly Glu Ile Asn Arg Val Ala Ala Cys Leu Arg Lys Leu
        2900                2905                2910

GGG GTA CCG CCC TTG CGA GCT TGG AGA CAC CGG GCC CGG AGC GTC CGC    8784
Gly Val Pro Pro Leu Arg Ala Trp Arg His Arg Ala Arg Ser Val Arg
        2915                2920                2925

GCT AGG CTT CTG GCC AGA GGA GGC AGG GCT GCC ATA TGT GGC AAG TAC    8832
Ala Arg Leu Leu Ala Arg Gly Gly Arg Ala Ala Ile Cys Gly Lys Tyr
2930                2935                2940

CTC TTC AAC TGG GCA GTA AGA ACA AAG CTC AAA CTC ACT CCA ATA GCG    8880
Leu Phe Asn Trp Ala Val Arg Thr Lys Leu Lys Leu Thr Pro Ile Ala
2945                2950                2955                2960

GCC GCT GGC CAG CTG GAC TTG TCC GGC TGG TTC ACG GCT GGC TAC AGC    8928
Ala Ala Gly Gln Leu Asp Leu Ser Gly Trp Phe Thr Ala Gly Tyr Ser
            2965                2970                2975

GGG GGA GAC ATT TAT CAC AGC GTG TCT CAT GCC CGG CCC CGC TGG ATC    8976
Gly Gly Asp Ile Tyr His Ser Val Ser His Ala Arg Pro Arg Trp Ile
            2980                2985                2990

TGG TTT TGC CC                                                    8987
Trp Phe Cys
      2995

(2) INFORMATION FOR SEQ ID NO:138:

(i) SEQUENCE CHARACTERISTICS:
          (A) LENGTH: 2995 amino acids
          (B) TYPE: amino acid
          (D) TOPOLOGY: linear (ii) MOLECULE TYPE: protein (xi) SEQUENCE DESCRIPTION: SEQ ID NO:138:

Met Ser Thr Asn Pro Lys Pro Gln Lys Lys Asn Lys Arg Asn Thr Asn
 1               5                  10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
    50                  55                  60

Ile Pro Lys Ala Arg Arg Pro Glu Gly Arg Thr Trp Ala Gln Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Ser Trp Gly Pro Thr Asp Pro
            100                 105                 110

Arg Arg Arg Ser Arg Asn Leu Gly Lys Val Ile Asp Thr Leu Thr Cys
        115                 120                 125
```

-continued

```
Gly Phe Ala Asp Leu Met Gly Tyr Ile Pro Leu Val Gly Ala Pro Leu
    130                 135                 140

Gly Ser Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Val Pro Ala Ser Ala Tyr
            180                 185                 190

Gln Val Arg Asn Ser Thr Gly Leu Tyr His Val Thr Asn Asp Cys Pro
        195                 200                 205

Asn Ser Ser Ile Val Tyr Glu Ala Ala Asp Ala Ile Leu His Thr Pro
210                 215                 220

Gly Cys Val Pro Cys Val Arg Glu Gly Asn Ala Ser Arg Cys Trp Val
225                 230                 235                 240

Ala Met Thr Pro Thr Val Ala Thr Arg Asp Gly Lys Leu Pro Ala Thr
                245                 250                 255

Gln Leu Arg Arg His Ile Asp Leu Leu Val Gly Ser Ala Thr Leu Cys
            260                 265                 270

Ser Ala Leu Tyr Val Gly Asp Leu Cys Gly Ser Val Phe Leu Val Gly
        275                 280                 285

Gln Leu Phe Thr Phe Ser Pro Arg Arg His Trp Thr Thr Gln Gly Cys
    290                 295                 300

Asn Cys Ser Ile Tyr Pro Gly His Ile Thr Gly His Arg Met Ala Trp
305                 310                 315                 320

Asp Met Met Met Asn Trp Ser Pro Thr Thr Ala Leu Val Met Ala Gln
                325                 330                 335

Leu Leu Arg Ile Pro Gln Ala Ile Leu Asp Met Ile Ala Gly Ala His
            340                 345                 350

Trp Gly Val Leu Ala Gly Ile Ala Tyr Phe Ser Met Val Gly Asn Trp
        355                 360                 365

Ala Lys Val Leu Val Val Leu Leu Phe Ala Gly Val Asp Ala Glu
    370                 375                 380

Thr His Val Thr Gly Gly Ser Ala Gly His Thr Val Ser Gly Phe Val
385                 390                 395                 400

Ser Leu Leu Ala Pro Gly Ala Lys Gln Asn Val Gln Leu Ile Asn Thr
                405                 410                 415

Asn Gly Ser Trp His Leu Asn Ser Thr Ala Leu Asn Cys Asn Asp Ser
            420                 425                 430

Leu Asn Thr Gly Trp Leu Ala Gly Leu Phe Tyr His His Lys Phe Asn
        435                 440                 445

Ser Ser Gly Cys Pro Glu Arg Leu Ala Ser Cys Arg Pro Leu Thr Asp
    450                 455                 460

Phe Asp Gln Gly Trp Gly Pro Ile Ser Tyr Ala Asn Gly Ser Gly Pro
465                 470                 475                 480

Asp Gln Arg Pro Tyr Cys Trp His Tyr Pro Pro Lys Pro Cys Gly Ile
                485                 490                 495

Val Pro Ala Lys Ser Val Cys Gly Pro Val Tyr Cys Phe Thr Pro Ser
            500                 505                 510

Pro Val Val Val Gly Thr Thr Asp Arg Ser Gly Ala Pro Thr Tyr Ser
        515                 520                 525

Trp Gly Glu Asn Asp Thr Asp Val Phe Val Leu Asn Asn Thr Arg Pro
    530                 535                 540
```

-continued

```
Pro Leu Gly Asn Trp Phe Gly Cys Thr Trp Met Asn Ser Thr Gly Phe
545                 550                 555                 560

Thr Lys Val Cys Gly Ala Pro Pro Cys Val Ile Gly Ala Gly Asn
            565                 570                 575

Asn Thr Leu His Cys Pro Thr Asp Cys Phe Arg Lys His Pro Asp Ala
                580                 585                 590

Thr Tyr Ser Arg Cys Gly Ser Gly Pro Trp Ile Thr Pro Arg Cys Leu
            595                 600                 605

Val Asp Tyr Pro Tyr Arg Leu Trp His Tyr Pro Cys Thr Ile Asn Tyr
610                 615                 620

Thr Ile Phe Lys Ile Arg Met Tyr Val Gly Gly Val Glu His Arg Leu
625                 630                 635                 640

Glu Ala Ala Cys Asn Trp Thr Arg Gly Glu Arg Cys Asp Leu Glu Asp
                645                 650                 655

Arg Asp Arg Ser Glu Leu Ser Pro Leu Leu Leu Thr Thr Thr Gln Trp
            660                 665                 670

Gln Val Leu Pro Cys Ser Phe Thr Thr Leu Pro Ala Leu Ser Thr Gly
            675                 680                 685

Leu Ile His Leu His Gln Asn Ile Val Asp Val Gln Tyr Leu Tyr Gly
690                 695                 700

Val Gly Ser Ser Ile Ala Ser Trp Ala Ile Lys Trp Glu Tyr Val Val
705                 710                 715                 720

Leu Leu Phe Leu Leu Leu Ala Asp Ala Arg Val Cys Ser Cys Leu Trp
                725                 730                 735

Met Met Leu Leu Ile Ser Gln Ala Glu Ala Ala Leu Glu Asn Leu Val
            740                 745                 750

Ile Leu Asn Ala Ala Ser Leu Ala Gly Thr His Gly Leu Val Ser Phe
            755                 760                 765

Leu Val Phe Phe Cys Phe Ala Trp Tyr Leu Lys Gly Lys Trp Val Pro
770                 775                 780

Gly Ala Val Tyr Thr Phe Tyr Gly Met Trp Pro Leu Leu Leu Leu
785                 790                 795                 800

Leu Ala Leu Pro Gln Arg Ala Tyr Ala Leu Asp Thr Glu Val Ala Ala
                805                 810                 815

Ser Cys Gly Gly Val Val Leu Val Gly Leu Met Ala Leu Thr Leu Ser
            820                 825                 830

Pro Tyr Tyr Lys Arg Tyr Ile Ser Trp Cys Leu Trp Trp Leu Gln Tyr
            835                 840                 845

Phe Leu Thr Arg Val Glu Ala Gln Leu His Val Trp Ile Pro Pro Leu
850                 855                 860

Asn Val Arg Gly Gly Arg Asp Ala Val Ile Leu Leu Met Cys Ala Val
865                 870                 875                 880

His Pro Thr Leu Val Phe Asp Ile Thr Lys Leu Leu Leu Ala Val Phe
                885                 890                 895

Gly Pro Leu Trp Ile Leu Gln Ala Ser Leu Leu Lys Val Pro Tyr Phe
            900                 905                 910

Val Arg Val Gln Gly Leu Leu Arg Phe Cys Ala Leu Ala Arg Lys Met
            915                 920                 925

Ile Gly Gly His Tyr Val Gln Met Val Ile Ile Lys Leu Gly Ala Leu
930                 935                 940

Thr Gly Thr Tyr Val Tyr Asn His Leu Thr Pro Leu Arg Asp Trp Ala
945                 950                 955                 960

His Asn Gly Leu Arg Asp Leu Ala Val Ala Val Glu Pro Val Val Phe
```

```
                965                 970                 975
Ser Gln Met Glu Thr Lys Leu Ile Thr Trp Gly Ala Asp Thr Ala Ala
                980                 985                 990
Cys Gly Asp Ile Ile Asn Gly Leu Pro Val Ser Ala Arg Arg Gly Arg
                995                1000                1005
Glu Ile Leu Leu Gly Pro Ala Asp Gly Met Val Ser Lys Gly Trp Arg
               1010                1015                1020
Leu Leu Ala Pro Ile Thr Ala Tyr Ala Gln Gln Thr Arg Gly Leu Leu
1025                1030                1035                1040
Gly Cys Ile Ile Thr Ser Leu Thr Gly Arg Asp Lys Asn Gln Val Glu
                1045                1050                1055
Gly Glu Val Gln Ile Val Ser Thr Ala Ala Gln Thr Phe Leu Ala Thr
                1060                1065                1070
Cys Ile Asn Gly Val Cys Trp Thr Val Tyr His Gly Ala Gly Thr Arg
                1075                1080                1085
Thr Ile Ala Ser Pro Lys Gly Pro Val Ile Gln Met Tyr Thr Asn Val
                1090                1095                1100
Asp Gln Asp Leu Val Gly Trp Pro Ala Pro Gln Gly Ser Arg Ser Leu
1105                1110                1115                1120
Thr Pro Cys Thr Cys Gly Ser Ser Asp Leu Tyr Leu Val Thr Arg His
                1125                1130                1135
Ala Asp Val Ile Pro Val Arg Arg Arg Gly Asp Ser Arg Gly Ser Leu
                1140                1145                1150
Leu Ser Pro Arg Pro Ile Ser Tyr Leu Lys Gly Ser Ser Gly Gly Pro
                1155                1160                1165
Leu Leu Cys Pro Ala Gly His Ala Val Gly Ile Phe Arg Ala Ala Val
                1170                1175                1180
Cys Thr Arg Gly Val Ala Lys Ala Val Asp Phe Ile Pro Val Glu Asn
1185                1190                1195                1200
Leu Glu Thr Thr Met Arg Ser Pro Val Phe Thr Asp Asn Ser Ser Pro
                1205                1210                1215
Pro Val Val Pro Gln Ser Phe Gln Val Ala His Leu His Ala Pro Thr
                1220                1225                1230
Gly Ser Gly Lys Ser Thr Lys Val Pro Ala Ala Tyr Ala Ala Gln Gly
                1235                1240                1245
Tyr Lys Val Leu Val Leu Asn Pro Ser Val Ala Ala Thr Leu Gly Phe
1250                1255                1260
Gly Ala Tyr Met Ser Lys Ala His Gly Ile Asp Pro Asn Ile Arg Thr
1265                1270                1275                1280
Gly Val Arg Thr Ile Thr Thr Gly Ser Pro Ile Thr Tyr Ser Thr Tyr
                1285                1290                1295
Gly Lys Phe Leu Ala Asp Gly Gly Cys Ser Gly Gly Ala Tyr Asp Ile
                1300                1305                1310
Ile Ile Cys Asp Glu Cys His Ser Thr Asp Ala Thr Ser Ile Leu Gly
                1315                1320                1325
Ile Gly Thr Val Leu Asp Gln Ala Glu Thr Ala Gly Ala Arg Leu Val
                1330                1335                1340
Val Leu Ala Thr Ala Thr Pro Pro Gly Ser Val Thr Val Pro His Pro
1345                1350                1355                1360
Asn Ile Glu Glu Val Ala Leu Ser Thr Thr Gly Glu Ile Pro Phe Tyr
                1365                1370                1375
Gly Lys Ala Ile Pro Leu Glu Val Ile Lys Gly Gly Arg His Leu Ile
                1380                1385                1390
```

```
Phe Cys His Ser Lys Lys Cys Asp Glu Leu Ala Ala Lys Leu Val
        1395                1400                1405

Ala Leu Gly Ile Asn Ala Val Ala Tyr Arg Gly Leu Asp Val Ser
        1410                1415                1420

Val Ile Pro Thr Ser Gly Asp Val Val Val Ala Thr Asp Ala Leu
1425                1430                1435                1440

Met Thr Gly Tyr Thr Gly Asp Phe Asp Ser Val Ile Asp Cys Asn Thr
        1445                1450                1455

Cys Val Thr Gln Thr Val Asp Phe Ser Leu Asp Pro Thr Phe Thr Ile
        1460                1465                1470

Glu Thr Ile Thr Leu Pro Gln Asp Ala Val Ser Arg Thr Gln Arg Arg
        1475                1480                1485

Gly Arg Thr Gly Arg Gly Lys Pro Gly Ile Asn Arg Phe Val Ala Pro
        1490                1495                1500

Gly Glu Arg Pro Ser Gly Met Phe Asp Ser Ser Val Leu Cys Glu Cys
1505                1510                1515                1520

Tyr Asp Ala Gly Cys Ala Trp Tyr Glu Leu Thr Pro Ala Glu Thr Thr
        1525                1530                1535

Val Arg Leu Arg Ala Tyr Met Asn Thr Pro Gly Leu Pro Val Cys Gln
        1540                1545                1550

Asp His Leu Glu Phe Trp Glu Gly Val Phe Thr Gly Leu Thr His Ile
        1555                1560                1565

Asp Ala His Phe Leu Ser Gln Thr Lys Gln Ser Gly Glu Asn Leu Pro
        1570                1575                1580

Tyr Leu Val Ala Tyr Gln Ala Thr Val Cys Ala Arg Ala Gln Ala Pro
1585                1590                1595                1600

Pro Pro Ser Trp Asp Gln Met Trp Lys Cys Leu Ile Arg Leu Lys Pro
        1605                1610                1615

Thr Leu His Gly Pro Thr Pro Leu Leu Tyr Arg Leu Gly Ala Val Gln
        1620                1625                1630

Asn Glu Ile Thr Leu Thr His Pro Val Thr Lys Tyr Ile Met Thr Cys
        1635                1640                1645

Met Ser Ala Asp Leu Glu Val Val Thr Ser Thr Trp Val Leu Val Gly
        1650                1655                1660

Gly Val Leu Ala Ala Leu Ala Ala Tyr Cys Leu Ser Thr Gly Cys Val
1665                1670                1675                1680

Val Ile Val Gly Arg Val Val Leu Ser Gly Lys Pro Ala Ile Ile Pro
        1685                1690                1695

Asp Arg Glu Val Leu Tyr Arg Glu Phe Asp Glu Met Glu Glu Cys Ser
        1700                1705                1710

Gln His Leu Pro Tyr Ile Glu Gln Gly Met Met Leu Ala Glu Gln Phe
        1715                1720                1725

Lys Gln Lys Ala Leu Gly Leu Leu Gln Thr Ala Ser Arg Gln Ala Glu
        1730                1735                1740

Val Ile Ala Pro Ala Val Gln Thr Asn Trp Gln Lys Leu Glu Thr Phe
1745                1750                1755                1760

Trp Ala Lys His Met Trp Asn Phe Ile Ser Gly Ile Gln Tyr Leu Ala
        1765                1770                1775

Gly Leu Ser Thr Leu Pro Gly Asn Pro Ala Ile Ala Ser Leu Met Ala
        1780                1785                1790

Phe Thr Ala Ala Val Thr Ser Pro Leu Thr Thr Ser Gln Thr Leu Leu
        1795                1800                1805
```

-continued

```
Phe Asn Ile Leu Gly Gly Trp Val Ala Ala Gln Leu Ala Ala Pro Gly
    1810                1815                1820

Ala Ala Thr Ala Phe Val Gly Ala Gly Leu Ala Gly Ala Ala Ile Gly
1825            1830                1835                1840

Ser Val Gly Leu Gly Lys Val Leu Ile Asp Ile Leu Ala Gly Tyr Gly
                1845                1850                1855

Ala Gly Val Ala Gly Ala Leu Val Ala Phe Lys Ile Met Ser Gly Glu
            1860                1865                1870

Val Pro Ser Thr Glu Asp Leu Val Asn Leu Leu Pro Ala Ile Leu Ser
        1875                1880                1885

Pro Gly Ala Leu Val Val Gly Val Val Cys Ala Ala Ile Leu Arg Arg
    1890                1895                1900

His Val Gly Pro Gly Glu Gly Ala Val Gln Trp Met Asn Arg Leu Ile
1905            1910                1915                1920

Ala Phe Ala Ser Arg Gly Asn His Val Ser Pro Thr His Tyr Val Pro
                1925                1930                1935

Glu Ser Asp Ala Ala Ala Arg Val Thr Ala Ile Leu Ser Ser Leu Thr
            1940                1945                1950

Val Thr Gln Leu Leu Arg Arg Leu His Gln Trp Ile Ser Ser Glu Cys
        1955                1960                1965

Thr Thr Pro Cys Ser Gly Ser Trp Leu Arg Asp Ile Trp Asp Trp Ile
    1970                1975                1980

Cys Glu Val Leu Ser Asp Phe Lys Thr Trp Leu Lys Ala Lys Leu Met
1985            1990                1995                2000

Pro Gln Leu Pro Gly Ile Pro Phe Val Ser Cys Gln Arg Gly Tyr Lys
                2005                2010                2015

Gly Val Trp Arg Val Asp Gly Ile Met His Thr Arg Cys His Cys Gly
            2020                2025                2030

Ala Glu Ile Thr Gly His Val Lys Asn Gly Thr Met Arg Ile Val Gly
        2035                2040                2045

Pro Arg Thr Cys Arg Asn Met Trp Ser Gly Thr Phe Pro Ile Asn Ala
    2050                2055                2060

Tyr Thr Thr Gly Pro Cys Thr Pro Leu Pro Ala Pro Asn Tyr Thr Phe
2065            2070                2075                2080

Ala Leu Trp Arg Val Ser Ala Glu Glu Tyr Val Glu Ile Arg Gln Val
                2085                2090                2095

Gly Asp Phe His Tyr Val Thr Gly Met Thr Thr Asp Asn Leu Lys Cys
            2100                2105                2110

Pro Cys Gln Val Pro Ser Pro Glu Phe Phe Thr Glu Leu Asp Gly Val
        2115                2120                2125

Arg Leu His Arg Phe Ala Pro Pro Cys Lys Pro Leu Leu Arg Glu Glu
    2130                2135                2140

Val Ser Phe Arg Val Gly Leu His Glu Tyr Pro Val Gly Ser Gln Leu
2145            2150                2155                2160

Pro Cys Glu Pro Glu Pro Asp Val Ala Val Leu Thr Ser Met Leu Thr
                2165                2170                2175

Asp Pro Ser His Ile Thr Ala Glu Ala Ala Gly Arg Arg Leu Ala Arg
            2180                2185                2190

Gly Ser Pro Pro Ser Val Ala Ser Ser Ser Ala Ser Gln Leu Ser Ala
        2195                2200                2205

Pro Ser Leu Lys Ala Thr Cys Thr Ala Asn His Asp Ser Pro Asp Ala
    2210                2215                2220

Glu Leu Ile Glu Ala Asn Leu Leu Trp Arg Gln Glu Met Gly Gly Asn
```

-continued

```
           2225                2230                2235                2240

Ile Thr Arg Val Glu Ser Glu Asn Lys Val Val Ile Leu Asp Ser Phe
                        2245                2250                2255

Asp Pro Leu Val Ala Glu Glu Asp Glu Arg Glu Ile Ser Val Pro Ala
                        2260                2265                2270

Glu Ile Leu Arg Lys Ser Arg Arg Phe Ala Gln Ala Leu Pro Val Trp
                        2275                2280                2285

Ala Arg Pro Asp Tyr Asn Pro Leu Val Glu Thr Trp Lys Lys Pro
                        2290                2295                2300

Asp Tyr Glu Pro Pro Val Val His Gly Cys Pro Leu Pro Pro Lys
    2305                2310                2315                2320

Ser Pro Pro Val Pro Pro Arg Lys Lys Arg Thr Val Val Leu Thr
                        2325                2330                2335

Glu Ser Thr Leu Ser Thr Ala Leu Ala Glu Leu Ala Thr Arg Ser Phe
                        2340                2345                2350

Gly Ser Ser Ser Thr Ser Gly Ile Thr Gly Asp Asn Thr Thr Thr Ser
                        2355                2360                2365

Ser Glu Pro Ala Pro Ser Gly Cys Pro Pro Asp Ser Asp Ala Glu Ser
                        2370                2375                2380

Tyr Ser Ser Met Pro Pro Leu Glu Gly Glu Pro Gly Asp Pro Asp Leu
    2385                2390                2395                2400

Ser Asp Gly Ser Trp Ser Thr Val Ser Ser Glu Ala Asn Ala Glu Asp
                        2405                2410                2415

Val Val Cys Cys Ser Met Ser Tyr Ser Trp Thr Gly Ala Leu Val Thr
                        2420                2425                2430

Pro Cys Ala Ala Glu Glu Gln Lys Leu Pro Ile Asn Ala Leu Ser Asn
                        2435                2440                2445

Ser Leu Leu Arg His His Asn Leu Val Tyr Ser Thr Thr Ser Arg Ser
                        2450                2455                2460

Ala Cys Gln Arg Gln Lys Lys Val Thr Phe Asp Arg Leu Gln Val Leu
    2465                2470                2475                2480

Asp Ser His Tyr Gln Asp Val Leu Lys Glu Val Lys Ala Ala Ala Ser
                        2485                2490                2495

Lys Val Lys Ala Asn Leu Leu Ser Val Glu Glu Ala Cys Ser Leu Thr
                        2500                2505                2510

Pro Pro His Ser Ala Lys Ser Lys Phe Gly Tyr Gly Ala Lys Asp Val
                        2515                2520                2525

Arg Cys His Ala Arg Lys Ala Val Thr His Ile Asn Ser Val Trp Lys
                        2530                2535                2540

Asp Leu Leu Glu Asp Asn Val Thr Pro Ile Asp Thr Thr Ile Met Ala
    2545                2550                2555                2560

Lys Asn Glu Val Phe Cys Val Gln Pro Glu Lys Gly Gly Arg Lys Pro
                        2565                2570                2575

Ala Arg Leu Ile Val Phe Pro Asp Leu Gly Val Arg Val Cys Glu Lys
                        2580                2585                2590

Met Ala Leu Tyr Asp Val Val Thr Lys Leu Pro Leu Ala Val Met Gly
                        2595                2600                2605

Ser Ser Tyr Gly Phe Gln Tyr Ser Pro Gly Gln Arg Val Glu Phe Leu
                        2610                2615                2620

Val Gln Ala Trp Lys Ser Lys Lys Thr Pro Met Gly Phe Ser Tyr Asp
    2625                2630                2635                2640

Thr Arg Cys Phe Asp Ser Thr Val Thr Glu Ser Asp Ile Arg Thr Glu
                        2645                2650                2655
```

Glu Ala Ile Tyr Gln Cys Cys Asp Leu Asp Pro Gln Ala Arg Val Ala
           2660            2665            2670

Ile Lys Ser Leu Thr Glu Arg Leu Tyr Val Gly Gly Pro Leu Thr Asn
           2675            2680            2685

Ser Arg Gly Glu Asn Cys Gly Tyr Arg Arg Cys Arg Ala Ser Gly Val
           2690            2695            2700

Leu Thr Thr Ser Cys Gly Asn Thr Leu Thr Cys Tyr Ile Lys Ala Arg
2705            2710            2715            2720

Ala Ala Cys Arg Ala Ala Gly Leu Gln Asp Cys Thr Met Leu Val Cys
           2725            2730            2735

Gly Asp Asp Leu Val Val Ile Cys Glu Ser Ala Gly Val Gln Glu Asp
           2740            2745            2750

Ala Ala Ser Leu Arg Ala Phe Thr Glu Ala Met Thr Arg Tyr Ser Ala
           2755            2760            2765

Pro Pro Gly Asp Pro Pro Gln Pro Glu Tyr Asp Leu Glu Leu Ile Thr
           2770            2775            2780

Ser Cys Ser Ser Asn Val Ser Val Ala His Asp Gly Ala Gly Lys Arg
2785            2790            2795            2800

Val Tyr Tyr Leu Thr Arg Asp Pro Thr Thr Pro Leu Ala Arg Ala Ala
           2805            2810            2815

Trp Glu Thr Ala Arg His Thr Pro Val Asn Ser Trp Leu Gly Asn Ile
           2820            2825            2830

Ile Met Phe Ala Pro Thr Leu Trp Ala Arg Met Ile Leu Met Thr His
           2835            2840            2845

Phe Phe Ser Val Leu Ile Ala Arg Asp Gln Leu Glu Gln Ala Leu Asp
           2850            2855            2860

Cys Glu Ile Tyr Gly Ala Cys Tyr Ser Ile Glu Pro Leu Asp Leu Pro
2865            2870            2875            2880

Pro Ile Ile Gln Arg Leu His Gly Leu Ser Ala Phe Ser Leu His Ser
           2885            2890            2895

Tyr Ser Pro Gly Glu Ile Asn Arg Val Ala Ala Cys Leu Arg Lys Leu
           2900            2905            2910

Gly Val Pro Pro Leu Arg Ala Trp Arg His Arg Ala Arg Ser Val Arg
           2915            2920            2925

Ala Arg Leu Leu Ala Arg Gly Gly Arg Ala Ala Ile Cys Gly Lys Tyr
           2930            2935            2940

Leu Phe Asn Trp Ala Val Arg Thr Lys Leu Lys Leu Thr Pro Ile Ala
2945            2950            2955            2960

Ala Ala Gly Gln Leu Asp Leu Ser Gly Trp Phe Thr Ala Gly Tyr Ser
           2965            2970            2975

Gly Gly Asp Ile Tyr His Ser Val Ser His Ala Arg Pro Arg Trp Ile
           2980            2985            2990

Trp Phe Cys
     2995

(2) INFORMATION FOR SEQ ID NO:139:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "linker used in the
            construction of pS3-56c100m."

(xi) SEQUENCE DESCRIPTION: SEQ ID NO:139:

CCGGGCGAGG GGGCAGTGCA GTGGATGAAC CGGCTGATAG CCTTCGCCTC CCGGGGGAAC          60

(2) INFORMATION FOR SEQ ID NO:140:

(i) SEQUENCE CHARACTERISTICS:
        (A) LENGTH: 56 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "linker used in the
            construction of pS3-56C100m."

(iv) ANTI-SENSE: YES (xi) SEQUENCE DESCRIPTION: SEQ ID NO:140:

GTTCCCCCGG GAGGCGAAGG CTATCAGCCG GTTCATCCAC TGCACTGCCC CCTCGC          56

(2) INFORMATION FOR SEQ ID NO:141:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "linker used in the
            construction of pS3-56c100m"

(xi) SEQUENCE DESCRIPTION: SEQ ID NO:141:

CATGTTTCCC CCTAATGAG          19

(2) INFORMATION FOR SEQ ID NO:142:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "linker used in the
            construction of pS3-56c100m"

(xi) SEQUENCE DESCRIPTION: SEQ ID NO:142:

CGACTCATTA GGGGGAAACA TG          22

(2) INFORMATION FOR SEQ ID NO:143:

(i) SEQUENCE CHARACTERISTICS:
        (A) LENGTH: 307 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (B) CLONE: 31

(ix) FEATURE:
        (A) NAME/KEY: CDS
        (B) LOCATION: 1..306

(xi) SEQUENCE DESCRIPTION: SEQ ID NO:143:

GAA TTC GGG TCC GTC ATC CCG ACC AGC GGC GAT GTT GTC GTC GTG GCA          48

```
Glu Phe Gly Ser Val Ile Pro Thr Ser Gly Asp Val Val Val Ala
 1               5                  10                  15

ACC GAT GCC CTC ATG ACC GGC TAT ACC GGC GAC TTC GAC TCG GTG ATA      96
Thr Asp Ala Leu Met Thr Gly Tyr Thr Gly Asp Phe Asp Ser Val Ile
             20                  25                  30

GAC TGC AAT ACG TGT GTC ACC CAG ACA GTC GAT TTC AGC CTT GAC CCT     144
Asp Cys Asn Thr Cys Val Thr Gln Thr Val Asp Phe Ser Leu Asp Pro
         35                  40                  45

ACC TTC ACC ATT GAG ACA ATC ACG CTC CCC CAA GAT GCT GTC TCC CGC     192
Thr Phe Thr Ile Glu Thr Ile Thr Leu Pro Gln Asp Ala Val Ser Arg
 50                  55                  60

ACT CAA CGT CGG GGC AGG ACT GGC AGG GGG AAG CCA GGC ATC TAC AGA     240
Thr Gln Arg Arg Gly Arg Thr Gly Arg Gly Lys Pro Gly Ile Tyr Arg
 65                  70                  75                  80

TTT GTG GCA CCG GGG GAG CGC CCT CCG GCA TGT TCG ACT CGT CCG TCC     288
Phe Val Ala Pro Gly Glu Arg Pro Pro Ala Cys Ser Thr Arg Pro Ser
             85                  90                  95

TCT GTG AGT GCC CGA ATT C                                           307
Ser Val Ser Ala Arg Ile
            100
```

(2) INFORMATION FOR SEQ ID NO:144:

(i) SEQUENCE CHARACTERISTICS:
        (A) LENGTH: 102 amino acids
        (B) TYPE: amino acid
        (D) TOPOLOGY: linear (ii) MOLECULE TYPE: protein (xi) SEQUENCE DESCRIPTION: SEQ ID NO:144:

```
Glu Phe Gly Ser Val Ile Pro Thr Ser Gly Asp Val Val Val Ala
 1               5                  10                  15

Thr Asp Ala Leu Met Thr Gly Tyr Thr Gly Asp Phe Asp Ser Val Ile
             20                  25                  30

Asp Cys Asn Thr Cys Val Thr Gln Thr Val Asp Phe Ser Leu Asp Pro
         35                  40                  45

Thr Phe Thr Ile Glu Thr Ile Thr Leu Pro Gln Asp Ala Val Ser Arg
 50                  55                  60

Thr Gln Arg Arg Gly Arg Thr Gly Arg Gly Lys Pro Gly Ile Tyr Arg
 65                  70                  75                  80

Phe Val Ala Pro Gly Glu Arg Pro Pro Ala Cys Ser Thr Arg Pro Ser
             85                  90                  95

Ser Val Ser Ala Arg Ile
            100
```

(2) INFORMATION FOR SEQ ID NO:145:

(i) SEQUENCE CHARACTERISTICS:
        (A) LENGTH: 121 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (B) CLONE: p131jh (ix) FEATURE:
        (A) NAME/KEY: CDS
        (B) LOCATION: 2..94

(xi) SEQUENCE DESCRIPTION: SEQ ID NO:145:

```
T TAT CAC AGC GTG TCT CAT GCC CGG CCC CGC TGG ATC TGG TTT TGC         46
  Tyr His Ser Val Ser His Ala Arg Pro Arg Trp Ile Trp Phe Cys
   1               5                  10                  15

CTA CTC CTG CTT GCT GCA GGG GTA GGC ATC TAC CTC CTC CCC AAC CGA       94
Leu Leu Leu Leu Ala Ala Gly Val Gly Ile Tyr Leu Leu Pro Asn Arg
             20                  25                  30

TGAAGGTTGG GGTAAACACT CCGGCCT                                         121
```

(2) INFORMATION FOR SEQ ID NO:146:

(i) SEQUENCE CHARACTERISTICS:
        (A) LENGTH: 31 amino acids
        (B) TYPE: amino acid
        (D) TOPOLOGY: linear (ii) MOLECULE TYPE: protein (xi) SEQUENCE DESCRIPTION: SEQ ID NO:146:

```
Tyr His Ser Val Ser His Ala Arg Pro Arg Trp Ile Trp Phe Cys Leu
 1               5                  10                  15

Leu Leu Leu Ala Ala Gly Val Gly Ile Tyr Leu Leu Pro Asn Arg
             20                  25                  30
```

(2) INFORMATION FOR SEQ ID NO:147:

(i) SEQUENCE CHARACTERISTICS:
        (A) LENGTH: 2219 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..2217

(xi) SEQUENCE DESCRIPTION: SEQ ID NO:147:

```
GCG GTG GAC TTT ATC CCT GTG GAG AAC CTA GAG ACA ACC ATG AGG TCC       48
Ala Val Asp Phe Ile Pro Val Glu Asn Leu Glu Thr Thr Met Arg Ser
 1               5                  10                  15

CCG GTG TTC ACG GAT AAC TCC TCT CCA CCA GTA GTG CCC CAG AGC TTC       96
Pro Val Phe Thr Asp Asn Ser Ser Pro Pro Val Val Pro Gln Ser Phe
             20                  25                  30

CAG GTG GCT CAC CTC CAT GCT CCC ACA GGC AGC GGC AAA AGC ACC AAG      144
Gln Val Ala His Leu His Ala Pro Thr Gly Ser Gly Lys Ser Thr Lys
         35                  40                  45

GTC CCG GCT GCA TAT GCA GCT CAG GGC TAT AAG GTG CTA GTA CTC AAC      192
Val Pro Ala Ala Tyr Ala Ala Gln Gly Tyr Lys Val Leu Val Leu Asn
     50                  55                  60

CCC TCT GTT GCT GCA ACA CTG GGC TTT GGT GCT TAC ATG TCC AAG GCT      240
Pro Ser Val Ala Ala Thr Leu Gly Phe Gly Ala Tyr Met Ser Lys Ala
 65                  70                  75                  80

CAT GGG ATC GAT CCT AAC ATC AGG ACC GGG GTG AGA ACA ATT ACC ACT      288
His Gly Ile Asp Pro Asn Ile Arg Thr Gly Val Arg Thr Ile Thr Thr
                 85                  90                  95

GGC AGC CCC ATC ACG TAC TCC ACC TAC GGC AAG TTC CTT GCC GAC GGC      336
Gly Ser Pro Ile Thr Tyr Ser Thr Tyr Gly Lys Phe Leu Ala Asp Gly
            100                 105                 110

GGG TGC TCG GGG GGC GCT TAT GAC ATA ATA ATT TGT GAC GAG TGC CAC      384
Gly Cys Ser Gly Gly Ala Tyr Asp Ile Ile Ile Cys Asp Glu Cys His
        115                 120                 125

TCC ACG GAT GCC ACA TCC ATC TTG GGC ATC GGC ACT GTC CTT GAC CAA      432
```

```
                                          -continued

Ser Thr Asp Ala Thr Ser Ile Leu Gly Ile Gly Thr Val Leu Asp Gln
130                 135                 140

GCA GAG ACT GCG GGG GCG AGA CTG GTT GTG CTC GCC ACC GCC ACC CCT         480
Ala Glu Thr Ala Gly Ala Arg Leu Val Val Leu Ala Thr Ala Thr Pro
145                 150                 155                 160

CCG GGC TCC GTC ACT GTG CCC CAT CCC AAC ATC GAG GAG GTT GCT CTG         528
Pro Gly Ser Val Thr Val Pro His Pro Asn Ile Glu Glu Val Ala Leu
                    165                 170                 175

TCC ACC ACC GGA GAG ATC CCT TTT TAC GGC AAG GCT ATC CCC CTC GAA         576
Ser Thr Thr Gly Glu Ile Pro Phe Tyr Gly Lys Ala Ile Pro Leu Glu
                180                 185                 190

GTA ATC AAG GGG GGG AGA CAT CTC ATC TTC TGT CAT TCA AAG AAG AAG         624
Val Ile Lys Gly Gly Arg His Leu Ile Phe Cys His Ser Lys Lys Lys
            195                 200                 205

TGC GAC GAA CTC GCC GCA AAG CTG GTC GCA TTG GGC ATC AAT GCC GTG         672
Cys Asp Glu Leu Ala Ala Lys Leu Val Ala Leu Gly Ile Asn Ala Val
210                 215                 220

GCC TAC TAC CGC GGT CTT GAC GTG TCC GTC ATC CCG ACC AGC GGC GAT         720
Ala Tyr Tyr Arg Gly Leu Asp Val Ser Val Ile Pro Thr Ser Gly Asp
225                 230                 235                 240

GTT GTC GTC GTG GCA ACC GAT GCC CTC ATG ACC GGC TAT ACC GGC GAC         768
Val Val Val Val Ala Thr Asp Ala Leu Met Thr Gly Tyr Thr Gly Asp
                    245                 250                 255

TTC GAC TCG GTG ATA GAC TGC AAT ACG TGT GTC ACC CAG ACA GTC GAT         816
Phe Asp Ser Val Ile Asp Cys Asn Thr Cys Val Thr Gln Thr Val Asp
                260                 265                 270

TTC AGC CTT GAC CCT ACC TTC ACC ATT GAG ACA ATC ACG CTC CCC CAG         864
Phe Ser Leu Asp Pro Thr Phe Thr Ile Glu Thr Ile Thr Leu Pro Gln
            275                 280                 285

GAT GCT GTC TCC CGC ACT CAA CGT CGG GGC AGG ACT GGC AGG GGG AAG         912
Asp Ala Val Ser Arg Thr Gln Arg Arg Gly Arg Thr Gly Arg Gly Lys
290                 295                 300

CCA GGC ATC AAC AGA TTT GTG GCA CCG GGG GAG CGC CCC TCC GGC ATG         960
Pro Gly Ile Asn Arg Phe Val Ala Pro Gly Glu Arg Pro Ser Gly Met
305                 310                 315                 320

TTC GAC TCG TCC GTC CTC TGT GAG TGC TAT GAC GCA GGC TGT GCT TGG         1008
Phe Asp Ser Ser Val Leu Cys Glu Cys Tyr Asp Ala Gly Cys Ala Trp
                    325                 330                 335

TAT GAG CTC ACG CCC GCC GAG ACT ACA GTT AGG CTA CGA GCG TAC ATG         1056
Tyr Glu Leu Thr Pro Ala Glu Thr Thr Val Arg Leu Arg Ala Tyr Met
                340                 345                 350

AAC ACC CCG GGG CTT CCC GTG TGC CAG GAC CAT CTT GAA TTT TGG GAG         1104
Asn Thr Pro Gly Leu Pro Val Cys Gln Asp His Leu Glu Phe Trp Glu
            355                 360                 365

GGC GTC TTT ACA GGC CTC ACT CAT ATA GAT GCC CAC TTT CTA TCC CAG         1152
Gly Val Phe Thr Gly Leu Thr His Ile Asp Ala His Phe Leu Ser Gln
370                 375                 380

ACA AAG CAG AGT GGG GAG AAC CTT CCT TAC CTG GTA GCG TAC CAA GCC         1200
Thr Lys Gln Ser Gly Glu Asn Leu Pro Tyr Leu Val Ala Tyr Gln Ala
385                 390                 395                 400

ACC GTG TGC GCT AGG GCT CAA GCC CCT CCC CCA TCG TGG GAC CAG ATG         1248
Thr Val Cys Ala Arg Ala Gln Ala Pro Pro Pro Ser Trp Asp Gln Met
                    405                 410                 415

TGG AAG TGT TTG ATT CGC CTC AAG CCC ACC CTC CAT GGG CCA ACA CCC         1296
Trp Lys Cys Leu Ile Arg Leu Lys Pro Thr Leu His Gly Pro Thr Pro
                420                 425                 430

CTG CTA TAC AGA CTG GGC GCT GTT CAG AAT GAA ATC ACC CTG ACG CAC         1344
Leu Leu Tyr Arg Leu Gly Ala Val Gln Asn Glu Ile Thr Leu Thr His
            435                 440                 445
```

-continued

```
CCA GTC ACC AAA TAC ATC ATG ACA TGC ATG TCG GCC GAC CTG GAG GTC        1392
Pro Val Thr Lys Tyr Ile Met Thr Cys Met Ser Ala Asp Leu Glu Val
    450                 455                 460

GTC ACG AGC ACC TGG GTG CTC GTT GGC GGC GTC CTG GCT GCT TTG GCC        1440
Val Thr Ser Thr Trp Val Leu Val Gly Gly Val Leu Ala Ala Leu Ala
465                 470                 475                 480

GCG TAT TGC CTG TCA ACA GGC TGC GTG GTC ATA GTG GGC AGG GTC GTC        1488
Ala Tyr Cys Leu Ser Thr Gly Cys Val Val Ile Val Gly Arg Val Val
                485                 490                 495

TTG TCC GGG AAG CCG GCA ATC ATA CCT GAC AGG GAA GTC CTC TAC CGA        1536
Leu Ser Gly Lys Pro Ala Ile Ile Pro Asp Arg Glu Val Leu Tyr Arg
            500                 505                 510

GAG TTC GAT GAG ATG GAA GAG TGC TCT CAG CAC TTA CCG TAC ATC GAG        1584
Glu Phe Asp Glu Met Glu Glu Cys Ser Gln His Leu Pro Tyr Ile Glu
        515                 520                 525

CAA GGG ATG ATG CTC GCC GAG CAG TTC AAG CAG AAG GCC CTC GGC CTC        1632
Gln Gly Met Met Leu Ala Glu Gln Phe Lys Gln Lys Ala Leu Gly Leu
    530                 535                 540

CTG CAG ACC GCG TCC CGT CAG GCA GAG GTT ATC GCC CCT GCT GTC CAG        1680
Leu Gln Thr Ala Ser Arg Gln Ala Glu Val Ile Ala Pro Ala Val Gln
545                 550                 555                 560

ACC AAC TGG CAA AAA CTC GAG ACC TTC TGG GCG AAG CAT ATG TGG AAC        1728
Thr Asn Trp Gln Lys Leu Glu Thr Phe Trp Ala Lys His Met Trp Asn
                565                 570                 575

TTC ATC AGT GGG ATA CAA TAC TTG GCG GGC TTG TCA ACG CTG CCT GGT        1776
Phe Ile Ser Gly Ile Gln Tyr Leu Ala Gly Leu Ser Thr Leu Pro Gly
            580                 585                 590

AAC CCC GCC ATT GCT TCA TTG ATG GCT TTT ACA GCT GCT GTC ACC AGC        1824
Asn Pro Ala Ile Ala Ser Leu Met Ala Phe Thr Ala Ala Val Thr Ser
        595                 600                 605

CCA CTA ACC ACT AGC CAA ACC CTC CTC TTC AAC ATA TTG GGG GGG TGG        1872
Pro Leu Thr Thr Ser Gln Thr Leu Leu Phe Asn Ile Leu Gly Gly Trp
    610                 615                 620

GTG GCT GCC CAG CTC GCC GCC CCC GGT GCC GCT ACT GCC TTT GTG GGC        1920
Val Ala Ala Gln Leu Ala Ala Pro Gly Ala Ala Thr Ala Phe Val Gly
625                 630                 635                 640

GCT GGC TTA GCT GGC GCC GCC ATC GGC AGT GTT GGA CTG GGG AAG GTC        1968
Ala Gly Leu Ala Gly Ala Ala Ile Gly Ser Val Gly Leu Gly Lys Val
                645                 650                 655

CTC ATA GAC ATC CTT GCA GGG TAT GGC GCG GGC GTG GCG GGA GCT CTT        2016
Leu Ile Asp Ile Leu Ala Gly Tyr Gly Ala Gly Val Ala Gly Ala Leu
            660                 665                 670

GTG GCA TTC AAG ATC ATG AGC GGT GAG GTC CCC TCC ACG GAG GAC CTG        2064
Val Ala Phe Lys Ile Met Ser Gly Glu Val Pro Ser Thr Glu Asp Leu
        675                 680                 685

GTC AAT CTA CTG CCC GCC ATC CTC TCG CCC GGA GCC CTC GTA GTC GGC        2112
Val Asn Leu Leu Pro Ala Ile Leu Ser Pro Gly Ala Leu Val Val Gly
    690                 695                 700

GTG GTC TGT GCA GCA ATA CTG CGC CGG CAC GTT GGC CCG GGC GAG GGG        2160
Val Val Cys Ala Ala Ile Leu Arg Arg His Val Gly Pro Gly Glu Gly
705                 710                 715                 720

GCA GTG CAG TGG ATG AAC CGG CTG ATA GCC TTC GCC TCC CGG GGG AAC        2208
Ala Val Gln Trp Met Asn Arg Leu Ile Ala Phe Ala Ser Arg Gly Asn
                725                 730                 735

CAT GTT TCC CC                                                         2219
His Val Ser
```

(2) INFORMATION FOR SEQ ID NO:148:

(i) SEQUENCE CHARACTERISTICS:

-continued

```
      (A) LENGTH: 739 amino acids
      (B) TYPE: amino acid
      (D) TOPOLOGY: linear (ii) MOLECULE TYPE: protein (xi) SEQUENCE DESCRIPTION: SEQ ID NO:148:

Ala Val Asp Phe Ile Pro Val Glu Asn Leu Glu Thr Thr Met Arg Ser
  1               5                  10                  15

Pro Val Phe Thr Asp Asn Ser Ser Pro Val Val Pro Gln Ser Phe
             20                  25                  30

Gln Val Ala His Leu His Ala Pro Thr Gly Ser Gly Lys Ser Thr Lys
         35                  40                  45

Val Pro Ala Ala Tyr Ala Ala Gln Gly Tyr Lys Val Leu Val Leu Asn
 50                  55                  60

Pro Ser Val Ala Ala Thr Leu Gly Phe Gly Ala Tyr Met Ser Lys Ala
 65                  70                  75                  80

His Gly Ile Asp Pro Asn Ile Arg Thr Gly Val Arg Thr Ile Thr Thr
                 85                  90                  95

Gly Ser Pro Ile Thr Tyr Ser Thr Tyr Gly Lys Phe Leu Ala Asp Gly
                100                 105                 110

Gly Cys Ser Gly Gly Ala Tyr Asp Ile Ile Ile Cys Asp Glu Cys His
             115                 120                 125

Ser Thr Asp Ala Thr Ser Ile Leu Gly Ile Gly Thr Val Leu Asp Gln
130                 135                 140

Ala Glu Thr Ala Gly Ala Arg Leu Val Val Leu Ala Thr Ala Thr Pro
145                 150                 155                 160

Pro Gly Ser Val Thr Val Pro His Pro Asn Ile Glu Glu Val Ala Leu
                165                 170                 175

Ser Thr Thr Gly Glu Ile Pro Phe Tyr Gly Lys Ala Ile Pro Leu Glu
                180                 185                 190

Val Ile Lys Gly Gly Arg His Leu Ile Phe Cys His Ser Lys Lys Lys
            195                 200                 205

Cys Asp Glu Leu Ala Ala Lys Leu Val Ala Leu Gly Ile Asn Ala Val
210                 215                 220

Ala Tyr Tyr Arg Gly Leu Asp Val Ser Val Ile Pro Thr Ser Gly Asp
225                 230                 235                 240

Val Val Val Val Ala Thr Asp Ala Leu Met Thr Gly Tyr Thr Gly Asp
                245                 250                 255

Phe Asp Ser Val Ile Asp Cys Asn Thr Cys Val Thr Gln Thr Val Asp
            260                 265                 270

Phe Ser Leu Asp Pro Thr Phe Thr Ile Glu Thr Ile Thr Leu Pro Gln
        275                 280                 285

Asp Ala Val Ser Arg Thr Gln Arg Arg Gly Arg Thr Gly Arg Gly Lys
290                 295                 300

Pro Gly Ile Asn Arg Phe Val Ala Pro Gly Glu Arg Pro Ser Gly Met
305                 310                 315                 320

Phe Asp Ser Ser Val Leu Cys Glu Cys Tyr Asp Ala Gly Cys Ala Trp
                325                 330                 335

Tyr Glu Leu Thr Pro Ala Glu Thr Thr Val Arg Leu Arg Ala Tyr Met
                340                 345                 350

Asn Thr Pro Gly Leu Pro Val Cys Gln Asp His Leu Glu Phe Trp Glu
            355                 360                 365

Gly Val Phe Thr Gly Leu Thr His Ile Asp Ala His Phe Leu Ser Gln
370                 375                 380
```

```
Thr Lys Gln Ser Gly Glu Asn Leu Pro Tyr Leu Val Ala Tyr Gln Ala
385                 390                 395                 400

Thr Val Cys Ala Arg Ala Gln Ala Pro Pro Ser Trp Asp Gln Met
            405                 410                 415

Trp Lys Cys Leu Ile Arg Leu Lys Pro Thr Leu His Gly Pro Thr Pro
                420                 425                 430

Leu Leu Tyr Arg Leu Gly Ala Val Gln Asn Glu Ile Thr Leu Thr His
            435                 440                 445

Pro Val Thr Lys Tyr Ile Met Thr Cys Met Ser Ala Asp Leu Glu Val
450                 455                 460

Val Thr Ser Thr Trp Val Leu Val Gly Val Leu Ala Ala Leu Ala
465                 470                 475                 480

Ala Tyr Cys Leu Ser Thr Gly Cys Val Val Ile Val Gly Arg Val Val
                485                 490                 495

Leu Ser Gly Lys Pro Ala Ile Ile Pro Asp Arg Glu Val Leu Tyr Arg
                500                 505                 510

Glu Phe Asp Glu Met Glu Glu Cys Ser Gln His Leu Pro Tyr Ile Glu
            515                 520                 525

Gln Gly Met Met Leu Ala Glu Gln Phe Lys Gln Lys Ala Leu Gly Leu
            530                 535                 540

Leu Gln Thr Ala Ser Arg Gln Ala Glu Val Ile Ala Pro Ala Val Gln
545                 550                 555                 560

Thr Asn Trp Gln Lys Leu Glu Thr Phe Trp Ala Lys His Met Trp Asn
                565                 570                 575

Phe Ile Ser Gly Ile Gln Tyr Leu Ala Gly Leu Ser Thr Leu Pro Gly
                580                 585                 590

Asn Pro Ala Ile Ala Ser Leu Met Ala Phe Thr Ala Ala Val Thr Ser
            595                 600                 605

Pro Leu Thr Thr Ser Gln Thr Leu Leu Phe Asn Ile Leu Gly Gly Trp
            610                 615                 620

Val Ala Ala Gln Leu Ala Ala Pro Gly Ala Ala Thr Ala Phe Val Gly
625                 630                 635                 640

Ala Gly Leu Ala Gly Ala Ala Ile Gly Ser Val Gly Leu Gly Lys Val
                645                 650                 655

Leu Ile Asp Ile Leu Ala Gly Tyr Gly Ala Gly Val Ala Gly Ala Leu
            660                 665                 670

Val Ala Phe Lys Ile Met Ser Gly Glu Val Pro Ser Thr Glu Asp Leu
            675                 680                 685

Val Asn Leu Leu Pro Ala Ile Leu Ser Pro Gly Ala Leu Val Val Gly
            690                 695                 700

Val Val Cys Ala Ala Ile Leu Arg Arg His Val Gly Pro Gly Glu Gly
705                 710                 715                 720

Ala Val Gln Trp Met Asn Arg Leu Ile Ala Phe Ala Ser Arg Gly Asn
                725                 730                 735

His Val Ser (2) INFORMATION FOR SEQ ID NO:149:

(i) SEQUENCE CHARACTERISTICS:
        (A) LENGTH: 1018 base pairs
        (B) TYPE: nucleic acid
        (C) STRANDEDNESS: single
        (D) TOPOLOGY: linear (ii) MOLECULE TYPE: cDNA
```

(vi) ORIGINAL SOURCE:
        (C) INDIVIDUAL ISOLATE: Human 23

(ix) FEATURE:
        (A) NAME/KEY: CDS
        (B) LOCATION: 1..1017

(ix) FEATURE:
        (A) NAME/KEY: misc_feature
        (B) LOCATION: 70
        (D) OTHER INFORMATION: /note= "A heterogeneity may exist -
            nucleotide 70 = G or C and  amino acid Xaa = Ala, Pro,
            Gly, or Arg"

(ix) FEATURE:
        (A) NAME/KEY: misc_feature
        (B) LOCATION: 71
        (D) OTHER INFORMATION: /note= "A heterogeneity may exist -
            nucleotide 71 = C or G and amino acid Xaa = Ala, Pro,
            Gly, or Arg"

(ix) FEATURE:
        (A) NAME/KEY: misc_feature
        (B) LOCATION: 75
        (D) OTHER INFORMATION: /note= "A heterogeneity may exist -
            nucleotide 75 = C or A and amino acid Xaa = His or Gln"

(ix) FEATURE:
        (A) NAME/KEY: misc_feature
        (B) LOCATION: 140
        (D) OTHER INFORMATION: /note= "A heterogeneity may exist -
            nucleotide 140 = C or G and amino acid Xaa = Ser or Cys"

(ix) FEATURE:
        (A) NAME/KEY: misc_feature
        (B) LOCATION: 141
        (D) OTHER INFORMATION: /note= "A heterogeneity may exist -
            nucleotide 141 = T or A and amino acid Xaa = Ser"

(ix) FEATURE:
        (A) NAME/KEY: misc_feature
        (B) LOCATION: 162
        (D) OTHER INFORMATION: /note= "A heterogeneity may exist -
            nucleotide 162 = C or T and amino acid Xaa = Leu"

(ix) FEATURE:
        (A) NAME/KEY: misc_feature
        (B) LOCATION: 263
        (D) OTHER INFORMATION: /note= "A heterogeneity may exist -
            nucleotide 263 = C or T and amino acid Xaa = Ala or Val"

(ix) FEATURE:
        (A) NAME/KEY: misc_feature
        (B) LOCATION: 292
        (D) OTHER INFORMATION: /note= "A heterogeneity may exist -
            nucleotide 292 = T or C and amino acid Xaa = Cys or Arg"

(ix) FEATURE:
        (A) NAME/KEY: misc_feature
        (B) LOCATION: 309
        (D) OTHER INFORMATION: /note= "A heterogeneity may exist -
            nucleotide 309 = C or G and amino acid Xaa = Arg"

(ix) FEATURE:
        (A) NAME/KEY: misc_feature
        (B) LOCATION: 359
        (D) OTHER INFORMATION: /note= "A heterogeneity may exist -
            nucleotide 359 = C or T and amino acid Xaa = Thr or Ile"

(ix) FEATURE:
        (A) NAME/KEY: misc_feature
        (B) LOCATION: 411
        (D) OTHER INFORMATION: /note= "A heterogeneity may exist -
            nucleotide 411= T or C and amino acid Xaa = Leu "

(ix) FEATURE:
        (A) NAME/KEY: misc_feature
        (B) LOCATION: 419

```
         (D) OTHER INFORMATION: /note= "A heterogeneity may exist -
             nucleotide 419 = G or A and amino acid Xaa = Ser or Asn"

(ix) FEATURE:
         (A) NAME/KEY: misc_feature
         (B) LOCATION: 429
         (D) OTHER INFORMATION: /note= "A heterogeneity may exist -
             nucleotide 429 = C or T and amino acid Xaa = Leu"

(ix) FEATURE:
         (A) NAME/KEY: misc_feature
         (B) LOCATION: 521
         (D) OTHER INFORMATION: /note= "A heterogeneity may exist -
             nucleotide 521 = A or C and amino acid Xaa = Gln or Pro"

(ix) FEATURE:
         (A) NAME/KEY: misc_feature
         (B) LOCATION: 590
         (D) OTHER INFORMATION: /note= "A heterogeneity may exist -
             nucleotide 590 = A or G and amino acid Xaa = Asn or Ser"

(ix) FEATURE:
         (A) NAME/KEY: misc_feature
         (B) LOCATION: 615
         (D) OTHER INFORMATION: /note= "A heterogeneity may exist -
             nucleotide 615 = A or G and amino acid Xaa = Val"

(ix) FEATURE:
         (A) NAME/KEY: misc_feature
         (B) LOCATION: 619
         (D) OTHER INFORMATION: /note= "A heterogeneity may exist -
             nucleotide 619 = G or A and amino acid Xaa = Ala, Thr,
             Gly, or Ser"

(ix) FEATURE:
         (A) NAME/KEY: misc_feature
         (B) LOCATION: 620
         (D) OTHER INFORMATION: /note= "A heterogeneity may exist -
             nucleotide 620 = C or G and amino acid Xaa = Ala, Thr,
             Gly, or Ser"

(ix) FEATURE:
         (A) NAME/KEY: misc_feature
         (B) LOCATION: 700
         (D) OTHER INFORMATION: /note= "A heterogeneity may exist -
             nucleotide 700 = T or G and amino acid Xaa = Phe or Val"

(ix) FEATURE:
         (A) NAME/KEY: misc_feature
         (B) LOCATION: 764
         (D) OTHER INFORMATION: /note= "A heterogeneity may exist -
             nucleotide 764 = C or G and amino acid Xaa = Ala or Gly"

(ix) FEATURE:
         (A) NAME/KEY: misc_feature
         (B) LOCATION: 781
         (D) OTHER INFORMATION: /note= "A heterogeneity exists -
             nucleotide 781 = G or C and amino acid Xaa = Gly or Arg"

(ix) FEATURE:
         (A) NAME/KEY: misc_feature
         (B) LOCATION: 792
         (D) OTHER INFORMATION: /note= "A heterogeneity exists -
             nucleotide 792 = C or T and amino acid Xaa = Ala"

(ix) FEATURE:
         (A) NAME/KEY: misc_feature
         (B) LOCATION: 796
         (D) OTHER INFORMATION: /note= "A heterogeneity exists -
             nucleotide 796 = C or A and amino acid Xaa = Arg or Ser"

(ix) FEATURE:
         (A) NAME/KEY: misc_feature
         (B) LOCATION: 888
         (D) OTHER INFORMATION: /note= "A heterogeneity may exist -
             nucleotide 888 = T or A and amino acid Xaa = Ser or Arg"

(ix) FEATURE:
         (A) NAME/KEY: misc_feature
```

```
        (B) LOCATION: 889
        (D) OTHER INFORMATION: /note= "A heterogeneity may exist -
            nucleotide 889 = A or T and amino acid Xaa = Thr or Ser"

(ix) FEATURE:
    (A) NAME/KEY: misc_feature
    (B) LOCATION: 903
    (D) OTHER INFORMATION: /note= "A heterogeneity may exist -
        nucleotide 903 = C or A and amino acid Xaa = Cys"

(ix) FEATURE:
    (A) NAME/KEY: misc_feature
    (B) LOCATION: 933
    (D) OTHER INFORMATION: /note= "A heterogeneity may exist -
        nucleotide 933 = G or A and amino acid Xaa = Ala "

(ix) FEATURE:
    (A) NAME/KEY: misc_feature
    (B) LOCATION: 962
    (D) OTHER INFORMATION: /note= "A heterogeneity may exist -
        nucleotide 962 = C or G and amino acid Xaa = Ser or Cys"

(ix) FEATURE:
    (A) NAME/KEY: misc_feature
    (B) LOCATION: 965
    (D) OTHER INFORMATION: /note= "A heterogeneity may exist -
        nucleotide 965 = C or A and amino acid Xaa = Ser"

(ix) FEATURE:
    (A) NAME/KEY: misc_feature
    (B) LOCATION: 1002
    (D) OTHER INFORMATION: /note= "A heterogeneity may exist -
        nucleotide 1002 = C or G and amino acid Xaa = Leu "

(xi) SEQUENCE DESCRIPTION: SEQ ID NO:149:

GGC TTC GCC GAC CTC ATG GGG TAC ATA CCG CTC GTC GGC GCC CCT CTT          48
Gly Phe Ala Asp Leu Met Gly Tyr Ile Pro Leu Val Gly Ala Pro Leu
 1               5                  10                  15

GGA GGC CGT GCC AGG GCC CTG SSG CAM GGC GTC CGG GTT TTG GAA GAC          96
Gly Gly Arg Ala Arg Ala Leu Xaa Xaa Gly Val Arg Val Leu Glu Asp
            20                  25                  30

GGC GTG AAC TAT GCA ACA GGG AAC CTT CCT GGT TGC TCC TTT TSW ATC         144
Gly Val Asn Tyr Ala Thr Gly Asn Leu Pro Gly Cys Ser Phe Xaa Ile
        35                  40                  45

TTC CTT CTG GCC CTA CTY TCT TGC CTG ACC GTG CCC GCT TCA GCC TAC         192
Phe Leu Leu Ala Leu Xaa Ser Cys Leu Thr Val Pro Ala Ser Ala Tyr
    50                  55                  60

CAA GTG CGC AAC TCT ACG GGG CTT TAC CAT GTC ACC AAT GAT TGC CCT         240
Gln Val Arg Asn Ser Thr Gly Leu Tyr His Val Thr Asn Asp Cys Pro
65                  70                  75                  80

AAC TCG AGT ATT GTG TAC GAG GYG GCC GAT GCC ATC CTA CAC GCT CCG         288
Asn Ser Ser Ile Val Tyr Glu Xaa Ala Asp Ala Ile Leu His Ala Pro
                85                  90                  95

GGG YGT GTC CCT TGC GTT CGS GAG GAT AAC GTC TCG AGA TGT TGG GTG         336
Gly Xaa Val Pro Cys Val Xaa Glu Asp Asn Val Ser Arg Cys Trp Val
            100                 105                 110

GCG GTG ACC CCC ACG GTG GCC AYC AAG GAC GGC AAA CTC CCC ACA ACG         384
Ala Val Thr Pro Thr Val Ala Xaa Lys Asp Gly Lys Leu Pro Thr Thr
        115                 120                 125

CAG CTT CGA CGT CAC ATC GAT CTG CTY GTC GGG ARC GCC ACC CTY TGC         432
Gln Leu Arg Arg His Ile Asp Leu Xaa Val Gly Xaa Ala Thr Xaa Cys
    130                 135                 140

TCG GCC CTC TAC GTG GGG GAC CTT TGC GGG TCC ATC TTT CTT GTC GGT         480
Ser Ala Leu Tyr Val Gly Asp Leu Cys Gly Ser Ile Phe Leu Val Gly
145                 150                 155                 160

CAA CTG TTT ACC TTC TCT CCC AGG CGC CAC TGG ACG ACG CMG GAC TGC         528
Gln Leu Phe Thr Phe Ser Pro Arg Arg His Trp Thr Thr Xaa Asp Cys
                165                 170                 175
```

```
AAC TGT TCT ATC TAT CCC GGC CAT ATA ACG GGT CAC CGC ATG GCA TGG        576
Asn Cys Ser Ile Tyr Pro Gly His Ile Thr Gly His Arg Met Ala Trp
            180                 185                 190

GAT ATG ATG ATG ARC TGG TCC CCT ACG GCG GCA TTG GTR GTA RST CAG        624
Asp Met Met Met Xaa Trp Ser Pro Thr Ala Ala Leu Xaa Val Xaa Gln
            195                 200                 205

CTG CTC CGG ATC CCA CAA GCC ATC TTG GAC ATG ATC GCT GGT GCT CAC        672
Leu Leu Arg Ile Pro Gln Ala Ile Leu Asp Met Ile Ala Gly Ala His
        210                 215                 220

TGG GGA GTC CTG GCG GGC ATG GCG TAT KTC TCC ATG GTG GGG AAC TGG        720
Trp Gly Val Leu Ala Gly Met Ala Tyr Xaa Ser Met Val Gly Asn Trp
225                 230                 235                 240

GCG AAG GTC CTG GTA GTG CTG CTT CTA TTT GCC GGC GTC GAC GSG GAA        768
Ala Lys Val Leu Val Val Leu Leu Leu Phe Ala Gly Val Asp Xaa Glu
                245                 250                 255

ACC CAC CGT ACC SGG GGA AGT GCY GCC MGC AGC ACG GCT GGA GTT GCT        816
Thr His Arg Thr Xaa Gly Ser Xaa Ala Xaa Ser Thr Ala Gly Val Ala
            260                 265                 270

AGT CTC TTC ACA CCA GGC GCT AGG CAG AAC ATC CAG CTG ATC AAC ACC        864
Ser Leu Phe Thr Pro Gly Ala Arg Gln Asn Ile Gln Leu Ile Asn Thr
        275                 280                 285

AAC GGC AGT TGG CAC ATC AAT AGW WCG GCC TTG AAC TGM AAT GAC AGC        912
Asn Gly Ser Trp His Ile Asn Xaa Xaa Ala Leu Asn Xaa Asn Asp Ser
    290                 295                 300

CTT ACC ACC GGC TGG TTA GCR GGG CTT TTC TAT CAC CAT AAA TTC AAC        960
Leu Thr Thr Gly Trp Leu Xaa Gly Leu Phe Tyr His His Lys Phe Asn
305                 310                 315                 320

TST TMA GGC TGT CCC GAG AGG TTG GCC AGC TGC CGA CCC CTS ACC GAT       1008
Xaa Xaa Gly Cys Pro Glu Arg Leu Ala Ser Cys Arg Pro Xaa Thr Asp
                325                 330                 335

TTT GCC CAG G                                                         1018
Phe Ala Gln (2) INFORMATION FOR SEQ ID NO:150:

(i) SEQUENCE CHARACTERISTICS:
        (A) LENGTH: 339 amino acids
        (B) TYPE: amino acid
        (D) TOPOLOGY: linear (ii) MOLECULE TYPE: protein (xi) SEQUENCE DESCRIPTION: SEQ ID NO:150:

Gly Phe Ala Asp Leu Met Gly Tyr Ile Pro Leu Val Gly Ala Pro Leu
  1               5                  10                  15

Gly Gly Arg Ala Arg Ala Leu Xaa Xaa Gly Val Arg Val Leu Glu Asp
                 20                  25                  30

Gly Val Asn Tyr Ala Thr Gly Asn Leu Pro Gly Cys Ser Phe Xaa Ile
             35                  40                  45

Phe Leu Leu Ala Leu Xaa Ser Cys Leu Thr Val Pro Ala Ser Ala Tyr
     50                  55                  60

Gln Val Arg Asn Ser Thr Gly Leu Tyr His Val Thr Asn Asp Cys Pro
 65                  70                  75                  80

Asn Ser Ser Ile Val Tyr Glu Xaa Ala Asp Ala Ile Leu His Ala Pro
                 85                  90                  95

Gly Xaa Val Pro Cys Val Xaa Glu Asp Asn Val Ser Arg Cys Trp Val
            100                 105                 110

Ala Val Thr Pro Thr Val Ala Xaa Lys Asp Gly Lys Leu Pro Thr Thr
        115                 120                 125
```

```
Gln Leu Arg Arg His Ile Asp Leu Xaa Val Gly Xaa Ala Thr Xaa Cys
    130                 135                 140

Ser Ala Leu Tyr Val Gly Asp Leu Cys Gly Ser Ile Phe Leu Val Gly
145                 150                 155                 160

Gln Leu Phe Thr Phe Ser Pro Arg Arg His Trp Thr Thr Xaa Asp Cys
                165                 170                 175

Asn Cys Ser Ile Tyr Pro Gly His Ile Thr Gly His Arg Met Ala Trp
                180                 185                 190

Asp Met Met Met Xaa Trp Ser Pro Thr Ala Ala Leu Xaa Val Xaa Gln
        195                 200                 205

Leu Leu Arg Ile Pro Gln Ala Ile Leu Asp Met Ile Ala Gly Ala His
    210                 215                 220

Trp Gly Val Leu Ala Gly Met Ala Tyr Xaa Ser Met Val Gly Asn Trp
225                 230                 235                 240

Ala Lys Val Leu Val Val Leu Leu Phe Ala Gly Val Asp Xaa Glu
                245                 250                 255

Thr His Arg Thr Xaa Gly Ser Xaa Ala Xaa Ser Thr Ala Gly Val Ala
                260                 265                 270

Ser Leu Phe Thr Pro Gly Ala Arg Gln Asn Ile Gln Leu Ile Asn Thr
    275                 280                 285

Asn Gly Ser Trp His Ile Asn Xaa Xaa Ala Leu Asn Xaa Asn Asp Ser
290                 295                 300

Leu Thr Thr Gly Trp Leu Xaa Gly Leu Phe Tyr His His Lys Phe Asn
305                 310                 315                 320

Xaa Xaa Gly Cys Pro Glu Arg Leu Ala Ser Cys Arg Pro Xaa Thr Asp
                325                 330                 335

Phe Ala Gln (2) INFORMATION FOR SEQ ID NO:151:

(i) SEQUENCE CHARACTERISTICS:
        (A) LENGTH: 1018 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (C) INDIVIDUAL ISOLATE: Human 27

(ix) FEATURE:
        (A) NAME/KEY: CDS
        (B) LOCATION: 1..1017

(ix) FEATURE:
        (A) NAME/KEY: misc_feature
        (B) LOCATION: 244
        (D) OTHER INFORMATION: /note= "A heterogeneity may exist -
            nucleotide 244 = T or C and amino acid Xaa = Ser or Pro"

(ix) FEATURE:
        (A) NAME/KEY: misc_feature
        (B) LOCATION: 256
        (D) OTHER INFORMATION: /note= "A heterogeneity may exist -
            nucleotide 256 = T or C and amino acid Xaa = Tyr or His"

(ix) FEATURE:
        (A) NAME/KEY: misc_feature
        (B) LOCATION: 311
        (D) OTHER INFORMATION: /note= "A heterogeneity may exist -
            nucleotide 311 = A or G and amino acid Xaa = Glu or Gly"

(ix) FEATURE:
```

```
        (A) NAME/KEY: misc_feature
        (B) LOCATION: 393
        (D) OTHER INFORMATION: /note= "A heterogeneity may exist -
            nucleotide 393 = A or G and amino acid Xaa = Arg "

(ix) FEATURE:
        (A) NAME/KEY: misc_feature
        (B) LOCATION: 404
        (D) OTHER INFORMATION: /note= "A heterogeneity may exist -
            nucleotide 404 = A or G and amino acid Xaa = Asp or Gly"

(ix) FEATURE:
        (A) NAME/KEY: misc_feature
        (B) LOCATION: 429
        (D) OTHER INFORMATION: /note= "A heterogeneity may exist -
            nucleotide 429 = T or C and amino acid Xaa = Leu"

(ix) FEATURE:
        (A) NAME/KEY: misc_feature
        (B) LOCATION: 471
        (D) OTHER INFORMATION: /note= "A heterogeneity may exist -
            nucleotide 471 = T or C and amino acid Xaa = Phe"

(ix) FEATURE:
        (A) NAME/KEY: misc_feature
        (B) LOCATION: 498
        (D) OTHER INFORMATION: /note= "A heterogeneity may exist -
            nucleotide 498 = C or A and amino acid Xaa = Ser "

(ix) FEATURE:
        (A) NAME/KEY: misc_feature
        (B) LOCATION: 606
        (D) OTHER INFORMATION: /note= "A heterogeneity may exist -
            nucleotide 606 = A or G and amino acid Xaa = Ala "

(ix) FEATURE:
        (A) NAME/KEY: misc_feature
        (B) LOCATION: 842
        (D) OTHER INFORMATION: /note= "A heterogeneity may exist -
            nucleotide 842 = A or G and amino acid Xaa = Gln or Arg"

(ix) FEATURE:
        (A) NAME/KEY: misc_feature
        (B) LOCATION: 867
        (D) OTHER INFORMATION: /note= "A heterogeneity may exist -
            nucleotide 867 = C or T and amino acid Xaa = Asn "

(ix) FEATURE:
        (A) NAME/KEY: misc_feature
        (B) LOCATION: 913
        (D) OTHER INFORMATION: /note= "A heterogeneity may exist -
            nucleotide 913 = C or T and amino acid Xaa = Leu or Phe"

(ix) FEATURE:
        (A) NAME/KEY: misc_feature
        (B) LOCATION: 930
        (D) OTHER INFORMATION: /note= "A heterogeneity may exist -
            nucleotide 930 = A or G and amino acid Xaa = Val"

(ix) FEATURE:
        (A) NAME/KEY: misc_feature
        (B) LOCATION: 1008
        (D) OTHER INFORMATION: /note= "A heterogeneity may exist -
            nucleotide 1008 = T or C and amino acid Xaa = Asp"

(xi) SEQUENCE DESCRIPTION: SEQ ID NO:151:

GGC TTC GCC GAC CTC ATG GGG TAC ATT CCG CTC GTC GGC GCT CCT CTT       48
Gly Phe Ala Asp Leu Met Gly Tyr Ile Pro Leu Val Gly Ala Pro Leu
 1               5                  10                  15

GGG GGC GCT GCC AGG GCC CTG GCG CAT GGC GTC CGG GTT CTG GAA GAC       96
Gly Gly Ala Ala Arg Ala Leu Ala His Gly Val Arg Val Leu Glu Asp
             20                  25                  30

GGC GTG AAC TAT GCA ACA GGG AAC CTT CCT GGT TGC TCT TTC TCT ATC      144
Gly Val Asn Tyr Ala Thr Gly Asn Leu Pro Gly Cys Ser Phe Ser Ile
         35                  40                  45
```

```
TTC CTT CTG GCT CTG CTC TCT TGC CTG ACC GTG CCC GCA TCG GCC TAC      192
Phe Leu Leu Ala Leu Leu Ser Cys Leu Thr Val Pro Ala Ser Ala Tyr
 50                  55                  60

CAA GTA CGC AAC TCC TCG GGC ATT TAC CAT GTC ACC AAT GAT TGC CCT      240
Gln Val Arg Asn Ser Ser Gly Ile Tyr His Val Thr Asn Asp Cys Pro
 65                  70                  75                  80

AAT YCG AGT ATT GTG YAC GAG ACG GCC GAC ACC ATC CTA CAC TCT CCG      288
Asn Xaa Ser Ile Val Xaa Glu Thr Ala Asp Thr Ile Leu His Ser Pro
                     85                  90                  95

GGG TGT GTC CCT TGC GTT CGC GRG GGT AAC GCC TCG AAA TGT TGG GTG      336
Gly Cys Val Pro Cys Val Arg Xaa Gly Asn Ala Ser Lys Cys Trp Val
                100                 105                 110

CCG GTA GCC CCC ACA GTG GCC ACC AGG GAC GGC AAC CTC CCC GCA ACG      384
Pro Val Ala Pro Thr Val Ala Thr Arg Asp Gly Asn Leu Pro Ala Thr
                115                 120                 125

CAG CTT CGR CGT CAC ATC GRT CTG CTT GTC GGG AGT GCC ACC CTY TGC      432
Gln Leu Xaa Arg His Ile Xaa Leu Leu Val Gly Ser Ala Thr Xaa Cys
    130                 135                 140

TCG GCC CTC TAT GTG GGG GAC TTG TGC GGG TCT GTC TTY CTT GTC GGT      480
Ser Ala Leu Tyr Val Gly Asp Leu Cys Gly Ser Val Xaa Leu Val Gly
145                 150                 155                 160

CAA CTG TTC ACT TTC TCM CCC AGG CGC CAC TGG ACA ACG CAA GAT TGC      528
Gln Leu Phe Thr Phe Xaa Pro Arg Arg His Trp Thr Thr Gln Asp Cys
                165                 170                 175

AAC TGC TCT ATC TAC CCC GGC CAT ATA ACG GGA CAC CGC ATG GCA TGG      576
Asn Cys Ser Ile Tyr Pro Gly His Ile Thr Gly His Arg Met Ala Trp
                180                 185                 190

GAT ATG ATG ATG AAC TGG TCC CCT ACA GCR GCG CTG GTA ATG GCT CAG      624
Asp Met Met Met Asn Trp Ser Pro Thr Xaa Ala Leu Val Met Ala Gln
                195                 200                 205

CTG CTC AGG ATC CCG CAA GCC ATC TTG GAC ATG ATC GCT GGT GCT CAC      672
Leu Leu Arg Ile Pro Gln Ala Ile Leu Asp Met Ile Ala Gly Ala His
210                 215                 220

TGG GGA GTC CTA GCG GGC ATA GCG TAT TTC TCC ATG GTG GGG AAC TGG      720
Trp Gly Val Leu Ala Gly Ile Ala Tyr Phe Ser Met Val Gly Asn Trp
225                 230                 235                 240

GCG AAG GTC CTG GTG GTG CTG TTG CTG TTT GCC GGC GTC GAT GCG ACA      768
Ala Lys Val Leu Val Val Leu Leu Leu Phe Ala Gly Val Asp Ala Thr
                245                 250                 255

ACC TAT ACC ACC GGG GGG AAT GCT GCC AGG ACC ACG CAG GCG CTC ACC      816
Thr Tyr Thr Thr Gly Gly Asn Ala Ala Arg Thr Thr Gln Ala Leu Thr
                260                 265                 270

AGT TTT TTC AGC CCA GGC GCC AAG CRG GAT ATC CAG CTG ATC AAC ACC      864
Ser Phe Phe Ser Pro Gly Ala Lys Xaa Asp Ile Gln Leu Ile Asn Thr
                275                 280                 285

AAY GGC AGT TGG CAC ATC AAT CGC ACG GCC TTG AAC TGT AAT GCG AGC      912
Xaa Gly Ser Trp His Ile Asn Arg Thr Ala Leu Asn Cys Asn Ala Ser
                290                 295                 300

YTC GAC ACT GGC TGG GTR GCG GGG CTC TTC TAT TAC CAC AAA TTC AAC      960
Xaa Asp Thr Gly Trp Xaa Ala Gly Leu Phe Tyr Tyr His Lys Phe Asn
305                 310                 315                 320

TCT TCA GGC TGC CCC GAG AGG ATG GCC AGC TGT AGG CCC CTT GCC GAY     1008
Ser Ser Gly Cys Pro Glu Arg Met Ala Ser Cys Arg Pro Leu Ala Xaa
                325                 330                 335

TTC GAC CAG G                                                       1018
Phe Asp Gln
```

(2) INFORMATION FOR SEQ ID NO:152:

(i) SEQUENCE CHARACTERISTICS:

```
            (A) LENGTH: 339 amino acids
            (B) TYPE: amino acid
            (D) TOPOLOGY: linear (ii) MOLECULE TYPE: protein (xi) SEQUENCE DESCRIPTION: SEQ ID NO:152:

Gly Phe Ala Asp Leu Met Gly Tyr Ile Pro Leu Val Gly Ala Pro Leu
 1               5                  10                  15

Gly Gly Ala Ala Arg Ala Leu Ala His Gly Val Arg Val Leu Glu Asp
             20                  25                  30

Gly Val Asn Tyr Ala Thr Gly Asn Leu Pro Gly Cys Ser Phe Ser Ile
         35                  40                  45

Phe Leu Leu Ala Leu Leu Ser Cys Leu Thr Val Pro Ala Ser Ala Tyr
 50                  55                  60

Gln Val Arg Asn Ser Ser Gly Ile Tyr His Val Thr Asn Asp Cys Pro
 65                  70                  75                  80

Asn Xaa Ser Ile Val Xaa Glu Thr Ala Asp Thr Ile Leu His Ser Pro
                 85                  90                  95

Gly Cys Val Pro Cys Val Arg Xaa Gly Asn Ala Ser Lys Cys Trp Val
                100                 105                 110

Pro Val Ala Pro Thr Val Ala Thr Arg Asp Gly Asn Leu Pro Ala Thr
                115                 120                 125

Gln Leu Xaa Arg His Ile Xaa Leu Leu Val Gly Ser Ala Thr Xaa Cys
            130                 135                 140

Ser Ala Leu Tyr Val Gly Asp Leu Cys Gly Ser Val Xaa Leu Val Gly
145                 150                 155                 160

Gln Leu Phe Thr Phe Xaa Pro Arg Arg His Trp Thr Thr Gln Asp Cys
                165                 170                 175

Asn Cys Ser Ile Tyr Pro Gly His Ile Thr Gly His Arg Met Ala Trp
                180                 185                 190

Asp Met Met Met Asn Trp Ser Pro Thr Xaa Ala Leu Val Met Ala Gln
            195                 200                 205

Leu Leu Arg Ile Pro Gln Ala Ile Leu Asp Met Ile Ala Gly Ala His
            210                 215                 220

Trp Gly Val Leu Ala Gly Ile Ala Tyr Phe Ser Met Val Gly Asn Trp
225                 230                 235                 240

Ala Lys Val Leu Val Val Leu Leu Phe Ala Gly Val Asp Ala Thr
                245                 250                 255

Thr Tyr Thr Thr Gly Gly Asn Ala Ala Arg Thr Thr Gln Ala Leu Thr
            260                 265                 270

Ser Phe Phe Ser Pro Gly Ala Lys Xaa Asp Ile Gln Leu Ile Asn Thr
            275                 280                 285

Xaa Gly Ser Trp His Ile Asn Arg Thr Ala Leu Asn Cys Asn Ala Ser
290                 295                 300

Xaa Asp Thr Gly Trp Xaa Ala Gly Leu Phe Tyr Tyr His Lys Phe Asn
305                 310                 315                 320

Ser Ser Gly Cys Pro Glu Arg Met Ala Ser Cys Arg Pro Leu Ala Xaa
                325                 330                 335

Phe Asp Gln (2) INFORMATION FOR SEQ ID NO:153:

(i) SEQUENCE CHARACTERISTICS:
        (A) LENGTH: 1019 base pairs
        (B) TYPE: nucleic acid
```

```
        (C) STRANDEDNESS: single
        (D) TOPOLOGY: linear (ii) MOLECULE TYPE: cDNA (vi) ORIGINAL SOURCE:
         (C) INDIVIDUAL ISOLATE: Human 27

(xi) SEQUENCE DESCRIPTION: SEQ ID NO:153:

CGGCTTCGCC GACCTCATGG GGTACATTCC GCTCGTCGGC GCTCCTCTTG GGGGCGCTGC      60

CAGGGCCCTG GCGCATGGCG TCCGGGTTCT GGAAGACGGC GTGAACTATG CAACAGGGAA     120

CCTTCCTGGT TGCTCTTTCT CTATCTTCCT TCTGGCTCTG CTCTCTTGCC TGACCGTGCC     180

CGCATCGGCC TACCAAGTAC GCAACTCCTC GGGCATTTAC CATGTCACCA ATGATTGCCC     240

TAATTCGAGT ATTGTGTACG AGACGGCCGA CACCATCCTA CACTCTCCGG GGTGTGTCCC     300

TTGCGTTCGC GAGGGTAACG CCTCGAAATG TTGGGTGCCG GTAGCCCCCA CAGTGGCCAC     360

CAGGGACGGC AACCTCCCCG CAACGCAGCT TCGACGTCAC ATCGATCTGC TTGTCGGGAG     420

TGCCACCCTT TGCTCGGCCC TCTATGTGGG GGACTTGTGC GGGTCTGTCT TTCTTGTCGG     480

TCAACTGTTC ACTTTCTCCC CCAGGCGCCA CTGGACAACG CAAGATTGCA ACTGCTCTAT     540

CTACCCCGGC CATATAACGG GACACCGCAT GGCATGGGAT ATGATGATGA ACTGGTCCCC     600

TACAGCAGCG CTGGTAATGG CTCAGCTGCT CAGGATCCCG CAAGCCATCT GGACATGAT     660

CGCTGGTGCT CACTGGGAG TCCTAGCGGG CATAGCGTAT TTCTCCATGG TGGGGAACTG      720

GGCGAAGGTC CTGGTGGTGC TGTTGCTGTT TGCCGGCGTC GATGCGACAA CCTATACCAC     780

CGGGGGGAAT GCTGCCAGGA CCACGCAGGC GCTCACCAGT TTTTTCAGCC CAGGCGCCAA     840

GCAGGATATC CAGCTGATCA ACACCAACGG CAGTTGGCAC ATCAATCGCA CGGCCTTGAA     900

CTGTAATGCG AGCCTCGACA CTGGCTGGGT AGCGGGGCTC TTCTATTACC ACAAATTCAA     960

CTCTTCAGGG TGCCCCGAGA GGATGGCCAG CTGTAGGCCC CTTGCCGATT TCGACCAGG    1019

(2) INFORMATION FOR SEQ ID NO:154:

(i) SEQUENCE CHARACTERISTICS:
        (A) LENGTH: 1019 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
         (C) INDIVIDUAL ISOLATE: HCV1

(xi) SEQUENCE DESCRIPTION: SEQ ID NO:154:

CGGCTTCGCC GACCTCATGG GGTACATACC GCTCGTCGGC GCCCCTCTTG GAGGCGCTGC      60

CAGGGCCCTG GCGCATGGCG TCCGGGTTCT GGAAGACGGC GTGAACTATG CAACAGGGAA     120

CCTTCCTGGT TGCTCTTTCT CTATCTTCCT TCTGGCCCTG CTCTCTTGCT TGACTGTGCC     180

CGCTTCGGCC TACCAAGTGC GCAACTCCAC GGGGCTTTAC CACGTCACCA ATGATTGCCC     240

TAACTCGAGT ATTGTGTACG AGGCGGCCGA TGCCATCCTG CACACTCCGG GGTGCGTCCC     300

TTGCGTTCGT GAGGGCAACG CCTCGAGGTG TTGGGTGGCG ATGACCCCTA CGGTGGCCAC     360

CAGGGATGGC AAACTCCCCG CGACGCAGCT TCGACGTCAC ATCGATCTGC TTGTCGGGAG     420

CGCCACCCTC TGTTCGGCCC TCTACGTGGG GGACCTGTGC GGGTCTGTCT TTCTTGTCGG     480

CCAACTGTTC ACCTTCTCTC CCAGGCGCCA CTGGACGACG CAAGGTTGCA ATTGCTCTAT     540

CTATCCCGGC CATATAACGG GTCACCGCAT GGCATGGGAT ATGATGATGA ACTGGTCCCC     600
```

-continued

```
TACGACGGCG TTGGTAATGG CTCAGCTGCT CCGGATCCCA CAAGCCATCT TGGACATGAT 660

CGCTGGTGCT CACTGGGGAG TCCTGGCGGG CATAGCGTAT TTCTCCATGG TGGGGAACTG 720

GGCGAAGGTC CTGGTAGTGC TGCTGCTATT TGCCGGCGTC GACGCGGAAA CCCACGTCAC 780

CGGGGGAAGT GCCGGCCACA CTGTGTCTGG ATTTGTTAGC CTCCTCGCAC CAGGCGCCAA 840

GCAGAACGTC CAGCTGATCA ACACCAACGG CAGTTGGCAC CTCAATAGCA CGGCCCTGAA 900

CTGCAATGAT AGCCTCAACA CCGGCTGGTT GGCAGGGCTT TTCTATCACC ACAAGTTCAA 960

CTCTTCAGGC TGTCCTGAGA GGCTAGCCAG CTGCCGACCC CTTACCGATT TTGACCAGG 1019
```

(2) INFORMATION FOR SEQ ID NO:155:

(i) SEQUENCE CHARACTERISTICS:
(A) LENGTH: 1019 base pairs
(B) TYPE: nucleic acid
(C) STRANDEDNESS: single
(D) TOPOLOGY: linear (ii) MOLECULE TYPE: cDNA (vi) ORIGINAL SOURCE:
(C) INDIVIDUAL ISOLATE: Human 23

(xi) SEQUENCE DESCRIPTION: SEQ ID NO:155:

```
CGGCTTCGCC GACCTCATGG GGTACATACC GCTCGTCGGC GCCCCTCTTG GAGGCCGTGC 60

CAGGGCCCTG GCGCACGGCG TCCGGGTTTT GGAAGACGGC GTGAACTATG CAACAGGGAA 120

CCTTCCTGGT TGCTCCTTTT CTATCTTCCT TCTGGCCCTA CTCTCTTGCC TGACCGTGCC 180

CGCTTCAGCC TACCAAGTGC GCAACTCTAC GGGGCTTTAC CATGTCACCA ATGATTGCCC 240

TAACTCGAGT ATTGTGTACG AGGCGGCCGA TGCCATCCTA CACGCTCCGG GGTGTGTCCC 300

TTGCGTTCGC GAGGATAACG TCTCGAGATG TTGGGTGGCG GTGACCCCCA CGGTGGCCAC 360

CAAGGACGGC AAACTCCCCA CAACGCAGCT TCGACGTCAC ATCGATCTGC TTGTCGGGAG 420

CGCCACCCTC TGCTCGGCCC TCTACGTGGG GGACCTTTGC GGGTCCATCT TTCTTGTCGG 480

TCAACTGTTT ACCTTCTCTC CCAGGCGCCA CTGGACGACG CAGGACTGCA ACTGTTCTAT 540

CTATCCCGGC CATATAACGG GTCACCGCAT GGCATGGGAT ATGATGATGA ACTGGTCCCC 600

TACGGCGGCA TTGGTAGTAG CTCAGCTGCT CCGGATCCCA CAAGCCATCT TGGACATGAT 660

CGCTGGTGCT CACTGGGGAG TCCTGGCGGG CATGGCGTAT TTCTCCATGG TGGGGAACTG 720

GGCGAAGGTC CTGGTAGTGC TGCTTCTATT TGCCGGCGTC GACGCGGAAA CCCACCGTAC 780

CGGGGGAAGT GCCGCCCGCA GCACGGCTGG AGTTGCTAGT CTCTTCACAC CAGGCGCTAG 840

GCAGAACATC CAGCTGATCA ACACCAACGG CAGTTGGCAC ATCAATAGTA CGGCCTTGAA 900

CTGCAATGAC AGCCTTACCA CCGGCTGGTT AGCGGGGCTT TTCTATCACC ATAAATTCAA 960
```

```
CTCTTCAGGC TGTCCCGAGA GGTTGGCCAG CTGCCGACCC CTCACCGATT TTGCCCAGG 1019
```

(2) INFORMATION FOR SEQ ID NO:156:

(i) SEQUENCE CHARACTERISTICS:
(A) LENGTH: 339 amino acids
(B) TYPE: amino acid
(C) STRANDEDNESS: single
(D) TOPOLOGY: linear (ii) MOLECULE TYPE: peptide (vi) ORIGINAL SOURCE:
(C) INDIVIDUAL ISOLATE: Human 27

(xi) SEQUENCE DESCRIPTION: SEQ ID NO:156:

| | | | | | | | | | | | | | | |
|---|---|---|---|---|---|---|---|---|---|---|---|---|---|---|
|Gly|Phe|Ala|Asp|Leu|Met|Gly|Tyr|Ile|Pro|Leu|Val|Gly|Ala|Pro|Leu|
|1| | | |5| | | |10| | | |15| | |

Gly Gly Ala Ala Arg Ala Leu Ala His Gly Val Arg Val Leu Glu Asp
          20                  25                  30

Gly Val Asn Tyr Ala Thr Gly Asn Leu Pro Gly Cys Ser Phe Ser Ile
      35                  40                  45

Phe Leu Leu Ala Leu Leu Ser Cys Leu Thr Val Pro Ala Ser Ala Tyr
 50                  55                  60

Gln Val Arg Asn Ser Ser Gly Ile Tyr His Val Thr Asn Asp Cys Pro
 65                  70                  75                  80

Asn Ser Ser Ile Val Tyr Glu Thr Ala Asp Thr Ile Leu His Ser Pro
              85                  90                  95

Gly Cys Val Pro Cys Val Arg Glu Gly Asn Ala Ser Lys Cys Trp Val
             100                 105                 110

Pro Val Ala Pro Thr Val Ala Thr Arg Asp Gly Asn Leu Pro Ala Thr
             115                 120                 125

Gln Leu Arg Arg His Ile Asp Leu Leu Val Gly Ser Ala Thr Leu Cys
 130                 135                 140

Ser Ala Leu Tyr Val Gly Asp Leu Cys Gly Ser Val Phe Leu Val Gly
145                 150                 155                 160

Gln Leu Phe Thr Phe Ser Pro Arg Arg His Trp Thr Thr Gln Asp Cys
                 165                 170                 175

Asn Cys Ser Ile Tyr Pro Gly His Ile Thr Gly His Arg Met Ala Trp
             180                 185                 190

Asp Met Met Asn Trp Ser Pro Thr Ala Ala Leu Val Met Ala Gln
             195                 200                 205

Leu Leu Arg Ile Pro Gln Ala Ile Leu Asp Met Ile Ala Gly Ala His
 210                 215                 220

Trp Gly Val Leu Ala Gly Ile Ala Tyr Phe Ser Met Val Gly Asn Trp
225                 230                 235                 240

Ala Lys Val Leu Val Val Leu Leu Leu Phe Ala Gly Val Asp Ala Thr
             245                 250                 255

Thr Tyr Thr Thr Gly Gly Asn Ala Ala Arg Thr Thr Gln Ala Leu Thr
             260                 265                 270

Ser Phe Phe Ser Pro Gly Ala Lys Gln Asp Ile Gln Leu Ile Asn Thr
 275                 280                 285

Asn Gly Ser Trp His Ile Asn Arg Thr Ala Leu Asn Cys Asn Ala Ser
 290                 295                 300

Leu Asp Thr Gly Trp Val Ala Gly Leu Phe Tyr Tyr His Lys Phe Asn
305                 310                 315                 320

Ser Ser Gly Cys Pro Glu Arg Met Ala Ser Cys Arg Pro Leu Ala Asp
             325                 330                 335

Phe Asp Gln (2) INFORMATION FOR SEQ ID NO:157:

(i) SEQUENCE CHARACTERISTICS:
        (A) LENGTH: 339 amino acids
        (B) TYPE: amino acid
        (C) STRANDEDNESS: single
        (D) TOPOLOGY: linear (ii) MOLECULE TYPE: peptide (vi) ORIGINAL SOURCE:

(C) INDIVIDUAL ISOLATE: HCV1

(xi) SEQUENCE DESCRIPTION: SEQ ID NO:157:

```
Gly Phe Ala Asp Leu Met Gly Tyr Ile Pro Leu Val Gly Ala Pro Leu
1               5                   10                  15

Gly Gly Ala Ala Arg Ala Leu Ala His Gly Val Arg Val Leu Glu Asp
            20                  25                  30

Gly Val Asn Tyr Ala Thr Gly Asn Leu Pro Gly Cys Ser Phe Ser Ile
                35                  40                  45

Phe Leu Leu Ala Leu Leu Ser Cys Leu Thr Val Pro Ala Ser Ala Tyr
    50                  55                  60

Gln Val Arg Asn Ser Thr Gly Leu Tyr His Val Thr Asn Asp Cys Pro
65                  70                  75                  80

Asn Ser Ser Ile Val Tyr Glu Ala Ala Asp Ala Ile Leu His Thr Pro
                85                  90                  95

Gly Cys Val Pro Cys Val Arg Glu Gly Asn Ala Ser Arg Cys Trp Val
                100                 105                 110

Ala Met Thr Pro Thr Val Ala Thr Arg Asp Gly Lys Leu Pro Ala Thr
            115                 120                 125

Gln Leu Arg Arg His Ile Asp Leu Leu Val Gly Ser Ala Thr Leu Cys
130                 135                 140

Ser Ala Leu Tyr Val Gly Asp Leu Cys Gly Ser Val Phe Leu Val Gly
145                 150                 155                 160

Gln Leu Phe Thr Phe Ser Pro Arg Arg His Trp Thr Thr Gln Gly Cys
                165                 170                 175

Asn Cys Ser Ile Tyr Pro Gly His Ile Thr Gly His Arg Met Ala Trp
                180                 185                 190

Asp Met Met Met Asn Trp Ser Pro Thr Thr Ala Leu Val Met Ala Gln
            195                 200                 205

Leu Leu Arg Ile Pro Gln Ala Ile Leu Asp Met Ile Ala Gly Ala His
            210                 215                 220

Trp Gly Val Leu Ala Gly Ile Ala Tyr Phe Ser Met Val Gly Asn Trp
225                 230                 235                 240

Ala Lys Val Leu Val Val Leu Leu Phe Ala Gly Val Asp Ala Glu
            245                 250                 255

Thr His Val Thr Gly Gly Ser Ala Gly His Thr Val Ser Gly Phe Val
            260                 265                 270

Ser Leu Leu Ala Pro Gly Ala Lys Gln Asn Val Gln Leu Ile Asn Thr
        275                 280                 285

Asn Gly Ser Trp His Leu Asn Ser Thr Ala Leu Asn Cys Asn Asp Ser
290                 295                 300

Leu Asn Thr Gly Trp Leu Ala Gly Leu Phe Tyr His His Lys Phe Asn
305                 310                 315                 320

Ser Ser Gly Cys Pro Glu Arg Leu Ala Ser Cys Arg Pro Leu Thr Asp
                325                 330                 335

Phe Asp Gln
```

(2) INFORMATION FOR SEQ ID NO:158:

(i) SEQUENCE CHARACTERISTICS:
        (A) LENGTH: 339 amino acids
        (B) TYPE: amino acid
        (C) STRANDEDNESS: single
        (D) TOPOLOGY: linear (ii) MOLECULE TYPE: peptide (vi) ORIGINAL SOURCE:
    (C) INDIVIDUAL ISOLATE: Human 23

(xi) SEQUENCE DESCRIPTION: SEQ ID NO:158:

| | | | | | | | | | | | | | | |
|---|---|---|---|---|---|---|---|---|---|---|---|---|---|---|
|Gly|Phe|Ala|Asp|Leu|Met|Gly|Tyr|Ile|Pro|Leu|Val|Gly|Ala|Pro|Leu
1| | | |5| | | | |10| | | | |15| |

Gly Gly Arg Ala Arg Ala Leu Ala His Gly Val Arg Val Leu Glu Asp
            20                  25                  30

Gly Val Asn Tyr Ala Thr Gly Asn Leu Pro Gly Cys Ser Phe Ser Ile
            35                  40                  45

Phe Leu Leu Ala Leu Leu Ser Cys Leu Thr Val Pro Ala Ser Ala Tyr
 50                  55                  60

Gln Val Arg Asn Ser Thr Gly Leu Tyr His Val Thr Asn Asp Cys Pro
 65                  70                  75                  80

Asn Ser Ser Ile Val Tyr Glu Ala Ala Asp Ala Ile Leu His Ala Pro
                85                  90                  95

Gly Cys Val Pro Cys Val Arg Glu Asp Asn Val Ser Arg Cys Trp Val
            100                 105                 110

Ala Val Thr Pro Thr Val Ala Thr Lys Asp Gly Lys Leu Pro Thr Thr
            115                 120                 125

Gln Leu Arg Arg His Ile Asp Leu Leu Val Gly Ser Ala Thr Leu Cys
 130                 135                 140

Ser Ala Leu Tyr Val Gly Asp Leu Cys Gly Ser Ile Phe Leu Val Gly
145                 150                 155                 160

Gln Leu Phe Thr Phe Ser Pro Arg Arg His Trp Thr Thr Gln Asp Cys
            165                 170                 175

Asn Cys Ser Ile Tyr Pro Gly His Ile Thr Gly His Arg Met Ala Trp
            180                 185                 190

Asp Met Met Met Asn Trp Ser Pro Thr Ala Ala Leu Val Val Ala Gln
            195                 200                 205

Leu Leu Arg Ile Pro Gln Ala Ile Leu Asp Met Ile Ala Gly Ala His
 210                 215                 220

Trp Gly Val Leu Ala Gly Met Ala Tyr Phe Ser Met Val Gly Asn Trp
225                 230                 235                 240

Ala Lys Val Leu Val Val Leu Leu Leu Phe Ala Gly Val Asp Ala Glu
            245                 250                 255

Thr His Arg Thr Gly Gly Ser Ala Ala Arg Ser Thr Ala Gly Val Ala
            260                 265                 270

Ser Leu Phe Thr Pro Gly Ala Arg Gln Asn Ile Gln Leu Ile Asn Thr
            275                 280                 285

Asn Gly Ser Trp His Ile Asn Ser Thr Ala Leu Asn Cys Asn Asp Ser
 290                 295                 300

Leu Thr Thr Gly Trp Leu Ala Gly Leu Phe Tyr His His Lys Phe Asn
305                 310                 315                 320

Ser Ser Gly Cys Pro Glu Arg Leu Ala Ser Cys Arg Pro Leu Thr Asp
            325                 330                 335

Phe Ala Gln (2) INFORMATION FOR SEQ ID NO:159:

(i) SEQUENCE CHARACTERISTICS:
        (A) LENGTH: 587 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
         (C) INDIVIDUAL ISOLATE: Thorn (xi) SEQUENCE DESCRIPTION: SEQ ID NO:159:

| | | | | | |
|---|---|---|---|---|---|
| GAATTCGCAA | TTTGGGTAAG | GTCATCGATA | CCCTTACGTG | CGGCTTCGCC | GACCTCATGG | 60 |
| GGTACATACC | GCTCGTCGGC | GCCCCTCTTG | GGGGCGCTGC | CAGGGCCCTG | GCGCATGGCG | 120 |
| TCCGGGTTCT | GGAAGACGGC | GTGAACTATG | CAACAGGGAA | CCTTCCTGGT | TGCTCTTTCT | 180 |
| CTCTCTTCCT | TCTGGCCCTG | CTCTCTTGTC | TGACCGTGCC | CGCTTCAGCC | TACCAAGTGC | 240 |
| GCAACTCCAC | GGGGCTTTAC | CATGTCACCA | ACGATTGCCC | CAACTCGAGT | ATTGTGTACG | 300 |
| AGGCGGCCGA | TGCTATCCTG | CACGCTCCGG | GGTGTGTCCC | TTGCGTTCGC | GAGGGTAACG | 360 |
| CCTCGAGGTG | TTGGGTGGCG | ATGACCCCCA | CGGTGGCCGC | CAGGGACGGC | AGACTCCCCA | 420 |
| CAACGCAGCT | GCGACGTCAC | ATCGATCTGC | TTGTCGGGAG | CGCCACCCTC | TGCTCGGCCC | 480 |
| TCTACGTGGG | GGACCTGTGC | GGGTCCATCT | TTCTTGTCGG | TCAACTGTTC | ACCTTCTCTC | 540 |
| CCAGGCGCCA | CTGGACGACG | CAAGGTTGCA | ATTGCTCTAT | CGAATTC | | 587 |

(2) INFORMATION FOR SEQ ID NO:160:

(i) SEQUENCE CHARACTERISTICS:
        (A) LENGTH: 587 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
         (C) INDIVIDUAL ISOLATE: EC1

(xi) SEQUENCE DESCRIPTION: SEQ ID NO:160:

| | | | | | |
|---|---|---|---|---|---|
| GAATTCGCAA | TTTGGGTAAG | GTCATCGATA | CCCTTACGTG | CGGCTTCGCC | GACCTCATGG | 60 |
| GGTACATACC | GCTCGTCGGC | GCCCCTCTTG | GAGGCGCTGC | CAGGGCCCTG | GCGCATGGCG | 120 |
| TCCGGGTTCT | GGAAGACGGC | GTGAACTATG | CAACAGGGAA | CCTTCCTGGT | TGCTCTTTCT | 180 |
| TTATCTTCCT | TCTGGCCTTG | CTCTCTTGCT | TGACTGTGCC | CGCTTCAGCC | TACCAAGTGC | 240 |
| GCAACTCCTC | GGGGCTTTAC | CATGTCACCA | ATGATTGCCC | TAACTCGAGC | ATTGTGTACG | 300 |
| AGGCGGCCGA | TGCCATCCTG | CACACTCCGG | GGTGTGTCCC | TTGCGTTCAC | GAGGGCAACG | 360 |
| TCTCGAGGTG | TTGGGTGGCG | ATGACCCCCA | CGGTGGCCAC | CAGGGGCGGC | AAACTCCCCA | 420 |
| CAACGCAGCT | TCGACGTCAC | ATCGATCTGC | TTGTCGGGAG | CGCTACCCTC | TGCTCGGCCC | 480 |
| TCTACGTGGG | GGACCTGTGC | GGGTCTGTCT | TCCTTGTCGG | TCAACTGTTT | ACCTTCTCTC | 540 |
| CCAGGCGCCA | CTGGACGACG | CAAGGTTGCA | ATTGCTCTAT | CGAATTC | | 587 |

(2) INFORMATION FOR SEQ ID NO:161:

(i) SEQUENCE CHARACTERISTICS:
        (A) LENGTH: 585 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
         (C) INDIVIDUAL ISOLATE: HCT18

(xi) SEQUENCE DESCRIPTION: SEQ ID NO:161:

```
GAATTCGCAA TTTGGGTAAG GTCATCGATA CCCTTACGTG CGGCTTCGCC GACCTCATGG      60

GGTATATACC GCTCGTCGGC GCCCCTCTTG GAGGCGCTGC CAGGGCCCTG GCGCATGGCG     120

TCCGGGTTCT GGAAGACGGC GTGAACTATG CCAGGGAACC TTCCTGGTTG CTCTTTCTCT     180

ATCTTCCTTC TGGCCCTGCT CTCTTGCCTG ACTGTGCCCG CTTCAGCCCA CCAAGTGCGC     240

AACTCCACGG GGCTTTACCA TGTCACCAAT GATTGCCCCA ACTCGAGTAT TGTATACGAA     300

GCGGCCGACG CCATCCTGCA CACTCCGGGG TGTGTCCCTT GCGTTCACGA GGGCAACGTC     360

TCGAGGTGTT GGGTGGCGGT GACCCCCACG GTGGCCACCA GGGATGGCAA ACTCCCCACA     420

ACGCAGCTTC GACGTCACAT CGATCTGCTT GTCGGGAGCG CCACCCTCTG CTCGGCCCTC     480

TATGTGGGGG ACTTGTGCGG GTCTGTCTTT CTTGTCGGCC AACTGTTTAC CTTCTCTCCC     540

AGGCGCCACT GGACGACGCA AGGTTGCAAT TGCTCTATCG AATTC                     585
```

(2) INFORMATION FOR SEQ ID NO:162:

(i) SEQUENCE CHARACTERISTICS:
        (A) LENGTH: 657 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (C) INDIVIDUAL ISOLATE: HCV1

(xi) SEQUENCE DESCRIPTION: SEQ ID NO:162:

```
GGGTGGGCGG GATGGCTCCT GTCTCCCCGT GGCTCTCGGC CTAGCTGGGG CCCCACAGAC      60

CCCCGGCGTA GGTCGCGCAA TTTGGGTAAG GTCATCGATA CCCTTACGTG CGGCTTCGCC     120

GACCTCATGG GGTACATACC GCTCGTCGGC GCCCCTCTTG GAGGCGCTGC CAGGGCCCTG     180

GCGCATGGCG TCCGGGTTCT GGAAGACGGC GTGAACTATG CAACAGGGAA CCTTCCTGGT     240

TGCTCTTTCT CTATCTTCCT TCTGGCCCTG CTCTCTTGCT TGACTGTGCC CGCTTCGGCC     300

TACCAAGTGC GCAACTCCAC GGGGCTTTAC CACGTCACCA ATGATTGCCC TAACTCGAGT     360

ATTGTGTACG AGGCGGCCGA TGCCATCCTG CACACTCCGG GGTGCGTCCC TTGCGTTCGT     420

GAGGGCAACG CCTCGAGGTG TTGGGTGGCG ATGACCCCTA CGGTGGCCAC CAGGGATGGC     480

AAACTCCCCG CGACGCAGCT TCGACGTCAC ATCGATCTGC TTGTCGGGAG CGCCACCCTC     540

TGTTCGGCCC TCTACGTGGG GGACCTATGC GGGTCTGTCT TTCTTGTCGG CCAACTGTTC     600

ACCTTCTCTC CCAGGCGCCA CTGGACGACG CAAGGTTGCA ATTGCTCTAT CTATCCC       657
```

(2) INFORMATION FOR SEQ ID NO:163:

(i) SEQUENCE CHARACTERISTICS:
        (A) LENGTH: 427 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (C) INDIVIDUAL ISOLATE: EC10

(vii) IMMEDIATE SOURCE:
        (B) CLONE: clone 2

(xi) SEQUENCE DESCRIPTION: SEQ ID NO:163:

```
GAATTCGGAC GACGCAAGGT TGCAATTGCT CTATCTATCC CGGCCATATA ACAGGTCACC      60
```

```
GCATGGCATG GGATATGATG ATGAACTGGT CCCCTACGAC GGCGTTAGTG GTAGCTCAGC      120

TGCTCCCGAT CCCACAAGCC ATCTTGGACA TGATCGCTGG TGCTCACTGG GGAGTCCTGG      180

CGGGCATAGC GTATTTCTCC ATGGTGGGGA ACTGGGCGAA GGTCTTGGCA GTGCTGCTGC      240

TATTTGCCGG CGTCGACGCG GAAACCCACG TCACTGGGGG GATCGCCGCC AAAACTACGG      300

CTAGCCTTAC TGGTCTCTTC AATTTAGGTG CCAAGCAGAA CATCCAGCTG ATCAACACCA      360

ACGGCAGTTG GCACATCAAC AGGACGGCCT TGAACTGCAA TGATAGCCTC AACACCGGCT      420

GGAATTC                                                                427

(2) INFORMATION FOR SEQ ID NO:164:

(i) SEQUENCE CHARACTERISTICS:
        (A) LENGTH: 480 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
         (C) INDIVIDUAL ISOLATE: HCV1

(xi) SEQUENCE DESCRIPTION: SEQ ID NO:164:

CTCTCCCAGG CGCCACTGGA CGACGCAAGG TTGCAATTGC TCTATCTATC CCGGCCATAT       60

AACGGGTCAC CGCATGGCAT GGGATATGAT GATGAACTGG TCCCCTACGA CGGCGTTGGT      120

AATGGCTCAG CTGCTCCGGA TCCCACAAGC CATCTTGGAC ATGATCGCTG GTGCTCACTG      180

GGGAGTCCTG GCGGGCATAG CGTATTTCTC CATGGTGGGG AACTGGGCGA AGGTCCTGGT      240

AGTGCTGCTG CTATTTGCCG GCGTCGACGC GGAAACCCAC GTCACCGGGG GAAGTGCCGG      300

CCACACTGTG TCTGGATTTG TTAGCCTCCT CGCACCAGGC GCCAAGCAGA ACGTCCAGCT      360

GATCAACACC AACGGCAGTT GGCACCTCAA TAGCACGGCC CTGAACTGCA ATGATAGCCT      420

CAACACCGGC TGGTTGGCAG GGCTTTTCTA TCACCACAAG TTCAACTCTT CAGGCTGTCC      480

(2) INFORMATION FOR SEQ ID NO:165:

(i) SEQUENCE CHARACTERISTICS:
        (A) LENGTH: 192 amino acids
        (B) TYPE: amino acid
        (C) STRANDEDNESS: single
        (D) TOPOLOGY: linear (ii) MOLECULE TYPE: peptide (vi) ORIGINAL SOURCE:
         (C) INDIVIDUAL ISOLATE: HCT18

(ix) FEATURE:
         (A) NAME/KEY: Duplication
         (B) LOCATION: 115
         (D) OTHER INFORMATION: /note= "There exists a
             heterogeneity at this position - Xaa = Tyr or His"

(xi) SEQUENCE DESCRIPTION: SEQ ID NO:165:

Arg Asn Leu Gly Lys Val Ile Asp Thr Leu Thr Cys Gly Phe Ala Asp
1               5                   10                  15

Leu Met Gly Tyr Ile Pro Pro Val Gly Ala Pro Leu Gly Ser Ala Ala
            20                  25                  30

Arg Ala Leu Ala His Gly Val Arg Val Leu Glu Asp Gly Val Asn Tyr
        35                  40                  45

Ala Thr Gly Asn Leu Pro Gly Cys Ser Phe Ser Ile Phe Leu Leu Ala
```

```
            50                  55                  60
Leu Leu Ser Cys Leu Thr Val Pro Ala Ser Ala His Gln Val Arg Asn
 65                  70                  75                  80

Ser Thr Gly Leu Tyr His Val Thr Asn Asp Cys Pro Asn Ser Ser Ile
                 85                  90                  95

Val Tyr Glu Ala Ala Asp Ala Ile Leu His Thr Pro Gly Cys Val Pro
            100                 105                 110

Cys Val Xaa Glu Gly Asn Val Ser Arg Cys Trp Val Ala Val Thr Pro
            115                 120                 125

Thr Val Ala Thr Arg Asp Gly Lys Leu Pro Thr Thr Gln Leu Arg Arg
130                 135                 140

His Ile Asp Leu Leu Val Gly Ser Ala Thr Leu Cys Ser Ala Leu Tyr
145                 150                 155                 160

Val Gly Asp Leu Cys Gly Ser Val Phe Leu Val Gly Gln Leu Phe Thr
                165                 170                 175

Phe Ser Pro Arg Arg His Trp Thr Thr Gln Gly Cys Asn Cys Ser Ile
                180                 185                 190

(2) INFORMATION FOR SEQ ID NO:166:

(i) SEQUENCE CHARACTERISTICS:
        (A) LENGTH: 192 amino acids
        (B) TYPE: amino acid
        (C) STRANDEDNESS: single
        (D) TOPOLOGY: linear (ii) MOLECULE TYPE: peptide (vi) ORIGINAL SOURCE:
        (C) INDIVIDUAL ISOLATE: JH23

(xi) SEQUENCE DESCRIPTION: SEQ ID NO:166:

Arg Asn Leu Gly Lys Val Ile Asp Thr Leu Thr Cys Gly Phe Ala Asp
  1               5                  10                  15

Leu Met Gly Tyr Ile Pro Leu Val Gly Ala Pro Leu Gly Ser Ala Ala
             20                  25                  30

Arg Ala Leu Ala His Gly Val Arg Val Leu Glu Asp Gly Val Asn Tyr
         35                  40                  45

Ala Thr Gly Asn Leu Pro Gly Cys Ser Phe Ser Ile Phe Leu Leu Ala
 50                  55                  60

Leu Leu Ser Cys Leu Thr Val Pro Ala Ser Ala Tyr Gln Val Arg Asn
 65                  70                  75                  80

Ser Thr Gly Leu Tyr His Val Thr Asn Asp Cys Pro Asn Ser Ser Ile
                 85                  90                  95

Val Tyr Glu Ala Ala Asp Ala Ile Leu His Ala Pro Gly Cys Val Pro
            100                 105                 110

Cys Val Arg Glu Asp Asn Val Ser Arg Cys Trp Val Ala Val Thr Pro
            115                 120                 125

Thr Val Ala Thr Lys Asp Gly Lys Leu Pro Thr Thr Gln Leu Arg Arg
130                 135                 140

His Ile Asp Leu Leu Val Gly Ser Ala Thr Leu Cys Ser Ala Leu Tyr
145                 150                 155                 160

Val Gly Asp Leu Cys Gly Ser Ile Phe Leu Val Gly Gln Leu Phe Thr
                165                 170                 175

Phe Ser Pro Arg Arg His Trp Thr Thr Gln Asp Cys Asn Cys Ser Ile
                180                 185                 190
```

-continued (2) INFORMATION FOR SEQ ID NO:167:

(i) SEQUENCE CHARACTERISTICS:
       (A) LENGTH: 192 amino acids
       (B) TYPE: amino acid
       (C) STRANDEDNESS: single
       (D) TOPOLOGY: linear (ii) MOLECULE TYPE: peptide (vi) ORIGINAL SOURCE:
       (C) INDIVIDUAL ISOLATE: JH27

(xi) SEQUENCE DESCRIPTION: SEQ ID NO:167:

```
Arg Asn Leu Gly Lys Val Ile Asp Thr Leu Thr Cys Gly Phe Ala Asp
1               5                   10                  15

Leu Met Gly Tyr Ile Pro Leu Val Gly Ala Pro Leu Gly Ser Ala Ala
            20                  25                  30

Arg Ala Leu Ala His Gly Val Arg Val Leu Glu Asp Gly Val Asn Tyr
        35                  40                  45

Ala Thr Gly Asn Leu Pro Gly Cys Ser Phe Ser Ile Phe Leu Leu Ala
    50                  55                  60

Leu Leu Ser Cys Leu Thr Val Pro Ala Ser Ala Tyr Gln Val Arg Asn
65                  70                  75                  80

Ser Ser Gly Leu Tyr His Val Thr Asn Asp Cys Pro Asn Ser Ser Ile
                85                  90                  95

Val Tyr Glu Thr Ala Asp Thr Ile Leu His Ser Pro Gly Cys Val Pro
            100                 105                 110

Cys Val Arg Glu Gly Asn Ala Ser Arg Cys Trp Val Pro Val Ala Pro
        115                 120                 125

Thr Val Ala Thr Arg Asp Gly Asn Leu Pro Ala Thr Gln Leu Arg Arg
    130                 135                 140

His Ile Asp Leu Leu Val Gly Ser Ala Thr Leu Cys Ser Ala Leu Tyr
145                 150                 155                 160

Val Gly Asp Leu Cys Gly Ser Val Phe Leu Val Gly Gln Leu Phe Thr
                165                 170                 175

Phe Ser Pro Arg Arg His Trp Thr Thr Gln Asp Cys Asn Cys Ser Ile
            180                 185                 190
```

(2) INFORMATION FOR SEQ ID NO:168:

(i) SEQUENCE CHARACTERISTICS:
       (A) LENGTH: 192 amino acids
       (B) TYPE: amino acid
       (C) STRANDEDNESS: single
       (D) TOPOLOGY: linear (ii) MOLECULE TYPE: peptide (vi) ORIGINAL SOURCE:
       (C) INDIVIDUAL ISOLATE: PBL-Th (xi) SEQUENCE DESCRIPTION: SEQ ID NO:168:

```
Arg Asn Leu Gly Lys Val Ile Asp Thr Leu Thr Cys Gly Phe Ala Asp
1               5                   10                  15

Leu Met Gly Tyr Ile Pro Leu Val Gly Ala Pro Leu Gly Ser Ala Ala
            20                  25                  30

Arg Ala Leu Ala His Gly Val Arg Val Leu Glu Asp Gly Val Asn Tyr
        35                  40                  45

Ala Thr Gly Asn Leu Pro Gly Cys Ser Phe Ser Leu Phe Leu Leu Ala
    50                  55                  60
```

Leu Leu Ser Cys Leu Thr Val Pro Ala Ser Ala Tyr Gln Val Arg Asn
65                  70                  75                  80

Ser Thr Gly Leu Tyr His Val Thr Asn Asp Cys Pro Asn Ser Ser Ile
                85                  90                  95

Val Tyr Glu Ala Ala Asp Ala Ile Leu His Ala Pro Gly Cys Val Pro
            100                 105                 110

Cys Val Arg Glu Gly Asn Ala Ser Arg Cys Trp Val Ala Met Thr Pro
            115                 120                 125

Thr Val Ala Ala Arg Asp Gly Arg Leu Pro Thr Thr Gln Leu Arg Arg
        130                 135                 140

His Ile Asp Leu Leu Val Gly Ser Ala Thr Leu Cys Ser Ala Leu Tyr
145                 150                 155                 160

Val Gly Asp Leu Cys Gly Ser Val Phe Leu Val Gly Gln Leu Phe Thr
                165                 170                 175

Phe Ser Pro Arg Arg His Trp Thr Thr Gln Gly Cys Asn Cys Ser Ile
            180                 185                 190

(2) INFORMATION FOR SEQ ID NO:169:

(i) SEQUENCE CHARACTERISTICS:
        (A) LENGTH: 192 amino acids
        (B) TYPE: amino acid
        (C) STRANDEDNESS: single
        (D) TOPOLOGY: linear (ii) MOLECULE TYPE: peptide (vi) ORIGINAL SOURCE:
        (C) INDIVIDUAL ISOLATE: EC1

(ix) FEATURE:
        (A) NAME/KEY: Duplication
        (B) LOCATION: 59
        (D) OTHER INFORMATION: /note= "There exists a
            heterogeneity at this position which can also be Phe."

(xi) SEQUENCE DESCRIPTION: SEQ ID NO:169:

Arg Asn Leu Gly Lys Val Ile Asp Thr Leu Thr Cys Gly Phe Ala Asp
1               5                   10                  15

Leu Met Gly Tyr Ile Pro Leu Val Gly Ala Pro Leu Gly Ser Ala Ala
            20                  25                  30

Arg Ala Leu Ala His Gly Val Arg Val Leu Glu Asp Gly Val Asn Tyr
        35                  40                  45

Ala Thr Gly Asn Leu Pro Gly Cys Ser Phe Ser Ile Phe Leu Leu Ala
    50                  55                  60

Leu Leu Ser Cys Leu Thr Val Pro Ala Ser Ala Tyr Gln Val Arg Asn
65                  70                  75                  80

Ser Ser Gly Leu Tyr His Val Thr Asn Asp Cys Pro Asn Ser Ser Ile
                85                  90                  95

Val Tyr Glu Ala Ala Asp Ala Ile Leu His Thr Pro Gly Cys Val Pro
            100                 105                 110

Cys Val His Glu Gly Asn Val Ser Arg Cys Trp Val Ala Met Thr Pro
            115                 120                 125

Thr Val Ala Thr Arg Asp Gly Lys Leu Pro Thr Thr Gln Leu Arg Arg
        130                 135                 140

His Ile Asp Leu Leu Val Gly Ser Ala Thr Leu Cys Ser Ala Leu Tyr
145                 150                 155                 160

Val Gly Asp Leu Cys Gly Ser Ile Phe Leu Val Gly Gln Leu Phe Thr
                165                 170                 175

```
Phe Ser Pro Arg Arg His Trp Thr Thr Gln Gly Cys Asn Cys Ser Ile
            180                 185                 190
```

(2) INFORMATION FOR SEQ ID NO:170:

(i) SEQUENCE CHARACTERISTICS:
        (A) LENGTH: 192 amino acids
        (B) TYPE: amino acid
        (C) STRANDEDNESS: single
        (D) TOPOLOGY: linear (ii) MOLECULE TYPE: peptide (vi) ORIGINAL SOURCE:
        (C) INDIVIDUAL ISOLATE: HCV1 (chimpanzee)

(xi) SEQUENCE DESCRIPTION: SEQ ID NO:170:

```
Arg Asn Leu Gly Lys Val Ile Asp Thr Leu Thr Cys Gly Phe Ala Asp
1               5                   10                  15

Leu Met Gly Tyr Ile Pro Leu Val Gly Ala Pro Leu Gly Ser Ala Ala
            20                  25                  30

Arg Ala Leu Ala His Gly Val Arg Val Leu Glu Asp Gly Val Asn Tyr
        35                  40                  45

Ala Thr Gly Asn Leu Pro Gly Cys Ser Phe Ser Ile Phe Leu Leu Ala
    50                  55                  60

Leu Leu Ser Cys Leu Thr Val Pro Ala Ser Ala Tyr Gln Val Arg Asn
65                  70                  75                  80

Ser Thr Gly Leu Tyr His Val Thr Asn Asp Cys Pro Asn Ser Ser Ile
                85                  90                  95

Val Tyr Glu Ala Ala Asp Ala Ile Leu His Thr Pro Gly Cys Val Pro
            100                 105                 110

Cys Val Arg Glu Gly Asn Ala Ser Arg Cys Trp Val Ala Met Thr Pro
        115                 120                 125

Thr Val Ala Thr Arg Asp Gly Lys Leu Pro Ala Thr Gln Leu Arg Arg
    130                 135                 140

His Ile Asp Leu Leu Val Gly Ser Ala Thr Leu Cys Ser Ala Leu Tyr
145                 150                 155                 160

Val Gly Asp Leu Cys Gly Ser Val Phe Leu Val Gly Gln Leu Phe Thr
                165                 170                 175

Phe Ser Pro Arg Arg His Trp Thr Thr Gln Gly Cys Asn Cys Ser Ile
            180                 185                 190
```

(2) INFORMATION FOR SEQ ID NO:171:

(i) SEQUENCE CHARACTERISTICS:
        (A) LENGTH: 139 amino acids
        (B) TYPE: amino acid
        (C) STRANDEDNESS: single
        (D) TOPOLOGY: linear (ii) MOLECULE TYPE: peptide (vi) ORIGINAL SOURCE:
        (C) INDIVIDUAL ISOLATE: JH23

(xi) SEQUENCE DESCRIPTION: SEQ ID NO:171:

```
Thr Thr Gln Asp Cys Asn Cys Ser Ile Tyr Pro Gly His Ile Thr Gly
1               5                   10                  15

His Arg Met Ala Trp Asp Met Met Met Asn Trp Ser Pro Thr Ala Ala
            20                  25                  30

Leu Val Val Ala Gln Leu Leu Arg Ile Pro Gln Ala Ile Leu Asp Met
        35                  40                  45
```

```
Ile Ala Gly Ala His Trp Gly Val Leu Ala Gly Met Ala Tyr Phe Ser
    50                  55                  60
Met Val Gly Asn Trp Ala Lys Val Leu Val Val Leu Leu Leu Phe Ala
65                  70                  75                  80
Gly Val Asp Ala Glu Thr His Arg Thr Gly Ser Ala Ala Arg Ser
                85                  90                  95
Thr Ala Gly Val Ala Ser Leu Phe Ser Pro Gly Ala Arg Gln Asn Ile
                100                 105                 110
Gln Leu Ile Asn Thr Asn Gly Ser Trp His Ile Asn Ser Thr Ala Leu
                115                 120                 125
Asn Cys Asn Asp Ser Leu Thr Thr Gly Trp Val
    130                 135
```

(2) INFORMATION FOR SEQ ID NO:172:

(i) SEQUENCE CHARACTERISTICS:
        (A) LENGTH: 139 amino acids
        (B) TYPE: amino acid
        (C) STRANDEDNESS: single
        (D) TOPOLOGY: linear (ii) MOLECULE TYPE: peptide (vi) ORIGINAL SOURCE:
        (C) INDIVIDUAL ISOLATE: JH27

(xi) SEQUENCE DESCRIPTION: SEQ ID NO:172:

```
Thr Thr Gln Asp Cys Asn Cys Ser Ile Tyr Pro Gly His Ile Thr Gly
1               5                   10                  15
His Arg Met Ala Trp Asp Met Met Met Asn Trp Ser Pro Thr Ala Ala
                20                  25                  30
Leu Val Met Ala Gln Leu Leu Arg Ile Pro Gln Ala Ile Leu Asp Met
                35                  40                  45
Ile Ala Gly Ala His Trp Gly Val Leu Ala Gly Ile Ala Tyr Phe Ser
    50                  55                  60
Met Val Gly Asn Trp Ala Lys Val Leu Val Val Leu Leu Leu Phe Ala
65                  70                  75                  80
Gly Val Asp Ala Thr Thr Tyr Thr Thr Gly Gly Asn Ala Ala Arg Thr
                85                  90                  95
Thr Gln Ala Leu Thr Ser Phe Phe Thr Pro Gly Ala Lys Gln Asp Ile
                100                 105                 110
Gln Leu Ile Asn Thr Asn Gly Ser Trp His Ile Asn Arg Thr Ala Leu
                115                 120                 125
Asn Cys Asn Ala Ser Leu Asp Thr Gly Trp Leu
    130                 135
```

(2) INFORMATION FOR SEQ ID NO:173:

(i) SEQUENCE CHARACTERISTICS:
        (A) LENGTH: 139 amino acids
        (B) TYPE: amino acid
        (C) STRANDEDNESS: single
        (D) TOPOLOGY: linear (ii) MOLECULE TYPE: peptide (vi) ORIGINAL SOURCE:
        (C) INDIVIDUAL ISOLATE: Japanese isolate (T. Miyamura)

(xi) SEQUENCE DESCRIPTION: SEQ ID NO:173:

```
Thr Thr Gln Gly Cys Asn Cys Ser Ile Tyr Pro Gly His Ile Thr Gly
```

```
1               5                   10                  15
His Arg Met Ala Trp Asp Met Met Asn Trp Ser Pro Thr Thr Ala
                20                  25                  30
Leu Val Val Ser Gln Leu Leu Arg Ile Pro Gln Ala Val Met Asp Met
            35                  40                  45
Val Ala Gly Ala His Trp Gly Val Leu Ala Gly Leu Ala Tyr Tyr Ser
50                      55                  60
Met Val Gly Asn Trp Ala Lys Val Leu Ile Val Met Leu Leu Phe Ala
65                  70                  75                  80
Gly Val Asp Gly His Thr Arg Val Thr Gly Val Gln Gly His Val
                    85                  90                  95
Thr Ser Thr Leu Thr Ser Leu Phe Arg Pro Gly Ala Ser Gln Lys Ile
                100                 105                 110
Gln Leu Val Asn Thr Asn Gly Ser Trp His Ile Asn Arg Thr Ala Leu
            115                 120                 125
Asn Cys Asn Asp Ser Leu Gln Thr Gly Phe Leu
        130                 135
```

(2) INFORMATION FOR SEQ ID NO:174:

(i) SEQUENCE CHARACTERISTICS:
        (A) LENGTH: 139 amino acids
        (B) TYPE: amino acid
        (C) STRANDEDNESS: single
        (D) TOPOLOGY: linear (ii) MOLECULE TYPE: peptide (vi) ORIGINAL SOURCE:
        (C) INDIVIDUAL ISOLATE: EC10 (Italy)

(xi) SEQUENCE DESCRIPTION: SEQ ID NO:174:

```
Thr Thr Gln Gly Cys Asn Cys Ser Ile Tyr Pro Gly His Ile Thr Gly
1               5                   10                  15
His Arg Met Ala Trp Asp Met Met Asn Trp Ser Pro Thr Thr Ala
                20                  25                  30
Leu Val Met Ala Gln Leu Leu Arg Ile Pro Gln Ala Ile Leu Asp Met
            35                  40                  45
Ile Ala Gly Ala His Trp Gly Val Leu Ala Gly Ile Ala Tyr Phe Ser
    50                  55                  60
Met Val Gly Asn Trp Ala Lys Val Leu Ala Val Leu Leu Leu Phe Ala
65                  70                  75                  80
Gly Val Asp Ala Glu Thr His Val Thr Gly Gly Ile Ala Ala Lys Thr
                85                  90                  95
Thr Ala Ser Leu Thr Ala Leu Phe Asn Leu Gly Ala Lys Gln Asn Ile
                100                 105                 110
Gln Leu Ile Asn Thr Asn Gly Ser Trp His Ile Asn Arg Thr Ala Leu
            115                 120                 125
Asn Cys Asn Asp Ser Leu Asn Thr Gly Trp Asn
        130                 135
```

(2) INFORMATION FOR SEQ ID NO:175:

(i) SEQUENCE CHARACTERISTICS:
        (A) LENGTH: 139 amino acids
        (B) TYPE: amino acid
        (C) STRANDEDNESS: single
        (D) TOPOLOGY: linear (ii) MOLECULE TYPE: peptide (vi) ORIGINAL SOURCE:
      (C) INDIVIDUAL ISOLATE: HCV1 (chimpanzee)

(xi) SEQUENCE DESCRIPTION: SEQ ID NO:175:

Thr Thr Gln Gly Cys Asn Cys Ser Ile Tyr Pro Gly His Ile Thr Gly
1               5                   10                  15

His Arg Met Ala Trp Asp Met Met Met Asn Trp Ser Pro Thr Thr Ala
            20                  25                  30

Leu Val Met Ala Gln Leu Leu Arg Ile Pro Gln Ala Ile Leu Asp Met
            35                  40                  45

Ile Ala Gly Ala His Trp Gly Val Leu Ala Gly Ile Ala Tyr Phe Ser
        50                  55                  60

Met Val Gly Asn Trp Ala Lys Val Leu Val Leu Leu Leu Phe Ala
65                  70                  75                  80

Gly Val Asp Ala Glu Thr His Val Thr Gly Gly Ser Ala Gly His Thr
                85                  90                  95

Val Ser Gly Phe Val Ser Leu Leu Ala Pro Gly Ala Lys Gln Asn Val
                100                 105                 110

Gln Leu Ile Asn Thr Asn Gly Ser Trp His Leu Asn Ser Thr Ala Leu
            115                 120                 125

Asn Cys Asn Asp Ser Leu Asn Thr Gly Trp Leu
130                 135

(2) INFORMATION FOR SEQ ID NO:176:

(i) SEQUENCE CHARACTERISTICS:
        (A) LENGTH: 9379 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: misc_feature
        (B) LOCATION: 345
        (D) OTHER INFORMATION: /note= "A heterogeneity may exist
            at this position which is A or G"

(ix) FEATURE:
        (A) NAME/KEY: misc_feature
        (B) LOCATION: 351
        (D) OTHER INFORMATION: /note= "A heterogeneity may exist
            at this position which is A or C"

(ix) FEATURE:
        (A) NAME/KEY: misc_feature
        (B) LOCATION: 846
        (D) OTHER INFORMATION: /note= "A heterogeneity may exist
            at this position which is T or C"

(ix) FEATURE:
        (A) NAME/KEY: misc_feature
        (B) LOCATION: 1319
        (D) OTHER INFORMATION: /note= "A heterogeneity may exist
            at this position which is A or G"

(ix) FEATURE:
        (A) NAME/KEY: misc_feature
        (B) LOCATION: 2126
        (D) OTHER INFORMATION: /note= "A heterogeneity may exist
            at this position which is A or C"

(ix) FEATURE:
        (A) NAME/KEY: misc_feature
        (B) LOCATION: 3659
        (D) OTHER INFORMATION: /note= "A heterogeneity may exist
            at this position which is C or T"

(ix) FEATURE:
        (A) NAME/KEY: misc_feature
        (B) LOCATION: 3669
        (D) OTHER INFORMATION: /note= "A heterogeneity may exist
            at this position which is G or C"

(ix) FEATURE:
        (A) NAME/KEY: misc_feature
        (B) LOCATION: 4146
        (D) OTHER INFORMATION: /note= "A heterogeneity may exist
            at this position which is C or T"

(ix) FEATURE:
        (A) NAME/KEY: misc_feature
        (B) LOCATION: 4680
        (D) OTHER INFORMATION: /note= "A heterogeneity may exist
            at this position which is G or A"

(ix) FEATURE:
        (A) NAME/KEY: misc_feature
        (B) LOCATION: 9080
        (D) OTHER INFORMATION: /note= "A heterogeneity may exist
            at this position which is A or G"

(xi) SEQUENCE DESCRIPTION: SEQ ID NO:176:

```
CACTCCACCA TGAATCACTC CCCTGTGAGG AACTACTGTC TTCACGCAGA AAGCGTCTAG     60

CCATGGCGTT AGTATGAGTG TCGTGCAGCC TCCAGGACCC CCCCTCCCGG GAGAGCCATA    120

GTGGTCTGCG GAACCGGTGA GTACACCGGA ATTGCCAGGA CGACCGGGTC CTTTCTTGGA    180

TCAACCCGCT CAATGCCTGG AGATTTGGGC GTGCCCCCGC AAGACTGCTA GCCGAGTAGT    240

GTTGGGTCGC GAAAGGCCTT GTGGTACTGC CTGATAGGGT GCTTGCGAGT GCCCCGGGAG    300

GTCTCGTAGA CCGTGCACCA TGAGCACGAA TCCTAAACCT CAAARAAAAA MCAAACGTAA    360

CACCAACCGT CGCCCACAGG ACGTCAAGTT CCCGGGTGGC GGTCAGATCG TTGGTGGAGT    420

TTACTTGTTG CCGCGCAGGG GCCCTAGATT GGGTGTGCGC GCGACGAGAA AGACTTCCGA    480

GCGGTCGCAA CCTCGAGGTA GACGTCAGCC TATCCCCAAG GCTCGTCGGC CCGAGGGCAG    540

GACCTGGGCT CAGCCCGGGT ACCCTTGGCC CCTCTATGGC AATGAGGGCT GCGGGTGGGC    600

GGGATGGCTC CTGTCTCCCC GTGGCTCTCG GCCTAGCTGG GGCCCCACAG ACCCCCGGCG    660

TAGGTCGCGC AATTTGGGTA AGGTCATCGA TACCCTTACG TGCGGCTTCG CCGACCTCAT    720

GGGGTACATA CCGCTCGTCG GCGCCCCTCT TGGAAGCGCT GCCAGGGCCC TGGCGCATGG    780

CGTCCGGGTT CTGGAAGACG GCGTGAACTA TGCAACAGGG AACCTTCCTG GTTGCTCTTT    840

CTCTAYCTTC CTTCTGGCCC TGCTCTCTTG CTTGACTGTG CCCGCTTCGG CCTACCAAGT    900

GCGCAACTCC ACGGGCTTTT ACCACGTCAC CAATGATTGC CCTAACTCGA GTATTGTGTA    960

CGAGGCGGCC GATGCCATCC TGCACACTCC GGGGTGCGTC CCTTGCGTTC GTGAGGGCAA   1020

CGCCTCGAGG TGTTGGGTGG CGATGACCCC TACGGTGGCC ACCAGGGATG GCAAACTCCC   1080

CGCGACGCAG CTTCGACGTC ACATCGATCT GCTTGTCGGG AGCGCCACCC TCTGTTCGGC   1140

CCTCTACGTG GGGGACCTAT GCGGGTCTGT CTTTCTTGTC GGCCAACTGT TCACCTTCTC   1200

TCCCAGGCGC CACTGGACGA CGCAAGGTTG CAATTGCTCT ATCTATCCCG GCCATATAAC   1260

GGGTCACCGC ATGGCATGGG ATATGATGAT GAACTGGTCC CCTACGACGG CGTTGGTART   1320

GGCTCAGCTG CTCCGGATCC CACAAGCCAT CTTGGACATG ATCGCTGGTG CTCACTGGGG   1380

AGTCCTGGCG GGCATAGCGT ATTTCTCCAT GGTGGGGAAC TGGGCGAAGG TCCTGGTAGT   1440

GCTGCTGCTA TTTGCCGGCG TCGACGCGGA AACCCACGTC ACCGGGGGAA GTGCCGGCCA   1500

CACTGTGTCT GGATTTGTTA GCCTCCTCGC ACCAGGCGCC AAGCAGAACG TCCAGCTGAT   1560
```

```
CAACACCAAC GGCAGTTGGC ACCTCAATAG CACGGCCCTG AACTGCAATG ATAGCCTCAA    1620
CACCGGCTGG TTGGCAGGGC TTTTCTATCA CCACAAGTTC AACTCTTCAG GCTGTCCTGA    1680
GAGGCTAGCC AGCTGCCGAC CCCTTACCGA TTTTGACCAG GGCTGGGGCC CTATCAGTTA    1740
TGCCAACGGA AGCGGCCCCG ACCAGCGCCC CTACTGCTGG CACTACCCCC AAAACCTTG     1800
CGGTATTGTG CCCGCGAAGA GTGTGTGTGG TCCGGTATAT TGCTTCACTC CCAGCCCCGT    1860
GGTGGTGGGA ACGACCGACA GGTCCGGCGC GCCCACCTAC AGCTGGGGTG AAAATGATAC    1920
GGACGTCTTC GTCCTTAACA ATACCAGGCC ACCGCTGGGC AATTGGTTCG GTTGTACCTG    1980
GATGAACTCA ACTGGATTCA CCAAAGTGTG CGGAGCGCCT CCTTGTGTCA TCGGAGGGGC    2040
GGGCAACAAC ACCCTGCACT GCCCCACTGA TTGCTTCCGC AAGCATCCGG ACGCCACATA    2100
CTCTCGGTGC GGCTCCGGTC CCTGGMTCAC ACCCAGGTGC CTGGTCGACT ACCCGTATAG    2160
GCTTTGGCAT TATCCTTGTA CCATCAACTA CACCATATTT AAAATCAGGA TGTACGTGGG    2220
AGGGGTCGAA CACAGGCTGG AAGCTGCCTG CAACTGGACG CGGGGCGAAC GTTGCGATCT    2280
GGAAGACAGG GACAGGTCCG AGCTCAGCCC GTTACTGCTG ACCACTACAC AGTGGCAGGT    2340
CCTCCCGTGT TCCTTCACAA CCCTACCAGC CTTGTCCACC GGCCTCATCC ACCTCCACCA    2400
GAACATTGTG GACGTGCAGT ACTTGTACGG GGTGGGGTCA AGCATCGCGT CCTGGGCCAT    2460
TAAGTGGGAG TACGTCGTTC TCCTGTTCCT TCTGCTTGCA GACGCGCGCG TCTGCTCCTG    2520
CTTGTGGATG ATGCTACTCA TATCCCAAGC GGAGGCGGCT TTGGAGAACC TCGTAATACT    2580
TAATGCAGCA TCCCTGGCCG GGACGCACGG TCTTGTATCC TTCCTCGTGT TCTTCTGCTT    2640
TGCATGGTAT TTGAAGGGTA AGTGGGTGCC CGGAGCGGTC TACACCTTCT ACGGGATGTG    2700
GCCTCTCCTC CTGCTCCTGT TGGCGTTGCC CCAGCGGGCG TACGCGCTGG ACACGGAGGT    2760
GGCCGCGTCG TGTGGCGGTG TTGTTCTCGT CGGGTTGATG GCGCTGACTC TGTCACCATA    2820
TTACAAGCGC TATATCAGCT GGTGCTTGTG GTGGCTTCAG TATTTTCTGA CCAGAGTGGA    2880
AGCGCAACTG CACGTGTGGA TTCCCCCCCT CAACGTCCGA GGGGGGCGCG ACGCCGTCAT    2940
CTTACTCATG TGTGCTGTAC ACCCGACTCT GGTATTTGAC ATCACCAAAT TGCTGCTGGC    3000
CGTCTTCGGA CCCCTTTGGA TTCTTCAAGC CAGTTTGCTT AAAGTACCCT ACTTTGTGCG    3060
CGTCCAAGGC CTTCTCCGGT TCTGCGCGTT AGCGCGGAAG ATGATCGGAG GCCATTACGT    3120
GCAAATGGTC ATCATTAAGT TAGGGGCGCT TACTGGCACC TATGTTTATA ACCATCTCAC    3180
TCCTCTTCGG GACTGGGCGC ACAACGGCTT GCGAGATCTG GCCGTGGCTG TAGAGCCAGT    3240
CGTCTTCTCC CAAATGGAGA CCAAGCTCAT CACGTGGGGG GCAGATACCG CCGCGTGCGG    3300
TGACATCATC AACGGCTTGC CTGTTTCCGC CCGCAGGGGC CGGAGATAC TGCTCGGGCC     3360
AGCCGATGGA ATGGTCTCCA AGGGGTGGAG GTTGCTGGCG CCCATCACGG CGTACGCCCA    3420
GCAGACAAGG GGCCTCCTAG GGTGCATAAT CACCAGCCTA ACTGGCCGGG ACAAAAACCA    3480
AGTGGAGGGT GAGGTCCAGA TTGTGTCAAC TGCTGCCCAA ACCTTCCTGG CAACGTGCAT    3540
CAATGGGGTG TGCTGGACTG TCTACCACGG GGCCGGAACG AGGACCATCG CGTCACCCAA    3600
GGGTCCTGTC ATCCAGATGT ATACCAATGT AGACCAAGAC CTTGTGGGCT GGCCCGCTYC    3660
GCAAGGTASC CGCTCATTGA CACCCTGCAC TTGCGGCTCC TCGGACCTTT ACCTGGTCAC    3720
GAGGCACGCC GATGTCATTC CCGTGCGCCG GCGGGGTGAT AGCAGGGGCA GCCTGCTGTC    3780
GCCCCGGCCC ATTTCCTACT TGAAAGGCTC CTCGGGGGGT CCGCTGTTGT GCCCCGCGGG    3840
GCACGCCGTG GGCATATTTA GGGCCGCGGT GTGCACCCGT GGAGTGGCTA AGGCGGTGGA    3900
CTTTATCCCT GTGGAGAACC TAGAGACAAC CATGAGGTCC CCGGTGTTCA CGGATAACTC    3960
```

```
CTCTCCACCA GTAGTGCCCC AGAGCTTCCA GGTGGCTCAC CTCCATGCTC CCACAGGCAG    4020

CGGCAAAAGC ACCAAGGTCC CGGCTGCATA TGCAGCTCAG GGCTATAAGG TGCTAGTACT    4080

CAACCCCTCT GTTGCTGCAA CACTGGGCTT TGGTGCTTAC ATGTCCAAGG CTCATGGGAT    4140

CGATCYTAAC ATCAGGACCG GGGTGAGAAC AATTACCACT GGCAGCCCCA TCACGTACTC    4200

CACCTACGGC AAGTTCCTTG CCGACGGCGG GTGCTCGGGG GGCGCTTATG ACATAATAAT    4260

TTGTGACGAG TGCCACTCCA CGGATGCCAC ATCCATCTTG GGCATCGGCA CTGTCCTTGA    4320

CCAAGCAGAG ACTGCGGGGG CGAGACTGGT TGTGCTCGCC ACCGCCACCC CTCCGGGCTC    4380

CGTCACTGTG CCCCATCCCA ACATCGAGGA GGTTGCTCTG TCCACCACCG GAGAGATCCC    4440

TTTTTACGGC AAGGCTATCC CCCTCGAAGT AATCAAGGGG GGGAGACATC TCATCTTCTG    4500

TCATTCAAAG AAGAAGTGCG ACGAACTCGC CGCAAAGCTG GTCGCATTGG GCATCAATGC    4560

CGTGGCCTAC TACCGCGGTC TTGACGTGTC CGTCATCCCG ACCAGCGGCG ATGTTGTCGT    4620

CGTGGCAACC GATGCCCTCA TGACCGGCTA TACCGGCGAC TTCGACTCGG TGATAGACTR    4680

CAATACGTGT GTCACCCAGA CAGTCGATTT CAGCCTTGAC CCTACCTTCA CCATTGAGAC    4740

AATCACGCTC CCCCAGGATG CTGTCTCCCG CACTCAACGT CGGGGCAGGA CTGGCAGGGG    4800

GAAGCCAGGC ATCAACAGAT TTGTGGCACC GGGGAGCGC CCCTCCGGCA TGTTCGACTC    4860

GTCCGTCCTC TGTGAGTGCT ATGACGCAGG CTGTGCTTGG TATGAGCTCA CGCCCGCCGA    4920

GACTACAGTT AGGCTACGAG CGTACATGAA CACCCCGGGG CTTCCCGTGT GCCAGGACCA    4980

TCTTGAATTT TGGGAGGGCG TCTTTACAGG CCTCACTCAT ATAGATGCCC ACTTTCTATC    5040

CCAGACAAAG CAGAGTGGGG AGAACCTTCC TTACCTGGTA GCGTACCAAG CCACCGTGTG    5100

CGCTAGGGCT CAAGCCCCTC CCCCATCGTG GGACCAGATG TGGAAGTGTT TGATTCGCCT    5160

CAAGCCCACC CTCCATGGGC CAACACCCCT GCTATACAGA CTGGGCGCTG TTCAGAATGA    5220

AATCACCCTG ACGCACCCAG TCACCAAATA CATCATGACA TGCATGTCGG CCGACCTGGA    5280

GGTCGTCACG AGCACCTGGG TGCTCGTTGG CGGCGTCCTG GCTGCTTTGG CCGCGTATTG    5340

CCTGTCAACA GGCTGCGTGG TCATAGTGGG CAGGGTCGTC TTGTCCGGGA AGCCGGCAAT    5400

CATACCTGAC AGGGAAGTCC TCTACCGAGA GTTCGATGAG ATGGAAGAGT GCTCTCAGCA    5460

CTTACCGTAC ATCGAGCAAG GGATGATGCT CGCCGAGCAG TTCAAGCAGA AGGCCCTCGG    5520

CCTCCTGCAG ACCGCGTCCC GTCAGGCAGA GGTTATCGCC CCTGCTGTCC AGACCAACTG    5580

GCAAAAACTC GAGACCTTCT GGGCGAAGCA TATGTGGAAC TTCATCAGTG GGATACAATA    5640

CTTGGCGGGC TTGTCAACGC TGCCTGGTAA CCCCGCCATT GCTTCATTGA TGGCTTTTAC    5700

AGCTGCTGTC ACCAGCCCAC TAACCACTAG CCAAACCCTC CTCTTCAACA TATTGGGGGG    5760

GTGGGTGGCT GCCCAGCTCG CCGCCCCCGG TGCCGCTACT GCCTTTGTGG GCGCTGGCTT    5820

AGCTGGCGCC GCCATCGGCA GTGTTGGACT GGGGAAGGTC CTCATAGACA TCCTTGCAGG    5880

GTATGGCGCG GGCGTGGCGG GAGCTCTTGT GGCATTCAAG ATCATGAGCG GTGAGGTCCC    5940

CTCCACGGAG GACCTGGTCA ATCTACTGCC CGCCATCCTC TCGCCCGGAG CCCTCGTAGT    6000

CGGCGTGGTC TGTGCAGCAA TACTGCGCCG GCACGTTGGC CCGGGCGAGG GGCAGTGCA    6060

GTGGATGAAC CGGCTGATAG CCTTCGCCTC CCGGGGGAAC CATGTTTCCC CCACGCACTA    6120

CGTGCCGGAG AGCGATGCAG CTGCCCGCGT CACTGCCATA CTCAGCAGCC TCACTGTAAC    6180

CCAGCTCCTG AGGCGACTGC ACCAGTGGAT AAGCTCGGA TGTACCACTC CATGCTCCGG    6240

TTCCTGGCTA AGGGACATCT GGGACTGGAT ATGCGAGGTG TTGAGCGACT TTAAGACCTG    6300
```

```
GCTAAAAGCT AAGCTCATGC CACAGCTGCC TGGGATCCCC TTTGTGTCCT GCCAGCGCGG    6360

GTATAAGGGG GTCTGGCGAG TGGACGGCAT CATGCACACT CGCTGCCACT GTGGAGCTGA    6420

GATCACTGGA CATGTCAAAA ACGGGACGAT GAGGATCGTC GGTCCTAGGA CCTGCAGGAA    6480

CATGTGGAGT GGGACCTTCC CCATTAATGC CTACACCACG GGCCCCTGTA CCCCCCTTCC    6540

TGCGCCGAAC TACACGTTCG CGCTATGGAG GGTGTCTGCA GAGGAATATG TGGAGATAAG    6600

GCAGGTGGGG GACTTCCACT ACGTGACGGG TATGACTACT GACAATCTCA AATGCCCGTG    6660

CCAGGTCCCA TCGCCCGAAT TTTTCACAGA ATTGGACGGG GTGCGCCTAC ATAGGTTTGC    6720

GCCCCCCTGC AAGCCCTTGC TGCGGGAGGA GGTATCATTC AGAGTAGGAC TCCACGAATA    6780

CCCGGTAGGG TCGCAATTAC CTTGCGAGCC CGAACCGGAC GTGGCCGTGT TGACGTCCAT    6840

GCTCACTGAT CCCTCCCATA TAACAGCAGA GGCGGCCGGG CGAAGGTTGG CGAGGGGATC    6900

ACCCCCCTCT GTGGCCAGCT CCTCGGCTAG CCAGCTATCC GCTCCATCTC TCAAGGCAAC    6960

TTGCACCGCT AACCATGACT CCCCTGATGC TGAGCTCATA GAGGCCAACC TCCTATGGAG    7020

GCAGGAGATG GGCGGCAACA TCACCAGGGT TGAGTCAGAA ACAAAGTGG TGATTCTGGA     7080

CTCCTTCGAT CCGCTTGTGG CGGAGGAGGA CGAGCGGGAG ATCTCCGTAC CCGCAGAAAT    7140

CCTGCGGAAG TCTCGGAGAT CGCCCAGGC CCTGCCCGTT TGGGCGCGGC CGGACTATAA     7200

CCCCCCGCTA GTGGAGACGT GGAAAAAGCC CGACTACGAA CCACCTGTGG TCCATGGCTG    7260

TCCGCTTCCA CCTCCAAAGT CCCCTCCTGT GCCTCCGCCT CGGAAGAAGC GGACGGTGGT    7320

CCTCACTGAA TCAACCCTAT CTACTGCCTT GGCCGAGCTC GCCACCAGAA GCTTTGGCAG    7380

CTCCTCAACT TCCGGCATTA CGGGCGACAA TACGACAACA TCCTCTGAGC CCGCCCCTTC    7440

TGGCTGCCCC CCCGACTCCG ACGCTGAGTC CTATTCCTCC ATGCCCCCC TGGAGGGGGA     7500

GCCTGGGGAT CCGGATCTTA GCGACGGGTC ATGGTCAACG GTCAGTAGTG AGGCCAACGC    7560

GGAGGATGTC GTGTGCTGCT CAATGTCTTA CTCTTGGACA GGCGCACTCG TCACCCCGTG    7620

CGCCGCGGAA GAACAGAAAC TGCCCATCAA TGCACTAAGC AACTCGTTGC TACGTCACCA    7680

CAATTTGGTG TATTCCACCA CCTCACGCAG TGCTTGCCAA AGGCAGAAGA AGTCACATT     7740

TGACAGACTG CAAGTTCTGG ACAGCCATTA CCAGGACGTA CTCAAGGAGG TTAAAGCAGC    7800

GGCGTCAAAA GTGAAGGCTA ACTTGCTATC CGTAGAGGAA GCTTGCAGCC TGACGCCCCC    7860

ACACTCAGCC AAATCCAAGT TTGGTTATGG GGCAAAAGAC GTCCGTTGCC ATGCCAGAAA    7920

GGCCGTAACC CACATCAACT CCGTGTGGAA AGACCTTCTG GAAGACAATG TAACACCAAT    7980

AGACACTACC ATCATGGCTA AGAACGAGGT TTTCTGCGTT CAGCCTGAGA AGGGGGGTCG    8040

TAAGCCAGCT CGTCTCATCG TGTTCCCCGA TCTGGGCGTG CGCGTGTGCG AAAAGATGGC    8100

TTTGTACGAC GTGGTTACAA AGCTCCCCTT GGCCGTGATG GGAAGCTCCT ACGGATTCCA    8160

ATACTCACCA GGACAGCGGG TTGAATTCCT CGTGCAAGCG TGGAAGTCCA AGAAAACCCC    8220

AATGGGGTTC TCGTATGATA CCCGCTGCTT TGACTCCACA GTCACTGAGA GCGACATCCG    8280

TACGGAGGAG GCAATCTACC AATGTTGTGA CCTCGACCCC CAAGCCCGCG TGGCCATCAA    8340

GTCCCTCACC GAGAGGCTTT ATGTTGGGGG CCCTCTTACC AATTCAAGGG GGGAGAACTG    8400

CGGCTATCGC AGGTGCCGCG CGAGCGGCGT ACTGACAACT AGCTGTGGTA ACACCCTCAC    8460

TTGCTACATC AAGGCCCGGG CAGCCTGTCG AGCCGCAGGG CTCCAGGACT GCACCATGCT    8520

CGTGTGTGGC GACGACTTAG TCGTTATCTG TGAAAGCGCG GGGGTCCAGG AGGACGCGGC    8580

GAGCCTGAGA GCCTTCACGG AGGCTATGAC CAGGTACTCC GCCCCCCCTG GGGACCCCCC    8640

ACAACCAGAA TACGACTTGG AGCTCATAAC ATCATGCTCC TCCAACGTGT CAGTCGCCCA    8700
```

```
CGACGGCGCT GGAAAGAGGG TCTACTACCT CACCCGTGAC CCTACAACCC CCCTCGCGAG    8760

AGCTGCGTGG GAGACAGCAA GACACACTCC AGTCAATTCC TGGCTAGGCA ACATAATCAT    8820

GTTTGCCCCC ACACTGTGGG CGAGGATGAT ACTGATGACC CATTTCTTTA GCGTCCTTAT    8880

AGCCAGGGAC CAGCTTGAAC AGGCCCTCGA TTGCGAGATC TACGGGGCCT GCTACTCCAT    8940

AGAACCACTT GATCTACCTC CAATCATTCA AAGACTCCAT GGCCTCAGCG CATTTTCACT    9000

CCACAGTTAC TCTCCAGGTG AAATTAATAG GGTGGCCGCA TGCCTCAGAA AACTTGGGGT    9060

ACCGCCCTTG CGAGCTTGGR GACACCGGGC CCGGAGCGTC CGCGCTAGGC TTCTGGCCAG    9120

AGGAGGCAGG GCTGCCATAT GTGGCAAGTA CCTCTTCAAC TGGGCAGTAA GAACAAAGCT    9180

CAAACTCACT CCAATAGCGG CCGCTGGCCA GCTGGACTTG TCCGGCTGGT TCACGGCTGG    9240

CTACAGCGGG GGAGACATTT ATCACAGCGT GTCTCATGCC CGGCCCCGCT GGATCTGGTT    9300

TTGCCTACTC CTGCTTGCTG CAGGGGTAGG CATCTACCTC CTCCCCAACC GATGAAGGTT    9360

GGGGTAAACA CTCCGGCCT                                                9379
```

(2) INFORMATION FOR SEQ ID NO:177:

(i) SEQUENCE CHARACTERISTICS:
        (A) LENGTH: 3011 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Duplication
        (B) LOCATION: 9
        (D) OTHER INFORMATION: /note= "There exists a
            heterogeneity at this position - Xaa = Lys or Arg"

(ix) FEATURE:
        (A) NAME/KEY: Duplication
        (B) LOCATION: 11
        (D) OTHER INFORMATION: /note= "There  exists a
            heterogeneity at this position - Xaa = Asn or Thr"

(ix) FEATURE:
        (A) NAME/KEY: Duplication
        (B) LOCATION: 176
        (D) OTHER INFORMATION: /note= "There exists a
            heterogeneity at this position - Xaa = Ile or Thr"

(ix) FEATURE:
        (A) NAME/KEY: Duplication
        (B) LOCATION: 334
        (D) OTHER INFORMATION: /note= "There exists a
            heterogeneity at this position - Xaa = Met or Val"

(ix) FEATURE:
        (A) NAME/KEY: Duplication
        (B) LOCATION: 603
        (D) OTHER INFORMATION: /note= "There exists a
            heterogeneity at this position - Xaa = Leu or Ile"

(ix) FEATURE:
        (A) NAME/KEY: Duplication
        (B) LOCATION: 848
        (D) OTHER INFORMATION: /note= "There exists a
            heterogeneity at this position - Xaa = Tyr or  Asn"

(ix) FEATURE:
        (A) NAME/KEY: Duplication
        (B) LOCATION: 1114
        (D) OTHER INFORMATION: /note= "There exists a
            heterogeneity at this position - Xaa = Pro or Ser"

(ix) FEATURE:

-continued

```
         (A) NAME/KEY: Duplication
         (B) LOCATION: 1117
         (D) OTHER INFORMATION: /note= "There exists a
             heterogeneity at this position - Xaa = Ser or Thr"

(ix) FEATURE:
         (A) NAME/KEY: Duplication
         (B) LOCATION: 1276
         (D) OTHER INFORMATION: /note= "There exists a
             heterogeneity at this position - Xaa = Pro or Leu"

(ix) FEATURE:
         (A) NAME/KEY: Duplication
         (B) LOCATION: 1454
         (D) OTHER INFORMATION: /note= "There exists a
             heterogeneity at this position - Xaa = Cys or Tyr"

(ix) FEATURE:
         (A) NAME/KEY: Duplication
         (B) LOCATION: 1471
         (D) OTHER INFORMATION: /note= "There exists a
             heterogeneity at this position - Xaa = Thr or  Ser"

(ix) FEATURE:
         (A) NAME/KEY: Duplication
         (B) LOCATION: 1877
         (D) OTHER INFORMATION: /note= "There exists a
             heterogeneity at this position - Xaa = Glu or Gly"

(ix) FEATURE:
         (A) NAME/KEY: Duplication
         (B) LOCATION: 1948
         (D) OTHER INFORMATION: /note= "There exists a
             heterogeneity at this position - Xaa = Leu or His"

(ix) FEATURE:
         (A) NAME/KEY: Duplication
         (B) LOCATION: 1949
         (D) OTHER INFORMATION: /note= "There exists a
             heterogeneity at this position - Xaa = Ser or Cys"

(ix) FEATURE:
         (A) NAME/KEY: Duplication
         (B) LOCATION: 2021
         (D) OTHER INFORMATION: /note= "There exists a
             heterogeneity at this position - Xaa = Gly or Val"

(ix) FEATURE:
         (A) NAME/KEY: Duplication
         (B) LOCATION: 2349
         (D) OTHER INFORMATION: /note= "There exists a
             heterogeneity at this position - Xaa = Thr or Ser"

(ix) FEATURE:
         (A) NAME/KEY: Duplication
         (B) LOCATION: 2385
         (D) OTHER INFORMATION: /note= "There exists a
             heterogeneity at this position - Xaa = Tyr or  Phe"

(ix) FEATURE:
         (A) NAME/KEY: Duplication
         (B) LOCATION: 2386
         (D) OTHER INFORMATION: /note= "There exists a
             heterogeneity at this position - Xaa = Ser or  Ala"

(ix) FEATURE:
         (A) NAME/KEY: Duplication
         (B) LOCATION: 2502
         (D) OTHER INFORMATION: /note= "There exists a
             heterogeneity at this position - Xaa = Leu or Phe"

(ix) FEATURE:
         (A) NAME/KEY: Duplication
         (B) LOCATION: 2690
         (D) OTHER INFORMATION: /note= "There exists a
             heterogeneity at this position - Xaa = Arg or  Gly"

(ix) FEATURE:
         (A) NAME/KEY: Duplication
```

(B) LOCATION: 2921
(D) OTHER INFORMATION: /note= "There exists a
    heterogeneity at this position - Xaa = Arg or Gly"

(ix) FEATURE:
    (A) NAME/KEY: Duplication
    (B) LOCATION: 2996
    (D) OTHER INFORMATION: /note= "There exists a
        heterogeneity at this position - Xaa = Leu or Pro"

(xi) SEQUENCE DESCRIPTION: SEQ ID NO:177:

```
Met Ser Thr Asn Pro Lys Pro Gln Xaa Lys Xaa Lys Arg Asn Thr Asn
1               5                   10                  15

Arg Arg Pro Gln Asp Val Lys Phe Pro Gly Gly Gly Gln Ile Val Gly
            20                  25                  30

Gly Val Tyr Leu Leu Pro Arg Gly Pro Arg Leu Gly Val Arg Ala
        35                  40                  45

Thr Arg Lys Thr Ser Glu Arg Ser Gln Pro Arg Gly Arg Arg Gln Pro
    50                  55                  60

Ile Pro Lys Ala Arg Arg Pro Glu Gly Arg Thr Trp Ala Gln Pro Gly
65              70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Ser Trp Gly Pro Thr Asp Pro
            100                 105                 110

Arg Arg Arg Ser Arg Asn Leu Gly Lys Val Ile Asp Thr Leu Thr Cys
            115                 120                 125

Gly Phe Ala Asp Leu Met Gly Tyr Ile Pro Leu Val Gly Ala Pro Leu
        130                 135                 140

Gly Ser Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Xaa
                165                 170                 175

Phe Leu Leu Ala Leu Leu Ser Cys Leu Thr Val Pro Ala Ser Ala Tyr
            180                 185                 190

Gln Val Arg Asn Ser Thr Gly Leu Tyr His Val Thr Asn Asp Cys Pro
        195                 200                 205

Asn Ser Ser Ile Val Tyr Glu Ala Ala Asp Ala Ile Leu His Thr Pro
        210                 215                 220

Gly Cys Val Pro Cys Val Arg Glu Gly Asn Ala Ser Arg Cys Trp Val
225                 230                 235                 240

Ala Met Thr Pro Thr Val Ala Thr Arg Asp Gly Lys Leu Pro Ala Thr
            245                 250                 255

Gln Leu Arg Arg His Ile Asp Leu Leu Val Gly Ser Ala Thr Leu Cys
        260                 265                 270

Ser Ala Leu Tyr Val Gly Asp Leu Cys Gly Ser Val Phe Leu Val Gly
    275                 280                 285

Gln Leu Phe Thr Phe Ser Pro Arg Arg His Trp Thr Thr Gln Gly Cys
    290                 295                 300

Asn Cys Ser Ile Tyr Pro Gly His Ile Thr Gly His Arg Met Ala Trp
305                 310                 315                 320

Asp Met Met Met Asn Trp Ser Pro Thr Thr Ala Leu Val Xaa Ala Gln
            325                 330                 335

Leu Leu Arg Ile Pro Gln Ala Ile Leu Asp Met Ile Ala Gly Ala His
            340                 345                 350

Trp Gly Val Leu Ala Gly Ile Ala Tyr Phe Ser Met Val Gly Asn Trp
```

-continued

```
            355                 360                 365
Ala Lys Val Leu Val Leu Leu Phe Ala Gly Val Asp Ala Glu
    370                 375                 380

Thr His Val Thr Gly Gly Ser Ala Gly His Thr Val Ser Gly Phe Val
385                 390                 395                 400

Ser Leu Leu Ala Pro Gly Ala Lys Gln Asn Val Gln Leu Ile Asn Thr
                405                 410                 415

Asn Gly Ser Trp His Leu Asn Ser Thr Ala Leu Asn Cys Asn Asp Ser
                420                 425                 430

Leu Asn Thr Gly Trp Leu Ala Gly Leu Phe Tyr His His Lys Phe Asn
                435                 440                 445

Ser Ser Gly Cys Pro Glu Arg Leu Ala Ser Cys Arg Pro Leu Thr Asp
    450                 455                 460

Phe Asp Gln Gly Trp Gly Pro Ile Ser Tyr Ala Asn Gly Ser Gly Pro
465                 470                 475                 480

Asp Gln Arg Pro Tyr Cys Trp His Tyr Pro Pro Lys Pro Cys Gly Ile
                485                 490                 495

Val Pro Ala Lys Ser Val Cys Gly Pro Val Tyr Cys Phe Thr Pro Ser
                500                 505                 510

Pro Val Val Val Gly Thr Thr Asp Arg Ser Gly Ala Pro Thr Tyr Ser
                515                 520                 525

Trp Gly Glu Asn Asp Thr Asp Val Phe Val Leu Asn Asn Thr Arg Pro
530                 535                 540

Pro Leu Gly Asn Trp Phe Gly Cys Thr Trp Met Asn Ser Thr Gly Phe
545                 550                 555                 560

Thr Lys Val Cys Gly Ala Pro Pro Cys Val Ile Gly Gly Ala Gly Asn
                565                 570                 575

Asn Thr Leu His Cys Pro Thr Asp Cys Phe Arg Lys His Pro Asp Ala
                580                 585                 590

Thr Tyr Ser Arg Cys Gly Ser Gly Pro Trp Xaa Thr Pro Arg Cys Leu
                595                 600                 605

Val Asp Tyr Pro Tyr Arg Leu Trp His Tyr Pro Cys Thr Ile Asn Tyr
    610                 615                 620

Thr Ile Phe Lys Ile Arg Met Tyr Val Gly Gly Val Glu His Arg Leu
625                 630                 635                 640

Glu Ala Ala Cys Asn Trp Thr Arg Gly Glu Arg Cys Asp Leu Glu Asp
                645                 650                 655

Arg Asp Arg Ser Glu Leu Ser Pro Leu Leu Leu Thr Thr Thr Gln Trp
                660                 665                 670

Gln Val Leu Pro Cys Ser Phe Thr Thr Leu Pro Ala Leu Ser Thr Gly
                675                 680                 685

Leu Ile His Leu His Gln Asn Ile Val Asp Val Gln Tyr Leu Tyr Gly
                690                 695                 700

Val Gly Ser Ser Ile Ala Ser Trp Ala Ile Lys Trp Glu Tyr Val Val
705                 710                 715                 720

Leu Leu Phe Leu Leu Ala Asp Ala Arg Val Cys Ser Cys Leu Trp
                725                 730                 735

Met Met Leu Leu Ile Ser Gln Ala Glu Ala Leu Glu Asn Leu Val
                740                 745                 750

Ile Leu Asn Ala Ala Ser Leu Ala Gly Thr His Gly Leu Val Ser Phe
                755                 760                 765

Leu Val Phe Phe Cys Phe Ala Trp Tyr Leu Lys Gly Lys Trp Val Pro
770                 775                 780
```

-continued

```
Gly Ala Val Tyr Thr Phe Tyr Gly Met Trp Pro Leu Leu Leu Leu
785                 790                 795                 800

Leu Ala Leu Pro Gln Arg Ala Tyr Ala Leu Asp Thr Glu Val Ala Ala
                805                 810                 815

Ser Cys Gly Gly Val Val Leu Val Gly Leu Met Ala Leu Thr Leu Ser
                820                 825                 830

Pro Tyr Tyr Lys Arg Tyr Ile Ser Trp Cys Leu Trp Trp Leu Gln Xaa
                835                 840                 845

Phe Leu Thr Arg Val Glu Ala Gln Leu His Val Trp Ile Pro Pro Leu
    850                 855                 860

Asn Val Arg Gly Gly Arg Asp Ala Val Ile Leu Leu Met Cys Ala Val
865                 870                 875                 880

His Pro Thr Leu Val Phe Asp Ile Thr Lys Leu Leu Leu Ala Val Phe
                885                 890                 895

Gly Pro Leu Trp Ile Leu Gln Ala Ser Leu Leu Lys Val Pro Tyr Phe
                900                 905                 910

Val Arg Val Gln Gly Leu Leu Arg Phe Cys Ala Leu Ala Arg Lys Met
                915                 920                 925

Ile Gly Gly His Tyr Val Gln Met Val Ile Ile Lys Leu Gly Ala Leu
    930                 935                 940

Thr Gly Thr Tyr Val Tyr Asn His Leu Thr Pro Leu Arg Asp Trp Ala
945                 950                 955                 960

His Asn Gly Leu Arg Asp Leu Ala Val Ala Val Glu Pro Val Val Phe
                965                 970                 975

Ser Gln Met Glu Thr Lys Leu Ile Thr Trp Gly Ala Asp Thr Ala Ala
                980                 985                 990

Cys Gly Asp Ile Ile Asn Gly Leu Pro Val Ser Ala Arg Arg Gly Arg
    995                 1000                1005

Glu Ile Leu Leu Gly Pro Ala Asp Gly Met Val Ser Lys Gly Trp Arg
    1010                1015                1020

Leu Leu Ala Pro Ile Thr Ala Tyr Ala Gln Gln Thr Arg Gly Leu Leu
1025                1030                1035                1040

Gly Cys Ile Ile Thr Ser Leu Thr Gly Arg Asp Lys Asn Gln Val Glu
                1045                1050                1055

Gly Glu Val Gln Ile Val Ser Thr Ala Ala Gln Thr Phe Leu Ala Thr
                1060                1065                1070

Cys Ile Asn Gly Val Cys Trp Thr Val Tyr His Gly Ala Gly Thr Arg
                1075                1080                1085

Thr Ile Ala Ser Pro Lys Gly Pro Val Ile Gln Met Tyr Thr Asn Val
    1090                1095                1100

Asp Gln Asp Leu Val Gly Trp Pro Ala Xaa Gln Gly Xaa Arg Ser Leu
1105                1110                1115                1120

Thr Pro Cys Thr Cys Gly Ser Ser Asp Leu Tyr Leu Val Thr Arg His
                1125                1130                1135

Ala Asp Val Ile Pro Val Arg Arg Arg Gly Asp Ser Arg Gly Ser Leu
                1140                1145                1150

Leu Ser Pro Arg Pro Ile Ser Tyr Leu Lys Gly Ser Ser Gly Gly Pro
                1155                1160                1165

Leu Leu Cys Pro Ala Gly His Ala Val Gly Ile Phe Arg Ala Ala Val
    1170                1175                1180

Cys Thr Arg Gly Val Ala Lys Ala Val Asp Phe Ile Pro Val Glu Asn
1185                1190                1195                1200
```

-continued

```
Leu Glu Thr Thr Met Arg Ser Pro Val Phe Thr Asp Asn Ser Ser Pro
            1205                1210                1215
Pro Val Val Pro Gln Ser Phe Gln Val Ala His Leu His Ala Pro Thr
        1220                1225                1230
Gly Ser Gly Lys Ser Thr Lys Val Pro Ala Ala Tyr Ala Ala Gln Gly
    1235                1240                1245
Tyr Lys Val Leu Val Leu Asn Pro Ser Val Ala Ala Thr Leu Gly Phe
1250                1255                1260
Gly Ala Tyr Met Ser Lys Ala His Gly Ile Asp Xaa Asn Ile Arg Thr
1265                1270                1275                1280
Gly Val Arg Thr Ile Thr Thr Gly Ser Pro Ile Thr Tyr Ser Thr Tyr
            1285                1290                1295
Gly Lys Phe Leu Ala Asp Gly Gly Cys Ser Gly Ala Tyr Asp Ile
        1300                1305                1310
Ile Ile Cys Asp Glu Cys His Ser Thr Asp Ala Thr Ser Ile Leu Gly
    1315                1320                1325
Ile Gly Thr Val Leu Asp Gln Ala Glu Thr Ala Gly Ala Arg Leu Val
1330                1335                1340
Val Leu Ala Thr Ala Thr Pro Pro Gly Ser Val Thr Val Pro His Pro
1345                1350                1355                1360
Asn Ile Glu Glu Val Ala Leu Ser Thr Thr Gly Glu Ile Pro Phe Tyr
            1365                1370                1375
Gly Lys Ala Ile Pro Leu Glu Val Ile Lys Gly Gly Arg His Leu Ile
        1380                1385                1390
Phe Cys His Ser Lys Lys Lys Cys Asp Glu Leu Ala Ala Lys Leu Val
    1395                1400                1405
Ala Leu Gly Ile Asn Ala Val Ala Tyr Tyr Arg Gly Leu Asp Val Ser
    1410                1415                1420
Val Ile Pro Thr Ser Gly Asp Val Val Val Ala Thr Asp Ala Leu
1425                1430                1435                1440
Met Thr Gly Tyr Thr Gly Asp Phe Asp Ser Val Ile Asp Xaa Asn Thr
            1445                1450                1455
Cys Val Thr Gln Thr Val Asp Phe Ser Leu Asp Pro Thr Phe Xaa Ile
        1460                1465                1470
Glu Thr Ile Thr Leu Pro Gln Asp Ala Val Ser Arg Thr Gln Arg Arg
    1475                1480                1485
Gly Arg Thr Gly Arg Gly Lys Pro Gly Ile Asn Arg Phe Val Ala Pro
    1490                1495                1500
Gly Glu Arg Pro Ser Gly Met Phe Asp Ser Ser Val Leu Cys Glu Cys
1505                1510                1515                1520
Tyr Asp Ala Gly Cys Ala Trp Tyr Glu Leu Thr Pro Ala Glu Thr Thr
            1525                1530                1535
Val Arg Leu Arg Ala Tyr Met Asn Thr Pro Gly Leu Pro Val Cys Gln
        1540                1545                1550
Asp His Leu Glu Phe Trp Glu Gly Val Phe Thr Gly Leu Thr His Ile
    1555                1560                1565
Asp Ala His Phe Leu Ser Gln Thr Lys Gln Ser Gly Glu Asn Leu Pro
    1570                1575                1580
Tyr Leu Val Ala Tyr Gln Ala Thr Val Cys Ala Arg Ala Gln Ala Pro
1585                1590                1595                1600
Pro Pro Ser Trp Asp Gln Met Trp Lys Cys Leu Ile Arg Leu Lys Pro
            1605                1610                1615
Thr Leu His Gly Pro Thr Pro Leu Leu Tyr Arg Leu Gly Ala Val Gln
```

-continued

```
                1620                1625                1630
Asn Glu Ile Thr Leu Thr His Pro Val Thr Lys Tyr Ile Met Thr Cys
                1635                1640                1645

Met Ser Ala Asp Leu Glu Val Val Thr Ser Thr Trp Val Leu Val Gly
    1650                1655                1660

Gly Val Leu Ala Ala Leu Ala Ala Tyr Cys Leu Ser Thr Gly Cys Val
1665                1670                1675                1680

Val Ile Val Gly Arg Val Val Leu Ser Gly Lys Pro Ala Ile Ile Pro
                1685                1690                1695

Asp Arg Glu Val Leu Tyr Arg Glu Phe Asp Glu Met Glu Glu Cys Ser
                1700                1705                1710

Gln His Leu Pro Tyr Ile Glu Gln Gly Met Met Leu Ala Glu Gln Phe
    1715                1720                1725

Lys Gln Lys Ala Leu Gly Leu Leu Gln Thr Ala Ser Arg Gln Ala Glu
    1730                1735                1740

Val Ile Ala Pro Ala Val Gln Thr Asn Trp Gln Lys Leu Glu Thr Phe
1745                1750                1755                1760

Trp Ala Lys His Met Trp Asn Phe Ile Ser Gly Ile Gln Tyr Leu Ala
                1765                1770                1775

Gly Leu Ser Thr Leu Pro Gly Asn Pro Ala Ile Ala Ser Leu Met Ala
                1780                1785                1790

Phe Thr Ala Ala Val Thr Ser Pro Leu Thr Thr Ser Gln Thr Leu Leu
    1795                1800                1805

Phe Asn Ile Leu Gly Gly Trp Val Ala Ala Gln Leu Ala Ala Pro Gly
    1810                1815                1820

Ala Ala Thr Ala Phe Val Gly Ala Gly Leu Ala Gly Ala Ala Ile Gly
1825                1830                1835                1840

Ser Val Gly Leu Gly Lys Val Leu Ile Asp Ile Leu Ala Gly Tyr Gly
                1845                1850                1855

Ala Gly Val Ala Gly Ala Leu Val Ala Phe Lys Ile Met Ser Gly Glu
                1860                1865                1870

Val Pro Ser Thr Xaa Asp Leu Val Asn Leu Leu Pro Ala Ile Leu Ser
    1875                1880                1885

Pro Gly Ala Leu Val Val Gly Val Val Cys Ala Ala Ile Leu Arg Arg
    1890                1895                1900

His Val Gly Pro Gly Glu Gly Ala Val Gln Trp Met Asn Arg Leu Ile
1905                1910                1915                1920

Ala Phe Ala Ser Arg Gly Asn His Val Ser Pro Thr His Tyr Val Pro
                1925                1930                1935

Glu Ser Asp Ala Ala Ala Arg Val Thr Ala Ile Xaa Xaa Ser Leu Thr
                1940                1945                1950

Val Thr Gln Leu Leu Arg Arg Leu His Gln Trp Ile Ser Ser Glu Cys
    1955                1960                1965

Thr Thr Pro Cys Ser Gly Ser Trp Leu Arg Asp Ile Trp Asp Trp Ile
    1970                1975                1980

Cys Glu Val Leu Ser Asp Phe Lys Thr Trp Leu Lys Ala Lys Leu Met
1985                1990                1995                2000

Pro Gln Leu Pro Gly Ile Pro Phe Val Ser Cys Gln Arg Gly Tyr Lys
                2005                2010                2015

Gly Val Trp Arg Xaa Asp Gly Ile Met His Thr Arg Cys His Cys Gly
                2020                2025                2030

Ala Glu Ile Thr Gly His Val Lys Asn Gly Thr Met Arg Ile Val Gly
                2035                2040                2045
```

-continued

```
Pro Arg Thr Cys Arg Asn Met Trp Ser Gly Thr Phe Pro Ile Asn Ala
    2050                2055                2060
Tyr Thr Thr Gly Pro Cys Thr Pro Leu Pro Ala Pro Asn Tyr Thr Phe
2065                2070                2075                2080
Ala Leu Trp Arg Val Ser Ala Glu Glu Tyr Val Glu Ile Arg Gln Val
                2085                2090                2095
Gly Asp Phe His Tyr Val Thr Gly Met Thr Thr Asp Asn Leu Lys Cys
                2100                2105                2110
Pro Cys Gln Val Pro Ser Pro Glu Phe Phe Thr Glu Leu Asp Gly Val
                2115                2120                2125
Arg Leu His Arg Phe Ala Pro Pro Cys Lys Pro Leu Leu Arg Glu Glu
                2130                2135                2140
Val Ser Phe Arg Val Gly Leu His Glu Tyr Pro Val Gly Ser Gln Leu
2145                2150                2155                2160
Pro Cys Glu Pro Glu Pro Asp Val Ala Val Leu Thr Ser Met Leu Thr
                2165                2170                2175
Asp Pro Ser His Ile Thr Ala Glu Ala Ala Gly Arg Arg Leu Ala Arg
                2180                2185                2190
Gly Ser Pro Pro Ser Val Ala Ser Ser Ser Ala Ser Gln Leu Ser Ala
                2195                2200                2205
Pro Ser Leu Lys Ala Thr Cys Thr Ala Asn His Asp Ser Pro Asp Ala
    2210                2215                2220
Glu Leu Ile Glu Ala Asn Leu Leu Trp Arg Gln Glu Met Gly Gly Asn
2225                2230                2235                2240
Ile Thr Arg Val Glu Ser Glu Asn Lys Val Val Ile Leu Asp Ser Phe
                2245                2250                2255
Asp Pro Leu Val Ala Glu Glu Asp Glu Arg Glu Ile Ser Val Pro Ala
                2260                2265                2270
Glu Ile Leu Arg Lys Ser Arg Arg Phe Ala Gln Ala Leu Pro Val Trp
            2275                2280                2285
Ala Arg Pro Asp Tyr Asn Pro Pro Leu Val Glu Thr Trp Lys Lys Pro
            2290                2295                2300
Asp Tyr Glu Pro Pro Val Val His Gly Cys Pro Leu Pro Pro Pro Lys
2305                2310                2315                2320
Ser Pro Pro Val Pro Pro Pro Arg Lys Lys Arg Thr Val Val Leu Thr
                2325                2330                2335
Glu Ser Thr Leu Ser Thr Ala Leu Ala Glu Leu Ala Xaa Arg Ser Phe
            2340                2345                2350
Gly Ser Ser Ser Thr Ser Gly Ile Thr Gly Asp Asn Thr Thr Thr Ser
            2355                2360                2365
Ser Glu Pro Ala Pro Ser Gly Cys Pro Pro Asp Ser Asp Ala Glu Ser
    2370                2375                2380
Xaa Xaa Ser Met Pro Pro Leu Glu Gly Glu Pro Gly Asp Pro Asp Leu
2385                2390                2395                2400
Ser Asp Gly Ser Trp Ser Thr Val Ser Ser Glu Ala Asn Ala Glu Asp
            2405                2410                2415
Val Val Cys Cys Ser Met Ser Tyr Ser Trp Thr Gly Ala Leu Val Thr
            2420                2425                2430
Pro Cys Ala Ala Glu Glu Gln Lys Leu Pro Ile Asn Ala Leu Ser Asn
        2435                2440                2445
Ser Leu Leu Arg His His Asn Leu Val Tyr Ser Thr Thr Ser Arg Ser
    2450                2455                2460
```

```
Ala Cys Gln Arg Gln Lys Lys Val Thr Phe Asp Arg Leu Gln Val Leu
2465                2470                2475                2480

Asp Ser His Tyr Gln Asp Val Leu Lys Glu Val Lys Ala Ala Ala Ser
            2485                2490                2495

Lys Val Lys Ala Asn Xaa Leu Ser Val Glu Glu Ala Cys Ser Leu Thr
                2500                2505                2510

Pro Pro His Ser Ala Lys Ser Lys Phe Gly Tyr Gly Ala Lys Asp Val
            2515                2520                2525

Arg Cys His Ala Arg Lys Ala Val Thr His Ile Asn Ser Val Trp Lys
                2530                2535                2540

Asp Leu Leu Glu Asp Asn Val Thr Pro Ile Asp Thr Thr Ile Met Ala
2545                2550                2555                2560

Lys Asn Glu Val Phe Cys Val Gln Pro Glu Lys Gly Gly Arg Lys Pro
                2565                2570                2575

Ala Arg Leu Ile Val Phe Pro Asp Leu Gly Val Arg Val Cys Glu Lys
            2580                2585                2590

Met Ala Leu Tyr Asp Val Val Thr Lys Leu Pro Leu Ala Val Met Gly
        2595                2600                2605

Ser Ser Tyr Gly Phe Gln Tyr Ser Pro Gly Gln Arg Val Glu Phe Leu
    2610                2615                2620

Val Gln Ala Trp Lys Ser Lys Lys Thr Pro Met Gly Phe Ser Tyr Asp
2625                2630                2635                2640

Thr Arg Cys Phe Asp Ser Thr Val Thr Glu Ser Asp Ile Arg Thr Glu
            2645                2650                2655

Glu Ala Ile Tyr Gln Cys Cys Asp Leu Asp Pro Gln Ala Arg Val Ala
            2660                2665                2670

Ile Lys Ser Leu Thr Glu Arg Leu Tyr Val Gly Gly Pro Leu Thr Asn
    2675                2680                2685

Ser Xaa Gly Glu Asn Cys Gly Tyr Arg Arg Cys Arg Ala Ser Gly Val
        2690                2695                2700

Leu Thr Thr Ser Cys Gly Asn Thr Leu Thr Cys Tyr Ile Lys Ala Arg
2705                2710                2715                2720

Ala Ala Cys Arg Ala Ala Gly Leu Gln Asp Cys Thr Met Leu Val Cys
            2725                2730                2735

Gly Asp Asp Leu Val Val Ile Cys Glu Ser Ala Gly Val Gln Glu Asp
            2740                2745                2750

Ala Ala Ser Leu Arg Ala Phe Thr Glu Ala Met Thr Arg Tyr Ser Ala
        2755                2760                2765

Pro Pro Gly Asp Pro Pro Gln Pro Glu Tyr Asp Leu Glu Leu Ile Thr
    2770                2775                2780

Ser Cys Ser Ser Asn Val Ser Val Ala His Asp Gly Ala Gly Lys Arg
2785                2790                2795                2800

Val Tyr Tyr Leu Thr Arg Asp Pro Thr Thr Pro Leu Ala Arg Ala Ala
            2805                2810                2815

Trp Glu Thr Ala Arg His Thr Pro Val Asn Ser Trp Leu Gly Asn Ile
            2820                2825                2830

Ile Met Phe Ala Pro Thr Leu Trp Ala Arg Met Ile Leu Met Thr His
        2835                2840                2845

Phe Phe Ser Val Leu Ile Ala Arg Asp Gln Leu Glu Gln Ala Leu Asp
    2850                2855                2860

Cys Glu Ile Tyr Gly Ala Cys Tyr Ser Ile Glu Pro Leu Asp Leu Pro
2865                2870                2875                2880

Pro Ile Ile Gln Arg Leu His Gly Leu Ser Ala Phe Ser Leu His Ser
```

```
                    2885            2890              2895
Tyr Ser Pro Gly Glu Ile Asn Arg Val Ala Ala Cys Leu Arg Lys Leu
                2900            2905            2910

Gly Val Pro Pro Leu Arg Ala Trp Xaa His Arg Ala Arg Ser Val Arg
            2915            2920            2925

Ala Arg Leu Leu Ala Arg Gly Gly Arg Ala Ala Ile Cys Gly Lys Tyr
        2930            2935            2940

Leu Phe Asn Trp Ala Val Arg Thr Lys Leu Lys Leu Thr Pro Ile Ala
2945            2950            2955            2960

Ala Ala Gly Gln Leu Asp Leu Ser Gly Trp Phe Thr Ala Gly Tyr Ser
            2965            2970            2975

Gly Gly Asp Ile Tyr His Ser Val Ser His Ala Arg Pro Arg Trp Ile
        2980            2985            2990

Trp Phe Cys Xaa Leu Leu Leu Ala Ala Gly Val Gly Ile Tyr Leu Leu
            2995            3000            3005

Pro Asn Arg
    3010
```

(2) INFORMATION FOR SEQ ID NO:178:

(i) SEQUENCE CHARACTERISTICS:
        (A) LENGTH: 80 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic polynucleotide
            probe"

(xi) SEQUENCE DESCRIPTION: SEQ ID NO:178:

```
TCCCTTGCTC GATGTACGGT AAGTGCTGAG AGCACTCTTC CATCTCATCG AACTCTCGGT    60

AGAGGACTTC CCTGTCAGGT                                                80
```

(2) INFORMATION FOR SEQ ID NO:179:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic polynucleotide
            probe"

(xi) SEQUENCE DESCRIPTION: SEQ ID NO:179:

```
CTGTCAGGTA TGATTGCCGG CTTCCCGGAC                                     30
```

(2) INFORMATION FOR SEQ ID NO:180:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic polynucleotide
            probe"

(xi) SEQUENCE DESCRIPTION: SEQ ID NO:180:

```
TTTGGCTAGT GGTTAGTGGG CTGGTGACAG                                     30
```

```
(2) INFORMATION FOR SEQ ID NO:181:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic polynucleotide
            probe"

(xi) SEQUENCE DESCRIPTION: SEQ ID NO:181:

AAGCCACCGT GTGCGCTAGG GCTCAAGCCC                                    30

(2) INFORMATION FOR SEQ ID NO:182:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic polynucleotide
            probe"

(xi) SEQUENCE DESCRIPTION: SEQ ID NO:182:

CAGGATGCTG TCTCCCGCAC TCAACGT                                       27

(2) INFORMATION FOR SEQ ID NO:183:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic hybridization
            probe"

(xi) SEQUENCE DESCRIPTION: SEQ ID NO:183:

AGTGCAGTGG ATGAACCGGC TGATAGCCTT                                    30

(2) INFORMATION FOR SEQ ID NO:184:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic polynucleotide
            probe"

(xi) SEQUENCE DESCRIPTION: SEQ ID NO:184:

TCCTGAGGCG ACTGCACCAG TGGATAAGCT                                    30

(2) INFORMATION FOR SEQ ID NO:185:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic polynucleotide
``` probe"

(xi) SEQUENCE DESCRIPTION: SEQ ID NO:185:

CAGGATGCTG TCTCCCGCAC TCAACGTC                                              28

(2) INFORMATION FOR SEQ ID NO:186:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic polynucleotide
            probe"

(xi) SEQUENCE DESCRIPTION: SEQ ID NO:186:

TCCTGAGGCG ACTGCACCAG TGGATAAGCT                                            30

(2) INFORMATION FOR SEQ ID NO:187:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "hybridization probe for
            isolation of clone 33c"

(xi) SEQUENCE DESCRIPTION: SEQ ID NO:187:

ATCAGGACCG GGGTGAGAAC AATTACCACT                                            30

(2) INFORMATION FOR SEQ ID NO:188:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "probe for isolation of
            clone 8h."

(xi) SEQUENCE DESCRIPTION: SEQ ID NO:188:

AGAGACAACC ATGAGGTCCC CGGTGTTC                                              28

(2) INFORMATION FOR SEQ ID NO:189:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "probe for isolation of
            clone 7e."

(xi) SEQUENCE DESCRIPTION: SEQ ID NO:189:

TCGGACCTTT ACCTGGTCAC GAGGCAC                                               27

(2) INFORMATION FOR SEQ ID NO:190:

(i) SEQUENCE CHARACTERISTICS:
        (A) LENGTH: 30 base pairs (B) TYPE: nucleic acid
        (C) STRANDEDNESS: single
        (D) TOPOLOGY: linear (ii) MOLECULE TYPE: other nucleic acid
        (A) DESCRIPTION: /desc = "probe for isolation of
            clone 14c."

(xi) SEQUENCE DESCRIPTION: SEQ ID NO:190:

ACCTTCCCCA TTAATGCCTA CACCACGGGC                                              30

(2) INFORMATION FOR SEQ ID NO:191:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "probe for isolation of
            clone 8f."

(xi) SEQUENCE DESCRIPTION: SEQ ID NO:191:

TCCATCTCTC AAGGCAACTT GCACCGCTAA                                              30

(2) INFORMATION FOR SEQ ID NO:192:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "probe for isolation of
            clone 33f."

(xi) SEQUENCE DESCRIPTION: SEQ ID NO:192:

TCCATGGCTG TCCGCTTCCA CCTCCAAAGT                                              30

(2) INFORMATION FOR SEQ ID NO:193:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "probe for isolation of
            clone 33g."

(xi) SEQUENCE DESCRIPTION: SEQ ID NO:193:

GCGACAATAC GACAACATCC TCTGAGCCCG                                              30

(2) INFORMATION FOR SEQ ID NO:194:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "probe for isolation of
            clone 7f."

(xi) SEQUENCE DESCRIPTION: SEQ ID NO:194:

AGCAGACAAG GGGCCTCCTA GGGTGCATAA T                                            31

(2) INFORMATION FOR SEQ ID NO:195:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "probe for isolation of
            clone 11b."

(xi) SEQUENCE DESCRIPTION: SEQ ID NO:195:

CACCTATGTT TATAACCATC TCACTCCTCT                                30

(2) INFORMATION FOR SEQ ID NO:196:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "probe for isolation of
            clone 14i."

(xi) SEQUENCE DESCRIPTION: SEQ ID NO:196:

CTCTGTCACC ATATTACAAG CGCTATATCA                                30

(2) INFORMATION FOR SEQ ID NO:197:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "probe for isolation of
            clone 39c."

(xi) SEQUENCE DESCRIPTION: SEQ ID NO:197:

CTCGTTGCTA CGTCACCACA ATTTGGTGTA                                30

(2) INFORMATION FOR SEQ ID NO:198:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "hybridization probe used in
            isolation of clone 12f."

(xi) SEQUENCE DESCRIPTION: SEQ ID NO:198:

TGCTTGTGGA TGATGCTACT CATATCCCAA                                30

(2) INFORMATION FOR SEQ ID NO:199:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid (A) DESCRIPTION: /desc = "hybridization probe for
              isolation of clone 35f."

(xi) SEQUENCE DESCRIPTION: SEQ ID NO:199:

AGCAGCGGCG TCAAAAGTGA AGGCTAACTT                                          30

(2) INFORMATION FOR SEQ ID NO:200:

(i) SEQUENCE CHARACTERISTICS:
          (A) LENGTH: 30 base pairs
          (B) TYPE: nucleic acid
          (C) STRANDEDNESS: single
          (D) TOPOLOGY: linear (ii) MOLECULE TYPE: other nucleic acid
          (A) DESCRIPTION: /desc = "hybridization probe for
              isolation of clone 19g."

(xi) SEQUENCE DESCRIPTION: SEQ ID NO:200:

TTCTCGTATG ATACCCGCTG CTTTGACTCC                                          30

(2) INFORMATION FOR SEQ ID NO:201:

(i) SEQUENCE CHARACTERISTICS:
          (A) LENGTH: 30 base pairs
          (B) TYPE: nucleic acid
          (C) STRANDEDNESS: single
          (D) TOPOLOGY: linear (ii) MOLECULE TYPE: other nucleic acid
          (A) DESCRIPTION: /desc = "hybridization probe for
              isolation of clone 26g."

(xi) SEQUENCE DESCRIPTION: SEQ ID NO:201:

TGTGTGGCGA CGACTTAGTC GTTATCTGTG                                          30

(2) INFORMATION FOR SEQ ID NO:202:

(i) SEQUENCE CHARACTERISTICS:
          (A) LENGTH: 30 base pairs
          (B) TYPE: nucleic acid
          (C) STRANDEDNESS: single
          (D) TOPOLOGY: linear (ii) MOLECULE TYPE: other nucleic acid
          (A) DESCRIPTION: /desc = "hybridization probe for
              isolation of clone 15e."

(xi) SEQUENCE DESCRIPTION: SEQ ID NO:202:

CACACTCCAG TCAATTCCTG GCTAGGCAAC                                          30

(2) INFORMATION FOR SEQ ID NO:203:

(i) SEQUENCE CHARACTERISTICS:
          (A) LENGTH: 15 base pairs
          (B) TYPE: nucleic acid
          (C) STRANDEDNESS: single
          (D) TOPOLOGY: linear (ii) MOLECULE TYPE: other nucleic acid
          (A) DESCRIPTION: /desc = "primer based on clone 11b."

(xi) SEQUENCE DESCRIPTION: SEQ ID NO:203:

CTGGCTTGAA GAATC                                                          15

(2) INFORMATION FOR SEQ ID NO:204:

(i) SEQUENCE CHARACTERISTICS:
          (A) LENGTH: 20 base pairs

```
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer based on clone 7e."

(xi) SEQUENCE DESCRIPTION: SEQ ID NO:204:

AGTTAGGCTG GTGATTATGC                                                 20

(2) INFORMATION FOR SEQ ID NO:205:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic polynucleotide
            probe for isolation of clone 13i."

(xi) SEQUENCE DESCRIPTION: SEQ ID NO:205:

GAACGTTGCG ATCTGGAAGA CAGGGACAGG                                      30

(2) INFORMATION FOR SEQ ID NO:206:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "probe for the isolation of
            clone 26j."

(xi) SEQUENCE DESCRIPTION: SEQ ID NO:206:

TATCAGTTAT GCCAACGGAA GCGGCCCCGA                                      30

(2) INFORMATION FOR SEQ ID NO:207:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "probe for the isolation of
            clone CA59a."

(xi) SEQUENCE DESCRIPTION: SEQ ID NO:207:

CTGGTTAGCA GGGCTTTTCT ATCACCACAA                                      30

(2) INFORMATION FOR SEQ ID NO:208:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "probe for isolation of
            clone CA84a."

(xi) SEQUENCE DESCRIPTION: SEQ ID NO:208:

AAGGTCCTGG TAGTGCTGCT GCTATTTGCC                                      30
```

(2) INFORMATION FOR SEQ ID NO:209:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "probe used for isolation of clone CA156e."

(xi) SEQUENCE DESCRIPTION: SEQ ID NO:209:

ACTGGACGAC GCAAGGTTGC AATTGCTCTA        30

(2) INFORMATION FOR SEQ ID NO:210:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "probe used for isolation of clone CA167b."

(xi) SEQUENCE DESCRIPTION: SEQ ID NO:210:

TTCGACGTCA CATCGATCTG CTTGTCGGGA        30

(2) INFORMATION FOR SEQ ID NO:211:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:211:

GGTGACGTGG GTTTC        15

(2) INFORMATION FOR SEQ ID NO:212:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic polynucleotide probe"

(xi) SEQUENCE DESCRIPTION: SEQ ID NO:212:

GGCTTTACCA CGTCACCAAT GATTGCCCTA        30

(2) INFORMATION FOR SEQ ID NO:213:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic polynucleotide probe"

(xi) SEQUENCE DESCRIPTION: SEQ ID NO:213:

TTTGGGTAAG GTCATCGATA CCCTTACGTG                                              30

(2) INFORMATION FOR SEQ ID NO:214:

(i) SEQUENCE CHARACTERISTICS:
         (A) LENGTH: 15 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "primer"

(xi) SEQUENCE DESCRIPTION: SEQ ID NO:214:

GAAGCCGCAC GTAAG                                                              15

(2) INFORMATION FOR SEQ ID NO:215:

(i) SEQUENCE CHARACTERISTICS:
         (A) LENGTH: 27 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "synthetic polynucleotide
             probe."

(xi) SEQUENCE DESCRIPTION: SEQ ID NO:215:

CCGGCGTAGG TCGCGCAATT TGGGTAA                                                 27

(2) INFORMATION FOR SEQ ID NO:216:

(i) SEQUENCE CHARACTERISTICS:
         (A) LENGTH: 30 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "synthetic probe used for
             isolation of clone CA205a."

(xi) SEQUENCE DESCRIPTION: SEQ ID NO:216:

TCAGATCGTT GGTGGAGTTT ACTTGTTGCC                                              30

(2) INFORMATION FOR SEQ ID NO:217:

(i) SEQUENCE CHARACTERISTICS:
         (A) LENGTH: 30 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "synthetic polynucleotide
             probe used for isolation of clone 18g."

(xi) SEQUENCE DESCRIPTION: SEQ ID NO:217:

CCATAGTGGT CTGCGGAACC GGTGAGTACA                                              30

(2) INFORMATION FOR SEQ ID NO:218:

(i) SEQUENCE CHARACTERISTICS:
         (A) LENGTH: 30 base pairs
         (B) TYPE: nucleic acid
         (C) STRANDEDNESS: single (D) TOPOLOGY: linear (ii) MOLECULE TYPE: other nucleic acid
        (A) DESCRIPTION: /desc = "synthetic probe used for
             isolation of clone b5a."

(xi) SEQUENCE DESCRIPTION: SEQ ID NO:218:

ATTGCGAGAT CTACGGGGCC TGCTACTCCA                               30

(2) INFORMATION FOR SEQ ID NO:219:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligo dT-primer adapter"

(xi) SEQUENCE DESCRIPTION: SEQ ID NO:219:

AATTCGCGGC CGCCATACGA TTTAGGTGAC ACTATAGAAT TTTTTTTTTT TTTT    54

(2) INFORMATION FOR SEQ ID NO:220:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer JH32"

(xi) SEQUENCE DESCRIPTION: SEQ ID NO:220:

ATAGCGGCCG CCCTCGATTG CGAGATCTAC                               30

(2) INFORMATION FOR SEQ ID NO:221:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer JH11"

(xi) SEQUENCE DESCRIPTION: SEQ ID NO:221:

AATTCGGGCG GCCGCCATAC GA                                       22

(2) INFORMATION FOR SEQ ID NO:222:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "polynucleotide probe JH34"

(xi) SEQUENCE DESCRIPTION: SEQ ID NO:222:

CTTGATCTAC CTCCAATCAT TCAAAGACTC                               30

(2) INFORMATION FOR SEQ ID NO:223:

(i) SEQUENCE CHARACTERISTICS:
        (A) LENGTH: 30 base pairs (B) TYPE: nucleic acid
            (C) STRANDEDNESS: single
            (D) TOPOLOGY: linear (ii) MOLECULE TYPE: other nucleic acid
            (A) DESCRIPTION: /desc = "synthetic probe used for
                  isolation of clone 6k."

(xi) SEQUENCE DESCRIPTION: SEQ ID NO:223:

TCTTCAACTG GGCAGTAAGA ACAAAGCTCA                                    30

(2) INFORMATION FOR SEQ ID NO:224:

(i) SEQUENCE CHARACTERISTICS:
            (A) LENGTH: 54 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "dT-primer adapter"

(xi) SEQUENCE DESCRIPTION: SEQ ID NO:224:

AATTCGCGGC CGCCATACGA TTTAGGTGAC ACTATAGAAT TTTTTTTTTT TTTT         54

(2) INFORMATION FOR SEQ ID NO:225:

(i) SEQUENCE CHARACTERISTICS:
            (A) LENGTH: 28 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "primer"

(xi) SEQUENCE DESCRIPTION: SEQ ID NO:225:

TTCGCGGCCG CTACAGCGGG GGAGACAT                                      28

(2) INFORMATION FOR SEQ ID NO:226:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "primer"

(xi) SEQUENCE DESCRIPTION: SEQ ID NO:226:

AATTCGCGGC CGCCATACGA                                               20

(2) INFORMATION FOR SEQ ID NO:227:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "probe used for isolation of
                  clone p131jh."

(xi) SEQUENCE DESCRIPTION: SEQ ID NO:227:

CGATGAAGGT TGGGGTAAAC ACTCCGGCCT                                    30

(2) INFORMATION FOR SEQ ID NO:228:

```
    (i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "linker"

(xi) SEQUENCE DESCRIPTION: SEQ ID NO:228:

GATCCTGGAA TTCTGATAAG ACCTTAAGAC TATTTTAA                              38

(2) INFORMATION FOR SEQ ID NO:229:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "adaptor in an expression
            cassette."

(xi) SEQUENCE DESCRIPTION: SEQ ID NO:229:

AATTTGGGAA TTCCATAATG AGACCCTTAA GGTATTACTC AGCT                       44

(2) INFORMATION FOR SEQ ID NO:230:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:230:

Asn Leu Gly Ile Arg
1               5

(2) INFORMATION FOR SEQ ID NO:231:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic linkers"

(xi) SEQUENCE DESCRIPTION: SEQ ID NO:231:

GATCCTGAAT TCCTGATAA                                                   19

(2) INFORMATION FOR SEQ ID NO:232:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic linker"

(xi) SEQUENCE DESCRIPTION: SEQ ID NO:232:

GACTTAAGGA CTATTTTAA                                                   19
```

(2) INFORMATION FOR SEQ ID NO:233:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic linker"

(xi) SEQUENCE DESCRIPTION: SEQ ID NO:233:

GATCCGAATT CTGTGATAA                                                  19

(2) INFORMATION FOR SEQ ID NO:234:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic linker"

(xi) SEQUENCE DESCRIPTION: SEQ ID NO:234:

GCTTAAGACA CTATTTTAA                                                  19

(2) INFORMATION FOR SEQ ID NO:235:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic linker"

(xi) SEQUENCE DESCRIPTION: SEQ ID NO:235:

GATCCTGGAA TTCTGATAA                                                  19

(2) INFORMATION FOR SEQ ID NO:236:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic linker"

(xi) SEQUENCE DESCRIPTION: SEQ ID NO:236:

GACCTTAAGA CTATTTTAA                                                  19

(2) INFORMATION FOR SEQ ID NO:237:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "adaptor for expression
            cassette"

(xi) SEQUENCE DESCRIPTION: SEQ ID NO:237:

```
ATTTTGAATT CCTAATGAGA CTTAAGGATT ACTCAGCT                            38

(2) INFORMATION FOR SEQ ID NO:238:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "adaptor for expression
            cassette"

(xi) SEQUENCE DESCRIPTION: SEQ ID NO:238:

AATTTGGAAT TCTAATGAGA CCTTAAGATT ACTCAGCT                            38

(2) INFORMATION FOR SEQ ID NO:239:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "linker for vector pS3-34."

(xi) SEQUENCE DESCRIPTION: SEQ ID NO:239:

AATTTGGAAT TCTAATTAAT TAAG                                           24

(2) INFORMATION FOR SEQ ID NO:240:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "linker for vector pS3-34"

(xi) SEQUENCE DESCRIPTION: SEQ ID NO:240:

ACCTTAAGAT TAATTAATTC AGCT                                           24

(2) INFORMATION FOR SEQ ID NO:241:

(i) SEQUENCE CHARACTERISTICS:
        (A) LENGTH: 56 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PCR primer"

(xi) SEQUENCE DESCRIPTION: SEQ ID NO:241:

GAGTGCTCAA GCTTCAAAAC AAAATGGCTC ACTTTCTATC CCAGACAAAG CAGAGT        56

(2) INFORMATION FOR SEQ ID NO:242:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PCR primer"
```

(xi) SEQUENCE DESCRIPTION: SEQ ID NO:242:

GAGTGCTCGT CGACTCATTA GGGGGAAACA TGGTTCCCCC GGGAGGCGAA        50

(2) INFORMATION FOR SEQ ID NO:243:

(i) SEQUENCE CHARACTERISTICS:
        (A) LENGTH: 59 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PCR primer"

(xi) SEQUENCE DESCRIPTION: SEQ ID NO:243:

GAGTGCTCAA GCTTCAAAAC AAAATGGGGC TCTACCACGT CACCAATGAT TGCCCTAAC        59

(2) INFORMATION FOR SEQ ID NO:244:

(i) SEQUENCE CHARACTERISTICS:
        (A) LENGTH: 53 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PCR primer"

(xi) SEQUENCE DESCRIPTION: SEQ ID NO:244:

GAGTGCTCGT CGACTCATTA AGGGGACCAG TTCATCATCA TATCCCATGC CAT        53

(2) INFORMATION FOR SEQ ID NO:245:

(i) SEQUENCE CHARACTERISTICS:
        (A) LENGTH: 53 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PCR primer"

(xi) SEQUENCE DESCRIPTION: SEQ ID NO:245:

GAGTGCAGCT TCAAAACAAA ATGAGCACGA ATCCTAAACC TCAAAAAAAA AAC        53

(2) INFORMATION FOR SEQ ID NO:246:

(i) SEQUENCE CHARACTERISTICS:
        (A) LENGTH: 53 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PCR primer"

(xi) SEQUENCE DESCRIPTION: SEQ ID NO:246:

GAGTGCTCGT CGACTCATTA ACCCAAATTG CGCGACCTAC GCCGGGGGTC TGT        53

(2) INFORMATION FOR SEQ ID NO:247:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PCR primer"

(xi) SEQUENCE DESCRIPTION: SEQ ID NO:247:

GAGTGCTCAA GCTTACAAAA CAAAATGGCA CCAGGCGCCA AGCAGAACGT CCAGCTGATC       60

(2) INFORMATION FOR SEQ ID NO:248:

(i) SEQUENCE CHARACTERISTICS:
        (A) LENGTH: 59 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PCR primer"

(xi) SEQUENCE DESCRIPTION: SEQ ID NO:248:

GAGTGCTCCT CGAGGTCGAC TCATTACTCG GACCTGTCCC TATCTTCCAG ATCGCAACG       59

(2) INFORMATION FOR SEQ ID NO:249:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PCR primer"

(xi) SEQUENCE DESCRIPTION: SEQ ID NO:249:

GGATCCGCTA GCGGCGCCAA GCAGAACGTC CAGCTGATCA ACACC       45

(2) INFORMATION FOR SEQ ID NO:250:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PCR primer"

(xi) SEQUENCE DESCRIPTION: SEQ ID NO:250:

GGATCCAAGC TTTTACTCGG ACCTGTCCCT ATCTTCCAGA TCGCAACG       48

(2) INFORMATION FOR SEQ ID NO:251:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:251:

Lys Glu Pro Gly Gly Gly Gln Ala
1            5

(2) INFORMATION FOR SEQ ID NO:252:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:252:

Glu Pro Gly Gly Gly Gln Ala Val
1               5

(2) INFORMATION FOR SEQ ID NO:253:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:253:

Pro Gly Gly Gly Gln Ala Val Gly
1               5

(2) INFORMATION FOR SEQ ID NO:254:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:254:

Gly Gly Gly Gln Ala Val Gly Gly
1               5

(2) INFORMATION FOR SEQ ID NO:255:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:255:

Gly Gly Gln Ala Val Gly Gly Val
1               5

(2) INFORMATION FOR SEQ ID NO:256:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:256:

Gly Gln Ala Val Gly Gly Val Tyr
1               5

(2) INFORMATION FOR SEQ ID NO:257:

(i) SEQUENCE CHARACTERISTICS:
        (A) LENGTH: 8 amino acids
        (B) TYPE: amino acid
        (C) STRANDEDNESS: single
        (D) TOPOLOGY: linear -continued (ii) MOLECULE TYPE: peptide (xi) SEQUENCE DESCRIPTION: SEQ ID NO:257:

Gln Ala Val Gly Gly Val Tyr Leu
1               5

(2) INFORMATION FOR SEQ ID NO:258:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:258:

Ala Val Gly Gly Val Tyr Leu Leu
1               5

(2) INFORMATION FOR SEQ ID NO:259:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:259:

Val Gly Gly Val Tyr Leu Leu Pro
1               5

(2) INFORMATION FOR SEQ ID NO:260:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:260:

Gly Gly Val Tyr Leu Leu Pro Arg
1               5

(2) INFORMATION FOR SEQ ID NO:261:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:261:

Gly Val Tyr Leu Leu Pro Arg Arg
1               5

(2) INFORMATION FOR SEQ ID NO:262:

(i) SEQUENCE CHARACTERISTICS:
        (A) LENGTH: 8 amino acids
        (B) TYPE: amino acid
        (C) STRANDEDNESS: single
        (D) TOPOLOGY: linear

```
        (ii) MOLECULE TYPE: peptide (xi) SEQUENCE DESCRIPTION: SEQ ID NO:262:

Val Tyr Leu Leu Pro Arg Arg Gly
1               5

(2) INFORMATION FOR SEQ ID NO:263:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:263:

Tyr Leu Leu Pro Arg Arg Gly Pro
1               5

(2) INFORMATION FOR SEQ ID NO:264:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:264:

Leu Leu Pro Arg Arg Gly Pro Arg
1               5

(2) INFORMATION FOR SEQ ID NO:265:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:265:

Pro Lys Ala Arg Arg Pro Glu Gly
1               5

(2) INFORMATION FOR SEQ ID NO:266:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:266:

Lys Ala Arg Arg Pro Glu Gly Arg
1               5

(2) INFORMATION FOR SEQ ID NO:267:

(i) SEQUENCE CHARACTERISTICS:
            (A) LENGTH: 8 amino acids
            (B) TYPE: amino acid
            (C) STRANDEDNESS: single
```

(D) TOPOLOGY: linear (ii) MOLECULE TYPE: peptide (xi) SEQUENCE DESCRIPTION: SEQ ID NO:267:

Ala Arg Arg Pro Glu Gly Arg Thr
1               5

(2) INFORMATION FOR SEQ ID NO:268:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:268:

Arg Arg Pro Glu Gly Arg Thr Trp
1               5

(2) INFORMATION FOR SEQ ID NO:269:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:269:

Arg Pro Glu Gly Arg Thr Trp Ala
1               5

(2) INFORMATION FOR SEQ ID NO:270:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:270:

Pro Glu Gly Arg Thr Trp Ala Gln
1               5

(2) INFORMATION FOR SEQ ID NO:271:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:271:

Glu Gly Arg Thr Trp Ala Gln Pro
1               5

(2) INFORMATION FOR SEQ ID NO:272:

(i) SEQUENCE CHARACTERISTICS:
        (A) LENGTH: 8 amino acids
        (B) TYPE: amino acid

```
            (C) STRANDEDNESS: single
            (D) TOPOLOGY: linear (ii) MOLECULE TYPE: peptide (xi) SEQUENCE DESCRIPTION: SEQ ID NO:272:

Gly Arg Thr Trp Ala Gln Pro Gly
1               5

(2) INFORMATION FOR SEQ ID NO:273:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:273:

Arg Thr Trp Ala Gln Pro Gly Tyr
1               5

(2) INFORMATION FOR SEQ ID NO:274:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:274:

Thr Trp Ala Gln Pro Gly Tyr Pro
1               5

(2) INFORMATION FOR SEQ ID NO:275:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:275:

Trp Ala Gln Pro Gly Tyr Pro Trp
1               5

(2) INFORMATION FOR SEQ ID NO:276:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:276:

Ala Gln Pro Gly Tyr Pro Trp Pro
1               5

(2) INFORMATION FOR SEQ ID NO:277:

(i) SEQUENCE CHARACTERISTICS:
            (A) LENGTH: 8 amino acids
```

```
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:277:

Gln Pro Gly Tyr Pro Trp Pro Leu
1               5

(2) INFORMATION FOR SEQ ID NO:278:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:278:

Pro Gly Tyr Pro Trp Pro Leu Gly
1               5

(2) INFORMATION FOR SEQ ID NO:279:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:279:

Gly Tyr Pro Trp Pro Leu Tyr Gly
1               5

(2) INFORMATION FOR SEQ ID NO:280:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:280:

Tyr Pro Trp Pro Leu Tyr Gly Asn
1               5

(2) INFORMATION FOR SEQ ID NO:281:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:281:

Pro Trp Pro Leu Tyr Gly Asn Glu
1               5

(2) INFORMATION FOR SEQ ID NO:282:

(i) SEQUENCE CHARACTERISTICS:
```

(A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:282:

Trp Pro Leu Tyr Gly Asn Glu Gly
1               5

(2) INFORMATION FOR SEQ ID NO:283:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:283:

Pro Leu Tyr Gly Asn Glu Gly Cys
1               5

(2) INFORMATION FOR SEQ ID NO:284:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:284:

Leu Tyr Gly Asn Glu Gly Cys Gly
1               5

(2) INFORMATION FOR SEQ ID NO:285:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:285:

Tyr Gly Asn Glu Gly Cys Gly Trp
1               5

(2) INFORMATION FOR SEQ ID NO:286:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:286:

Gly Asn Glu Gly Cys Gly Trp Ala
1               5

(2) INFORMATION FOR SEQ ID NO:287:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:287:

Asn Glu Gly Cys Gly Trp Ala Gly
1               5

(2) INFORMATION FOR SEQ ID NO:288:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:288:

Glu Gly Cys Gly Trp Ala Gly Trp
1               5

(2) INFORMATION FOR SEQ ID NO:289:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:289:

Gly Cys Gly Trp Ala Gly Trp Leu
1               5

(2) INFORMATION FOR SEQ ID NO:290:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:290:

Cys Gly Trp Ala Gly Trp Leu Leu
1               5

(2) INFORMATION FOR SEQ ID NO:291:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:291:

Gly Trp Ala Gly Trp Leu Leu Ser
1               5

(2) INFORMATION FOR SEQ ID NO:292:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:292:

Trp Ala Gly Trp Leu Leu Ser Pro
1               5

(2) INFORMATION FOR SEQ ID NO:293:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:293:

Ala Gly Trp Leu Leu Ser Pro Arg
1               5

(2) INFORMATION FOR SEQ ID NO:294:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:294:

Gly Trp Leu Leu Ser Pro Arg Gly
1               5

(2) INFORMATION FOR SEQ ID NO:295:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:295:

Trp Leu Leu Ser Pro Arg Gly Ser
1               5

(2) INFORMATION FOR SEQ ID NO:296:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:296:

Leu Leu Ser Pro Arg Gly Ser Arg
1               5

```
(2) INFORMATION FOR SEQ ID NO:297:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:297:

Leu Ser Pro Arg Gly Ser Arg Pro
1               5

(2) INFORMATION FOR SEQ ID NO:298:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:298:

Ser Pro Arg Gly Ser Arg Pro Ser
1               5

(2) INFORMATION FOR SEQ ID NO:299:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:299:

Pro Arg Gly Ser Arg Pro Ser Trp
1               5

(2) INFORMATION FOR SEQ ID NO:300:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:300:

Arg Gly Ser Arg Pro Ser Trp Gly
1               5

(2) INFORMATION FOR SEQ ID NO:301:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:301:

Gly Ser Arg Pro Ser Trp Gly Pro
1               5
```

```
(2) INFORMATION FOR SEQ ID NO:302:

(i) SEQUENCE CHARACTERISTICS:
         (A) LENGTH: 8 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO:302:

Ser Arg Pro Ser Trp Gly Pro Thr
1               5

(2) INFORMATION FOR SEQ ID NO:303:

(i) SEQUENCE CHARACTERISTICS:
         (A) LENGTH: 8 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO:303:

Thr Val Pro Ala Ser Ala Tyr Gln
1               5

(2) INFORMATION FOR SEQ ID NO:304:

(i) SEQUENCE CHARACTERISTICS:
         (A) LENGTH: 8 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO:304:

Val Pro Ala Ser Ala Tyr Gln Val
1               5

(2) INFORMATION FOR SEQ ID NO:305:

(i) SEQUENCE CHARACTERISTICS:
         (A) LENGTH: 8 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO:305:

Pro Ala Ser Ala Tyr Gln Val Arg
1               5

(2) INFORMATION FOR SEQ ID NO:306:

(i) SEQUENCE CHARACTERISTICS:
         (A) LENGTH: 8 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO:306:

Ala Ser Ala Tyr Gln Val Arg Asn
1               5
```

(2) INFORMATION FOR SEQ ID NO:307:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:307:

Ser Ala Tyr Gln Val Arg Asn Ser
1               5

(2) INFORMATION FOR SEQ ID NO:308:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:308:

Ala Tyr Gln Val Arg Asn Ser Thr
1               5

(2) INFORMATION FOR SEQ ID NO:309:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:309:

Asp Cys Pro Asn Ser Ser Ile Val
1               5

(2) INFORMATION FOR SEQ ID NO:310:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:310:

Thr Pro Gly Cys Val Pro Cys Val
1               5

(2) INFORMATION FOR SEQ ID NO:311:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:311:

Glu Gly Asn Ala Ser Arg Cys Trp

```
1               5
```

(2) INFORMATION FOR SEQ ID NO:312:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:312:

```
Thr Gln Leu Arg Arg His Ile Asp
1               5
```

(2) INFORMATION FOR SEQ ID NO:313:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:313:

```
Leu Val Gly Gln Leu Phe Thr Phe
1               5
```

(2) INFORMATION FOR SEQ ID NO:314:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:314:

```
Arg His Trp Thr Thr Gln Gly Cys
1               5
```

(2) INFORMATION FOR SEQ ID NO:315:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:315:

```
His Trp Thr Thr Gln Gly Cys Asn
1               5
```

(2) INFORMATION FOR SEQ ID NO:316:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:316:

```
Trp Thr Thr Gln Gly Cys Asn Cys
1               5
```

(2) INFORMATION FOR SEQ ID NO:317:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:317:

```
Met Met Met Asn Trp Ser Pro Ile
1               5
```

(2) INFORMATION FOR SEQ ID NO:318:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:318:

```
Asp Met Ile Ala Gly Ala His Trp
1               5
```

(2) INFORMATION FOR SEQ ID NO:319:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:319:

```
Leu Ala Gly Ile Ala Tyr Phe Ser
1               5
```

(2) INFORMATION FOR SEQ ID NO:320:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:320:

```
Leu Ile Asn Thr Asn Gly Ser Trp
1               5
```

(2) INFORMATION FOR SEQ ID NO:321:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:321:

```
Ile Asn Thr Asn Gly Ser Trp His
1               5
```

(2) INFORMATION FOR SEQ ID NO:322:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:322:

```
Ser Leu Asn Thr Gly Trp Leu Ala
1               5
```

(2) INFORMATION FOR SEQ ID NO:323:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:323:

```
Phe Asp Gln Gly Trp Gly Pro Ile
1               5
```

(2) INFORMATION FOR SEQ ID NO:324:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:324:

```
Asp Gln Gly Trp Gly Pro Ile Ser
1               5
```

(2) INFORMATION FOR SEQ ID NO:325:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:325:

```
Gln Gly Trp Gly Pro Ile Ser Tyr
1               5
```

(2) INFORMATION FOR SEQ ID NO:326:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:326:

Gly Trp Gly Pro Ile Ser Tyr Ala
1               5

(2) INFORMATION FOR SEQ ID NO:327:

(i) SEQUENCE CHARACTERISTICS:
       (A) LENGTH: 8 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO:327:

Trp Gly Pro Ile Ser Tyr Ala Asn
1               5

(2) INFORMATION FOR SEQ ID NO:328:

(i) SEQUENCE CHARACTERISTICS:
       (A) LENGTH: 8 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO:328:

Gly Pro Ile Ser Tyr Ala Asn Gly
1               5

(2) INFORMATION FOR SEQ ID NO:329:

(i) SEQUENCE CHARACTERISTICS:
       (A) LENGTH: 8 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO:329:

Pro Ile Ser Tyr Ala Asn Gly Ser
1               5

(2) INFORMATION FOR SEQ ID NO:330:

(i) SEQUENCE CHARACTERISTICS:
       (A) LENGTH: 8 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO:330:

Pro Asp Gln Arg Pro Tyr Cys Trp
1               5

(2) INFORMATION FOR SEQ ID NO:331:

(i) SEQUENCE CHARACTERISTICS:
       (A) LENGTH: 8 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO:331:

Asp Gln Arg Pro Tyr Cys Trp His
1               5

(2) INFORMATION FOR SEQ ID NO:332:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:332:

Gln Arg Pro Tyr Cys Trp His Tyr
1               5

(2) INFORMATION FOR SEQ ID NO:333:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:333:

Arg Pro Tyr Cys Trp His Tyr Pro
1               5

(2) INFORMATION FOR SEQ ID NO:334:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:334:

Pro Tyr Cys Trp His Tyr Pro Pro
1               5

(2) INFORMATION FOR SEQ ID NO:335:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:335:

Lys Ser Val Cys Gly Pro Val Tyr
1               5

(2) INFORMATION FOR SEQ ID NO:336:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:336:

Ser Val Cys Gly Pro Val Tyr Cys
1               5

(2) INFORMATION FOR SEQ ID NO:337:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:337:

Val Cys Gly Pro Val Tyr Cys Glu
1               5

(2) INFORMATION FOR SEQ ID NO:338:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:338:

Arg Ser Gly Ala Pro Thr Tyr Ser
1               5

(2) INFORMATION FOR SEQ ID NO:339:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:339:

Asn Asn Thr Arg Pro Pro Leu Gly
1               5

(2) INFORMATION FOR SEQ ID NO:340:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:340:

Asn Thr Arg Pro Pro Leu Gly Asn
1               5

(2) INFORMATION FOR SEQ ID NO:341:

(i) SEQUENCE CHARACTERISTICS:
            (A) LENGTH: 8 amino acids
            (B) TYPE: amino acid
            (C) STRANDEDNESS: single
            (D) TOPOLOGY: linear

```
        (ii) MOLECULE TYPE: peptide (xi) SEQUENCE DESCRIPTION: SEQ ID NO:341:

Thr Arg Pro Pro Leu Gly Asn Trp
1               5

(2) INFORMATION FOR SEQ ID NO:342:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:342:

Arg Pro Pro Leu Gly Asn Trp Phe
1               5

(2) INFORMATION FOR SEQ ID NO:343:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:343:

Pro Pro Leu Gly Asn Trp Phe Gly
1               5

(2) INFORMATION FOR SEQ ID NO:344:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:344:

Pro Leu Gly Asn Trp Phe Gly Cys
1               5

(2) INFORMATION FOR SEQ ID NO:345:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:345:

Leu Gly Asn Trp Phe Gly Cys Thr
1               5

(2) INFORMATION FOR SEQ ID NO:346:

(i) SEQUENCE CHARACTERISTICS:
            (A) LENGTH: 8 amino acids
            (B) TYPE: amino acid
            (C) STRANDEDNESS: single
```

```
            (D) TOPOLOGY: linear (ii) MOLECULE TYPE: peptide (xi) SEQUENCE DESCRIPTION: SEQ ID NO:346:

Gly Asn Trp Phe Gly Cys Thr Trp
1               5

(2) INFORMATION FOR SEQ ID NO:347:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:347:

Asn Trp Phe Gly Cys Thr Trp Met
1               5

(2) INFORMATION FOR SEQ ID NO:348:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:348:

Trp Phe Gly Cys Thr Trp Met Asn
1               5

(2) INFORMATION FOR SEQ ID NO:349:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:349:

Leu His Cys Pro Thr Asp Cys Phe
1               5

(2) INFORMATION FOR SEQ ID NO:350:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:350:

Tyr Ser Arg Cys Gly Ser Gly Pro
1               5

(2) INFORMATION FOR SEQ ID NO:351:

(i) SEQUENCE CHARACTERISTICS:
            (A) LENGTH: 8 amino acids
            (B) TYPE: amino acid
```

(C) STRANDEDNESS: single
            (D) TOPOLOGY: linear (ii) MOLECULE TYPE: peptide (xi) SEQUENCE DESCRIPTION: SEQ ID NO:351:

Ser Arg Cys Gly Ser Gly Pro Trp
1               5

(2) INFORMATION FOR SEQ ID NO:352:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:352:

Arg Cys Gly Ser Gly Pro Trp Leu
1               5

(2) INFORMATION FOR SEQ ID NO:353:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:353:

Cys Gly Ser Gly Pro Trp Leu Thr
1               5

(2) INFORMATION FOR SEQ ID NO:354:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:354:

Gly Ser Gly Pro Trp Leu Thr Pro
1               5

(2) INFORMATION FOR SEQ ID NO:355:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:355:

Ser Gly Pro Trp Leu Thr Pro Arg
1               5

(2) INFORMATION FOR SEQ ID NO:356:

(i) SEQUENCE CHARACTERISTICS:
            (A) LENGTH: 8 amino acids

```
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:356:

Gly Pro Trp Leu Thr Pro Arg Cys
1               5

(2) INFORMATION FOR SEQ ID NO:357:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:357:

Pro Trp Leu Thr Pro Arg Cys Leu
1               5

(2) INFORMATION FOR SEQ ID NO:358:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:358:

Trp Leu Thr Pro Arg Cys Leu Val
1               5

(2) INFORMATION FOR SEQ ID NO:359:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:359:

Leu Thr Pro Arg Cys Leu Val Asp
1               5

(2) INFORMATION FOR SEQ ID NO:360:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:360:

Thr Pro Arg Cys Leu Val Asp Tyr
1               5

(2) INFORMATION FOR SEQ ID NO:361:

(i) SEQUENCE CHARACTERISTICS:
```

```
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:361:

Pro Arg Cys Leu Val Asp Tyr Pro
1               5

(2) INFORMATION FOR SEQ ID NO:362:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:362:

Arg Cys Leu Val Asp Tyr Pro Tyr
1               5

(2) INFORMATION FOR SEQ ID NO:363:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:363:

Cys Leu Val Asp Tyr Pro Tyr Arg
1               5

(2) INFORMATION FOR SEQ ID NO:364:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:364:

Leu Val Asp Tyr Pro Tyr Arg Leu
1               5

(2) INFORMATION FOR SEQ ID NO:365:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:365:

Val Asp Tyr Pro Tyr Arg Leu Trp
1               5

(2) INFORMATION FOR SEQ ID NO:366:
```

```
        (i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:366:

Asp Tyr Pro Tyr Arg Leu Trp His
1               5

(2) INFORMATION FOR SEQ ID NO:367:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:367:

Tyr Pro Tyr Arg Leu Trp His Tyr
1               5

(2) INFORMATION FOR SEQ ID NO:368:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:368:

Pro Tyr Arg Leu Trp His Tyr Pro
1               5

(2) INFORMATION FOR SEQ ID NO:369:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:369:

Tyr Arg Leu Trp His Tyr Pro Cys
1               5

(2) INFORMATION FOR SEQ ID NO:370:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:370:

Glu Ala Ala Cys Asn Trp Thr Arg
1               5

(2) INFORMATION FOR SEQ ID NO:371:
```

-continued

```
    (i) SEQUENCE CHARACTERISTICS:
         (A) LENGTH: 8 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO:371:

Leu Ser Pro Leu Leu Leu Ile Ile
1               5

(2) INFORMATION FOR SEQ ID NO:372:

(i) SEQUENCE CHARACTERISTICS:
         (A) LENGTH: 8 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO:372:

Ser Pro Leu Leu Leu Ile Ile Ile
1               5

(2) INFORMATION FOR SEQ ID NO:373:

(i) SEQUENCE CHARACTERISTICS:
         (A) LENGTH: 8 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO:373:

Pro Leu Leu Leu Ile Ile Ile Gln
1               5

(2) INFORMATION FOR SEQ ID NO:374:

(i) SEQUENCE CHARACTERISTICS:
         (A) LENGTH: 8 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO:374:

Leu Leu Leu Ile Ile Ile Gln Trp
1               5

(2) INFORMATION FOR SEQ ID NO:375:

(i) SEQUENCE CHARACTERISTICS:
         (A) LENGTH: 8 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO:375:

Leu Ser Thr Gly Leu Ile His Leu
1               5
```

```
(2) INFORMATION FOR SEQ ID NO:376:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:376:

Val Gly Ser Ser Ile Ala Ser Trp
1               5

(2) INFORMATION FOR SEQ ID NO:377:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:377:

Gly Ser Ser Ile Ala Ser Trp Ala
1               5

(2) INFORMATION FOR SEQ ID NO:378:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:378:

Ala Arg Val Cys Ser Cys Ile Trp
1               5

(2) INFORMATION FOR SEQ ID NO:379:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:379:

Trp Val Pro Gly Ala Val Tyr Thr
1               5

(2) INFORMATION FOR SEQ ID NO:380:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:380:

Val Pro Gly Ala Val Tyr Thr Phe
1               5
```

(2) INFORMATION FOR SEQ ID NO:381:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:381:

```
Pro Gly Ala Val Tyr Thr Phe Tyr
1               5
```

(2) INFORMATION FOR SEQ ID NO:382:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:382:

```
Gly Ala Val Tyr Thr Phe Tyr Gly
1               5
```

(2) INFORMATION FOR SEQ ID NO:383:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:383:

```
Ala Val Tyr Thr Phe Tyr Gly Met
1               5
```

(2) INFORMATION FOR SEQ ID NO:384:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:384:

```
Val Tyr Thr Phe Tyr Gly Met Trp
1               5
```

(2) INFORMATION FOR SEQ ID NO:385:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:385:

```
Tyr Thr Phe Tyr Gly Met Trp Pro
1               5
```

(2) INFORMATION FOR SEQ ID NO:386:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:386:

Thr Phe Tyr Gly Met Trp Pro Leu
1               5

(2) INFORMATION FOR SEQ ID NO:387:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:387:

Leu Ala Leu Pro Gln Arg Ala Tyr
1               5

(2) INFORMATION FOR SEQ ID NO:388:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:388:

Arg Val Glu Ala Gln Leu His Val
1               5

(2) INFORMATION FOR SEQ ID NO:389:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:389:

Val Glu Ala Gln Leu His Val Trp
1               5

(2) INFORMATION FOR SEQ ID NO:390:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:390:

Glu Ala Gln Leu His Val Trp Ile

```
1               5
```

(2) INFORMATION FOR SEQ ID NO:391:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:391:

```
Ala Gln Leu His Val Trp Ile Pro
1               5
```

(2) INFORMATION FOR SEQ ID NO:392:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:392:

```
Gln Leu His Val Trp Ile Pro Pro
1               5
```

(2) INFORMATION FOR SEQ ID NO:393:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:393:

```
Leu Ala Val Phe Gly Pro Leu Trp
1               5
```

(2) INFORMATION FOR SEQ ID NO:394:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:394:

```
Gln Gly Leu Leu Arg Phe Cys Ala
1               5
```

(2) INFORMATION FOR SEQ ID NO:395:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:395:

```
Met Ile Gly Gly His Tyr Val Gln
1               5

(2) INFORMATION FOR SEQ ID NO:396:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:396:

Thr Gly Thr Tyr Val Tyr Asn His
1               5

(2) INFORMATION FOR SEQ ID NO:397:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:397:

Asn His Leu Thr Pro Leu Arg Asp
1               5

(2) INFORMATION FOR SEQ ID NO:398:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:398:

His Leu Thr Pro Leu Arg Asp Trp
1               5

(2) INFORMATION FOR SEQ ID NO:399:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:399:

Leu Thr Pro Leu Arg Asp Trp Ala
1               5

(2) INFORMATION FOR SEQ ID NO:400:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:400:
```

```
Leu Ala Pro Ile Thr Ala Tyr Ala
1               5
```

(2) INFORMATION FOR SEQ ID NO:401:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:401:

```
Thr Cys Ile Asn Gly Val Cys Trp
1               5
```

(2) INFORMATION FOR SEQ ID NO:402:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:402:

```
Leu Val Gly Trp Pro Ala Pro Gln
1               5
```

(2) INFORMATION FOR SEQ ID NO:403:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:403:

```
Cys Pro Ala Gly His Ala Val Gly
1               5
```

(2) INFORMATION FOR SEQ ID NO:404:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:404:

```
Pro Ala Gly His Ala Val Gly Ile
1               5
```

(2) INFORMATION FOR SEQ ID NO:405:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:405:

Ala Gly His Ala Val Gly Ile Phe
1               5

(2) INFORMATION FOR SEQ ID NO:406:

(i) SEQUENCE CHARACTERISTICS:
          (A) LENGTH: 8 amino acids
          (B) TYPE: amino acid
          (C) STRANDEDNESS: single
          (D) TOPOLOGY: linear (ii) MOLECULE TYPE: peptide (xi) SEQUENCE DESCRIPTION: SEQ ID NO:406:

Gly His Ala Val Gly Ile Phe Arg
1               5

(2) INFORMATION FOR SEQ ID NO:407:

(i) SEQUENCE CHARACTERISTICS:
          (A) LENGTH: 8 amino acids
          (B) TYPE: amino acid
          (C) STRANDEDNESS: single
          (D) TOPOLOGY: linear (ii) MOLECULE TYPE: peptide (xi) SEQUENCE DESCRIPTION: SEQ ID NO:407:

His Ala Val Gly Ile Phe Arg Ala
1               5

(2) INFORMATION FOR SEQ ID NO:408:

(i) SEQUENCE CHARACTERISTICS:
          (A) LENGTH: 8 amino acids
          (B) TYPE: amino acid
          (C) STRANDEDNESS: single
          (D) TOPOLOGY: linear (ii) MOLECULE TYPE: peptide (xi) SEQUENCE DESCRIPTION: SEQ ID NO:408:

Ala Val Gly Ile Phe Arg Ala Ala
1               5

(2) INFORMATION FOR SEQ ID NO:409:

(i) SEQUENCE CHARACTERISTICS:
          (A) LENGTH: 8 amino acids
          (B) TYPE: amino acid
          (C) STRANDEDNESS: single
          (D) TOPOLOGY: linear (ii) MOLECULE TYPE: peptide (xi) SEQUENCE DESCRIPTION: SEQ ID NO:409:

Val Val Pro Gln Ser Glu Gln Val
1               5

(2) INFORMATION FOR SEQ ID NO:410:

(i) SEQUENCE CHARACTERISTICS:
          (A) LENGTH: 8 amino acids
          (B) TYPE: amino acid
          (C) STRANDEDNESS: single
          (D) TOPOLOGY: linear (ii) MOLECULE TYPE: peptide (xi) SEQUENCE DESCRIPTION: SEQ ID NO:410:

Val Pro Ala Ala Tyr Ala Ala Gln
1               5

(2) INFORMATION FOR SEQ ID NO:411:

(i) SEQUENCE CHARACTERISTICS:
             (A) LENGTH: 8 amino acids
             (B) TYPE: amino acid
             (C) STRANDEDNESS: single
             (D) TOPOLOGY: linear (ii) MOLECULE TYPE: peptide (xi) SEQUENCE DESCRIPTION: SEQ ID NO:411:

Ala Thr Leu Gly Phe Gly Ala Tyr
1               5

(2) INFORMATION FOR SEQ ID NO:412:

(i) SEQUENCE CHARACTERISTICS:
             (A) LENGTH: 8 amino acids
             (B) TYPE: amino acid
             (C) STRANDEDNESS: single
             (D) TOPOLOGY: linear (ii) MOLECULE TYPE: peptide (xi) SEQUENCE DESCRIPTION: SEQ ID NO:412:

Gly Val Arg Ile Thr Thr Gly Ser
1               5

(2) INFORMATION FOR SEQ ID NO:413:

(i) SEQUENCE CHARACTERISTICS:
             (A) LENGTH: 8 amino acids
             (B) TYPE: amino acid
             (C) STRANDEDNESS: single
             (D) TOPOLOGY: linear (ii) MOLECULE TYPE: peptide (xi) SEQUENCE DESCRIPTION: SEQ ID NO:413:

Val Arg Ile Thr Thr Gly Ser Pro
1               5

(2) INFORMATION FOR SEQ ID NO:414:

(i) SEQUENCE CHARACTERISTICS:
             (A) LENGTH: 8 amino acids
             (B) TYPE: amino acid
             (C) STRANDEDNESS: single
             (D) TOPOLOGY: linear (ii) MOLECULE TYPE: peptide (xi) SEQUENCE DESCRIPTION: SEQ ID NO:414:

Arg Ile Thr Thr Gly Ser Pro Ile
1               5

(2) INFORMATION FOR SEQ ID NO:415:

(i) SEQUENCE CHARACTERISTICS:
             (A) LENGTH: 8 amino acids
             (B) TYPE: amino acid
             (C) STRANDEDNESS: single
             (D) TOPOLOGY: linear -continued

```
        (ii) MOLECULE TYPE: peptide (xi) SEQUENCE DESCRIPTION: SEQ ID NO:415:

Ile Thr Thr Gly Ser Pro Ile Thr
1               5

(2) INFORMATION FOR SEQ ID NO:416:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:416:

Thr Thr Gly Ser Pro Ile Thr Tyr
1               5

(2) INFORMATION FOR SEQ ID NO:417:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:417:

Thr Gly Ser Pro Ile Thr Tyr Gly
1               5

(2) INFORMATION FOR SEQ ID NO:418:

(i) SEQUENCE CHARACTERISTICS:
            (A) LENGTH: 7 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:418:

Asp Ala Thr Ser Ile Leu Gly
1               5

(2) INFORMATION FOR SEQ ID NO:419:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:419:

Thr Ala Gly Ala Arg Leu Val Val
1               5

(2) INFORMATION FOR SEQ ID NO:420:

(i) SEQUENCE CHARACTERISTICS:
            (A) LENGTH: 8 amino acids
            (B) TYPE: amino acid
            (C) STRANDEDNESS: single
            (D) TOPOLOGY: linear
```

(ii) MOLECULE TYPE: peptide (xi) SEQUENCE DESCRIPTION: SEQ ID NO:420:

Gly Glu Ile Pro Phe Tyr Gly Lys
1               5

(2) INFORMATION FOR SEQ ID NO:421:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:421:

Val Ile Lys Gly Gly Arg His Leu
1               5

(2) INFORMATION FOR SEQ ID NO:422:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:422:

Leu Gly Ile Asn Ala Val Ala Tyr
1               5

(2) INFORMATION FOR SEQ ID NO:423:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:423:

Gly Ile Asn Ala Val Ala Tyr Tyr
1               5

(2) INFORMATION FOR SEQ ID NO:424:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:424:

Cys Asn Thr Cys Val Ile Gln Thr
1               5

(2) INFORMATION FOR SEQ ID NO:425:

(i) SEQUENCE CHARACTERISTICS:
            (A) LENGTH: 8 amino acids
            (B) TYPE: amino acid
            (C) STRANDEDNESS: single (D) TOPOLOGY: linear (ii) MOLECULE TYPE: peptide (xi) SEQUENCE DESCRIPTION: SEQ ID NO:425:

Gly Arg Gly Lys Pro Gly Ile Tyr
1               5

(2) INFORMATION FOR SEQ ID NO:426:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:426:

Arg Gly Lys Pro Gly Ile Tyr Arg
1               5

(2) INFORMATION FOR SEQ ID NO:427:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:427:

Pro Ala Glu Thr Thr Val Arg Leu
1               5

(2) INFORMATION FOR SEQ ID NO:428:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:428:

Ala Glu Thr Thr Val Arg Leu Arg
1               5

(2) INFORMATION FOR SEQ ID NO:429:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:429:

Glu Thr Thr Val Arg Leu Arg Ala
1               5

(2) INFORMATION FOR SEQ ID NO:430:

(i) SEQUENCE CHARACTERISTICS:
        (A) LENGTH: 8 amino acids
        (B) TYPE: amino acid

```
        (C) STRANDEDNESS: single
        (D) TOPOLOGY: linear (ii) MOLECULE TYPE: peptide (xi) SEQUENCE DESCRIPTION: SEQ ID NO:430:

Thr Thr Val Arg Leu Arg Ala Tyr
1               5

(2) INFORMATION FOR SEQ ID NO:431:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:431:

Gly Val Phe Ile Gly Leu Ile His
1               5

(2) INFORMATION FOR SEQ ID NO:432:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:432:

Val Phe Ile Gly Leu Ile His Ile
1               5

(2) INFORMATION FOR SEQ ID NO:433:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:433:

Glu Asn Leu Pro Tyr Leu Val Ala
1               5

(2) INFORMATION FOR SEQ ID NO:434:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:434:

Asn Leu Pro Tyr Leu Val Ala Tyr
1               5

(2) INFORMATION FOR SEQ ID NO:435:

(i) SEQUENCE CHARACTERISTICS:
        (A) LENGTH: 8 amino acids
```

```
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:435:

Leu Pro Tyr Leu Val Ala Tyr Gln
1               5

(2) INFORMATION FOR SEQ ID NO:436:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:436:

Pro Tyr Leu Val Ala Tyr Gln Ala
1               5

(2) INFORMATION FOR SEQ ID NO:437:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:437:

Tyr Leu Val Ala Tyr Gln Ala Thr
1               5

(2) INFORMATION FOR SEQ ID NO:438:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:438:

Leu Val Ala Tyr Gln Ala Thr Val
1               5

(2) INFORMATION FOR SEQ ID NO:439:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:439:

Val Ala Tyr Gln Ala Thr Val Cys
1               5

(2) INFORMATION FOR SEQ ID NO:440:

(i) SEQUENCE CHARACTERISTICS:
```

(A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:440:

Ala Tyr Gln Ala Thr Val Cys Ala
1               5

(2) INFORMATION FOR SEQ ID NO:441:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:441:

Tyr Gln Ala Thr Val Cys Ala Arg
1               5

(2) INFORMATION FOR SEQ ID NO:442:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:442:

Gln Ala Thr Val Cys Ala Arg Gln
1               5

(2) INFORMATION FOR SEQ ID NO:443:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:443:

Ala Thr Val Cys Ala Arg Gln Ala
1               5

(2) INFORMATION FOR SEQ ID NO:444:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:444:

Thr Val Cys Ala Arg Gln Ala Pro
1               5

(2) INFORMATION FOR SEQ ID NO:445:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:445:

Pro Pro Ser Trp Asp Gln Met Trp
1               5

(2) INFORMATION FOR SEQ ID NO:446:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:446:

Pro Ser Trp Asp Gln Met Trp Lys
1               5

(2) INFORMATION FOR SEQ ID NO:447:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:447:

Ser Trp Asp Gln Met Trp Lys Cys
1               5

(2) INFORMATION FOR SEQ ID NO:448:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:448:

Trp Asp Gln Met Trp Lys Cys Leu
1               5

(2) INFORMATION FOR SEQ ID NO:449:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:449:

Asp Gln Met Trp Lys Cys Leu Ile
1               5

(2) INFORMATION FOR SEQ ID NO:450:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:450:

Gln Met Trp Lys Cys Leu Ile Arg
1               5

(2) INFORMATION FOR SEQ ID NO:451:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:451:

Met Trp Lys Cys Leu Ile Arg Leu
1               5

(2) INFORMATION FOR SEQ ID NO:452:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:452:

Lys Pro Thr Leu His Gly Pro Ile
1               5

(2) INFORMATION FOR SEQ ID NO:453:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:453:

Pro Thr Leu His Gly Pro Ile Pro
1               5

(2) INFORMATION FOR SEQ ID NO:454:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:454:

Thr Leu His Gly Pro Ile Pro Leu
1               5

-continued

```
(2) INFORMATION FOR SEQ ID NO:455:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:455:

Leu His Gly Pro Ile Pro Leu Leu
1               5

(2) INFORMATION FOR SEQ ID NO:456:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:456:

His Gly Pro Ile Pro Leu Leu Tyr
1               5

(2) INFORMATION FOR SEQ ID NO:457:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:457:

Gly Pro Ile Pro Leu Leu Tyr Arg
1               5

(2) INFORMATION FOR SEQ ID NO:458:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:458:

Val Val Thr Ser Thr Trp Val Leu
1               5

(2) INFORMATION FOR SEQ ID NO:459:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:459:

Ile Ile Pro Asp Arg Glu Val Leu
1               5
```

-continued (2) INFORMATION FOR SEQ ID NO:460:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:460:

Ile Pro Asp Arg Glu Val Leu Tyr
1               5

(2) INFORMATION FOR SEQ ID NO:461:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:461:

Glu Cys Ser Gln His Leu Pro Tyr
1               5

(2) INFORMATION FOR SEQ ID NO:462:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:462:

Cys Ser Gln His Leu Pro Tyr Ile
1               5

(2) INFORMATION FOR SEQ ID NO:463:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:463:

Ser Gln His Leu Pro Tyr Ile Glu
1               5

(2) INFORMATION FOR SEQ ID NO:464:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:464:

Glu Lys Gln Lys Ala Leu Gly Leu
1               5

(2) INFORMATION FOR SEQ ID NO:465:

(i) SEQUENCE CHARACTERISTICS:
           (A) LENGTH: 8 amino acids
           (B) TYPE: amino acid
           (C) STRANDEDNESS: single
           (D) TOPOLOGY: linear (ii) MOLECULE TYPE: peptide (xi) SEQUENCE DESCRIPTION: SEQ ID NO:465:

Lys Gln Lys Ala Leu Gly Leu Leu
1               5

(2) INFORMATION FOR SEQ ID NO:466:

(i) SEQUENCE CHARACTERISTICS:
           (A) LENGTH: 8 amino acids
           (B) TYPE: amino acid
           (C) STRANDEDNESS: single
           (D) TOPOLOGY: linear (ii) MOLECULE TYPE: peptide (xi) SEQUENCE DESCRIPTION: SEQ ID NO:466:

Glu Ile Glu Trp Ala Lys Leu Met
1               5

(2) INFORMATION FOR SEQ ID NO:467:

(i) SEQUENCE CHARACTERISTICS:
           (A) LENGTH: 8 amino acids
           (B) TYPE: amino acid
           (C) STRANDEDNESS: single
           (D) TOPOLOGY: linear (ii) MOLECULE TYPE: peptide (xi) SEQUENCE DESCRIPTION: SEQ ID NO:467:

Ile Glu Trp Ala Lys Leu Met Trp
1               5

(2) INFORMATION FOR SEQ ID NO:468:

(i) SEQUENCE CHARACTERISTICS:
           (A) LENGTH: 8 amino acids
           (B) TYPE: amino acid
           (C) STRANDEDNESS: single
           (D) TOPOLOGY: linear (ii) MOLECULE TYPE: peptide (xi) SEQUENCE DESCRIPTION: SEQ ID NO:468:

Glu Trp Ala Lys Leu Met Trp Asn
1               5

(2) INFORMATION FOR SEQ ID NO:469:

(i) SEQUENCE CHARACTERISTICS:
           (A) LENGTH: 8 amino acids
           (B) TYPE: amino acid
           (C) STRANDEDNESS: single
           (D) TOPOLOGY: linear (ii) MOLECULE TYPE: peptide (xi) SEQUENCE DESCRIPTION: SEQ ID NO:469:

Trp Ala Lys Leu Met Trp Asn Glu

```
1               5

(2) INFORMATION FOR SEQ ID NO:470:

(i) SEQUENCE CHARACTERISTICS:
         (A) LENGTH: 8 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO:470:

Ala Lys Leu Met Trp Asn Glu Ile
1               5

(2) INFORMATION FOR SEQ ID NO:471:

(i) SEQUENCE CHARACTERISTICS:
         (A) LENGTH: 8 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO:471:

Leu Pro Gly Asn Pro Ala Ile Ala
1               5

(2) INFORMATION FOR SEQ ID NO:472:

(i) SEQUENCE CHARACTERISTICS:
         (A) LENGTH: 8 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO:472:

Leu Phe Asn Ile Leu Gly Gly Trp
1               5

(2) INFORMATION FOR SEQ ID NO:473:

(i) SEQUENCE CHARACTERISTICS:
         (A) LENGTH: 8 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO:473:

Ala Ala Pro Gly Ala Ala Thr Ala
1               5

(2) INFORMATION FOR SEQ ID NO:474:

(i) SEQUENCE CHARACTERISTICS:
         (A) LENGTH: 8 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO:474:
```

```
Ile Leu Ala Gly Tyr Gly Ala Gly
1               5

(2) INFORMATION FOR SEQ ID NO:475:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:475:

Val Asn Leu Leu Pro Ala Ile Leu
1               5

(2) INFORMATION FOR SEQ ID NO:476:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:476:

Pro Gly Glu Gly Ala Val Gln Trp
1               5

(2) INFORMATION FOR SEQ ID NO:477:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:477:

Gly Glu Gly Ala Val Gln Trp Met
1               5

(2) INFORMATION FOR SEQ ID NO:478:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:478:

Glu Gly Ala Val Gln Trp Met Asn
1               5

(2) INFORMATION FOR SEQ ID NO:479:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:479:
```

```
Gly Ala Val Gln Trp Met Asn Arg
1               5
```

(2) INFORMATION FOR SEQ ID NO:480:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:480:

```
Ala Val Gln Trp Met Asn Arg Leu
1               5
```

(2) INFORMATION FOR SEQ ID NO:481:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:481:

```
Val Gln Trp Met Asn Arg Leu Ile
1               5
```

(2) INFORMATION FOR SEQ ID NO:482:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:482:

```
Arg Gly Asn His Val Ser Pro Ile
1               5
```

(2) INFORMATION FOR SEQ ID NO:483:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:483:

```
Ala Ala Ala Arg Val Thr Ala Ile
1               5
```

(2) INFORMATION FOR SEQ ID NO:484:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:484:

Ala Ala Arg Val Thr Ala Ile Leu
1               5

(2) INFORMATION FOR SEQ ID NO:485:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:485:

Ala Arg Val Thr Ala Ile Leu Ser
1               5

(2) INFORMATION FOR SEQ ID NO:486:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:486:

Arg Val Thr Ala Ile Leu Ser Ser
1               5

(2) INFORMATION FOR SEQ ID NO:487:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:487:

Val Thr Ala Ile Leu Ser Ser Leu
1               5

(2) INFORMATION FOR SEQ ID NO:488:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:488:

Thr Ala Ile Leu Ser Ser Leu Val
1               5

(2) INFORMATION FOR SEQ ID NO:489:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:489:

Ala Ile Leu Ser Ser Leu Val Thr
1               5

(2) INFORMATION FOR SEQ ID NO:490:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:490:

Ile Leu Ser Ser Leu Val Thr Gln
1               5

(2) INFORMATION FOR SEQ ID NO:491:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:491:

Leu Ser Ser Leu Val Thr Gln Leu
1               5

(2) INFORMATION FOR SEQ ID NO:492:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:492:

Ser Ser Leu Val Thr Gln Leu Leu
1               5

(2) INFORMATION FOR SEQ ID NO:493:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:493:

Ser Leu Val Thr Gln Leu Leu Arg
1               5

(2) INFORMATION FOR SEQ ID NO:494:

(i) SEQUENCE CHARACTERISTICS:
        (A) LENGTH: 8 amino acids
        (B) TYPE: amino acid
        (C) STRANDEDNESS: single
        (D) TOPOLOGY: linear

```
        (ii) MOLECULE TYPE: peptide (xi) SEQUENCE DESCRIPTION: SEQ ID NO:494:

Leu Val Thr Gln Leu Leu Arg Arg
1               5

(2) INFORMATION FOR SEQ ID NO:495:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:495:

Ser Glu Cys Thr Ile Pro Cys Ser
1               5

(2) INFORMATION FOR SEQ ID NO:496:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:496:

Glu Cys Thr Ile Pro Cys Ser Gly
1               5

(2) INFORMATION FOR SEQ ID NO:497:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:497:

Cys Thr Ile Pro Cys Ser Gly Ser
1               5

(2) INFORMATION FOR SEQ ID NO:498:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:498:

Thr Ile Pro Cys Ser Gly Ser Trp
1               5

(2) INFORMATION FOR SEQ ID NO:499:

(i) SEQUENCE CHARACTERISTICS:
            (A) LENGTH: 8 amino acids
            (B) TYPE: amino acid
            (C) STRANDEDNESS: single
            (D) TOPOLOGY: linear
```

```
        (ii) MOLECULE TYPE: peptide (xi) SEQUENCE DESCRIPTION: SEQ ID NO:499:

Leu Met Pro Gln Leu Pro Gly Ile
1               5

(2) INFORMATION FOR SEQ ID NO:500:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:500:

Met Pro Gln Leu Pro Gly Ile Pro
1               5

(2) INFORMATION FOR SEQ ID NO:501:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:501:

Pro Gln Leu Pro Gly Ile Pro Glu
1               5

(2) INFORMATION FOR SEQ ID NO:502:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:502:

Gln Leu Pro Gly Ile Pro Glu Val
1               5

(2) INFORMATION FOR SEQ ID NO:503:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:503:

Leu Pro Gly Ile Pro Glu Val Ser
1               5

(2) INFORMATION FOR SEQ ID NO:504:

(i) SEQUENCE CHARACTERISTICS:
            (A) LENGTH: 8 amino acids
            (B) TYPE: amino acid
            (C) STRANDEDNESS: single
```

```
            (D) TOPOLOGY: linear (ii) MOLECULE TYPE: peptide (xi) SEQUENCE DESCRIPTION: SEQ ID NO:504:

Pro Gly Ile Pro Glu Val Ser Cys
1               5

(2) INFORMATION FOR SEQ ID NO:505:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:505:

Gly Ile Pro Glu Val Ser Cys Gln
1               5

(2) INFORMATION FOR SEQ ID NO:506:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:506:

Ile Pro Glu Val Ser Cys Gln Arg
1               5

(2) INFORMATION FOR SEQ ID NO:507:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:507:

Pro Glu Val Ser Cys Gln Arg Gly
1               5

(2) INFORMATION FOR SEQ ID NO:508:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:508:

Glu Val Ser Cys Gln Arg Gly Tyr
1               5

(2) INFORMATION FOR SEQ ID NO:509:

(i) SEQUENCE CHARACTERISTICS:
            (A) LENGTH: 8 amino acids
            (B) TYPE: amino acid
```

```
        (C) STRANDEDNESS: single
        (D) TOPOLOGY: linear (ii) MOLECULE TYPE: peptide (xi) SEQUENCE DESCRIPTION: SEQ ID NO:509:

Val Ser Cys Gln Arg Gly Tyr Lys
1               5

(2) INFORMATION FOR SEQ ID NO:510:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:510:

Ser Cys Gln Arg Gly Tyr Lys Gly
1               5

(2) INFORMATION FOR SEQ ID NO:511:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:511:

Cys Gln Arg Gly Tyr Lys Gly Val
1               5

(2) INFORMATION FOR SEQ ID NO:512:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:512:

Gln Arg Gly Tyr Lys Gly Val Trp
1               5

(2) INFORMATION FOR SEQ ID NO:513:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:513:

Arg Gly Tyr Lys Gly Val Trp Arg
1               5

(2) INFORMATION FOR SEQ ID NO:514:

(i) SEQUENCE CHARACTERISTICS:
        (A) LENGTH: 8 amino acids
```

```
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:514:

Gly Tyr Lys Gly Val Trp Arg Gly
1               5

(2) INFORMATION FOR SEQ ID NO:515:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:515:

Ile Met His Thr Arg Cys His Cys
1               5

(2) INFORMATION FOR SEQ ID NO:516:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:516:

Val Gly Pro Arg Ile Cys Arg Asn
1               5

(2) INFORMATION FOR SEQ ID NO:517:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:517:

Gly Pro Arg Ile Cys Arg Asn Tyr
1               5

(2) INFORMATION FOR SEQ ID NO:518:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:518:

Pro Arg Ile Cys Arg Asn Tyr Trp
1               5

(2) INFORMATION FOR SEQ ID NO:519:

(i) SEQUENCE CHARACTERISTICS:
```

(A) LENGTH: 8 amino acids
          (B) TYPE: amino acid
          (C) STRANDEDNESS: single
          (D) TOPOLOGY: linear (ii) MOLECULE TYPE: peptide (xi) SEQUENCE DESCRIPTION: SEQ ID NO:519:

Arg Ile Cys Arg Asn Tyr Trp Ser
1               5

(2) INFORMATION FOR SEQ ID NO:520:

(i) SEQUENCE CHARACTERISTICS:
          (A) LENGTH: 8 amino acids
          (B) TYPE: amino acid
          (C) STRANDEDNESS: single
          (D) TOPOLOGY: linear (ii) MOLECULE TYPE: peptide (xi) SEQUENCE DESCRIPTION: SEQ ID NO:520:

Ile Cys Arg Asn Tyr Trp Ser Gly
1               5

(2) INFORMATION FOR SEQ ID NO:521:

(i) SEQUENCE CHARACTERISTICS:
          (A) LENGTH: 8 amino acids
          (B) TYPE: amino acid
          (C) STRANDEDNESS: single
          (D) TOPOLOGY: linear (ii) MOLECULE TYPE: peptide (xi) SEQUENCE DESCRIPTION: SEQ ID NO:521:

Cys Arg Asn Tyr Trp Ser Gly Thr
1               5

(2) INFORMATION FOR SEQ ID NO:522:

(i) SEQUENCE CHARACTERISTICS:
          (A) LENGTH: 8 amino acids
          (B) TYPE: amino acid
          (C) STRANDEDNESS: single
          (D) TOPOLOGY: linear (ii) MOLECULE TYPE: peptide (xi) SEQUENCE DESCRIPTION: SEQ ID NO:522:

Arg Asn Tyr Trp Ser Gly Thr Glu
1               5

(2) INFORMATION FOR SEQ ID NO:523:

(i) SEQUENCE CHARACTERISTICS:
          (A) LENGTH: 8 amino acids
          (B) TYPE: amino acid
          (C) STRANDEDNESS: single
          (D) TOPOLOGY: linear (ii) MOLECULE TYPE: peptide (xi) SEQUENCE DESCRIPTION: SEQ ID NO:523:

Asn Tyr Trp Ser Gly Thr Glu Pro
1               5

(2) INFORMATION FOR SEQ ID NO:524:

```
        (i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:524:

Tyr Trp Ser Gly Thr Glu Pro Ile
1               5

(2) INFORMATION FOR SEQ ID NO:525:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:525:

Trp Ser Gly Thr Glu Pro Ile Asn
1               5

(2) INFORMATION FOR SEQ ID NO:526:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:526:

Thr Pro Leu Pro Ala Pro Asn Tyr
1               5

(2) INFORMATION FOR SEQ ID NO:527:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:527:

Glu Glu Tyr Val Ile Arg Gln Val
1               5

(2) INFORMATION FOR SEQ ID NO:528:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:528:

Glu Tyr Val Ile Arg Gln Val Gly
1               5

(2) INFORMATION FOR SEQ ID NO:529:
```

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:529:

Tyr Val Ile Arg Gln Val Gly Asp
1               5

(2) INFORMATION FOR SEQ ID NO:530:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:530:

Val Ile Arg Gln Val Gly Asp Phe
1               5

(2) INFORMATION FOR SEQ ID NO:531:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:531:

Ile Arg Gln Val Gly Asp Phe His
1               5

(2) INFORMATION FOR SEQ ID NO:532:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:532:

Arg Gln Val Gly Asp Phe His Tyr
1               5

(2) INFORMATION FOR SEQ ID NO:533:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:533:

Asp Asn Leu Lys Cys Pro Cys Gln
1               5

```
(2) INFORMATION FOR SEQ ID NO:534:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:534:

Glu Ile Glu Leu Asp Gly Val Arg
1               5

(2) INFORMATION FOR SEQ ID NO:535:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:535:

Ile Glu Leu Asp Gly Val Arg Leu
1               5

(2) INFORMATION FOR SEQ ID NO:536:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:536:

Glu Leu Asp Gly Val Arg Leu His
1               5

(2) INFORMATION FOR SEQ ID NO:537:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:537:

Leu Asp Gly Val Arg Leu His Arg
1               5

(2) INFORMATION FOR SEQ ID NO:538:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:538:

Asp Gly Val Arg Leu His Arg Phe
1               5
```

(2) INFORMATION FOR SEQ ID NO:539:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:539:

Gly Val Arg Leu His Arg Phe Ala
1               5

(2) INFORMATION FOR SEQ ID NO:540:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:540:

Val Arg Leu His Arg Phe Ala Pro
1               5

(2) INFORMATION FOR SEQ ID NO:541:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:541:

Arg Leu His Arg Phe Ala Pro Pro
1               5

(2) INFORMATION FOR SEQ ID NO:542:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:542:

Leu His Arg Phe Ala Pro Pro Cys
1               5

(2) INFORMATION FOR SEQ ID NO:543:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:543:

His Arg Phe Ala Pro Pro Cys Lys
1               5

(2) INFORMATION FOR SEQ ID NO:544:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:544:

Arg Phe Ala Pro Pro Cys Lys Pro
1               5

(2) INFORMATION FOR SEQ ID NO:545:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:545:

Phe Ala Pro Pro Cys Lys Pro Leu
1               5

(2) INFORMATION FOR SEQ ID NO:546:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:546:

Ala Pro Pro Cys Lys Pro Leu Leu
1               5

(2) INFORMATION FOR SEQ ID NO:547:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:547:

Pro Pro Cys Lys Pro Leu Leu Arg
1               5

(2) INFORMATION FOR SEQ ID NO:548:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:548:

Pro Cys Lys Pro Leu Leu Arg Glu

```
1               5
```

(2) INFORMATION FOR SEQ ID NO:549:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:549:

```
Cys Lys Pro Leu Leu Arg Glu Glu
1               5
```

(2) INFORMATION FOR SEQ ID NO:550:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:550:

```
Lys Pro Leu Leu Arg Glu Glu Val
1               5
```

(2) INFORMATION FOR SEQ ID NO:551:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:551:

```
Pro Leu Leu Arg Glu Glu Val Ser
1               5
```

(2) INFORMATION FOR SEQ ID NO:552:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:552:

```
Leu Leu Arg Glu Glu Val Ser Phe
1               5
```

(2) INFORMATION FOR SEQ ID NO:553:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:553:

```
Leu Arg Glu Glu Val Ser Phe Arg
1               5

(2) INFORMATION FOR SEQ ID NO:554:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:554:

Arg Glu Glu Val Ser Phe Arg Val
1               5

(2) INFORMATION FOR SEQ ID NO:555:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:555:

Glu Glu Val Ser Phe Arg Val Gly
1               5

(2) INFORMATION FOR SEQ ID NO:556:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:556:

Glu Val Ser Phe Arg Val Gly Leu
1               5

(2) INFORMATION FOR SEQ ID NO:557:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:557:

Val Ser Phe Arg Val Gly Leu His
1               5

(2) INFORMATION FOR SEQ ID NO:558:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:558:
```

```
Ser Phe Arg Val Gly Leu His Glu
1               5
```

(2) INFORMATION FOR SEQ ID NO:559:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:559:

```
Phe Arg Val Gly Leu His Glu Tyr
1               5
```

(2) INFORMATION FOR SEQ ID NO:560:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:560:

```
Arg Val Gly Leu His Glu Tyr Pro
1               5
```

(2) INFORMATION FOR SEQ ID NO:561:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:561:

```
Glu Pro Glu Pro Asp Val Ala Val
1               5
```

(2) INFORMATION FOR SEQ ID NO:562:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:562:

```
Gly Arg Arg Leu Ala Arg Gly Ser
1               5
```

(2) INFORMATION FOR SEQ ID NO:563:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:563:

Leu Ile Glu Ala Asn Leu Leu Trp
1               5

(2) INFORMATION FOR SEQ ID NO:564:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:564:

Ile Glu Ala Asn Leu Leu Trp Arg
1               5

(2) INFORMATION FOR SEQ ID NO:565:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:565:

Glu Ala Asn Leu Leu Trp Arg Gln
1               5

(2) INFORMATION FOR SEQ ID NO:566:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:566:

Ala Asn Leu Leu Trp Arg Gln Glu
1               5

(2) INFORMATION FOR SEQ ID NO:567:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:567:

Asn Leu Leu Trp Arg Gln Glu Met
1               5

(2) INFORMATION FOR SEQ ID NO:568:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:568:

Leu Leu Trp Arg Gln Glu Met Gly
1               5

(2) INFORMATION FOR SEQ ID NO:569:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:569:

Leu Trp Arg Gln Glu Met Gly Gly
1               5

(2) INFORMATION FOR SEQ ID NO:570:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:570:

Val Glu Ser Glu Asn Lys Val Val
1               5

(2) INFORMATION FOR SEQ ID NO:571:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:571:

Glu Ser Glu Asn Lys Val Val Ile
1               5

(2) INFORMATION FOR SEQ ID NO:572:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:572:

Ser Glu Asn Lys Val Val Ile Leu
1               5

(2) INFORMATION FOR SEQ ID NO:573:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:573:

Glu Asn Lys Val Val Ile Leu Asp
1               5

(2) INFORMATION FOR SEQ ID NO:574:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:574:

Asn Lys Val Val Ile Leu Asp Ser
1               5

(2) INFORMATION FOR SEQ ID NO:575:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:575:

Lys Val Val Ile Leu Asp Ser Phe
1               5

(2) INFORMATION FOR SEQ ID NO:576:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:576:

Val Val Ile Leu Asp Ser Phe Asp
1               5

(2) INFORMATION FOR SEQ ID NO:577:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:577:

Glu Ile Ser Val Pro Ala Glu Ile
1               5

(2) INFORMATION FOR SEQ ID NO:578:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:578:

Arg Glu Ala Gln Ala Leu Pro Val
1               5

(2) INFORMATION FOR SEQ ID NO:579:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:579:

Glu Ala Gln Ala Leu Pro Val Trp
1               5

(2) INFORMATION FOR SEQ ID NO:580:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:580:

Ala Gln Ala Leu Pro Val Trp Ala
1               5

(2) INFORMATION FOR SEQ ID NO:581:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:581:

Gln Ala Leu Pro Val Trp Ala Arg
1               5

(2) INFORMATION FOR SEQ ID NO:582:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:582:

Ala Leu Pro Val Trp Ala Arg Pro
1               5

(2) INFORMATION FOR SEQ ID NO:583:

(i) SEQUENCE CHARACTERISTICS:
        (A) LENGTH: 8 amino acids
        (B) TYPE: amino acid
        (C) STRANDEDNESS: single

```
        (D) TOPOLOGY: linear (ii) MOLECULE TYPE: peptide (xi) SEQUENCE DESCRIPTION: SEQ ID NO:583:

Leu Pro Val Trp Ala Arg Pro Asp
1               5

(2) INFORMATION FOR SEQ ID NO:584:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:584:

Pro Val Trp Ala Arg Pro Asp Tyr
1               5

(2) INFORMATION FOR SEQ ID NO:585:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:585:

Val Trp Ala Arg Pro Asp Tyr Asn
1               5

(2) INFORMATION FOR SEQ ID NO:586:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:586:

Trp Ala Arg Pro Asp Tyr Asn Pro
1               5

(2) INFORMATION FOR SEQ ID NO:587:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:587:

Ala Arg Pro Asp Tyr Asn Pro Pro
1               5

(2) INFORMATION FOR SEQ ID NO:588:

(i) SEQUENCE CHARACTERISTICS:
        (A) LENGTH: 8 amino acids
        (B) TYPE: amino acid
```

```
          (C) STRANDEDNESS: single
          (D) TOPOLOGY: linear (ii) MOLECULE TYPE: peptide (xi) SEQUENCE DESCRIPTION: SEQ ID NO:588:

Arg Pro Asp Tyr Asn Pro Pro Leu
1               5

(2) INFORMATION FOR SEQ ID NO:589:

(i) SEQUENCE CHARACTERISTICS:
          (A) LENGTH: 8 amino acids
          (B) TYPE: amino acid
          (C) STRANDEDNESS: single
          (D) TOPOLOGY: linear (ii) MOLECULE TYPE: peptide (xi) SEQUENCE DESCRIPTION: SEQ ID NO:589:

Pro Pro Pro Arg Lys Lys Arg Thr
1               5

(2) INFORMATION FOR SEQ ID NO:590:

(i) SEQUENCE CHARACTERISTICS:
          (A) LENGTH: 8 amino acids
          (B) TYPE: amino acid
          (C) STRANDEDNESS: single
          (D) TOPOLOGY: linear (ii) MOLECULE TYPE: peptide (xi) SEQUENCE DESCRIPTION: SEQ ID NO:590:

Pro Pro Arg Lys Lys Arg Thr Val
1               5

(2) INFORMATION FOR SEQ ID NO:591:

(i) SEQUENCE CHARACTERISTICS:
          (A) LENGTH: 8 amino acids
          (B) TYPE: amino acid
          (C) STRANDEDNESS: single
          (D) TOPOLOGY: linear (ii) MOLECULE TYPE: peptide (xi) SEQUENCE DESCRIPTION: SEQ ID NO:591:

Pro Arg Lys Lys Arg Thr Val Val
1               5

(2) INFORMATION FOR SEQ ID NO:592:

(i) SEQUENCE CHARACTERISTICS:
          (A) LENGTH: 8 amino acids
          (B) TYPE: amino acid
          (C) STRANDEDNESS: single
          (D) TOPOLOGY: linear (ii) MOLECULE TYPE: peptide (xi) SEQUENCE DESCRIPTION: SEQ ID NO:592:

Ala Glu Leu Ala Ser Arg Ser Glu
1               5

(2) INFORMATION FOR SEQ ID NO:593:

(i) SEQUENCE CHARACTERISTICS:
          (A) LENGTH: 8 amino acids
```

```
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:593:

Glu Leu Ala Ser Arg Ser Glu Gly
1               5

(2) INFORMATION FOR SEQ ID NO:594:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:594:

Leu Ala Ser Arg Ser Glu Gly Ser
1               5

(2) INFORMATION FOR SEQ ID NO:595:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:595:

Ala Ser Arg Ser Glu Gly Ser Ser
1               5

(2) INFORMATION FOR SEQ ID NO:596:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:596:

Ser Arg Ser Glu Gly Ser Ser Ser
1               5

(2) INFORMATION FOR SEQ ID NO:597:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:597:

Ala Glu Ser Tyr Ser Ser Met Pro
1               5

(2) INFORMATION FOR SEQ ID NO:598:

(i) SEQUENCE CHARACTERISTICS:
```

(A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:598:

Ser Asp Gly Ser Trp Ser Thr Val
1               5

(2) INFORMATION FOR SEQ ID NO:599:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:599:

Val Val Cys Cys Ser Met Ser Tyr
1               5

(2) INFORMATION FOR SEQ ID NO:600:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:600:

Val Cys Cys Ser Met Ser Tyr Trp
1               5

(2) INFORMATION FOR SEQ ID NO:601:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:601:

Cys Cys Ser Met Ser Tyr Trp Ile
1               5

(2) INFORMATION FOR SEQ ID NO:602:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:602:

Cys Ser Met Ser Tyr Trp Ile Gly
1               5

(2) INFORMATION FOR SEQ ID NO:603:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:603:

Ser Met Ser Tyr Trp Ile Gly Ala
1               5

(2) INFORMATION FOR SEQ ID NO:604:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:604:

Met Ser Tyr Trp Ile Gly Ala Leu
1               5

(2) INFORMATION FOR SEQ ID NO:605:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:605:

Gln Lys Leu Pro Ile Asn Ala Leu
1               5

(2) INFORMATION FOR SEQ ID NO:606:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:606:

Lys Leu Pro Ile Asn Ala Leu Ser
1               5

(2) INFORMATION FOR SEQ ID NO:607:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:607:

Leu Pro Ile Asn Ala Leu Ser Asn
1               5

(2) INFORMATION FOR SEQ ID NO:608:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:608:

Pro Ile Asn Ala Leu Ser Asn Ser
1               5

(2) INFORMATION FOR SEQ ID NO:609:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:609:

Ile Asn Ala Leu Ser Asn Ser Leu
1               5

(2) INFORMATION FOR SEQ ID NO:610:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:610:

Asn Ala Leu Ser Asn Ser Leu Leu
1               5

(2) INFORMATION FOR SEQ ID NO:611:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:611:

Ala Leu Ser Asn Ser Leu Leu Arg
1               5

(2) INFORMATION FOR SEQ ID NO:612:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:612:

Leu Ser Asn Ser Leu Leu Arg His
1               5

(2) INFORMATION FOR SEQ ID NO:613:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:613:

Ser Asn Ser Leu Leu Arg His His
1               5

(2) INFORMATION FOR SEQ ID NO:614:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:614:

Asn Ser Leu Leu Arg His His Asn
1               5

(2) INFORMATION FOR SEQ ID NO:615:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:615:

Ser Leu Leu Arg His His Asn Leu
1               5

(2) INFORMATION FOR SEQ ID NO:616:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:616:

Leu Leu Arg His His Asn Leu Val
1               5

(2) INFORMATION FOR SEQ ID NO:617:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:617:

Leu Arg His His Asn Leu Val Tyr
1               5

(2) INFORMATION FOR SEQ ID NO:618:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:618:

Arg His His Asn Leu Val Tyr Ser
1               5

(2) INFORMATION FOR SEQ ID NO:619:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:619:

His His Asn Leu Val Tyr Ser Thr
1               5

(2) INFORMATION FOR SEQ ID NO:620:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:620:

His Asn Leu Val Tyr Ser Thr Ile
1               5

(2) INFORMATION FOR SEQ ID NO:621:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:621:

Asn Leu Val Tyr Ser Thr Ile Ser
1               5

(2) INFORMATION FOR SEQ ID NO:622:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:622:

Leu Val Tyr Ser Thr Ile Ser Arg
1               5

(2) INFORMATION FOR SEQ ID NO:623:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:623:

Gln Lys Lys Val Thr Phe Asp Arg
1               5

(2) INFORMATION FOR SEQ ID NO:624:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:624:

Lys Lys Val Thr Phe Asp Arg Leu
1               5

(2) INFORMATION FOR SEQ ID NO:625:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:625:

Lys Val Thr Phe Asp Arg Leu Gln
1               5

(2) INFORMATION FOR SEQ ID NO:626:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:626:

Val Thr Phe Asp Arg Leu Gln Val
1               5

(2) INFORMATION FOR SEQ ID NO:627:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:627:

Thr Phe Asp Arg Leu Gln Val Leu

-continued

```
1               5

(2) INFORMATION FOR SEQ ID NO:628:

(i) SEQUENCE CHARACTERISTICS:
         (A) LENGTH: 8 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO:628:

Phe Asp Arg Leu Gln Val Leu Asp
1               5

(2) INFORMATION FOR SEQ ID NO:629:

(i) SEQUENCE CHARACTERISTICS:
         (A) LENGTH: 8 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO:629:

Asp Arg Leu Gln Val Leu Asp Ser
1               5

(2) INFORMATION FOR SEQ ID NO:630:

(i) SEQUENCE CHARACTERISTICS:
         (A) LENGTH: 8 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO:630:

Arg Leu Gln Val Leu Asp Ser His
1               5

(2) INFORMATION FOR SEQ ID NO:631:

(i) SEQUENCE CHARACTERISTICS:
         (A) LENGTH: 8 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO:631:

Ala Ser Lys Val Lys Ala Asn Leu
1               5

(2) INFORMATION FOR SEQ ID NO:632:

(i) SEQUENCE CHARACTERISTICS:
         (A) LENGTH: 8 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO:632:
```

```
Arg Lys Ala Val Thr His Ile Asn
1               5

(2) INFORMATION FOR SEQ ID NO:633:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:633:

Lys Ala Val Thr His Ile Asn Ser
1               5

(2) INFORMATION FOR SEQ ID NO:634:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:634:

Gly Arg Lys Pro Ala Arg Leu Ile
1               5

(2) INFORMATION FOR SEQ ID NO:635:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:635:

Arg Lys Pro Ala Arg Leu Ile Val
1               5

(2) INFORMATION FOR SEQ ID NO:636:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:636:

Lys Pro Ala Arg Leu Ile Val Phe
1               5

(2) INFORMATION FOR SEQ ID NO:637:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:637:
```

Pro Ala Arg Leu Ile Val Phe Pro
1               5

(2) INFORMATION FOR SEQ ID NO:638:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:638:

Ala Arg Leu Ile Val Phe Pro Asp
1               5

(2) INFORMATION FOR SEQ ID NO:639:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:639:

Arg Leu Ile Val Phe Pro Asp Leu
1               5

(2) INFORMATION FOR SEQ ID NO:640:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:640:

Leu Pro Leu Ala Val Met Gly Ser
1               5

(2) INFORMATION FOR SEQ ID NO:641:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:641:

Pro Leu Ala Val Met Gly Ser Ser
1               5

(2) INFORMATION FOR SEQ ID NO:642:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:642:

Leu Ala Val Met Gly Ser Ser Tyr
1               5

(2) INFORMATION FOR SEQ ID NO:643:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:643:

Ala Val Met Gly Ser Ser Tyr Gly
1               5

(2) INFORMATION FOR SEQ ID NO:644:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:644:

Val Met Gly Ser Ser Tyr Gly Glu
1               5

(2) INFORMATION FOR SEQ ID NO:645:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:645:

Met Gly Ser Ser Tyr Gly Glu Gln
1               5

(2) INFORMATION FOR SEQ ID NO:646:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:646:

Gly Ser Ser Tyr Gly Glu Gln Arg
1               5

(2) INFORMATION FOR SEQ ID NO:647:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:647:

Ser Ser Tyr Gly Glu Gln Arg Val
1               5

(2) INFORMATION FOR SEQ ID NO:648:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:648:

Ser Tyr Gly Glu Gln Arg Val Glu
1               5

(2) INFORMATION FOR SEQ ID NO:649:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:649:

Tyr Gly Glu Gln Arg Val Glu Glu
1               5

(2) INFORMATION FOR SEQ ID NO:650:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:650:

Gly Glu Gln Arg Val Glu Glu Leu
1               5

(2) INFORMATION FOR SEQ ID NO:651:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:651:

Lys Thr Pro Met Gly Phe Ser Tyr
1               5

(2) INFORMATION FOR SEQ ID NO:652:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:652:

Thr Pro Met Gly Phe Ser Tyr Asp
1               5

(2) INFORMATION FOR SEQ ID NO:653:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:653:

Pro Met Gly Phe Ser Tyr Asp Thr
1               5

(2) INFORMATION FOR SEQ ID NO:654:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:654:

Met Gly Phe Ser Tyr Asp Thr Arg
1               5

(2) INFORMATION FOR SEQ ID NO:655:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:655:

Gly Phe Ser Tyr Asp Thr Arg Cys
1               5

(2) INFORMATION FOR SEQ ID NO:656:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:656:

Phe Ser Tyr Asp Thr Arg Cys Glu
1               5

(2) INFORMATION FOR SEQ ID NO:657:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:657:

Ser Tyr Asp Thr Arg Cys Glu Asp
1               5

(2) INFORMATION FOR SEQ ID NO:658:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:658:

Tyr Gln Cys Cys Asp Leu Asp Pro
1               5

(2) INFORMATION FOR SEQ ID NO:659:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:659:

Leu Thr Glu Arg Leu Tyr Val Gly
1               5

(2) INFORMATION FOR SEQ ID NO:660:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:660:

Thr Glu Arg Leu Tyr Val Gly Gly
1               5

(2) INFORMATION FOR SEQ ID NO:661:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:661:

Glu Arg Leu Tyr Val Gly Gly Pro
1               5

(2) INFORMATION FOR SEQ ID NO:662:

(i) SEQUENCE CHARACTERISTICS:
            (A) LENGTH: 8 amino acids
            (B) TYPE: amino acid
            (C) STRANDEDNESS: single (D) TOPOLOGY: linear (ii) MOLECULE TYPE: peptide (xi) SEQUENCE DESCRIPTION: SEQ ID NO:662:

Arg Leu Tyr Val Gly Gly Pro Leu
1               5

(2) INFORMATION FOR SEQ ID NO:663:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:663:

Asn Ser Arg Gly Glu Asn Cys Gly
1               5

(2) INFORMATION FOR SEQ ID NO:664:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:664:

Ser Arg Gly Glu Asn Cys Gly Tyr
1               5

(2) INFORMATION FOR SEQ ID NO:665:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:665:

Arg Gly Glu Asn Cys Gly Tyr Arg
1               5

(2) INFORMATION FOR SEQ ID NO:666:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:666:

Gly Glu Asn Cys Gly Tyr Arg Arg
1               5

(2) INFORMATION FOR SEQ ID NO:667:

(i) SEQUENCE CHARACTERISTICS:
        (A) LENGTH: 8 amino acids
        (B) TYPE: amino acid

```
          (C) STRANDEDNESS: single
          (D) TOPOLOGY: linear (ii) MOLECULE TYPE: peptide (xi) SEQUENCE DESCRIPTION: SEQ ID NO:667:

Glu Asn Cys Gly Tyr Arg Arg Cys
1               5

(2) INFORMATION FOR SEQ ID NO:668:

(i) SEQUENCE CHARACTERISTICS:
          (A) LENGTH: 8 amino acids
          (B) TYPE: amino acid
          (C) STRANDEDNESS: single
          (D) TOPOLOGY: linear (ii) MOLECULE TYPE: peptide (xi) SEQUENCE DESCRIPTION: SEQ ID NO:668:

Asn Cys Gly Tyr Arg Arg Cys Arg
1               5

(2) INFORMATION FOR SEQ ID NO:669:

(i) SEQUENCE CHARACTERISTICS:
          (A) LENGTH: 8 amino acids
          (B) TYPE: amino acid
          (C) STRANDEDNESS: single
          (D) TOPOLOGY: linear (ii) MOLECULE TYPE: peptide (xi) SEQUENCE DESCRIPTION: SEQ ID NO:669:

Thr Ser Cys Gly Asn Thr Leu Ile
1               5

(2) INFORMATION FOR SEQ ID NO:670:

(i) SEQUENCE CHARACTERISTICS:
          (A) LENGTH: 8 amino acids
          (B) TYPE: amino acid
          (C) STRANDEDNESS: single
          (D) TOPOLOGY: linear (ii) MOLECULE TYPE: peptide (xi) SEQUENCE DESCRIPTION: SEQ ID NO:670:

Ala Ala Cys Arg Ala Ala Gly Leu
1               5

(2) INFORMATION FOR SEQ ID NO:671:

(i) SEQUENCE CHARACTERISTICS:
          (A) LENGTH: 8 amino acids
          (B) TYPE: amino acid
          (C) STRANDEDNESS: single
          (D) TOPOLOGY: linear (ii) MOLECULE TYPE: peptide (xi) SEQUENCE DESCRIPTION: SEQ ID NO:671:

Ala Phe Thr Glu Ala Met Thr Arg
1               5

(2) INFORMATION FOR SEQ ID NO:672:

(i) SEQUENCE CHARACTERISTICS:
          (A) LENGTH: 8 amino acids
```

```
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:672:

Phe Thr Glu Ala Met Thr Arg Tyr
1               5

(2) INFORMATION FOR SEQ ID NO:673:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:673:

Thr Glu Ala Met Thr Arg Tyr Ser
1               5

(2) INFORMATION FOR SEQ ID NO:674:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:674:

Glu Ala Met Thr Arg Tyr Ser Ala
1               5

(2) INFORMATION FOR SEQ ID NO:675:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:675:

Ala Met Thr Arg Tyr Ser Ala Pro
1               5

(2) INFORMATION FOR SEQ ID NO:676:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:676:

Met Thr Arg Tyr Ser Ala Pro Pro
1               5

(2) INFORMATION FOR SEQ ID NO:677:

(i) SEQUENCE CHARACTERISTICS:
```

```
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:677:

Asp Leu Glu Leu Ile Ile Ser Cys
1               5

(2) INFORMATION FOR SEQ ID NO:678:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:678:

Leu Glu Leu Ile Ile Ser Cys Ser
1               5

(2) INFORMATION FOR SEQ ID NO:679:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:679:

His Asp Gly Ala Gly Lys Arg Val
1               5

(2) INFORMATION FOR SEQ ID NO:680:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:680:

Asp Gly Ala Gly Lys Arg Val Tyr
1               5

(2) INFORMATION FOR SEQ ID NO:681:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:681:

Gly Ala Gly Lys Arg Val Tyr Tyr
1               5

(2) INFORMATION FOR SEQ ID NO:682:
```

```
    (i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:682:

Ala Gly Lys Arg Val Tyr Tyr Leu
1               5

(2) INFORMATION FOR SEQ ID NO:683:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:683:

Gly Lys Arg Val Tyr Tyr Leu Thr
1               5

(2) INFORMATION FOR SEQ ID NO:684:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:684:

Lys Arg Val Tyr Tyr Leu Thr Arg
1               5

(2) INFORMATION FOR SEQ ID NO:685:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:685:

Arg Val Tyr Tyr Leu Thr Arg Asp
1               5

(2) INFORMATION FOR SEQ ID NO:686:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:686:

Val Tyr Tyr Leu Thr Arg Asp Pro
1               5

(2) INFORMATION FOR SEQ ID NO:687:
```

(i) SEQUENCE CHARACTERISTICS:
    (A) LENGTH: 8 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:687:

Tyr Tyr Leu Thr Arg Asp Pro Thr
1               5

(2) INFORMATION FOR SEQ ID NO:688:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:688:

Trp Glu Thr Ala Arg His Thr Pro
1               5

(2) INFORMATION FOR SEQ ID NO:689:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:689:

Glu Thr Ala Arg His Thr Pro Val
1               5

(2) INFORMATION FOR SEQ ID NO:690:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:690:

Thr Ala Arg His Thr Pro Val Asn
1               5

(2) INFORMATION FOR SEQ ID NO:691:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:691:

Ala Arg His Thr Pro Val Asn Ser
1               5

(2) INFORMATION FOR SEQ ID NO:692:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:692:

Arg His Thr Pro Val Asn Ser Trp
1               5

(2) INFORMATION FOR SEQ ID NO:693:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:693:

His Thr Pro Val Asn Ser Trp Leu
1               5

(2) INFORMATION FOR SEQ ID NO:694:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:694:

Thr Pro Val Asn Ser Trp Leu Gly
1               5

(2) INFORMATION FOR SEQ ID NO:695:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:695:

Pro Val Asn Ser Trp Leu Gly Asn
1               5

(2) INFORMATION FOR SEQ ID NO:696:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:696:

Val Asn Ser Trp Leu Gly Asn Ile
1               5

(2) INFORMATION FOR SEQ ID NO:697:

(i) SEQUENCE CHARACTERISTICS:
       (A) LENGTH: 8 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO:697:

Asn Ser Trp Leu Gly Asn Ile Ile
1               5

(2) INFORMATION FOR SEQ ID NO:698:

(i) SEQUENCE CHARACTERISTICS:
       (A) LENGTH: 8 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO:698:

Ser Trp Leu Gly Asn Ile Ile Met
1               5

(2) INFORMATION FOR SEQ ID NO:699:

(i) SEQUENCE CHARACTERISTICS:
       (A) LENGTH: 8 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO:699:

Trp Leu Gly Asn Ile Ile Met Glu
1               5

(2) INFORMATION FOR SEQ ID NO:700:

(i) SEQUENCE CHARACTERISTICS:
       (A) LENGTH: 8 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO:700:

Leu Gly Asn Ile Ile Met Glu Ala
1               5

(2) INFORMATION FOR SEQ ID NO:701:

(i) SEQUENCE CHARACTERISTICS:
       (A) LENGTH: 8 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO:701:

Gly Asn Ile Ile Met Glu Ala Pro
1               5

(2) INFORMATION FOR SEQ ID NO:702:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:702:

Asn Ile Ile Met Glu Ala Pro Thr
1               5

(2) INFORMATION FOR SEQ ID NO:703:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:703:

Ile Ile Met Glu Ala Pro Thr Leu
1               5

(2) INFORMATION FOR SEQ ID NO:704:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:704:

Ile Met Glu Ala Pro Thr Leu Trp
1               5

(2) INFORMATION FOR SEQ ID NO:705:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:705:

Met Glu Ala Pro Thr Leu Trp Ala
1               5

(2) INFORMATION FOR SEQ ID NO:706:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:706:

Glu Ala Pro Thr Leu Trp Ala Arg

```
1               5
```

(2) INFORMATION FOR SEQ ID NO:707:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:707:

```
Ala Pro Thr Leu Trp Ala Arg Met
1               5
```

(2) INFORMATION FOR SEQ ID NO:708:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:708:

```
Pro Thr Leu Trp Ala Arg Met Ile
1               5
```

(2) INFORMATION FOR SEQ ID NO:709:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:709:

```
Thr Leu Trp Ala Arg Met Ile Leu
1               5
```

(2) INFORMATION FOR SEQ ID NO:710:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:710:

```
Leu Trp Ala Arg Met Ile Leu Met
1               5
```

(2) INFORMATION FOR SEQ ID NO:711:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:711:

```
Trp Ala Arg Met Ile Leu Met Thr
1               5

(2) INFORMATION FOR SEQ ID NO:712:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:712:

Ala Arg Met Ile Leu Met Thr His
1               5

(2) INFORMATION FOR SEQ ID NO:713:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:713:

Arg Met Ile Leu Met Thr His Phe
1               5

(2) INFORMATION FOR SEQ ID NO:714:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:714:

Met Ile Leu Met Thr His Phe Glu
1               5

(2) INFORMATION FOR SEQ ID NO:715:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:715:

Leu Asp Cys Glu Ile Tyr Gly Ala
1               5

(2) INFORMATION FOR SEQ ID NO:716:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:716:
```

```
Asp Cys Glu Ile Tyr Gly Ala Cys
1               5
```

(2) INFORMATION FOR SEQ ID NO:717:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:717:

```
Cys Glu Ile Tyr Gly Ala Cys Tyr
1               5
```

(2) INFORMATION FOR SEQ ID NO:718:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:718:

```
Glu Ile Tyr Gly Ala Cys Tyr Ser
1               5
```

(2) INFORMATION FOR SEQ ID NO:719:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:719:

```
Ile Tyr Gly Ala Cys Tyr Ser Ile
1               5
```

(2) INFORMATION FOR SEQ ID NO:720:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:720:

```
Asp Leu Pro Pro Ile Ile Gln Arg
1               5
```

(2) INFORMATION FOR SEQ ID NO:721:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:721:

Leu Pro Pro Ile Ile Gln Arg Leu
1               5

(2) INFORMATION FOR SEQ ID NO:722:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:722:

Pro Pro Ile Ile Gln Arg Leu His
1               5

(2) INFORMATION FOR SEQ ID NO:723:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:723:

Pro Ile Ile Gln Arg Leu His Gly
1               5

(2) INFORMATION FOR SEQ ID NO:724:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:724:

Ile Ile Gln Arg Leu His Gly Leu
1               5

(2) INFORMATION FOR SEQ ID NO:725:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:725:

Ile Gln Arg Leu His Gly Leu Ser
1               5

(2) INFORMATION FOR SEQ ID NO:726:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:726:

Gln Arg Leu His Gly Leu Ser Ala
1               5

(2) INFORMATION FOR SEQ ID NO:727:

(i) SEQUENCE CHARACTERISTICS:
           (A) LENGTH: 8 amino acids
           (B) TYPE: amino acid
           (C) STRANDEDNESS: single
           (D) TOPOLOGY: linear (ii) MOLECULE TYPE: peptide (xi) SEQUENCE DESCRIPTION: SEQ ID NO:727:

Arg Leu His Gly Leu Ser Ala Phe
1               5

(2) INFORMATION FOR SEQ ID NO:728:

(i) SEQUENCE CHARACTERISTICS:
           (A) LENGTH: 8 amino acids
           (B) TYPE: amino acid
           (C) STRANDEDNESS: single
           (D) TOPOLOGY: linear (ii) MOLECULE TYPE: peptide (xi) SEQUENCE DESCRIPTION: SEQ ID NO:728:

Leu His Gly Leu Ser Ala Phe Ser
1               5

(2) INFORMATION FOR SEQ ID NO:729:

(i) SEQUENCE CHARACTERISTICS:
           (A) LENGTH: 8 amino acids
           (B) TYPE: amino acid
           (C) STRANDEDNESS: single
           (D) TOPOLOGY: linear (ii) MOLECULE TYPE: peptide (xi) SEQUENCE DESCRIPTION: SEQ ID NO:729:

His Gly Leu Ser Ala Phe Ser Leu
1               5

(2) INFORMATION FOR SEQ ID NO:730:

(i) SEQUENCE CHARACTERISTICS:
           (A) LENGTH: 8 amino acids
           (B) TYPE: amino acid
           (C) STRANDEDNESS: single
           (D) TOPOLOGY: linear (ii) MOLECULE TYPE: peptide (xi) SEQUENCE DESCRIPTION: SEQ ID NO:730:

Gly Leu Ser Ala Phe Ser Leu His
1               5

(2) INFORMATION FOR SEQ ID NO:731:

(i) SEQUENCE CHARACTERISTICS:
           (A) LENGTH: 8 amino acids
           (B) TYPE: amino acid
           (C) STRANDEDNESS: single
           (D) TOPOLOGY: linear (ii) MOLECULE TYPE: peptide (xi) SEQUENCE DESCRIPTION: SEQ ID NO:731:

Leu Ser Ala Phe Ser Leu His Ser
1               5

(2) INFORMATION FOR SEQ ID NO:732:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:732:

Ser Ala Phe Ser Leu His Ser Tyr
1               5

(2) INFORMATION FOR SEQ ID NO:733:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:733:

Ala Phe Ser Leu His Ser Tyr Ser
1               5

(2) INFORMATION FOR SEQ ID NO:734:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:734:

Phe Ser Leu His Ser Tyr Ser Pro
1               5

(2) INFORMATION FOR SEQ ID NO:735:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:735:

Ser Leu His Ser Tyr Ser Pro Gly
1               5

(2) INFORMATION FOR SEQ ID NO:736:

(i) SEQUENCE CHARACTERISTICS:
        (A) LENGTH: 8 amino acids
        (B) TYPE: amino acid
        (C) STRANDEDNESS: single
        (D) TOPOLOGY: linear

```
        (ii) MOLECULE TYPE: peptide (xi) SEQUENCE DESCRIPTION: SEQ ID NO:736:

Leu His Ser Tyr Ser Pro Gly Glu
1               5

(2) INFORMATION FOR SEQ ID NO:737:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:737:

His Ser Tyr Ser Pro Gly Glu Ile
1               5

(2) INFORMATION FOR SEQ ID NO:738:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:738:

Leu Gly Val Pro Pro Leu Arg Ala
1               5

(2) INFORMATION FOR SEQ ID NO:739:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:739:

Gly Val Pro Pro Leu Arg Ala Trp
1               5

(2) INFORMATION FOR SEQ ID NO:740:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:740:

Val Pro Pro Leu Arg Ala Trp Arg
1               5

(2) INFORMATION FOR SEQ ID NO:741:

(i) SEQUENCE CHARACTERISTICS:
            (A) LENGTH: 8 amino acids
            (B) TYPE: amino acid
            (C) STRANDEDNESS: single
```

```
        (D) TOPOLOGY: linear (ii) MOLECULE TYPE: peptide (xi) SEQUENCE DESCRIPTION: SEQ ID NO:741:

Ala Ala Ile Cys Gly Lys Tyr Leu
1               5

(2) INFORMATION FOR SEQ ID NO:742:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:742:

Ala Ile Cys Gly Lys Tyr Leu Glu
1               5

(2) INFORMATION FOR SEQ ID NO:743:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:743:

Ile Cys Gly Lys Tyr Leu Glu Asn
1               5

(2) INFORMATION FOR SEQ ID NO:744:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:744:

Asp Leu Ser Gly Trp Glu Thr Ala
1               5

(2) INFORMATION FOR SEQ ID NO:745:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:745:

Val Ser His Ala Arg Pro Arg Trp
1               5

(2) INFORMATION FOR SEQ ID NO:746:

(i) SEQUENCE CHARACTERISTICS:
        (A) LENGTH: 16 base pairs
        (B) TYPE: nucleic acid
```

(C) STRANDEDNESS: single
        (D) TOPOLOGY: linear (ii) MOLECULE TYPE: other nucleic acid
        (A) DESCRIPTION: /desc = "primer derived from clone
            81"

(xi) SEQUENCE DESCRIPTION: SEQ ID NO:746:

CAATCATACC TGACAG                                                      16

(2) INFORMATION FOR SEQ ID NO:747:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer derived from clone
            81"

(xi) SEQUENCE DESCRIPTION: SEQ ID NO:747:

GATAACCTCT GCCTGA                                                      16

(2) INFORMATION FOR SEQ ID NO:748:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer from clone 36"

(xi) SEQUENCE DESCRIPTION: SEQ ID NO:748:

GCATGTCATG ATGTAT                                                      16

(2) INFORMATION FOR SEQ ID NO:749:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer from clone 37b"

(xi) SEQUENCE DESCRIPTION: SEQ ID NO:749:

ACAATACGTG TGTCAC                                                      16

(2) INFORMATION FOR SEQ ID NO:750:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer JHC 7"

(xi) SEQUENCE DESCRIPTION: SEQ ID NO:750:

CCAGCGGTGG CCTGGTATTG                                                  20

(2) INFORMATION FOR SEQ ID NO:751:

```
    (i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer ALX 80"

(xi) SEQUENCE DESCRIPTION: SEQ ID NO:751:

TTTGGGTAAG GTCATCGATA CCCTTACGTG                                     30

(2) INFORMATION FOR SEQ ID NO:752:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer JHC 6"

(xi) SEQUENCE DESCRIPTION: SEQ ID NO:752:

ATATGCGGCC GCCTTCCGTT GGCATAA                                        27

(2) INFORMATION FOR SEQ ID NO:753:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer JHC 13"

(xi) SEQUENCE DESCRIPTION: SEQ ID NO:753:

AATTCGCGGC CGCCATACGA TTTAGGTGAC ACTATAGAAC CCCCCCCCCC CCCC          54

(2) INFORMATION FOR SEQ ID NO:754:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer 156e16B - derived
            from clone 156e"

(xi) SEQUENCE DESCRIPTION: SEQ ID NO:754:

CGACAAGAAA GACAGA                                                    16

(2) INFORMATION FOR SEQ ID NO:755:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer K91/16B - derived
            from clone K91"

(xi) SEQUENCE DESCRIPTION: SEQ ID NO:755:

CGTTGGCATA ACTGAT                                                    16
```

(2) INFORMATION FOR SEQ ID NO:756:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "sense strand primer
            ag30a16A"

(xi) SEQUENCE DESCRIPTION: SEQ ID NO:756:

CTCTATGGCA ATGAGG                                                        16

(2) INFORMATION FOR SEQ ID NO:757:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "sense strand primer
            156e16A"

(xi) SEQUENCE DESCRIPTION: SEQ ID NO:757:

AGCTTCGACG TCACAT                                                        16

(2) INFORMATION FOR SEQ ID NO:758:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer 202aEnv41a"

(xi) SEQUENCE DESCRIPTION: SEQ ID NO:758:

CTTGAATTCG CAATTTGGGT AAGGTCATCG ATACCCTTAC G                            41

(2) INFORMATION FOR SEQ ID NO:759:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer 156e38B'"

(xi) SEQUENCE DESCRIPTION: SEQ ID NO:759:

CTTGAATTCG ATAGAGCAAT TGCAACCTTG CGTCGTCC                                38

(2) INFORMATION FOR SEQ ID NO:760:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer 156e38A'"

(xi) SEQUENCE DESCRIPTION: SEQ ID NO:760:

CTTGAATTCG GACGACGCAA GGTTGCAATT GCTCTATC                                38

(2) INFORMATION FOR SEQ ID NO:761:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer 59aEnv39C"

(xi) SEQUENCE DESCRIPTION: SEQ ID NO:761:

CTTGAATTCC AGCCGGTGTT GAGGCTATCA TTGCAGTTC                               39

(2) INFORMATION FOR SEQ ID NO:762:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer CA216a16A - derived
            from clone 216"

(xi) SEQUENCE DESCRIPTION: SEQ ID NO:762:

TGAACTATGC AACAGG                                                        16

(2) INFORMATION FOR SEQ ID NO:763:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer CA216a16B - derived
            from clone 216"

(xi) SEQUENCE DESCRIPTION: SEQ ID NO:763:

GGAGTGTGCA GGATGG                                                        16

(2) INFORMATION FOR SEQ ID NO:764:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer CA84a16A - derived
            from clone 84"

(xi) SEQUENCE DESCRIPTION: SEQ ID NO:764:

AAGGTTGCAA TTGCTC                                                        16

(2) INFORMATION FOR SEQ ID NO:765:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: other nucleic acid
            (A) DESCRIPTION: /desc = "primer CA84a16B"

(xi) SEQUENCE DESCRIPTION: SEQ ID NO:765:

ACTAACAGGA CCTTCG                                                           16

(2) INFORMATION FOR SEQ ID NO:766:

(i) SEQUENCE CHARACTERISTICS:
            (A) LENGTH: 16 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "primer CA84a16C - derived
                from clone 84"

(xi) SEQUENCE DESCRIPTION: SEQ ID NO:766:

TAACGGGTCA CCGCAT                                                           16

(2) INFORMATION FOR SEQ ID NO:767:

(i) SEQUENCE CHARACTERISTICS:
            (A) LENGTH: 16 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:767:

Met Asn His Ser Pro Val Arg Asn Tyr Cys Leu His Ala Glu Ser Val
1               5                   10                  15

(2) INFORMATION FOR SEQ ID NO:768:

(i) SEQUENCE CHARACTERISTICS:
            (A) LENGTH: 4 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:768:

Met Ala Leu Val
1

(2) INFORMATION FOR SEQ ID NO:769:

(i) SEQUENCE CHARACTERISTICS:
            (A) LENGTH: 15 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:769:

Met Ser Val Val Gln Pro Pro Gly Pro Pro Leu Pro Gly Glu Pro
1               5                   10                  15

(2) INFORMATION FOR SEQ ID NO:770:

(i) SEQUENCE CHARACTERISTICS:
            (A) LENGTH: 12 amino acids
            (B) TYPE: amino acid
            (C) STRANDEDNESS: single (D) TOPOLOGY: linear (ii) MOLECULE TYPE: peptide (xi) SEQUENCE DESCRIPTION: SEQ ID NO:770:

Met Pro Gly Asp Leu Gly Val Pro Pro Gln Asp Cys
1               5                  10

(2) INFORMATION FOR SEQ ID NO:771:

(i) SEQUENCE CHARACTERISTICS:
        (A) LENGTH: 41 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:771:

Ile Ile Pro Asp Arg Glu Val Leu Tyr Arg Glu Phe Asp Glu Met Glu
1               5                  10                  15

Glu Cys Ser Gln His Leu Pro Tyr Ile Glu Gln Met Met Leu Ala Glu
            20                  25                  30

Gln Phe Lys Gln Lys Ala Leu Gly Leu
            35                  40

(2) INFORMATION FOR SEQ ID NO:772:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:772:

Asp Arg Gly Trp Gly Asp
1               5

(2) INFORMATION FOR SEQ ID NO:773:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:773:

Phe Asp Gly Asp Ser Tyr Ile Phe Gly Asp Ser Tyr Ile
1               5                  10

(2) INFORMATION FOR SEQ ID NO:774:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:774:

Cys Cys Arg Ser Cys
1               5

(2) INFORMATION FOR SEQ ID NO:775:

-continued

```
    (i) SEQUENCE CHARACTERISTICS:
         (A) LENGTH: 20 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "primer ssc5h20A - derived
              from clone 5h"

(xi) SEQUENCE DESCRIPTION: SEQ ID NO:775:

GTAATATGGT GACAGAGTCA                                            20

(2) INFORMATION FOR SEQ ID NO:776:

(i) SEQUENCE CHARACTERISTICS:
         (A) LENGTH: 34 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "primer ssc5h34A - derived
              from clone 5h"

(xi) SEQUENCE DESCRIPTION: SEQ ID NO:776:

GATCTCTAGA GAAATCAATA TGGTGACAGA GTCA                            34

(2) INFORMATION FOR SEQ ID NO:777:

(i) SEQUENCE CHARACTERISTICS:
         (A) LENGTH: 74 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "probe derived from clone
              5h"

(xi) SEQUENCE DESCRIPTION: SEQ ID NO:777:

CCCAGCGGCG TACGCGCTGG ACACGGAGGT GGCCGCGTCG TGTGGCGGTG TTGTTCTCGT    60

CGGGTTGATG GCGC                                                  74
```

What is claimed is:

1. A polypeptide immunoreactive with an HCV antibody wherein the immunoreactive portion reactive with said HCV antibody is a segment of an HCV polypeptide less than or equal to 20 amino acids, wherein the amino terminal amino acid of the segment is amino acid 1940 of FIG. 72 (SEQ ID NOS:137–138).

2. An immunoassay reagent comprising a polypeptide according to claim 1.

3. A method for detecting the presence of antibodies immunoreactive within hepatitis C virus (HCV) proteins in a sample, said method comprising:

contacting an immobilized immunoassay reagent according to claim 2 with said sample, and detecting antibodies bound to said reagent.

4. A method of making a polypeptide according to claim 1 wherein said polypeptide is prepared by recombinant expression or chemical synthesis.

5. The polypeptide of claim 1, wherein the immunoreactive portion reactive with said HCV antibody consists of amino acid 1940 to amino acid 1947 of FIG. 72 (SEQ ID NOS:137–138).

6. A polypeptide immunoreactive with an HCV antibody wherein the immunoreactive portion reactive with said HCV antibody is a segment of an HCV polypeptide less than or equal to 20 amino acids wherein the amino terminal amino acid of the segment is amino acid 1218 of FIG. 72 (SEQ ID NOS:137–138).

7. An immunoassay reagent comprising a polypeptide according to claim 6.

8. A method for detecting the presence of antibodies immunoreactive within hepatitis C virus (HCV) proteins in a sample, said method comprising:

contacting an immobilized immunoassay reagent according to claim 7 with said sample, and detecting antibodies bound to said reagent.

9. A method of making a polypeptide according to claim 6 wherein said polypeptide is prepared by recombinant expression or chemical synthesis.

10. The polypeptide of claim 6 wherein the immunoreactive portion reactive with said HCV antibody consists of amino acid 1218 to amino acid 1225 of FIG. 72 (SEQ ID NOS:137–138).

* * * * *